US012529110B2

(12) United States Patent
Zwarthoff et al.

(10) Patent No.: US 12,529,110 B2
(45) Date of Patent: Jan. 20, 2026

(54) METHOD OF DIAGNOSING BLADDER CANCER

(71) Applicant: ERASMUS UNIVERSITY MEDICAL CENTER ROTTERDAM, Rotterdam (NL)

(72) Inventors: Ellen Catharina Zwarthoff, Rotterdam (NL); Annechiena Geertruide Van Tilborg, Gouda (NL)

(73) Assignee: Erasmus University Medical Center Rotterdam, Rotterdam (NL)

(*) Notice: Subject to any disclaimer, the term of this patent is extended or adjusted under 35 U.S.C. 154(b) by 0 days.

(21) Appl. No.: 17/571,248

(22) Filed: Jan. 7, 2022

(65) Prior Publication Data

US 2022/0205047 A1 Jun. 30, 2022

Related U.S. Application Data

(60) Continuation of application No. 15/076,544, filed on Mar. 21, 2016, now Pat. No. 11,220,714, which is a division of application No. 13/265,376, filed as application No. PCT/NL2010/050213 on Apr. 20, 2010, now abandoned.

(60) Provisional application No. 61/170,928, filed on Apr. 20, 2009.

(51) Int. Cl.
*C12Q 1/6886* (2018.01)

(52) U.S. Cl.
CPC ..... *C12Q 1/6886* (2013.01); *C12Q 2600/154* (2013.01)

(58) Field of Classification Search
CPC ............ C12Q 1/6886; C12Q 2600/118; C12Q 2600/154; C12Q 2600/16; C12Q 2600/116
See application file for complete search history.

(56) References Cited

U.S. PATENT DOCUMENTS

| | | | | |
|---|---|---|---|---|
| 5,786,146 | A | 7/1998 | Herman et al. | |
| 6,017,704 | A | 1/2000 | Herman et al. | |
| 6,200,756 | B1 | 3/2001 | Herman et al. | |
| 6,265,171 | B1 | 7/2001 | Herman et al. | |
| 2002/0198371 | A1 | 12/2002 | Wang | |
| 2008/0254447 | A1* | 10/2008 | Foekens | C12Q 1/6886 435/6.16 |
| 2009/0054260 | A1 | 2/2009 | Sidransky | |
| 2009/0305256 | A1 | 12/2009 | Pfeifer et al. | |

FOREIGN PATENT DOCUMENTS

| | | |
|---|---|---|
| WO | 1997046705 | 11/1997 |
| WO | 2002081749 A2 | 10/2002 |
| WO | 2005082144 | 9/2005 |
| WO | 2006088940 | 8/2006 |
| WO | 2008083098 | 7/2008 |
| WO | 2008140532 | 11/2008 |
| WO | 2009036922 | 3/2009 |

OTHER PUBLICATIONS

Lofton-Day (Clin Chem, 2008, vol. 54, p. 414-423).*
Greiner (Am Soc Human Genetics, 2007, pp. 1-18).*
Tan (Molecular Oncology 2009, 3, 425-438).*
Di Lorenzo (Cancer, 2010, 1893-1900).*
Aleman et al., "Identification of PMF1 methylation in association with bladder cancer progression," Clin. Cancer Res. (2008) 14(24):8236-8243.
Benjamini et al., Behav Brain Res, vol. 125, 2001, pp. 279.
Bibikova et al., Genome Res, vol. 16, 2006, pp. 383.
Blaveri et al., Clin Cancer Res, vol. 11, 2005, pp. 4044.
Bracken et al., Genes Dev, vol. 20, 2006, pp. 1123.
Brazma et al., Nat Genet, vol. 29, 2001, pp. 365.
Brazma, Scientific World J, vol. 9, 2009, pp. 420.
Catto et al., "Promoter hypermethylation is associated with tumor location, stage, and subsequent progression in transitional cell carcinoma," J. Clinical Oncology (2005) 23(13):2903-2910.
Cortese et al., "DNA methylation profiling of pseudogene-parental gene pairs and two gene families," Genomics (2008) 91(6):492-502.
Cottrell, "Molecular diagnostic applications of DNA methylation technology," Clin. Biochem. (2004) 37:595-604.
Derks et al., Cellular Oncology, vol. 26, 2004, pp. 291-299.
Dulaimi (Clinical Cancer Research, 2004, vol. 10, 1887-1893.
Dyrskjot et al., Cancer Res, vol. 64, 2004, pp. 4040.
Dyrskjot et al., Nat Genet, vol. 33, 2003, pp. 90.
European Partial Search Report for Application No. 19159895.2, mailed Jan. 21, 2020, 21 pages.
European Search Report for Application No. EP 16152123.2, mailed Oct. 24, 2016, 17 pages.
Fan et al., Cold Spring Harb Symp Quant Biol, vol. 68, 2003, pp. 69.
Febbo, "Epigenetic events highlight the challenge of validating prognostic biomarkers during the clinical and biologic evolution of prostate cancer," J. Clin. Oncol. (2009) 27:3088-2090.
Feinberg, "The history of cancer epigenetics," Nature Reveiws (2004) 4:143-153.
Friedrich et al., "Prognostic relevance of methylation markers in patients with non-muscle invasive bladder carcinoma," European J. of Cancer (2005) 41(17):2769-2778.
Frommer et al., Proc. Natl. Acad. Sci. USA, vol. 89, 1992, pp. 1827-1831.
Gonzalgo; Liang, Nat Protoc, vol. 2, 2007, pp. 1931.
Herman et al., Proc. Natl. Acad. Sci. USA, vol. 93, 1996, pp. 9821-9826.
Herman; Baylin, Current Protocols in Human Genetics, vol. 10, 1998, pp. 10.16.11-10.16.10.
Hogue et al., J. National Cancer Institute, 2006, vol. 98, pp. 996-1004.
International Prelinimary Report on Patentability and Written Opinion for PCT/NL2010/050213, Issued Oct. 25, 2011.

(Continued)

*Primary Examiner* — Sarae L Bausch
(74) *Attorney, Agent, or Firm* — McNeill PLLC

(57) ABSTRACT

The present invention relates to a method of diagnosing cancer in a subject comprising detecting in the DNA of said subject at least one hypermethylated CpG island associated with said cancer, wherein an elevation in the level of methylation in said CpG island of said subject, relative to the level of methylation in said CpG island of a control subject, is indicative of said CpG island being hypermethylated.

19 Claims, 9 Drawing Sheets

Figure 1A:
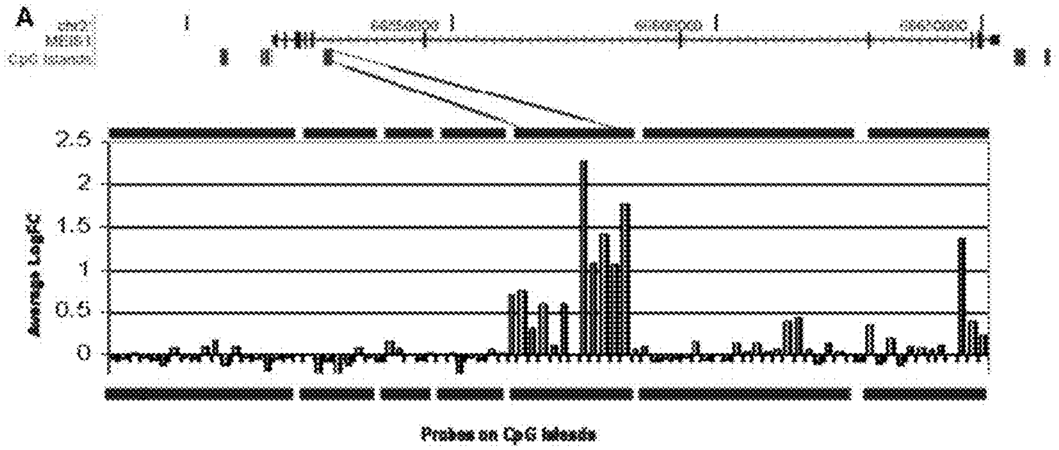
Figure 1B:
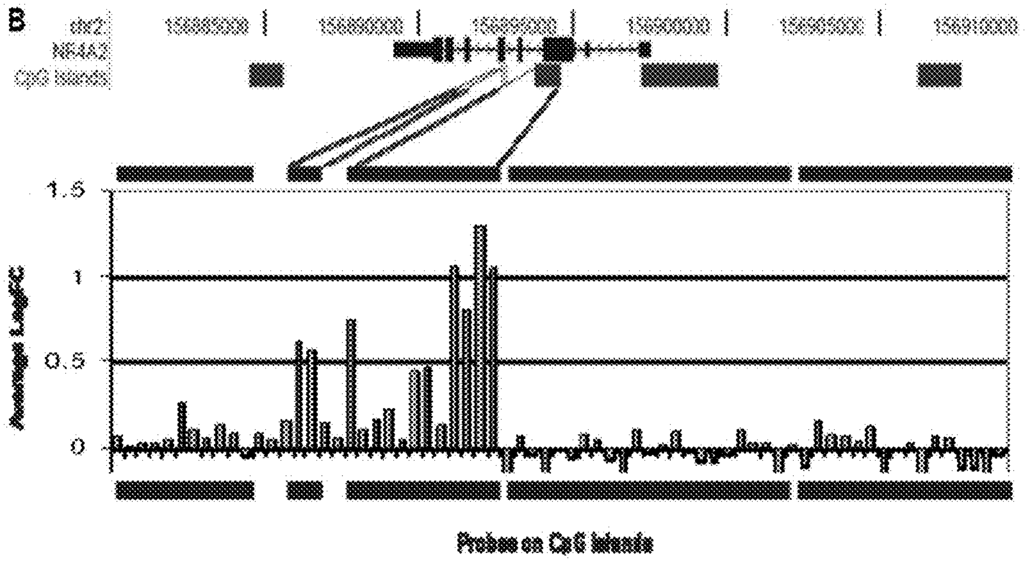
Figure 1C:
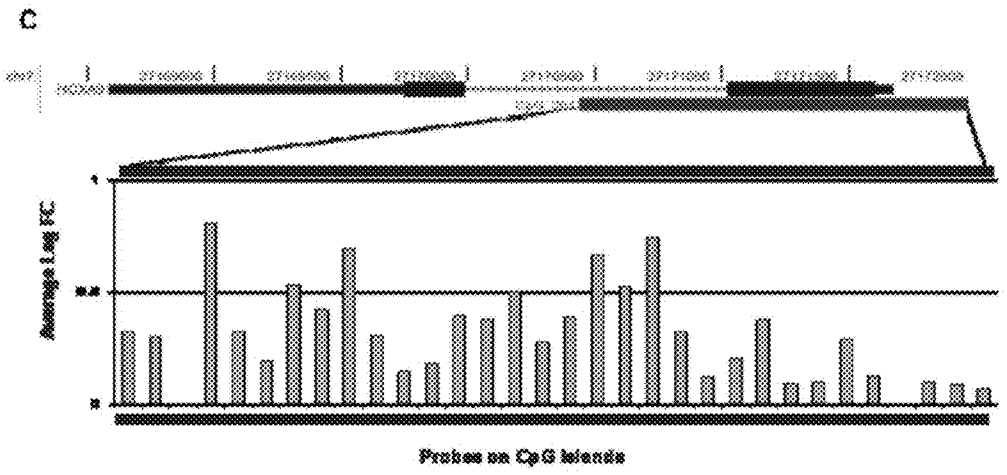
Figure 1D:
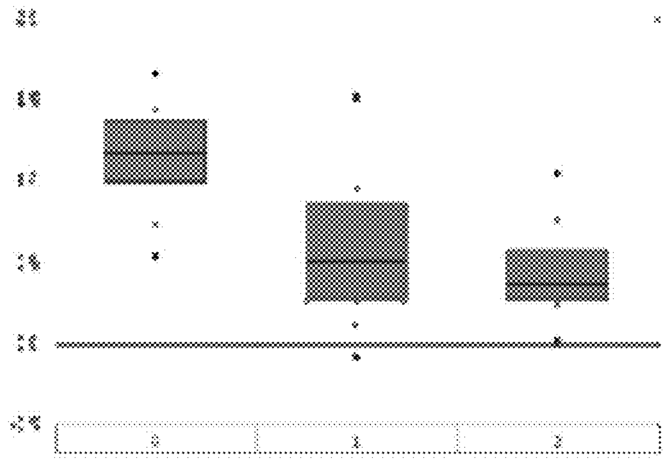
Figure 1E:
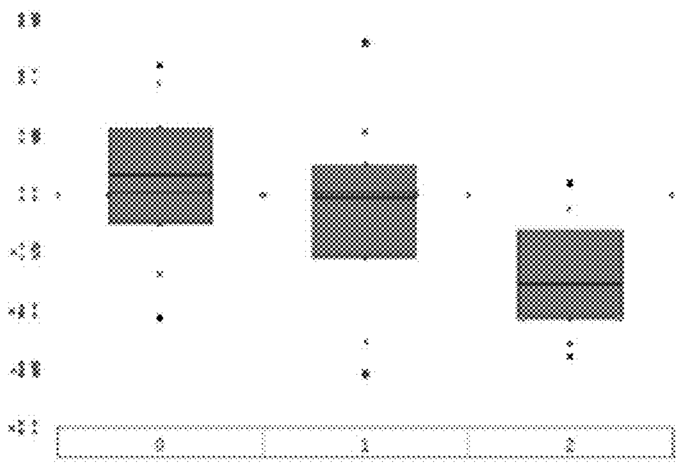
Figure 1F:
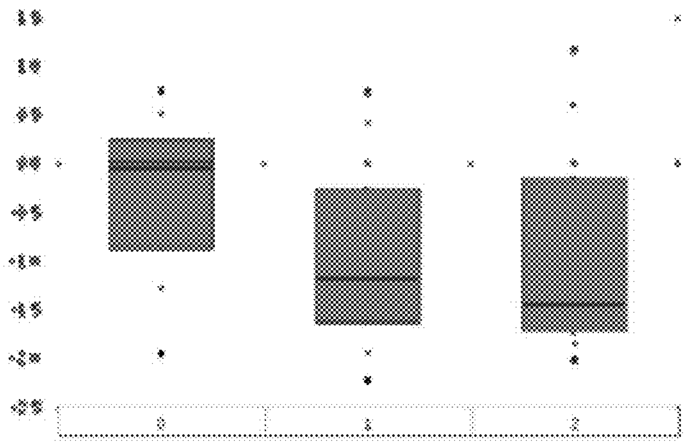

Specification includes a Sequence Listing.

(56) References Cited

OTHER PUBLICATIONS

Irizarry, "The human colon cancer methylome shows similar hypo- and hypermethylation at conserved tissue-specific CpG island shores," Nature Genetics (2009) 41(2):178-186.
Jones et al., "The fundamental role of epigenetic events in cancer," Nature Reviews (2002) 3:415-428.
Kim et al., "Epigenetic markers as promising prognosticators for bladder cancer," The Japanese Urological Association (2009) 16(1):17-22.
Kitamura, "Analysis of tissue-specific differentially methylated regions (TDMs) in humans," Genomics (2007) 89(3):326-337.
Lee et al., Cell, vol. 125, 2006, pp. 301.
Lin et al., "Increase sensitivity in detecting superficial, low grade bladder cancer by combination analysis of hypermethylation of E-cadherin, p16, p14, RASSF1A genes in urine," Urologic Oncology: Seminars and Original Investigations (2009) 28(6):597-602.
Lindgren et al., Oncogene, vol. 25, 2006, pp. 2685.
Lurkin et al., PLOS One, vol. 5, 2010, pp. e8802.
Modlich et al., Clin Cancer Res, vol. 10, 2004, pp. 3410.
Negraes et al., "DNA methylation patterns in bladder cancer and washing cell sediments: a perspective for tumor recurrence detection," BMC Cancer (2008) 8:238, 12 pages.
Ohm et al., Nat Genet, vol. 39, 2007, pp. 237.
Pike et al., "DNA methylation profiles in diffuse large B-cell lymphoma and their relationship to gene expression status," Leukemia (2008) 22:1035-1043.
Rakyan et al., Genome Res, vol. 18, 2008, pp. 1518.
Rauch et al., "High-resolution mapping of DNA hypermethylation and hypomethylation in lung cancer," Proceedings of the National Academy of Sciences, vol. 105, No. 1, Jan. 8, 2008, pp. 252-257.
Raju et al., "4023: Genome-wide analysis of CpG island methylation identified OTX1, OSR1 and ONECUT2 as biomarkers for recurrent bladder cancer detection in voided urine," Cancer Research, American Association for Cancer Research, US. vol. 72, No. Suppl. 8, Apr. 15, 2012, p. 4023.
"Remington's Pharmaceutical Sciences", 1991, Mack Pub. Co.
Roupret et al., "A comparison of the performance of microsatellite and methylation urine analysis for predicting the recurrence of urothelial cell carcinoma, and definition of a set of markers by Bayesian network analysis," in: Investigative Urology, Klocker et al. (eds.) The Authors Journal Compilation © BJU International (2008) 101:1448-1453.
Salem et al., "Progressive increases in de novo methylation of CpG islands in bladder cancer," Cancer Research (2000) 60(9):2473-2476.
Sanchez-Carbayo et al., J Clin Oncol, vol. 24, 2006, pp. 778.
Schlesinger et al., Nat Genet, vol. 39, 2007, pp. 232.
Schouten et al., Nucleic Acids Research, vol. 3, No. 12, 2002, pp. E57,13.
Smiraglia et al., "Excessive CpG island hypermethylation in cancer cell lines versus primary human malignancies," Human Molecular Genetics (2001) 10:1413-1419.
Smith (2007, Epigenetics 2:3, pp. 161-172).
Smyth, Stat Appl Genet Mol Biol, vol. 3, 2004.
Tada et al., "The association of death-associated protein kinase hypermethylation with early recurrence in superficial bladder cancers," Cancer Research (2002) 62(14):4048-4053.
Tommasi (Breast Cancer Research, 2009, 11: R14, pp. 1-17).
Van Oers et al., Clin. Cancer Res, vol. 11, No. 21, 2005, pp. 7743-7748.
Verma et al., "Genetic and epigenetic biomarkers in cancer diagnosis and identifying high risk populations," Critical Review in Oncology/Hematology (2006) 60:9-18.
Widschwendter M et al., Nat Genet, vol. 39, 2007, pp. 157.
Wu et al., "DNA methylation profiling of ovarian carcinomas and their in vitro models identifies HOXA9, HOXB5, SCGB3AI, and CRABPI as novel targets," Molecular Cancer (2007) 6:45, 10 pages.
Yan et al., Methods Mol Biol, vol. 200, 2002, pp. 87-100.
Yang et al., Nucleic Acids Res, vol. 30, 2002, pp. E15.

* cited by examiner

D

E

F

Legend: 0-Normal; 1-MI-BC; 2-NMI-BC

METHOD OF DIAGNOSING BLADDER CANCER

CROSS-REFERENCE TO RELATED APPLICATION

This application is a continuation of U.S. application Ser. No. 15/076,544, filed Mar. 21, 2016, which application is a divisional of U.S. Ser. No. 13/265,376 having an international filing date of 20 Apr. 2010, which is the national phase of PCT application PCT/NL2010/050213 having an international filing date of 20 Apr. 2010, which claims benefit under 35 U.S.C. § 119 (e) of provisional application U.S. Ser. No. 61/170,928 filed 20 Apr. 2009. The contents of these documents are incorporated herein by reference.

REFERENCE TO A SEQUENCE LISTING SUBMITTED VIA EFS-WEB

The content of the ASCII text file of the sequence listing named "2022-01-017_170826.00151_Sequence Listing.txt" which is 526,600 bytes in size was created on Jan. 7, 2022 and is electronically submitted via EFS-Web herewith and is incorporated herein by reference in its entirety.

FIELD OF THE INVENTION

The present invention is in the field of bladder cancer diagnosis, and in particular the methods for predicting the progression of bladder cancer tumors. The invention provides diagnostic methods and diagnostic compositions for use in such methods. The invention further provides therapeutic targets for treating specific forms of bladder cancers.

BACKGROUND OF THE INVENTION

Bladder cancer is the fifth most common cancer in the western world with an incidence of 20 new cases per year per 100,000 people in the U.S. Unfortunately, these statistics do not include superficial pTa bladder cancer, which represents the most common type of bladder cancer. In the Netherlands, the incidence of both superficial and invasive bladder cancer is estimated as about 30 new cases per year per 100,000 people. This is in accordance with data from global cancer statistics for the western world. Superficial bladder tumors are removed by transurethral resection. However, up to 70% of these patients will develop one or more recurrences, and it has been estimated that 1 in 1,450 people is under surveillance for bladder cancer in the United Kingdom. Cystoscopy is an uncomfortable, invasive, and expensive procedure, but currently remains the gold standard for detection of recurrences. Because patients have to be monitored perpetually and have a long-term survival, bladder cancer is the most expensive cancer when calculated on a per patient basis.

Hence there exists a need for an inexpensive, noninvasive, and simple procedure for the detection of bladder cancer. Cytology done on voided urine is a noninvasive procedure with up to 100% specificity. Unfortunately, this method is limited by its sensitivity, which is especially poor for low-grade tumors. Because of this limited sensitivity, alternative methods need to be developed for the detection of tumor cells in voided urine.

SUMMARY OF THE INVENTION

The present inventors have found that the methylation of a number of specific CpG islands (CGIs) in the DNA of cells shaded in the urine of a subject is indicative of the present of a tumor, in particular a bladder tumor. Thus, aberrant methylation of these CpG islands in the DNA of a subject may be used as diagnostic and/or prognostic marker as well as a therapeutic target.

The present finding has been found to be particularly advantageous in the case of bladder cancer diagnostics (including disease prognosis and prediction of disease recurrence and progression), since the detection of methylation may occur in DNA (of cells) in a sample of urine obtained from the subject to be diagnosed. In particular urothelial cells present in said urine sample are used for this purpose. The skilled person will understand that diagnostic methods as indicated herein may make use of any body sample in which DNA comprising the aberrant methylations as defined herein can be detected, including biopsies of cancerous tissue, or tissue suspected of being malignant.

The present inventors have demonstrated the suitability of using methylation of specified CpG islands as diagnostic markers in bladder cancer diagnostics, such as for:

- detection of recurrent cancer in DNA isolated from patient urine, and
- detection of primary cancer in DNA isolated from patient urine.

Thus, in a first aspect, the present invention provides a method for diagnosing cancer in a subject comprising detecting in the DNA of said subject at least one hypermethylated CpG island associated with said cancer, wherein an elevation in the level of methylation in said CpG island of said subject, relative to the level of methylation in said CpG island of a control subject, is indicative of said CpG island being hypermethylated. The presence of a hypermethylated CpG island might indicate that the subject is at risk of, or suffering from, a cancer.

Preferably said CpG island is selected from the group consisting of the CpG islands listed in Table 1, Table 2, Table 3, Table 4, Table 5, Table 7, Table 9, Table 10 and Table 12.

In a preferred embodiment of methods of the invention, said cancer is bladder cancer.

In another preferred embodiment of methods of the invention, said method comprises detection of recurrent forms of cancer in DNA isolated from patient urine and wherein said at least one CpG islands methylation associated with cancer selected from the group consisting of the CpG islands listed in Table 1, Table 2, Table 3, Table 4, Table 5, Table 7, Table 9, Table 10 and Table 12.

In yet another preferred embodiment of methods of the invention, said method comprises detection of primary forms of cancer in DNA isolated from patient urine and wherein said at least one CpG islands methylation associated with cancer selected from the group consisting of the CpG islands listed in Table 1, Table 2, Table 3, Table 4, Table 5, Table 7, Table 9, Table 10 and Table 12.

In still a further preferred embodiment of methods of the invention, said DNA is obtained from a urine sample of said subject.

In another preferred embodiment of methods of the invention, said bladder cancer is non muscle-invasive bladder cancer. Alternatively, said bladder cancer is muscle-invasive bladder cancer. In a further preferred embodiment, said method provides detection of differential methylation of one or more of the genes provided in Table 7. Differential methylation of one or more of the genes provided in Table 7 is used to discriminate between subgroups of bladder cancer, such as between NMI-wt and MI and NMI-mt groups.

In a preferred embodiment of methods of the invention, general inflammatory cells in urine, preferably lymphocytes, are detected by methylation of at least one of the CGIs listed in Table 9. Table 9 indicates a number of CGIs methylated in blood but not in bladder cancer. The differential methylation of these CGIs, which can be detected in DNA (of cells) in a sample of urine obtained from the subject to be diagnosed, and in particular in urothelial cells present in said urine sample, are useful for the detection of lymphocytes in urine, or in general inflammatory cells in urine, which is indicative of cystitis. Positive detection of the presence of inflammatory cells in the urine can be used to diagnose infection or non-infective inflammation of the urinary tract and kidney.

In a preferred embodiment, said method comprises detection of recurrent cancer in DNA isolated from patient urine. This method entails the detection of specific CpG island methylations associated with recurrent forms of the cancer.

In another preferred embodiment, said method comprises detection of primary cancer in DNA isolated from patient urine. This method entails the detection of specific CpG island methylations associated with primary forms of the cancer.

The present inventors have further demonstrated the suitability of using methylation of specified CpG islands as prognostic markers in bladder cancer diagnostics, such as for:

- prediction of disease course based on analysis of tumor-derived or urine derived DNA, including:
  - prediction of invasive potential of non-muscle invasive urothelial carcinomas;
  - prediction of urothelial carcinoma-specific survival, and
  - prediction of presence/absence of lymph node and distant metastases caused by urothelial carcinomas Thus, in a second aspect, the present invention provides a method for the prediction of the recurrence, progression or prognosis of cancer, in particular bladder cancer, comprising detecting in the DNA of said subject at least one hypermethylated CpG island associated with said cancer, wherein an elevation in the level of methylation in said CpG island of said subject, relative to the level of methylation in said CpG island of a control subject, is indicative of said CpG island being hypermethylated. The presence of a hypermethylated CpG island might indicate that the subject is at risk of cancer recurrence, progression of a cancer, and/or poor prognosis. A preferred method for the prognosis of a risk of cancer recurrence, progression of a cancer, and/or poor prognosis comprises detection of one or more methylated CpGs in CGIs of the genes listed in Table 12B, whereby the CGIs are preferably chosen from GPR103, DBC1 and/or GATA2 genes. Said cancer is preferably bladder cancer.

In a preferred embodiment of said method for the prediction of the recurrence, progression or prognosis of cancer, said CpG island is selected from the group consisting of the CpG islands listed in Table 1, Table 2, Table 3, Table 4, Table 5, Table 7, Table 9, Table 10 and Table 12, preferably from Table 5 and Table 10.

In aspects of the present invention the methylation of dinucleotide in or methylation level of a CpG island may be determined by any method available to the skilled person. Preferably said method comprises methylation-specific PCR (MSP). Alternatively, or additionally, use may be made of a multiplex ligation-dependent probe amplification (MLPA).

The present inventors have further demonstrated the suitability of using methylation of specified CpG islands as markers in bladder cancer diagnostics for prediction of therapeutic response, such as for prediction of failure or success of (neo)-adjuvant therapies.

The present inventors now envision as part of their invention the use of demethylating agents capable of specifically demethylating the CpG islands associated with tumor, in particular bladder cancer, as defined herein. They may also be of use as priming therapy for chemotherapeutic regimes.

Hence, the present invention provides a method for the treatment or prevention of cancer, in particular bladder cancer, comprising administering to a subject in need of such treatment a therapeutically effective amount of a demethylating agent capable of selectively demethylating at least one of the CpG islands methylations associated with cancer as described herein.

Clinical outcome of demethylating agents may depend on specific methylation profiles.

The present invention further provides pharmaceutical compositions comprising demethylating agents capable of selectively demethylating at least one of the CpG islands methylations associated with cancer as described herein.

The present invention further provides diagnostic compositions comprising PCR primers and reagent or probes capable of selectively hybridising under stringent conditions to hypermethylated CpG islands as defined herein.

DETAILED DESCRIPTION OF THE INVENTION

As used herein the term "CpG island" refers to genomic regions that contain a high frequency of CG nucleotides. In mammalian genomes, CpG islands are typically 300-3,000 base pairs in length. They are in and near approximately 40% of promoters of mammalian genes (about 70% in human promoters). The "p" in CpG notation refers to the phosphodiester bond between the cytosine and the guanine. CpG islands are characterized by CpG dinucleotide content of at least 60% of that which would be statistically expected (~4-6%), whereas the rest of the genome has much lower CpG frequency (~1%), a phenomenon called CG suppression. Unlike CpG sites in the coding region of a gene, in most instances, the CpG sites in the CpG islands of promoters are unmethylated if genes are expressed.

As used herein the term "CpG island methylation" refers to a methylation of at least one CG dinucleotide in a CpG region as defined herein. Hence, the methods of the present invention include the detection of at least a single CG dinucleotide being methylated in a CpG island as defined herein.

As used herein the term "hypermethylated CpG islands" refers to a CpG island exhibiting an elevation in the level of methylation, relative to the level of methylation in the same CpG island of a control subject. Again, the level of methylation includes the presence of a single methylated CG dinucleotide in the CpG island as compared to the control situation, in which the same CpG island is unmethylated. Also, methods of the invention include embodiments wherein the methylation of a single CG dinucleotide in a CpG island as defined herein is detected among other methylated sites.

As used herein, "cancer" shall be taken to mean any one or more of a wide range of benign or malignant tumors, including those that are capable of invasive growth and metastasis through a human or animal body or a part thereof, such as, for example, via the lymphatic system and/or the blood stream. As used herein, the term "tumor" includes both benign and malignant tumors or solid growths, notwithstanding that the present invention is particularly directed to the diagnosis or detection of malignant tumors and solid cancers. Typical cancers include but are not limited to carcinomas, lymphomas, or sarcomas, such as, for example, ovarian cancer, colon cancer, breast cancer, pancreatic cancer, lung cancer, prostate cancer, urinary tract cancer, uterine cancer, acute lymphatic leukemia, Hodgkin's disease, small cell carcinoma of the lung, melanoma, neuroblastoma, glioma, and soft tissue sarcoma of humans; and lymphoma, melanoma, sarcoma, and adenocarcinoma of animals.

The term "bladder cancer" as used herein refers in general to urothelial cell carcinoma, i.e. carcinomas of the urinary bladder, ureter, renal pelvis and urethra. The term includes reference to the non muscle-invasive (NMI) or superficial forms, as well as to the more dangerous muscle invasive (MI) types. Also included in the term is reference to the primary forms as well as to recurrent forms of the cancer.

The NMI types may further be subdivided into $FGFR3^+$ and $FGFR3^-$. Mutations in the fibroblast growth factor receptor 3 (FGFR3, indicated herein as $FGFR3^+$) occur in 50% of primary bladder tumors. It is known (e.g. Van Oers et al. 2005 Clin. Cancer Res; 11(21), pp. 7743-7748) that an FGFR3 mutation is associated with good prognosis, illustrated by a significantly lower percentage of patients with progression and disease-specific mortality. FGFR3 mutations are especially prevalent in low grade/stage tumors, with pTa tumors harboring mutations in 85% of the cases. These tumors recur in 70% of patients. Efficient FGFR3 mutation detection for prognostic purposes and for detection of recurrences in urine is an important clinical issue. Thus, in preferred embodiments of the present invention the method of diagnosis includes further the step of detecting an FGRF3 gene mutation. This additional step may be performed prior to, during or after the step of detecting the hypermethylated CpG island as indicated herein. The detection of the FGFR3 gene mutation as indicated in Van Oers et al (this reference is expressly referred to and incorporated herein by reference in its entirety for the methods and mutations to be detected as described therein) indicates the cancer is very likely of the non invasive type.

"Subject" as used herein includes, but is not limited to, mammals, including, e.g., a human, a non-human primate, a mouse, a pig, a cow, a goat, a cat, a rabbit, a rat, a guinea pig, a hamster, a degu, a horse, a monkey, a sheep, or other non-human mammal; and non-mammal animals, including, e.g., a non-mammalian vertebrate, such as a bird (e.g., a chicken or duck) or a fish, and an invertebrate.

A method of the invention can be performed on any suitable body fluid, such as for instance on abdominal fluid, pleural fluid, bronchial fluid, pericardial fluid, blood, serum, milk, plasma, sweat, tears, urine, peritoneal fluid, lymph, vaginal secretion, semen, spinal fluid, cerebrospinal fluid, ascitic fluid, saliva, stool, sputum, mucus or breast exudate. Preferably, a method of the invention is performed on blood, serum, plasma or ascitic fluid, more preferably serum. Depending on the methods employed, the skilled person will be capable of establishing the amount of sample required to perform the various steps of the method of the present invention. Generally, such amounts will comprise a volume ranging from 0.01 μl to 100 ml or more. Preferred samples are urine samples.

In even more preferred embodiments of aspects of the invention the cell fraction of urine, preferably tumor cell fraction, is used. Urine cell fractions may be obtained by filtration or centrifugation. The cellular DNA may subsequently be analyzed, for instance upon extraction of the DNA from the cells, although in situ methods performed on whole cells are also envisioned.

The skilled physician or biologist will be familiar with the various ways of providing a sample of a body fluid from a subject, in particular an urine sample. Urine collection and preparation of the sample for CpG island methylation analysis suitably comprises for instance the collection of a urine sample were collected into a 50 ml centrifuge tube. The sample may optionally be used for additional tests, such as dip stick tests for leucocytes, erythrocytes and nitrite as routinely performed in the art. The cells in the urine are suitably spun down for 10 min@3000 rpm; 4° C. An amount of supernatant is suitably stored at −80° C. for later use. The cell pellet may then be washed, for instance by adding a suitable amount of PBS (phosphate-buffered saline), such as 10 ml, to the cell pellet. After mixing and centrifugation (e.g. 10 min@3000 rpm; 4° C.), the PBS may be discarded. The cell pellet may then be resuspended in PBS (e.g. 1 ml) and transferred to a microcentrifuge tube. The suspension is then suitably centrifuged (e.g. 5 min@6000 rpm; 4° C.). The supernatant can then be carefully removed and the cell pellet may be stored in a −80° C. freezer until DNA extraction.

Commercial systems for DNA isolation from blood, urine and tissue are available form various suppliers of molecular biological reagents. Special reference is made to the DNeasy® Blood & Tissue Kit and DNeasy® 96 Blood & Tissue Kit available from QIAGEN GmbH, Hilden, Germany.

The term "therapeutically effective amount" as used herein refers to an amount of a therapeutic agent to treat, ameliorate, or prevent a desired disease or condition, or to exhibit a detectable therapeutic or preventative effect. The effect can be detected by, for example, chemical markers or antigen levels. Therapeutic effects also include reduction in physical symptoms. The precise effective amount for a subject will depend upon the subject's size and health, the nature and extent of the condition, and the therapeutics or combination of therapeutics selected for administration. Thus, it is not useful to specify an exact effective amount in advance. However, the effective amount for a given situation can be determined by routine experimentation and is within the judgment of the clinician.

For purposes of the present invention, an effective dose will be from about 0.01 mg/kg to 50 mg/kg or 0.05 mg/kg to about 10 mg/kg of the polynucleotide or polypeptide compositions in the individual to which it is administered.

The present invention also pertains to pharmaceutical compositions comprising demethylating agents as defined herein.

A pharmaceutical composition can also contain a pharmaceutically acceptable carrier. The term "pharmaceutically acceptable carrier" refers to a carrier for administration of a therapeutic agent, such as a polypeptide, polynucleotide, and other therapeutic agents. The term refers to any pharmaceutical carrier that does not itself induce the production of antibodies harmful to the individual receiving the composition, and which may be administered without undue toxicity. Suitable carriers may be large, slowly metabolized macromolecules such as proteins, polysaccharides, polylactic acids, polyglycolic acids, polymeric amino acids, amino acid copolymers, and inactive virus particles. Such carriers are well known to those of ordinary skill in the art.

Pharmaceutically acceptable salts can be used therein, for example, mineral acid salts such as hydrochlorides, hydrobromides, phosphates, sulfates, and the like; and the salts of organic acids such as acetates, propionates, malonates, benzoates, and the like. A thorough discussion of pharmaceutically acceptable excipients is available in Remington's Pharmaceutical Sciences (Mack Pub. Co., N.J. 1991).

Pharmaceutically acceptable carriers in therapeutic compositions may contain liquids such as water, saline, glycerol and ethanol. Additionally, auxiliary substances, such as wetting or emulsifying agents, pH buffering substances, and the like, may be present in such vehicles. Typically, the therapeutic compositions are prepared as injectables, either as liquid solutions or suspensions; solid forms suitable for solution in, or suspension in, liquid vehicles prior to injection may also be prepared. Liposomes are included within the definition of a pharmaceutically acceptable carrier.

Once formulated, the pharmaceutical compositions of the invention can be (1) administered directly to the subject; (2) delivered ex vivo, to cells derived from the subject; or (3) delivered in vitro for expression of recombinant proteins.

Direct delivery of the compositions will generally be accomplished by injection, either subcutaneously, intraperitoneally, intravenously or intramuscularly, or delivered to the interstitial space of a tissue. The compositions can also be administered into the nervous system. Other modes of administration include topical, oral, suppositories, and transdermal applications, needles, and particle guns or hyposprays. Dosage treatment may be a single dose schedule or a multiple dose schedule.

Specific aspects of the present invention relate to the CpG islands indicative of certain forms of cancer emerging for instance from the following comparisons:

A) CpG islands hypermethylated in non muscle-invasive (NMI) bladder cancer (BC) that are FGFR3 wild type, herein referred to as NMI-BC wt, vs. muscle-invasive (MI) bladder cancer herein referred to as MI-BC (n=31)
B) CpG islands hypermethylated in MI-BC vs. NMI-BC wt (n=11)
C) CpG islands hypermethylated in all bladder cancers (n=62)
D) CpG islands hypermethylated in NMI-BC-FGFR3 wild type vs. NMI-BC-FGFR3 mutant (n=31), and
E) Hypermethylated CpG islands predicting progression of disease or death of disease (resp. n=3 and n=11)).

The methods of the invention comprise the detection of hypermethylated CpG islands in the DNA of a subject. As indicated, hypermethylation is a relative term indicating that the methylation level of the respective CpG island is higher than or elevated with respect to the methylation level of the corresponding CpG island in a healthy control subject.

The methods of the invention comprise the detection of at least one hypermethylated CpG island in the DNA of a subject. Since there are many CpG island indicated herein whose hypermethylation is indicative of cancer, in particular bladder cancer, the method preferably entails the detection of at least 2, 3, 4, 5, 6, 7, 8, 9, 10, 11, 12, 13, 14, 15, 16, 17, 18, 19, 20, 21, 23, 24, 25, 26, 27, 28, 29, 30, or more, such as 35, 40, 45, 50, 55, 60, 65 or more hypermethylations in the DNA of a subject. In such instances, it is possible to speak of a CpG island methylation profile. In such a profile, the percentage of positively detected CpG islands is preferably at least 50%, more preferably at least 70%, more preferably at least 90%.

The CpG island methylation profiles may comprise of between 2-25 CpG islands for diagnostic purpose, such as determining whether a bladder cancer is present, and/or whether it is an NMI or MI type.

The CpG island methylation profiles preferably comprise of between 2-25, more preferably more, such as between 50 and 150, for instance about 100 CpG islands for diagnostic purpose, such as determining the prognosis of an NMI to develop into a more aggressive MI type of tumor. Thus, the present invention provides for a prognostic method for determining whether an NMI type bladder cancer can develop into an MI type.

It is also possible to use a method of the present invention to distinguish between a primary or recurrent form of the tumor.

The skilled person is well aware of the various methods that have been developed to analyze DNA methylation. Amongst these methods are restriction enzyme- and sodium bisulfite based approaches, as well as multiplex ligation-dependent probe amplification (MLPA) approaches.

Restriction-enzyme based methods are based on the inability of methylation sensitive restriction enzymes to cleave methylated cytosines in their recognition site. The identification of the methylation status relies on Southern hybridization techniques or PCR and is based on the length of the digested DNA fragment. The inability to digest methylated sequences results in longer fragments, indicating a methylated CpG dinucleotide. Restriction-enzyme based methods are simple, rapid and highly sensitive and are suitable for genome-wide methylation analyses as well as marker discovery techniques.

Preferred methods for application in aspects of the present invention is sodium bisulfite ($NaHSO_3$) based detection of DNA methylation. Such methods are essentially based on the fact that treatment of single-stranded DNA with sodium bisulfite results in sequence differences due to deamination of unmethylated cytosines to uracil under conditions whereby methylated cytosines remain unchanged. The difference in methylation status marked by bisulfite reactivity can accurately be determined and quantified by PCR-based technology. Bisulfite sequencing techniques (such as described in Frommer et al. Proc. Natl. Acad. Sci. USA 89 (1992), 1827-1831) provide qualitative data on the methylation status of 5-methylcytosines in the amplicon between the sequence primers and thus requires primers specific for bisulfite converted, but not specific for unmethylated or methylated DNA. This approach provides detailed information on the methylation status of all CpG-sites.

A methylation-specific PCR (MSP) assay for determining the methylation status of CpG islands may be used. Such methods are for instance described in Herman et al. 1996 (Proc. Natl. Acad. Sci. USA 93 (1996), 9821-9826) and Herman and Baylin (Current Protocols in Human Genetics 10 (1998), 10.16.11-10.16.10). The MSP assay is based on the use of two distinct methylation-specific primer sets for the sequence of interest. The unmethylated (U) primer only amplifies sodium bisulfite converted DNA in unmethylated condition, while the methylated (M) primer is specific for sodium bisulfite converted methylated DNA. Using MSP, 1 methylated allele may be detected in a background of 1000 unmethylated alleles. MSP is very suitable for analyzing the methylation status of CpG dinucleotides in a CpG-island. The method may also be applied for high-throughput analysis of clinical samples. The most critical parameters determining the success and specificity of MSP, i.e. bisulfite conversion, primer design and PCR as well as several post PCR validation approaches are discussed in Derks et al. 2004 (Cellular Oncology 26 (2004) 291-299). Methylation Specific PCR (MSP) is described in great detail in U.S. Pat. Nos. 5,786,146, 6,017,704, 6,200,756 and 6,265,171 and International Patent WO 97/46705.

Commercial systems for DNA methylation analysis using MSP are available form various suppliers of molecular biological reagents. Special reference is made to the EZ DNA Methylation-Startup™ Kit and EZ DNA Methylation-Direct™ Kit available from Zymo Research Corp. Orange, CA, U.S.A.

Use can also be made, alone, or in combination with any of the above, of the MLPA technique. The MLPA technique is for instance described in great detail in Schouten et al., 2002 (Nucleic Acids Research 3(12) e57, 13 pp.).

Also, use can be made of a microarray chip to which DNA of a subject is hybridized. Such arrays for CpG islands are for instance commercially available from Agilent Technologies Inc., Santa Clara, USA.

Herein below are provided the following Tables:

Table 1. Coordinates of selected regions containing relevant CpG islands based on Homo sapiens full genome as provided by UCSC (hg18, March 2006). These CpG islands are aspect of the present invention as hypermethylation of these regions is associated with cancer, preferably bladder cancer and/or certain forms of said cancer.

Table 2. CpG islands differentially methylated in NMI-BC wt vs. invasive BC. These 42 CpG islands are aspect of the present invention as hypermethylation of these regions is associated with either NMI or more aggressive MI forms of the cancer. Hence, these regions are particularly indicated for use in diagnostic methods wherein typing of the cancer is relevant. The table provides data on CpG islands hypermethylated in non muscle-invasive (NMI) bladder cancer (BC) that are FGFR3 wild type, herein referred to as NMI-BC wt, vs. muscle-invasive (MI) bladder cancer herein referred to as MI-BC (n=31) as well as CpG islands hypermethylated in MI-BC vs. NMI-BC wt (n=11).

Table 3. CpG islands hypermethylated in (bladder) cancer. These 62 CpG islands are aspect of the present invention as hypermethylation of these CpG islands is associated with (bladder) cancer.

Table 4. CpG islands hypermethylated in NMI-BC FGFR3 wt vs NMI-BC FGFR3 mut. These 31 CpG islands are aspect of the present invention diagnostic markers for typing of (bladder) cancers and in particular indicate the relevance of FGFR3 mutations in bladder cancer. These 31 CpG islands may be used for diagnosis of FGFR3 wt primary and recurrent tumors in for instance urine. These 31 CpG islands may also be used for detection of FGFR3 wt tumors in patients with a FGFR3 mt (mutant) primary tumor. Alternatively, these 31 CpG islands may be used for the identification of recurrences that progressed to muscle-invasive disease or to stage pT1 or to high grade (WHO 2004 grading system) or G3(WHO grading system 1973). These 31 CpG islands may also be used to present specific targets for therapy in NMI-BC tumors that are FGFR3 wt.

Table 5. CpG islands potentially involved in progression and death of disease. These 14 CpG islands are aspect of the present invention as hypermethylation of these regions is associated with prediction of the recurrence, progression or prognosis of cancer of cancer, in particular bladder cancer.

Table 7 (including Tables 7A and 7B) indicates differentially labeled CGIs between subgroups of bladder cancer and/or between subgroups of bladder cancer and a reference sample (i.e. blood).

Table 9 indicates a number of CGIs methylated in blood but not in bladder cancer. The differential methylation of these CGIs, which can be detected in DNA (of cells) in a sample of urine obtained from the subject to be diagnosed, and in particular in urothelial cells present in said urine sample, are—apart from the purpose indicated herein for diagnosing bladder cancer—also useful for the detection of lymphocytes in urine, or in general inflammatory cells in urine, which is indicative of cystitis. Positive detection of the presence of inflammatory cells in the urine can be used to diagnose infection or non-infective inflammation of the urinary tract and kidney.

Table 10 provides a list of hypermethylated CGIs that show 3 or more CpG dinucleotides highly methylated in a specific CGI. This list comprises 82 CGIs representing 71 genes and 11 CGIs not directly associated with a gene. A preferred gene from Table 10 is MEIS1, showing the highest degree of methylation with a fold change of 4.8 and an average fold change of 2.2 across the 10 probes that were present on the array for this CGI.

Table 12 (including Tables 12A and 12B) provides a list of CGIs that are differentially methylated between tumors and urine from non-bladder cancer control. These genes represent potential biomarkers for urine tests.

LEGEND TO THE FIGURES

FIG. 1A-FIG. 1F. Methylation pattern and expression of selected genes. (a) MEIS1, (b) NR4A2 and (c) HOXA9. (d), (e), (f) are Box plots representing the expression profiles which were taken from oncomine FIG. 2A-FIG. 2B. Comparison of differential methylation between subgroups. (a) Unsupervised analysis performed on all probes present on the 244K array without selection: PCA showing the distinct bladder tumor groups cluster separately (Red-MI, Blue-NMI-mt and Green NMI-wt), (b) Venn diagram showing the number of CGis that are differentially methylated FIG. 3A-FIG. 3C. Semi-supervised analyses between bladder tumor subgroups involving hierarchical clustering and PCA. (a) Clustering and PCA of NMI-mt and NMI-wt tumors, (b) Clustering and PCA of MI and NMI-wt tumors, (c) Clustering and PCA of NMI-mt and MI tumors.

Figure 4A:
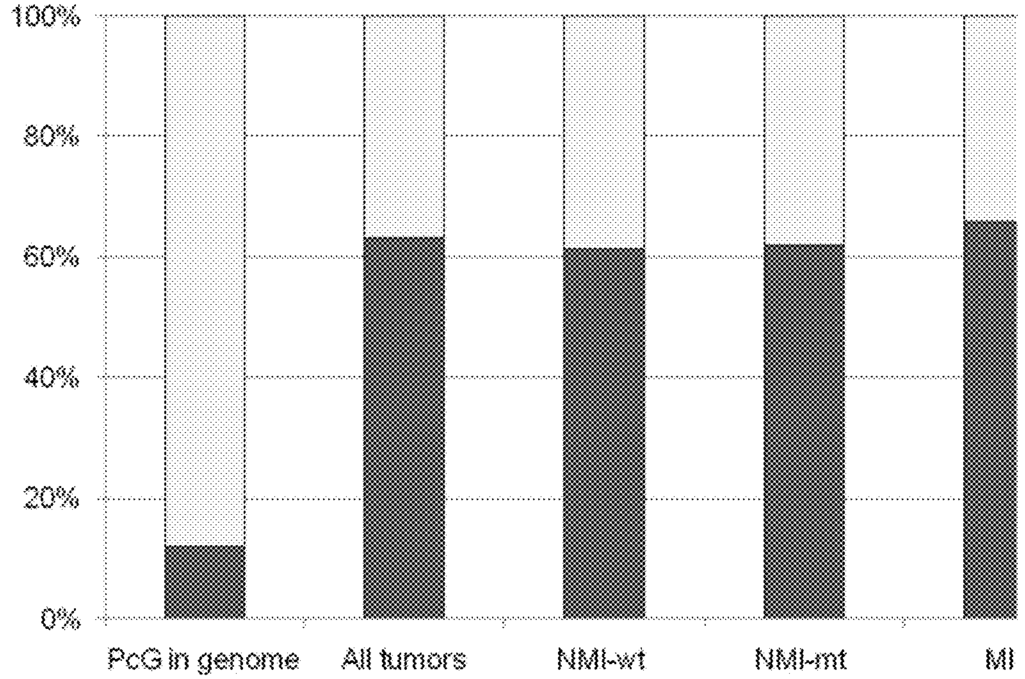
Figure 4B:
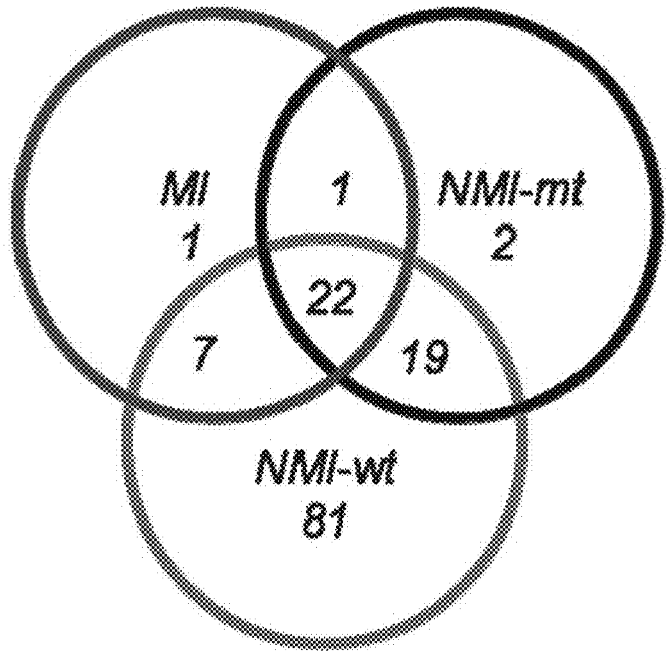

FIG. 4A-FIG. 4B. Most methylated gene-associated CGis are targets of polycomb complexes. (a) Overrepresentation of PcG genes in BC methylated CGis. (b), Venn diagram showing the overlap in PcG target genes between bladder cancer subgroups.

FIG. 5A-FIG. 5D. Hierarchical clustering of GGMA data of all the investigated samples. B. Heat map showing the probes which are methylated in all tumor subgroups vs. blood and urine; C) Methylation of two CpGs in the MEIS1 CGI (black peaks: methylated CpG, red: not methylated. IM, in vitro methylated DNA; RTI 12, T24, J82: bladder cancer cell lines; PU: patient urine; NU: normal urine; NB: blood), D) KM curve for progression to muscle-invasive disease based on a combination of methylation of GRP103, DBC1 and GATA2.

TABLE 1

Coordinates of selected regions containing relevant CpG islands based on *Homo sapiens* full genome as provided by UCSC (hg18, March 2006)

| | | |
|---|---|---|
| chr1: 119333484-119333719 | chr1: 149638545-149639227 | chr1: 160220156-160220709 |
| chr1: 178464743-178471598 | chr1: 2072175-2072389 | chr1: 2106293-2106715 |
| chr1: 232106869-232108183 | chr1: 33385564-33385979 | chr1: 41122328-41122880 |
| chr1: 47672249-47672972 | chr1: 68288825-68289104 | chr1: 71284766-71286392 |

TABLE 1-continued

Coordinates of selected regions containing relevant CpG islands based on *Homo sapiens* full genome as provided by UCSC (hg18, March 2006)

| | | |
|---|---|---|
| chr10: 21828640-21829645 | chr10: 22804715-22807056 | chr10: 73437163-73438385 |
| chr10: 7449476-7449790 | chr10: 7489383-7495345 | chr12: 113657930-113659205 |
| chr12: 118612357-118612674 | chr12: 94776044-94776377 | chr13: 113930978-113931584 |
| chr13: 34950488-34951119 | chr13: 49595986-49600287 | chr13: 94152191-94153185 |
| chr14: 36205192-36206099 | chr14: 37746906-37747538 | chr14: 53488428-53488700 |
| chr15: 94688798-94689131 | chr15: 94696311-94696840 | chr15: 94705727-94706054 |
| chr15: 94712480-94712812 | chr16: 52873104-52882105 | chr16: 52873104-52882105 |
| chr16: 85098883-85102729 | chr16: 86294154-86294408 | chr16: 87372445-87372729 |
| chr17: 24303411-24303889 | chr17: 34157398-34159854 | chr17: 44074280-44075233 |
| chr17: 56827843-56838048 | chr17: 58865328-58865618 | chr17: 73932992-73933361 |
| chr17: 75377960-75381951 | chr17: 75531280-75531546 | chr18: 5186244-5187389 |
| chr18: 68359955-68362770 | chr19: 4059891-4060207 | chr19: 42586165-42586705 |
| chr19: 63420090-63420541 | chr19: 63784504-63785085 | chr2: 104835284-104839920 |
| chr2: 105864220-105865009 | chr2: 111591678-111597436 | chr2: 115635091-115637285 |
| chr2: 124498611-124499725 | chr2: 156892636-156892878 | chr2: 156893736-156894685 |
| chr2: 171384729-171385226 | chr2: 176737610-176738187 | chr2: 19424445-19425131 |
| chr2: 43251514-43251780 | chr2: 45249374-45251726 | chr2: 63134470-63134933 |
| chr2: 66525936-66527222 | chr2: 70984709-70985764 | chr2: 72224630-72228512 |
| chr20: 22505518-22507240 | chr20: 22510737-22514165 | chr20: 22514762-22515148 |
| chr20: 35582018-35583550 | chr20: 54012011-54014085 | chr20: 60061693-60062033 |
| chr21: 33316999-33322115 | chr21: 36990008-36995832 | chr21: 37857725-37858416 |
| chr21: 43350621-43351134 | chr3: 129688131-129694023 | chr3: 148591199-148594390 |
| chr3: 62330280-62330608 | chr3: 62331767-62332398 | chr4: 111780013-111780343 |
| chr4: 122520930-122521740 | chr4: 155881084-155881434 | chr4: 177159356-177159814 |
| chr4: 40134579-40135662 | chr4: 9756136-9756429 | chr5: 115810975-115811393 |
| chr5: 122461778-122463450 | chr5: 134390896-134393045 | chr5: 135442969-135443206 |
| chr5: 140724146-140724826 | chr5: 174091287-174092335 | chr6: 101023927-101024343 |
| chr6: 1549606-1560865 | chr6: 21704622-21705099 | chr6: 26312699-26313302 |
| chr7: 121727243-121727884 | chr7: 1481682-1482268 | chr7: 155266364-155266696 |
| chr7: 155288454-155292175 | chr7: 156895132-156895886 | chr7: 2082782-2083345 |
| chr7: 27164708-27165039 | chr7: 27219187-27220360 | chr7: 2724511-2724848 |
| chr7: 27251165-27252762 | chr7: 32768010-32768497 | chr7: 55040457-55041024 |
| chr7: 8449587-8450236 | chr7: 96488158-96489591 | chr8: 132985505-132986242 |
| chr8: 142288380-142288718 | chr8: 57520625-57522095 | chr8: 65661156-65662687 |
| chr8: 9798161-9799053 | chr9: 121170908-121172141 | chrX: 39749470-39754050 |
| chrX: 50040955-50041296 | | |

TABLE 2

CpG islands differentially methylated in NMI-BC wt vs invasive BC. Provided for each are: ID; Comparision; Coordinates of selected regions containing relevant CpG islands based on *Homo sapiens* full genome as provided by UCSC (hg18, March 2006); Chromosome; GeneName; Location relative to gene Sequence.

7; I vs SW; chr1:41122328-41122880; 1; chr1:041122606-041122650; Unknown
CGGATGTGCGTGGACTCTGCGGGCGGGGCGCCCGTAGTCTCCCTCCTTCGCACCCCGGGCGCCTGGGAACCT
CCTCGCGCGTTTGGCCACTCGCTGCTCCTGGCAGTAGGGGCTTCGGGCCCCGCCGTGTCCCCACCCAGGTAT
GGGGATGCGGAGTTGATGGGTGCGGGGCGCTGGGAGGGGGCAGATGAAAGGGGCAGTCGAAAGGGGGCCA
TGCGCGCCGAGCGCAGCCGGGTCATTAGCCGCGGGTGTGAGCGGCGGGGCAGGCTTATCGCCCATCCAGGC
CTGGCGGGCGGGCGGTCCCCGACGCGGCTGCCGCCGCCGCCCGCGGCAGAGGGCACGGCGGTTCCCACGCT
CGGGCCCTGGTTCGGGGGCGTTCTCGGGACGGCGTGGCCGCGCTCACCACCACCGCGGAGGCCGGGCTGTA
ATTAGGATAATTGCGCTGCTCCCAGCCTGGGGCAGCTCAGGACCCGGCTGCACCGCGCTGGCCCGGGACGGG
CGGGGGCAGGGGGTGGCGGGGCCCGAGCGATACAGCCCCTGGCGCAGTCCG (SEQ ID NO: 1)

61; I vs SW; chr10:73437163-73438385; 10; CHST3; INSIDE
CGCCCAGACCGGCCGTGGCGGGGCCCCGGCGCCACGTGCTGCTCATGGCCACCACGCGCACCGGCTCCTCG
TTCGTGGGCGAGTTCTTCAACCAGCAGGGCAACATCTTCTACCTCTTCGAGCCGCTTGGCACATCGAGCGCAC
AGTGTCCTTCGAGCCGGGGGGCGCCAACGCCGCGGGCTCGGCCCTGGTGTACCGCGACGTGCTCAAGCAGC
TCTTCCTGTGCGACCTGTACGTGCTGGAGCACTTCATCACGCCGCTGCCCGAGGACCACCTGACTCAGTTCAT
GTTCCGCCGGGCTCCAGCCGCTCCCTGTGCGAGGACCCCGTCTGTACGCCCTTCGTCAAGAAGGTCTTCGAG
AAGTACCACTGCAAGAACCGCCGCTGCGGCCCCCTCAACGTGACGCTGGCCGCAGAGGCCTGCCGCCGCAAG
GAGCACATGGCCCTCAAGGCGGTGCGCATCCGGCAGCTGAGTTCCTGCAGCCGCTGGCCGAGGACCCCCGCC
TGGACCTGCGCGTCATCCAGCTGGTGCGCGACCCCCGGGCCGTGCTGGCCTCGCGCATGGTGGCCTTCGCCG
GCAAGTATAAGACCTGGAAGAAGTGGCTGGACGACGAGGGCCAGGACGGCCTGAGGGAAGAGGAGGTCAGC
GGCTGCGGGGCAACTGCGAGAGCATCCGCCTGTCCGCGGAGCTGGGGCTGCGGCAGCCCGCCTGGCTGCGG
GGCCGCTACATGCTGGTGCGCTACGAGGACGTGGCACGCGGGCCGCTGCAGAAGGCCCGCGAGATGTACCG
CTTCGCCGGCATCCCCCTGACCCCGCGGTGGAAGACTGGATCCAAAAGAACACGCAGGCGGCCCACGACGGC
AGCGGCATCTACTCCACGCAGAAGAACTCCTCGGAGCAGTTCGAGAAGTGGCGCTTCAGCATGCCCTTCAAG
CTGGCCCAGGTGGTGCAGGCCGCCTGCGGCCCTGCCATGCGCCTCTTCGGCTACAACTGGCGCGGGACGCCG
CCGCCCTCACCAACCGCTCAGTCAGCCTGCTGGAGGAGAGGGGCACCTTCTGGGTCACGTAGGGGGGCCGG
GGCCCCGTATGCCCCTCCTCGTGAAAGGCCTGCCCCGTCTTTCTGCCGCAGCCCTCGCAGAGGGCGGGTGCA
CAGCGCCATGACGGGCAGCGCCTCCTGTAGCAGTAGGGCCCCCAGCCAGCGCTCCAGCCAA (SEQ ID NO: 2)

TABLE 2-continued

CpG islands differentially methylated in NMI-BC wt vs invasive BC. Provided for each are: ID; Comparision; Coordinates of selected regions containing relevant CpG islands based on *Homo sapiens* full genome as provided by UCSC (hg18, March 2006); Chromosome; GeneName; Location relative to gene Sequence.

97; I vs SW; chr12:118612357-118612674; 12; CIT; INSIDE
CGGGGTCCTCACGGCTCCCGCAGGCAGCCGGCCCCTGCTGCTGTCTTCAAACAGCCTCCCGGGGGACCGCTC
TCTCCGCGTGCTGAGCATCCGGCCGGGGGACTTCTCTCGCTCCAGGGGGCGGCCAGAGACTTGTCCCTGCGC
AGCTCGGTCCGCCCCTCGCGGTAGCGGTGGGGTGTGCTTGGCTCTCGCGGGTGGCTGGGGCCTTCGGGCGG
CGCTGGGCTGGAGGCCACGCGCTTGGTGATGTGCTCGTTGTACGTGGGTGGGCCTCGCTTGTTGGGGCTGCT
GGCGACACAAGAGAACGTAGGGAGCTGCG (SEQ ID NO: 3)

162; I vs SW; chr17:34157398-34159854; 17; PCGF2-PSMB3; DIVERGENT_PROMOTER
CGAGAGGACCCGGACCCCGGCGGGGAAGGGCGCCCTCCCCCGGCCTCGCGGCCGCCCCAAAGCACATCCCC
TTCTGCCGGCCCCAAGTCCCCGCGCGTCCACGGCGCCCCTGTGCCCACGGGAGAGCACCCCCGCCCAGATGG
AAAAGGGGGTAGACCGGGCAGAGCGAGAGGCGGCTTTGGCTCGTGGGGAGCGGCGACCCAACCCAGCGCGC
ATCCCGCAAGCCCTCCCGGCTGCCCCGGACCTTCCCCCTCGCTACCTCGGAACAGGGTCTGCCCGGGGGCTG
CTGCACAAAGAGGGGTGGTCGAGGGAGACGCCAAATCGTTAAGACGGGGAGCCCGTTTCGGCCATCTTGGAA
GAGAGGAAAGGGAAAAAGGGACAGAAAAAAGGGAGAAAGAAAGGCGGACGGGGCAAGCTGGGCTAGGGACT
GACGGGGCGCGGGGGGTGCGAAGGCAGGATCGGCTCAGAGCCCCCCCTCCCATCGGGGCTTGCGAAGAACG
GCCGGCCCCCATCCCAATCCCCAGAGGGTTACAGGCCAGGAGAGGGAAAGGCAGGGGGAGTCCGCTCCGCT
TACCTGGGTTCGGGGTCCGGTGGGTCTCGGGGAGGGGGGGATGGGAGGGAGGGAGGGAAGGGAGGGGAGG
GGGCCGCAGCCGTGTCGCTCGCCCGGGCGGCGGGAGGGGAGAAACCTACGGTAAGAAAGGAGTTTGTGAAA
GCGGCTTGGGGTGGGAGGGAGAGGGGAGGGGAGGGGACCGAGGGGGGAGGGGAGGGACCGGAGTGTGGG
GGGGAGACAAAATGGCTTTTTTCCTCCAGACAAGGTAGGTCCCGCCCACCACTCACCCACGTGACCTCATTCC
TTCAGGATGCTGGCAGAGACGGGAAGAGGAGGGGGAGGCTGGCGCGGCCGCTCCCCGCCACCGGCTGCCGG
GTCCCTAGCCAGGACGAGACCCCTCCCTTCCCATGCGGCCGCCCCGACCCCGGAGGATGGATCTCTTATGTT
ACCTTCCGCAGTTAGCCCCCCTCCCTTCAAAATATGGGTTCCCCCCACTGACACTGTGATGCCCATCCCTAAC
TGGGGCGCCTGGAAAATGGTGAAATGGGGACTGGGCTGAAAGGTGGCTCGTGGTCCTCCACGCCCCGGCCTA
GACCAAAGGGCGCGGGGTCCGGCGGGGGACGCGACGCCTTCAGCCAGGCGTCCGAGCGATTTTCATT (SEQ
ID NO: 4)

169; I vs SW; chr17:56827843-56838048; 17; TBX2; INSIDE
CGGAGGCGGCACAGCTGGAGCCCGGATTGTGGCACGCCGTCACCGTGCTGCTCCGGGGAATCCCGACCCGC
TCCCTGCGAAAGCGTTTCCGAACGCGAACCCAGAGCCTGTGAACGCGCCGGCAAGCCCCCACTCCCCCACCG
CCGCCCGTCGCAGGTGGGCCCGTCCTAGGGGTCCTTCCTGCGCTCTACCCCGTCTCTCAAGTCACTCAGTCG
ATCGCCCCGTTCACGCTCCCGTGATCCCAGACATCCATAACCACGATCTCGCCTCCATGCACATCCAACGCAC
GACGGTGCACAACGTGCACCTGACTTCTGCGGACCAGGTGTCTCAAGCGTACAGCGGCCACCCGCGGAACCG
CGGCCCGGGGCCAGTGAGTCGTCTGCAGCTCCCCGGGTTAGGGGATTCCCCAGAACTCCGGGAAAGTCACCC
GAAGTCCATCCGGGATGCGGCCTTGGTTCTCGGCCGCGTATCTCGCCCTTAGGTGCAGAACGACGCCCTTCC
AGGGCCCACAGCTGCCAGGCTGGGCCTTGCCCTCGCATCCCCCGGGAAGACCAGGGACGGGGCCACACAGG
CCGTGGCTGCGGAGACGCTTCCCCGGGCCACCCCGCGACCAGGAGGGAGTCGAGCCGCCCGCTCTCCCGCG
TCCCCCGCCCCATCCCAGCCAGTTGGCCCCACCCTGCGCGGGATAATTGGGACGGGAGGGAGGCGACGGGA
GGGCGGCGGCTCCAGAGAGACTGCGCGCCTGTCAGCGGCAATTTGTTTAAGTGGACGGGACGGGCCGGGCC
GCTGCGGGCTGGGGTCACCGAGGCCGCGCCCCCACCCCAACCAGACCTGGGACCGCGGGGGAGCCCGGTCC
GGCCGCTAAACCGGGCTGGCTGGCGCCAGGGCTCCGGGAGGTGCGGTCCGGCGGGGAAGCCGTGATGGGAA
GCGACTCTGTCCAGGGAGTGTCCTTCACCACCACACTCCTCACGTCCAGGCAGTGATGACGGCCTGGCGGCA
CCCTCACAGCGGGCCCATAGCACGGGGCCACACACGTCCCCTGAGCTTAGCCTGGGCACATTCGTCTGCCAC
CGAGGGCTTAAGCCAGTCTGCAGCCCGCGCCCCGTCACTCGGACGCAAGTCCGTCGTCCGCTCTGCCACGCG
GCCGCACAGCCCGGCTTCCTGCTGCCCACTGCCCGCGGGGTCACGCAACCCCGGCCCTGCACA (SEQ ID
NO: 5)

270; I vs SW; chr21:37857725-37858416; 21; chr21:037857850-037857894;
Unknown
CGATTTCCGCAGATTTCCTGCTGGAACGTTCTCTCGGGCCTCAAGTTTTCCTGAGAGGACGACGTGGAGAGTG
GAGACAAAGATGCTCAAAAGCCAGGAAATCGCAGGCTCGGAAGCCCCCACGCATCCTCTGAACGCAGCGCCA
TCTCGGGGCTGCGGCGGGACCAAGCGGGACGCTTGCAGGCTGTCGGCGGCGGGGGCCGCGAGCCGCCGGCG
TAGGCCGCTCCAGCTGGAAGACCCCACCGCTAGGGTTCCAGGGGGCTGCGGACGCTTCCGAGGGGCCCAAG
GCGAAAGAACGCGCCCGCTTGTCGGCCACGTGACCGTCCCCGTCCGCGTCCGCAGCGACCACGTGACTGTGC
GTCCGCGGCGTCGATTGACTGGGAGCTCCCTGGCCACGCCCTAAGCGCCAGCCCCGGGCTTCGGGGGGCGG
TGCTGCTGCGGTTGCCATGGCGTCTTCCGAGCGCGCAGGCGGGGCCCAGAGTAGCTTTTCGGGTATTTGCTA
CCGGCTCTCGGTAGGGCTGGTCACCTTTGCTTGCTGAGCTTCGCGCCCTGCGTCCTTTGGTCCCCAGCAACTT
GCAGGGCAGCCGTCCCTCATGAGGCCCTCCAGCGAATGCCCTAAAGCTCCGAAGTTGCTCCGGAGGAAACAG
GCTTGCTCCGAGGGTGCACGTCCTTACTGCCCGTGACGTCG (SEQ ID NO: 6)

271; I vs SW; chr21:43350621-43351134; 21; CBS; INSIDE
CTGCTGCACTTGTAAAGTGGGTGCTTCTCAGCTTCATGGTTTGAGGGGTGCAGCCAGCTTCGGCCTAAGTGGT
GTTGAGGGTCGAGGACCCAGCACCCCCACACGGGAAGCGCGGTGTCCCGCCTTCAGGCTGGAGTACTCTGGC
ACCCTCTGGGGTCCCGAAGTGCCTGAGTACCTGTTTGAGCCGCGTGTAGGTGACTGCGCACCTGTTTGAACT
GCGTGTAGGTGACCGCGCACCTGTTTGAGCTGCCTGTAGCTGACCGGGCACCTGTTTGAGCTGCCTGTAGGT
GACCGCGCACTGTTTGAGCTGCCTGTAGGTGACTGGGCACCCGTTTGAGCTGCCTGTAGGTGACCGCGCACC
CGTTTGAGCTGCCTGTAGGTGACCGGGCACCCGTTTGAGCTGCCTGTAGGTGACCGGGCACCCGTTTGAGCT
GCCTGTAGGTGACTGGGCACCCGTTTGAGCTGCCTGTAGTGACCGCGCACCCGCTTGAGCTGCCTGTAGCTG
ACCGCG (SEQ ID NO: 7)

283; I vs SW; chr4:40134579-40135662; 4; FLJ20273; INSIDE
CGCGTTGTAGGGGTAGCCGTAGTAGGCCAGTGTGTAGGGGTCGCAGGAGTACACGTAGCTGGGCTGCTGCG
CTGCCTCAGCCGCGCCGCCGCCCCTGGCTGCCTTCTGGTAGCGCGAGTACTGCTCCTGTCCACGGGCTTGGC
CAGCGTGACCTCCAGGCACGAGCCCTCCAGCTCAGTGCCGTTGAGGTTGTTCATGGCATGCACGGCATCCTC TABLE 2-continued CpG islands differentially methylated in NMI-BC wt vs invasive BC. Provided for each are: ID; Comparision; Coordinates of selected regions containing relevant CpG islands based on *Homo sapiens* full genome as provided by UCSC (hg18, March 2006); Chromosome; GeneName; Location relative to gene Sequence.

GCGGCTGGTGAAGTGCACGAAGGCGTAGTCGCGGATCTTCTTGACGCGCTCCACGCAGCCGGGGTTGAACTG
GCCGAAGCTCTTTTGATGGTGTCCTCGGTGGTCTCGATCATGAGGTTGCGCACGTAGAGGATCTTCACGGTCT
CCATCACGTCCTCGTCCACGTCGATCTCAGGTTCGGCCCAGTCCACGGCGATCTGGTGGCCCCACAGCTGGA
TGCGGCCAGGCATGAGCTTGCGGCGAGCCATGGCAGCCGGCGGTGGCTCTCGTACTCCACGAAGGCGAAGC
CGCGGTTCTTCATCTTGTCGGCCGCGCTGGCGTAGACGATCACGTCCAGCACGCCCTCGGTGACCTTGGCAA
TCTCCTCCAGGATTTCCTCGCGCTTCTTCATCTTGGGGATCCCGCCGATGAAGAGGCGGCAGTTGTCCCGCTG
CAGCACACGCCGAGCAGGCGGCCCGGGCGGATCTCGTAGTTGTTGAGCTCACGCACTGCGCGCTTGGCCTCG
TGCTTGTGGCAGTACATGACGAAGGCGTAGCCGCGGTTCTTGCCGTCAAAGTCCATCATGAGGCGCAGCTCG
TAGATGCGGCCCACGGCCTCGAAACGGGCACCAGCTCGTCCTCGTACACGTCGCGCGGGATCTTGCCCACGA
AGACCTCGCAGCCACGCTGCGGGTCGGGCCCTCCCAGCCGGGCGGTGGGCCGCCGTACTTGCGCTGCCCG
TTCTCTTGCACCATGCTGTAGCCCGTGCGCTCCATCAGCGCCAGCAGTGCTGCTCGTTGGGCGCGCCCGCCA
CGCCCTCGGGCACCTTGGCGGAGGACCCGGCGGCCGAGTCACTGCTCATGGCTGCGGTGGAATCCTCTGCG
(SEQ ID NO: 8)

357; I vs SW; chr7:27219187-27220360; 7; chr7:027219187-027219246; Unknown
AAGTCTGGAGATAATTATGTCGTACAGTCGCAAACATTATTCCGTTCTTACTGTAAACGGCCCCGGCCACCTT
TACGAGAAACCAGGAAACTTCTGAGAGTTACTAGCAGCGTTTACGCGGGCAAACGAGTTCTTTTTCTTTCTCT
CCCGGATTGTTCGAAGTATCTATCGGGCGGCTTCGATGCCAGGTTCAGAGGCGCGCCAGGGAGAGGGCGCCC
CGCAGAGGAGCGCAGCGGAGAGGCCTACGCAGGTCCCCGGTGCCCGCGGCCCTCGGAGGCCGGGCCCTGCG
TCTTGGCCAGCACTGGGTGGCAGCTGAGGCTGGTGGCCCGGAGCCCTCGCGGCCGCGGGCAGGCCCCTTCTT
GGGCAGGGTCGGGCACTCCCGCTGTCCAGGGCTCTTCGGCACCCTCCTTCCAATCAGGTCGCTCTCCCCTGC
TCCCCAGACTCAACTCCTCCGAAGCTGCTCCAGGTTGAATGTGACCGCTAGGCCGACTCCCTGGGCCCGCGA
GCAGTTCTCGAAAGGTGCGGACTGAGCCCTTTCTGGGGTGGGGTGCGGGTTGGTTCTCGCAAGTGTGACCCA
GGGTGAACTTGCTATTTCGGGTCCCGGGTGCTGCAGGGCCAGGAGAACAGCTGGGATGGGGGACCCCGCCT
CCACCCTCGGGCCGGCACGTCCGCGCCCTGTCAGGTCCCCCTCCCTCCTCTATGATGGCCAAGGCGTGCGCC
AGGGCTATCCGGGAACCTTGTAAGGCCTCGTGCTGGCACCTAACCCCACTCGCGGCACACTTCCTCTATGTAG
TCTGCGGCCCCGCCTGCCAAATAGAGTGACCAGTGCAGGGACAGAATGCCAGGCTGGTGGCCGACCGCCTGA
GGGACAAAGGCGAGCATTCACAAGCCAACAGCAGACCCCTGCCCCCCATATTTCCATTTCGCTCAGGCTTTTA
GGACAAAATCAACAAGGCCGCAGAGTGGTGCAGGCGCTCACCCCGGGTGCAGCCTGGGGAGCCACTGGTTC
CGCGACCCTGGGCATGAAACTCCTCAAGGGCGGCCCTCGAGACGCAGGGGAGAGGATGCTGCCGGCGCCTG
CCCGAGGGCTTCTCTGCGGGAAGCGGGCAGGCACCCCACCGGAGTCATTGCCGGGACCCTCAGCGCAACGC
GGGCCTGTTCCTCTCG (SEQ ID NO: 9)

373; I vs SW; chr7:156895132-156895886; 7; DNAJB6; INSIDE
CGGAGATGGCGCGTCTGGATTCAGGGAGATCGTGCGGCCAGCTTCCCTCCCTCTGCTCTGGATGGGGGCCGG
CCGCCGCCGCTCACTCACGGCTCTCTCTCTCCCGCTGTGCCTGCAGGTGTGGCCGCGACGATGCCCTCGCTG
AGGAGCGCATGCGGAGAGGCCAGAACGCCCTGCCAGCCCAGCCTGCCGGCCTCCGCCCGCCGAAGCCGCCC
CGGCCTGCCTCGCTGCTGAGACACGCGCCTCACTGTCTCTCTGAGGAGGAGGGCGAGCAGGACCGACCTCGG
GCACCCGGGCCCGGGACCCCCTCGCGTCCGCAGCAGGTGTGCAAAGGGAGGCAGCCGTGGAGCAGGCGCAG
AGTGAGACTTCTCTGGGTGCCAGAGGACAGCGAGGACACAAACCGCGCCTGGGCTGCTGTGTTCTGACCTGA
GCGGGCGTGGGCGGTCGGGCGGGGCGGGAGGAGGTAGCCTCCTCTGCTCCTCTCCCGCTCGCGGCGCCCCA
CGCCACGGTGGCTCCGGGCCCCCCACCGTTAAAACGGGGTCCGCGTGTCCTGTACGCAGCGTGTTGCTCCGC
AAAGGATGACAGAGCTGCCACGGCAGTGCGAGGTGCTGCTTTTACCGTAGACGTGCCTTTTCGTAGCTTTAG
CGTAGAGCTTGAGGCCTGTGGCTTAGGCCGGGTGGTCTCGTGCTGGTGGGGTCTGCGTTTGCCCCTGCCCCT
CCGTCAGCTTCACCTTCTCGTGCCTTCTTCTGCG (SEQ ID NO: 10)

389; I vs SW; chr8:132985505-132986242; 8; chr8:132985506-132985550;
Unknown
CGTAACGGGCGTGGGTCGTCCGTCGCGCCGCCCGGCGAGGAGTGGGCTGGCGGCGGTAGCTGTCGCCCGCT
TGGTTGCGTGACCGCGGGGTCCGCGTCCGCTCCCTCCACCCTTCGCCCTTCGCCCTCGCCTCGTTCCGGCCTC
CGCGGCCCAGCAACGGCCGTCATGGTGCCGTCGGCGCTCCCTGCGCGGCCCCGCTGAGCCTCGGTGCGGCG
GCGAGCGCGGTCGAGATCGCCATGCCTACCCGTGAGTGGCCGGCCGAGGGCCGGGGGCGTTGGGAGGCGAC
TGCCTGCGCGACGGCTTGGGCCGGGTACTCCTCCCGGGCGGCTGGGGAGGCTGGGCCGCGCTGAGCAGAGC
CAGGAAGTGTCTGCGAGCGGCGGAGTTAGTTTCGTTTCGGCTTAGCCTTCCGGAGATGGCGTGAGCCCGTTG
CACGGATCGGGAAACTGAGGCCCGAACGTTAAGGGAACTGCGGGACGCGCTGTTAGGAGGCGGCAGAGCTG
GTGGTAACCTGACCCGTGGGATTTCAAAGTTAAAGCCCTTTTCCCACGGCCACACGGCTTCGTGGGACTTTAT
GGAAATATTGAAAATAACTGCGGTACCATTGTCAGTCCCTTCTCACCTCGGGCCGGACGTCGCTAGTGGAGC
GCCGGCCCCGAGTCCCTTCCCGCGGCCGCCAGACAGACCCCCGACAGCCTAACTCGGCGTCCGTATCGCCGT
CGGGGCGGCTGAAGTCG (SEQ ID NO: 11)

12; SW vs I; chr1:68288825-68289104; 1; DIRAS3; INSIDE
CGGAGGCACGAACCAAGCAGCCTAGAAGACAAATGCGCTGCTCGGAGAGACTGCCGCGGCAACCAACTGGA
CACCCCAAGAGCTCACTCCTCCGCGGTTTTATATTCCGACTTGCGCACAGGAGCGGGTGCGGGGGCGCAGGG
AGTGTGGGTAACAGGCATAGATTCCGCTTGCGCAATACGTGGTAAGAAACCAGCTGTGAGGGGCTGGCCCAA
CGCAGAGCGGCGCGAGGTCCGCTTGGCATCTACAACAATCGAGGGGCTAGTCCAGAAGTTCAAG (SEQ ID
NO: 12)

15; SW vs I; chr1:71284766-71286392; 1; PTGER3; INSIDE
GCTCAGCTAGTAAGTGAGGAGCTCAGCTCTGAAGCTGTAACCAAGACCGCGCGGGCAGGAGGAAAGGACACT
TCAGCGCTCTGCGGTTGCAAACACACCCCTGCGGGTGCTGCCACTTAGCAAAGTCTAGGTTCCCGCTTACTCG
CACACGCATCCTGACTTCCCCCAACCCTGGAACTACCTACCAGGAGCGGAGACCAGCAGACCGACAGCACGC
ACATGATCCCCATAAGCTGAATGGCCGTCTCGGTCGTGATGCGGCCCCACTGGGCACTGGACTGAGATGCCG
TGGCCTTGGCCGGCAGCGGGACACCAGGGCCTTAATGGTGGCCAGGTTGCAGGAAAAGGTGACTGTCAGCG
CCAAGAGCCCCAGGAAGGCAAAGGCAGAGGCGAAGAAAAGGTTGCCCCAGTTATGCGAAGAGCTAGTCCCGT TABLE 2-continued CpG islands differentially methylated in NMI-BC wt vs invasive BC. Provided for each are: ID; Comparision; Coordinates of selected regions containing relevant CpG islands based on *Homo sapiens* full genome as provided by UCSC (hg18, March 2006); Chromosome; GeneName; Location relative to gene Sequence.

TGCCCCCTCGCCCGGTGCTGATGAAGCACCACGTCCCGGCCACTGGACGGTGTACTGGCCCACGCCCAGCAC
CGGCAGCAGGGCGAAGGCGAGCACGGCCAGCCACACGCCGAGCAGCACAGCGCGGGTGGCACGCGTCTTCA
TGTGGCTCGCATACCAGTGCGGCGCCCTGATGGCCAGCGCCCGCTCGACGGCCATGGCGCTGGCGATGACAA
CGAGGAGAGCCCGAAAACAGTCATGGTCAGCCCGAAAAAGGTGCAGAGCCGCCCCGACGGGTCGATGTGCT
CCCAACGCTGCTTGGACAGGTACACGACGATGACGACCGGGGTGGTGAGAAGCTGCCCGACCAGGTCGGTG
AGCGCCAGCCAGCCGATGCACAGCAGAAGGACTTCTTGCGCTTGCTCTCCCGGCGCCGGTAGCTGCGCGACA
CGAGCAGCATGGCCAGTGCGTTGCCCACGAAACCAGTGAGCAGCATGGTGATCGGGAAGGCCACGGACACC
GATCCGCAATCCTCGCCAGACCCTGGAGGGCGCGTGAGGTTGCCCCGCGCCTCGGGGAACGCTCGGGCGCC
CACATGCCTGTGTAGGAGTGGTTGAGGCGGGTGCAGAAGGGGGCATCCCCTCCGTAGCCCCGGGTCTCCTTC
ATGTTGGCTTCGAGGTGAGGAGGGGATGGCGTCCAGAGAGCCGCAGCGGGAGGGGGCAGACGCGGCGCGG
GCGGCGGCGGAGGTGGCGTTTACCGCGGCTGGGGCTGGGCTGCCCCCCATGGTGCGGGGCGCAG (SEQ ID NO: 13)

21; SW vs I; chr1:119333484-119333719; 1; TBX15; INSIDE
ATTCTTAATTCCCACACCTCTTCCCAAGTTACGCCACCGGTCGAGGACGGCAGGAGACCCCCGAGTGCAGAG
AAAGCTCAAACCGGCAGCGAAGTCGGTCCTAGCCAAGCTGAAAAAACGTCTCGGATTCGCGGACAGCGGCCT
AGACACAGCCCGATCTTCCAGTCCTAGTGCCCTGGTCGAGACGGTTCTATCCTTTTGCAAAGAAGCCGGAAAG
AGCTGGGTCCCGGGGGCG (SEQ ID NO: 14)

26; SW vs I; chr1:178464743-178471598; 1; LHX4; INSIDE
CGGGGTGGGCTTCCCGCGCCTGCAGCCCGGAGGCGTCGAGCGCCTGATGGAGCGTCAGAGGAGACCTCGTC
CCAGCGTTGGGCCTTCTGTTGTATTTCTGCCAGAAACTCGCGTTGAGGAGAATTTGTTTAAGCGTTTCTCTAC
CTGTCCATGCATCTCGTAAATACAGTAAGCATGGCAAGCCCTTTCGCTGGTTAACCCCGGCGTCCGTGTGCTC
ACTGCCGCCCTGCACGCACGAGGTCGCGGATGGTTCAAAGCACCCGCGGTGGCAGCCGGAGAGGCAGAGCG
GGCTCTAGGGACTAAGACAGGGCCGAGCTGGACGACTGGTGGCAGGGCGGCCGGGGAGGCCCCGCCGCGGG
GAGGTTTGGGCCCCCTACCCTGCGGAACTGGAGGCAAGTGCGGACTCCGGCTGCAGGCCGCGGTCTGCGGG
GACGCGCGCGGGGGGCCTGCGTCCCGCCACCTCCGCGCACACCCCTGGTCCCCTTCCCCAGCCCGGGCCGG
CGCCGCCCGCCGCGTGACTCGCGCGTTCCGGGCCGAGTACGGGCTGTCCCTTGGCCCAGCCTCAGCCAGACG
CGGGGGAGAGAGAGCAGGGGCTGGGAAGTGCCGGCAGGAAAGGAATTGGCCAGGGGAAAGAGGAGGAGGA
GATAGATGGAGTCATCGGTTACGGAGCGCGCTCCGTCCGGCGGAGCGAAGCCGGGGACCGAGAGCGCGCAA
GGCGAAGACACAGCGACGCAGCCCCGTCCCCGGCCTCCGGACCGCCTGCCCCGCTCGGCCCCGGCTCGGCT
CCGCCCCGCCCCTGGGTCCGAACGGAGGAGGAGGAGGACACGAGCCGCGCGGGCTTGGAACCCCACGAAGAC
CCGCAAACCCAGGGCGCCGCCGTCTCCGACCACCTGCTGCCGCGGCAGGCCATCAGCAGAATTTATACCCAG
GGCGCGAGCCCGCCACGGCTGGGCGGAGGCGGAGGCGGAGGCGGGGAGGGGGGGGGGGTCCGGCTTGCGA
GGCCCCGCCCCGCTCCCTGCCGCCCCGCCCCCCTCCGCCCCGCCGGCCTCACTCGGGGCGCCGGGACCCCCA
CTCCCTCCGGGGTCGGCTGCCCGCCGCCGGGTTGGGGGATGTGCCGAAGGGCGGGCCTCCCTGCGGAAAGC
GACGTCACGGCCGCTCCTCAGTGTGAATGAATCAAAACGCCCGGGTGACCGCGGCCTCCCGGGCGGCC (SEQ ID NO: 15)

40; SW vs I; chr10:7449476-7449790; 10; SFMBT2; INSIDE
AAACCACTCTGAAAGAACTGTGAGACCTTTGCACTAAGACCATTAGGGATTCTACGCAAGGTTCTCTCTGCTC
CTTGCAAAATTACAGGCGTCATGAAGGATGGCGGCTCGTAAATCGAAGCCTTTGAACAGGGGCTCACCGTCC
GGCGGCATCAACACCTTGTTGTTCTGTGTGCACCACCCCACGGGGTGCAAATCCGCGATGACTACGTCACAC
CAGAAGTCGGCCCTGCGGTCCTCCCCGTAACCGCAGTAGCGCAGAAGCAGCAGCTGCCCGCACGTGGTAATG
ATCGTGGCCACCAGTACGTGTCCG (SEQ ID NO: 16)

41; SW vs I; chr10:7489383-7495345; 10; SFMBT2; INSIDE
CGGCAACCGAGCCAGATCCAAGAGGGGTCGGCCTCGTCTAAATTGGTTTCCCACCAATGGCCTCGGATCAGC
CGCGGCTGTGCTGCGGGAGCCCTCAGGACGCGGCTGGGGTTGGTGCGCGGGGCCCGGAACCCCAAACCCGG
CTCGGTTCGGCAAGGTTCAGGGAGACAAGGTAGAGAAGGCTGGGGTGAGCGAGAAGTCGGGCGGCCGATCG
TCAGGGCCACGAGCCTCGCCTTGCCTTCTTGGAATCCCACCCAACTTTAAAGGCCCAAAGATCCTGAAAATTC
CGAAAGCGAAACGCGAGCTGGTCTCCAGAAGTTTGAGAACGGTCTCCCAGGCTTTCCAGCGTCGTCCCGGGA
TTCTCGGACACCACAAACGCCATCAACCACGAGCACCGGTGTCCGTGGCTATTGCCCCGAATGGTCCCCATCC
GCGTCCCCGGGAACTCCCTCGGCTTTTCGCGCATCCAGGCCCCAGCCCCAGCTACTGGTGCGCCCCGAGCCC
CTAGGTGCCAGAGCGGTGGTCGGCCGGGCTCCTGCCCAGTCTCGGCTCCTCCCTCCTCCCCACCAGAAGGAA
AAACTTGGGCCCTTCGAGAACCCTGTGGAATGTTCTTTGTAATCAACTGTACATCCGCTTCCACGGCCGGCCT
CGTGCAAAATCGCGGGTTTCGGGGCCTTGGAGCAAATTGCGCTTGTCAGCGGCGACGTCAGGAGGACAAGGG
GAGGGGTTCGCGGCTGAAACTGCAGCTTCGCAGCACAGAGCCATTTTAGGCTGCTCCCCACCTCGCGGGGCC
CATGGGAAAGCCGGCCCCGGGAGGCGCGCCCAAACGCAGGCTGGAGGAGCCACGGACGCGTCCTGGCCGGC
GTGTCGCCATCGTTCAGCCTCGCTGCCCAGGTGGGAGGGGTCACCTGCCGCGGGGTCTCCAAGCCAGTGCCG
CTTGCTCCCGGCCCCCACCCACTGACAGCACGGCGTCCGAGTGACCCTGTCAGCCTCGTTCTGCGCTCCTGC
AAACCACGTTGCTGCGCTAACTACAAACCTGGCCAACATGTCTTTGTAACCCTATCATTTAAAAACGCTTCCA
GGCACCTGGCCGCTGCCAGATCAGGTTCGCGGCCCGGAGGAGGTCCTCCCACCTGCCCCCGCCAGCCCCG
GGGACCGGCGCGGCCTCCGTGTGGCCCCCGCCCACGAGGTCCCTCGGGCAGGAACCG (SEQ ID NO: 17)

112; SW vs I; chr14:37746906-37747538; 14; SSTR1; INSIDE
CGGAAAAACTCGAATGTCGCCCTGCCGTTCCTGGGGTTGGTGACAGGTCTGGTCATCGCACGGCGGCAGCTC
CTCACCTGGATTTAGAAGAGCTGGCGTCCCCGCCCGCCCAAGCCTTTAAACTCTCTCTGCCAGAACCCGCCAA
CTCTCCAGGGTACAAAGTACAGCAGGGACGCGGGTGGAGCCCTTCCAAGCGGCGCAGCCTTATCTTTCCCGA
GTGAACACCTAGGTGGATTCCCAACACCGCGCCTGGCACGTTTCTGGAGGGAGTCTCAAGCTCCTCCAGAGC
TCCCAGCTGCCGTCCTCGTTTCTGCAGTCGATATTCCTGTGGGAGACACGGGGGGCTCTGAGCGCTACGAGC
TTTATTAAGAGATTTGCGAATGGTTCACTCAGGTCCCTGAACACTCCCAATAGCCTAAGCTGCCTGCTGTGTT
ATAGCGCAGAAGCCCCTAACGCACGGTGGTTGTCCTTCTTCTCATAACGCTCGCAGCTTAGGGCCAGTTTCCG TABLE 2-continued CpG islands differentially methylated in NMI-BC wt vs invasive BC. Provided for each are: ID; Comparision; Coordinates of selected regions containing relevant CpG islands based on *Homo sapiens* full genome as provided by UCSC (hg18, March 2006); Chromosome; GeneName; Location relative to gene Sequence.

CGATTCTAAGAGTAATTGCGTGGGCACCTGTGCTGGGGCCAGGCGCAAAGAAGGGAGTTGGTCTGCGCGAAG
ATCGTCAACCTGCTAACAGACCGCACATGCACTTTGCACCGACCATCTACG (SEQ ID NO: 18)

118; SW vs I; chr14:53488428-53488700; 14; BMP4; INSIDE
CGGTAAAGATCCCGCATGTAGTCCGGAATGACGGCACTCTTGCTAGGCTGCGGGCGGCGGCGCAGCCCAAAC
ATCTGCAGAAGTGTCGCCTCGAAGTCCCGCAGGAGCTCATGGCTCTGCCCTGAGCGCGTCCTCCCGCGTGGC
CCTGAATCTCGGCGACTTTTTCTTCCCCGTCTCAGGTATCAAACTAGCATGGCTCGCGCCTCCTAGCAGGAC
TTGGCATAATAAAACGACCATCAGCATTCGGTTACCAGGAATCATGGTGTCTCTG (SEQ ID NO: 19)

147; SW vs I; chr16:52873104-52882105; 16; IRX3; PROMOTER
CGCGAGGATGGGCGGGCTCCACGTCTGGGGGCGCTGTGAGCAGGGCCAGAGCGAAACCTCAGTCTGAGTTT
ACGAACTGGGAAGGAGCCTGAACCCCAGAAACACCGTTAACAAAGAGGGCGAACGCAGGGAGCCGAGGAGA
CGTCTCCTTGGCCTCTGGGGAAGGGGCTGGAGGAGCGAGCCAGCTGAGAAGCGGCTTTGCCGGGTGTCCACT
AGCGGTTCGCCAGCCCTCTGTGCGCCCGCAGAGTGACGCAGAGGCCGACACAGTCCCCTCCCCACTCGCCCC
TGGGGCGCCGCCGACCTTGATCACCCCCTTCGCGGAGGGAACTCCCAAGGCGCGGCGCTGGCCGCTGGGTC
CGCATGGCCCAGTCCTGTCGGGCTCCGCTCTGCTGCCGCCGAGCTTCGAAGGTGTGCAGTGTTGAGCCGTGT
CTTGTTCCGTGGCTTCGAGGGGTGTGCGCGCTTCCTATACCTCCCGGAACGCGCGAGATAGTCACACGCGCC
ACTTTGAGGGTCAAACACCCCGCATCTGGCCACACTGTACCTTTACTAACGTGGGGAGGGGGCAAAAAAATG
TGTCTCTCCTTCTTACCCCGAGGTGTCACTCGCCCAAACACTCCCTACAACTTCTTCAAGTCAAACTTGGCAA
GGTTGGCTGGCTGACTGCGAGAGGAAAAAGAGGGCGCGGAGGGGGCGCGGCGCGCGGCCGGGTGTAGAGG
CCACGGAGGCGAGGCGCCGAGCGTCCCCTTTGTCCTGTAGAGGGAGCTCCAGCCCCAAATTTCCCTGCTGCC
TCCCCCGGCCCGCCCACCCCAGGCCCGCTGGAGCCGGAATCCCGGCTGGAAAGGTGCGGCGGTCTGACACC
CCCGCAACCCCCGCGCCGGGGCCTTAGCAGGATGCCTCTTCTAGGGCACGTGGGAAAACCCACCAGGGTGCC
AAGACGCACAGATGCTCCCAGGACCCGGGCTCCCCAACTCTCAACTAGAGCTGGGCGTCACACATCATCTAG
AGGATTATGTACCCCTAGGCGACCCTCTTCTCCATATCCGCCTCCACCGTCACCCCACACCCTGGCATCTATA
AAGAGGGAAGGGGGGCAACCGGGTTGGAAGGAGGATGGAATCTGGGCTTGCACAGCCTCTTATAGGTAACA
GTGAGAAAGCCTAACTGTGTCGATCAAAGAATGGGGACGAAGGGAGTGATGAGAACACGACC (SEQ ID NO: 20)

151; SW vs I; chr16:85098883-85102729; 16; FOXF1; PROMOTER
CACACACACACACACAAAAGTTGGGAGAGAATGTGAGAATGCTTGTGTTCGTGGACGCGTGCGCACGTATGG
AGCGGCGGTACCTATGATTATTTGCGCGTGGCGCCTGGCTATGCGTGGGCGAACGGCAGTGGAGAACATGTG
GGCGTGCATGAAGTGTGCACTTAAACCAAAGTGTGCCCTCCCCGTTGGGCAGGCCTGTGTGTTGGTCCAAGG
GTTGGGAGCGCCTGAGCTGTGTGAGGGTCGCTGGGAAGGGTGTTTGAGGCCGTGGGCGGTGCGGAGCGTGT
CTGTGTGCGCGGGGCTGAGCTGGTTGTGTGAAGTGGTAGCGGGTCTGCCAGAGAGCGTTTACCTGCGTGAAT
GCACAACCACACACTACGGGTCACGTCCCACACTCATTCTTTCCCTAGGCGGGCCAGGCTGTCTGCACGCGG
AGACCCAGAGAGGCCAGCGGAAGGGCAGCGCGGGAAGGCGCTCTCTTCTCCCGCGAGCGCAGATCTGGCGG
AGGAGGCGGCGACTGCCCGGCAGGCTGCGCCGGCGAGCCCCCCAGCTCCTCTCACCGACGTGCCAGGCGCC
CCGAAGGCGACAGGCGTCTCCCGCCGAAAATGAAGGCGTCCGAGCCAGGAAGGTGGGGGCGGGTAGTTAGG
GGAGACAAGGAGTCCGGAGAAAACCGAGAGGCGGGTAGGCTTTGAACGCGCCGCGCCGCGGGCCGTGCTGC
GAGCCCGGCACACGCCTCTCGCCCCAGCTCGCGCTGGGGCTTGGCCTCTAGGCTCTTCGCGATGACCCGCGA
AAACACCCCTCGCCCCCCTCTTCTCAACCGGAACCCTGGAGGGAGAGGCCGCGCCCGGCCAGCAGTCGCTGC
GAGAGCAGCACTCACCTGGGTCTGTGCGCGCCGCGATGCGCCGGGGCTCCTGCGCTGTCCTGCGCTCCGCTC
TCGGCACCACCTTTCGTGGCTCCACCGCCCCCAGCCCGCACCCGAGCGCTGAGGTGCAAGGGCAGGTCTGCG
TGCGAGCCCCCTGCGGGCTGGCAGCCAGGTGCGCGAGGGCCGCCCTTGCCGGCGCTCCCAGCCCGCGCTGT
CTGCTCTCAGGAACCTGGCCTGGCGCGCAGTGTCAGAGGCCCCGCGGCGGCGGCAGGCCGAGCCCACAGGG
GCATTAGGCCAACTCCCCCTCCCGCCCTGCGCACGCGGAATTCTCTATTATTATTATTAAAGAA (SEQ ID NO: 21)

180; SW vs I; chr17:75377960-75381951; 17; CBX8; DOWNSTREAM
CGAGCAGGAGCAGGCGCGGCCCCGGATGTGGAGCCAGGCTTTCGGGAGAGCCCATTTCTACAGGGATTCGG
CCCGACGGGTGCCGGGCCGAGCTCGCTCGGCCTTTGTTAGTTTCGGCGCCGCTGATTGATCGCCTAATCCAG
TGGACCCTGAGAAGAACAGACTGGGCTGCCAATGGCCCGACCCCACGCCGCCGCGACCTGCCCGAGGGCAC
CGGGAGCGATGGGTGCGGAGGGGCTGGGAGGACGGTCATCCGGGCGGCTGGACCTCTCCTTCCTCCCCTCC
GCCTTCGTGGCTCGGCGCCGGGCCTCAGGGAGGACGCAGAGGGGGCGCCCGTGGCGGTGGGCGCCCAGCGG
TACCTTTGGGTCGGGGGAGGTAAGGCTTTCTCAGCTCGGGTTCGGAACCAGAAAGCCACCGGCCCCCCGGG
GGTAAGGGGTGGGCGCCGGCGACCCGGGCCGACGCCGCCACCTCAGAGGGCGCGCGCGTCCCACCAAGGTC
GGCCGCCGGCCCTTCGGACGGACGAGGGAAAAGCCAGCCGCGGCTCCAGGGTGCCCGAGACTCAATCGCAC
CACCTGCACCCCGGCCACCTCCGCCTCCGAAGTCTCAGGAGGAAAGCCCCGACCCAGCCCGCAGCCTCTCTC
GCGCGTTCAGGACCCGAGGCTGCGGGCAGCCGCCTTCCACGACGGACAGCACGGAGTCCCGCCGGGCCCCG
AGCCACGCCAGTCTCGGACTTCAGCTGGGTCCGAGGCTCCTCTGGGCCTGGAGGGCTTTTAGAGGAGAAGAG
GAAACCAGCACAGGAGCCCCAGAGGGCCGGACAGGTCTGTGCGCCAGCGGCCCGGGCGCATGGCACAGTGC
CTGGATCAGGATTGGTGCGAAGCCAGCATCAAACGGACAGAAAATGAATCCGATCCGACACTCTAGGAAGAG
CATGAACCTTCCAATCCAACCAATGTTTGTGCGAGGCCAGGTTCCCCGCCGCGGTGGCCCACAAGCCAGCCC
TGTCCTCGGGACGCAAGGTAACCAGTCCGGCTGGAGGCCGCCACGCACGCCTGGTCTCTGCAGTTGTGGCGG
ATTCCCAGGGACTCTGCCCAGGAAATGGAAACCCGTGAGGGCGCTCCTCAAAGCCGAGGGTGGTGATGGCCA
GCGAACCCGAAAAAGGGCAGGGTGGGCGCCCTCCCATCCGCTTAAGCAGTAGCCCATTCCACTGC (SEQ ID NO: 22)

187; SW vs I; chr18:68359955-68362770; 18; CBLN2; INSIDE
CGCGCGCGCAGGTCCCCGCCCCTCTCCCCGGGCTGGGGGCGGGGTGGGCAGGCCGACGGCTGACCTGGTCG
AAATAGATGGTCATGGTGCGGTTGCTCATCTCGGACGGCTCGTGGTTGGTGCTCCGGTGGCGGAGAAGGCCA
CCTTGGCGCTGCCGGAGCGCACGGAGATGCCTAGGGAGGAGGTGACGGCGCCGTCCGCCGACGGGCTGGAG
TCGCACACCACCAGGCACTTGCCCTCCAGCACGATGGGCTCCGTGTCGTTCTGCGCCCGCACGGGGCAGCAG TABLE 2-continued CpG islands differentially methylated in NMI-BC wt vs invasive BC. Provided for each are: ID; Comparision; Coordinates of selected regions containing relevant CpG islands based on *Homo sapiens* full genome as provided by UCSC (hg18, March 2006); Chromosome; GeneName; Location relative to gene Sequence.

GCGGGCAGTAGCACAACAGCAGGGCCAGCGCCACCCCCAGGCAGGATCCGCAGCCGCCCGGCTCGCGCAGC
GCCCCCCGGCGCCCGGGCATCATCAGCCGCAGCCCGAGTGGCCCCCGGCCGGGCGCCTGCATCGGGACTGG
TGGGAGGCGGCGCGCGGGGGTGGAGGCCGGCGCCGGCGCGAGCGCGCGGAAGGGCGCGAAGGAACGCGCG
GAGCTCGCAGCAGCCTCCGGGGGCCTTCGTCCCCGGCTCTGACGTTCAAGGCCAGGGTCGTTCTCAGAAGAA
AGGCGCCTGTGAACCTGTCAGGGCACAGAACCCAAAGCCTTACACCGGGAGGTGGAGCCACCGGGAAGAAG
GGGACTGGGAGCAGGTGCCTGCGGCTCGGGGGTTCTCCCCGAAGGCCACCCCCTTGGTCCCGCGCACAGCC
AACCCGCTTTCCGATCTGGCACAACAGGTCCGGAGAAACGCCCGGGCGCAGCTGGCAGCGCATCCCTGAAGG
CTCCCGAGCAGCGCGCGGGGCTGCGACGAGGAGGGGGCCGCGCTTCTGCAGGTCCTCGTCGCTAAGACGGG
CCCCGAGACCCTCAGAAGGCGTCACCGCCACCCCGCCCATTCACCAGCGCGGAGGGGGCTAAGACGCAGGC
AAAGAAAAACCTACGAATGCTTGCCTTCTCGCCTTCATCTCACAGCATTTCCTTGGAGCAGACCAAGGAACCC
TTTTCCTATCCCTTGTTTCCCTGCTATCCTCTATTTTTCAATCCTCGAGATGTTTTTAAAGTCCATTTAAGTCCC
TTTGGTACAGATTTTATCTGTTTTCCACCCACAGAACAAATCCCAGGAATCTCCTTGGGGCGAATAAGATTAC
TAGGGGGGAAATACACCACACACACACACACACACACACACACACACACACACACACACA (SEQ ID NO: 23)

200; SW vs I; chr19:42586165-42586705; 19; ZNF569; DOWNSTREAM
GGAAGTATCTTGGCCTGCACGCGGTTTACATCATTGGGAGCACAGGCCTCGCCCTCCGAACTACGAGGCCCA
GAGCCCTTCGCGCCGAGCGTTTCCCGCCTTTCCCCTGTCTCAAGTCATTGCCCAGGGCCACTGCGGGCCGTTC
CTGCCTGTCCGTGGAGCTGCGGCCCCCGTGTTCCCAGGGTGAACGAGCACGTGCGAGGCGGTGGTGCTTGTA
TCCGGGATAACCAGGTAGGGCGGCTGCATGCTTCATAGAGGCCAGCCTGTGCCGACCGGGAGCTGTAGGACG
GTCTGTGTCTGGGCTGCTTATGGGTATTCGCGTGCGTCTGCCGGTGCGCGGTCCGAGCCTACTCACGAGAGC
GTGTGTGTGTCTTCTGTCTCGTGTTGCTATGAGGTTTGCATCTGTGTGGCTGGAATAGCTTGTTTGTGGGGGC
CCGCGCGTGACCTGTGTGTGCGTTACTGTGTGTGTCTAGGCAGGATAGTGACGGGCCGTGTGACTGTGACGC
CATCATCAGGTTGGTGAGATGGCGTGACCGCG (SEQ ID NO: 24)

207; SW vs I; chr19:63420090-63420541; 19; ZNF274; DOWNSTREAM
CGAGGGAGGACGACAAGCGGGGACGTTGGCGGAGGGGTTAATGGCGGAGTCGCGATCCAGCCGAGCCCACA
ACTCTGGGAGGCTGGTTCTGCCTCTCTCCCGAAGCGTCGCCCGGCTAAGCTTCGAGACCAGGACACACAACC
GCCGACTATTCCAGAGCCCACAGTCGGCTTCACGCTGGAGGCCGGAAACGACACGTCCCCAAAGCCCGCGCG
CGCGGCCCGCCAGAACTGACCTACCCAATCACCGCACCGCTGCGATCAAGCGGCGACACACGTTGCCGGGTA
AGAGTCACGCTTGGCAAATAAGCAACCTGCCTCATCCAATCAGCGTCTCGCCTGCCCGGTTAGTTCCTTGTCT
TGCCCAACCAGATTCTTGCCTCCTCCATACCGCTACTTGCGTGTGCCGGTGCCTGGCCCAATCAGCGTCTTGC
GCCTCTTCTCGCTCCCG (SEQ ID NO: 25)

223; SW vs I; chr2:72224630-72228512; 2; CYP26B1; INSIDE
CGCTTGTTGCGGTGGATGTCGCCAATGGAATTGGACACCGTGTTGGGGCCCAGCAACATGCGGGTGCTGCGA
GGCCACTCGGTGCTCACGAGGTGGTGCTCGCCCATGAGGATCTTGCGCACGTTCTCGCGCCGGTCACGCGTA
TCAGCGGCCGCCCCAACAAATGCGTCTTGAACACGTTGCCATACTTCTCCCTCCGCGACGACTGGAAGCCAG
AACCCTGCGGGAGCCACACCCGGGTCTCTCTCAGGGTGCACTTCTGCAGAGGGCCCGCGAGGGAGGGGCGG
CGGACCCCAACCGGGGTACAGTCACCTGCCCCCTCTCCCCACCAAACACACTCACACAGACGAGCACGCAGG
TTTTATTTTTCATAGCGTGCACAAGAACTGCGAAGTAGGGCCTAGAGGATAATAAATAATGCAAGGAGGCGGA
GGCCCAGGGGCACCCCCAGGAGGCTGTTTTTTGGTAATGCTTTCGAGAGGAAAGAGGTATCCCGGACAGCTG
GACCCGAAGCGGGAGTCTCCGCCCCCACCCCCACCCCCACACCCCCACCCCGCGCTCGGGAGCCTCTCGGAA
TAAATATTTCCAGGCTCCGGGCCACGGGCTGGCGAGACCCCGCGGGGTGGCCGCAGGCCAAAGATTATTATA
GCGGTAAGCGGTCGGTGCCCGGAGGCAGCAACTACAGATGGGGGTTGGAGTTTCCTCCGCTCTCCGGTGTGG
CCCGCGCAGGGACCCGGCGGCCCTCGGAGGACTCTGCAGGGCGGGGTCACGGGCCCAGAGCCGCGATTTTC
CTAATGCATTTTGCCCTGGAAATACGGAGACGGACTTTGGTTGCCGCCCTGGAGTTTGGAACCCGAGCGCGG
GGCGGGGCGGGACCGGGCAGGGCGACCCGCGCAGGTAACCAGATCCCCGGTGGTGGCGGCGCAAGCCGAG
GATGGCGGGGCCGGGGCCGGCCGGACTCTCGAAACGGCTGGCGGAGCCGGCCGGCGCGGGTACCGGAAACC
GTGGAGACCTCAGAGGGGCGGGGGCAAGGGCGTCCCGCTCACCTTTGACGTCGGCACTAGTTACCCCACCCC
ACGTTAACCCTTCTCCTGCCGGGGCAGCACCCGGCGCAAAGGGGAGGGGCGCCACCTGTCTAGCCGCCCCGC
CTGCCAGCCCAGAGCGTACCGACTCGGGCTCCAGATCTACCCGCTCCTGCACCCCCGAGGG (SEQ ID NO: 26)

227; SW vs I; chr2:104835284-104839920; 2; POU3F3; PROMOTER
CGCTCGGCAGAGGCACGATACAGCGGGAGAGAAGGGCAGGCCCGTTCACATTTTAATCGGAGCGCACCGGC
GGCCGCTCCTCGGCTGCGTCCTGGGCTGCCGCTCGGGCTCGGGACTGCCAGATGCAGCTCTGGCTGGGGGC
GGCGGGCGCAAGCGGGCGCACCCGCAGCTAGGGGTGCGGGGTGCACGCACACGCACGCTCATTAAGAGCCA
TGTATTTATTGAATGTCCGAGTTGGGTTAGTTCATTGGAAATCCCCGAGGAGGGCTCAATTTGCCCTTGTTTT
CGTTGCCACTTTCCTTTTTTCTTGGTTCGCTGAGGTTCCTCTGTGCAGCGTTTCCGCTTGGCCGCGTCCCCCC
ACCCCACCCCACCCCACCCCCGCTTCTCTCGCCTACCGGGTGCACTCCCCCTCCCATCCCCCTTAACTCTTTC
AGCTGGGTTAGAGCTGAGAAAGCATTTGTCGCCGCCAGCCCATCCACCACGCAAATCCATCTGAGACAGAAA
GGAAAGAAAAAAAAGCACCACCATGCCTAAGAATAGAGAGCGAGCAAACCCCCCCACCGCTAATCACACACA
CACACACACACACACACACACACACACGAGGAAGCGGTGGAGCAGAGAAGGGCGCGGCTAGCCGACCCG
GTTCTTTCGCCCGGCTCCTGCTGCCACAGGGAATTCCTAAAGCCATTGGGGTCGAATACACTTACGATGAATC
TATGGGGGAAGGTCGGACTGATTGCTTTTCAAATACATCGCACGGCTCCGCTGACCGGCACCCTCCAAACTCA
CAAGGGCACGCACGCTACTTGCCGAATCCCAGAGGAGGGAGGAGGGAGGAAGGGAGGGAGAGCGAAGGAG
GGAGAGAGGGGGTGGAGGAGCCAGGGAGCGGCGGCAGCGAGCGGTCCGTCTCGCACGCGCGGGCACCGCG
CTGGTCCTGGGCTGCAGGTTTCCCAGATGATGGCATCCGAGAACTTAAACAAAGGGGCTGCCGCCGGCGCGC
AACGGCTGCGGAAAGTTGCGGTGGCGGATTTCCAAGGAGCGTGGCCACGACCAGAGCTCTTGGCGATGCGA
GCCCCCGCTTCCCACCCCCGCCGATCAGAGAAGGGGGCCGGCTGGTGAAGGGAAGAGGAAACTTTGAAACCA
CTGGGGACACACTGTCTATAGGTATTAGCTTGAATGGTACATCCGTGCCGCGCGCTTTACA (SEQ ID NO: 27)

TABLE 2-continued

CpG islands differentially methylated in NMI-BC wt vs invasive BC. Provided for each are: ID; Comparision; Coordinates of selected regions containing relevant CpG islands based on *Homo sapiens* full genome as provided by UCSC (hg18, March 2006); Chromosome; GeneName; Location relative to gene Sequence.

235; SW vs I; chr2:124498611-124499725; 2; CNTNAP5; PROMOTER
GACTCTCATCACTACCACACCCATGTGTCTTTCCTCTCTCCGTCTCCCTGAGACGCCAGTGAACCACCTGGGC
TTGGAATCCAGAGCCCCGGAACACCTTGCAGTACTTGCCCGAAGCAACGCGCCACAGCGGGAGGGAGACGCA
GACGCGAAGACCGGCGAGAGGATGTGCGGTGGGAGTAGCTGCGGGGTCTGCAAGCAGGGGAGCGCGCACAA
CGTTAAACCTTGAAACCAGAAATCCCGATCCTATCGAGACCCATCAGCTTTTCCCATTTGGGAACGAGCGCAG
GGGAAATTAATGCGTAATTCAAGCTCTGTTTTCCCCTCCCCTCCAAAGGTGAGGTGGGGGAACGCGTCTCGTT
AGCTCATTACAAAGCTTTCCGTGGGAAATTCCCTCTTCCTAATGCGTCTGTCTTGCAACTCCTATTAGCATCCT
TCGACAGCGGCCTTTGAAAATCTCCTTTAAATTTCATACCTCTACTCGTTTCCCAAATGGGGGGAAGGGAAGA
GAAAGCCGGGGGGTAGAGAGAATTTCCTTCCCCTTTCCCTCCCAGGTAGCCAAAGCGCACCGCAGCGGCTTG
GCTTCCTGGAGGAAAAGCGCCCGAGCGGGGCAAAGACCCGCCCAGGCTGCTCTTATAGGCGACGCGGGGCG
GGCCTGGCTGGGGGCGGTGCCGCGCGGCCCCGCTCGCCTATAAGGAGCTGTCCGCCACCCGGGTGCTGATT
CCAGCTCTCGCGCCCGACGAGGTGGATTTGGCTGTCCACCGAGCTCCGGCGCCTGTCGTTCTAATTGGGTTT
GGATTTGCACCGTTAAGGAGGGGGAAGAGAAGGAAGAGGCGGGCGAGGAAGGCGAGTCCAGCTAGCGGCTG
TTGCGGGGACCGTAGCCCCAGCTGCAGCTCCGAAGAATCCCCCGCCACGGTTTCGGTGGAGCGTCTGGGCAC
GGGATGGAGTGAAAGAGCGAGTGCCTCTCCAAGCGGGGGTGGGAGGGGGCAGGCTGTGCAGAGGAGAGAGA
CAGCGAGAAGAAGCCGCGGCTGGCTACTGCGAATTTGGGATTCGATTGGGAGGGACCGCTCACTCGGGGGA
AATGGATTCTTTACCACGGCTGACCAGCG (SEQ ID NO: 28)

257; SW vs I; chr20:22505518-22507240; 20; FOXA2/C20orf56; DOWNSTREAM
CGTACCCGGCTCTCAAAGGCACGGCACCTTTGAATTAGGTTGCGGAGTGGCCTGGGCGAGGGGACCCGGGG
CCATCAAAGGCCCGAGGGAAGGCCGTGGGGCGACACCCGTCTAATGACAAGTAATTAAGGATTCGACGCCGC
GCATTACCAGCGGAACGGGAGGCATTAATTATTTAAAAACGATTAGCCTTGCCGTGTGTCCTGCAGGCGTCCC
ATCATGTTCAGCGAAGATAACCAGCCACCCGAGGCGAGCCGGGGCTCGGAGGGCGGCGGGCGCGCTCCCCA
GCAGGCTTCGGGGCGGTGGACACGGGCGCACAGCCCAAGGCACCAGGGAAGGAGGAGGAGGGGGCCACCAAG
GGTCCCCACACAGGAAGGTGACTACATAACACTGACCCTGCTGAACAACGAAACAGATTTCTGCCCACTTGG
GTTCGAAGTCTGGTGACTGCGGCGCAGATGGGAAAAGCTTTCGGTCGGGGGTGGTGGGCAATTTCCATGTGC
CAGTTCCCTGTCGCATCAGACCAAAGACCCAAAGTAACCCAGCCAGGCACGGGCCTCTCACAGTGCCTGCTA
CCCAGGCGTTTAAAGAAAAGACCCCAGAGAGAATGTGGATCTGGCGTGGGGGCAGGGATTGGGGGGGGGCC
TGGTAGACACCTGGGGAAATACAACTTTATGAGGTTTCAAGGGGCAGCAGCAGAACTACTATTTTTCCGAGGT
CCACGCCTTTCCGCAGGCGGCGGAAAGACGCGGCTGGTTCTGTTGGGTCCTACAAACTCGCGTCCTCCGGAA
TTCCCGAGGGCAAGCCCGGCACGCGCAGCGTGCTCCTGCCCGTGGAAGGGGGGAAATCGGCGACTGGGTTG
CAGGGAGAATGCGATGATAAATGGCCCTGCGTCTGCTTTCTGACTTTCTCTCCTGGACCCAGCTCGTAACCCC
AGAGGCTCCCCAACCTGCCTGCCGCCAAGCACGGCTGTGCGCAAAAGGCCACCACCGCTTCCTGCAGCCAGA
GCTAAGGTTCACTCGCCTCTTAGAAAGGCGCGGCCCCTCCCCTGCTGCTGCTTGATGACGATCCCCATCGTCT
CCTCGGCCTGCCTGTGTCCGAGAAAGAGTTGAGACTGGACTCGAACCCCTGCGCGCCAAGGGGAGGGCGTCA
CCATGCTCCGCCTCAGCCTCTTCAAACTCCCATGCACCACGCACATCATTTTCTGCTGA (SEQ ID NO: 29)

262; SW vs I; chr20:54012011-54014085; 20; CBLN4; INSIDE
CGACGTCCAGGGACCAGGTGCCCTTCGGCTCCCGCCGACCTGTTGCTCGAAACTTGCCCTGAGCTCTCGCTG
CCGGGCTCTGGGCTCCCAAGCCTCTCCCCCGCCGCCGCAGCAGCCTCTTTTAGGGCCCGGAAGAAATGGGAG
CCGGGGCTGGTGAGAGGGGTAGGAAGAGGGACGGTAGAAGTTTCAGACCCAGGCATATTTGGGAAGGCGAG
TGCTTTACATGATTCCCCATTTCCCAATCGGACCAGCTTAGCCTGGGCAGGCAGCCTCGTGCTGAGGTGCCTG
GAGACCGCCCACCCCTAGGTGCTCGCTTCCCCCCGGGTCTGACCTGATCGAAGTAAATGATGCGCGTCTTGTT
GCTCATCTCGGATGGCTCGTGGTTGGTGCTCCGCACCGCCGAGAAGGCGACCTTGGAGTTGGCCGCCCGGAC
CGATATCCCCAGCGGGGAGGAAGAGGAGCCCTTGGAGTCGTGGCCGGGTTCGAGTCGCACACCACCAGACA
CTTGCCCTCCAGCACGATGGGCTCCGTGTCGTTCTGTGCCCAGACGGGCAGCCCCGGCAGCGTGAGGACCAG
CAGCACGGCCGGCACCGCGGACAGCGCCCGGCGCCCGGAGCCCATGGTGAGCCGTGTGGGCAGCCGCGCCG
GCTGGCGCTGGTGCTCGCCCGCGTCGCCTCCTACCCCGGGATCCCGGTGCTCGGGAAGATGCTAGCGGCTAG
GTCGACAGCGCTGCAGGAGCGACGGCGGCGGCGGCGCGCACACTTCCACCAATTCTGTGGCTTGAAGTCAAA
GTCTCCCCTCGAGCTCTCTCGCTGCTCTGTTACCTTTGTCCTTTAAGGAGCTCATGCAGCACCCTTTACCCTAC
TCTCCTCCGCCCAAGAATCAGCCCTGCCTGGGGCCCCTGCACCCACTCTGGTTCCTAGACATCTGAAAGTCAT
CAAACCCTCACATTCACACCTCAAGGCAAAAAATAATAATAATAATAAATCTCACCCCAAACTCAAGCACCAC
CAGCTAAACCACGGAGCAGGAACAAAAAGAGGGGACTCAAAGAGAAGCCACAAGGGTGGCGGGTGCCCAGC
GGCGCGGGTGCCAGTCCTGTCTGGCTTGCGGCAGGGACGAGTTACAGAGGCAGAAGGTCCTTCCCAGGCTGA
GAAGACGCGAGGCTGTGTTCATGGCCAGGACGCCAGCGACTCCCACTTTCGCCTG (SEQ ID NO: 30)

268; SW vs I; chr21:33316999-33322115; 21; OLIG2; PROMOTER
CGGTGCCGGGAGCCTTGCCTCCCGCCGCCACCCCTGGTCAGCTCTGCGCAAGAACGTCGTTCTGTTTGGCAG
CCAGGCCGAGACGCAGCCTGAATGTGAGCAGGAACTCGGAGAAGGGAAGGGAGAGATCAGAAAGAAGGCCC
GGGAGGGACCCGGGAAGCAGTGGGAGGTCTGCGCCCTGGAGCCCCGCGAGAGCCCGCCGGTTTGGCACGGG
CTCCTCCCGGGCCGCCCGGCGGTCCAACAAAGGCCGGCCCCGACACGCACCCGGTCTTTTGTGGGAGAGAAA
CACAAAGAAGAGGAAAAACACGGAGGAGGCCAACAGCACCAGGACGCGGGGGCCAACCAGGAACTCCCGGA
GCCGGGGCCCATTAGCCTCTGCAAATGAGCACTCCATTCCCCAGGAAGGGGCCCCAGCTGCGCGCGCTGGTG
GGAACCGCAGTGCCTGGGACCCGCCCAGGTCGCCCACCCCGGCGCCGGGCGCAGGACCCGGACAAGTCCTG
GGGACGCCTCCAGGACGCACCAGGGCAAGCTTGGGCACCGGGATCTAATTTCTAGTTATTCCTGGGACGGGG
TGGGGAGGCATAGGAGACACACCGAGAGGTACTCAGCATCCGATTGGCACCAGGGCCAAGGGAGCCCAGGG
CGACACAGACCTCCCCGACCTCCCAAGCTACTCCGGCGACGGGAGGATGTTGAGGGAAGCCTGCCAGGTGAA
GAAGGGGCCAGCAGCAGCACAGAGCTTCCGACTTTGCCTTCCAGGCTCTAGACTCGCGCCATGCCAAGACGG
GCCCCTCGACTTTCACCCCTGACTCCCACTCCAGCCACTGGACCGAGCGCGCAAAGAACCTGAGACCGCTTG
CTCTCACCGCCGCAAGTCGGTCGCAGGACAGACACCAGTGGGCAGCAACAAAAAAAGAAACCGGGTTCCGGG
ACACGTGCCGGCGGCTGGACTAACCTCAGCGGCTGCAACCAAGGAGCGCGCACGTTCGCCTGCTGGTGTTTA
TTAGCTACACTGGCAGGCGCACAACTCCGCGCCCCGACTGGTGGCCCCACAGCGCGCACCACACATGGCCTC TABLE 2-continued CpG islands differentially methylated in NMI-BC wt vs invasive BC. Provided for each are: ID; Comparision; Coordinates of selected regions containing relevant CpG islands based on *Homo sapiens* full genome as provided by UCSC (hg18, March 2006); Chromosome; GeneName; Location relative to gene Sequence.

GCTGCTGTTGGCGGGGTAGGCCCGAAGGAGGCATCTACAAATGCCCGAGCCCTTTCTGATCCCCACCCCCCC
GCTCCCTGCGTCTCCGAGTGACAGATTCTACTAATTGAACGGTTATGGGTCATCCTTGTAAC (SEQ ID NO: 31)

276; SW vs I; chr3:148591199-148594390; 3; ZIC4; INSIDE
GGCCGGCCGGCCTTCCTTCCTTCCGCCCTCGCCCTCTTCATGCCTCAGAAACGTGGCCTACTCTGCATTCGGT
GTGTGCGGAAGCAGCAATCACAGAGGCAGCCCTAATACCGGAGGCGGCGGCGGCGCAGCAGGGCCAGGTGG
TAGCTCGGGGCTGAGGATCGCGGCGGGGGCAGCCGCTATGGGGCCCAAGCCCTGACACACGTACCATTCGCT
CAAGTCGGCGGTACGCGCCGCCACCGCCGCCGAGGAGGCCACCTGGGACTTGTGGCCGCAGTCCGACGAGG
GCGACACGAGGGAGACGGTGTAGCCGAATCGTAGCCAGAGCTGGGCGGCGGCGAGCGCCCGTGCACCTTCA
TGTGCTTACGCAGCGAGCTGGGGTGCGTGTAGCACTTGTCGCAGCCCCGCACCTTGCACGTGTATGGCTTGT
CGCTAGTGTGCACGTGCGAATGCTTCTTACGGTCGCTGCTGTGGCGAAGCGCCGCTCGCAGCCCTCGAACTC
GCATCTGAAGGGCTTCTCGCCTGGCGGAGGCAACGCAGAGACATTAGTGCTTGTGGGTCGTGTTCCCGTCAG
GTGCTTGCCACCCTCCCCCATTCGTCTCTCATTTTCTGGAAAAGAACTACAAAATATTTTCAGAAATCCTTTCC
ACGGCGCCTCAGGTCGAGCACCCCTTTCCCTCGTGCAGAGAGCGCCCCCGGTGCCCTCTCTTGAACGCCTCC
ATCCCTCCCGCCTTCCTCCTCTGGGCTCATGGGGAGGGTATGGAGGAGGAGCGACAGTGACTCCATCTTAGT
CGAGTTTCCATCCTCGAAAATCCGATCCACTCGGGTTGTTTCCTCCAAATTTTCTCCACTTGGAACCAGAAGC
ACCTCTGCTCGGAAATACATTAACGGAGGAGCTCACAATATAGTTAACGGGGAAGCTCACATCTGCTCGATTT
AAAGTTGCTGTTTCAGACTAACTTCTCTGCCGCTACCCCGCCCAGCCGTCATCCCCCCCACCCACCCCCATCC
TGGCCCAAATTGTTTCCTAAAGTAGGTTTTGCGCAAACGCCAAAGCGATGAAATAATTTAAGGATGCGCAGCC
GATGCACATTGTGTGTGCATAAAGTGGATTCGTGCTGCAGGGAGAGGTATTCTGAGCAATGATTCACTTCAGA
AGGATTTTTACAGGAATGGAGCCCCCTCCCTCTTTCCTTCTACCCCCTGAGG (SEQ ID NO: 32)

285; SW vs I; chr4:122520930-122521740; 4; GPR103; INSIDE
GAAATGTTCTGGAGCATGGTGACGGGAATGCAGAAGAAGGTGATGAGCAGGTCACTGAGCGCCAAGGAGCA
GATAAAGATGTTGGTGACGGTGCGCATGGCCTTGCTGCGGGTCACCACGTAGAACACAGAGCATTGCCAAAG
AGCGCCAGGGCGAAGATGAGCACGCCGGTGAGCACGAGGGCCAGCTTGGCGCGTCCCGGCAGCTCTGGGGT
GTAGACGAGCGGTCGCAGCCGGTACAGAGCGATGAACTGCTCCCGCGTCAGGTTGTGGTCCCGCAGCAGCCG
AGAGAACTGCTCCGGGTAATGTTAAGCGCCTGCATTGCTGTGCGCTCCCGGGACGCGGGGCCACCGCCCGCT
ACTGGCTGGCCATCCGCATCTGCGGGGCAGCGAGGGCTTCGGGGGACCAGCCGGAGGCCGCCTCCCTTCCTC
TACTCTGGAGTCAGCCGCGCGGGAGGGCTCTAGGCTGCACCCGGGAGGTTCGGGAAAGGAGAGCAGCTCAG
GGATCAAACCCACGATAAAGAGGCGGGAAGCCAAAGCACTGGGAGACTCGATCTCAGTGACCAAAAAATGTT
CGCGGTTCAAATAAAGTTCTTCCCTTGCTCTTCCCTAAGGCGAGGCGCCGCCACGGTCTGGGGTGCTGGACG
CCACGCGAGGGTCCTGGCGCCTCTGGCTCCCCGCCTTCTGGCCATGCGATGCGGACGCCGGACCCGCTTGGG
GAGCGGTGGAGGGTGGGGCTGAACTCGGTGACGCCTCCCTCACACCCAGCTTCAGTGGCGCCAACGCCGCTT
CCCCGCACCCTCAGGGCG (SEQ ID NO: 33)

293; SW vs I; chr4:155881084-155881434; 4; LRAT; PROMOTER
GAAGATGAGGTGCAGAAGTAAGCTGGGACCTGTGAGCCTCAATTTCGGCCTCTTCTGCGCTGAGACCCAAGC
GGATCTTGCTTGGCCTGTATGCGTTACTGGGGAAATGGACGTGGGCCTGAGCGCGCAGGTGCGAGGGCGCT
GCCCCGGGGCCGACCACCCTGCGGGGACACTGTAGCTGTCATTCCTTCTTCTGCAGGCGGTAGGGGAAGCG
GTGGCCAAAGTGGGAGTCGACCGCTCAGCACAGTCTGTCTGAGTGTTGACCAGGAAAGTCCAGGCTCTTTCT
AAATCTCGCCGCAGACCTGGTGACGCATTCGCATGTATTTAAGGCGTTTGCACGCAGAACG (SEQ ID NO: 34)

296; SW vs I; chr4:177159356-177159814; 4; GPM6A; INSIDE
CTTTACTCTTGGAGAAATCCCTCACAACAAAGGACAAGGGAGAAGCAAGGGGGAGGGGCGCCCAGTGGACTT
GGCTGGAAGAAGTGAGCGGGCTGGGGTTGGAAGAGTAACTCGGGCTGCGGGCTGACGCAGTCGGCAACCGC
GGAAGAGCAGCATCTCCCCTGCGCCTGTGGATACGCCAGTCCAGGGATGGCGAGTGCTTTCTCCTCCCCAGC
TTCTCCCTCGCTCTTCGAGGTGACTCGTGGGACCCTGCGTCCTAGTGCTGGGTGTGAATCGGCTATTTCACAC
CCAGTTCTTCCCCCCTCCGCCACACGCAGTCACATTCCTGGAGCTATTCCAAGCTGCCTCCGCTAAGCACCGA
ATAAGCGGACCCTGCCTGGAAACTTGAGCGAAGCTGAACTGCGCCGAACTCCACCGTCCAGTGACCCGAGCC
AGTGTGGACGCCCTTTTAATCACG (SEQ ID NO: 35)

317; SW vs I; chr5:140724146-140724826; 5; PCDHGA5; INSIDE
CGCTGTGCGAGCCAGGATCCGGGCAGATCCGCTACTCGATGCCGGAGGAGCTGGACAAAGGCTCCTTCGTCG
GCAACATAGCCAAGGACCTTGGGCTGGAGCCCCAGGAGCTGGCGGAGCGCGGAGTCGCATCGTCTCCAGAG
GTAGGACGCAGCTTTTTGCCCTGAACCCGCGAAGCGGCAGCTTGGTCACCGCGGGCAGGATAGACCGGGAG
GAGCTCTGCGCTCAGAGCCCACTGTGTGTGGTGAACTTTAACATCTTGGTTGAGAACAAAATGAAAATTTATG
GAGTAGAAGTAGAATAATCGATATTAATGATAACTTCCCGCGTTTCCGGGATGAAGAGTTAAAAGTAAAAGTT
AATGAAAATGCGGCTGCAGGGACACGGTTAGTGCTTCCCTTCGCGCGGGATGCGGATGTGGGTGTGAACTCT
CTCCGGAGTTACCAGCTCAGCTCCAATCTGCACTTCTCTTGGATGTGGTAAGCGGAACTGATGGACAAAAGTA
TCCGGAGCTGGTGTTGGAACAGCCCCTAGACCGCGAGAAAGAGACTGTTCACGACCTCCTCCTCACAGCTTT
AGATGGCGGAGACCCGGTACTCTCCGGCACCACGCACATCCGTGTTACGGTCCTCGACGCAAACGAAATGCG
CCCCTGTTCACCCCATCCGAGTACAGCG (SEQ ID NO: 36)

333; SW vs I; chr6:101023927-101024343; 6; SIM1; PROMOTER
CGAATCGGGAATTGGCATTCCGTAAGGGAGCGGAGGGCCTCAGGCCACTAGGCAGCTCCGAACGCGGGGAA
GCGGGAGCAAAGATGAGCTCAGAGCGAGGGTTGCCGGCGCCACCCTGGGCTGCGCATGAGGGGCCGTGGAC
CCGCCCCGAGACTCAGTGACAGTCGCAGCTTAACCCCGTTGGGGGCGCCGCCCCGCTGAGGTGGTTGCGTCT
CCAAGTCGTGAGCCTCCAATAGCTGCTCCCGCTTTCGCGTCGCAACCCCAGGACCCCGGGAAATTACCACTGT
GCTCGTCTGGGCGGAGACCCGGTGCTTCGGAAGCCTGGGGCACATGCCTGGGTCCCACCCTAGACTCACCGC
CTCTGGGCCCGAGACATGGGAATCTGCCCTTGAATATCTGGGCGCCTTTGCTGTTA (SEQ ID NO: 37)

TABLE 2-continued

CpG islands differentially methylated in NMI-BC wt vs invasive BC. Provided for each are: ID; Comparision; Coordinates of selected regions containing relevant CpG islands based on *Homo sapiens* full genome as provided by UCSC (hg18, March 2006); Chromosome; GeneName; Location relative to gene Sequence.

367; SW vs I; chr7:121727243-121727884; 7; FEZF1; DOWNSTREAM
CGCTCCACAACCCGGAAGGAGCTCAGGCCGGACTTGGCGTGAGGGTCCCTGCGGGGCTGGGTCACCTACCC
GTCCGCGATCACCCCACAGGGGCTGTTAGTAATCTCCCTGCTTCCTAGGCCGTTGAAAGCACTCAGGTCACCC
ACTCTCGGTGACCAGAGCGGTCAGTCTTTCCCCGCCATGAAATGTGAGTTCGGGTGGCAGCCGCCGCGCCCC
TGCAGTGTCCCCTGCACATCTCCGGTCTCGGTCTCGCCTTTCTCAGCTCCGCGCCGCCTTTTCCTGGGCGCCG
CAGGACTCATGAAGTGAGGCGGGGCCACAGATTTAAGTTTATTCCCCGCAACTGTCGGGGCGGTCCCGGAGC
TGGTGAGGACGCGCTACGGTGGGTGCAGAAAGGAGATCCCTGGACTCTGTAGAACCTGGGCCCGCGGTGTG
GACCGATGGTGGATTCTCCGCGACAACAGCCCTGGAGGGGAGAGTGGGCCGGGGGAGGGGCCACGGGGCCC
CTGAGGCCTGCGGGGCTGGCCGCACTGGCCCCGGGCCTGGCGGGGTGGTGGAGTCCGAAGCGGCGAGGCGA
GGACCCCGGGGCCCGCTCCCCCCAGTCGCCCTCCCGGGATGTGGCCCCGCTGCAGTAGCACTACG (SEQ ID NO: 38)

376; SW vs I; chr8:9798161-9799053; 8; hsa-mir-124a-1; PROMOTER
CGGGCTCCGGTGCGGGACAGGCAGCCGGAGGGAGCTCCAGACCCCTCCCCTCGCGCCCGCGGCCGCTGCGC
GGAGGTCTGCGGAGGGCGCCTGGCTCGGTCGGTCGCTCCTTCCTTGGCGGGCCCTCCCGACCCACGGTGCTC
AGCCAGCCCCATTCTTGGCATTCACCGCGTGCCTTAATTGTATGGACATTTAAATCAAGGTCCGCTGTGAACA
CGGAGAGAGAGGCCTTTCTCCTGAGGAAGGAAAGGAGGAAGGAAGGAAGGAAAGGTGAAAGAAAGGAAGAG
GGGTGGGTAGAAATGGAATAAGAAAACCAGGAAAAAGAAATAAAAAGCGGCGCGTGTGCGTGCGCACTGACA
GCGGGGAGAGGGATGGGGGTGGGGAACGCCGGAGGAAGGGACCACAGCATCCTCCCCGCCGCAGCTCCCCC
AATCACACAGACAATGAGATAACAGCGACGTCTTCCAAAGGTCTTTGTTCTCCCCCATCCTTTCGCATCCAGG
CTTTTTCCTGCAAAGCGGAGGGGGTGGAGGGATGGGGGTGTGGGTGGAAGTGGGAGACGGAGGGGTGCCTC
CCCCGTGTTAATTACCCCGGCTCCCCTCGCCCCTTTCCCCGCGCCTCGCCTCCCCTGCAGCTCCAGACATGAA
AAAACAACATCGACCCCACCTCGCCCCAGCGCAGCAACCCACCCACCCATGTCGCCCTCTGCTTCGCCCAGG
AAACTGAAGGGGACTAGGAGGAGGAAGAAGAGAGCGAAGGACAAGGAGAGCAGCGGGGACTCGGCAGCGG
CAGCCGGGGCAGGGCGCGCGGCCGCCCCTCTTTACCTCCATCGCTGAGTGGGGGCGCAGCCGGGCCGGGCG
TGCCGCAGGGGCGAGTTGCCGCGGTCCG (SEQ ID NO: 39)

380; SW vs I; chr8:65661156-65662687; 8; BHLHB5; DOWNSTREAM
CGCGCGCGCGCACCCGCACGCAGTCTGCAATGCCCTCACCAGTCCCCGCAGCTGGGCAACCCCTCCAAGA
CCCTGTGTTACGCTTAAATTCCTCTCCCTCCTATCGTACCCACCATCCATCCTTAAGCAGGGAGGCCGAGACT
CACAGAATTCCCTTCTCCACCAACTCGCACTCTTGGTCTAGCACGCGGAAACCGAACCTTTCTACGCGGCCCG
ACCTTGCGATTGCTCCAGCATGAGTGGCATTGACTTTTCCAATGTAATGACTTATGAAAGATATAATCATGTG
TTAAATTGATCCTCCGTTTAACTGTTAATGGTGTGCTCTGGGCACATTTACGTATTTGATGCTATGGTAACTAA
TTACCACTAGAAAAAAGGATAATACACTTCCCAGACTTTGAAAAATAATCATGAGTTCACTTCCCGGCTCGCA
GCACATCGTGGCGGCCCTGCCGGGAGGAGCGAGAAACGAGTGGAAACCCGAAAGTGTGCTCATGGAATGCA
GGAGGTAATGAATCCTGGTCAGGTGAGACTACTTAGTCAAACCTTTAATGAAAACGTGATTCACATGGAAAGC
AGGAGTGGGAGGGAACAACTACACAAAGGTGCCTTTAAACAAAATTAAATGGCAAAACCTGCTATCAGAAAC
ATGAATAGGTTTCTTTCAATTAAAATGCAGGTAAGACTAAATTATCCACGTGCCAAGCAACTTTACATCAATTA
ACATTTTTTTGTTGTGTGGGCAAAGTAAATGAGCCCGGCTCCTGTGCTCTCTGTATTGGCATATACAACTTGA
AAGTCTCTGGATTTCCAAGCCAATGAGCTGCAGGTTTATTTAAATTCGGCCTTTTAAATCAAACTTTAGACACA
GTAGGTGGAAGGAGGGAAAGAGAAGGAAAAACAAGGAGTCAGTAACTTCAGTTTAACAGTAGAAACAACTCT
TACGGTGAGAGTCTTTTTTGCCCGGCAAATCTCTGGCTCTCTGATCGACTGGTGTTTAGAACCAAGGTTCCAG
TAAACAGGGCTGGGTAGGATAACGAGGAGAGTGTTTGTGCTGGGACCTGGCAGGACTGGAGGAGGAAAGGA
GCCGCCTTCCAGCAGGTCCAGCATCCCTAGGTTGCAAACACACCAAATGACGTCCACGCAGCACTCGCCCCA
CCGCGCTGTTTTTGCTTGCGCAGTGCTCCCGAAGGGATTCGGGATC (SEQ ID NO: 40)

398; SW vs I; chr9:121170908-121172141; 9; DBC1; PROMOTER
CGTCGGGAGCGCGCGGGGACACACACGCCACTCACTCAAACCCGCAATTAGCCCTTTGAGCCCCAGGCACAG
GAACCCCCTCCCTAGAACTGGAGAAGACTTGGAGGCGGCGGGGCGGCCAGGTGAAAGCGGACAAGGGTGCC
GGTAGGGGGAGGGGCAGAGGAGCGCGGGGACGCCCCGAATGCGGCCCGGGGCCGGGTCCAAGGGCAGCGG
GGCTGCGGGGCGCTGCACCCGGCGCCGCCTTACCTGGAGTCAATGTCCGTCTTTGGCGGAGAGCTGCGGGA
GGACGCTTTTTATTCGCTCGGTGGGAACTTGGGAGAGCCCTGCGTGCAGCTCGCATTCCGGGCACGGCGCGG
GGACTGCAGGCGTGGGGTACCTGGCTCCTAGCAGCCTGGCTCATACTCAGCCGTAAAGTCCCCTTCGCTGG
TCCCGAGGACAGGCATGAATCCCGGCTCCGGAAGGCGGTCACTCTCCCTCTGCCTCCCGGCTCTCTCGCTCT
CGCTCTCGCTGTTGCTCGCTCGCTCTCTCCCTCTCTCGCGGGTTCGCTCGCCTGCGCTCTCCTCCTCCCCGCG
CGCCAGATCAGTTTGCAGCCGTGGGGTCCGGGAGCGAGGCGGCTGGCGAATGGAGAGGGAAGTCCAAGTGG
CCGCGGTCTCCGGGCGGGGAGCGGCGGAGGCCGGGCTACGCCGGGGGAGGGACTTAGCCGGCGACGGCCG
AAAATGAATGGGGGAGCGGCGGCCGGGGGGCGGGGAGGGAGGAGCTGAACGCCGGGGTTGCTTCCGAGGA
GTGTTTTGTACATCTTTAGGCGGAGGAGGAGAGAAGCGAGAGGAGGAGAGACGGGAGGCCGCCTCGAGGGA
AGGGCGGCCCGGGTGGGCTGGGGCTGAGCCGTAGGGAGTTTCGTGGGTCTGGGGCGTGTAGGGTGTTGTGT
CTATGCGCACGAGCATCCAAAGGGACCGCGCATACGCGCAAACCCGGAATCCTGGTGCCCTAAGCGTGACTG
TACTGTGTGTGTCGCGAGTACCTGAGTGTTTCTGGGGCGGCAGGTGTTTCCACGGCCGCGTGGATCCATCGA
GTGTGGGTTTTGTCTCGGGAGTTGCCCGTGTGGGTCCGTTTGTGTCTGCGCGTCTCTCTGTGAGTGTTTGACA
CTGTTTGTTTCTCTCGTGTGTAGGCGAGAGCCCACGTAACCTCCCAGAATGAAGCAAGAGCTTCTC (SEQ ID NO: 41)

403; SW vs I; chrX:50040955-50041296; X; CCNB3; PROMOTER
GCGTGTCGCAGCTGTGCACGCTGATTGGTCCTCTGCTGGCCAATCACCACTGCACTTCATGACGGCTGTAGTT
TTCAAAATCCCAACTGGGCTGGTGGAGGGTCGCAGGTGTCAGGTTGAGACGGACCGAGTCGCTATAGTAAGG
AGCTCCGTTCATTTCCTTGGCCTCTCCTGGTCTAGGGGTGCGTCGATGGTCTTTGCTGTCTGTCCTCGATCTC
GGTGTGAGGTAGGCGCCTTTGGGCAAGTACTGCTGGCTCCAGCGTCCGGCTCTGTCGCCTGCCAGTGGGTCC
TTGGGCGTCCTCCAGCCCCTTGCTGAATTCTGTTGCTGGGATGCGCGGCG (SEQ ID NO: 42)

TABLE 3

CpG islands hypermethylated in (bladder) cancer. Provided for each are: ID; Comparision; Coordinates of selected regions containing relevant CpG islands based on *Homo sapiens* full genome as provided by UCSC (hg 18, March 2006); Chromosome; GeneName; Location relative to gene Sequence.

2; ALL; chr1:2072175-2072389; 1; PRKCZ; INSIDE
CGGGCGCGGGAGCTACGCCAAGGTTCTCCTGGTGCGGTTGAAGAA
GAATGACCAAATTTACGCCATGAAAGTGGTGAAGAAAGAGCTGGT
GCATGATGACGAGGTAGGTGCCGCTTCTCATGGGGCCGGGGGCCC
GGGAACGCGCTGCCCTGGGGCCTCCTCCGGGCTTTAGCGGAATTA
ATCCATGCACGAGAGACCTAGCCTCACGTTGACG
(SEQ ID NO: 43)

3; ALL; chr1:2106293-2106715; 1; PRKOZ/P7162; INSIDE
CGAGGAGTCGGTGTGAGGCCGCGTGCGTCTCTGTCGTGGACACGC
GTGATTGACCCTTTAACTGTATCCTTAACCACCGCATATGCATGC
CAGGCTGGGCACGGCTCCGAGGGCGGCCAGGGACAGAGCTTGCGC
CGAGACCGCAGAGGGAAGCGTCAGCGGGCGCTGCTGGGAGCAGAA
CAGTCCCTCACACCTGGGCCCGGGCAGGCCAGCTTCGTGCTGGAG
GAACTTGCTGCTGTGCCTGCGTCGCGGCGGATCCGCGGGACCCTG
CCGAGGGGGCTGTCATGCGGTTTCCAAGGTGCACATTTTCCACGG
AAACAGAACTCGATGCACTGACCTGCTCCGCCAGGAAAGTGAGCG
TGTAGCGTCCTGAGGAATAAAATGTTCCGATGATGTGGAGCTCCT
CTGATGCCTTTTTTC
(SEQ ID NO: 44)

6; ALL; chr1:33385564-33385979; 1; chr1:033385935-033385979; Unknown
CGGACGTTAAGCCGCGTCCAGGGCTCCGTGCAGGCGCTGTACTGG
TTGCCATCGTGCATCACGATGCAGTAGAAGCCGCGGCTGGGCTGG
ATCTGGATGCTGCCCTTGCGGCTTGCGGCTTCGTGTGCAGCCCGA
TCACCCACTGGGTCTTCTCCGCCACCACCACCTCCCAGTAGTGGA
CGCCACTACTGAAGGCTTCAGAACCCAGCACCGACACCTCCACAT
CGAAGCGCTTTGGCGAGTCCTGCAGTGGCTGTGGGTGCAGTTGCC
GTAAGCCACAATGGTGCAGTCGTCCGACAGGATCAGGCGCTGGTG
GGCTGTGCCCGGGTCCAGGGTTAGGGCGGCTGGCACTGTGGGGGT
TGGAGGAGGGAGAGAAGATGAGTGGGGAGAAGGCTGTGGCCCACC
ATGCAGTG
(SEQ ID NO: 45)

8; ALL; chr14:7672249-4767297Z; 1; FOXD2/MGC12982; PROMOTER
CGCGCCGGCTTTGCCCGCTTTCCCTGAGGGTGTCCAGTTTTGTGAA
TAAAATTAGAGAAATCTGCGGGCGTAGTTCCCCAAGCCCAGCTCA
GGCTTCCGTTTGCAGCCCGGCGCTGGCCGAGCTCGAACGCTGAAA
AGGGCCGCGTGCAATCGTTCCGCTGTGCCTCAGGACAAACTCCGC
TTCAAGCCAGTGCCGCTCTCCGGCAGTTTCCTGATTGACTTAATT
AGATCCGCATAATCGCTGGAGGGCTTTTCTTTCCCAGACCGAGAA
CAGCTCATTTATGGGGACCAAAAGGAAGAGAGGGAGAGACGACCC
GGACGCCACTGATAGCAACGTACTCTTCGCAAAAAACACTCAGTA
ACTAGTGGAAAAGCCCAACAGGCATCCCCCTCCGCCCGCAACGCT
TCCTCCCAATTGTTCTGGGCTGCACGAGGGAGATGGCCGGGCCGT
GGAACAGATGCAGAAGGAGGCCCGGCACGACCAGAGACGCTGTAA
CCAAGACCCGCAGAGCCTGTGGCTTCCCGCTCTTTGGCGGTGCAG
CAGGCATGGTGCTGGAGCCCAAGGCTTCTGGGAAAGAGTCCAGGT
TTTCGCGGAGGGAGCGACGGACTCACGCGGGATCGCAGGCACTGC
TGCAAGACGCCGAACAGGCTGAGCCGGTAGGCGAAAGAAGTAGGG
TCACAGAAGAAGCAAAGAAAACGAAATAAATTCCGAATCCCGCG
(SEQ ID NO: 46)

50; ALL; chr10:21828640-21829645; 10; C10orf114; PROMOTER
CGTCCGGGAGCCTCCGCAACTCGCATTTCCCAGTCGCAACCCTGG
GTCATTCCTGCCTCCGTCCCAGCTCCCGGACAATTCCCAAAGCCA
AAGGCGTCGAGCGTGTTACTGGCTCCCACCAGCCCAATTAATAAT
CAGCTTAACTCGTGGAGGCTTTGAGCCCCAGTGCTCCGTTCCCTG
AAGCCTCCCAGTGCGGAGCCCGGCTCCTGCGAGGACATCCTTGGA
GGGGGGCCGGGGCGCAGGGACGGATTTCCTGGGAAAAATGTCGCT
GGCGTGTTGCACCTAGAGGGCTGTGGGCAAGGAGGCACGCACCAA
TGTCCCAGTTCTGGGCTCTCAGATCGGGATTCCTCCAAAATCGCG
ACAGCCGCTCAGGTGCTGGGTGCTCACGTTGGCAGCACAAGCGCC
AAATGCACGACCCCGCGCGCCGCGCGCGACCTCCACGCACACTTA
GAGCCGAGGTGACAAGGGAAGGCGGCGGGGGTGGAGCCGCTCTCT
GGTGGAGCATGATCAATCACTTTAAAGGGTTCAAAAGTTCAAGTT TABLE 3-continued CpG islands hypermethylated in (bladder) cancer. Provided for each are: ID; Comparision; Coordinates of selected regions containing relevant CpG islands based on *Homo sapiens* full genome as provided by UCSC (hg 18, March 2006); Chromosome; GeneName; Location relative to gene Sequence.

CCCCTTTGGAGGGGAGAGGTAATGCTTCCCGCGGCCTGCTTCTCT
CTGAGACCCGCGGGTTCCCGGCAGCCGCGCAACCACTGGGGATCT
CGGCTGCCGCTTGCGGGAGCCCCTTCCGGGGAACACGCTCTCGGG
CCGCGCAGCCGGGCGAGGTTGACGCAGCTGCTAGGGGGCAGTTTG
GCTTCCCCGGGAGTACCGGAGTCGCTCGGCAAAAACGTGATCTCA
GCCTGCAGGGCCCGGGGCGCGCGCTTTTCCCTTTCTCAGCAACGG
GAAAGGCCTGTTGGCAGAGGCCGGCGGAGTGCTGGCGGCCTGGCG
GCTGGAGGCTTCGGCGGAAACCTGAGCTCCCTGCGACCTGTTCTG
CTAGCAGGGGCGGGGGAGAGCCCCAATAAGCCGCCCCAGAGGCGA
CCGTGCAAATTCCTAAGAAAAAGCCCTCTAGAAAACACCAAGCCC
TTCCAAAAG
(SEQ ID NO: 47)

54; ALL; chr10:22804715-22807056; 10; chr10:022806090-022806137; Unknown
CGTCGGCGCTAAGCAGCTCTGGAAACGGGCAGACCCAGCTGTGCA
GCGATGTCCAGTGTCGCCGCATCTGCCCCGCGGGGTGCAGCATGA
GTCTTCCTTTGTGGCGTGCGGCTCCATCGGAACGCGCTTGCGACG
ACAAATTCCTTTTTTCCCCCCCGCAGTTAACAGTTCTGGGGCAGA
GGCTGGTGGAGAGGTCCAGAGCCCACTCAGACCGAGATGAAGATG
AGGAAAAGCATGAGCAGGAAGAGGCTGGCGGCTGCGGCGCCACAG
GGAAGAGCTCGGTGCGCGGCGCAGCCTCCCGCGACCGCGACTCCT
GGGCTGCGTCGAGGAGCCGCGTTGCCATAGGAACCGTAGCGGCGC
CCCAGTGAAACCCTGCGTTCGGACAGGAGAAGCTAACCGGGCCGC
CCACTCCCACCCGCGCTTCCTCCCCGCCCCCACCGGCCGTGCGCG
AAAAGCAGAGATCCGAGAACCGCGTGCGGTACAAACGGCAAAAGC
TTCGCGCGCATTTTCCGGGAGTTGAGCGCGCGGCCGCAGGCGGGA
ACCTACCGCTCTCAGGCTCCCAGCCCGGGCGCTACGACCCTGTGG
GCGCCGCCTGTGCAGCCCCTCCTTCCAGCCCGCTCGGGCGCATCC
CCCAGGCCGGGCCAGCGACGCGGGCACCGGGAGCCCCTCCCCCGG
TCCGGGCTTTGGCCCACACCCGGGGACCGCGGAGTGGGAAAGGAA
CCAAAGCGCGGCGCCTGGCCGACCGCGGACGAAATTCGAGGCCGG
AGGGCGTTTTCTTTTTTGCAAAATTGCCCCAAAGCCAGGGCCCAT
GTACCTACTGTCTCCTTTGCCCCACATGCTCCAAGAAAATAAGAC
ACATTCTACCCCGAGTCCTAATTATTGGGCCATTTCCTTAACGCG
CGGTCTGTCCCCGTGGGCAGAAACATACTGCGAGATGCAGTTTGG
TAATTAACAAAGAGACGAGACCTAACTGGGCTTCCGAAATGCTGG
ATACTGCGGCCGGGTCGCCCCGCATTCGGGCATCGCGCGGTTCCC
GGCCTTCGGGACGTTCCGGCCCGGCCGGACTTTGACCGCTGGCGA
ATTAGGAGAAACGCAGAAGGCGGACGCTCCCCAATTTCCCCATCG
AGCCTTCTCCTCCCGAGTCTGCGAAGCCCCTGGCTCAGGAGACAC
CGGCTCCGCGCCTGGGCCTGCAAATCCGCTTCCAGCGAGCGCAGG
CCTGTCGCTCC
(SEQ ID NO: 48)

87; ALL; chr12:94776044-94776377; 12; SNRPF; PROMOTER
GTTACTTCCCAAAGGGCGTGTTCTCCAAGAACTGCATTTAGCATT
TCAGATCAGAGTGACCCGAACTCAATAGGATTACGACAAAAACTA
GTGAGATTCAGATAACACCGTTACATCGAAAGTTTTATCCGTGAC
AGAGGAAATATTGCTTACGCCCTTAGGTAATTTCAAATGCACGTA
TGAAGGCCGTGCGGGTTTCTGCAGGCGAAGCAAAAGAAAGGTGGG
GCCGGCAGGGTCGTGGGGCGGGGGTGGGGCATGACACCTATCCCA
GACGCAACTCGACCTCGTTTGCAAGAAATTCTGTATCCAACTCTC
TTCAGTGCGTTTCGCCG
(SEQ ID NO: 49)

94; ALL; chr12:113657930-113659205; 12; chr12:113657930-113657987; Unknown
GTTCAGTGGTTTATAGAAAATTTCTTTCTCTCTCTCAGGTCCACT
AAGACCGAGAGAGAGAGAGAAGTCGACTCTGGCACACCCGGGCGA
GGGGCTGCCGGGATTCGGGAGCTGGCGCGGTTGATTTTTCCGAGA
ATCCTCCACTTGGGGTGACGTCGGGCAGCGCGCGCGGGCCGTGAG
GTTAATGCCCAGGCTTTTCTCTAAAGCGTCCGGGAATGATCCGGC
GAATAAAACGGGTGTCTGCAAAGTTAATGAATTGTACAGGAGGCT
GAGGGTGGGGACTTCGACCCGGGGAGCCAGAGGCGGTTCTGGTGG
ACGCTTCCCCGTGCGCCTAGGGGTGCGCTGGGCTTTCCCAGCCGA
GGTCTGCAGAGCGCACCGCGTGAGCTTCATCGATCTCATCTTCTT
CCAAGTGGGAGGAGGTGGAGATGCTGGGAGAGTTGTGGGGAGTTG
GGAGTGGGTTGGAGGGGGACTGTCTAGATTCTACTCTGGAGGATC
CAATCACGTGGTGCTGTTCCCCTGCCTAGAACTTCAAGGTTTCCA TABLE 3-continued

| CpG islands hypermethylated in (bladder) cancer. Provided for each are: ID; Comparision; Coordinates of selected regions containing relevant CpG islands based on *Homo sapiens* full genome as provided by UCSC (hg 18, March 2006); Chromosome; GeneName; Location relative to gene Sequence. |
|---|
| ACGGTTTGAATAAAACCCAAACGATGCCCGATGTCCAACGAACGA ATGATCTAGCCTCGGCCTACTTCTCAGGACTTAGCTTTGTCCCTG CCCGCGACTTCCCGCTGGGAACGTCGTCCCCGCCACCACCGCTCT GCTTAGGTTCGAACTCTGGGCCACTCTTCCTACTCCCTCTGGTTT CCAGCAGGAGAAGCGCTTCGGAGGAGGGGGCTAGGGGCGCTCAAC CTCCCGGGTTAGAGGAAATGCAAGTTGGGCCAATTTCGCCCTCCA GACTCCGAGGCGGATAGGCCCAGGGGGCAGCGGCCTTGCCCGGCG GCCACTGCCCTCCTCCTCCCCGCGCCCCCTGGCTAGGCTTTGAA GAGCTCATTTTAAGAACTTTTCCATTTTCCTTTTGGAGGCGTGTT GTTCTTCTCAGTCACCTCGCTTTTTTTTTTTTTATGAGCTTCAGC GCTGATCTGCACGTTCTTCCCTCCGTGTAATTTCAATTTGAACTC TCCCCAGAGCGGCCTTTTCCCTCTTGTTGCCTGCCAAGTCGTTTA AGGCTAAGCAAACATTCTTCCTCCCTCCCGTCCGCGCGAGTCTCG GTCTACACCCGCGAGGGGAGGCGGAGGCGGTTACTCCGAGAGTTC CGGTGGGTTGGAGCCTTTCAGCAGCCGCCTTCAGACTGTTTGGGA GCCGAAAAGCG (SEQ ID NO: 50) |
| 99; ALL; chr13:34950488-34951119; 13; MAB21L1; PROMOTER CTTTGCCGTCATCGCGGGTGAATGCACCACTACCTTTTGGCAGTT GGAGGGGAGACCCATCAGAGCCGGAGAACCTGCAGCCACGACGGC GAGGATGTGCAGTGGTCTCTGGGGAAACGCCGCCTTCGCCCTCAC CCGGCGCGTGTGGCCCTGTGCCGTCCGCTCGCCGCCTCTCTCTCG CTGCTCCGCATTCCCGTGCCCTCTTACTTTCCTCTCTGGGCTCAA GATCGCTACGCTTTATTTCTGCGTGAGCTTATTTGAAACCTTACT TGGTGTCCCGGCTTACTCTCCACGTCTGCTCCAGACCACGGTCTG CCCACGCACCCCTCAGCCTGCACCGCCCACGTCCGGCCCAGGTGT GGTCGCAGCCAAGCCCCAGCCGCGGGCCCCTGCGCCCTGGCTCTC TCCCTTGGGTTCAGGCCAGAGATGCTTGCCCCAAGACCTCGCCCC TTGCCTTCTTGGGCCACCTGCAGAACACCCTTGGTTGTCAAGGAC GTGAGACAGCCGAGGACGGGGAGGCCCCAGGGCTGTTCGGGGACC TTAAGTGGGTCCAACGGGAAGGACGCGGGCCTGCGAGGATGCCG GTCGGGCCTGGCTGGAGCCAGGCGCGCAGGTGGCGCATCTTCG (SEQ ID NO: 51) |
| 102; ALL; chr13:49595986-49600287; 13; chr13049599159-049599206; Unknown CGGGCGGACGAATGGACGGATTCGAGCGAAGCTTATTTCCCTTCT CCTAACGCATCTACCTATAAATAGCGCTCACCGCGCTGAGTCACC AAAACCCCGAGTTTCCCCAAATAGCGCGTAACGACTGTGGGATCG CGTCCCTCGGGGCTCTGTGACAGACTCCAACCACACACCCGCTGG GCTGGACTGCGGGCCCACACGGCCCAGCGGGTCTCTCACCACCCG GCGCCCCAGGGACGCGGGCGAGGCCGCGGTGTCCGGACGAGTCGA CAGCGTCGGACTTCCCGCGCGCGGACGGCGCTCTGGGGAAGGAGG AGCCGGCGGGCGGCTGGACCTGGCCTTGACTGCGCGGGGTCCGCC CCCGCCCCCTCGGGAGCGCAGAGTTGCGGGGGGCCGGCACAGCCT CCGCCCTGCGCCGCCCGCTCACACAATGGACGCGTCGGGAGGGG GCGGCCGCGGCTCCCATTCCGGTCCCAGGGCGGGGACTCCGGGCG GCGGGAGAAGCAGTCGGGCTGGGGCCAGAAGGAAAACCCCCTCTC CCTCTGCCCACTCAAACTGCGAAAGGGCTCCAGCCGGCGGTGCCA GGGGCTGGGGAGCAGCTGGGGAGGGAGCGGAAGTGCCACCCCCTG CAGTCAAGGGTGGTGACGTCACCCCTGCAGCCAGCCTGTAGGGGG GTGTCTGTACATCACATGACCCGGCCCCCCTCTCCCCGCCGAAGC CCGCGCGCGCGCTCTCTCCCCCAGCCCCGACTCCCACCTCTCCCC CGCCCCCTCTCCCCAACTTTCGCCCTCCCCGCTCCGGCACCGTGT CAACAGCGCCAGCTCCGCCCCCTCCCCGCGCCCTGTGGAACCGCC ACGGCGGCGCGGCGGGCGCTCGCGCTCAGGTCCGAGGCTCCGAGA AGCGAGCGTGCCCCGGTTCCACCCTGCCCCCCAGCTCAGTGCTGC TGGCTGCGTGGGCACCAGAGCCAGGGGGCACGGCGGCGTGCAGCG ACAGCGCTTCTCTGCTCCATCCTCCCACAGCAGTTAGAGGACGAA GCTGAGGCGCCGGGTCCGAGCTCGGAGGGAGCGAGGCGCATGCAC GGCCTCCGGGCCCTGACGCGTAGCCTCCGGGGTCGGCCCACGGG CGAGAGAAGCAGCCGGGAGCCCCTCCTCGACCCCAGCAAGGCGGC CCGCGCCTCCGCTCTCCCTACCGCCCGGGTGGCGCACGCCAGTCC CCGTCTTTGGC (SEQ ID NO: 52) |

TABLE 3-continued

| CpG islands hypermethylated in (bladder) cancer. Provided for each are: ID; Comparision; Coordinates of selected regions containing relevant CpG islands based on *Homo sapiens* full genome as provided by UCSC (hg 18, March 2006); Chromosome; GeneName; Location relative to gene Sequence. |
|---|
| 103; ALL; chr13:94152191-94153185; 13; SOX21; DOWNSTREAM CGGAAGCCTCATCCCGCCAAGCCTTCGCCTCCTCGCTGAGACTCT GAGCTGCGCTGGGGTTGGCGGGCACCCGATTCCGCCCCGGCCCAG ACCGGTCACTCAGTGTGTGCATATGAGAGCGGAGAGAAGCGACCT GGAGGCCATGGGTGGGGGCGGGTGGTGAAGCTGCCGAAGCCTACA CATACACTTAGCTTTGACACTTCTCGTAGGTTCCAAAGACGAAGA CACGGTGGCTTCAGGGAGACAAGTCGCAAGGGCGACTTTCCAAGC GGGAGATGGTGAAGTCTTTGGACGTGTAGTGGGTAGGTGATGATC CCCGCAGCCGCCTGTAGGCCCGCAGACTTCAGAAAACAAGGGCCT TCTGTGAGCGCTGTGTCCTCCCCGGAATCCGCGGCTTAAACATTC TTTCCAGCTGCGGGGCCAGGATCTCCACCCCGCGCATCCGTGGAC ACACTTAGGGTCGCCTTTGTTTTGCGCAGTGATTCAAGTTGGGTA ACCCTTGCTCAACACTTGGGAAATGGGGAGAATCTCCCCCCCCGC AACCTCCCGCACCCCAGGTTCCCAAAATCTGAATCTGTATCCTAG AGTGGAGGCAGCGTCTAGAAAGCAAAGAAACGGTGTCCAAAGACC CCGGAGAGTTGAGTGAGCGCAGATCCGTGACGCCTGCGGTAGCTA GGGCATCCAGGCTAGGGTGTGTGTGTGCGGGTCGGGGGGCGCACA GAGACCGCGCTGGTTTAGGTGGACCCGCAGTCCCGCCCGCATCTG GAACGAGCTGCTTCGCAGTTCCGGCTCCCGGCGCCCCAGAGAGTT CGGGGAGCGGTGAGCCTAGCCGCCGCGCGCTCATGTTTATTCACG CGGCCTTGAGCAGCCGAGCTCCAATCCATATTAATCAACCGCTCG ACCTACACAAGTCTAAGTTTACGGAGAAAACCTAGTCCCCGAAA GGAAGAACAGCAATCCGGACAAGCAGTTGGCGCCTTTGTCCCG (SEQ ID NO: 53) |
| 107; ALL; chr13:113930978-113931584; 13; chr13:113931540-113931584; Unknown CGACCCAGCCCCCGAGGAGAACCCAGAACCGACCCAGCCCCCGAG GAGAACCCAGAACCGACCCAGCCCCCGAGGAGATCCCAGAACCGA CCCAGCCCCCGAGGAGAACCCAGAACCGACCCAGCCCCCGAGGAGA TCCCAGAACCGACCCAGCCCCCAATGAGATCCCACAACCGACCCA GCCCCCGAGGAGATCCCAGAACCGACCCAGCCCCCGAGGAGACCC CAGAACCGACCCAGCCCCCGAGGAGACCCCAGAACCGACCAGCCC CCGAGGAGATCCCAGAACCGACCCAGCCCCCGAGGAGATCCCACA ACCGACCCAGCCCCCGAGGAGACCCCAGAACCGACCCAGCCCCCG AGGAGATCCCAGAACCGACCCAGCCCCCGAGGAGATCCCCAACCG ACCCAGCCCCCGAGGAGATCCCACAACCGACCCAGCCCCCGAGGA GACCCCAGAACCGACCCAGCCCCCGAGGAGATCCCACAACCGACC CAGCCCCCGAGGAGACCCCAGAACCGACCCAGCCCCCGAGAGATC CCACAACCGACCCAGCCCCCACGGAGAACCCAGAACCGACCCAGC ACCTGGGCAACATTCTGC (SEQ ID NO: 54) |
| 111; ALL; chr14:36205192-36206099; 14; PAX9; INSIDE TCAGAGAATTTGGAAAGGCCTACTCTGAGGGGAGTAAAACTTCAC CAGGCCCTGGGCTGGAAGCACAGGAGGTCGCGGCTGGGCCCAGCG CCCTCGGGAGGCCAAGGGCAGGGAGCCGACCCAAGGTTAAGCCCT CCAGCTCTCCGTCGCGGGTTTGGGTCCCGTCTCAAGAGTGGGGCG CGCGGGCTGGGCCTCCGGCCTGACACCCTCTCTTCTCTCCATCAG TGAGCGACAGCTCCCCCTACCACAGCCCCAAGGTGGAGAGTGGAG CAGCCTGGGCCGCAACAACTTCCCCGCCGCCGCCCCGCACGCGGT GAACGGGTTGGAGAAGGGAGCCCTGGAGCAGGAAGCCAAGTACGG TCAGGTGAGGAGGCGAGGGTCAGGCCAGGTGGGCCGCGTGCGGCG GGGATTTAGGCGATGGAACACTTTGTGATGGGTCCCTTTCTGAGC TTCCCGCGAGAGAAGCCCAGGCTGGCGTCCCTTTGCTGCTACGAG CCAGATCCTTCGTGGACTGGGGCGAAGCAGAGGCCTGAGCTTGGA AGGCGGAGCTGGGGCCTCGACCCCCGCCAGGGGCCGGGAGCGCTC GTCAGGGCGCTGGGGGTCTGGGGCGGCAGCTCCCCGGGGCGAGGC TCTGGGAAGCGCCTCCAGGCCTGTCGGCCTCCGGGAGCTTGGGAG GCGGCTCCCGAAGCCCTTTCGGCGGCTCTCGTTGGGGGTAGAGTT AACCAAAGAAGGCGCTTCTGAAGGGCCGAGCGGAGCAGCCCTGGG GCCTCAGAGCCGCGCCCCTCACGCCCGCGAAACGCGCGCCCCGGTC TCGGCCCCACGGTGCGACTGCGGCTGCGGGGTCCTCACGTTCGGA CTTTCTCTCCGGTGGCTCTCGGACAAACACGCTTGGCCAATCCTG CG (SEQ ID NO: 55) |

TABLE 3-continued

CpG islands hypermethylated in (bladder) cancer. Provided for each are: ID; Comparision; Coordinates of selected regions containing relevant CpG islands based on *Homo sapiens* full genome as provided by UCSC (hg 18, March 2006); Chromosome; GeneName; Location relative to gene Sequence.

130; ALL; chr15:94688798-94689131; 15;
NR2F2; DOWNSTREAM
CGCTACGAATGTAAGATGAATTTAGTGGCGCGGCTGCCTCCCTGA
ATCCGAACGGTAATGATGGATTTATCAACGGGGATTCGCCTTCAG
CCCAGCGAGGGAGGTTTACTCAGCAAATATGTCGGCGGCACCCAC
CCAAATGCAATCATTTGACCCCCTGCGGACGATAGCTGCCGTGCC
CCTTCCCACCGCTGGTCCTGCTTGGCCAGGGTCGCTGGGGGCCAG
AGGCCGGCCCGGATGACCAGAGAGGTGGCCTCACGGATCCTTGGC
CTCTCGCCCCCTCCTCTGTTTCCTCCTCTCAGCTTGAGGCTCTCC
TGGCAAGGGGGATCGAT(SEQ ID NO: 56)

133; ALL; chr15:94696311-94696840; 15;
chr15:094696796-094696840; Unknown
CGGGGGGGTGGGGCGTGGAGGGCGGCCTGAGTGCCGCGCCTGGCC
CCTGCCCTGGGTGCGCACCAGGCCGCGAAAGCCGGGGGCCGCCTT
CTCGGCTGCTGAAGCCCGGGAGTCAGTCAAGCGCCCTTGGCACCG
CGAGGGAGGCGCACCTCGCCTGGTGCAGAGTTGCCGCGACCCGAG
CGGGAGGAGGCACAGGACGCAGGGCTCCTGGCCTGGCTGTGGGCT
TGGCCTTGGCGCACTAAGCGCTCCCCATCTGCCCGAGCTGGCCTC
CGCGGCCCTCTCGGCCCAGTCTACGTTCGTTTAAGGACTTCAGCG
CGAAGAAGAGCGAACGTGGCTAGAACCTGTTGACCTCTCCTCTGG
CCTGGAAGTCCGCACAGCTCGTGGCAACACTGGACGGACGGTTGT
CAGGGGACGACCGCGGGCAGGTGGGGAGGAGGCCTTGGTCTGGCT
CCTGGATTCCACCCTGGGACGGAAGGGGAAGCGGAAACCTTGACC
TCAGCCACACAAGGACACCTATCTGGCTGTCT
(SEQ ID NO: 57)

134; ALL; chr15:94705727-94706054; 15;
chr15; 094705808-094705853; Unknown
CGCCTGCTGCCTGCCGTGGGGCCGCTCCGAGGTGCCAGGAACTCC
GGTAAGGGTCCCGGCGGCGGCAGCCCGGGAGTGGGCAAAGAGGGA
ACATGCGTGTATTTCAAAGAAACCAGCGCGGTCTCTGACTTCCCT
GTCTTCGCTCTCCACCCCCGCTCCCCCTCAACACACACATAATAT
AACAGACGCGAAGATAATCCTGCCATCTGGCAAATCCCAAATTTG
GTGACCAAGCTCGGAAAGCAACAGCGACGGCTCATCCCGGAGTAG
GTGGCTGGTCCTGCCGGACTCTCCGGAGCTGGGGCAAGGGCCGTG
GGCTCTGCCCG(SEQ ID NO: 58)

136; ALL; chr15:94712480-94712812; 15;
chr15094712480-09471253E Unknown
TAGGACCTGAAATTGCAGAGACATAGAAAATCAATACGTGGTCGG
GAGTCAACTGCGCGCGACCAAGGGCTCTGCCCTCCCTCTCTCCGT
TGATTTGGACGCTGGGAAGCTGCCCGCCGTCCTTCCCACCCCCTT
TGCCCAGCCTTGGCAAGACCTCTCCGGAAACATACTCGCGTTAAG
GAACTGGGAAAGCTTCCTGGCCCGGAGCTAGGAGCCCGACGTTGG
GGCTCCTTGCTGAGTGAGACGCTCAGTCCTGTGCTCCCGCCCCGC
CCCAGGCGCCCAGTCCCGCTGGGATCCATCTCCTCAGCCCCGGTT
TCCCGCTCTGCGAGCG(SEQ ID NO: 59)

145; ALL; chr16:52873104-52882105; 16;
IRX3; PROMOTER
CGCGAGGATGGGCGGGCTCCACGTCTGGGGGCGCTGTGAGCAGGG
CCAGAGCGAAACCTCAGTCTGAGTTTACGAACTGGGAAGGAGCCT
GAACCCCAGAAACACCGTTAACAAAGAGGGCGAACGCAGGGAGCC
GAGGAGACGTCTCCTTGGCCTCTGGGGAAGGGGCTGGAGGAGCGA
GCCAGCTGAGAAGCGGCTTTGCCGGGTGTCCACTAGCGGTTCGCC
AGCCCTCTGTGCGCCCGCAGAGTGACGCAGAGGCCGACCAGTCCC
CTCCCCACTCGCCCCTGGGGCGCCGCCGCACCTTGATCACCCCCT
TCGCGGAGGGAACTCCCAAGGCGCGGCGCTGGCCGCTGGGTCCGC
ATGGCCCAGTCCTGTCGGGCTCCGCTCTGCTGCCGCCGACTTCGA
AGGTGTGCAGTGTTGAGCCGTGTCTTGTTCCGTGGCTTCGAGGGG
TGTGCGCGCTTCCTATACCTCCCCGGAACGCGCGAGATAGTCACA
CGCGCCACTTTGAGGGTCAAACACCCCGCATCTGGCCACATGTAC
CTTTACTAACGTGGGGAGGGGGCAAAAAAATGTGTCTCTCCTTCT
TACCCCGAGGTGTCACTCGCCCAAACACTCCCTACAACTTCTTCA
AGTCAAACTTGGGCAAGGTTGGCTGGCTGACTGCGAGAGGAAAAG
AGGGCGCGGAGGGGGCGCGGCGCGCGGCCGGGTGTAGAGGCCACG
GAGGCGAGGCGCCGAGCGTCCCCTTTGTCCTGTAGAGGGAGCTCC
AGCCCCAAATTTCCCTGCTGCCTCCCCCGGCCCGCCCACCCCGGC
CCGCCTGGAGCCGGAATCCCGGCTGGAAAGGTGCGGCGGTCTGAC TABLE 3-continued CpG islands hypermethylated in (bladder) cancer. Provided for each are: ID; Comparision; Coordinates of selected regions containing relevant CpG islands based on *Homo sapiens* full genome as provided by UCSC (hg 18, March 2006); Chromosome; GeneName; Location relative to gene Sequence.

ACCCCCGCAACCCCCGCGCCGGGGCCTTAGCAGGATGCCTCTTCT
AGGGCACGTGGGAAAACCCACCAGGGTGCCAAGACGCACAGATCT
CCCAGGACCCGGGCTCCCCAACTCTCAACTAGAGCTGGGCAGTCA
CACATCATCTAGAGGATTATGTACCCCTAGGCGACCCTCTTCTCC
ATATCCGCCTCCACCGTCACCCCACACCCTGGCATCTATAAAGAG
GAAGGGGGGCAACCGGGTTGGAAGGAGGATGGAATCTGGGCTTGC
ACAGCCTCTTATAGGTAACAGTGAGAAAGCCTCAACTGTGTCGAT
CAAAGAATGGGGACGAAGGGAGTGATGAGAACACGACCCCGCCAC
CGCGCAGGCTA
(SEQ ID NO: 60)

153; ALL; chr16:86294154-86294408; 16;
KLHDC4; DOWNSTREAM
CGTGTGACACTTTGGAACGCTTCTCTCGTTACAAACCAGCGTCTT
TACTGAAGGTCCTTCCGCTGCAGAGCTGCGCAATGGATGTGTGGA
CAGAGCTAGTCGGCACGTGGAGGCTCTCCTGGTTTTCAGCAGGAA
ACGTGCTGTGAGCAGGAATCGCGAGTGAGTTCCATGGCGTCCCCG
GGTCAGCGCGCGTGCAGGAATCGCGAGTGAGTTCCATGGCGTCCC
CGGGTCAGCGCGCGTGGGGTCCTGTCTCG
(SEQ ID NO: 61)

155; ALL; chr16:87372445-87372729; 16;
chr16087372616-087372660; Unknown
CGGCGGGGAATCGGGTGGCCACGCACGTCGGCCTAAGGGGCCCTG
GCAGCGCCCGGCAGGACAGCCGTCCACTGCACACCTCAGAGCCGG
CACCCGGGACGGTCAGCGTCCCCATGGGCCCGGCACCGCAGCTGC
CCAGATCCTCACCCGCACACAGGAAGGGTCCCTGCAACCCAGCGT
CCACCGTGGAGAAACATGAACGTGAGCAAAAATACGGCCTGCGGT
GGGTGTGCGACCCCACACAGAAGGGCGAGAGGCTCGTGGCCATCC
CACACACTGGGAG
(SEQ ID NO: 62)

165; ALL; chr17:44074280-44075233; 17;
hsa-mir-196a-1; PROMOTER
TTTCGCTAGATCATTTGTTAATTGTGGGAAGGAAGGACGCATCCG
GGGAGAGGAGATCCAGGGCTGGAAAAGTGGGTGAGCGGCGCTGGC
GCAGGCGGCCAGGAGAGAGCAGATGAACCGTTCGTTAGAGCAGCG
AGGTAGTCGTGAGCGCTGAGATCCAGAGACTAGGACCCACTCCCT
CTCTGAGCAGCAAATTGGGAAGAAGATGCTCACTCGGTAAGGGCG
AGGGAGCCCGGCATGGCGCCCCACCACGGGCTCGGTCTTCTGCGC
GCCAAGATCCCGCTTGGGGCGAGGCGTTGGGTCAGCGTTTAGAGC
CACTCCCTGCGCTGGTGGCTGGACATAGCCTCCCTATCCCACCTC
ATCTTCCCCCATCCCCGACAGAGGAGGTTGTGAATCTACGGCCCT
TGACGTTGAGGCGTCGGAGGGCGCACCTTTGTAATTGCGGCCTCC
CTTCGCCCCTTAAGTGCCGCTTCTGGGCGCCTAGGCTGGATATGA
AAGCCCCGTTCCTAATCCTCTGCTCTGGTCCCCTCCTCTGACTGC
TGGGACTCTAAGCTAGGCCCTCCCCAGGTTCCATCACTGCGGCGC
CAACCCGCGGCTGGGCTGTCCGCAAGAGGGAGTTGAAGGCGCGCG
GAATCCCGAGGTGCAGCTGACCCTCCTCTCAACGCCGACTCGCCG
CTCCCGCCCGGCCACCTCCCTGTCGGGCAGACTTCCTGTTCTCCT
GCTCACAGCAGGGAGGCAGTCGCCGAGCCGGTCAGCAGCGTGCAC
GGAGATCTTCACTCTGCGCCCAGCCCCGGGACACAGGTGCAGTCT
CCAGCGGAGCACTGCGGAGTGCGCGCCGTCGAGCACTAGGGAATC
CTAGACGGAGGACTTGGTCCATTCCACGCAGTCCCAGGCAGGTCC
GCAGCGGAGGGACGCAGCGGTCTCCAACTCCTGGTCACGACTTGG
CG
(SEQ ID NO: 63)

172; ALL; chr17:58865328-58865618; 17;
CYB561; INSIDE
AGAGGAGGCGGAGACCTGACCCCAGAAAGCAGCACTCAAACAGAT
GCAGCTGCACCCACGCGCCCGCCTGCTGCCAGAGCCACTCTCCGG
AGCCTGCAGTCCTGAAGACGCCTCAGCAGGGGCAGGCAGAAGACA
CCCCGCGAACCCCCAGGGCCGGCCGGGCGCATCACTGGGAGCCGG
GGCTATCTCCCTCCGTCAGCGTCTTGAAGTCCATGGAGAGGGCCT
GCTCTTCCGCCTGGGAAGGCCGCTTCCAGTCGGCCCGGTCAAGAT
GTAGAGCACCGCCCCACCG
(SEQ ID NO: 64)

TABLE 3-continued

| CpG islands hypermethylated in (bladder) cancer. Provided for each are: ID; Comparision; Coordinates of selected regions containing relevant CpG islands based on *Homo sapiens* full genome as provided by UCSC (hg 18, March 2006); Chromosome; GeneName; Location relative to gene Sequence. |
|---|
| 176; ALL; chr17:73932992-73933361; 17; DNAH17; INSIDE<br>CTTCTGCAGACAGACAAGAGCCCTCCTTACCTTCCATGAAGAGTC<br>CGTACACGTAGGAGCCCTCTCGCGGAGGAGCGGTCATGTCCTCTC<br>GGTTTTTCTTGGTCACCTCGACAGACAGACACATCTTTCCAGGGG<br>CCACTCGTTCTTCCTGGCCATGGACTGCATGATGGCCGTGAGGAA<br>CGACTGGGGGTTGAAGAAGCCGGCCAGCCACACGGTGGTGGGCAG<br>GGCAAAGTCTGTCGTCCAGGCCTCGAGTTCCTGCAAGGCACACGA<br>GCCGCTAGGAGGAGAGGACATAGAATGACATGGGAACGACCGGGC<br>CTTGGCCGTTCTGAGCAGGGGTCACGCCAGAACCTTCCACGGGCC<br>ACTCAGCG<br>(SEQ ID NO: 65) |
| 181; ALL; chr17:75531280-75531546; 17; TBC1D16; INSIDE<br>CGCCTCACGGGGCCTGCCAGCAACGCGCTGTGTGCAGCAGGAAGC<br>CCACGCCAGGTCCTGACGGCTGCATCCTGTGTGCTCTCCGGCCTG<br>GCCGCCTCAAGACACGCCACCTTTGATGCACACGCGCTCCGGAGG<br>CACAGGAAGGACGGGGGCACTGGGAAGTCCATGTTTAGTCTCCTG<br>ACGTCGACCACACAAACCAGACGGAACGGTGTCCCCGGCCCAGGC<br>TGAGCGGAGCACACCATGAGGGCAGAGGCTACAGGTGATC<br>(SEQ ID NO: 66) |
| 183; ALL; chr18:5186244-5187389; 18; chr18:005186349-005186393; Unknown<br>CGTCGGACGTTCACAACGACCACGCTTTTCCCCGCTTCCTCGATT<br>AGCCTGGCCTCCCTTGCTCCAGTGGGGCGGACTCAAATGCGCACG<br>CACGCACACGCCGCCAAGCCGGTCAACCGCAGACAAACTGACTCT<br>TCGCCAACTAGTAGCCACGGAGAGCAGCAAAGGGACCAAGGTCCT<br>TCACCGCCTGCTCCAAAAAGACACGGCAACCTCCAGCGGCGCCGC<br>AGTAGCTGCCTCTGTGCTGCAGCCTCCGGTCGGAGTTTAGGTCTA<br>ATTCCTTAAGAAGTATCGCTCCTCTGCCCTTCGTCCTACTCCCCT<br>TGGCTTCGCCCACTTCGCCTCCTTCTCCTCGGGAGGCCAGGAGGA<br>CCCGGGTCACTTTGCCAATTCTGCGGAGGGGGAAGTAGCGTGAGG<br>GAGATTCCCACGCAAGTAGCCCGAAGCCCACTACTCTTTGCCCCA<br>CCTCTCCACTCTCTTGCCCGTGTAGGTGCCGGTGCTGCTGGCGAA<br>AGTCCCAGTTCTTAAGGCTCCTGAGCTCGGAAGGGGTGTGAGGAG<br>CCAGATGGGAAGAGAAGCAGCGGGACGAGGGCGAGGAAGGGCTGG<br>AGATTGTTAGAGGACAGATGGGGCGGGACTGGGGAGAGGGGCGAA<br>GGCGACGCGCCGAGGCACTCCTCCGCCCCATGAGCACAGACGTAA<br>CTCCGAAACGCGCAGATGGCCGTAAGGTAAAGAGGCCTTTTTTC<br>CCTCTCCTCTCCGTCCTCTACCCTGCTCCCCTCCTAGACACTTGG<br>TGAAAAAGCAAGGTGCGGTGTACCTGGAGCGAACACCATGATTCT<br>TCCAGCCGCTACGCCCCCAGATTAAGAGAGAAAGACAGGCAGACG<br>GAGGATGGGAAGAAGGCCGGACTTGGCGGGGTCCGGTGCAGGAGG<br>GCGCGCTGGGCGGGCGGCGGGCGGGGCGGTCAGCACCCCGGACGC<br>TCCCGCCGCTAGATCCTGGGGCCGCAGCTCCAGCCGCCGCCGCGC<br>GCTCTGCCTCCACAATGCGGCCACAGCGGCGGCGGGAGGAGGAGG<br>GTGAATCCCCGCTCAGTCCATCCCTCATTCCTGTGCCAGCTCGGG<br>ACGTACACTGCTGCTTAGGGAGCAAAGCACTTCCACCGCTTTCAC<br>GCGACGAAGGTCG<br>(SEQ ID NO: 67) |
| 193; ALL; chr19:4059891-4060207; 19; MAP2K2; INSIDE<br>GACCACAAAGCGCTTCCTCATCCTTTCCTCGCCCTTTGATGCCGC<br>CGGCAACGTGACTCTGCGAGCAGCGGGGCAGACGCCAGGTCTCCC<br>TCGCAGGCGGGAAAGGGGCTCCAAGGCGGGTGCTGCCTGCTCGGG<br>TCACATGGCTACGTGGGGGCCTTGCTCAAATTCACTTCCTGCCTT<br>CATTACAAAACTGTCAAAGGGGATCGCACGTTTGCAGGGTGTCAC<br>CCAAGCATTCTGGTTTTGCAAACGACGCTGTGCGGCAGCGGTCTG<br>ATACCTGATGAGCTCGGTGTGGCGGGGTCGGCAGCATTTCCTCCG<br>(SEQ ID NO: 68) |
| 209; ALL; chr19; 63784504-63785085; 19; MGC2752; INSIDE<br>CGGTGTCTGGAGGAAGCGGCGCGGACAGTCTCCCGCTCCACCGTG<br>TCGGGCCTGAAGAGGCCGCTGAACGCTCGCGATTACTGAGGCATC<br>TGGTAGGATCGCAAGGCCATCAACCTACAGGTGAAGCCGAGGCGC<br>TGTGGCGCTTTGAAGCCGGAGAGAAGCTCAGTAGAATCGGGAAGG<br>CGCTGGGGCTGTCCAACTCCACCTTGGCCACCATTCGTGACAACA<br>AGGAAAAGATCTGGGCGAGTTCCCAGGAGGCCACACTGAGGCGGC<br>CACCAAGTTGACGCGTGGCCGCAGCCTGGTGATGGAGAACATGGA<br>GCAGCTGCTGAGCATGCGGATGGAGGACCAGAGCCAGCGCAACAT<br>GCCCCTCAGTGTGGTGCTCATTCGGGAGAAAGCCCACAGCCGTTC<br>GAGAACCGCAAGCAGGAGCAGGGCGAGGGCGCCTAGCCCGAGAGC<br>TTCGGGGCCGGTCGAGGGTGATTCGCTGGCTTTAAGGCGCGCCAC<br>AGCTTGAGCAGCATCGGGGCCAGCGGCCCAAGAACGCAGCTGCAA<br>GAATCCAGCGTTAATGCGCAGGGTGATCCCGGAGGGCG<br>(SEQ ID NO: 69) |
| 210; ALL; chr2:19424445-19425131; 2; OSR1; PROMOTER<br>CGGCCGTTCGGTGCTGCGGTATCCCATCCCCCGCCTGTTTAAGAG<br>AAATTGATCACGTTAAGCGGGCCCTGCGTCGCTGCGCAGTGCCCG<br>GACTACCGCTTGGATGGATTGACAAGGGAAGGACGCAGACACCTA<br>AGAGCAACAAGGGTACTTTTTAAGCGAGGTTACATGTGTTTAGGA<br>CTCGCGAGGACGTCACGTTTCGAATTTGGTAAAAGTCCTCGGTAG<br>CTAGGACCCAACAGTTCTGCCCTCCTGGAAACCCAATGAGGTGAC<br>AAAACTCCCATCTCATTACTGGGAGTCCAGCGCACTCCGCCACCG<br>CGGCTGCAGCTTCTGCTAGCTCGGAGCCTGCGGACTCCAGCCGGC<br>GCGAACTCCGCCGCGACTCTTTCTGGCTCTCTCGCTCACGCCTTC<br>GGGGCGGAACCGCGGGCGCCGGAGTGGTCCCAGACTCGGCTGGGA<br>CCGGGCAGCCTAGAAGAAGGGTCCCCTCAGTAGAGACCAGGCCTC<br>CAGCTCTCCGTCCGGCGCTCCGCTCCACAACCCGCCAGTCATGTG<br>AGGTCCGTCAAGGGAGCGATCCCTCCGTCTGCCCGGGCTTCCGGG<br>CTGTGGACCGCACTGAACCCAGTCCCGCAGCAAGCCCTGCTGCCG<br>CCTTTTCCTGGGCACGCCTGCGGTGGTGACGGCCCGCTGCTATGT<br>CTCCACG(SEQ ID NO: 70) |
| 212; ALL; chr2:43251514-43251780; 2; chr2043251514-043251559; Unknown<br>AAACACAGTGCCGCAGTGAAAGTGGGACAAACGCGCCTGTGTGCA<br>TCCTGGCCGAGGTGCCGGAGGAAGCGTGGTCGGGGCAGAAGTGTT<br>AATGGGCCTCCTTCCTGCCGTGCCCTGCCCGTGCCAGTCCTCGGT<br>GCTCATCCCGGCTCCCTGAAATGCTCGCTTCCACTCAGGGCCAGC<br>GCACTCCCTCCACGTCCCTGGCCGCAGATCTGTCCTGCTTTGACA<br>AATAACCCGCTCAGCCTTCGGGTTTATGGTTTTTCCGTCG<br>(SEQ ID NO: 71) |
| 214; ALL; chr2:45249374-45251726; 2; chr2045251412-045251456; Unknown<br>CGCTCCCTTTCCCGCACACGCATTGCTGCCTCCTCTCGGGCTTGG<br>TTAATGAGTCTGTGCGCCAAGCCAGGTCGCTCCGGGCAGTTCGCG<br>CTTCCGCGCCTCGGCACTCGGATGACCGTGTCCTATTGTCTCTCT<br>CGTGAATGTCGCTGAAAAAAAATAAAAGTTTGTTCTAAGCCCGTG<br>GCATTTCCGCGCGCAGATGGAAAGGCAAGTGGGAGAGGAGGGTGC<br>AGGTGCGGGGCGGGCGCGGCGGCCCCTTCAGGCGCCGGGGCTGGG<br>CTGCCCCCGGCCGGGAGCAGCTCCGCTCCGCGCACGTGGCTGTGG<br>GCGCTGCGGACGGGGGACGGCAGGCGGGGGACGGCAGGCGGGGAG<br>TGGAGGGTGCAGTGCCCGCAGGTGCCGACGGCTTCCTCCAGAGCC<br>CTTCGCGCCGCGCCTTGCCTGGCTGGTGGCGCGGGGAAACCATGG<br>CAGCATTGCGGCTCCGGCGGGCGGGCTCTGCGCGGGGCCCCACCG<br>AGCTTTCCGGGAGCCTCTCCCGCAGCCGATGGGCATCTAGGGCGC<br>AGAACGAAGAGTGGGCGCCGAAACGGGTGTAGGCGCTGGAGGCCG<br>ACGGGGAGGCCCGGGGCGGTCAGGCTTCTCGGTAGAGAGGGCCGT<br>GCACCTCGCGGCCTGCGGGCTAAGGCGGGGAGCCGCTCCTGGGCG<br>GCCGGGCGCGCGGACTGGAGGGAGGGAAGCGCCACGGACTGGGGA<br>ACCGGGGTGACGGGGAGACGGGGGGGCTGGTGGGGTGAGGTCGGC<br>GGGCAGCAGCCAAGTGTTCTGCAGCTCCGAACCCCGCCACCCCTG<br>GGCGAACGGAATGGCACCCGCGGAGACGGGCGGGGACGGGCGAAA<br>GCGGGTTTGCTCCGACCCGAAGCTGAGCCCGGGTTGGAGGGCGAG<br>ACCGTAGGCGAGAATGGCCGCGCGGGCTGGGAGACCCGGGCCGTA<br>TGGAGTGAGTGGAGCCGCCCGAGGTAGGGTAGTTGGGGATGGTAG<br>TTGTGAAGACAGTCGGAGTCTAGCTCCGGGCAGACGAAACACCGG<br>GGCGCGCCAGGGTCCGTTTCCTCCTTCTCTCTGCTTTCCCACCAC<br>CCTGTAGATACGGAGCCAGCAGTCGGGCTAGAGCGGAGGCTGAGG<br>GTCGCGGTTCCAAGGGCGGTCTCTCGCCCCGGGTCAGGCCCCACC<br>CCGCGGTGGCGGTCGCGTGGCGCTGTCCTGGAGTTGAGCTGTCCC<br>GCGCCGCGGCC<br>(SEQ ID NO: 72) |

TABLE 3-continued

| CpG islands hypermethylated in (bladder) cancer. Provided for each are: ID; Comparision; Coordinates of selected regions containing relevant CpG islands based on *Homo sapiens* full genome as provided by UCSC (hg 18, March 2006); Chromosome; GeneName; Location relative to gene Sequence. |
|---|
| 217; ALL; chr2:63134470-63134933; 2; OTX1; INSIDE CTCGAATCTTGGAGACACTGGCTTCTAGTCGCACATCTGCACTTTCTCCCACCTGTGGCCTCTCAGGCTCGGCCGCCCGAGGGAGTTTCTTTTATTCCCAGTTCGGCTTTCTTTTGCGAAGGCCGAGTCTGGGCCTGCCAGGGGCCTGCCCGAGTCCTCTATCGCGGGTCCACGTGGCCACCAATGACCCGCGGCGCCCCCGCGTGTCCCCGCAGCCACTCCGCGGAAGCAGCGGCGGGAGCGCACCACCTTCACGCGTTCACGCTGGACGTGCTCGAGGCGCTCTTCGCCAAGACTCGCTACCCTGACATCTTCATGCGGGAGGAGGTGGCGCTCAAGATCAACCTGCCGGAGTCTAGAGTCCAGGTGCGCACTCCCCGGGCTCCAGGGTCTGGGTAGGGAGCTGAGGCTGCTCGGGGAAGGTCTAGGAAGGCTCTTGAGTAGTTCTTGAGGAGACCATC (SEQ ID NO: 73) |
| 220; ALL; chr2:66525936-66527222; 2; MEIS1; INSIDE CGGTTTGGAGAGGGGAGCGCAAAGCGCTGGACGCATGCGGTACAGTGCCACGGCCGCCGGTGGGCTCCACTGCCCTGGGGAGCTGAGGCGCGACGAATGAAGCACCAGGGCGCCTGGTGGGCGCCAGTCTCCGGTCTGGAGCCTGCTGGCCTGTCCCTCCGGGGCGCTGAACCCCTAGTGCGGCGTCCTGGGGGCCGGGCAGGAAGGATGGCCTCTCCACCTGTCTGCGAATGCAGCCCAGCCAGTTTGAGCCTCCGCAGAGGTGCGCTCCGGGACTGGGCGCTTCTCGTGCTGTGAGAACGCTGGGCCTTGTTAGCTCATTAACCCCTCTGTCTCTAGGGCCCGTTGGCGGCACGGTTTATTTTATTTTACCTGTTTTCCTCGGAGGGCGCGAAGACTCCACCCGCGCGGGGACCTGGGATCGACGACTTTGATACTAGGCGGTATCCCGGAGGGCTAAGTCGGCGGAAATCCACTTGACCTTGTAGCGTTAGTCCTTTCTTTTCCTTTCCTTTCCTTTTTCTTTCTTCTCTCTTCCTATTTATTTATTTATTTTAAAAATAGGATTAAGACACCAGTAGAAGCTGTAATCCCGTTCCTTCCCCCACTCCCAGTCTTCCGGGCCGCCTGGAGGTCCCTGCCGGAGAGAGCCACTTTGGCGGGCGCAAGCCCCTGGGCGCCCTCTCCTGACCGCCGCGCTCTCGGCTCGGCTTGGCTGTTCCGGGCTCCCAGAGGCTAGGGGAAGCGAGGGGCGCCAGGGGCTTCCCGGCCTCAGCGTGGGGCGAGGTCCCGGCTGCGACCCCGGAGAGAGGGAGAGGGGGGCCATGATGCTAGGCGTCGAGGCGAGGGTTGAGCCTGTTTGGCTTCAGAGAACGATGCGGGTTCGACCGGAAGCGGGGCGCGTGTTCTAGGGGCCCTTGGGTGGATTAGGGGGCGCCAAGAGGGTTAGGCGAGGAGAGGCCTGGCCACCCAGTTGCTAGACTTTAGGCCGCACTCCAGGAAGGAGCAGTCGGCTTCCTTCCTAGGCCGCTTCTATTGCGCGCCACTCCTTGAATCTAAGCATTTTCCACTCCAAGAACCGTTGGGAGAGAGGGGAGAGCGGAGCAGAGTCTCTAGGCCCCCAGGGCCGCCTCCCGGGGTGGCCACGCCTGCCGGTAGCGAGCCGAGATTAGCTAGGTCTGTGCTCGGGCCTCAGCGGTGGCCCTGGCTCTTCCCTAAGCAGCGGG (SEQ ID NO: 74) |
| 222; ALL; chr2:70984709-70985764; 2; VAX2; INSIDE CGGGCGCATAACAGGCACCCCGCACATCGCACCGCGGACGCAGCGATCCTCCCATTTGTACCCTAAGGCCTGAGAAGGCCGCTCCACACCTCCGCGTGCACAGTCCCTAGACCAGTGAGGGCGGGGAGGGGAAATCCTTTTGTTTTATATTGGAAACCTTACGCCAAAGGCAGGCAGGAAGCAACCAAAGGAACAACAGGCCGCCTGAGCCGTGGCTCAAACAGCACAGGGCAGTGGCCGAGCACCAGGCTTTTCGGTGGAGCGGGATACCAGCAGGCAGAAGAGGTGGACAACTCTGACCGCAGACTCCCTACAACCCCGCGATCGATGCTCCACCTGCACGCTCAAACGCACCTGTTTCCCAAATTAATCCAGACGCGAATTTAACGACCGATTTTGTAGATCCGGGAAATTCTGTCCACCAGCGTCACCCAACACAGCAACTTTTACAGACAATGCGTGGCGTCCGTTCCTGCTCACCCAAAGCGGCCTCTCTGGGCTGACAGCCACCCCTGCGGGTCCTCAAACCCCACTCAAACCCTCCGAACCCCTGTGTCTGGGAGCAGTAGGGTGGGATGACTGCAGGATCCCTTGAAGAAGTGACTCGCTGCAACCCCACCACCAGCAGCAAAAACGCTTTCACCCGGGAGCTGCATGGATGCGCGGATGGCGGGGGCTGAGGGGACGCGTGAAGCCCAGGCCTCTTGCTTGGGCTGGGCGATTCCCGCCGTGGGACGGGTGGGATTGACCTTAGTGGAGTCCAGTCCTTCGGAGAATCCGCGGGCAGTCGGGACCCACGCTCCGGAACACCCAAGTCCGAACTCGTACACACAGCACAATGGCGTGCAGCCGCCGGGGCCCTAACTCCCAGAGACGCGTCTGAAGAAGCCATACAAGGGGGCGCAGCTTCGGGGCTCTGGCTGGGAGGTTACTGCAGGGACAGCGCCTCGCCTCCAGCAGCCGGGTCCAGGCTCAGGGCCGGCCGGCCTCTGCTCGCTTTCTGCTTGGATTACCAACAGCCACTGGGCTTGGGGAGATCGGCCGGGCCG (SEQ ID NO: 75) |
| 230; ALL; chr2:105864220-105865009; 2; NCK2; INSIDE CGGCAAGACGCGCAGGAAGACCAGCGCGCGGGATGCGTCCCCCACGCCCAGCACGGACGCCGAGTACCCCGCCAATGGCAGCGGCGCCGACCGCATCTACGACCTCAACATCCCGGCCTTCGTCAAGTCGCCTATGTGGCCGAGCGGGAGGATGAGTTGTCCCTGGTGAAGGGGTCGCGCGTCACCGTCATGGAGAAGTGCAGCGACGGTTGGTGGCGGGGCAGCTACAACGGGCAGATCGGCTGGTTCCCCTCCAACTACGTTTGGAGGAGGTGGACGAGGCGGCTGCGGAGTCCCCAAGCTTCCTGAGCCTGCGCAAGGGCGCCTCGCTGAGCAATGGCCAGGGCTCCCGCGTGCTGCATGTGGTCCAGACGCTGTACCCCTTCAGCTCAGTCACCGGGAGGAGCTCAACTTCGAGAAGGGGGAGACCATGGAGGTGATTGAGAAGCCGGAGAACGACCCCGAGTGGTGGAAATGCAAAAATGCCCGGGGCCAGGTGGGCCTCGTCCCCAAAAACTACGTGGTGGTCCTCAGTACGGGCCTGCCCTGCACCCTGCGCACGCCCCACAGATAAGCTACACCGGGCCCTCGTCCAGCGGGCGCTTCGCGGGCAGAGAGTGGTACTACGGGAACGTGACGCGGCACCAGGCCGAGTGCGCCCTCAACGAGCGGGCGTGGAGGGCGACTTCCTCATTAGGGACAGCGAGTCCTCGGTAAGTGCGCTGCGCCCACAGCTCCGGCTGCAGGCAGTAAATGCGCCTTGCGCGGTGGGTCTGTGTGCCGCG (SEQ ID NO: 76) |
| 232; ALL; chr2:111591678-111597436; 2; FLJ44006-BCL2L11; DIVERGENT_PROMOTER CGACTCGGTGAAGGATGATGCCCGGAGGGTGATCTCGACCTTTAACATTCCACACACCTACCTCCACGCACCAATCGCCGGAATCTCCAACCCGCGGGCCGCGTGGGCTTTCTACCCTGCACCGCTGAGCCGCGGCCACGGGAAGAGGCGCGCTCCCGGCGGCCCAAGCTGGGAGCCAAGCTCTAACGGGTGTGGCGGGAAGTGTGGTGGCCCGCCAGCAGCTGCCACGACGCTCGCTCCACCGACGCCCAGAGCTGTGGCCGGGCCGGGGGCTGGCACCCGCTGGGCCGCCACTCTCGGGGATTTTGGTGGCAAAGCGGAGGTCCCGCCGAGGCTGGCGAGGTGCGCGGCTGGCTGCTAGGAAAGAGATCCAGACGGTCGCCTGGTGCGCTGGATCCCGTGCCCTTTCCCTGAAACCCAGCCTGGCCTGACTGCAACCTCTCCCAACTTCAGTGCCGGATCCCCTAGACAATCAGGGTGGGCTCCCCGCTGCGAGCGCGCCCCACAGCCGGGTGCCGCCAAAGGTCTCCTGCTGTAGCGGTGACTCACATTCCCAGTGATTTAGAAAAACTGTGGTGCCGAGTGAAGAAGCAACACCCTTAGACAAGAAJAGCTCCACTCTTTCCGCGAGCGGGAAAAAAGGTTTGGTTCAGCAGTGATGCTATTTCAGTGAATCAGACGCTCTGGGGCTCTGCAAGGAAACGCACGGACTGGGAGAAGGAAGTGGGAGCCTAGAGTTTTGCTCTCGGCAAAACAAGAACTCGGCTTGTCCTCCCAGGCCGGCGGTTTCCTACGGCAAGACAAGGCGCGGAAAACATTTTTACCATCTGACGCTGTAGTCTGTCCTTTAGAAGAGAATAGGTGAAAAGTTTAATAAAGAAATTAAGCGATGTGGAAGTCGTTCCCGCTGCTTGCAGAGGGTGGGGAGCGGGCCTGGGCAATTTCGGAACTAGGAGAGACCACGTCGGCAAAGCCTGTGGTCCCGAACAAGGGCCATGGATTTCCCATTTCTCAGATCCCGGCTGCCCGACTTCATTCTTGTTTCTTTCAGCACAAGCCATCCCCCTTCTCCCTCCCTCCACGTCTCTTGGCAGAGACAGAAAGGGACACCGCTCTGCCCGCGTCCAGCGCGAAGGAGGTGACCTAAAACCCATGGCCCTTCTCACACTGCGTTCTCTGCGCTCCGGCCCAGTTCCGGAGGACCTCCCG (SEQ ID NO: 77) |
| 238; ALL; chr2:156892636-156892878; 2; NR4A2; INSIDE CGGGTTGGAGTCGACATGGGCCCTGACGAGGGCACTGATCAGACTCACCGGGGGCGAAGGGGGAGAGGGCTCCTGTGGGCTCTTCGGTTTCGAGGGCAAACGACCTCTCCGGCCTTTTAAACTGTCTTGCGAACCACTGCAAAGGAAGAGCCCTGTTAGCGCCGCTTTTCCGAGCCCAGGCCCAGCTGCTGCCTCGGTCCCTCCCCGGGGAAGGCCGCAGCCGCGGGGCACCAGGCTGAGCG (SEQ ID NO: 78) |

TABLE 3-continued

| CpG islands hypermethylated in (bladder) cancer. Provided for each are: ID; Comparision; Coordinates of selected regions containing relevant CpG islands based on *Homo sapiens* full genome as provided by UCSC (hg 18, March 2006); Chromosome; GeneName; Location relative to gene Sequence. |
|---|
| 240; ALL; chr2:156893736-156894685; 2; NR4A2; INSIDE TCCTAACCAATTTCATTCTGAACAGGGAAGACAGCTCCTAGCACATGCAAATGACCCTCTTCCAACTCCGGCTCCAGCAACTTCGGGCGGGGGCCAGCCGGGTCGGCTGAATGCGAGGGGGATGCGACCTGGCCTCCCAGTCTTTCTGCTTCCCTTTCTCAGACACCCGGAAGTCCCCGCCGCAGCCCATGGTCTCCTGCAGGGCAGCTTCGGCGGACCCCGGAGAGCTGGGCAGTCCCGGGAGAGCTGGGGCTGGGCTACTGCACCAAGGCAGAGGGCACACTCCGAGGTCCCGGGCACTAGGGGCTCCCTACCTGCCTACTCCGCTCCCGCCATTGCTCACCTTAAAGAAGCCTTTGCAGCCCTCACAGGTGCGCACGCCGTAGTGTTGGCAGGCCGGTTGTCCCCACACACAGCGCACAGCCCCTCGTTGGAGGGGGGAGCCCCGCGACGGCGGTGAGGGCACCTGCGTGTCGAGCAGCTGAGACGCGTGGCCGATCTGCAGGCCCGGGAAGCCCATGGACGCGGGCTTGCGATGGGGTTGGGCACAGCGAAGGTCTGCCCGTCCACCACGTGGTGGCTGCCGGCGGGCTCCGGGTTCATGGGGACGTGCAGGGGCCCGTCGAAGCGCATCTGGCAACTAGACACCGGGGTGCCAGGGGGCGATTGCTTAAGGAGAAGAGGGAGAGGCGGGAGACTGGCGTTTTCCTCTGCTCGATCATGTGCGTAGTGGCCACGTAGTTCTGGTGGAAGTTGTGGAGAGATCCCGGGTCGTCCCACATGGGGCTGTGCTGCACCTGGAAGCCCGGGTGGTGGGCGTCGGGGGCGAGGAGGGCTTGTAGTAAACCGACCCGGAGTGCGGCATCATCTCCTCAGACTGGGGGGGCAGGTGGCTGTGTTGCTGGTAGTTGTGCATCTGAATGTCTTCTACCTTAATGGAGGAC (SEQ ID NO: 79) |
| 245; ALL; chr2171384729-171385226; 2; GAD1; INSIDE ATACAATTACCCACACAACAAAGAGGGCCTCGGGAGAGTCGCCAGCCCTGGTAGCATATGAACCAGGCACCGGCGTTGGAGCTGGCCAGGGCAGGGCGGGAGGAACGCGAGGCCTGCGCGCCTTTGTTGGTGCTTTCGCCTTGATGGATTTCTTTTCTGACGCTTTCCACATTTCCCGCTCCCTTTTGCCGCCTGGGGGTGGGGGTGGGGGGTTAGCGGGCAGTTGTGTTAATTTGCCCTCCACTCCCGGCGCCCTTACGGAATCCCGGTGGCCGCCAGTCGCCGGCGCAAATGCCAAGTCACCGGTAGGAGACACAACAGAGGCGATGACCTGAATCCGCACGTGGCCTGGTTCGCCTGGAAGCTGCCAAAGCGAAGGCAAGAGAGCCCGGGACCCTGTGTAAAACAGCAAGCAGCACGTGTCCCAGGCACACTGTTGCGGGCCCTTAGCCTAGCTACGCATCCGCACCCCAGGCTTCAAAGGCGCGCTGGGCG (SEQ ID NO: 80) |
| 254; ALL; chr2:176737610-176738187; 2; HOXD3; INSIDE GAAAGAGATCCGTGGGCTTCTGACCCTGGTTTAGGCAAAACAGGGGGAGGCGCCGAGACCAGCTCGAGCACT AGCGGATTTTGAGAGAAACTGACCGCAACCTCCATCGCCTTCCCCCTCTCTTTCACTTGGATGGGCTGACTCTACCCGTCGGTGATTTACGACGATTGCAGCGCTAGTCACAGCCTGGCGCCTGGTGTCCCCTCCCTTCCCAAGCCCCCTCAGCTTTTCCACTGCCACCGGCGTACAAGCAAGTGCCGAGCGGCCTCCGCAAGTCGGACTAGCCTCCCGGCGTCCGAGGCCACCACGGGCAGCAGATTTTTGGTCCCCAGCGAGGCTGCGCGCGTTCGTCCCGCCTCCGACCGCCGAGCAGAGCTGCTAGCAGAAGCAGGCGCCGGTACTTTATATAATCCTGCTGCTCGCAGGGTGCAAGAGCGGGAAAAGTGCGGAGTAGGGAATTCTTTTGCTGCGCTGCCTCCTACGCGGAGCCTGCTTTCCACTGCTGAAAAGTGCCGGGCCTTGGGAAGTGTTTTTCTTTCATTCCTTACCGAAGCGTTTACTGCCGCCGTGGTCG (SEQ ID NO: 81) |
| 259; ALL; chr20:35582018-35583550; 20; NNAT; PROMOTER CGGCTGGCTACCGGTGCGCGGGGACCACACTCACAAACCGCATTCCGGTCTTCCCGCCCGAAAATCCGCGCTGTGCGAGGGACCCACAAGACTGGCGGTCTAAAAGGGACCCGCCTCACTTGGAAACGGGCTGCGGTAGCCACAACCCTCCGGTAGCGGTAGCGTAACCCCGTTCGGTGATCCAGCCGCACAGCGCAACGGGTACAAAGAACCCCACTGGCTAAGGCCGACCTACCAGGGCTTGGGGGAGGGGGAGCGGAAGACGAGGTCGAAACGACCTGTCCAGCAGAAAACTATCCCCAAGCATATTCCAACCACTTCTCCGTAGAGCTCATTCCTTCCGTGCATACGAAGGGCGCCAATCCTTCCTGTATCCCTCCTACAGATACCGGGTGACTACGCTTTTGCGCCCAAAGCGCAGTGCTCTGGCTCAGCTCCCTACAGTAGCGACCTCCACCGCAGATTCTCATCTCCTCGCTACCGTAAGAGAGATGTAAAGAATCAGACGGGTTACGCGCTCAGGCACCCTCATGAAGAGAGGACCTGGGCTTAAAACTCATTCAGTATCAGGAAAAGAGCGCCGAGCACGGGCCTATTATGCCAAAGCTTCTGAAAGGGGCACCACGTTTTTTGCTCTATGGGGCAGATGACCCCTCCCTAATTTCGGTTTTCATCCATCCCCAAGGTAGGCTTTGGAGTGGCACCGGAGACTGAGCTCAAATTTGCAGGCCAGGGACTGGGGAGAAGGGCGCCACACTAAGAGACCTGCACCCCCATTCTCGCCCTGTACTCTACCCAGAGTCGTGGTCCCCTCCATTTTAAAGCAAAATCCAAAAGCAAGCACGGCGGAATCTTCTGGAAGGGGGGCTAAGATGGAACTCAGGAGGCGGGGGTCGGTATGGAAAGAGCAGATGGATTATTTTTTTCCTCTCCTGGCGAATGAGGGCGCCCCCAGCCACCCCTCCTCATAAACACCCCCCAAGGCGCGCATGCGCACTTAGGTGGCGGGCGGGTACTTAAGGCGCGGCCACCGCGGCTGCGGCAGTGCGCCCAACAGCGGACTCCGAGACCAGCGGATCTCGCAAACCCTCTTTCTCGACCACCCACCTACCATTCTTGGAACCATGGCGGCAGTGGCGGCGGCCTCGGCTGAACTGCTCATCATCGGCTGGTACATCTTCCGCGTGCTGCTGCAGGTAAGTCTGACGGGGTTTCGGTGGGAGAGGGT (SEQBIDNO:K) |
| 267; ALL; chr2060061693-60062033; 20; TAF4; INSIDE CGTCTAATCGATGGTGGGGCGAAGGGAGAGCCACGGCGGCCCTGAGTGCAAGCACCATCCTGAAACCAGGAGCCCATGAGGCCGCGGGAGCCGGAGGACCAGGACCGCCCTCGCACTGCCCTGTGACAGCTCCCGGCCCAGCTCTCTGCCGCTCTGGATCCGTCACTAAGCAGCTCCATTAAGTGCCCGGTCAGGCAGGAGCGGCAGGGAAACACTGGGGCACCCACATCTGAACAGAGAAGATGCCCACCTTGAGAAGGTACCTGGAGAAGGGAGCCACGAGCGACGTTTATGCTGAGAAGCGGCATCCGTGCACCTCACCTCCGCCCGTCCACGCCG(SEQIDNO: 83) |
| 281; ALL; chr49756136-9756429; 4; chr4009756149-009756196; Unknown CGCTCGGGTGGCCGAGTTACACCTGGCTATAAGTCATCCCGTGCACCTGACTAAATGCATCCCGTGCACCTGACTAAATGCGTCCCGTGCACCTGACTAAATGCGTCCCGTGCACCTGACTAAATGCTCCCGTGCACCTGACTAAATGCGTCCCGTGCACCTGACTAAATGCGTCCCGTGCACCTGACTAAATGCGTCCCGTGCACCTGACTAAATGCGTCCCGTGCACCTGACTAAATGCGTCCCGTGCACCTGACTAAATGGTCCCGTGCACCTGACTAAATGCGTCCCG (SEQEDNO:84) |
| 284; ALL; chr4:111780013-111780343; 4; PITX2; PROMOTER CGCGGAGAGACACAGGGAGAGGGAAGGGAGTTGCGCTGAAAAGACGCAAAGATACGCGCGTGCAACTCCCTCCCCTTTCAGGTTTCAGAGGTTTGCAAACCAGGGCTGAGAGGAAGGGGCTCGGGAACTCACGTTCCTCTCGCCCCCCTTCTGTCTGGAGTCTCGCCCGCCAGAGGCTGGTTAACCCCAGTCCCGGCCGCCGCAGACACTGCGCTGAGCTTTTGGGTCCTCGCCTTGCCCAGCGCCAGTGCAGCTGAAGTGAGAGCTGGTGGGAAATGCAAATGGCTCCTGGAGAAATAGAAGATACAGAATGATTCTCATTCCCTCCT(SEQIDNO: 85) |
| 302; ALL; chr5115810975-115811393; 5; SEMA6A; INSIDE CGCGGCTGCCGCGGCTGGGCTTCCGCTTCTGCTGCAGCGTTGGGGTTGACTCTGGGGTGGGGAGGGCCGTCAGGTCCAGGTGGTGCTGGTCTGCTTTAATGAGCATCTTGGCCGTGTTGCCGGGAGTGCGAGCTTGCCGTTGTGCATGAGTGGCGTGAGGATGGCCTCCGGCTTTGGGTCTTTGGATTGAGTGTCCCCAAAGAGGCCGCTGAGCTTGGTGACGCTGCTCATGGAGCCCCGGCGCGAGTGGGTGAGCTCCTTCTCTTGCGCTGCACCACAGCCACGTCTTTGCGCCGATGATCACAGACGCAGTAGACGGTGATGCCCGAGAAGACGGCCCCCATGACGAAAGCCAGGATGACTGCAATGGCCAAGAGGGTGACGGGAACCAGCTGGTCGGGCCTTTGAGGTAACTT (SEQ ID NO: 86) |

TABLE 3-continued

CpG islands hypermethylated in (bladder) cancer. Provided for each are: ID; Comparision; Coordinates of selected regions containing relevant CpG islands based on *Homo sapiens* full genome as provided by UCSC (hg 18, March 2006); Chromosome; GeneName; Location relative to gene Sequence.

304; ALL; chr5:122461778-122463450; 5; chr5:122462228-122462286; Unknown
CGGCCAAGGCTGGCGGCGGCAGGTACCCGGGTGCCCCGAGGGCCA
CCCGCCGCCCCGCTCTGGCGCATCCATCAGTGGCCAGCTTTCACC
GTGTCTGCCAGGCGGGACTCGCCAGGTGTCAGGCTCATGCCATAA
GCCTGACACTTGCGCGGGGTCGCCGTGGCTCCTCAGGGAAGCTGG
GCCAAGGAGGCTGGGTCGCGCCGGCGGGCGCCGAGGCCACCTTCT
CGGGGCAGGCCATCCGCGCTGAGGCGCAGACACGGCGGTCCTCCA
GGCCCATTAATAACCCGGAGGGCGCTGCGATCCGACAGCGCAGTC
GCCACAGGCTCTATTTCCCGTGGCCGCCTGCCTCCTTCCAGCCCA
GTTCGAGTGGAGGGATACTGGGCGCCCACTACCGCCCGGCCGGAG
GGTGGGGGTCCCTCTCGCGCAGGCTGCTTTGGAGAGTGTCGGAGA
GAGACAGCTTTATCTACAGCTTCACCCATTGTATAGCACAACAGA
ATCGCATTTAGCCTGGAGAACAGCCGTCGGGGCAGGAGTTGTGCC
TTCTCTAACAATTAGGCTGATCGTTAAATTTGCTATTCCTTTCTT
CCGGCGTCTAGGGAGAGCGTGCACACCAAACCCTCCAGAACAGCA
CCCCGGTCCCCCACCCCGCCCCACCTGTCCCCGCCCTGCTTAGTG
CCTGGAGGGAGAACTGACTGGTCGCTTGAGGGACCCCATTTCGGG
CGCGCCCTTGGAGTCCTGGGGCTGCGGCTCCTGCTCTACCGGGCT
GCAGGCTTGCTCTGCCCCGTCCCGTGGCGTTTGGGAGGCAGTGAG
GAAGCCTCCGAGTCTCTGGGTCGAAGGAAGTGCGAATGGCACCCG
CGATAGACTGGCCGTCTCCCCCACCCCGCCCCGTCTGGTGATTTT
AAATCGTCTCCTGTGTAATTGTAAAAAGAGGAAAGCTGAATACCA
GACGACCAGTATAGAATCTCTTCGAGACAGCAGATTGGGCAAGAG
ACGGGCTTTTTTTCGCAATACAAGGATAAACACATCCTGAAACTC
CAGATAGAAACCTCAGGAATGGGCGAGAGGGTCAGAAGGAACGAA
GACAGTAGGGAAGAGAGAGAGAGAGACAGAGACAGAGGGAGAGAT
GCAGAGAGACTGAAACGGGAGGAAGAAGCCTGGAACTGTCGGTTC
CGTGGAGAGCGGACATGCTATCTGCGCCCAGATCCGAAGGCTTTT
GGGGAGCCTAG
(SEQ ID NO: 87)

311; ALL; chr5134390896-134393045; 5; PITX1; DOWNSTREAM
CACAGAAGAAAAGGCAACCCCAGGCATAAAGAGGCTCTCAGCAGC
CCCTGCCCGAACGCTCCTGGCAGGCAAGGGCCCCATAGCACCCTG
GGGCCTCGAGGGTCACCGCAGACCCGGCCTGGGAAGAACCCGTAG
AGTCCCGCAGCCGCGGAGGGAGGGGGTTCTCGCTAAGGCGTCCCG
CGGACAACGCCGAGAGGCACAGCTTAGCGGGTGCGCACCGGACAG
GCTCGCAACGCAGGACGGTGCCCTCATGGGAGCCAGGCGAGCAGG
TCAAGAATGGTGGTGGGGAAGCGGGGTAGGCAGACCTCGGCGGGG
GCTGCCTCGGCGCTCTGCTCCTACCCAAGGGGCCCGGTTCCCTTT
CTACCCACAGTTCCCTTTCTATCCGCCTCCCTCCTCAGCCAATGA
AGCAGTCGGGGCTCAGCAGTGCTTAGCACGCTCGGACTATGGTTT
TAATAGACGTACATGGACAAGTCGATATAGACAGATTTATTACAG
TCAGTCCAACATACACAGGGACGCTGTAAACAGGGGCGCGGCCGG
AGAGCGGGTGTGCAAAGTGGGCGCAGGGCCCTGGGGCCGCGCCCC
TTGCTCTGCCGGCTCGACTCTTGCACGGCGGGCGGTGAGGAGGGG
GCTGTTCGCCCAGACAGAGGGCCACCTCCTAGCCCGGGAGCGAGC
AGAGGGCCTGGGCCTGCAGCTAAGCTCAAGGCTGGGGTGTTCTGA
GATGGACCTCCCCCACCTCCCGCCAGGCCCGCACTGCCCGCTGTC
GCTCCGTGGCCTTAATATAGGGCTCGGGGCGCGGGGCCAGCAGG
CTCTACCAGGCGCGCCGGGGCCGTGTGCGGCTCCACTGAGTGCCC
GATCCTGGGCTGGGGGCACCGTCCCCCCAAACCCAACGCCCGCCC
CAACACGGATCCGACTCGAGCTAAGGCGCTCTCGGCCGGGCCTGC
TCGGAGAGGGCAACTTGGTTTGTACGGGGTCGGGAAATCCTAGGC
AAGTCCAGGCCCCGCACATCCAGTCCGCAGGCCCGCCACTCAGT
CCGGATCCAGCGCGGCGGGGACGCGGGATACGAGGTCGTCCTCCC
CGGCCGCTGGGCCTCGGCGCTCGCCTACCGCGCCGCGTGCCCTCC
GCGGAGTGGGCCTCCGGGGCCCGTGGGAACACACACACCACCCGC
GCCATCCCGAGAGAAATTGCAACTCATCCATTTTTTCGCGGCACT
TTCTCCGACGT(SEQ ID NO: 88)

314; ALL; chr5:135442969-135443206; 5; chr5135443148-135443192; Unknown
CGCGCGGGACCGGAGGCGCACACCGGAGGGGAGGTGCCCCCACCA
AAATTTAAGTGCGGCGCAACATGCACCACAGGTAGGGGCACTACC
AGGGCAAAAAGACTTGGTGAATGCGAGGGCCGGGCCTATCAAAGG
TGCGTATGGTGGTACCAGAGCAAGGCGGAACAGCTGCTCAGTGGT
CCGCAACCGGGTCAAGGGACAAGAAGACGATTCTGGATTGTAGGC
CGCCCGAGAGCG(SEQ ID NO: 89)

319; ALL; chr:5174091287-174092335; 5; MSX2; DOWNSTREAM
CGGTGACTCGGAACAGAGGCAGAAAGGATGCGAGGACTTCTTGCT
GCGTAAACAGCGCGGCGGGCAGATTGGCACCTGGCACCTACCAGG
ACTGGCGCTTCGTCCCGCGTTTCCAT
TGTGCCCGCACCACTTTGAAAGTGGGCGCCGGAAACTCCGTTTTT
CTTATGGGGCCGGGGTCGGCAACGTGGTTCAGAGGTTTCACAAG
CTCCAGCACAGAAGTGATCCAAACCGAGGGGTCGGCTCGAAGTCG
GAGGCTGATTTTTCTTGCTCAGTCGCTCCGCCGGAGCTGAGCCGC
TGGAACGACCCAAACCTACCTGAAAGCGCGTCTCTGCAGTCCCGC
TGGACTTCTCCGGCTCGAACTCCTAATCTCAGCCCGGAATCCAGC
CATATTCATTTAAGATTGCGTTTTCCAAAGGCCAAAGCCTTTCCC
GGTTTCGTCATCAGCCGCCAGGTTGGGTCCCTAATTAGCCTGTCC
ACCGAGCTTCCTTCCCGGCGCCGCTTGGACCCCGCAGCCCCGGGC
GATCTCAGCCCGGGGGGGAATCCGGAGACGCCGGCTCCGGGTTAA
GACTCTGCTCGTCCCCAGGAGGACGGGGTCGCGATCCAGAGTGCG
ATCCGGAGAAAAGGGCTGCATCTTGCGTGGCTGGCGGGTTAGACT
GGAATCCGTCTGGGGACTGCGCACCATCCCCATCGCTCCAGACGC
CGAAACAAAACCTGAGGCTCGGAGAGGGGAAAAAGAGTTGTTCAG
GCTCGAACATACGCATCCCAGCCTCATAGGTGGATGGGGTTACCG
AGCTGAGAACCAAGCCGAGGTCCGCGAAGCCGGGCCGCCCCCTTG
CTCTGGGCCTCCCTTCAAGCCTGCAGTCTGGGGATGGGTTCCGAG
TCACCGCGGTCCGGGCCTCGGTCAGGCTTGGTCGGGCACACAGGG
CGTTTCAGAGGCCAGATGACAACCTGTGGCGGCAAAAGGACTCTC
CCTCACCAGGGACCCGCGAAGGCGCGCATTGCAAGATGTTAGCGT
GCGGGCTTTAGATATCCTTGCGTCCG
(SEQ ID NO: 90)

324; ALL; chr6:1549606-1560865; 6; FOXC1; PROMOTER
CGGGGTCCCACGCGGGCGGCGCGGTCTTCCCCAGGCCTCCTTCTC
TGGAGACCCGGTTCCCAGGGGACGCTGTGCGGGGACAGGCGGAGC
CGGCCCTTGGAGCCCGGCGCGGGCAGAGGCGCCGCGGGACAACGC
CTCCGACGGCAGGGGGCGCTCGTAGCACGCGCAGTGCGCGGTGCG
GGCGCCCAGGACGGCTGCCTGGCCCCGGGTTCCCGAGGCGCGGGA
CCTGCCGGGGTGAGGTGCCCCCAGCCTGAGAGCCCCAGCTGGGTC
GGCCAAGGGGCCTCCGGGCTTCCACATCGTCCCTTTTTCTGCTGA
CGCTCGCGGGGAAGCGGCGGGAAGCCTGTGAGGGGCGGCCTGGGA
GCAGACGGACCACCAGGTCACCGGCGCGCGCTGCCAGGCCCGACC
CACTCGCGAGGACCAGCGGTTCCCGGAGGCGTCGGCCCTCAGGTC
CTCGGGGGAGGCCGGCTGCACCGAGCCGGGTGTCGGCCTTGTCCC
TGTCCTGAGAGGTGCAAACACCGGCCCCGGCCCAGGCCCCGGGGC
TCCTGCCCAGAAGGCTCAGAGCTGGGGGCCGACCGCGCCTTACCC
GCAGGAGGCCCGGCGGTGCGTCCGCGTTGGTGCCACTCCCCGGCC
GGGGTGAGGGACGTCGGAAGGAAGGTCCCAGGGCGCAGGGTCCGC
GAAGGGAGCACTCGGAAGGAAGGCTGGCTGCGGCCCCGGCGCCTG
GGTCCGCTGCGGCGCCGGGCCGGAGACCTGGGAACAGCCAGCCAC
CTGCAAGGTTGCAGCCCACCTCACCCCGCCGGCGGCTCCGGGCTG
TCTGTGGGTCTGTCTCACGGGGCAAAGCCTTTCTTCCCACACCCA
CAGCCAAGGCGCGTCCGTGCAGGGGCACACGCCTTCTGCTCCAGC
CCCAGGAAGGCGCTTTCGCCCTGCAGTCCTCCGACGGCCGGCTCC
GCCGCACCGCGCACCCTGGCTCCGGCAGACTCTGGGGCCTGGGGA
CTCGCCCACCCTGCGCGGCGCGCCCCCCACATGAGCCGAGGTTGG
GAGGCTGCGGGGCCTCTGTCCTCCCAGGCCGTGGAGTGCGGCGGC
GCTCTGAGTCCGCTGGGGACCTGGATGGAGAGAAACTGGGGCTCG
TTCGCGCACACATGCACCATTTGTTCTTTCCGATCATCTATCCCT
TTACGAATTTTATTTTTATTCCGGATTGTTAATGCAAGACGACAG
TTGAATCTCCA
(SEQ ID NO: 91)

339; ALL; chr7:1481682-1482268; 7; chr7:001481829-001481873; Unknown
CGGCCTGCGGTGGGGAAGCGGGTACGGGAGGCCCAGCTCTCCCCA
CCAGGGTCACTGGAGAGGAGCAGACGCAGCCGTCCGCCAAGACCC
GGGCACGAGTCCCCAGCAGCTGTCACTGCCCCAAACTAACGTGAC
CCCACGTCCACCAGCAGGTGAACAGATAAACCAACGGCCGATCCA
CACAATGGCAGGCCACCCAGTGCCCACAACACCACGACTCTCCAG
ACTGTGCGAGCAGAGCACCCGCAAGCTCCCTCGGTATAAACTCAA
CGCAGACAAACCCACAGGGCCACAGGGCGGCGCGGACTGGGAAGG TABLE 3-continued CpG islands hypermethylated in (bladder) cancer. Provided for each are: ID; Comparision; Coordinates of selected regions containing relevant CpG islands based on *Homo sapiens* full genome as provided by UCSC (hg 18, March 2006); Chromosome; GeneName; Location relative to gene Sequence.

GGCAAGAGGGGTAGCCGGCGATGGCCATGTACACTGTGGCCTCCG
CCCTCCCTCCCTGCCCGGCCAGGGCACCTGGGACGGCGGGGGGAG
CGGCAGAGTTGCGCCCTCACCTTGCAGACGCTGCTGCTGGCAGCC
CCTTCGCTGTGCAGTAGGACCTCAGGCACGGGCACCCGCAGCTCC
GGCCGCTGTAGGTAGAGCTGCAGGAGAAGGTCTCGGCAGCCCTGC
CCAGCACGCTGGAAGAGGTGGAGCAGGGCTCACCAGGCGGACG
(SEQ ID NO: 92)

340; ALL; chr7:2082782-2083345; 7;
MAD1L1; INSIDE
AACACAGTTATGACACAGTGAGCCCACAGCACAGTTAGCCTGCAG
CACAGTGAGCCCGAGACACAGGTATGACACAGCGAGCACATGGCA
TGGTGACCCTGAGACAGGGTTACGACTTGGTGAGCCCCAACATGG
TGAGCCCAAGACGGTTACGACATGGTGAGCTCACGGCACAGTGAG
CCTGAGATGGTTACGACACGATGAGCCCGCAGCACGGTCAGCCTG
AGACGGTTACAACATGGTGAGCCTGTGGCACGGTGAGCCAAGACA
GGGTTACGACATAGTGAGCCCACAGCATGGTCAGCCCGAGACAGT
TATGGCACAGTGAGCCCGCGGCACGGTGAGCCCGCAGCATGGTGA
GCCCGAGACGGTTATGACACAGTGAGCTCACGGCACGGTAGCCCG
AGACAGAGTTACGACTTGGTGAGCCCGCGGCATGGTGAGCCCAAG
ACAGAGTTACGACTTGGTGAGCCCGCGGCATGGTGAGCCCGAGAT
GGTTACGACATGGTGAGCTCGCAGCACGGTGAGCCTGCCATGGCC
TCAAGGGTTAAGATGTAAAC
(SEQ ID NO: 93)

345; ALL; chr7:2724511-2724848; 7; AMZ1;
DOWNSTREAM
CTTCTCAGCAAAGGCCAACACGTCTTTCTCGAGTCCAAGACCATC
TCCCGTTCAAGGGCCCTCACCGCGCTTTGTGAGTCTGTCTCGTGG
GCCTCCTTCAGTGGTCTGTGACCAGCGGGAATGAATGGGACGTGT
TTTGTTCAGCCCTGACTCTTGGACGCTGGTGGCAGCCGCGGGCGC
CCACTCACCTGGCACGTGGACGAAGGTGATGAGCGCGGCTGACGG
CTCCCGGGGGCAGTGTGGGGTCCAGTCTGAAGCCGACGCCCTCTC
GGTCAGGCTTTCAGCAGCAGAAGGCAGTGGACTCTTCACCATTTC
TTCCAACACTTTCTCACGTAG
(SEQ ID NO: 94)

349; ALL; chr7:8449587-8450236; 7; NXPH1;
INSIDE
AAACTGAGGCAACCAACTTATTCGCAAGAGTAAAACCCTATGGGG
AGAAGCGATTCCTGCCCCTCTTCCCCCGGCGAGGAACACGGCTGG
AGCCACCCAGGCGCCTTCCAGGCTAAGGCGCCTTTAGGGCGCGCA
GGGGTGAGGGAGAGGGTGGGGAGAGTCCTAATTATTATGAATTTC
TAAAGGCGCAGTAATTATTCACGGGGAGCAGGACAAACCATGGCT
AGGCAGGGAAATCGATATATTTGCTATCGAAAGTTCCTGCTCGCC
TTTAATGCAGACGAATGGGGGATGCAGCCTCATTATTTTCCGTGG
TTAGGCTCGCCAGCGTGGGGCCTGATGCAGCGTGAAATCTATCAT
CATTAGACCCGGGATGGAGCGGCGGGGGGGAGTTTCTCTTACTTA
CCAAACCGCAACAACAAACAAACAACGACGAACAACCGCCCCCTA
CAAACACTCATTCTCACACAACGTTGCCCTACCTCCCTCGCCGCT
TGCCCTGGCCGCTGTTGCACACTCCCCTGGGGGCTGTCTGACGCC
CTAGAGCAGACACTGCGGTCACTTAAAGTGCGCCCAGTTCCTCCA
CCGCAGCGGTCACACCGTTGATTTGATCCAGAAATAAGACGGATA
GTACCGAGCGTTGGCG(SEQ ID
NO: 95)

354; ALL; chr7; 27164708-27165039;
7; HOXA7; PROMOTER
CGCCGCCGCCGTCTGTCTAGACTCAAGCGACTGAAGGGGCCAACA
GAGCTGGTGTTTAAAGTAGAACCTGCCCAGTCCAACAGCCCGAGC
AGGGAGCGATTTCGGGGATCGCGGGAAGGAACGCACTCGCCAAGG
GAGGGCCGGGTGCCCTCGCCACCGGCTCATTCCTGCTCCGGTTTT
GCCCGATGCGCGTCCAGGAGGTTCTGGCAGGACGCACTGCCCCTC
TGCCCCGGCCAAGGAGGATGCGGATACTGCCCGCAAGGTTCGGCC
TTTATGGACCCAAGTCAGCCAACTGGGCCGAGTCCTGCGGACACC
GAAACCTCCCTTTCG(SEQ ID NO: 96)

358; ALL; chr7:27251165-27252762;
7; EVX1; INSIDE
CGCCTGTGCTCTGGACTCGCTGTGCAGGGTCCGGCTCCGAGGCGC
TGGTCGGCAGTCCGAACGGAGGGAGCGAGACCCCCAAGAGCAACG
GCGGCAGTGGTGGGGGCGGCTCGCAAGGCACCCTGGCTGCAGCGC
CAGTGACCAGATGCGTCGTTACCGCACCGCCTTCACCCGAGAGCA
GATTGCGCGGCTGGAGAAGGAATTCTACCGGGAGAACTACGTATC
CAGGCCGCGGAGATGTGAGCTGGCGGCCGCCCTAAACCGCCGGAA
ACCACCATCAAGGTATGCGGGGTCCAGGCTGGGGAGGCGGGTGTG
CACCTATTTAGCGGGAAGTAAATGCCAACTGCCAACTCCCTGAAA
CGCAGGCCAGGAATCTGGGCCTGGGGTCTCCCTGCCCGGGCGTGC
AGATTGACCCTCGTGACAGCTCCTAGGCAGGCATTGCTGCCATGT
GGCTGACTCTGTCCCTTTCCTGGTTAAATAGACAAGGGGTGGGCG
TGGGGGAAGGGGATAGAGTGCCTGTGCGGGTGACAAGGAATTTCT
GGGGACACGCTCTCTGCGGCCGCAGACCAATTGAGTCCATGTCCT
TTCACTGCTCCTCCCATACACACACTGGCCTCTGGCACCCCGGGG
GCCTGGCCACCTGGGCAGAAGGAAGGAGGGAGCGGGCTGGATCAC
TCCCCAAACCTCTCTCGGAGGGATTCCAGCTCCAGGTGGTGGTGG
TGGGGTCGGTCTCTACCCGGCTGGTGTCTGCTTTGGCTGTTCCTG
CCCTGCGAACACTGTCCCCGGAGCGGGACCAGACTACTGGCCCTG
AGCATCGGGCCAAGTCCAGCTACTGAACCTGCTCCGCTCCTCTCC
CCAGGTGTGGTTCCAGAACCGGCGCATGAAGGACAAGCGGCAGCG
CCTGGCCATGACGTGGCCGCACCCGGCGGACCCCGCCTTCTACCT
TACATGATGAGCCATGCGGCGGCCCGCGGGCGGCCTGCCCTACCCC
TTCCCATCGCACCTGCCCCTGCCCTACTACTCGCCGGTGGGCCTG
GGCGCCGCATCCGCCGCCTCCGCCGCCGCCTCGCCCTTCAGCGGT
CGCTGCGCCCGCTCGACACGTTCCGCGTGCTGTCGCAGCCCTACC
CGCGGCCCGAACTGCTGTGCGCCTTCCGCCACCCGCCGCTCTACC
CCGGGCCCGCGCACGGACTGGGCGCCTCTGCCGGCGGCCCCTGCT
CTGCCTCGCCT(SEQ ID NO: 97)

359; ALL; chr7:32768010-32768497; 7;
chr7:032768257-032768301; Unknown
CGGACTTGTCCCCGCAGCCCTTGCGGACCTCCTGGTCGTCATGGC
GACTGTGAAATGTGGGGTGGGGAGCATGCGTTCGAAGCCATTTGC
GCGGGCAGTCCCTGCGTGTCCCCCCACGTGCTCCCCACACTCGCA
GGACCCCCGCCTCCGAGCTTCCCTGAGCGTGCAGCTTCCAGTGAG
GGCAGCCCCACGCACAGCCCCCCACACCCTCCCCAACGCCTTCAG
CCCCCGGTGCGCGTAGTCCCCAAGCCCACACGTGCACTTCCACCT
TGCGGCAGCTGCACGTACAGCCCCCCACACGCTCCCAGCCCCACT
GGCGCAGAACCCATCACCGCTCGCCCTTCACGCGCTTCACTGGGA
GTGCAGCCCCCACCCCGAGCGCGCAGCTCCACGCAGCCTTCCACA
CTCTCCCCAGCGCCTGCAGCACCCCCAGTGCGCACAGCTCTGCCA
GTCGCTTCCCCGCGTGCCGCCCCTGCACCACTTCG
(SEQ ID NO: 98)

362; ALL; chr755040457-550410247;
chr7:055040965-055041024Unknown
CGAGCACGGCCTCGGAGGCTGAGAGGCCTGGGAGGCAGGGCCGCG
TCCTGCGGGCTCCACGAGAGCCCTGTGAAATGCCAGTCAGATCCT
GGCCCAGTGCCCCAGGTCCTCCCGCAGCCTCGGCAAACCCTCCCC
CGGCGCTGGAAACCTTCCCCTGCCAGGCGCAGAAGGCCGCGCGCA
AGCACGCAGCTCACAGTCACCGCCACCTGCTCTGAAACCCCAGGT
TCAGCGCAGGATCAGAGTCCCCCATCCCCACCCCACGCAAGGGAC
GCAGGATTGACAGCGACCCTGAAGAAATGCAGTCGAGAGCTATTG
TGAAAGGGCGCTGGCCCGGAGGCCCCCCAGCCCGCGCAGGACAGG
CCAGTTAATCGCCTTGGTCCCAGGCCCCTATTAGCGTGTCATCTG
CGACAGCAGGACACGCCTTCCCATGCCAGCCGCTTTGGGGCCCGT
GCGGCCCTTTTTCCCTCGCAGCTGCTGCAACAAATAGCAGTTCTT
TTGAGGGAAGGAACAGTGTGGTCCTCAAAGTTCATAATGAAAATC
TTGGAGAAAAGTCATAGTTGCTAA(SEQ ID NO: 99)

364; ALL; chr7:96488158-96489591; 7;
DLX5; INSIDE
CGAGCGGGACGAGCCCTGGGGCTCCCACACCGCTGGAGACTGCGG
CGAGTTACACGCCATTGGGTCGCTGGAGCTGGGACTGTGCTCCGG
GGGCATCTCCCCGTTTTTCATGATCTTCTTGATCTTGATCTTTTG
TTCTGAAACCAGATTTTCACCTGAGTTGGGGAACAAAGGCACACG
TTACCGGGACACTCAGAGGTCGCCCGCGCCTTCCCCGGGGCGGCG
ACTGGAGGCATCTTCGGACCTCTGGGCGGCCCAGCCCTCCTGGCG
TCTCCCCGCCGCGCTTGCGGCCTACCGCCAAGAAGCTATGCCTTAGG
CAAACCATGGAGCTCTGGCCCCAGAGGGCGCCCTGGCCGGCTCGG
GGCGCCCCGGCCCAGCGAGGCCACGACCCCAAGGCTTGTTTTTGT
TTGGGCTGGGGGTGGGGGACGCCAGCGCGGCGGGTGTGCGCCCGA
GTGTCCTCGGCGGCGGCGCGCCTCGTGTAAGCCTGCGCAGGACGC TABLE 3-continued CpG islands hypermethylated in (bladder) cancer. Provided for each are: ID; Comparision; Coordinates of selected regions containing relevant CpG islands based on *Homo sapiens* full genome as provided by UCSC (hg 18, March 2006); Chromosome; GeneName; Location relative to gene Sequence.

GCGGAACGCGGCGAAGGTCTCCAAAACAATCGCGCGAGCCGGCGG
GGAAGGGGCGTGGGGCGGGCTACGCGCGCCTGTGGTCAGAAAAAG
GAGCGAGCTCCCAACCTCCCGTCCTACTCCCTTCACTCCCTCTGC
AGCTCAGAGAGGCCAGAATCTGACTGCAGCTCTTGGCGGCGCTCG
AACATTCTTTATGCTTCCGTAGGCCCCAGCTGGGTTGGAGGAGTA
AAAGGAATGGGACAATCCAGGAAGACTTCTCACGTACAATAGCGC
CCCCCACCTCGCGACCCTTCGGTGGCCGTGGCCTGAAGCTCCGTA
GGCTCAGGGCACGACCCTTCAGTTTCTCCGCTCCAGGCGACGTTC
TCAGCCTTTTCTTAGCCTGAGACCACCGCGAGAACACCAGGCCTT
GCTCACCCCCGAGGAGGCTCTACATTGTTAAGAAAACCAGATACT
GCTCTGGGCTGCCTAGGCCGCCCTAGAAATAACCCTCCGCTTGCT
TTCAACCCGCGAAATTGGCCCCACAGCTCCGGAGGCCCGCTACGG
GGTGGGGGCGGGGGGCGCGGTTAGTGGGAGGTATCTCCAGACCGT
GATGAATACCATCCCCACCGTCTCAAGGCCTGACTCACCGAGTTA
AAGCATAGGGGCTGATGTCTTTGGGTCTGTTAGTTTCTCACGGGT
ACTGTCAAAACAGCTCCAGTCCCATCGAGACTGAACCGCGCGACC
AACCAGACGTG
(SEQ ID NO: 100)

369; ALL; chr7:155266364-155266696; 7;
RBM33; INSIDE
CGATTCAAAGATGCCGGCGTCCCGCAGTGTGCGGTTCGTGCCCTT
AACCACCCGCTTCTTTGTTTCCCGCCCCTCTGCTTTCGCAGGAGC
TCTTGTGCTTGAGTTCAGTGTTAGTGGTAGCGTGGCTACTCCACT
TGGAGGTGGCGGCCGTCTGACCGTGTGTTACTGCTTTGCCGACGG
GGCCTCCCGGCCCTGATGCGTGTACACTCTGCGGGCTGCACCGGG
TGGCTCTGGTTGGGGGCGAAGCTGTGTTGACTGGGAGACGTTGGA
AATTGAGACATGGAGAGATGACGGGAGTGCGTTTCTCTGGGTTTG
ATCTCCATCCTGTTTT
(SEQ ID NO: 101)

371; ALL; chr7:155288454-155292175; 7;
SHH; INSIDE
CGCGGTGGCCCCCGCACCCGGAGCGTCGGCAGCACCTGGAGCGGT
TAGGGCTACTCTGCCGCCGCCGCCCCCGCGGTCCCCGCCGCCGCT
GTCCCCGCCGCGGTCCGTGCGCGCGGGCGCCAGTGCACCAGGAGC
GCGTGCGCCAGGCGGAAGGGCGCGAAGGCCCGGTGCGCCCAGCTG
TGCTCCTCGATGACCGCGTAGCACGAGGCCAGCACCCGGTTGATG
AGAATGGTGCCCTGGGCCGTGAGCGGCGCGTAGGCGCCGCGGCCT
CCTCGCTTAGGGTCACGCTGTGCACAGCGGCGGGCAGGAGCCGGC
GGTCCCCGTCACGCTCGGCCACCACGTACACGCGCTGGCCCGGGC
GCACGCGGCTGGCGAACAGCGCCCGAGGCCCCAGTGCGCCCCGGA
AGGCGGCCCCGAGCCCGAGGACGCCTCGGGCTCCCCGGTGGCCGA
GTCGTTGTGCGGCGCCACAAAGAGCAGGTGCGCGGCGGTGAGCAG
CAGGCGCTCGCGCGGCTCCCGCGTCTCGATCACGTAGAAGCCTTC
TTGGCGCCGTCGTCGCGGTCCAGGAAAGTGAGGAAGTCGCTGTAG
AGCAGCCGGCCCTGGTCGTCCGCCGCCAGCACGCGGTCCCCGGGG
CTCAGGTCCTTCACCAGCTTGGTGCCGCCCTGCTCCAGGTGACCG
TGGCCGAGCCCGGGAAGCAGCCTCCCGATTTGGCCGCCACCGAGT
TCTCTGCGGGTGAGGAGAAGGGAAAGAAGAGAGGACAGGGCATTG
AGTTCCGAGAGGGAGGCGCGTCTCGGGGAGGAGGGCGCACGCTGG
TGCCCGCGCTCCTAGGCCAGGGGTGCGCAAGGCGCGGGGCGGGGC
GATTGATTCCAGGCGGGTCCCGCACACACCTCCCTCCCCCAACCC
CACTGCCCCAGGGACAGGATTCCGACACATTCCTTAACGACTCCT
AAGTCTGGGCTGGCGGTCACAGAGGTTGGCTGGCGTTTCCTGCAG
AGGCCGGTGACACTCTTTCCTTCCGCCTTCCTCCAACCCCACCCC
CAGCTCCGCACACACCCGGCCTCGCCGCGAATCCATCCAGAGGGG
TTTGCTCTGCACTTGGATTCCTCAGGAAGCCTCCTTGAGCTCCCG
CGGGCGCCGGGCGCACCCTCCTTCCCTCCCGCCCCGGCGCGGGGC
GCGGCGCCTGCTCGCGCACTCAGCACCCGGGCTGCGCGGCGGAAA
CCCTGGCCCGC
(SEQ ID NO: 102)

390; ALL; chr8:142288380-142288718; 8;
SLC45A4; DOWNSTREAM
CGCACGGCCTCCTCGTCCCTCTCGGGCAAGGCTATCAGCCAGAGC
ACCTCCCCTTTGACACTGACCGGCGTCCCCAGCCCCGCCTTGTTA
CTGCATCCGTCTGAGGTACAAGGTTAGAAGCCACAGAACCCGAGC
TGCAGCCTGACCCACACAAGCTGCGGGCGCAATGGCGCTTTGCAG
ACAAGACAGCCTGCCCGTCTGCCCTTCTTCTCGGCTTCCCTTAAG
ACACAAGGTGACGACACGGACGGTTTCAAGTGAGTGCATCTGGAA
ATAATCTCAGTGCAGGGGAGGGGTTGAGGCCAAAGATGTCGTGAC
CTGGTCCCCGCTGTGGCCAGGC
(SEQ ID NO: 103)

402; ALL; chrX39749470-39754050; X;
chrX039752648-039752692; Unknown
CGAGGTATAAAGACCAACGCACGACGGGCGCCGGGGCGCCGTCAC
CTGCCTGGGTTAACAGTTCCTGCCGCGGGGGCAGGGAGAAAGGCG
CTAGAGGGGCGCGGGGTGCCGGCGGGGCCGAGCCCGGGCGCGGGC
GAGCCCTGGGTGCCAGGCCCTGCGCCGCACGCCACTCTCGCAGCG
CTGCCGCCGGGAAAGTGCCGGCGCTGGCTCTCCCTCCCCTCCCGG
GAATAGCGGGCGCAGGCACGCACATCCACACACATCCAACACACA
CACACACCGCACACTCACACACCCGGGTGGCCGCGCGGGGCTCCG
AGCCGCGCAGGCCTCCTTGGCAGACATCTTCCTGTGGGAGGATTT
CAAACGAGCCGTGAAAGCCAGAAACTACACGGGTTACAACTCCGG
AATCCCTGGCCGGCCTCGGCCTCCCTCCCCACCTCCGGCCCGGCC
CCCTCCGTTCGGCCCGTGGCCAGGAGCCCCACCAAAGGACAAAGC
TCACACGCCGAAAGCGCGGGGAGATCCGGGGGCGCAGAGATGCCC
CGACGGCCCTTCTACCTTCTGACCCTGGGACCCACGGCCAAGTGC
CGCGCAGCCGAGGTCGGCCTTGCTGATCTGTGGTGGCCCAGGGCG
ACCCGAAGCGCACCGGCTTCAGGGTGCGCCCTGGCCAGGGCTGGG
GTGGAGGGTCACATAAGCCACCTGGCATCCGAGGGTGGCCGCCTC
GCCCCCTCAACGCCGCTCTCCAGGGAAGGAGGCGGCGGGGTCACC
AGGGCGCAGCTGACAGCCCCAGGCCCCGGCCAGGGCGCACCCAAA
GAAGAGGGAGGCTGCTGCCTGAACTGGCCTGGGGGCAGAGGGAAG
TGGGCCCCGCGCTGTGGAAGGCCCCAGGCTGGAGCGCCGGGGACA
GCTGTCCAAGCGGCGAGGGCTAGGAGTGGCCTCGCCTAGCGCTAG
CCGGCCAGGCCCTGGAGGTGCTCCGCGCCTTCTCGGCCAAAAGCC
AGCTCCGCGCCGCTGGCGGAGTGGGAGGGAGGCGGCCAGGCGAGC
GCCCCGCCTTCGTCGCCCGCGGTCACAGGGGCAATTACACTCCTG
CTGCAGACGGTTACCAGCTCGCCCGCGCATCCCTCTCTCGGCTCC
CCTCTCCTCCCCTCTCCTCTCCTCCCCTCCCCTCCTCCGCGGAAC
TGCTGGCTCCATATTAGCGAGGGTGCCCTGGCAGCGCGACCGAGG
CAACTACCCCT
(SEQ ID NO: 104)

TABLE 4

CpG islands hypermethylated in NMI-BC FGFR3 wt vs mut. Provided for each are: ID; Comparision; Coordinates of selected regions containing relevant CpG islands based on *Homo sapiens* full genome as provided by UCSC (hg18, Mar. 2006); Chromosome; GeneName; Location relative to gene Sequence.

4; SW vs SM; chr1:2211959-2212429;
1; SKI; INSIDE
TAGGCAGGAGGAGGAGGAGGAAGAGGGCACCTGCTGAGATACTTC
ACTGGTCTGAGGGCCCCTTCTGCCCCAGCTAGCGCTTGGGTGAGG
GTTGGGCTTGCGGAGCCGTCCTGTAAAGCCGGGGATGCAGGACGC
ATTGTCACCCCCTCCTGCCGCTCTTACGAAACACTCTTAATTGAG
TCCGATTCTTGGTGAATCAGCCTTCCAAGAACCGCGACCGCAGCA
TCCTGTGCCGCTTCTGTGTTCCGCATTTTTCTCTTTCTGCAGCGT
TTCCTCTCATTCTGGATGGAAAGCCTGTTTGTCTCCCTCAATCTT
TGGCGAGGGTGGCAGGCAGCCAGGCGGCCATTACGGGCCGCGCCT
CCCACCAGCCAGTCGCTGGCAGGAGCGTCCGGGGAGGGAGCAGAC
CCCGTTCACCCTCACCCCAGAACTGAAGCAGCGAGGGGACCCAGA
CGAGCTGGAATGCAGGCG
(SEQ ID NO: 105)

5; SW vs SM; chr1:2226303-2228929;
1; SKI; INSIDE
CGCGCTCCGCCAGCAAGACCTGGCGTCTGCAAAACACAGGCGTGA
GGGGCGTGCTTACTAATGCCTGGTGTTCCAGAAGGCGGCTCCCGC
CAGGCCTCCCGAGTAGGAAGGAGAGGGCTCGGCCCGCCAGACACA
CACACACCCACCTGCACACGCTGCTTCTCTGGGCTCTGCCTCACG
GTTCTCACGCTGCAGCTCCGGTCTCGCGCCTCCTTTTACGTTGTT TABLE 4-continued

| CpG islands hypermethylated in NMI-BC FGFR3 wt vs mut. Provided for each are: ID; Comparision; Coordinates of selected regions containing relevant CpG islands based on *Homo sapiens* full genome as provided by UCSC (hg18, Mar. 2006); Chromosome; GeneName; Location relative to gene Sequence. |
|---|
| TAGGTTTCTTTCTGACATGACTGAGGGAAGTGCGGTTCACAGGCA<br>GAGCTGCCTGGGGAGAGAGGTGGCAGGCGGCCCGTTGTTCACCGG<br>GCCCCGGCCTCGCTAAATTCACACCTCGGCGGCGTCTGGCAGCTT<br>CCGCGGCGTGGGCTTTAGCACAACACAACCCCGTCGGCCCTCAGA<br>GCTGCAGGGTTGCCGACGTGCCCTCCTGCGCGTGCCAGTCCCTCG<br>CCCCAGCCGTCCCCCGCCACTGTTGTCCTTGATTCTGGTTGGAGG<br>TGTGATTTCCCACATACATATTCATGTGGTGTGTTTGCAGCGTGG<br>GGTGTGAGTCACACGGATATTTTAATGGGGAGAGTGGGGGGGCTT<br>GCGGAGGCGCCGGGCGGATGGACGTGTCCATCTGGCTCGTGGGGA<br>GACCCGGGGCCCTCAGATGGTGCGATGTCTGAGGCTGCCCTCCTC<br>ACATTGATGGGAGCCAGGGCCTACTTGGCTTGCTGCCCCCAAGGG<br>GAACGTGGCCCTAGATACCGGGGGAGGCCCCGCCGCAGCCTCAAG<br>TGACTGACTCAGGCCCCCAGGTTAGCACAGCTGCCACAGGCCTGG<br>CGGAAACTCCGGATGGGGGTCTGAAAAGCCTTTGTGGGGTCGGGG<br>CACCACACGGGTTGGGCTGATGGCGCGCTGGGGGCGGGCTCCAG<br>GGCACATTGTCAGATAGATGACCCCACGGGGTGGGCTGAGGACTG<br>CTGGTCAGGTGAGGGGTGTGCTGGGACCGGCTGGGCAGTGACCCC<br>GAGCCGCCTCCGGCCCCCAGGAGCTGGAGTTCCTACGCGTGGCCA<br>AGAAGGAGAAGCTGCGGGAGGCCACGGAGGCCAAGCGTAACCTGC<br>GGAAGGAGATCGAGCGTCTCCGCGCCGAGAACGAGAAAAGATGAA<br>AGAGGCCAACGAGTCACGGCTGCGCCTGAAGCGGGAGCTGGAGCA<br>GGCGCGGCAGGCCCGGGTGTGCGACAAGGGCTGCGAGGCGGGCCG<br>CCTGCGCGCCAAGTACTCGGCCCAGGTATGCGGGTGGGGAGACTG<br>AGGCACGCAGCACGGTGGGCGTGAGCCGCCGTGGGCCCCGGTGGC<br>CAGTCCTGCCCAGCCGGAA<br>(SEQ ID NO: 106) |
| 19; SW vs SM; chr1:92718496-92725197;<br>1; GFI1; INSIDE<br>CGAGTGCACGGCTTTGTGCTGCTCCAGGCTCACCGCGTGCCCGAA<br>GGTCTTGCCGCACATCTCGCAGGCAAAGGGTCTGGTACCGCTGTG<br>GGACCTGCGCACGTGCACCTCGAGCCCGTGCGGCGTGAGAACACC<br>TAAGGCGGGTGGGGCCAGAGAGAAGGCCGCTGAGAGGGGCCGCGG<br>GGCGCAGGCGAGGCGCGGGTAGGGGAAGCGGGCGCACGGCAGGCG<br>AGGTGGTGAGCTCGGGAGCCTCACCTTGCTGCACTTGATGCACTT<br>GTAGGAGCCGCCGCCCAGCAGCGGCGGGTGCACAGCAGCTCCGAC<br>TCCACCTTGACGCCCAGCGCCCTTGTCTGCGTGCAGCCCGTGGCCA<br>CGCTCGGGGTACAGCAAGCCCGCCGCTGCCGTGGGCCTCTCATAC<br>AGCCCGGCTGCCGCAGACCCGAAGTCGCCGTAGAGCCCTAGGCCA<br>GGGCCAGGGTGGCACCGGCCCCTGCGCTGCAGCTCCCTGGCGCCC<br>CGGCCCCCGCGCCGCCGGCAGCCCGCTTCGGGCCGTACAGCGCGG<br>CCGGGTGGCCAGGCTCCGGGGCGGGTTCGCAGAAGAGGCCCAGGC<br>CAGCGCCACGCTCCAGGGCCCCACACGGTCGGTAGCTTGCACCAG<br>GTGCCGCAGGTCAGAACCCGCCAGGCCGCTCCATGAGTACGGTTT<br>GAAAGGCAGGGGGAAGGGCTGGGCTTCGTCCAGCGATGGGCACAT<br>TGACTTCTCCGAGGCTGTGGAGGCACAAGGGGAGCGTCCGGTCAG<br>GCTTCAGACGGCAGAGCGGAGGCGCCGGGCTGCGGCTGCGAGCGT<br>GGCGTGTTCGCGGACTGCGGGGCACCCAGCGCTTGTAGAACACTG<br>CGTGCGCCAGGTGCCAGGCTCGCCCCAGGGTAAAACGTGGCCCGG<br>GCCCTGGGGCCTCGCAGGCCACTATAGGAGGCAGAACAGTAAACA<br>GATCATTAAAAGACCTCGGGAGAGGAGGTCGTAAATTCTGTGCGA<br>GTGCAGCGGAGGCGCTCGGCGTTCCGAGGATCTTTTCTGGCTGGA<br>CCCGCGCACCTGGAGATCCTACAGGGAAGGGCGCATCTATAAATG<br>CCCGTAGTTGAGCTGTTAAGAAGGAGAAGGTGGCGGCGTTCGGCC<br>CCTCACAGCACTCAAGGGCGGAAGGGTCCAGCCACCAGCGCAGGC<br>ACTCTCCCAGCCCCTACATGTTCCCATTCAATTCTTTTTCTTCCC<br>AGAATCCAAGAGGAAGGAGGGAGAAGGTCCATAAATGCGGCCCCG<br>AACTACCCGAAAGGCTGCTGTCGAATAAACCCGAAGGTATTAAGA<br>TTTCACGAAGTTAAGTGCC<br>(SEQ ID NO: 107) |
| 24; SW vs SM; chr1:163590111-163590435;<br>1; LMX1A; INSIDE<br>CGAGAGGCCCGGCCACCGGCTCGGGAGCTGGGCCGGTCGCTTTGG<br>GAGCGGATGAGGAAGGTTAGGAGAAGCAGCGAGATAGATCCCAAT<br>TTTACAATTCTATTTTCTTTCGGTAGGGTCTCGGCGTCTGGGCCA<br>CGTTGAGAGCGAACGTGGGCCGAGCGGAGGACACAGAGTAAAAAG<br>CGACGCCCGCTGTATACATAAATCCGCACCCGCTGCCCGCCCGGG<br>TACTGCCTGCTCTGGCTTCCGCTCTCTTCCGAGGCTGGGCAAGTC<br>CAAAAGTTCCCGAAAGGGGGGTCAAAGAGGGGCGCTCAGTGCACG<br>TGATTTCG<br>(SEQ ID NO: 108) |

TABLE 4-continued

CpG islands hypermethylated in NMI-BC FGFR3 wt vs mut. Provided for each are: ID; Comparision; Coordinates of selected regions containing relevant CpG islands based on *Homo sapiens* full genome as provided by UCSC (hg18, Mar. 2006); Chromosome; GeneName; Location relative to gene Sequence.

| |
|---|
| 29; SW vs SM; chr1:219134035-219134808;<br>1; BLX1; DOWNSTREAM<br>TTCTTCCCTCTTTACTCCATTCCCTAACTCCTGCCTCGTAGGCAG<br>CGGTGGGGAGCCGCAGGCTGCTCCCCGAGTCCCAACGCTACTAGG<br>GTGCTGTAACAGTGATGAGGCGGCGTTGCAGTCTGGCAGGCGCTG<br>CAGCGGGCACCAGCTACGTTTTGCTGTCGGCGGCAGTTACCCGGA<br>CGCAAGTTAAGGGGTAGGCGCGCAGAGGCGGTTGGAGGCGGGCGG<br>CCGGCCCCTGACCTCGGAGAGCTGCGCCGAGCAGGGCGGAAAATT<br>TATGGTCTGTGTACACTTTCTGCTCCAGAGCCCCGCGCACCAGAA<br>GGATGGGGCCCTGCGAGCGCGCCCCAGGCCGCGAGCTGGGGCCGC<br>AGGCGCCACGGCCATGTATAGTGCCCACCCGACTCTGTTCTGCAG<br>CGCTGTGGTCATAAACCTTCCCTTAGAGGGCGCGGCTGTAAACGA<br>AAGTCCGGCGAGAGGTGGATGCAGGCCTTGCCGCCCGGACCCTCA<br>GGTATAATTCTGGAAACTTGCACGGAAGCCTGGGTCCCGCCATCT<br>TCCCTGTTGTGGTGGGGTAAGAGGATAGTTTATACTGGCTGTTTG<br>GAATCCCGCGCGGTGGATGCAAGGTGGGATTCCAGCCAGCGACGC<br>GCCGCGTGGCCGGGAGTGCAGACAGGTCACCGGTCCCCGGGTGTC<br>TGGACCGCGCCGCTTCCTACTGGGCTTACTTCGGGATCTAGACTT<br>CGGCCTCCGTCCTTGCAAGGGCCCAGATTTGATTCCGGTTCGTCG<br>AGGCG<br>(SEQ ID NO: 109) |
| 35; SW vs SM; chr10:845627-845967;<br>10; LARP5; INSIDE<br>CGAAACCCTCGAGGAGCGACCACATGACCCCCGCGCTGTGAGCTG<br>CTGGCGGCCAGCGCCCTCGCCTCGATTGTCTGCAGCCCTGTAGTG<br>GGCCGCGAGGCACGCAAGCCGCAACTACAGCTCGCCACGGGGCAC<br>ACAGACAGGCATGCACCACCACTACCCGTCGCCCGGATACACTGA<br>ACTGGTTTTGAAGCCTGAACTGCAGAGATCCTAATATAGCAACGC<br>AGGACGTTTACGGCCACCCGCCAGTGACAGCCGGTGATGTGATGA<br>CAGGAGGGCCTGGGTGAAAATGCAAGACACTCACTCTCAGAGAAC<br>GACGACTCCACTTGAAATTCATGT<br>(SEQ ID NO: 110) |
| 38; SW vs SM; chr10:3150889-3151107;<br>10; PFKP; INSIDE<br>CGGCCGGGTGGGGACCGGCGTGGCGTCCTGCGGACCGCGTGGAGT<br>TTGGGGTGTCTGACATCGTTCTCCACGTGGCTATTTTCAGCGTTC<br>TCCCGGGGAAGTACTTGGAAGAGATCGCCACACAGATCGCACGCA<br>CAGCATCAACGCGCTGCTGATCATCGGTGGATTCGAGGTACGTTA<br>CCGTTTCTCTCTTGCCGGTCTTGCAGGTGTGAGCCGCG<br>(SEQ ID NO: 111) |
| 42; SW vs SM; chr10:7489383-7495345;<br>10; SFMBT2; INSIDE<br>CGGCAACCGAGCCAGATCCAAGAGGGGTCGGCCTCGTCTAAATTG<br>GTTTCCCACCAATGGCCTCGGATCAGCCGCGGCTGTGCTGCGGGA<br>GCCCTCAGGACGCGGCTGGGGTTGGTGCGCGGGGCCCGGAACCCC<br>AAACCCGGCTCGGTTCGGCAAGGTTCAGGGAGACAAGGTAGAGAA<br>GGCTGGGGTGAGCGAGAAGTCGGGCGGCCGATCGTCAGGGCCACG<br>AGCCTCGCCTTGCCTTCTTGGAATCCCACCCAACTTTAAAGGCCC<br>AAAGATCCTGAAAATTCCGAAACGAAACTGCGAGCTGGTCTCCAG<br>AAGTTTGAGAACGGTCTCCCAGGCTTTCCAGCGTCGTCCCGGGAT<br>TCTCGGACACCACAAACGCCATCAACCACGAGCACCGGTGTCCGT<br>GGCTATTGCCCCGAATGGTCCCCATCCGCGTCCCCGGGAACTCCC<br>TCGGCTTTCGCGCATCCAGGTCCCCAGCCCCAGCTACTGGTGCGC<br>CCCGAGCCCCTAGGTGCCAGAGCGGTGGTCGGCCGGGCTCCTGCC<br>CAGTCTCGGCTCCTCCCTCCTCCCCACCAGAAGGAAAAACTTGGG<br>CCCTTCGAGAACCCTGTGGAATGTTCTTTGTAATCAATGTACATC<br>CGCTTCCACGGCACGGCCTCGTGCAAAATCGCGGGTTTCGGGGCC<br>TTGGAGCAAATTGCGCTTGTCAGCGGCGACGTCAGGAGGACAAGG<br>GGAGGGGTTCGCGGCTGAAACTGCAGCTTCGCAGCACAGAGCCAT<br>TTTAGGCTGCTCCCCACCTCGCGGGCCCATGGGAAAGCCGGCCCC<br>GGGAGGGCGCGCCCAAACGCAGGCTGGAGGAGCCACGGACGCGTC<br>CTGGCCGGCGTGTCGCCATCGTTCAGCCTCGCTGCCCAGGTGGGA<br>GGGGTCACCTGCCGCGGGGTCTCCAAGCCAGTGCCGCTTGCTCCC<br>GGCCCCCCCCACTGACAGCACGGCGTCCGAGTGACCCTGTCTAGC<br>CTCGTTCTGCGCTCCTGCAAACCACGTTGCTGCGCTAACTACAAA<br>CCTGGCCAACATGTCTTTGTAACCCTATCATTTAAAAACGCTTCC<br>AGGCACCTGGCCGCTGCCAGATCAGGTTCGCGGGCCCGAGGAGGT<br>CCTCCCACCTGCCCCCGCCAGCCCCGGGGACCGTGCGCGGCCTCC |

TABLE 4-continued

CpG islands hypermethylated in NMI-BC FGFR3 wt vs mut. Provided for each are: ID; Comparision; Coordinates of selected regions containing relevant CpG islands based on *Homo sapiens* full genome as provided by UCSC (hg18, Mar. 2006); Chromosome; GeneName; Location relative to gene Sequence.

GTGTGGCCCCCGCCCACGAGGTCCCTCGGGCAGGAACCGCCGCGC
GACCTCTGTTCAGCGGCCGCGTCCTGGCCACGGGCGACCCCTGTC
GGGAACCCTGTTCCCGGCTAAGTGCGTTCCCGCATTCCGGTGGCT
CTCACCCGAGCTCGCGTTT
(SEQ ID NO: 112)

44; SW vs SM; chr10:013553837-13554175;
10; C10orf30; INSIDE
TACAGTTGATACCCACCATCCCCATCATCGCTATTAGAATTGGGG
TCAATACCCATCATCACTGTTAGACTTGAGGCCGATACCCGTCAT
CACTGTTAGACTCGGGGTCGATATCATCATCACTGTTGACTCGGG
GTCAATACCCTTCATCACTGTTAGACTCGGGGTCGATACCCGTCA
CCACTGTTAGACTCGGGGTCGATACCCGTCATCACTGTTAGACTC
GGGGTCGATACCCGTCATCACTGTTAGACTCGGGGTCGATACCCG
TCATCACTGTTAGACTTGGGGTGATACCCATCATCGCTCTTAGAC
TCGGGGTTGATACTC
GTCATCG
(SEQ ID NO: 113)

45; SW vs SM; chr10:13556159-13556753;
10; C10orf30; INSIDE
CAACATCTGTCATCGCTGTTAGATTTCGGGTCAATATCCATCATC
GCTGTTAGACTCGGGGCCGACATCCGTCATCGCTGTTAGACTCGG
GGTCGACACCCATCATCGCCGTTGGACTCGGGGCTGAACCCGTCA
TCGCTGTTAGATGCGGGGTCGATATCCATCATCGCTGTTAAATTT
GGGGTCGATATCCGTCATGACTGTTAGATTTGGGGTCGATATTCC
TCATGACTGTTAGACTCGGGGCTGATATCTGTCATGACTGTTAGA
CTCGGGGCCGATATCTGTCATCCTGTTAGACTCGGGTCAATACCC
GTCATCACTGTTACACTCGGGGCCGATACCCGTCACCGCTGTTGG
ACTCGGGTCGATACCCGTCACCGCTGTTGGACTCGGGTTGATACC
CGTCACCGCTGTTGGACTCGGGTCGATACCCGTCACCGCTGTTGG
ACTCGGGCGATACCCGTCATCGCTGTTGGACTCGGGTCGATACCC
GTCATCGCTGTTGGACTCCGGTCGATATCCGTCATCAGTGTTGGG
CTCAGGTCGATACCCGTCATCAGTGTTGGACTCGGGTCGATACCC
ATCATCG
(SEQ 1D NO: 114)

47; SW vs SM; chr10:15294510-15295293;
10; C10orf38; INSIDE
CGACAGCTTCACAGTAGGATTATTGTGATAAAAATGACTCAAGCG
ATGCAAAAAGTTTCATCTGTTCCCAGAATCCGAGGGAGAACTGAG
GTGATCGTTAGAGCATAGCGACATCACGTGCGGTTTCTAATGTCC
CTGGTGGCGGATACGCCGAGTCCTCGGAAGGACATCTGGACACCA
CTTTCAGCCACCTCCTTGCAGGGGCGACATCCGCCAAAGTCATCC
TTTATTCCGAGTAATAACTTTAATTCCTTTCTAACATTTACACGG
CAAACAGGAATGCAGTAAACGTCACGTCCGTCCCACGGCTGGGCT
GCCGTTCCGTTTCCTCCACGAACGGGTACGCGCTTCCATGAGAAA
GGATATTTGGCAATTTTATATTCCACAGTCAGGTGGGTCTGCGAT
AGCTCATTTAATGTTAAACGCCATCAGGGGCCTCTCCTCCCGTTT
CTGCCAGGGCTTTTCTTGTCTTCTCCTTGGTCATCATCATCATCG
TCTTCCTCTTCCTCGTGGGCAGATCTTCTCTGGTGGGGGCTGGCT
GCTGGCTCCGAGGGGGCATCCGCAGTCCGTCTGGTCGTCTCCTCC
TGCAGGCTGGGCAGCTGGCCACCACTTCTCCGACTCGCCCCTCCA
ACAAGCATCGCAGGGCACTGTCCTCGGGGGTACAGACCGTGGTCC
CACATTCGCTACCACTCTGTTCCACGTCATCCAGGTACACGAGCT
GCGTGTAGGCCGTGCTGTCTGGGGCTCGAGGCTCTTTCTGCTGGT
GCTCTTGGACGGGCG
(SEQ ID NO: 115)

64; SW vs SM; chr10:88112905-88117344 10;
GRIDL INSIDE
CGTGAACGCCCTCGCCTCGCACCTGTGGCGCCTGCCGCGGGGCCC
GACCGGAGGCAGTGGCTGTGGACAAGGGCGGCCCCGGCGTAGGCC
AGGATTTCCCCGCAGCCGGACCGGCCCAGCTCCGCTCTTTCCTGG
GCGAACAGCGCCCACCTCCGGCCCAGGCGGCGGCGCCTCCGCCCG
CGGCGCGGACAGCGAGAGAGAAACCGGCTCCTCCAAACCTGGTGG
AGGAGCGCTGCAGAGAAGCGCCGGGCTGAGGCTCTGGGGGCCGCG
GGGCGCGAAACGCCGCGCCTACAGGTTATGCCCGGGAGAAGGAGA
CAGGTCGGGCTCCAGCCGCTGGGCGCTCCTCACCTCGAAGCGAGG
AAAACACCGGGCCACTGAGATCAGGGGAGGTGCGCCCGATACAGG
TACCCGGCACGCAGACACGCCCACCCCCAAACACCGAGAAACAAA
GACTGCCCGAGCCACGCACGCCTGCGCGGCCAGCGCTGGGCGCAC TABLE 4-continued CpG islands hypermethylated in NMI-BC FGFR3 wt vs mut. Provided for each are: ID; Comparision; Coordinates of selected regions containing relevant CpG islands based on *Homo sapiens* full genome as provided by UCSC (hg18, Mar. 2006); Chromosome; GeneName; Location relative to gene Sequence.

ACCCGCGCCCACACAGCCCGAAGGGCGCCACGCAACCCGCAAGAA
CACCAGCTCCCCGCGCTCGCAGGCTCTCCGTGCCGGCCCGCAGCG
CAGAGCAGTCCCGGCGCCGCTGCCTAGGTGGGCCGGGAAGGCGCG
CCACCGCGCATGGCACCGCGGCTGCCGAGGAACAGAGGGTGCCCT
GCGCAGCCCAGCTCGTCCCAACCCCTCCGGTGCCCACTGCTGCGA
CGCCTCGCAGGCCGTGTCCCAGTGGGCCCTGGGCACAGCGGTCAC
TCACCTTCCTGCACAGCCTGGATGGGTTGTTGGCCTCGATGACCT
TGATGGAGTAGGTGATCTTCTCGCTCTGCAGGATGTCATCGTTGA
GGCTCAGGTCGGATACCGCCAACTGGAACACCCTGTCGTCCTTGG
CCGCGTTCTCCTCGAAGATGGCACCTGGAGGAGAGAAGGGATCAA
GACCGGACTGGACAAGAACCCTCTCCCCGCTTCCCTTGGCCCGAG
GGTCAAGGCACTCGCAGACCGATGATTGCCGGGTGGTGGGAAGTC
TGAACTGGGATTTCAGCTTGGCGGGGTAGATTAAGGCTCTCCGAT
CTCCACCTGCACAGGAATATGTTCCCCTCCCCCCACCGCCCTCAG
CGCACACGTGCACACAGTTGACATGAGTTACACATGCACATCCCA
CAGGCTGCCACCAGGTCACACACGTGTCTCACAACCAAGGCACCA
CATGTCCTAGCCATGCTCCACACAAGGGACTAAGCCAAGCTGGGG
TGGCCCCAGGCAGCGCCCAAATCCTTGACATGGTTCCATAAATCC
CATCCCAGGAGCCAGGAAG
(SEQ ID NO: 116)

71; SW vs SM; chr10:102986025-102986636; 10;
LBX1; PROMOTER
CGGGGGGCGCCGGGCGCAGGCCGGGCATGGGGCCTGAGCTTAGGC
CAGGTGGAAAGGTGGAAGGACCTAGTGGGGACAGACGAAGAGACC
GAGGAGCCGCCCGCCCGGCTAAATGGACACAGGAAAGCCTGAGTC
AGGCTTCTCATAATAAATAAACTGCACGTGAATAATTCAGCAGTC
GCGCGGGGGCCGGTTGCATCAGCGCCGCCGCCGCCGCGCGGCGCC
CAATTCCCCGCGGAGGGGAGTAGCCAATTAAGGCACTTGAAAAGG
GAGTCGGGTGGAAGATCCCCCGCCACCAGTATCCTGGATTTACCC
AGGTCGAGTTCAGAGAGCCTCCCCGGTCCCAACCCCCTCGGGCCC
CATGGGTCAGGGGGCCGCCTGCTGGGAAGTGCTACCTCAGCTAAG
CCGCTCAGGTGTCCCGAGACTCCGGGCAAGGGAAGACAGGCGGCG
AGACGGACCAGAATAAGGGATGCGGACGTCTGACCTGTGGAAAAC
CCAGCATCTGCAGTGCCCAGCCGCACAGGGAACGTGGGCGGCGTG
GTTCCAAGCACAGTGAAGACGCCAGGCTCGGATCTGTGCTCAGAG
CCGGGATCCCTCCGGGCTGCTTCG
(SEQ ID NO: 117)

108; SW vs SM; chr14:28317076-28317375;
14; FOXG1B; DOWNSTREAM
CGTAGCGACGACGTGGTCCTTGTAGGACCAAGCATTCTTGGCATT
CTGTCGAGATTGAGATTCCAGAGCATCGGATGAACGGGACTTATA
GCTAAGGCGTACTCACCCACCCCTCCCTTCGTCTTTTACGCACGC
AGCAACTCGTCCTCACGTGCATAGGGGTAGTGGACAGTGTTGACT
TGAATTGCTGTCCCTCGTTCCAAGCCTTTCCTGTGAATGAACCCG
AAAACACTCGACAGGTCGTGAATAATCGTTTTAATGAGTGTGCAA
AGCGTGCGACGGGGTGCACCGACTGTCG
(SEQ ID NO: 118)

126; SW vs SM; chr15:58079172-58079459;
15; FOXB1; PROMOTER
CGCTGGCGGGGGTAGGGGGTGTGGGTGGGTACGGAGTCCTTTCAC
TGCCCGTCGGCAGTTGGCACCAGAGCGGAAAGTGTGTCCCCTCCC
CCGCCTCTCTCCCTTGGGCAGTTTGATTTCCCGCCAGCTCAGTCG
GAGTGGCCTGGAAGAGCGGGCTCAAACTCCAAAGGCAGTCGTGGG
AGAGTCGTAGCGGATACGTTTCCCCTGACATGCGCCGGGTGCTCG
TCTCTGCCCCCCACCCGCCCCCAAAACCCAAACCTGCAAGTCGAT
GTTGTCCGGTGACCCCG
(SEQ ID NO: 119)

127; SW vs SM; chr15:58083339-58085812;
15; FOXB1; PROMOTER
GTGCCTAAAGTTACCTAACGATACAAACCGGATACAACGCAGAGG
AAACAGAATACCCCAGCCAAGCAATTTCCATGTCAAACATCATCC
GCGCGGCTGCTCCATCTGTGAACGTGAGTGGTCGCCTGCTCCCTC
TTCCGCGGCGGCCGCTTCCTCATACCTTCACACGGCGCACACCGG
CCGGCGCGTCCAGCTGCCTGCCCAGTGGCCGAGGCTCTTCCCCCT
CGCCCAGTCTTGAGCTGGAAGTGATTCCTATTGGCCAAGGTGTCC
ATGTAAATAGGTGTGAAAGAAACAGAGCTGGCCGGGCTCTCCCTT
CTCGCTCAGTCCCCTCCCTCTGCAGCCCCCGCTCCCCCTCCTCTT
CCTCCTCCTCCCAAGGCGATTGTCATATGATAGCTAAGAAGTGGC TABLE 4-continued

| CpG islands hypermethylated in NMI-BC FGFR3 wt vs mut. Provided for each are: ID; Comparision; Coordinates of selected regions containing relevant CpG islands based on *Homo sapiens* full genome as provided by UCSC (hg18, Mar. 2006); Chromosome; GeneName; Location relative to gene Sequence. |
|---|
| ACATTAATGAAGCGCCGCTACAGGGGTCTTTTCTGCTCCTGTCAC<br>CGCTTAAACTATCAGATGGTTCGAGGGAGGACATGGAGGCAGCCA<br>CCTAGCTCAGCGGAGACGCGGAGCCCACAGCAGCGCCCTCCGGAG<br>CCCTAACACGTCGCTGCCACCATCCGCGCCGGGACTCCGCAGCCG<br>AGCTCGGCCGCCCGCAGGACGCTCCAGGAGCGTCGCGACCGGGCG<br>GCACGGGACGCTGCGGGGCTGAGCTCAAGAGCCCAGGTTCGCGCC<br>GAGTCCAACCGGACCCGGACGCTGCGCGCGGAGTGCGCGTCGAGT<br>GCGCGCCGAGAGAGAAGCGGCGCGCAGCGGCGTCCTCCCGGATGC<br>GGACGCGCAACTTGAAGCAACTTAAGGTGAGCAGCTCTCTGTTCC<br>GTCCCTGCCCCCTATTCTGGCCCCAGTACCGACTTACTTCCCGGC<br>TATCCTCGCGCCGTTCGCCGGCTTCCCCTCCCGCGCCCACTAAGC<br>CCGCAAAGTTGCTGGCGAAAGAGTCCGGGCGCTGGCTGATCGAGC<br>GCCGCAGCCCCACCCCCGACCCCCGAAGTCTGTTACTCGGTCTGG<br>CTGACCCCGCCGGTGTCTCTGTGCATCCATGCTACCTTTCCCTAT<br>TACCCACCCCCTTCCCAGATCCGAGCAGTCCGCCGGCCCGCGCGG<br>ACCCAGAGCAAGAAGAGGGCGAGGAAGAAGATGCCTCGCCCGGCC<br>GCAACACGTACAGCGACCAGAAGCCGCCCTACTCGTACATCTCGC<br>TGACCGCTATGGCCATCCAGAGCTCTCCCGAGAAGATGCTGCCGC<br>TGAGCGAGATCTACAAGTTCATCATGGACCGCTTCCCCTACTACA<br>GGGAGAACACGCAGCGCTGGCAAACAGTCTGCGCCACAACCTCTC<br>CTTCAACGACTGCTTCATC<br>(SEQ ID NO: 120) |
| 167; SW vs SM; chr17:47590175-47591465;<br>17; CA10; INSIDE<br>CGACGGGAAAACGGGGGGAAGGGGGGAGCCCGACACGGCACACAC<br>ACATACACACTCGCACACACTTCCGAGCGAGTGCACACTCGCACT<br>CCCACCCGACAGCCGGCCAGGGACAGTCACCCCCAAGTCAATATC<br>GCAGTTTGAATTGTTCCGGCAAATCTCCCCTCGGGCTCGACGGAT<br>GTGCGCCCCAGATGTGCTGACACATGTCCGATGCCTCGCTGCCTT<br>GGAGGTCTCCCCGCTCGCGTGTCTCTTCTCTTCGCACCAGCGGCG<br>GAAACCGCACTAGCAGCGGCGGGGCGGCGGCGGCGGCAGCAGCCA<br>CCTGAAGCCACCAACACTGGGCTCTTCCAGCAAAAACGAGACCCC<br>GATTCGTCTGGCGCCCCAAGAAGACATAGACGATAGCCCCCCGCC<br>GGGCTGCGCCGTGCAATTCCGGGCTCCCGGGAGCGCGTAGCTCGC<br>TGGCTAACCCAGGCAGTCCGCGGCAAGTTGCCCTCGAAGTCCGCC<br>CCCCTCACCGGGGCATGGTCGGAGGGTGGCTGCTGCGCTCCGGGG<br>CAGTTCTTCTCCTGCTTCCGGGGGGCGGGGAAGGAGCAGACACAG<br>CAGACACACAGAGAAAGAGAGGCAGGGATTATTGCCCAAACCGCC<br>AGCCGCCGGCAGCCTCCGCCGACCCTCCCTGCTCCCCAGGTCCGC<br>GCGCAGCCTGCAGCCTCTCAGCCGGGTTCCGGCAGTGCGTCCAGG<br>GCGCCGAGGGGAAGGGCTGGGCCCCGGGGACTGGGGCGCGGTGGG<br>GGCACACAGACTCTCCAGGTCGGCGCGCCCTTCCTGCTCCTCTGC<br>TATTTTCCTGAACTCCCCAGAACCCCCAGTTGCCTGGCTTCCATC<br>GCCCGCAACTAGCGCCGCTGTCGAGATTTTCCGCAATACAACTGC<br>AGGGGTCGTTATTTCCTCGCCTACGGATCCCTACGCTTCCCAACT<br>CAGAGAGAGGAGGACAGGTGGGGGCGGGAGGGGGAGGAGGAGAAG<br>GAGGCTTGGCCAGGTGAGCGTCCTCGCCGCCGCCGGGCGTCCCAG<br>CGTCAGCTCCGCAGCCCGGCACCCGGGGGCGGAGGCAGGAGGCCC<br>GGGCGGGGAGGTGAGGCTGAGCGCGGCCATGAGGAGGGGAGGAGG<br>AGGCTGGGTGTCACAGCTTCAGGCCACCTTGGCCGCCGCCTCGGC<br>CCCAGTCCCTGGCAGCCGCCTCCGCACTCCGCCCCGCCCTGGCTG<br>CCTCTGTTACCCTCCAGGATTTTCGAGTTTCTCTTCTTAAAAAGA<br>ACTTCGTGCTGCGGGTTCGGCGG<br>(SEQ ID<br>NO: 121) |
| 174; SW vs SM; chr17:67623575-67623903;<br>17; SOX9; PROMOTER<br>CGTGGGTCCGCCTACCCCAAGCACTTTTTGTGACGTCACAGCTCC<br>GAGGACCATCCGGGGGCTTTACTCTCGCGGAAGCCCAAAAGTTGG<br>GGTTTGACCTCATGACCTTGGCCTTCCCGGGGGGCGGAGGCCCTC<br>GGGACAGGACGCGCTGTCCCCGGAGTCCGGAGCTCAGGCCAGTGG<br>CAGTCGACCCAGCCCCCGAGACTCCCTCACGCCGCTCCAAAACCA<br>AAACGGAGCCCAACACGAAGCTGGGTGAAGCCGTAGCTTGCAGGA<br>GCCAGGGAGATGCGCTCTGCCCGGACTTCCCGGGTCCTGTTGAGA<br>CGGAAAGGATCG<br>(SEQ ID NO: 122) |

TABLE 4-continued

CpG islands hypermethylated in NMI-BC FGFR3 wt vs mut. Provided for each are: ID; Comparision; Coordinates of selected regions containing relevant CpG islands based on *Homo sapiens* full genome as provided by UCSC (hg18, Mar. 2006); Chromosome; GeneName; Location relative to gene Sequence.

| |
|---|
| 175; SW vs SM; chr1767627870-67631593;<br>17; SOX9; INSIDE<br>CGACTCGGCTGACGTTTTTGACCCGGCCAGGAGGCAAAGACCAAA<br>ACGTCAGAGCAGTAGCCCTGTTACTGAGGAGCGTCGGCAGGGTCG<br>CGGGTAGAGGGGGCTGGAGAATGACTTGTCAGAGCTCAGGTCGAT<br>GTGGCGCGGGGCGGCCTCGAGAGCGCCGGGCTCCTGCGTGGCCAC<br>GGCCGCCGCTGCCAACCTTCGCGGGGACTTAGCTTTGCTTTCCAT<br>TGACTCCCTTTGCAAAAGCGCAGCAGAATCCTGACCAGCCGCACC<br>AGCCCCGGCGAACCCGAGCATGTAATCTATTTATATGGATTATTA<br>CGGAGGAACAGCGGGCGTTGAGTCACCAAAACATTTGCTTCAAAA<br>GACTATTTCTAAGCACTTTTGCAGGCAGGCAGGCTCGCTCCAGGC<br>GCGTAAACTCGGCTACGCATTAAGAAGCGGCTGCTTTTCGAATAC<br>TGCAAACCCAGCTAAGTCCCCGGTGCCGCGGAGAGAGCAGTGAAA<br>AGAAATGTCGGAGGTGGGGGTAGATCCTAGTCTAGACACACACAC<br>TTGCGCGCACACACACACACACACACACAAGATTCGCGCGGAGAA<br>GGCACTAAAATTCTGGCATTCCGAGAGTACGACAAACTACACACT<br>TGGAAGTCCCGGGTCCCCCGCCTTCCCCGCAGCACCCCCCGCCCC<br>CCCACCCTACCGTCCGCCCTTTGGCTGCGATCCCCTCCCCTCTCC<br>TCCCCTCCCGCCTCGTCACCCAGCCCAGTGCCACAATCCTCCTCC<br>CTCCCCAAAATCGGGTCCAATCGCTGCCTGCCAACCCTGGGACTG<br>CTGTGCTGTGATTGGCGGGTGGCTCTAAGGTGAGGCGGAGTATTT<br>ATTAAAGAGACCCTGGGCTGGGAGTTGGAGAGCCGAAAGCGGAGC<br>TCGAAACTGACTGGAAACTTCAGTGGCGCGGAGACTCGCCAGTTT<br>CAACCCCGAAACTTTTCTTTGCAGGAGGAGAAGAGAAGGGGTGCA<br>AGCGCCCCCACTTTTGCTCTTTTTCCTCCCCTCCTCCTCCTCTCC<br>AATTCGCCTCCCCCCACTTGGAGCGGGCAGCTGTGAACTGGCCAC<br>CCCGCGCCTTCCTAAGTGCTCGCCGCGGTAGCCGGCCACGCGCCA<br>GCTTCCCCGGGAGCCGCTTGCTCCGCATCCGGGCAGCCGAGGGGA<br>GAGGAGCCCGCGCCTCGAGTCCCCGAGCCGCCGCGGCTTCTCGCC<br>TTTCCCGGCCACCAGCCCCTGCCCCGGGCCCGCGTATGAATCTC<br>CTGGACCCCTTCATGAAGATGACGACGAGCAGGAGAAGGGCCTGT<br>CCGGCGCCCCCAGCCCCAC<br>(SEQ ID NO: 123) |
| 199; SW vs SM; chr1942586101-42586705;<br>19; ZNF569; DOWNSTREAM<br>CGATTGGGGCCTCAGCCTTAGTTCTTCCAGCTGGACCCTGGGATG<br>GTGCGGGGCTGTGGCTCTGGGAAGTATCTTGGCCTGCACGCGGTT<br>TACATCATTGGGAGCACAGGCCTCGCCCTCCGAACTAGAGGCCCA<br>GAGCCCTTCGCGCCGAGCGTTTCCCGCCTTTCCCCTGTCTCAAGT<br>CATTGCCCAGAGGCCACTGCGGGCCGTTCCTGCCTGTCCGTGGAG<br>CTGCGGCCCCCGTGTTCCCAGGGTGAACGAGCACGTGCGAGGCGG<br>TGGTGCTTGTATCCGGGATAACAGGTAGGGCGGCTGCATGCTTCA<br>TAGAGGCCAGCCTGTGCCGACCGGGAGCTGTAGGACGGTCTGTGT<br>CTGGGGCTGCTTATGGGTATTCGCGTGCGTCTGCCGGTGCGCGGT<br>CCGAGCCTACTCACGAGAGCGTGTGTGTGTCTTCTGTCTCGTGTT<br>GCTATGAGTTTGCATCTGTGTGGCTGGAATAGCTTGTTTGTGGGG<br>GCCCGCGCGTGACCTGTGTGTGCGTTACTGTGTGTGTCTCAGGCA<br>GGATAGTGACGGGCCGTGTGACTGTGACGCCATCATCAGGTTGGT<br>GAGATGGCGTGACCGCG<br>(SEQ ID NO: 124) |
| 204; SW vs SM; chr1957082579-57083180;<br>19; ZNF577; INSIDE<br>CAGCAGACCCCTTTTTAAGTACGCATGTGATAAGCAATGAACACG<br>AACTGCCCAGAGCAGTCTCCAACACTGACACGATTCGCTTCCCCA<br>CCACGACGCCCTAGCGCTACTGTGCAACGAAGACCTCCAAGCACT<br>GGTTCCAATGCGGAGACCATGGGCTCCCAGACTCTGGGAACTCCA<br>ACACGACTGCGAAACGAACTCCGAGCGAGGACTCCCCGAGAGCTC<br>CCCGCAACACGGACCTCACGCGCTAGCGAACAACAGAAAGCGCGC<br>TCTCCCTGCCCCTGAACATTCCCAGAAGCCCACGCAGACCAGACC<br>GATGACCTGTCTCCACTGCTGGAGGCGAGTCAGGGACCCGAAGTC<br>TCTAAACACTCGCCTCTACCCGCCGCCCCGCGAACCCCACACACT<br>GCAGACGCGACACTCGCAAGTTTCGGGGATGGCGGCCGGCGAGGG<br>CATACTGCGTCTTTCCGGAGACACGGAATACGGCACCAGCCGTCC<br>CTTTATGATGCAATATGTCTGCGCCCAGGGGACGCTTGCTGGGAG<br>CAGCCATTTTCAACCCTACTGCCGTAGAGCAGGCGGAGTCCCTCT<br>TTTCGCG<br>(SEQ ID NO: 125) |

TABLE 4-continued

| CpG islands hypermethylated in NMI-BC FGFR3 wt vs mut. Provided for each are: ID; Comparision; Coordinates of selected regions containing relevant CpG islands based on *Homo sapiens* full genome as provided by UCSC (hg18, Mar. 2006); Chromosome; GeneName; Location relative to gene Sequence. |
|---|
| 233; SW vs SM; chr2:119329502-119332035; 2; EN1; PROMOTER<br>CGAGGAGGCTGCAGGGACGCGCATGGAAGAGCCGGTGCGTGGGAG<br>GGTTTGCGGGGGGGACATCGCGCCCCCTAGGGGTGACCCCAGTGG<br>GTCCCGTGTGCTCTCCGCGGAGCCGGCGGAGCCTTGTCTCTGCAC<br>CCGGCGCGCAGCGGCCCCTTAAACAGTGGAACCGTGAGGCCGCTC<br>TAAGCCGAAGGGCTGGAATCTGGGTTTCTCGGGTTTTATTTTAGA<br>CCATTCGGCACCAAGCCCGAGCTCCCCCGCCGCACCGCTTCCAGT<br>CCCCTTTCTTTCCATAGAGCGACCGAAGCCGGCGGTGGCGCAGGG<br>AGCCGAGTCTGATGAGCTCGCGGGCGGCTGAAGGCCGGCTTCCCT<br>GTGGGGAACGCGCCACCTGTCGGCGCCAGTGAGAACTGCGTCTGT<br>GTGGCGCCCTCGGGGTATTCGGGGCTGCGGGGAGATGTGTGCCTG<br>AAGCCCTCGCTTGCGGTGGGGACGTCCGGCCTCTTTCCTGGCAAT<br>TGACCCCTGAGGCGGGAGAGACAACGGAATTCCCACAAAGGGATC<br>CTTCTCGGGATCTCCCCACCTCAAGACAGCTAAAGCTGGAGGAAA<br>AGCCCCTCCGGGGGGTGGGGGGTGCGGGTTTGCCCTGGATTCCGA<br>AAGCAGAAAATACCCGAGCCACACAGGGACGGCGCCGCGTTGGT<br>AGTCGGGGCTACGTTCCTACTCCCTCTACCTCCCCCGCGCTGTGT<br>GACCCTGGGCGGAACCCCGCTGCTCTCTGGGCCTCAGTGTTCTTA<br>TTCGTAAACTGAGGGCGTTGGAGAGATTGGTCCTCTCCCAACTCT<br>GACCTTGAAACTGATACTGAATCTGAGCAGCGTCTGTAGACACCT<br>GTGCCTTGCCTTCTATTTCTAGCCTTGAATAAATCCTGGACTTTT<br>ATGTGCCATTTATATCCTAATCTCATATATATTTAATGTATAACT<br>GCTGCCATATTGTTTTCTCAATTGTCTAGGTTTTCATTTGGATGG<br>GGTTAGGATGGTCCAAATTATCCCGATAAGTGCCCATTAACTTAA<br>ACCTTTTTAAAAAATGAAACCAGTAAAACTTCATTCACTTTGCAG<br>TGTGGACACTGCTGGAGAGCACCCATGTCGTGGGTCCGCGAGGAC<br>ACAAGGAGGGGCTTAGAGACATGCGGGAGGCTTAGATGAGAAGAC<br>AGCACCCGGGCAGCGGTCAGTGTTAGAGAGAGGACCCGTAAGAAG<br>GGCCGAGGCTAGAGGGAGAGCGAAGACTGAGCCAACGACGCACCT<br>GAGCCCTGGGGTGGGGGTGGAGCGTGGCTCCTAACCCAAATCTCC<br>CTGCCAGGCAGTGTCCGAC<br>(SEQ ID NO: 126) |
| 264; SW vs SM; chr20:54633629-54640196; 20; TFAP2C; PROMOTER<br>ACCATGAGCTTCCAGTTCCTACGGGTGAGAAAAGAGGTGTCTGTG<br>TGGAGGGCAGGTGCGACCCCGGGGGCTAGCAGAGAGGAGAGGCTG<br>CGGGAGGACTCGCTGCGAAGGGCGAGGGGTGGCGCTGGTGGGACG<br>GGCGCCTGGGGCCGTGCAGGGTGGCTCCTGGGTGCTGCCCGGGCT<br>GCCTGTCGCCCAGTACTGGCGCAGGAAGACGGGTCCGCGCAGCGT<br>CTGGCAACAGTGGCCTGCTCCACGCCTGGAGGCGACCAAGTTCTG<br>AGTTAAAGGCGCCGGGCTTAGCGGGAAGTGTATGGCGACCCAGAA<br>CACGGAGCGGAGAAGGCCTCAGGGGACACGAGGCTACCGCCTTAG<br>TCCTCGGGCCTGCGCTCCGAGCGGTTAGGGTGCGTACGGATGGGC<br>TCCGGGATGTTAGTGGAGAGGTGACAGGAGTCTACCATCCCACGG<br>CCAAGCGGTGAGGCCTCCGGCGGGCGGGGGTCCCCCCCGGGGCAG<br>GGCAGGGGGAGAGTCAGGCATGTCTCTAACGGGCTCCCTAGTAGA<br>ACCGCTAGGAAAGTGGCCTTCAACCCTAGGCACCTTTGTGGCTTT<br>CAGGTAGTTGGGCGACTAAAAATTCACTTTTGCCTGCGTGAAATG<br>GGACAGGTGGTTGTCAGGTTAGAGACTGTGCCCACGAAGTCTCGT<br>TTGGCGGGCCGGGACTGACGTGGACCCGGGCCCTCCTCGGAAGCT<br>TGGGAACCTGTGAGCCCCTCAGCTCCTCGCCTCACTTTGCCTGTT<br>TGAAAAAAGGAGTTGTTTGAGAGAAGAGTTAAGGCTCAAAAGGTT<br>CTAAACGAAGAGCATGCGGCCTGACGCGGAGCGCAAAGAAGCGAG<br>CAGTGAACTGAATCTGGTGGGACTGAGACCAGAGGCGTCTGTATG<br>CGGCGGCCGCTTCGCGCCCTATTAAAGCAATCTGTTATTTACGAT<br>AATCATTTTGTAATTATTTTGGAGTGGCTGTGACTTGATGTCTGT<br>GGTGCCCCAGGGCATGCCCTTACTGGACATAGATACTTCAGGGTG<br>CCCTTTGACGCCAGTGTCGGTCCAGTGGGTGCCAGTGCCGCGAAG<br>GGAGGGTGGCGGGCGTGAATGCCCCCTCCTCCTGGGTTGCCGCAG<br>GCCCCGGCCTTTCCACCTTGCTTGATCCTGGCGGGTCTGCCACTT<br>ACTGAGGTCCCTACCGGCGCTCACGTTGTCCCGAGAGGCGGGACA<br>AACGTCCGGCGCGTGGCGCGGAGTCTGCGAAAGCGCTCGGGGGCC<br>TCCATCTTCTGCTCGGGAGTCCCTCCCTGGGGCGGGAAGAGGAGT<br>CGCAGATCTGCCCGAATCT<br>(SEQ ID NO: 127) |

TABLE 4-continued

| CpG islands hypermethylated in NMI-BC FGFR3 wt vs mut. Provided for each are: ID; Comparision; Coordinates of selected regions containing relevant CpG islands based on *Homo sapiens* full genome as provided by UCSC (hg18, Mar. 2006); Chromosome; GeneName; Location relative to gene Sequence. |
|---|
| 280; SW vs SM; chr3:148619483-148620015; 3; ZIC1; DOWNSTREAM<br>GAGTGCGTAAAGGGAAATTTTTGCATTGGTGGATTTATTGAAAGC<br>ATGGAAACAGTCTTCGGGGGTAGGTGTAGGGGGTGCAACAGCGAG<br>ACTTCCCCACAACACCTCCACCGAAGGCTGGGTCGTCGCGTTTGA<br>GGGACCCTCCCGCCACCCCGCAGCCTGGCGGGGCGCTTTCCAAAT<br>CGTCGCGGCAGGCTCTGGCCGGGCAGGGCGAGATGTGCGCATGCG<br>CGGCCTGTGGCCCGAGGTTCCACGTGCTGATGAATATGCATGAGA<br>CTCCCCCGCCCTCGCGGGCTAGGAGAGAACCAAGCAGAGGCTCCG<br>GCCTGTGAAAGTCGCTGGCTAGGCTCCCAAAATAGTGCGGCGGGG<br>TAGCTGCACGTGTTTGTTTTCAAACCGCGCTGGTTTAAGTGAGTT<br>CACACTGCGGAGCCGACAGCAGAGGGTAGAGCAACCTGGGGCTGC<br>TGCCATTGAACGGCGAGTTGAGCGGGCCTGTCAGGGCCTCTCCGC<br>CGAGGGCCGGGGGCTGCATGGTGCTCGAGCCCCAG<br>(SEQ ID NO: 128) |
| 289; SW vs SM; chr4:134288613-134289892; 4; PCDH10; PROMOTER<br>CGCGTTGCCCCTGCGCCTCCGGAAGGGGCACTCACAGCTGGTCAA<br>GCGCGTCCTTCGGAACTCGGGGAGGCTCCGTTGGGGCTTACACAG<br>AGCTAAGCCCTGGGCCAGGGAGGATGGATGCAAGTACGTGCATGT<br>GCAAACGTGTTCGCAGATACCCGCAGCGGTGCACACTCGGGCCCC<br>TCGTGTGCACGGGCCCTGCCCACCACCCCGCCCGCGTTCGCCGCC<br>GCCCCACTGTCCTCATCCCGCGGGCTGACCCCAGGATTGGCAGAA<br>ATCAGTGGTCTAATCTAGCATGTGGGTAAGGGATCGATCTCCAAT<br>TGCCAATAGAJAATAGCCGGTGTTCCCAGCCGCTGCGTGGCACTT<br>GGCCGCACAAGGCGCAGGGATATCAGAGGCGCTTTGCAGCGCTTG<br>GCGGTGCTGTGTGCCGGATGCCCCAGAGCCCGGCGTTAGGATGCG<br>GGCTTGTAGGAAGCGGCTCAAATCAACTCCTCAGTCACTGATGAA<br>CGCGCTCACGGCTGAAGCTAGGTCCTCGAGTGAGTTAATCTACT<br>TGGTAAGTATTTTGTGAATATGTATTTTGGGAGGAAAGAAGCACG<br>TCGAACGCGTCTGCCCGTCTGTAAGCGCGTCATCCCCACATCCTT<br>TAGCGTGAATTCCTCCGCTTTTTAGGAGTCACCTCCACCCCCTAC<br>TCCGTATGCTTCGCGCCTTTCCTCACGGCCCCGTCAGACCCCCTC<br>ACCTTTAGATTGACACATGCCATATAATACTCACTTTTAAAATGC<br>CCTGCCAGTCTCTCTAGGGTCCCTTAATTAGGTAACCCTTGCCAA<br>TTAGTGGGCCCTGCGCTACTTTTTCCCTTCTCGATGATTTATTTC<br>CATGATGCGTATTAGGGAAAATACCTTAAAGGAAAAAGAATGTTA<br>GCATCATTGGAAATCCCGCTCCTAGGAGAGGATATCGCAGCTGTG<br>CTATTATGTTTTCGCATTTGCTGATGCAAACAGGGGAACCTCTCT<br>ATTCCCTCCCCATTACCTGCGGCTGGGGACTGGGAACTTTCCGCG<br>GCATTGTCCCCAGCCAGCGCCTCGGACCTGCGGGGCTGTTCTCG<br>CTCTCACACTCACACTCACCCCGGCCGCCGGGCGAGAGTTCTGTC<br>CCGCCCCGCCCGGCTGCCGCGTGACGTGTCTGTTTGGCGGCCAGT<br>TTGGCCAATCATCGGCAGCTCGGTGGGTGGTGCTCCTGGGCGATT<br>GGTTGGCAGAATGAGGGCGCTGCGCAAAAACGGAGAAGCCGAGCG<br>CTCG<br>(SEQ ID NO: 129) |
| 290; SW vs SM; chr4:134291113-134293078; 4; PCDH10; INSIDE<br>CGGAGCCAGACCTGACGGTGGAAATCTCTGAGAGCGCCACGCCAG<br>GCACTCGCTTCCCCTTGGAGGAGCGCATTCGACCCAGACGTGGGCA<br>CCAACTCCTTGCGCGACTACGAGATCACCCCCAACAGTACTTCTC<br>CCTGGACGTGCAGACCCAGGGGGATGGCAACCGATTCGCTGAGCT<br>GGTGCTGGAGAAGCCACTGGACCGAGAGCAGCAAGCGGTGCACCG<br>CTACGTGCTGACCGCGGTGGACGGAGGAGGTGGGGGAGGAGTAGG<br>AGAAGGAGGGGGAGGTGGCGGGGAGCAGGCCTGCCCCCCCAGCAG<br>CAGCGCACCGGCACGGCCCTACTCACCATCCGAGTGCTGGACTCC<br>AATGACAATGTGCCCGCTTTCGACCAACCCGTCTACACTGTGTCC<br>CTACCAGAGAACTCTCCCCCAGGCACTCTCGTGATCCAGCTCAAC<br>GCCACCGCCCGGACGAGGGCCAGAACGGTGAGGTCGTGTACTCCT<br>TCAGCAGCCACATTTCGCCCCGGGCGCGGGAGCTTTTCGGACTCT<br>CGCCGCGCACTGGCAGACTGGAGGTAAGCGGCGAGTTGGACTATG<br>AAGAGAGCCCAGTGTACCAAGTGTACGTGCAAGCCAAGACCTGGG<br>CCCCAACGCCGTGCCTGCGCACTGCAAGGTGCTAGTGCGAGTACT<br>GGATGCTAATGACAACGCGCCAGAGATCAGCTTCAGCACCGTGAA<br>GGAAGCGGTGAGTGAGGGCGCGGCGCCCGGCACTGTGGTGGCCCT<br>TTTCAGCGTGACTGACCGCGACCAGAGGAGAATGGGCAGGTGCAG<br>TGCGAGCTACTGGGAGACGTGCCTTTCCGCCTCAAGTCTTCCTTT<br>AAGAATTACTACACCATCGTTACCGAAGCCCCCCTGGACCGAGAG |

TABLE 4-continued

CpG islands hypermethylated in NMI-BC FGFR3 wt vs mut. Provided for each are: ID; Comparision; Coordinates of selected regions containing relevant CpG islands based on *Homo sapiens* full genome as provided by UCSC (hg18, Mar. 2006); Chromosome; GeneName; Location relative to gene Sequence.

GCGGGGGACTCCTACACCCTGACTGTAGTGGCTCGGGACCGGGGC
GAGCCTGGCTCTCCACCAGTAAGTCGATCCAGGTACAAGTGTCGG
ATGTGAACGACAACGCGCCGCGTTTCAGCCAGCCGGTCTACGACG
TGTATGTGACTGAAAACAACGTGCCTGGCGCCTACATCTACGCGG
TGAGCGCCACCGACCGGGATGAGGGCGCCAACGCCCACTTGCCTA
CTCTATCCTCGAGTGCCAGATCCAGGGCATGAGCGTCTTCACCTA
CGTTTCTATCAACTCTGAGAACGGCTACTTGTACGCCCTGCGCTC
CTTCGACTATGAGCAGCTGAAGGACTTCAGTTTTCAGGTGGAAGC
CCGGGACGCTGGCAGCCCCCAGCGCTGGCTGGTAACGCCACTGTC
AACATCCTCATAGTGGATC
(SEQ ID NO: 130)

309; SW vs SM; chr5:133887842-133891327; 5; PHF15; PROMOTER
CGAGAGAAGGTGAGCTCGGCGGGCGCAGCGGGTTGGGTGGGTGTG
GCCCGCGGCTCCGGGAACAGACCCAAGGCCCCGCCACCGCCGGCT
AGCAGCCCGACAGCCCGCCCGCCTGGCGAGCGCAGGCCTTCTTCC
AGAAACTGCGAGGATCCGAGCGTACTGTTTGTGCACCACAAGGTC
AAGTCGGGAAGTGGAGCCGGAGGAGGAGGGGCGAGGAGGCGAAGG
GTGGGGAGAGGGGCGCCCCGCTTCCTCGCCATGTGCCAGCCTTTG
GAAGTTACCCCTCGGTTTTTAACTTTCGGGGTAATGGGAAGGAAG
AGCAAGGAGGAAGGGGTCGCCCCGGGGCAAAATCCTGCTGGGGCC
AGGATGTGCAACCACCCACCCACCCGCTCATCACTGCCTTCTCCA
CCCCCCGGAAATGCGGGGCAGCGCTAGGCGCCAGGAGGCACCCGG
GAGGGGGAGGGGGCGACGAGCCCAATGGGGACCCTCTCTACGGAC
CGCCCCTCTTTTCTTGAGGTCGCCTACAATTTCAAGTTCCCCCGC
CCGGAATGTTAGTTTTCCATTTGGAGTGGGTGCGGGGAGGAGGGC
CGCGCCCCCTCCCCAAGACTCGCGTTCGCCCCTCCACCCCCTCCT
GCCAGCACTTTCTGCTCACTTCTGGTGCTGCAAAACGCCACGCAA
TTTATTCGATTCGCATTTTAAAACCAGCGATTCAGAAGCAGGGCC
TAGGGCGAGGGTCTTCCAGCGCTGGAGCCCCGGGGGGCGGGGTGC
TCAGTGCAAACCTCGTTCCCTCGCGAGTGTCGCCTCCAGGCTGTT
ATTTGCAAAGAAACGTCTTTTTGACGCAGGGAGAAATGGCAAATT
TTAAGTACGTCATTAATATGGCGCCAAAAGATTTTTTTAAGTATA
AGCTCGCTTTTTTTTTTTTTTTAAGGTTGCGGGGGGCGCCGCCCGG
GTCTGGGCGCGTAGGGGGCGGGGTGTGAGCAGAAAGTGTGAGTGA
AAGAGTGGAGGGGCGGGGTATGTGTGTGAGTGTGTGAAGTGTGAG
CAGACCTGATGGGACTTGCACGGGCGCAGCCGCCGCTCGGGCCCG
GCCCTGGGGACAGGGCGGGCTAGGGGCGCCCCAGAGTCATGGGGA
GTCCGGGCCCAGGGTGCCAGCAGGCGTGGTGGTGGGGCTGCGAGG
GAGGGCACCCTTCCCCCACGGGGCCCGCAACGCTACCTGGACTCC
CCGCCGGAGCCAAACAACTGGGCGGGGGGTTGGGGGGGCGGCGAC
GGGGGTGTCGGGAGCGGAGATCGAGTGAATAAGAAAAAAGTGGCT
ACTCCCCCTCCCTCGCTCC
(SEQ ID NO: 131)

328; SW vs SM; chr6:5080084-5080849; 6; LYRM4; INSIDE
ATCCCTATTCCTTCTCCTTCCTCTCCCTTGGTAACGGCACTCCTA
GGGCTGTGGAGGGTGCGGTTCACTCCTGGGACTGTGGAGGGTGCG
GATCACTCCCGGGACTGTGGAGGGTGCGGATCGCTCCGGGGCTGT
GGAGGGTGCGGATCGCTCCCGGGGCTGTGGAGGGTGCGGATCGCT
CCCGGGGCTGTGGAGGGTGCGGATCGCTCCCGGGACTGTGGAGGG
TGCGGTTCACTCCCGGGACTGTGGAGGGTGCGGATCGCTCCCGGG
ACTGTGGAGGGTGCGGATCGCTCCGGGGCTGTGGAGGGTGCGGTT
CTCTCCCGGGGCTGTGGAGGGTGCGGTTCACTCCCGGGGCTGTGG
AGGGTGCGGTTCACTCCCGGGGCTGTGGAGGGTGCGGTTCACTCC
CGGGACTGTGGAGGGTGCGGATCGCTCCTGGGGCTGTGGAGGGTG
CGGTTCATCCCGGGACTGTGGAGGGTGCGGATCGCTCCCGGGACT
GTGGAGGGTGCGGATCGCTCCCGGGGCTGTGGAGGGTGCGGTTCT
CTCCCGGGGCTGTGGAGGGTGCGGTTCACTCCCGGGGCTGTGGAG
GGTGCGGTTCACTCCCGGGACTGTGGAGGGTGCGGATGCTCCTGG
GGCTGTGGAGGGTGCGGTTCACTCCCGGGACTGTGGAGGGTGCGG
ATCGCTCCTGGGGCTGTGGAGGGTGCGGATCGCTCCAGGTGTGAT
TTTCATGGGAATGGAACTGGCTCCCTAGGTGGTGTTCATTTC
(SEQ ID NO: 132)

379; SW v SM; chr8:65653638-65653908; 8; BBLHB5; PROMOTER
CGAACGCCGGGGGAGGGACGGTGGGAGGGGTGCGGTG
AGCGAGGGGCTGCCCTGCATGTAAACAGCCTCGGGGTCCCAGACG
AGACAAGTGGGACCGCTCAAGCCTGCAGAACCCCCGGTCTCGGTC
CAGGCACAAGAGCCTCCCGTAGCCCCGCCTGATCTTTCTCAGTCT
TTAGGTTCCAGGACATCCAAAGGAGCGTAGGTAACCGACGTCTAC
GTAGTATTTCTGTCCCCGGAAGACTGGATCTCAGGGAATTATTAT
GGAAGATA
(SEQ ID NO: 133)

386; SW vs SM; chr8:72916429-72917309; 8; MSC; INSIDE
CGGGGCAAGGGCGCGTTCCCTATCGCAGGATCACTTGCTATGGTA
AGCCGCCCACCCTGCGCGCTCCTCCGCGCGGGGAAGAACCTGCGC
GGCAGGACGTGGTGTTGGAGTTGGGGCGCCCGGAGCGGGAGTGGG
GAGACCTGATGCAGAGAGTCTGGAGTCGGAGCTGGGGGTGCTGCA
GGTAGGAGCAGGAGCGGGGCGGAGAGGGAGGCCCGAAGAAGACCC
CACACAGGTTGGCGCAGCGGGGCTTGGGGAGGCTTCAGCCCAGAA
GTGGAGAGGGTTGACAGACGCCGCCTGATTAGAAAAAGCCGGGAG
CTTGGGAAGGAGACGGGATTGAAGAAGCCACCCGGCAGGGAGGCC
GAACGGCCCAGAGCTCTCCGGGTAAAACCCGCCTGCGGTGATCTG
GGAAGTGTGTCTCCACCTAGCCCTGCGAGCAGCGGCCTTCCTCCC
GCCCGTTGAAGGGCGCTGTGCTGGAGTACGAACCCGGCCCAGAGA
AGCCACTCGCCCTTCTTTGTCACTTAAAACCCTGTCCCGACGCGG
ATCTCACGTCTAGACCTCTGTCTTTAAAGCGGATGTAGAGCGCGT
TCTAACCGTTCCCTAACCATTGTGTCACCGCGAAAGGCGGGGCTG
TGTGGAACCGTCCCGCACGTGTGCGATGAATCTGGCTCCGCTGAG
AACGGATCCGTGGGCTGTCTGGCGCGGGCTGGGGCAGCAGCCGAG
AGTTAGTCTACAGAGCTAGGGCCCGAGGGTGGACCTGCGTCCGCG
TCTCGTCACGAAAGGAAGCTCTTTGGAGAGGCAAAACGTGGTCG
CCCAGATCCGGCGCAGCTGTAGCCGTGGGCGCTGTGCAGTGACAG
CCACACCCGCCACCTGTCACG
(SEQ ID NO: 134)

400; SW vs SM; chrX:2845926-2846236; LARSD; INSIDE
TTTCTCATCAGGATACAGTTCCAGCGTCGCACAAACCCGAAGGAG
GAGTACCAAGAGATGAAAAACAGGCAGCCCACGCCGGCCATGCCG
GTGACTGCTCTCGCGGAGACAGAGAAGAAACCGCAGGCTGGCCGG
CAGCCAGGGTGAGAATCCCCAGCGCCAGGAACTGGGTGTAACCCC
AGAGCTGCGCCCTCAGGGCGGCGTCCACTTCGGGGGGCCTGCCTG
GGTCACAGTCGTTTGTGAGCGTGAAGGGCATGCCGTAGAAATAGT
CAAATCCGTGGTTCAGGGGGTGTGGCAGTGATCCCCGCG
(SEQ ID NO: 135)

TABLE 5

CpG islands potentially involved in progression and death of disease. Provided for each are: ID; Comparision; Coordinates of selected regions containing relevant CpG islands based on *Homo sapiens* full genome as provided by UCSC (hg18, March 2006); Chromosome; GeneName; Location relative to gene Sequence.

406; DOD/alive; chr2:115635091-115637285; 2; DPP10; PROMOTER
AAAAAAGAAATGAGTATCAGAGTCTTATCATCATTACAGTTCTTA
TGGTTTTTAACCGACCTTTAGGAGTTCCACCGACGTGACCCAAGC
AGCTGGTAGGAGAATCTGGGCTGGATTCGGAAGGCGCGCTACAGG
ACGCCCGCTGCCCCGGATCGGAAGGCGCAGCACCTCAGGCCACAA
TCTCAGACACGCCCTCGGGTCCCGACAGGTGTTGCCCGCCTCCCA
CGGGGCTCCGGGACCCCGGTCCCCGGGCTGCCCCCTGCCTTCTGG
GGCGCTGGAGCGCGCGCAGTGGCGGAGCTGAGCCACCCAGTGCTT
CGCACGGGCGCGCTCCGCTTCTCCGGGTTTTAGCGGAAGCCTGCG
GGGGGCGGGGTAACCGCGGAAGCCGGCGGCCGTGGGCGCGCGGGT
TGGGGGCTCTCGCGCCGCTCCGGGCTCTCCCCCCCCCCGGCTGCG
GTTGCCGAAGAGAGGCCGGAGGCGGCGCCCGGCTGCTCCACCTGG
CGCGCTGAGCACCGCGCGGGGAGCCCCCGGGGGCGGGCGGTGGGG
GGCGCGGACTGCGGGAAGAAGGCACGAGGCGTCGCCGCAGCTCGG
TCAGGGGCCGGGGCCCCGCCGCTCGCCGCTGCACTAACTTGCCGC
TTGGTCTCGCCTCCCGCCGCGGCTCGCTGCGCTTTGGGTGGCGGG TABLE 5-continued CpG islands potentially involved in progression and death of disease. Provided for each are: ID; Comparision; Coordinates of selected regions containing relevant CpG islands based on *Homo sapiens* full genome as provided by UCSC (hg18, March 2006); Chromosome; GeneName; Location relative to gene Sequence.

GGGCGGGGAGAGCGGGGAGTCAGAGGGTCTGCGGTGGCCGAGGGA
GGGACCCTACGACGGGGAGCCCGCCCGGTGCCGCTCTTCTTCCCC
TCCCCGCCCCTCCGCTCCCCCCACCCCGTCCCTTCCGCCGATTCC
GGGAGGACGGGCGCCCGTGACCTGCGAACGCTGCCAAGTGACGGT
CCCCGAGTCTGAAGCGCCCGCGAGGAAGCGAGCGCCAGCGCGGGC
CGCCGGCGATGACGGCCGCGAAGCAGGAGCCGCAGCCCACCCCGG
GGGCCAGGGCGAGCCAGGCGCAGCCGGCGGACCAGGTGAGAGCGG
CAGCCGCGGCCAGGCCCTCCCGGGAGGGGTGGCTCCAGTGCGCGC
TCCGCCCGCCTCCCGCTTCCCAGGCTGGGCTCCCGCGCCTCCCTC
TTCTCACCCTCCCCCGCCCCGCCCCAGTTCCAGGCTCTCCTGCTT
CTCCACGGACTCTGCGGGAAGTTAGAGCCTCTGCTGCGCTCCGGG
GCCCGGCGAGAGGATGCGCAAGGTGGAGAGCCGCGGGGA
(SEQ ID NO: 136)

407; DOD/alive; chr3:62330280-62330608;
3; FEZF2; INSIDE
AAAATTGGTGCATTTAGGAAGGAAATGCTATAAACGCCTAATTCC
TTCTCGTTCTTTGGGGTTGCTGAGCTGACCTCGCCGCGAGGGGAG
AGGGGGAAAAAAACGCGCACTAATGATTCTGTTTATTAGTTATAT
ATGTATATATTCCGTGTTCGCTTGTACAGGAGGATTTACATGGCT
GTATAAAGATGGCTAGGGGCGCCGCGCTCTTCTGGGGCGCTCACG
GTGACAGGCTGGGGTTAAAACTGGCTGCCCCAGGAGAAGCGGAGG
CCTGGAATTAAATACGTTTCGGCGCACTGATTTAAATAAGTTTCC
TGAATATACAAA
(SEQ ID NO: 137)

408; DOD/alive; chr3:62331767-62332398;
3; FEZF2; INSIDE
AGAGCTTCCCCCTACACCAGGCACAACCCGATTCTAAAGAAATGC
TGCGCCCGCGCCTGCAGATTTCGCCTTCTCTCTCCAGATCCCTCT
TTGCCTTCCTGCCAGCCAGCCGCGACCCGAGTCCTGAGTGAGGTG
AGAAGAGAAGGCCTCGCCTGGCACGTTACCTTTTTGGTGAAAGCC
TTTGCCGCAAAATTCGCAGACGAAGGGCTTGTAGCCCGCGTGGAT
GCGGATATGCGTGTTGAGCGTGGAGCTGCGGTTGAACGCTTTGCC
GCACTGGTTGCATTTATGTGGCTTTTCCTAGGAAAGGGGCGAGTG
CACAGTAAGGAGAGGCCACCTCGGGAACACCTGGAAGGGACATCC
CCCCCACCCCCACTCAACCCTAGAGGGTAAGGGATAATCTTTGGC
CATCGTATCCCCGGTGTTATCACTAAGATTCTGGGGGTTGCGCGC
GGGCTAGGCCCGACCCGGGGGCACGTACCTGGGTGTGGATAATTT
TGTGCCTGCAGAGCGTGCTGGCCTGGCGAAAGCCTTTGCCGCAGA
CTTTGCACACGAACGGTCTGGCTCCGGTGTGGACCGGCATGTGGC
GGGTGAGATTATAGTGAGCGTTAAACACCTATGGAAAGACATGG
(SEQ ID NO: 138)

409; DOD/alive; chr20:22514762-22515148
20; chr20:22514762-22515148; Unknown
ATCTTTTGCTGCTGAAATGCAGATGGTTTGGACACTTCATAAAGA
GGGCATTAATAAGCCCGCCGAGTGAGCGCCAGGGCGGGATTCTCC
CACAAATTCAAGGTCTGTATCTCCGCGGAAGCCGTGCTATCGGTC
CCCCGAGTGCTGAAGGCTCCCACGAGGGGCAGGCCAGCCCGGTGC
GCCAGGGAAGGAGCTTGATGGTGTGTACGGCTACGTAGTGAACGT
GGAGGTGTGCGCAGCGGAGTCAGAGGGGCTAGATCCCCAGCATTT
CCCACGGGGTCCCACCTAGCGCGTGGATGGAGCAACTTCATCACT
CCACCGAGGGCAGGGAAAGAGGAGTAAGCATTGGAGCTCAAAGAA
TGAGCAATTTTTCAAAGCTTTCTCC
(SEQ ID NO: 139)

410; DOD/alive; chr20:22510737-22514165;
20; FOXA2; PROMOTER
CGGGTGGTTGAAGGCGTAGTGGTGTTCCGGCTTCAGGTGGGCCTC
AGGCGGCAGGCCCGGGTGGTGGGGCGGGCCCAGCAGGTGGGCCGC
GGCCTGCTGCTGCTGCCCGGGAGAGGGCGCCGGCTCTGGGGGCTC
AGCGCCGCAGCCGGCGTCCCCTTCAGCTCTCCCAGGCCCCCTCGC
TTGTGCTCCTGGCACGGGGAGGCGCTCGAGTGAGGCGACTCGGTG
CCCGCCGGAGTCTCGGAGGCCGGCCCGGCGGCCTCCCCGAGTTGA
GCCTGTGAGGCCTGGGCTCCGGCGGCCGCTTCTTGCCGCTGCCGG
CGGCGCCTGCGGCCTCCTTCAGCGCCAGCTGCTTCTCGCACTTGA
AGCGCTTCTGGCGGCGCAGGTAGCAGCCGTTCTCGAACATGTTGC
CCGAGTCAGGGTGCAGGGTCCAGAAGGAGCCCTTGCCGGGCTTGT
CGGGCGAGCGGGGCACCTTCAGAAACAGTCGTTGAAGGAGAGCGA
GTGGCGGATGGAGTTCTGCCAGCGCTGCTGGTTCTGCCGGTAGAA
GGGGAAGAGGTCCATGATCCACTGGTAGATCTCGCTCAGCGTCAG
CATCTTGTTGGGGCTCTGCTGGATGGCCATGGTGATGAGCGAGAT
GTACGAGTAGGGCGCTTTGCGTGCGTGTAGCTGCGCCTGTAGGTC
TTGGGGTCGCGGGCGCGGCTCAGGCCCGCCTGCCCGTACATGGGG
CTCATGGAGTTCATGTTGGCGTAGGGGGCCAGGCCGCCCATGGCC
CCGGCCGCCTGCCCCCCGAGCGGGCTCAGGCTGGGACTCAAGTGC
GGCCCATGCCCGCCACGCCGGCCGCCCCGGCCGAGCCGCCCATGC
CCGCCATGGCGCCCGCGCCGGGGGACATCCCCGCCAGGGACGGGC
TCATGCCAGCGCCCACGTACGACGACATGTTCATGGAGCCCGCGC
TCATGTTGCCCGAGCCGCTGCCCATGGCGGCCGCCGACATGCCAT
GTACGTGTTCATGCCGTTCATCCCCAGGCCGGCGTTCATGTTGCT
CACGGAGGAGTAGCCCTGCGGACAGAGCCCCGGGAGGGAGGCGAC
AGCGTTAGCACCGCGGCTGGAGGGTGCCCAGACCTCCCACCCACC
GCCCAGGCCTCCGCGTCCGGGGAGGCCTCCGGGGGCCCTTTCGTC
CCCGATGGCCCAGTCTCCGGACTCCGAGTCTGTTTCATT
(SEQ ID NO: 140)

411; DOD/alive; chr8:57520625-57522095;
8; PENK; PROMOTER
ACAGAGGACTTCTCGGGGTTCCCGAATTCCCAGGGTTAAAACAAA
CTTGGTTTGTGCGGCGACACCGCTACCCTTACCGGTCCCCAGATA
GTCGCGGATCCCCGAAGCTAAGAGCCAGGGCAGGACTCAGTCAGT
GTTCCAGGAACAGCTGAGACACCCAGGTCACCACGGGCTCGCGCC
GCTGCGGCTCCGACCCGGTGCGAACCGCCATACGCGCCGCGCGGT
GGGCCGGAGGCAGTCCGCGTACTGTTGCGGAAACTCTGTCTCACA
AGGTGCGCAACACTCGCCGCGCGCAACACCACCAGGAAGTTGATG
TCGGCCGGGCGCACTAGGCGGTAGCTGCACGTCGCGCAATCCTGG
CTGCATTCGGCCCGCACGGTCGCCAGGAGCCCGGGGCCGAGCAAC
AGCAGCCAAGTGCAAAGTGTCAGGAACCGCGCCATGGACTGCGAG
GAGAGAGGGACGCGTGCTTCGGCCTGCCTGGGCGCAGAACGGGGT
CCCTCGGCAGGACCCTCGCCGCGACAGCCTCAGCAGGGGATCGTC
GAGCAAAAGCCCGCAGGAATGCTCCTTTCTGGGCCCCGCCCTCC
CGGCCGACAGCTTTTAGGTAGACGTGGAGGCGACTCAGATCGCCT
CGCGGTTCCCGGGTGGCGCGGTCGCCCCCAACGCGAGGCTGCCTG
GGGCACCCGGCTCTTTTCCTGGGCGTCCGCGGCCCAGGGCAAGAT
TCCGGAGAGAACGCCGCAGACCAGGGGCGAGAGAGCGGGAGCCGG
GGGAGGCAGGACATTGACTGGGGTCACAAAGAAGAACCAGGGAAC
GCTGTGGGGAACCCATGCAATGAAATGTGAAGGGAAAGAGGGCGG
GCAGACGTCCCCAAACCCGCTCAGCAAAGACAAGCTTCGGGCAAA
TTCACTCACGTTGACGCTGTTCGGATGGAGCAGGCCAATTGGAAA
AGCCGGGTTCAGACACGACTCTAGAGGGAAGAGAAGAAGGCAGTG
TGAGGAGGGCGGGCGTCGGGGAGAAGCGGGCCCGGGTGTGCTGGC
GGACGTAGGGCCTCACCGTCGCGGTCCTCAGCGTCTCTGCGGGGT
CACGGGCCAGGCTGCGGGGCTCTGAGCGCCTGCCTCGCCGTCCCG
GGGCTTAACGGCTGCTGGAGCCACTTTATAATTACCCCAAACCGA
AGGAGGCGCGCGCGCCCCAATCGCCGGCGGGCTGCAGCT
(SEQ ID
NO: 141)

412; DOD/alive; chr17:24303411-24303889;
17; PHF12-SEZ6; DIVERGENT_PROMOTER
GATCTGCTCTTCAAGAGGAAGCCTAAAGTGGAGAGTTTGTAATCC
TGACAACGCCCAGCTACCTGCGTACCCCGGACTCCAACTCCCAGT
TTGCAACGCCAAAGGGTCTAAAGGGCGAACGGGGGCGATTGCATC
CTGGGAGCAAGAATCGCGATAGGTCTGATGGATTGTGGGAACTGT
AGTTCCATGTGCGTGCGATGCACTCTATGGTAGGATAGACCCGGG
GAAGAGTCATTTGCCGGCCAGGAAGGGATACTTTTGAGAGCGTCA
GTGCTGCATGCCGGGATTTGTAGTCTGAGGCCCGCCTCGCATTCT
GGGCGGGGATTCATGCTCCTTTTCAGGGCGCCCGCTCCTCCCCTT
GGTATTGCCGTCAGAGATGGGCGGTTGGTTATTGCTGCCTGATGG
TGGATGAAGCAGTGGAAAAGAGAATTGTATCGTTGTGCTTGACAC
TAGGGGTTTAGTTGGAATTGTGCTTC
(SEQ ID NO: 142)

413; DOD/alive; chr1:149638545-149639227;
1; PSMB4; PROMOTER
TAGGATTACTGCATGTTCAGCTACGACCTCATCAACATGGCTGCT
GGAAGTCGTCTACAGGAAAAAGAAAGAAATGACACTGAAGGATCA
CTTCCGCTTCCGTTGGCGCAAGCGCTTTCATTTTTTCGCTACCGT
GACTAAGATGGAAGCGTTTTTGGGGTCGCGGTCCGGACTTTGGGC
GGGGGGTCCGGCCCCAGGACAGTTTTACCGCATTCCGTCCACTCC TABLE 5-continued CpG islands potentially involved in progression and death of disease. Provided for each are: ID; Comparision; Coordinates of selected regions containing relevant CpG islands based on *Homo sapiens* full genome as provided by UCSC (hg18, March 2006); Chromosome; GeneName; Location relative to gene Sequence.

CGATTCCTTCATGGATCCGGCGTCTGCACTTTACAGAGGTCCAAT
CACGCGGACCCAGTAAGTTCTCGGCGCTTCGTTTGCGTAGCGGGA
GGGACCGTGGGGCCTGGTGCTGCCGGCTGGTTTTGAGAGCCCGGG
AAGGTGAGGCGGGGACCCCGGGGGCGCGCGAACGGCAGGGGAGCT
CAGGGCGCGGAGTCCTGGAGAATGCAGAATAATTGGAAGGAATTA
TAGAAAATCAGAAGCGCAGCTAGTGCGCGGAAAGAGGGCGCAGTC
CATCCCCCCTCTCAGCTCCCACCGTTCTCACTCTTTAGGAACCCC
ATGGTGACCGGGACCTCAGTCCTCGGCGTTAAGTTCGAGGGCGGA
GTGGTGATTGCCGCAGACATGCTGGGATCCTACGGCTCCTTGGCT
CGTTTCCGCAACACTCTCGCATTATGCGAGTCAACAACAGTACCA
TGCT
(SEQ ID NO: 143)

414; DOD/alive; chr21:36990008-36995832;
21; SIM2; PROMOTER
TCCTTAGTGACAAGGTCTCTGATCTCCTGCTGCCACTGCAATAGC
CTCTCCCATCCCGCGGGGAACGGCCGGAGTTCTTCCCTTGATCTC
TCCCGAGTCGGCTTCCGCTGGGGATGGATCGCAGGTAGCGCCGGC
GCGGCCTGGGGAAGAACAGTTGCGGAGCATCTGAAGCGGAAAATC
CAAGCAGATGTGAGGCGATCCGGGCCCGCCTCGTTCCTCTTGGGG
CCTGAATTTCTTCCAGATAAGTTTCCTAATGGAACATTTCTAAGA
GGTGGGGTACGAGGCGGCTTGCTCGCACGGCAGTGGGACAGACTG
CGGGTGGGGACGTACTGAGAGGTCCGGACCTCAATGCGTCCGACC
CGTCTCCACACCGCCCTTTTCCAGCCCCCAGTCTCCTTTCATTCC
CTACTCTTCAGGCTCCTTTGGGGCCAGTGGGTGAACCGCCATTTA
GAACGGTGCCTCGGACTCGGGGTCGTGCGCTCCATCTCTGCCTCC
CCCCTGGGGCCCGCGAGGCTGGTCCGGGCTTTCTGAGCTGGGCGT
TCGGCTTTAGGCCCAATACCTGGACCAGGAATTTCTTCTCCCCGC
GCCAGAAGGGAAAGACATAGGAGGTGTCCCAATCTGCGGTCACCG
CCGATGCTCCTGACACTCTAGTGAGCACCTGCCCGGTACTTTTCC
ATTCCAACAGAGCTTCCAGCTTCATACTAACTATCCCACATACGG
CCTGTGGGTATTAGCTCTAAGTGTCCTTTTCCGAGGGCCCGAGGC
TCCCCCTCCAGCAGGGAGAGCTCCGGGACGGCCCCCACCAAGGGT
TGGGTTCTTCCTTCACAATTCCACAGAGGCATCCCTGTCCTTCCT
ACCTGGGAAACCTCGAGGTGCGGTGCCCGTGTACTTCTGGTACTT
TGCGTGGTGCCATCAGGGACCCCAGAGCCACAGCTGCGTGTGTGT
GTGGATGTGTGTGTGTGTGTGCGCGCGCGCGCGTGTACGGCGAAG
GATGTGCTTGGGGGAGCCGAGTACACAACGTCTGCTTGGGCAGCT
GCTGGGCAGGCGTTGGGCCTGGAGGTATCTCACACCCACGTATCT
TCCAGTCTTCAAACACGGCATTGCTCTGCCTCCCGTAGCGCGCTT
CGAACCTGCCTCGCGGACACGTGAACAGAGGCTGCCCTGGGAAGA
TAAGTGCGCTTTCCCGTAAAATCCGGGAAATTTGCCTTG
(SEQ ID NO: 144)

415; DOD/alive; chr1:232106869-232108183;
1; SLC35F3; PROMOTER
AAGTACTGAACTGGGAGCGGCAGGGTTTGAGTCAAAAGAGAAGGG
TGGAGGAGCGCGTCCGGTGCCCCAAGGCTTCCAGGCGGAGCGCGG
GCGCGAGGTGCGGGCTCCGGGGCGGAGCGCACGCCCGGAGGCGGG
AAGTGGGCAGCAGCGCCCCCGCCTGGCCCCTGTGCGCCCCGACCC
GACGCCTCCCCGCCCGACCAGGTGCCTCGAGAGCGCACAGCTGGG
AGGGCTCTCCCGGTCGCGGCGAGACTCACGCCTGCGGTGTGCTAG
GGCGGCGGCGACGGTGACGGGCGTGGGGCCGGCGCTGCCTCGGCT
GCCGGGTCGTTGCGGCGAGCGCGCGGGCCGGCCTGGAGTCACCGG
GCTGAACCGCCGCGCCTGCATCGTGCCGCACGCCGCGGAGGCGCT
CGGGTACAGACCGCGCGGGCGCGCACAAAGCGGCCCGGGGCGGCC
GGCGCGGCGCAGACCCTCGGTGGCAGCGCACTCCAGTCTTCCCAG
GCTAGCGGCTGCAGGGAGCTCCGGCCCGCGGCCCCTCCGCCTCAA
GTCTGGGAGCTGCCGGTCCCACTCTGTCTTTGCCTATGGGGATTC
GAGAGTTTCCCAGCGGCGCACCCAGGGGCAAGAGCATTGCCGTGT
GAGTAGCGCCCCGGCGTGGGTGAGCGAGCCGGCGGGCGGGAGGCC
GGAGCGCCGGGGTAGCCCTTTGCAGCTGGGACACTGGGCAGTCTG
AGGCTCGGGGAAGGGCGGCGCGCGGTGGAGCTGCTCGGGAAGT
TTCAGTCATTCTTTCCCTCGCCACTCGCCCCAACCCGCACTGCCC
CGAGAGCCCAGGATAGGGCACTGGGGACAGCTGCCCGGGGAAGTG
GGTGAGTGGCGGCGGGAAGGGAGGAGCGCGGGCTCTGCCGCGGCG
CTCGCCCCCGGAGGGCCCCGGCCGCGCTCTTGCTCTCGCCCTGGG
ATCTGCTCCTCACGAATCCCCTCCTCTCTGTCCATGCTCCCCTGC
CCACCCACCTGCCCGTGGCGCCTGCGACCGCAGTGGCATGAGGAG
GTCACCGGACGTCAGCCCCCGGAGACTGTCCGACATCAGCCCCCA
GCTCCGGCAGCTCAAGTACTTGGTGGTGGACGAGGCGATTAAGGA TABLE 5-continued CpG islands potentially involved in progression and death of disease. Provided for each are: ID; Comparision; Coordinates of selected regions containing relevant CpG islands based on *Homo sapiens* full genome as provided by UCSC (hg18, March 2006); Chromosome; GeneName; Location relative to gene Sequence.

GGATCTGAAATGGTCGCGCTCCGTGGAGGATCTCCCAGCGGGCCG
GTGGGGCTCACGTCCATCGAGGAGCGGATCCTGCGCATC
(SEQID NO: 145)

416; DOD/alive; chr6:21704622-21705099;
6; SOX4; INSIDE
TGCATCACCACCTTGGTTTTGTTTTATTTTGCTTCTTGGTCAAGA
AAGGAGGGGAGAACCCAGCGCACCCCTCCCCCCCTTTTTTTAAAC
GCGTGATGAAGACAGAAGGCTCCGGGGTGACGAATTTGCCGATGG
CAGATGTTTTGGGGGAACGCCGGGACTGAGAGACTCCACGCAGGC
GAATTCCCGTTTGGGGCTTTTTTTTCCTCCCTCTTTTCCCCTTGC
CCCCTCTGCAGCCGGAGGAGGAGATGTTGAGGGGAGGAGGCCAGC
CAGTGTGACCGGCGCTAGGAAATGACCCGGAACCCCGTTGGAAGC
GCAGCAGCGGGAGCTAGGGGCGGGGGCGGAGGAGGACACGAACTG
GAAGGGGGTTCACGGTCAAACTGAAATGGATTTGCACGTTGGGGA
GCTGGCGGCGGCGGCTGCTGGGCCTCCGCCTTCTTTTCTACGTGA
AATCAGTGAGGTGAGACTTCCAGAC
(SEQ ID NO: 146)

417; p-np; chr1:160220156-160220709; 1;
OLFML2B; INSIDE
TTGGGGTTGTAGTCTATCTGGGTCGTATAGGAATACTCATTCTCG
AACAGCAGCCTGGGGACGATCTGTGTGTTGGTGTGGGTGTCGAAA
GCGTAGGAGATGTTGGCATTCCGCTGGTTGTAGCTATCACGGCAT
ACAGCACCCCACAGATGACGAAGCAGTTGCCGTAGAAATTCCTCC
GGAGCCCCGTGCGCCATGTGGTCTCCTTCTGTGTGCTCAGGTCCG
CGGCATTGAGCTTGCTCAGGACAATGACCTCCTGGCTGAAGCCCT
CATCGTCCAGGGCCGGGTAGATGAGCCATGGCCATTCTCGTCCAC
AGCAAAGTCCACGTCTGAGTGGCCCTGCCATCGCCAGGGGGTGGC
CTCCTCGTAGGCCACGTCATGCAGCATGGCCCAGGCAGCCACGTA
GCGCTGCTTCAGGTCGTACTTGATGATGTTGCGGGTGAAGGCGCG
ATTGTAGTAGAAGGCGCCATTTATACCACGTGGCCTGTGCCGATC
CAGCTGTACGGGAGCTTGTAGGAATTGCTCCAGCGACCTGCAGGT
GGGGAGAAAAC
(SEQ ID NO: 147)

418; p-np; chr3:129688131-129694023; 3;
GATA2; INSIDE
TCACAGGCCAGCTGGAAGTGGGCAGAAACCCTGTGGGTCCCAGAC
CCTCCCCAATCGGCCGCTGCTCCCACCTCTCCCGCCCCAATTTTT
CAGCAGCTCGATTCCTGCGGATCCTACATCCGGGAAGAAGCAGAC
GGGCCCTCCTCCCCTCCCTCGCCTGGCGCGCGGCGCCTGGGTTCT
CATCACCACGGGCCCAGTGCTCACCGTGCGCGGGGCTGTAGGAGA
CGCGCGCCCGCGCGTGAGCGGGGTTGGCATAGTAGGGGTTGCCCT
GCGAGTCGAGGTGATTGAAGAAGACGTCCCCTCGTCTGGAGGCAG
CAGCTGCGCGGGTTCCATGTAGTTGTGCGCCAGGCCCGGGTGGTG
TGAGTCGGGGTGCTGCGCATTCAGCACGGCCGGGTGCGCCATCCA
GCGCGGCTGCTCGGGCGCCACCTCCATGGCCGGCGGCGGCGGCTC
AGGGTCTGGGTGCAGACGGCACGGCCCTGCGCGAGGAAGGGGGAG
TGAGGCGTGCCGCCAGCGCCTGACACCCCCCAAAGTCCCACCACG
AGGTGTCCCGCACGCCACGGAGCCCCAGCCCAGATCCGGCGAGAA
AGAGCACCAGTCCCGGGTGGAGGAAAGCCCAAGGCTCAAAACGA
AAGGAAGGCGGGGAGGGGGTTCAGCCACGCACACTCACGTGGTGA
CCCGCGGCTCCAGAATCACACACCCGTGCACATGGGGTCACGCCC
GGGGACGGGTCCCGACACCAGTGACCCCAACAAACGCACAGAGCA
GCACTTCAGTCAGACACTCACACTGAGCCCCCCCGCCCGGTAGAC
AAACAATGAACACAGACTCAAAAGTTGGAGACAGGCGCCCGGGCA
CCCAGTGTGGCACTTGATCCCAGCGACACGCACACACCCACACTT
GGCGCCAGATACACATACTGATCTCAACCCCGAAAACATGCACAC
GCAGCCCCCTGAGCGCAGTACTAAGCGGCACAATCAGGACCTTCA
ACAAAGCACACCAAAGCAGTCGCCCGCAGCCTGGCCCCCCGCCCT
AAGTCCCCCCAGAGTCCCCTCAAAGCTAGGAGCGCCCCAGGCCCC
CAGCCGGCTCTCAAACCCCAAACTTACACACGCAGCCGTGGGGAG
GGGAGGGACTCGGCCTCTGAGAGTGAAGGAGTTCGGCGGGAGCCC
CGAGGGCGACGGGCCCAGGGACAGCACGTCCGGAGGCTG
(SEQ ID NO: 148)

419; p-np; chr6:26312699-26313302;
6; HIST1H4E; INSIDE
GTCTGATCTGTGAAGGGTAGGGCCAGCAGGCAGCACCAAAGTTCC
CGTATGCGCGTTTTCAGTCTTCATTTAGGTCCGAATTCCCGGCAT TABLE 5-continued

| CpG islands potentially involved in progression and death of disease. Provided for each are: ID; Comparision; Coordinates of selected regions containing relevant CpG islands based on *Homo sapiens* full genome as provided by UCSC (hg18, March 2006); Chromosome; GeneName; Location relative to gene Sequence. |
|---|
| ATAAGAATACTACCGTCGCTTGTTTTTCAGATTTTTGGGCTATTT TCGTTGGTGTGTTGGTCATGTCTGGTCGCGGCAAAGGCGGAAAGG GACTGGGTAAAGGAGGCGCTAAGCGTCACCGTAAGGTCCTGCGAG ATAACATCCAGGGCATTACCAAGCCTGCCATCCGGCGCCTTGCTC GTCGCGGGGGTGTCAAGCGCATTTCTGGTTCATCTACGAGGAGAC TCGCGGGGTTCTGAAGGTGTTTCTGGAAAACGTGATTCGTGATGC TGTGACTTACACGGAGCACGCCAAACGCAAGACAGTGACAGCGAT GGATGTGGTCTACGCGCTGAAGAGACAGGGACGCACTCTTTACGG CTTCGGCGGCTAATGCTACCGTTAAACGACTCAGCATCTCGACTT CCCAAATCAAAGGCCCTTTTCAGGGCCGCCCACAGTTTTCCGCAA AAGAGCTCATGACTTGTTAGACGATTGGTTGGTCTCTTTATAAGT TAATTGTTCCTGTCAA (SEQ ID NO: 149) |

TABLE 6

| Primers and probes for MEIS1 MS-SnapShot. | | | | | | |
|---|---|---|---|---|---|---|
| BSP Primers (MEIS1) | | | | | | |
| Fwd. 5' GGGTTTTTAGAGGTTAGGGGAA 3' (SEQ ID NO: 150) | | | | | | |
| Rev. 5' CAACTAAATAACCAAACCTCTCCTC 3' (SEQ ID NO: 151) | | | | | | |
| MEIS1 A/B SNAPSHOT Probes | | | | | | |
| Probe | Sequence (5'-> 3') | Size (bp) | Strand | UM | MT | μM* |
| MEIS1 A | T21 GGAGAGGGGGG TTATGATGTTA GG (SEQ ID NO: 152) | 45 | sense | T | **C** | 0.2 |
| MEIS1 B | T14 GTTTGTTTGG TTTTAGAGAA (SEQ ID NO: 153) | 34 | sense | T | **C** | 0.2 |

TABLE 7A

| Differentially labeled CGIs between subgroups relative to blood | | | |
|---|---|---|---|
| CGI | Gene Name | Probe location | Subgroup |
| chr01-2072175-2072389 | PRKCZ | chr01: 002072146-002072190 | NMI-mt vs Ref |
| chr01-2106293-2106715 | PRKCZ | chr01: 002106497-002106541 | MI vs Ref |
| | PRKCZ | chr01: 002106664-002106715 | NMI-wt vs Ref |
| chr01-47672249-47672972 | FOXD2 | chr01: 047671905-047671953 | NMI-wt vs Ref |
| | FOXD2 | chr01: 047672191-047672235 | NMI-mt vs Ref |
| | FOXD2 | chr01: 047682633-047682689 | MI vs Ref |
| chr1: 63554983-63563059 | FOXD3 | chr01: 063559476-063559520 | NMI-mt vs Ref |
| | FOXD3 | chr01: 063559476-063559520 | NMI-wt vs Ref |
| chr01-68288825-68289104 | DIRAS3 | chr01: 068289060-068289104 | NMI-wt vs MI |
| | DIRAS3 | chr01: 068290072-068290116 | NMI-wt vs Ref |
| chr01-71284766-71286392 | PTGER3 | chr01: 071284980-071285024 | NMI-wt vs Ref |
| chr1: 90955098-90955445 | BARHL2 | chr01: 090955137-090955181 | NMI-mt vs Ref |
| chr01-119333484-119333719 | TBX15 | chr01: 119333484-119333528 | NMI-wt vs MI |
| | TBX15 | chr01: 119333569-119333613 | NMI-wt vs Ref |
| chr1: 163590111-163590435 | LMX1A | chr01: 163590167-163590226 | NMI-wt vs Ref |
| chr1: 173258989-173259419 | MRPS14 | chr01: 173259418-173259462 | NMI-mt vs MI |
| chr01-178464743-178471598 | LHX4 | chr01: 178470479-178470532 | NMI-wt vs Ref |
| | LHX4 | chr01: 178470597-178470641 | NMI-wt vs MI |
| | LHX4 | chr01: 178470597-178470641 | NMI-wt vs NMI-mt |

TABLE 7A-continued

| Differentially labeled CGIs between subgroups relative to blood | | | |
|---|---|---|---|
| CGI | Gene Name | Probe location | Subgroup |
| chr1: 196153712-196154414 | LHX9 | chr01: 196154203-196154247 | NMI-wt vs Ref |
| chr1: 219117072-219117487 | HLX1 | chr01: 219117515-219117568 | NMI-mt vs Ref |
| | HLX1 | chr01: 219121301-219121352 | MI vs Ref |
| | HLX1 | chr01: 219134113-219134157 | NMI-wt vs Ref |
| chr1: 241719037-241719368 | SDCCAG8 | chr01: 241719439-241719492 | NMI-wt vs Ref |
| chr02-19424445-19425131 | OSR1 | chr02: 019415391-019415435 | NMI-mt vs Ref |
| | OSR1 | chr02: 019424965-019425009 | NMI-wt vs Ref |
| chr02-45249374-45251726 | SIX3 | chr02: 045013420-045013464 | NMI-wt vs Ref |
| | SIX3 | chr02: 045015982-045016033 | MI vs Ref |
| | SIX3 | chr02: 045015982-045016033 | NMI-mt vs Ref |
| | SIX2 | chr02: 045085251-045085298 | NMI-wt vs Ref |
| chr2: 54536404-54537878 | SPTBN1 | chr02: 054536311-054536361 | NMI-wt vs Ref |
| chr02-63134470-63134933 | OTX1 | chr02: 063134470-063134515 | MI vs Ref |
| | OTX1 | chr02: 063134470-063134515 | NMI-mt vs Ref |
| | OTX1 | chr02: 063134803-063134847 | NMI-wt vs Ref |
| chr02-66525936-66527222 | MEIS1 | chr02: 066525898-066525942 | MI vs Ref |
| | MEIS1 | chr02: 066526023-066526067 | NMI-mt vs Ref |
| | MEIS1 | chr02: 066526791-066526835 | NMI-wt vs Ref |
| chr02-70984709-70985764 | VAX2 | chr02: 070985519-070985563 | MI vs Ref |
| | VAX2 | chr02: 070985519-070985563 | NMI-wt vs Ref |
| chr02-72224630-72228512 | CYP26B1 | chr02: 072227412-072227461 | NMI-wt vs Ref |
| | CYP26B1 | chr02: 072227537-072227583 | NMI-wt vs MI |
| chr2: 73004709-73005568 | EMX1 | chr02: 073004783-073004827 | NMI-wt vs Ref |
| chr2: 85213468-85216104 | TCF7L1 | chr02: 085215511-085215555 | NMI-wt vs Ref |
| | TCF7L1 | chr02: 085216153-085216212 | NMI-mt vs Ref |
| chr02-105864220-105865009 | NCK2 | chr02: 105864372-105864417 | NMI-wt vs Ref |
| | NCK2 | chr02: 105864443-105864487 | NMI-mt vs Ref |
| | NCK2 | chr02: 105864906-105864950 | MI vs Ref |
| chr02-111591678-111597436 | FLJ44006-BCL2L11 | chr02: 111592037-111592081 | NMI-mt vs Ref |
| | FLJ44006-BCL2L11 | chr02: 111593125-111593170 | NMI-wt vs Ref |
| chr02-115635091-115637285 | DPP10 | chr02: 115636612-115636656 | NMI-wt vs Ref |
| chr2: 119329502-119332035 | EN1 | chr02: 119330694-119330738 | NMI-wt vs Ref |
| chr02-156892636-156892878 | NR4A2 | chr02: 156892639-156892683 | MI vs Ref |
| chr02-156893736-156894685 | NR4A2 | chr02: 156894489-156894533 | NMI-mt vs Ref |
| | NR4A2 | chr02: 156894576-156894620 | NMI-wt vs Ref |
| chr02-171384729-171385226 | GAD1 | chr02: 171384729-171384773 | MI vs Ref |
| | GAD1 | chr02: 171385019-171385063 | NMI-mt vs Ref |
| | GAD1 | chr02: 171385019-171385063 | NMI-wt vs Ref |

TABLE 7A-continued

| Differentially labeled CGIs between subgroups relative to blood | | | |
|---|---|---|---|
| CGI | Gene Name | Probe location | Subgroup |
| chr2: 172653235-172653630 | MAP1D | chr02: 172653288-172653332 | NMI-wt vs Ref |
| chr2: 174907710-174910885 | FLJ46347 | chr02: 174910857-174910905 | NMI-wt vs Ref |
| chr2: 176652334-176656692 | EVX2 | chr02: 176655532-176655591 | NMI-mt vs Ref |
| | EVX2 | chr02: 176656139-176656183 | NMI-wt vs Ref |
| | EVX2 | chr02: 176656517-176656563 | MI vs Ref |
| chr2: 176720618-176720921 | hsa-mir-10b | chr02: 176720535-176720594 | NMI-mt vs Ref |
| | hsa-mir-10b | chr02: 176720535-176720594 | NMI-wt vs Ref |
| chr02-176737610-176738187 | HOXD3 | chr02: 176737609-176737653 | NMI-mt vs Ref |
| | HOXD3 | chr02: 176737609-176737653 | NMI-mt vs MI |
| | HOXD3 | chr02: 176738050-176738094 | NMI-wt vs Ref |
| | CENTG2 | chr02: 236438664-236438711 | NMI-wt vs Ref |
| chr3: 11721578-11721824 | VGLL4 | chr03: 011721492-011721547 | NMI-wt vs Ref |
| chr3: 12983649-12984210 | IQSEC1 | chr03: 012983600-012983644 | NMI-wt vs Ref |
| chr3: 25680561-25681574 | TOP2B | chr03: 025681366-025681410 | NMI-wt vs Ref |
| chr03-129688131-129694023 | GATA2 | chr03: 129692644-129692688 | MI vs Ref |
| | GATA2 | chr03: 129698463-129698509 | NMI-wt vs Ref |
| chr03-148591199-148594390 | ZIC4 | chr03: 148592447-148592499 | NMI-wt vs Ref |
| chr3: 148613030-148613264 | ZIC1 | chr03: 148613058-148613102 | NMI-mt vs Ref |
| | ZIC1 | chr03: 148619483-148619541 | NMI-wt vs Ref |
| chr4: 4910534-4911092 | MSX1 | chr04: 004910620-004910670 | MI vs Ref |
| | MSX1 | chr04: 004910620-004910670 | NMI-mt vs Ref |
| | MSX1 | chr04: 004910620-004910670 | NMI-wt vs Ref |
| chr4: 30330303-30333940 | PCDH7 | chr04: 030333744-030333788 | NMI-mt vs Ref |
| | PCDH7 | chr04: 030333834-030333878 | NMI-wt vs Ref |
| chr4: 41678680-41678940 | WDR21B | chr04: 041678597-041678646 | NMI-wt vs Ref |
| chr4: 85636684-85639823 | NKX6-1 | chr04: 085637474-085637518 | NMI-wt vs Ref |
| chr4: 94974810-94975333 | ATOH1 | chr04: 094974874-094974918 | NMI-wt vs Ref |
| chr04-111780013-111780343 | PITX2 | chr04: 111780048-111780092 | NMI-mt vs Ref |
| | PITX2 | chr04: 111780288-111780343 | NMI-wt vs Ref |
| | PCDH10 | chr04: 134291474-134291518 | NMI-wt vs Ref |
| | NR3C2 | chr04: 149586403-149586447 | NMI-wt vs Ref |
| | TRIM2 | chr04: 154436244-154436288 | NMI-wt vs Ref |
| chr04-155881084-155881434 | LRAT | chr04: 155881084-155881128 | NMI-wt vs Ref |
| | LRAT | chr04: 155881330-155881378 | NMI-wt vs MI |
| | HAND2 | chr04: 174687934-174687985 | NMI-wt vs Ref |
| chr4: 184255825-184258373 | FLJ30277 | chr04: 184255924-184255968 | NMI-wt vs Ref |
| chr5: 360287-360592 | PDCD6 | chr05: 000360593-000360637 | NMI-wt vs Ref |
| chr5: 1161803-1162051 | SLC12A7 | chr05: 001162056-001162100 | NMI-wt vs Ref |

TABLE 7A-continued

Differentially labeled CGIs between subgroups relative to blood

| CGI | Gene Name | Probe location | Subgroup |
|---|---|---|---|
| chr5: 3647468-3656054 | IRX1 | chr05: 003654466-003654525 | NMI-wt vs Ref |
| chr5: 5192442-5193941 | ADAMTS16 | chr05: 005192514-005192558 | NMI-wt vs Ref |
| chr5: 6790705-6791004 | POLS | chr05: 006790682-006790728 | NMI-wt vs Ref |
| chr5: 54554812-54555385 | UNG2 | chr05: 054555175-054555219 | NMI-wt vs Ref |
| | UNG2 | chr05: 054555391-054555442 | NMI-mt vs Ref |
| chr5: 114542616-114544119 | TRIM36 | chr05: 114542773-114542817 | NMI-wt vs Ref |
| chr05-115810975-115811393 | SEMA6A | chr05: 115811349-115811393 | NMI-wt vs Ref |
| chr5: 127899858-127900162 | FBN2 | chr05: 127900012-127900056 | NMI-wt vs MI |
| | FBN2 | chr05: 127900012-127900056 | NMI-wt vs NMI-mt |
| | FBN2 | chr05: 127900101-127900154 | NMI-wt vs Ref |
| chr05-134390896-134393045 | PITX1 | chr05: 134390896-134390940 | MI vs Ref |
| | PITX1 | chr05: 134390896-134390940 | NMI-wt vs Ref |
| | PITX1 | chr05: 134391093-134391137 | NMI-mt vs Ref |
| | TRPC7 | chr05: 135720277-135720321 | NMI-wt vs Ref |
| chr05-140724146-140724826 | PCDHGA5 | chr05: 140724562-140724606 | NMI-wt vs Ref |
| chr5: 140780945-140781256 | PCDHGA11 | chr05: 140781192-140781236 | NMI-wt vs Ref |
| | PCDHGA12 | chr05: 140791316-140791360 | NMI-mt vs Ref |
| | PCDHGA12 | chr05: 140791441-140791494 | NMI-wt vs Ref |
| chr5: 141235749-141238152 | PCDH1 | chr05: 141237048-141237094 | NMI-wt vs Ref |
| chr05-174091287-174092335 | MSX2 | chr05: 174091297-174091341 | NMI-wt vs Ref |
| | MSX2 | chr05: 174091410-174091454 | MI vs Ref |
| | MSX2 | chr05: 174091473-174091517 | NMI-mt vs Ref |
| chr6: 1326743-1330210 | FOXF2 | chr06: 001329813-001329866 | NMI-mt vs Ref |
| | FOXF2 | chr06: 001329813-001329866 | NMI-wt vs Ref |
| chr06-1549606-1560865 | FOXC1 | chr06: 001551371-001551415 | NMI-mt vs Ref |
| | FOXC1 | chr06: 001551429-001551473 | NMI-wt vs Ref |
| | FOXC1 | chr06: 001551500-001551559 | MI vs Ref |
| chr6: 5947471-5950124 | NRN1 | chr06: 005947569-005947613 | NMI-wt vs Ref |
| chr6: 10498025-10498551 | TFAP2A | chr06: 010498473-010498517 | MI vs Ref |
| | TFAP2A | chr06: 010498473-010498517 | NMI-wt vs Ref |
| | TFAP2A | chr06: 010498811-010498870 | NMI-mt vs Ref |
| chr6: 22677564-22678684 | HDGFL1 | chr06: 022677587-022677632 | MI vs Ref |
| | HDGFL1 | chr06: 022677587-022677632 | NMI-mt vs Ref |
| | HDGFL1 | chr06: 022677587-022677632 | NMI-wt vs Ref |
| chr6: 25834434-25834701 | HIST1H2AA | chr06: 025834650-025834695 | NMI-wt vs Ref |
| | HIST1H2BA | chr06: 025840937-025840981 | NMI-wt vs Ref |
| chr6: 41176454-41177326 | NFYA | chr06: 041177112-041177165 | NMI-wt vs Ref |
| chr6: 50895246-50896050 | TFAP2B | chr06: 050896068-050896112 | NMI-wt vs Ref |

TABLE 7A-continued

| Differentially labeled CGIs between subgroups relative to blood | | | |
|---|---|---|---|
| CGI | Gene Name | Probe location | Subgroup |
| chr6: 75968300-75968853 | COL12A1 | chr06: 075968669-075968713 | NMI-wt vs Ref |
| chr06-101023927-101024343 | SIM1 | chr06: 101024299-101024343 | NMI-mt vs Ref |
| | SIM1 | chr06: 101024299-101024343 | NMI-wt vs Ref |
| chr6: 101953488-101953856 | GRIK2 | chr06: 101953514-101953560 | NMI-mt vs Ref |
| | GRIK2 | chr06: 101953514-101953560 | NMI-wt vs Ref |
| chr6: 108592365-108597232 | NR2E1 | chr06: 108595517-108595561 | NMI-wt vs Ref |
| chr6: 126122028-126122524 | HEY2 | chr06: 126122132-126122176 | NMI-wt vs Ref |
| chr6: 166499964-166503413 | T | chr06: 166502963-166503011 | NMI-wt vs Ref |
| chr6: 169801163-169801511 | WDR27 | chr06: 169801059-169801108 | NMI-wt vs Ref |
| chr7: 1029023-1029492 | hsa-mir-339 | chr07: 001029489-001029533 | NMI-wt vs Ref |
| chr07-2082782-2083345 | MAD1L1 | chr07: 002083155-002083200 | MI vs Ref |
| | MAD1L1 | chr07: 002083155-002083200 | NMI-wt vs Ref |
| | MAD1L1 | chr07: 002121288-002121332 | NMI-mt vs Ref |
| chr07-2724511-2724848 | AMZ1 | chr07: 002724511-002724555 | MI vs Ref |
| | AMZ1 | chr07: 002724511-002724555 | NMI-wt vs Ref |
| | AMZ1 | chr07: 002724629-002724673 | NMI-mt vs Ref |
| chr07-8449587-8450236 | NXPH1 | chr07: 008449587-008449636 | NMI-mt vs Ref |
| | NXPH1 | chr07: 008449587-008449636 | NMI-wt vs Ref |
| | NXPH1 | chr07: 008450192-008450240 | MI vs Ref |
| chr7: 19113449-19113833 | TWIST1 | chr07: 019113860-019113907 | NMI-wt vs Ref |
| chr7: 27149139-27152087 | HOXA5 | chr07: 027150566-027150625 | MI vs Ref |
| | HOXA5 | chr07: 027151311-027151355 | NMI-mt vs Ref |
| chr07-27164708-27165039 | HOXA7 | chr07: 027164869-027164913 | MI vs Ref |
| | HOXA7 | chr07: 027164869-027164913 | NMI-mt vs Ref |
| | HOXA7 | chr07: 027164944-027164988 | NMI-wt vs Ref |
| chr7: 27170441-27172987 | HOXA9 | chr07: 027170467-027170515 | NMI-mt vs Ref |
| | HOXA9 | chr07: 027170467-027170515 | NMI-wt vs Ref |
| | HOXA9 | chr07: 027170998-027171042 | MI vs Ref |
| chr7: 27198331 -27199622 | HOXA11 | chr07: 027198283-027198327 | NMI-wt vs Ref |
| chr07-27219187-27220360 | EVX1 | chr07: 027245650-027245694 | NMI-wt vs Ref |
| chr07-27251165-27252762 | EVX1 | chr07: 027251482-027251527 | MI vs Ref |
| chr7: 35263447-35264743 | TBX20 | chr07: 035263668-035263712 | NMI-wt vs Ref |
| chr7: 96469320-96469736 | DLX6 | chr07: 096469212-096469266 | NMI-mt vs Ref |
| | DLX6 | chr07: 096469526-096469572 | MI vs Ref |
| | DLX6 | chr07: 096469776-096469827 | NMI-wt vs Ref |
| chr07-96488158-96489591 | DLX5 | chr07: 096489129-096489173 | NMI-mt vs Ref |
| | DLX5 | chr07: 096489475-096489520 | MI vs Ref |
| | DLX5 | chr07: 096489536-096489591 | NMI-wt vs Ref |

TABLE 7A-continued

Differentially labeled CGIs between subgroups relative to blood

| CGI | Gene Name | Probe location | Subgroup |
|---|---|---|---|
| chr7: 119702299-119702721 | KCND2 | chr07: 119702676-119702723 | NMI-wt vs Ref |
| chr07-121727243-121727884 | FEZF1 | chr07: 121727241-121727285 | NMI-wt vs MI |
| | FEZF1 | chr07: 121727336-121727380 | NMI-wt vs Ref |
| chr07-155288454-155292175 | SHH | chr07: 155291537-155291581 | MI vs Ref |
| | SHH | chr07: 155291593-155291637 | NMI-mt vs Ref |
| | SHH | chr07: 155291751-155291795 | NMI-wt vs Ref |
| chr7: 158509937-158510390 | VIPR2 | chr07: 158509989-158510033 | NMI-wt vs Ref |
| chr08-9798161-9799053 | hsa-mir-124a-1 | chr08: 009798455-009798508 | NMI-wt vs NMI-mt |
| | hsa-mir-124a-1 | chr08: 009798593-009798644 | NMI-wt vs Ref |
| | hsa-mir-124a-1 | chr08: 009800023-009800077 | NMI-wt vs MI |
| chr8: 10624024-10624296 | SOX7 | chr08: 010624244-010624300 | NMI-mt vs Ref |
| | SOX7 | chr08: 010624319-010624366 | NMI-wt vs Ref |
| chr8: 11597006-11600365 | GATA4 | chr08: 011599544-011599588 | NMI-wt vs Ref |
| chr8: 25955253-25955609 | EBF2 | chr08: 025955446-025955495 | NMI-mt vs Ref |
| | EBF2 | chr08: 025955446-025955495 | NMI-wt vs Ref |
| chr8: 55532724-55535078 | SOX17 | chr08: 055533948-055533992 | NMI-wt vs Ref |
| chr08-65661156-65662687 | BHLHB5 | chr08: 065661235-065661282 | NMI-wt vs MI |
| | BHLHB5 | chr08: 065662258-065662302 | NMI-wt vs Ref |
| chr8: 72916429-72917309 | MSC | chr08: 072917197-072917241 | MI vs Ref |
| | MSC | chr08: 072917336-072917380 | NMI-wt vs Ref |
| chr8: 140700279-140700514 | KCNK9 | chr08: 140700520-140700564 | NMI-wt vs Ref |
| chr08-142288380-142288718 | SLC45A4 | chr08: 142288398-142288442 | NMI-mt vs Ref |
| | SLC45A4 | chr08: 142288610-142288657 | MI vs Ref |
| | SLC45A4 | chr08: 142288610-142288657 | NMI-wt vs Ref |
| chr8: 145014900-145015187 | EPPK1 | chr08: 145015195-145015240 | NMI-wt vs Ref |
| chr9: 959530-963276 | DMRT3 | chr09: 000959621-000959665 | NMI-wt vs Ref |
| chr9: 21979774-21980108 | CDKN2A | chr09: 021979951-021979995 | NMI-wt vs Ref |
| chr9: 23812413-23812667 | ELAVL2 | chr09: 023812373-023812424 | NMI-wt vs Ref |
| chr9: 37024136-37028341 | PAX5 | chr09: 037024964-037025008 | NMI-wt vs Ref |
| chr9: 101621613-101627382 | NR4A3 | chr09: 101627386-101627439 | NMI-wt vs Ref |
| chr10-7489383-7495345 | SFMBT2 | chr10: 007491431-007491476 | NMI-wt vs Ref |
| | SFMBT2 | chr10: 007491576-007491626 | NMI-wt vs NMI-mt |
| chr10: 13556172-13556753 | C10orf30 | chr10: 013556159-013556211 | NMI-wt vs Ref |
| chr10: 15294605-15294858 | C10orf38 | chr10: 015294592-015294641 | NMI-wt vs Ref |
| chr10-21828640-21829645 | C10orf114 | chr10: 021828885-021828929 | NMI-wt vs Ref |
| | C10orf114 | chr10: 021828954-021828998 | NMI-mt vs Ref |
| | C10orf114 | chr10: 021829373-021829417 | MI vs Ref |
| chr10: 76825135-76839606 | ZNF503 | chr10: 076834917-076834976 | NMI-wt vs Ref |

TABLE 7A-continued

Differentially labeled CGIs between subgroups relative to blood

| CGI | Gene Name | Probe location | Subgroup |
|---|---|---|---|
| | ZNF503 | chr10: 076837381-076837425 | NMI-mt vs Ref |
| chr10: 88112905-88117344 | GRID1 | chr10: 088115612-088115656 | NMI-wt vs Ref |
| chr10: 94441310-94441717 | HHEX | chr10: 094441395-094441439 | NMI-mt vs Ref |
| | HHEX | chr10: 094441744-094441795 | NMI-wt vs Ref |
| chr10: 99068802-99071038 | FRAT1 | chr10: 099070245-099070298 | NMI-wt vs Ref |
| | FRAT1 | chr10: 099070376-099070420 | NMI-mt vs Ref |
| chr10: 101277153-101277910 | NKX2-3 | chr10: 101277900-101277957 | NMI-wt vs Ref |
| chr10: 102974173-102980053 | LBX1 | chr10: 102975940-102975999 | NMI-wt vs Ref |
| | LBX1 | chr10: 102976227-102976273 | NMI-wt vs MI |
| | LBX1 | chr10: 102976227-102976273 | NMI-wt vs NMI-mt |
| chr10: 106389558-106392802 | SORCS3 | chr10: 106392567-106392611 | NMI-wt vs Ref |
| chr10: 124891898-124892607 | HMX2 | chr10: 124892023-124892067 | NMI-wt vs Ref |
| chr10: 128863581-128864054 | FLJ45557 | chr10: 128864100-128864145 | NMI-wt vs Ref |
| chr11: 22319439-22319953 | SLC17A6 | chr11: 022319657-022319701 | NMI-wt vs Ref |
| chr11: 31776637-31777992 | PAX6 | chr11: 031776609-031776653 | NMI-wt vs Ref |
| chr11: 68274244-68274755 | MTL5 | chr11: 068274304-068274348 | NMI-mt vs Ref |
| chr11: 117983446-117987106 | PHLDB1 | chr11: 117984800-117984844 | NMI-wt vs Ref |
| chr12: 1844001-1845219 | CACNA2D4 | chr12: 001844114-001844158 | NMI-wt vs Ref |
| chr12: 40253533-40253742 | PDZRN4 | chr12: 040253480-040253529 | NMI-wt vs Ref |
| chr12: 52726910-52727810 | HOXC4 | chr12: 052727781-052727833 | NMI-mt vs Ref |
| | HOXC4 | chr12: 052727781-052727833 | NMI-wt vs Ref |
| chr12: 79634857-79635257 | MYF5 | chr12: 079634813-079634857 | NMI-wt vs Ref |
| chr12-94776044-94776377 | SNRPF | chr12: 094776044-094776094 | NMI-wt vs Ref |
| chr12: 95164929-95165298 | ELK3 | chr12: 095165171-095165220 | NMI-wt vs Ref |
| chr12-113657930-113659205 | TBX5 | chr12: 113325125-113325174 | NMI-wt vs Ref |
| chr12: 113609113-113609535 | TBX3 | chr12: 113609153-113609207 | MI vs Ref |
| | TBX3 | chr12: 113609259-113609303 | MI vs NMI-wt |
| chr13-34950488-34951119 | MAB21L1 | chr13: 034950488-034950532 | MI vs Ref |
| | MAB21L1 | chr13: 034950709-034950765 | NMI-wt vs Ref |
| | MAB21L1 | chr13: 034950955-034950999 | NMI-mt vs Ref |
| chr13: 35817738-35819004 | SPG20 | chr13: 035817882-035817927 | NMI-mt vs MI |
| chr13: 57101588-57102323 | PCDH17 | chr13: 057101685-057101729 | NMI-wt vs Ref |
| | PCDH17 | chr13: 057105585-057105629 | NMI-mt vs Ref |
| chr13-94152191-94153185 | SOX21 | chr13: 094152286-094152330 | MI vs Ref |
| | SOX21 | chr13: 094152463-094152507 | NMI-mt vs Ref |
| | SOX21 | chr13: 094152463-094152507 | NMI-wt vs Ref |
| chr13: 105943410-105943788 | EFNB2 | chr13: 105943362-105943406 | NMI-mt vs Ref |
| | EFNB2 | chr13: 105943488-105943532 | NMI-wt vs Ref |

TABLE 7A-continued

Differentially labeled CGIs between subgroups relative to blood

| CGI | Gene Name | Probe location | Subgroup |
|---|---|---|---|
| chr13: 111763361-111764235 | SOX1 | chr13: 111764262-111764315 | NMI-wt vs Ref |
| chr13: 112249708-112249928 | TUBGCP3 | chr13: 112249984-112250030 | NMI-wt vs Ref |
| chr14: 19992581-19993863 | APEX1 | chr14: 019993551-019993604 | NMI-mt vs MI |
| chr14: 23710894-23712060 | REC8L1 | chr14: 023711936-023711980 | NMI-mt vs Ref |
| chr14: 28317076-28317375 | FOXG1B | chr14: 028317289-028317343 | NMI-wt vs Ref |
| chr14: 33338698-33340189 | NPAS3 | chr14: 033339869-033339913 | NMI-wt vs Ref |
| chr14: 36122289-36122589 | NKX2-8 | chr14: 036122225-036122274 | MI vs Ref |
| | NKX2-8 | chr14: 036123184-036123232 | NMI-wt vs Ref |
| chr14-36205192-36206099 | PAX9 | chr14: 036196442-036196486 | NMI-mt vs Ref |
| | PAX9 | chr14: 036205602-036205647 | MI vs Ref |
| | PAX9 | chr14: 036206112-036206171 | NMI-wt vs Ref |
| chr14: 37137198-37138958 | FOXA1 | chr14: 037137114-037137159 | NMI-wt vs Ref |
| | FOXA1 | chr14: 037137543-037137587 | NMI-mt vs Ref |
| chr14: 56347822-56348040 | OTX2 | chr14: 056347712-056347756 | NMI-wt vs Ref |
| chr14: 60045486-60047933 | SIX6 | chr14: 060046995-060047041 | NMI-wt vs Ref |
| chr14: 60173732-60174416 | SIX1 | chr14: 060173710-060173754 | NMI-mt vs Ref |
| | SIX1 | chr14: 060179528-060179574 | NMI-wt vs Ref |
| chr14: 98781593-98783184 | BCL11B | chr14: 098782637-098782681 | NMI-mt vs Ref |
| chr15: 50867751-50870991 | ONECUT1 | chr15: 050870481-050870525 | NMI-wt vs Ref |
| chr15: 58083428-58085812 | FOXB1 | chr15: 058084349-058084393 | NMI-wt vs Ref |
| chr15: 62984853-62985116 | ANKDD1A | chr15: 062984784-062984834 | NMI-wt vs Ref |
| chr15: 65902540-65909629 | LBXCOR1 | chr15: 065908791-065908850 | NMI-wt vs Ref |
| chr15: 72206924-72210097 | ISLR2 | chr15: 072206870-072206914 | NMI-wt vs Ref |
| chr15: 74414579-74414893 | ISL2 | chr15: 074414745-074414789 | NMI-wt vs Ref |
| chr15: 88158407-88159577 | ANPEP | chr15: 088158433-088158477 | NMI-wt vs Ref |
| chr15-94688798-94689131 | NR2F2 | chr15: 094688839-094688885 | NMI-wt vs Ref |
| | NR2F2 | chr15: 094688901-094688949 | MI vs Ref |
| | NR2F2 | chr15: 094689087-094689131 | NMI-mt vs Ref |
| chr16: 727072-727328 | NARFL | chr16: 000727383-000727427 | NMI-wt vs Ref |
| | CBLN1 | chr16: 047869472-047869516 | NMI-wt vs Ref |
| chr16-52873104-52882105 | IRX3 | chr16: 052879704-052879750 | NMI-mt vs Ref |
| | IRX3 | chr16: 052879918-052879974 | NMI-wt vs Ref |
| | IRX3 | chr16: 052880382-052880426 | MI vs Ref |
| | IRX5 | chr16: 053528320-053528364 | NMI-wt vs Ref |
| chr16: 66071900-66072846 | ATP6V0D1 | chr16: 066071973-066072017 | NMI-mt vs MI |
| chr16-85098883-85102729 | FOXF1 | chr16: 085098933-085098977 | NMI-wt vs Ref |
| | CNTNAP1 | chr17: 038089272-038089316 | NMI-mt vs Ref |
| | CNTNAP1 | chr17: 038089272-038089316 | NMI-wt vs Ref |

TABLE 7A-continued

Differentially labeled CGIs between subgroups relative to blood

| CGI | Gene Name | Probe location | Subgroup |
|---|---|---|---|
| chr17-44074280-44075233 | HOXB5 | chr17: 044026017-044026069 | MI vs Ref |
| | HOXB5 | chr17: 044026017-044026069 | NMI-wt vs Ref |
| | hsa-mir-196a-1 | chr17: 044074404-044074448 | NMI-wt vs Ref |
| | hsa-mir-196a-1 | chr17: 044074457-044074501 | NMI-mt vs Ref |
| chr17-58865328-58865618 | CYB561 | chr17: 058865281-058865326 | MI vs Ref |
| | CYB561 | chr17: 058865281-058865326 | NMI-wt vs Ref |
| | CYB561 | chr17: 058865512-058865556 | NMI-mt vs Ref |
| chr17: 67627870-67631593 | SOX9 | chr17: 067630891-067630945 | NMI-wt vs Ref |
| chr17: 71582000-71585125 | GALR2 | chr17: 071583191-071583235 | NMI-mt vs MI |
| chr17-75531280-75531546 | TBC1D16 | chr17: 075531439-075531483 | NMI-wt vs Ref |
| chr17: 75936057-75936582 | C17orf27 | chr17: 075936313-075936368 | MI vs Ref |
| | C17orf27 | chr17: 075936313-075936368 | NMI-wt vs Ref |
| chr17: 76404186-76404427 | KIAA1303 | chr17: 076404103-076404162 | MI vs Ref |
| | KIAA1303 | chr17: 076404103-076404162 | NMI-wt vs Ref |
| chr17: 77537903-77538626 | ASPSCR1 | chr17: 077538538-077538583 | NMI-wt vs Ref |
| chr18: 894579-899574 | ADCYAP1 | chr18: 000899042-000899087 | NMI-wt vs Ref |
| chr18-5186244-5187389 | ONECUT2 | chr18: 053259508-053259552 | NMI-mt vs Ref |
| | ONECUT2 | chr18: 053259508-053259552 | NMI-wt vs Ref |
| chr18-68359955-68362770 | CBLN2 | chr18: 068361299-068361343 | NMI-wt vs MI |
| chr18: 74837994-74842232 | SALL3 | chr18: 074838538-074838582 | NMI-wt vs Ref |
| chr18: 75565313-75565933 | CTDP1 | chr18: 075565319-075565363 | NMI-wt vs Ref |
| chr19: 898548-898981 | ARID3A | chr19: 000898650-000898694 | NMI-wt vs Ref |
| chr19-4059891-4060207 | MAP2K2 | chr19: 004059891-004059935 | NMI-wt vs Ref |
| | MAP2K2 | chr19: 004060122-004060166 | MI vs Ref |
| | MAP2K2 | chr19: 004060122-004060166 | NMI-mt vs Ref |
| chr19: 9131907-9132918 | ZNF317 | chr19: 009132692-009132736 | NMI-wt vs Ref |
| chr19: 12985960-12986259 | NFIX | chr19: 012986040-012986084 | NMI-wt vs Ref |
| chr19-42586165-42586705 | ZNF569 | chr19: 042586544-042586592 | NMI-wt vs Ref |
| chr19: 55553586-55553895 | NAPSA | chr19: 055553837-055553881 | NMI-wt vs Ref |
| chr19: 57082654-57083180 | ZNF577 | chr19: 057082979-057083023 | NMI-wt vs Ref |
| chr19: 60283718-60285792 | EPS8L1 | chr19: 060285492-060285536 | NMI-mt vs Ref |
| chr19: 60907042-60907388 | EPN1 | chr19: 060907107-060907151 | NMI-mt vs Ref |
| | EPN1 | chr19: 060907320-060907364 | NMI-wt vs Ref |
| chr19: 62043096-62043807 | PEG3 | chr19: 062043010-062043054 | NMI-wt vs Ref |
| chr19: 63321122-63322053 | ZNF329 | chr19: 063321824-063321868 | NMI-wt vs Ref |
| chr19-63420090-63420541 | ZNF274 | chr19: 063420437-063420481 | NMI-wt vs Ref |
| chr19-63784504-63785085 | MGC2752 | chr19: 063784639-063784683 | NMI-wt vs Ref |
| | MGC2752 | chr19: 063784804-063784848 | MI vs Ref |

TABLE 7A-continued

| Differentially labeled CGIs between subgroups relative to blood | | | |
|---|---|---|---|
| CGI | Gene Name | Probe location | Subgroup |
| | MGC2752 | chr19: 063784804-063784848 | NMI-mt vs Ref |
| chr20: 9444472-9444893 | C20orf103 | chr20: 009444951-009444998 | NMI-wt vs Ref |
| chr20: 21433933-21444714 | NKX2-2 | chr20: 021439947-021439991 | NMI-wt vs Ref |
| chr20-22505518-22507240 | FOXA2 | chr20: 022505822-022505866 | NMI-wt vs MI |
| chr20-22510737-22514165 | FOXA2 | chr20: 022505888-022505938 | NMI-wt vs Ref |
| chr20-22514762-22515148 | FOXA2 | chr20: 022507864-022507908 | NMI-wt vs NMI-mt |
| chr20: 23294035-23294650 | GZF1 | chr20: 023294489-023294536 | NMI-wt vs Ref |
| chr20: 25011839-25013525 | VSX1 | chr20: 025011908-025011952 | NMI-wt vs Ref |
| chr20-35582018-35583550 | NNAT | chr20: 035582918-035582969 | NMI-mt vs Ref |
| | NNAT | chr20: 035582918-035582969 | NMI-wt vs Ref |
| chr20: 36785545-36790786 | SLC32A1 | chr20: 036787891-036787941 | NMI-wt vs Ref |
| chr20: 38749965-38753401 | MAFB | chr20: 038753128-038753174 | NMI-mt vs Ref |
| | MAFB | chr20: 038753269-038753318 | NMI-wt vs Ref |
| chr20: 49542203-49542863 | NFATC2 | chr20: 049542266-049542311 | NMI-wt vs Ref |
| chr20-54012011-54014085 | CBLN4 | chr20: 054013134-054013178 | NMI-wt vs Ref |
| chr20: 54411932-54412178 | CSTF1 | chr20: 054412143-054412187 | NMI-wt vs Ref |
| chr20: 55680656-55681057 | TMEPAI | chr20: 055680906-055680952 | NMI-wt vs Ref |
| chr20: 56860125-56860442 | GNAS | chr20: 056860480-056860524 | NMI-wt vs Ref |
| chr20-60061693-60062033 | TAF4 | chr20: 060015181-060015225 | MI vs Ref |
| | TAF4 | chr20: 060062094-060062139 | NMI-wt vs Ref |
| chr20: 62371744-62371958 | PCMTD2 | chr20: 062371900-062371944 | NMI-wt vs Ref |
| chr21-33316999-33322115 | OLIG2 | chr21: 033318624-033318681 | NMI-wt vs Ref |
| chr21-36990008-36995832 | SIM2 | chr21: 036991619-036991663 | NMI-wt vs Ref |
| | SIM2 | chr21: 036999107-036999151 | MI vs Ref |
| chr21-43350621-43351134 | HSF2BP | chr21: 043902052-043902096 | MI vs Ref |
| | HSF2BP | chr21: 043902052-043902096 | NMI-mt vs Ref |
| chr21: 45511336-45511549 | POFUT2 | chr21: 045511551-045511595 | NMI-wt vs Ref |
| chr21: 46892946-46893236 | PRMT2 | chr21: 046893181-046893225 | NMI-wt vs Ref |
| chr22: 18453364-18453931 | DGCR8 | chr22: 018453720-018453764 | NMI-wt vs Ref |

TABLE 7B

Sequences of differentially labeled CGIs between bladder cancer subgroups relative to blood CGI: 561 range = chr1:63554983-63563059
CGGGCAGGCCCAAGCTGCGATGTGGAGAATTCGATGTCCGAGCGACCTCCTCGGAGGAGTGGGTCGAGTTAAATA
TAACCGCGCGAATGGAATGGCGCTAAAAATAAGGCAGCAGCTGGCCTGTCCACAGCCCTGTCCCGGGAGGGGCGG
GGGCCCCAGTGGTCTTGGGCAGGAAGGCCGCGTCCGGCCCAGGGGCGAGAAGGCTGCGGCGTCCGCAGCCAGGGC
TGGAAGGCCTGGGAGGCCGCGCTCTGTGGGCCCCGGGGCCTCCATTCGGGCTGGGTCGCGGGCCTGGACGGGGAC
TGTCCAGAGGCATCCGAAAGCCAGGCCAACTTGCCTGGACGTAACAAGACGGAAGGGCTGGGCGCTGAGGTCCTG
CCAGCCCGGCCGCCAGAGGGAGCTGAGCGCCAGAGGAGGACAAGCCGAACCCTTCAGGAGGCCGGGCGTCTCCGG
AGACCGAAGCGCCGGAGGACCCGAGGAGGTCTGCCCCGCGCGCTGCTCTGGAGACTCCCGGGGCGGGTGGCGCTC
GGCCTTTCCGCTCCCTTCCTTCCCACAAGTCCCTTCCCGCGCGCGCCCCACGGCCCTGCCCGCCCTCCCGCGTCA TABLE 7B-continued

| Sequences of differentially labeled CGIs between bladder cancer subgroups relative to blood |
|---|
| GCGCCCCAACCGTCAAGCCAGCAATTGAAACGTTTCCAAAACGGTCTATTTATTTGCTCCCAATAAATCGATCGG<br>CGGTGATTAAAGAATCGATGTGGCCTGGGTGGGCGAGTCGCTTGAGGGGAGGGATTGGGGGCTTTCGCCCGGCGC<br>CTGCAGGGAGGCCGAGGGCGGGCGCGGGCCTGAGGGAGGCGTGTCCCGCCCGGGCCACACCCGAGGACCCGACAC<br>CTGGGCTGGCAGGCCCCGGCAGGCAGCGTTCCCTCCGGCGGAGAGGGGCGCGCGCCCGCCGCCTGCTTTCCTCGG<br>CCCCTCTCGCCTTTCTCGCGCGCCGGGGAGGCTGTGGCCGCCAGTGGCTGCGGAGCTGCTCAGAGGCTTTTGTTG<br>CTCCTCGGCCGGCTGAATGGGGATTTTGTAAAGCGGGACAGATAAAAATGAGCAGCATCATATTGTTTGACAGAA<br>TGATCTCGCATGATGAAGTGTCGGCTCCGAAGGGGGTGAAAATGGTGAATTCCTAAAAACCCAGCCCTGGGCTCC<br>TCCTCGAGCTGCCGGTAGCCTGGAGGGACCCAGCGGACAGCCGGGCCTGGCCGCATCGCTCCAAACGGTGTCAGA<br>AAGACTCCGGCTTTCAATGCCAAGTCATTTTTAAGCCCCGATCCTGTCCAGGACCTTTCTCCTCGTGGATGAAAA<br>GAACAATTTTCGAGAGAAAGGCTCGTTTTTATTAAATCCGACATGCTGCTGATAACTCCATGCTAATGTGAAATA<br>ATTAACATAATAGCCATAATTAAAAGCACGCTAACAATGCCATAAATTTATCACACAATTTTACTAGCTTTCTGC<br>CCCTAACTGCTCTCTCATCGTTAATTAAACGTGTTGCCTTTTACAGAATGGATGTTTATATATTTCCAATATAAA<br>TAAATTCGAAACCATCCTCTCTCTCTTCCTCTTTCTCTCCTCCTTTCCTTTTGGTCTCTCGCCATTTACAGGCAC<br>GCCTTGGCGTGGACCCTGAGTGGCAGACATCTTGAAAATAAATGAAGTTTTGAGATGCAAATCCAAACAAGAACA<br>TTAAAATAGCCTCTTTTTTTCCACCCCGAAAAGATCCGGAGAGGTATACAAGGGGGTAGTGGTGGGTAAGAGAGT<br>TGAAAATCCCCCGCTTTGGGAAATGGAAGTAATCTGGGTGGGTTGGGGCCTTGGGTACCACCTCTGCCCTTTCCC<br>ACCTTCCTTGGTGGCGGCCATCCAGACAAAGAGGCCGGTAATAGTTTAACAAATCTATGAAGATTTTCAAGAAGC<br>AGCAGACTTTGATTGTTGCGGGCGCGGGGGTGTTGGGGAGAAAGGAGGGGAATTTTTCTAATAGTCCCACCCACG<br>TTTTGCTCCCTCTTGGACAAAGAGTAACTACTCTTGGTGGGGGACGCGCCCTTCACTCCGCGGAACCTGGTCCCA<br>ACTCCCCGTATTGTAAGAAAAGTGCACCCGCGCGCGGGCATGATGATTCTATCTCACATCGCGCCAACGACTTAT<br>TCAAGCCACTGGCACTGTCTCTGACTTAAAAGAGGAGAAAAGAGGCATATGGGTTCACTTGGGCCTGGTGAGGGG<br>TAGGTGGGCAATTCCCGCCTTCCGCACTCTAACCGTGCCCCTCCTCCAGTGTTGACCACCTAAGAACCCAAAATG<br>AGCTGTAATTAATTTCCCTTTCTCCATCATAAATTTTTCTATCCATTTCTTCCCCCCCATCCCCCCACTGGACGC<br>ACACACTAAATCTCCCCTCCCCTGGAGACGTCTCAATTTCCTTCCTATCGATCCGGACTCCATTCTTCTTGCCTC<br>CTGTTGCTAGAACCTAGATCCCCACTCCCCGCACCCCTCATTCCCACCGCGTCCAGGTGGCTTTCCCAGCGGGGT<br>ACCATGTACTCTGCCCGCTCCAGAGGAACCGAAGGGGTTTCATTCCATTCTCCTTTGGTTGAAACATTTCAAACA<br>TTTGAGCAGGTGAGGCAGCTGGCTGCCATCTTCCTTTTTAAATCTCTCCTGGGAAGTTCGCTTGTTGAGACTCAA<br>AGAGTCACTCAAACTCATAATTGCGTGTGTGTGTCTACTCATTCTCCCTCTATCTCTCCAATAACCCTTTGAGAC<br>TCAGAAACTTTTTATCCACATACACCCTTTATCACATTTTCTTCCCCCCACTACATGTGTCTCACTTTCTCTCTG<br>TATCTGTCTCGCTTCTTCCGTCTCTGTCCTACAGCTTGGCGGTAACTGACGACCTGTGAGCTTTTAGCTGCAAAC<br>TGCAACTACGCGGCAAACAATTTATTTAGCCCGACATCTAGCCGGTCTCCGGCAGGACCCTGCACCGCGTCGGGA<br>TCGGACCCTTCCGCTGGGGCGGCCTCCTGCGTCAAGGCCAGCAGGAACCTTCCTGTCGCCCTCCCCGGCCGCCGC<br>TTCGCCTCCTTCCCGCCCCCGGAGGTTGTGCAGGCGCTATGGTCCGCCTGGAGGGAGAAAGCCGGCGGCCGGTTC<br>CTGAGCCGAGAGCGGCCGCGGAAAAATCCTCTGCCTCCGCTGGAAATCGATATTAGGCCGGCGCGGGCGCGGGAC<br>GTCGGGGCCGCAGCCAGTAGGTTGTGCACGTCTCATCATTTAGCTAATCGAGTCGAAAAGTTTCTGTAAGGGCCG<br>GACCCAGCATCAGATGGTAACACTGATTGAACAAGAGATTAGCACAATAGATCTCTAACCGAGGGGAAGCGTTGC<br>TTTTCACGCTACGCGCCGTAATTAATGGTATGAATCAATTAATTTGACTTTTATTGTGTCGAAGGAAAAAAGCGC<br>AACAAATGGAACCGGCAGCTGGGAGTTGTTCGTCCTCCACCCCCTTCCCCAGGGAGGTTCCAAGGAGACACCGGG<br>GAATGGACGGATCAGGCTGGGCCGTGGCAGAGGGAGGGTAGGAGGCAGCGACCAGCAGCGTGGAGGGAGTCCAGA<br>GAGCTAGCCTCTGCGGACGGCGGAATCGAAATTAGGCTCATTTGGAGACTACTTCGAGACCGGTGAGGGGAGCCC<br>TGTAGCCACCATCCTCCGGCGCGCATCCACACATACTAGTCCACGCGGGCCCAGCCACCAAGGCCGCGGCAGGGC<br>CAGCGCTGCGCCCCGGGCCCCTGCCTTTAGGGCTGGGCAACCCAAGCAGAGCAAAGGAGGTTCCTGAATGTGTAA<br>ATTTCCGCTTTTTAGCTTTTTTTTTTTTTTTTTTTGGACCTTCCGACACTTCGGTTGCTGAGGCAGTTGCAGACG<br>CGACCTCTGCAGTCCTGGGCGATGGCCAGCCAGCTCAGCTCGGGTCGGTTTCGCGGAAAGCTGTCTAGACGGCAT<br>TGTAAACGGTTCGGAGCCTGCGGGCCACAAAGCTGTGGAGCTACGGAAATCAACTCTGAGATGCGTTTTAGGGCC<br>GTGTGCAACCTCGGGATCATTTAGATAAAGAAAAACTGTGGAGGTTGGCGGGCGTCTCAGGATAGTGTCACCACC<br>CCCTACCCTGCTCCCAGCCTCAGATGAGTAGTGTTATATCCTGGGAAACTGTCTAATGGGGATGAAAGTCAATCT<br>GTGTGTCTCAATGCCTGTAATGAAGCAAGTTTACAGATTTTTAAATTTTTATTTTTATTTTATTGAATTATTTTT<br>GGTGTGTCTAGGCCAAGGAAAGAGGAGATCGTGGGTGGGGAAACAGACTGAGGGAATCAGAAGCACCACTGTCCA<br>TCCGGAATTAAATCCACATCCCAGCATCTTCTGCAAATATTTCACTAATTATTTCCTCTCGGAACTCCTCCCCTC<br>GTGCTCCTTCCTCTGGTGAGGCCGGCGCTCCCCTCCCAGGCCGCAGCGGACAGACAGGGATTGGGTTCCGTGTGC<br>CTGCCACACCAGGCAGGCTCTTGCGGCTCCCAACTAGGCGGCCTAAATGAGGGAGGAAAGAGGAGGCGCATCGCT<br>GATTCACCGCGTCAAGAGCACTGACTTTCCTTGGAGGTGTGAGGTCCACGCACCCCAGCCACGCACTTGGGGGTC<br>GGTTTGCGGTGCCTCCCCCTCCAGTCCCAGTGAAATCCCCACAGTTTTTCCTACTATCACTGACTTGCCTTGCAC<br>TCCGCGTGCATTGGCCACACATCCTCGCCTCCTCCACCCGCTCCGCCGCCGGTTTTCTTGGAAGTTAAATCTTGG<br>AGGATTTGTCCACACCTTAAGAGAAGAAAATCCACGTTAGCTGGCAGCAACGGAGATCCCAGCATGCTGGCATGC<br>CCAAGTCTGCCCAGGTTCCCCCAAGGCCATGCCCGCCGCCCGGGAAGTCACTGCCCGCACCCCTCACGTTTCTTC<br>AGCCGCCCCTGGGCGCTGCGTCTAACCTGAAGACACCAGGCCTCTTCCCGGATCCACTCGACTTACCCAGGCCGC<br>TGCCAATCCCAGCTCCTTCCCCAGCGCCTCATTTCCGATTTTTTCATATGCTAAGTCGTTTAACAACTCCAAGTA<br>GCCAGTTATGGCTTCTTTATTTATAGGTTCCCTGCTATTTTACGTCGTTTTTATTTCTCTCGGCAACTATTCTAG<br>TAGATTAATCAATAGCCATTTTCTGACCTTCGGGAACCCCAGCTGATGCTTTTTGTGGCCGCACGAAAAAATACA<br>TACAGGAAAACACGCCCGCATCAAGCCGGGAAAGAGCAGGTAGGACCTGAGTGGTTTGGTTGGGGGAGGGGGAAA<br>AAGACATCTCAGCAGGTGTCTTCCCCGGAATGAGCACTGAGGCCAGAGGGGAATCTGAAATCTAATTAGCAGGAG<br>GGAGCCGGGTGCGCTGCTCTTACTCTTTAAAGCTAAAAACAATGAAACAAAAAGCAAAACAGAGACTAAGTTTTG<br>CTTTTTAAAACACGATATGGGAACCTCGTTCTAGGTCGCCCAGTCCCTGTCTAAGGAGTGTGACAAAGTGGGGGG<br>GAGAAGGGCGGAAGGGAGAGGGGGCGGGGAAGGCAGGGCAGCGACAGTCGCACAGTCCCGCGGACGCTCCCAGGC<br>CCACGCCCTGACTCGCTCACACCCACCCACACTCACACCCACCCGCTCCCTGGGCCCCAGGGCCCGGATCCAGCC<br>TGGGTGGGGGGGTCTCCGGGCGGGCCGCAGCGCCCTCCGTGCCCCGGGGATGCTGGCGCACAGTGCGGAGCGGAG<br>TTGCGCGTCTCTCGTCCCTTTGTTGACAATTCCCTGAACCAACTTGAGTTTGGCCGGCTCGGCCGCGGCCCTGAC<br>GTCACGCACGGTCACGTGGCCCCGCCTCCCGCTGGATCTTTAAGTAGAAAGTAATCTATCAGGCCAGTCCTTAAA<br>ACGGGACTTTCGACTACCGGGGCTTCGGCGTCCCTGACACCCAGCCCCCTGCCCCCCCGCTACTGTCCCTGCCCG<br>CGCCCTCCCGAGCTGCTCGGCGCCCGGCGTCCCGCGCCCGCCTGGACCGCTCCTGCGCCCCACGCCAGGGCCAGA<br>GGCCGAGGAAGGCGGGCTAAGTGAGGGGGCGCGGCGTGGAGAACCGCCGGGGCCGGGAGCGGTAGCGAGCGCCTA<br>GTACCGAGCGCCAGGGACGGCAGGAGTTCGCGGAGCGCGGCCGCTGGGGGCGGACGGCAGAGCCCGCGCCACGCG<br>ATGCGGGGCCGCCGAGTGTGAGCTGAGCCCAGCGGGCCCCAAGCCACCTGCGGCCCCCTCCCCTCTCCCTGCCCC<br>CCATCTTTCGGGGGCACTCAAACCCTCTTCCCCTGAGCTCCGTGGCAGCCCCCGAACACCCTCATCGCCCGCTGC<br>CCCCTCCCCGCCGCCGCTACCAACCCCGAGGAGGGATGACCCTCTCCGGCGGCGGCAGCGCCAGCGACATGTCCG |

TABLE 7B-continued

| Sequences of differentially labeled CGIs between bladder cancer subgroups relative to blood |
|---|
| GCCAGACGGTGCTGACGGCCGAGGACGTGGACATCGATGTGGTGGGCGAGGGCGACGACGGGCTGGAAGAGAAGG<br>ACAGCGACGCAGGTTGCGATAGCCCCGCGGGGCCGCCGGAGCTGCGCCTGGACGAGGCGGACGAGGTGCCCCCGG<br>CGGCACCCCATCACGGACAGCCTCAGCCGCCCCACCAGCAGCCCCTGACATTGCCCAAGGAGGCGGCCGGAGCCG<br>GGGCCGGACCGGGGGGCGACGTGGGCGCGCCGGAGGCGGACGGCTGCAAGGGCGGTGTTGGCGGCGAGGAGGGCG<br>GCGCGAGCGGCGGCGGGCCTGGCGCGGGCAGCGGTTCGGCGGGAGGCCTGGCCCCGAGCAAGCCCAAGAACAGCC<br>TAGTGAAGCCGCCTTACTCGTACATCGCGCTCATCACCATGGCCATCCTGCAGAGCCCGCAGAAGAAGCTGACCC<br>TGAGCGGCATCTGCGAGTTCATCAGCAACCGCTTCCCCTACTACAGGGAGAAGTTCCCCGCCTGGCAGAACAGCA<br>TCCGCCACAACCTCTCACTCAACGACTGCTTCGTCAAGATCCCCCGCGAGCCGGGCAACCCGGGCAAGGGCAACT<br>ACTGGACCCTGGACCCGCAGTCCGAGGACATGTTCGACAACGGCAGCTTCCTGCGGCGCCGGAAACGCTTCAAGC<br>GCCACCAGCAGGAGCACCTGCGCGAGCAGACGGCGCTCATGATGCAGAGCTTCGGCGCTTACAGCCTGGCGGCGG<br>CGGCCGGCGCCGCGGGACCCTACGGCCGCCCCTACGGCCTGCACCCTGCGGCGGCGGCCGGTGCCTATTCGCACC<br>CGGCAGCGGCGGCGGCCGCGGCTGCTGCGGCGGCGCTCCAGTACCCGTACGCGCTGCCGCCGGTGGCACCGGTGC<br>TGCCTCCCGCTGTGCCGCTGCTGCCCTCGGGCGAGCTGGGCCGCAAAGCGGCCGCCTTCGGCTCACAGCTCGGCC<br>CGGGCCTGCAGCTGCAGCTCAATAGCCTGGGCGCCGCCGCGGCCGCTGCGGGCACAGCGGGCGCCGCGGGCACCA<br>CCGCGTCGCTCATCAAGTCCGAGCCAAGCGCGCGGCCGTCGTTCAGCATCGAGAACATCATAGGTGGGGGCCCCG<br>CGGCTCCTGGGGGCTCGGCGGTGGGCGCTGGGGTCGCCGGCGGCACTGGGGGTTCAGGGGGCGGCAGCACGGCGC<br>AGTCGTTTCTGCGGCCACCCGGGACCGTGCAGTCGGCAGCGCTCATGGCCACCCACCAACCGCTGTCGCTGAGCC<br>GGACGACTGCCACCATCGCGCCCATTCTTAGCGTGCCACTCTCCGGACAGTTTCTGCAGCCCGCAGCCTCGGCCG<br>CCGCCGCTGCTGCGGCCGCCGCTCAAGCCAAATGGCCGGCGCAATAGGGACGCGCCAATGGCCGGGACCCAGGGT<br>CCGGCGGCGGCCTCGAGCAACAAATGCACCTCCAGGCTGCGCGCCCTGTCCCAAGCCCGGTCCCGGTCCCGCTGC<br>CCAATCCTGGACTCTGCCTCTCCCCAATTTCCTTTCCCCTGAGCCCCCAACGCCTACCTTCCGCGGCCTCCATCC<br>CCTCGCGCACACCTAAGCTGGTCGAGCAAACTCACCGCGCGCCCGCCGGGGATAGCTTTCCATACAGGTAAAACC<br>GAAAACCGAATTTTCCAAAAATGCACCCCGACGGCGCCTGCTCTTAGTACCG<br>(SEQ ID NO: 154) |
| CGI: 26 range = chr1:90955098-90955445<br>CGCGTCTGCTACCAGATGCGGCTCCGGGGGCTCCATGGTGACTGAGATAGGAGAAGAAGGCGCCGTCCCTACGGT<br>ATCAATCTCCGAACAGGGAGATGGGGTGGCTCTGACTCCTAAAATCCGCGGTCCTGGCCTCACCGAGCGGGCGGAA<br>ATCTCCATTCATCATGCCTGGGCTGCCTGAACTGGCACTGGACAAAATCGTGTCTATTCCAAAACTCGACCCGCT<br>GGCCCCTTCCATTGTCATTGCTACATGAGGTCCACGCCACTCCGCCGTTCAGCAGCCGCCCCGAACCAGCGAAGA<br>AAGCTATCGATCGTAAAACAAAATAAACACCAAACAATGTTGCCGCCG<br>(SEQ ID NO: 155) |
| CGI: 29 range = chr1:163590111-163590435<br>CGAGAGGCCCGGCCACCGGCTCGGGAGCTGGGCCGGTCGCTTTGGGAGCGGATGAGGAAGGTTAGGAGAAGCAGC<br>GAGATAGATCCCAATTTTACAATTCTATTTTCTTTCGGTAGGGTCTCGGCGTCCTGGGCCACGTTGAGAGCGAAC<br>GTGGGCCGAGCGGAGGACACAGAGTAAAAAGCGACGCCCGCTGTATACATAAATCCGCACCCGCTGCCCGCCCGG<br>GTACTGCCTGCTCTGGCTTCCGCTCTCTTCCGAGGCTGGGCAAGTCCAAAAGTTCCCGAAAGGGGGGTTCAAAGA<br>GGGGCGCTCAGTGCACGTGATTTCG<br>(SEQ ID NO: 156) |
| CGI: 32 range = chr1:173258989-173259419<br>CGCGGAAGAGGGCGGAAGGAGAACCCCTGGACTGGTCCTCACCGAGCACTACAGGTGGCAGAGCCGTGGGGGACC<br>CGTGGGTTATGAGATTCAGCGGTGAGGGGTAGCGGTGTGGATAAAAGTAGAGGCCTGACCTGCTTGAACGTCCGC<br>AGCAGCGAGCCCAGCATGAAGGCCGCCATGTTGTCCGCTACAAACTACAAACCGCTGAAACTTTATTGACACTGC<br>CGAATAGCGCAGGACACGAGGGGCGGGGCCTGGGCCGCCTGGGGCGGAGCTGGGAGGTGGGTGGGAATGTGGCCT<br>ACAGGAAAGCGGGGTTAGTTTTGGGATCGGAGCTCTCGCGATATTTCACGGAACTTGGGCAAATGACAAATCTGA<br>AGGCGCCGCGTTGATGCTGATGGCGCAGCCAGACCCGCCCCGTGTGTTGCAGCCCG<br>(SEQ ID NO: 157) |
| CGI: 58 range = chr1:196153712-196154414<br>CGTCTGGCCAAAGGCGCCCAGCTCAACGGCCGCGACGCGGTAAGGAAGGGCTCCGCCGCGGCGGTAGCCGGGCAC<br>CCCTGCGCCCTCTGTTAAACCAAGCCGACTCCCTGGCCGGTGGAGAACCGGAGCGGCGGGTCGTAGAGACGTCCG<br>CTTGAGGGTGGCGGGTGAGTTTTCTCCCGTCCACCTATGCCTACAGGGCTAAGAAACGGTCGTTTTTCTGAATCG<br>AAATGTCTGCAGCTGGCTATCCTCCGTCGCAGCTGATTCCGAAAGAGCAGGGAGAGGAACTGGGAGGAGGTGGGA<br>TGGGGGGTGGTGGCATTCTCTTCTACAGACCTCAAGGTTCCCTTGATTCCGGGGCAGGCGTCTCCCCGGCGAGGA<br>TCCGCAGCTCCGAGGGCAAGCTGGGCATAAGCAATAGGAGGACGGCGCGCTGCCGAGGCGTCCGAGCCAAGCAGG<br>AGCCCAGGTGGCCTTAGTCTCTGGGCCTGATGACCGGACCTGTGGAGTAGATTCCGACGCGACTGGGTCATTTCC<br>AGTTCTCTAGACGCTCGGGGCTTGGACCCCTAACCGAGAGAATCTCAGGGTTTCTGGCATCCCGACTCAGTCCC<br>TCTAAGGAGACAGCACTACGTTTAGCGCCAGGACCCGGCGGGTGTCATGTGTAGGGGGAAATCAAATAAAACATA<br>CGGAGGAGCGCGGCACCCAGTCGAAACG<br>(SEQ ID NO: 158) |
| CGI: 43 range = chr1:219117072-219117487<br>CGGCGGGGGTCGCTCCAAAGACTTGTATTTCGCGTTTGCCTCCGGGAGCTGGGAGTAAGGCCTTGGATGGCGCCG<br>ACGCGGTTGCGAGGAAGCTGAGGCCTGGGAGAGCAAGGGGCGCGCAGGCGAAGTTGCAACTTGCACTCCAGCCGC<br>GGGCCTGGCGGAGAAAGGGAGGCTCGCGGCGCCGCGAGGAGTCGGCGGGCCTCGGGGCCTCGCTTTCGCCGCATC<br>TGCCCAGCGCTCCGGGCCTTGAATCTCGGCAGATGCGAGTTGTGGGCACCTAGGGAACCCTGAGGACTCGCATTC<br>CCCCGGGTCTGTATCCCGTGCCCACCCCGGAGCGTCGCAAACCTTGGAAAGGGTGAAAGCTGATAGGGGAGTCTT<br>ATTTCTTAAGAGAGAGGGTGAGGGCGCGCGGCGCTGCCTCG<br>(SEQ ID NO: 159) |
| CGI: 25 range = chr1:241719037-241719368<br>CGGAAGAGGTGGACCGGCTGCGGACCCAGGTACTGTGCAGAACGCGGCGCAGGTGGGAGTCCTTGGGCGGGCGTC<br>TACAGGTGGATCTTTTATGCACCTCAACAGGCCGGCTTTCTCACGGATCACATCGGTTAGCAGTAAGCTGGGAGG<br>GAGGTCCCGAAGACTGTGCTGGGCACAGTGCAGGACCCAGAGAAGCGGAGCCATGGGCCCGTCCTGGTGAGGGAG |

TABLE 7B-continued

Sequences of differentially labeled CGIs between bladder cancer subgroups relative to blood TTAAAGTCCGTGCAGGTGAACAGACCCCGGCCCGCGAATCAACGAACCACACCGAGTGCCAAGTTGCGCCGTGCA
GGCTGCGGAGGGTGCGAGAGCAGGGAGAAGCG
(SEQ ID NO: 160)

CGI: 132 range = chr2:54536404-54537878
CGAACGCAACATCAAGGGCGAAAAGAGGCTGCACAAATCACGTAGAAAATTAGACCGCCTCTTTCCATGGCGATA
ATCGAATTAGCCTCAAATTAAACGTGAAATTGGCCCTCTCCGGCTGTGGAGACAAAGCCCCTATTGTCCTGCTCG
GGTAGCGGCAGCAGCAGTGCCCACCCCGCCCCGGCCAGCCTGGTCGGTCCCCGCCGCTGGGAGGATGAGGTCCGG
GCTGGACCCGGGAAGAGCCTCAGCTGGAGAGGACGTGGACGCGCCCGAGGCTCGGCTCCCTGGGCGGCTGCGGGG
CTCCGGGCAGGAGGAGAGGGCGGGCGAAGCAGAGGGAGCGGGCGGGAGTGGGGAGGGAGGAGTGCGGAGGGCGGA
GGGCGTGCGGGAGGGATCCCGGGAGTGCGCTTGTGTGTGTGTGCGCGCGCGCCCGCCCCGCGCGCTCCTCTCCCC
GCCCCTCGCCCCCTCCCTGCGAGCGCCCTCCTCTCCTCCTCCCCCGCCCCCCGCGCTCCCGCCCAGCCCCCGGA
ATCAGTGCCGCTGTTGCCGTGCAGGCTGCGGATTCCTCCAGTCCCTCCCTCGGCCGCCTCTCCTCCCGGAGCGAG
CGCGCAGCCCTGCGCAGCAGCGCCCACTGGTCCCGTCCTGTGAGCCCCGGCCCAGCCGCGGACAGACCCGCGGA
GTCGCCTCCCGGCCCACCCGCCCGGCCGCCGAGGAGCGGGAGGAGGACGGGACCCCGGCGCCCCCACCCCATCCC
CGGGAGGTAGGTAGGGGGCCCGAGGCAGGGAGATGCCAACTCACTGGGGCTGCCTCCCGGGTGGGCTCCGCGGCG
GCGGACGGGCGGGAGGAGGGGCGCGGGCCCAGGGCCGGAGGACGCCGCTGCCCGCCTGCCCTGCGCCCGGGGAGC
CGCGTGGGGGCAGGGAGGCTGCAAAGCCCGGGCGGGGGCGGCGCGGGGAGCCCGGGTCGCGGGTGCTCATTGGTA
CTCGGATGATGCGGGACGAGGGGCGGCAGGCTCTGCGGTGAGGCGGCAGCAGACCCGCCGTGCGCACCGCTGCCG
TCCGGCCCCAGCCCCGGCGCGGCGCGGCGATTCCTCCTCCCTGCCTCCGCCGGCGCCTCCCTGCAGCCGGGCGCG
GCGGCCCCTGACGCGGAGGCCCCTGGCGCGGAGGTGGGTGCGGAGCGGACAGCGGACAGCCGGAGGGTCTATTTT
CAGGTGCCCTCTCTGTGGCCCCGCGGGTGGGGAGCGGGGGCGGCGGTGACAGGGCCGGGCTCTGCGCGTAGCGGT
GCAGGGGATGCGGCCAGGCGTGGTCCCGGCTGCGCCGCGCTGCAGCTGAGCCGGAGGCGGCGGCCCCGCGCCCCC
ACCTCCGCCCCATCCCTGCGCTTGCTACCCTCGTGCGCCCGCCCCCCCCCGCCCTTTCTGCCGTCCCCACTCTC
CCAGGGCTGGGCGTGAGCCGCCTCCGGGCGCCGAGCCGCCGCTGCGCCCG
(SEQ ID NO: 161)

CGI: 77 range = chr2:73004709-73005568
CGCGTTCCCCCGCGGAGTGGCTCTCGAGTGCGGGGAGGTGTTGCGGAGGGGAGTGGACTTAGGGAAGGGGCGGCA
AAAGGGCAAAGGGAGAAATGGCGTGTGTGTGCGTGTCAAGGAATGGAGAGGGCAGGGCGCTTGGGAGCAGGGCGC
GAGGCCAGGCTCTGTTGGGCCCCGGCTCACGGCGCCCCTTCTCTCTGTCTGTACCTGCGTGTGTTGCCGTCGGCG
GCGGGGCCGCAGCCAGCGACGTGCCCCAGGACGGGCTGCTTCTGCACGGCCCCTTCGCACGCAAGCCCAAGCGGA
TCCGCACGGCCTTCTCGCCCTCGCAGCTGCTGCGGCTGGAGCGCGCCTTCGAGAAGAACCACTACGTGGTGGGCG
CCGAGCGGAAGCAGCTGGCCGGCAGTCTCAGCCTCTCCGAGACGCAGGTAATCACCCCCGGTCGCGGCCTGCCCT
GCGCCCGGAGCCCGGGTGGAGGTGAGGGTGCGCGGGTGCAGGAGAGGCCCTGAGCCCGCCCCAGCCCAGCCCTGC
TGGGTTCCAAAAGGCCCCCATTCCCCGCGGCGCTGCGGTCAAGCCCGTCTTTAGAGCCTCTTCCTCGAGACTGCG
TGCAGCCTGCTGAGCCCGCAGGACTTTTGTCAAGCGCTAAAGACCTAGCAGGAGGCAGAGTAAATGCAAACTGTA
TCCCGAGCCCGGCTCCCAAAGCTCCTCACGGGGGGACCAGGTTCCCTGGAGGAAGCGGGTCGCCTCGGGAGCGGG
CAGCGCAGGCAGCACCGAGGCCACTGGAGCTGGCTCCAGCCCTGGCATTCCTGCAGCCCTTTTCCCGCCACTGTG
TCGGGGCGCTCATAGTCCTGCGGGGAGCCGGTCCG
(SEQ ID NO: 162)

CGI: 221 range = chr2:85213468-85216104
CGGGGGTCGCGTTGGAACCCCACAGGAAAAAGGCGCGGAAAGCCGCCGGGCATTTTCCGGGGTTCCATAGATGTC
CCCAGTGTCCTAGTCCGTGCATCAGCTCGCGCACTCGGAGGGACTCTAGGCAGGGGGAGGGCCCCGCGGCCAGTA
TGTGCGTCCGAGGCTTTCCCGCAGGGGGCAGTGCCGCCCGCCCGCGCGCCGATACGGTGGGAGGGGGTGGGAACC
TGCGCGGAGTTCTGGAGGTTCTTGGGAGAAAGTTAGGGGATGCGGAGGGGTGGGCGCAAGACTTCCAGGACTCC
AGGGAGGCCGTGGGGAGGGCCGCCGAGGGTGCAGTGTGAGGCGCAGGAGGGGGTTGGGGGCGGTGCACGTTGCAG
GGAGACGCAGCCCCTGGAAGATGCGAGTGTGAACGTGTGAGTGTGAGTGCGTGTGTATGTGTGTGTGTGCGCGCG
CACCGCAGCTCTCCGGGTTCCGCGAGGCGCGCGGGTGTCAGCTTGCAGCCGGGGCTCCTCCCTCCGGCCCCCCTG
CCCAGCCCGGCGGTCCCTCCTCCCTCCCTCCCCGCTCGCCCCTCCCCGGCGGGCCAGGGGCTGGGACGCCCCGGC
GGAGCAGGCGGCGGCGGTGGCGAGTTGGGGAGCCCTAGGCTCGGCGCTGCCGGAGGGGCCCGAGCCGAGCCGCCT
GCGCCCCGGCCGGGCAGCGCCGGGCCCGCTTCCCGCGGGGCCACGCCCTGTCAAACTTTGTTGCGGCGGCTAGCG
CAGCGGGCCCGCAAGCGGGCGGGAGGGGCGCCGGGCCGGGCCGGGCAGGGCGCGGGCGGCTAGGGGCTCCGAGAG
CGGCGGCCCCGGCCCGCGGCCCCACCATGCCCAGCTCGGCGGCGGGGGCGGCGGCGGCGGCGGCGGCAGCGGGG
GAGGCGGCGGCTCCAGCGCCGGGGCGGCCGGCGGAGGGGACGACCTCGGGGCGAACGACGAGCTGATCCCCTTCC
AGGACGAGGGGGGCGAGGAGCAGGAGCCGAGCAGCGATAGCGCCTCGGCGCAGCGGGACCTAGACGAGGTCAAGT
CGTCCCTGGTCAACGAGTCGGAGAACCAGAGCAGCAGCTCGGACTCGGAGGTAAGGAAGCACCGCGGCCACCCCC
GGGGGATCCCGGCCCTGCGTCCGCTCACCCGCTCTTGCCTTTGTGTCTCCTCCGCAGGCGGAGAGGCGCCCGCAG
CCCGTCCGGGACACTTTCCAGAAGCCGCGGGACTATTTCGCCGAAGGTATGTGCCCGCTGGGACAGCCCCCCACT
CTCGATTCCCGCTGCGCTCCGCTGCTCAGCCCGGGCGGCCCACCGTCCCCCTTGCTTGGGTGGACGCACCCTTGC
CCTCCGCCTTTATTGGCGGCAGCCCCCGTGGGGCGCGCGTGGGGGGCGCTGGGGTCCCCAGCTCCCGCCTCGAGC
CCCCTGCCGCGGCGCTGTCAGTCCCGGGGGCCTGGGCCTCACCTCGCCTTGGTCTTGTTCGCAGTGAGAAGGCCT
CAGGACAGCGCGTTCTTTAAAGGACCCCCGTACCCTGGGTACCCCTTCCTGATGATCCCGGACCTGAGCAGCCCG
TACCTCTCCAACGGACCCCTGTCTCCCGGAGGAGCGCGCACCGTGAGTGCCCGTCGGGCGCGCCGGGGAGGGTGG
GAGGCCGCGGCCCGCAGGATGCGCCCCCGGGCTTGGCCATGGAGTGGGGATGGGGCCTTCTGCGCCGATCCCAA
GCAGAACTTGTTTGCGGAGTTGAACTACTCTCTGGCGGCCGAGCGCGAGGCTGCGCTGGCCAGTGCCTGGATGAA
AGTAAAGTTACTTTAACTTTTCCCCTCTTGCGGGTTGAGGTTTTGGAGTCCACCTCTGGGATCTTCCTTGGCCTC
CAGAATTCTTCGCCTGCACCGAAGGAAACTTGGATTTGTGCCCGCTTTGGGGGGGTCTCGCTTTCCTTCTTGGAA
ATCGGTCAGCTTTCTCTGGCAGTGGGGCAAGGGGCCTAGGGAGCTGGGTTGGCGACGTTGTCCTCCGACTCCGGG
TTCACTGGGCGGCTGCAGGCTGGTTCCTAAGAAACCCAGTTTTCGTGGCGGGTTATTCACAGCCCCCGTTCCCAC
CCCCAGCCCTCGCACCGGGGCCTCAGCTTTTCTGCGGAGCTAGCTCCGAATTTTAAACTCGCGTAGATGATTTCG
AGGCGACCCAAGGCATTCTTCAAGTTGAGGAACTTGGCTTTTTCCCCCTTTTGTCGCCTGCTTTTCTCATTTAAA
GCGAGCGCTGCGACACTTTAAACCTGTTAATGGGCGCGTATTGTGTGCTGCCCGCTGGCATTTAGAGCGGTGATT
AAGCAAATTGACCGGGCCCCAGACGACGTGCAAATGAGGGCGGATTCCTTCGCCCCCTCTCTCTGGCTCTAAACT
CCCGCCCCCCGCGTTGCGAGGGGCGCAGCTGGGGCTGGCGAGGCCTTTGTGTCCCCCAAGCCGCCACTCCACCC
CTAGGCTCCCTGCCCAGGTGCTGGGTCCGATGACAGATGTTGGGTGAACGCCTACCTACTGTGTGCCAGGTTCCC TABLE 7B-continued Sequences of differentially labeled CGIs between bladder cancer subgroups relative to blood GCGTGCTGCTGCTTGGGCGCGATGTGAATCGTAGTAGTTCTTTGCTTCCCGCCCAGATTCCCATTGCCTGCCACT
TCGCTGTCGACG
(SEQ ID NO: 163)

CGI: 173 range = chr2:119329502-119332035
CGAGGAGGCTGCAGGGACGCGCATGGAAGAGCCGGTGCGTGGGAGGGTTTGCGGGGGGGACATCGCGCCCCCTAG
GGGTGACCCCAGTGGGTCCCGTGTGCTCTCCGCGGAGCCGGCGGAGCCTTGTCCTCTGCACCCGGCGCGCAGCGG
CCCCTTAAACAGTGGAACCGTGAGGCCGCTCTAAGCCGAAGGGCTGGAATCTGGGTTTCTCGGGTTTTATTTTAG
ACCATTCGGCACCAAGCCCGAGCTCCCCCGCCGCACCGCTTCCAGTCCCCTTTCTTTCCATAGAGCGACCCGAAG
CCGGCGGTGGCGCAGGGAGCCGAGTCTGATGAGCTCGCGGGCGGCTGAAGGCCGGCTTCCCTGTGGGGAACGCGC
CACCTGTCGGCGCCAGTGAGAACTGCGTCTGTGTGGCGCCCTCGGGGTATTCGGGGCTGCGGGGAGATGTGTGCC
TGAAGCCCTGCGCTTGCGGTGGGGACGTCCGGCCTCTTTCCTGGCAATTGACCCCTGAGGCGGGAGAGACAACGG
AATTCCCACAAAGGGATCCTTCTCGGGATCTCCCCACCTCAAGACAGCTAAAGCTGGAGGAAAAGCCCCTCCGGG
GGGTGGGGGGTGCGGGTTTGCCCTGCGATTCCGAAAGCAGAAAATACCCGAGCCACACAGGGACGGGCGCCGCGT
TGGTAGTCGGGGCTACGTTCCTACTCCCTCTACCTCCCCCGCGCTGTGTGACCCTGGGCGGAACCCCGCTGCTCT
CTGGGCCTCAGTGTTCTTATTCGTAAACTGAGGGCGTTGGATGAGATTGGTCCTCTCCCAACTCTGACCTTGAAA
CTGATACTGAATCTGAGCAGCGTCTGTAGACACCTGTGCCTTGCCTTCTATTTCTAGCCTTGAATAAATCCTGGA
CTTTTATGTGCCATTTATATCCTAATCTCATATATATTTAATGTATAACTGCTGCCATTATTGTTTTCTCAATTG
TCTAGGTTTTCATTTGGATGGGGTTAGGATGGTCCAAATTATCCCGATAAGTGCCCATTAACTTAAACCTTTTTA
AAAAATGAAACCAGTAAAACTTCATTCACTTTGCAGTGTGGACACTGCTGGAGAGCACCCATGTCGTGGGTCCAG
CGAGGACACAAGGAGGGGCTTAGAGACATGCGGGAGGCTTAGATGAGAAGACAGCACCCGGGCAGCGGTCAGTGT
TAGAGAGAGGACCCGTAAGAAGGGCCGAGGCTAGAGGGAGAGCGAAGACTGAGCCAACGACGCACCTGAGCCCTG
GGGTGGGGGTGGAGACGTGGCTCCTAACCCAAATCTCCCTGCCAGGCAGTGTCCGACGAGCATCGACGGCAGGCG
TCGAGACCAGTGCAGGGTAGCTCAGACCTCAAGCCACGCTTGACCTTTCCATGAAATGAATAAAACTCGAAAGCC
AGGGAAAGGGGACAGTACTTTGATCCGGAGATCGCTTATAACCTCTGCTTGGAGTTCCGAGTTCGTGCGGCTCAA
GGGAGGCTACAGTCCAGCAAGCTCTGGGCTCCAAGCGTGGGGACGGCAGCCCCCAAGCTTGGCGCACCCCTCGGG
AAGCCCCGGAACGGTCCTCGCCAGACATAGCCGGCTGTCCTGGTCCTTAGCTTCAGGCTGGCGGCGCAAGGCCAG
AGCGGCTGCCTTCTAGGCACCTGGGTGGAGGTCTCGCATAGCATTCCCTGAGAAGCGAAACTGCCCTTGGGGCCG
CAGCGAGCCTGCCACATCGAACTGGAGACCCTCTGCTTTCGGGATAGATGGGACGTTTCTGCTCTGTCCTTCTTG
GAGTCCCGGAATCGTTCTGGGGCCGCGTGCTGCCTGGAGGCGGTGAATTTCAGGGTCTTGAGAAGCCGCGCACAC
ACGGGATTCTGGGCGAGCGTCCCGTCTCTTAATTCCTATTAAGAGACGGGAAAATCGAGGGACTGGAGGTCCCAT
CATTGTCGCGTGAGCAGCCTCCTGAACACCAAGCGAGACCTGAGGGTTCCGCTGGGGCCTCGCCCTGACACCCGG
GCCCTCCGTGTGGTCGAGAGTTTGCGCCCGCTCCCGCTAGGGCAGCGAGGTCCCACTTGCGGCCGGCTGGGGCAT
GGTGGCACCGGTTGTCTACTCCCCACTTGTGACACCGACAGCTTCCAACTCCTCAGACCCACCCCGTGGAATTCT
GGACTTTGTGAGGGCCGCCGGGGTCCTGGCCCTGGGGTCAGCTGCCATCTGACTAAGCCAGGACGGCGGAGCTCC
AGGCCTTGCTCCAGCACTGCCGGTGCGTCGGGGCCCGCGGAGAGCCCAGGGCGGGAGCTGTGGGCTGAGCCGGGT
GGCCGCGTGGACACAGATGCCCGGCCGGACTGAGCGGCAGCCAAGACTCTCCGTCCATCCCGCCGCTGGACTCGA
CTCTCCCAGACCCGCCACGGAACCCAGATTTGAGCACGCAAGATAAAGACGCCAGAGGCGAGTGCGCGGCGGAGA
ACTGGCCGCGACACGGGAAGCTTCTGGGGCGCAGAACGCTGGCTCCGACTCGCGCGGCG
(SEQ ID NO: 164)

CGI: 36 range = chr2:172653235-172653630
CGACGGCGCGCTTGTGGCCCGGCCGGAGCTTGCGTGCGCGTTCTGACGGCTGGGTGCTGTGTTACAGGTCGGCGC
AGTTCGAGCACACGGTTCTGATCACGTCGAGGGGCGCGCAGATCCTGACCAAACTACCCCATGAGGCCTGAGGAG
CCGCCCGAAGGTCGCGGTGACCTGGTGCCTTTTTAAATAAATTGCTGAAATTTGGCTGGAGAACTTTTAGAAGAA
ACAGGGAAATGACCGGTGGTGCGGTAACCTGCGTGGCTCCTGATAGCGTTTGGAAGAACGCGGGGGAGACTGAAG
AGCAACTGGGAACTCGGATCTGAAGCCCTGCTGGGGTCGCGCGGCTTTGGAAAAACAAATCCTGGCCCTGGACTC
GGTTTCCCAGCGCGGTCAACG
(SEQ ID NO: 165)

CGI: 295 range = chr2:174907710-174910885
CGCCCTCGCCCCCCCCCCGCAAGTATCCCCCACTACTCCCCCCCACCCCCGCGGCCCTAGCTAGCTGACTTGACT
GGCACGCGCCGGGAGCCCGGGCTCGGGCCCCTCGGAGCGTCTGATTGGCTGCGGGGCAGCTCCGGTCTGCTCTGC
CTGCGCCCTCATTGGGCGAGAGGCGCAGCCAGCGGCACTTCAAAGCGGGTGCTCCTCGCACTTAGGCTGAGTTTA
GCCGGCGGGAGCCTGGAGTCCGCTCGGCACGAGCGCGGGGACGCGGGAGCCGCGCGGGACCCAAGCAGTTTTTCC
GAGCAGCCGCCAGGCTCAGCCCCGCTCCCAGCCTCGCTGCGCAGCCAGAGACCTGCTATGGCCACGTCTATACTC
GGGGTAAGTCGCAAGCGCGGCAACGCATTTGCTTGTTTTAACCGGAGTAATTTTTCGTTATGGCTTCTGGGGTCT
GCGGCTCCGGAGAAACTGTTGCTGCTAGACTGCAGCTTCAGCTTCTATTAGCACTTTCCACATTTCTGGGACTGA
TTTTTCCCCAAGTTTTTGGAACCCAGAAAGATGCCTTTGCAAGAAAAGGCCTTCTTAATCAAGTCCTTTTTCATT
TGGTTTCAAAAAAAAGCTAGAGGTTTCTTTTCTTCCCCTCGTGATTTATACCCCATCCCCCGCATTGCTTTGGGG
ATTTTGTTGCAATTATGCGACAATGGTGTTTCCAGAAAACAGTCTTAATCGTTTTGCAGTCCATCTAGTCACGCT
AATAAACATTTACATTTCCGCGGCTCCCCAATTCGCCCATGACTTTGAAATCTGTCTCTGGCCGCTTATCCTCGG
ATTATTGTTTTCATAATCGCTGTTTTTGTGTGTATGTAAACTTTAAAACCAAACGTTTTCTATTAAAAAAGAAAA
GTCAAGTCGTAGCCACCCTGGGAGAGCTGCAAGTTTCGCCCGTCCCTGGCAGCTGTTTCGGCCGCCTCCGCCCTC
ACCCGGTGTTTGTTGTCTCTGGTCTCTGTGTTTACCTTCGCGCTTCACCCCGAAGGGCGACTTGGGGTCTTCTGG
GAGATGAGCCGGTTTACGGCGACAACCCAAGTCCGGTTGTAGGCAGGGTTGCAGCGGGGAACACGGAGGCATCTT
TGATTTATAGCCTCAGCGAAGTGCAACTTTCCGGCGCCTGGACCTTCGCCCGGGTGATCGCCCCTGCTCCGCGCC
CGGTGCGGCGACTCCTCCGCGGGCGCGTGGGGAGGAGGCGCGAGGCGGGGAGCCAGGACCCCCCGGGAGCAGCCG
CAGGGGACGAGGCTGCTCACGGGTGCACTTTGTTTCTTCCCCCACTTCCTCTTGCCCTCCTCCTTCTTGCTCCCT
CCCCCATCCCACCCACTCTAGGAAGAGCCGCGCTTCGGAACGACCCCGTTGGCCATGCTGGCGGCGACCTGCAAC
AAGATCGGCAACACGAGCCCGCTGACGACGCTGCCAGAGTCGAGCGCCTTCGCCAAAGGCGGCTTTCACCCCTGG
AAGCGCTCCTCGTCCAGCTGCAACCTCGGCTCCAGCCTCTCGGGCTTCGCGGTGGCCACCGGGGGCCGTGGCTCG
GGCGGCCTGGCGGGCGGCTCGGGCGCCGCCAACAGCGCCTTCTGCCTGGCCTCCACGTCGCCCACGTCGTCCGCC
TTCAGCAGCGACTACGGCGGCCTCTTCTCCAACTCGGCGGCTGCCGCGGCGGCAGCGGCCGGGGTGTCCCCGCAG
GAGGCGGGTGGCCAGTCGGCCTTCATTTCCAAGGTGCACACGACGGCAGCCGACGGGCTGTACCCGCGCGTGGGC
ATGGCGCACCCGTACGAGTCCTGGTACAAGTCGGGCTTCCATTCGACGCTGGCGGCCGGCGAGGTGACCAACGGC
GCGGCGTCGTCGTGGTGGGACGTGCACAGCAGCCCGGGCTCGTGGCTGGAAGTGCAGAACCCCGCTGGGGGGCTC TABLE 7B-continued Sequences of differentially labeled CGIs between bladder cancer subgroups relative to blood CAGAGCTCGCTGCACTCGGGCGCCCCCAGGCCTCGCTGCACTCGCAGCTGGGCACCTACAACCCCGACTTCAGC
TCGCTCACGCACTCCGCCTTCAGCTCCACGGGCCTCGGCTCCTCCGCCGCCGCCGCCTCCCACCTGCTCTCCACC
AGCCAGCACCTGCTGGCCCAGGACGGCTTCAAGCCGGTGTTGCCCTCCTATTCGGACTCCAGCGCCGCCGTGGCA
GCCGCCGCCGCCAGCGCCATGATATCGGGCGCCGCGGCTGCCGCCGCCGGGGGGAGCTCGGCACGCTCTGCCCGC
CGCTACTCGGGCCGCGCCACCTGCGACTGCCCCAACTGCCAGGAGGCGGAGCGGCTGGGCCCGGCCGGGGCGAGC
CTGCGGCGCAAGGGCCTGCACAGCTGCCACATTCCGGGCTGCGGCAAGGTGTACGGGAAGACGTCGCACCTGAAG
GCGCACCTGCGCTGGCACACGGGCGAGCGGCCCTTCGTGTGCAACTGGCTCTTCTGCGGCAAGCGCTTCACGCGC
TCGGACGAGCTGCAGCGGCATCTGCGGACTCACACGGGCGAGAAGCGCTTCGCCTGTCCGGTGTGCAACAAGCGC
TTCATGCGCAGCGACCACCTGAGCAAACACATTAAGACGCACAACGGGGGCGGCGGGGGCAAAAAGGGCAGCGAC
AGTGACACGGACGCCAGCAACCTGGAGACGCCCCGTTCCGAATCCCCCGACCTCATCCTGCATGACTCCGGCGTC
AGTGCCGCCCGGGCGGCGGCAGCGGCGGCGGCGGCAGCGGCGGCGGCGGCGGCGGCCTCCGCGGGAGGCAAG
GAAGCAGCGTCTGGCCCCAACGACTCTTAGAGGCCGGGCGAGAGGCGCGAGCACACAAGCGAGTAGAGACACCGA
GAACGAACGAGAGGTTCGGAGGGCGAGCGAGCGGGAGGCGGGAGGGCAGGGGCTTCAGTGACGCCCCCAGGGCCC
GGGCTGGGCGCGAGGTGGAGCCGCTCAGGGCTCCCGGGCTGCGGTTCGCCCGCTGTGCGAGGAGCTCCCCTCTGC
CTTCCGCGCCCGGATAAGAATCGAACGCGTGGTCCGGAAACAAAAGCGAACCATCCTCCGACACAAACACTTTAA
AAACTGTACTCCCAGACGTACACATACACCGGAGACCTACAACCACAAGCACGCACACTCGCGCGCGCACACACA
TACCACTCGCCCAAACTTCTCGAGCG
(SEQ ID NO: 166)

CGI: 289 range = chr2:176652334-176656692
CGAAAAGGAGGCGGCGCAACGGCCACCCCTTCCAGCACCTCGGCTTTGTCCTTCCCGGGGAAGGCGGCCACATCC
CTACCCGCCTTGCTCCTGAACGTAGTAAACAATCTCACAAACAACCACCGCTGCCCACGCTCTCCATCCGTCCTC
CCGGCCTTATCAGACCTCCGTTCTCCCGCACTCTTCGGGCAGGGTCCCTAATAAGCTCAGGCTGAAAGAACGTTT
GCCACCTCCCCCACCCTCGTTGAAAGAAAAGGAAGAAAAACAGCAGCAGCGAGAAACCTCCGGGGCGACTCCTCC
CCCGCCCCCAAGCACCAGCGCACAGCATCCCCCTCTGTCTTTGTTGTGGTTCTCCGTTGCTTCGGGCCACGCCGT
TCAGCCAAGCAACCCGGACCTGAGAGTGCACAGCCAGGACTAGCTTAGGGGGCGAGGGGTTGGTCTTTGGGAAAC
CAAGCGCTCAGGACAGAGGTGGAAAGTGGGTCCCGGGAGCCAGAAAAGAGAGAGAAGGGCAGACGGCTGGGTGGC
AAATACAAAAATAGAAATAATTTAGGGGGATGCCCGCCAGGCTTTTGCGCCTGCTCCTTCTCCCCCAATTCGGAG
CAGGTTCCCTTCGGCCTCCCGCGCCCCGGGGCGCCCCCTGGCGGCAGCGGCAGCAGCGGGCAACGCGCGGAGGGC
TCAGGGGGCGCACAGGGGACTCCCGGGCACACTCAGAGAGGCGGGCGCGGCCCCCTGGCGGTGGCGACGTAGTTA
TCTGGTGAGCGGAGCCTCGTCCCTCTGGTCCGGCGGGCTCACGGCCGTCTTACTAAGCACCGCGGCCGAGTAGGG
CAGGAAGCCGCTCTCGGAACGCGGCGCCGCCGCGCTGCAGCCGAAGTCCGAGCCTCCCCCGGCCCCGGCGCCCCC
GCCGCCGCCGCCACCACCACCACCGCCGCCGCCACCGCCACCCCGGGAACCCAGGGCTGCGGCAGCTGCTGCCGC
GGCTGCCGCCGCCGACTGACTGCTGTGGCAACTGAGGCACGAGCAGGGTGCAGAGCCGCCGCTGGGGGGCGCGCC
GGCCGCCGCCGCCGAGGAGGCCGCAGCCGCTGCGGCTGCCGCGGCTGCCGCGGCAGAGGCCGCGCTGTTGAGCCC
CGCGGCGGCCGCGGGAGCCTGGTAGAGACCAGGGTGGCGGAAGCTACACAGCAGCTCCGGCCGAGAGTAGGGGTG
CGAGAGGGCGCGGAAGGTGTCCAGTGGCCGGATGGAAGTAGCGAAGGGCGACGAAGCCGCGGCCGCCGCGCCTGA
GGCTGCAGCCGCGGCCGCCGCCGCCGTGACGCCCACGTGCGGGTAGTAGTGCAGCGGCACGTGCGAGTGGAAGGG
GTAGGGCAGGCTTCCGGTGGCGGCCGCGTGCGTCATCATGTAGGTGTAGAAGCTGGGGTCGGCTGGGTGCGGCCA
GGACATGGCCAGGCGCTGCCGCTTGTCCTTCATGCGCCGGTTCTGGAACCACACCTGCGGGGAGAGACGCGCCGC
AGCCTGGGTTAGGGAGCGCCCCGTGTTCCCAGCTCCTGTCCCAGGACCTCTGCCCCTTCCGGACCTCTGAATGGC
TTGGTCTACTTCTCTCCGACCAAGCCCAACCCCGAGTACCCTGTGGTCTCCCAGCTGGGAAAGTGTGGACGGCAG
TGTGTGGACCGCCGTGGGCACACCGTCCTCAACGAAGAGGGTCCTCTCCCCCGCGTCCGGCTGCTGCTGCTCCTC
AGGCTTTTATTCCCTTACTTCTTGCTGCACTTTTTTGTCCCAATCCAACCTTTCCTCTCCCTCCCGCCACCCACC
AGTGCCGGTCTCGCTGAGCACCCGTCTCTCAATCCCAGGATTTGTACGGGGATTCTGGGCAGCCTTTGAAGAGAG
GCTGCCGCTCAGCTTTTCTGAGAGGTCGCCGCGCGAAGTCTTGAGCCCTCCGAACTGCAAGGACCTGCCCCTAGG
GGCACGGGTCCGATTTTGATATTGAAGGGATGATTTTGTTGGAATCGTTTGCCTTAAATGAGTGGGTAGAGCAAT
GTCTCCATAAACGGGGAAGGGGACGTTTCCACCCCTCCCAACACTATCTAATAAAGACATCATTCGTCACAACTC
TAAATTAAAGAAAGCCCGATCAAACCAGAGGGAGACTTCCACACTCCTCCCCTACCCCGTGGAGATTTTTTCTTT
TTTCTGCAGTGTCGAACGCTCCATGAAGGGCTCACCAAATCGCCTAACCTCCCGGCTATCTCTCCCAGACGTATA
ATAAAATTAATAACCTAAAGTTATATATAAATAAGGACAATTTCGTTGCATTTTTCCCCGCAGGAGGTTGCCCTT
TTTTCGTTGCCCAAGAGGAAAATGTTCAGGAAACTACTGTCTCAAACCAATCGATTTTAAAGATACAGTATCCTT
TTCTCCGTGTAACGATTTATGCGGAAAATAAATCTCCAAGCTCAAGAGCAAATGAAAAGTTTCACCTCTGGTTCC
TGCTTGAGGAACAAAGACCAACTGGGCTTGCCGCCTAGGGGAAAGTGGGGCCGTGGGTATGGGCGAGGGGGCATC
TGGCCAGGCGTTGGGCACAATGGAGCAGGGGCGAGTGCTTTCAGCATTGGAGTCACCATTCGGGGGCCTTCTTAG
ATCCGTCAGGCCGGACAACCGTTCGGATTCGGTGGCCGGGAAATAAATAAGCCAATTCCTTTGGTGACTACCCCC
CGCGGATTTCCAGACCCTTAGCTAAATCTAGCCACCCAGAAAGGGGAAAGGGGAAAAAGAAACAATCAACCCAGA
TGCCCCCGGGGAGGCCAGAGCAGGCATGCACTGGAATTGATACCTTGATGGTGGTTTCGGGCAGGTTGAGTGCCG
CGGCCAGCTCGCACCGGCGGGGCCGCGACACATAGTTCTCCCGGTAGAACTCCTTCTCCAGGCGCGCGATCTGCT
CGCGGGTGAACGCCGTACGGTAGCGCCGCACTTGATCCGCGCCAGAGCCGGAGCCACCCAGCGCCGCGCTCCCGC
CGCTGCCTCCGCTGCCTCCATGCAGGCTTCCGAGGCCTGAGCCCGACGCCGACGTCGTGGTGCCGGCAGCCGAGC
CGCTCTCTGCGTACCCTGGCAAACAAACGACCAACAGCGCATGAGTGGCTGTAGGACCAACAGCCCGGCGCTGGC
GCTGCGCGCGGATCGGGGAAGCCCCGTCAGGAAGGAGAGTCGCTGCCGGAATTGATGGGGTCTGTCATGCTTACA
AATTGCTGCCGTTAATGGAATCAATAAAGTTTGGGGAGCCCTTCATAAGCAAATAATAGAAACGGAATTAGGAGA
TTTCTTTTTTAATAATTAGAAATTTTCAACCAAGGAGGAAAAGTGGCCGAGGGAAAATGCCTACCTCTGGGCGCA
GTTTGGGAAGCTCTGGGTTTCCCATGGTCTGGAGACCGCAGGGCAGCTTTTTATACGGCCTCTAACCTTTATCTG
AGTCTTCGGGGTTTCAAATATTTTAAGAGTTCCAACACAGCAGTAGCTCAAACCCAAGCCAATAGGGGGTGAAAT
ATACTTTTCAACTCTTTCTCCCGCTGACCTAAACAGAGACGCCGGCGAGGCTTCCTCCGACTTACCCAGAAGAAT
GCCCCCTCCAGCCCTGAGGGCACAGGGGCAGGGGAGTTCAGAGTAGTTGCCCAGGGTACCTTTCCCAAAAGCAAC
TCGGCTGCTGACTAGGGGTCTACCGGCTCGCTCGGGCTCTTAGACACGAGCGCAGAAACATTTTCTCGGACTCAG
GAGCGAGGGCGGGTGGGCCTGGTGTTCCAGGCTCCGCAGGCCTGAGCCTGGCGGGAAAGCTCAAGGAGCAGAACT
GGAAGGCACGGTCCCAGACATGCGTCCCGCCCCCGCCCGTGCTAGCTCGGTGTAGCTTGCCTGTGGAGGGTCTGA
GAGGGGAAAAGGCACCGGGAAAGGCTGGCGGGGGCCGCGGAGGAGCAAAGAGGATGGGACTGGAGAGCGCGGTGC
GGCCGGCGCGGTTACCTTTGCCATTGTTTTCCTTAAGCTGAGCGGCGCCGAGGCCCCCGGGGGAGCGAAGCGCGG
AGCAGCCCACCTCCACGTCGCTGCTCATGTCGGCCTCAGCGGCCGCCTCTGAATAATGGCCCGGCTTCTTGCGGC
TCTCGGCGGCGGAGGAGATTTCGGAGGAGACGGTGCTTTCGCTGCCCGTGTGCTGCAGGTTGAACAAAGTGTCTA
TTTCGAATTTGCCCTTGGCGGGGAGTTCTCCCAGAGCGCTGTGCAGGGGGGCAGACGGCAGGCGCGGGCTTAGGC TABLE 7B-continued

| Sequences of differentially labeled CGIs between bladder cancer subgroups relative to blood |
|---|
| GAGCCGGGTGCTGCGAATTTTCCAGGGCCTCGAGCACAGCATTGCCAGCCGAGTTGGACAAATTGGAGAATCTCT TGCCCGCCG (SEQ ID NO: 167) |
| CGI: 25 range = chr2:176720618-176720921 CGCCGCTGTAAGTACCTTCCCGCTTCTTCCGAATCGCGAAGAGACGGTACTGATCGCGGGGAAGTGGTGGGCTAA GGGGCCAAGCCAGCGGAGTGGGCGGATAGAAGAAAGGCCCTGCCTCCCCCACCCCACCCCCACCCTCCACCCCCG GCCTCGCTCTGCGAGGTTAGCCCGCTTCGGGAGGTGGAGGCGCTAAATCGAGGTCCCGGAAAGCTTTTCTGGGGC CTGGTTCACAGACACCTGCCTGAGAGAACGGTCCGCGGGGTCTCGCCCTTGTCTCCTTGGGCCTCCCTAGACCTT CGCG (SEQ ID NO: 168) |
| CGI: 20 range = chr2:236438623-236438823 CGAATCCAGTCCCGGCCGGCGCTTTGAAGCCTGTGCTGTGCGATTTTCTCAGCAGTGAGGTAGGAATAGACGCGG CTAATGACAGGAAGGTCGCGCGGGTGAGCTGACCTGTGTGTGGCGCAGCCTTGGGTTCCGCAAATAGGGCACCCA CAGTAACACGTGTGGCGCCGACCCCGCCGTGCGCAATCGGGGCTTTATACG (SEQ ID NO: 169) |
| CGI: 22 range = chr3:11721578-11721824 CGATGGGACCGCGGCTTGACACGCATTAAGGAGCCACTGAAAACTCCATCTAAGCAGAAAAGCGGCTTAGTCATC CATGCGTTCTGGGCAAGTTATCCTGGCCGCACCACGTGGAACGGAGTAGATAGAGCTCGGGAAGCTGAGCGCAGG GCGGACAACGGGAAGGCCAGAGCCGTGGGCAAGCACGCGGAGGGCAGCGAGGGGCACTGGCACCGGAGCCGCGGG GAGGCAGGAAAACGCAGAGGCG (SEQ ID NO: 170) |
| CGI: 68 range = chr3:12983649-12984210 CGCTCCTGTCCCAAGGGCGCGTCTCTCTCTCCCACGCACAAACTCGGGTCCTGTTTGCTCTTCTCTCACCCAAAC CCACAGTCTGGCGGACGCACCCCGCCCCGCAGGCAGCTTTCTCTCGCACGCCGGGCGCCCGGTCCCGACGGTCAC CCGCACTCCCGCACAGGCATCCCCACAGCCTGCGCCAGCCCACCGCTCAGCACCCGGGAAGGCCGCTCGCCCCGC GCCGCGCCCTCACCCGCTGTCAAGCTCTAGCTCCAGAAGGGACTGGGTCCTCTCCGAGTTGCAGTGCAGGCACCA CATGGCGGCCGCAGTGGGAGCGGGCCGGGCCGGGAGCCGGGACCCAGGCCCAGCAGAGGCCGCCGACTCCCGCCA GCGAGCCGCCGGATCCCGGGGCCGACACCCGGCCACCCGGAGACCCGACCACCCGCCACGCGATCACGTCGGGGC TCCTGGTCCAGCGTCCGCCGGCTCCCGCGGCTCCGGCCCCAAGTCCGAGCCCCAGGCCAGCCAAGCCCGCCCCTC CGCCGCCGCCCGCTTGGCGCAGCGCGAGGCCGGGCCG (SEQ ID NO: 171) |
| CGI: 120 range = chr3:25680561-25681574 CGCGGGGAGCGGGCTGGAGGATTCTGCAAGCACAGGCCCCTATGGAGCGCCCGTTCGGGGGACGGGATTTCCCTC CCTTTCCCCTCCCCCGCCCGTTCGGAATTCCGCCCCCGCCGCGGGCCCGGAACAATGCAGCCGCCCGTCCCGGGG ACCAGCCACTTACCACCCAGGTCAGTGCCCCGTTGCCGCCGCCCACGCCGGCTCCCGCGCCGCAGCCACCCGACT TGGCCATGGCGAGTGCCTCCAGCTCACAGGCCCTGAGGCCGCAGCCGCCGCTCCCGCCTCCCTGCGGGCCGCTGG GCCCCGCCGCTCCGCACCCACCGCTCCACTCGCCGCACTCCTAGCCGCGCCGACCCCCGCGCCCCATCGCGAAGA TCCGGAGCGGACGTCCAGCCGAGCCCGCTGAGGAGGCCGCGCCGCCGGCTGCCCTCAAACTCGAGGCGCGGCGTC CGCGTCGCCCGGGCCTAGCGCGGCGGCTGAGGAGAAAGCAGGGAGCGACCGGCGGCGGCCGAGCGGCGGCGTTGC CTTCTCGCCCGCCCGCGGGCGCCGCTGCAGGCCGGGCTGAAGCCCGGGCGTGCGAGCCGCGAGGGCGGCCGGGGA GCCCGAGGCGCTCGGACGTGGCGAGGACGCAGAGGTGCCTTGTCCTTCTCACACTCCGCGAAGGCCAGCCACTCG AGTCGCCAGAGTAGTCGTCCCGGTCGCCGCCGCTGCTTCAAAGGCAGCCTTAGCCTCGCTGCAGCCCCGATTTCC TCACACACACACACCGAGAGGGACAATAAACAGAGCCGCCGCCGCCGCCGCCACGGTCACCTCCCTCTTGTCCGG CATAACACCGCACACACACATTTGCACACCGGGGAGAGAGGGAGGGCGCGGCGGCCGCCCCCGCTGTCAGTCAGC GCCATGCTGTCCAATCCGGGCCTTGTCGCCACAGCCTCTCGGCCAATCCCAAAATTCCAAGCCCCCTGGAGGGGC GGGACCCGAGGGGGGAAACGTCATTGCGGGTAGCAACCG (SEQ ID NO: 172) |
| CGI: 23 range = chr3:148613030-148613264 GACCGGCGCTTCGCTAACAGCAGCGACCGCAAGAAGCACATGCACGTGCACACGAGCGACAAGCCCTATCTTTGC AAGATGTGCGACAAGTCCTACACGCATCCCAGTTCGCTGCGCAAACACATGAAGGTAATCGCCGCACTCTCGTCG CCCCCTTTGAGGCAGGAGCTCTCTTGGCTCTCGGCTTGGGGTCGGGCGGCGAGTGGCAGACAGGCGGTGGCGGGA GCCAGAGGAA (SEQ ID NO: 173) |
| CGI: 41 range = chr4:4910534-4911092 CGGGCAAACCTCCGGAGGCCCCGGTGCACCGCGCGTCCAGCCGGCCCAACTCGAGCTAGAAGCCCCAACCACTGC CCAGTGCCTGAGTTGCAGTCTTGGGTCCTTTAGAAACCTGGAGATGTGCGTAAAATTCAGATGCCGGTATTCCCG AACTTCCCCAGGCCTCAGCATATCTCGGCGGCCTGTGGACAGATGGGAGGCTACCAATCGCTCCGGCGTCCGCAG CCCGACCCCTGCCGCCAGACCCCGGACGTCTTCCGGATAATAAAGTTCCCGCTCTAATTCATTTTCCCTAATCTG GACGCCCCTAATCTACAGCTTTTATTGCGCCCAGTTAAAAGTCGAGGGAATTCGCTGTCCCTCCGCGCTCGGATA ATTACCCCTAAATGGCCACGGCAGCCCCTTGTGTTTCCTGGAGATTAGAACCCCGCAGTCATCAATGGCAGGGCC GAGTGAGCCGCCAATCACCTCCGCTCACTCCCTGAGAGCCGCTGGCCTGGGCCGCAGGAGGAGAGGCCATAAAGC GACAGGCGCAGAAAATGGCCAAGCCCCGACCCCG (SEQ ID NO: 174) |
| CGI: 300 range = chr4:30330303-30333940 CGAGCGCGGCGGCTGGCTGACGCTCCCTCCCGCCTCCTTATCCCGGGCCCTCCTCCCTCGCTCTCTCCTAGTGTG TAGTTTCGGCGGCTCGGCTGCTACTGCCGCCGCCGCTGCAGCAGCAGCGTCAGGGACAAGCCTGATCCGTGAGCG AGCGAGCACCCAGCAGCAACCACCACTTTGGGCAACTTGCGGGTTTCCTGCTCGCGGGTAGCGAACGGGAGATTC CCACTAGCGGTTCAGTGTCTCCGAGCCGCTGCAGCCCGAGGGGCGGCGGGAGCGCCCGCACCAGACTCTCCCAGA CGCGAAAAGGGACGAGACAACTGCGGAATTCACCAGCCGTGCCAGGGCACTTCCGAGGCCACAACCGACTGACAC |

TABLE 7B-continued

Sequences of differentially labeled CGIs between bladder cancer subgroups relative to blood TTTTTCTCCCCTTGGCAAACTGGATTTTTTTTTTAAGCTACTTGGCAGCTGTCTCTGACTCCACCTCCCCCTCC
ACCCCCGCCCGAAAGCCTTTGGCTTTTCTTCGGAAATCCAGACAGAATTGGGCATCTTTGTTAATTGCCGTTGGG
GACGCCCGGCCGTGCGCTTTCGCCGGCTAACGTCGCCTGTGCTCCGAGCCTGGTTTGCTCACCTTTGAACTGCAA
AGGGATCAAGTTCAGCTTGAGTTCCCTGCATTGGGAAGGAGAGAGAGCGTGCAAGAGAGCGAGTGGGAGAGGGGG
AAAGGGGAAAGGAGAGGAGGGAGGAGAGAGAGGAGGGAGGAGAGAGAAAGGGAGGGAGGGAGGGGAGGGATCGAG
AGAGAGCGGGGAGAGAGAGGCTGCAATCTCCTCCCTGAATCGCGCACAGCGCTGCAGATCCCACTGCTCCGACAT
GCGGGCCGAATGCAGGTGAGAAAAGGCACGGACTCTGCGGCTGCGAACCCAAACTTGGGCACCGCACGGTGCGCA
CTGCTCAGCCTTCGCCCCCGTGGGCGAAAGGCTGCTGCGGTTTCAGGCGGCTGCTTCGTGACTAATGACCTTGCG
CAGAGTTGTTAAGAAAAAAGAGAAACCCGCGCTCTCCGGGGTGAGAAGGGACTGACTCTGGGCGTCTCTGAAGAT
GGCTCGGGCTTCTCTTTGGCGCGCCGGGGGGACCCTGACACTGACCGCTCTGTGACGCGAGTAGTCTCCCCTGCA
CCGTGCCCGAAGCGACGTGCCGGGGGATTTTTCATTCTCGATCTGTTGACTGGCTCCCCCGCTGCATGAGCAGAG
TCGGAGTTGAGACTGGCTTGTTGCTGGCCCCAGCGCCTGGTGCAGGAAGCGACTCACGTTTGTCTGGGTGGCCGG
AGCCGGAGCAGAGCCTGGGTTTGGAGTGAGTGCCTGGAACGTGAATTGGACTCAACTCGAGTAGCAGCAAAGACC
AGCGGGCTGGCAGGCGGGGGAGGCTGCAGGCTCATTCCCCACCTCTTCCCAGCCCCACTGCCCGTCTGCCGGAGC
GGTTCTGGCCCCTTCCGACAGAGCGGGGACTAGAGCCGGGGATTCTCCGCCCGCTGAGGGGATGACTCTGGGTTG
GGGGAGCGCCGAACCCGCGGCGCGCAGTGTCCCGTGAACTGTGAGTACTGCGACTGAACGGCGGCAGGCGAGCGG
GCGATTAGCACCCATTGCATGAATTATGAAACAATAACTTTCGGAAGAAGCAGGAGGAAAAAAAGAAGCATCTAT
CGCTGCCCTCCCACCCCCATTCCCGGCCAACTCTCCACGCCGCTTTTGCCCCCTCCCTCCCCTCCCTCTCGCTCC
TTCCTTTCCGGGAGAGGGGAGAGGACTCGGGGGAGGGCAGGCGGCCGGCCCCGGAGGAGGGGGGCGCCGAGGGGG
CTGTGGTTAGAAGGAGCAGTAGCAGCAGCAGCAGGAGAAGATGCTGAGGATGCGGACCGCGGGATGGGCGCGCGG
CTGGTGCTTGGGCTGCTGCCTCCTCCTGCCGCTCTCGCTCAGCCTGGCGGCCGCCAAGCAGCTCCTCCGGTACCG
GCTGGCCGAGGAGGGCCCCGCCGACGTCCGCATCGGCAACGTGGCTTCAGACCTGGGCATCGTGACCGGATCGGG
TGAGGTGACTTTCAGCCTGGAGTCCGGTTCCGAGTACCTGAAGATCGACAACCTCACTGGCGAGCTGAGCACGAG
CGAGCGGCGCATCGACCGCGAGAAGCTGCCCCAGTGTCAGATGATCTTCGACGAGAACGAGTGCTTCCTGGACTT
CGAGGTGTCGGTGATCGGGCCCTCGCAGAGCTGGGTGGACCTGTTTGAGGGTCAGGTCATCGTGCTTGACATCAA
CGACAACACGCCCACCTTCCCGTCGCCCGTGCTCACGCTCACGGTGGAGGAGAATCGGCCGGTGGGCACACTTTA
CCTGCTGCCCACAGCCACCGACCGCGACTTCGGCCGCAACGGCATCGAGCGCTACGAGCTGCTCCAGGAGCCCGG
AGGCGGCGGCAGCGGCGGCGAGAGCCGGCGCGCCGGGGCGGCCGACAGCGCCCCCTACCCCGGGGGCGGCGGGAA
CGGCGCGAGCGGCGGCGGCTCGGGAGGCTCCAAGCGGCGGCTGGACGCATCAGAGGGCGGCGGCGGCACCAACCC
CGGCGGCCGCAGCAGCGTGTTCGAGCTGCAGGTGGCGGACACCCCGGACGGCGAGAAGCAGCCGCAGCTGATCGT
GAAGGGGGCGCTGGACCGCGAGCAGCGCGACTCCTACGAGCTGACCCTGCGAGTGCGCGACGGCGGCGACCCGCC
TCGCTCCTCGCAGGCCATCCTACGGGTCCTCATCACCGACGTGAACGACAACAGCCCCCGCTTCGAGAAGAGCGT
GTACGAGGCCGACTTGGCTGAGAACAGCGCCCCGGGGACCCCCATCCTGCAACTGCGCGCAGCCGACTTGGACGT
GGGGGTCAACGGGCAGATCGAATACGTGTTCGGGGCGGCCACCGAGTCGGTGAGGCGGCTGCTGCGCCTTGACGA
GACGTCCGGCTGGCTCAGCGTCCTGCACCGGATCGACCGCGAGGAGGTGAACCAGCTGCGCTTCACGGTCATGGC
CCGCGACCGCGGGCAGCCCCCCAAGACCGACAAGGCCACCGTGGTCCTTAACATCAAAGACGAGAACGACAACGT
GCCGTCCATTGAAATCCGCAAGATTGGGCGCATCCCCCTCAAGGACGGGGTGGCCAACGTGGCCGAGGACGTTCT
GGTCGACACCCCCATCGCTCTGGTGCAGGTGTCCGACCGAGACCAAGGCGAGAACGGGGTGGTCACCTGCACCGT
GGTGGGCGACGTGCCCTTCCAGCTCAAGCCAGCCAGCGACACCGAGGGCGACCAGAACAAGAAAAAGTACTTCTT
GCACACCTCGACCCCTCTGGACTATGAGGCCACCCGGGAGTTCAACGTGGTCATCGTGGCGGTGGACTCAGGCAG
CCCCAGCCTCTCGAGCAACAACTCCCTGATTGTCAAGGTGGGAGACACCAACGACAACCCGCCCATGTTCGGCCA
GTCGGTGGTGGAGGTTTACTTCCCTGAGAACAACATCCCGGGCGAGAGGGTGGCCACGGTGCTGGCGACAGACGC
AGACAGCGGTAAGAACGCCGAGATCGCCTACTCGCTGGACTCCTCTGTGATGGGGATCTTTGCCATCGATCCCGA
TTCTGGGGACATCCTGGTCAATACCGTGCTGGACCGCG
(SEQ ID NO: 175)

CGI: 21 range = chr4:41678680-41678940
CGTCACCAGTTACTCCCGTTTAGCCAACGAGCTGCGTGTGAGCTGCATGGAGCGGAAAAAGGTCCAAATTCGGAG
CTTGGATCCCTCCTCTTTGGCGAGCGACCGATTTAACTTCATTCTGGCGAGTACCAACAGCGACCAGCTCTTCGT
AGTGAACCAGGTCGAAGTCGAAGGCTCCAAGTACGGCATCATCAGCCTGCGAACTCTGAAGATCCCTTCGTTCCA
CGTGTACGTGCTCAGAAACCTCTACGTCCCCAACCG
(SEQ ID NO: 176)

CGI: 217 range = chr4:85636684-85639823
CGCAACTTCCCGCAGTTACTGCCGCTCAGCCGCACTAAGGAGGTCCGGAGACTTGGAAGAAACTTCGGAGACTCG
CTGAAAGGCGAAGAACTGAGCGAGAAAAGGACCCCAGGCTGGGCCCTGAAGTCCACCTGGAAGGCTGGGAGCCTC
CGCGGCGCTGCGGCCTACTACCCCGAAGACTAGCGTGATCTTGGGGCAACTCAGTTTGCCTCAAGCAAGGTCTTT
GCGGGATGGTACATTTTCCCCAGGCCGTGTCCCTTCATCTCACTCTTCTCCTGGCTCGCTCTTGTGTTAGGGTGT
TGAGCTCCACGATGTCCCCAAATGTGCCCGGACGCAGCGTGTGCCAGCCCCCAGAGTGGAGGCAGGTGGGAAAGC
GCGGGCCCAGCGCTGGTGAGCGGCTGGAAGCGCTCGCCCTGCCCTGGGGACGCTGGACTGTCTTCAATGGGCTCA
CCCAGGCCGAGTGTACTCGGGCGGCGAGGGCGAAGAGGTGAGGTGGGGACACCCCAGGCGGAGACGTGCATGCAA
ATACACTCACTTCCCGGGCGGTGGAGGGCTCACCGCTGCCGGCCTCACTGCTTCGAAGAGAGGCAGCGGGTTAG
GCTGGCGAAGGCGGAATGGGGCGCTGGACGACAGGGAGGAGCCGGGAAAGCAGAGATGCAGTGGCCTCTCCTCCC
CTCTCCTCCCCATCTTTCTAATCCAGGCCAGGCCTGCGGTCCTGGCCAGGCCGTTTCAGGAACAGCCAGGGCCTC
GGACGAGACACACGTCCCTCACCGCGTTGTGGTCCACACGAACACACACACACCGGCTCAGCCCAGGCGTACTCA
AGACTTAGAGAGAGGGAGGCGCTTGGATACAGCCACGCGAGCTCAGAAAAGCGAGAATCCCTTTCTGGAAGCCCT
GGCCCAACCTAACTGGTGTGATTCCGGCGCTGTCAAACTACTGGGGCGGGCCACAGGATGGACTGAGCGGCATGC
ACACCAGGGGCCGCGACCCGGGAGTGGGCAGAACAGGCACGGCAGGCAGGCATCGGGGCGCGGGTGGTAGTACTC
ACGAGGGGTACAGGCCAGGCGTGCGTCCCTCCAGGGCGGGCTCTGCATCACTCCGGGCCAGAAGATGGGCGTCCG
GCCAGGCAGCTCAGCCAGCGGCTTGGGGTACCGGCCCACGGCGGCCACGGCCGCGGCGCTGGGGCTGAAGTAGAG
CCCGGGCGGCGGCGGCGGCGGGCTCAGGCTGCTAAAGCGTGGCAGTCCGGCCAGCAGCCCCGCCGGGGATGAGGC
GGCGGCTGCGGCCGCGGCAGCAGCCGCGGCGGCGGCAGAGGCGGAGGAGGCAGAGGCGGACGAGGAAGAGGAGGA
GGAGGAACCGGAGGGCGAGGCGGAGGGCAGGGCGGCCCCCGAGGCCACGGGCATGGAGGGCCGGCTCAGGATATC
GTTGATGCCGTGTGGGGTGGCGGCCGAGAGCTGCTGCGGGGGGCTGCCGAGGGATGAGAGCCCCCCCGTGGCCGG
GGGCTTCAGGCCGCCTGGGTTGTGGGTGCCCAGAGGCGGGGAGGGCGACGAGGAGGACGACGACGAGGACGAGGA
GGAGGGGGGGCCGGCAGGCAGCGGGGGATACGCGGCAGGTACAGCGGGGTCTTCATCTCGGCCATGCTGTGCAG
GGCGGCCAGGGGAGGGCTGCTGAGCAGGAATGCGCTCTGCCGGGTGCCCTCCATTGCCCCCACCGCTAACATCCC TABLE 7B-continued Sequences of differentially labeled CGIs between bladder cancer subgroups relative to blood ACGGCCACGCCGGAGACCGTAGCCTTGCAGCGAGGGCGCTGGCTGGTGCCCCCCGCGGGGCTCAGAGGAGCCGGA
AGCGCCGAGGGCGCGAGCGGAGAGGCACTCGGCGCGCCCGGAGGCGAGCTGCCAACTGAACCAAAAATGCCGCTG
CCGGGAGTTGCTCGCCTAGCTGCGCAGCAGAGATGTCCAAACCCTCCACGCGGGAGGCGGCAGCTCGCCGAGAAA
AGCAGGCGTCCCGGCGGGCTAGGCAGTCCTTTCGTTCCGCGAGTCCTAGATTCGATCCCTGGCTATTCTCTCTTC
CTCACTTTTCCTAGCTGTTCAAAGTGCGCTACTTCTCATCTTCTGCCCCCGGGAAATAAGCAAAACAAAACCCAG
GCTGGCTCCGGAGAGTTTGTAGCAAAGTTAGTTGCCGAATCTCCACTTTGAAGTTGGAGGGTGGGGGTGGCTTGC
TTTCTTTGGGGAGGTTCAAAGGACGCCTTGTGCAGCCCGTGGCGCTCCTCTGATCTTACTGGGATGCTCTGCTCT
TTCGGTCGCGCGGCTGATTCGCATTCGACGCTCACTGTGCCCGGGGAGAAAGCGCATCCAGCCCGCGGGAGATCT
AGCCTCTGTGCGGGCTTCCTCCGCCCACGCTGCCCCGGGCTGCTGCGCCAGAAAGGGCAGTGCCACGGATCCCCG
CGGCTCCCAGGTCCTCACCTCCACCCGCCTTGCCCTCTGGCCCACGGGGCACTGGAGTTGCAATATTGAAAAGAA
AAAGGGGGAGGAAAAACACAGAAAAACAAAAGACTAAGTGTGAAAAGTCTGACGGCTGGGTTTCGGCGCCGCTCG
TCAGTCCACTTCTGCAAACGGGCCCGGCGACCCCCGCCCCACCCCCGCTCCCTCTCTCCCTCTCACTCTCAGCCT
TTGACTCTCCTCTCTGGCATTTTCTTCGCGGCTTCCCAGGCTTCGGTCTTCTAAGTCCTGTCCTCTGGCCAAACT
GACCCTCTCCGCGGCTCCTCCGCTCTTTCTCTCCTTTCCTCTCTCCCTCCGGGCCTGACAGTTCAGATGAAGCTC
TCAAAGGTAATAAAACATTTGCATCACTCCCTACCCCTCTTTAGCTGGGGGACGAAAGGGAGGGGGAAGTGGGGG
ACCAAAATGAGAACTTTGAGGGACGTCACTCCGAGGCTGCGGGGGCCGGCGAGCCGGGCGCAGGCCGGGGGCGTA
ACCACCGTGTCCAATAGCTCGCCGCCTCGATCCTTGCGTCGCCCCTGGGGCTCGCCCACTCGGGGGCGCCGCACC
CTCTGATTGGCTGAGGCGGGCCAGGCGTAGGGCCGCGCCCGCCTAGTCCCCTCCCGCTCCCTACTTCTTTCTCCT
GTGGGCGGGGCCAGGAGGGGCGGGAGCTGGTGAGTGGTGCGGTTCCGCGCTGGGGCCAGTGGCCG
(SEQ ID NO: 177)

CGI: 39 range = chr4:94974810-94975333
CGCGGTGCGGAGCGTCTGGAGCGGAGCACGCGCTGTCAGCTGGTGAGCGCACTCTCCTTTCAGGCAGCTCCCCGG
GGAGCTGTGCGGCCACATTTAACACCATCATCACCCCTCCCCGGCCTCCTCAACCTCGGCCTCCTCCTCGTCGAC
AGCCTTCCTTGGCCCCCCACCAGCAGAGCTCACAGTAGCGAGCGTCTCTCGCCGTCTCCCGCACTCGGCCGGGGC
CCCTCTCCTCCCCCAGCTGCGCAGCGGGAGCCGCCACTGCCCACTGCACCTCCCAGCAACCAGCCCAGCACGCAA
AGAAGCTGCGCAAAGTTAAAGCCAAGCAATGCCAAGGGGAGGGGAAGCTGGAGGCGGCAGAGGCGGCGGCGGGAG
AGCTGTGGGGTTGTTCAGGAAAAGTTGGGCTGGGGGCTGAGGCACCTGAAGCAGTGAACCAGGACTAGGTAGGAA
GCAAGAGCATCCTCCTGCGCAAGCGGAGACGCAAACGCGCTCCTGAACCCATGCAACCGCCCGGCCCAGCGCCG
(SEQ ID NO: 178)

CGI: 162 range = chr4:134291113-134293078
CGGAGCCAGACCTGACGGTGGAAATCTCTGAGAGCGCCACGCCAGGCACTCGCTTCCCCTTGGAGAGCGCATTCG
ACCCAGACGTGGGCACCAACTCCTTGCGCGACTACGAGATCACCCCCAACAGCTACTTCTCCCTGGACGTGCAGA
CCCAGGGGGATGGCAACCGATTCGCTGAGCTGGTGCTGGAGAAGCCACTGGACCGAGAGCAGCAAGCGGTGCACC
GCTACGTGCTGACCGCGGTGGACGGAGGAGGTGGGGGAGGAGTAGGAGAAGGAGGGGGAGGTGGCGGGGGAGCAG
GCCTGCCCCCCCAGCAGCAGCGCACCGGCACGGCCCTACTCACCATCCGAGTGCTGGACTCCAATGACAATGTGC
CCGCTTTCGACCAACCCGTCTACACTGTGTCCCTACCAGAGAACTCTCCCCCAGGCACTCTCGTGATCCAGCTCA
ACGCCACCGACCCGGACGAGGGCCAGAACGGTGAGGTCGTGTACTCCTTCAGCAGCCACATTTCGCCCCGGGCGC
GGGAGCTTTTCGGACTCTCGCCGCGCACTGGCAGACTGGAGGTAAGCGGCGAGTTGGACTATGAAGAGAGCCCAG
TGTACCAAGTGTACGTGCAAGCCAAGGACCTGGGCCCCAACGCCGTGCCTGCGCACTGCAAGGTGCTAGTGCGAG
TACTGGATGCTAATGACAACGCGCCAGAGATCAGCTTCAGCACCGTGAAGGAAGCGGTGAGTGAGGGCGCGGCGC
CCGGCACTGTGGTGGCCCTTTTCAGCGTGACTGACCGCGACTCAGAGGAGAATGGGCAGGTGCAGTGCGAGCTAC
TGGGAGACGTGCCTTTCCGCCTCAAGTCTTCCTTTAAGAATTACTACACCATCGTTACCGAAGCCCCCCTGGACC
GAGAGGCGGGGGACTCCTACACCCTGACTGTAGTGGCTCGGGACCGGGGCGAGCCTGCGCTCTCCACCAGTAAGT
CGATCCAGGTACAAGTGTCGGATGTGAACGACAACGCGCCGCGTTTCAGCCAGCCGGTCTACGACGTGTATGTGA
CTGAAAACAACGTGCCTGGCGCCTACATCTACGCGGTGAGCGCCACCGACCGGGATGAGGGCGCCAACGCCCAGC
TTGCCTACTCTATCCTCGAGTGCCAGATCCAGGGCATGAGCGTCTTCACCTACGTTTCTATCAACTCTGAGAACG
GCTACTTGTACGCCCTGCGCTCCTTCGACTATGAGCAGCTGAAGGACTTCAGTTTTCAGGTGGAAGCCCGGGACG
CTGGCAGCCCCCAGGCGCTGGCTGGTAACGCCACTGTCAACATCCTCATAGTGGATCAAAATGACAACGCCCCTG
CCATCGTGGCGCCTCTACCAGGGCGCAACGGGACTCCAGCGCGTGAGGTGCTGCCCCGCTCGGCGGAGCCGGGTT
ACCTGCTCACCCGCGTGGCCGCCGTGGACGCGGACGACGGCGAGAACGCCCGGCTCACTTACAGCATCGTGCGTG
GCAACGAAATGAACCTCTTTCGCATGGACTGGCGCACCGGGGAGCTGCGCACAGCACGCCGAGTCCCGGCCAAGC
GCGACCCCCAGCGGCCTTATGAGCTGGTGATCGAGGTGCGCGACCATGGGCAGCCGCCCCTTTCCTCCACCGCCA
CCCTGGTGGTTCAGCTGGTGGATGGCGCCGTGGAGCCCCAGGGCGGGGGCGGGAGCGGAGGCGGAGGGTCAGGAG
AGCACCAGCGCCCCAGTCGCTCTGGCGGCGGGGAAACCTCGCTAGACCTCACCCTCATCCTCATCATCGCGTTGG
GCTCGGTGTCCTTCATCTTCCTGCTGGCCATGATCGTGCTGGCCGTGCGTTGCCAAAAAGAGAAGAAGCTCAACA
TCTATACTTGTCTGGCCAGCGATTGCTGCCTCTGCTGCTGCTGCTGCGGTGGCGGAGGTTCGACCTGCTGTGGCC
GCCAAGCCCGGGCGCG
(SEQ ID NO: 179)

CGI: 308 range = chr4:149582663-149586506
CGGATTACGCAGCCACTTCTCCCTGCAAAGTGCACGCTCCCGCGCCGCGGCCGCACGCCGAGCACGGCAAGCGGT
GCCCCGCCGCGCGCCCCTACACACCTGCCTCGGCCGGGGTCCGTCTCTCGCCGTCTACCTGTTGCAGCGCTTGCC
ACCGCCACGAAACCCCTGCTGCGGAGCCCCCCTAAATCCAACCACATCCAGGCCAGCGAGTGCCGCTCTCCCTGC
AGCGGGAGAGCCCGAGGCAGCAACGCTCTTGCACCCAGGTGACTGACTGCACGGGCTTCCTCTGAGCAGCCTGAA
GTTGGCTCCCGTCTCCCGGGCCCAATGACACCCCGGGCGCGGAGGGGCTGAGAGGAGGGGGCAGGGGCAGGGGCA
GGGCCAGGGCGGGCAAAAAAGGGAGGGAGAGAGGGCGGGCGAAAGCCCGGAGGGGGAGTGGGCCAGCTGGAGGGC
TGGCCCTTTTAAAAGCGGGTCACATGTCCAGATAAAGTTCAGGTTGCTATCCCGCCCCCCTGAACCCTTCCTATT
GGCCCGAAGAGAAGCAAGGCTCCACGCCGCACGGGTCAGGCGGGCTTCTTATTGGACAATCCAGGCTGTCAGTCA
CCAGGCGGGCGACATGACTGATACAAAGTTGCTGCGACACAGCCTGGACTCGGCAGCTTCCTTAAAGCCGCAGCC
GCGGCGGGAGCTTGGGGTGCCGGGCGGTGGCTACATCAGGCGGCCTCCGCACGCTGCCCCCACCCCCATCGCTCG
GCCGCCCCAAACTTGCTTACGTCCACCCTGCTCTCCTTCTGACCGACCCCAGGATATCTGGAGAGATGTGAAAAG
TGTGCTGACGCGGAAGAAGTCGGTTTTTCCGCGAGCAAAGTGTCGTCCCCTCACGCTCTCCACCTGCAGCTCCAG
GTGAGCTGCAGCCCAGACCCTGGCGCCGCCCAACAGCGTCCGCGCGCGGGGAGGACTCTGGGTGGGCTTCACCCG
ACCCTCGAGGTTCCTCTCCCAGCCCCTTTCCACTGTCTCCAGAGTTACCTCTCAGCAGAGCAGCAGCAGCCTTCG
CTGCCAGCGAGCAAGACGATCACGTTCACTCGATTTGAATTTAGTTGTTTTAACCGTGCTGGAAAAACCCTTTAA TABLE 7B-continued Sequences of differentially labeled CGIs between bladder cancer subgroups relative to blood ACACAGCTTTCCTCCCATCCCTTAGACCCCTAACACCAAAAAAAAAAAAAAAAAAAAAAAAAAAAAAAAAAGAGAGA
GAGAGAAAGATAAATGAAAGAAGTGGCAGGGTCAAGAGCTGCTCCTCTACTTCCTTATAATTTTGTCACTGTACT
TACTACTTTAGTATTGGATTTTTCCACTAGTTCAATTTGAAAGCAAGCTTACCATCGAGGATATTCACGTTATAA
TGGGTGGAGGGGGTGGGTCACATAAGTGGGAGAAACAGACAGGAGGGGGGGAAGGAACCAAACTGTTTTCTAAGGA
TCGGTTGTCTGCATGAAGAAATTTCGGTTTCCCTCCAACCGCCCCCTCCTCGATTCTCCTCCCGCCCACCCAAAT
GCTGCAGTTACTAAGCAAAAGGATGGGGTTCCTAACTTTGATTTCTAAGGACTTTTAGGCTTCTCATGTAAGGCC
CCGTTTTAGGCTCCCCGCTGGCCCGGAGTCAGCATCAGTGACGTATACACCTAAATCTGGTCCCCCGGCCCTCGG
CGACCCGCAGCCCGGCGGCGGCAGCTGTGCGGCCTCCCGCCTCACCCTCGCTTCGCGCCCGCCAAAGCCCGAGGC
GGGGGACCGGGGGACACCCTGTGCCCAAAGGCCCCTCCTCTCCTTAACAGTTAGTTAAGCTCCGGGATTCCGGAC
CCCTAACCCAGGGCTGAGACTTGAACTCTCAGCCGCTCCAGTCAGGAACTCCCTGGAGATAGGGGCGACAGCGGC
AGCGCCGCGAGCTGGTCCTGACCCCAGACTCTAATGCCCCTCGGTCCCCAGCTTGGAGCTGCCCCCGGCGTCCCC
GCAGCCAGGAGTCCCCGCCGAGCGTCCCAACTTTCCCGCGGGGCCCACCGTCACGCGCACTCTCCCGGCCCAGCG
AACTGGGCATCGATCTCACGTCGGCAGAGCGCGGGCGGCGGGCGGGAGCAAGGGGAGTCCCGGACCTAGAGCCTG
GGCACGCGAGGCGGCGGCGGCTCCGCAAGCGTTGCCGAATTATTCATTATTAAAGGAATGGACGTGTCTCTTTTA
CTAAGTTTTTATCTCCTTTGAGGAGGGCCGGTCTTGCCCTGGATCTCAGCTTCTTGCAAAATCTAGGTTAGAACC
GTGCAGGGGCAGCCGCCGCGATCACTCGCCCGCCACCCAGCACCCTTGCCCCAGGGCCGCCAGCGGGCAACTCGT
CTCCTGCCCGCATCCCACCTCGCCTCGCCAACCCGCGCCCTCTGCCCTGGGCGCGCAACCTGCCTTGCCCGGGGC
CGCCCCTGCGCTCTCCGGACCCCCTCTCGCCGCTGTCAGCGCAAAGTGACTGTCGCTGCACTCACCTTTTCTAGG
ACATGGTGGGGAGGCTGGGGCGGGGGAAGGGGAACGGCTAGACTCCCGCCGCCGCTGCTGCCGCCGCCACCAGCA
AGTCCAATATTGGCTGATCGGCGGTGAGGATGGAGAGGATGATAATCCCGGCAGTGGCAGTCGCCCTGCTGACGG
TGGGTAGAGCAATAGTGCTGTTACCCTACAAGAGGCGGCGAGGCAGCGGCGCCAAATCGCGCAGAGGGGGACGCG
GGCACCCGCCCGCCCCCAGCGGCGGCGGCCGGGCCTCTGGCGGGCCCCTCTCCCGGGGCTGCGCGTCCGCTCGGC
GTTGACAGCGGCGTCCCTGGGAGCCGGGAAGTCCGGCAGGAGGATCCCGCGCCCGCCGCTCCGCAGCGCCACTCT
CCGCGCCCCCTCCCCGGGCCCTGGGTGGCCGGTGACAGCTCCGGCGGCCGAGCGCGTGTGTGAGGGGGCGGTCGC
AGGGGGAGCCTGCGCCCCCCTCCCCGGGTCACGCCCTCACGAGCGGGAGGAGGCGGCACCGCGTCCGGCCACCCG
CGGGTGGGAAACGGGCAGGGGCGCCGGCAGCCGCCCTCCCACTACGGCCACTGACAACCTGGAGGCCAAAGGAAA
ACTGAGCCCAAATGCACGCACCCCCTTCAGCCCTGCCCGCAGCCCTCCAAAGTCCGGCCCTGACCTCGCGCCCGG
CTTCAGGTGCAGTTCCCACCTGCGGGGGGAGGCGAGGGCTGGGGACCTCGCGCGGGGGGCGGGAGGGAAAAGTTT
TCTTTTCCTGCTCCTCGGCTGCCCACCCCGCCAGGCTGCTCCTCTCCCCGCCCCTCTCGGGCTCGCCGCGCCTCT
GCCCCACCCCCGCCGTGGGGGGGCGCCGAGGAGGGAGCGGGCGTCTGTGCGCGGAGGCGTGCGGGGAGCTGGCTG
GGGCGCTGCGGTCGCGACCGGTCCCCTCGCTCTGACGGCGGCTCAGACGCCCGCGGAGGCGGCTCGGCGGGGCAA
GCCGAGGAAGGGGCCGAGAGCCGGGACCCCTCCTCCTCCGCTCGCGGCGCGCCGCGCGCCCCCGCGTCTCCTGGC
GCGCCCCCGCGCCCTCGTGCCCGCTCGGGCAGACACCTACGCAGACGCGAAAGTGAAAGGGGGGCGACTGGGCCC
GGCAGGCGGGCGGCCGGCGGCGCGCGGGCACGCGGCAGGGGACAGAGGATGGATGGGTGAACCCGGATCCCGGGA
TTCTCCCGCGCCCGCTGCCCCTCTGCGGAGCCTCCCCGGAGTCCCACGCCCCCACCCCGGCCACGGAGATCACCA
CGTCAGGAGATATGTATGCGTGTGCATGTGTGTGCGCGCGTGTTCACGCGCGTGTGCGAGGTACGCTTCTGCCCC
AGACTCTTCCCCCGCACCG
(SEQ ID NO: 180)

CGI: 44 range = chr4:154436043-154436665
CGAGAAGCTGAACGAGCTGGCCGACCAGGACTTCCCCTTGCACCCGCGGGAGAACGACCAGCTGGATTTCATCGT
GGAAACCGAGGGGCTGAAGAAGTCCATCCACAACCTCGGGACGATCTTAACCACCAACGCCGTTGCCTCAGAGAC
AGTGGCCACGGGCGAGGGGCTGCGGCAGACCATCATCGGGCAGCCCATGTCCGTCACCATCACCACCAAGGACAA
AGACGGTGAGCTGTGCAAAACCGGCAACGCCTACCTCACCGCCGAACTGAGCACCCCCGACGGGAGCGTGGCAGA
CGGGGAGATCCTGGACAACAAGAACGGCACCTATGAGTTTTGTACACTGTCCAGAAGGAAGGGGACTTTACCCT
GTCTCTGAGACTCTATGACCAGCACATCCGAGGCAGCCCGTTTAAGCTGAAAGTGATCCGATCCGCTGATGTGTC
TCCCACCACAGAAGGCGTGAAGAGGCGCGTTAAGTCCCCGGGGAGCGGCCACGTCAAGCAGAAAGCTGTGAAAAG
ACCCGCAAGCATGTACAGCACTGGAAAACGAAAAGAGAATCCCATCGAAGACGATTTGATCTTTCGAGTGGGTAA
GGAGAGGGCTTCTGTGCCCGACG
(SEQ ID NO: 181)

CGI: 122 range = 0hr4:174686622-174688044
CGGCGGGTACGTTGGGGATGCACTCGCGCAGTTCGGCGAAGGCGCTGTTGATGCTCTGAGTCCTGCGCCGCTCCT
TGCGGTTGGCGGTGCCTCGGCGCTTCACCGGGCGCGGCCCCCCCAGGCCCGGGGGCCCGGCGCCCGGCGGCACCC
CCCCGTAATGGGAGTGGTCCAGGCCGGCGGCGCCGCTGGCATACTCGGGGCTGTAGGACAGGGCCATGCTGTAGT
CGGGGGGCGACATCTCGGGGTGGCCGATGAGCCAGCCATGGAAGTAGGGGTTCTCCTCATGGCTGCAGCGGCTGG
CGGCGGCGGCGGCAGCTGCGGCGGCGGCGGCGGCAAACGGGTAGCCCTCGTGGTGCACCACCGGGTGGTGGGGAA
AACCACCTACCAGACTCATTTCGCCCTCCGCGCCCCTCCACGCGCCCCAGCGTGCGCGCAGCCCCGCCGCGCCCT
CGGCCCGGGCCCCTGCCTCAGCGCTCGGCGTCCTCCCCCACCCCCCACCCCCCAGCCCCCGGGCGCCCGGGCCCG
CCCGGCAGCCGCAGAGGGGGGCTGCTGCAGCCCGGGCCCCGTCCCCCCGCCTGGCCAGCCGGGCCCGCCTCAGCAG
CGCTGCGGCCGCCGGCTCCCCATGGGGCGCGGCGAGCTGGTCCTGGCACCGTGCGCCCCTGGCCGCCGCCGCCGC
CGCCTCCGGTTCCCGCCTTGCTCCACGGCCCGCGCTTCGGCTCCTGCTTCCCGGGCTGCTGCGCGGAGGCAGAAT
CCTCTCGTGCTCATACAAAGGTGCCGGGGCTCCCGCGAGGCTGGTACGCGGAGTCTCGGGAATCCAAGCCCGGGC
CGCGGTCCTGGCACCGAAGCTAACCCGGAATCCAGGGGCGAGTCTGAGCCGCGGCTGGAGGAGCCGGTCCAGCTG
TGCCGGGGGGCGGCGGGGTCGACTGCTCACTGCAAAGCTACCTCCGTGCGACCCTCCCCTTCCCGCCTCTTCCCC
TCCCCCCACCAGCCCGATCTGGGTTCTTGGGCGCTTATTGTTTTAATGAAATTTTTGGTTGTTGTTGTTTTGGTC
CTTAAATGTGATTTTAGCTGCGAGTAACGTGTCCTCGCTCCTCTCGCGCTCTCTCGGAGGGTTTTCAGAGAGGTC
TCAGTGCATCCATTTTCTCAGATCCTCTCCTTTCGGGGCAAGGATCTGGGGCCCTGAATGAGCCTTGGAGCTCGA
AGACCGCGGCTCGGGCTCTCGGAGGGCTCTGCGCGGTGGCCGAGGAAGCTCCGGGGTGACGGCGGTGGTTCTCCT
GGGCTGGACGACGTGAGGGGAGCAAGCGGATTTTCCCAGCAAGATCTCCATGTACAGCTACATCTTTAGGGCCGC
TCGGGTTAATATATGTCGTCAGAGGCTCCTCACGCCAATCCCGGGGCGGCAGGGGCGGCGCCTCGAGCTCTCG
(SEQ ID NO: 182)

CGI: 245 range = chr4:184255825-184258373
CGAGATTGGCCGCAGATGCCCCGACGGGATGGCCTGGGGAGCCGAAAGCTGTCCCCAGCCCCGGACAGCTACTGC
CCACGCCGCGCAGGCCAGCCTCACACAGTAGCGAATCTCCTTCACGCGACTTCCTCGCAGGCCTGTGAACCCGCA
GGGGAGGCGGAGGTCGGTTCAAACCCTGCGAGAGCCCCTGCCCAGCGCGGAGTCCTGCACACGGTGGAAAGTCCT TABLE 7B-continued Sequences of differentially labeled CGIs between bladder cancer subgroups relative to blood TACGCATTAGCGGGCAGGATTAAACGACTTCACACCACGAGGTGCAAGACTGGGCTTCGGGGCCTTCCTCGGTGT
TGCTATTTTAAAAGAAGCTGCTCAGTAACCCAGAAGAAGATGACGGGGGACGGTGGTGTAGACCCGGCTGGAGAG
GAGTCCAGGGCCTGGGAGGCGCCCCCTCTGACTGAGGGGCTGGGGACCCTGAAGCTTGGCGTCCAGGCCCCGCCA
GCGCTGCACCCGGCATTGTCCCGCCTGGGGCAGGCGTCCGGTCCCTCGGCAGTGCGGGCCAGCACGTACGTAGTA
GCTGCTGAATAAATAAATGCCTATGCAACAGGGAACGTCCCGGCCCACCCCGGCCGGGCCAGGGCCTAGGAAGGG
CGGGCGTCCGGCGCCGCCGTGGGTCCCTCCGGCGTGGCCGCCCACACCTCCTGGCCACGGCGGGGCTGCGGTGGG
GGGACATCCTGGGGCGGGCGGCTGGACGGAAGGGACTAGAGTCGGGGCGCGTCCACGGCCAACCGCCCCGAACCA
AGCAGGGGAGGCCAGGGACCAGGAGCTTCCGGGGCCCCGCGGCTGGAGCGCCCGGACGCGAAGGGGCGGCGGGTG
ACGGGGCGCGGTGCGGGCGGCTACAGGGCCGGACGGGAGTTCCTCCGCTTTCCGCCGCGCGGCTCGCGGTCTCAG
CCGAGGTCATCGAGGGCCAGGAGCCCTGGCGGAGGCCCCGCCGTCCCGGACCCACCGACGCACTCCCAGGGCTTG
GCGCTTTCCCACCACCCCGGACCGCCCTTGGGGTGCCGGAGGGGCTCGGGGCGCGGCGTGGGGAGCCTTTGTGCC
CTCTCCGCTTGTTGAGGTTTTTTCTCCGGAGGAGAGCTCCCCGCCCGCCACCCCTTTCCTCTCGAAAGTTTTGTG
GTTTCCCTAGAAGACGAAAGAGGTTGAGAAGGTTGCGGAGACTTTTGCAATCTTCCCCGTCCAGAAACTCTAAAA
CCTCTCGGCGTTTGGCCCAGGGGAGCTATCTGGGGTCAAGGGGAGGGAGCTGGCCGCACATTCCTTCGCCCGCCT
TCCTCCCACCTGGAGCCGCGGCCCCGCGGGGCAGTGCGTCCGAGCTGGTGCGGCGACGCCGGCAGCGGCGGGGTT
AAGCTCAGGAATGCGGCGCGAGGAATGCGCATGCAGATGAGGCGGGCGGGCGCATGCTAATCGCATGCAAATGAG
GGGCCCGCCGCTGCCGCGGCAGCGCCGCAGCTTCCCGGATCCGAGCCCAGACGGCGGCGGCTCCGGCAGCCTGGG
CGCCGCGACCCTCGGCGGCCAGAGGGGGACGGGGCGGAGGAGGAGGAAGAGGCGGAGGCAGCGGCGGCGAGGGGG
AGGAGGGTTCGCTCGCCGGCTCCGACGCAGACATGGTGGACTGATCCGCAGCGGGGCCGCGAACAGCGTTTCCTG
AGGCACCTCCCGCGCGTGGTTCCGCCGCGCCCCGCGCCCTGCGCCCCTCAGCCCCTCGCCGGCGCCCGCGTCGCG
GGTTGGCAGCCTAGCCCGGCAGCCGCGTTCCCGCCGCGTCCCGCGCCCGGTACCTATGGAGGCGCCGCTCGCCGG
CGAGGCCGCCGACCATGCCTAGGAGGGCCGGGAGCGGTCAGCTGCCGCTGCCCCGGGGCTGGGAGGAGGCCAGGG
ACTACGACGGCAAGGTCTTCTACATTGACCACAACACCAGGAGGACCAGCTGGATCGACCCCCGGGACAGGTGGG
CGCCGGCCGCGGGGGCGCGGGCCCGTTCGGACACGGCGGCTGTTGTCCCGGAGACCCGGCCGCGCGGGGGGCTGG
GGCGGCGCCGGCCCGCGGTGCCCCGAGGGGTCCCGGGAGGGATGTGGGGCTGGCTGCTCCGGCGGGGCCGAGGAG
CCGCCCGTACCCGGGCTCCTCCGCCCACCGGCTTCCCGACGCCCCTCCGGGGACCCGGCCCCGAGGCAAGGCTGG
AGTCGCTGCCCCGGGCCGACGCCGCGCGCCAGGCTAACGGACCCGAGGGGCCACCTGAGCCCTGTTAGGAACTTC
CCTAGGCTTCGAGGTGCCCACGTGGAGGCTGCAGGACACCTTCGGCCTCTGGGCGGCGGGGGTGGGCTAGGGCCT
CACTGCCAGTTGGGGAACGAGCCCTCCGGGCCACCTGTGGCATCCCTCAGGCCGTCCTTGGCGCGGGAGCCTGGG
CTGCGAGCTCTTGGCGGGGGCGCCCAGACTGGCCGGAGGTCCCGAGCTGGGAAGGGGCTCCCGCCCCCCGCCGGG
CCCTGCTAGTGGGTGTGACTGACTTTGCCCCTCAGAGTTTAAAAACGCGCGTTTGGGGGTTTCGCTGTCTGTCG
(SEQ ID NO: 183)

CGI: 33 range = chr5:360287-360592
CGTGCGCCTCAGAAGGGGCGTTAGGCAGAACGCGTGCCCATTCTCAGGTGTGCTCGGCGTGTGTGTGCTCGGCGT
GTGTGTGCTCGGCGTGTGTGTGCACACGTGTGCCGTGCGCCTCAGAAGGGGCGTTAGGCAGAACGCGTGCCCATT
CTCAGGTGTGCTCGGCGTGTGTGTGCTCGGCGTGTGTGTGCACACGTGTGCCGTGCGCCTCAGAAGGGGCGTTAG
GCAGAACGCGTGCCCATTCTCAGGTGCGCTCAGCGTGTGTGTGCTTGACGCGTGTGCACACACACATGTGACGGT
GTGCCG
(SEQ ID NO: 184)

CGI: 18 range = chr5:1161803-1162051
CGACCGGCGTGCACCGTCTCGCCATTCCCAAGGGCAGTGCAGAGCATGGCACCCAGCACCCGACAGGCGAGGACG
GCCCAGGACAAAGCGGCAGCTCTAGCTGTCCTCAGATTTTGGGAGGGGGCTCCCAACACGGACACGGTAGGTAGT
TGGAGCAGGAGGGACGGGCAGGCCACTGACCACGCAACCGGGCCTCTGTCAGCGGCCAGGGGCAGAGGGAGGCAG
GACCGCCCCTGGACAACCGACACG
(SEQ ID NO: 185)

CGI: 584 range = chr5:3647468-3656054
CGAGGCTCCGTGAAGAGAGGGAAGCGAGGCAGGGGGTGAAGGGACCGCCTGGCCGGTGTCCAGGATACGGGTGGC
TCAAACCACCAGCAGAACAGCATGCCGACTCTGGCCCGATGGCCGCCTTCATCCCGTAGCCCCAACCCGGCCTAA
AGCCGAGAAGACGCCAGAGTGCGCTGCTGAAATTCCCGCGGAGTCCGGTGTGCTGGAGAGCCGCAGCGGGGTGAA
CTCCCGGCCCCGTCTCTGCGTAGGAGGTGGTTCGCAAAGTGGCCCCGGGAGCCGGGACTGGTACCCGGTTCCCCA
CGGCACCGTCCGGAGCTCTCCAGCCACGAGGCGCAGAAGTGGCCTGCCAGCGCCTTCCCAGGCTCAGGGAGGCGA
GGAGGCCCGTGCACTTGGCATCTTCTCCCGGGAGCCGCACGGCCAGGGCCGCGGCGAAACGGAGCCCATCTCAAG
TGCGCCGCGCCTGGCCGCGTCCTGTAGCCCGACGAGGCTGAGGATGGAGAGGGGAGACGCAGGGAGAAGAGGGAC
GCGGGACTTGGACCCAAGAGGCCGCTCCGTTGCCGGTCTGGCGGCGGCGCCGACTCGGGTTCGCGCGTTCCACAC
AAGTTTCCTGTCTGCCTCTGCACACCTGGTGGACAAACCGGGCGTCCAGGCCACACCGTCTTCCCCCTTCGCGGG
GGCGCGGGGGATGTTTCCCTCCGGCTGCCAGGGGGCTTTCTGGGTGAAGAGAAAGCCCCTCCCCCCGCGTCTCCC
CCACCCCTCCCTCCGAGAACCCGCGGCGCCGACTGCGCCTGCTTCCCCCGAGCTGGCGACTTCTCCGCGGGATTT
GCCCTCGCTCAAAGTTTGCACAATTGAAAGAGCCCGCAGAGCTCGGCCGCTCCCCGCTTCCCCAAGGGCGGCGAG
GCCGGTCATTGGCAGACGATCGGTTACTACCCAGTAGGGGCCCACGGGAACCCGCATCTGGAGTCGGGGGTGTCA
CGCCACGCCGGTTCAGTGGCTCGCGGAGAGCGTCCGGGTGCACTTCTGCCAAAGATGTCCCCTGGAGGCCCCGGC
CGCGCGGGACTCGGGGGAGAGGCCGCTCCCCCCTCGCTGTCACCAGCGTCCAGGCCGCCGGCCCCTTCCCCGCTG
CCCAAACAGTAGAAAAGCAGGCGCCAAGTTGTTTTTGTTAAAAAGGGGACACACCTCGGCCGCGAAACTGCAAAC
CCGGTGTCAGACAGCTGTAAACCCGTGTCGACAGGTTGTCAGACAGCTGCGGGGGCTGGTCGGGAAGGAGCCCAC
GGCCTCCGGGCCCACACCCCGCCGCCCCGACGCGCGCGCCCACCGCGAGAGTAGCTGGCCGGGCCGGCACGGGGC
ACCACGTGCTCGCGGGAGGGGCGGGAGCGGCCGGCGAGGGCGGGCGGGAGGCAGGGAGGGGGCGGGAGGGGAGCC
AGGGGCGGGGCCTGCGCTCAAGGGGATGCCAATCAAAGCATCAACTTCAAATTGTGTCTGAAAGCCCCGCCGCCG
AGCGGAGGGCGGCCGCCGCAGTCGGCGCGCGATTGCGGATCCGGGCGCAGCCGGGAGCCGGGCGCCTGCGAGCAC
CGGGCAGAGGAGCCGCGACCGGCCTCCATCTCCCGGCCCGCCCGAGCGCGCCCGGCCGGCCGCCCGCTCCTCCCT
AGACCCCTCGCGGCGCCCCCTGCAACCCCCTCCGGCCGGCCTCCGCCTCCCTCCCCGCGCCTTTAATACTCGCCC
CCGGGCGCCTACGGCGGCGAGCGCCCGGGGGTGCTGGCCGCGGCCGCTGCGGCGGCTGCCGCCGCCTCGTCGGGC
CGACCGGGGGCCGCGGAGCTGGGCGGCGGGGCAGGCGCGGCTGCAGTCACCTCGGTGCTGGGCATGTACGCGGCG
GCGGGGCCGTACGCGGGCGCGCCCAACTACAGCGCCTTCCTGCCCTACGCCGCGGATCTCAGCCTCTTCTCGCAG
ATGGTGAGTGCGCCCGGCCTCCCCCGCTTCTCCTCTGTCTCACCCGCGCCAGGGCAAGGGTGGCGGGTCGCCCGG
GAGGGAGAGACTACGGGTGGACCTGGTCCGGAAGAGGAACTAGAAAGGTCCGGGGGCAGGTTCCCGGTGGCCGAG TABLE 7B-continued

| Sequences of differentially labeled CGIs between bladder cancer subgroups relative to blood |
|---|
| GCCGCGGCCCCCGGGGACGCAAGAGGGCTGGGAGGCCGGGCGGGTGACGGCTGGGCCATCTCGGCCTGGGAAAGC |
| GGAAGGCCCGGGCCAGGGAGCGGGTAGCGAGTGAATTCAGAGAGGCCGCAGAAGCAGGCCCGTGGAGCGGTGCCC |
| GCGCTGGAGGTCGGGGGCAAACTCGCCTGGCTCGGCCAGGGCGCCCGGGCAGGCCCACGGGGTTCCTGCAGGTCG |
| GCCCGGCGTAGCGTAGCAGGACTTCCCTTCCTGGCCGCGGGTTCCACTCGCGCGGCCTCTTTAGTTTTCGAACCG |
| AGTCTGGAAAACTTGGTTTTCTCCCTCTTTAGCAGCTCCGAGATAGTTGTATCCGAGTTTGCCAGACAGACCCCT |
| TCTAAGCCTGGTAGAGTCAATCAAAATAATCTTAACAATAGAGGTCCAAAGGGATGGAGAGGTCTCTCCACGGCG |
| TGAGTGCGAATTTGAGATTAAACAAAAATTAAGTTGCAGTAATGTGCTGGTGTCTGAAACGGTGTTTGATTTTAC |
| TTTTGTAAGTTGCCCAAGTTTTCATTTCATTTGCACAGAAAGAAAAGCACTTTTCTTCCTGCGTTACATAATGGA |
| GGATTAAAGAAAACAGTGTCCCTTGGCTTAAAACAAATGGTGTCCTCTTAGTCTCCCGTCCCAGTGGGCGTTAGA |
| TGTCGGGGCAGGCGGCTGCACACTTAATTCTCCGCGGGGGCATTGGCCTGTCTGCCGGTCCAAATCATCCATTTT |
| CCTTGGTCTGACTGCAAGGTCGGTGCTTAAACTTCGGACGGCTGGTGAATTGTGCGGCGGGCGCGGGGCCCTGGG |
| AGGCAGCCCCCTCCTGGGTCGCTGCCCGCGGGATAAAGCAATTTCCAAGCACCCGCGATATCTCCCCGCTCCCCG |
| CAGGAGAAGCGGGGAGTAAACGCCCCTCAAGTGTGCACAAGCAAAGAGCGGGTTTCCCTGTAACTTTTCTTGTAG |
| TTTTGAAAGAAAGCGGCCCGGCTGCCTTTCAGGTCTCTTACTATCGAAAAAGATCAGCCCCCATTTTGTTCAGGC |
| GGCGGGGAGGCCGGGACGCGATGAGAGATTTACAAGGTGTCCTTTCAAAAAGAATTCCCAGTGGAGACGAGGCTG |
| AAACGTCTTCTTTACAATTACAACCAAAATAATTAGAAAAGCGCAAAGTACATTTTGGAACGATTGGGCAAAAAC |
| GAAATCTAGCCGCAGAAATGTTTTCTCTGCGGCCTCAGTCACCAAACTAATTAGTCCAAGAAATCTTCTGGTCTT |
| TACAACTTTCTCAGAGTCCGGAACTCCCTTTGCTAACATTGCAACTAGACCATTTTTTCAGAGGATGAATATTTT |
| TTACAGAAATTGCGAATGCAGTTGTGTGCCATTTGGGAACCCTGCCTGTGTTTGCGGGGGAGGGAGAGAGCTTCA |
| GTGTGAGGACCTGCACCCTTTGTGGAGAGCTGGGGAAGGGAGATGTTTGCTGTTCTGAGTTGTTTTTCCCACCTA |
| GAGGGATAATATGTAAAAATTATTCCCACCCAAAAGGTGTGTGTTTCTCCAGCTCTCCCACTGGTTCTGAGAGAG |
| TAAACTCAAACCCAAACCCTGATTCTAGGCCTAGGTTTCCAAGCCATTATAATTGGGTGTTTGGAAGTCAAAAGA |
| TAAAATTGTATTTGAATGTCTGTCTGCGCAATTTATGGTAATAATGAGGCCTAATGAGGTTGTTAGAAAGATAAA |
| ATGTTATTTACCAAAAAACCTGATGGGATAATTTGACTTGCTGTGTTTTACTACTGATTATAAAAAGAATATCGA |
| TTGCAAATAAATCAGCGCCTCTAAATGCCTGCAAACAGCTAGTGTTTGCTCCCTCCAGATCAAAGTCAAACTTAA |
| GAGATGAAGTAACTGAGAAGAGGCCTAGGATACTGAACCGGTTCCCCTCCTGGCCGCCGGTGGCTCCCAGCCCTT |
| GCGTTAATATTTTACAGGCTAAGCCTTCCTTTTGTATTAAAAAAAAAAAATGGTGTTTTTGTTATTGTTGTCGATG |
| ATGGCCGGGATTAAAATTTTAAATTACCTGTCACCTCTAAAGACCTTTTAATGTGGGTAAACCATTATATGCAGA |
| TTAATTTGGAAGGCAAAGGACTGTGCTTTCGTTTTAAATTGCTGGCGGATTTAGACCGGTAGAAAACCCGGGATG |
| GTTTATTTTGATTGAGCCCCCTCTGGGTGGCAGAGAGGAGGCTTGGGCTCTGGGCCCTTTACGTTTGGAGAAATG |
| GCTTTATCAGCTCAGTTGAAAGGTTTTTCCCTCTAGCTAGTGAAAGATAAACTTGGAAATGCAGGTTTCTCCAGC |
| GGTTGGTGGTGGGGACAGGGGTCGCCTAGGGAACTTGCAGGGGCCGCGGCCTCTGTTGTGCTCTTCTGGAGAGTG |
| CACTGTTTGTGGAACTTTTCTAGAGTGGCAAAAACGATCTCCACTGTCGGTGAAAGGGCAGTTCCTGAAGTCAGC |
| TCATGGTCCTGGCTCCCCTTCTCCCCAGCAGTGAACTGGGGGTGACTTCCTGATCTGCCCAGCACAGGAGAGCCC |
| CGCAAAGCGCCTGGGAGGCCCTCGAGTCCATTGAAGCGGCTGCTTCCCACTCTCCCGTCTTGGGGACTCATGTCT |
| CTCTCTCTCTCTCCCTTTCTCTCTCCACTTCCCTCCTCTCTCTCCTCGATGGATCTGCCCTGTGGCTTCAGGGCT |
| CGCAGTATGAACTGAAGGACAACCCTGGGGTGCACCCCGCCACCTTCGCAGCCCACACGGCGCCGGCTTATTACC |
| CCTACGGCCAGTTCCAATACGGGGACCCCGGGCGGCCCAAGAACGCCACCCGCGAGAGCACCAGCACGCTCAAGG |
| CCTGGCTCAACGAGCACCGCAAGAATCCCTACCCCACCAAGGGCGAGAAGATCATGCTGGCCATCATCACCAAGA |
| TGACCCTCACGCAGGTCTCCACCTGGTTCGCCAACGCGCGCCGGCGCCTCAAGAAGGAGAACAAGGTGACATGGG |
| GAGCGCGCAGCAAGGACCAGGAAGATGGAGCGCTCTTCGGCAGCGACACCGAGGGCGACCCGGAGAAGGCCGAGG |
| ACGACGAGGAGATCGACCTGGAAAGCATCGACATTGACAAGATCGACGAGCACGATGGCGACCAGAGCAACGAGG |
| ATGACGAGGACAAGGCCGAGGCTCCGCACGCGCCCGCAGCCCCTTCTGCTCTTGCCCGGGACCAAGGCTCGCCGC |
| TGGCAGCAGCCGACGTTCTCAAGCCCCAGGACTCGCCCTTGGGCCTGGCAAAGGAGGCCCCAGAGCCGGGCAGCA |
| CGCGCCTGCTGAGCCCCGGCGCTGCAGCGGGCGGCCTGCAGGGTGCGCCGCACGGCAAGCCCAAGATCTGGTCGC |
| TGGCGGAGACAGCCACGAGCCCCGACGGTGCGCCCAAGGCTTCGCCACCACCACCCGCGGGCCACCCCGGCGCGC |
| ACGGGCCCTCCGCCGGGGCGCCGCTGCAACACCCCGCCTTCCTGCCTAGCCACGGACTGTACACCTGCCACATCG |
| GCAAGTTCTCCAACTGGACCAACAGCGCATTCCTCGCACAGGGCTCCCTGCTCAACATGCGCTCCTTCCTGGGCG |
| TTGGCGCTCCCCACGCCGCGCCCCATGGCCCTCACCTTCCTGCACCTCCACCACCGCAGCCGCCGGTCGCTATTG |
| CCCCGGGGGCACTCAATGGAGACAAGGCCTCGGTCCGCAGCAGCCCCACGCTCCCAGGTACAGCTCCAGGCCGCG |
| TCCACCTGTCCCCTAGCTGGGAATGCAGAGGCCTGGCTAGGTGTGGTAGCGTGGGGTGCAGCATGAGCCGGGAGG |
| GTACCAGGCAGTGGCCGCTGAGCCCTGGGGCTGCGCTTAATCCCTGCTTCAATTTAGAAAGCCAGACAAGGCCCT |
| AGGGCTCTCCCAAGAGAGCTTTGCCCTACCGGCGGGCCTGCTACGGGGTGGTGGTGGGGTGAGGGGTGACGTTTT |
| TCGGCGAATCTGCCTGGGCAGCCGGCAGAAGTTGGTGGGAAGGAGGCCTGGGACCTCTCCCGCCCGTCTCTCCGT |
| CCTAACTCTGCCTCTTCCGATCTCTCGCAGAGAGACCTCGTCCCCAGGCCAGATTCGCCGGCACAGCAGTTAA |
| AGTCGCCCTTCCAGCCGGTACGCGACAAGTGAGTGCTGTTTGCTTTTGCTATGGGAGAAGGCGGTGGGGAGGGGG |
| GAGGAGGAGTGGTCGGGACCCGGGCGGAGCTGGCTGGGTGGCGGTGGGGGTCGCGCAGTCCTAGTTGAAGGAGCG |
| CTCCCCGCCAGCCCTGGGCGCCGGGCGAGCCGAGGAGACTGGAGTTTCTCCCCAGCCGGGAGCCGCGCTGGCTGT |
| CGACCCCGCCCCCAGGGCTCCGCTACTGGAACCGGCGTCGCCCGGCGCTGCGTCCCCCACTCACAGTGCCCCTGT |
| CTTCTTGTCTCGCTGTGTTTCCCATGCAGCTCTCTGGCCCCGCAGGAGGGAACGCCGCGGATCCTAGCAGCCCTC |
| CCGTCCGCCTGATTAAGGGTCTTCTTTTACTTTTGCGGGGGGGAGGGGGGAGGAGTTGGGGAGGGAGGGAATGTG |
| GGAGGAATTAAGACAAATATTTCAGACTGGTGTAAAGGACAAATATGACAACGACGTCAAGGACTCGCATCCGTC |
| GCTTTCTGCAGAAAGGGGCTTCTTCGGTCCCGAGCTCGCGTCCAGGTGGCCAGGCCTCTGCCGGCGGCTCCAGTG |
| GCTGCGATTATCGGGTTCGGTAAATGCCCCCACGTGCTTGTGTCTCTTTCCCCCCTTTTCTGTATATAGAGTGGT |
| TTCAGATTGTAAATAGCGCGTCAGCGAACTTGTCTAAATCATATATTTTTGTCTAATAAACTAAATGAAATGACA |
| CCCCCTCCCCGCTCCTGCTGCTGTGTGCCTGTCCAGCGTGTGTGTGAGTGTGTGTTTGTGTGTGAATGTGTGTGT |
| GTGAGTGTCTGTGTGGCAGAAACAGAGACAGAGAGAGAGAAGTGGGGGATACAGGGATCCTGGAACCCTGGGTGG |
| GACCCAAGGGTCTGTGGCTGGGGGAGATGGGCTTCTCAATGGGGGCCTTTAGAGACTGTTGCCACCCAAGACGCA |
| GGTGCTTTAAACATCTCTTCGTTGTTTGTGGTTGTTGTTGAATTTTTAAATATTGTCACTGTGGCAGTTTCTTGC |
| TGGCAGTTCAATTGCTTTCACGAACATTTTTCTGAGACATAATTTTCTCAGGACATAAATAAGTTCAATTTGAGG |
| CAGTTTTACAAAACGATTTTATAACGTCGGTAAAAACAGAGGAAAAAGAATTTTTATTGCGACCCCAGAGGAGAA |
| CTTCGGATTAGAAACCAGTTTACAACTAGTTGTCTCAACGGCGCATCGTGGCGCCTGGTCGTTTTCTGAGTTGAG |
| TGTGAAAATAATGGAGTATCGCTTTGCATGTATTTTTAGTGATTCGGTTAAATCAAACACGGGAAGAAATTGGAA |
| GGCTCTTTAAAACTCCACAGATGGGCCAGCCGGGATGCGGTGCGGGGCTTCTCTGCGGTGTGAGGTGTGAACGAG |
| GGGCTGAGGCTGTGGTGGGAAGCGAGAAAGAGGAGGTGGCTTTGGTCTCCCAGGGAAGCCCCTTTACACTTGGGC |
| TCCACGGACTGCGTCCTTTGCCCTCAGGCGCGCGCACCGCGGGAGTCCAGAGCAAATTGCCCTTAGATGGCCGCG |
| GCCGGGCAGCGGGGAGGCAGCTGGGAGCAGCGATGTTGGGAAACACTCGCAGCGGGGCTGGCCTCGGGCGCGCGC |

TABLE 7B-continued

Sequences of differentially labeled CGIs between bladder cancer subgroups relative to blood GAGTGGGGAAAGGCCTAGGAGCCTGGACATCGCTGCGGATCCGGGACATCAGCATCAGTGGGTTCGGAGCGGGAC
GCGCGCCACGCGCCGCAGCAGGCACCTTCAGGAGGCTTTGCGGACCCGGCGCGGGGCCTTCAGGGCGCAGGCGAC
TCAGCGTTGAATGCGTGAAAACTGAGCCAGCAAACATTTCCAAAACTGCCAGCGAGGATGTGGGCTGCCGGGAAA
AACGGTCTAGTGGGGACAGGGCCGAGTCCCGAAGTCAGAGCCGAGTCCCGAGGTCAGAGCGGCCGTCCTCCGCTC
GCACCCCCAGCCTGTGACCCGCCCTTCCCGGCTTGCTCGAGACCCACTGGCGCCAGTGCTGCGCGTGGGGACTCC
GTGCATGGCCGAAGCGAGGGGGAAAGTCGGGGCGCTGGTGTCTTTTCAGAGGTTCCAGGAAAGAGGGAGGCTCGC
GTTAGGACTAGGAGGTGCCAGTCCACGGCTCCTACCCGCTCCCGACGCCCGCATCCTTCTACAGCCCTCCACCCC
GTTCCTGGTCCCTGTAGAGGGGAAGGTCCTCTCCCTGCCCCGAGGCGGGAGGAAAAGCGGCGAAGAGGAGGCTCG
AAGGGCGCCGCGTAGGGCAAGTGGGCCGAGGACACCG
(SEQ ID NO: 186)

CGI: 140 range = chr5:5192442-5193941
CGTGTACTCGCGCACACGCAGTCAGGTGTGGATGTACACCCGCGCACACCCAGGCACATGTACACCCGCGCGCTC
ACACACCCCATCCAGCTACAGCAGAATTCTGGCCAGGCTGTTGACCGCACACCTGCTGCCTCCTTGGCCACCCTG
TCCACACAGTAGCCCGATCGACCCCCGTGGCGGCCGAGACCCAGGCCCATCCGCAGCCCTGAGACCTCCCTAGGG
ATTGCACCCAGCAGCCAGTCACCGGCCTCCGCGGCCTGGCCAGTTGAGGGTGGCCGTGACCGCGGGGCCAGGAGC
GCCGCCACATCTCGGGGCAAATGGCGCGGGGGAAGAGTTTCCTCCTCAGCCTCCCCGTCTCCGATCGCTCCGCAA
ACTCCAGAGCGAGGCACGCGCCTTTAAAGGCAGGTCCGCGGCTCTCCCACGTCCTGGCGCCCGGTTTTCCGCACC
CAGTGTCCCCACAGCTGTGCCCGGGCACAGAGGCGCGGCCAGACCGCACTCCGCGGGCTGCAGGTGTCCCGGCCT
CTGGCGGCGCCGGTGCGGCCCGGAGGTGGGAGCCCGCGGAGCCACTGCAGTAGCTGGAGTCCCGCCGAGTCCCCA
GCCCCAAGGCAGGGCAGGAGCGCGCACCGGCCGGAGGTCCATGCTGAGCATCGCCCGCGCCGGTGCCCGGCAGCC
TCTCCAACTGTGTGGTCCCCGCGCGGGCAGAGAGGCACGGACTGCAGGCCGTGGGCAGCTCCATCTTCCCGCGTC
CTCCTCCTCTGGCGCTGCCCGCTGTCTCCCGCCTTCCCTCTGCTCCCCGCTCGCCTCCGCCTCAGCGCCCCGCTG
ACCTCGCCTCCTCCCCTCTGCTCTTTGTCCCTGCACTCTCCCCTCCTCGGTCCTCTGACCCCCCCGCCCTCACCT
CCTCCCCTCCTCTCTCCCCTGCCCGCCCCGCGCTCTCCCACCGCTCCCGCCGCCCCCGCCGCCGCGGCTGCCACT
CCGCCCCCCGCGCCGCACGGAGCTTCAGTAATAACCCCGGCGCGGCGGCGGAGTCGCTGTGGGGAATCCTCCCGC
GCTCTGCCTGGGTCGGGTCCTCCCTGCCCGCTCGCACGCTGCCGGCCGGGGACCCTCCGGTGGCCCCTAGCCCCT
CGGAGCGCTCCTGGATGAAGCCCCGCGCGCGCGGATGGCGGGGCTTGGCGGCGCTGTGGATGCTGTTGGCGCAGG
TGGCCGAGCAGGTGAGTCCCGGGCGCTCCCACCAGCGCGGAAACCGCGGGTCCGGACAGCTGGAGGCGAGTCCCC
CGCGGCTCCTCTCCCGCGGACCCCGCCGTCTCACCGCGATGTCGCCGCTGTTTTCCGCAGGCACCTGCGTGCGCC
ATGGGACCCGCAGCGGCAGCGCCTGGGAGCCCGAGCGTCCCGCGTCCTCCTCCACCCGCGGAGCGGCCGGGCTGG
ATGGAAAAGGGCGGTAAGTCCGTGAGGTGGGGGCTTCTAATCCTTGCCATTTAGCAGCTCGTAATCTCCGTGCCG
(SEQ ID NO: 187)

CGI: 21 range = chr5:6790705-6791004
CGGATCGAAACTGTGGTGAAAGACCTTTGGCCGACGGCTGATGTGAGTATGTTCTTTGGAGTTCTGTGTCGCACG
TCACGTGCGAGTAAATTTAAATACCCTGTGATGATGATGTGTCGGCTAGATCCACACAGACCTTTTCTCGTTGGC
CCGAGGCAGCAGTTCTCCAAGTGTGCTTTGAGAAGGCCTCCGTTGCCTGGAATGCATGGCCCCCGGCGCACCTGC
ACCTGCTGTCTTAGACACCTGCGGTGGCCGCACATCTTCGTGATGCTGGCGCGCACTCAAGTGCGAAGACCATCG
(SEQ ID NO: 188)

CGI: 54 range = chr5:54554812-54555385
CGGGCTCGGCGGCGGTCTGCTCGCACTTACGTCGCCAGCCCAGTCTCGTACCCGAAAATTCAAGCCCCATCCGAG
ACAGGGAACCCAGCAGGCTTGCACTGCCACGGTGGGGAGCGGGACGCACGGAGCACGACACTGACTGGGGGAAGG
GGGCAGCAGTTCGCGGCTCCTGCAGAGCAGCTGCGTGGCGGGAATGGGTCCTTCCACCGGCGGTGCGGCGGCCCCT
GCGCCGGCTCCGGGCAGCCGAGTAGCCCGCCACCCACCAACTAGCTAAGCAGCCGCCTCTGTGAAGCTCGGCGGT
TCCCTGTGCGCCTGCGAAATTTTGACTCCGACTCACCAGCGACCGGCCACCGAGCCGCCGCTGTAGGAGCTGAGA
GCACGTCTTGAACACCGGATCTTTCCACCCAAGACCCGACAGCGTGCAGGGGCCTCGAGCAGTAATTTGAGGCCG
CGTTTCCCGCCAAGGTTTGGCCCCAGCTAACCGCCCCACCCATGCAACCGAGCGGGAAGAAAGCTGTGATTCGAG
GGGCCAGGAGAATACGGGAAAAGCTTCTGTTCTGCGCACAGCCAGTGCG
(SEQ ID NO: 189)

CGI: 129 range = chr5:114542616-114544119
CGCGCACAGGGAGTCGAGTGCTCCTTTGTGCCATCACCTCTTCTCGAAGCTCCAGGCGCAGAGGGCAAACGCTGA
CGCCCTTTCCCGCCTTCTCTCCGTCTGCGAGTTCCGGAGGGCAGTGCACTGTGCAGCCTCCGTACTTCCCGACAC
GTTCCGCCTGCAAACCACTTAGGAGCTTCTGCCGGCAATTTCTCGGATGCAGCGCGGAGCCCAGCCTCCCGCACT
GACTCAGGCCCGGCACCACCCCGCCTGCTGAGGGCGTCGTCGCGGGCGCCACCGACGGCGCCAGCCTGCGTTCCT
AAAGGCTCCAGGACAGGTGTGGGGCTGAAATCCCGCTCCTCCAGCATCTTCCCCTCCCTACCAAAAGAAGGCTGC
TTTAAATATTCCCGGCCTGGAGCAGCAGCAGCTAAGGACCTGGAAAGAGGCCCGAAAAGGCCAGGGCAGGGCGAA
CGAACGTGCTGTCCCTATTTACCGGCCACACGCTCTGACTGCGGGCTGACCCTGATCGCACACTTCGAGCCTGTT
CACTCGCTGGGCGGACCCTCCCTCCACGCTCCGCGCCCAGGCAGGCGAGGTCACCCACTCGAAGTCACCACGTTT
GAGTAGCCCTGGTTGGTGGGGCAGCGCCCCCTTGGCCAACGCCCCGCCCTCCTCTCCATCTTCCGACGCTGGGCT
CTCGCCCTTCGGCGTCCGAGAGCCCCTATTGCTGCCCAGCTGGCCCCAAAAGCGTCCGAAAGTCCCCTCTTGGCT
TATTTCAGAGATGCCACGCAATAAAGAAAAGGCGGCTACTTTGCATTCCGCAGCTGCTGGGACGCCCGGGCTGCG
AGCGCGGCTCCTGGATTCCAGCCTCCCGCCCTTCCCAGGCGCTGGAATGGACACGGACGCCCACAGTGGCGGGCC
AGGTAGTGCCGGAGTCGGGGGCCCAGGCCGCGGCGCCCCGCGCCTCATCACTTACCTTGCCTTTAGCTATCAATT
CCATGATGTAGCCAAATTCACTCATCTCCCCAGACTCCGACATGTTTACACCCCTTCACAAACTCTGGAGGACCG
ACGCGGGTGTATCGAATTTGTCCTTTCTTTTCTCTTTTTCTGTTTTAGTCTGAGTTTTGCCGAGCTCCCCGCCC
ATAAGCTGTTAACCAGGAAAAGAGGGGAAGCGCCGGGGAAAGCAAGAAGCGGGCTTGGGTGAAATGAAGGCCATC
GAGGGCTCCCGGGCAGCCTCGCCCGGCTTGCTAGGATCCGGGTGCAGCGGTCGGGGCTGCGCGATCTAACGGAAC
AAACGAGGGCGGCGGCGGCGGCAGCAGAGGCCGTGAAACCCTCACCAGGCGGAGCCGGGCGCGCGGAGGCCCCGC
CTCCTCGGGGGTCGCGGCAGCGGTTCGGACCGCAGCGGAGACAAACAAACGCGCACACAAAGCGGGTCCGCACTC
GGCTCAGCGCGGCCCCAGCTAGACATTCCCCGGCCTTTATCGCATGCCGGCAGGTTGGCCGTCCCCGGCTCTCGG
CGCG
(SEQ ID NO: 190)

TABLE 7B-continued

Sequences of differentially labeled CGIs between bladder cancer subgroups relative to blood CGI: 21 range = chr5:127899858-127900162
CGCGTCCCGATTATCAGTGCAATGTGATCACTTGATTTTAAACGCAACTATGCGTCCAAATGGCTGAGTGCAAGA
GGTCGGCCGGAGATAGGGCCGAGTGCGCTGCCCCAAGCTGCGATCCCTGCCAAGCACTCACGGACAATGCACTGG
TTTCCTCCAGGGAGCGTCTTCCATCCAGGGCAGCAGTAGGAGTGGAATCTGGAGCCGCACACGTTGGGCCTGTGA
TGGACAAGCGCGGTCACGTAACAGATAGGTAGAGGGATGCAGCAACATATAAACGGTCTTCGTAAGCAATGCCCC
GAGCG
(SEQ ID NO: 191)

CGI: 56 range = chr5:135720297-135720941
CGCCAGTCCTTTGTAGGCGTTCATGCGCGAGCGCGAGTGGCTGAAGGAGTCTTTCCGCTGTTTCTCGGTGCACTC
ATTGCACTTGCAGAAGTAGTCGTGGGGCCGCTCGATGCGGGCGCCCTTGAGCAGCAGGATGTGCACGATCTCATA
CTCCTGGCAGTGCGCCGCCAGGATGATGGGCGTGATGTCGTGGGAGAAGCGCGTGCCGTCCTCGTCGTAGGCATA
GAAGTCGTCGTCGCGCAGCTCCTGTTCCAGCGGGCTGAGCGTCAGGCGCTGGCCTCGCGCGAAGGCCGGGTGGTT
GAGGATGGCCTCCACGATGCGCACATAGCCCTTGCTGATGGCCAGCAGCAGCGCGTCCCCCACCCGTGCCAGGTT
CTCCTTCTTCAGCAGCAGCTCCGTGACCTCTAGGTGCTCGTTGCCCACGGCCAGCTGCAGAGCGTTCTGCCCCAT
GTAGTCCACACAGTTGAAGTTAAGGGTCTTGGACTCCTCCAGCATTTTCCGGACCACCGGGATGTTGCCATACTC
AGCCGAGTCCAGGAAGCGCTCCTCCTCGGGCGTCAGACTGGTGCCCTTCTCGTTGAACATGTAGGCGGGACCCCG
GATGGCCTGGCGACGGCCCTTCTCCCTCAGCGTTGTGTGCCGGCG
(SEQ ID NO: 192)

CGI: 29 range = chr5:140780945-140781256
CGAGAAACCGCGGAATATCGGCTTAGAGCCTGCCATGGCGAATCGGCTACAGCGCGGGGACCGCAGTCGGCTGCT
GCTGCTGCTGTGCATTTTCCTGGGGACGCTGCGGGGGTTCCGGGCCAGGCAGATCCGATATTCGGTGCCAGAAGA
GACCGAAAAGGGCTCCTTCGTGGGCAATATCTCCAAGGACCTGGGGCTGGAGCCCCGGGAGCTGGCGAAGCGCGG
AGTCCGCATCGTCTCCAGAGGGAAGACACAGCTTTTCGCTGTGAATCCGCGAAGCGGCAGCTTGATCACGGCAGG
CAGGATAGACCG
(SEQ ID NO: 193)

CGI: 182 range = chr5:141235749-141238152
CGCGGCGTCTTCCTGCACGAAGCGACCCAAGCAGCCCCAGTCCGCACCGCCTTGGTCAGCGGGCGCTCCCAGCAC
ACACCCAGCGCGCGGAGCGACTCCTCCCAGAGGACGCCGAGTGTGTGTGTGTGTTGCGGAGATTAGGGGGTGGCG
GGGGGGACGGCGGCAGTTTCTTGGGCTCTGGCGGCCCCACCCCCACCCCGGCAGCGCCCAGCCTCCAGGAACCCA
AGGCAAGGCTAGGGCGCGGCGTGGTGAGAACGCGCTTCGGCTAGTGGGGGGAGCCCTTGCGCCCCCCGCACCCAG
GCCACCGCGGGGAATCCCTCCTCCCCGGCATCTCCGGCCTCGGCCTAGGGTCCCCCGCAAGCCGGAGCCGGCGCG
AGCGGCGCAGCGGGCGCCAGGAGGGGGCGGGGAGGGAGCCGGCGCCGGAATCACAAAGCCGCGAACCCGGCTAGG
CGGGGACATTCTCATAAAACCGACCCTCTCGTGGCGAGCAGAGGGGGTTTTTTGCCCTACGCTCAATCCTCCAAG
GCCTCAGTGCCGCCCCCAGTCTTTCCTGGCAGAAGAAATAGTAGCCGACCACTGTTGGGGAAACTGAGGCCAGAA
TTCTGACTTACAGAGGGTAGCTGGGGGGAAGGGGTGCGAGACCACCTCGCCTACAAATTCTGCTCCTATGCCTGC
CGCGATCTCCGTTCTGGCTCCAGGGCCTGCCCGCGCACACACTGGCCTACAGCGGGGACCAGGCGGAGGGGGCGC
TCAGGTGTGAGACGAACCCAGGTGTGCGGGACCCACCAAGGTGTGTGGGACCCAGGTGTGCTGGAGACCCAGGTG
GCTCAGAAAACTCAGCTAAATGGCTGGAAGAGGGTCGCAATCACCGTCCCAGGCTAGCACCCTCTACAAAGGAAC
CTGGGGCCCCAGAGCTCCGGGGAGGCGGGATGGCTTGGCCAGCCAGGTCCAGCTTGTTCCCGGAACACCAGCCGG
TTCGGCCCGGGAGTGGGGGTTGGGGAGGCGCCGACTGGGAAGCCGGCAGGCCGGCCCAGCCTTCCCGCTGTGCCG
ATATTTACAATAATAATGTCGCGATTAACGTGGCGGGGCGCTTGGGGCTCGCCGAACGACCCCGGCGGCTTCTCC
TGCCTGAATCTGGACTCCGAGAGAGAGGAACGGAGTGTGTGTGTTTGTGTGTATGCGCTGCAGGGTGTAATGTAA
TGTGACACTGTTGGTTTAAGGTGTGTGTGACACCCAGTGTTAAGATGGGTGAAGCAGTGGATTCTGTGTTTGTGA
CCGTGAGGCGCTGCTGTAGGTGCCAATTCCTGTGTTAGAGTGTGTGCCATCAAGCGTGTGCTGAGATACTGGGTT
GTGTGTTTGTGTGGGTGCAGTAGAGGGGTGCAAGGAGACCTGTGCTGTGTACCTATGTTCTGGCCAAGAAGTGGG
TAAGATGATATATGCTAGGGTGTGTTCCTTAAAGGAATGTGGGGGGTGGCTAGGTTTTGAGGGTTCATCTAGTGA
ACTGTGGCTGTGACACTCGTACATGAGGGCACGAGATTGTGTTTGTGTGTCCACGTCGCGGGGTGTCACACCCGG
TTGTGTTATTGCTCTGTAAAGCCACGGGTTGTGTGTCGGTGCTGCTGATCGTGCAGACACTGAAGCGGATTCTGA
GCTGGCGACGGTGCCCCAGTGGGCGCTGGTGTGCGGGAGGTATGTCTGTGTGCACATATGCAGGGATGTATGTAT
GTGTGTATATATGTCCACGGTCTGGCCCTCTGGGTGCCCGCGAGAAGCTGGAAGCGGCTGAGTGAGCCGAGGTAG
TTGCCCAACAAGTGTGTATGTATGTGTTGTGGACAACGGTCCTTGCTTGCTCCGTCCTCCGGGAGACCCCCACCA
AACTGGGGGCCGCGCGCTTCCCCAAACCCATCCTCCACGCCGCGCGCTCCTGGAGTCTCCTTATCCCCGTCTCTC
CGAGCGCGCCCAGGTTTGGGACGCGGGGACTAGGGTTCTGCTCAGCACCCCCTCCCCTCCCTCGGCTTCTCGCCG
CGGACCTGGGAGGACGGAATCCCTCAGCCGCATCCCCTGCTATGGGCTCCCAGCAGCCCCCACCTCAGCCCCCTC
GCGCCGAGCTCGTGTTGGGCCCCCGCGGCCTCGCTCCGCCGAGCGCCCCTCCCTCAGCTCCCGCCGGCCATGACC
GCTTCGGGCCCCAAGCCGCTGCTGCCTCCACCGCCGCCGGATCCTTACCCGCCTCCGGGCAGCGCCGGCCGCCCG
CCCCGCTGTCCATGAGCCGCCGCCGGCCCCGGCCTGGGCTGCGGCTCCGCACGGCTGGGGCTGGAGCTGCAGTTC
GGGCTCCGGCTCCGGCTCCGGCTGGCTCTGGGCGCAGCAGCCCGGCGGCTTTGCGTCCGCGCCGCGCTCCCGCTC
CCCG
(SEQ ID NO: 194)

CGI: 263 range = chr6:1326743-1330210
CGCCGCGCAGAGTCGGCCGAATCCAGCTTCTCCAAGGGCGGGCGGGTGGGATGATTTGTTGATTTGCTTGTTTTC
CACCAAACCGCAGGGCACCTCCAGGAGCTCCGGGACAACTTACAAATGAAGACACAGAGCCCCCGTCCCTTGCTT
CAGAGAACCAAATAACGGAACTGAATGATCGTTTCTTCAGCAAAGCCTAAAGACGCTTGCGTCCCGCGGAGAGGT
GCCCACGCGCGACTCGGCTGCCCCCTCTTCTTGCGGGTCCGGGTAGGGTAGGGCGGGAACGCGGGACGTGCCCTA
AGCGGGCCAGCCGAGCGCGAGACAGGCGATGCTGCAGAAGCCTGCCCGCCTGCGGGTCACACACCGGCCGGCCTC
GGCTGCAGGGGTTGCGGGGCCACGGGTCGCGGGGCGCCGGGAGCCGCGAGCAGGTGACGGCCGCGCCGGGCAGCC
CCGCGGGCCGCGATTCCCGAGAGCCTGGCGCCACCCCGCGGAAGCCGGAGGAACTGCGGCTTCTTCCCGCTCCCG
CGCGGAGGGGGAGAGGGAGGCGCAGCGCGGAGGGGAGAGGGAGGCGCAGCGCGGAGGGGGAGAGGGAGGCGCAGCGC
GGAGGGGAGAGGGAGGCGCAGCCCGCACCGCGCAATCCCGGGGCTCTGGCGGGAGGGAAGGTGACTTGCGTGGGA
CGACTCCAAGAGGCCAGGCCCGGCCTTCGCAGTTCACCCACGAGGATACCGCGACCAAGCCACCAAAGCACTCTC
TGGCCAGGCCGAGACCCCTTTTCCCCCGGGCCCCAAGAGAAAAAAGCACTTTCTCCTAAAACACGAACTCCCCGC TABLE 7B-continued Sequences of differentially labeled CGIs between bladder cancer subgroups relative to blood GGAGGGGCCCGGGGCTGCCTGGCACGGGGCAGGGTGTGCGGCTGCCGTGCGGGCGCGGGCCAGAGTCACGTGGAG
GCAGGCGGAGAGGGCGAGGGGGCCCCCGTAAATCATCCTGAGGGATTTTTGGCCCAAGTCCCTGTTTCCGAAAGG
TTGCGGGACGGCTTTGACGTTGATTATGTAGCTGTTCTCTTTTCAAGTGCGCGCCCCTCCCCACCGCAGCCCGTC
TGGTGTGCGAGGATTGTGTTTGAAAGGGAGGAAGCATCCTTGAAGTGGTGGGTGATGGATTGTCTAAACCCTTCT
GGGACGTTCTGGGTGGGGGTTTTCGAGGCAGCTCATCAATAAAGACCCCCCTGGAGAGAAGGGGCGGCTGGAGAC
CAGCCCCCGCCGCGCAGCCCCGAGGCCCCAGGCCTGGAACACAGTCCTCGGTGTGGGGCACAGGGCGTGAGGGGA
GGATGAGCTCCCCCTGAGCAGATGGAGATTTCTCCTTGCCTGGGCCGTTTGACCCCCAAAGCCTTGCAGACTGGC
CGCGTGGGTGCCATGGGGCGATTTCTTGGGAAAGGAGGGCAGCAGAAAGGCCCGTGGGCTCTCAGCGCCTTGGAG
TCAGGGGAGCAGGAAGGGGAGTGGAGGTGCGGACACGCCTCCAGCCACCGTGCTCCCCTAGGAGGATCTCCCTTC
AGCCCCTGTAGAACCCTGCATCTCAACCACCCTCGTGCATGTGGTTTACCTTGGCATAGATTTCCAAGCCGCTAC
AGAAAACCTGTCCACCTCCCCCAAGGTGGAGGCGGGAGTTGGGAGGCAGGGGTGCTGGAAAGGGTCACCTGGCTC
AAGCCGACCCCAGGTCTGACGGGCGGAGAGCCTCGAGGGCCACGCCCCAGGCCAGTGGTGTCCTCTGAGGCCGCA
AAGCCGACTGGCTTCTGGAGGAGCAGCAGCCTCGGCCTCAGCCTCGGCTGGGAAAAGACGCAGTCGGGGCCCTCC
GTGCTCCAAACTTGAACTACTCTGGGTCCCCACGAGGAGGAGGCTGCCCTGGGGTCAGAAACTCCGACGGAAATG
AAGGGGAGGGGGCGTAGGTTCCCTGGCACAGCTCGGCCTGGAGAGGCAGCCTGGGGGCCCAAACTCATCTAGGGC
GCGCCCGGAGCTTCCCCGGCCTCTCTTGGCCCATCGCGAACGAGCTCCCCTCCCCGACTGGGTCGGCCTCGGGCG
CCTTTCGCCTTCGCAGGCCGCCGGGGTTCCGCGGAGGGCTTGTGTCCCTCCCTCCCGCCGCCGCAGCCCGCCCGA
AGGTCAGGCCGCATCCGGGGCCCGGGGCCTTTGGCCAGGCTGCGGGGAGGGGTGGGGTTGGGGGGCTCCCCAAAG
CAGCTTCTCGGAGGCGGCGTCGGGGCGCCCTGAGGTCCCTAGTCGGCCTCTGGGCGCCGAGCACGTTTTATTTAT
CCCCACAGAGGATGCTGGAGGACAAAAGAAATATTTGGACGTCAGAGCTGATTTATATTTTTGGAAGAGCTACGT
TTCCTTTTCTGAAGAGAAGCGAGCGCGCCCCATATCCTGAGCTCGGCGGGGAGGACGAGAGGGGAGTTTTGATGC
GCCAGGAAGTTCATCTATCGCCCAGGCGCTCAGGACCCGGCGCCCCGCCGAGTTCGCCGCCCTCGGAAATATTTA
TTTATTTGGGGGAAGGGAGGGCAGCGGGGAGGAGACCAGCCAGACGGGAGAAGAAAGCCCTGCCCGGGCTGGGTT
GGGACCTCCAGGGCGCTTCCCCGCGCGGCCGCAGCCGGCCAGCCTCTGGTCTCGGTTGGAGGGCATCGCAGGCGC
GGCCTGGCGACCTCCGGGCGCCTTTGGCTGGTGTCTTCCGTAGCCCTCGGCGCGCACCCTCCCGCGTGCAGTGCC
CGGAGTGACCTCTTCAGGCCCCGCGGGCGCCTCCTGGGTGGGCCCCGCGGCCCCTCCAACCCTGCCCAGCGTGTG
TGCGCGGCCTAGCCATCTTTCTCCCCAGCCTGGGAAGGCGGGCGGGAGGAGGGGATCCGAGGCCGGGGGCCGCGG
AGCAAAAGGCACGCGGACCCCTAAACGACCCCCGAGCGTTGCCACAGCCGGGAGGGCGGAGGGAAGGTGTGCAGA
GCTCGGGGGTCTCCCAGGACGCAGCTTGGCTCCTACCGGTTTCCAAGGCATCTGCAAGCTCTGTCCTGCGACCTA
AAGCATGGGGACGTCCCTTCCAGCAGCATCAGTGGGCGAAAAGTTAACATGCTGAGGGCCACCGGCACCCACACT
TGCTTCCAGGAATACTTGCGGTACAGGCTTCCTGACTTATTTTCTTTAGCCGCTGGGTGCCCCCCCTTCTTCCCC
CGTTGGGAGACGCAGACCGACTCTGTTCCAACCTAAGCCCCTTCTCTCTGCCTTTTGGACAAAGCGGGCCGCCTC
TGCTCTCCACTCACTCCCCGCAACCCCGCAACTCGCCACCCCTAAACGCAGCGGGCTGTAGGCGAAGTCGAAGAG
GTGCTCCGCCTGGTACCGCGGCCTGCGCACTGGGATCGGGGCCTGCAGGCCGCTGGGCTGGCTCCTGGGATCATC
CCAAGGTTTTGGTCTCGCAACCGAGGGGACCCGCGCCCGGCAATTTGGGAAGTGCGGAAATGGGGTGAGGCCGGT
CTTCGCTTGAGGGTCTCG
(SEQ ID NO: 195)

CGI: 190 range = chr6:5947471-5950124
CGATGCGGATTCGCGCTGGCGCTGAACGCTGAGCGCAGGCGGGGAGGCTCGGCACTCTCCGACCTCAGTAGCGCC
CCCAAAACCGAAGTCCAGCCGGCCAGAGAGGACACTTACGTGCACACGGTCTTGATGTTCGTCTTGTCGTCCAGG
CCCTGCGGGTAGTTGGCCATGCTGTCGCCCAGCTTGAGCAAACAGTCCGAAAAGCCCTTGAAGACCGCATCGCAC
TTGCCCGCTGCTCTCACGGCCTGCACCAGATACGCTGCGGGGAGGAGGGAACACCGGTCAGCAGCGCCACGACCC
CGCCCTGCCGCCCACTGCCCTTTCCTGCGAGACCCTGGCTCCGCGCGGCCTCATCGCATCGGGCGGCCTCTCCCA
GCGCCCAGCCTCGGGGCTCGCCAGTGTTAAAGGTGAATGAAAGACGTGACCCAGGAATGCCCGACCTGCAGCTAA
CGCTGCGTCTAGTGCAAATTGTCGGTGTGTGAGCAGGTGTGGGTGGGTGGGAGGTAGGTGAGTCCATTCCTTTCC
TCCAGCTCCCTCCCGCATCTCGCTCCGTATCTTTTTCTGTTTCCATCGCCCCCTCTTCTCACCTCCCTCATCCCT
TTTATTTCTCTTTCTCCTCGCTCCCTCCTTCGTCTCCCAACACTTCCCCAGCAAGCCCTGTCACAGCTCTCGCAA
TGCGATCTTCCATTTTGAGGTGACAGAAGGGGTCTCGGCTGCAGCGTGCGGGGGCGAGAACGGGGTGGGGAGACG
ACAGGGCGTGGGGTCACGCAGCTGAACCCAACGCCACATCACGAGAATAAGCCTCAGGCTTGGCGCTCTGTCCTT
GGTGGGCGCTCAGCAAACACTGCTGAATGAATGAACGAATATAGTCCCTGGAAGCCACCAGCAGTTACCGAAATG
GATTGTTTCATTATAAAACCGATTGCCTACCGTGGACTCTGTATTCCGAGTGAGACCCTCGGATGCACCCTCTCC
CGCCCCGCTGGAAAGAGGGCAGCCTGGACGTCCTGAGACCTGGCGCGGATGATGAGTGGTCTGGAGAGGAGAAGG
CCAGAGGCCGGGCGGGGTCACGGATGAGTCTGCCTGGGTCACCTCCGCAAAGGCCAAATCCACGAACCTCGGGCC
TCTTTCTCTCCTCCTCCCCTGTCCGCCACTCGGCTCCCCAGACACCCTTAACAACCCACCCGCCCGCCAAAAAGC
CCGCCTACACTCCGGACGGCAGCGGGGAGAGGCTGTTCTTCTCCAGGTGCCAGCCCTGCTGCTGAAAGTGAGCTC
GCCGCGGCCCGGGGCTCCTGGCCCCAGCTCAGGACTCCCTGCAGAGAGCAGGCAGGGATAAAAGCTGAGCGGCGG
GAGGAGGAGGAGGAGGAGGAAACACAGGCCGCACGAAGGTCCAAGCCCCAAGCCCCCAAGCCCCCGGCCTCTGGA
CGGCCAAACCCCGAGGCGCGGGACTGGAAGGACAGGTACCAGGCTGCGGGCGCGCGGCTGTGGCCATCTCTTTCC
GCCCTGAGGCCGACGAACCCGGCTGGAAGCTGAGTGCCTAGCGGCCCAAAGCAGCCCGGGCGCCGGGAGGGCGCC
AGAGAAGCACAGCGTTAGGGCGGGGAAGAAAGGGTGAATCTCAGAATCGAAATCCGCACTGGCGCCCACGACCCT
GGGCGCCGGCCTGGTCCTCGGCAGCTTTCTGGCGGCTGCGCTTGTGTGTGAATGTGTCCCGGGAGGACCGGACAC
CTCAATCCCCCGGCCCCCAACGCGGGCGCCTGTCCGCGAGCGCCGGGCCAGACGCCGAAGAGGAAGGTGACCGAA
CCCGTAGCAGCTTCCGAGAGCGTACCCGTTTGCAAATTGCTGCAGGAAGAGCGAGGCGGGCCTTGCGCTTTTTAA
TCCGGAACGGGAAGCACTGGGGAAGGGACCGAGGTTAACTTCGACCTCCGCTGGGGCAGATACGTAAACCTTCTC
AAACCTCCGAGTTCACCTTACAGCGAACATTAAATACCCTTGCGACTACAATACTAACAAATCGAACACTGACGT
AAAATCTTAAGAATAAACGAATCTTTGTTCTGATAGAGCTCGTTCAAAATGGAAATACACTCCACACATCTTCCT
CTATAACGCATGTCACAAATACAGCTTTGCAGAGAAGAAACGAAATAAAATAAAGTCCAATCTCCCCGTCCACGT
CTCTCCCCACCCCTTGCCTACACCCCCAAAACTCAGTGGCGAAAGAAGCCCCTAAAATGCATTGACATTTTTTAA
GGGGAATTGGGGCTCGCCGGGGGCGGGAGCGCTCTTGTCACGTTATCTTCCCAGGCGCTGCTGGAGAAGACCCTG
CACACCGCGCATGTGTGAGTGTGTGCTGTGTAAAATAAGTCGTGAACATTTCTGTCTTTTAAAACTGTGACTCCT
TGGACTCTAGCCTTCTCTGGGAGGCCGGGAGGCTGCGCGCGGGACGGATTTTGCAGGCGCACGCGTCCCAGCAGG
TCGCAGCCCGTGGGTCCCTCGCTGTCCTTCCTGAACCCCGCTTAGGCGAGACTCTAGCGGGTGACCCTGGCTCCT
TCCCTGTCCTCTCTGCCGTCCCCTTCTTGTGCGGTTTCCATCCGTTCATTCATTCGTTCGACCTCTCATTCATTC
CGAACTTCCTCCTGCTGCGTCTTCTTTCG
(SEQ ID NO: 196)

TABLE 7B-continued

Sequences of differentially labeled CGIs between bladder cancer subgroups relative to blood CGI: 40 range = chr6:10498025-10498551
CGTTTCGGGTGCGGGGTGCTGATGCTGCTTTTTTGTTGTTCGTTTGCGCTCGCGCTCGCTCTCGCTCTCTCTCTG
CATCCCCCTCACCCCTTTCTCGGAGACTGAACTAAGTGAAAAGTTGTTTCAATAATCGCAGCTCTCTGCTCCGC
CAGGGCCGAGGGAGGCGGGCGGAACACGGAGGGTGTTTTGTTAAATGCTCCCGTCGTTCGCAGGGGCTGGGACTT
GATAAAAGGAGACAGTTTTCTGAAAAGATTTGATTGAAATGGCGTGTGCCAGGGCTGATGGGAGCCAGCGAGGGA
CAAAGCGCCGAGAATCCATGGACACTCGAGCAATTATGCCTCCACGCTGAAGGTGGATTAGCGCGCTGGAAAGAA
GCATATGTTTGGCCCGGGGCGACACTTCCCCCCGGCTGAGCTTAGAGAATGGGAGCGCGGAGAGCGGCTGGACCC
GGAATATCAACTATCTGCGAAGCCCCCCCTTCTAGCCCAACTCCGCCAGCCTCCCCGCCCCCGCCGGGGAAAAGT
CG
(SEQ ID NO: 197)

CGI: 100 range = chr6:22677564-22678684
CGTCCGAGGGTGGGTCCAACGGGCTTCGAGTGTTCGGGAGATAATGCACACTTCGCAGTGGATCTTCTCGGGGCC
CCGAGCGTTGCCCGCCCATTAGGTGGCGCCGGTCCCCTCGAACAGGTCGCTCAACAACTCCCGCCCAGCAGCCGC
CCTTACTGCGCGCGCGCAGACTTCGGCGTCTACTTCCGGTGTGGCCCAGGCGGGGTCCGCAGAACCAGCTATGTC
GGCCTACGGCATGCCCATGTACAAGAGCGGGGACCTGGTGTTTGCCAAGTTAAAGGGCTATGCCCACTGGCCGGC
GAGGATAGAGCACATGACCCAGCCCAACCGCTACCAGGTGTTTTTCTTCGGGACCCACGAGACGGCCTTCCTGAG
TCCCAAACGCCTGTTCCCGTACAAGGAGTGCAAGGAGAAGTTCGGCAAGCCCAACAAGAGGCGCGGCTTCAGCGC
GGGGCTGTGGGAAATCGAGAACAACCCCACGGTCCAGGCCTCCGACTGCCCATTAGCCTCAGAGAAGGGCAGCGG
AGACGGGCCTTGGCCGGAGCCCGAGGCCGCAGAGGGCGACGAGGACAAGCCGACCCACGCTGGTGGCGGCGGCGA
CGAATTGGGGAAGCCGGACGACGACAAGCCCACTGAGGAGGAGAAGGGGCCGCTGAAGAGGAGCGCGGGGGACCC
GCCGGAGGACGCCCCCAAACGACCCAAGGAGGCAGCCCCCGACCAAGAGGAGGAGGCGGAGGCGGAGAGGGCGGC
GGAAGCGGAGAGGGCGGCGGCGGCGGCGGCGGCGACGGCCGTCGACGAGGAGAGTCCGTTCCTCGTGGCGGTGGA
GAACGGCAGCGCCCCTAGCGAGCCGGGCCTGGTCTGCGAGCCGCCTCAGCCAGAGGAGGAGGAGCTCCGGGAGGA
AGAAGTCGCGGACGAGGAGGCCTCCCAGGAGTGGCATGCCGAGGCACCGGGCGGCGGAGATCGCGACAGCCTGTA
GTTACCAGCGTTTCCAGAAGAGCCCCTGCCCCGTTCCTGCTGCGGCCTGGCCGTTCTTGGGGAATCTGACCACGG
CGTGCAAACTGGGACTGCCTTTCCCTCTCCTCAGCCCGTCCTCCTCCAACCCGCGCTCCTTTGCCCTGCCG
(SEQ ID NO: 198)

CGI: 20 range = chr6:25834434-25834701
CGCCGCCCAAAAGCTTATTGAGTTCCTCATCATTGCGGATCGCTAGCTGCAGGTGGCGGGGAATAATGCGAGTTT
TTTTGTTATCGCGAGACGCATTGCCTGCCAGCTCAAGGATTTCTGCTGTGAGATACTCTAACACTGCCGCCAAAT
ACACTGGTGCGCCTGCCCCTATCCGCTCTGCATAGTTTCCCTTACGAAGCAGACGATGGATCCGGCCTACGGGAA
ACTGCAAACCCGCTCTAGAAGAGCGAGACTTAGACTTGGCGCG
(SEQ ID NO: 199)

CGI: 71 range = chr6:41176454-41177326
CGGCTTTATCGTAGGAGCGTCTTCGCCTCCCCCGTTTCCAGTAGAAAAGACAGCTTTGCTCCTTTGAAAGCGCAG
ACCGCCGCACCTCCAGCCCCTTCTCCCCGGGGAAGTAGGCCCCGCTAAGAATGTGGGAAGGTGGTGGGGCGGCGA
CTGAAGTCGCTTCCGATTGGCGTTGTCCCAAGGAAGCCTGCGCGGATTGATCGGCGGCAGGCCTCCAATAGAGCC
TGCTAGGCGGATTGGCTGCTACGCGGCTGGGCCCTGTTTCCGGTACCTAGGCGGGCAGCCATGGTGACCGGCGAG
CGGCATGCGACGCCGCCTCTGTGGCCTGTGGAGGCCCGCTTGGCGGCGCTGCTTCCCGACCTACTGGTCTTTCGG
AAGCCTCGGGGATGGGAACCCGAGCTCGCCACGGCCCAGGGCGTCCTCCTAGGCGTCCATGTGACGGGTGAGGGC
GACGGCCGGCACTTGCACTTAAGTCTCCTGGCCTGCGGGAGAGGCGGCCGTTGGGTCTAAGCCCCTGGAGGCCTC
GACGGTTACAGGCCTAGCCTCCCGCGAGCTAAGGCACAGTTTAACTTCGTGCTGCGGCTTCCTTAGGAAACTTTG
AGTATCTTCGTTTTAGCGTGGGAGGACATCTTTTGGGATGAACCGGCTCAGTCCTTGAGCTCACCCCAAAGATGA
TGAAATTGAAACTCAGAGGAAAGGATTTTTACAGGACCACGCCCCGGGCTTTGAACCCGTTTTTCCCAACCCCGA
GCATTTTCTATTAAGCGTTCTGTTTCAATTATTTTATTCGTTCAGTTAATTCGTTCTTGGCGTCATAAGTATATG
CCCGCCGTTGTTCTGGCCGTAGCTATCTAGCAGCCACTCCGCGAGTCG
(SEQ ID NO: 200)

CGI: 68 range = chr6:50895246-50896050
CGTCCGAACAGAAATCGCAGCCGCCTCCTGTGTGGGCATCTTTCACGGAAATTTCTGCCCACGTTCAATGCGTAC
GGGTCTCTAGCACTGAGGCTAGCTCAACTCTTCGGGGCAGGAGAAGTTGCGCCCAGCCAGGAGGACGCCAGCCGC
CTCCGGGGCCCGGACCGCGCTCGCCAAAGCCCTTTTCCGGCTCGGGCGAGGGCTGACGCGGCCAGACGGCTCCGC
TACTCGCGGGCGAGGCGGACTAGGCGGACGAGGCGGCCGAGGCGGGCGAGGTGGGAGAGGCGGGCGAGGTGGGAG
AGGCGGCCGAGGCGGGCGAGGCGCGGGGCGCGCGGCGGGCCAGGCTGGGGACCGGGAAGCCCGCGGAGCCTCGCT
TTTAAGCGGAATGGTCTGGGACAGCCCCAGGTGGTTGCCAGGGGAAGGGAGGAAGGGAAGGTTCTGCTGAGACGT
CGAGGTTGGAAATAAAAACTTCGGAAAGGCGAAGCGGATTTAGAAAAGGAGGGAAGTCGAGGCGGGCGAAGCGGG
CCATGGAGATTGCTAAGAGGAAAAGTTGGAGAGAAAAGGAAGGAAGAGAAGCAGACTCCCGGGTGGCGGGCGCGG
GCCGCTAGGTCAGACGAAAGGTGGAGGGATGCAGAGGCTCCCCAAAGAGCCGAGAAAGACACGCGACCCCTCCGG
ATCGGGACAGCTCCTGAAAGCCCGGCGCAGAGCCGCCTCGAAGATCCTAAGAGTGGGCGACTCACAGGCGCGGCC
GGCAAGCTCCTGGGGGACTCGGGCTCGGACGAGCGCCCACAGGCAGCGCCTGGCG
(SEQ ID NO: 201)

CGI: 43 range = chr6:75968300-75968853
CGGCGCCGTTTTGGAAACCCATCTCGGAGCGCCCCACTGCCTCCGCGGGAAGGTCCGACGCACCCGGCTGTCCCT
GAGGGAGGCAGGATGGAGCAAGGGCAGGACACTGGAGGTGGTGCCCAGCAACTCCGGCGCGCGCTTGCTTCCCAG
GCTGGAAACCTTGGCCCAGGCTCAACCTGTCTGAGCTGGACCAGTCCAGGCCACGCGCCTTGGAGCCCTGCTAAC
CAACAGGGACAGCCGCGACCCTAGGTCGTGCGAACACCTGGGGTCCCGGATCTCCGCTTGCCTGCCATCATCCCC
CAGGCTGCTTGGCTGCTGGCTCATCTGCCCGCACCGTCCGCCCCGCCGACTGAGCTCCCCACAAAGCACACAGAG
GCGCAGAGCCAGCGCTGTTGGAGTCTTTTATTGTGTTCTGTCACCGAGGTCGCAGCCCCGAGCCAGGTGGTTGGT
TACCAGCCAAGCGAGCGAGTGCGCCCGCTCTTCGGGGCTCCTGGGTGCCACCCGGAGGTGTCCTGTTGGTTGCGC
TGATTAGAGCCGTCGCCCCCTCTCGGGCG
(SEQ ID NO: 202)

TABLE 7B-continued

| Sequences of differentially labeled CGIs between bladder cancer subgroups relative to blood |
|---|

CGI: 27 range = chr6:101953488-101953856
CGCCTTTTGTGCCGGGCTGTGGCTCGCTATCGACATCTCGTCCGTTACCAAGGCTGGGTTTCCTACTGATTTCCC
TCCTCCTCTGCTTTCACAGGCTCGCGCGGCCGGACATTGTGGGTGTGCGTGCTGGATTTCTCCCGGATGCTCTCC
GACTAACATGGATGTCCCACCATTCCTTGCAGTGGAAGGTTGTTCCTTGGCGCAGTGAGTGAAGAACATGCAGCG
ATTGCTAATGGGTTTGGGAAGCGGAGACTCCTTCCTCTCTCTATGACCATGCCGTGATCGTGTCTGCGGTCACCA
CTCGACGCATCCTCATTTCTACCCGAACCCAGGAGCCGAACGCTAGATCGGGGAAGTGGGTGCCGTGCG
(SEQ ID NO: 203)

CGI: 318 range = chr6:108592365-108597232
CGCCGAGTTCGAGAAAGCGCTACGCCGCCGGTCGGGCTAGCTCCACAAGCGGCTGTACAAGTTGGCTGTCAAAAA
ACGCTGATTTCTCCTCCTGTCACCTAATAAACCCCTACGCGCTTATGGCCTCGTCCCACAATCCCCCAATCTCGT
CCCAATTCGAAAAACCGAGGAGGAGGGAATAAACTGAGAGATAAAGATCCCCCCATCTTGCTCTTTCCCCGGGAC
CCCAGCCTTGGTCGCGGCGCCCCACTAAGGAGGACACAGGCTCTGGTGTGTGTGGTGTGCGAGACCCCGAGCTCG
AGGCCGAGCCAAGGCTGGGCAGAAAGTTGCAATCACGTGCTGTCGGAGCCCACTGGAGCGCACAGCCCGCTCCCC
CTGGGACGCCCAGGCGGAGGACCTGCTGCGCCCTCCCAGGGCTCGGGGGACTCCAGCATTCACTTGCACGCACAG
GCGAACTCTGATTGAAAGCCCGGGATGACACCGAGTCTGGAGAAAGAGGGACCGGGGGGTGGGCTGGCGGAATTG
CAGAGCGCCGGCCACAGCTCCCCTCCCCGCGAACGTCGAGCGGAGGGCGGGAGGTGTAACCTCTGACCTCTGGCC
GGGTCCACGCCCTGAGGAGGGACTGGCAAGCTCTTGTTCGACAAGTTCAAGCTGCCGAGAGAGCTTAAATAGAAT
TAATCTCTTAGAGATCGGGGATCATCGCTCCCTCGGCATGCGCTCTCCCAGCGCCGCGCACAGAGCAAGGCGCGA
GAGAGCTCAGGAATCGCGGGAAGGCAAGCGGAATGGGGAGGGGGTAGGGGATGAGGGCCTCTCTTCACTATTCCT
CCGCCCGGAGAGCGGGAGCCCGCAACGCCCGCCGAGGACGAGCGGCGGGAGGGAACGCTCTGCCCTCCAGCCGCC
CCGGTGCAGATAATGGAGGCGACAAGAGATTCGCTCAGCGTCGGATGGGCCAGCTCTGCTTGGGGAAGCTGGCGG
CATCCTCCCCTCGGCTGGTGCCCAAACCCACTGCGCGAAGGCCGAAGGAACGCGGAACCTCCAGAAGACCCCATC
CTCAGCCCTGACTTTCCGTAGATATGTGCAAAATGAGTAAATTACTCACCTCGGGCCAGATCCAAGTTTTACCCA
ACAGAAGGGGCACCGGACCAAGAATGAACCAACTCACATGGCCATGTCCGGCGCGCACAATCACACGCCAGCACA
CAGCCACCCAATTTCTTCCGCGAATCTATCTGGCACTCTGGAGAGAGGGGGAAAAGCGTTTTGAGAAAGCCCCGT
CACCCCTCCCCTTCCTTCTTGCCGTGAAATATACGAATTCATTTTTATTACGAGCCGCACCGTCCTCACCATCAC
GCACGCACAGAGCCACACTCCCATATTCACACTTTCTAACTCGTAAGCTCCGACAGCGCCTGCATTTTCTTTGGG
AGCCGCTTGGAGGTTCATTAATATCATTAGCATTTAACCCCCTCCCTCTTCCCATCCCCTCCCCGCACATGGCTG
ACGTCAGACCCCGCCAGGAGTTGGGGGAAAAGCTAAGTGGGCCAGGGACGCCCTATTCCCCTCCCCGCGGCTGCC
TGTCAGAGCGCTTCTGGAGATATTACAGGGGACCCAGCCCGCAGCGACAGGCACAAAGTCACGGGGTAATGAACT
TCGGGGACCCTTCGCCGCTGCGTGCGCGGCTCTCCCCGGAAACCCGGACCTGGCCGCCTCTTCCCTCGGAAGATT
TCCCAGCAATCTAGTTTTCCCACTCTGCGCTTGGGTTCCGGCAGCGCGGAGCCCGTCTGCCTCTGAGACTGCGGT
AGTGTTTTCCTTCTTTCCTTGGGAGACCAGCGGTCGGCAGAGATTGCCCACACTCTGCATGCCTATGTAGAGGGA
GAGATCGAAGACTGAGTGACAGGAATGGGGAAAAAGAGGGATTTCGCTCCGTAGGAAGGCCATTTTCGTGTCTCC
ATCTCTGTCTTTCAACATCCCTCTCTTGCTGTTCTTCCTTCTTCCTCAGTCTTCCTGTCCATCTCTCCATCTGTC
TGTCCATGTGTGTGTCCATATCAAGCAGCATTCCCAGCAGCTGCGGTTTTGCAAGAGCCGGGAAGAAACTTAAGG
ATGCTTAAATTTCCACTGTTGGACGAATTCTGAGCGCCCAGGGAGCAGCGCAGCGCGCGACTGACACCCACCTGT
CCCGCCCAGGAGCCTTGCAGGCTGGAGGGCAGCTGGAGAGCGGCGGCGCCCGGCGGCGAGGCGGGCGCTGCCGGC
CGGGACTCGGGCAGCGCCCACCAACCGCTCCGCCCCGGGACAGCCAGCATGAGCAAGCCAGCCGGATCAACAAGT
GGGTACCTCTCGGGCCGCCGTGGGGCCTAGGCGCGCAGCCTGGGGCGAGCGAGCGGGGAGGCTGGGGGAGGTCCT
GCCTGGAGCGCTGCGAATCTGAGCCCCTGAGAGGGATTCCAGCGGGCGTGTGCGTTCGGCCCAGACCTGTAGACC
GTGAGTTGGAGCATTTCGTGGAGAGGGGAGAGCCGTTTCGTTGCCTCTGGATTGCTTGATCCCCCCTGTCTGGTG
CGGTGAGAAGGTTACGACCCGCGCAGCCCACCAGTCGGATGAGTTGTCTCCATTTAGCCGCCAGGTGCTGGATGG
GGGGGCCATGGGGGCGGGAACTGGGCCGCAGCTCCAGGCGGTAGCACAATAACACACTCGCTCAAAACTCCGAGC
TCCAGCGCGCAAAAGCAACTCTGTGCAAAGCGGATTTTGAATGGAATGCTTTGCACCCCGTTTCTAGCTATTTCA
AATAATCCTGCAAACTGGGAAGCAGAAACAATTTAAAAGTCACATTTTCCTTAATCCTAAATCCGCGTAGGTCAT
AACTGGGGAATTTAAAGTATGGCGAACCACTCTAGCAAAGAGAGGACCAAATCCCTAATCCCAAGGACTTTTCGA
GCCGGAGCCCAGCAGAGGCAGGAGTGCGCGGCCTGCTCCCTCCGTGCGCTTCTCTCCTTCCTCGAACTTCCTTAG
CTGCCGGCTCTCCGAACGCCAGGCCGCAGCTGACCTCTCACCACCCCGAGACTCACGAGCGCAGGGCTAAGTGTG
TGTGCGAGGGCATTTGCTTGCACCCTGCCTGCGGAACCCAAGAATGTGCAGGCCCGAGCCAGCGTTGAGCAGGCG
CGGTCACGGTGCTCAGATCTCCCGGGGGCATTTCAGTTCCCGCCATCCAGTGGCCCACGGCTGCGGGCTCCAGGG
TCTGAGGCTGGGGACTACCGTTGCCGCCGCAGTCCCCATATCCCGAAGTTGCCTTGCTGCTTGTGTTGTTTTCGC
AGATAGCATTTTTGGCGCTCTGTGCGTTCCTTCCCTCCCCCTCCCCCTTTCACTCGCCCTCATTGTCCTGAGTCT
TTGAAAGTTGGGAGAATCGGAGATACTTCTGAGGACTGGTAATGAAGTCTCACTTAAGTGGGATGCAATTCCCGC
CCTCCTACCCCCCTCCAAGAAGGAGGTTGTGTTTTCATTTTGTTTTGCTTTGGGTGCTGACCTTTAAAAAATTAG
AGCAAAATGAACGTGAACAAAAAGAAAAGGAGAAATGTTTCGAGCTGGGGCAGAGGGAGCAGAGAAGGAGCCCTC
ACCGCGGCCGGAATGCAGAGCGGACCCTGGCCCAGGACTGGGTTTCCCTTTAGGCTCGGGCCTACCCTGGCCCTC
GCTGTTGGAATCTCCAGGAGGTAAAGCGACCTCGATTTTTGTTGCCCGCATTCCCGGGCGTGAGTGTCCTTCCCA
GGAGGCTCAGGAGGCCGTTTCTGTTGCATTCTGAGCCTCCGTTGCAAAAACTGAAGCCCGTGGGTCTCGGCAGGC
CTCCTAGCTCGCTCGCCCCGGGACAGGCCCTCGCCTACACCCCTGGAAGTAAGGAGCCCCGGGCTCTTTCGTCCT
TTTCGGGGTGTGGAGCCCCTGGGGCCCTTGAAAGGTGAGGCCTCAGAGGCGAGGGAGGGGTGAGCGGGGAGCTCT
GCCCGCCTGCGGCTGCGCCCCCGCTGTGGACTAGGAGGCAGGCCAACCCTCCGGACTTTGGGGGAAAAACCACAG
CGGGCTCCTTGCGGAAACTTTGGCCGTTCTAACTTGCCAAGAGCCTGAGTGAGGCCTTGGAAGCCTCCAGCCCCG
GCTCAGGTCGGGACGCGGCTGCTGAGCTTTCTCAGGCCCGCAGGACAGCGGCCCCCGCCGGTGGCGCCGCTGCAT
TTAGGCCCTTTCCAGACCGGTGGCGGCAGCCAACCCGAGACTTGCGTCCCTCGGGCCCGGGGCAGCTAGGAGGTC
GGCGCGCAGCGGGCCGGGTCAGGACTGGGTCGAGCAGACAGAGCTGCAGCCCCCGCCTTGCCCGGCTTCTCGCGG
CTGGAGAGCAGAGCGATGTCACCCGGAGCCCCGCCTGGGTGGTAACGAGACCCTGGCCAGTCACCCCTGCAGCCC
AGACTAACTTCTTTCAACAGCCTCTGATGGTAATTACAGTAATCGAAGCTGCCATATATCTTTAGGCAATTATGA
CACACAAAAAGCCCCGAGGGGACCCCCTGGCGAGGGAAGTTAAGAACGGTTTTCCAGCTTCAGGAAACTCCGGCT
CGCCTCACGTCGGAGCTCGCTCGGCTTGCTAAATGAGAGGAGCTTTGCAACGGGGTCAACCAGCTTGTCTCGTGA
CCCCAAGTCACCTTAACGTGGCTGGGTGGCGGAGTCTGAGGCACAGGCCCGCTATGCCCCGGAATTTTCGCGTCC
CTCCCTCCTGGGCCCCGCCCCAGCCCGGTTGCCTGTTTCTAATCTGCCCCGGGAGCCGCGGCTCAGAGGTCTGCT
CAGAGGCAGGACTCGCACTGGTGGTGGCCTAGAGGGCAACAGTCCGGAAGCTCGGGCGGGGGAATCCG
(SEQ ID NO: 204)

TABLE 7B-continued

Sequences of differentially labeled CGIs between bladder cancer subgroups relative to blood CGI: 38 range = chr6:126122028-126122524
CGCGGTACCTGAGCTCCGTGGAAGGCCTGGACTCCTCGGATCCGCTGCGGGTGCGGCTTGTGTCTCATCTCAGCA
CTTGCGCCACCCAGCGGGAGGCGGCGGCCATGACATCCTCCATGGCCCACCACCATCATCCGCTCCACCCGCATC
ACTGGGCCGCCGCCTTCCACCACCTGCCCGCAGCCCTGCTCCAGCCCAACGGCCTCCATGCCTCAGAGTCAACCC
CTTGTCGCCTCTCCACAACTTCAGAAGTGCCTCCTGCCCACGGCTCTGCTCTCCTCACGGCCACGTTTGCCCATG
CGGATTCAGCCCTCCGAATGCCATCCACGGGCAGCGTCGCCCCCTGCGTGCCACCTCTCTCCACCTCTCTCTTGT
CCCTCTCTGCCACCGTCCACGCCGCAGCCGCAGCAGCCACCGCGGCTGCACACAGCTTCCCTCTGTCCTTCGCGG
GGGCATTCCCCATGCTTCCCCCAAACGCAGCAGCAGCAGTGGCCGCG
(SEQ ID NO: 205)

CGI: 270 range = chr6:166499964-166503413
CGTCGCCTCCCGTTCAAGCAGCGTCCCTTCCCACAACCCCCGTGCAGAAGGCGCAGCGCGGCCCCCTCCTCGCTG
GTCCCAGACCTGGCGGGCTCCTCACACCTACCTGGCCCCCTCCGTTGAGCTTGTTGGTGAGCTTGACTTTGCTGA
AGGAGACGGGAGCCTTCATCCAGTGGGCCCCGAAGTTGGGCGAGTCGGGGTGGATGTAGACGCAGCTGGGCGCCT
GCGGCTCCGGCTTGCCCCCCGGCACCCATTCCCCGTTCACGTACTTCCAGCGGTGGTTGTCCGCCGCCACGAAGT
CCAGCAGGAAGGAGTACATGGCGTTGGGGTCCAGGCCAGACACGTTCACCTTCAGCACCGGAAACATCCTCCTGG
AAAACACGGGGCGGGCGCAGGAGGACCCCGACACTGACCAGGTAGGCCGGAGGCAGAAGCTGGGCACAGAGGCCT
CAGTTATTTCGGGGCACAGAGGAGCCCCCTGGGGAACGTCCGAGGGTGACTCCCAAGCTCCCCCTTCCCCGAGCC
CTGCCAGGTCCAGGTGGCCTCCTCACCATCTCCACGGCCTCGGGAGGGAGGGGAGGAGAGGACCTGGCGAAGGGT
TTCAGTGCAGGAGGCCACATCCCGCGGGGACAGGCGGGGACCAGGGCGCGCCTCGCGGGTCCCGGGATGCCTCCG
AGGTCGGGACACCGAAGTGCGCGTTCCTCCTCCCCAAGCTTCCGCGGAGAAAGCCCCAGAAGAGGGGCTTGTAGA
AATGCACTCGAGGGAGTTAACCAGAGCGGGAACAAACACAAAGCCCTCCTCCAGGAGAAAAAGGGTTCGACCTCC
GGGAACTTGCCAGGTCCCCCAGGCTGCCCAGGCGCTGGAGAGCGCGGCGCGCGCGGGCTCCGGACGCGCACCCAC
CTGCCGTTCTTGGTCACGATCATCTCATTGGTGAGCTCCTTGAAGCGCAGCCACAGCTCGCTCTCCTCCAGGCCC
ACGCGCAGTTCGCGCTCTGTGGGGTCGCCCTTCTCGCTGCCCGCCTGCAGCTCATTCTCCACGGCGCTCAGCAGG
TGGTCCACTCGGTACTGCAGGCTCTTTCCCGCGCTCTCGGTGCCAGGGGAGCTCATCCTCCCGTCCGGCTCCCCT
CCCCGCCGTCCCCGAAGCCCAGACTCGCTACCTGAGATCCACCTTCCCTGCTCTTGGCCGCCGCCCTTCCGAGAA
AAGGGGCCCCTTGGACCGAGACCTGCGACGGCTCCCGGGTCCCGGGTCCCGGCACAGACCCGGGAGGAGGGCGCG
GACCAAGACTTGGGGGGAGGGGACGGGGGCAGAGGGGTGGGGAGAAGTTATTCCACTTGAACTCCCCAAGGCTCT
ACTAGTGTAGGTCTCTGGGGACCGAAATTCAGTGCCCTCCCCATAAATAGAGCCGCGGCGGCAGCGCTGGGGTGC
TCGGCGGATTGGGCCGCGCACGCTTTGAAGTGCCGGGCAGCCTCCCATTGGCCGAGAGCGGCCATATCAGACCCA
GCCGGGCGGGTCTGGGAGGCCGGGGGCCAACAATGGGCTCCCGCACGCCTGTTTCATGTAAATCCGGGGCCCCAG
CCCTGCGAGCCCCGGCCCAGCCCCTACACCCCGCCCTTCTCCAAATGTTTGCACCTCCATCAAAGCGGCGGGGC
AAGCCCCGGAGGAAGGTAAGCTGGACGCCCCGGCCTGCCCCAGCCCGCCCCAGCCCGCCCCAGCCCGCACTTCCG
CGAGGGGCTGCCCGGCAGCCTGCGATGCTCCCTGATTCCCGCGCGGGGTCCTCCTCGCTTTCCCAGCGCGCCCGG
ATCCCGCAGCCGCGCCAGGCTGGAACGTTCGCGCGGCCTCACCTGTCCCCGCTCCAGGCGCGCCTCCCTCCCCTC
CCAGGGACGAGCGCATTTGGCCGGGCTTTGGGATGCGCCGCGCTCGTCTCGCCGCAGTAGTAGTGCTGTTCTCGC
GCCTCCGATGCCTCAACTCTCCAGTCTGGCAGTTTCCGGTGCACCTGTCCCCACACGTCCCTCGCCCACGGAGCC
CCAGGCGGCGTTACGCACACCCAGGATCGTGGATCAGCCTGCCCCGGCGTCGGGTGTCCCCGCGGCTCTCACCAT
CTGGAAAAGGAAGGTCCGCGCGCAGAGAGGGAAATGGACGGAAATAAGCAAAAGCAAAACAACCCCTTCTGAGAA
GTGTCCTCCTCGCTCTCTTATAAAAACAGGACTTGTTGCCGAGGTCAGCGCGCGCATCGAGTGTGCCAGGCGTGT
GCGTGGTTTCTGCTGTGTCATTGCTTTCACGGAAGGTGGGAGAAGGTCGGGGCTGGCGGGGTGGTCCGGACTAGT
GGGACTCGGGGCGCTTTCCCCGCCCGGCCCAGCGCCAAGCGGTGTCGGCAGCGGTTGTTTTATTACCTTTCGGTG
AGAACTTACGCGAGGAGAGCGAAGGAGAGGTGACAATGAGCAGGAAATAGTTCAGTGGGGTCTCTTTAAACAGTA
ACATTCCTCCTAAAACGGGAGCCCAGGAAGGGGGAAGGAGGCAGAAGCTCCCCCTTCCAAGGCCTGGCTTTGCGC
TTCTGCACACCTCGCCCATTCGCTGGACGAGGGCCTGCCTCGGGTAGCAGCCTCTGTTTCCCGGTCTCCTGAGCG
GGCACCCCAGCCCCAACCCCTCTAGAGAAAGCCTGCGCATCGGGTGGGGCAGCGAGTTCAGAGGAGTCTTGCGCC
CTAGCAAGGGGGCTTTCCCGCGGACATGGTATCTGCGCCCCGCGCTAAGTCTCCCCTGCCCCCTGCCCCCTGCCC
CTCGCCCCTCGCCCAGCCGGGCTCGCTCCGGGGTCGGAATTGCTGGGGAAGCCGAAGGAGGGATCCCCGCCCGG
GACTCGAGGGATCGACCCGCCTCGCGGTATGCGGAGGGCTGCCAGGAGCCAGTCCCGGGGAAGGGTGCCTGCCGC
CCGTGGGGGACAGGGCTCCTTCTCTCCCTTCTCCAACTTACACCGACGAGTCAGGAAGCCGGAGCGTCTAGTCCC
TGTCCGCATTTCTCAGTGTCTTTTGATGTCTGGGATGCATGGATATTCCCAGGGGGCTGACCCGAGGTGGGGAAG
TTTCCTTCTAGAAAGAGGCACCAAAAGGACCTCATTTGCTCCTGACGCCGGACCCTCCTGACACGCCTTCACTGG
CTCATCGGGTCCTGGGCTTTGGGGGAGAGCGTGGTGCGTGTTACTCTCCTTACTCCGGGTATTAAAATGTCTAAG
AGGTCATCGCTTTGGCCCAAGGCCTCCCGAGGATAAGATAAAAGGGAAAAGTGGAGGGGAGGTGAAGGAGGAACG
AGGGTGGGTCCCAGGCAATTGAGGGCCTCGGAACCCTAGGCACGGGAGCGAAACCTCTCCTGCGGCTTCAGGGCA
AAGGAGTCCCGAAGGCTGGATCCCTCCCCTGCGCTCGGACGGCGTCGCGGCCGCTTTTCCCACAGTCGGGAAGCG
(SEQ ID NO: 206)

CGI: 25 range = chr6:169801163-169801511
CGCGGCCGGGTTGATCTCCAACACGGCAATCTTCCCGCCAAAGAGGGAGGCCAGCAAGCACAGCACCTGCAGGGA
CGCGGTTTCAACATCGTTAGCGACACCACCCAGTAAAAGCAGACGAAACGTGCATCCGCACACGTATCCTAACAG
CTGCTTCATTCTCATAGCAGCGACATCGCCCTGTCACTCCTAAAACGTTTTTACACACAAAATCCCGTTTACTCA
GCCAGTCGTTACAGGATCACTCTGAAGAAAGAAGAAATCAGAGGCACGTCTCATAGACAGGGAGGGCCGCGTCTC
AGGACTGACCTTTTGATCCGCAGTGCGGTTCCTCAGGGCACACGATCCG
(SEQ ID NO: 207)

CGI: 40 range = chr7:1029023-1029492
CGCATACGAGTCCAGGGGCTGCTACAAAGCGCGGCGACGTCTCCGCGGCGAGCTGGCCACTCCATGGTCCCGGCG
CAGACACTGGGGCAGGCGCCGGCTCTGTCGTCGAGGCGCTCACAGGCAGGCACACGTGAGCTCCTGGAGGACAGG
GAGAGCGGCCGCCCCGCCCCTGCGGAGCACAGGACGCTTCCTGCCACCCCTGCAGAGCATGGGACGCTTCCTGCC
ATGGTGCCGTGGCAATGGGTGGCACCTGCCTGTGGCCCCTTCTCAGAAGGACGTTTTAAACGCGTGAGGTCTGAT
GCACAGCCACAGGGAGACACAGACGAGCAGATGTGGGCATCCGAGTATTTACAAGGTCTGGTGGCTCCTGCAGCC
GCGACACGGGCTGAGCGCAAGTGATGTGTGAGGTGTCCCCAACAGATGGCACGGGGAGCGCCCACACCCGCCACC
GCGGGGTCTGCGGAAGCTCG
(SEQ ID NO: 208)

TABLE 7B-continued

Sequences of differentially labeled CGIs between bladder cancer subgroups relative to blood CGI: 26 range = chr7:19113449-19113833
CGCTTCTAAACCCAATACGCTTTTCTGGAGTCCTCGGAACAGCTGGCCGGGGCTTTTAGCACACGGGACGGGACC
TTCGCCTTTGCCTGTTTTTTTTTCGACCAGGAGAAGCAGGTGCGAGAGTCTGGGGCTTAGGAGGTGGAAGGCGGG
GAAAGAGAATCCACTAGGTCCTCGTGTAGAGAACAACAGTCGCTCCTTAGATATTACTCCAGGACGGAAACCTGA
TTGCAAACCGCTGTTCCTTCGAAACTTGCAAAACCCGGAACAGAAAACTCCCGCCCAGCCAATTTTAGCTCTCGC
TGAACTCTCCCGCCTGCGTTACGTTTGCACAGCAACTCTTTGTAAATGTCCGAGTCCTCTCGGAGGAAAGATCGT
TAGGGCGACG
(SEQ ID NO: 209)

CGI: 207 range = chr7:27149139-27152087
CGAGAGCCGCGTCCCCGCGGTCGCGTGGATTTAGAAAAAGGCTGGCTTTACCATGACTTATGTGCAGCTTGCGCA
TCCAGGGGTAGATCTGGGGTTGGGCGGGCGGCGCCGGGCTCGGCTCGCTCTGCGCACTCGCCTGCTCGCTGCTGG
CAGGGGCGTCCTCCTCGGCTCCGGACGCCGTGCCAACCCCCTCTCTGCTGCTGATGTGGGTGCTGCCGGCGTCGG
CCGAGGCGCCGCTGGAGTTGCTTAGGGAGTTTTTCCCGCCGTGGTGGCTGTCGCTGCCGGGCGAGGGGGCCACGG
CGGAGCAGGGCAGCGGATCGGGCTGAGGAGAGTGCGTGGACGTGGCCGGCTGGCTGTACCTGGGCTCGGCGGGCG
CCGCGCTGGCGCTGGCAGCGTAGCTGCGGGCGCGCTCTCCGGAGCCAAAGTGGCCGGAGCCCGAGCGGCCGACGC
TGAGATCCATGCCATTGTAGCCGTAGCCGTACCTGCCGGAGTGCATGCTCGCCGAGTCCCTGAATTGCTCGCTCA
CGGAACTATGATCTCCATAATTATGCAACTGGTAGTCCGGGCCATTTGGATAGCGACCGCAAAATGAGTTTACAA
AATAAGAGCTCATTTGTTTTTTGATATGTGTGCTTGATTTGTGGCTCGCGGTCGTTTGTGCGTCTATAGCACCCT
TGCACAATTTATGATGAATTATGGAAATGACTGGGACATGTACTTGGTTCCCTCCTACGTAGGCACCCAAATATG
GGGTACGACTTCGAATCACGTGCTTTTGTTGTCCAGTCGTAAATCCTGCCTGATGACCTCTAGAGGTAAACTCGT
GCACTAATAGGGGAGTTGGGTGGAGGCGAGGGGGGTGGCGCGCGCGCCCCGGGCGCGTGCCCGCCGCCAGTTGCC
GCCGTTCAGCCGGACTCGAGCGCCACCCGCTGGAGGCAGGGCTCATCGCCCAGCTTCCGACCGGGGGCTGCAAGG
GCCGGGGTCGAATTGAGGTTACAGCCCATTATGGCAAAATTATTGCATTTCCCTCGCAGTTCCATTAGGATGTAC
CAATTGTTAGGCCGTCAGCTGCCGATCGCGCGCCCGGCGAGGATGCAGAGGATTGGGGGGAGGTGGTGACTTGCA
TTTTATTTACAACAACTTTATTTCCCCCGTTTTGCAGCCCCTCTTATTTTTGTGTCGAGGTTGGGGTCGGTACTG
ACCGTCCTGCCAGCAGCTCTGAATTTTGAAAATACAGATATCACCTTCGGGGAAGGGGGAAAGCCATTTAGCCAA
TTGGAGAAATAAATCCTGCCCGCAGCAGCAGCAGCTACAATTACGGCTCTGTTTTTGCGAGCGCATGAGGGACAG
TGTCCCTGCCGCTCTTAAATGACAGGCGTCTATTAAAGATAGCTTTTGTGTAGTGTTTCTCCAAGGCGAGGTCAA
ATTCCATACACTTTTATAACCGTAGTCGATTTTTCTTTCGTGTGAATATGGTTTTCGTGTCATTAGTTTGCGATT
TGATTTGCTTACGTATCCAGCCTGGAAAATCTTCATCACAGGGTCCGGTTCCTCGAGCCAGCCGGGCCCCAAGTC
GGAGGGTTCTCCTTGAACCCAGCGAGTGGGCCCAGGCTCCCTGCAGCCACAGAGGCTGCCTGGGGTCTGGGGATC
CGTGGGGCGGGTTACTGGGGTCTTGCTTAGACCTCCAGGAGTAAAATGAGGGCGATAATGGAAGCATTCCTTGGC
AGTGCCTAGTATCTCTGTAGTTATTTTCCACGGCTCCGAAAGACTCAAGTAAATCACAAATATAGCTGAGAGGCA
AGTGGAGTCTCCCCGCTGGAGGCCCGGCGTTGCAGGCGCCCCTGGCACGTCTGGAAGCCAGGACTCTGGCGGCTC
CCATGGCCCTGGGCCCCTCGTTGGGTCCTGAACGCTGCTGTGGCGGCGACGCGGGCGCTATCGGAGGCTGGGAGC
GGGAATCCGGAGCCGGGAGCCTACCCCGGGCTGTAATGTTCCACCCGCGCCCAGGTTAACTCGCCTCGGCTGAGG
CTGCTTCTCTTCCACTGACGGTTGCACACGCGGGACCGAGAGACTGGGCTCTGTTGGGGCCCCCTTTGTTCCTCG
AGCTTCCTTCCTGTTCTGGGAGGCGGCTTGGGAGGCCGCGACAAGGCCGGGCTCCAGCTCTTAGACCCCCTCTTT
CCACTGGCCAGAGATGATTTGATGATGCCCTTCGGGACTTACTGGCGAGGGACTTAGGCAGAGACGCCCAGACAC
GAAACGGGGCTCGGCCCAGGGCTCTTTCCTCCCCAGCAGCCCCGCGTCCCGAGGTCGGGGAGCTCAGAGACACTA
GCACAGGAGCCCCAGACGCATTCAGGGCGCACCCCAGAACTCCGGAGCCGGTTTGGGCATCCTTGTGGAGCGGGA
CTGGGTGTGTGCAGTGCGCCCCGCTCCACCGCTGGTATTGGCTGTGTGTGAGGTTTTGTTTTGTTTTGTTTTGTT
TTGTTTTGTTTTGTTTTGTTTTGTTTTGTAAGAAATAAATGCACAGACGCTTGCAAAGCTCCGGGCTCCCCTGAA
GCTGCGGAAGCCCCCAGATGGGAGCAGGCGGGGAGAAAAGTTGGGGAACAGGCGAGGGCAAGGGGGCAAAGCCGA
AGGAGGTTGCAGCGCTGGCCTGGTCCCTGCCCAGGCATCTACTCGCCCGCCTTTGCCTCTGAGTCCTCCCCGCTG
GGCTGCGTGGAATTGATGAGCTTGTTTTCCTTTTTCCACTTCATGCGGCGGTTCTGGAACCAGATCTTGATCTGG
CGCTCGGTGAGGCAGAGCGCGTTGGCGATCTCGATGCGGCGGCGCCGTGTCAGGTAGCGGTTGAAGTGGAACTCC
TTCTCCAGCTCCAGTGTCTGGTAGCGCGTGTAGGTCTGGCGGCCTCGGCGCCCATGGCTCCCATACACAGCACCT
ACGAGCAGAAACGGCCGGGCGCCG
(SEQ ID NO: 210)

CGI: 201 range = chr7:27170441-27172987
CGGAGCTGGGCAAGCCGTCAGGGCGCCCTAAGGCCGCTGATCACGTCTGTGGCTTATTTGAATAATCTGTCATGG
GGACCCTTGTGGCCCGGGTCGCCCGCAGCCTCATCTTGGCAGGATTTACGCCGCCACTGGCCGAAGGCAAGAAGT
GGAAGGAATCGGCCGTCTCCCCCAGCGTCCCAGCTCCGGCTGCCCTGGCTGCCGCCGCTCACGGACAATCTAGTT
GTACAAAAGGCTCTCTGGGCTGCACTGCTTTCGAAGAACGGCCCAAAGTATCTCGGTCCTGGGCCTGGGCAGCCA
AGGAGAGGGGCGGCCAGTCTTGGCTCGTCCCGAAGTGCCCGCCCCGCCCCCTCTCGCTGCAGCAGCCGCCTCCTC
TCCCGTAGCCCTGCGGGCCGCTCTTCACTGCTCTCCAGACTTGGGGCCCTATCTGAGGCGTCCCAAACACCAACT
TCTGGCTCCTGGCCCCAACTCGAGAGGCTTCCAGCGAGGACGAAGGCAGGCTCGAGAGAAACCTGGCGGGCCAGC
AGATCCGGGAGGCCGGCGTGGAGGCGGCGGCGGATTTGAAGGGAGGAGACACTTACTGGGATCGATGGGGGGCTT
GTCTCCGCCGCTCTCATTCTCAGCATTGTTTTCAGAGAAGGCGCCTTCGCTGGGTTGTTTTTCTCTATCAACTGG
AGGAGAACCACAAGCATAGTCAGTCAGGGACAAAGTGTGAGTGTCAAGCGTGGGACAGTCACCCCTTCTGGCCGA
CAGCGGTTCAGGTTTAATGCCATAAGGCCGGCTGGAGGGCAAGCCCGCGAAGGAGAGCGCACCGGGCGTGGGCTC
CAGCCAGGAGCGCATGTACCTGCCGTCCGGCGCCGCCGCCGCCACGGGCGCCTGGGGGTGCACGTAGGGGTGGTG
GTGATGGTGGTGGTACACCGCAGCGGGTACAGCGTTGGCGCCCGCCGCGTGCACTGGGTTCCACGAGGCGCCAAA
CACCGTCGCCTTGGACTGGAAGCTGCACGGGCTGAAGTCGGGGTGCTCGGCCAGCGTCGCCGCCTGCCGGGGAGG
CTGGCCCAGGGTCCCCGGCGCATAGCGGCCAACGCTCAGCTCATCCGCGGCGTCGGCGCCCAGCAGGAACGAGTC
CACGTAGTAGTTGCCCAGGGCCCCAGTGGTGGCCATCACCGTGCCCAGCGCCTGGCCCGCCCGGCCCGACCCACG
GAAATTATGAAACTGCAGATTTCATGTAACAACTTGGTGGCACCGGGGGGGAAGTACAGTCACCTAATAAGTTGC
CGGCGCCCGCGCCCCATTGGCCGTGCGCGTCACGTGCCCGTCCAGCAGAACAATAACGCGTAAATCACTCCGCA
CGCTATTAATGGTCCGATGTTTTGCAGTCATAATTTTTATAGCAAAAGCCATATGTTTTTATGTAAAGGGATCGT
GCCGCTCTACGATGGGGTTTGTTTTAATTGTGGCCAACGACGATTAAAAGATCAAATCTAGCCTTGTCTCTGTAC
TCTCCCGTCTCCCCCCCATACACACACTTCTTAAGCGGACTATTTTATATCACAATTAATCACGCCATCAAGAA
GGCGCGGGTCCCGCGTGCGAGTGCGGCCAGCGGAGCCCCTCACATAAAATTAGACAATAATTGAAGCCATAAAAA
AGCAGCCAAATCGCATTGTCGCTCTACTGTATTTAAATCTATATTTATGATATTTCATAAGGAGTTATTGTTTCA
GAAGCCACACAGGCTGGCGGGAAGTCGGAAACGACCAACAGATTCGTTTGCCTCGCCGTGGCTCCCAGCTGTAAA TABLE 7B-continued

| Sequences of differentially labeled CGIs between bladder cancer subgroups relative to blood |
|---|

AATTTACGAGGACTTGGAAAGGTTAGACTGTTGTGTTTGGTTGGCGAGCTCCCTGTAAATAATCCCTGCGGTCCC
CGGGAGAGGCGAGTTTACCCGCGGCCGCCCTCGAAAAGTCAAATTCAACGCAGGATCCGTCCCAAACGGAGCCGC
CGCCGGCCCTACCAGGGCACTCCAGGCAGGGACCGGCCGCTCAGGGAGTACCGCGGGTGTAGGTCCCCACAGCTA
CCCGCCTGGAGCGAGGGGCGCCCGGGCAACCCTTAAATTCGCCTTTGCTACGAGGACCCCACGGAGGAGCTGGCC
AGGAGGGAGCGGCCAGCCGCCACCAGGGCGAAGGTTTTGAGGGCCTGGTTGGTTGTGCGGCGCGCTCGGTCCCCG
GCCCTCGACCCCACGCACACGCGCGCCCAGCCCGCCTTTCTCATCAGCTGGCAATCAGGATTCCCAGGCGCAGGC
GGCTGGCGACCCAGCCCTGTGCTCCAGCCTCAGAGGCTCTAACCATGAGCGCTGCAAGCCTGGTTGCGCTCCGTG
AATCCCAGCTGGGGAAAAAACTACAAGTGGCATGAATGGAAGGCAAGTTCGGTTTGGGAAAAGGCAGCCTCGCCT
AAGAGACCCCGCAGCTCCGGAACCTGGGAGGCCCGCACCGATGTGGCCTGTCCCGGGGCCGCGTGAGCCTTTCAG
GGCTCCTTCCTCCCTTTCCAGCTGCTACTCCGGGCCTCGCCTTGGTTACCTACGGGGCCCGGAGACTCGGCG
(SEQ ID NO: 211)

CGI: 114 range = chr7:27198331-27199622
CGGCGGCAGCGATCGGCCCTGACCATAGAGGCGGCCGTGGCGCGGAGGACTTGACCTTTACGGCACGAGAGGAGG
GCGCTGGCTGAGCCGCAGGGAGGGGGACGCTGCTCTCTCCAGCCTCCTCCACCCAATAGCAGTCCGCTCGACCCA
CGCCAGCTGCGCGCTCACCCCCTTTCCCCCTCCATTTTGTGCAGTGTCCGCAGACCCGCGGCCGGAAACAAAGCC
CCCAGCCCTGCTCTCACCACCCTTCTTGCAAGCTGCTGTCGCCAACCCCCCAGACCAGAGGCTCAGAGCTAACGC
TAAGCCCCTTAAGGCCCTCTCCAGGGCCCTCTTCTCTCGCCAGCCGCCCTCAGCCAGCTCCTGACCCCAGCCGCC
CTCAGCCAGCTCCTGGGTACCACTCTGGGTGCCAACCGGGACCTGCCGGTGCCACGGTCCCGTGCGCCGGGTCCC
GGCCTCGGGCTGCGGGCGGCTTCGGGGCCTACAGCCCAGCGGCGCGGAGCGTGGCAGAGGCGCGGGGCGCAGCGC
AGCCCGAGGCTGCCTCCCGCCCGGGCGGACGGCGCGGCCGCTGGGGTGCACAGCGTAGCCCCGCGTGCCCGGCTC
GCTCTCCGTTCCCTCGGATAGCTCCCACCGCTCGGCTCCGGGCTCAGAAAGCGGAAGTATTTGGTAGAGAAAAAC
ACGGTTTCTTTTCAGCTCGTCTCAAAATCCCTTTTAGAGAAAATGCTCCTGTCAAGTTTTATTTCCCGTTGCAAA
CCACCTTCCACGCTGCCAAGAATTAAGACCGGGAGAGATTAAATACCCGATTATTCTCCTGGGGAGGGCGGGGCG
GGGCCGGGAAGTGGGCACCCACACCAAACATTCCTTGAAGTAGGCTTGTCCTGATCCAGCCGCGCCCGGGGAGCC
CCACGAAGGCCCGCGCGGCCTGCGGTGACGTCAGCCTGCAGTTGCGGGGCCACTCACCCGCACAGACACGGCCCT
TGCTGTTCCGCGCCGGGACCTCCGCCAGCCGTCCTGCCGCAGCCCCGACTGGCCCGCGTGCCGTCAGAGGGAGGC
CCGCTTTACACCGGCCTGAGCCTCCATTTGAGTAGGGGGTTCTTGTAGAAGCGTGGAGGGTTTGGGGCCGCGCC
TCTGTCCCCGAGGGGCGCGACATCAGGTAGCTCTCCGAGTTCACACCCCAGTACCTGGGGGAGGACCTATGTCGC
CGCATAACCGCCCGCAGAGGTTTGGAAATCTCTGAGACCCGTTGTAATTATTTCTGCCCAGTGGATCCGGCTCTT
CAGCGTCACGAGAGCCG
(SEQ ID NO: 212)

CGI: 111 range = chr7:35263447-35264743
CGGTTTCCGGCTTTTGGACAATGGTCCCTCGCTTAACGAATGCTAACGAATGCTCCCTTAGCTGGGAGCTGCAGG
GACCGGTCCCGGCAGGTCTAACCAACCGTCCGCAGGCGCCGTGGTCGAGAGCAGAGCCGAGACGGCGGGGCAGGG
TGCCAAGCGGAGGGCACAGCCTGGCAGCCACCGTTGGCGGCAGGAGAGAATGGGAGAAGGGAGACCCGCTTCTCA
GCACAAGGGCATCTGTCTACTCCCGAACATGGCCGGAGATTCCTGTCCACAGCCTCCCTCCAGCTCTTTCTGGTA
GACACTTTAAAAGCGACATTAACGGGCTTCGGTGCCTTTGGATTCCTAAATTAGGTTTACGGAAAAGGAAAGACT
TCCCAAGAACAGTGAGAAGAGGAACTGCAGCCCCTCCAAGGCCGCTGCGGCGCGTTCCCGGGGCGCGCCGAGAGC
AGCGCGCGGCTCCGTGCCCCGTGGGGAGCGCGCGGCGCGGCCTTGGATTTCACCGCGAGTCGGGAGGGCGGGTCT
GAGCCTTGCCTCCCAGGATCCTTCCGACGAACACCCCGCGGGTTTTAGTTTATCGAGCCAAAGTGGTCCCGGAGA
AGCGCTCCCTCGCAGCCAAGCTGCAAGAAGTGGCCGGGAACCTACAGGCCTCGGGCCGACCCAGGAAGCCTCCGC
ACCAGAAAGCTCGAGGAGCCCTTACCCAAGTCTTGCTCGAAGGGCAAAGCAAAGAGCCAGCACCCCTGAGTGTCA
CTGAAGTTCCTGGATGGGGTGTGAGTGCGCGCGTTCCGTCCGAGACCTCAGTCTCGCCCAGCTATAGAGCCGATA
AAGGGATGTCTTGTGGGCGTAAGGCGCTTCGCGCCCATCTCCAAGGCCGATGTGGTCAGGAGGTGAGGGGAAATG
TCCTTCTGGCAGAAGCCCGCGGTGCTGCGACGTTGACCCGCCTGGCCTCAGGCTCAGGGCGGCGGGCAGCCCAGG
GCACATGTAGTTTCAGCAGCCGCGCTACGTGGGCGGGGGACCCCAGGCCACCCCACGTGTCCGCCCTGGGCCTCC
TCCGGGTCCCAAGGCGCGGCGCCTCCAGGCCTTGTAGCGTCTTCCCCGGGTCCCCGCGCGCCAGGCCCCGCAGCC
TGCTCACAGGACAGCCCTCGGGGCTGCGACCCTCTCGCTCCTCCCCGCGGCCACTCGCTCCCCGTTCATCCCCCA
CGAGCTCACTACCGCAGGGACCGGCCCTCAGAGCCCCGGGCCTCCTCCCGGCAGTGGAAGAATCAGCGTGCTAAC
ATTGTGTGCAAAACTCGCAGCG
(SEQ ID NO: 213)

CGI: 30 range = chr7:96469320-96469736
CGAGGGCCTTGCCCGCCCTCCTCCTCCCACCCGCAAGGGTTGGCCCGCGTTCCCCTGCGGGCGAGACAAAGAAGC
AGGAGCCAGGACCCGGCTGGCGCCTAACCCGGCGCCGGGGCCTTGAGCCCCTGAGGTGTGCGCCTTCCTGCAAGG
CCCCAAAGAACCCGAGTTTTTGCCCCTTGCTGAAGGGTTGGAAGTGCGGGCTGGACTAGTGCAAACAAGAGTGAC
TCCAACCGCCTTACTTCAGCTCATTACCGTCACCCATGAAAACGGAATGAAGGACTGGGAAGCCAATCTGCCGCG
TTCAATTGGAGAGAAATGACTGTCGGAAGAGGCCCTGCGGTAAATAGCCTCTGAGCCGCGAACTCTATGCGCCGT
GGCCGGTGGCAGAGGCCACACCTGGCAGCCACTCGTGGCGCG
(SEQ ID NO: 214)

CGI: 32 range = chr7:119702299-119702721
CGGAAATCATCGGCGACTGCTGTTATGAGGAGTACAAGGATCGCAGGCGAGAGAACGCCGAGCGCCTGCAGGACG
ACGCGGATACCGACACCGCTGGGGAGAGCGCCTTGCCCACCATGACTGCAAGGCAGAGGGTCTGGAGGGCCTTCG
AGAACCCCCACACCAGCACGATGGCCCTGGTGTTCTACTATGTCACGGGGTTTTTCATTGCCGTCTCTGTCATCG
CGAATGTGGTGGAAACAGTGCCGTGCGGATCAAGCCCAGGTCACATTAAAGAACTGCCCTGTGGAGAGCGGTATG
CTGTGGCCTTCTTCTGCTTGGACACGGCCTGCGTCATGATCTTCACAGTTGAGTATTTGCTTCGCCTGGCTGCAG
CGCCTAGTCGTTACCGTTTTGTGCGTAGTGTCATGAGTATCATCGACG
(SEQ ID NO: 215)

CGI: 42 range = chr7:158509937-158510390
CGTCCTCCGACGCGAGATGGCTGTGTGCCACCGACTGTCCAAATGCCCTGCCAATGCCATCGTGAAGCATCCGTG
TGAAGGAAAAAGTCCACCTTACCGTGCGCTGTGGCATCGATCAGGCGTGTGGACAGTCGCAGGCACGCAGCGGTC
TCCCAACATCAGGGCACACCGCGATCAGGTGTGTGGACAGTCGCAGGCACGCAGCGGTCCTGCAGCAGCAGGGCG
CACCGCGATCAGGTGTGTGGACAGTTGCAGGCACGCAGCGGTCTCCCAGCATCAGGGCACACCGCGATCAGGTGT TABLE 7B-continued Sequences of differentially labeled CGIs between bladder cancer subgroups relative to blood GTGGACAGTCGCAGGCACGAAGCGGTCCTGCAGCAGCAGGGCGCACCGCGATCAGGTGTGTGGACAGTTGCAGGC
ACGCAGCGGTCTCCCAGCGTCAGGGCGCACCGCGATCAGGTGTGTGGACAGTCGGTGGGCACGCAGCGGTCTCCC
AGCG
(SEQ ID NO: 216)

CGI: 20 range = chr8:10624024-10624296
CGCAGGAGGGCTCGGCCTGGGACCCCCTCTGCGGGCCTGCGGCTTTAGCCAGCAGAAAGAGGGGCGTCAGTCCTA
TCCCCAAAGTTCCGCCTCGGGAAAGAGCCCTGAGCTCTGAACTCCGACGAAAAAAGGAAGGGCTCTGTTCCGGAC
CGGGTGGGGTTTGGGAAGGGTAGAGCCGGCCTCGGGTGCCCTTCTTACAGGGCCTGTCTCCCGCTGCGTGCACCA
AGTGCTTTGAAAGTTTTTCGCGGATTAAAACGAATAAAAACCTCGTCG
(SEQ ID NO: 217)

CGI: 221 range = chr8:11597006-11600365
CGAGGGTGAAGGATCGCCGCAAGGCACCGCACCTCCCGCTGCAGCCCATCCCGCACTACTAGGAGAAGCCGGCGT
AGGAGCGCCGCCTGTGTCCTTGGCTGTGGGGAGGACGTCAGATGGCACCCCGCCAGACACTAAGCCCCAAGCCCC
TGGCTTGTTGCTAAGAAAATTCACTGCCCGGTCCAGACTCAGCCCTTTTCGCCCTTTAAGGGTCGCGCGTGGGAG
GCAGCTCTGAGACCCCGGGTAGCGCTGGAGCCACAGATTTCCTCCGAGAAAAGAAAGGCCGGGATAGCTTCCCGC
TCGCCCAAGCCCAGATTTTCCACTCTCCAGGAAGGCCTTGCAGGTCCCTGCCGCAGGCCTTGGCTTCGCGCCTCT
CTCGCTCGCCCCCCACGAAGATGATTGCCGGTTTCAAACCGGGAGCAGGGAGTCTGCTTCCTTCTCCGCTGAGTC
CGAAGGATCGCAGATTGGAGCGTGCTCCGGAGACCGCTTTTCCGCAGCGCCGGCCTCCGAGATCCCCAGCACCCC
TTCAGCCTTAAGTTCCCACGTTTCGGGTCCGTGGCGCCAATTCTGCTAAGTAGCAGGCTAGGAATTGGGGGAAGT
CGGAGAAGAAACCCTAAGTGTGTCGCCCCCAGCTTCCGGGATGCAGGCCCGCCGGGGTCTAGAGGGGCGGCTGCC
GTGCGTCCAGCCTGTGCGCAGGCCTTTCGCCGCTCGGCGCCCCAGGCAGCCTCAGTTTCCTTTCCTCTGTTTGCG
CCCCAGTGAACCTCCGCACCTCTCATTCAGGGAAGAGAATTCCCCGCGCAGCCGCGCTCGTTTCTTCCTCTGGGA
TTTTCCTGAGAATCCCCAGGAGTTGGCCACGATCCCATGGGGGGTTTCCTTCTACCCAGCCCCGCGTCCTGGCCT
CGTCCTTAACCCCCGGGTTGCCTTCACTCAGGCTGGGAATCCACGATTGATTTCCTACTACGGAAGCGGGTGGCG
TTCCCAGCCTGCTTTCGGAGCAGCACGGGTTTCGTGCAGGGTGTTATCCCGACCCCTTCCCCCATCCCTCTAATC
TGGCTTGAGAAGCCCGTGCTGGAGAGAAAAACGCGGCCTTAAAAAAAAAAAAAAGTTTAACCGAAAGCGTGAGAG
CCACCCGCCGGCTGTTATCTGGGGCTGAAGGCTGCGGTAATCGATGGGTTATTTTTACGCGGTAATAGGGCCCTG
TGATTGCTCTATTAACCTTTAGACCTGTCTGAGGGACTCTCCGGCTCGCAGCCCCGCTGCGCTGGGGCCTCCAGG
CTCTGACGCCGACTCCCAACTCAGGCCTGACACATTCCCCTCCCCCATACCCTGGAAGAGCCCCCTCCATGAAGA
AGCTCCCCTGGACCGCCTGGCTCCCCAGCCCTTGCCACGTCCCTTGGATTGGTGCAGAGCCGCCGCAGGCTGCAG
AAAAAAGGGGGAAAGATTAGAAGAGAGGAGGCCACAGGAGATGGGAAGTGTCGCCAGGAAGGGATGCAGATTGCA
TAAATACATAAAATTGAGGCTGAGGCCTGGGCTCCCGACCATCTCCCTGGGATTTTGGGAAGGCAAAAGGGAGGC
TTCGGTCTCTACGCTCTGATTTTAGGAGGCAGTCTGGGTGTCTCCTGAACCTCCAAGGAATCCGGGGCTGGGAGG
ATCCCCACTACCCCTGCCCAGGAACTAGCATCCAGCCGGGCACCCCGGGTGACCCAGTGCCCCACACAAGATCGA
GAGTTGAGCCCAAGAGGTCACCTTCTTCTCTACTGGCCCCGCCCCTCGCCCGCCGCTGCGGGATGAGGACCACAG
GAAGGGGGGGCGGGGAGGGAGAAAGGGAACTCATTAATAAAGCTGACCCTGGGCACCACAGCGAACCCAATCGAC
CTCCGGCTGGGTTGCGGGTGATTCCCCGCTCCCTGGCGGTAGCACTTGGGCATTTTCCGCGGAGACCCCAGAGCC
TGGACTTTGCCTGCTGGGGGAGCTTTCCGCACAGTCCCGCAGCCTGCGCCCAGCGGAGGTGTAGCCGGGGCCGCG
CACCCCCGCCCCGCCCTTGCACGTGACTCCCACAGGCCAGTCAGCGCCCTAGGGCCGAGTTGCTGGGCCGGGGAC
CCGAGCCGCGAGCTGGGGACTTGGAGGCGGCGGCGCAGGGGCCGCGAGAGGCTTCGTCGCCGCTGCAGCTCCGG
GGGCTCCCAGGGGAGCGTGCGCGGAACCTCCAGGCCCAGCAGGTAGGGCTTTTTTCTTCCCTTTCTTTGCTCCTT
CCCGCGGTCCCCCAAACTCGGAGCTTCTCCGCCTTTGCTTGTCTGGAGGTAGAGAGGTAGCTAGTGGGAGGAAAA
GAGACGTGCGCTACTCACTTCACCGAAATTGCCCAACCCCTGCTCTGCTTTTGACTTTGCCTTAGCAACTTCTTT
AAGTCAAAGTAAGACTTGGGGGCAAAACAGAGAAATATTGGAAGCGCCTTTGGATTCTTTCCGTGTGAACTTGAA
CGCTTTCAATCCCTGTCCCCGTGTGCACATTCTCCAACCCTTGTTTGCATATCGCAGGCCGGGGCCTGGGTGGTG
ATGGTGGCCGCGTGAAGTTACCGGGACTGACGGGCCCGGGACAGGCTGCACGGCAGCTCGCACATGGAGGGAAGT
AGACGGAGGCTTGTCGCCCACCAGCGACTCCGGGGACGCAGGGTGGCAGTGCCAGGCAGCTCCGCTGGGCCTCAG
GGGCCCCCGGGAGCCGCTCTGAGGTGCGGAGAGGCTGCTGAGTGGCGGAACTATTCATGCCCTTTCTGGCCGGCC
TCCTCGCCCTCGGGGCTGGGGTCCAGGGACTGAATGCTCCTCTGGAAGCTCACCACCCCACCTGCCCGCGCTGCT
TCTACCTGAAACTGGCCAAGGGCCCGAGCCCGGACCGGAGCCGTGACTTCCCTCCGCCGGCCACGGGGCTGCCCG
GATCCGCCGGGTTATGTCGCTTGGCTTTGGGCTCAGGGGTCACCGTGGGCAGAGGGGGGTGCCGGGGTCGCGGAC
TGCCACCAGGTTGAGGAAAGGAGGGGCCTTTTGGCTGGGGAAAGAGCGTGGTGGGGGACCCGCGGCCGATGGAAT
CCCTGGGGCAGCGCGGCCCGCACCGTGGAGGTTGGGGAAGCGCCTCGGGGAAGTGTTTCCTGTGTTCCCAGAAAA
GGAAGACAACCGAGAGCAGGTTTCAGGCTTTTAAAGAAAGCCTGGGGTGTGGAGGTGATGCTCCGCACACGTCTG
TGTCTCCTCCCCTGCTGCGGCCGGCTTGGTTGTGCCGGCTAGCGTGCGACCGTCCTCCTCGCTGCAGGCCGAGAG
CGGAGGCGTAAACCCAGGCCAGCGAGGAGTGTCCTATAAAGGGACGGGGACTTTTCGGCG
(SEQ ID NO: 218)

CGI: 25 range = chr8:25955253-25955609
CGTTTGCTCCGCCGTCAGTCCATAACCAGGCGCTACTAAGGCCTCCAGGCTCGGTGCGCAGAGCCGGGAGCGCTC
CTCCAGCTCCAGGTTGGGGGAGTCGGGGTGGAGGAGGTTCGGGAAATCGACTGATTTAGAGGCTGGGGGTGAGT
AGCCTCGATTTATCATCCCTGATGGTGAGAGTGGAAAAGTGTCGCGAGAGTGACAGATGGAATCTTTAGTGCTTC
GCAAGAGGGAGTTATTAGGCCGCGGGGTTTGGGGGGTACTTTCCGCTTACTTTGTCATTCTCCACAAAGTCCACG
AAGGCCGTCCGCTCGATCTCCACCGGCTGGCCCTGCCTGTCATAGAGCGCCAGGACG
(SEQ ID NO: 219)

CGI: 233 range = chr8:55532724-55535078
CGCTCGGTATGTTCATCTAAACGACCTTGGGCAAGTACGTCGATTCCAAGGTACAATCAGCCCTCCCAGACGGCT
TTTCGAGTCTCCCTAACCCCGGTGGGAGAGGACGCGGCGCCAGAGCCCAGCTCCGGCTAGTTTTCCCGGGGGCAG
GTGTAGCCTTGGGCGCGGGGCCGGGGGAGGGGCAAGGGGCGGGCGTGGGGTTGGACTGGGACGTGGGACTCGGAC
CACGGCCTGGGCGTGGGCCTAACGACGCGGGACCGGCCCAGCCCTCGCCGCTCCATTGGCCACATCTGTGCAGAAA
AGGCCCCGCGGCCCAGGGGCGCCCGCAGTGTCACTAGGCCGGCTGGGGGCCCTGGGTACGCTGTAGACCAGACCG
CGACAGGCCAGAACACGGGCGGCGGCTTCGGGCCGGGAGACCCGCGCAGCCCTCGGGGCATCTCAGTGCCTCACT
CCCCACCCCCTCCCCCGGGTCGGGGGAGGCGGCGCGTCCGGCGGAGGGTTGAGGGGAGCGGGGCAGGCCTGGAGC
GCCATGAGCAGCCCGGATGCGGGATACGCCAGTGACGACCAGAGCCAGACCCAGAGCGCGCTGCCCGCGGTGATG TABLE 7B-continued Sequences of differentially labeled CGIs between bladder cancer subgroups relative to blood GCCGGGCTGGGCCCCTGCCCCTGGGCCGAGTCGCTGAGCCCCATCGGGGACATGAAGGTGAAGGGCGAGGCGCCG
GCGAACAGCGGAGCACCGGCCGGGGCCGCGGGCCGAGCCAAGGGCGAGTCCCGTATCCGGCGGCCGATGAACGCT
TTCATGGTGTGGGCTAAGGACGAGCGCAAGCGGCTGGCGCAGCAGAATCCAGACCTGCACAACGCCGAGTTGAGC
AAGATGCTGGGTGAGTCCGAGTCGCAGACCCAGGCGGCCGGGCGCGCTGGCGCGAATCGCTAGGCCGATTTCTTA
AACCCCAAACTGTTCTTTGCGAGCCTGACGCCCAAAACCAGGGGTGTGTAGCGGCCACGTCCTTTCTTAAGGCTC
TGGGTTCCCTTCCCGCTTCCCGCCCTCCGACCCTCCAAAGCAGCTTTCCGCCTTGCTCTCCGGCTCCCGGATTCC
CCAGGTGGCCGGGGGCGCGGGTCCAACGGCTCTGGGAAGGCGACTTCCCGGCACCTCCGGGCGGCGCGAGAGCAC
CCTTGGCCCTGAACTGGGCCGGTTGTGTCCATCCCTCGACCCCTTCCCTAGTTAGGTGTCCTTTTCTGTTTTTCG
AACGACCGGGTGATGGGTGAGCGGAAAGCCGCTTCCAGGAGACCAAAAGAAAGGGGTGCCTTTAGAGGACGGGTG
TTCCCCAAGGGCTCGGACTCAGGAGTCCCAGATCTCCCTCTTTAACTTCACCCCGGTTGCGCAATTCAAAGTCTG
AGGGGGGAGGTGCGTCCAGGTGGGGCCAGGTGGGGCCTGGAGCGGGAGCGCAGCCGATAAGCCCTGCGCCCCTCT
CCCCCTTCCTTCCACTGTGCAGGCAAGTCGTGGAAGGCGCTGACGCTGGCGGAGAAGCGGCCCTTCGTGGAGGAG
GCAGAGCGGCTGCGCGTGCAGCACATGCAGGACCACCCCAACTACAAGTACCGGCCGCGGCGGCGCAAGCAGGTG
AAGCGGCTGAAGCGGGTGGAGGGCGGCTTCCTGCACGGCCTGGCTGAGCCGCAGGCGGCCGCGCTGGGCCCCGAG
GGCGGCCGCGTGGCCATGGACGGCCTGGGCCTCCAGTTCCCCGAGCAGGGCTTCCCCGCCGGCCCGCCGCTGCTG
CCTCCGCACATGGGCGGCCACTACCGCGACTGCCAGAGTCTGGGCGCGCCTCCGCTCGACGGCTACCCGTTGCCC
ACGCCCGACACGTCCCCGCTGGACGGCGTGGACCCCGACCCGGCTTTCTTCGCCGCCCCGATGCCCGGGGACTGC
CCGGCGGCCGGCACCTACAGCTACGCGCAGGTCTCGGACTACGCTGGCCCCCCGGAGCCTCCCGCCGGTCCCATG
CACCCCCGACTCGGCCCAGAGCCCGCGGGTCCCTCGATTCCGGGCCTCCTGGCGCCACCCAGCGCCCTTCACGTG
TACTACGGCGCGATGGGCTCGCCCGGGGCGGGCGGCGGGCGCGGCTTCCAGATGCAGCCGCAACACCAGCACCAG
CACCAGCACCAGCACCACCCCCCGGGCCCCGGACAGCCGTCGCCCCCTCCGGAGGCACTGCCCTGCCGGGACGGC
ACGGACCCCAGTCAGCCCGCCGAGCTCCTCGGGGAGGTGGACCGCACGGAATTTGAACAGTATCTGCACTTCGTG
TGCAAGCCTGAGATGGGCCTCCCCTACCAGGGGCATGACTCCGGTGTGAATCTCCCCGACAGCCACGGGGCCATT
TCCTCGGTGGTGTCCGACGCCAGCTCCGCG
(SEQ ID NO: 220)

CGI: 74 range = chr8:72916429-72917309
CGGGGCAAGGGCGCGTTCCCTATCGCAGGATCACTTGCTATGGTAAGCCGCCCACCCTGCGCGCTCCTCCGCGCG
GGGAAGAACCTGCGCGGCAGGACGTGGTGTTGGAGTTGGGGCGCCCGGAGCGTGGAGTGGGGAGACCTGATGCAG
AGAGTCTGGAGTCGGAGCTGGGGGTGCTGCAGGTAGGAGCAGGAGCGGGGCGGAGAGGGAGGCCCGAAGAAGACC
CCACACAGGTTGGCGCAGCGGGGCTTGGGGAGGCTTCAGCCCAGAAGTGGAGAGGGTTGACAGACGCCTGCCTGA
TTAGAAAAAGCCGGGAGCTTGGGAAGGAGACGGGATTGAAGAAGCCACCCGGCAGGGAGGCCGAACGGCCCAGAG
CTCTCCGGGTAAAACCCGCCTGCGGTGATCTGGGAAGTGTGTCTCCACCTAGCCCTGCGAGCAGCGGCCTTCCTC
CCGCCCGTTAGAAGGGCGCTGTGCTGGAGTACGAACCCGGCCCAGAGAAGCCACTCGCCCTTCTTTGTCACTTAA
AACCCTGTCCCGACGCGGATCTCACGTCTAGACCTCTGTCTTTAAAGCGGATGTAGAGCGCGTTCTAACCGTTCC
CTAACCATTGTGTCACCGCGAAAGGCCGGGGCTGTGTGGAACCGTCCCGCACGTGTGCGATGAATCTGGCTCCGC
TGAGAACGGATCCGTGGGCTGTCTGGCGCGGGCTGGGGCAGCAGCCGAGAGTTAGTCTACAGAGCTAGGGCCCGA
GGGTGGACCTGCGTCCGCGTCTCGTCACGAAAGGAAGCTCTTTTTGGAGAGGCAAAACGTGGTCGCCCAGATCCG
GCGCAGCTGTAGCCGTGGGCGCTGTGCAGTGACAGCCACACCCGCCACCTGTCACG
(SEQ ID NO: 221)

CGI: 17 range = chr8:140700279-140700514
CGGCCGCCCCGATGCACAGCGTCCCCATGCAGGAGAAGAAGCCCACAGTCACCATGTTCTCCATAGACACGTCAG
TGTTGCGCATGCCACAGCACTTCTTAATGCGCTTCAGCAGGTAGCGCACGAAGGTGTTCATGCGCTCGCCCAGGC
TCTGGAACATGACCAGTGTCAGCGGGATGCCCAGCACGGCGTAGAACATGCAGAAGGCCTTGCCCGCATCGGTGC
CAGGTGCAGCG
(SEQ ID NO: 222)

CGI: 21 range = chr8:145014900-145015187
CGCTGACCACCTGCCGCAGGGCCGCAGCCCTCCCAGACCGACAGAGTGCCACCAGCTCCCGCCGCTTGTCAGCGC
CAACGTATTCGGAGAGCAGCAGGTCCCAGAGTGACACGCTACACCCCTTAAACCTCCCTGTGCTGACGGGCACCT
TCATGGCCCTCAGAGCCACCGCGGTGTGGTCGTCCACCTCAAGCACTGTGTCTGAGGGCAGTGGCAACAGCAACA
ATCCGGTCTCGGAGTCGCACACGCAGCGCTCCCTGAGCTGCTGGTAGGTCACCTGGTCCCGCG
(SEQ ID NO: 223)

CGI: 260 range = chr9:959530-963276
CGTGTGCCCTTCGGCGGGCGGCTGTAGCTGTAGCTGTTGTGACGGCTACGGCGGAGGCTGCGGCCGCGCGGGGAA
TGGAGCCGGACCGCGGAGTCGTCACCTCCAAGGTGTTTCTAGTGGCCTCCTGGAAGATGATCCCGCGCCCACCTT
GCCGGCGTGTTCGCGGGCCCCTGCCCACTGCCCCCCCTCTTTCTTTAGGTCTGGCTTTTGAGGATCCCGGAGTCT
TGCAGCTCCCGCCATTCCGCAGATAACCTCCGCACACTTAATTGTGACCCGCGGGGTGGTCGGAGAAGCTCCGCA
CGCGTCCTCAGTGGGAAAGTGTCCCCTCTCAGCACTGCCCCCTTCAGTCCCCCTGCATTTCTGGAAAGTCAGGCA
AGGCCCAGGTAGGCTGCCAGTGCACTCTCAGCCTTGACTGAGCACCTTTCGGGCCTCTGGTGAGCCCCGAGAGCC
AGGTTTGGCTCGGCAGAGCGGGCTTGGGCTGCGCAAGCAATGCGCATCGTGGCCGCCTGCACCCTGGGAACTAGG
CCTGTCCAGTGGGCAGCATCCTCATTTTTGAAAAGGCCCTTCTAAACCCACCGGCCTCGCCTAACGCCGTTTGGT
GCTGCATCCGAGCGGCCTCACGCGGTCCCCTGGAAGGGCCACTCCCAGCGGGAGGGCGGGGCCCGGGACCTGCGC
TGGCCACGCAGGGTCTCAAGCTGACCGGAAGACCCGGCTTTTGGCCTGTGTCCAATAGCCCCAGAAGAGAGGGGT
CTGGAGCCTTCCTCCCACGCGTAGTGACGCTCAGGTGTCCTCGGGTTGTTAGTCTTGACCCAGGAGAGTGCAAGA
CAGGCCCAAGGCCTGGGGGGATTGCGTTATGAATGTCCAATTCTAAACACAAGGTAGAGCACAGACAGTACATCC
TCACGGCTGGATTTTAACCGTATTTTAATAAACACATTCGAGGGGGTGTCAGTTTCCCCAAGCTCTGCCCCCTTC
CGCGGGCGGGATCCATGGTGTGTGCAGTGTAAGAGTGCGCAGAACGCGTGTGTTCAAGTGTGGGCGTGGCAGGCG
TCGTGTGCTCGCCCCGCGCACTGTGCGGATCGCCCAGACAGCCTTGACAGGTTTTTGCAGATGTTTGGGTGCTAC
GGTGTGGGGAAACCCAGGCAGGAGCGCCAGGCCTAATTCTCCTGGACTCTTGGTGAGCGGCCGCTACTCCACGAG
GGGCTAGAAGCAAAGGGGGCACGCGCTTTTCCCCAGGCCGCCTCTTGCTGCCGCAGTGGCTGAGGGCGCTGATGA
CCCCTCCCCGCTTCCAGCGGACTTGACCCGCGGGCTGACAACCCACCGCGACAAGCAGGCGGCTGGGTTCGCGCC
GCCGCCCCGGGGCCCTTGGCTCAAATTTCACCTCGAGTCCTGCAGACCCTGCGCCACTGAATTGGGGCCCAGGAC
GCCCTTGGTGACACTCGCCTTCTTGCTGCCACAACCACCGTCATACCCGCAGCCGGGGCTCCCTCCGCTAACCAC
GCTTGGAGACCCCAATCGGGGACAGAGGTGGGAGTCAGACCCCCCCTGGCCTGCACTGCCGTTTCCCTCGATTCT TABLE 7B-continued

| Sequences of differentially labeled CGIs between bladder cancer subgroups relative to blood |
|---|
| TGCGGAAACAAGACTCCCGCCCACACATAAAAATGCAGCTCCCGGCCACCGGGCGCCGGTGGCTCACGCCTGTAA<br>TCCCAACACCTTGGGAGGCCGAGGCGGGCGGATCACTTGAGGTCAGGAGTTCGAGAGCAGCCTGACCGACTACTA<br>AAAATACAAAAATTAGCCAGGAGTAGTGGTGCATGCCTGTAATCCCAGCTACTCGGGAGGCTGAGGCACAAGAAT<br>CGTCTGAACCCGGGAAGCGGAGGGAAGCAGCGAGTCGAGATCGCGCCACTGCACTCCAGCCTGGGCGACAGAATG<br>AGATTCCGTCTCAACAAATAAATAGAAATAAAAATATGCAGCCCCCTCCGCTCCACTTGAACTTTAATGCTGAAC<br>CGGTTTCCCACGTATACGTGTATCGCACCGCATTTTGACGCTTTGCATCGAGTCGCATTAATGGCGCTTTTGAGA<br>ACGCGTCGTCGCGCTTTACAGAGAAACCCTACGGGCAGCCTGTGGAGGGGTAGGGGATATTCATTGGCTTTCCCT<br>GCTGGGCCCCGTCCGCCGGGCGGGTTAGGGTCGTGGCAGCCTGCCCGCGCGCCGCTGACTCTGGAATTTTGTCCG<br>GGAAACTGGCGTAGGGCCCTGGCTCTCCCTTCGCCCTCCGCGCACACGCGGACGAGGCCTTAGATCCACAGCCTT<br>TTCTAGGCCCTGCGCCTTTGAAGCTGGGCCACTGCCAACCGCTCGCGATTCTCACCTTCAACAGTCGCCCCCTTA<br>CCCCTCCCCCACCCGCCTGCCCTCGGGAGCGGGTCGCCTCCACTCCACCACCTGTTTAAGTTCCTCCCCCTCGGC<br>GCCCCTCCAGTCCCCACCCCGGCCCCGGTCCAAAAAACCAGCAAACGGAACTTTTCCACAGTTGAAAGCCGCGGC<br>CCGCGAGGCCGGGCTGGGAGGGGAAAGCGGGGCGTGTCTGGGGGGCGGGGCCCCGAGCACTCCGGAAGTTGCCCC<br>GCCCAGGAGGCTCCTGGGAAAGTGAGGAGAGGGCCCGGGCCTACTTTCGTCCTGGTGTGGCGCCCCTCAGCCTCC<br>CCTCCTCCCAGTTCCCGCGCCTCCGCAGGGCGCCTCGGCCTGGCCTCCAGGCAAAGTTCGCGCCCCCTGTTCCTG<br>GGGTGTCGGCCGCGCGGGCCGTTTCCCTTCATTACTCCCGGGCCCCTGAATCCGAACGCTTTCCCAGAAGCGCGC<br>AAATCCGCTTGCTTTCCCCGCGGCTGGGCTTTGTTCAGGGACAGCAAAGGAGGAGGCGGGAGGCTGGTGAGGTTT<br>TCTGGAAAAGGGGCTTGTCCCGAGGAGGAAGTGCCCCAGATCCCTGAGAGCCAACGCTCTGGGGAGAAGAAACTT<br>TCCTTCTCCCTTGAATGTTGCTCAGATTACCTAAAATTATTTTTTCAGCCCTTGTGTTCTAAAGTCGCAGGGTAA<br>AGGTTATCTTAAGACTTAACATCAGCGCTGCTCATTTGTACGTTGGTGGAGACGTGCCTTTTTTCCTTTGCACTT<br>AAGGTGGACAGGGTCTGCGACGCTCCCTTCCAGGACGGTGTGGGGAAGCGGCCGACGTCCCCAGCCGGACTCACG<br>CCCTCCTACTACTGGGCGTCGGCTCCGCCGCGGGCGCTCCCGACAGGGAGCTGGAGTCGGACGAGCGGCTGCCCC<br>CAGGGCCTCCAGGAACCGCGGCCCAGCGGGGAGCGCCCCAGGCTAGCGCTTTTCCAGTTCCCTTCGAAAGCGCGG<br>GGCTGAGGTCGCGGCGCTGGGCCCTCGGATGAAGCCGTGCTGTAGCTACACCTGAACCCCGCGAAAGGCTGGCGC<br>GGTCGTGTATCCAGGCTGGGTCTGAGGAATCCGCAAGCGGGAGAGCGCTAACTCCTAGGCGTGAGCCGCTGCTGG<br>CTTCGAGAGTTCGAGAACATGAAGGACCTGGCTTCTCCCGCCCGGTCGGCTTAGGGCCAGCGAGGTCACAGGCCG<br>TTCTGCTCTCCCTGTTTGTCCCCAAAGGCCTCGGCACGTGGGGATCTGGAGCAGGCCTCAGGCTGCGACCCGTCT<br>CTTCCCCTACCAAAATTATGTGGGAACAGCGGTCCAGGACCTTCCCCTGTTCAGCGGTATCCCCGGGCCGGTGAC<br>CCCGGGGTTCAGTCGTCTCCCCGACCCCAAGCGGCCTCTGCTTTCCACCCCTCGCCCCGGAGGGCGGCTTCG<br>(SEQ ID NO: 224) |
| CGI: 25 range = chr9:21979774-21980108<br>CGCGGCCAGTGAAATCCCAATCGTCTTCCACGTGGAACCCCAGGTCCGCAGTTATGATAACGGATCACATCGCTC<br>CTGCGGAAAGTGCGCGCGGTGGAGTGATAATTGGACCTAGCGTCTAAATTCTTGTTGGAGGACCTCGTTCCAGCT<br>GCCAGTTAAGCCTCTGGGATCCGCAGCGTCTCTAGGAATTGAGAGAGTGGGGAAGTTAGGATCCAGGAGGAGGAT<br>GGTGGGGGCTGAGGAGTGGAGGAGCAGCGTGCATCTCATCTCTTGTCGCCGGGCGGGCGCTCTTTCGGGTCCAGG<br>GCCCTTGCACCCCCAGCGTGGCTCCGGAGGCGGCG<br>(SEQ ID NO: 225) |
| CGI: 20 range = chr9:23812413-23812667<br>CGACTATGCAAACGCTTGCCGCTAGCCGCATCCTTCTATCGCCCCCCAACTCAAGACCCGAAATGGCCAACTCTT<br>CACCGAGGGGGCGTCCCATCGCTGCCTTGCCTTGGCCCGCCCCTTCGCCAAGCTCAATCCCTTTTCCCCAGAAAA<br>ACCTGTGCCTGTCCTCAGACCCGGCCCCACGGCTGGAAGTCAAAACCCACCCCGGAGCCACGCGGCTGGAGCACG<br>TTTTTACACCTGCTCGGCCGCTTAATTACG<br>(SEQ ID NO: 226) |
| CGI: 278 range = chr9:37024136-37028341<br>CGCTCACAGGTCGGAATAATTCAAGCCTTCCGCTCCCCCGCCGAGCTGGGGTAGCTGATCACTGAGCTGAAACTA<br>AACGTTTTAGGTGGAAAAAAAGCGTCCGAAGGCACCGTGAAATGATTAAGGAACTAAAGAGCTTCTCGCCATGTG<br>AGATCATGTCCTGTTCTCGCCAACATCACAAGATGTCCCCAGACACGCCGCGCCCCCAGCGCGCCGCCCCACACT<br>GCCGGCCCGGAGCGAGGAAAGGGTAGGCGCTGCGCGGCCGGGCCTGCTCAGCGCGCCAGACGTGGCGGACCCGGC<br>CCGGCCGGAGTAGAGCGGGAAGCCGGGAGAGCAGCAGTGCTGCTGCCGCGCCGCCCCAGACTTTTATAGGGGTTG<br>GGGGGAGGGAAGGAAGGCTTCAGCCTGCGCCGGGCGCTAGCCAGCGCACCTACGGGAAGGGGCAGACCGAAGCGG<br>AGCCCGGGAGCCCGGGTCTTCCAGCCGCACCTTCTATTAAGACATGCGCTTGGGGGTCGCGGCCCTCTGCGCTGT<br>GCGCGGGGCCTGTGACATCTCCATGTGCAAACCCCGCTGCTTAGACGAGCGCAGGCCGGGTTTTTGTTTTTGAAG<br>AAATTAACTGCTCGGCCAAGCAGGTGCTTTTGAAAGGGGTTGCAAAGGCTGGCAGTGTTGCCAGGCACCGAGGCG<br>ACGTTCCGGTTTACTCCGATTCACCCCTAGGGCGGCGCCCGACCCCAGGGTTCCCAGCCATCCAACCCCCACCCC<br>AATTTGTTGGGGTCCTGACTATTGCTGGGCCCCTGACCCTAGGGCAGCGCCAGATCCCTAAAGCCCCCAGGTCCC<br>ATCCAGTCTTCTAGTCCCAGAACCCCTCCCCACATCAAGTTCCATTCTGGCCCAGAGCATGGAGGTTAAGCTGTG<br>AAATACTGGAGATGAAATCCGGGCTTCCGCTTTGGAGCACCCGGGCAGAGCAGAACATCTCAGTAGTTTCTGGAG<br>ATTGGCGGGAGTTCCAGACACCTTACCCCGGCCCATAAGTGGAATCGCATTGCCCTCGAGCCCTGAGACGTTGTG<br>GAGTCCCAGAGCCCCAGGACTTGATTCCAGAGAGGAAATCAGATCCACAGAGACCGAGCAGAGGTGTGGCATGTC<br>CAGCCCTCTCTCTTCGGGCCAGACTCAAGCCTCCCCTCCCTGTTCCCCTCCCCAGCCTTGAGTTAGTTCAGCTGC<br>TGGGCCTAGCCACTGAAAGCCTGTGGGGCCCTGCAGCGGGGTGGTCGCAGGGGAAAGGTTCTCCAGGGCGGGGGA<br>GCGCTCCGTAGGAGGACTCCTGGCCCGCCGGACAATGGCAGTTTTGGAGAGTGAATCGTCCTCAGCAAGAGTGTT<br>GTTTGTTTTTTGGAGGGGGTGGTCACGAGGCTGGGTCGCAACCTAGGGGGAAGAGCCTAGAGCTCGAGGAAAGGG<br>GGGCCCCCGGCGGCAACTGGACATCACATATCCACTGAGCAGATTTCGCCACAATCGGAAATGTGGCTGTGGATT<br>CCCGGGCGGCCCCCCCACCAAGTGGTCTGCGCAGTTCCCCAGCGCCGCCTCCTCCCTGCAGCCTGCGGGCCCGTG<br>TCCCTACCCCGAGATTTGATTTTTGGCCATCTCCGAGTGCTCGACTCTTTCCCTCCGCAGCCCAGCCCCAGCCCA<br>GGCTTCCCGCCCTCCCGCCTCGCCCGCGCCGGGAGGCAGCGCCTGGGAGGAGCGGCCTGTCCGCGCCTGGAGATC<br>AAAAGCCCTCCCGGAATTGACATTTCACCCCGGGCTGGGGGCGGGGGGTGTTGGTGTTTTGTTGTTGTTGTTGTT<br>TCCATTTAGAGGGCTTGTTTTGTTTTTGTTTGTTTTCTGTGAGTTTTCATTTTTCCATGGGATATTCTTTTGTTT<br>CGGGTGTTTTGCGTGTTGTTTTTTCGTGGGATTGATTTTAGCGGGTTTTGCTCTGTAAGTCCTGGTCTTTGGGGT<br>GAGTTTTGATTTTGTGTAATTTTGTACTTTGTCCTTGTAGGCTGTCTTTTTGTGTGTCGTTTGTAAGGCTTTTCC<br>TTCTCCGCGGTGTTTAGATGTGTTTTGATTTGGTGTGAGTGGGTGTCGTCTGTGTGTGTGTTGCCTTAGGGAATT<br>TCGTGTTGTGTGTGTTTTGTTTCCTTCGATTTGAATTTTATTTTTTTGAACTGTACGTTTTGGTGGGGGATCGGG<br>TTATATTTTCATGTGTTGTCTTTAGTTTTTGTGTTTGTGAGATGCGCTGGTGAGAGTTTGCGTGTGTATTTTGGC |

TABLE 7B-continued

| Sequences of differentially labeled CGIs between bladder cancer subgroups relative to blood |
|---|
| TTTTGTGGGGCTTTGGGATTAGGGAGGGGACATCAGCCGCTACTCCGTTCCTGCCCGCACCCATGAAGGGCAGAG<br>GATTAGGCCAAGCATCACGAATCGTAGGTTCGCCGTGCTCCGCCGCTTCGCGCTCTGGACGCTCGAGACCAGCGG<br>GAAACAAATGTGGTTCCCGAGGGGGCGCCCGCTGGTCGTCAAAACCTCGCGGGCCCGGAGGCGCCGCTGCTGGGT<br>CAGAATCGCAGAGCCCCCCTCGCGGGTACCGAGGCCCAGCCGCCGTCCCCTTGCCCACCCTCTCCCCTGTGAGT<br>CGGTCTCCCCTTGCGCCTGGCCAGCATGCTTCGGACCGTCCGGACTCCCGCAGCGTTGGCCCAAGGGGCGGCTCC<br>CCTCGGCGGAGCAGGTGACGAACCACTTCGGAGGACACGGAATTGACACTGCGGCCCTAGAGATACGGGACAAGG<br>GGCCAGAACGCGGGGAGTCTAGGCTCAGATCGGAGTCGGGATCCCGGGAAAATCCCCCATCTCCCTTGCCCGCAG<br>CCCTAGAATCCCAGAAACCCAACTCCGCGCAGCTTTCGGTTTGGAGAGCCCGCCCTGGTTTGCAAGCACAGATAC<br>ATGTGCCCACACCCGAACACACGCAGACACCGCCAGAGAGCGAGACAGCGAGCGGGCGCCTCCGTAGCAGCGGCC<br>TGCGGGGCGGAACCGGAGCTGGCGCCGCCTCAAGGGGAAACCGAACTGTAGTGACCGGAAATGTCCCCAGGACAG<br>AATAAGCCATTCCTTCTGTCCACGTTGCCAGGACTTCTCCAGCTCAACACACCTTGGTTTGTTTAATGTTACACG<br>AGGGAGAAGATTTAGAGGCAGAGACACATGCTGGCTCAATCGGCGAGGAAATACGAGCAGAGTCTAAACAGAAAG<br>AAATATGGAACGGGGGGAGACTAGACTGTGGGGAGGCAAATTGGAGGCCCAGAAAAGGGGCTGGTGCGGAAGCT<br>CCTCCAGGCCCCTGGGCGCTCTGGCATTCTGTGAGAAGGAGAAAGCAGAAGCCGAGAACAGAGAGTGACAGGAAA<br>AGAAAAGAGACGCAGAAGGGGTGGCCTAGGCACGCTGCGAGCTGCCCTCCAGCTAAGACGCTGCGGGCAAGGGA<br>GGGGGAGGCCGACATCGCCAGGCGAGGGGCCAAGGTCGGGCTCTTTAACTCAGCCAGGAAACATCGTTGGGGGCT<br>CCAGGGCTCGTGGAGCCCGAACTGGGGCTCATTTCCGGCCCGATGCCCCTCTTCCCCAGACCCCTAGCCCGGAAT<br>CCAGCAAAGGCTGGGCCATCGCCGTCCGCCACTGGGCCTCCCTCTGTGCGAGCCCTGGGAGAAGCCTCAGGGAAC<br>GACTCTGGCACTGGGGCTCGGCCCCGGAGCTAGCGCAGAGCGTGGGTGGGAGTCGACATCCAGGCAGGAGGCAAA<br>GAAGAGGCCCCGCCCTAAAGCCGAGGGCCCAGTTCTTCGAAAGCCTGTGGCCGGAGCTGGACTCACAGGATTCGG<br>GGTCCGTACAGCGCGCACGTGGTACCGCATCTTCGGCAGGCGGCGCCCCTAATGCCCAGCCCCGCCCTGCTTCGT<br>TTGCCGGGCCTGAACTGTGTCAGCATTGAGGGTGGACGCCGAGTCGCGGCGAGTTGGTCCCTTGCGGTATAAACT<br>TGGGGCTTCCCTAGGGGCGGTGCCGGGATGGATGGGGGCGCCTCTCCACCTGCAACTCCCCCAGCGCAGAGCGCA<br>AAAAGTGCACATCGCGGGCCAGCCGTCGCCTCGGGGTTTCAGGCGGCGCCCGGGGCAAAAAGGAGCTGAGGATTG<br>GTTTGGGTCAAAACACCCATTTCAGTTGGCAGTGGGGTCCTCTGCGCCTACAGGGCTTCGAGCTCCGGGTGCGGG<br>CTCACTGGGGCACCATGTGCCAGCGACTCGCCACCCGGAAATACTTGGGTTGCGCTAGAATACGCAATGGTCTG<br>TGTTCG<br>(SEQ ID NO: 227) |
| CGI: 392 range = chr9:101621613-101627382<br>CGGGCCGCCACCGCCGCCTCGGCTCCTCCGTGACGTCCGGGAAGGGTATCCCCGGCACTCAGGAAGTGGTGGCCG<br>CGGGCAGCTCCGCCCCCACGCGACTCGGGGCTGGCCGAGCTGCCGGGTGGTAGAACCGCCGGGCCTTCCGCAGGG<br>CGGGCGGGGATCACCGTCTCCCCACCTCCGTGCGCACACACATGCACGGGCCTCGCGCCCCGCTGTCGCCCGCGC<br>CTCGCCCTGCTCACTTCTCACAGCCCGCGCCGGACGAAGAGAGCCGCCAGCGCCCCCCCTCTCTCCCACGGCTCG<br>CACCCACTCACCCCGACCCCCGGCGCCGAGCCCGGCCCCTCGTCGCCGGTCACCAGACCTGGTCGAACCGAGTCC<br>AAGATGGCGACTCCGCCCCCGCCCCCTCCGCACTCCCGGCGGGGTCAGGGCGCCCCCTCACGCGGCGGGCTCGCG<br>CCCGAGACCCGGCTAAAAATAGCCAGGCCCGACTATATTTGGTTCGGCCGGATCCTGGCGCGGCCGCGCGCTCCC<br>CGCCCCGCCCCGCCCCGCCCCGCGCGCCCTGCCCCGCCCCGCGCGGCGTTGAATGGAGAAGGGGCGGGGGTGACC<br>GAGGGGAACCTACTCCGCTATCTGCGGCGCGCGCCGGCGGCGGGTCCCGGCCAACCGCCGAATTTAGTAACATCG<br>CCTGCGTCAATCACGCGCCTCGCGTGCGTCAGCGCCGCGCGGCTCCAGGTCCTGCTCCCCCCCTTCAAGCCTTTG<br>AATGGATACAATGTAGCAGCGCCCTCCTTCCTTCCGAGGCTGGATTGGAACCCGCCGCAGTGCAGAGACTCGGTT<br>GCTCTCGGCTGGGTCAACTTTCGGGGCATTCTCCCACGATCCTCTCCGCACCACCGTGTCTGAATTGGAAGTGGA<br>GGCGAAGAAAGATATACATGCCATATTTACCTATATGTAGTTTGTTTTCAAGTTTCTGGTCCTAGCTCGAACCTT<br>CTTCGATTCTGAAATGTGTGCTGTCTACAAAGGAATCTTGTATCTCCCCTCGGCGCAGCGCCCCCCGCCCCCGCC<br>ACACACACACAAATTGGGACAGGTCAAACATATAAAACGGTATTTGTGATTCAAGCGGACCACATGGGGACCACT<br>CTATCTGCATTGTTTCACTCAAATATTTTCTCCTGTCCAAAAATTCATTTCTGAAAGAGACTGCGTTCACTCAGC<br>AGCAACCTTTGGGACTAGGGGTCTTTAACTCTGATAAATTTTGTTTTCATCAAGAAATTTACACTTAAATTTATC<br>ATTTCCAGGAAGAAATTGCTCTCCTTCATACAGTCACCCAGGCTTTCGGCACACCATTTCATGACAAATGTGTCC<br>GAGGAGACCAAAGCAAATCCCCTAGCGAGGGACTGACTAATAAGTCCTGTTGATTGATTTCGAAATGTTTAATTT<br>GGGAGATGTGGGCGGAGGGCATCTACAACCATCAAAAAGTGAAAGTGCTAGTTGAGAGTTCCATTTCTGACCCGG<br>TGCCGGGGAGGAGGAATGATTTGCAATAGTCAGACCCGCTCAGCTGTTCAACACGTGTGTGTTTGTTTTACACAC<br>AGAGTAGTTTCTGCTGCAGCGCGCGTGTGCATGATGGATGTGCACTTCGCTGGGTTATAACGTGTCCAGTTAAGA<br>AACCCACGCCGTACGTGTAAAGAAATCAAACCTTATCCCCGGAACCATCTGCATCCCTGTGTGAAACACGCACCC<br>AGTAAATGATGCGGGGAGGGGGGATTAGCCTGGGCGCAGAGGACCGGAGCAACGTAAACAGCTTTAGAACCTATG<br>CAAGAGGAAAGTGCAGCTGCACCTCAGGGCGTCTTCGGGCTGGTGCCAGACGCCTTCTGCACCGGCTGCCAGGTC<br>ACTGGAGCTGGTCAGAAGCTGGCTGGCGGAGCCTTCCCTTTCGGAAGAGCTGTCCTCTCCCTTACCCCCCTCGCC<br>CTGGCTCCGTGCCTCGGGGCAGCCTCGGAGGCGCGCCAGCAGCACTCCTCCAACTCTACTCCACCCGAGCCTGAC<br>AGCTGGGCGGTCCCGCCTGACCCGTGGGCAGGCCGCTGCACCCTCCCGCAGACGCACGCCCTGGCGAGCGGTTCC<br>GCTGCAAAAAGAGAAGCCCCCAGGCCGGGGCCGGCCGTGCGGCGGAGTTTCCATTGTGCGGCCGTGCGACTGGCC<br>GAGGAACGCGCGCGCGCGCGCGCGCACACGAACACACACACCCTCCCTCGCACACGCGGAACCGGCTGGGCCAGG<br>GGAGGGAGGAGGAGGGTGACGTAGCGTCCCATGGCGTCACATTGACGTCTCGCATTCCAGGCACTCTATGGAGAG<br>GCCGCTAGGGCTCCTGTGGCATAAATGACGTGCCGAGAGAGCGAGCGAACGCGCAGCCGGGAGAGCGGAGTCTCC<br>TGCCTCCCGCCCCCCACCCCTCCAGCTCCTGCTCCTCCTCCGCTCCCCATACACAGACGCGCTCACACCCGCTCC<br>CTCACTCGCACACACAGACACAAGCGCGCACACAGGCTCCGCACACACACTTCGCTCTCCCGCGCGCTCACACCC<br>CTCTTGCCCTGAGCCCTTGCCGGTGCAGCGCGGCGCCGCAGCTGGACGCCCCTCCCGGGCTCACTTTGCAACGCT<br>GACGGTGCCGGCAGTGGCCGTGGAGGTGGGAACAGCGGCGGCATCCTCCCCCCTGGTCACAGCCCAAGCCAGGAC<br>GCCCGCGGAACCTCTCGGCTGTGCTCTCCCATGAGTCGGGATCGCAGCATCCCCCACCAGCCGCTCACCGCCTCC<br>GGGAGCCGCTGGGCTTGTACACCGCAGCCCTTCCGGGACAGCAGCTGTGACTCCCCCCCAGTGCAGATTTCGGGA<br>CAGCTCTCTAGAAACTCGCTCTAAAGACGGAACCGCCACAGCACTCAAGTACGTATGAGATTCGCCCAGTTAATA<br>AGGGGACTTGCTAAAAAAGTTGGCTTGCTGGGAAGCGTCGCTCCTGAAATTGACAACTTTGAGTGTGGGGTTCCC<br>TCCCCTGACCTTGCCGCCCGGCTCCGGCTTTGCTAGCCCAGCGGCCCGTAGGTTCTGATCTGAAACTTTTCCCCT<br>GTAGTGGGCCCGCGGGGATCTCTGGAGCTCGTGGGATTCCTCCCCCCACTCGAAGAGGCGAAAAGCCTCTAACAA<br>AGAGGAGGACCGGGATTTGTGCTATAGCGGCTCCAGCGATGTAATTCAGGGTATTTCGGCTCTAGTTGTCATGGT<br>AATGATGCTCTCGGCGGCGGCGGCGGCGGCGGCAGCGGCAGCGGCAGGGAGTTGCAGCTCCGGTGATGAACGGCA<br>GTAATTTTCCTGCCTTTTAAGTAGGATTGAAAATAGGAGCTCTGGTGGGTCCAAGTAAATGTTGCTAATGGTGGC<br>ACCGAGCTGGTTCTCTGGAAGGAAGCTTAGGAGGGAAGGGCCTAGGCAGCGACGGCCAGAGTTTGCAGACGCACT<br>CGGAGGACCTCAGGAAAGAGGGCGTAATTGTAGGAATGTGGCTTATTGTATTGAAATGAGCCTGGGGTTCCACTA |

TABLE 7B-continued

| Sequences of differentially labeled CGIs between bladder cancer subgroups relative to blood |
|---|
| GGCACGTCTGCCTGTCGTCGCTGACATGCCGGTTTACACTTTTCCCTTAGGAGGTAAATCGGGTGTAATTGGCGA CTCCCGCACACTGACACGTGTGGGGACGGTGTCCCTCTCCTCTGGACGTTGGCTCGGTGTGGGAAAGGCATGCTT TTTCACGGACAGAACTCGCGCTTTTGGAGAAGTTGCTCCGAGTGTTTTACTCTTAGTAGAAATGAAAGTTCTCGG TGGTGAGACGAGAGCGGTCATGCGAGCGCAGCCTGCGGAGACTGACTTCCAAAGGCACCTCTCCAACCTGTTGGA AGCCTCGGGGCAGTGGTGAGGAAGAACGCATTTGTCCCTTGATTTCCAAAAACGTTCTTGGAGATTGCCTTTTAT TTATTTATGCGTCCGGATTCTCCAGAGGGAAGAGCTGCGAGGAGTTAGTAATCAGAAATGTCGGGCTGTGATCCC AGGGCCTTGTGGTGCTGGGAGAGAAGAACAGGGAGCCGTCATTCCATCGCGAGTCCAGTGCCGGATCTCCTTTTC CCACGACCGGGAAATATTTTATAGAATCAAGTTAGGGAAAGAAAAAGCTGCCTAACGTGGCTGATGGGCACAATG AATGAAGTTACTTTATTCGAGTTATTTTCGCTGAACAAGATGCTCGCAGAGTTAGTATCAAAGCCTCCTTAGGCC ACAGCAACCTCCACGTCCGCTCCGCCCCCCACCCCCCGGCACCCATCCACCCCTTTGCCTGGGACCGTGCGCTCA CAGAAATTCTTCCCCGCGGTTTGTCTAGTCTCCCTCGGTCTTTCTGAGAATCTCAGTCTTTCCCTTTCTGTCAGT CTCTCCCTCGCTCCTCTTGCCCCCGCCCAACCTCCGCCCCCGCTCCCCAGGGTTGGAAACTCCGCAGAGGAGCCC CGGTCACAATGGTGCGTTTCACGGTTTCCTCCACACACTTCACCACCGGGAGGGGAACACGGGGGTGTTCCTTTC GTCTGCCCACGAGAAAGAAAGGGGCTTTGACAGAGGTAGTTATTTCTTCCTAATTTACAACCCCAAGGCTCTGTG CTCCCGGCCCCGGCGGCCGCAAGCAGGAGCGGCGGAACGTGTTTCCAGGCACTGAGGCTTTGCCTAGGTAACCGG CCGCTTGTGGGGTGGAGAGAGCGGCGGGGCGCTGGGCTGGGCTGGAGGAAAGGCTGTGTGGGTCCCTCCCGCGAA CGCTGGGCGCTCGAGGGGAACTCCTTCGTTGGGGAGAGGCGGTCCCCGCCCACCCGAGTTCTGAGGCCTCCTCTC AGAGAACGACTCCGCTTGAAAGGCCCTCAGGGAATGCGGGACGGGAATGCGGGCACCCACTGAAGGGGCGGGTGG GGGATTGCTGGAGACCCCCATTGAAGATGCGGGGAGACGGGAAGCACGTGCTACAGCCGTGGGAAGATCCGCTTC TACCCGCGCTACATCGAGCGCAAGCTTTCCGTCCGAGCAGCTCCAGCTGGGGCTGGGGGTGGCAAGGGAATCCCC CATTTCCTGGTCGTCGAGGGTTTCCTGGACCTGGGAGCCCCGAGTCCCTTTCTCTCTTCCTGCAGGCAAGCCCCG GGCTCAGGGGCGCCAGGAGATGACCCTCGTGGCCCCGCGCACCTCGGAGGTTTTTGGTTTGGTTTGATTTGGGGT TTTTCGGTCCCTGTTCCCACTCTTCGAGCTGCGCCCACCCCGGGCAAAGGGGGCGCTATAGGCCGGAGTTTGGGC ACCCAGTTCCTTCCCTGAGGCCTGCTGAGCTGCGCTTTCAGCTACAAAGTTTCGCTGAGGCTGTGGGCTGAGACG CTGGTCCCGGAGCTGCGCTCGGCGCCCTCAGGAATGTGCCCCCGCTAGGCCGCTGGGTGGCCAGGAGCCTCCAAG CCGCCCACCCTCGAAGACACCGCCCTCTGGGTGCAGGGGACCTGCCTCCGCTCGTCCCATCAGCCGCTAACGCCG TCCGCTTCGTCCCCTTGCTTCCAGCGCCAGCCTTCTCATCGCTGTGCCCTTTTGTTTGCTTGACCCCTGGCCCTC GAAACTCGCGGCTAATAGAAGCGAAGCTCCATTAGCATTTAGAATGAAAAGCGCAGACTTTCTTAATTCCTCGGG GCATTCATGCATTCGTTCCGGACCTTGTGCATTTCCTATGCAACGTGTAAAATTTGTATTTGAGGGGTGGGGGCG GGCGGAGCTGGAAAATGGCTTTTTTCCGCTGGTGAACACTCACTGACCCCCCGTATTCGGGCGGAGCTCG (SEQ ID NO: 228) |
| CGI: 56 range = chr10:13556172-13556753 CGCTGTTAGATTTCGGGTCAATATCCATCATCGCTGTTAGACTCGGGGCCGACATCCGTCATCGCTGTTAGACTC GGGGTCGACACCCATCATCGCCGTTGGACTCGGGGCTGATACCCGTCATCGCTGTTAGATGCGGGGTCGATATCC ATCATCGCTGTTAAATTTGGGGTCGATATCCGTCATGACTGTTAGATTTGGGGTCGATATTCCTCATGACTGTTA GACTCGGGGCTGATATCTGTCATGACTGTTAGACTCGGGGCCGATATCTGTCATCACTGTTAGACTCGGGTCAAT ACCCGTCATCACTGTTACACTCGGGGCCGATACCCGTCACCGCTGTTGGACTCGGGTCGATACCCGTCACCGCTG TTGGACTCGGGTTGATACCCGTCACCGCTGTTGGACTCGGGTCGATACCCGTCACCGCTGTTGGACTCGGGTCGA TACCCGTCATCGCTGTTGGACTCGGGTCGATACCCGTCATCGCTGTTGGACTCCGGTCGATATCCGTCATCAGTG TTGGGCTCAGGTCGATACCCGTCATCAGTGTTGGACTCGGGTCGATACCCATCATCG (SEQ ID NO: 229) |
| CGI: 22 range = chr10:15294605-15294858 CGTTAGAGCATAGCGACATCACGTGCGGTTTCTTAATGTCCCTGGTGGCGGATACGCCGAGTCCTCGGAAGGACA TCTGGACACCACTTTCAGCCACCTCCTTGCAGGGGCGACATCCGCCAAAGTCATCCTTTATTCCGAGTAATAACT TTAATTCCTTTCTAACATTTACACGGCAAACAGGAATGCAGTAAACGTCCACGTCCGTCCCACGGCTGGGCTGCC GTTCCGTTTCCTCCACGAACGGGTACGCG (SEQ ID NO: 230) |
| CGI: 987 range = chr10:76825135-76839606 CGCTCCCAAAGCCACGCGAAAGTGGAAGCGCGGGGCCTCGGGATGCCCATCCAGCCGGCTGCCCGCGCGCTGGCC GGGGTTCCAGGACTCCTTCCTGCTCCGCCGGGCTCTGCAGCGCCGCCTGGTGGACACGCGGCGCTCCGCCCGGGC TCCAGCCGCCAGCCGGCGCGCCGGGGATCCCGCGGCTGTTCGGGAAAAAGCTGGAGAGAGTCGGGGGGCGCGCCT TGGGGAGGGGCATTTGTCCCTCCGAGGAGGCTCGCACCTCGGCCTGGACACGCAGCAGATACTGGCACCCACCCT TCACTTACCGCGCGCCCGGGGTGACTCGGATCCGTCCAACACGTCGGGGAATCCTTTCTGTCCTCACCCCCGGGC GCCCCAGCGCCGGAACGCTGCTGCCTCTGTGTAGCTGCTCCCGGAAGGAGTTTCATCAAACTTTTAAGGGGCTTT GGTTTTGGGTTGTGTTGATAAAATACCAAGAAGGGGCATGAAGGCACGAACGTCCCGGGTTCGTCTCCCTGCTGG TCCCAAGCCTGAATCCCAGGGCGGGGGAATGTCTAGGTCCTTCCGGGCCGGCAAGGTGTGGTCGCTCAGGGACCC CTGTCCGAAGACGCTAGGGAAAAGAGGCACAGCCTGTGGGTCGCAGTGGCCAGGAGCGCGTGGCCGCTGCTGGTG AGAGAGTGGTAGACGCCTGGCTTTCAGGTCCTGAGCTGCGGGCACCGGAGCGTGGGACCCCGGCTGCAGCACCGC CACGCGCTCCCGCCCTCCCACCTGCAGGGCGGGGGATGTCTGTCCAAGAGGCCGGGGCGACAAGCCCGCCGGCCA GGATTCTCAAGGAACCAGGCCCAGCTCAGCCTCTCTCGGCGGGACCAGAGTGGACCGGGGCCGCGGCGTCCGAA GACGCTGCGGGCCAGGGGTCCTCCTCGGCGCCAGCTCCGTTTCCTGGGGTCTCGCGACGTCCGGACATCAGGGTC GGGGGTGTGGAGACGGCGGCGGAGCCAGAGTCCCCACCAAGTCAGTTCCAGGAGGCGGCCCGCGCGCTTCCCGCA GTGTCCGGGAGGTCGCTGGGGGTGGCTTTGCGTGCAACCCGGGTAAAGGCCCTGCAGCCGTGAGGCTGGCGCTGG GAGGAGGGTGGAAAATCTCAAAGTCACCAATCCCGGTGCAAATGGCGGCAGGGGCCGCGGGCTGTCGGACGCAGG CGAGAGGCCAAAGGCTGACTTCGCGCGGCCGTGAGTCCCCAGAGGCAACAGGGGTACCTGAGCGCCGAGGGGATC CCGAGACTCGGAGAAACCGGAAGAGCCTGACCCCAGGGAGCGGAGAGTTTGGGGTGCGCTCTCAGAGCTGTGACT CCACGGTCCCGGAATCCTTGGAAAGGGCGCTCTGGGCTCAGAGCTCCCAACTAGCCGGAGGACCTGGGCTAGCGC CCAGGCCTGGAGCGTCTGGGAGGGGGCGCTGGGTCTCGGCCCCCCTCCCCCCAAAAGGGACTGAGACTTTTTTCT GCGTGCTTCCTTCGGCGCTTCGGGCAGCTCTGTCCTGCGGCCCAAGCTGGGGAGAAGACAGCGGCCCGCGCCACA GGGAGCTGCGCCCGGACCCAGACTCCCGCCGCGCTTCTGCAGAGCGGAGCCCTAGGTGCCCACCTGGTAGCCCCA GAAAGGCCGGACCTGGGCGCCGGGACGCTCGCGGGGCCGCACTTGGAGGGGCTTTCCGGGTCCTGGCCGGGCGGG CTCTCCTGCGGCGCGGAATGGAATAGAGCGCCGGCTGCAGAGCCACCCGGACGGGGAAAAGCAGCGGTGGCGCCG GCCAGCCCCGGGTCCCGACTCTGGAGGGAGGAAGGAGCGGGCGGGTGGGGGTGGGGGTGAGGGCGAGGGTTGCGG GGAGCGTTTAGAAGGCCCTGGGCAGCCAGAAGAAGAAAAGAGGACGCACTCTCCCCTAGGGACCAGAGGGTCCCT |

TABLE 7B-continued

| Sequences of differentially labeled CGIs between bladder cancer subgroups relative to blood |
|---|
| GCGTACTCCCCCCAGGCCCGGGACACAGGTTCCCCCAGCGCCCCTCCGCCTCCCAGTCTATTCGGCTTGCCCCAG |
| CGCGCTGCCCCACGTCCCCGAGGCCCCGGCCCAGGCCCAGCCGGCGAGTCCCGGCCTGCTCCACTCTGCACAAAA |
| CGAAACCCAAATGCCCAAAAAGCTCAGGAGGGAAATTTAACAAAAACCCTGTCCCCCGCCCCACACCCCCTTTCA |
| CTTTTAACAAGCCAGCTGCCAAGAGAAAATTGAAATAAAAACGAAATGATAGATAGCGGAGGACACTATTTTCCA |
| AATGGTGAAATATCCTCTAAAAATATGTTCCCCAAGGCCAACTTCGCGGCTGGTAGCCCCTTCCGACGCCTTTGC |
| CTCCCAGAAAATCACAACAAAGCGATCGGAAATTCAGCCACGGTCCCGGGAAGAAGGAGTAGCAGTGAGGCCCCG |
| GAACCCACTGCGGCCGAAACTGCCATGCTCTCTTTAACCAAAATAAAAAAGATAAGAAGAAGAAGTAAAACCCTT |
| TAATACATCAAATATACGGAATTTTAATCTTTAAAGCGATACATTGTCTATTATTTTAGTACATGACGTAAACCT |
| TGTCCCCTTCTCAGCGGGTGGACTTAAAAATTAAAAATAGTTAAGTGTTCCTTTTAAAGAACAAAATAAGGCAAA |
| TGAGGTTTTGGAATAGAATTTTTTCTTTTTCTTTTTTTTTTTGTTGTTTTCTTCCAGAATACATACAAAAAAATA |
| CCCATTCTCTTCGATGGTATACACCTTAAAAATAATTGCAATTTGAAATCAGAGCTGACAAATTGTGACTTTTTT |
| TTTCATTTTTTTTGTAACAAACATGCATGTAAATTTGTGTTTCAATCAGACATTAAATAACGTACAATACAATCA |
| TAGCAATTTTAAAGTAACATTAAAGAGAAGACCTCTAGTTCTGTGGCGGTTTTGCTTTTATTTATAATCTACAAG |
| GGATGGGAGGGTTTGTTTTCCACATTTTTACCCTCAAGTTTTAAAATTTTTCCCACCTCCTTTTTACCTACAGAG |
| CTCAAACTAAATAATGCACTTTTGAACCACCGGTCCGCTTGGAGCTAACATAAATAAATACCAGTGTCCACCGAT |
| GCAGTCCTCAGATGAACACTTTCTCAATTATTTTTTCCTTTTTTTTTCTATAAAAAGTCAAATGATATTTTTTCA |
| ACTTTTATAAAGTTTGGGTGGGGAGGTGAAAGTGGGGAGAAGGGGAGTGTCCCACCGGGTCTCGGTCGCTGCTGT |
| CGGGTAGATAGATACGGTATACATTTCTTTCCTTTCGTGGCCCGAGTCCTCCCCACGCGCGGGTGTCAGCAGCCT |
| GGGCCGTGATCCCGCCTCTCCCTGGACTCCTCCCCTCCCCCTCTCCCTCCTCTCCCTCGCTCGCCCTCCCGGCCG |
| CCCTCACTGATACCCCAGCGCCGAGGCGGTGGTCAGTCTCTGTCCGTAGAGGGCGTAGGGGGAGTAGTACGGTCC |
| GGTGGCGGCGGGCACCGGCACGGGGGCGCCAGGCGTGGGAAGCGGGCTCTTGGAGTAGGGGTGGTAGCGGCTGCT |
| GAGTCCCAGCGCGTGGTGGGGGCTGCGCAGCGCCAGCGTCCCAGGGCTGCCCGGTGCGCCCGAGGTGGGGATGTG |
| CATGTGGCAAGCCATGGCGGCCGCGGCAGCGCTGGCCAGAGACGACGAGCTGGGGTAGCCCGACAGCAGTTTGTC |
| TGTCCCGGGAAATGCCGTATGGGTCCGCAAGTGGCTCAGCAGCTCTTCGGACGTGGCGAAGCGCTTGTCGCACGG |
| CCCGTTGGCCGACACCCAGTTGCAGATGTGGGGGAGTGGGTCGTTAGGGAGCATAAAGCCGTAGGGGTAGAGGGG |
| GTGGCCGGCCAGGGAGGGCGGTGTGGCGCCAGCAGCCGCGGCGGCCGTTAGCGAGGAGTGCACACCGTGCAGCGG |
| GTGCGTGGGGTACACCAGCGGGTATCCGGACTTCAGCGCCGCAGCCGCAGCAGCCGGATCATGTGCGCAAGAAGC |
| GCTGGCGGCCGCCGCCCCTGCCAGGTGGCTAGCGCAGTGGTAGCTGAGGCAGTAAGGGTCCCGGCACAAACTGGC |
| TGTCATCACGGACGGCGGAGACGCTCCGGCCAAAGGGCTGGAGCCGGCCGGCTTACTGCAGCCCAGAGACCCGGC |
| CGCGGCCGCCGCCAGCTGCGCCCCCACCAGGCTGCCCGGCTTGGTGGGGTCAAGTGCCACGCCGTGTGGCAGGAA |
| CTGGGGCGGGTAGCCGGCGTAGGCCCCGGCCAGGCTGCCTGGGTAGGTCATACCCGCGGGAGGCAGAGGGAACAC |
| TGTCTGGCCCGGCTTGTAGGGTGACACGGGAGCCACCAGCCCAGAGCCCAACACTGAGGAGGAGGTGGGCGCGCT |
| GGGGCCGGAGCCGGAGCTGGAGCCCGATGAACCGCCGCAGTCCGAGCCCAGAGCCTTGCCTCCCGGGCCCCCATC |
| CGGATGCTGGTTCACATCCACATTAATCCCGCCGCCGCAGCTAATCCGGCCGTGTGCCAGCCCCGTGGGTCCCCC |
| TTCGGCCGAGGCGCCCCCGGTGCCCTTGCCACCGCCGCCCACGTCGGTGTCTTTCTTGTCGTCCTTGCCCTCCGG |
| GGCACCCCCGGCCGAGGACAGCATACCTCCCGGCGAGCAGGCCGAGGCGCTGGAGCTCGGGCTGCCTGTCCTGGG |
| CGTGAATGGCTGGCAGGTGGCGCTCGGTACCCGGAATCCCGACTTCTCCGACGAAACACCCCCGCCGCCGCCCCC |
| GCCACCGCCACCGCCTCCACCGCCGCCTCCCGGCTCCTTCTTATCCGAGCCGGGTTTGGAGTACGGCTTGAAACT |
| CGACTTGTCCTCCACGCCGATGTCGCTCAGCTTCAGGGGGCCCGATTTGGTGTCCTTGTCGCCCGCAGCACCGCC |
| GCCGGCACCGCCCGCGCCGCCCCCGTTGGAGGCAACCGAGGAGAGTTTGGAGGAGGGCGAGGGGTCGGGCTTCCC |
| GATCTGCGAACATGTTTGCGCCAACAGCGCCAGCGGGCTCTTCTTGGCATCGAGCTGCGGGGTCAGACGATGGGG |
| GGGGAGCGTCACACAGAGAAAGAAGTGGAAACCCTTTAGAATCCTGGCTTCTGGGGTTCAAATGCCTCTCCGCAA |
| CAGCCCACGAAGATCCTCCCAGCCCCAAGGCGCAATTCTAGGCGGCACCCCCTCTTCAACACCCACTCACAAACA |
| TTCTCGCCGTTGGGAAAGGCAGCAGATTGCTCCCCCCGCCCAACCACCACCCCCAGCAGCATCTTTCCTGCCCTC |
| TCTGAGCGCTAACTAGATTTTTAAAGAGCAAAATGTTTTGGTTTTCGGTTCCTAGACCCAGAACTGTACCCCCTC |
| CCCACAAACACTCCTTAATTCTTCAGAGTAAGGGCTCGGGCGGCTGGCGCCTCAGAGGCTGTGTGCACACACTGG |
| CTTCTGCGGATACGAAGGACGGCGACTTTGGAACCGTATTTCAGACCTCCGCCTGCCTTCGGTGCCGAGTGAAGG |
| GGCCTGGGTCGGGGTAGGGGCTTTCATATCGAAAGGAGAAACAAGTATTGGCAGCCTTGCTCCCTAGCATGCACG |
| CCCCATTCCACTTCCTCCCCCTTTTCCGCCCTAGTTTTGAGGTACGGAAGCAGTAGCCTCTTCCCCCATTCGGGA |
| GCTGAATCACTCCGACCCCCCCACCTCCGCCCAGATCCCGAGAAAAAGAAAGCCCTAGGGTGGCAGCCAGGGTAG |
| TGGTCCCAGTGCGATCCAGAGAGAGGGTCCTTACCTCGATGGGGCTGACCGGCGTGGAAGGCAGGGGCTGCAGGT |
| ACTCGGGGTGCAAAATGTGGCCAGTTCGTGCCGTCAGCATCTTCAGCACCTTGATTGGCAGGCGGTTGGCCTGGC |
| GCAGGGGGTCAGAGGGGGGCACGGCGTGCACAAAAGGCTTGGTGCTGCCGGCCGGGGACGAGCCTGGGCCGGGGC |
| CGGAGCTATTTCCAGAGAGCGCGCTGGTCCAGGCAGGGTCTGCACCGCCGCCTCCGCCTCCGCCGCCGCCGCCGC |
| CGCTGTGCTTACTGCTTCTTAGGGCAGAAAGCGAGGGCGCTGTGCTCATGACCCACCCGCGCGCATGGGAGCAGC |
| GGGGGGGAGGGCTCCGGGAGGCGCGGGGCGGGCTCGGGGCTGCGCGCTCGCCCCGGGAGCAGGAGCAGCGGGAGG |
| AGGAGGAGCTGGCGCGGCGGCCACGGGCGCCCAGCGCGCCTTCTCGGCGCCTGGAGCCAGACGCGAGTAATCCTG |
| GGTGGCCCGCAGCGGAGCCGTGGCCGGGCTAGAGGAGCCGGCTGGACTGCGGGAGTGCCGGGCGGCTCGCGGTGT |
| CCGCCTCGGGCTGCTCCCCTGCGCTGCGTTCTCGCGGCCCCGCGCCGGCGCTGCGCTCTGCGATGCGAGCCGCTG |
| CGTGTCCAGCCGGGGCTCTGGCGAGGAAACTCACTTCAAAAGCAGCTGCACCAAGGGGGAGATTAAAGCCTTTGC |
| CGCCTTCCAATCAAATGGGAGCCCGAGGTGATTGGAGGGTCAAGGGGATGTGACGCGTCCCGCGCCGCCGCCGCC |
| GCCGCTGCCAGGACTCTCAGTGCCGGTTTTAATGGGCAGCTCCCTCTTCGCCGCCCCCCTGTGTGTCCCCTCCCT |
| CGATTTCGCTGGGAGGACGAGATGGACATTTATTCTACGTTTGCCATCCGCCGCCTCCCTCTTTTTTCCTCCTCG |
| TCGTTCTTCCTTTCCCCAGCTCGAAAATAAACTGAAACCTTCTTTTGAAGGGGGGTGCGCGTGAGGAACAGACTG |
| CGGGGGGTGTCCAGAAGGAGCACCGGTGGGAGTGTGGACACCGGCCGGACTGTCAACTCCAGGGGCGAAGGGAAC |
| CTGCACACCCAGTGTTTTTTCCTTCGCAGTAATCGAGATCCCGCGCGGCGCAGCGCAGCCACCAGGGTAAGAAGG |
| CAAGGTGGGGAGCCGGAGCTGGAAGAAGCCCGCCCGCCCGCTCTAATTTCCTCAGATTCCGCGGCGGAGAAACCA |
| GAAGCTAGATGGGCAGTCGCAGCGGCGGCGGCTCAACACCGCGAGGAGCGCTGGGCTCTCCGCCCTTCCCGGCCA |
| CGTGACGCCCGGGGACGCGTAGATTGGGGCAGCAGCGGGGGTCACATGTTTCCTCTGTTTCACCCTCAGTCTGTC |
| CCCCAACCCCCCATTCTTACTCTCCCACCCTGTTTTCCTCCCTCCCCCCCTTCTTTGGGCATCTCCACCCCTCCA |
| TCAATTGTCAATGTTCCTCGACCGCAATCAATCAGTTATTTGTCAGCTCTTGTCAATCCTCCCGTGATTTATGTC |
| AGCTTTTGTTGCTGATTACAAGGCGGGTGCGACTTGAAGGGAAAAAGAGAGAGGGAGAGAGAGACGGAGAGGAAG |
| GAGGAGATTGAGAGGGAACTGGAGGAGGGGAAAAGAGGAGCGGCCTCCTGGGATGGGGGTGGGGTGGGGGCTCTA |
| AGAAAAAGAATGAAAGAGGCGCACGGTGTCAGGAAAATGAATAGCGAGAGTAAAGTGCGCAGGTGCGCCCAGGGC |
| GCCGAGAGGGGCGCGCAGGCCTGGAGTGTGCGCCTGCCCTCTCGGTGTCGGAGAGACGCCCTTCCACCTCTGGGA |
| GCCTCGGTCTGTTGGGGTCGCGGAGTTCGGGCGCGGCTCCGGGTACCCGAGACCAGCGGCGGCAACTTCTAACAC |
| GGGAGATTTCCCGCCACCCCACCCCGCCGCCGCGAGTCCTCGCGGGGCGTGTTGCGTGCGGAGGTCAGGCTGCCA |

TABLE 7B-continued

| Sequences of differentially labeled CGIs between bladder cancer subgroups relative to blood |
|---|
| CCCTCTGTAGTTCCCTAACCCCAAACTCGGAGACTTCTAAGAGCCACACCACCAAGGAACTTCTAGTCCTGGAGG |
| TCAATGGTGGGGCAAACCTCGCCTCAATTCTTTGACCCCCTCGGGTCGTAAGCAGGGCTAAGAGGCTGCGAAGAA |
| GAGGCCTGGCCATGGGTGTATGGGGGAAGAAACATCTCAGGCTCACTCATGCCCCCTCCCCGACCTTCTCCCACC |
| TGCCGCCATCCCCGCAGGCTGGGGAGCCAGGGTAACTCGGGGCTGCTCTCTCGAATTTATTGGAACGCCGAGTCG |
| GAATGAGCTGCGCTAGGAGAGCCGAGGGAAGGAGCGAGAGAGGGAGGGGGCGGCTGCCTGTGGGAACGCGGGTTC |
| TTCCAGGGAAGCGGAGCGGGACTGCCGCGTTCCCCTCGATTTGCACCGTCACTCGGGTTGTTTGGGAAGAAAAGG |
| GGAGGCGCTGTGCGTGCCACCGGGTACCTGGACCTGGATGCCCAGTGTGTATGCATGCCTGTGGCGCTGCGTGAG |
| TTATCGGGGCTCTGATAGCGTCCGGAGCGGGTTCGAGGGTCTCCTCCAGGAACTCGCAGAAATTAGAGGGGGTGG |
| GGAGGAGGACACACCCCCTTCCTCGGAACGACTTAGAAGACTTTGAATCTCCCCTCCTCCGCTTTTCCGCCCCGG |
| CTCTTCTTTTGTTGTCAAGTCCTTTTGATAAATGGTGGGGCTGGGAGCTCTGGGAGTCGGGAGCCAGTCTGTGCC |
| CGCGTGGGGGGCGGGGGCCGAGCCTGGAGACCCGGTTTCGACCGGCGCGCACCTGGGGCTGAGCCGGGTGCGCGC |
| GGGGGTCGGGTCTGGAACTGCCCTTGGTATGCTCGCCCTCTCCTCTTGGCCCATCTCACTCCCCTCCCCCACCTG |
| ACTCCCCTCCCCGGCTTCTTTCTCTGTCTCCCACTCCGCACGGGTACCGAGAACTTTCCGGGGTGAGTTTTAGAA |
| TTTGCTCCTAGGCATTCTTTTTCTGCGTTTGGATTTTATCCCTTGATTCTTTGGGTTGGTAAACTTTATGAAATG |
| GTAACTTGACTGAAGCTCATTTGGAGAGAAGAGGGGAGTGAGGCGGTGTGTGCTTGGGGCTGGTGTTTGTCAGTG |
| TGAGCGTGTAAGAGCACACCTGCATTCAAGGGGGGTTTGTAGTGTCCGTGCGACATCTGAGGGAGGTGAGTCGGCG |
| AGCGGGTGGCGAGGCCCCACGCTGAGGGAGGCGGTTGTCTGGTCTCCGGGGAGCAAGTCCCAGGTGCGCGTTTCG |
| GAGGGCGGGACAGTCCTACGCTGTCTCTGCGGGGCAGCGCGTCTGTGAAGCACTCTTATCCTTCGGGTGTGTCCA |
| TGTGTGCCTGGTTACTGAGTGCGCGGCCGTCTAGGTGTCGACCCAACCAATGGTAGTGCTCCTAACGCCGCGAGC |
| CCACCTTTGGGCCGCTATCGCCGCGGCCTCCCCGCGAGGCCCGGGCACTGAAATTCTGGGGCCTGCGACAGGGCC |
| GGGGGGGACGCAGCCAAGGGCGTCCCTCCCCAGCCTCCAGACTCAGCTCTTCCCCCTCTCCTCTAATTCCAGCAG |
| CTTATTACGCCGGCGGCTCAGGGGAGGCAGCCTCAGCACCTGAAGCCTGGGGGGGCCGTGGAGTGGCTCCTGCGT |
| CCCCCGGTGTGGCCACACACGCTCGTGGGGCTGCGCTGTGCTGCGTGGGTGCGGGTCGTGGTCAGCGTGCGTTCG |
| CTTTTCTCAAAACTCCACTCCGAGGGTCCGAGCGCATGGGGGCGCCTGGGGGCCTGCGCGCCCGGGGCTTTTGGG |
| AGGCGCCAGCGTCCGAGCCTGCGCACCTCGCGCAGGAGGCCAAACCCCCGAAGGCCGGCGCGGGCCCGGGAGTGG |
| GGGCCATTAATTACTCTGCGCCAGGCCTAAAGCCTCCAACCCCCAGCAGCAGTTGGCGTGGATGTCCTGCGGATT |
| TTATTTGCAAACAATGGAAATGATTTGTTTTCTCTAAAAAAGGAGTGGGCAAGGCAGATATTGGAGGAGGGGGTG |
| GGAGGAGGAGAAGGAAGGGGAAAGAGCTGAGGAAAAAAGTTTGAAAATGCCTTGAACTATTCACTGTCGAGATGG |
| CTAATCAGTATTGAGGCCGGAGGGCAGGCGGGCCGCCTTTCACCGCCGCTTCCCTTTCATCTCGGGCTCGGCGGA |
| GGCGCTCAATTAAAAGCCTATCAGTTTGTAAGTAAATCAACGCCTATCAGAGTTGTCACATCAAACAAAACGATT |
| ATTATTGCAGCCCGCCTCCCCTATTAATCTCCCTCGAAGATAATCCGCCTGACAGGTCAGGCCCGGCGAGCTGGA |
| AAGCCTGGCCCAGAGCACCCAAACAGTCCCGGACTGGCGCGCGCCCCCGGGGGCTCCCCACCCCTGTCCTGCCC |
| CGCCTCGCGGTCCCTGGGAGCGGGGAGAGAAAGCGCGCGCGGAGGCCTCTGCACCCAGGTCCGCCCCACCTGACT |
| GGGAGCAAGGCCCAGATTCGCGGGGCCAGTAGGGGACAGTCCCGCGCGGCCCTCGCCGCTGCTCGGGGCAGGGGA |
| GAAGCCTGGCGTGCAGGAGCCGCGGCCCGGCCCGGGGTCTCGCCACGGCCTGCGCTCTCCTCGGCTCTCATTTAT |
| TTTCTTCCTCCCTTCTTTTTGTTTTCTCTCCCGCGTCTTTCTGGGCTCCCCCATCTTTTTCCTTCATTTCCTTTT |
| CCTTTTCCCTTTTTTTTACTTGCCAGGGAGTATTTCCCATTCTGGCTCTCTCTTCTTGGTGTGCCGTATAAACCT |
| TTCTTGCGCAGCCACACTGCCTGGAGTAGGATGTTCTCAGGGCCCGGGTTATTTCTCCCGGGTTGCCCCAGGAGT |
| GTGCAGTTCCCAGAAACTCATGGCAAAGTCCTCTATAATCTCTTTCCGAGCAGGGGCTCTGAGAAGCTCTGCGCC |
| TGTTTAAGGGTTGGGTGGGTTTGGAGGGGTGAAGAGGAAAAAGAGGGAGAGAGACTGGTGGACAGTTGTCCTATT |
| CTGGAATTAGTATTTTGCCTTGGAATTTCATAGCTGTAACGTTGCCGACCTCGCTGTTGGCGTTGCCCGGGCTTT |
| TCAAATATGTAGATAAGACTCAAGGGGGCATCCAGGCCTCAGTAGTGACTATGTGTGTGTGGGTGGGTGCCTGAT |
| ACAAGTAAATACACCCAGATAACTGCCTCTGTGGCCTCAAGTTAGTGTCCCAAGAGTTTGGGTGGGGCCTCGCTT |
| CTAGAAGGCGCAAAAATCGTGGCCTTCTTCCCAGTGGCCTCCGGCTTCCTGCTTTGGGATGCCTCGGAATCGAGC |
| CGGACCCGCCTTTTTCTGCGCTCTTCCTCCACATCTGTAGGCCCAAACGGCCACTGCCGGAGCCAGGTGGAGCCA |
| GGATTGAGGGGTAGCTGAAGTGTCTGTGACGAAAGGGCTGCCCGAGGGAGCCCAGGCCTGCCACCTCATATGTCG |
| GGTTCAGTGCGCCGCGAAGGCTCTCCGCGCCTGTATCTCGGAGGACCCCCAGAGCGCTGCAGTATTGGGCGTCAG |
| GGCCGAGCCTCTCGCAGCAGTCACGCCGCAGTCCGAGGCCACGGACATCCAATAGAGCCCACTTCAACTTGCATG |
| GTGCATGGGGTCCAGGACCGGTGGCCCCCACACAGGGTTTCCCAAAGCCTCTCCATTTGTCTGCACTCTCCACTG |
| CCGACCTTGTAGGAAATTTATTTCCATGCCCAGAAATATTGTTTGGACACAGTGGCTCGGTTATCTTCGCGCCTG |
| CTTTTCTTAAATACATTTATTTCACCTCTGCCACGCTGCAGATATTTAAAGATCTGTAGATACCGTAACCCTCAG |
| CGATGCGGGACTCACTCTGGTTATAGATAATATTCTCTGGGTGGTTATTTGAACATAAGTTCTATCTCCAGCCCA |
| GATGACACCCAAGCAGGGGCTGTAAAGGACACTTGCTCTAGAATGTTTTCAACTGAAATATATGTCCACACACGG |
| AGAATTTAAGAGTATTTTTATATTTCTCTCTAGATCTAAATATTCAGATGTGTTAATTACATGCCCTAGAAGCTG |
| GAAGCGATCAGTGGTGTTCACACTGGACGTGGAGCTGTTTGTATAATTTTCATCTCCCTGCACTTAAACATGACT |
| CTCAGTCTAATAAATTCAACCTTGTCATTTTTAGAATCGACGGGATTTCTCTGGCTGTCGTTTGCGCTGCATTTA |
| TCCGAATACATCCAGCTCGCAGGCATCCTGCAAGAAACGGCTCCCGGCTCGCGTGTACGCCGACACCTCGGCCCA |
| ACGCAGGACTCGAGGTGGTTTCTAGTGCCCGGGTGGCTGCAAGTCTGCCCTCCGAGGGAGGCTGGACAAGCGGCG |
| CCCCCAGGTCGAGCGGCCTCTCGCTGCCTGGCAGTGCCTGGCAGCCCCCACCTCTGCCAGTGCTTCGGAAACCCG |
| CCTGGCCAGGTTCGCCCGCGGTGAAAAATGAAAGCAAATTCCCCAACAGAGGTAGCCGGAACTTTCCTCGACGAA |
| GGCTCCCTCCTGCGCCTGTGTCTGGAGAACCCCCAGAGCGCTGCAAGTTAGCAAGAGAGATTCGATGGCGGCTCT |
| GGAAGGCGCACGAAGGGTGGGGCGGGGGAGCAAAGAGGCCACTGGGTGACCCAGCCTGGTCCGGGGTGAAACGCT |
| AGAGAAGGCGCCTCGCCTTCCTTATTTCAATGCAACTCCTCGGCCCCAGACGGTAAAAATAGTTTCCAAGCTGCC |
| GCGGACGCCCAGGATGTGTTTGCAGAGATCAAACTGGGGAGGAGGCAGCTTTGTAAAAGTTGCAGAAAGATTAGC |
| CGAGAAGCGTCCGCCCGGCGGGGCTCAAGAAAGCTTGGGGACAGCTCCATGTTCCTTGGGGCGGAATGGCCCAAG |
| AATTGGCCTGGGTAACCCCCTGCCCAGTTCTCTGTCCTCACTTCGAGCCAGTGCTTAAATAACTTCCCGCCGCCT |
| GCCCTGCAAACTTCCCGGCGCGGCGCCGTTGAGGCCAGGACACAGCAAAGGCTAGCAAAACCCCGCCGCGGCGCG |
| CTCGGCCCCGGCCCTGAGAGGCTGCGCGGGTGGGAGGACCAGTGTGGTTTCTGCTCCCACTCGGCTGCCCAGACC |
| CTCAAGACCGATCCCCCAACTCCTGGGAGCGGGTGCTTCCCTCTGGGAGCCGAGATCTTGCGGGGCCAGCGAGGG |
| CGCAAAGTGCGCGCGCTGGCCCGCGCGGGGGCGGCCGCGCGTCTCTCCGCGGGGCCTGTCGCCAGGCCGGCCGCG |
| GCGCGTGAGTGATGAGGGCAGAGAAGGGCGCCCATAAATCGCGGGTGTCAGGGCGAAAAACTCTCTTTATTGTCT |
| GCGTGATGGATGGGCCCGGGGACGAGACACCAAATACTTCGTATCGCCTTTAAATGGGAACACATTTTCCGCGGC |
| CATAATTCATGTTTTTAAATAGAAAGTTTGAAATGTTGCCTATATTTCACCAGCCCTGACATATTTATGAATCG |
| CTCCCTGCATGCAAATATCATTACTTAAAGCGCCGGGGAGAGCGCGGGGGAGGGGAGGAGGCGCGGTTCCCGGGG |
| CGTGGGGGTGGTGAACCGGGGAAATATCGGTGGAGGGGGGCCATCTCCCTAAAGGGCAGAGGGTGAGGTGCGGTG |
| AATAGCCGTATCCGGAAACCGAGCGTGCCCCGGGCTTCTTTCCCGCCGCCAGACCCCGCACAGCCGCCCTGGGAC |
| GTTTTTCGAGGCTTGGGACCTAAGACGGGTCCCCGGACCCTGCTGGGAAACCAGGGGGCGTTTTTCGTCCCTCTC |

TABLE 7B-continued

| Sequences of differentially labeled CGIs between bladder cancer subgroups relative to blood |
|---|
| TGAGGCCATTATCCAAGCTGAAACCACCTTTTATAAGAAAAAAGTTTAAAGAAAAAAAATTTAACAAACACAAAT<br>AATAATAATAACCCAACATGTTTCGCGTTCTTTGCCACTGCATCGATTTTATTGATTTTCATTCTGCAAACCTGG<br>GAATGTGCGCGCTCGGGAGGGGAGGCTGTCAAAACCCAGTCATCGCGGGGACTGGATGGGGGACAATTCTCCGAC<br>GCCGCGGCCTGGACCCGCCCCCACCCAACCGGCGCACCACCTCCCAGGCACCACGGAGCCTGCGCAAGCTGCGGG<br>GCCGTAAAGGAACCGGCCCCCAATCTCCGGGGCTTCAGTCCCGCCCCTCTCTCCCCCCAGTGCCCTGCAGCGCTC<br>CCAGGGTCCGTGTCTGCCCTCCCCAAGCCCCCACTGTCAATACAATCCCTGTTAAAAAAAAAAAATCTTTTTAGA<br>GCCAGGCACGTGCCGTCGGCCTCTCCCCTGCCCGCCTGGCCCAGGAGGCGCCCACACCTGCGCCCTCACTTGCCG<br>AGACTTTTACCTGTGCAGTCCCCGGCGGCGCCTGCAGCCGCGCAGGTAACCGAGAAATGGAAGGGAGGGCTGGGG<br>AGTGAGAAGGACAGAGAGCACCGCCCGACACAACCAGACGCGCGGACCCGGGGCCTCCTCTCTGGACCGGTGCTG<br>GGGCCCTGGTAGAACCAGCTCCGGGAGCCGAAATTGAGCCATGAAGAGTGGGCCGAGGGAGGGGCGAGGGGAACG<br>GGCCTCAGGAGGGAGGGGCGGGCCCGGCGGCACTTCCGTTGGGGGTGGGGCTGCGGGCTGCCGCGCCGGTCCCGC<br>CCCTCCGCCGCGCGGGCCCGCCCGCTCCAGGCCAGGCTCCGCCCCCACCGACTCGGAGCTGGATCTCAGGCCACG<br>GCGCCCCCCCAGTCGCGCCCCCAACCCCGGAGGCCTCGGGCTGAACCGGGTTTCGCAGGAGGGCACAGGGCG<br>(SEQ ID NO: 231) |
| CGI: 356 range = chr10:88112905-88117344<br>CGTGAACGCCCTCGCCTCGCACCTGTGGCGCCTGCCGCGGGGCCCGACCGGAGGCAGTGGCTGTGGACAAGGGCG<br>GCCCCGGCGTAGGCCAGGATTTCCCCGCAGCCGGACCGGCCCAGCTCCGCTCCTTTCCTGGGCGAACAGCGCCCA<br>CCTCCGGCCCAGGCGGCGGCGCCTCCGCCCGCGGCGCGGACAGCGAGAGAGAAACCGGCTCCTCCAAACCTGGTG<br>GAGGAGCGCTGCAGAGAAGCGCCGGGCTGAGGCTCTGGGGGCCGCGGGGCGCGAAACGCCGCGCCTACCAGGTTA<br>TGCCCGGGAGAAGGAGACAGGTCGGGCTCCAGCCGCTGGGCGCTCCTCACCTCGAAGCGAGGAAAACACCGGGCC<br>ACTGAGATCAGGGGAGGTGCGCCCGATACAGGTACCCGGCACGCAGACACGCCCACCCCCAAACACCGAGAAACA<br>AAGACTGCCCCGAGCCACGCACGCCTGCGCGGCCAGCGCTGGGCGCACACCCGCGCCCACACAGCCCGAAGGGCG<br>CCACGCAACCCGCAAGAACACCAGCTCCCCGCGCTCGCAGGCTCTCCGTGCCGGCCCGCAGCGCAGAGCAGTCCC<br>GGCGCCGCTGCCTAGGTGGGCCGGGGAAGGCGCGCCACCGCGCATGGCACCGCGGCTGCCGAGGAACAGAGGGTG<br>CCCTGCGCAGCCCAGCTCGTCCCAACCCCTCCGGTGCCCACTGCTGCGACGCCTCGCAGGCCGTGTCCCAGTGGG<br>CCCTGGGCACAGCGGTCACTCACCTTCCTGCACAGCCTGGAATGGGTTGTTGGCCTCGATGACCTTGATGGAGTA<br>GGTGATCTTCTCGCTCTGCAGGATGTCATCGTTGAGGCTCAGGTCGGATACCGCCAACTGGAACACCCTGTCGTC<br>CTTGGCCGCGTTCTCCTCGAAGATGGCACCTGGAGGAGAGAAGGGATCAAGACCGGACCTGGACAAGAACCCTCT<br>CCCCGCTTCCCTTGGCCCGAGGGTCAAGGCACTCGCAGACCGATGATTGCCGGGTGGTGGGAAGTCTGAACTGGG<br>ATTTCAGCTTGGCGGGGTAGATTAAGGCTCTCCGATCTCCACCTGCACAGGAATATGTTCCCCTCCCCCCACCAG<br>CCCTCAGCGCACACGTGCACACAGTTGACATGAGTTACACATGCACATCCCACAGGCTGCCACCAGGTCACACAC<br>GTGTCTCACAACCAAGGCACCACATGTCCTAGCCATGCTCCACACAAGGGACTAAGCCAAGCTGGGGTGGCCCCA<br>GGCAGCGCCCAAATGCCTTGACATGGTTCCATAAATCCCATCCCAGGAGCCAGGAAGTTCCCCGGGAGGGTGGTG<br>TCCCCCACCCAAATCCCAGGACAGAATGATGGGTCCTTCTCCATGCACGTCCCCTGCTGAGTGGAGCTGAGCGAA<br>GCAGGTCTACAGTTGGCTTTCCTGCGCAGAGGGGTCTTCCTTAGGCAGGGGCTTCGGATGGCCTGCAGCTTGGAT<br>GACTGTGACGCTGCCCGGCCTGGCGCCCTGAGCTCAGCCTCCTACTCTCCATCCTTCCCCACTCCCATTTCCTGT<br>ACGTCTGTCGAGGGGAGTGGGGGAAGGGGACTTGTGTCCTAGGCGCCTCCACGTTCAGATCTAGCGGAGCTGGGG<br>GTCCCAGAAGGAGCTGCTCTTGAAGGGCTTTCTAGAACCGCGGACAGCTCCTCCAGGGCGCCCTCCGGCTGGCGC<br>TTTGTGCGCCTAGCACAGCTTCCACGGACCCTGCGCTTCCAGCCGAGATCAGTGCGACCAGCCCGAGCCTAGTCC<br>TGCAACCTGGACAGCTCTGGAGTCAGCCACCCACATCCCGCCTCACCAAGCCTCGAGGGTCCCTGAGGTCCCGGA<br>GCTAGGCCCAGTGATCCCTCGAGCTGGGGGCTGGGTAGGAGGAGGGAGGCCCGGATTCCTCACTACACCCGGAGC<br>CGGCGCCGCAATGCTGACCGCGAGACCCGCACCCCTCCAGGGCGGGAAGCAGGTTTGGTCACGGGCCCCTGAGGA<br>GGAATCGTAGCTCTCCGAGCCCAGGCCTAGTCCTCACCACCCCACTCCACCACCCACCCTCCCGCCTTGTCCCGT<br>CCTCCTCGCCTTCAACACCTCCCAACCCCCAGTTTCCCTGTGCTCGCTGGTCTTTCCCAACTTCCGGAAAGACGA<br>CTGCGGAGGGACTCCCCCAAAGCGACCGCTGTCAGCCCCCCAACTCGGCCCAACTTCCCGAGATTCCTCCCGTGT<br>TGCTCCCAACTCCCACCCACTCCCCCTCGGCGCGCCCACTCCCCCTCGGCGCGCCCCCTCCTCCTCTGCGCTTTC<br>ATCTTCTCTCCCGGTTCTCTCTCTCTATCCATCTCTTCCCGCTCAGCATCCCCCTACCCCCCGCTGCCCACGCTT<br>CTTCCCTCGGCTCCCACCACCCAGACCGTCTGGGCCCCCAAGACTTGGACCACGCAAAACTCTAGGACTGTCCAG<br>GATGGGGATGCAGTCGCCACAACCAGATACACACGCACTCACACATACACCAAGGGCTACACAGACACACACCGG<br>AGAAGCAGGCAGACACTGTGTCCACTCTAACAGGCTGACAGACAGTCGTGCACGCACCAACACACGCTCAGATGG<br>CCCCACACACCCCAACACCCTCTCACAGTAACACCGACACCGTGCCAGGCGCACACAGCGACACACGCTGACAAC<br>ACGCACCCACACACATTCACACACGGTTCCGGTCCGGCCTCTTTGATCTTGCCCTGCCAACTTGGCGAGCCCCCC<br>GCTGTACCTCCCCCTGCCCCCCGCTGCTCTGAGCTGCGCAGAAGGGCCCTCCCGACCCGCCGACGGCCCCGCTAA<br>GGGCGCGGGTCTCGACGCGCGTCCATCCCGGTGTTCCCCGAAGCGTCGGCCCTAAGTGTCGGTAGAGGCCGCGGG<br>GCCCCGCGCGGAGATCGGAGCCCCGGGGAGCGGCAAGCAGCCAGCGGGAGCGCGGCGCGGCCGGTGCACAGCTCC<br>TCCGCCGGGCGGCGCGGCGCGGCCCTTCGGGGGAGCACCGCCCGCCGAGCCCCTCGGCCCAGGGAAACGCCAAGT<br>TTGGACGCCGCGCACCCCCTGCCCCGTTGGGGCCCCCGCCCAGCCTCGGCCCGGCCTCCAGCCGCGCTTACCGAT<br>GTGGATGATGGAGTCGGCCCGCACCGACACGCACTGGCATATCCAGGGGAGAAGCCACAGCGTCAGCGCTTCCAT<br>GTCCCCCGGGCGCGCGGCTCATCCACCCGGGCCCGGGGCGAGGCCGAGGGCAGCGCGAAGCGGGGAGGCGCTGGT<br>CCCGGTGCAGTCCCGGGCCGCTCCCCGGGAGAGCCGAGCCCGCCCGTGCGTCTTCCCCCGCGCGCCCGCCCCTGC<br>GCCCTGCGCCCGCCCCAGCCCAGCCCAGCCCAGCCCAGCGCGGTCGGGCTCCCGCTCCGGCTCCGGTGGCGGCTG<br>CGGCGGTGCTGGCAGCTTGAGCCCAGGCCGGCGCGGCGGGGGCGGCCCGCGGCTGTGGCAGCGGCGCTTCCCGCG<br>GCTAGAGCGGCTTCGGGGGAGGCTGAGGCGGTGGCGGCGGCGGCCGGGCCGGCGTGGCGGCTCTGGGCTGGCTGT<br>GTGTCTGAGCCCCGGCGAGGAGCGAACTGCGGAGGACGCCCCCTCCCCTCCCCCTCCCCCTCAGCTCCGCTCCCC<br>CTCCCCTCCCTGCCCGCCTCCCTCCCCTCCGCCCGCCTCTCTACCACGTGACTGCGGAGCCTCAGCCTCGCCGCG<br>CGGCTCTCGCCCGCTCGCGGCTCGGAGGGGGCGCCGGGTGCTCCACGCTCCCGGCTCGGGGGACGCTCGGAGACC<br>GGCACAGCGGCGGGGACCGGCCTGGGCTGCGGCGCGCCGAGCTCTGACGGTTCGGGCCTCCTTCTCCGGTTCGCC<br>AGGGGCGGGAGAATGGAGGAGGGCCGGCCGCTAACTGCCCTCGAGGGGCTCCCGAAGCGCCCTGGCGACCTCAGC<br>AGCCGCGCGTCTCGGGTCATGTCCCCGGCCGAAACAGACCGTTCCTCGTGGAGTGGGACCTGGGGAGCAAGAAGA<br>GAGACCGGGGCGGGGCGCCGGGCCAGGCCCCAGGACAGCTGGGGAGCCAGAGGGGGCCGGCCGCCGCAAGCATCT<br>CAGAGTAGAGCCCGGGCCGTGGGCTCGAACCCTGGCTGGCCGCGCGGACCTCGGCGGGCGCCCATCCCCCGCTCC<br>ATGGGCAGCGCGCTCAGCCGGGAGTCGGGCAAGAGGCTCGGACTCTGAAGCCCAATTCATGGCCGGAAACCAGCG<br>CAGCCGTGACCGCGGCGCCTGGACGTGAGGAGCCTTCCAAGCGGCCGGCGGGCTCAGACTCCGACCCTGCACGGA<br>GCTTTCATGTGCGAGCCCGGGCGAAGAGCCCGCTCCTCGCGGCCACAGCGGAACAGGGCTCCCTCCGCCTCCGGT<br>GCCTGCCTCGGGCCG<br>(SEQ ID NO: 232) |

TABLE 7B-continued

| Sequences of differentially labeled CGIs between bladder cancer subgroups relative to blood |
|---|

CGI: 34 range = chr10:94441310-94441717
CGAGGGTTTGATGATGCGGCCCGAGCCTGGCTGTGGTCGCCTGTCGGGGCTGGAGCGGGACCCTCAGCCGGGCCG
GGCCTGGGGGCTAACGTTTTCACAGTGCGCCCTGAGTTTCCTTGGGTTACTGCTGGGACCGCGCAGGAGGAAGCA
AAGAGTTTTTCGAGCTAGACCAACAGGAAACACATTGACGGAAATGTTGCCATAGCCCATGGGGTGGCTTTAACT
GGCCGCCCCCGCGGGCTGGGTGTGAAATCAGAGGAGGCCGCGGCTCCCCCGGCCAGGATTGGAGGCTCCTCGCGC
AACCTAATGCGGGTGTCCGGGCCCGAGCGCTTCCCGCGCAGCCAGGCCTTGTCGGTGCAGCAGCCCCGCTCCTCC
CCAACACGCACACACCCGGTGTTCGCAAGTGCG
(SEQ ID NO: 233)

CGI: 182 range = chr10:99068802-99071038
CGCGCCCGACTGCGGGAGCCAGGATCAGGTCCCCAGGGCGCCCTTGCAGACAGCACCCTGAGCGAAGGAGCTCAG
AAGGCAGTCCGGCTTCACCCAGACCCCCAATCCCACAGAAGCGCCGTCCCCCAGCGGCACAGCACCCCCTCCCCG
GCGCGGTGGTAGGGCCCGACGTGACGTCACCCATTGTTTACAAATCAACCCGAGCCGGCAGGATTCCGGCTCCCG
CGGCTGCAGGCGCGCGGCTAGAGTGCCTGGCGGGCTCCGGCTTCCGCGTCCGCCCCGGCCCCGGTCCAGACTTAG
TCTTCAGCTCCGCGCCCGCTCCGCCGCGGCCCACCGCGCCCGCCGGCAGCCGAGCCCCCAGCGACGCCCGCACAG
CTCCGGGTGCCCAGACAGGGGGCCATGCCGTGCCGGAGGGAGGAGGAAGAGGAAGCCGGCGAGGAGGCGGAGGGG
GAGGAAGAGGAGGAGGACAGCTTCCTCCTACTGCAGCAGTCAGTGGCGCTGGGCAGCTCGGGCGAGGTGGACCGG
CTGGTGGCCCAGATCGGCGAGACGCTGCAGCTGGACGCGGCGCAGCACAGCCCGGCCTCGCCGTGCGGGCCCCCG
GGGGCGCCGCTGCGGGCCCCGGGGCCCCTGGCTGCGGCGGTGCCGGCGGACAAGGCCAGGTCCCCGGCGGTGCCG
CTGCTGCTGCCGCCCGCGTTGGCGGAGACTGTGGGCCCGGCGCCCCCTGGGGTCCTGCGCTGCGCCCTGGGGGAC
CGCGGCCGCGTGCGGGGCCGCGCTGCGCCCTACTGCGTGGCCGAGCTCGCCACAGGCCCCAGCGCGCTGTCCCCA
CTGCCCCCTCAGGCCGACCTTGATGGGCCTCCGGGAGCTGGCAAGCAGGGCATCCCGCAGCCGCTGTCGGGTCCG
TGCCGGCGAGGATGGCTCCGGGGCGCCGCCGCCTCCCGCCGCCTGCAGCAGCGACGCGGGTCCCAACCAGAAACC
CGCACAGGCGACGACGACCCGCACCGGCTTCTGCAGCAGCTAGTGCTCTCTGGAAACCTCATCAAGGAGGCCGTG
CGAAGGCTTCATTCGCGACGGCTGCAGTTACGTGCAAAGCTTCCCCAACGCCCGCTCCTGGGACCTCTGTCGGCC
CCGGTGCATGAACCCCCTTCGCCTCGCAGCCCTCGCGCGGCCTGCAGTGACCCTGGCGCCTCCGGGAGGGCGCAG
CTCAGAACTGGCGACGGCGTTCTTGTGCCTGGCAGCTAACACGCCCGGGGTGGCCACAGCGCCAGCCTCAGACTG
GAGGGCAAGGGGTTCCCTTGAGGGCTGCAGTTCTACTCAGGCTGGTGGAGAACTCTGGCTTTTGGAAGCGAGAGT
AAAAAGCTAATGACGAGGAACCGAAAAATCGCGAGTGTTTCGCGGGTAACTGGGGTTGAGGGCCAAAATATTTGG
AATGAAGGACTTTGGCCCTATTTAAGGCAGATTTTACAGAGCGCACCTCAAACGTACAAGTCAGTAGGACTCCTT
ATTTGGCGTGACCCGACCTGGCCGCGGAGCCTGCATTTCCTCGCAGCCTCTCAGTGCCCTCCAGCCCCGCGACCA
TGTGGCCACAATCCACGCTTCTCCGGATCGCGGTGCGCCGGAACCACGGAGGATGATGCCAGTTACTTGCTTTAC
CTTTTCAGGGCTGGCTCCTGATCCACTTTGGGGGAGGAGAACATGAGTAGATAATTTCAGGGTGCAGCCCAATCT
GCCAGACTTAAAAAAACCATCTTGTGTCTTTGGAGGTGCTGCTTAATACCAAACATGCGGTGCCATGAAGGGACC
CTTTGGGGGTTGAATAGGAGTTAACCCCTGCGCTCTCTTTGCAACTGTCTCTCTTCTCAGAGTGGTGGGGGAAGG
CTGTACGACACGGGTGGGGAAAGGAGGTGGGGGCGGGGAGTATTGAATGGTGGTGGAAGGGTAGAGAGGCGCGGA
GTGAACCCCACGCCCTGTCTAAAGTGTATTTTCAGAGCCGGCCCGCCTCTCCTCGGTTCAAGGTCACTGTTTCCT
GGGCACGCACTGGGTTGCGGGACAGAGTAGCCAGGTTCTGCCGGTGCTCGGAGAAGAGCGCAGTGTTTTGCAAGT
GCTGGAGTCTCCTGAGGACACGCGCGTCGCCGCCACCGCGGGTGTGGGAAAGCGCGGACGTGCTGGGCGGCTGTG
CTTCGGTAGGCGACCACCGCCCCTGGCCGCGCTCCGGGCTTTCACGGAAACTCCCGAGACCG
(SEQ ID NO: 234)

CGI: 56 range = chr10:101277153-101277910
CGTGCACGGGCTTGGAGACGGGGCGCCAGTACCAGGCAGGGCACAATGAGGCTTGGGGCCCTTACAGTCGCTGCA
ACCTGGAGGTACCGAACCGGGGACTCCGACCTGACATGCAGGCGAGGCTGCGAGGTCCAGAGCCTGGACCTGGTT
CCTAGGGAGCGCCACTCCTTCTGACCCCTGTGGCGTGCGTCCTGGCGCGCCGCACCCGCCTGGTGCCTCGGCCCT
CTCTGCTGTTCCCTGGCTGATTCTGAGCAAGGCCAGCAGCCCACGGCCCCACCCGACCCCCACATCTCCGCAGGG
TCAGGCGAGCCGAGCAGGAACTGCGCCGGGGCAGTGGTGATGGCTGGGCGTCCCTGCAGCTTCAGGGGCCAAGGG
CAATCGGGGGGCTAGGCCCGCAGACCTGGCCGTCCGCTGACGCAGCGAAGGTCTAGCGGAACCTTGGGGATCGCT
CTCCCAGTGCCGACCGAAGGCCCGGACCTCCAGGCTGGACGCGGCGAAGGCCGCATAAGACGTTACTTAAACATG
TTACTTAAACAAGACTGCAGTAAACGTTTCTTTCCAAGTGAGAAAGGTCTTTTTCGTTCTCAGACGGTTTGAAGG
TGTTTGTGCCAACGTGACCCCCGGGGAGATTTGGAGGAAGCTTTCTACGTCCTAGGAGGCTGAGATCCCACGGAG
CCGGTTTACGGTTGAGAGCAGACAGTTTCGAGTAGATAGCGCTGGAAGAGACACGAAGAATCTCTCTTGCTTCTT
GGAACGCG
(SEQ ID NO: 235)

CGI: 403 range = chr10:102974173-102980053
CGCTTTAACTAGACGGGCGGATAAATGGCCCCGTTTCTCCTCAGCCCCGACGCGCCTGCTTAGCTGCGCGCCCCG
CGGGCGCCGCAGCTCGGGTGGGCTCAGCCCTGGGGCCGCCGCCCCCAGCCCAAAGGGACCCAGCGGGGCCAGGCC
CAGGGCCGCGAAGCAGAGAGCGGCCGGAGGTGCCAGGGCCGCTTCATTGGGATTCATGAGCGTGTTGGGCGGGCG
GCCTGGGGCTTCGGGCGCGGGGCGGGGGCCGAGTGGGGGGGTGCGCACGGCGGGCGCAGATGCCCGGGTGACCGA
CCCGCCGTGGTCCCTGCGCCGCCTTTGTGCCGAGGAGGCGCGCGCGGGGACCTAATCCATCAAATTGTCTACAAA
TTGTGAAGAAAATTCAAAAACCATATGGTCGCCAGCGCCGGCGCGCTCTGGGCTGCGGAGGGCCGCGGCCGTGCC
CGCACCGGGAGCCGCGGGGGGCTGGGCCCGGCTATTGTCGCCTGTCAGCGGCCGCCCAGGCCCATTCGTCCCGGC
CTTCATGGTCCGCGCTCCGAATTACAGACCCATCCATCCTAAGAGAGGGCAATTTTTGTCGCCCGGGAGGAACCA
GCCGCACGCCTGCCCCGCTGCCCTGCCGTCTCCTTCCTTCTCTGCTCCTTCTCTCTCTTCTCCTCTCTTCCCATT
CTTTTTTTCTCCCTCTGTCTCTGTCTCCCTTTCTCCGTTTCTCTGTTTCTCTCTCTTTTTCCTCTTTTTCTCCGT
CCTGTCTCTGTGGCTCTCCGCTTTCTCTCTCTGCTTTTGGAGTGTCTTTCTGTGCTCCTATTTTTTTTTCCTGTT
TCTCTCTGTCTCTTCGTTTCCTCCTGGACACGCACGTTCCTGGCTCGGGCCCGGGGGCCCATCGCCGCCCGAGA
CCAGATGCGCATTTCTCACATCAATTTTGCGGAGAAAGAGAGCCCAGCGGCCCGGAGGCGGGACCCCACTCCGGT
GACAGCGGCTACTCGCCAGCCCAGCGACAACAAAAGCCCGGAGAGAAACCCGCTCTGTCCAGGAAAGTGAAAGCG
GCCTCAGCCCCCGCCCCAGCCGGCCTTGGGGCGCCGCAGACCCGAGAGAGTCCTTGCAAGATCCATACCTCTGCC
CCCAGCGGTGTGCCGGGGTGTGGAGGCAGAATTGGTTAATGTTGCCAGAAATTCACACCAGCTCCCAGACGCTTG
GGCTTACAGTTCCAGGTGCCCACATTGAAATTCAGCCTGGCCTTGATGCCTTTAGCCTTTGGCCCCCGACTCCCC
AAGGATGAGGCCCTCGGGGCTAGAATCGAAACTTGGGAACCCAAGGCTCCACCCCGCGTCTGACTGAGTGATACC
TGCAGCGCTCCCGGGGCTCAGCCCTGTTTTCGGGGAGTGCAGGGAGAATGCCCTTGGGTCTGGGGTGGGATGCAG TABLE 7B-continued

| Sequences of differentially labeled CGIs between bladder cancer subgroups relative to blood |
|---|
| GAAATGCAGGGCAAGACCCCCTCCCACCCTTTGTTCAACACAAATTAATGTTGTACTGTGGTGTGCCCCCACATA<br>CACAGGCATTTTCTCCCAGCATTTCACGGCTCGTTTTTACCCCGACCTGGCGAAGCCCGCTTCTCTCCCGATTT<br>AGCAGCTGCCTCAGGTTTATGGGCAAGAGGCGCCTCCTCCTGCTGCTTCCCCCTCGCCCTTCACTCTTAAGCCTG<br>TCCTGAAAATCCCCCCCAAATCTCCAAGGCTAGGGCGACCGGCACGAAGAGCGGCAAGAAGCCCAGCCTGCCGCT<br>GCTTCTCGGAAACGGGCCCACCACTCAGACACGGTCGCCGCCGGTTCTAGTAAAATGGCAAAGACTTTATTTATT<br>GGAGAAAGAGGCCTTGGGTACAGTCTAGGGAGGAGAGGGGAAGGGAGGAGCAGGGAAGGGGCACTCGCAGCCCAC<br>TCACATCCAGCCACCCTCCTCTGGCCAAGTCGGGTAGGAGTGGGGTGTTCGAAGTGGCAAGAGAGACCCAGAGCT<br>GTGGAGGAGGTGAGGTGAGGGCTTGGGTCGGCCTCCTCTCTGTCTCTGTCACATGCAAAAAAATTCTAAAAAGAG<br>TACAAAATAATTATAGGGCTTTGGGTTCTGTTTTCGATAGTTGGTTGGTTGGATTTCCCCCTGCATTGTCCCTAA<br>GAGCCGGACTCCAACAGTCAGTCCGAGGAAATGCGGGAGGGAGGGAGGAATCTTAAAAACAGCATTAGTGGGCAT<br>TAGGAGGCAGAAATGGCATCGAAAACAGACTTTTCTCTCAGAGGGTGGGGAGGAAAGATCGATTTTGAAACTTGC<br>AAGTCAGGACCTGACTGCCCACCTCTTCCCCTCCCACATGAGGAAAAAAGGCCCGAGGAAATAGAAGTCAACTGC<br>AATAAGGCCGAGGGAGGCGAGGAAGGAGCGGGCCGGTGCATTCGCCACATGCAGAGAAAAATCAAAACAGCCGGA<br>GCTGCCACTCCCCTAGACCGCAGGGTTAGTGTTCCCCGCCCTGGTTTCTGTCTCGCCCTCAGCAAACCCGGCAGC<br>CCGAGAGCTTTGAAAACATCGAAATCTCCGAGATTTAAAAAATAATAATAAAAGAAAGGAAAAATCAGGCTGCGG<br>TGGGAAGAACCCGCTATATAGGTTTAAATATTTATATAGAAGCCATACAGAATTGCACGGCGAGGGCTTCCGGGG<br>CGGCGGAGGCCGCTGGTGGCGGCCGGCCCGGCCGGCCAGCCTGGGTTTATTGCTTCGAGAGGGAAGAGGCGGCTG<br>CCAGGAGCCGAGTCCGGGGCCGGGGACAGGGGAGGAGGCGGGAGTTGGCAGAGGAGGTCCCAGCTCCCCTCGGCG<br>GTCCGGTCCGGGAGGCGTTGGGCTTTCGAGCGCTAGGAGCCCAGGGCGGCGGAAGACCCGGGGCGCCGCTCAATC<br>GTCCACGTCGATCTCTTCGTCTTCCTCGTCCTCCGAGCAGTCCTGGCTGCTGGCCGGCTGGTCCGTGAGCGGAGA<br>GGCAGGCGAGAGCTGCAGGGCGCCAGCGCCCGGGGCCTTCGGGGCGCCTGGGGGGAGGACCGGAGAGCCGGGCCT<br>CGACTTGGCCCTGCCGCAGCCGCCGCCACCGCCGGCTGTGGCCTCCGAGTTCTGCTCGAGTTCGGCCAGCGCCAC<br>GATGTCCATCTGCCCGCTGGGGCCCAGTTTCTTGGCGGACTCTACGTCGGCCTTCATCTCCTCCAGGTCCCGCTT<br>GAGCTTAGCGCGCCGATTCTGGAACCAGGTGATGACTTGCGCGTTGGTGAGGCCCAGCTGCTGCGCGATTTGGTC<br>GCGATCGGCGGGGGACAGGTACTTCTGGTATAGAAAGCGCTTTTCCAATTCATAGATCTGGTGGTTGGTGAAGGC<br>CGTGCGCGACTTTCGCCGCTTCTTAGGGGTCTGCCGCTGCCCAAAGATGGTCATACCGTCGCGGCCTGGGAGGAA<br>AGGACAGTGTAGGCTCGCGTTGGGAGAGAGGAAGCCCACCCTGGCTCTCGCCCCCGTAACTCCGTAACCCACCCA<br>GGCCTGTCCGGCCTGCAGTCTACCAATGTTCCCTTCTCAGATTTAATTCAGCCTCCAGGACCAGGGCAAGTCTTG<br>GCTATGGCAAACCATCTCCTGTCTTTGGTCTCCCAGAAGTCCCTAGGAAAAATTGTTTTGGTCTCTGCCCCCTAC<br>CTAAGAGTTGGTTTGAAAGACCCAAAGTCTCTAAGGGTATGAGAAAGCCAGACAGAGACACCCTAATTGCGGTGT<br>GAATGTTGGTTCTCCATCCCTTCCCAATCACTTCAACTCTACCCTACCCATAAGGTCCCCGGCAAAAGACTCTCG<br>ATTCCCCACGCCGAGTAGCCGGGCTAAGAGCGCCCAGGACACTGGGAACGCAAGGGAGCCCGGCAAAGCAAGCAG<br>ACTGCGGAAAGAGCTTGGCCACCCTTCTCCTGCCACCCCCCAGCTCTGGCCTACCCAGAGGTCCCTGGGAAATAA<br>GGATTGGGTCCCGTCCCACATATCTTCACTCCCATAAGCAGCTGCTCAGGCTGGAAGGCCCTGGCGGCCGGAGAG<br>GGCAGAGGCGAGCAGAGGCATAGGGGACGAAGCGCGCAGGGCACAGGGCGCGAGGCGCTGGGTGCAGGGGAACCC<br>AGCAGCTGCGCCTACCTTCGGCTGCCTGCAGAACGCTGACCTCCAGCCCCTTAAACGTCTTGCTGGCGAGCTCCT<br>CCAGCGCGCACAGCGGCGAGGTCTGCGAGAGCAGCGCGCGGCCCGCCAGGGGCAAGCCGCCCTGCGCGTGCTTGT<br>CCGCGGCGGCCAGCAGGTGCGCCGCCCCGCACAGCGAGTAACTTCTCCGCACAGACGGCTTGTTGAGGATGTCCT<br>CGATGCTGAACGGCGTCAGTGGCTTGTTGGAGTTGGCAGGCGGAGGCAGGTGGTCCAGCGGGCTGCGCCGCCGCT<br>CCTCCCCCGGCGCCGCCTTGCCGTCCTCCTTGGAAGTCATCTCGGCCTTGTTCGGGGTCCCGGCCGGGGCGGCTC<br>GGGCCGCGGGGACCCAGCCCGCGGGCAGCTCGGGCGCCGGACGGCGCGGGCAGGCAGCGGCGGGTGGAAAGGAGG<br>CCGCACTGGGCAGGGCGCGGGCCGGGCGCGGGGCCGATTAGCGCGGCGGCTGAGGAGGGGAGAACAGCGCGGGGC<br>CCCGGGAAGAGGGCGCTGACGCGGGCGCCGCTGCTGCTGGGGCTTCCAGCAATCCGGGGCCGGAGCCGGGGCGCG<br>CTGCGCGGGGCTCCAGTTTCGCCAACCCCGGTGCTATTTAAAGGTGTCAGGTGGCTCGGCAGTGGCTCCTGGCCC<br>CGGGTCCTGGCGGCCGCAGTTGGAAGAGCCGAGGCGAGGGCGCCGATCCCGGACTGCGAGGGAGGCGGAGAGACG<br>GGGCAATTGACTATTGCTAACAAGTTAGCCTTGATCGCGGTGTAATCAATTATCTGCAGCGGCACTTCTTTCTCT<br>TTCTCTCTCCTTTCTCCCTTTTTCCTCTCTTCTTTGCCTCTGTTCTCTCCTCCTGTTCTCGCTCTCCCTCCCTCC<br>CTCTCTCTTCTCTCTTCTCTGCTCCCCCCTTCTCTCTCCTTCTCTCCCTCTCCCTCGCCCTCTCTTTCACTCTCT<br>GTCTGTCCAATGCAGGCGGCTGTAAGTTGGGAAGCTCATTAATTAGCGGGCCGGGGGTAGGAGGAGCCGGCTGGA<br>ATTAGCCTGCCTAATGCGCCTGTCAGTCCGGGCGCTGCGCTGCGTTCGGCCCGAGCTGTTTGTAAATTACATTAG<br>CTGCTCCTTTATTGCACCCGAACCTCGGGCGACTGAAAAGCCACCGCCCCCACCCCAAACTGCGAGCCGCGCTCC<br>TGGCGCACCCGCCTCCCGCCGGCCTAGCTGCAATGACCGCACCGGCCCGAAGGTCTCGGTCTCTCCGACCCGGGA<br>TGTGGAGCCCGAAAGAGTGGTGGGAACCCCAGCCCGGGAGGGACGCGGCCGCCGCTCGGGCCAGGTAGGACCAGG<br>AGCCCGGGTGGGCCCCGCTGCCACCCAGAGTGGACTTTGCGGAGCTGAGATCAAGAGCCCAGCGCCTCTACCTCT<br>GACCCTCTTGCCCCTCACCCCACTGCCTGGGCGACGCGCCTGGGGAGAGGGAATCTGAAGCCCTCCTGCGCTGGC<br>CCGCAGGAGGTCAGAGCCGGCTGCGCAGCCTTGGGTGGGCGACGCGGGAAGGGGGTGGAGGACCCCAGGGGTTGG<br>GGGAGGGGGCTAGTCGGAGAGCTCAGCCTTCTCCACGCGGAGAGGCGGAGGAGGGAATTGTTGGCGGCTCTGGAC<br>GCCTCTCCCCGGCCTGATTCCGAAGCGGCCGCCCTACCTCCTCCGGCAATCTTGCTCACTTTCCTCCGGCAGCCG<br>CTCCCCAGGCTGGCTGGGGCCACCAACGGCCTGATGATGGGCGTCTGAAGAGTAGCCAGGCCAGGTGCCGGGGCT<br>AACGGGGCCGGCTCCGTGCCTCCCTGCTGCG<br>(SEQ ID NO: 236) |
| CGI: 295 range = chr10:106389558-106392802<br>CGGTCACGAAGGATCTCAGCTGCACCAAGCGCGCAGGCTACACTCCTGCAGTAGCGGATTGGGGACCAGATAAGC<br>CCACGCGGCTCCCGCCTGAGTACCCTCTTAACTGGCGGCCGACACTTTGAAACAATTGAGTCCGTTCAGAAACGG<br>ACTGGGGAGAGTGAGGGCACGACCTCAAAATCCTAGGCAGCAAAATGAGGTCTGGATCCTCCCTGGAAGAACAGA<br>CATCTCGACTACTCTCTCGCCCCACCTCTGGCCGGGAGGTCGGGGCAAGGAGAATCCCTCAACCGAGAAGATCTG<br>GCAAGTCCCCGATCCCACCGGGGCCTTCCGCCTCTTTTCCCTCATCCCCTAGGAGGCTTTATCAGGTTCTAACCG<br>CTTGTAGTGGGGGCCGTGGGTGCTCGGGGCGCCAAGAGGAGGGGGCTGCCGAGAGCGGCCTGCCTAGTTCTCAGC<br>ATTGCCTCTTTGACCACTCGCAGGCTCCTGGAAATGCAAACACAGCCCGTGCGTGATCCGCACGCGACCAAAAGC<br>CGAGCGCACACCTCCCGCCCCCGCCCCACTTGCCATCGCTCACACTAACGTGCACACATGCTCGTGCAAACGCGC<br>ACGCACGGAACCGCGCGCCCCCTCACACCCAGCCGCGCTCCCGGCCCGGCTCAGCCAGGTGCCCCCACGCGGCAG<br>CGCCCGGTCTGCCCGCCGGCCCCCTGCGAACCCCTCGCCTCACGCCCGCCTGCCTGCGCGCACGCACGCGCACGC<br>ACGCATTCCCCACGCCCCCGCGCGGGGGCGCAGGCCTTGGGTGGCGGGGTTTGGCCGGGAGCCGGCCGGGCCAGG<br>GAGCGGCGAGCAGAGTCCAGGGTGCATCCCGCGCTTGGCTTCCGTGCGCAGCCTCCCCGCGCGGAGGCACCTGGC<br>TCCCTCTCGGCTCTAGAACGCGAACAGTTGGCGTTGAGCACACAACTCCTCCTCCTTCTCCCCCGAGACCCCTGT<br>ACCCTCCCCGCGCGCCATCTCCCGCCCCTCATAACAGGCCCGAAGAGTAAACCCCCAAACGCGTCCAGAAGCGGC |

TABLE 7B-continued

| Sequences of differentially labeled CGIs between bladder cancer subgroups relative to blood |
|---|
| TCCCAACTCTTCGCCGGGAGCACGTTGGAGGCTGGATTTCGGAGAGACTCGGGATTGGGGTCTATTGCCGGCCCC<br>TCCTGGATCCGGCTTGATTTTCATATTTTAAGAAGATTTTCTTATTACCTTTGATTACTCCTTTTTACCAAATTT<br>CTGGAGGAGCTCAGTGGGGAGGATTGGGGGGAATCTGATTTTAAGAAAGAAAGCACCGAAGGGGCAATTATTAAT<br>TTTCCTCGGGTTTGGAATCACCCTCTGGACAAGAGAACGGGCGAGCGGGAGCTAGGAGGGAAGAGTGGAGAGGAC<br>CGGCGAGGCGCGCCAGCCGGAGCCACCTCCTTCCCGGCCGCCCCCTCCCCACTCCCCCTACACACACACGCTCGC<br>TCGCTCGCCGGCGCGCGCACACCCCCCGCGCCGGACCCGCACCTCGGCGGGCGCCACACACTCGGCAGCCCGAGC<br>CGCGGTAGCCGCAGCGGGATGGAGGCGGCGCGCACGGAGCGCCCCGCAGGCAGGCCGGGGGCGCCGCTTGTCCGG<br>ACGGGGCTCCTACTCTTGTCGACGTGGGTCCTGGCCGGCGCCGAGATCACTTGGGACGCGACAGGCGGTCCCGGA<br>CGCCCGGCGGCCCCGGCTTCGCGGCCACCGGCGTTGTCTCCACTCTCGCCGCGGGCAGTGGCCAGCCAGTGGCCG<br>GAGGAGCTGGCGTCGGCGCGGAGAGCCGCCGTGCTGGGGCGCCGGGCCGGACCAGAGCTGCTGCCCCAGCAGGGC<br>GGCGGCAGAGGCGGTGAGATGCAGGTGGAAGCCGGAGGGACATCACCGGCAGGCGAGCGGCGGGGCCGGGGCATC<br>CCAGCTCCTGCCAAGCTTGGCGGCGCGAGGAGGAGTCGCCGGGCGCAGCCCCCAATCACCCAGGAACGCGGGGAC<br>GCCTGGGCCACTGCTCCGGCCGATGGTTCCAGAGGAAGCCGTCCCCTTGCTAAGGGTTCCCGGGAGGAGGTGAAG<br>GCGCCGCGGGCTGGGGGGTCGGCGGCTGAAGACCTCCGGCTGCCCAGCACCTCCTTCGCGCTGACCGGGGACTCG<br>GCCCACAACCAAGCCATGGTGCACTGGTCGGGACACAACAGCAGCGTGAGTACCCACCCGGCGGCGGGTCCGCCT<br>GTTTCCTGACACCGAAGGGGAATGGGGGGGTGGGTGGGAGCGAGGGACAGATAGTTGCTCGGGGGTCGAGGCGGG<br>GGACGCCTCGACTTTTCGAGATAACAGGTTTGTCCGATTCCCCCCACGCCCCCAACAGGTTAACGGAGTTTGTTG<br>TTAGACGCTGTGTGTGTTTGTTTACTGGAGACCCTAGGCTTCGGCCGCCGGGAGGGGGAGTGGAGGAAGGGGCTTC<br>TTAAAGATGAGTGGGGGAGGGATCTGTGCTCACTTTCTCCAATACTTGGCTTGGAGGGTCAGTTTTCCTGTTTGC<br>GGGGTGCTTGAATTCTTGGATGAGAAAAAGGGCTGACTTGGGGCGGGAGCCGCTGAACAGACCGATTCCTGCGGC<br>TGCCGGGCTCCCCCTACCCCCACCCCACCCCCACCCCCCCTCCCGTCACGCGAAAGGGAACCCGGAAGGCCATTC<br>GGACTCCCAGCCTCCTGCTCGCCTCGGGGTCGCTGCTATCCGCTCCAGGCGCGCAGTCCTCCAGCCCAAGAGGGA<br>GGCTCGGCCAAGTCGGCCCCCAGCCTTGGCCTTCAGGTAACCCCGGTTCCTCCTTCAAAGTCCAGGGAGCGGCCC<br>TGGAAAGCCGTAGCAGAGGCCGTAAAAAAAAGTTTAAAGCGTGAAGCGAAATTCCACACCCATCCAGCGCTCATG<br>CCACACCGCTCGCCCTCACGCACGCACAGGCACACGGAAGTCGCTCAGCAGAAAACTCTCGACTTCACCATTGCG<br>TCCTGCGCCACAAACGGCTCCCTGAGCGGAGTTGGGTGCCTGAGCTTCCTGCACACCTCTCCACCCGCTTTTCCC<br>CGCCACCGGGTTCTCCTGGACAAGGATGTACCGAGAGGTGGCGTCGTTGAGCCCGGTCTGGCCTACTCCGGCATT<br>CCGAACTGGGCGCCCGACTGAGCATCGCGCCTGCCTGGCAGCTGCAGCGGCCCGCAGCGCGTGCCCGGAGGGGCT<br>CCCCCTACCTCGCCGGCACCCAGCGCTGTGCAGCCAAGCAAAGAAAAGGCGGGGGACAGGTTCCCACCATCTCCC<br>CGACTTCCCTCCCTCCCGCG<br>(SEQ ID NO: 237) |
| CGI: 56 range = chr10:124891898-124892607<br>CGGGCGCTCATTCTGAGCCGCGACGCCCCCTCAACAGGCTCCCGGCACCGCAGAGCCAGAGGCCACGCGGTGAGA<br>ACCCCAGTGCGTGCGCTCTTCTTGTGTGAGAGGCCGGAGGTAGAGTTGGGAGAAAGAGGAGCCGGCGAAAAGGTT<br>AGTGGGATCTGCTTTCCCTTCTGCGGCCTTCTGGGCCAGCTAGGGCCTGGGAGATGGGGACCAGGGTCGGAGGCT<br>TGGGGGCGGGAGGGCGGTGCTGCCGGCTGCTTCCTGCAAGCGGTTTGAAGAGGCATCGCGTTGTCCGGCCGCCTG<br>CGCAAGGGCCACGCGCTGCTGCTTTCACCCCCTTGCGCCCGCGGGGCACCTGGACTCCCCTTAAGAGTCCCCGTG<br>GGGCCTGAGCTTCTGCTGGGCGCTACGCTGCCCTCCACGATTCCATTTTGCCCCATTTACTCGGGTCGTCCACTT<br>CCCGCGGCTCAGTGACCCAGCCAGGGGGCGTCTTCCGCTAGCGGTCCAAATGTAGACTCCGCAAAGAGGCTAAGA<br>AGACCTGTCTACCCGGGTGCGCGCGATGGGGTCAGGGTGTAAGAACCAGGAGCCTCATAGAAACCTCTGCTTGGG<br>GTCCAAAGCCCAGCCGGGCACTCCCAGAGGACAACATCCGCCCCCCGCATGTACACGTGGCCCCGCAGGACCCAGC<br>CGCAGGGCTCCCACGCTCGGCTCCCCGCCCTCTCG<br>(SEQ ID NO: 238) |
| CGI: 32 range = chr10:128863581-128864054<br>CGACCACTTCCGTATGAGGCACGATTCGTTGGCATTCTTCACCTGCAGCAACCGCTGTGGGACTAGGCTGGTTCC<br>CCAGCCCCGGCGGGGTGTGAGTCTGCGACGGCTGCTCACTACATTCGGGGGACAGGCACTGCATCGGGGGTGAGC<br>AGGCCAGGGCAGTTTCCGAGGGCGCCTGGAGCCCGTTGAGATGTGTGGCTCTCCTCCGCTCGTCATCTGCCGGGC<br>AGAGTGACCACTGGCTGGCGGCTGCAGAGTCTGACAAACCAGGCTCGGGGGCCCTGGCACTGAGGGCAGGTGCGT<br>AAACGGTGGCAACCTCCGTTTTAAACACCCTCCTGAGGGCAGGTGGAGCGGGCTCCTCGGAGTTTGGCCTCCCCC<br>GGTCCTGCTTGGCCCTCCCGAGCAGCTGGTAATCGGGCTCTTCGGATGGAGGCCGAGTGGAGTTTTGGAGCGCAG<br>CTTCTCCATAGCTGAGCGGCTCCG<br>(SEQ ID NO: 239) |
| CGI: 38 range = chr11:22319439-22319953<br>CGCCGCCGCCGCGGCCAAGGGCACCTGCAGAATGTGAGAGAGCCTGGGAGGTCTTGCAGCTTGGTGTCACCCCAC<br>CACCCTAATCCCCGAGGGTGGGGGGAGGTCGACGGCCCTCCTCCCAACCCCGACGGGTCCTGAAAAATGGGAATG<br>GGTCAGCATCGGGGGTACCTAAGCCGCCAAGTCCTTGACTCGCCCCTGCTCTGCCGCGCAGGGTGCTGGAGAAGA<br>AGCAAGACACCGGGGAGACAATCGAGCTGACGGAGGATGGGAAGCCCCTAGAGGTGCCCGAGAGGAAGGCGCCGC<br>TGTGCGACTGCACGTGCTTCGGCCTGCCCCGCCGCTACATTATCGCCATCATGAGCGGCCTGGGCTTCTGCATCT<br>CCTTCGGTATCCGCTGCAACCTGGGCGTGGCCATTGTGGACATGGTCAACAACAGCACCATCCACCGCGGGGGCA<br>AGGTCATCAAGGAGGTGGGCAACGTCTGGCCGCCCTGGCTCCTGCCCTTCGGCCATGCGGCCTCG<br>(SEQ ID NO: 240) |
| CGI: 98 range = chr11:31776637-31777992<br>CGGGAACGTGAAGCGAAGCTCACCACCGGTGCCCGCTACCCCCACGCCGGCAACTCTGTGCTTCGTTTGGCCCAC<br>GTGTCCTCCCCACGCAACTAGGGGCGACGGTCCTGTGCCTGAGGTGACAATCACCCCCCAAAAACCTCACTTGCG<br>GGTGGGGGGGTGGTGATTGCCAGTTGACCCAGAATTTTCTAGCAACTAGGCGCGTTAAAGTGAAAAGCCCCTGGA<br>CTAGCTCCACCTCCGGCCCCAACCATCACAGGCGGACCCTAGCTGATTTGACTCTCACTTCCCGCCCTCAGACTG<br>CCGGCGACGAAAATCCGCCCGAATCGGGCGCCACCTCTGGTGGAAGCTGCTGTCCTCGGCTTCTGCCCAACTCCA<br>AGAAGCGGAAGGGGGGTGTATCCTGCGCCCCAAGCTCATGGGAGCCCACGCACCGGGGAGAGCCCGGAGTGGAGG<br>CTCTGGGCTCAGCCCTCCCAGGCCTAGGCCACCGTGCCCTGAGTCCCTCCCCAAGACTTCTCGGACTAAGTGGGC<br>CAGACTCTTGTCAGGGGAGGGATCACCAGGACCTCAGATTGCTGGGGGCGGAGGGGTGGACGCTCGTGAGTGCGA<br>AGTTCGGGTGTCACTTGGGTGTGTCCAGTGTCTACAAGTGGGAATCCTACGGTTTCAAAAGTCAGGCAGGGATGG<br>GGTTGCCTACACTCGGTGGGGTCAATCGCTAGTCTCACCAGAGGCGGAGCGGGCCTGGGGGCCCTCTGAGCTCG<br>CGGAGGCGGCGGGTTCGGGGCCCGTGCGGGCGGGGTCGCCCAGGGGAGCCCGGGCCCCGCGCGTCAGGAGGCCTC |

TABLE 7B-continued

Sequences of differentially labeled CGIs between bladder cancer subgroups relative to blood CGCCGGCCGAGCGGCCGCGCTGGGAAACAAGAAGCGAGCGCTTTGCTCCCTATCTTCCCAGTGTCCGTCCTATAT
TGTTTTCTGCTCTTAAAACTGACATGTCTAATTGGCAATTGGTGCCGAATCGTGTCCAGAGGTCTCTTGTGGAAC
ATTTCTACAGCTGTCTCCTTCAACTAGACGCTTATTCATGTCGCCTTAATGAGAAACAAAACGTTCTCTAATGAG
CAATTACAGAGCGACAGGATTGTTCCCATAACAAATTCTTGCGAGTGACAGAAGCATCCTTTGTACCAGATATTT
CGCATACTGTTACCGATTTTCCCTTCCCTCGCCCGACTCCATGGAGGCGCCGGGCATCCGGAGCCGGTCCGAGAG
CTCACGGATGCGCCGGCAGCCTCCTCGCAGTCCCGCGCGCCGCCCCTGGCCCCGAGCCCCTCGGCTCCGTTGTGC
TCCTGGGAGTGAGACGCCACGTCCCATTATCCCGCATATTATCTCCTTGTCACGAGGACAACAAATACCGATTAA
TCTTCG
(SEQ ID NO: 241)

CGI: 61 range = chr11:68274244-68274755
CGGACGCCCGGGTGGGAGGCTCCTTCCAGGACCCAGGCGCCCAGGGGCAACACCGCCGGGCTGCGGTGCGCGGGT
AGCAGCGAGGACAGGAAGTGCACGTTGCAGGCGGGCGGCTGCGGGGCCTGCAGGAGCGCGACGTCCTCCAGCGCG
CTGAGCTCTGGGATCCCGGGGTACTCCCCGAGGAGCTCCCCGCCGTCGCTGTCGCCCCCCGCGAGCTTCGCCTTG
ACCTGGCCCTTGCAGTCGGCGCCCAGCGCGGGGTTGAACGCGTGCAGGACGGGTTCCTTGGGGTCCGCCGGGCCC
AGGTACGCTTCTTTGAAGACGTGGAACTCGTCCTCCTCGTACTTCACGGGGGCCTTCAGGCCGATGTTCTCCGAA
GCGAACGGACCCTCGGGGCTTAAGAGCTCCGTCACCATCGCATCCTCGGGGCTGGGCAGCCCGCCCGGCAGAGGG
CCCTCCTCCATGGCGCAGGGCGGCGGGGCGGGATGGCGGGGGCCGCGCACCTGCAACACGCG
(SEQ ID NO: 242)

CGI: 269 range = chr11:117983446-117987106
CGGACGGGACGGGGACGGGGGCGGGGACTGGCGGGAGGGGGGCGGGACAGGCTCGCTCTCCTCCTACTTAGCGA
GCTCCCGGGGAAAAGCAACGGTGTCCTCCTAAGCCTGAGGCCACCGCGACCGAGCCGAGCCAGGCTAAGGGACCA
GTGTCTCCCTGCCCCCCCCCACCTCTAGGTAAGAGCGCCCCGTCCCACTACACTTGCGGGTCCCATTCGCTGCG
GTGCTAGGACTGGATAAGGGGAAGTCCCCGGGGCCTGGCGAGAGCCCTGAGATCAGCTCTAGGCTAGGGAGCTCG
GCAGAAACCCGTGGGGGAGAGAGGGCACCCCAGGTGAGTGCGTGGGGGCGAAAGGAGCGTTATGGGGAGTTTTCC
TGTGAGCCTCTTGCTTTTGCCTTCCCTCGGCCGCTGCCAACGCCACCGCCAGAGGGGGCCGTGACGCTCTCCCCCC
CTTGGAGAAACTCTGATCCTGGCCCTATCCAGACTCTCCCGCCGGCACCCAGGCGGCCGGGCGGACACTCGCGGG
GTATCGGGCGGCGAGCGCGCGCGCGGGTTTTCGTCCTCCAGCGCCCCACACCTCCCCCTCTCCGCCCACAGCAGG
ACCTTGGGGCGGGGGTATCTCCTGTGACGTCTCCCCGCCTGTCCCCAGGCCGGCCGCCTTGATGGACCAGGAAGG
GATTCGGAGTCCGGCTCAGAGTCTTGAGCGTCTAGGAGGGCTGCCTGGGGGTGTCCAGGAGATGGGAAGCCCGCC
TGGGGCCTCCCAGGCACTCCCCAAGGCCCCACGTCCTCGGGGGCCGGGGAGGCCGCCTGGGGCGCCTTGCCACGC
CCGCGCGGTCCCTATTGGAATCCCTAGCGGAGTTCCCCGAGCGGAGGCTGACCCAAGTCATCCGGGCTCCCCCGG
GATAGGGAAGTGCGGGCGGGCGGCTGGGTAGGGGCGCCGGCGCAGGGTGGCCGAGTCGCCCGCTAGCGCTTCCGC
CGAGGCAGGCTCGAGTGGGGACTTGGCCGGGCGACCGCACAGCCCTGCCGGGGACCCACGGCTCTGGGGCGGGGC
TGCATTCTGGGCCGTTAGCTCAGCGGTCCTGGAGCCTCCCGAGGCTGACTCATCGGGCGGCGGGCTCACCCCCCA
GCCGTCAAACGCAAACGCAGGCGCCCCACCACGCCGGGCTCCCACGCGGCACACACGCACGCCTCCGCGACACTT
CGCACACCTACGTCCCTGCGTCACGCCACCCAGACACACCCGGACCCGCCCACACGCCGAGGCCTTCCCACGCAC
TCCATGCCTTACGCCTCACAGGAAAGCGCCCCGCGCTCACGCAGCCCCTCACACCCGCAGCCCCGCTTACACGCG
CCCCAGCTCACACATGCACCCCAGTCACACAGCCTACCTCACACACGCACCCCAGTCACACACACAACCCAGCTC
ACACACGTACCCGTCACACATGAGGCCCCAGCTCACACACGAAGCCCAGCTCACACACGCAGTCCCAGCTCTCAC
ACACACACCCCAGTCAAACACGAGGCCCCAGCTCACACACGAAGCCCAGCTCACACACACTGCCCCAGTTACACA
GCCCAGCTCATGCAAGCAGCCCGTCACACACACAGCCCAGCTCACACACACAGCCCAGCTCACACAAGCAGCCCG
TCACACACACAGCCCAGCTCACACACACAGCCCCAGTTATACACACACAGCCCAGCTCACACACGCAGCCCGTCA
CACACACAGCTCAGCTCAATACACAGCCCAGCTCACACACACAGCCCCAGTTACACACACAGCCCAGCTTACACA
CACAGCCCAGCTCACACACACAGCCCATCACACACACAGCCTATCACACACACAGCTCAGCTCAATACACAGCCC
AGCTGACACACGCAGCCCAGCTCACACATACACTCCAGCTCACACACGCAGCCCGTCACACAGCCCCAGCCACAC
ACACAGCCCAGCTCACACACGCAGCCCAGCTCACACATGCAGCCCCTCACACATGCAGCCCCAGTCACACACAC
AGCCCAGCTCACACCGCAGCCCCAGCTCACACACGCGGCCCCTCACACACATTCAGCCGCCCTTCCCGCAGCTGC
CAGGCTCGGAACGGGCGGTGTCTGTGGGGGCCGCCCCGTTTCCCGGCCGCGCAAACAAGCGGCTCCTTCTCTCTG
CCCCGCCAAAGAAAGGCCGCTTGTCAGGGGCGGGCGGGCAGGCGGCAGCGGCAGGCGCCCAACACTGCGGCCTTG
TCCCACGCGGGCAGCCTGGGCAGGAGCAGGCCGAGGGGTGCAAGGGGCCGCTACCTTGCGGAAACCTCCCTCCCT
CGGCCCTGCGGACCGCGGAGAGGCACCTTTCCACCACCGGACACCCAAGCAACAGCCCTCGCTCCATCCGCGCTC
TCCCGGCTCCCCCTCTCCTCGGGCCGCCCATCTCTCCTCTCTTCCGCCTTTGGGGTCCCGGTGGGCCCCAGCCTC
CCTCTCCTTCGCCCCATCTCCCCGCCCGTCAGCCTCCCCTCCGCTGCCCTCGCGCATCCCCAGTGTTCCCGTCTG
TCGTCGCCTCCACTTGAGGACCCGCCTGTCCTTTCTTCCCCCGACCCCTCCACCTCTGTGTTCTTCAGTCTCCCC
GCATCCTCTGCCCTCGGTCTTCCCCTCCCCAGCTTGCATTTTTTCCCATCTCTTAGTCTGCCTTTCATTTTCCCC
TTCACATCCCGGTGGCTCCCCTTCCCCGCCCCGTCCCTCTGCACACCCCCATTCATCTCTGTCAGGTTTTTCTCA
TCCTTAAGTTCTCTCGTCCCCTCCCCACTCGGGCGTCCCCCGCTGGGCTCCCCGCCTCAGTTTCCTTCCCTTCC
TGACTCCTTCCTCTGACGGCGGCCCTTTCTCGAGGGCGGATGTGCGCCTGGAGGGCGAAGGCGGCGGCCGAGAGG
ACCCCAGCTCGGCCTGGCGGGCCTCTGGCCACAGCCATGCACCGCTTGGGCCGAGGCCGAGGCCGACCCCCAGGG
ACACAGGTGAGGCCGGGCGACCCGCGGGGCTCCGGGGAGCGCCCGAGCAGTGGCCCCGCGAAGGGCCGGGTCTGG
TGCTCTGGGGCTGGCTTTGGACCTCTCGTCCTGGGACTCCGTGGGAGCCCGGGAGCTGTGTCAGTGCCCGTTGGT
GCTGGAGCCAGTCGGCCCTTCCTTGGCCTCCTTCAGGCGGGGGCCAAGACCCCCGAGAGTTCACTCTGGGTGCTC
CACTCGGCGGAGAGGGCTTCAGACTGGTGTCCCGCGTGGCTGGGGTGTCGGCGCATTCCCGCGGGGGAGGAGGCC
GAGGGCCCGGGCCGGGGTCACCTGCCGGCGCCCCGGCCTTGCGCACAGAGGGCCTTGCCTGTCGCTCGTCAAATC
CAGACACCTGGGCCTCCGCCACTCGGCTGCCGGGGCGGCACTGGGGCGTCTGTACCCAGCGTGCGGGAGGGCACC
CAGGGCCGGACGCGCACCGCAGGGGTCTTTTTTTGGCCGCGGGGCCGGGCGGGCGGGTAATGACAGCCGGGTTGC
TGGGGAGCCGCGGGCCAGATGGAAGCGGGGCCGCAGGTGAGGGACGTCCCTCGCGTAGCGCCACTCAGCCGCCGG
GGCCAGAGCGGGAGTCAAGGTGAGGGCGCCCCCAGGTGGCCGCTCTCGGCCGCGGCGATCG
(SEQ ID NO: 243)

CGI: 97 range = chr12:1844001-1845219
CGTGCGGGTGACTCCTCTTCCTGCCGACAAGGTGGGCGATGAGAACGAGGAGGCCCAGTCCCACCAGGGCGCCGC
CGACGGCGATGGGGATCGGCGTGTTGTTCTCGCCCAGCAGACGCTCCTCCGCAGATCCGAACTGGTTGCCTTCCA
CCTTGAAAGCCTGGCCCCACACTGGGAATATGTTGATTGAAAACGCCTTCGTGCCGCGGACACGCTCCGCTCCGG
CTGTAGAATTGCCGATGGCTGCCCGCAATGCTCGCAGGGAGTCGTTGGCAGCTTTAAAAGTGGGGTCTCTGGGGT TABLE 7B-continued

| Sequences of differentially labeled CGIs between bladder cancer subgroups relative to blood |
|---|
| CAGGAAGAGTCGTATTCAGCTGGATTCCTCGTAGGAAAATCCGGCTAGAACCTGCATTCATCCCCAACCGGAAGC CCAGGACCGTGGTGCCCTCGCCGCGCCGCTCCCGGGTCTCCAGGTGGGCGCCGCGCTCCCGCTGGCTGAGGTCAT GCCCAGGTCACCGTCGCGTGGTCCCTCCTCTCTGGGTGAGGTTCAGCTGCAGTCCCGCGCTGGCCGGCAGGCAGG CCCCGTGGGTGCCGCTCACGCTGTACCTGGCCACGGAGGGGAGAAGGGGCTCTCGGCGCCGTGGCGGGGAAGGCG CGTCTTGCTCGTGGCGCGTCTCTCCCTTGCTGAAGCTGCTGTTGGAAATCTAGGCCTGGATCGGGGCACCGCGGA GCCTGATGGTCTCGCTGTTCGTGCGGACCTGGGGCCTTGATATCTGGTAGAGATTCCACAGTCCTGATTTCCTT GGAGCTTGCACTGAGGAAAATGTGTGTGTCTGACAAGTTGTAAACAAAACTCATGAGCTGGACGCTGTCACGTGT CGCACTTCTTGTGAAATGGAAGGTCAGTGTCTGTCTTCCTCCAAAGCACAATCGCGTGCCTGGGGTCGGAAGTGT TCTCTTTACTGCAAGAGCCACTGTCAAGCACTTCCGCATTGGATGGCAGGTCAAAGGTCACATTCTTAGAGCCAC TCTTAGAGTCGTAGTTCATCGAGAAGGCAGCGAAGCTGGCCATTACGCAGGCTGTCCCGTTGCCCTTTTTCACCG CATCCGCTGCGGCTGCACCACGCACGAGGCCCAGCAGCAGCAGCAGCACCAGGGGCAGCCGGGGGCTCCACCAGA TGCAGCCCGGGCGGCAGGCGCGAGGGGAGCCGGTGTGTGGGGAACCGGGGCGCGGGGAGGCGGTTGCGGGGCGCT GGCCTGAAGGACGGTGGCG |
| (SEQ ID NO: 244) |
| CGI: 16 range = chr12:40253533-40253742 |
| CGACGGGACACGGTACATCACAAAGAGACCCGTGCGAGACCGAATCCTGAAGGAACGTGCCTTAAAGATCAAGGA AGAGCGGAGTGGCATGACCACAGACGATGACACCATGAGCGAGATGAAAATGGGGCGCTACTGGAGCAAAGAGGA GAGAAAGCAGCACCTGGTTAGGGCCAAAGAGCAGCGCCGTCGCCGTGAGTTCATGATGCG |
| (SEQ ID NO: 245) |
| CGI: 79 range = chr12:52726910-52727810 |
| CGTGTTCCCGGGCGGAGGTGCGCGCAGCCACCCCAGGCTGCTGCCAGGTGCCCGCTGGGGCTGCCAGGGCGAGGA GGCCTCTGGGCTGTGGAGCGAAAGTCAGATCCACCGCCTACTGCGGGGTAGGGGCCGCAGTGGGGACCGCCAGCC CTGTGGTCCCTCTCGCGCTGACTGGCGTAAAGTTGTGGCCGAATTCGCATCTCTTCTGGTGCTTCTCGCCCGCCA GCGCAGGGCCCAGGTGTTTGAGGCGAAGGGGCTCTAGCTCCCCGCAAGCCTGGAGCCAGGCGTCGCGCTTCCTCC GGGCTTAATCCAGACCTTTCAACACACACCTCATTCGGGGGAGGAGAAAAGCACAGGACCGCGGAGAGCCCAGCT TTGAGGCCAGGCCTGAAGGGATAACCCACACAGGGAACGTTTTCCTATCAGAGAATAATGGAGCACAAAATAATT CAGAAAGCGAATGGGCAGGACCACAGCCTGAGAGTCCCGCGCCGCGGGGCCGCTGCAGAGCCGGTCTCCCGAGCA CCGCGGCAGGACCATTTCGTTGGAATGTAGGGCGAGGCCGAAGCCCGCCCCGGACCCAGGCCGCGAGGTGCGCGC CGGCCGCCGAGGGGCCGCCTGTAAATTACAGCCCGCCGGGAGGACTCGGAAATACACAAAAGGAGCCGAAAGATT TAAACAGTCGGAGGCAGAGGCGTCCCGAGGCGGCCAAAGCGGAAATCAATCACGTAATTAAAACAGGGAGGGGAC GAAGCCCAAGGCTGGGGTCCCGGGTTCGGAGGAGGCGGCCAAGGTGCAGGCCGAGGCTGGCGAGCGGCTTAGGG ACGTGGCTCGCCCGCCAGGACCAGAGCGCGCGGAGGGGCTTCGGGGAAGTTTATAACACATCGCTATTGATTCCC G |
| (SEQ ID NO: 246) |
| CGI: 32 range = chr12:79634857-79635257 |
| CGGAGCGACAGACTAGGGAGCTCCGCCCGGGATTTGCCCATCGGCGGAGGCGCCAGGCTCCCGTTTCTCCCCATC CCTCTCGCTGCCGTCCAGGTGCACCGCCTGCCTCTCAGCAGGATGGACGTGATGGATGGCTGCCAGTTCTCACCT TCTGAGTACTTCTACGACGGCTCCTGCATACCGTCCCCCGAGGGTGAATTTGGGGACGAGTTTGTGCCGCGAGTG GCTGCCTTCGGAGCGCACAAAGCAGAGCTGCAGGGCTCAGATGAGGACGAGCACGTGCGAGCGCCTACCGGCCAC CACCAGGCTGGTCACTGCCTCATGTGGGCCTGCAAAGCCTGCAAGAGGAAGTCCACCACCATGGATCGGCGGAAG GCAGCCACTATGCGCGAGCGGAGGCG |
| (SEQ ID NO: 247) |
| CGI: 30 range = chr12:95164929-95165298 |
| CGCGGTGGAGATCAGCCGGGAGAGCCTTCTGCTGCAGGACAGCGACTGCAAGGCGTCTCCGGAGGGCCGCGAGGC CCACAAACACGGCCTGGCCGCCCTCAGAAGCACGAGCCGCAACGAATACATCCACTCAGGCCTGTACTCGTCCTT CACCATTAATTCCCTGCAGAACCCACCAGACGCCTTCAAGGCCATCAAGACGGAGAAGCTGGAGGAGCCGCCCGA AGACAGCCCCCCCGTGGAAGAAGTCAGGACTGTGATCAGGTTTGTGACCAATAAAACCGACAAGCACGTCACCAG GCCGGTGGTGTCCCTGCCTTCCACGTCAGAGGCTGCGGCGGCGTCCGCCTTCCTGGCCTCGTCCGTCTCG |
| (SEQ ID NO: 248) |
| CGI: 35 range = chr12:113609113-113609535 |
| CGCGCGAAGCAGAGAACGAGAGGAAAGTTTGCGGGGTTCGAATCGAAAATGTCGACATCTTGCTAATGGTCTGCA AACTTCCGCCAATTATGACTGACCTCCCAGACTCGGCCCCAGGAGGCTCGTATTAGGCAGGGAGGCCGCCGTAAT TCTGGGATCAAAAGCGGGAAGGTGCGAACTCCTCTTTGTCTCTGCGTGCCCGGCGCGCCCCCCTCCCGGTGGGTG ATAAACCCACTCTGGCGCCGGCCATGCGCTGGGTGATTAATTTGCGAACAAACAAAAGCGGCCTGGTGGCCACTG CATTCGGGTTAAACATTGGCCAGCGTGTTCCGAAGGCTTGTGCTGGGCCTGGCCTCCAGGAGAACCCACGAGGCC AGCGCTCCCCGGACCCCGGCATTAGGCGCCAGCTGCCGGCTATCTGCG |
| (SEQ ID NO: 249) |
| CGI: 121 range = chr13:35817738-35819004 |
| CGCAATAATGCTGCGTCACGAAACTGCGCATTCCAAGAGAAACTTTTCTCAGGCCCAGAATTAAGTCGGAGGGAT CCGCCGCGCAGCTCAATCCCTAGGAAGCATGAAAGAATGTATTGTAAAGAGTAAAATCACGCGCAATCCATCCCA ATATAACCGCAGTTGTTCGTGGGCCTTCTTGCAGAGAAAGGCTGCCCAACCTTGACGGGGCCATGGGCGCTGCGG GAGGGCAAAAGACCACAGAGATCTGCGAAGCCAAAGTAAACAACGGGGTTGGGGCGGCGAGAATGATCAATAGCG ATGCTCCGAAAGGACTCCGCGATAGGAATCGAGCGGGAAGGATTCCCTCCATCCTAACAGTCCATGGGTTAAGAG GCCGAAGCTTCCCTAAATACCACACTCCCGCGAGAGAAGGGACTGAGAACAACTTCTCAAACTATTCTCTCTCGA AATCGCTCCCTTCCTCGAAAATTCCATCTCTGAGACTCGGATGAGGTCCCCACCCCCTCCACCCTTGTCCCGTGA CCGTCGCCCGCTCAGCCTCCCAGCCGAGTCCGCGGGGCCTGGGGCGCCCACCCCGCCCACCCAAGGGACCGCGCA GGGGTGAACTCCCCCGCGCCCCACCTGCGCCTTCCAGACCTCGGGCGCCCCGGCGTTGCCTCGAGAGCTCCCTGC GCGGCCGCCGCGGCACGGACCAGCTCCCACTCCCTTACACTGGGCGCCGCTGCGCTCGCCGGGGGCCGGTCCCGA GGTTCCCAAGGCCTCGCGCGCGCGCTTGCCGTGGCAACCAAGACGTTCCACGACGCGCGCTCTCGAACGCTTCGC GTCACGCGGCCGCGCGGCCCCGCCCGTCGGCCTCGCTCCCGCCACAGAGCCCGCAGCACGCCGCCGCCGCAGCCT AGGTCACGTGAGTACCCACGCGCGCGTCTTGCCAGCGGATTCATCACCGGCCTGCTCAGACTAGGTTCTGCCCAC |

TABLE 7B-continued

Sequences of differentially labeled CGIs between bladder cancer subgroups relative to blood TCTGACCTTCTAAATGGTACGTGGGAGGACGTCCGTCCCCTTCGGACCCAAGAGTCACCGTAACACTCTAGAAGG
GGAGAAAAGGAGCGAGGGCGGCAGGCGACAGAGAACCTCGCGAGTCAGCGGCCCCGCGCAGACCCCCCCAGGCAC
GGTCCCCTGCGGCCACGTCGGCTGCTCGGCGCCTGCGCAATCTCTTTCTCTCCAGCGAAACCGAGGCCTCCGGAG
AGCCTAGTAGAGAGTGTGGGCAGTGAGCGCTTGTAGCCGCTAGAGGGAGCGCTGGGCACAGTGCACG
(SEQ ID NO: 250)

CGI: 58 range = chr13:57101588-57102323
CGCGGCATGTTCGTACCAGCGCGGGCAGAAACGGGCTCACGAGCGCCCTCGAATTCACACACACTCACCGAAATA
CACATCTCAGCCCGTGGAAGCGCATTCACACACACCCACGTACACTCCTCCGCACCTCATTCAGATGGGTCCACG
CGGAGTCAGGGCTGCGCTTCCCTTGGCATGGGCGTGTGTGCGGCGAGGGCGTGTGTGCGTGCGTGTGTGAGAGTG
TGTGTAGAGAAACCCTTTAGGCAGACCGCAGCTACGTTATTCTGCAAGCATACTGCGATTCCCGATTCCGTGTAT
GTAGGACCACAAAAAAATTAAATCGCTGTTAAACTTTTTTTTGTAAATTCTCTTTTCCGAAGGAAGGCGCTGGAA
GAGCTACTCCCGGTGGTTAAAGGCCCGGGAGACCTGGTGGCGAATCCTGGGGCGCGTCCGCTTTGGCGGAGCGCT
GGGCTCCGCTAGCCGGACTGGTTCCCCATCTAACTGATCTAATCAATGACTCCGAAGAGCCGGGGCTCCTGGCCC
CGCCCCCGCCATCCTCTTCTCCGCCTCCCATTGGACGCGGGCCGAGAAGGCAGGGCCTTGCTCCTCGCTCGGATT
GGCTGACAGGGAATCAGTATCAATGTTTAAGCGGCGGCGTGAGGTGAATAGAGTCAGTCAGCAAGAGACGCTGGG
GAGAGAGCAGGGATCGCGAGCCCGGCGGATGCGGCAGCGGCGGAAGGCGGCTGGGGAGACG
(SEQ ID NO: 251)

CGI: 30 range = chr13:105943410-105943788
CGCCGGGCTCTGCGGGGGCATCTCCTGGACGATGTACACCGGGTGCCCGTAGTCGCCGCTGACCTTCTCGTAGTG
AGGGCAGAAGACGCTGTCCGCAGTCCTTAGCGGGATGATAATGTCACTGGGCTCTGAGCCGTTGTTGTTGCCGCT
GCGCTTGGGTGTGGCCAGTGTGCTGAGCGACAGCGTGGTCGTGTGCTGCGGCGAGTGCTTCCTGTGTCTCCTCCG
GTACTTCAGCAAGAGGACCACCAGCGTGATGATGATGACGATGAAGATGATGCATCCTGAAGCAATCCCTGCAAA
TAAGGCCACTTCGGAACCGAGGATGTTGTTCCCCGAATGTCCGGCGCTGTTGCCGTCTGTGCTAGAACCTGCAGA
CGCG
(SEQ ID NO: 252)

CGI: 74 range = chr13:111763361-111764235
CGCTCCCAGCCGGCAGCCGCTCTGGGCGTGCACCCGCCACGCGAAGCCAGAGGTTGGACGACGCAGCCGGCCAGG
CGCGGCTCCCGGGGGACCCCGAAACCGCCTGTGGCTCAGGCCCTACTTGGCAAGAAGAGACTGGGGAGTGAGAGG
AGGGGTCACTCTTGCTCTCTCGCACAATAGACTTCCCGCAGGCGAGTGCGAACGGCCTTTTGCTTCCTCCTTCTT
TTCCAGGACCCTTAGCGACAGGAGAGGAAGAGAAGCGGCCCGGCGGTTTAATTGCCAATTTCCTGATGCAGCCAC
AGGGCCCAGCAGCGGCTCAGCCTAGGCCACCGGGTCCAGGCCTCTAGGCAATAGGCCCGGCGCCCCCTCCAAGCA
CCGTTTCCCGCCGACCCCGCAGTCATCACTGTGAGCTCGAGAGTATGGGCAGCCTGTGGTGCCCTGAGGCGCCGG
GCGCTCGGCGCATCCGCCGTGCCCACAGCGCTGAGGACCAACTAGGGCTGCCCTCGGCCAGGGGCACTGTGCCCG
TTTGAGTGGCACTCGGACCTGGCGAGGGGTGGAAGCCCAGGTAGAGCTCGCGTCTTTAAGAGCCACCCGACAGAA
CTGCGCGCTACATCTGCGCCAGCTGGGCTGGGTGGGAACAGCGCAGAAATACTCCCGTGCCGGGGCGTACAGGGC
AGGTAGGCCCAGCAGAGAGTCTTCTCGGAAAGTTTCCCACAAAAGAAGGGCCGGGCAGGCCGAGCGGCAGGAAAA
GCCGGTGCTCAGCGGCGAGGCCCGAGAGGTCTGGCATCCGGCGGCCTCCCAGCTTTGCTCGGGTCTCCCGCCGCC
TCTCTCCAGAGCCGCCCGTAGCTCCGTGGGGCGGAGGGCGCAATGCCCCG
(SEQ ID NO: 253)

CGI: 28 range = chr13:112249708-112249928
CGATTCCTATCGAATCAACACGGCCATTAAGGACAAAAACGGGCAGGACACAAAAGCAAGCCTGGATGGCGCACC
CTACAAACGAGTTCTGAAACAAAGCGAGTGCCAGACGCGCGTGGGAAAGACGCGCGTGGGAAAGACGTGCATGGG
AAAGTCGCGCGTGGGAAAGTCGCGCGTGGGAAAGTCGCGCGTGGGAAAGACGTGCGTGGGAAAGACGCGCG
(SEQ ID NO: 254)

CGI: 87 range = chr14:19992581-19993863
CGTGACGTAAGTCCGCCGCGGGTTCGCCAGCACCTTGCCATCCCGCACCACGCCCACGCCAATCTTATTGGCGCT
GCCTTCAAAACCCAGCACCGCCGGCATGGCGGAGGCTGGGAGAAAACGCCGACAGGACTCCTGGCAATGTCAGGA
GCTGTGGAGGTCCTCACTAGTCCGCGCTGGGCCGCAGCTTTCCGGAGCGCAGAGGAAGCTGGCCAGCCTGCAGAT
AGCACTGGGAAAGACACCGCGGAACTCCCGCGAGCGGAGACCCGCCAAGGCCCCTCCAGGGACCTGTCTTCCTAA
CTGCCAGGGACGCCGAGCCAACTCTGTGCCTTACATTCGTATCCGTTTTCCTATCTCTTTCCCGTGGTCCAGCCC
AGCCTTCTCCACTGTTTTTTTCCCTCTTGCACATAGTTAGAATCTTAAGTCAGTGTCACACAATGTGCTGTGCAT
CTGGCACAACGATAAACAGCCCGAGGGAGGGTTGGGGACCTAAGTGTCCTAGAGAATTAGAGGAGGGAGGCGAGG
CTAAGCGTCTCCGTCACGTGGTGTCAGACAGACCAATCACGCGCATTCTTCGGCCACGACAAGCGCGCCTCTGAT
CACGTGACCAGGTCCGCTACCCACGTGGGGGCTCAGCGTGCACCCTTCTTTGTGCTCGGGTTAGGAGGAGCTAGG
CTGCCATCGGGCCGGTGCAGATACGGGGTTGCTCTTTTGCTCATAAGAGGGGCTTCGCTGGCAGTCTGAACGGCA
AGCTTGAGTCAGGACCCTTAATTAAGATCCTCAATTGGCTGGAGGGCAGATCTCGCGAGTAGGTACAAGGCACT
ATGAAATGATCTAGTTTCGTGGGTGAGGGGCTGAAGGGCCTATGATGCACGGAGGCGGGGAAAGGATTTAGAGAT
AACGTGGTTTGAAAGGCGGGACCTGGTGCGGGGACGCTCTTGGGAGGAGTCTTCTCCCCAGCCTTAGCTGGTTTC
ATGATTTCTTTGCGTCTGTAGGCAACGCGGTAAAAATATTGCTTCGGTGGGTGACGCGGTACAGCTGCCCAAGGG
CGTTCGTAACGGGAATGCCGAAGCGTGGGAAAAAGGGAGCGGTGGCGGAAGACGGGGATGAGCTCAGGACAGGTA
AGGGAATGAAATCAGCCCTTCTTCCTAGAAGCTGCGGCGGGGGTGTTTGTCATTCCCTTGATGTACGGTAAGTAC
GGGCCGACTCATTTTTGCAGGGGTTTGTGAAGAAGTCGCAGGAACCGTAGGCTTTCGTTGGGTCTATAGTTAACG
CCGGATCG
(SEQ ID NO: 255)

CGI: 79 range = chr14:23710894-23712060
CGCCTGTTACTAGAGGCGAGAACCGGAGCCCATTGGTCGGAACACCTCACAATGGACCCCAGCGGCGCGCAAAAT
CCTTATGATTGGTTTGCTGGCTGCCTCGGGAGACCCTGTTGCCAGGATACTTGGCGTTCCCGACCCGACCCCCGT
TCCCCATTGGCTGTCAGGGCAAAAGCCGCCATCTAATGAGGAGCGAGGTGCGGTGCCCCGAAGCGCTCGCTTCCC
GCGGTGCGATCTAGTCCTGCAGTAGGCGGCCCGGGGCCACACCGCGGCCGCCCAAGCCAGTGCAAGGCCCAGGGG
CCTGACATCGCTCCCAGCGCTCGAGGACCGAGGCCTGCTGTGGAGGACACCGTGCTCCCTCGGGACCTGCTCTGG
ATTCCGGCCCGGACGTCCCCTTGGAGCTCTGCATCTCCAACCTGGAACCCAACCCAGAAGTCTCAAGTTTGACGC TABLE 7B-continued

| Sequences of differentially labeled CGIs between bladder cancer subgroups relative to blood |
| --- |
| ATCACGTGGCGTGCGGATCCACTGAGGGTCCACAGAGAGGGGCGCCCATCTCCTGCGTCTCAGTTATCCTGGTAA TTGTGTATCTGCCCATTGTTCGTTGCCTCATTAACTTGGCTTTCTAGGTGCACCCACCTTGCCACCAGAGAAGTC CAAATCCTGACTTCTCTCCAAGGTGTTGGGAATTCTGTGCCCTAAAGAATTCCGACTCAGATCCGAACGGGGATC TGGTGGAATCGAGGGTGAAAGACCAGAGGGACAATGTTCTACTATCCCAACGTGCTTCAGCGCCACACCGGCTGC TTTGCCACCATCTGGTAAGGGCGGGGCCCGTTGGCGCGCGATGGCGGACGCTGCCCGGGATCCCAGCCTGACAGC TCCCCCTCCATCCCCATTCTCCCACCTTCCCCACCCACTTCAGGCTGGCGGCGACTCGCGGCAGCCGGTTGGTGA AGCGCGAATACCTGAGGGTGAATGTGGTGAAAACCTGGTAAGGCCCAGAAAAGGGAAGGAGGGCCTGGTGCGGGG GGTGAGTTAGGGGATGGGGTGGCCAAGACTGTGGGCCCACTCCTGGACGCAGCGGTAATCAGGGCGCATTGTTCC CCAGCGAGGAAATCCTCAATTACGTGCTGGTACGAGTGCAACCCCCGCAGCCCGGCCTGCCGCGGCCCCGCTTCT CCCTCTATCTCTCAGCCCAACTTCAGATCGGTGTGATCCGCG |
| (SEQ ID NO: 256) |
| CGI: 23 range = chr14:28317076-28317375 |
| CGTAGCGACGACGTGGTCCTTGTAGGACCAAGCATTCTTGGCATTCTGTCGAGATTGAGATTCCAGAGCATCGGA TGAACGGGACTTATAGCTAAGGCGTACTCACCCACCCCTCCCTTCGTCTTTTACGCACGCAGCAACTCGTCCTC ACGTGCATAGGGGTAGTGGACAGTGTTGACTTGAATTGCTGTCCCTCGTTCCAAGCCTTTCCTGTGAATGAACCC GAAAACACTCGACAGGTCGTGAATAATCGTTTTAATGAGTGTGCAAAGCGTGCGACGGGGTGCACCGAGCTGTCG |
| (SEQ ID NO: 257) |
| CGI: 147 range = chr14:33338698-33340189 |
| CGAGAACTCCAAGTCCGACGAGAAGGGGAACCAGTCCGAGAACAGCGAAGACCCGGAGCCCGACCGGAAGAAGTC GGGCAACGCGTGTGACAACGACATGAACTGCAACGACGACGGCCACAGCTCCAGTAACCCGGACAGCCGCGACAG CGACGACAGCTTCGAGCACTCGGACTTTGAGAACCCCAAGGCGGGCGAGGACGGCTTCGGTGCTCTGGGCGCGAT GCAGATCAAGGTGGAGCGCTACGTGGAGAGCGAGTCGGACCTGCGGCTGCAGAACTGCGAGTCACTCACGTCCGA CAGCGCCAAGGACTCGGACAGCGCAGGCGAGGCGGGCGCGCAGGCCTCCAGCAAGCACCAGAAGCGCAAGAAAAG GCGGAAACGGCAAAAGGGCGGCAGCGCCAGCCGCCGGCGCCTGTCCAGCGCGTCGAGCCCAGGCGGCCTGGACGC GGGCCTGGTGGAGCCCCCGCGGCTGCTGTCCTCCCCCAACAGTGCCTCGGTGCTCAAGATCAAGACGGAGATCTC AGAACCCATCAATTTCGACAATGACAGCAGCATCTGGAACTACCCGCCCAACCGGGAGATCTCCAGGAACGAGTC CCCCTACAGCATGACCAAGCCCCCCAGCTCTGAGCACTTCCCGTCCCCGCAGGGCGGCGGCGGTGGGGGTGGCGG TGGCGGGGGGCTGCACGTGGCCATTCCCGACTCGGTCCTCACCCCGCCCGGCGCCGACGGCGCGGCCGCCCGCAA GACTCAGTTCGGCGCCTCGGCCACCGCGGCCCTGGCCCCCGTCGCCTCCGACCCGCTGTCACCCCCGCTCTCGGC GTCCCCGCGGGACAAGCACCCCGGGAACGGCGGCGGGGGCGGGGGCGGGGGCGGCGGCGCGGGGGGCGGCGGCCC CAGCGCGTCCAACTCCTTGCTGTACACTGGGGACCTGGAGGCGCTGCAGAGGTTGCAGGCGGGCAACGTCGTGCT CCCGCTGGTGCACAGGGTGACCGGGACCCTGGCCGCCACCAGCACGGCCGCGCAGAGGGTCTACACCACGGGCAC CATCCGCTACGCGCCCGCCGAGGTGACCCTGGCCATGCAGAGCAACCTGCTGCCCAACGCGCACGCTGTTAACTT CGTGGACGTTAACAGCCCCGGCTTTGGCCTCGACCCCAAGACGCCCATGGAGATGCTCTACCACCACGTGCACCG GCTCAACATGTCAGGACCGTTCGGCGGCGCAGTGAGCGCAGCTAGCCTGACGCAGATGCCCGCCGGCAACGTGTT CACCACGGCCGAGGGACTCTTCTCCACGCTGCCCTTCCCCGTCTACAGCAACGGCATCCACGCGGCACAGACTCT GGAGCGCAAGGAGGACTGAGGCGCCGCCCGTCCTGGGCCCGGCCAGGCCCCGCTTGGAGGAGGCATCGTCGGCAT TTTCGTTTAGACCTTTAATTCTAGCACTTTGAATTCGAGCAGGTCAGCGTCTTCTCTCGCCACGACG |
| (SEQ ID NO: 258) |
| CGI: 22 range = chr14:36122289-36122589 |
| CGCCCGGCCGCTGCCGATCTCGGAGCTCGGAGGCCGAGCTCCACAAATTTGGGTCCAGGCCCGCTTTAGAGCCCC TGGGCGGGGGCGCTTCTCAGGGCATCCTGTGAGGGCTTTGAGGCCTCCTTGGAGTCGCCAGATGAACTGGTGCCG CCTGTGCGCCTTGGCCCCATAGCCTCAACGGCACTCTCACTGCCTGGGCTTTGGTCTTTGCCCAGGAGCCTGCCC ATGGCCTACGCTCCCCGCTCGCAGCATGGCAGACCCTGACGAGGCTGCCCGCCTTGGTCCGGGAATGGACCGATC G |
| (SEQ ID NO: 259) |
| CGI: 123 range = chr14:37137198-37138958 |
| CGGGGCAGGGTACCCGCGAGGGCAGGCACGTGGCGGCTCCTGCGGTGTCCCGGGTTAAACTTGCCTGTGTTTAAG ACGGGTCTGCGACAGCTTGGGGCGGTCCAGGTCGCGGGGAGGGCGGGCTCCTCAAGTGGGGGATCCGCGGCAGTG AGGACTGTAGGGTGCGCGGGTACTCCGGGTAGCCGCCAGCGGAGGAAGCGGCTCCGCCCTTCCCGGAAGCTGCCC TTGCTACACCCGTGGGGCCTGCTCCCGGCGCAGTCCCGCAGTACCTGAGCGGCACTCGGTCCTTTGACCACGCTT GGCTGCCTCAGCTTACACTTCCCAGCAGGATCTGGCTGGGAGCCCCTTCCTCAGATATTCACCAGGCAGGTAGAA GCAGAGGGAGACGACGGCGAAAGGTGGAAGGAGAGGCCGCGGCCTCGGGCCTCGGGCCCCGGGCCCAGACGGCGG CCTCTCGCGGCGACAGGGTCCTTCCTATTTAGCAGGACCGCAGGGTTGGCAGACAGCAGGGCCTGGGCCGGCGGG GCTCTGCGGTGCCCATTCGAGTCTCTCCAGGGCTTCCCTCTGTGGCTGTCCCTCGCCTGCCCCCTTTCCTTGCCT ACCCTTCCCTGGACGGGGTTGTTGTCAGGTGACGGCTTCAGCAACCCAGCCATGCTTGGTGTGGAGTGGTTCGAG TTCCTCCGCGGGCCCCCACCCCCCACCCAGATAAGAAGCTTAAGTCCTCCTTCTGCAGGGGAGAATCGGATGCAA TGAAACTAAGACCTGTGGTCGTTAACGCGGTTCAAAGCCGACCCCAACTGGGACACGGCTCAGCTTAGAAGTGAG GAAGGCCTGGGACGCTGGAAACAAGGGGTCACACGTGCGTGTGCCTGGCCTTCGCAGGTGGATGTGTGCGCCGAG CTGGGGAAGGGGCCAGGGAGCCGCGAGACTGCGGTCCCCCGCGAGAGAGAAGTATGGGCCTGGCCAGGGTTCGAA CTCCGTTCCTTCGCTGCCTTCCTTTTATTTTTCTTCCTCATCTTCCTTCCTCTCTCCCTTGGTTCCATCATTAAA TCTTTAAGGGATTAATTCACAACTCTGTAGTAGGTAGGGGCCCTGGGACCACTTGACGGGCCTTTGCAGGCAGTT CTGTACAGAGTCCTAACCCGTAACGGGCCTCAACCCCGGCTGTGTGTGCGTGTGCTTGTGTCTGTGTGTCTTTGT GTGTAAAAGCAACGCATAAACATACCCAGGGCTTTCACTTATTTTATTGAAGCAAACAAACAAAAACAGCCACTG GGTTTGTCTTTTCCCCTACTCCTGCCTGAGCGCCGCCGGGTTTCTGAGCTGCTCCGGGCGCGGACCTAGCTCACC CGCAGCCGGATGTCGGAGCCGGAGCTGCTCCCCACCCGGCCTCGCCCGCGGGCGACAAAACCGTCCCTCTGGCCA CGGGAGAGCATCGCCTTGCCAAAATCAACTCGCATTTTCATGTATTCAAATGAGAAAGACTGAGAAGGGCGATTT CCCCTGCTGGGCAGTCGACAGCGTTGGAAGGAAGAAGTGCCCCCTAGGGCCTCGCGGAAACGGGAACAAACCTCC CTCGAGGCCCCCGGAACCGATATGGCGACCCCGCCCAGACCTGGGTCCCCGCGGCCGCGCGCGTCTCCCGCCGTT GTGGCCCCCGAGTTACTGACTTTTGTTCACACCGGTCAGCGCCTGTTGGAGGACGTGCTCAGCCCCAGCCGGTCC CTCCTCATCCAGCCGATCCCCCTCCTGGGGAGCGCG |
| (SEQ ID NO: 260) |

TABLE 7B-continued

Sequences of differentially labeled CGIs between bladder cancer subgroups relative to blood CGI: 20 range = chr14:56347822-56348040
CGGGCCTCGAGGATGCGAGTGTGAGGTCGACAAGATATCGTGGAAGAGAGCGAACGAGGGAGGCCCCCGTTGGAA
ACAGTTTCTGTGTTAGAACAAACGCCACCAAACGACCGACACTGCGAGGCCTGGAGCTACCTGGGCTGGCGCCGC
CCGAGCCCCGGGCTGCGAGCCCAGAGGCTGGGAAGTGATGGGACCTGGGGGCCCGAGCCGGAGAGTGCG
(SEQ ID NO: 261)

CGI: 178 range = chr14:60045486-60047933
CGGCGGGCGCTGTCGAGCACGGGGAGGTGCTGAAATAGTCCTGGCGTGCTGATTCAAGCTTTGATTGGCAGAGCC
ACCCGGTGACTGACAGGGGGTCTCCATGGCGCCCGCGCCGCCAATCCGCCCACCCCAATAGCGGAGCCAGCTCGC
CTGCCGGCGTGCCTGAGCCGAGCCGAGCCCGAACCCCAAGCCGCGGAGCCAGCACCTCCTCCAGTCGGGGTCGTC
CGCTCCCGGCCGTTGAGCCACCGCCGCCACCCGGTAGTGTGTCCCGCTGCCCCAATCCGCCTCATCAACAAGCGC
CTGGCACACTCAGCCAGGCCCGCGGGCATCTGCTGCGTGTCCCGCTCCGGGCTCAGTGCCCTCGCCGCCGCCGGC
ACTGCCTCGATGTTCCAGCTGCCCATCTTGAATTTCAGCCCCCAGCAAGTGGCCGGGGTATGTGAGACCCTGGAA
GAGAGCGGCGATGTGGAGCGCCTGGGTCGCTTCCTCTGGTCGCTGCCCGTGGCCCCTGCGGCCTGCGAGGCCCTC
AACAAGAATGAGTCGGTGCTACGCGCACGAGCCATCGTGGCCTTTCACGGTGGCAACTACCGCGAGCTCTATCAT
ATCCTGGAAAACCACAAGTTCACCAAGGAGTCGCACGCCAAGCTGCAGGCGCTGTGGCTTGAAGCACACTACCAG
GAGGCTGAGAAGCTGCGTGGAAGACCCCTGGGACCTGTGGACAAGTACCGAGTAAGGAAGAAGTTCCCGCTGCCG
CGCACCATTTGGGACGGCGAACAGAAGACACACTGCTTCAAGGAGCGCACGCGGCACCTGCTACGCGAGTGGTAC
CTGCAGGATCCATACCCTAACCCCAGCAAAAAACGTGAGCTCGCCCAGGCAACCGGACTGACCCCTACGCAGGTG
GGCAACTGGTTCAAAAACCGCCGACAAAGGGACCGAGCGGCTGCAGCCAAGAACAGGTCGGTACCTAGAGGCCTC
CGCGCTTTGAGCGCACCGGGGAGGAGGCGGGTGGAGGCACCTCTGGCGCCCTTACCCAGTCCCTGGCGACTCCAA
TTCAGCAGGAGTTGGGAGCGCGGTCTGTCTTGGGTTAAGAGCCCTGCGTTCTGGGCTCCTGGCCGGGAGTTCCCT
TGCCGGCTCTGCTTCCCCACCCGCTGGCTCCCCACGCCTGCGGGCAGCTGCAGCAGCTGGTCCCGGTCACCAAAC
CAAGGCTTCACTGGGACGGAGAGGGGAAGAGAAATAAAAAATTAAAATCCTACAAACAGTTAGGGACCCCAAGAC
CCAAAGCTAATTCTTGTCAGCCTGGGCACAGGCTCCTACTATTAATCGAAGCCTGGCTTATTAGCAATGTGTCGG
TTTCATGTTAATTATCATTTTCAAAGCCCAGGTATATCCCTCCCTAATGCTTTGAAAACAGTTTTCAATGGACTT
TTGAGAAATGGGAAGTCGAGTTTTCCTCTTCCCATGCGCTGCCTGCCTGCCACTCTTGTCTCAAAACAGCAAACTAGTC
CGTGGGCCGAGGCTTTTCGTTTCCCGGAGTGTGGATCTCGATTAGCCAAACATTTTGCGGAAGAGCCCGGCCTCA
TCCCCCAGGCCCAAATGCTCCTTACAATCCTTTTTGCCTTTAGGTCGGGCCGACCCGATCCAACGCGATCGCGGG
AGCACTTGCTCAGGCGTAAGCCCCAGGCAGACGCACCGTTAGAAATGGTATCCCATGTCCCTGGGACCGATCTGT
CCTTGTCACCCACACTTCGTTTATTTCCTGACAGTCCTGTAAATCTCCCAAAAGTGCACAACAAACAGGGAGGAC
ACTGCAAGCCCAGTATATAAAAGACCTGGGAGCTGCGGCGCTGAGAAAGGGCGCGAATCATGGTGGGGCACAACA
GTAGGGACCCGCGGAGGGGCGGCCGCGGACTCCTGCCCGACCTCTGTCGCCTTGCCGAGTAATCCTCGCCTTAAC
TGCTGGGGTCTTCGGAAGAACCTCTAGCCGCCGGGCTGGAGGGACGCAGGAGGTGGTGGGGGCGGGCGACGGGCG
GCTGTGTTACGAGCTGTGACCCGTGTTCCCTTTCTTCCCCGTAGACTCCAGCAGCAGGTCCTGTCACAGGGTTCC
GGGCGGGCACTACGGGCGGAGGGCGACGGCACGCAGAGGTGCTGGGCGTCGCCACCAGCCCGGCCGCCAGTCTA
TCCAGCAAGGCGGCCACTTCAGCCATCTCCATCACGTCCAGCGACAGCGAGTGCGACATCTGAGTTGCCCATCCA
GGATGCTCAGAAGCAGATTCCAGTGTAAAAACGAGAAAAACAAAATGAAAGAGGGGAAGAAGATGAGAGACCTGC
AAATCCAGCGCCACAGAAGCCAGGTGACCAGGGACCCGCGGGCTCGGGTTGCCGTTTCCCGCCCCACCCCGCGGC
CGGCCTGGCTTCACTGGCGCCCTTTGGCCGCGACCACGGGAACCAGCG
(SEQ ID NO: 262)

CGI: 54 range = chr14:60173732-60174416
CGGCTAGGCTGCGCCTGCATCAGGCGTGGTGATTGGCAGGCGCCTACGGCCCACGCAGAGATGGCCGCGTGGGGG
TCGGAGCGCCAACTTCTCAGCTCCCCTTCTCCCATGACCCTCACCCCCCACACCATCTTCAGCCGCCCACTGGGA
GCTTCCTCCACCCCTACCCCCCAGTGCCGGCGAGGCCCCCTGGCAGATGGAAGCTGCTGACTGATGGGGGCTGCC
GAGCGCGAGGGAGCTGAGTGAGGCCCTTGCGCCCTAGGCGGTTGCACCCCGGACCCCTGCAGCTGTGGACGCCGG
AGCTGTGCGCAGTCATCCTGAGCCAGCCCGCGGGGCCCGATCGGAAGGGACGCCTCTCCTAAGAGCTGGCCTGGA
GTCCTGGAGCCTCCAAGCGGGCAAGTAGGGGCCGCAAAGGCTGGGCTGGGCCTCCGCTGAGGCCCTCGGGGGCCT
CTGGGCCCTCATGGCCTGGAGGCCGCGCGGCCCAAGCCCCTAGAGCAGAGGCCGCGCTAGCCTGCAGGGGTCGAC
GCAGGGCCGGAGGCAGCGGCTTTTCCTTCCCACTCCGGGTTGACCCTAAAGACACGATTTAACGTGGCGGCGGCA
GCTGCCCACGCTGTCTGGAGGAGCAGGGCGCCTGGGATGCGGCGGCGAAACTGGCCCGGAGGGGGGCCCAGGCCT
CACGCGCCCG
(SEQ ID NO: 263)

CGI: 133 range = chr14:98781593-98783184
CGGAGGCTCCTTCCGTCCCGGCCTCACCTGGATCCCGGGAACCGCCCGCTCTGTCCCGCCAAGGTGGGCTGAGGA
AGACGGCGCCACTCATCAGGGCAATGGCGGCGGGCGGAAGAGGGATCCCCGTGCGCCCCCAGCACCCGGGACGAA
TGCCACCCCGGCGAAGCGACCCGACCGGCGCGCACGGTTTCGGGGAGGGGACCACTTCCACATTCCCCATGCCCG
AGAAGGTCACCCACCCGGGAGAGCGCCCAAGGGCCAGAGAGGAGGCGACTGGTGGAGGAGGGGCGGCCCCGTGCG
CACAAAGGGGCCCGGGGCCGGCAGGCTCCCCGCCCTTGACCTTGGGTCTCCGCCTCCATCCATCTCCGCCGGCTG
CCAGGGAAGGGGGCTGGCCCGGGGCCAGAGGCGTGCTCGCTGGGCTGCTGCTGGGCTGGGGACCGACGGGGGCGG
GGGGGAAAGGAGCCGGGAAAAAAGACTCCAGGGCTGCAGAGTGCTCCGAGGAAGCCTGCATTCCACCACCTTCAG
GAGCCGGTCCCGAGGCGGCTCCGATTCACTGCATGCCCCCCGCCCCCCAAAGCAAAAGTTGCACGGATGCACGAG
GGAAACCCCTTCCCAAAGCTAGCCCTTCGACTCGCCCACCCCCCGCCTTCCTCGGACCCAGGCCGAGTGGGGGAG
GGGAGTGTCAGGGGAGGAAGAAAGGAGCGCGCCTTCCCAGCGAGGCCAGACGCGGGCTGGGTCAGCTGCGCCTCC
GCCCGCCCCTCGCCGCCCGGCTCAGGCAGCTGCTCCATTAAGCCCCCGAATTATGCATGGACCTTGAGCCCTCTC
GGCCCTCCCGCCCCACCAAGGCACAATCAACGTGCGCAGCGGGCGCGGGTCAAAGAGAGAGGGAAGGAGGTGGAC
GATGGGCGCAAGGCCGTGGGCGAATCAGAGGCCGGCGGCCAGGCGGGGGCCAGGCGCGCCCGCAGGCCTGGGAAC
AGTGCCGAGGAGCCTCCCGACCCGGCCAGGGCCAGCCGGGAAAGGGGCACCGCTCGCAGGGGAGGCCCCCGCGCA
GTTTTGAAGTTGCCAAAGTGTCCGCGCCGTGCCGGGTGCGGGGTCCGGGAGATGCAGCCGCCCCCGCGGAGCTCT
GCGCCCCTGGCCTCGGGGAAGGCCATTGTGTTCTCCTGTGTGGCAATGAAGGGGGCTATGGACCCCAACCATTGA
GCCCTTGGAGGGAGGGGCCTGAAGACCCCTCGGGCAGGGCGGGGGAGGCTGTCTTGCGGGCGGCGGAGAGGATGG
GTATGATTTGCTCGGGATAGGCACCGTCGCGGGGAGGGGAGGAGGCCAAGCTTGAGGAGGGGCTGCTGGAGATGG
AAGGAAGTGAGAGGAGACTTGCAAGTTGCAAACGTCGGGGAAACCGGAAAATTGCAGTAGCGGGGAGGCAGGTGG TABLE 7B-continued Sequences of differentially labeled CGIs between bladder cancer subgroups relative to blood CGCCCAGAGGTTCGAAAGCAGAATTGGGAGGACTTCGATGTCCACCTCGCAGACAGTGACCCAGGCCCCAGAGGG
CTCCGCAGCCTGGAGCCTCGCGTCCCGCCTCCCCGCAACACGCTGTTTTCAGCGTTCCAGACCACAGCGCTGCAG
TCTACGCTGCCCTGACG
(SEQ ID NO: 264)

CGI: 248 range = chr15:50867751-50870991
CGCCAAAAGAATGAGCGCGGGAGGGGGTCACAGCAGCCAGTTCGGCCAAACATCGACGCTGCTCCGGCACGCTCC
AGCCCAGCGCCTGGGATGTGTCAGAGGTACCTGCGAGGAACATTTGCGTGCGATTCCACGCACGCGTTGCATCCC
TCTTCCCAAACCCGGATCGCTGAACTGAGAGGTGGCGCAGAGTGTCTCACCAGGTGCGGGGATTTCTCTCCGCCT
CAGGCCGTACGAGCTTCCCTCGCTGTCCCTGAGCGCAAATGAGCCTCTTCAGTCGCCGAGGCCCGGCCGCTTAGC
TCTCGGAGCCTTCCACAGCCCAACACCCTGAGCCCTGGAGTAGGCAATTTGCTCCCACAGCCCTGTGCTGGCCCT
TCCAGGCACAGGGAGTCCCCCTTCTAGGGGTAGGGGCGGGCGGGATGAAGCGCACCCAGCCCTCTCTCCTACCCT
TCCTCCTTTGGTCCCTTCGGCTTTCGTGTACCTTATCTCCCGCGCGCCCAGCTCCTTGGCCGGCTCACCTGCTAA
GCGGAGCGCGGACATGCGCTGGAACTCCGGCTCCTGCAGCCACTTCCACATCCTCCGGAAGGTCTCCCGGCCGGA
TTTGAGTTTGCTCCAGGGTTTGGGGTTGCGCAGCAGGTCCGAGAGGGTCCCCTGGGAGCGGCAGAGCACCCTCTG
CGCGAAGATGGCCTGTGGGATGCTGTAGCGCTTGAGCTCGGTGGTGATACGCTGCGCCACCTCTTTGGTATTGAT
CTCTTCCATCTGCCCTGAATTACTTCCATTGCTGACCTGCGCGCCGGTCACCGAAGGGTTGGGCTCCCGGGCTGT
GCCCAGGAGTTGCCCGTGGCCCTGGGCGTTCAGGTGGGCGTGGGGATGGTGCGGAGGAAGGCCGTTGATGGGCAC
CATGCCGGCCGAGGTGGGCGTGAGGTGCTGCTCCCCGTGGCGGCCGAGCATGGCCGGGTGGTGGGCTTCGAAGCC
GTTGGGGGTGAGCATCTTGTCGGTGGGCATGGCGGCCCCCGGGTGGGCATAGTGGGGGAGCCCTTGCTGGGAGTT
GTGGATGCTGCCCAGACCGGAGCTGGAGAGGGGCGAGAGGCTCTGGCCCATGCCGGCCACGTCCTTGTGGTAGGG
GGTATAGAGGTTATTCATGGAGGCCAGCCCGCGCTCATCCCGCATGAGCGTGAAGCTACCGCTCACGTTGCCCGC
CAGGCGCTGGTGGTGGTGCGGGTGGTGGTGGTGATGGTGGTGGTGGTGATGGTGGGGGAACTTGTCCGAGACTGT
GGAGATGGGAGGCAGCGGCTGCAGAGGGGTCAAGGTGGTGTAGGTGGTGGGCATGCTCATACCTGGGGGAGTCTC
GCAGGCCATGGTCATGGTGGGATGCAGGGGGCCGGCCAGGCTGTGCTCAGGGGCCCGGTGGTGGTGGTGGTAATC
TCCGCCGCCGCTGCCGCCGTCCAGCAGGGACGCCATGCCCATGGAGCGCGGGTGCGCGGGGGGCAGGTGGCTGCC
GCGGTGCGCCACGGAGCTGCGCGCGTGGGGGCTGCCGCCCAGCAGGTCGGCAGGGGCGGGCACCGGCTCATGGCT
CACCCCGTGCAGCTCGCCGATCGCTTCCATGGTCAGCTGCGCGTTCATCGTGATCCGGGCGAGCAGGCGGCGGAC
ACAACATCGATGTGGCCAGGCAGAGGCGGCGAGGGGCGCACGGAGTCCGGTCTTCACATCGGCTGCTGGCGACTG
TTGCCTTCCTTCCTCTCACTGTGGGGCTCTGTCTCTCTCTCTCTCTCTCTCCGTGTGTGTGTGTCCGTGTGTGCG
TGTGCGTGTGTGTGTGTGTGTGTGTCTCGCCTTCCCTCTTACCCCCCACCTTCCCCTCTGCGTCCTCGGCTTTTT
TTTTTTTAATATTAATTTCCAAAGAGGATCCGCGCCGTTGGGAGAGCGCAGTGCCCCAGCCCGCCCGCCTCGGCC
ACCTCTCGCCCCTCTCTTTCTTAAAATTCTGAGGTCTCCGGCTCCCCTGCCGCGGCCCGCGCGCCTGCCGCGTCT
GCTGCCTGCCCGCCCCGCTGGCCAGCTTGAGCCATGGCTCTGTTACTGTTACAGACTCTGTGGCCGCGGTTCGGT
AGCCGCCGCCGCCGCCGCCGCAGCGGCCCGCCCTCACGCCCGCCAGGCGCAGCGCGCATGCGCGAGGCCCGCCCC
CGCCCCCTAGGTCGCGGCGCGCCAGGCCCTTGGCGTCCCGGTACAAATGAAGGAGGGGGCCCAGCGCCTTCCCTG
CGGCGCTGGATGGCCAGGGAGCTGCGGGCACGTGCGAAAGATTGGCGCAGAGCGCGACCTGGGGCCGCCGCTGCA
ATCCCAGGAGACTCGCGCCTGGCTCGCTCGCCTCCCTTGCTTGAGTGGGCTCTGTCCTCCCAGCCCGGGGACGCT
GCAGCTTGCCCGGGGAGCTGGGGACTGTGTCATCACCCCTTCGGCTCTAGCCCACTAAGCTTTATTTCCCGGGGG
GCTGCTGGGAGTGCGCTTTCCCACCCTTGAATTCACGGCCTATTGGGGGATGGGGGTTGGGGTGGGGTGGGGTGC
AGATTGCTTAAAGGGCTGGGTCCGTTTGGCGGCCGTTGACCCGGCACCCTTCGTCCTCCCAGATACATACTTGCC
CACCCTTTCTCATCCATGCCCTGGGGAGAGGAGTAATCAGTGCCAAGAATCCCAGTTCGGGCCATACCTCACTGT
CCCCCGCCGCCTGGCTCCTTCTCCCGCTCAGCTCATAATTAAGGCTGTGCGTCCGCTTCGCCGATGACTCGGCCT
GTGGAGGGGGGCGAGGGAGAGCGGAGGGAGTGCCCTGGAGGGTACCCATGTTAACTTCCGGGTGCTGGTGGGGCC
GTGGAGGCTCGGGCCGTCCCTGCGGTTACTCCCAAGGCCCTCCTGCTAAAGCACCCGGAGGCGGTTGCTTTCCAG
AAGTACTGACGCAGACAGGGTGGACGCCGGCGCGCGGGTCTCCGCTTGGCCCCTAGGGACGCCCTTTTCCCGGCG
TCCCCGAGAGACGCCTCCAGATTTGAAAATCAATTCAGCTTCGGGAGTAATTTCGCCCTTCCCACAGTCACGCTC
CAATCTGGAATCGAACCTGGTCTTTGGGCCTGGTGGGGACGTGTGCGGAGGCCCCCAGTTTGAGACGTACACCCG
GCCGCCACATGCCGCG
(SEQ ID NO: 265)

CGI: 226 range = chr15:58083428-58085812
CGCGCGGCTGCTCCATCTGTGAACGTGAGTGGTCGCCTGGCTCCCTCTTCCGCGGCGGCCGCTTCCTCATACCTT
CACACGGCGCACACCGGCCGGCGCGTCCAGCTGCCTGCCCAGTGGCCGAGGCTCTTCCCCCTCGCCCAGTCTTGA
GCTGGAAGTGATTCCTATTGGCCAAGGTGTCCATGTAAATAGGTGTGAAAGAAACCAGAGCTGGCCGGGCTCTCC
CTTCTCGCTCAGTCCCCTCCCTCTGCAGCCCCCGCTCCCCCTCCTCTTCCTCCTCCTCCCAAGGCGATTGTCATA
TGATAGCTAAGAAGTGGCACATTAATGAAGCGCCGCTACAGGGGTCTTTTCTGCTCCTGTCACCGCTTAAAACTA
TCAGATGGTTCGAGGGAGGACATGGAGGCAGCCACCTAGCTCAGCGGAGACGCGGAGCCCACAGCAGCGCCCTCC
GGAGCCCTAACACGTCGCTGCGCACCATCCGCGCCGGGACTCCGCAGCCGAGCTCGGCCGCCCGCAGGACGCTCCA
GGAGCGTCGCGGACCGGGCGGCACGGGACGCTGCGGGGCTGAGCTCAAGAGCCCAGGTTCGCGCCGAGTCCAACC
GGACCCGGACGCTGCGCGCGGAGTGCGCGTCGAGTGCGCGCCGAGAGAGAAGCGGCGCGCAGCGGCGTCCTCCCG
GATGCGGACGCGCAACTTGAAGCAACTTTAAGGTGAGCAGCTCTCTGTTCCGTCCCTGCCCCCTATTCTGGCCCC
AGTACCGACTTACTTCCCGGCTATCCTCGCGCCGTTCGCCGGCTTCCCCTCCCGCGCCCACTAAGCCCGCAAAGT
TGCTGGCGAAAGAGTCCGGGCGCTGGCTGATCGAGCGCCGCAGGCCCCACCCCCGACCCCCGAAGTCTGTTACTC
GGTCTGGCTGACCCCGCCGGTGTCTCTGTGCATCCATGCTACCTTTCCCTATTACCCACCCCCTTCCCAGATCCG
AGCAGTCCGCCGGCCCGCGCGGACCCAGAGCAAGAAGAGGGCGAGGAAGAAGATGCCTCGGCCCGGCCGCAACAC
GTACAGCGACCAGAAGCCGCCCTACTCGTACATCTCGCTGACCGCTATGGCCATCCAGAGCTCTCCCGAGAAGAT
GCTGCCGCTGAGCGAGATCTACAAGTTCATCATGGACCGCTTCCCCTACTACAGGGAGAACACGCAGCGCTGGCA
GAACAGTCTGCGCCACAACCTCTCCTTCAACGACTGCTTCATCAAGATCCCGCGGCGGCCGGACCAGCCAGGCAA
GGGCAGCTTCTGGGCGCTGCACCCAAGCTGCGGGGACATGTTCGAGAACGGCAGCTTCCTGCGGCGCCGCAAGCG
CTTCAAGGTGCTTAAGTCCGACCACCTGGCGCCCAGCAAGCCAGCCGACGCGGCGCAGTACCTGCAGCAGCAGGC
CAAGCTGCGGCTCAGCGCGCTGGCGGCCTCGGGCACGCACCTGCCACAGATGCCCGCCGCCGCCTACAACTTGGG
CGGCGTGGCGCAGCCCTCGGGCTTCAAGCACCCCTTCGCCATCGAGAACATCATCGCGCGGGAATACAAGATGCC
TGGGGGGCTGGCCTTCTCCGCCATGCAGCCGGTGCCCGCTGCCTACCCGCTCCCCAACCAGTTGACTACCATGGG
CAGCTCGCTGGGCACCGGCTGGCCACACGTGTATGGCTCCGCCGGCATGATCGACTCGGCCACCCCCATCTCCAT
GGCGAGTGGCGACTACAGCGCCTACGGCGTGCCGTTGAAGCCGCTGTGCCACGCGGCGGGCCAAACGCTGCCCGC
CATCCCCGTGCCCATTAAGCCCACGCCGGCCGCCGTGCCCGCGCTGCCTGCGCTGCCAGCGCCCATCCCCACCTT TABLE 7B-continued Sequences of differentially labeled CGIs between bladder cancer subgroups relative to blood GCTCTCGAACTCGCCGCCCTCGCTCAGCCCCACGTCCTCGCAAACAGCCACCAGCCAAAGCAGCCCCGCCACCCC
CAGCGAAACGCTCACCAGCCCGGCCTCCGCCTTGCACTCGGTGGCGGTGCACTGACCCGCAGGAGCCCACGCCCC
CTCTCGTTCTCCTCCCCACCACCTCACTCGCCTTCCCTGGCTCCCAGTCCTGCCGGCCCCCACCTGGGACCGCCA
CCCTAACTTGTTCATTTCACCTTCGGCCAACCCGCCTTGCCCCAAGAGAACTTTGTTTTGGACCCAGGAGACCAA
ACACAAACTTGCAGATGGGCCGAGAGGCGCGTGGGAGTTGTCCTCGCCCCCACATCAAGGAAGGCCGGGGCCACC
TGAGCCGAACCATCCCCTCCCTGAGGCCCCGAAACCCCCTCCTATTTGACCGGCGGGGGAAACCCTGTCACCCCC
TCTTCGCCGAGAAAAGCGCGTCTTCCCTCCGCCCAGATCGGCGGAGCCCCGAACTCTGCG
(SEQ ID NO: 266)

CGI: 22 range = chr15:62984853-62985116
CGCGCCCCTCTGGCCTCCATCACTGTCGTGCCGGTCGTGGGGACAGATGGGAGGGAATTACGGTATTTACAGCTG
CTCTTCGCCGGCTCTTGCTCCCCCGCGTGTCGACAACCGAAACTGCAGCGAGGCCCAGAGGCCTCTGCCCACTCC
CCTCGGAGTTCCAGGAGGACGCTAAGCGCGAGAAGCCAGGCTCAGGGAAACTGAACGCCCATACGCTCCTAGTCC
CTCTCACCTGGATCCTCTGCGTCAGGTTACGTGCTTGCG
(SEQ ID NO: 267)

CGI: 541 range = chr15:65902540-65909629
CGGGACGCAGGTGCAGGGTGCTGGACGCAGGTGTGCGGCCGCTTACCTGGGGCGTGCAGGCCTTGGGCTGCGGGG
AGGCGGCGGGCGCCGCGCGTGGCCCGCGGGCGGGCGGACCCGGGGAGGGCGCTAGCGACTGCGCGGGCGGTGGGT
GTGGCGCCCCGGCTCTCAGCTGTCAGGCGCGCCTGCCCCGCCACTCGGGCTGTGACCGCGCCGTCCCCGCCGCCG
CGCCATGCGCTCCAGGCTTCGGCCTCTTCTTCCGGCCAGTCCCCGGCCTCGGGGTCAACGGCTCAGGGTTCGCAT
CTCCGCGCCCGGGGTCCCGGCGCCCCGTGCCCGCTGAGAGCGGGAGGGGCCGCGGGTGGGAGCGCGGAGAACCAG
GGAGCACGGCTGTGCGCGCGCGCGGGGAGGGGCCGCGCCGTCACCCGGAGAGCCCGGCGGATCCCGGACTCCCGC
CCGCCGCTCCTCCCGCCGCGCACCTCCGCTCACCGCTCGCCCGGCTCCAGCCGCCGCCGCACTGTGAGTACCCAC
GTCCGGTAGCCCGCCGCCCCCGCGCTCTGCTCCTGCAGCTTTTTTTTCGTTTAGTTCTGATTTGGGCTCCTGTGG
CTGTTGTTTTTATGATTATACCTAAAGACACCACCGCCTCGCTCCCACCACTGCCAGTCTCCCGCTTCGCTGCCC
TCCCCAAGCTCGTCCATCTAGCTCCGGGAGCCGACGGGGGTTCCTCAAGCTGCTCTGGCTGCTGCTCCTTGTCGC
TGCATATGGCTCTTCGCCTGTGCTTTCCGCTTTGGCCCCCGAAATTCCGTTCCTTTCCTAGGGACCCCCTTCTTC
TGACTCCGGGCCCGGACCCCCCTCCTCTCACTCAGGGAAAACCGCGCAGGGACCCAGGACCCTCAACTGGGGTAC
GCTCTCGGCTCGGGCGCTGTCTTCACTGTATGCGGGCCAGGCATAGTTGCCGATTTCGAGAAACCGAGAAGCTGT
CATTTCCCAGCGCTGCGCGCCCTCCAGCCACCTCCAGGAGGGCGCGAGGCTTGTCAGCCGGGGAGTTAGGACAGT
GTTTTTGCCTCCTACAATGATATAAAGGACTTCAACGCGAAATAAGGGTCAACTTATTTTAGTTCGATCCTCGGA
GATAAAGATGAAACAGACAGATAATACATAAATAGCTTGATACTTGAAGAAGGTACAAAACAGATGAGAGAAAGA
GGAACGAGCCGGCAGAGACAGCTCAGGGACAGATAAGATCGACAAATGAGGGTCTCCTAGACAAATAGAGAAGAA
GGGAGAGAGACAGATAAACAGAAGATTCCAGTCTCCTTGCTGAAGGCTTTTGAACTGGGATCCCCTGTCTGGAGC
TGCCCCTCTGAAAACGGAGTTACATTCAGGGCCGACTGCAGGGGAGGAGCCCTCAGGGTTGGGCTGCCCTGGCCG
CAGGAGCGCCTGCAGCCTTGGGCCGGATGGGAGCCTGGCTTGTCTGAGGACATGTGGCTGGGTCAGGCGACCTAG
AGGGCCCCAAACATCAGTCCCCAAGTACCCCCGCTGCTGAGGTCTGCCTGCACAGCTCCCTCCCTGCCTCAGCCA
GAAAGCAAAGTGCAAGGACCAGCAGCAACTTGTGTGCCTGGAGCCTTGCAATGGCTACGAAGATGGCTGAGATTC
CTTCTAGCCCATATGAGCCGGGACAGCGAGGCATGAAGGATACTCAGAGAGGTGATGCCCCTCAAAGAGGAAGCC
CAGAGCCCCGAATCCTGCAGTTGGCCCGAGTGGGAAACGTATATCTGAAGGAGGAAAGCTCAAGGAGTGGGCGAC
TGGAAGCTAAGAAGTGGATCCCAACAAAGTTCCTTGAGAACCTCTCTGTCCCACACGTTGACCTCGGTGGAAACC
AGCTTTGGTCTGGAATACAGCTAAAAATGCAGAAAATGTGGTTAGAACTGCAGGATCCTGGTCTCACTAATAGCT
GGAAAGAAAACGGTTTATATATCCAGCCGAAATCTTTCTGCTCAACGAACGCGGGCGCCAGCCGTGAGAGGAGAA
GCTCGGGTTTGTGGAAACTGGCAATGTTGTCCCCTGAAGCCGGCTCGGGCACCAAGCTGGGTGCGGTGGGGGCCG
CGCTAGGTCCGGGTGCGCACCGAGCGCTTTGGAGAGGGTCAGGTTCAGCACCGCGAACAGCGGTAGCCTCCGCCT
CTCTCCTTCCCTGGCAGACACGGTTCCCTCCTCCTTCTCCTCACCCCCCTCCTTCTCTTCACCCCCCTCTACCCC
CTGCTGTCTGGAGATGGGCAGTGACCGCCCCTCCCCCCTCCCCACCCCTCCTTGCACTGCCCCCGCCCGCCCGCG
TGCATGCGCGACTGAGCAGAGGGGCGGCCGATCCCCGAAGTCCGGGCTTCAGGACCCGGGCCGGCAGCACCGGCT
GCGAGGGTTGCCGAAGGCGCACGGATCTGGGCGCTGAAAAAGCCAGGATTTGGCAATGGCTTTGCTGTGTGGCCT
TGGGCAAGTCACTCTGCGTATCTGGGTTTCACTTCCTTCCCAATCCGAAAACGGGATTGGGTTCCTTGCAGCCCG
GGCATTCCTGAGGTCTCCTTTACCCCTTCTCCTCCCCCAAGCCCCGGGGGCTGTTGTTAACGGCGCCAACATGGG
TCTGAGTAACAAAAGACGCCTGTCCAGGGGGTGAATGAGTTTGGACTCCCCACTGCCAAGTATCCCCCGCGCGCC
CAACTCGGAGCGCCCTGCTGGGCGGGCCCGAGCCTCGGCGGCGGCGCTGAAAATGGCTCATCTGCTCTCTGCTTT
CTCTATTTCGCAGGAGCGGCGGCATGGAGGCTCTCACCACTCAGCTGGGGCCGGGGCGCGAGGGCAGTTCCTCGC
CCAACTCCAAGCAGGAGCTGCAGCCGTACTCGGGCTCCAGCGCTCTCAAACCCAACCAGGTGGGCGAGACGTCGC
TGTACGGGGTGCCCATTGTGTCGCTGGTCATCGACGGCCAGGAGCGCCTATGCCTGGCGCAGATCTCCAACACCC
TCCTCAAGAACTACAGCTATAATGAGATCCACAACCGCCGCGTGGCCCTGGGCATCACGTGCGTGCAGTGCACGC
CGGTACAGCTGGAGATTCTGCGTCGGGCCGGGGCCATGCCCATCTCGTCGCGCCGCTGCGGCATGATCACTAAGC
GAGAGGCCGAACGCCTGTGCAAGTCGTTCCTGGGCGAGCACAAACCACCCAAGCTGCCCGAGAACTTCGCCTTCG
ATGTGGTGCACGAGTGCGCGTGGGGCTCGCGTGGTAGCTTCATCCCTGCGCGTTACAACAGCTCTCGTGCCAAGT
GCATCAAGTGCGGCTACTGCAGCATGTACTTCTCGCCCAACAAGTTCATCTTCCACTCGCACCGAACACCCGACG
CCAAGTACACGCAGCCCGATGCCGCCAACTTCAACTCCTGGCGTCGTCACCTCAAACTCAGTGACAAGTCGGCCA
CAGACGAACTGAGCCATGCTTGGGAGGACGTCAAGGCCATGTTTAATGGCGGCACGCGCAAGCGGACCTTCTCCC
TACAAGGAGGCGGCGGAGGCGGTGCCAATGGCGGGTCGGGTGGGCAGGGGAAGGGTGGTGCTGGCGGCGGTGGCG
GCGGTGGCCCAGGGTGCGGTGCAGAGATGGCCCCAGGCCCGCCGCCCCACAAAAGCCTGCGCTGTGGCGAAGATG
AGGCTGCCGGGCCTCCGGGGCCACCTCCACCCCACCCGCAGCGCGGACTTGGCCTGGCGACTGGAGCTAGTGGCC
CGGCGGGCCCAGGAGGGCCCGGTGGCGGCGCCGGCGTACGAAGCTACCCGGTGATCCCGGTGCCCAGCAAAGGCT
TTGGGCTCCTGCAAAAGCTGCCCCCACCACTTTTCCCCCATCCTTACGGCTTCCCTACGGCCTTCGGCCTATGCC
CCAAAAAGGACGACCCGGTTTTAGGCGCGGGCGAGCCAAAGGGCGGTCCTGGCACTGGGAGCGGCGGCGGCGGCG
CGGGGACAGGCGGGGGTGCGGGGGGCCCGGGAGCCAGCCACTTGCCCCCGGGGGCAGGGGCGGGCCCGGGCGGCG
GCGCCATGTTCTGGGGGCATCAACCCTCCGGGGCAGCCAAGGACGCAGCGGCAGTGGCTGCAGCGGCCGCCGCCG
CCACTGTGTACCCGACGTTTCCCATGTTCTGGCCAGCAGCAGGCAGCCTCCCGGTACCGTCCTACCCCGCTGCTC
AGAGCCAAGCCAAGGCCGTGGCGGCAGCCGTGGCGGCGGCAGCGGCGGCGGCAGCGGCAGCTGCTGGCAGCGGTG
CCCCAGAGCCCCTGGACGGTGCCGAGCCAGCCAAAGAGAGTGGCCTCGGCGCGGAGGAGCGCTGCCCGAGCGCTC
TGTCCCGCGGGCCCCTGGACGAAGACGGCACGGACGAGGCGCTGCCACCGCCCCTGGCCCCGTTGCCCCCGCCGC
CCCCGCCGCCCGCACGCAAAGGCTCCTACGTGTCGGCCTTCCGGCCGGTGGTCAAGGACACCGAGAGCATCGCTA TABLE 7B-continued Sequences of differentially labeled CGIs between bladder cancer subgroups relative to blood AGCTCTACGGGAGCGCCCGGGAGGCGTACGGCGCGGGGCCTGCTCGGGGGCCGGGACCCGGCGCTGGGAGCGGCG
GCTACGTGAGCCCGGACTTTCTGAGCGAGGGCAGCTCCAGCTACAATTCCGCCTCGCCCGACGTGGACACCGCGG
ACGAGCCCGAGGTGGACGTGGAATCCAACCGCTTCCCCGACGACGAGGACGCCCAAGAGGAGACCGAGCCCAGCG
CACCCAGCGCAGGGGGCGGCCCAGACGGTGAACAGCCCACTGGACCCCCTTCCGCCACCTCCTCTGGCGCGGACG
GTCCCGCAAACTCTCCCGACGGCGGCAGCCCCCGCCCCCGGCGCCGCCTCGGGCCACCCCCAGCTGGCCGGCCCG
CATTTGGGGACTTGGCAGCCGAAGACTTGGTGCGGAGACCTGAGAGGAGCCCGCCAAGCGGCGGCGGCGGCTACG
AGCTGCGAGAGCCTTGCGGGCCCCTAGGAGGCCCCGCGCCGGCCAAGGTGAGCCCCGCGCCCGCCCCGCCAGTGG
CGCCTTCCCACCTACCCTGTGCGCGGCAGGGCTGCGGGGCCGGGCGGAGAACGGGAATTTTGTTCCGCGCAGGCG
TGGGAGCAGCAGGCCTCGGCCACTCTCCGCAGGCCCAGCCTTGGGCGCGCTGCGAAACTGGGCCCACCCGCACCC
TCCAGTGAGGGTTTCGAAGGGAAGGGAAGCTGGGGGCGGCGGGAGGACTGGGGAACTTGTGTGCTTTGTTTTTGT
TGATGGGAATGGGGAGGAGACCGGCTGAGACTGCCAGACACAGAGACAGAAAAGGGGTGTGGAGAAAGAAAGAGG
AGGTAAGAAAGGAACCCAGAGCCAGAGAAAAGCGCTCGCCCGGGTGGGCATCAGAGCCCCAAGGAAGAGGAGAAG
AGAGGACAGTGTGGCCTCTCCCTGAGTCGGGCCCCAGCAGTACCGGGTCCCCGGAATCTCCCACCACCCCAACTC
GCAGTTTTCCGAGTCTCTTCGCACTCCCGCCTTGGGAACCACAGGGTTCGTTGCTGGGAAGCTGTCTCGGGACCG
CGTGCGGAGCGGGAGGGGGGCTCTCAAGCTGGCAGGGCCGGGGCTTGAGGGGCAGGATGCAGCCAGGCTGGAGTC
GTTGGCCATTTTGAAAGTGAGTGCGCATACCTGTACATTCGGTTCATTAAAACACGAATCATTAACCGGATGCGA
AAGGCGTCATTTATGCCGCGGACGGGGCACTGGCGGGAGGGAAAATGCCTAAAAGGAGGCGGGTGCAGAGGGTGG
AGGACACTTTGAACGCCCCTCGGCTTGGGAGCCGCTTTGTGTTTAGAGTAATTTTCCCGAGGGCGCTAACAATTA
CCCTGAATCTACAAGGGGGCAAGGGTGCGCCGCGTGCGTCACTGTGCCCGCTCAAGTCCAGCGGGCGCACCAACC
TTTGCCACTCCGTCGGCTTTCCCTCTTGGCCGCGGGGTAGGGCTGGGCGTCTTTGGGCCGCCGCAGGGCGCCACC
CTAATCGCCTGTCATTTCTCGGCCGTCGCAGGTGTTCGCGCCCGAGAGGGATGAGCACGTGAAGAGCGCGGCGGT
GGCGCTGGGGCCCGCGGCCTCCTACGTCTGCACCCCCGAGGCCCACGGTAACGCCTGTCGCGGCCGCTGGCCACT
GTAATGGGGGAACCGCAGACAGAGGGCCGGGGTCAAGGAAGGCCTGCGAAGGAAGACAAGGAGAGAGACGCAGAG
AAAGAGGGAGAGGGAAAGAAAAATAATGAAAACAAGGAAGCTAAGCTAGTACTCCCAACAACTTCCAATCTTTAG
TTACTTAAAAACAACAGTGACAACGCCCTCTCCACCACACGCACACACATGCTGCAGTACACCCAGACACGGCGT
TAAACCCTTAACAAAATCACGCCCGACACGGCCTTCAAATCCTCTCATTTATTCAGCAAGTGTGTTTGGCCGCGG
GGTCCCCTTTGGCTAGGCCGGATCGGGGCGGAGGATGGGGGCACATGGCCGCGCGCTTGGGTACCCCAGAAGCGC
CAGGGTAGCTGAGGCCCATCGCGGGGTGGTGGGGGCCGCCCTGCACTTGCGCGCCTTACCAGGTTCCTCACAGAG
GAGGGGTTGGGGGCAGCGGAAAATCGGGCAGGTCGAGGCAGCCGAACCCCGGACGATGTCCCCCCACCCACCCCG
AAGGTCGCAGCCTGGGCCGCGTTCTCAGCAGGAGTCGGGCGGACAGACCCGGCGGCCACGCGCGCTCGCGGTGCC
CCAGTATCTGCGCGCGATGTAGGTCGCTCGTCCCTGGTGGGCTCGGCTGCTCGCCTAGCTCTTTTCCAAGGGGCT
GGGGCGGGGGCCTGAAGCCCGGAGATGAGCAGACCAGGCGCGGGGGTGGGGGGTGCCCGGCCCAAAGCCTCAGGG
CGCGCTCCTGGGCGCACAGCCGGGAACCAGAGGCGGCCACGACGCTTTTAATTAGGGCTGGGGCGCCCCGACCGC
GGCAGCTCCGGCAGTATCCGGGTCACGGTTTCTTTGCCTCTCTTGAAATTCGGTTTGTTGCCTTCAAGAGCCAGA
TAAGGAAGACAATCACTCGCCCGCCGATGATTTGGAAACG
(SEQ ID NO: 268)

CGI: 216 range = chr15:72206924-72210097
CGGGAAGTAAAGCCTCGGGACTTTGGTTAAGCGCGCCCCACTGGCGTATCGCGCCGCGGGACTGCAGAGCCGTGA
GCAGCGGTCGCCTTGGTGCAGGGTTCCAGCCACATCTTCCTCGCCCAGCCAGCACCCTCTGCCGTTGACCCGCCT
CTGCGCCCGGCAAGCGGCTTCCAGCAGGGGGCGCGCGGACCAGGCTTGGGCCCTAGAACAGCGCGGATGGAGT
CGCTGGAGCAAGTCCCCAGATCCAACCGGTTTCAACCCTCCCCACCCTCCCGACGCTCCGGGTTCGCGACGTTGA
AGTTAAGGGTCGATCCGCAGAAAGCGGCCAGGGGCTCCAGCTCTCCATTCCTGGGTCTGTCTGGGGTCGGCTCCA
GCCTGGTTAGAAGCCTTAGTCTGGATTCGGCAGATTCTGAATCTGGGACCCTCTGCGCTAGCGGCTTGGAACCTT
GTCACCCTCCCCTCCCCCACCCCTACTTCCACACACCTGATTAGTTGTCTGTTTCTTTAATGATCAAAGACGTGG
GCGGCGGCGGGATGAGGTCTTGGTTCCCGGCTCCACAGCCCTCCCTAACTGTCATTATTAACGTTATAAACATTA
GACCCGCTTCTGCGCGCCGGACGGCGCCGGACGAGGTGCGCGCAGTCTTCTAGCTGAGCTCGGAGGCAGATCCAG
AAGTCGCGGCTCCCACCCCAGGCCTCGGCGGACTCTGCCTGGGGCGACTCGGGCTCCAGCCCTGCCCGGGCGGGC
ACTGGGCTCTCCAGGGTCGAAGGCAGGGGTAAGGGGCGTCTTTCCCCCAGGGCAGCCTCCGGGAACAAAAGCATT
TGCTGTAGAGTGAGCTAGAGCCTCCGGGCCCGCGGGAGTCAGCTCCCGCCCAGGGGTGGTCACCGCGTCCTTAAC
CACCCCAGGAGCCCCGTCTCCCTGCCGAACTCCTTGGCTTCTGCAACCCTGTCAAGACAGCAAGGAAAGGGGGTC
TTCCCTGGTCCTCGGGCCCCGAAGTTTCGGGGTTGCTTATAGGACGGGTTCCTGCAGTCCAGGGAAGCTCTGGGC
AGATAGCGAGCCCATTCTCCCTTCCATTACCCAGATTCTGCCTCCCTGCGGAAGGCAAAAAAGAAAGAAAGAAAA
TAGGTAAAAACCGGCGGAGGGCCTTGAGCCTCCCCGCCTGGCGCCCCTCACTCAGTCCCGAAAAGTCCCCTGGAC
ACGCCATGCCGGACCGGACTCAGCTCCCGCTGCTGGGCCCCTGCCTCCAAATATCCTTCCCAGGCACAGGCTCCC
AAGACCGCCCCCTCAGGGTTCCCAACACCCGGACAACTGCCCAAGACGCCGCTCCCCGCCCCCACCCCCACCTTG
TTCGGCAGACAAAGAAGGGTGTGCTGGCCCCGCCGTCTGCCTCCTTCTCCCGACCCCACAAGGCCTAGAAACCTC
AGGGACTCACCCCGGGCTAGGGACCCAATCCTGGCTGTCCCACCACAGGATCCCCGGCAGGGACGGGTCACAGTG
CTCTCACCCCTCGACCATTTTCGAAGACACCTTCCCTGAAAGGCGCCTTGCGCCCTCCCCATGGGTCGGCGGGGG
GGGACTCCAGGCCCGAGCAGGCGGTGTGAAGTTCTGTGTTCTGAACTGGGGCTGAGCAAGATGCGATGGTCTCAG
CCCGCTGGGCCGCCCGTAGCGACGGCAGGAGTAGGGGAGAGGGAGGGACGCTTGGAGTGTGAGCGCACCAGTCTG
TTCATATTTAATTTACAAAGCAGCCTCGGAACCCCGGGCCGGGTGGTCTCTTTAGACGCTGCGCTCTTAGCCTGT
CTCTCTTCCCCACCCCCTCCCCTAGCTCATTAAGATGCTCAACACTCAAATCGGGGTATTGATCTCCACGGAAGC
CCCAAACCCTCGCCATCGAGAGACCCCCATGGCCCGGGGTGATGGCTGTGGGGCTTGGTGCTCCCAGAGAGCTCA
GTGGCTACAGAATGGGTGGGGATTCTGCGTGTCTCCCGGAGCCTGAACCCCTTTCCTGGTTATGGCCGGTAGCTG
TCTCCAGGGCTAACGTGGGCAGCGCAGGGGGGCGGAAACCGGGTTTTAGCCAAATGCCTCGACATCGCCGCGCCT
CCGCCTCCTCGTCGCTGAAAGAAATGTCGGGGTTTCATCAGAGCTAGGGAGCGACAGTCGGGAACAGCGAGTCTG
CCGAAGCCGGCTGTTGTGTGAGGGTGTGAGACGGCGGGGCGGTGAGGGGCCACCGCGGCTTGGGGGATAGTGCGT
GTGGGGTTGACCGTGTGTCTGCTTGAGAGGCTGTGAAGATATGGGGGGCAGATATGGGAGAAATGCTCGGGCCTG
AAGTCCCCAGCCCACCGTGCTCAAGAGTAGCGGACGTTTTGCCACCATCCTTGTCTGTGCTACTGTCTGCTGCAG
CTTCCGTGCCCCGTTCTCCTGGAGCAGGCAAGACCTGGAGTGAGGTGCTTGGGTGCGCTCGAGAGAGCTTCCCCC
TGCTCCACCTGTCCCGCGGTGCGCGCAGGCCAACGCGTCGGGCAGTGGGCTTCAAGCGCTGGTTTAGCCACAAAA
GACCAGAAGTAAAGAGTTCCGGCTTAAGAGGCTGGGCAGGGCTGCGGTGGGCTGGGGAGGGGGGTGTCCCTTCCC
AGCACGCCCTGCAGGGCTGTGCGTTCTGGTGTCGGGTTAGACTAGCAGGCGGGGCGGGGGGGTTGGGGCGGCGGG
GCGGGGGAGACTAGGGCTTATATCAGCCCAGATCCAGGCAAAAATGGTAGGGAGGGTGCGGCGCTCTGCTAACAC
TATCAATTATGCATCATGTTGAACGTGGCTTCGGGGAGGAGGCGGCTAGCAGCGGGGGTGCGGAGGGAAGGGT
CCGCGCGAGCTCGGCTGCGCGCAGCTCAGCGGGTCCCGCTCGAAGTCTGTCGGTGCCACCGCCTGCATTTGCAAA TABLE 7B-continued Sequences of differentially labeled CGIs between bladder cancer subgroups relative to blood AAGAGTTTAAAGGCAAAGACACGCCTTCCCCCCCCACTTCAGCCGCGCGCCTTTCCTTCCCCCAAATTCCTCAAA
GATGGTTTGTCTCACGTGTTGCAGGGCGTAAAAGCGGCTTGCATTCAATTAGCAGCGAAGCTCGCGGGCGCTGGC
GGGACAGGCGCGTGAGGGTGAGTTCGCGTGAATGTGTGTATGCGTGTGCGAGAGGAGAACGGTAAGTGTCCCGGG
TGCAGGTGTGCCCGTGAAAATGCG
(SEQ ID NO: 269)

CGI: 32 range = chr15:74414579-74414893
CGGAGCTCAAAAGCCGGACGCTACTGGACGAGGCTTAAAGCGCTCGCCCCAGCGCGGGGCCGGTGAGGAACGTTC
ACCGTGGACCATGGTCGAATAATGTTAGCGTGCACTCGGGGCCTCGCCCTAGCCTTCTGCAAAGCCTCGGCCTGC
GCCCTCGGCTGCATCCGTTTCGACGCCAACCAACCTCATGCTCTTAGTAGAACGGCAGTAGCGACCGCGCCCTCA
GGCCCACAAGCCCGAAGGTCTGGGCAGGGTCTGGAATGGCGGTGGAGACACTTTATCCGCAGGCGTTTCACCTCG
CGCCCCACCCAGGCG
(SEQ ID NO: 270)

CGI: 109 range = chr15:88158407-88159577
CGGCATCTTGGCCGGGTTGTAGGAGCGAGGGAGAACGCGACTGTAACGCGGGCGTTGAGCACCTAGAGTTCCCCT
TCCTCTTCACTGAGAGCTGCGGCGGAGGCTTTAGACCGAGGAGCGAGATCTAAGGTTAAAGAAAGGGCCTCTGAG
CCCAGTGTTGGCCAGAGACCCCACAGGCGGGCCGGGTTCGCCCTTTGCCTTCGGCCGCGCCCCACCCACCAGGGA
CAGAGTGGCCGCGGCCGAGCCGGGTCCACCCGCCGCAGCTTAGCTCCGCTCCGCCGCCCTCCCCGTCCGTCCTCC
CCAGGCTCCCGTCGCCCTCGCCCACCCTGGGGCCCCCTCCCCAGATGGGAGCCCCTCCGACCCCTGCGAGGCCCG
CTGGGGACCCACTTGACCGCGAGATCGTAGTGGGAGCTCGGCCAAAAGAATTCTTCGCTTTCCCTGGCCCTCAGT
TTACCCATCTGGGAAGAGGGGCGTCGCGGCCGCAGAAGTCCAGCTCCGCACGCGCCAAGCGCTGGGTCTGCAGCT
CCCTCGGTTCCCGCGCACCCAACTGCCCCACGACCCCTACCCGCGCCCGCAGCCCCCGCCCTCCCGCCCCACTTG
CCTGGGCCGCCGGGCGCTGGAACCTGGACCCTGGACCCTGGCGGGTTCCGAGCTGCGCCGCCGCCGTCCCTGCCC
CTCCAGCACTGGACTCCTCCTTTCCCGTCTTTTTAAAGGGAAGTAACCGGACCCGACCACTACTCCACCCGATTC
ACCCCTAGCGGGCCGCCCGCCCGCAGCTCCGCCCGGGCTCCTCCCCCGTCCGCCCGCGGCTTCCCGGGAGCCCCC
CAGGGCTCCTCCGCTCCTCCGACGGCCCGGCCTTCCCCCCGGGGCCTGGGATGCACCAGGGCTCCTGCTGCCCCC
GACGGGGTCCCTGTCGCCGCAGCCCGCGGGACCCGCCGGCCACATCTGGACGGCATCTGCCGCGGGGGAGGGGCT
CAGAGCCTCGCCCTGAGTGTCCCGCAGGGAGCCTTGTGCATCCGGGGCAGGAAGCCAGCGCATCCCGTGCAGACG
GGTGGTGCAGATAACGGACCCGCCACAGCACGCAATTCAACTTTCTTGGTACCTGGGACTCGTAGTTCAGAAGGC
GCAGTAGCACGACCTTGCGAAAAAGCACCGGAGTCGGGAACACGCG
(SEQ ID NO: 271)

CGI: 21 range = chr16:727072-727328
CGCCACCCGCACGACGGACGTCGGCACCACACGAGCTGCCCTTGGCAAAACGCGTTGTCGGCTGCTGGGATGGAT
TTCAGGTTAAAGCAGAGTCACCAGGCCGACCACTGCTTACCTTGTTAGCATCTAGAACCTTCTTCAGCTCCTCGT
GGCTCTGCTGGGTGATAAGCACGGTCTCTGCGGAGGTGATGCAGCCGCTGCACGCCAGGCAGTCGTTTAGCGAGA
CCTTGGCCTTCTCCAGCCTCCGGGTCCCGCCG
(SEQ ID NO: 272)

CGI: 61 range = chr16:47868915-47869809
CGGGTCCACTCCTCACTCGCGAAGTCCCTATCTATCTCTGTGGGTCCCGGAGGCACAGGGCTGCAAGGGCGCCCG
CTAGAGCTGCTCCACGGCTTACCGGATTGCATGCGGAGAAGAAACGGGCCCGGGTTTCAACAGAGGCCCCGTGCT
CCGTGAATTTCTAACTCGAACCAGCCGCTGGGATAAATCCGAGAAACGTTGTTTATTGTGCTATTATTAACTTTC
CCTTCTCCCCACGCCCCTAGAGGAAATAAAATTCATTCCTGAATATTGGGCCAGGAAAACGTTTCTCTGAAAGGA
ACCACAACTGCAGGGGACCACCCGGCTGCAGCTCCCAGCTCCCGGCCCTTCGCCCTAGGCTGCCCACTCGCTCCG
GCTCCCGACCTCCCCGCTGCCGAAGCAACTGGGTCAGCCTTTCAGACTTAAAACGAAGTCGTTTATTTCATTTTT
GCTTTCACATTATGTTCCGATACAATCAAAACTCCTGGACGAACCTCTTGAATAAAGTCCTGTGAATGAGCGGAA
TCATAGGTCCTGGGCGCCCGAGTATGCGGCGGGTGGACTCCGGATTCAGAGGCGGTGTATAAAACATACGCTGCT
TCGGGAACTGCGAGGGGGACGCGGTGGGAGACATCCGGGGACAGAAGGCCTGAGGAGTCTGCCGCTCCAGGCAGG
GTCGTTTGGGTCCTCAAACTGGGACTATTCCTGATGCATTTGGAATGCAAAGAAAAAAATCAAACTTCGCTCCTG
GGCCGGCGGCCGCGCCTGGCCTAGCAAGATTTCGGCCACATTTCTTACGTTTCCGCCAAAGCTGTGAACACAGGC
GAATGCAGTGCTGGTCCCCGGCCTGGCGCAGGAAGGAGCGCAAGGCCGGCTTTGCAAGGAAGCCCTCGCG
(SEQ ID NO: 273)

CGI: 179 range = chr16:53527803-53530347
CGCGAAGGCTCGGGGCTGCGAGCCGAATGCCCGCCGAGCTGCCTGGGAACGGGAACCGCGCACCCGGGAACGCCA
GGCGTTTCTCTTCATCCAGGAACGGCGCGGAGAGCCTCCGGCTGGGGAGCTAAACCGCTGGGGACTCCGCGGCTG
CTGCCTGAGTCGCTGTCCGCTGCCCGCATCCCTTCCGCCCTGGGCCTCTGCACGGTCTGCGGTTTTCTGTGCGCA
CTTGGTCTTCAGTACTAGCACCCAATTACGTCTGGGTTTTTCTTCTTTACAGAGCTGGGTTTCGGTGGCCACCAG
CTTTTCTGGTGTTTAGTGACTCTGAGTTTGGAGGTGGCCTACCAGGCAAACGGGGATTCAGGGCATTTAGGAAAC
GTCTTCCGCGCTTAATCCCAGAAGTGGTTGCGTGTCCGTACGATCCCAAGTTCCTCCCGGAGCCTCTTCTTTGCT
GCGTCTCGGGCCCTCCAGCAGGCGAAGCCTCTTAGACGCGCTGGGAAACTTCCGGCGTGTTCGGGGCTCAGGGT
TTCTTCTCAGGCATGGATTGGGGCGCAGAAGTTGCGCGAGGCAGCGCCTAAGGTCCCGAGGTGCTGAGACTGTGC
TGGCGTTTGCCACCTGCCCCTGGCTAGGCCGTTTCTGGGCCCCAAGAAACGCCTACCTTGGCACTTAGGGACCAG
AAGCCTCTGGATGTCTAGCAACAGGGGTCACGGGATCACTGCGTGGGGTCTCTGTAAGCAGTCCCCTGAGGCAGT
GCAAAACCGGAAACCTGCTCTGTGCGGGGCCGAATCAGTTCATGGGATTTGGGAGTCAGGAGAGACGTCTTTCTC
CTCCCAGCTCCTACACTCCGGGTACCAAGGCCCGAAATGCCGTTCCCCCAGCCCGGGTGCGGGGTCTGCAGCAAG
GCCTCCTGATTTGCAAACCCCTCCGGGCTGCTTATTCCTGGTGCCATGCGCAGCCCTTGGGACCTAGAAGATTGT
GGGGGAGGGAAGGTCGCACGTGCGGTTTTGGCACCGACCGTGCCTCCTAGTCCACCTGTCCCCCACAGCTAGCTG
CCAACTCGGACGGAAGCGCGGAACAGCGCAATGCAAACCGCCCAAAGTGAAAGGAATGTAATTGCGCTCCCATGA
CAGAGCCAGACGCGGATGCAGTTTAGGAAGGGCGCCGCCTACCGGCCCCTGGGAGCCATGCGATTCGAAGGGAGG
GGGACCTAGAGGAGACCCCCGCTATCCCCCCACCCACCGTGGGGCCTTAGCTTTGAACTCCGGCCCGGACAAACT
TAAACTGCTTCGCCACCCCAACGCGCCACAGCCCTGGACCTAAGACCCAGTTAGCATTGGGAATTTGGGGAGCAG
GGCCCACGACTAGAACAAAGTTAACCCTACCGGTTCCCGCCACGGCTTCGGCACATTTCAAAAAACCAGGCGCAG
GCAATTGAGAAATACGCTGCCGGCTGAAACAGCCTGCGGGTGGGGCTGCAGCCGTGCGCGCCCGGCAGTTCCCG
TCCCGCATCAGGTGTACGCACTTCCACTCCTGCGGGCCCTTCCACGCTCCAACTCTGGACCCCGCGCAGTTTTAA TABLE 7B-continued Sequences of differentially labeled CGIs between bladder cancer subgroups relative to blood TCTGCGGTTTGGGAAATGGGGGTGCTACCGTGCAACCGCGCCCTGAAAGACCGTTTTGGTCTTAAGAGCTTTTGG
CCTGTGGGGTGGACATCTGTAGAAAAAGGAAAAACAAAACAAAAGTAACCTCCCATTGCGTCGAACCCTCCTATT
CCGAAAAGAACTTTAATGAGGTTGGCTTGGCAAGGCCTGCGGTGCTTACCTCGGCTTCGCCCTACCCCGCCAGAA
GCCCTCATAGGTTGTATCCACTGGTCTCCCCCAGGTGCAGGGTTATTAGGGGAAAGGGGGGCGCGCCCTCGGGCT
GGATCTTTGTTTCCCTCGTCGCCCGGTCATCAAACAGGAGGGAAATCGGGCCCGACTGGGACCTTGCTGCCCGCC
TTCCCCTTAAACTGGCTAAAGCTTCAGGACTGTCCCTAGACCCACCCCGCGGGTCTTCCTTTGTGTCCAGGGCAT
AGCCGATCTCCTTTTCGTTTTCACGAGAACTGCGACTTGGGCCTCGGGCACTAGGCGAGCCCAGGTTGTGGCCTA
ACAGCAGATCGCCTCGGGAGCTTGGCTGCAGCTCTGCCCGCACCTCCAGCGCTGGGCGGCCTCTCGGGGCCAGTG
GGGATCTCTGGCCTCGTGTAGGCCACGGGCCCCAGCCCTGGGTCCCCAAGGCCGCTCGCCGGGCAGCGCTCGTTT
CCGGCACCGGGACGAGCCCAGCGCGCTCAGACACCACTTTCCCGGTGAAATCTGCTTTTATTTGCTCCGAGCAAA
CCTCGGGCTCTCAGCGCTCCCGCCTGATGGATGCAAATGTAAATGTGCACTTATTTAATTGGATCAGGCCCCAAG
ATAAAAGAGATAAACGGCTCCCCGCTTGCTAACTTATTTTCCTAGGCATGCAGCGCCGCGTGGAGGGGAAGCTAA
TGAAGGAGCAGCGCGGTGCTGGGCACTCGAGCTCTCCGCAGCCGTGGCACGCTGGCCGGCCGGCCCCGCG
(SEQ ID NO: 274)

CGI: 78 range = chr16:66071900-66072846
CGCAGGCCAACGCGAAGACACGATGATCCCAAAGACCTTAGTGTCTTGGCGGGGGGAGGGGGAAGAGGTGGGGGA
CTTTTCCGCTTAGCTTCCCTAAGGGTTGCTACGCGACAGCTCTCGGGCTACGTCAGGGTAAAGAGGTTTGTATGG
CCACACCTCGCACCGACCAACTACCCCCGAAACACCCCCTCCTCCCAAACTGCAGGGTGAGCACAGCGAGAGAAA
AGGTGGCCCAAGCAGAGGCGAACAACTGCGGTTCTTAAAGCCTTGTTTGAGTTTGGGCCCGCGCCGAGCCACAGC
TAGAGGTAGATCCCGCTCCTGCGCGTCCGCTATCAGCCCCAGGATTCCCAGAGAGGCCTCTCAGGCCCTTCAAGA
CCCCCCCTTCCGGCTTCCCGGCCTACACCTCTGAACCCTCAGGCCCCGGACAGCCTCTATCCCCGCCTTTCGCGG
CCCCGGCTCACCCTCTAGCGTCTCGCACTGCACCAGGTTGAGGTAGTCGGCCTGGCTGAGCACCCCGGCCTTCAG
GCCGCGCACCAGTCCCTCCAAGTAGCCATTGTCCACGTTAAAGTAAAGCTCCGGGAAGAACGACATGGCTGCTGC
GGGAGCGGCGGGACCGGAGAACCAGGACCGGCCGGCACGAATCGCGACTCCCCAGGTCAGCTGACGCTGCGTCCT
CAGCGGGCTGTCAAGTGCGTCAGGTGACGCGCAAGCGCCTCACGTGACCATAAGGGGGCGTGGCTCTGAGCGGTG
CCCGGCTTCCGGGTGGCTGCGCGGAAGCGCGGTGCAGGCGTGGGCTGGCCCTGCGGCGCCTGCGCGCTAAAAAGA
GGAAGTTTGAGGCCGGCCGCTTGGTGGCGCCTGTGGCCGCAGGGATTTGACTGGGCCTTCTCTAGCTTTCCCCGG
TTTGCTGCACTTGACGCTGCAGGGCGGGCGGGGTAAAGAAGGGAGCG
(SEQ ID NO: 275)

CGI: 39 range = chr17:38089258-38089793
CGGGGGTTGGGGGCACGGAAGGGGAAGCTTCGGTCGCTAAGTGGGCCGGCCTTTGGAAGGGTCTGGGAGGGGCCA
GCGCTGACTAACAGTCGGTTTCCCTACCCTAGACGGCTGCGACGAGGAGCTGGTGGGTCCCCTGTATGCACGCTC
CCTGGGCGCCTCCTCCTACTACAGTCTCCTTACTGCGCCGAGATTCGCCAGGCTGCACGGTGAGCTCCGCGGAAC
ATCAGCTGCCAACTGGCAGCGCACCGCGGAAGGGTGGGGGCCTCCGGAGGACTTCGGGGAGAGGGATAGCCGGTT
AAAGCTCCTGTCCTTTCTATAGGCATAAGCGGGTGGTCACCACGGATTGGGGATCCGAATCCCTGGCTCCAGATA
GACTTAATGAAGAAGCACCGGATCCGGGCCGTGGCCACACAGGGCTCCTTTAATTCTTGGGACTGGGTCACACGT
TACATGCTACTCTACGGCGACCGAGTGGACAGCTGGACACCGTTCTACCAGCGAGGGCACAACTCGGTACTCTGG
GCGCCAAGGCG
(SEQ ID NO: 276)

CGI: 69 range = chr17:44074360-44075233
CGGCGCTGGCGCAGGCGGCCAGGAGAGAGCAGATGAACCGTTCGTTAGGAGCAGCGAGGTAGTCGTGAGCGCTGA
GATCCAGAGACTAGGACCCACTCCCTCTCTGAGCAGCAAATTGGGAAGAAGATGCTCACTCGGTAAGGGCGAGGG
AGCCCGGCATGGCGCCCCACCACGGGCTCGGTCTATCTGCGCGCCAAGATCCCGCTTGGGGCGAGGCGTTGGGTC
AGCGTTTAGAGCCACTCCCTGCGCTGGTGGCTGGACATAGCCTCCCTATCCCACCTCATCTTCCCCCATCCCCGA
CAGAGGAGGTTGTGAATCTACAGGCCCTTGACGTTGAGGCGTCGGAGGGCGCACCTTTGTAATTGCGGCCTCCCT
TCGCCCCTTAAGTGCCGCTTCTGGGCGCCTAGGCTGGATATGAAAGCCCCGTTCCTAATCCTCTGCTCTGGTCCC
CTCCTCTGGACTGCTGGGACTCTAAGCTAGGCCCTCCCCAGGTTCCATCACTGCGGCGCCAACCCGCGGCTGGGC
TGTCCGCAAGAGGGAGTTGAAGGCGCGCGGAATCCCGAGGTGCAGCTGACCCTCCTCTCAACGCCGACTCTGCCG
CTCCCGCCCGGCCACCTCCCTGTCGGGCAGACTTCCTGTTCTCCTGCTCACAGCAGGGAGGCAGTCGCCGAGCCG
GTCAGCAGCGTGCACGGAGATCTTCACTCTGCGCCCAGCCCCGGGACACAGGTGCAGATCTCCAGCGGAGCACTG
CGGAGTGCGCGCCGTCGAGCACTAGGGAATCCTAGACGGAGGACTTGGTCCATTCCACGCAGTCCCAGGCAGGTC
CGCAGCGGAGGGACGCAGCGGTCTCCAACTCCTGGTCACGACTTCGGCG
(SEQ ID NO: 277)

CGI: 269 range = chr17:67627870-67631593
CGACTCGGCTGACGTTTTTGACCCGGCCAGGAGGCAAAGACCAAAACGTCAGAGCAGTAGCCCTGTTACTGAGGA
GCGTCGGCAGGGTCGCGGGTAGAGGGGGCTGGAGAATGACTTGTCAGAGCTCAAGGTCGATGTGGCGCGGGGCGG
CCTCGAGAGCGCCGGGCTCCTGCGTGGCCACGGCCGCCGCTGCCAACCTTCGCGGGGACTTAGCTTTGCTTTCCA
TTGACTCCCTTTGCAAAAGCGCAGCAGAATCCTGACCAGCCGCACCAGCCCCGGCGAACCCGAGCATGTTAATCT
ATTTATATGGATTATTACGGAGGAACAGCGGGCGTTGAGTCACCAAAACATTTGCTTCAAAAGACTATTTCTAAG
CACTTTTGCAGGCAGGCAGGCTCGCTCCAGGCGCGTAAACTCGGCTACGCATTAAGAAGCGGCTGCTTTTCGAAT
ACTGCAAACTCCAGCTAAGTCCCCGGTGCCGCGGAGAGAGCAGTGAAAAGAAATGTCGGAGGTGGGGGTAGATCC
TAGTCTAGACACACACACTTGCGCGCACACACACACACACACACACAAGATTCGCGCGGAGAAGGCACTAAAATT
CTGGCATTCCGAGAGTACGACAAACTTACACACTTGGAAGTCCCGGGTCCCCCGCCTTCCCCGCAGCACCCCCCG
CCCCCCCACCCTACCGTCCGCCCTTTGGCTGCGATCCCCTCCCCTCTCCTCCCCTCCCGCCTCGTCACCCAGCCC
AGTGCCACAATCCTCTCCTCCCTCCCCAAAATCGGGTCCAATCAGCTGCCTGCCAACCCTGGGACTGCTGTGCTGTG
ATTGGCGGGTGGCTCTAAGGTGAGGCGGAGTATTTATTAAAGAGACCCTGGGCTGGGAGTTGGAGAGCCGAAAGC
GGAGCTCGAAACTGACTGGAAACTTCAGTGGCGCGGAGACTCGCCAGTTTCAACCCCGGAAACTTTTCTTTGCAG
GAGGAGAAGAGAAGGGGTGCAAGCGCCCCCACTTTTGCTCTTTTTCCTCCCCTCCTCCTCCTCTCCAATTCGCCT
CCCCCCACTTGGAGCGGGCAGCTGTGAACTGGCCACCCCGCGCCTTCCTAAGTGCTCGCCGCGGTAGCCGGCCGA
CGCGCCAGCTTCCCCGGGAGCCGCTTGCTCCGCATCCGGGCAGCCGAGGGGAGAGGAGCCCGCGCCTCGAGTCCC
CGAGCCGCCGCGGCTTCTCGCCTTTCCCGGCCACCAGCCCCTGCCCCGGGCCCGCGTATGAATCTCCTGGACCC
CTTCATGAAGATGACCGACGAGCAGGAGAAGGGCCTGTCCGGCGCCCCCAGCCCCACCATGTCCGAGGACTCCGC
GGGCTCGCCCTGCCCGTCGGGCTCCGGCTCGGACACCGAGAACACGCGGCCCCAGGAGAACACGTTCCCCAAGGG TABLE 7B-continued

| Sequences of differentially labeled CGIs between bladder cancer subgroups relative to blood |
|---|
| CGAGCCCGATCTGAAGAAGGAGAGCGAGGAGGACAAGTTCCCCGTGTGCATCCGCGAGGCGGTCAGCCAGGTGCT<br>CAAAGGCTACGACTGGACGCTGGTGCCCATGCCGGTGCGCGTCAACGGCTCCAGCAAGAACAAGCCGCACGTCAA<br>GCGGCCCATGAACGCCTTCATGGTGTGGGCGCAGGCGGCGCGCAGGAAGCTCGCGGACCAGTACCCGCACTTGCA<br>CAACGCCGAGCTCAGCAAGACGCTGGGCAAGCTCTGGAGGTAGGACCCGGCGGGGGCGGCGCGGCAGGGTGGGCA<br>TCGCGGCGGCTGGGGGCGCTGGTCAGGGCTGATTTGCCCCGCCCCGCCTCCCATCGCCCGGGAGTTGCCGTTCCG<br>GGAGCCGGCGGGATGGGGTTGGGAGTGGGAATGGGGTGTAACTGTGGCTCAGAGTTTGACAAAGTTCTTGGGCTG<br>CTCGCGGGGACGCGGAGGAGGGGGGTGGTAAGTGGAAGAGGTGAGGGAGGTAGCTGGAGGATGGACGAAGACTGG<br>TGGGAGACGGAAGGAGGGGGCTGCCAGCCTGCTCTCCAGTCGCCTGGAAGCTCAATCGGGGCGGGGAAGTGAAAC<br>TTGCCTCCCTCCTACCCGGCCTCTTAAAACTGCACTCTCTCGTGCAGCCCCACTGTCCACGGAGATGGGGCAAGG<br>GAGAAACCGAGGTTGGAGGAGACCCTTGGCAGGAACTGGGAGGCGGGAGGAGGGAGGCTACTGGAAATAGGTGGG<br>AGTGTATGGTGGGGGGTGAGAATTGGGGACCTTCTTGCAGCTTAAGTAATTTGGGGGAAAGTTTTCAAAGGGGGT<br>TGGGGTTGGGGGCGGTAAGTCGAGCAGCAAAGGCGTTTAGGGGGCAGCACCGGGAGTCGTTTTCATCTCCAGCGT<br>TTCCAAAATAGAAATAGAAGGGGAGGGGAGGGAGGGGGCGGGGAGTGACCGCTCAGGTCAGACTGCAATAACTTA<br>TTTATTTATTTATTTTTAAGAAAAGTTATGAGCTGTGGTTGCAGGCAGGAGGGAAGATGGAGTTGTGTGCAGAGG<br>AAGCCGAGTGGTCTGGGTCGCCGCCTCCTCCCCGCCGACCTGACAGTTTGGCGGATTTCACTGACCCCTCTCCCT<br>CTTTTTCTCTGTGCCCCCCGCCCCGCCCCGAGCAGACTTCTGAACGAGAGCGAGAAGCGGCCCTTCGTGGAGGAG<br>GCGGAGCGGCTGCGCGTGCAGCACAAGAAGGACCACCCGGATTACAAGTACCAGCCGCGGCGGAGGAAGTCGGTG<br>AAGAACGGGCAGGCGGAGGCAGAGGAGGCCACGGAGCAGACGCACATCTCCCCCAACGCCATCTTCAAGGCGCTG<br>CAGGCCGACTCGCCACACTCCTCCTCCGGCATGAGCGAGGTGCACTCCCCCGGCGAGCACTCGGGTGAGTCGCCC<br>CTCGACCCCACCGGACAAGCTATCTCCGTCCCGCCTGGCACACCCCCTGCCCTCCGCCTGGGAGATTCTTCGTGG<br>GGACTTTATGCTTCCCGGGAGGGACACACTGCCCTTTGCGCCCGTCCCGCTCCCCTCTCTACCCAGAGCCTAAGA<br>GGCATCCAAACAACACACACACAAACACACACACCCCAACTCAATCCCAGCATCCGAAGAGATTAACTTTTTTAT<br>TGGGAGGTAAAATGCCCTTAACAGCCTTACAAGACCTCTCCCTTCTTCTCTGCTCCCCCACCCCAAAAGCACACA<br>CAGGGCTCTTACACAAGTAGCAATTAGGTCTTCCGGACCCTCCGGGCCCCAGACCCTCCCCTGATAAAAGGGGGC<br>TGTCCAGTGTGTACCGGCGGGTTAATCATTGGGCGACTTATCTCCGGTGCAGCGCGCCTCTTGCGCGGGTGCGGG<br>CCCTTATTACACTTTAGCAGCGAGGGAGGGTCCCCGGAGGGTGCCTAAGACTAGGGCGTCTGCACAGCCCTTGTT<br>GATTTTCTCGTGCTTGTTCTTTTATTGTCCACAGGGCAATCCCAGGGCCCACCGACCCCACCCACCACCCCCAAA<br>ACCGACGTGCAGCCGGGCAAGGCTGACCTGAAGCGAGAGGGGCGCCCCTTGCCAGAGGGGGGCAGACAGCCCCCT<br>ATCGACTTCCGCGACGTGGACATCGGCGAGCTGAGCAGCGACGTCATCTCCAACATCGAGACCTTCGATGTCAAC<br>GAGTTTGACCAGTACCTGCCGCCCAACGGCCACCCGGGGGTGCCGGCCACGCACGGCCAGGTCACCTACACGGGC<br>AGCTACGGCATCAGCAGCACCGCGGCCACCCCGGCGAGCGCGGGCCACG<br>(SEQ ID NO: 278) |
| CGI: 260 range = chr17:71582000-71585125<br>CGCCTCCGCCCCGCGTTTCCTCCCCCCGATCTCCCAGGGGTCCTCTTTTGAGGGCACCCCAGCCCCTCGACGGTC<br>CCGGGATATCCTGCACCCCTGCCAGGCTGCAGGGAAGCGCCGAGGCGCGCGGAGTGCGAGGTCCGTGCTCCCTGC<br>GGCGCGGCGCACACGCAGGGTCCGGGGTCGACCCCTCCACCGCTCCGGCGTCTGCCGGGGAAGTCAGTCCGCCTG<br>GTCAGCCCAGAACCCCCGACTGCGGGGGCTGGAGCTCGGAAGCAGGTACAAGCGCCACTCTCCGCCTGCGCCGTG<br>GAATGCGCGCCGGGACCACTCCGCAGCCCTTCCCCCAGCGCCGCCGGCCGCTGCTGGGGACAACCTCGCCCTCCT<br>GTCTCTTGCTCCTCCTCCTGACCCCAGCGCACCCCCATCCCCGCCCCAGATGAGGCAAGGCTCCCTCCGCCTTCA<br>GCCCGGCAGAGTCGCACTAGGAGTTGCAGCGGCCGCAGCCCCGGGAGCTTCCCGCTCGCGGAGACCCAGACGGCT<br>GCAGGAGCCCGGGCAGCCTCGGGGTCAGCGGCACCATGAACGTCTCGGGCTGCCCAGGGGCCGGGAACGCGAGCC<br>AGGCGGGCGGCGGGGGAGGCTGGCACCCCGAGGCGGTCATCGTGCCCCTGCTCTTCGCGCTCATCTTCCTCGTGG<br>GCACCGTGGGCAACACGCTGGTGCTGGCGGTGCTGCTGCGCGGCGGCCAGGCGGTCAGCACTACCAACCTGTTCA<br>TCCTTAACCTGGGCGTGGCCGACCTGTGTTTCATCCTGTGCTGCGTGCCCTTCCAGGCCACCATCTACACCCTGG<br>ACGGCTGGGTGTTCGGCTCGCTGCTGTGCAAGGCGGTGCACTTCCTCATCTTCCTCACCATGCACGCCAGCAGCT<br>TCACGCTGGCCGCCGTCTCCCTGGACAGGTGAGCCAGCGCCTTGGCCTCCCTGGGAGATGGGCATCCACGCGGGG<br>GATGGAGCGGGAGGCGGGACTGGGGACCAAGAAGGGACGCGCAGAGTGGGACAGGACACTAAGAAGGCAGTGGAA<br>GACAAGCGGGCGCGGAGGAGGAAAAAGAGGAATAAGAATGGGGGACCGTGGTGTCCCTCGGTTAGATGCGTCCTG<br>GGGCCTGGAAGCCTGGAGAATGTGGCTCTCCAGCGCCGCCCGTGCCTGACAACGCGCAGCGTTTCCCAGTACGAC<br>GCGTTTGTGCGCGTTCATCTCGCTTGAGCTTAATGCCCTCCGTGAGGGTGGGATAGGACAAAGTGCCCAATATAC<br>AGAAGAGTTGAGTTCCTAAGTAACTCGCTCAGAGTCGCCAGCCAGGGATCGGGTGCGTGAAGTGACCGTCTGTCT<br>CCTGCAGCCAACTTCAGGCGCCTCCACTGCGCTCGCCTCCAAGCCACGGTTTGGTTGGTTGGTGCAGCTGGCTCA<br>GGTCCAGGCTGTGGATCTTGGGTCCTTTGCAAGGATCCACTCCGGAGTCCCAGCGAGCGTGCCTAAAGGTCCCTA<br>GCTCAGTCCCAGCCCACTCTGCCTCTCGCCTCCAAACAAAACAAAACAAAATAAAATCCAAAACAAGTCGGGGCC<br>GGGAGAGGAGCGTGCCCTGGGGTTCTTCCTCCCCAGCCAGAGGAGAGCGAGAGACGCACATTCGGGAGAGCGCGG<br>GACTCAGGTGGAGCTTGAAAGGACACTGGGATGGTTCCTGGGGAGGAAATCCGGGTATTTCCCCTCTCCATCCTC<br>TGGAAAAACAGAGAGGCGAGGCCAGACTGCCCCCACACCTCCTGTAGCCACTGAGCGCGAAGTGCGTTGGTTCCG<br>AGCGCGCTGGTGGGATCCACAAAGCTCGCATTCTCTCAGGAATCCCCTGAGAAATTAACTGTCCCTTGCCCAACA<br>TGTCTTCTCCAGGCTGTCTGCTAGAGCCTCAGGCGCCTCCGCCCTCCCTCCCGCGGCACCGTCACCAGTGGGTAG<br>TCACAGCCTCCCGGAGCCCATAGCCGGTTCTCCAACCTTTAGTCTTCAGTGGCTTTGGGGTGCCCTCTCAGTGGA<br>GACTGTGGTTGCAGTCCCCGGGGGCAGCGGGAGAATGGCTTGAAGGCACACCTTTCCTGCTGCCGGGCCCGCCCC<br>ATTTCCAGGCTCCGCTGAGTGTCTGGGACACGCTGGGAGGCCCCCACCTCCGCCCTCACGCCGAGCCTCACCCCC<br>ACCTCCTCTGTGTGCGGTGTAACCATGCGCTAAGGACCTTCCTCGAGAGCAGCCTTGGGACCGAGGTGCAGGGGT<br>CGCGGCCCTCCAGCATGAATGTGCCCGCTCAGCCGACGTCTCCCTTCCCGGTCTGACCGCAGGTATCTGGCCATC<br>CGCTACCCGCTGCACTCCCGCGAGCTGCGCACGCCTCGAAACGCGCTGGCAGCCATCGGGCTCATCTGGGGGCTG<br>TCGCTGCTCTTCTCCGGGCCCTACCTGAGCTACTACCGCCAGTCGCAGCTGGCCAACCTGACCGTGTGCCATCCC<br>GCGTGGAGCGCCCCTCGCCGCCGCGCCATGGACATCTGCACCTTCGTCTTCAGCTACCTGCTTCCTGTGCTGGTT<br>CTCGGCCTGACCTACGCGCGCACCTTGCGCTACCTCTGGCGCGCCGTCGACCCGGTGGCCGCGGGCTCGGGTGCC<br>CGGCGCGCCAAGCGCAAGGTGACACGCATGATCCTCATCGTGGCCGCGCTCTTCTGCCTCTGCTGGATGCCCCAC<br>CACGCGCTCATCCTCTGCGTGTGGTTCGGCCAGTTCCCGCTCACGCGCGCCACTTATGCGCTTCGCATCCTCTCG<br>CACCTGGTCTCCTACGCCAACTCCTGCGTCAACCCCATCGTTTACGCGCTGGTCTCCAAGCACTTCCGCAAAGGC<br>TTCCGCACGATCTGCGCGGGCCTGCTGGGCCGTGCCCCAGGCCGAGCCTCGGGCCGTGTGTGCGCTGCCGCGCGG<br>GGCACCCACAGTGGCAGCGTGTTGGAGCGCGAGTCCAGCGACCTGTTGCACATGAGCGAGGCGGCGGGGGCCCTT<br>CGTCCCTGCCCCGGCGCTTCCCAGCCATGCATCCTCGAGCCCTGTCCTGGCCCGTCCTGGCAGGGCCCAAAGGCA<br>GGCGACAGCATCCTGACGGTTGATGTGGCCTGAAAGCACTTAGCGGGCGCG<br>(SEQ ID NO: 279) |

TABLE 7B-continued

Sequences of differentially labeled CGIs between bladder cancer subgroups relative to blood CGI: 38 range = chr17:75936057-75936582
CGAGAGCCTCTACGACGCACTCAACCAGTACTACGTCCACCTCGGCGGCCAGAAGTACGTGGACCTCGGTCTGGG
GACCCACCGCGTCAAATGTCGGGTTCACCCCAACTTCCGCCTGATTGTCATTGAAGAGAAAGACGTCGTGTACAA
ACACTTTCCCATCCCCCTCATTAACCGGCTGGAGAAGCACTATCTGGATATCAACACGGTGCTGGAGAAATGGCA
GAAGAGCATCGTGGAGGAGCTCTGTGCGTGGGTGGAGAAGTTCATCAATGTCAAAGCACATCATTTCCAGAAGAG
GCACAAATACAGCCCCTCTGACGTCTTCATCGGCTACCACTCGGACGCCTGCGCGTCTGTGGTGCTGCAGGTCAT
AGAGAGGCAGGGTCCCCGGGCCTTGACGGAGGAACTTCACCAGAAGGTGTCTGAGGAGGCCAAATCGATCCTGCT
GAACTGCGCTACGCCCGATGCCGTGGTCCGGCTGAGCGCCTACTCGCTGGGCGGGTTCGCAGCGGAGTGGCTGTC
G
(SEQ ID NO: 280)

CGI: 22 range = chr17:76404186-76404427
CGTCACGTGCAGAGCATCCTCCCGACTGGCGAGGTGGCTTCCACGTGCCCCGTCAATCAGGGCTGGACAGTCCGT
CACGTGCAGAGCATCCTCCCGACTGGCGAGGTGGCTTCCACGTGCCCCGTCAATCAGGGCTGGACAGTCCATCAC
GTGCAGAGCATCCTCCCGACTGGCGAGGTGGCTTCCACGGAGCGATTCTCGAGACCCGAGGGGCGTGGACACAGC
TTCTACGCAGGCAGTCG
(SEQ ID NO: 281)

CGI: 53 range = chr17:77537903-77538626
CGCGCGTCGGGCGCTGGGAAGGTGACTGTGCGTTGGGCGCGCTTGGTGGCCCCAGGGCTGGGCCTGCTCCCGTCT
GACAGTAGTGCCGCGCTGCATGGCACGGGTGTTGCGTTCGTGGGTGAGAGCGCTGAGGTCTGCACGTCGGGTCTC
AGTGGTCATGGGGATGGAAGCCACCCCAGTGGCTGTCGGGGTGAATGGAGGCCCCTGGAGATGGCAGCGGGTTAA
GCACGAGCACGGAATTCTCCCTCCCAAAACGGAACTCAGACAACAGTGACGGAGCCTAAGAGCAAAGCCAAAGCC
ACGGGCAGGGGTGAGCGGGACCCGAGGCAGGAGATGACGGAGCCTAAGAGCAAAGCGAAGCCACGGGCAGGGGTG
AGCGGGACCCGAGGCAGGAGGTGACAGAGCCTAAGAGCAAAGCGAAGCCACGGGCAGGGGTGAGCGGGACCCGAG
GCAGGAGATGACGGAGCCTGAGAGCAAAGCGAAGCCACGGGCAGGGGTGAGCGGGACCCGAGCCAGGAGTGGCGC
CGGGCAGGGAGGCAGGCAGCCCCAGGCGCTGTGTGGGCACTGGGTGAGAAGCAGGGATCCCGGCGCCCTGGCTCT
GTGCTGCTTCCTGAGACGAGAGTGGCAGAGGGCAAGAAGAAAACCAAACAGCGCGGGGAACAGAAGTCAGGAAAG
ATGAACGTCTGGAAGGAAATGCCCCTGGGCCGGGCGGTGCCCCCGGGCG
(SEQ ID NO: 282)

CGI: 330 range = chr18:894579-899574
CGGAGAGACCTCGGAGCAGAGAAGGCGCCGCCGACCCTCGCGGCTGCCTGGCCCGCGGCTCCTACAAAGGCGGGC
TAGCCGCCCGCCCTCTCCCTTGCCTTCCTCCCCTTCTTTTCTGACTTTCCCTCTTTCCCTTAATCGCCTGCTTCT
TCCTCCGGGTGGACTTACGGCCACCTTGCTCCTCCGCGCTTCACCTCATCGCCCCCTCTTTCTTTCTTCTGCCTC
TCTCTCTGCGCCCCCTTCTCTCCGTGTCACGCTCCCTCCTGGTTCTGCGCGTCTACAAACTTTTGAGCAGAACAC
GAGCCTCGGCAAACGAGTCCCGCAGCTCCTCCTGCTGCTCCCGCTGGTTCCTGCGGCTTCTGCTCAGACACCAAC
GCCAGACGGCGATGCCTCTCGGGTGGTGACTCCAGCGCAGGAACTTGAAGAAGCGCTTTGCCCGCCGTCCTACCT
GGCAGCTCTCCTGGCAGCGGGAGGAGTTGAAGGGTAAGGGAGGGAAAATCTTACCAAAGCGACCGGCTCACTCGA
CTGCTGATTCTTTCGCTTGGCATCGCGTCAGGGGAGTTAGCTTTCCTTCAGCCGGGTCTGGCTAGTTATTGGGCG
CCGGGTAGATGCATATATATATATATTTTTTTCTAACTATAGCAAGCAAGAAGTGGCAGGGCGCGCACCGGCTGTCG
CCAAGTGCTGTTCAACTCAGGGAGCCGGGGCTTCGCTCCGTCCCTCCCCCGGCTTCCAGAGCTTTTTGGGGTTGG
AGGGTGGGAGGCCAGGGGCGTTCTCACAGCTGTGTGTCCTCTTTCCCATCCTGCGCAGAATGACCATGTGTAGCG
GAGCGAGGCTGGCCCTGCTGGTCTATGGGATAATCATGCACAGCAGCGTCTACAGCTCACCTGCCGCCGCCGGAC
TCCGGTTCCCCGGGATCAGGTAGGTGCTGGCTGCCTGGCCCAAGCAGGAGCTGGGGCTTCCCAGGCACAGACGCT
TCCTCACGGTCTCCTTCCTGCAGTCCTTTGGGTCCAGACTACTAGCATCGCCCTCTGCGCCCCCGGTGCGCCTCC
GCCAGCCTCGGCTGGACAGCGGGTCCCCATTCTAGCCGAGGGTCTGGCAGGCTCCGCGACTGCTCGGACGCCTCC
CCCAGCCCTAGGCAGCTCAGGGTCCCGGGTAGAGCCAGTGAGCTTCTGGCCGCTGGAGAACCCCCCCTCCCCCAA
CCCGGCCCACAGGATGGGGGCAGGGCACGGCCCCTAGCTTGGTTTCTTTTACCTATTCTTGGGACGAGTTAGGAG
AACTTCAGCTCTGGAGCCTGGCCGGGGGTTGAGCGTGAAGCTCCCTCGGACTTTGCTTTGTTACTGCTTGTTCTG
GACTATCCGGGTGGGGTCTCTCTCTCTCCTCCACCCTTTCTTTTCATTTCATTCCAATTCTTTCCCCTGAAGAGC
TTTCTTTCAAGTGATCCGTGTTCCAACTGCATTTTGAATCCCAGGCTGTCTTGGGGGGCGTGCGGTGGGGAGGGT
GTTGGCCCGGTGTGATTGAGGAAAAGCGACTTAAGAGAGGGAAGAACAAGGACGAGACTGCGAAGGAGGGGGAAA
AACAGGCGCAAAGGAGGAGGAAGGGAAAGCCAGCAGGCAGGCAGGACCGGGAGAGCAGCCCTGCCTGGCCCGGGA
TGGAGGAACCTTGGCTTTTTTCTTAACCCCGGGTTTCTAACCGGCAGGCGCGGCCCAGGTTCCCGGAGGCAGCCC
CAGAGTCGCGGACCGATGTGCCAGGCTGTGGATGAGCCCTGGGTAGGGGAGGGTTCGTACCAGCGGCGCCTGGGG
CAGCGAGGAGCGCGCGTTCTGCCTGCGAAGCTGCCTTCTCCGAGCCCCGCCCAGGAACATTAGCTCTGGGGGGCC
GCTGATCATTGATTTGGACGGAGAGATGGGTTCTGGGTTCTGTATTAGGATTCCAGCATCTGGGCTCGAGGCAGG
GCAATATCCAGAAAGACCCCAGGGTTCGGGGTACCCGGGCCAGGGCTGAGGCGCATCGCCGAGCAAAGGCTGGGT
GCGAGGCGTGCGGAATGATGCGCTTGCCTTGCCCGGGCCTCTCCAAGGATGGAGAAAAGGCGAGTGAAGCAGCGA
AGTACGACTCCAACCCCGCCCAGAGAGTGCTACTAGCGCTGGCTGCACGCCAAGTCTCTCCAGGGGTCCAAAGCG
AGAGGGATTTGTTTTAACCCATCTCTACCCGTCCTGTGTCAAGAACGGAGGCTGTAGAGGGCGACTGCGAAGTCG
CCAGGCACTCGCTGGATCTCGGTCCCCCTCCTCGTGCTCTGGGGTTGAGATGGGGCACCGCCATCGATAACAGAT
CAGCGCGAACTATTCGTTTAGTGGCCTTAAAACACCCTGGTTTCACCCTCAGCTATTTTCAAGTTCCCGTGTGCC
TGGCACTTTCTCCGTGCGAGAAGCACCGGAGGGTGCGGACGCGCCACAGTCTGAGCCGCCGCCGAACTGGCTAAG
TTTAGGGGCATTTATTATTCATGTTCCTGCCAGATCCTCGCCTGCCCAAAATAGAAACCGAGGTTCTCCGTGACC
TACATCTGCTCGGAGAAGGGCTCCCCTGGGCTCGGAGGCTGGGGTGGGGGTGGCTGAGGAGTTGGCCCCCGCACG
CCCCACGCATCCTCTCCTTTGCTTTCTGGGCCTCCCCATTCGGGTCTTCGCGTGGGTCAGCGCCCGGTCTCCCAG
GGCCTTTCTCGTCCCCGCCCGTTGCTGCTTTGGGGAGGCTCGGGAGCCAGGCGGGGAGGGGGGCGGTCCTTTTCC
GTAGACAGGTGTGCGCGATCGGCGGAGACGCCTCGGTTTCCCAGCGCTTGTTGAGGCCGTGGCCCGCAGGACGAC
CCTTTACCCGCGAAGGGGGGGTGGGCGGGCCGCCCGGCGGGGTAGGAGTGGTTGGGTGTCGTTGCCTCCTCCTTA
CCTCTGCTCCCACCCCCAGTCCTGGGAGAAGAGGACAATTCTCAGCGGAGGACTTTTATCACCTGTGAAAATCCGC
GCGAGCCCCTTACTTTGGATCCTCGCCGAGCTGGGGAGGAACTTGCACTGACCACACCTTCTGTCCCCGGCCACC
CCGCAGGCCAGAGGAAGAGGCGTACGGCGAGGACGGAAACCCGCTGCCAGACTTCGATGGCTCGGAGCCGCCGGG
CGCAGGGAGCCCCGCCTCCGCGCCGCGCGCCGCCGCCGCCTGGTACCGCCCGGCCGGGAGAAGGTGAGATTCGCG
CGGCCTCGCGCACACCCGCGGCTGGGAGCTCGGGACTGCGGTGACGGGAGGGGCAGTGTGGTGACCCACCCAGGA TABLE 7B-continued

| Sequences of differentially labeled CGIs between bladder cancer subgroups relative to blood |
|---|

TTTTTTTTTTTTTCCCGTGAAAGTCCTCAAGCCTGTCCTCTCCCTGGCCCGATCCTATTGCAGCGACAGAAAATC
AGCAGCGGGCGGGTCTGTGTGGACCTGAGGGCCGCGTGGGGACCGAGGGGGGCTGTGGCCCAAAGAGTGGCAGTG
AGTGGCGTCAAGGAACCCACACTCCGCATCTGCCACTCCTAGAGCCGGGACTAGCTCCCGATCCTAGCAGTTGCT
CTCGAGATCATCCCGGGAGTTATTGGCGAGTTCTGGGCCTCTGGAGGTTTCCCTGTCAGCCTCCCCGGCCGCCGA
GGGGGCGCGCGCCCAACAAGGGGGTCTCTAGCGGCCACCTGGGGACAGAAACAGTGACCCTGGGCGCGCACTTTG
CCTCCCCGTTAGAGATGTCGCCCACGGGATCCTTAACGAGGCCTACCGCAAAGTGCTGGACCAGCTGTCCGCCGG
GAAGCACCTGCAGTCGCTCGTGGCCCGGGGCGTGGGGTAAGAGTTTGTGGAAGGATTAACCTGCGCGCGCCGGGG
TGGGTGCCTGTGCGGGGCGCGCGGGGCGGGCGGCGGTGGGTGCCCGTGGGGGCCAGGGTGAGTCTGCGCCCCTGG
GTCTGGGGTGGGCATCCGCCCACGGGTCGCAGTTGGAGATTTTGAAGTGGCACTTTAAATTTGCCCAGAGAGCTCT
GGAAGAGGCAAAAAGGGAACGCGAGCCAGGGAGTTTGATCCGTTTGAATGAAAAGAAAGAGAAACCAAACCAAA
CCTCTCAGTCATCCAAAACCTTCAGGCTTCCAGGGAGGTTTTGCTATAATTTTCTCTAAGCATGACTGTTTCTGG
GGGAGGGGAAAGGGGTGGTTGTATTTACTGAAAATTCAAATCGAAATAATAAATGGCCAAATGTGGACACTTATG
GACCCAAACAGTTTTGCTCACGCCAGAGAAACTGAGAGCACAGGGCTTGTGTGAAGCCTATCTCGGCAGAAGGCA
ACATTCTAATAAAGCCCGTGGGAAAACAGATTACATTTTCGCCATGAATAAGTCATGCAGTGAAAAATATTGCCT
ACAGCCTGTCGACTTATATTATTATCACGTTTTTCAACTCGGCGTGAGGAGGGAGAGGAGTGTTCATATTTGACT
AGGAATTGCAGGATCGATGCAAACTCCAGGGCAGCAGCCAGACTGGCATATGTAGGGCTCTCCGGTTACTTTCTC
TGTATGTCGCGGGTGAGAGGAACAGCGAGGACAATTTAGCGCAAACACACGAAGGGTCGGATCTCAAGGGGGCAG
CGCTGGGAGAAAGGTTAGGCTTGAAGCGCGCGTCGCCTGCCCGGATCTTATCCCGGGCCCCCTCCGCAGGGTTTG
GTGCCAGGAGATCCTGCGTGGGGAGGGGGGCATCGAGGGGCTGCCGTCTCGGCCCTCCCCACGGCTGCTTCCAGG
CAGAGGCGGGCGACGCGGTGGGCAGTGCGAGCCCCGGGCCCTCCCCGAAGGCTCCCGCGTGGGGTGGGGCCCGCC
TGCTCCCCGCGGCGATTGAACCTGTGTCTCCCGCCCCGCCACCCTCTTCCCGACCCCTTTGCTTGCAGTGGGAGC
CTCGGCGGCGGCGCGGGGGACGACGCGGAGCCGCTCTCCAAGCGCCACTCGGACGGGATCTTCACGGACAGCTAC
AGCCGCTACCGGAAACAAATGGCTGTCAAGAAATACTTGGCGGCCG
(SEQ ID NO: 283)

CGI: 338 range = chr18:74837994-74842232
CGCAGAAATTACTCGTGCGCACCATTTCCGCTGTGGGGGCATTCGTACAAGTTTCCGCTGCACACACAGCCTCCC
GGGCCCTCTCCTCCAAGGCTCTGCCGGATCTTCCAACGAAATCCCAGAGCAGCCTGCGCTGGGGAGCCCGCAAGT
CTCTCCAGATCTCTGCACCCCGCACCGCCCGGAATCTGGGACGGCGCCCACGCAGGGCTGGGCCAAGGGCAGAGC
TCGCACCCTGCCTTCACGCCCGGTTCACTTGCGTCCACGAAAGCAGCGTGCCGGCCTCCTCCATCTTCCCACTCG
CGCAACGCACGGCGACCCGCGCGACACTTCTGCAATCTGAAGGCTTGCTTCTTACAAATAAAGGGCCAGAGTCTC
ACACTTGCCTTCGTTGGAGGGACTTAGAAGATCCTCCCCACGTCCACACCTTGTAGGAAATGCAAAACAGATCGA
TGAAATTAAACAGTTGCATTTGGAAGCCCCAGAAAGACCTAAAGACATCGTGCCGGTTTGTTGGAGAGAGGGTTG
CGGGACAGGGGGAGCGGGCCTTACGCAACAGAAAAGGTGGGCACAGCGCGCTCAAAATGACCCAGTGAGGAGTTG
GTGCCGCCGGGCCAGAGGCTGCGAGTCCAGCTGGCTCTGGACTTGCTCCGCAGGCGTCAGACGCCGTGGGAACCT
GTGTCTGCTTCTTCTCTCCAAAGTGTATCGGTTAAAAAAAAATAAAAGTAGTAGTAGTAGTAGTGGTAAGGAAAA
AAATAAAAATAAAAAGGAGACACAATTAACCAGGTCATAAAAGCTAGGGCACCTTCGACCAGGGCTCTGGCCCTC
CAGCGATCGTTTTGCGTTGTTTCTCTTCTCAAAAGTAGTCTCAGACCCCTGCCTTTCCGCTGCAGCTCTGCGACT
TCCCCAAACTCCTTAATCCTGTAAATTCTGCAAGAAACTCCCATCCTGCAAGCTGCTTTTCCCCCTCCCCCCTGC
GTTCCTTTTTTCTCTCCCCACCCGCGCCGCCTCTCTATGCCCCTCTCTTCTCAGAAAAATTCCTGCCCCCCGCGC
GCCCCAAAGCCCGGGCTGCAAACTTTTCCCCGCCGGGCGCCTCTGCGCCAGATGCCGGAGCGTCTCCACAAAGCC
TGAGCATCTGCACAAGTTCGCAGCCTAACTGCGGGATAAAGACGTTTCCCCCGTAGCTTAACTAGAAAAGCGCCA
TCGATGGGTGTGTTAAACGGGATAACTAGAGATTTCAAACACCTTTTATTTGCCTGTCTTGAAAAAAAAATCTAA
ATGAATACGCCCGCTACCAAAAGGCAAAATAAAACCAACCTTAAGGGTTTTTGTTGTTTTTTTTTTTTTTTCAAAA
GTGGCGATAGGGACTGTTTGGACCTGACTCCAACCTGCGCCCTCCCTTCCTCTATGACCCTCCTGCGCTTTTCCT
GGAACCCAAAGCTCTGACTTCGTCAAACTTACACAATTAAAGGCAGGCGGAAGAACGCGGGCTGGGAAGCAAGCG
GGAAGATTCTAGAATGGAAGGGAGCCCGCCGAGCGCCGCGAGCCGCGCCAGGCCGGGTCCGATGGAGCAGGCGGG
GATTCCTCCCCCAGGCGGACCCCCGCCACCAGCCCTGCCGGGAGCTCGCGGCCTGCGGAGCGCCCGGGCTGGCCG
CTCACCGCCCGCTTCCCCCAGCGAACGACTCGGGGAAGCTCCAGGAGGCCATCTGTGCTGACGGTTCACACCAGA
CAGGACCACTTGCAAGGACAAAAATAAGAAATTTAGGAAACGAAAAAAGACGTACTGGGGCGAGGGGCGCGGGCG
CGGCGACGACGGGGCCGGGGGCACATCCTGGCGGCCGCTCGGGGAGAGAGGACACGCGCGGGAAGGAGCGCGGCG
GGTGCACGGCCGCGGGTGGGAGTACGCGCCTGTGCGCGCGGGGCGAGGGCGAGGGCGCGTGCGTGTGACCGCGGG
GAGGGGGCGGGCGCGTGTGCGGGGAGCGCGCCGCGCCAGGGGCCGAGTGTGTGGGGCCGATCCAGAAGTGCGCAG
CCCCCTCACCTGGCCCCCGTGTCATCCCCGAAATCCCGGGAAAGGGTGGGCCGCGCGCGGGAGTTTGGTGGAGTT
GGAACTTTCGGTCGCGCTCGCTGCCCACTCCGCTGGCGCCCGGTGGCCCGTGGTGAAGGGGGACTAGGGTGGGGA
ACACCGGGGCCCTGCGGTCCCCTCCCTTTCCTCTGTATTTAAGAAGCCGCCGGCGGCGCAGAGGCCCCAGGCGGCTG
GCGCGGGGGCGAGGCGGCCCGGTGGCAGCAGCGGGCGGGGCGGGCGCTCCGGAGTCGGTGGGCCCGCGGGTTGG
GGGGCGGGGAGAGGGGGGAGTGGAAGGGAGGGGGAACGCAGGGGAGGGAGAGGAGGGGAGGAGCCGCGCGGCCCG
CGCCGCTTCCGAACCGGAAAGTTGGTCTTGCCGAAGTCCTGCCACCCCGGCGTGCGCACTCCGCTCCGCTCCGGC
CGCGAGCCTCCGAGCCCGGCCGGCCGCCGGGGGAAGCCCGCGGAGGGGACGCGGGGCCGGGCGAGAAGGTCCGGA
GAGCGGGGGGCACCTGAGCCCGGGCGGGCCCGCCGCGCTGAGCGGCGCTGAGAGCCGCGGCGGAGCAGCGAAGGC
GGCCGGCCGACCCCGCGCGCCCGGAACAGGAGGCGCGGCGCCCGAGCGGCCCGGGCGAGACAAAGGCGCCGGGTC
GGAGCCCTGCCCGCGGCCGCTCGCTCCGGGAGGGGCCGCCCGGCGGCGGCGGCGGGGGGGGCGCGGGCGGCGGCG
CAGACACTCTATAAAGGGGCGAGCCCGGCGCGCCGGCGGAGACGGCGCCGCGCGGACGCCGCCAAAGTTTGCTGC
CTGCGCCCTGCGGAGGGACGGCCACCGCGGCCCGCGCCGCACCCGGGCCCCGCCACAGCCGCACCCGGGGCGGCC
GAGGAGCGCGGCGCCGGAGCCCGCGATGTGAGGCGGCGCCGGGCAGCGCGCGCCCCGGTCCCGAGGCGCCGCGGC
CCCCTCCTCGTCGGCGCGGCCGCTAATTGCGAGCGCGGCCTCATTTGCATAGGCCGCCGGAGTCCGCTGGAGCCC
GGCCAATCGGCGCGGCCCTCCGCTAATGGCCATGCATTATTCACCAGCCTAATTGCTCAGCCCCATGCGCGGCCC
GCGCAGCCGCCGCCGCCCCGCGCCCCGCGCCGCCCGCCAGGCCGCCCCGCGCCGTCCCCGCCGGCCGCCCC
GCTGATGCCGCTGCCCCGCGCGGGGCCGAGCGCCGCTAGCAGCATGTCTCGGCGCAAGCAGGCCAAGCCCCAGC
ACCTCAAGTCGGACGAGGAGCTGCTGCCGCCTGACGGGGCTCCCGAGCACGGTGAGGGCCGGGGCTGCGGGGTGG
CCGGGGGGTCTGGGGCTGCCCGTCCGGGCTGGGGAAGCGCGTGCGGCGGGAGCGGATGCGCGCGTCCGGGAGCGG
GAGAAAGTTCCCTGCTTCCTGCGGGCAAGCGTCCGCCCCGCGCCAGGCCGGCCGCGGGGCCCCGGGTACTTCGCC
GGAGCGCGCGCGGCCGCCGAGAGAGTTGTGGGCGAAGTAAACTTGGCTCCTCTCCTCGGAGTCGGGGAGCTGCCC
GCGAAGGGCGCCGAGGCCGCGGCCGGCTCGAGGACGGCTCGGAGGCCGGGGCGGAGGGAGTCCACGGTGCCTCC
GCCGCCGCGCCGCCCCCCAGGGTCTCTGCGCCAGGACGCTGAGGCCGGCGGCGGCGGGGAAGGCGACCGCAGCCC
ACCTACCGCTGGACGCGGGTTGGGGACCCCGCCGCCCGGCCAGCTTTGTTCGGGGGCCCGCGGCCCCTCCCGGGC TABLE 7B-continued Sequences of differentially labeled CGIs between bladder cancer subgroups relative to blood CCCCGCACCGCCTCGGGTGACCCGCGGTGTCCCAGCGCGTTGACGCAGCCTGTGATCCCTCGCGAGGCGAGGAGA
AGGTCGGGGGCTTGGCTCTGCCTAATGGCCGCCCGGGGAATTAAGCTGGGGGTGAGCGCAGCGGCGGCGGCCTGG
GCCTGGCCCCTGCTCGCGGCGTGTTTCCGGGGCGTTCGTTGCAGCGTCTGCGCGGGCCTTTTCTCTCCCGTCTTT
TTGGATCCGCCGAGGCCGGGCGCTGGAGACCTCGGCTTTGCAGTCATTTCGCTGGTAGGAGCGTCCTCTTCGAAA
CATCCAAGAGCAAAGGGCAGGCGCCGCGAAAGTTAAGAGACTGGCAAAGGGCTGGACTTCCCAGAGTGGCGCCTT
AGCCCCGCAAAGTTTGGGGCGCCCCCACCCCCTTCGTCG
(SEQ ID NO: 284)

CGI: 43 range = chr18:75565313-75565933
CGGGTGCAAACGCATCCTCTGTCCCACGTGGAGTGGTGTGTCCACACGCATGTCCTCTGTCCCATGCCCACGTGG
AGGGGCGTGTACACACGCATGTCCTCTGTCCCGTGTGGAGGGGCGTGTACACGCACACGTGTCCTCTGTCCCGTG
TGGAGGGGCGTGTACATGCTCACATGTGTCCTCTGTCCCGTGTGGAGGGGCGTGTACATGCAAACGTGTATCCTC
TGTCCCATGTGGAGGGATGGGCACATGTGTGTCTTCAGGACGCCTGTCTCAGGCACCCGTGTGTCTTCAGGACGC
CTGTCGGGCACACGCGTGTCTTCAGAACGCTTGTCTGGGGCACACGTGTGTTCTCAGGATGCCTGTCTCGGGCAC
ACAGGTTGCGGGGGCGGCCGGGGCTCCTCAGGCCTTTTCTCCCGACTGTTGCTACTATTCTTTTTAGGGCATCTT
TCACTTCCAGCTGGGCCGGGGTGAGCCCATGCTGCACACGCGCCTGCGTCCACACTGCAAGGACTTCCTGGAGAA
GATCGCCAAGCTGTACGAGCTGCACGTCTTCACCTTCGGCAGCCGGCTGTACGCACACACCATCGCAGGTCAGTC
AAGCCGCAGCCGAAGAGGCCG
(SEQ ID NO: 285)

CGI: 33 range = chr19:898548-898981
CGGGACCGTTTCACAGATGAGAAGACCGAGGTGCCAGGGTGGCGATCGCACGAAGGGCCCGTCACGGGAGAATGA
GGAGGGTCTGGCGTCAGCAAGCTCCCCCGGAATCTCGTGATCTGGAAATCCACAGAGAAGCACCTTCACCACGCC
AGCTTCCCGGGCCGCGCTTCATTGTCATTTCTGGAGAGTGTTATTAATATCCGCCCCGTGGGTGCGGCGCTGTGT
ATTTCCAGAGAGGGGACTCGGGGCCCATCAGGGCCGGGGGAGTGGAGCCGGCAGATGTTCGGCCCTGCCCAGAAT
CACTTCCCCAATTTCCCCACGCCCGGCGGGGCTCTCAGCATCTGCATCCGCCGAGGCCTGGCTGTGCTGACGGGA
ATTGAAAGGACCTCGTGGCTTAGGCAGGCGGGGGAGCCCCCCGGCTGGTCAGGTGCACG
(SEQ ID NO: 286)

CGI: 70 range = chr19:9131907-9132918
CGCCGCGACTATGGGGTAGCGTTCAAGGGCAGGCCGCACCTCACTCAGCACATGAGCATGTACGACGGGAGAAAA
ATGCATGAATGTCATCAGTGCCAAAAAGCCTTCACCACGAGCGCGTCCCTCACACGGCACAGGAGAATCCACACC
GGGGAGAAGCCTTACGAGTGCAGCGACTGCGGGAAAGCCTTCAACGACCCTTCAGCCCTTAGGAGCCACGCAAGA
ACTCACCTCAAAGAGAAGCCCTTTGACTGCAGTCAGTGTGGAAATGCATTCCGGACCCTCTCGGCCCTGAAAATC
CACATGCGAGTTCACACTGGCGAGAGGCCTTACAAGTGTGATCAGTGCGGGAAGGCTTACGGCCGGAGCTGCCAC
CTCATCGCACACAAGAGAACGCACACCGGAGAGAGGCCCTACGAGTGTCACGACTGTGGGAAAGCTTTCCAGCAC
CCCTCCCACCTCAAAGAGCACGTGAGGAATCACACGGGGGAGAAGCCCTACGCGTGCACGCAGTGCGGCAAAGCC
TTCCGCTGGAAGTCCAACTTTAATTTGCACAAGAAGAACCACATGGTGGAGAGAAGACCTACGAATGTAAAGAATGC
GGGAAATCCTTTGGCGATCTCGTGTCCCGGAGGAAACACATGAGGATTCACATCGTCAAGAAACCCGTGGAATGT
CGGCAGTGCGGGAAGACCTTCCGAAACCAGTCCATCCTTAAGACTCACATGAACTCTCACACTGGAGAGAAACCA
TACGGGTGCGATCTCTGCGGGAAAGCTTTCAGCGCGAGTTCAAACCTCACCGCACACAGGAAGATACACACGCAA
GAGAGACGCTACGAATGCGCCGCCTGCGGGAAAGTCTTCGGTGACTATTTATCCCGGCGGAGGCACATGAGCGTT
CACCTTGTAAAGAAACGAGTTGAGTGTAGGCAGTGTGGCAAGGCCTTCAGGAACCAGTCAACGCTGAAGACGCAC
ATGCGAAGCCACACGGGGGAGAAACCGTACGAATGCG
(SEQ ID NO: 287)

CGI: 25 range = chr19:12985960-12986259
CGGAAAGCGCGCTTTTCGGCAGAGCTGGTTAGTTTTTAATGCGGGCTTTTTTTTTCTCACCCGCCGTTCCCTCCG
CTCCGGTCTGATTCGCAAATCCCCAAACTGGCACAAACCGGGAAACTTGCGGCCGGCCGTTCTTCTCCCCGAGTT
GGAGACAGCCCTCTCCTCTTCCCTCCCCCGCCTCTGGGCCCTGACCCACTGCCTGGTTTGCGCTAGAGCCGTTTA
AAAAAGAAAGAAAGGAAGAAAGGAGCCGGGCTCTGGTACCCCGATGCCAGCCGAGGGCGCGTTTCCCAGGCGGCG
(SEQ ID NO: 288)

CGI: 35 range = chr19:55553586-55553895
CGCGACCACCCGCTGCGCATGCGCTTCACTTGGGCGTCACCCGGGGAACTGCGCCTGCGCAGTCTCTCCCCATCC
GAGGTCCGCTCCGCGAGTGCGAGCGCGCGCCAGGCCCACCCGGGCGCTGCTCTTCATGTCCCCGCGGTCGAAGAC
GGCCACATACGTCCCCAAGAAGACGTCACCGAGGATCCAGAAGGGCCCTGCAGGCGGAGGGACATCCAGGGCCTG
GAAACCGGACAAGCAGAGGCGGACGCCATTTCGAGTAGTCTGCAAGGCAACAAGACGACAACTGGGTGTCGCGGC
CACAAGGACG
(SEQ ID NO: 289)

CGI: 47 range = chr19:57082654-57083180
CGATTCGCTTCCCCACCACGACGCCCTAGCGCTACTGTGCAACGAAGACCTCCCAAGCACTGGTTCCAATGCGGA
GACCATGGGCTCCCAGACTCTGGGAACTCCAACACGACTGCGAAACGAACTCCGAGCGAGGACTCCCCGAGAGCT
CCCCGCAACACGGACCTCACGCGCTAGCGAACAACAGAAAAAAAAAAGCGCGCTCTCCCTGCCCCTGAAACATTC
CCAGAAGCCCACGCAGACCAGACCGATGACCTGTCTCCACTGCTGGAGGCGAGTCAGGGACCCGAAGTCTCTAAA
CACTCGCCTCTACCCGCCGCCCCGCGAACCCCACACACTGCAGACGCGACACTCGCAAGTTTCGGGGATGGCGGC
CGGCGAGGGCCATACTGCGTCTTTCCGGAGACACGGAATACGGCACCAGCCGTCCCTTTATGATGCAATATGTCT
GCGCCCAGGGGACGCTTGCTGGGAGCAGCCATTTTCAACCCTACTGCCGTAGAGCAGGCGGAGTCCCTCTTTTCG
CG
(SEQ ID NO: 290)

CGI: 159 range = chr19:60283718-60285792
CGAGGTGGGGGCGAGGAACCACCCGGACTGGGTCTCCATGGGCGGGGTCGTGGCTTAGGGCAGGGACAGGTGTAG
GGCGAGGGGTGAGTTCGGGGCGTGGACGTGCGTGGGTTCACAGGTGTGAACGGTAGCCGCACGTGGGCTGGGACT
GAGCTGAAAAATCGGCCAGGGGCGAGGCCCGGGTAGGAAGTGGGTGCGGCGTGGGGAGGCGTGGCCTGACGGTGT
GATTGGCAGGCGGAGCTGATCCGAGAGGACATCCAGGGGGCTCTGCACAATTACCGCTCGGGCCGCGGGGAGCGC TABLE 7B-continued Sequences of differentially labeled CGIs between bladder cancer subgroups relative to blood AGGGCGGCGGCGCTCAGGTGAGAGGGAAGAAGTTGGCAGGGTCTCTGGGAAGCCGGTTTCCCCTCCTTGTGCCTC
AGTCTACAACACCAGCCTGGAACAGAACAAGAGTTTTGCATGGAGTCAAGCACACCCTAGTCGAGTCTTGTCTGT
ACCTCCCAGACGAGCTGACCCCTTCTCCAGAACTCTGCTTCTTTTCTCTGTTCCCTGTCCAGGCCCTCAGTTTCA
CTCTAGAGAGGTGCTATCCCTCCGTATATCGGATTTCTCCCTACCTCGTTGAACTTGTTCACTCCCTTTGAGCCT
TTTGAGCCTGTGTGTCTCGTTCTGCGCCCTGGATTTCCCCCTCCCTGGACCCCTCAGTGGACCCAGTCTTGGTGT
CCCCGTCGCCCTCCGCAGGGCCACGCAGGAGGAGTTGCAGCGCGACCGCTCGCCCGCCGCTGAGACCCCGCCCCT
GCAGCGCCGCCCGTCAGTCCGCGCAGTGATCAGCACCGTAGAGCGGGGCGCGGGCCGCGGACGACCCCAGGCGAA
GCCCATTCCCGAGGCAGAGGAGGCGCAGAGGCCTGAGCCGGTGGGGACCTCGAGCAACGCTGACTCGGCCTCCCC
GGACCTGGGTCCCCGGGGTCCTGACCTGGCGGTTCTGCAGGCGGAGCGGGAAGTGGTGAGCCGCTAAGGAAGGGG
TCTGGGGGCAGGGCCAGGCGACTGGAGGCGGGGCTAGGGCGTGGAAGGGCGGGGCCGGCTGCGGGACGGGCGTTC
TCTGGTCAGACTTCTGCGTTATGGAAGAGGGGCTGGGTCGGGGGCGGGGCTTGGTTGTGGGGCGTGGCCAGGTGT
TTGGGGCGTGGCCTGATCTGGGGAAGTGTATAGGTGCTCAGGTTCAGGGCTTCGACGGGGATGGTTTTGGAACTC
GGGAGCCCTGAGCGTCCCCCTCCTCTGTCCCCTAGGACATCCTGAACCACGTGTTCGACGACGTAGAGAGCTTTG
TATCGAGGCTGCAGAAGTCGGCGGAGGCGGCCAGGGTGCTGGAGCACCGGGAACGCGGCCGCAGGAGCCGGCGCC
GGGCGGCTGGGGTAAGGGGCACCCTGGCGTGGGATCTGAACCCCCTCCCGATCTCTTCCAAATGTCCCCGCTCT
CCCCAGGCTCTCCCCTCCCGCCACTTGCCAGGGCTGACCTCACCGCCATCTTAACCGGGTGTCCACCTCTCTCTG
CCTGCCTGGTGCTGGCCCCGCGTCCCCATCGCCGCGCCCGTCTGCTCCCCTCAGAGGGCTTGCTGACGCTGCGGG
CCAAGCCGCCCTCGGAGGCCGAGTACACCGCGTGCTGCAGAAGATCAAGTACGCCTTCAGCCTGCTGGTGAGGA
CGCGCCCGCCCCTGGGCCGGGGCGCGGGCACGACGAACCTGTCCCGTCCCCGCACCCACGCCAACCACCTCCCTC
CCCACGCCCCAGGCCCGGCTGCGCGGCAACATCGCCGACCCCTCCTCTCCGGAGCTGTTGCACTTCCTTTTCGGG
CCTCTGCAGATGGTGAGACCCGCCCCAGGCCCTCGGGCCCCCCTGCAGCGGGAGGAATCGGGTTCGACTTGTAGA
AGGTGTGGCGGCACAGCTGCCCTCCTGCTCCCCTGACAGATTGTGAACACGTCGGGGGGGCCGGAGTTCGCGA
GCAGTGTGCGGCGGCCGCATCTGACATCGGATGCCGTGGCGCTGCTGCGGGACAACGTCACTCCACGTGAAAACG
AGCTCTGGACCTCGCTGGGGGACTCGTGGACCCGCCCCGGGTGAGGGGCG
(SEQ ID NO: 291)

CGI: 34 range = chr19:60907042-60907388
CGCTCCCCTGCGTTTCGGCTGCTGGCCCAGCAGAGGGCGCCGGAGAGCGGACGGAGCCGCAGGCGGGGTTGTGGG
AAGACGCTGGGATCCCGTGCGCGCTTGTGCTCCTTCCTTCTGGGCCAGCGCGCAGACTATCAACCGAGGTATTCA
GTCCCTCGGAAACCCAGTTCCTCCGTTTCCAGGCTTCTCGCCCACACGGAGACAGTCGCTCTCACACGTACCTCT
CGCGGGCTCTTACTCGTGGTCCCGGTCTCCTCCTGGTCCCCACCTTCCAGCCCAGCGCGCACACTAGACGGCACG
TGCTCTCCACGCTCTTTCTCCAGCGCCCCTTGCTCACCCGCCCCCCG
(SEQ ID NO: 292)

CGI: 61 range = chr19:62043096-62043807
CGCAGCAAGCCTCAGCCGCCCTTATTTAAGATACCGCCCGAGAGGGCGGGGAAAGAAAACCCCTACAGGCAGGAC
AGCCCTTCGCCCCTCCCACCACCACTGCGGCAAACAAGCCCCGCCCCCAGAGGGTAGCCGGGCACGCCGGCGCCG
CGAGGCCGATGGCACCCCGCAGGAAGGGGCATTTTCGCAGCCCCCAGACCCAGCCCAGGAGGCCCAGGGCTCCCG
AGAGCCGCATTCCGCCGTGGCAACAGGGATAGCATTGGTGTCGACCTTGCTGGACTTGCCGTGGCAGAGCCCCCG
GCTGTCTGCCCTAATGCCCCCGGTTTGCTGCGGTGGCCCCCGGCCAGTCAGAAAGGCGCGGAGACCCTGCAGCAG
CCCCTCAGACCCCGGACTGCAAGATGGCGGCACCAACGCAGCAGCCCGGGCTGCGCCCACCCCTGCCCCAAAAAG
GCACCAACCATCCACAGCCTGGCCGCCACTGTGCCCACTCTCGGACTGGGCAGCGGGCGGCCAAGTACCATGTCC
GCCAGCCCGCCCTGCCACAAGGGTCGCTGGCTTGCCGCGGGGTCTTGGGCTTGCGGCAAGACGGCCACTCTGGCC
CAGAGCCGTCGCGACACCAAGGTCCCGCGGGCAGGAGGCGCGCGGGGCGGCCGAAGGCGCACTCACCTCACCTCA
GTGCTGCGCAGCCTCGGGCACGAACAGCCGCCTAGCG
(SEQ ID NO: 293)

CGI: 94 range = chr19:63321122-63322053
CGCCCAACGAAGAGGAGGGAGTAGGGGTCCGCGCCCCACCACGAAAGGAGAGTAGAGGGCTCGCGCCCTGCGGGG
AGAGGCGTTAGGGGGTCCGCGCCCGGCGAGGAGATGCGCGTACCAGCCCCGCACGCCAAGGGGAGAAGACACGCG
GGACGGTCCGCGCCTGGCGGAGAGAGTTCCTCACGCCCGCCCCGCCGGGAACCACAAGCCAGCGCCCCTAACAAG
CCCCTGCCCAGAGCAGGGCTGCCGCGTACCCTCACAGACAGAAAGAGCGACCACGCAGCCACCGCCCAGCCCCAG
CCGCTCTGGAGTCCTTGACCCCACCCTCACTAGGCCTTGGCTCCGCGACCGGTGGGCGGGAACGGAGGAAACAGA
CCCGAGAGGCCGCGAGAGGACGGAACTCACTTCCCGCCGCCGTAGCGTCCTCGTCAGCTCGCCCTCCGACTCTCC
GCATGGGCGCGCAGAGTTCCCGGATGCGATATTCCGGTGACACCGGACGCTGGGGGCGGGGCCTAGTGCGACGAG
GGCGGGGCCGGGGCCGGCCCGGGGCGGGGCCGTGGCCGCAGCTGCCTGGCAGCCAGAACCTGGGAGCGCTCGCAG
TGCTGCCTTTCGGGGTTCTTTGTCCTTCGCTTCTGCTGGTAGGTGAGGTTTAACAGACGGAAAGACGCCGGGAGC
GCACGTGGGCTGCCTTGAGCCGCTGCGGACGAGCACCTTGTCTCTCAGGTTGACCAGCCGTATATCCGCTTGCGA
GCCTGCACCACCCTGGGCGCGCGTGGTCTCGGCAGAATCTCGTTCACACGGGTCCCACTCGTAGGCTGCTGTGTC
TCCTTCCTCTCACGGCGTCGGGGACTGGGGCCTGGAGTCACTCCTCTACAGGGGTGTGGAACGCGCCAATGGACG
CTGACACCTTCATGCGGTCGTTTAACGCTCCG
(SEQ ID NO: 294)

CGI: 35 range = chr20:9444472-9444893
CGCTTCCCTATCGGGGCTGCACGTAGAGCATCTAACCGCATGTTCCCGGAACCTGGGATGCGCGCGCGCAAAGGA
GCGCCCAAGCGTGCAACCCAGAGTTTGGACGCGCCGCCCTTTACAGCCCCCGCCCCGGGGCCGGGCGAGCTGAGG
GGGCGCGGGGCGTCTGTGTTCCCAGCTGATCACAGAACAGGCCGATATCGCATTGACCCGGGGAGCTGAGGTGAA
GGGCCGCTGTGGCCACAGCCAGTCGGAGCTGCAAGTGTTCTGGGTGGATCGCGCATATGCACTCAAAATGCTCTT
TGTAAAGGTAACTCCGAGCCCAGCGGGCAGAGGGGCCGCAGGCTCCGCGTGGGTGTGGGAAGTGGCGGCCCCTAG
GTTTAAGAACCCAGACGCTGCGGGGACGATTGAAGCGCACCTCCCCG
(SEQ ID NO: 295)

CGI: 671 range = chr20:21433933-21444714
CGCGGAGACATCTCGAGTCCCGCAGGTGTCTGAGCTGCGCTGCGCGCCCCAGCCGGGAAGCCTTTTCTTATCCAA
CCGCGCCGCCCCGCGGAAAGCCTGGGTACTGCAGACGCCCTCACCGGCCCACCGACAGCTGGTTTTGAAGCGGGG
GCTTAGAAAAGTAAAGGGGACAGTGTTTGGAGCCACGATGCCTTTGATGTGAGGCGGTTCCACCCAACAATCAAC
GAATCAAGCTGGAACTGCAGGCCCTACTTTTGTTGGGGGGAGGACCTTAAGGAATGTCACCCCCTTGTCCCCTAC TABLE 7B-continued

| Sequences of differentially labeled CGIs between bladder cancer subgroups relative to blood |
|---|
| CCTCTGCCCCACGCCCAGCCTCTCAGAAGGCACCAGGCGTGAGTAGAGTGCGAGGCGTCCACACCCTCGTGTCCC |
| TTCCATTCCCGGACACCTTTGCACCCTAGCCGAGGCCTCAGCACGGAGTGAGGGTTGCCTGGGGTGCCCTGCTGT |
| GTGTGGGGCGTTCTTGCCTCCCGGGCCCTGACCCCACGGTCTGGGTCGGCGAGGCGTCTCTCCCTGGCGTCTGGA |
| CTGTGCGCCTGCCCCGCTTCCAGGCGACGAACGGCAGGAGCCGGGGGTCCGGCGGGACCCGGATCCAGGGCGGGC |
| GGAAGGCGAGGGTCTCTCCTTCCCGGAACCCCCGCCCCGGAAACCTGCAACCAAACCGGGTCCCTCCTCCGCATC |
| GCTCCCGCGCTCCCGGGCCGCCTCCCCACGCGGGCACCCACTCTCCGGGCCCTCGCAGCACCGCCCTCTCCGCGT |
| CCACCCGCGCGGCCGACGCCGCCAGGGGCCCTGAGATCGCGGAGACAGCGCGCCCTGGCGCCTGGTGGGGCCCTC |
| CCAGTGGCCAGAGCGCTCCTGGACCAGTCGGCTGTGGTCTGTGCCCAAACACGATGGAAACCGGGGCTGGGACGG |
| GCGGTGGTACGCACGTGGAGGAGAAGAGGCATGGCGGGAAAACCACAGCCGAACACAGGTCGACTCGCACCTCCC |
| AGGCACCCGCCGCCGTCTGACTCGCGGCTCTCCCCAAGGTTCCGACTCGCCGCCACCTCTTGGCACCACTCACCG |
| GGCTCCGACCCGGGCCGCGAGTCCGCTGATGCGCAGCTGCCTCCGGCGGCTCCCGGGCTCTGCCCGGACCCGCGC |
| GCAGAGACGCTCGGGAACGCTGGGCTCGGGCGCCTCCTGGCGGCGGCAGCACGCGGCACACGCTCGGTTCTCCGG |
| CCCGAGGGGGCGCGTGGAGCGTACGCGGGATCCGCGCGCGGGCCTGGGCTGCTGGCCCACATTTCCCCGCTTGCT |
| CGGATGGCGGCGCTGAGGCCTATTCGCCTCTTTATTAATAACGATGCCTCGGGAGGGAAAAAATAGAGCCTTTAA |
| AAATCAGAGTGCGAGAGAGGAGTGTGTGTGTGTGTGTGTGTGTGTGTGTGTGTGTGTGTCTCGGGGCGTTGGTGA |
| AAGCAATAAAACTCAGATCGCTTCCTTGGCGAGATAGCGGCGGCTATAATGCGCCGGGGGGATCAGGGGTTTATT |
| TGCAGATCCTGGATAAAAGATGATATATCGACACGGTTTAGAGTGTCACTGCGCTTGGCCTCTCAGGGAGCCACA |
| AGTACATATTTCCTGAAATACCGCCCAGCACAGTATCTAATCCGCCCGCCACTTAACACCGGGAGGGGAACTTCA |
| GCAGCGCACAAGCGCGCTCCCGGTTTCCTGGTTCTGGGTGGGGAGAGCCCAAATGAGAAGGATCTGGTATGCCTA |
| GACGCCCCCTCCCCTGGCCTTTGTCTTCAGTCCAAGTAATCACTTAGCGATGGGCCTTAATAAATACGTCTGAGA |
| ACTGTCCTTATGCTCGGTAAATATTGGATTAGCTTTTCAATGACCAGGCTCTTGAAAAGGCTCGAGAAATACACA |
| CCAGGTCTCAACTAAGCCCAACAGTCAATAGGTAAGGAAATAAGTTATTTCCCCATCTGAGGTGGGGAATGTTGG |
| GAAGGGGGACTTCCACTCTTACCAAATTATCTGATTCTACTAAATATGACCGTTGTACTAAATAGGAAAGGGGGC |
| GCATCCAAGTTTCCCATTAGTCGGAATTTCCACCAGCTCAGTTCTGCTCATTAAGGGCCGAGTGACTTTGTGGGG |
| AACATATCTGGGTTCCAGTTTTTATTTCCACAGAGCTCAGCATAAACTATTTTTGTTTAGTACATATGGTTTATT |
| TGGGGACTGCTTATGGGAGTTTTGACCTGGCAATTGCAGGGGAGAAGGCATGACCCAAATTATTTCCGACTGCCT |
| CGCGCCAATTTGGACCGCTTAGAGGAGGCAAAAAATGGGCAAATTCCTTGGAAGCCCTGCTGTGTCTCCCTGGTA |
| CTGAATTTTGTAAGCACGCGATACAGGAGACATTGAAAATTAAAGAGGAAGTATCTCCCTCCTCCAACATGGGGA |
| GAGACGCTGTTGGAAGAAGTTTCTGAAGTGGTTTCCCATCGCACCAAGAGGCCAGTGGGATGGATCCCCGCGCAT |
| AATTCAAAGGAACGCGCGCGTCTTTAGCTCTTCGGGGTTGGTAACCAAGTGGTCCGGCCGGGCGCAAGTCGCCTT |
| GGAACCGGCTGCAGCCCAAGTCTAGCTGGGCCCGGGACTGAGCGGCACCCTTGGCCTCTCAGAACCTTTCTCGCG |
| GTGAGTGGAAGGGCGGCTCCGCGCGCGGGCGCTTCGGGGCCGGTCGGTTGCGAAATCAGGGGGTGGATTTTCATC |
| TACCCAGGAGCCGCTAAGCCCGTAGGGGACCGAGCATCACCCAGGCCCTGGGTACCCTGAGTTGCCTCCTGAGCC |
| CCAGGACGGTCCGATGGTGCAGAGCTCCCAGGCAGAAGTTAGTTTCCTGATACACACACAGCAGTGAGCAAAGTG |
| CGCACAAGTGAGCCAAACCCTGAAGACGCAGGTTCGCGGACTCCCATCCCAGCGTTAGAGTCAAGGAGACAGAAG |
| AGAGGAAGGAGAGAAGTGAGGAAGGGAGAGAGATTATGAGAAAAAGAGATTATGAAAGTAGAGAAAGAGATTATG |
| AGAGCGAGATTATGAGAAGAGAGAAAAAGAGAGATTTTGAGAGAGAGAGACAGAATGAGAGAGATCCAACTTTCA |
| GTGTCACGGGGCCTAGGCGGGGCAAGCGCCCTCCGAAGCCATCAAAGACAGGGGTGGCTTTTTCTCCCCTCCTCC |
| AGCCTCCTCCCCAATAGATATAGCACGAATTTTTAATGCGTCTTCCTTTCACAGACAACAATACAGGGTTTGAAA |
| GCCGGACACAATTTAGGTTTTGTGCGGGTCCCTCCTCGCGCTCCCTCGGCCCAGCTGGCCATATGGAATCCAGCA |
| TGGAGCCCGTGGATGACAAAGGGACCCAGTGACAGGCCCAACAAAACCCCAAGGAGACTTCTGCCTGACTCCGGG |
| ATTCACTGCCGGCGATAAGCGCGCTGAATGGTGCGGGGTGGGGCGGGGGGTGGGGGGCGGGCCCCTTCTCCTTCT |
| TCCCCTCTCTCTGTCCCCGCGATCCTTTCTCTGTCCCTTTTTAATATGCACGCCTCTAACATCTCCGGCTCCCAG |
| CTTTCCCATTGTGCGGTTTTGTACCGCCCGCTGTAGATTGGGCGAAGATAGACTGCTGAAGCGGACCCCGCGCCG |
| GGTGCGCTCCCAGGGCGCTGGGGTTAGGGCCACACAGGGCTCCGCAGGCGCTTTTATTGACTCCATGGGGACCCG |
| AGGACAGAGAGAGGCGGGCGCCGGGTCCACCTCCCGGGCTCCCGGCCGGCCACAGGAGCGCACACCCAGATTGCA |
| GGCCCGCGGTCCTGGCCACAGCTCCAAATTTGTCCTCAATGAGCAAGTGGTGGAAGCCTGCCAGGGTGAGGACCT |
| TCCACGCTTCCCCCTTCCTCTCTGGAAACCTGAGGGTCTCTTGTGATCATTCTCACCCTGGAAGCCCTGGGGCCT |
| GGAAAAGTCAAAATGGCCTCAGGCCTTCTGACAGCTCCGCTCCAAGAGACTTGAAACCCTCACCTTTCCTCCCAA |
| GAGGATTTTGGGATTAGGGGAAGTTGCAAGTGGATGTTGAGTGGTTAGTACCAGGGCAGGTTGGGCGTTCAATTA |
| TTGCACAACAACTATTTGGGAGAAATTCGTTGGCCTTTAAAAACAGTAAGACATAAGCCCCCAAACATTGCCAA |
| GCTAGTGTGGAGAACAAAGGGAGACCTTTTAGCATTTAGAAAAACTGCCCTTTCCCCGAGGATGAGCCCGGAGAT |
| GGGAAAGGACCTTTACTGGGGTATTAGAAAGACTTCCGAGCCCTCAATTATCCAGGGGCGGTGTGGAACGCGGGA |
| ATAAAGTGTCATCGCGTCCCTGGGCTGCTGCGCAGAGTGCTATCGACGCACAGATTTGGTCGCACGGATAATCAT |
| GTTTGCTTTAGATATTGAATTAAACCTGATCATCAACTACAGGGAGCGAGAAAGTCAGCTGGGACCGCTCCTTTT |
| GCCCGGCCTCCTCACTGCCACCCAACCCCCCAGCCTTGATGGTGCAGCTTCGGAGAGAACAGAGATACAATTTCC |
| AAATGCGCCGACGTTCAGTCCCTCAGCGTCTGCAGCACCCGCTGGGCTCTGAGCTAGAGTCCCAAGTATTTTTAG |
| AAACCCGCGAGATAGAGGAGAAAGGCTCATCCTCCAGTTGGCCAGGCTTCCTAAGACGCTCCCCCGCGTGGCCAA |
| GTGTGCGCCAGCATCTGCCAAGGAGATCTTCCTCCAGCAACAAGGGTGGGACGGAATCCGTTCCCCGCCGGAAAG |
| ATGGATGCGCCCTTCCCGGGCGTGCCCGGGGCTGTGTGCCCACTTCCCATCCGGGGAGCTCACCCCACCCCCAAA |
| CCTCTACTTCCTAGCAATCCACCCAGTTCCACGCTCAAGGGCTGACCTGGGGGGACCGCACACCCTGGTTCGGAC |
| CGCCGAACGCTGGAGGGAAGGAGGCCCGGGATCCAGTCCCCGGAGAGAGGCCTGGAAGCCCGGAAAGGATGGGAG |
| CGTAAGGGAAGGGAGAGGCATGGTTTGCTGGGATTGCCAAAGATTCTCGCTCCCTGGCTTCCTGGGGCCAAAGAT |
| CCTAGGGAGGGCTGCAGTATCCCCTCCCTCCCCCGAGCCCAGAACCCCGCGTACTTCCCCCAAGCCCCCTAAGCC |
| AAAGCCTCGCGCGCCCTGACCGTTCCCACCCCCAGCCTTAGCGGTCTCCTAGGTCAGCACCAGCCCGCAGATTTT |
| GAAAAGGAGTGGGGAGTGGGGAGAAGGCAGCCAGTCTTAACCTCAGACCCCCACCCACCCACTTTCTTAGCGTGA |
| GGTAAGTCAAATGTAACAAAGTGAAAGTCATCGAGTGTAGTGGCTTCAACAGCTTCTCAGGCTGAAGGAGCCACT |
| CATAGATTTGGGCCAGCGAGGGGGGTTTGCTCTCCTCGCCTTTGCGGCTCCCGAAGTCACTTTTCCTCCCGTAGC |
| CGGACGCTGCCGCCCGGGGTTCAGACAGCGCGCGAGACCAGGGGAGATGCGGGGGAGGGTGGGCGGCCCTGGGCT |
| TCCGGCCGACCGCTCGCAGGCCGGAGGCCGAGCGTTCTCCTCCCCGCCCCAATCCTAGGCGCGGGGTGCAGCCTG |
| TGGTCGGAGGGGCCTGCACCGGGAGCCCCGCCCGCCCCAGGGCCCCGGTACCCCCGGCCTCCCCGCCCGAGAGGA |
| ACCGCCTGTGGGAGCCCCGCGGGCGGCCGGGCCCGGCTCCCAGGCCCAGGCCTCCGGCCCGGCGCAGTAGGACAA |
| ACGGGAGGGCAGGGATTTTTTCTTTTTTTCTTTTTTAAACACAGGATTTTTATTAAAATTCTTATTTAAAAAATC |
| GAAAGCTTTCTGCGCCCGGCGCTGTTGGGGAACCGCGCCGAATAGCTGAGCTCCAAGTTCGGGGCTGAAGGCCCG |
| GAGGACAGGGCAGAGGGCTCCCTGCCTACAGGGTTTTCTTTTCCATATTTGAGAAATGTTTGCACAATAAAATAA |
| AAAGAGAAAGGAAGAAAGCAGGGGAAAACGCAAAAACAAAAACAAAACAAAAAACAAACCCAAACAAGCCACAAA |
| GAAAGGAGTTGGACCCAGACGGGAAACAGGCCGGTCCTGAAGGTCATTTTGGCAACAATCACCACCGATATTTAC |

TABLE 7B-continued

| Sequences of differentially labeled CGIs between bladder cancer subgroups relative to blood |
| --- |

AACGAAAAGCGAAATCTGCCACCAGTTGTCAGAACGTTTACATGGCCATAAATATTTAGCATTTTCTTATTTTTT
TTTAAAAAAAGGAAGAAATTCTCTGTATTTTTAAAGTGTTCTCCACTTGCTTTAGAAGACGGCTGACAATATCGC
TACTCACACAAACATATTTTACAAAATGCACGAAAGCAGGGGTGGGGGGTCGGTCTTTTTCTCGTTTTCAAGTGA
CGACATTAACGCTGGGACGGTTTGGTCCCCCCGGGGAGAGGCAAAGAAGCGAAGCTGCGCAAACATTCTGTAAAC
ACGGCGTAGAGTTCAGCCCTCTCCCAAGGTTCAGAAGGAGAGGCATGGGCAGAGCTGGGTGGGTGGAATCTGCCA
CTCCAAGGAGACGCAGGCAACCTCCCGGCGCCTCCCTAGTGGAGCCGAGAGTCAACTCGACTCCATAATAATAAT
TATAATAATAATAATAACCACCATAAGGACCGAGGCCTCCTCGCCGCCACCGCCGCCGGGGTGGGGCCTGGCCT
GGGGCCGCGAGTCTCGTTGGGGCGGCGCTCACCAAGTCCACTGCTGGGCCTGGACCAGGGGGTGTGCTGTCGGGT
ACTGGGGGGTGCTGGCCGAGCTGTACTGGGCGTTGTACTGCATGTGCTGCAGCGACTGCGCGCTGTAGGCAGAAA
AGGGAATGCCCGCCTGGAAGGTGGCGGCTGCCAGGTCCTGGGCTTTGAGCGCGTGACATGGTTTGCCGTCCCTGA
CCAAGACGGGCACGGCCACCCGGCGCGGCGAGGGCAGGGGCGTCACCTCCATACCTTTCTCGGCCCGGGCGCGCT
TCATCTTGTAGCGGTGGTTCTGGAACCAGATCTTGACCTGCGTGGGCGTGAGGCGGATGAGGCTGGCCAGGTGTT
CGCGCTCGGGCGCCGACAGGTACCGCTGCTGCCGAAAGCGCCGCTCCAGCTCGTAGGTCTGCGCCTTGGAGAAAA
GCACTCGCCGCTTTCGCTTCTTGCCGGCGTCCCCCCGCCGCCCGGGGTCTCCTTGTCATTGTCCGGTGACTCGT
CGGCCGAGGGCTCCGGGGACTTGGAGCTTGAGTCCTGAGGGGGCGCCCCGGCAGCCAGACCGTGCACTGGGGGGA
GGGGGAGAGAGAAGCGCGTCAGGCGTCTGGAGGCCGCGCGCAGCCTGCACCAGACTCGGAGCACCCTGGATCCTC
CGTGCGACCCTGGACCTCCGCGCCTGGCAGCCCAGCCCCGCTGCCTTTGCCATGACCCCTGCCTTCCTCTACGCC
TGACGAAGACGTCGGGACCTCCCAGGGTAAAGAGGGAAATCCGTAGGAGTGGGGGCTAGGGGCTCGCCTTTCAAG
GGGCTCACATAGTGTGGGTGAGAATTTGGGGGGGGAAGTGGCACTGAAGATCATCGCGGGTTAAGGGCTCCGGCG
CCCTTAAGCGGTTTCCTCTCCGGCGAGACGTGGGCAGATTTTTAAAAGAAATACCCCACAATCCCAGCATTGATC
GGCTCGGCCATTTAAGGCAGGTTTTTGGGGGCTTTCGTTTCTGCTTTCGGGCCTTCTAGACACCCCCTGCACTGC
ACAAAGCGTCCTCTATGATCGCGCAGGGGGCAGGGTGAGCTATTTATACCCGGGCCACCCGAAGCCTCCCCACCC
TCCACCCGTACCCGGACGAGGCTCGCTGGCTACCTCCAGGGCGCCAGGCCAGTCCCTCCCAGCGGCCGGAGTCCG
GGGGCTGCGGCTGGAGCCATCGGTCCGGGTTGACATCATATACCAGCCCCTGGGAGGTATAGCCCTTCTCCCTCT
TTCTCCTTAACTTCTCGCATTGAAAAAAATTTTGGAGACCAAGTTCTTTCCCGGAACTAAGGAGGCTTGAAGAGG
AGGGCAGAGGACATCCTATACAGGTGTTAAAAATCTTTCTACGGATCCGAGTGAGGGGGTCCGGGCTTACATGGC
CCCTTCCCCTTTCACTCCCAGCGTCCAACCCGGGCTGCGGCTGCAGGAATGGAGGGGACCACGGCCTCGGCAGCC
AAGTTTTGCTACTTACGGGAGTACTGAAGGCCCCTCGGTGCTGGCCAGCCAGCGCGTGTACGGGTTGTCGCTGCTG
TCGTAGAAGGGGTTCTTCAGGGGCAGGCTCTGCACCGCGTCCAGGGCGCCCTGCCCCAGCGGCCCGGCCCTCTTG
GCTGGCTCGGGCCCCTCGTTCTCTTCCTCCGGACCTTCGGCCACAGAGCCCTCCTCATCGTTGGTGTCCGGCAGG
TCTAAGATGTCCTTGACCGAAAACCCCGTCTTTGTGTTGGTCAGCGACATGGTTCGAGACCCCAAAATTTATGTC
GCAAAGTTGTAGCTTCACTTGGTCAATTCGTGGCGCTCCCCTGCCCCGGCGGGCGGGGGAGGGGGGAGTTGGGGG
GAGGGACTGGGGGAGGGGAGGGGGGAATTGGCTTTAATTATTGGGATAATTATTATTTTTAAAAAGAGAAAGAAA
CTGGGGATGGGGAGGAAAAAAATGAAGCCCAACCCAGTGCCTCTCTCTGTCTTCTTTGAAAGCACGCGGAAATGG
ACGCAGGAAGCCGGGCGGCCTGCGCGCCGAGCGCCGCGGGCCCCGGCCTTAGTTTCTAACTCCAGGAGGGGTGCC
AAGGCGGCGTCAGCTCGGGCTCCGGCGGCCGCTCGGCGCGCGGTGGCGGCTGGTGGCGAGGAAAAAAATGGGCCAT
TGCCCGAGCGATCAGTCCATATAAGGCTGGGCTCCACTCACGAACCTGGGGAGGCGGGGAGAGGGGGAGAAAGAG
AGGGAGGGAGGGAAAGAAAGAGGGAGGGAGGGGGGAGCGAGAGAGGGAGCGGGAGAAGGGTGGAAAAAAGGGGGAA
GAGACATTAAAAACGCAAAGGTTGGCCACGTGTGGGCGGGTCTTGGGAGTCAAGTGGATGAAGACAGTATTTGCA
GATGTGAAATTGTGGGTTTTGGGGAGCTCCGCGCTCCCAGCCAACGGCCCTCTAGAGCAAGATGAGAGGTGTAAC
GTGTCAATTAATTGCAAAGACGGGGCGAGCCTTTTTTTTTTTAAACCCAGTATTTACATACAAAGGGCCACCGCG
TCGCTCGCGAGTCCACACACTTGAAAGGGCCGTTTTAACAAATTGCATCTTAAAAAAGGTGGGGGTGGGGAGGAG
GAGGGGAGAAAACAAAACAGAAACCAGGAGGAGGGAAAAAATCCTCTTTAACATTCACCGGTTCCTACCTCCCCG
CCCCCGCGCGCCCACCCCCGGCAAGCCGGAAAATTGGCGATTTGTGGCGCCTTTGGAAAAGGGGGAGGGGGCGAA
GGCCGAGCTGCGGAAATCTCTCCTTTCCATCGTTGGTGGTTGCCTAAACAAGATCCGGTTCAAATGGCAAGAGCC
CAACTTCTGTAAGCCTCCTAGGTCAATATTTTGGTTGAGGCTTAAGGATGAGTGCTAGAAATGACAAGGCAAGTA
ATTGATTCCAGTTAACCGCGAGAGAGCCCAAAACCCAGGAGAGAGCTCCGCTCCGGGCCGGCCAGAGCCACCACC
AAGCGACCCGCCCCCTTCCAGCCGCCCTTTATTTGCTAAGACTCATTTATTTCCTTCACTCCGCCTCCCCCCAC
CTCCCACCCCCAACCCCCCGCCTCCACCTCTCTGCGGCCAAGGAGGACGCGCAGTTCACTTTCTGCTTTGCGGGC
GGTCCCGGGGAGGGGCGGGGTAAGAGTGAGGAGCTCCAACTTCGTCTGGGGTCGGACCCTGGCCCTGCTGCCTCTG
GGCTCTGCGGGCCTCTTTCCCCGGGTGGAGGAAAGGGCAGACGGCCCTGCTCTTTCCTGCCCTCTATTATCCCTC
CCTCTCCGGCCCCCTCCCTCTCCAGCCTCTGGCTAGAGGTGGAGCAGCGGGAAGGCGGCGGGGCGGGATTGCGGG
GGTGGGGGTGGGGGTTGTGTCTCCAGCCTGGGTGAAGACCCAGAAAGCTGCGGGGGAGGGGGGTCGCTGGGTGGC
CCGACGATGCCTCGTTTTCTCCCCAGTTTTCTTCTCCCACGCGAGTTCTTTAGTGTGGTCTCTTTTTGGACGCCT
TGGGTGCGTTCGGAGTACGCGCTCCACGTTTCCAGGTTAAGTCAGGTTAGTGTGAAGTTTCCAGCCACTCTCGGC
TCTGGGAACTGAACTTTCCCGGGACTTGCACTTCCTCCTCGGCGCTGGGGTTGGAAAAGACCACGCCGCATTTGC
CACCCCTTCTTCTAGTTAAAACTTTTTGGGGGGGGGGTGCAGGGGTGTAGATTGGCTACCTGATGCTCGTTCGC
CCCAGAGGAGTGTCAGGAAGGAGCTTTGTCTGGGGGCGGGGAGGGGCACAGAAGGCCACCCCTGCGGGGTCCAGG
TCTAGTCTTCCCACAACCTGGGCTCCTCCGCGCGGGCCAAGCTGAGCGCGCGGGCACCGGGTCCTCCTCGCGCGC
AGCTGCAGCGGACGCCGCCGCGCCCCAGCTGCCCCCGGGTTGCCAGCGCTGGGTGAGGGCACCTCTCCCCGAGCC
GCTCGGCGGCTTTCTGCAGCCCTAGCTGCCTCGCCCCCAGTATGTGACGTGGGTGACAATGGCCCAGGTTAGAGC
AAGCCCCTCGTCGGCGCGTCCTGGGTGGTCGGACCCGGGCAAACACAAATACAAACCGATTGCTAAGCTGCGGAC
AATGAGCGAAATGTAGACAAATGTCCCGCTCCCGTTGGAAGCCTTTGTCCCGGCTCG
(SEQ ID NO: 296)

CGI: 61 range = chr20:23294035-23294650
CGCCACGGCGTGGCCACCGAGGTGGTGTACCGCTGCGACACCTGCGGCCAGACCTTCGCCAACCGCTGCAACCTG
AAGAGCCACCAGCGCCACGTGCACAGCAGCGAGCGCCATTTCCCATGCGAGCTGTGCGGGAAGAAGTTCAAGCGC
AAGAAGGACGTGAAGCGGCACGTGCTGCAGGTGCATGAGGGCGGCGGCGAGCGGCACCGCTGCGGCCAGTGCGGC
AAGGGCCTGAGTTCCAAGACAGCGCTGCGGCTGCACGAGCGCACACACACGGGAGACCGGCCCTACGGCTGCACC
GAGTGCGGCGCCAGGTTCTCGCAGCCGTCCGCGCTCAAGACGCACATGAGGTACGCGGGGAGCCGTCCGGAGGGG
TCCCTGCGCACTGGAAGGGTGTGTCAAGCACTGAGGTCGTCCTGGGATTTGATGTCTCACTGCTTAATTTCTCCG
CTCCAAACCTGGGGCTTATTTCGAGACAGCGTTTAGTTCTCTGTCAAGGTACAGGGGCTGCGAGTGATGGCTCT
GCTCCCTTGTTCTGAGACCCCTGGGGCGCCCCTGCTGGCCGGGACGTCCCTCTGGTGGGACCGCGACAGCGGCCG
CGGGCTCGCCCCACCG
(SEQ ID NO: 297)

TABLE 7B-continued

Sequences of differentially labeled CGIs between bladder cancer subgroups relative to blood CGI: 118 range = chr20:25011839-25013525
CGCGCTTTGAACCCAACCAGCCCTCATCGCTCGGAGCCCTGCGTCCCCCGCTTCCCAATCCCAGAACCCCGGAAG
CAGATCTCCTCAGTCCCACTCCCTGAGGGTCCTACAGTCCGAGGTCCCGCAGCGAGGGAGGAGCAAACGCCTGAG
CTCCGCGGGAACCCGGCGCGGCTGCCTGCGCGCACGCAGGGACCGGAGCCCGAGCCTGGGCCCTGCAAAGTGGGT
CTCCCACTCGCTGCGCGTTCGAGTGGGGCCTCCGCTAAACATGCAGATTAAACAAGGGGCTTCCGATAAGGATAA
TTACAGGAGGCTGCGCATTGACTTTCCGTTACTAAAGGAAGACCCAAATCTCCCCCTTGCAAGCTGTTCCCGGGA
TTACCAAAACAATCACTTTCTTTTGAGATCATTGTCTTTTGAACCACTCCAGCTCGGGGCAGAACGCTTTAGACG
CTGGCGTTGTTTTCCGCTCCGCGAGGAATTTTCCCCCAGATTTATCTCTGGGTTTAGGGAAGGCGTTGGGCATTC
GGGACTGCGTAGTCGTTTGTAAATCCGAATTTGGGGTAGCAGTTAAGTGAGATACCTACGCTTCCACACAGTTTG
TAGCCCGAGACCAGTCAGGCAGGCAGGGTAGTCGATTCTAAGGTGGCCCGACCGGGGTCGCCCGCGAATGGAAAG
CCTAAGGGGCGAGGGCGGACGCGGGCGCCGTGCCTGCAGCCCCGGGTGCCGACCAAGTGGCCTCACCTGGGACAG
GTCTTGGGGTCTCCCTCCCCTAGGTCTCCCTGGAAGGTAGGCGATCACGGGAGTGACAGACCCCGAGTAGATAGC
CAGTGATCCAAAGACACCAAAAGGCCAGGCGGTAGGAGCCCAGCCTCAGACACTCTCTATAGTGACCGCGGCGCC
TCGGGAAGGATCGTCTTAAACTCATTTTGCAGGTGAGAGCAACTGGGACTTATTAACCCAGTCACATCGGACACA
GAGACGTGGCGAGGGCGACACAGAGCAGGAGACTCAATCAAGGAGCCCGTATTGGAGCTCTAAGGGGACTCAGAG
ATGCAGAAGGAACGAACTTCTAAGGGGTCTTGCAATTCCTGGACTGGGGCGTTCCTAATGCATCCCGGGACCCCA
ATGCCAGGGAGGGGCCTGCAGGACCCCAGCGGTGGGCGAGTTGTGTCCTGGGTCACCTTGTGTTTCGCAGCGTGG
CGGTGGCAGGAGCCCAGCGCGGGAGGACATTTTCATAGCCTCCTACAGTGAGAAACGCCCCCCACCCGACGCTGC
GCTCATCTGTGTCCCCGCTGTTGCCGGGGCTCTGGTATCCACTTGCGCGCCCTATGTGGTGGGGATCCACCCAGA
GCCCAGCGTCAAGTTATACGGGCGCTTCACTCAGCGTCAGCCAAGACCAGGGAAGCGCTTCTTGCCGTTTAGGAG
ACGTCTGCAAGAGATAAAAAGCTAGCCCACGATCCACCCACAATCCTCGTGTCCCCGGGGTGCCCTCGCAGTTGC
CAAACCTACGGGCCGCGTTTAGGGGAAGCCTCCGCGTCCTGGCGGCCAAAAGAATGGGCTCCTTCCAGCTTCCCC
CTACCGGATACCACCTGCAAATCTATTGCCAGAGGCGCAGCTCCCGCGAACGTTCCCGCCCCGGGCGGCCCCCAG
GAGTCGTTTTGGGTCCCTAAATCCGTTGAGGGTTCCG
(SEQ ID NO: 298)

CGI: 380 range = chr20:36785545-36790786
CGGCCGTCGGAGCAGGGCCCCAGCGCACCGCGAGCCTCTGCTTCCTCCGCCTTGCAGCGCCGCGAGCCCTTCTTT
CCTCCGCGCCTGGCCCCGTCTGCGCCCCTCTCGGCGTGGGCATTCGCAGACCCGCTAGGAGGCTGACGAGAGGTG
TCCTCATAGAGTCCTGCCTTCTTCCAGACCCCCAAACGAAAAGAAAGAGAAAAGCCAACCTTTCGCCTCCATTCT
GCACGCATTTGGAGAGCGGCTGGTGGCGAGCGATCCGCACAATCGCTTCCCTCGCGGCGTCCCTGGACGGGCGGA
GAGAACCCGGGTGACTGAGCCTGAGGCTGAGCTTCCTTGGGAGCGATCCATGCCAGCCACTTCTACCTTCAAGGG
GGACTCGCGGCCGGGTTTACGCGCGAAGGATGGGTGCCAGGGAAACTGACTTATAGACGACCCGCTCCGCGAGAG
ACTGACAACTCAGTCCTGCGGGCTTTCGGGGCGCCCAGACCAGTCCTTAGCCAGAGGATCTGGGGCTGCACAGCT
CCCGGACCCTGGAGGGGGTGGTCCGGGGGTGGGAGACTGCGAGCATCAGCCCACGCCGGCCCCCTCCCACCCTGC
GGCGGCGAGGTGGGAAGGGCCAGGATGCGAGCTTAGCACCTCCCCTAGAAATGCAGCACTTCGCCCCCCCACCTC
CCCTGCCCTCGGCGCTCCCTCTTTCACGCGCTCCCTCCCGCCTCCTTCCCAAGGGCGCCCTTCTTCTGCCCCCAG
CTCACGTCTGAATCCCTCGGCGCCCCTTTCTCTTCTCCTAGCCCCTTCCTCACGTCCCCTGCCTCCGGGTATTT
CCTCTCTCCAATCCCCCACCCCCGCACCGCCTGATTCCGAGGGGCGGGAGCGCATTGGGCTGCGCACGGGTGGGG
GCGCCGCGCCAGCTTCGCGTAGCTGCTCTGACGCCGCTGCCGCCGCCGCCGCCGCCGCCGCCCTCCGCAGCCCAG
CTCGCGCCCCGCGGCAGCTCCGCAGTGACACTAGCCACCACCGCCGCCGCCGCCGCTCCGCCAGACCTGCTGCCAG
CTTGCCCGGTCCAGCCCTGAGAGAGCCTCGAACGCCAGCTGCGAGGGTCATGAGCCAGAGAGCCCCGGGGCGCCG
CGCGGAGAGCAAGCGGAGATAGCGACTTTGCGCCCCCCAGCCCTCGCCTTCTTGCATCGCGTTCCCCGCATCCTC
GGGTCCTTCTGTCCTTTCCGCTGTCCCCACCGCCGCCATGGCCACCTTGCTCCGCAGCAAGCTGTCCAACGTGGC
CACGTCCGTGTCCAACAAGTCCCAGGCCAAGATGAGCGGCATGTTCGCCAGGATGGGTTTTCAGGCGGCCACGGA
TGAGGAGGCGGTGGGCTTCGCGCATTGCGACGACCTCGACTTTGAGCACCGCCAGGGCCTGCAGATGGACATCCT
GAAAGCCGAGGGAGAGCCCTGCGGGGACGAGGGCGCTGAAGCGCCCGTCGAGGGAGACATCCATTATCAGCGAGG
CAGCGGAGCTCCTCTGCCGCCCTCCGGCTCCAAGGACCAGGTGGAGGTGGTGGCGAATTCGGGGGCCACGACAA
GCCCAAAATCACGGCGTGGGAGGCAGGCTGGAACGTGACCAACGCCATCCAGGTAAGCGCGGGATTCCCAGTTCT
GCCTGTCCTCCCCCCTCCCAGCTCAGCGTGCCGGGCTCTGCCCCCGACAGTCGCCCGGTGATCTCGGCCTGGAGA
CCCCCTCCTGTACCCAGGAATCTCCCTTTCTCCATCCCTCCCAGCCCTGCGCGGGGACCTACGCCCCCAGGCGGT
GTTTTCCGCCCTAACCCACGCTCCCTCCCAACGGCACCAGCTGCAAGACCGCTAGGCTGAAGTTCGGTCTGAGAC
ACCTGTCCGGAGACACTGCAAAAGTGAAGGAAATGGGGGGAGGGAGCAGGAAGCGATGAGAAAGAAAGAAAATCA
GGATTGGAGGGCACGGTTTGGTCTTGGACTCTGGAACGGATTCACAGCTGCATTTTTGGGAGGAAAGAAGAAGGG
GAAATCGCTGAGGTCGGAGTCTCCTCCCCCCGCACACACGCATAGACACGCACACGTATATAGGCAGGCACACCA
CATGCCCACAGCCCCCCTTCCCACGAACAAAGGCGCAGGCACAGGCGCACACGACATGTATCTATATATAGACCA
CAGTACTATCCCCAAATGCACCTGCGTACACCCCTACAGCTCCACAAACAAAAGCATATACCTGCACATACCAAA
CACACGAATATTCGTTTGAACATATGCACACACACATGCACAGATGCATGCAGACAGGAACCAGCCTGCTCCCTT
GGGTGCGGCCCTGTTGGAGACATACAGGTATACACACGAAAGCACACACATGCTCCCACACAAACACATTTAG
TCCGCAATAATCCAGCATTACCTGTGCACAGACTCGCCCCTCTCGCCCGAAATCCCGGCTGCACCGCAAAGAGGC
GGCCAGCTCCTCCCCGTGTGACCCTGGCGAAGCCCTCTCCAGAGGCTAAGAATGGCCCCTGCTCTCTAGGCCCTC
TCCCCTTATTCCTAACCCCCCACTCCCCACCAGGCGGCGCAGGACTCCTACATAGGGAGCAGGTTTGGAGTCTTG
GCAACGACCTCCGAGCTAGCAGGGGCTGGCAGGCCGCAGCTTTCTGGGCCGAAGGAGACTTCAGCTCTAGGCAAC
CCCGGTCCCTTACAGCTTGGCCCCGCGGCGTCCCTGGAGCGCACTATCACTGGGGCCACGGAAGGCAGGTTTTCT
GGGAGCAGAGGCCTCCCAGGGGTTGTTCCATGTATGGGGTAAGCAGGACTCCACCGGGCCCCGAACACCAGATG
GCCCGACCCAAGGCGCTTTCCGCTCCGGGGCCCGGCGAGACGGCCTTGCTGGATCACGGACCCGGGGCTGCTCCC
GCCTTCGCTGTGCCCCGCGACTTCCCGGGGCGTCTTTCAAGGCTCCGTTTGATAGGCCCCAAGGGAGGCCAGGGC
AGGAGGCTGGAGGCTCGTAGGCCTCCGGGACCCTGGATTTCGTTAGCTCTTAGTCCCCGTGTGGATTCTAAACCC
TACAGCCCTGTCCGCCTGACCCTGAAGCTTCTGGTTCTAGACTCTTGCTCGGTTCGGCTTTCTGGCCTCCCTGGC
GCCTTCCCGCCAAGCTCCTCCTCCTGCTTGCCTCCCCAGCCTCCACTTAGTCCCCTTCCTTAGGTCTCGCCCTCG
CCTCACTCTAACTCCAGCCTTGTCCTAAGACTCTCAATTTCCAGCCCTGCTTCCTCCTCCCCGCGCGCTGCTCCC
CAAGCGTCTTCACATTGTCTCTGTTCTTGCCTCCCAGGGGCTTTGCCCCACCTTCAGCCCCTCTCCCTCTCTACC
CTATTTCCTTTTCGCCTCACAACTGCAGCCTTTAACGTTTCCTCCTCTGGTCTGAGCCTGAGACGCCCGAGTTTT
CCTCTTTAGCTCCCGTGCCCCATTCCAGCCCCACCACAAATCCCGTGCCCACTCTTTCCACTGGCCCAGGCCCAG
CTCACTACCTTTCTTAGAGCCCCTTTCCGACTACGCTCCCTTCTGTCCCTTCTCATCTCCTCCCCCAACTCCTCA
TTCTGTTCCTGTCCCCAGAAACCATCCCGAAGTATCTCCCTTCCCTCCTGTGGCTTCTCCCTATTCTCAGCCCTC
TCCCACCCTAGCCCTCTCGCTATCACCAGCCATTAGCGCACCTTTCCTTCTCAGATCCGTCCATACATCCCTCCC TABLE 7B-continued

| Sequences of differentially labeled CGIs between bladder cancer subgroups relative to blood |
|---|
| TCTCCATCTCTGGCTCGACACCCGGGCTCACTATTAGTTCCCCTACATCCACCCCGCAGCCTGCTCTTAACCTCT<br>CCTCCCCGGCGGCTCAGACCCAATTCTCAGTGTCCTTAGCGCCCCCTTCGGGCCACAGCGTTAAGCCACGCCCCC<br>CGGGCCCCTCATCCGTTGCCAAGTTCGCTGAGCGTCCGCGTCTGGTTGCCTCTCCGCCCCACAGGGCATGTTCGT<br>GCTGGGCCTACCCTACGCCATCCTGCACGGCGGCTACCTGGGGTTGTTTCTCATCATCTTCGCCGCCGTTGTGTG<br>CTGCTACACCGGCAAGATCCTCATCGCGTGCCTGTACGAGGAGAATGAAGACGGCGAGGTGGTGCGCGTGCGGGA<br>CTCGTACGTGGCCATAGCCAACGCCTGCTGCGCCCCGCGCTTCCCAACGCTGGGCGGCCGAGTGGTGAACGTAGC<br>GCAGATCATCGAGCTGGTGATGACGTGCATCCTGTACGTGGTGGTGAGTGGCAACCTCATGTACAACAGCTTCCC<br>GGGGCTGCCCGTGTCGCAGAAGTCCTGGTCCATTATCGCCACGGCCGTGCTGCTGCCTTGCGCCTTCCTTAAGAA<br>CCTCAAGGCCGTGTCCAAGTTCAGTCTGCTGTGCACTCTGGCCCACTTCGTCATCAATATCCTGGTCATAGCCTA<br>CTGTCTATCGCGGGCGCGCGACTGGGCCTGGGAGAAGGTCAAGTTCTACATCGACGTCAAGAAGTTCCCCATCTC<br>CATTGGCATCATCGTGTTCAGCTACACGTCTCAGATCTTCCTGCCTTCGCTGGAGGGCAATATGCAGCAGCCCAG<br>CGAGTTCCACTGCATGATGAACTGGACGCACATCGCAGCCTGCGTGCTCAAGGGCCTCTTCGCGCTCGTCGCCTA<br>CCTCACCTGGGCCGACGAGACCAAGGAGGTCATCACGGATAACCTGCCCGGCTCCATCCGCGCCGTGGTCAACAT<br>CTTTCTGGTGGCCAAGGCGCTGTTGTCCTATCCTCTGCCATTCTTTGCCGCTGTCGAGGTGCTGGAGAAGTCGCT<br>CTTCCAGGAAGGCAGCCGCGCCTTTTTCCCGGCCTGCTACAGCGGCGACGGGCGCCTGAAGTCCTGGGGGCTGAC<br>GCTGCGCTGCGCGCTCGTCGTCTTCACGCTGCTCATGGCCATTTATGTGCCGCACTTCGCGCTGCTCATGGGCCT<br>CACCGGCAGCCTCACGGGCGCCGGCCTCTGTTTCTTGCTGCCCAGCCTCTTTCACCTGCGCCTGCTCTGGCGCAA<br>GCTGCTGTGGCACCAAGTCTTCTTCGACGTCGCCATCTTCGTCATCGGCGGCATCTGCAGCGTGTCCGGCTTCGT<br>GCACTCCCTCGAGGGCCTCATCGAAGCCTACCGAACCAACGCGGAGGACTAGGGCGCAAGGGCGAGCCCCCGCCG<br>CGCTTCTGCGCTCTCTCCCTTCTCCCCTCACCCCGCCCCCACCAGCCCAGTGCGCCCTGCCGCCGCG<br>(SEQ ID NO: 299) |
| CGI: 315 range = chr20:38749965-38753401<br>CGCTGGTGGAGCCCGCCTCCCTGAAGCCGGAGTTGGCGAGTTTCTCGCACTTGACCTTGTAGGCGTCTCTCTCGC<br>GGGCCAGCCGGGACACCTCCTGCTTAAGCTGCTCCACCTGCTGAATGAGCTGCGTCTTCTCATTCTCCAGGTGGT<br>GCTTCTGCTGGACGCGTTTATACCTGCAAGACTGGGCGTAGCCCCGGTTCTTCAGGGTCCGCCGCTTCTGCTTCA<br>GGCGGATCACCTCGTCCTTGGTGAAGCCCCGCAGGTGGCGGTTCAGCTCGCGCACGGACATGGACACGAGCTGGT<br>CGTCGGAGAAGCGGTCCTCCACGCTGCCGTTGCCGCCCGCCGCCGTCGCCGAGGCCGTCGCGTGCGGCCCGGGCC<br>CGGGGTGGCTAGTGGGCAGCTGTTGCGCCGGGCTAGCGGCGCTGGACGGCGGCGGCGACGCTTGGTGATGATGGT<br>GATGGTGCGGGTGAGCGTGCGGGCCCAGCTCGTCGTGGGCCACGCCGGCGCCCGGGTACGCGTGGTGCGGGTGAG<br>GGTGGTGGTGATGGTGGTGGTGGTGAGCGCCGCGAAAGCTGTCGAAGCTTTGCAGCGGCTGTGGCACTGGGTGCG<br>AGCCGATGAGCGCTTCCACCGCGTCCTCGGGCGTCAGGTTGAGCGCCTCGGGGTTCATCTGCTGGTAGTTGCTCG<br>CCATCCAGTACAGATCCTCGAGGTGTGTCTTCTGTTCGGTCGGGCTGAAGCTGGGCGACGAGGGCACGGAGCTAC<br>ACGGAGTGCTGAGCGGTGTGGAGGACACCGAGCCGGCTGGCTGCAGGCGTGTGCAGGGCCTGCCCGGACGCTCCG<br>CGCGCCCCAGTGGCTCCTTCTTCACGTCGAACTTGAGCAGGTCGAAGTCGTTGACATACTCCATGGCCAGCGGGC<br>TGGTGGGCAGCTCTGGCCCCATGCTCAGCTCCGCGGCCATCGCTGAAGCGAGGCGCAGCCGCCGCTGCCGCCCGG<br>GAAACTTTGCGGCCGGCCGGAGCGCGCCGAGCCAAGCGCGGGGGGGAAGAGCGGAGAAGAGCTGGGGAGGCGGGG<br>AGCGAGGGCGCAGCGGGCCGGGGCCGCCGGCCAAGCCTTTGTCTGGGGACGCGGCGGCGCGCCGGAGAGTCCCGA<br>GGCTGCCTGCACCGCCCCAGAGCTCTGGGCTGTGCCCGCGCAGGGACCGGGCCGGGTAGAGTCGGGCGGGGTGGA<br>GAGGCAAGCGGAGCGCGCGGTGGGGCTGAGGGGAGGCGTGGGGCGAGTGCCCGTTGCTCGCTCTCTAGCTCTCTT<br>GCTCTTACGCTCTCTCGCTCGCAGCCGCTCGCAGCTCGGCGGTGCAGCTGTGCTGGATCCGGCGGCGCCGCAGCC<br>TTTTATCGCCTCCTGATGTCACTGGGGTGCGGGGGCCCGGGCGGCCCGGTGCGCGGGCCAATAGCTGCACGGCCT<br>CCGCGGCCCAGCGGCGCAGGGCGGGGCGCGCCTGACAGCTCCCCCGCCCCCCGCGTCAGCTGACTGGCGGCCCGA<br>GCGGCCCCGGAGCGGCGGAGGCCTGGCGGAGCGCTGGAGCGGAGTGGGACGGCCAGCCTGGGCCCACCCCCGTAC<br>CCTGCAGGTCCCGGCCCACGCACGCTCGCCTGGAGTGCGCGCCCCACCTCTAGGCCAAATCACCGCTTTCCCCTC<br>CTCGCGCACTCTCCTCCCTCAGTTCCCTTTGCACCCCACCCCCATCCCGTGTCACCCCCAAGGAGGCTCAGAATG<br>AGCGCCGGGACAACGCCTCCTGGGCCCTTTGTTCCCAAGCGGCCCCCGCCCAGTGGGCGACGCTCTGTGTGTCCT<br>CGCGGCTTCTGGCCGTGTGTGTCGTGCGTTCCTGTTTCTGGAGATCTGCGCGTATTTGTATGTTGGGGAGGGCGG<br>GCTCGAGGCTCCGAGAGTTGTGTTCAGACCCAACTCTTAACCTCAGGGGACCTTTCTCAGGCCAAGCGAGGGCCC<br>CTCCTGGCGGGTGCAGTCGCAGAGCCCTGAGGTTCGACTCCACTGGCCCCGCCGCTCCCCGCGTTCACCCCACCG<br>CACAATGTTCACAGTGAAGGCGACGGGAAAAGCAGCAGCCCAAAGGCTCTGAATTCCTCTTCCCCGCCACACGCA<br>CGGAATCCTGAGCCCCCGGAGCCTCGGGGCCGAGGCCGGCCCGGGACGGTGCTCCGAGTAGCTCTCCACTGCTGG<br>GGAGCCGGCCCTGTTTTTGTTTGAACGTTTTGTAACGATTAAGCAGATCCCGGCGTCAGCCCGCCGCGGAGAGGC<br>TCAAACAGGCATAAAGTGCGACCCCAAGTGGCCACTGTGCGCAAAGGCGCCGCGACCGCCCGGCCCACGGCCGGA<br>AGGCTTGGACGGCGCCTCGTACCCAGCCAGGTCTCCCCTACCTGGCCCAACCCAAGCCAGCCCAGAACGCATACT<br>ATGTGTGCACCAGAGCCCAGGACAGGTTCCCCTCGAGCGATGTACAGGTCCTCGGGTCCCGTCTTCGTACTCAGC<br>CGCGAGCCTCGAGCCGCGAGCTCCGCTCTGGTCGCCCCGTTGAAATTCCGTGCCCCAGCGTTCGGGGGTGCCCGT<br>CGGCTGCTCCCTGGGCCGGAAGGTCCTGGGCGGAGGAAGGCCGGTAGCCAAAAGTGGAAGCGCCACAGTGAAGCG<br>GCCCAGGGCCACCGGGTGAGAAACCTCCCGGAGGGCAGACGGGGAGACCGAAGCACACCGCACTAGGCATCCAG<br>ACTGGGCTTGGGAGCCGCGCACCCTCCCTACCCAGATCCAGGATGGCTAGAATTAACGGGTTCTTTCTGAGACCT<br>CGGCTCAGGCGCCGAAACCGGATAGATCGCGAATTCGCTGGACCCGGAGACCCGACCCGCCTCCCGCGTCACCTT<br>CTTCTTTCTAGCTTTGGGCGCGCGCAGCGAAAGGCAGGAGAGGCGCGCACTGGGTGAGTGAGTCCCGGCCGCTGT<br>CTGCGCTGGACCAGCCCGACTGACCTCGCGCGTAGGGGTCGCGTGAGCCACACCGGTGCAGACGCGCCTAGATTA<br>TTTTTAAATGTTAGAAGGTAAAATATTTGCCTCCAATTAATCTGAAAACTCTCTATTCTCTTGCGCCCTCGGAGA<br>GGCTGGGGTACGGCGTGGTATTGGGCCGCCTATTTTTAATAAAATGAGTGTATTTTAACTAAAACTTAACTCAAT<br>CTTGTGGGGTGGCAAATTAAATGCTGGAAGAGCGCGTCTACAACCCTCTTCGAGAAGCGTGCTCTCCGCAGAAAT<br>GAGTCGGCCGCCTGGAGAGAGAGCCTGGGCGGTGCCGCTGCGCAGCCCCTGCCAGTAGCTGGGGGTTGGGGACTC<br>GCACCTTGTAAATGTCCTCGTCTTGTTTGAACGCAGTGAGAGCACACTCGTTTCCAGATCACTCGGGACCGGGTG<br>TCTCGGATCTGTGCAGACTATGTATGGCTCCGGCCTCAGGCGGCCAGGGCGGGACAAGCACG<br>(SEQ ID NO: 300) |
| CGI: 43 range = chr20:49542203-49542863<br>CGCTGGCACCACCGAGCCCCGCCGCACCCCGCCGCTATTCTCAGGACGACCTGGGCAGCCCCCCAGCTTCTAGAA<br>AAGACACAGAGGAGACTGCGCAATCAACAGGCAGGAGTGTGCGTGAGTGCGGCATGACATGGGCACGCCACCCCA<br>GAGAAGTGGGCGCCTGCTGCGCTAAACGTCATCCGTCATCCTTTCGCTGAAAAGTTGGAAAACAAACAACAAAAA<br>CCCCGCCCAGCCTCATTTAATGCGAACCAAACACAAAAGCCACAGGGGAAAGCTTTTCCTCTCTGTGCTTCCCTT<br>TTCCGGCCGAGGAACACCACCAGCCAAGATAAGGGGACTGTGCGGGGCCCTCTGCGCGGCTTCAAAGGGCTGGCA |

TABLE 7B-continued

Sequences of differentially labeled CGIs between bladder cancer subgroups relative to blood CCCGCCCGGGCCCGCTCCCACTCCCACTGGCTAATGGGCTCCCCGCTCCAGCCCTTGGGGAGCAGGAGGCGGCCG
GGGCTCCATGCCAGGCGACTTGGAAGAGGTTTAAGGCTCACGCCACACAAGGGAGGAAGCTCGGCCTGTCAAGAG
GCGTGATAAAGCAGCCCCTTATCGCAGTTTTCCTTTCAACTGCCTCCAAGTGAGCGCCGGCCGGGGCTGGGCCTG
TCAAGGCCAAGCGTGTTCCTTTCATGTCGCCCTGGGTTCCTCGGTCAGCGACGTATCCACG
(SEQ ID NO: 301)

CGI: 20 range = chr20:54411932-54412178
CGCGGGTTTAAGTGGACGCCAGGTGCACCGGACACAGGCTGTGTTTAACCACACCGAGGACTATGTGTTGCTGCC
CGACGAGAGGACGATCAGTCTTTGCTGCTGGGACTCGAGGACAGCCGAGCGGAGAAACCTGCTGTCGTTGGGGCA
CAACAATATTGTACGCTGCATAGTGCACTCCCCCACCAACCCCGGGTTCATGACGTGCAGCGATGACTTCAGAGC
GCGGTTTTGGTACCGGAGATCG
(SEQ ID NO: 302)

CGI: 30 range = chr20:55680656-55681057
CGCACGCGCACGTGTGTGCCTGCATGCACTCACATGTGTGTTTCCAACCGGCCGACAGTGACGCACGTATGCCCT
CGCCACTCGGCAAGCACCTCGTGCTCCTTGGTAACCAGCAGATGTTTCTCTCAATTACTGATTTTCAAGAGCCTG
GTGTTTCCTGACATGAGCCAGGATGGCGGGCGGCGCCCAGGGGAGGGGAAGTGAACCGGGGCTCCGTTTCCAAGG
CTCTTGGACAAAAAGCGAAGCCCTGGATCAGGAAGCACAATGCGGCTGGTATTTAGCCGCTTCTCAATAGTGCCT
CATTCAATCCCCGGGGCCTCATTGATGCCCGCCGCGTGCTGGAGAGCCTCTGAGGGTCAGTCGGCGACGGGCACC
GTCTGGAGGGGTCTCGCCGCTAACCCG
(SEQ ID NO: 303)

CGI: 26 range = chr20:56860125-56860442
CGCAGCATGGTAGCGGGAGCGCAGCTGCGCGGGCAACCGCCGGGTTTGTGGCCGGTTGGCGGGCTCAGTGCCGCC
TCAGTGGGCTCTAGCAGTAGAAAAGTAAAGCGACTACCCTAAGATACCCAGAGCGAGAGGAGAGGGGCTAGAAGG
GTGCTGGAGGCAGGCTGTAGTGGGGCTAAAGGAGCTGACTGACCAGCGCTGCGGCCGGTGCCCGAAGCAGCGAGC
AGCGCACCTCAGCTCCGGTTGCCGCGCGGCATGGTATTTATCTGTGGGTTCAGTGCGCACAGCGTTGTCCAGTCT
CGAAACCACCCTAAACCG
(SEQ ID NO: 304)

CGI: 18 range = chr20:62371744-62371958
CGTGAGTGAGGGCGTGCACGGTGTGGGGTCCTGTGAGTGCGGGTGTGCACGGTGTGGGGTCGTAAGTTCAGGCGT
GCACGGTATGGGGTTGTGTGAGTGCATGGCGTGGGGTCTTGTGAGTGCGGGCGTGCACGGTGTGGGGTCTTGAGT
TCAGGCGTGCACGGTATGGGGTCGTGTGAGTGCATGGTGTGGGGTCGTCAGTGCGGGCATGCACG
(SEQ ID NO: 305)

CGI: 22 range = chr21:45511336-45511549
CGCAGGGCCCACGCTCCCGGCCTCTGGGACGCTCACGGCAGCCCCACGAGAATGATCACACGAGGGCCCACGCTC
CCGGCCTCGGGGACGCTCACGGCAGCCCCACAAGAACGATCACACGAGGGCCCATGCTCCCAGCCTTGGGGACGC
TCATGGCAGCCCCACGAGAATGATCACACGAGGGCCCACGCTCCCGGCCTCGGGGACGCTCACG
(SEQ ID NO: 306)

CGI: 24 range = chr21:46892946-46893236
CGCGGCCTAGAGCGGTGAGTGGGGTCTCGAGCGCATCCCGGGTGTTTGTGCCGAGGCTGGTGACGTCCGAGGTGG
CCTCTGAGTGTGCTGACTTGTGACCCTGAGCTGTTGGGGGCTCACCGGTGACTCCATGGTCTTGTTGAGCACCCT
GCACGTGGGGCTCAGGGTCGGTAAAATAGCAGTGCGTGGAGACCGCGTGCTAGAGGCCGTGGCGCCCGCGTACAA
TGAGTCGCAGACAGCACAGACGGGAGTAGGGCAGAATAGACAATATCCCGTGAATTGCGTGGGGCG
(SEQ ID NO: 307)

CGI: 38 range = chr22:18453364-18453931
CGCCAGCGCACAGCGCGGCAGGACGCGCCCGGGTCTCAGCGGACTTGTGCATGTTAGCTGTGTAGATTTATGTGA
GGGCTTGTAAAACTCTGGTCTTGTAAACTAGTCTTAAGCGCTTTTAATATGGAGACAGATGAGAGCCCCTCTCCG
CTCCCGTGTGGGCCCGCAGGAGAAGCGGTGATGGAGAGCCGAGCTCGCCCCTTCCAAGCGCTGCCCCGTGAGCAG
TCTCCACCACCTCCCCTGCAAACGTCCAGTGGTGCAGAGGTAATGGACGTTGGCTCTGGTGGTGATGGACAGTCC
GAACTCCCTGCTGAGGACCCCTTCAACTTCTACGGAGCTTCTCTTCTCTCCAAAGGATCCTTCTCTAAGGGCCGC
CTCCTCATAGACCCGAACTGTAGTGGCCACAGCCCGCGCACCGCCCGGCACGCACCTGCGGTCCGGAAGTTCTCC
CCTGACCTTAAGTTGCTTAAGGATGTAAAGATTAGCGTGAGCTTTACCGAGAGCTGCAGGAGTAAGGACAGGAAG
GTGCTGTACACAGGAGCAGAGCGCGACGTGCGGGCGGAGTGCG
(SEQ ID NO: 308)

TABLE 8

PcG target genes methylated in all bladder tumors or specific subgroups.

| All | NMI-wt only | NMI-mt only | MI only | NMI-mt and NMt-wt | MI and NMI-wt | MI and NMI-mt |
|---|---|---|---|---|---|---|
| DLX5 | ADCYAP1 | BARHL2 | TBX3 | CNTNAP1 | EVX1 | HOXA5 |
| DLX6 | ATOH1 | BCL11B | | EBF2 | GATA2 | |
| FOXD2 | BHLHB5 | | | FOXA1 | HOXB5 | |
| GAD1 | C20orf103 | | | FOXD3 | MSC | |
| HLX1 | CACNA2D4 | | | HHEX | NKX2-8 | |
| HOXA7 | CBLN1 | | | HOXC4 | SIM2 | |
| HOXA9 | CBLN4 | | | HOXD3 | VAX2 | |

TABLE 8-continued

PcG target genes methylated in all bladder tumors or specific subgroups.

| All | NMI-wt only | NMI-mt only | MI only | NMI-mt and NMt-wt | MI and NMI-wt | MI and NMI-mt |
|---|---|---|---|---|---|---|
| IRX3 | CDKN2A | | | MAFB | | |
| MAB21L1 | COL12A1 | | | ONECUT2 | | |
| MEIS1 | COL27A1 | | | OSR1 | | |
| MSX1 | CYP26B1 | | | PCDH17 | | |
| MSX2 | DMRT3 | | | PCDH7 | | |
| NR2F2 | DPP10 | | | PITX2 | | |
| NXPH1 | ELAVL2 | | | SIM1 | | |
| OTX1 | EMX1 | | | SIX1 | | |
| PAX9 | EN1 | | | SOX7 | | |
| PITX1 | FBN2 | | | UNG2 | | |
| PRKCZ | FEZF1 | | | ZIC1 | | |
| SHH | FLJ46347 | | | ZNF503 | | |
| SIX3 | FOXA2 | | | | | |
| SOX21 | FOXB1 | | | | | |
| TFAP2A | FOXF1 | | | | | |
| | FOXG1B | | | | | |
| | GATA4 | | | | | |
| | GNAS | | | | | |
| | GRID1 | | | | | |
| | GZF1 | | | | | |
| | HAND2 | | | | | |
| | HEY2 | | | | | |
| | HMX2 | | | | | |
| | HOXA11 | | | | | |
| | IRX1 | | | | | |
| | IRX5 | | | | | |
| | ISL2 | | | | | |
| | ISLR2 | | | | | |
| | KCNK9 | | | | | |
| | LBX1 | | | | | |
| | LBXCOR1 | | | | | |
| | LHX4 | | | | | |
| | LHX9 | | | | | |
| | LMX1A | | | | | |
| | LRAT | | | | | |
| | MAP1D | | | | | |
| | NFK | | | | | |
| | NKX2-2 | | | | | |
| | NKX2-3 | | | | | |
| | NKX6-1 | | | | | |
| | NPAS3 | | | | | |
| | NR2E1 | | | | | |
| | NR3C2 | | | | | |
| | NR4A3 | | | | | |
| | NRN1 | | | | | |
| | OLIG2 | | | | | |
| | ONECUT1 | | | | | |
| | OTX2 | | | | | |
| | PAX5 | | | | | |
| | PAX6 | | | | | |
| | PCDH1 | | | | | |
| | PCDH10 | | | | | |
| | PHLDB1 | | | | | |
| | PTGER3 | | | | | |
| | SEMA6A | | | | | |
| | SFMBT2 | | | | | |
| | SIX2 | | | | | |
| | SIX6 | | | | | |
| | SLC32A1 | | | | | |
| | SNRPF | | | | | |
| | SORCS3 | | | | | |
| | SOX17 | | | | | |
| | SOX9 | | | | | |
| | T | | | | | |
| | TBX15 | | | | | |
| | TBX20 | | | | | |
| | TBX5 | | | | | |
| | TFAP2B | | | | | |
| | TRIM2 | | | | | |
| | TRIM36 | | | | | |
| | TWET1 | | | | | |
| | VIPR2 | | | | | |
| | VSX1 | | | | | |
| | ZIC4 | | | | | |

TABLE 9

CpG islands (CGIs) methylated in blood but not in bladder cancer. Provided for each are: ID no.; Coordinates of selected regions containing relevant CpG islands based on *Homo sapiens* full genome as provided by UCSC (hg18, March 2006); GeneName; Location of the probe used; the Fold Change; and the sequence of the CGIs.

| No | CGI | Gene Name | CGI probe location | FC |
|---|---|---|---|---|
| 1 | chr19:53930240-53930625 | RASIP1 | chr19:053930330-053930374 | 2.66 |
| 2 | chr7:72883371-72883981 | CLDN4 | chr7:072883457-072883501 | 2.64 |
| 3 | chr22:26522794-26528592 | MN1 | chr22:026525238-026525282 | 2.21 |
| 4 | chr7:5614184-5614510 | FSCN1 | chr7:005614143-005614190 | 2.15 |
| 5 | chr16:66239477-66241425 | RLTPR | chr16:066241103-066241147 | 1.93 |
| 6 | chr5:551112-551430 | SLC9A3 | chr5:000551380-000551424 | 1.86 |
| 7 | chr19:6426223-6426998 | DENND1C | chr19:006427051-006427102 | 1.82 |
| 8 | chr3:32836146-32836433 | TRIM71 | chr3:032836466-032836511 | 1.78 |
| 9 | chrX:129301145-129301626 | SLC25A14 | chrX:129301313-129301357 | 1.76 |
| 10 | chr9:124027565-124030907 | LHX6 | chr9:124029663-124029718 | 1.74 |
| 11 | chr10:129424401-129427356 | FLJ46831 | chr10:129426989-129427033 | 1.71 |
| 12 | chr1:3147370-3148160 | PRDM16 | chr1:003147944-003147988 | 1.65 |
| 13 | chrX:128941527-128945710 | BCORL1 | chrX:128944842-128944886 | 1.64 |
| 14 | chr17:7584523-7585036 | DNAH2 | chr17:007584859-007584908 | 1.63 |
| 15 | chr1:27548507-27550603 | SYTL1 | chr1:027550188-027550232 | 1.6 |
| 16 | chr19:10304689-10307022 | ICAM3 | chr19:010306004-010306051 | 1.56 |
| 17 | chrX:129132628-129134108 | AIFM1-RAB33A | chrX:129133196-129133244 | 1.55 |
| 18 | chr21:45648960-45650662 | COL18A1 | chr21:045663489-045663539 | 1.53 |
| 19 | chr10:134864694-134865392 | KNDC1 | chr10:134865054-134865098 | 1.48 |
| 20 | chr9:129556229-129557670 | SH2D3C | chr9:129556146-129556190 | 1.48 |
| 21 | chrX:47305347-47306043 | ARAF | chrX:047305953-047305997 | 1.45 |

Sequence of the CGIs of 1 chr19:53930240-53930625
CGTGCGGGGCTGGGGCGGCGGTTACCTGGGCGTCCTGGTAGCCCTGGAGCAGCAGGAAGTAGGGGCGGTTGCTGGG
GGCCTGGATGAGGCACTGAGTCAACTGATCGAAGTCCCCGGGGTCTGCAGTTCCGATTTGGGCGTCGGCTGCCCCTG
GGGCCATGCTAAGTGCCTGCTGTCTCCGCTCCTGCTGCCGCCGCCGCCGCCCCTGAAGGCTAAGCTCCGACACGCTG
CGCCGCAAAGACAAGTTTTCTGAGCGCTCCTTGCCTCCAGACCCAGCTGGGGCCCCTGATCCGGTCCCCGGGCCAGG
ACTGGCCAGCGCTGCCCCACCCGACGCCGCCCGGGAGCGGTTCTTCTGTGGCCGCCACGAAGGGGCGCCGGTGCCT
GCG (SEQ ID NO: 309)

2 chr7:72883371-72883981
CGAACGTTAAGTCCGTCCCCAGCGCTTGGAATCCTACGGCCCCCACAGCCGGATCCCCTCAGCCTTCCAGGTCCTCA
ACTCCCGTGGACGCTGAACAATGGCCTCCATGGGGCTACAGGTAATGGGCATCGCGCTGGCCGTCCTGGGCTGGCTG
GCCGTCATGCTGTGCTGCGCGCTGCCCATGTGGCGCGTGACGGCCTTCATCGGCAGCAACATTGTCACCTCGCAGAC
CATCTGGGAGGGCCTATGGATGAACTGCGTGGTGCAGAGCACCGGCCAGATGCAGTGCAAGGTGTACGACTCGCTGC
TGGCACTGCCGCAGGACCTGCAGGCGGCCCGCGCCCTCGTCATCATCAGCATCATCGTGGCTGCTCTGGGCGTGCTG
CTGTCCGTGGTGGGGGGCAAGTGTACCAACTGCCTGGAGGATGAAAGCGCCAAGGCCAAGACCATGATCGTGGCGG
GCGTGGTGTTCCTGTTGGCCGGCCTTATGGTGATAGTGCCGGTGTCCTGGACGGCCCACAACATCATCCAAGACTTC
TACAATCCGCTGGTGGCCTCCGGGCAGAAGCGGGAGATGGGTGCCTCGCTCTACGTCGGCTGGGCCGCCTCCG
(SEQ ID NO: 310)

3 chr22:26522794-26528592
CGCCAACGTCTTGTCGTCGTCCGCGCTGTCCACCAGGGCCTTGTCAGCGGGCATGTACCAGGCAGCGCTGTGCTCTG
CCATCAGCGAGTCCAGGTCAATGGTGCTCATGGCGCTCTTGACCGCCTCGGAGCAGCAGCTGCCCAGCTCGCTGTCG
CCATTCTGCGCCCCTGAGGCCCCGACGGCGCACTCACCCTTCTTGCCACCCTTCAGCCCCAGAGGCTGGTCCTCGGA
GATGCTGAACTGCTGCCTCTGTAGCTGGATCTGCGCCTGAAGGATCTCCAGGGGGTGGATCTCGTCGGGTGGCGGGG
CGCCGCTGCTGCTCGTCGGGGTGCGGACCTGCTCCAGGCCCGGAGTGCCCGGATGGCCCGGGCCCCCACCGCCGCC
GTAGCTGTCAGGGGTCGAGGTAGAGTTAGACATGATGCCCAGGCCGAGGGCGGGCGGGGGCGCCTTCGGTCCGTGT
TCCCCGGCGCCTACCCCACGGGGAGGGAGTTTGGGCGAGCCGGTCACCAGGGGACTCCTGCTCGCTTTAACTAGTGC
CTGGGGGTTGTCAGAGCTGGACGACACCTCGTCCTCATTGGCGTAGCTCGTGCTCACCTCGTCCGAGGCGAACTCAC TABLE 9-continued CpG islands (CGIs) methylated in blood but not in bladder cancer. Provided for each are:ID no.; Coordinates of selected regions containing relevant CpG islands based on *Homo sapiens* full genome as provided by UCSC (hg18, March 2006); GeneName; Location of the probe used; the Fold Change; and the sequence of the CGIs.

CCACGTTTGGCGAACTACTGTCCGACTTGGCCCCGCCGTCCAGGGACCCAATGAGGTCCGGCTGATCCCCCAGGAGC
AACTCAGCCCCCTTCCCCCAGGATGGCGACGTGAGCGCCTTTTCGTGGGGCGTCGGTGCCCCGCGCGTCTCGCCTGC
GGAGCTTCCCCCGACGGCTGCGCCTGACGCTTGCTGCTGCCCTGGGCTCACCCCAGGTGCGCCCCCGCTGTCCGGAG
CCGCCGAGTACTTGTCAAAGAAGGTGCCAGGGCTCACGTGACCACTGTCCCTTTTTCTGCGACCCCGTCCCCGGCCG
CCGCCCCCGGAGACCGGCTTGCCGTCATTCCCCGACGTGGATTCCAGGGTGTAGTTGGGGGAGAGGCTGGTGCCGTC
CCCCTGGGCTGGAGGGTTGGGCGGCCCCGAGGCTTTGGAGCCGCTGCTACTGGTCCCGGACGGGCCTCCGGGTCCT
GGGGCCCCAGGAGCAGTCCCTCCTGGGAAGTAATCCGAGCCCGGGTTGCCGGCCACTGCCGCGCCGTCGGTCTCGTT
CTGGCTCAGTTTCCTCTTGCCCTCTGGCGGGTTCTTCTTGTTGAAGGTCACGTTGAGGTTGGGGGCCCCGAGGCTGG
CGATCATGTTCTGGCAAGCGGTGGAGAGCGCAGCCAGGCAGCTCTGGCCGAACAGGTTGTCCTTGGAGCTGGGCTTG
TTGAAGGAGCCCAGCGAGAGCGCGCCCAATTTACTGGCCGAGGTGCGCTGGCTGGGCTGGAAATCAGGCTGCGGCG
GGTAGGCACCCCCGCCACCGCCGCCACCAGAGCTGCCACCGCCCCCTCCCGCGCTGGGGGGCGAGTTCACGCCTGG
ACCGCTGTGCGGCGTGGACTGCCGGCCGGCTGCACCAAACGGAAAGCCCGGCTGGCCCCCGAGCGCAGACGTAGCA
AAGTCCGGCGGCGGGGGCCGGCGCTCCGAAGCAGCGCTGGGGAGCCCCACGCCCGCCCCGGGCGACTGCAGCTGAC
CCAGGCCTCCCAGACTGCCCCCGAACTGCAGGCCCGGTGAAGGCAGCGCGGGCACGTGGCCCTCTCCGGGCATCCT
CATCGGCTCCTGCAGAGGGCCCCGGAACAGCACCCCCGAGCCACCAGGCGGAGGAGGGGGCGCCAGGCTGGGGTCG
TGCGGGCCACAGTCAGCGGGCAGACCCGAGCCGCCCATCCTACGGGGCAGCAGGTCTCCGGGCGGCGGATGCGGAC
CTGAGAACCACGCGCTCTCTTGCGCCAAGTGCGGCGCCTGCTGCTCGAAGGTGCCCAGACGCCCGGCGCCCGTGCTG
CCGCCTTCGCGCTCAAAGTTCGGCTGGGCCAAGCCGCCCACCGGGCCGCCATGCACCAGGCCGCCCTGGCCCACGTC
CCCGGGGTGGCCTAGCTGAGCCAGGTTGGGCTGGCGCAGCCGCTGCTGCTGATTCCGCGACGCCATCTGCTTAATCA
TGAGGGCCGCGTTTTGGCGCTGCTGCTGCTGCTGTTGCTGTTGCTGTTGCTGCTGCTGCTGCTGCTGTTGCTGCT
GCTGCTGCTGCTGCTGCTGCTGTTGCAGGGACTGGTGGTCCGGGGCCGGATGCTGCAGGGGCGGCCCCGAAGGGAA
GCTGTCGGGCACAGGCGGTGTGAACTCGCCGGGTAGGCCTGGGTAGGCGGAAGGGGAGAGGTGATTATCCAGAGCG
CCGTTGTGCATGCTGCCGTTCCACGAAGCGCAGCGGTCCACTCCCGCGCTGCCCGGAAAGTCGAAGCGCGGCCTCTT
GGCCACGTTCATGTAGGGGGGCGCGTCGAAATGCTGCAGCCGCTGGTTGGGCGCCTGCTGCGGAGGAGGATGCTGC
ATGCTGAAAACAGGCTCGGAATAAGGGTGCATGCTCCGGTTCTCCAGCCGGTGGATGGGATACTCGAATTGCGCGTG
CTGGCTGGGCAGCATGGGGCCTCCGTCCTGCAGGCCGCCGCTGGGCGTGCCCGCCTCGCCCTGCTGGGGCCGAGGG
AGCGCAGGCGGGCACGAATTTTGTCGGACTAGAAGCCCGGGTGGCGGCGGCGGCTGCTGCTGTGGCGGCTGCTGCG
GGGGCTGCTGCTGAGGGGGTGGCGGGGCCTGCTGGGGAGGCTGCATTAACGGGTGCCTGGAGCCCACTGAGGGCTC
CAGACCCACAGGCATCTTTCTGGCCCCACTGAACCTCTCAAAGAACACACCATGCTGCTGCTGCTGCTGCTGGGGCT
GCTGCTGCTGCTGGGGCTGCTGCTGCGGTGGCTGGGCGTGCATTTTGGACAAGCCCACCATGCCCGCAGCTCTGGGC
ATGGCCGAGGCGCCCGGGAAAGCGCCCCCAGGAACCTGGCGACCCGCTGCATAATGAGGCAGCTGCCCTTCGGAGT
CAGAGGGCGAAAACATGTCAAAATGTCCCGAGGGCGCCTCGCCCGGGTAATTGTATTCCAGCGAGTCGACGGCTCCT
TGGTTCGTCACCCTCCGTGGCTCCAGACTGTGGGAATCGGAGCCGCTGGAGGACGGCAGGCCGTGGAAGGAGGCGG
CTCGGTTAGGGCTCTGGTCCAGCGGCAGGCATGGGGCCGGCACGGCGTGGCTGGAGGCACCTGAACTGTGGAAGTC
CGGGAGGTTCCCCGGTCGCTGCGGGCCGAAGCTCTCAGGCCCCTGGCTCTCCGCCATGTGCTCATAGCCCTCGGCGA
AGGGCGGCTGGCTGCCCAGGCCTCCGGCTGCGCCGCCGTAGCCGAGCAGGCGACCCCCGTGCAGGCACGAGGCCCC
GGGGTCCGGGCCACCGAAGTTGCCCCCAAAGTGGGGGTGATGCTGGTGGGGATGATGACTTCCCGGGTGGCCGTGG
TGAGGCTGCTGGCCGCCAAAGAAGCCGTGCACAGGCTGCGCTTGCAGCCCCCCTGCGTGCAACTCCGAGTGGCCGC
GCGCGTGGAAGCCGTAGGGCTCCATGTTCATGCCCAAGATCGGGGGTTCGCCCAGCGCGCTCATAGCAGGATCCACA
GGGCCAGGGGGCCCCCCAGTGTGGAAAGCCGGGGCCTTAAAGTGGGTGTTCATGCTCAGTCCGGTCTCGTTAAAGTT
CCTCTCGCCCTGGCCAGCGTTCCTGCTGTTGACCTGGGGCTCGAATTGGTCCAGCCCAAACATACTTGGCGGGGGGC
AGAGGGGGATCAATAGGGCATGACAGCCGGCTCTCCGCGGCGCGCCTCCGGCCAGCTACTCGTTCCAGCCCAGGATT
GGGCGCTCCGGGACGCTCAGCACCGCGGGGGCTCAGCGCGCACCTCCACCCCGCCTGATGTGAGGGACGGGGGGCG
GGGTATTAGCTCCTCTCCTGAAGCTCCGATTCTGCCCGGGGAGGGCCTCTCACATCTTGCGAGGCCGCGGGGCCTCT
AGGAGCCGTGTTGGGGGGCCCATGCCCCGGGCGGTTGTCACAGCCGCGGGTGGGTCTGCGGGGAGGGGACGAAGCC
GCGGATGAACGGAGACAAAAAGTTAAGTGGGGGGAATGGGGAGGGAAGGGGGTTGGGAGAGCAGAGCGATCACCTT
CTCAAGTCCGATTGGGTCTGCTGGGGAGCCCTCAGGACGCCGCCCGCAGCCTCCCGGAGTCCGTGGCAGAGCTGCTA
AGGGCAGGGGAGGGAGACCCTTCAAAGCCGCGGCTGGCGCCGGGCACCGACAGAGCGGTCCCTCCCCCCGCCCCCC
GGAGTCCCCGCGCCCCGCAGCCCGAGCCTCCACCGAGCACGATCCGCTCGCACAATCCCCGTAGGCTCCGGGCGAG
CGGCTGCTGCTTCTTCAGCGGGTCGGAGGACTGGAGGCTCCGCTCGGCATCGCCGGTGCCGGCCCCCGAGCCGAGG
ACGCAGAGGGGCTGCGAGGCGGCAGGCGCCGGGGGCTGGAGCCGAGGGTCGGGGAAAGGCGCGGCTCCTCTGCTC
GGCAGCGGGTGCGCTGCGTTCGGCGCGCAGCTTCGCGGCCACGTCCGCCGCCTGCCGCTTCTGTTCTCCGCCGTTGG
GTGTCTGAGTTCGCCGGAGTCTCCGCGCACCGTTGCAGGCGCGGGAGGGCAGCGAGACGAGGGGTTGGGTCGCTCC
AAGGCTCCGGTTCCCTGCCTCCGCGCTGAGGTGCTTCGCGAGTCCCTCTCGGACCTGAGGGAGGGGGGCGTACGCG
GGTCGGGGGGCCACGCCGGGCGAGCAGGCTAAGGCGTTCCCGCTGCGCTCTCAGAGCCCGGAATGGGGGGAGGGG
GGCGCGGGGGCAGCTCTGGGGGGTCTGCGCACCCCTCTCCCGACTAGCGGGGGGGCTCTGCGTGGGGCGTTCCGAG
GGTCTCGGCTCCCCTCTCTGTGTCTGCCTCTCGCCCAGCGCCGGGAGAAGCAGCAACAAGTTTTGCATTTCAGCAATC
AATTTCAGCCATTACATTTGCACCAATCAGCGCCGCCCAAGTTCCGGGCTCGGGGCGGGGCTCGCTCTTAAGGTGGT
CCGGGGTCCTGGCTGCCGAAGCCCCCGCCACGAACCCGCACTACCCCAGCTCTGGGGTCCCCTGCGCCCGCCTCTCC
TCGGGGTCCGGCGTCAGTGCGCTGGGGGCGCGCCCCGGCCTCCGGGCGCATCGAGCTGGAGAGGGTGCAGGCGGA
GGAGAATGGCGGGAGCTTGGCTTTGTTCACCCCCTTCCCATTCACACTGTTCCCAACTCCCCACCCCCAACTGGAGCG
AGACCCACCGGGTGGGCAGGGGGCGGGGAGGTGGGCGGTGAGCGGTACGGGGCGCTCAGACAATGAGGTCGCCAG
GCAAAGACCCTAGACTCGCCACGGAAAGTCGCTAAGTGTCTACTGCACTTCGGCTCCGGGGTGAACACTCCGTTCTC
CGCTAGCGGCGCCCAAGTTAGCCGGCCCTGGGATTTTCTTGGAGGGTAAAGCAGACGGGGAACCTCGAAGTTAGGGT
TCTCCTCGAGAGACCTGGGCGCTTGCTCACTCCTCCGTCACTAGGGCGTTCACAATTGTTCCCCTTCCCCACTGCCTG
GGGTTCCCGGTTCTCACCGGCCGGCGTGGGCTCCAAGGAGTCACAGTCACTCAGCCACTTTATGGGGGAGCACATCG
GTTGAGCCCAGTAACCGGAGCGACTTGCGAGGCGGCTGGGAACCCCGAGAAGACACGCACGAAGAGGGCGCACCCG
CCGGGCCGCACACCTTGCCCTGGGCCACCCGGTCCAAGACCCAGACCCTCTGCGGGTGCG (SEQ ID NO: 311)

4 chr7:5614184-5614510
CGCCTACCACGTGGCCGAGATTCCCGAGGCTGCAGCCAATGAGCAGCATAGTCCGATGGGGGAGGCTGGAAGGGCC
GTTCACGAGATCTCTCGGGAGGAATCGGTAGGAGCTGCCCAACTGAAAGGGACGGGGGAATAACCCGGGGCGAGGG
ACCTGCCCAGGCCCTGCCCTCTGGGGGGAAGCCAGGCCAGGGGCCGGGGGCATCTCTGGGGTCCCAGGTGAGATGC
GGGTCGAGGGAGCCAGGCCACGGTTCTCCAGACTCGCGTGGAGGCCACGAGCGTCTTCTGGAGGAGCGGGCACTGC
GCGGACCGGCAGACTCTGGGGCG (SEQ ID NO: 312)

TABLE 9-continued

CpG islands (CGIs) methylated in blood but not in bladder cancer. Provided for each are:ID no.; Coordinates of selected regions containing relevant CpG islands based on *Homo sapiens* full genome as provided by UCSC (hg18, March 2006); GeneName; Location of the probe used; the Fold Change; and the sequence of the CGIs.

5 chr16:66239477-66241425
CGTCCTAACGTACTGTCGTTCCTGAATCTCGCAGGCACCGACACTGCCCTGGACACTGTGAGGGGGTGCTCCGTGGG
GGGATGGATGACCGGCAGGGCGGACTGGAGGGCGGGACGGGGAGGGCTCGGTCCCCCCGCGGGTGTAGCCAACAG
CCTCCCCCCGCAGCTCTTCGCAGCGGTATCCCGAGGCTGCTGCACCAGCCTTACCCACCTCGACGCTTCGAGGAACG
TCTTCTCCCGCACGTAAGGGGGACCTGTCGGGGCCGGGGGAGGCTGCTGGAAGCCGCCTCCTTGCGGCCCCAGGCC
CACCTTCCCACTTCCCCCAGGAAGTCCCGCGCCGCGCCGGCCGCGCTGCAGCTCTTCCTCAGCCGCGCGCGGACGCT
GCGGCACCTGGGCCTGGCGGGCTGCAAGCTGCCGCCCGACGCGCTCAGGTCAGTGTCGGACCCCGGCCACGCCCCC
GCGGGCGCTCCCACCCTGCCCTGGCCTTCGCCCCTCCCCGCTCCTGCTTCTGTCGCTCCCACAACCTCCCCCAGATCC
TGGCCCTGCCTCCTTCGTTCGCACCCTGGAGCCCCCTGTCCCAGCTCCCGCCACCCCGTGTAACGTCCTCTCCCAGAG
CCCTTTTGGATGGCCTCGCGCTCAACACGCACCTCCGCGACCTGCACCTGGACCTCAGCGCTTGCGAGGTGAGCGCC
GGCCCCCAGAAGAGACCACACATTGGGAGAGGCGCTGGGAGGCGGAAGGGCAGGGCCGTGGGCCGCCTGCCCCTCC
CCACTCGCGGCCTAAGTGGGTCCCACTTCCCACCTCCCACCTCCCACATACAGCTGCGCTCGGCCGGCGCCCAGGTG
ATACAAGACTTAGTGTGCGACGCAGGCGCTGTGAGCTCCCTGGATCTGGCGGATAACGGTGAGGCTGCAGGAGAGCC
CATCCTCGCATCATCCACTCGATTCCCAATCCCCACCCTACCCTTGCAACTTCGCCTCGTGCGTGACCCGAGTCACCC
CCAGGCTTCGGCTCAGACATGGTGACTCTGGTGCTGGCCATCGGGAGAAGCCGGTCCCTGAGACATGTGGCGCTTGG
AAGGAACTTCAACGTCCGGTGCAAGTGAGCCCCCACCCTACTCCTGGGCCTCCCAGACAACACCCCACCACCCCTGT
CCCCCACAACTGCGGCCCCTGCCCACAGGGAGACCCTGGACGACGTCCTGCACCGGATTGTCCAGCTCATGCAGGAC
GACGATTGTGTGAGTTCACGGGACCTTGCAGGGCCTCGGGCAATTAGACCACTTTGGTCCTCCTTTCTCTTGTTCCCT
CAGACCCTGTGACCTGCCCTCACTGACCCCTGACTCCAGCCATCAATGGCTTTCTCTTAACCCCAGCCTCTTCAGTCT
CTGTCGGTGGCTGAGTCTCGGCTGAAGCTGGGTGCCAGCGTCCTACTCCGGGCCCTAGCCACCAATCCTAACCTGAC
CGCGCTGGATATCAGCGGCAACGCCATGGGGGACGCGGGCGCCAAGTTGCTGGCCAAGGCGCTGCGGGTCAACTCG
AGGCTCCGGTGGGCGGGGTCAGAGGGGTGGGACCAGCGGGCAGGGGGCGCGGTGGAGAGGAGGGCACCGGGCTAA
GGGGAGGGACTGAATGAGGCGGAGCAAATGGAGCAGGCTGACGAGGCGAATGGACTAGGCCGAGGGTTGGGTGGG
GCGTTGGGAAGCTCCGTCCCCGACTGAAGCCAGGCCCGGCCCAGGTCTGTGGTCTGGGACCGGAACCACACATCTGC
TTTGGGTCTGCTGGACGTGGCGCAGGCGCTGGAGCAGAACCACAGCCTGAAGGCCATGCCTCTGCCACTGAACGACG
TGGCCCAGGCGCAGCGCAGCCGCCCGGAACTGACAGCACGTGCAGTCCATCAGGTGGGCGTCCCCCTCTTCCCTTGC
CCTTCTCTGCACGGTAACTCCGTCCCTCG (SEQ ID NO: 313)

6 chr5:551112-551430
CGGATGCCGGCCTCCTGCCTCGGCCACCGCCCTCCTCTTCAAGGATGCTGTTTTGCCTCTGGTCGCTCTATCTTATCT
TTTTTCTCCGCACTCCTGGACGTCTCTCGGACCTTTCGCTCTGACAGTGGCTTGAGCCTCGGCCGCCACTTCCGCCCC
TGCTACTTCGGGGCCACGTCTCGGTCCGACGCTGAGGGGTGCTGCCAACCGTGTCTTCTCTGTGAACGTCCTCACGA
TGAACGCCCCCGTTCCACTTCCCACCCTGGAGCTGCTGCTTCCGTGACTCACATTCCGGCCATTTCCGTGGTGTGAGG
TACGGGCG (SEQ ID NO: 314)

7 chr19:6426223-6426998
CGTTACATTGCGATTCATTCAGGAACCCACGAGACCTCTCCCGCAGCGTCCCCGCTGCTCACCGGGCTGCAGACGAG
TGCGTCGCGGTACCCCCGAAGAGCAGGGCCTGGGCTTTGAGGAAGAGACGGGACACCCCTTCCCCGGGGGCCAGG
GCGACCTTCCTGAGCCGGAGCCTCAGCAGGGACACCTGAAGCACAAGGGAGTGGCCCTGAGTGGGCAGGTGTGGGC
CCCTCGCCTCCCGGGGCAGGAAGGTGGGAGGGGCGACACTGACCACGTCTGGAGGCAGCGCCTGCACGTCGTTAAA
GGTCGTCTCCAAGGTATTGGCGTCCACGTTCAGCACCACGACGTCCTCCAGGGCTTTTTCTCGTACTCTCTGCGGAAA
AGCGGGGTCGGCCGCTCAGAGCCCGGGAGTCCTTGGCAGAGGAGGGCATCTGGGGATGTAGAGGAAGGGGGAACCC
TCACGTCCCCGTCGTCTGGGTAGATCCACGCTCACCTCGGCGAGACTGGCGTGCACTCCAATGAGGTAGGGCATGGG
CGCGCTGCGGACCGAGGGGACGGGGTCATGCAGGCACCGCCCCCAGGGCCTGCCCACAGGCCCTGCCCCTCCCAGC
TGCCCTCGCTCACCAGCAGTAGTCCAGCAGGTGTGGGGGCAGCGTGGGGATCAGCACGTGCTCCCAGCGCATGGGG
TACAGGAGCGCGCAGGACGCGTGGACGCACGAGGTCAGCTGGGGAGCGATGGCGGGGCGTGGAGTCAGGGCCTGG
ACCCTCTAGCGCG (SEQ ID NO: 315)

8 chr3:32836146-32836433
CGTGAAATCGCCGTTCGTGGGCCCACGGCTGCACCCCGAGATAGAAGCGGAATAAAGGGACGACGTTACCTTCACCA
GCCTGAGTCTCTTGGGCCGCGCCCGCCTGCCCCGACTCCAAGCCCTACAGGAACCGGTTTCCCTGGTTAGGAGGTAT
CCACCCGGCTCAACCAGGGTCTCGACTTCCTTGGAAAAGACCAAGGCAGCCGTACGCTGCTGGAACGCCGGAGTGCA
AAGGCTTTTAGGGCTACATTGCAACCCTCGGGCTCGATTTCGCCCTTTGGGCTGTCG (SEQ ID NO:316)

9 chrX:129301145-129301626
CGTTGCCGCCTTTTTCGTACTGAGCGCGCAGGGCACTACGCCCACCACTCCCCTTGACCCACTCCTCAAGCCCTGATA
CCGGGGCGAGGCCCCTTCCTTTTCTAGTCCTTCTACGCGCCAGGTGGGTGGGTTTCGCGGTGACGAGGCGACACCTC
TTTCCCCTCTGGCGAGCACGTTAACTGGGGAAGCTACCAAATTCTCACGCCTTAGCTGCCCTGCCTCCACCTCCCGCA
AGTCCGGTTGCCCCTCTAGGCTTCTGCGCCTGCAGTGGTTCCGACCCTCGCCTTTAGAACTCTGCCGCTTCCGCCTCT
TATTTCGCGCCTTTGTTTTTAGTTTTGGAAGGGGCGGAGTTGAAATGGCTGCGCCGCGGTTGCCGAAGCAACGCTTTG
GTTACTTCCGTTGGTTTCAATGCTTCCGGGTTGGCGCTGCAGTGGCGTTTCCGACTGTGGGAGCCTCAGCTTCCCAGT
CGTCCGATGAGCCCG (SEQ ID NO: 317)

10 chr9:124027565-124030907
CGAGGCCCAGGCGAGTGGCCAAGACGCGGCAGGACAGGAGGATGCGCCTGGCTGCTCTCGGCTGCTGGACGCGGCC
TGCAGTAGGGAGAGCGCAGCCCGGGGTAATCCCACTCAGGGCTCCGGGTGCCCAGTTCTCCCACTTCCCATCCTGGC
GGCCTAAAGGCAAGGCCTAGACCCTGGAGAGGCCAAAGTCGGGCCAAAACAACAGCGAAGCTGGGACTGGAACAGG
CGCTGGGGGCCTGCGCATGACCCCAGGCTCAGAATGCGACACTCCAGTGACGCCGGGGAATGAGTTGAGATGGAGC
CGGAGACAGAGGTTGGGGTTCAGGACGAGGCGCTTGGGTATGGGATCGGATCTGAGACGGTTGCGGCGCTGGTGCT
TTGGGCTGGACCAGACTCGAACCCAGAGCGGAGCGAGGGTCAGAGCCAGGGCAAGAGTCCGAAGCCCAGCTCAGCG
TCCAGCCCGCGAGAGACCCCACCATGAATGACGTCCGAGTAGGGTTGGAACTCGAAGCCCGAACGCACTGGAAATGC
AGCCGGACGACGGCTGGGATCCGAGTGGGTCCGGGCCAGAAATGGGGACCTCAGAGCTCCACCGAGGCGCTCGAGG
TCAGAACTGAAGCCTGAGACTTAGGCAGGACCCGAGACAGAGCCAGAGACGATACCGAAACCCAATGGACCGCGAG
GACCGAAGGCAGATCCGGGGCGCAAACCTGTGCAGGCACTGGCGCGCTGCCTGGAGCTCTGGGTTCGCGCCGCTGA TABLE 9-continued CpG islands (CGIs) methylated in blood but not in bladder cancer. Provided for each are:ID no.; Coordinates of selected regions containing relevant CpG islands based on *Homo sapiens* full genome as provided by UCSC (hg18, March 2006); GeneName; Location of the probe used; the Fold Change; and the sequence of the CGIs.

GCGCCGGCAGGTTGGACCAGCGCTGCGCGCCGGAAGTGCACTCGGGACGCCGGGGTTCTGGAGGAGAGACCACACG
CCGCAAAAGTGGCCTCCGAATGCGCCCGGGGCCTGCCCTCGGCGACACTGCTGGCTCGGCGGCCGCAGCCTACCTG
AAGTAGTCCATCTTGCAGAAGATCTCCTTGTTCTTGATGTAGCAGCTGTTCTGCTGCCTCAGCGACGTGCGACACACG
GAGCACTCGAGGCACCGCACGTGCCAGATGAGGTTGTTGACCTGGGGACGGGGCGGGGACGGAGGTCGGCTCAGCG
CGGGCCTCTTTCACTCCGGGCCCCAGCCTTCCCGGTCTCATTTACAGTCAGAGGCGCTGAAGCTCAGAAGGTGCATG
CGATTCCCCTATTTTTCTCCCGTAATACTGAGACTCAGGGAAATGGAAATAAACTCTTCTTATTTTTCAGACGGAACCC
GGGGGCTCAGGCAGACCCTAAGTCTTGCCCAAAGCTTCGCAGTCGGGCAGCAGTGGAGCCAGGATTTGGAAGTAAGA
GGACCTGCGGTGCTTCCCTGCAGTCTCCTGCGCTGCGTCCCACGCCCCGACAACACGCACGCAACACCTACCCCTGT
CTCACCTTGAGCAGATATCGGTCCAGGATCTCGAGGCCGCAGCTGGAGCAGATGTTCTTGCCTGCAGACGGCACGGA
GGAGGCGGCAGAGGGCGGTGAGCAGACAGATGGCGTGCTGGGCGTACATGGGGAGGCCTGACCCTCGTCCTTGTCC
AGAGCTCCTGCCAGGGCCTCGGCGTCAGACTGAGCCTGCGGCGGGGGAGAGAAGGAGAGGAGCGCTGATCCGGGCA
CCCAGAGTTGGGGCTGCCTTGGAGACAAATCTGGGGCCCCCGAGCACCAATTGACAACGAAATCTCCCCAGGACAAT
GCGCCGTAGACTGAAGGACAGGGATGGAAGGGCCTATTGGAGAGGAAGGGACGGCCCCAACTTTTAACACGCGCAT
TCTGGGTGCTGGGAGCGGTTAAAGCCAACATTCCCTGCCGGAAAACCGAGGCTCAGAGAGGGGCGGCGCCCGCCGG
GAGTCCCCCAGAGCGTGAGCAGCAGTTCGTGGCCGGAAAACCTGGCCAGGTCCCCAGGGCCGGGCCGCTGGAGGAC
TGGGCACCGCAGGCAGGGCCAAACGGACTCACCATGGCGGGCGGCGCGGTCCCTTCAAGACAGCGGGTGGTCGCTT
TGCAGCCGGACCCTGGCTGGGCCATCACCTGGGGGAGGGGGGGAGGGAACGCAGGCGGCGGCGGCTGCTGAACTG
GCTCCGCACAGCCTGAGCCCAGCGCCTCCCCGCGCCTGTTATATAAACCGGCGCCGAACAATGAGTCCTAACTTTGT
AGTGGGCATTTAAAGCCCTTCCCCACAAAAGCGGTGTCTCTCTAATGAAGCAATTTGAATTTGGATTGGATTTTTTCC
CTCTCTCTCCCCCTCTCCCTGCACTTAACCCGTGGCTCTTGAAGTAATCGCTTAGTTCCCTTGCAATCCAAGCCTCTGA
GGGGGGAAGAAAAACACGCGCACACACACACAAACTACCTGCAATTAGAAATTGTCGTGAATGCCCAAGATAAGAGG
TAGCCAGAGTGTCAATTCCAACTGTCAATCAGTGAGATCCATCAGGCCGCCCAAAGAATTGCAAATTTGATTTTTTAA
TGGTAGTAATTAAAAATCGAATTTTTTCTCTCTCCACCCGCCCCCCCACCCCACTCCCCTTCCTCGCTCCCTTCTCCTC
TCGGCACAAAATGCAAAAAGGAGAAAAGAGAGAAAGAAAGAAAATAAAAAAGAGATGGGTGAGGGGCGGAGGGTGG
TTGAAGAAAAGAAAACCCCGAGCGCGGTGAGCACCCGCCCGCCCGCCCGCCTGACACGCGCGGCGAAATTGAAGCA
GCTATATTGACACGGATTCAGGCGCCTTTCGAGGGCCAGTCGGAGGGAAACCCGGAGCAAAAAGAGAGCGAGATCG
GGGCGAAACGGGACCAAAAAGAGAAAAGAGAGGCGCTCAAGGGGAGGAAAAAGCACCCTCCAGCCCCTCGGCGCGC
CGGGTACCGGCCCCGCGTCGGGATTCTCAGCGCTGCGCCGGCACAACCCCCGGCGCATCGGCGCTATCAGCGCCTAT
TCAGACGGACAATACCGGCCTCGCCTCCTCTTGATTCGCCTGTGTCTTTACTAAATCGCTTTTTGAGAAATTCCTCCAA
CATTTGCATAATGTGTTCCCGCTTTCCGCGACCCCCCCCCCCCGCTCGCGCGCGCTCCCACACTCACAAGCACACA
CTCACAGGCGCACCCTCGTACCCCTCCTTCCTGCAACCGCCCGCCACCCTGCTCGGCCCGGCTGGGTCCCGGACCCT
GCCCGACCCCGGCCCGGGCCGCTCACCCAGTCGTTCGCCGGCTCACCTGGTCGGTGGCGGGGCCGCCCTCGGCCGG
CAGCCGGCAGCCCTCGGGCAACGCCGGGGCGGCGTTCTCATGCTTCCAGTACATGGGCCGGGGAACCTCGGGCTCA
GCGGGCGCGCAGCGCGGAGAGCTGCGCCGAGGGGGACCACAGCCG (SEQ ID NO: 318)

11 chr10:129424401-129427356
CGCCTCTTTCGCACAGGTGCCCGACTCGGAGTCCGGGAGGCGGGCCCTCTTTCCAGGTACCCAGCCCAGCGTCAGCC
TGGGTCCATCCTCCGCCACCCCACAGCGCGGGGAGCAGGGGAGGCCGAAAGCCGGGCAGCTTGGGGGGCCGGGATA
ACCCGGGCTGCAGCAACCCCGGGCGGCAGCAGGACTGGAGAGCTGGTGTCGGACGCACTGCAGAGACGTCCCTGTT
TTCGGCGCGTCCTCCGACACCCAGCAGAGAGCTTGGCGCTCTCCGCTCTGCGCGCCCGAGGTCACAGCGCGGAGAAA
CCTGGCGGGGCCCCGGACTCCCCGGCTTGGGAAAAGCGATGACTGCCCTGAACTGCTGGGGCGTTCGAAATTTCCAG
GGTCCCGACCCTCCGTGGGGTACGCGCGACTTCGGCGCAGATGTCAGTCCGCTGCCTTCCGGGTTGAGGGAGCGAG
GACTCCAGACGACCCCAGGGCCGCTGTCCAGGCCCAGCCCCGCGTTCTCCACCTCGCCACCTCGCTCTGCGGCTCCA
GCCTGGAGATCTACGGACTTCATTGCGATCTCTTGCGCAGTGTAGTCGCCCTCTATCCCTAGCCCCGAGTCCCGGGTA
ACCCAGGGGCCCCGGCGAGGCGAGTTTCTTTGGGGCGAGATGTCCCGAGCCGAGCAAAGGGGCCGCGCATTGGACG
GGGCTCCCAAGCCACAGCCCTGGGGGCCTTGAGGAGTCGTGGTACGGTCCAGGGCAGTCGGGGCTGCGGGGCCCGT
GAAGCCAGACGAGGCTACGGACTTAGGGTCCCTGCAACCAAGACCGCGAGCGACTGTGGACTCGGGACGGATCGCA
CAAAGGAGGAAGGGGGAATCAGAGGGGCGTCCGGTCCAGGACGTGTCAGGCCTGGGCGGGGCGGAAAACTGACACC
AGGGCGAGGACAAGGATTTCGCTCCTCCAGGGCTGCCAGGGGAGGGGCTCGCCACCGTCACTCTCCATGGGCTCTG
GCCCCGACGGTGTTTAAAGGGCGGAGGGCTGGGCCGGGCTGGTCGCACCCGGGCGCTGCTGGCGGCCAAGCTGGAT
GGGTCGCCAGTGAGTTTCGGTGCGGCACCGCTGGCCCAGGCCCGGGCGCGGCTGGACATGGCCACCTACTGCGACG
ACCTGGGCCCCTCCTCGGCCCCGCCCGGCCAGGCCCAGGCCACCGCGCACCCCCCGGGCTATGAGCCAGGGGATCT
GGGCGCGGTGGGCGGGGGCCCCCTCCTGTGGGTGAACGCGCCAGCGCTCAGCCCCAAGTCCTACGCTTCGGGTCCC
GGGCCTGCGCCGCCCTACGCGGCCCCGAGCTACGGGGCTCCCGGCCCGCTCCTCGGCGCCCCGGGCGGCCTGGCGG
GCGCCGACCTCGCCTGGCTGAGCCTCTCCGGCCAGCAGGAGCTGCTGAGGCTGGTGCGGCCGCCCTACTCCTACTCG
GCGCTCATCGCCATGGCCATCCAGAGCGCGCCGCTGCGGAAGCTGACGCTCAGCCAGATCTACCAGTACGTGGCTGG
TAACTTCCCTTTCTACAAGCGCAGCAAGGCGGGCTGGCAGAACTCCATCCGCCACAACCTGTCGCTCAACGACTGCTT
CAAGAAGGTGCCCCGCGACGAGGACGACCCAGGTAACAGCGGCGCGCCGGCTCGCTCCGTCCAGGACTCCCCATCTT
CCCGCCGGGCCGCGGGCACTCCGGGGGTGGGAGCACCTTAGACAACCTAATTTCTCCCTGCGCGGTTGGGGATACCC
GGGGAGGAGGGAGAAGGGGAAGAAGTGCTTGGGCATGGACAGGTTCTCAGACAGCGGCTGAGCCCACCACAGGCCC
GCGTTTACAGTGCGGCGGTCCCGGGGCTCTCAATCTCTGTGCGCTCCTTCGGAGGAAGAAGCGGGAGAGCCAGCAAG
CTGGGTGACCTTGGAGTGACTCAACTTCCCTGGGCCTCAGTGCCCTACCTGGTAAAATGGGGAAGACAGCGCCTAC
CCCAAGGATGGGCAAAACAAATAGGATGCCCGTTTGGAAAGCTCTGGAGCCTACCTGGGGGCCTGGCGTGGTCTGCG
CTGTCCTTGGCAGAGCGGCTGGCGGAGTCCCACCATTAGCATCTCGCAGGCCTTCCTTCACCTTAACGGGGCTCGGC
CTTTCCCAGGGCTCCCTTCCTCCTCCTTTCTGGATTGTCACTTTCTTCCCAGTCCTGCTGTGGAGGCCCATCGGGTAC
AGAGTGCCCGTCAAGGGTGGAATGGGGGCGAGGACTCAGACCCTCTGTAAGGGCCAGCAGGGGATCTTTCTGAAGC
TGACCTCCTCGCTGGCTCACACCACGGCCCGTCAAAGCTCGAACCTTCTGAACTGGGCTGTTTCTTCTTCTGCAGGTA
AAGGCAATTACTGGACCCTGGACCCCAACTGCGAGAAGATGTTTGACAACGGGAACTTCCGAAGGAAGAGGAAGAGG
AGAGCTGAAGCCAGCGCGGCCGTGCGCTCGGGAGCCAGGAGCGTGGGAGGGGCCGAGGCGCCAGCGCTGGAGCCC
CCGAGCGCGGCTTGCCTGGACCTGCAGGCCTCGCCCTCTCCATCCGCACCCGAGGCCGCCACCTGCTTCTCCGGTTT
CGCTTCTGCTATGAGCGCTCTGGCTGGCGGCCTTGGCACCTTCCCCGGGGGCCTGGCGGGCGACTTTTCTTTCGGGA
GGCGGCCACCGACAGTCGCCACCCACGCTCCCCAGACCCTTAACCCCTCCCCTGGCTTCGCCCCTGGCCACCAGACC
GCGGCCGCCGGCTTCCGCCTCAGTCACCTCCTCTACAGCCGGGAAGGGACCGAAGTTTGAAGGGAGGCTGGAGGCT
AGCCGGGTGCGGGTCCAGAGGTGCTGAGCTCAGGCCTCCGGTTTCCCCTGGTGACAGCCCCACGTGTTGGCGTTGAA
GGCCTTGGTGCCCTGGGAGGAAGCGCAGAGCCGGGGGCGGCTCG (SEQ ID NO: 319)

TABLE 9-continued

CpG islands (CGIs) methylated in blood but not in bladder cancer. Provided for each are:ID no.; Coordinates of selected regions containing relevant CpG islands based on *Homo sapiens* full genome as provided by UCSC (hg18, March 2006); GeneName; Location of the probe used; the Fold Change; and the sequence of the CGIs.

12 chr1:3147370-3148160
CGGGGTGCGGGGAGGTTGAGAGCGCGGCGGCCGCTGCCAGCAATCGAGGAGCCAGCGGCGCGTGTGCTGAGGGCC
CAGCTAGCAAAATAAAGAGGGTTTTCAGCGGAGCGGCGGCTCAGGCGAGGCTGGGGGAGCCGGGGAGCGCGTCCCG
CCATTTTTCCAGCCGAGGTCAGCAGCGGGTGAAGGGGCGGAGTCCGTGGTGTTCCCAACTGCCCAGGCGGGCGGTG
AGATGGGGCAGGCGGTTCCGCAACGCGGCTCAGGCCCCAGCGCCCTGCCTGCAGGAGGCCGCTTCTTTCTCTGTTGC
CATCGGGCGCCGGTTTCCTCTTCCGGGGATGCAGGGCAGCTGGGGGGGCTCTGCCTCTGTGCGGCTCTTCCGTGGTT
CCACGCTGGGCTCCGGGGTGACCACAGTCCTCAGCAGCCCACACCCTCAGCCCGAAGGGGGCCCAGGCCCCGTGCC
CAGAGGATCCAGAGAGACAGCCGGGAGCCCAGCAGCTGTGGCAGCTGCCCCCACCACCACCCCGGGGCTGGCCAGG
TCCCACCTCCTGACGCCACACGGTATGACTGGGCCCTCCTGGTCAGTGCGTCGCATGTAACGCCTTCAACTATTGGG
GCCGGTGTTGGAGCATCCGTCTCTGCGTCCCCACCTGATGACAAGCTCCGGGGAGCAGGAGTGCTGGCCAAGCCCAC
GCACGGACCAAGCCCACGTCAGACTCCGCCAGAAAGGCAAGAAGGGCCTCCGCATGGCGTGACGGATGGGTTTATG
GGGGCATTCCATCCCACCCGGACGCTCG (SEQ ID NO: 320)

13 chrX:128941527-128945710
CGGAGCTTGAGCGCCAGAACCACGCACTGAGGTCGCCCAGGGTGGGGAAGTGGGGGGCCGGGGGAGGGGCGGGGC
ATCCGGCGGGGAGGTCTCCCCCACCGCATGCAAGACCCTTTGCCCCCCCACAACATACACTGAGGCTAAAACGGGGA
TGAGAGTCACACAGAGCAGGAGCGAAATCTTTCGCTCTCCGACCCGAACGGCGCGTTGCTCGACCCCCCCCTTCCTG
GAGCCAGGGGCTGGCCGAGGAAGGTGGCTCCGTTCTTCCCCCGTGGCCAGTGCGGGGTCTGCGGCTGCCCGGCGAG
GTTCCGGCTTCCCCGGGACTGGCAGGGGGAGCCCCGAGAACTGCAGGCCCGCCCCCCTTCCTCCTCCTCCTTCCCC
TCCTCCCCCACGTGTCCTCCCTGAGCCCAGCAGCCTGATCCCAGCACCCCCCGCCACCTCCCTCCTCCCGCTTCGCCC
GCTTCCCCGGCGGCGTGGAGAAGAGCAAAGTTGCGACAGCGGCCGGGGGCTCTGCCCAGGTAAAGGGGGCGCCGTG
AGGCGGGGGTGGTGGGGAACGGTGCGGCCCTGCGGCGGGGGCGGGGGGAGGATAAAGAAACTTGCTTCCCGCGG
CCCCCACCCCGCGTGGGTTCCGATCTTGCGTGGAACGAGCCCGCGTGGCGAGTCGCGGCAACACTGCCGGGACCGA
GGCCGGCACCTGGACCCGGACCCGGACCGCGCGCTTGGGCCGGCTCGGCGGGCGCAGGCAGCGGGCCAGGCCAGC
ACCCAGGCAAGGGCGGGGTGGGTGGCCGTACACCGGACCGAATCGGGGACTCCGGTGGCGTGGGCGCGGGCCGAA
CCCCGACCGGGCCGAGTTGGGTGGCGAAGTAGGACGTGGATTCGGGGGCGGGGCGCGGCGGGAGGGGGAAACCAG
GCCTGGCCAGACTGGCCTGGGCGTGGGGGCGGGGGGCGAGTTCGGGGCACTTGCTGGGCTCTGGACCGAGCGGTAG
GGCGGGGCGGCGCTAGGGGCTGGGCCGGACCCGCAGGGAGAGGGCGAGGGGAGGGAGAGCCGGGGGTGGAGTAG
GGGCGTGGAGTTGTGAGCGGGGTCTGGCCTCGGCCGGGGGCGAAGGTAGATCGGCGGGGCCGCGAGCGGAGGGAG
GGAGGCCCGCGGCGGCGCGGCGGCAGCGAAGGCCAGCTTCCGCGGAGTTTGTGCCCGGGCTTCCCGGGCTCTGGCC
GCCTCACGCGCACAAATGGGGCTAGGGGACTGAGTGGTAAGCAACTCCGAGTGTTAGACGGTGATCGGGCGGCGAT
TCCGGGAAAAGCGAGGAAAGACACAGTCTGCGATTGTGCCGCACCCCCCACCCACCTCTTAGCATCTGGATTCTGCT
CTCGTAGTGGGGGCCGCGGACCCTCCCCGCCACAGTCCTTTTACTCTCCAGCACTCCCACCGCCTTCCCCCCTTCTTCA
GCCATCTGACTCTCCTAGGGGTATGTGTTTTTGGGGGTGGACGGCGACGGGGGTGGGGGATACTTTCCTTCCCGTGG
CGGCAACCTAGTTCGTATCTTATTCCTACAAGGTAGCGTCGCTTCGAGTCGCATGGACATTGGGGTTTAGATAATTTA
CCCCCCACCCAAGCGATTTAATGGCTTTTAAGCAAAAGGCGAATACCTGGATTTCCATGGGAGGGATGAGGTTTGAA
GATTGGGATTCACCCCTAGCTCACTTCCACTACCAACCCCTCTTTCTTGTGAGCCACTTCCACGGGTATTCAAATCTG
GGGGGGAGGGGGGACGGGAGTATTAATATGCTTCTCTATTTCTACACAGGGTCGGCGTGGCGAAGGACGGCTAGCCT
TGGAGGGAAAGTAGCCACCAGTCCAACTCGGGTCGCCCCCACCATTATTTCGGTGAGGGGGCAACGCTAAGAAGGGG
ATACTGGTGGGTAGGGGCCCAGTATAAGGGAGGGGGCTGGGTAGTCGTCCCCAGAAGGACTCCGTGTCTTGGCGGG
GAGAGAGAGAGGCGAGCCCCGGCTTCAGGGGAGGGGTTCCGGGGAGGGAGATGGGGGGGTGGCGACGACGGTGGG
GGGGGGAGCGGGAAGAAGGGGGAGTCACGCCCTGCCTGCAAGGGGAGCCTCCCTCAGGCCCCTGGGAGAAGGGGA
CTGAATGCGTCTGTTCTCCGCTGCCCGGCAGAGGAGATCTGGGGTCTCGAGATTTGCACACTGGATCGGCACCAGTG
GCCTGAGAAAGTCAGGTCGGGGCATAAGGTGGAGAACGTTGGAAGAAAGAGAGAGAACCCTTTGGCCGCGGCTCAC
TGACCCTCTCCCTTCCTCAACCTCCCCCTTCGAGGGGCGTCGAGGTGGGGGGGGACGTGGGGCTCCTGCAGCCCCGC
AGATTGAGCGCCTCCGCCTCTCCCAGGAGTCTAGCTTTTTGCCCGGCTTGCTGCAGCCACTGCTGCCTCCCTCTCCGG
AATCCGCTCGGTCCTCTCAGCGATCCCCTCCTCCTCTCCTCCCCTCCCAGTGTCACCGGGGCTGCTTGGCTCTGCCCC
CTTCGCCGCCGCTTGCTCCCTGCTTTCGTCCCTCCCTCTCTTGCTCGCTCCCTCCCTTCGCCTCCTCCTCCCCATTCCC
CCCCACCCGCGTAGGCCGCATTCTGGGAGTTGTAGTCCGGTGGAGCGGGGGTTGGCGCCGCCCGCGGACCCAGCCG
GACTCCACTTCCCGTCGAGCCCTGCGACCGGCACCCACTCCACCAGGCTTCGCTCGCACACAGACACACACACACAC
CGCTCTCCCCCTCACTCTTTCGCTCGCCGCGGCTGCTGCCAGTGTGTGGCTCTGTCTCTCCTCCGCTTTGCTGAGCCC
TCCCTTCTTCCTCTCAGTTCCTCTAGAGTCCGACCGCCGCCGCCGCCGCCGAGAGAGAGGAGAAGGAGGTCGGTGGCGATAA
GGGGCGGAGGGGGGCATCAGATCGGGGCAGTATTAGGCGGGTGGCGGTTAAGAGGGAGTAAGAGGGAGCCCGGGT
GGCGGCCTGAGCCTCCCCGCGGAGCCGACCCGGGAACAGGTGCGTCTTTTTTCTCTCTCCCCCAATCCCTCCACCCC
TTTTGACTCCCCGGCTTTTTCGTATCCCCCACCCGCTTCTTTCTATCTTAAGCCTTTCTCCAACCCTGTTCCTTCTTTT
CCCTGCGGCCGCTCGGCTTGCCCCCGGGGGCGCCGTCCTCTTCGTGTCCCCGGACGTAGCGCTCCCTGGAGCTGGG
TATGTCTTCGCCCCTCCCTTCGGGACAGCTCCCTTCCACTTCCCACCTTCGTACCCCATCCCCTGACTTGCCCTACCCC
CTTCTCGACCCCCCTTCTCTCTTAGCCAGGTGAGACTCGTTCGCCACGATCCAAGAGAGTCTTCTTCCCGGCTGGGCGG
GGGTCTCCATGGAAACGGGGGTCGGTTGATCCTGGGGGGGAAACCATAGGAATTACCCCACTCCTCGGAAAGGGAG
GTGGAGGCTATGGTCTTGTTAACTACCTGACTCCAACCCCCGATCCAAGGATCCGACGATCCGAAGGGAGGCTGGCT
AGCAGGGCAGGGCGAGAAAAGGCTTTTTTTGGGGGGGGGGGGTGTCCGTGATGAAGTGTTGAAGAGACCGGGAGA
AAATGCCCTCCAACCTCAGAGGGGAGGTGCGACGGGTGCTCTTCAGGGCTGCTTTCTTCCCGGCGCTGGGGTGCGGG
AATCGTAGGGTAAGGGGTACCCCTAGGTGGCGGCGGGGCCTGGGTTCGGGAGTGGGAGTGCTGTGATGGGGGCAGG
GGCAATTATCCGAGTCCCTGGAAAAAAGGCGGGGATGACTTCGGAGCGCCCTGGCTCCGCTGCCCTCGCTCTAGGG
GCGGGGGCCGCCGGGCCGGGCGCGGCGGGGAGGGGGCTTAAATTGAAGGAAGATGAGATCGGGGGCAATTCATACT
AGCACCGGCAAGCCAGAGGGGAGATCCGGCGTGCAAGCCCTCCACCCGCTTCGCGCCAGGCCTGGAGGCAAGGGGT
CGGCGAGCGAAGCCGAGGGCTGGAAGGAGGGAGGCTCCGGTTACGGGGCCGGGTTTCGGGATCAGGGGCAATCCCC
CGGCCCTTGGAGAAGGAGGGAGAGGGATGGCCGCGAACCCCAGGGCTCCCCCACCCCGGGTCCTAAGGGGCGTGAG
GGACGGACAGCAGGCCCAGCGGAGCTGGATTCGAGCGGATCGCGGCCG (SEQ ID NO: 321)

14 chr17:7584523-7585036
CGAGTTGGTGCGGGACGTGCCGCACGGCGTGCTTCTGCTGGACACCTTCCACAGGCTTGCCTCCCGCGAGGTGCGGC
TGCCCCGCGGCTTCCTCGGCTTCCCGTCCCGCGTGCTTTCCTGGAGTCCCTCCTTCCGGAGGCCCTCCTGCCTCCACG
TGTGCCCTTCTCCATGTCCAGCATTCGGGCGCCTCTTGTCTTTCTTCTGTTCCCTGGCTTCGGCGTCCCCGGGAGTGT TABLE 9-continued CpG islands (CGIs) methylated in blood but not in bladder cancer. Provided for each are:ID no.; Coordinates of selected regions containing relevant CpG islands based on *Homo sapiens* full genome as provided by UCSC (hg18, March 2006); GeneName; Location of the probe used; the Fold Change; and the sequence of the CGIs.

GACTCCCGCAGCGGGGTGCAGCTTTCCTCTGGGATGAGTGACCGGAGGGAACCCGCCTTCCCGGGCACGTCGCCAG
CCTCTTCCTCTTCTTCCCTAGGCTATCAAGCGGACTTATGACAAGAAGGCGGTGGATCTCTACATGCTGTTCAATAGC
GAGCTGGCCCTGGTGAACCGTGAACGGAACAAGAAATGGCCAGACCTGGAGCCCTACGTGGCCCAGTATTCCGGAAA
GGCGCGCTGGGTGCACATCCTCCGGCGTCGCATCGACAGAGTCATGACCG (SEQ ID NO: 322)

15 chr1:27548507-27550603
CGAGGAGGCTGACCCGGAGCTGGAGCCCGCGTCGGGGGGAGAGCAGGAGCCGCGGCCCCAGCAAGCCCAGGTAGG
CGGGAGTGGCCCGTGGCTGCTCTCAACATCCGGAGCGGACTCCGGGCGGGGAGCGCTCCTGCCCAGGGCTGCGAGC
CGCCCGCGACCCAGGGCGCTCGGGGCAGGGGTGGGGAAAGAAGGGGCGCCCCGTCACTTGCCCCCTCTGCAGACCA
AGGCCGCGTCCCAGATCCTGGAGAATGGGGAGGAGGCCCCGGGGCCCGACCCCTCTCTCGACCGCATGCTCAGCAG
CAGCTCCTCGGTGTCCAGCCTTAACTCCTCCACGGTGAGGCGGGAGGGAGGGGACCCGGGCGGCCGGGGGGTGGAC
CCGTTCCGATGCGTAGCCCCTGCCTGCCCCTCCCTCGCCGCGGGACCCACCGCTGCAGCCCCCCAGCCTGCCACCTA
TGACCCGGGTCTGAAGCCTCCGCGCTGCCCGCGGCCCCGACGTGAGCCCTGCGAGCGGCCCTGACTCCCACCCACTC
CCGTCCGCAGCTGAGCGGCAGCCAGATGAGCCTGTCAGGCGACGCGGAGGCGGTGCAGGTCCGCGGCTCCGTGCAC
TTCGCGCTGCACTACGAGCCGGGCGCCGCCGAGCTGCGCGTGCACGTGATCCAGTGCCAGGGCCTGGCCGCCGCCC
GGCGCCGCCGCTCGGACCCGTGAGTGCCCCGCCGGCCAAGCGGGGCGCGGCTGTCACAGCCCAGCCCACCATTCAC
AGGGTCTCGGCCTCCTCGTCCTCATCTTCAAAATGGGAACAACAGCGTTATTGGGAGGCGTGCGATTAAGCGAGACA
ATCCCTGTAAAGCGCTTAGCACGAGGCCTGGCACGTGTTCGGGATGGTGGCTGGGGGAGCCCACAGGCAGGGGAGA
AGGCTCTGGGAGGGCCCCTCCTCACCTCGGGTTCTCACCTCCCCAGCTACGTCAAAAGCTACCTCCTCCCGGATAAG
CAGAGCAAGCGCAAGACGGCGGTGAAGAAACGGAATCTGAATCCGGTTTTCAACGAGACTCTCCGGGTGAGGCTGTG
ACCACGATGCGGTTCCCCGTTAATGAACTGGACGCCCCCTTCCTGCGGGGCTAGGTGGCAAGGGCAGCCAGTAACGT
CATTGCCCGGAGGATCGGCGGAGGGGGCCCATTAACTCGTTATCCAGTGTTGTCAGCCTCGTGGTGGGCGTGGTGAT
AGTGCAGGTCCCCATTAATGCCCTTAGGGGCTCCCCAGAATTCCATCATGGTAGGAACGCGGTAGGACCTGCCTCAG
CCAACTCGCGCAGCATCTACGCGGGCCACCAGCAGTGCTCCACTAAAGCTCACCTCCTGTCCTCAGTACTCCGTCCCG
CAGGCCGAGCTTCAGGGCCGCGTGCTGAGCCTGTCTGTGTGGCACCGCGAAAGCCTGGGTCGCAACATCTTTCTGGG
CGAAGTTGAAGTGCCCCTGGACACGTGGGACTGGGGCTCTGAGCCCACCTGGCTCCCCCTGCAGCCCCGGGTGAGG
CAGCCAGGCCGCGTGGGGAGACCTGCGGCCCGGGTCTCCTGCATTTACCCCACCAGGCTCTCCCGCAGCCCCCTCAC
ACCCCGCCTTCGACAGAACCTCCCCTCAACCTCTTAACCTCATGGCCCCAGGCGAAGCCCGGCCGGCCACGGCCCCT
TCCCCGAGGGCGCTAGGACCCCTAGGTTCTGCCCCTGCAGGCCCCGCCGTCTCTTCTAGCCGCACCCCATCCGGGTC
TGCAGACCCCACCCTCCTGAGGCCCCTTTCCATTAGCCCCTGCTCCACGATAAGCCCGCCTCTCGCAGGTCCCACCCT
CTCCCGACGACCTTCCGAGCCGCGGGTTACTCGCCCTGTCCCTCAAGTACGTCCCCGCCGGCTCCGAGGGTGAGTGA
CAGCCGGAGAGGCCAAGCTGGACACGCCCTGAAAAGCGGGAGACTCCAGTCCCCGGGTTTGGGGGCGGTGGACTCC
ATCCGTGTGCGGGCCTGAGCCGAGCCTCTCCGCAGGCGCAGGACTGCCCCCGAGCGGGGAGCTGCACTTCTGGGTG
AAGGAGGCTCGGGACCTCCTGCCGCTGCG (SEQ ID NO: 323)

16 chr19:10304689-10307022
CGCCCCCTTCCATTCCCCGCCCGCTTCCATCACTTGGTGTCGCCCAAGCCTGTGGTCGCCCCTAGCAACGCCCTCCCT
CACTTCGCAGTCGGTTTCCCCTTTCATCATCGCCCCCCCACGTCCCGCTCTTGGTCTCTCCCGATCCCGCGTGGATCC
GGTGCTTGGGCGCCCCCGCCAACGACCCCCGCGCACCTCAGCGTTGGTGTCGCCCGGTTCCCCCCGCGCACGCGCAC
CGTGGTATTTCCCGCCACGCTCCTACACCGCCCCCCCCAATACCTGGTTGGTCACGTCCCCCGGGAGGCCCCGGATC
AGTATCTTGCGGCGGTTACGGAACTGGCGCTCGGTGTGTTCCAGGCGTTTCCGGATCTCTTCTGGATCTAGAGGCGG
CAGCTCTTCTTCCGGCGCCCGGCGCTCCGCGGCATCGCCGGCTTCGACTTCGGCCCCAGACTTAGGGCTCAGCGGGG
GCCGGTGAGTAACGGACACGTCCGCCGCCATCTTGGGAAACCCGGCGCCTTCTGGGACCAGCGAGCCGGGGCGGAG
CGGCATAGAGCGGCAACGAGGGCGCGCCCGTCGATTGGCTGGGAGAAACCCCACCTCCTTCCCGCCCCCCTTGCCCC
GTTGGCTAAGCCCCAGCCCACCTCTCAAGAGTTCAAGCTGCGTCTGCGCGCCACAGGCCCCGCCCCCTTCCGTCGCA
GCGACGCTACTCAGTGGATGTGCACCTGGGTGGGAGAGACTTGCAGCGCGGGTGGAATCAAACCACAGATTAGGGA
GTTTGAAGGCTTTATTGGTGCGGAATCTGAGGGCACAGCCAAGCCCCCGCCAACTTTGATCCCGGATCCCAGCGTCA
CTCAGCTCTGGACGGTTCTTCCCCCATTGCTTCTGTCGGCTGCATAGACGTGAGGGGCAGATAGGTGCTCTCCTCCCT
AACATGGTAACTGCCGCTCCGTTGGTGCTCCCTGAAGACGTACATTAAGGCCAGTACGATAGTCACCACGCCCAGGG
TCAGTAACACCGCCACGAAGACGGGGACAAAGTGGGAGCTCCCAGCTGTGCAGAGAAAGCGCTAAGTCAATATGCGT
CCCTTCTGTCTCCAACCCCCCCGCCCCCCGGCTTACCGGTCCAGACCCGCAGCCCCGTGTTAGCTCACCCTCAATGTC
CATCACCACGACCAGGGTGTATTTGCCTCGTGAGCTGGACGCTTGGCACTGATAAGTACCATTATGTGTTACGTTGAC
GAAGAACGGGATCCCCACCGGCACCTCCCGGCTGGAGCCTTCCTTCAAACACCGCAGCTCGGGGTACGGGTTGCCCC
TGGCTTGGCACTGCAGGACGTGTCTCGTTTTATCTTTCCATTTCAAGTGCTGGGGGCATGTGGCTCGGTCAATTTTGG
GACCATCTGTGGAACCACCATGTGTGATCAGACACCCAACACACCCGAGGCACAGTGGTGCAGAGGAGCGTCTAATC
TTTCCAGGGCAGGGGTGGAGGGATTAAAGGTCAGGGTGACCGACTCACACAGGACTCGCAGCTGGACGCTACTGTTC
CTGTGCAAGAACTCGCCGTCCACCTCGAGAGTGGCACTGCAGAAGAAGCTGCGTCCGTCGTCACTCTCGGTAGCATT
TAGCTGAAGTTGAGCTGGCTGCCCCGGGGCCGCGGCCGGAACTCCGTCCAGCGTGACCTGGACTCGAGCCCCAGCC
ATGCAACTCACGGTCACTGTGGACCCCTCATGGGCGGTGGGCTCGCTGAGGTTCACAATGGGTCCTAGGAAGCCTAA
AGGCGGGGCATTGCCCAGGAGCTTAATGAACAGGACCTTCCTGTGGGTCAAGCCGCTCCCTCCGCCCTCCCCTTTCC
TCTCGGGATATCCGGGCCACGCTTTCGGCCGTTCAAGCCTCGCCCTCTTTCCGCGCTGTGTCCAGCTTCGGGCACTCA
GGCCCAACCCACGTTGCAACTGCTATTGGGGCAAGCCAGGCCCCACCTTTTCGGCTAGTCTCCGCCCCCTCTGCCAC
GCCCCCAGACTGCTGAGGCCGCGCCCCCTTCCCACGCCTCCTCTTACTAAAGACCGTCAAGTTCTCCCGGGCCTCCC
GTCTCTCGCCCCCTAGGGTCACGTTGCAGACGATCTCCCGGGCACCCTCCTGATCCGCGCGCGCCGTGGCTGTGGCT
GTGGCCGTTAGCGTGTCCCCGTGGTTCATGACTGTCGCATTCAGCATCTGGTCCCCCAGCGCCAGGTAGACCTGGGC
CTCTGAGGCTGGAAAAAGCCCGTCTAGGGTGCAGTCCACCGGCCACGACGTTTCCACCTCCAAGAACCGGGGGGCCA
CGAGGCGCGGGGGGGTCACG (SEQ ID NO: 324)

17 chrX:129132628-129134108
CGCGGCGGGCCTTCCCCATTGGCCAGCCAAACACAACCGACTGCGGCAGCCAATAGGAGCCGCTCTCCTGAACATTC
AGAGGATGGGTGCGCGTGGTGTGATAAGGGGATGTTGGCGCCTGGTACGCGCCCCCCTACATCTGGCAAGTCTGTAA
CAGAAACAGTTACACCCCCTACACACGCACACGCGTGCCCGCTGGCTCCCTCCTCTCAGCTGTACAGGCCCCGGACA
ACCCACTGCGTGTCTTGGCAGCGGCCTCCCAGGCTGCCTGGGGCCCGCGAGTGCACCTGCTCACTCATTAAGACAGA
GCATCCCTTTATCCCAAGGCGCGGGTCGGGTAGAGGGTGGGGGTAGAGGGGACGGGGTAGCGGGGACCGGGAAGG
CGCGGCTCAGCTGCCCGCTGCTCCCGAGGTGAAAGAGGTGCCTCCGCCCCCACCCCATCCCCGCAGAGTTGCGTTGC TABLE 9-continued CpG islands (CGIs) methylated in blood but not in bladder cancer. Provided for each are:ID no.; Coordinates of selected regions containing relevant CpG islands based on *Homo sapiens* full genome as provided by UCSC (hg18, March 2006); GeneName; Location of the probe used; the Fold Change; and the sequence of the CGIs.

TCCAGGGAGGCCGAAGTGATCCAGTGATGTCTTAAGGTGCAGCTCTTTGTCCTCCCCAGCTGTGCTCCCTGCCCGCT
GACCCCGTGCGCTCGAGCCAGTGGGGGTGGGGAGCCCGAAACCTATAACATAAACGGGGGCAAGGAGAAAGAAGTC
TATCCCGGGGTGGCGTGTGCCGCTGTCCCCACCCCGTCTCTTTCCTCCTGAGGCTTCTTCCCTCGGGTCCGTCCCGGG
AATGCAGGCAGGGGAGGGTGTGGGCCGAGGCGCGGCGGCGGCTGGAGCAGCGCGGTAGGGTCCTTCGCCAGAGCA
TCCGGTCCGAGGGCGCACACAGGCAGAAGGCTCGCGGCTCGTCCACTCTCCTCCCTCTCTCCTCCTCTCCCTGGCTTT
TGTGTTGGTGCCTCCGAGCTGCAAGGAGGGTGCGCTGGAGGAGGAGGAGGGGGGCCCGGAGTGAGAGGCACCCCCT
TCACGCGCGCGCGCGCACACGGTGCCGGCGCACGCACACACGGGCGGACACACACACACGCGCGCACACACACACG
CACAGAGCTCGCTCGCCTCGAGCGCACGAACGTGGACGTTCTCTTTGTGTGGAGCCCTCAAGGGGGGTTGGGGCCCC
GGTTCGGTCCGGGGGAGATGGCGCAGCCCATCCTGGGCCATGGGAGCCTGCAGCCCGCCTCGGCCGCTGGCCTGGC
GTCCCTGGAGCTCGACTCGTCGCTGGACCAGTACGTGCAGATTCGCATCTTCAAAATAATCGTGATTGGGGACTCCAA
CGTGGGCAAGACCTGCCTGACCTTCCGCTTCTGCGGGGGTACCTTCCCAGACAAGACTGAAGCCACCATCGGCGTGG
ACTTCAGGGAGAAGACCGTGGAAATCGAGGGCGAGAAGATCAAGGTGATCCAGGGGGTCAGGTCCAGGAAGGGTGG
GACCCGGGAGGGGACCTCGCCCGAGGCATAGCTCTAGCGGTTGTCGTCGTCCAGCGTCCAGCGCGTGGCGGTTTCG
CCTCTTGCTGAGCCGAGGACCCTCG (SEQ ID NO: 325)

18 chr21:45648960-45650662
CGCACGCCCCTCCTGTCTCGCGTCCGTCCCTCCGTGCAGCCGGGGCAGGACCCTGCAGGGGCCTTGCGGGCCGGAG
GTGCCGGCTTCCTCCTCCGTCCCGTCCCCCCGCGGTGACTCTATTCAAATCTCCCCCCTTCCCGCTGCCCCACCGGA
CTCAGGGGCTGGGGTCGTAGCCCGGCGGGCAGCGGTGTTCACCTTCCGCATAAACCTGGGCTTCCTCGCGGGGCAG
CCCCCGGGCCCTGTGCTGGGTCGCAGCCTCGGGCGGTTCCCTCGGGGCGGGACGTGTCCCCGTCCGTCCTCGCCCGT
CCCCGCCGCCCCCGGGTCCCGGCCCGCCCCGTCCTCGCAGCCGCAGGTCCGCTGCGGCGCCCGCCCCCCTCTCCCCT
CCCCGGGCCTTGCCCTGCTCGTCGCTCCGCCCCCTGCCCGGCCCCTGCCCGGCCCCGCCCCGCGCCCGCCCCCTGCC
CGCGCCCGCCCCGCCCCCTGCCCGGCCCCTGCCCGGCCCCTGCCCGCCCCCTGCCCGGCCTCCCAGCGGCGGCGGC
TGCAGCGCGGCGGTCCGAGCGGGTGCACCGCGGCGGAGGAGGCAGCATCCCGCGGCGCTGACGGTCCTGGGGAGA
GCATGGCGCCGAGGTGAGGCCGGGGCTGCGGGCAGGGGTTGGGGGACGCCAAGATGCGGCTGCGGGGGTCGCGGG
GGTCGCGGGGCTCGGCCGGGTCCTGCGGGGGTCGCGGGGGTCCTGCGGGGTCTGACCCGTGCCTGTCCCGCGCAGG
TGCCCCTGGCCATGGCCGCGGCGGCGGCGCCTCCTGGACGTGCTCGCGCCCCTGGTCCTGCTGCTCGGGGTCCGCG
CGGCCTCCGCGGAGCCAGGTAAGACCCGGGCGGGACGGGAAGGTTCGCGCCGGTGCCCGCCGGCCTCGCCGCCCTG
GCTGGGGTCCCCGCCCGGCTCCCTCACCCCCGCCCCGGCCGCTCTGGGTTCAGCCCCGGCCCTGCCCACGCGCGCAG
GAGGCGCCGGAGCCGGACGGAGCGGGGCGGGGTGGCCGGAGTCCCGCCCATTCATTCTCCCCGCGGGGTCCGGGCC
GGGAGGGGTGCGCGGTGCGAGCGGCCGGAGTCCCCGCGCGGGGACCGAACCTCCGCGGCCGGCGGGGTCGTCGGT
GCCGGGAGGGCTCGGGGCGGGGCCGCGGGGTCTCGGGAGACGCGGCCTCTGTCGCCGTCACGGCCTCGTCCCCGCA
GCGCCGGGTCCCGGGACTGACCGCGGGCGGAAGGCGGCGGAGCGCGGGGCGTCGTCTCCGCGTTTCCAACCTGTTG
AGGCTCCTCGCCGCGGGCCGGGCCTTGTGCGCCTCTGTCCCCGCCGCCCTCAGGCCTCTGTCCCCGCGCCCGCCGTG
GTGTCGGGTTGCGCGGTCCCCTTTGATGCCAACCGAGCGCCGCGCGGTCCGAGAACAATGCCCAGAAGCCGCTGCCC
CGCCGGCCTCGCCGCTTCCCGTGCGCGGCAAACGGTGCGCGGGGCCCGTGGGGACCTTCCTGCCTCCAACCCCGGG
ACCCAGTTCCCCACCACCTGCTAACCGGGGCCTCCTGCCTCCAGCCAGCCCAGCAGAGGCCCGGGGGAGGCGGCGG
GGACGCGGACCCCAGGGGAGCCCCGCCCAAAGGGCCTGGGTGCCTTGTCGCGGGTGGAATCCCACCCGGGGGTCCA
CGCAGCCAGCGCCTGCCTCCGACTCG (SEQ ID NO: 326)

19 chr10:134864694- 134865392
CGAGGACAGGGCCCGGCCCCACCCCGGGGCGAGTACGAGTTTGGAAGCAGTGAGGGCGCAGAGTGGGGCTCCATCT
GGGGAGAGGCCTCTCTCTGTCACCCGGCCCCGTGCGGCAGTTCAGGGTCCCAGCATCTCCCCTGCACTGGGAGGCGG
CAGCCGTGCCCGGGGGGCGCCCGTGGTGGGCGGGTGCAAGAGAGAAGGGCGTCGGGTGTGCAAGCACCACCGGCCT
CCCATTAACAGCCTGCCCGGGCTCCGCCCACAGGAGCCACTGTCCACGTAACCTGCGTCTCTTTCTTTCAAGGAAAAG
AGAAGCCAGCCATGGCCAGGACCAGCAGCAGGGCCCCCTGCTCACCCACCTCGGTGTCGGATGTGGACTCGGACGC
ACTGTCACGGGGAAACTTCGAGGTGGGGTTTCGGCCTCAGAGGTCCGTAAAAGCCGAGAGAGCGCAGCAGCCTGAG
GCTGGCGAGGACAGACGGCCAGCTGGCGGGGCCTCAGACGTGGAGGCAGTGACCCGACTGGCCAGGTCCAAAGGGG
TCGGCCCAGCCTTGTCCCCCGGCCCAGCCGGATTCCAGAGCTGCAGCCCCGGCTGGTGCAGCGCCTTCTACGAGGCC
GACTGCTTCGGGGCCGACGTCCACAACTACGTGAAGGACCTGGGGCGGCAGCAGGCGGACGGGGCCCTGCCCGACG
CCCAGAGCCCG (SEQ ID NO: 327)

20 chr9:129556229-129557670
CGAATGCAGCATCCCTGCGCTCGGCGCCCTGCTATTGGCCAGAGATGATCTCACCGCCTCCCGGCCTGCGCGCGCCT
GATTGGCCGGTGCGGGGATGCTGCGCTCCGCCGCCGGCGGGGCAGTCCTTCAGGCGGGCTCCGCGAGCGTGTGTGA
GCCTGGGGGAGCGAAGAGCCGACGCGCCTGGCATCTCCCAGGGGGCTCAGGGGGCAGGAGCGCGGAGACCCCCGG
ACAGGGTCTTAACCCCTTCCCGCCAGCCCGAGCCCAGCATCCCCTCCAGCTCCCCTCGGCGTCCCAACCCCAAGCAA
AGCCATCCCCAAAGGATGCTCCGCAGAGAGGCGGGGTCCGGGTCCTCCCCTCCACCCCCTTCCGTTTAACCCTCTCA
CCGCCGCGGCGCCGTCCTGCACTGCCCGGCCAGCTGGGCTGGGAGAGACCCGCGCCCCAGGCATGTCCAAGCCCAC
CTAGAGGGCGGGAGGGTGGCGGGCGCTCTGGCCCCAACCCTGGCATCCGAAGCATCCCCCGCGTTTCCTGCTCCTCA
CTCAGTCTTCAGATCCCAGTCCGGCGCCCCCGGTACAATGGGGAGCCAGGGTGCCCAGGTCAGCCGCAAGGGCCAG
CGTACCAGGCGGAGGACCGGCAGGACGCCGGAGACCCCATCTCCCAGTCCCCCCTGCCCCAGCTCTCTCCCTCCTGC
GGAGGAGGCAGAAACGGACCGGCATCTACCGCAGCCCAGAGTCCCAGGAGTGGCCGCCGAACCCTCACCCCGCGGA
GCGCCTGGGCGCCCAGAGGTGAGGCTGGGGTGACCCCGCCCCCTCCCCGGGTCGGCCGGGCCCAGCCCAGCCCGAC
CCTGCCGGGCGCCGCTGAGCTGCAGCTCCCCGGCTGGCTCTAGGGCCCCGGGCGGAGCGGCCGGGGGTCCCAGCCC
GGCGCGCGTGGCGGGGGCCGAGCCGCCCCCTCACCTGCACCTGCACGAAGGAGCCGCGGTAGAAGCAGCAGGCGGC
GGCCGACAGGGCACTCCACAGGCTGCACCGCTCGGTCATGGTGGGGCCAGGCTGCCGGGGCCGGGACGGTGTGGGG
GGGCGGTGGCCGGCGGGGCAGGGGCGCAGGGACCAACCGGCTAGGCACCGGCTGCGCGTGCCTCTCAGCGGCGCG
ATTACCTCATCGCCTTGTCGGGGGAGGAGCGGGGAGGCGGGGCGGGGAGACCCCACCCTCCAGCCGGCCAGGGGAG
GGGAGGGGGCCATTGTTCCTCCCTCCGCCCGCCCCCCGCTCCCAGCCCCTCGCCCCCCGCCCTCCAGTTCCGCGCGC
TCGGGCTGCCTGGAGCTGCGGGCGCGGAGCGGAGGACCTGCCAAGGAGGGTATTACCGGGGGCAGCGGGATCGGGT
GGGGACCCATGGGCCAGCGAGGGGAGGTTCTGCCTCCCCCACTCGCCGCACCTCTAACAGACCGGGAGCG
(SEQ ID NO:328)

TABLE 9-continued

CpG islands (CGIs) methylated in blood but not in bladder cancer. Provided for each are:ID no.; Coordinates of selected regions containing relevant CpG islands based on *Homo sapiens* full genome as provided by UCSC (hg18, March 2006); GeneName; Location of the probe used; the Fold Change; and the sequence of the CGIs.

21 chrX47305347-47306043
CGCCTGCGCGAGTCAGGACGAGCGCTTGCCCCAGATCTTGACGTTTCAGGCGGCCCCTCCTAATCCGGAACACGACT
CACATTCCGTTGGTCTTGCCTTGACAGACGTGACCCTGACCCAATAAGGGTGGAAGGCTGAGTCCCGCAGAGCCAAT
AACGAGAGTCCGAGAGGCGACGGAGGCGGACTCTGTGAGGAAACAAGAAGAGAGGCCCAAGATGGAGACGGCGGCG
GCTGTAGCGGCGTGACAGGTGAGGGCGGGCCCGGGAGGGCTCGGTTTCTGGAGCGGCTGCCGGGCACGGGCAGGG
AGCCCGGACCGAAAGCTCAGCTCCAGGATGGCTGCGCTTGGGCCCCGGCGTTCCCTGCCCGGAACCGGAGGAGTGG
TTTGACCCGGGGCGAGACCATCGTCGACAGCGGGGGTGGGGTGGGTAACAGGAATAGGCGGGCAAGGCTGCGGGTG
ATGGTTTCGCCCGCTGCTAGTGGTGGTGCGCCTGCGCAGAGCCGGAAGCCCTTTGGTAGGCGGGACCCGACCGAGT
GGTGCCGGGATTCCGTCTTAACCCCCGCTAAGGTGTCCAATGACCTTTCCTTACCAACTGCGGGGAGTGTGTGGAAA
CGCGGTTCACTCCCCGGTTTCCTTATTCTGGATCAGTGTCTGACCGCCCCCGCCGGGAGAATGTCAGGATTCTCGCCT
CT (SEQ ID NO: 329)

TABLE 10

Hypermethylated genes and CGIs in bladder cancer.

| Symbol | CGI | Fold Change |
|---|---|---|
| MEIS1 | chr2: 66525936-66527140 | 4.76 |
| NR2F2 | chr15: 94688798-94689034 | 2.93 |
| SOX21 | chr13: 94152191-94153185 | 2.8 |
| MAB21L1 | chr13: 34950554-34951119 | 2.68 |
| OTX1 | chr2: 63134539-63134851 | 2.67 |
| MGC2752 | chr19: 63784504-63785085 | 2.64 |
| IRX3 | chr16: 52873104-52882105 | 2.63 |
| PAX9 | chr14: 36205265-36206099 | 2.62 |
| FOXC1 | chr6: 1549606-1560865 | 2.5 |
| DLX5 | chr7: 96488158-96489487, chr7: 96489900-96490182 | 2.45 |
| NR4A2 | chr2: 156892636-156892878, chr2: 156893804-156894601 | 2.45 |
| CNTNAP1 | chr17: 38089258-38089793 | 2.35 |
| FOXF2 | chr6: 1338049-1339169 | 2.35 |
| HHEX | chr10: 94441310-94441717 | 2.33 |
| PRKCZ | chr1: 2072175-2072389, chr1: 2106293-2106661 | 2.31 |
| HOXA7 | chr7: 27164708-27165039 | 2.27 |
| MSX2 | chr5: 174091287-174092335 | 2.26 |
| SLC45A4 | chr8: 142288380-142288627 | 2.22 |
| FLJ44006-BCL2L11 | chr2: 111591678-111597436 | 2.21 |
| MAP2K2 | chr19: 4059920-4060207 | 2.2 |
| SHH | chr7: 155288454-155292175 | 2.19 |
| chr13: | chr13: 49605587-49606020 | 2.19 |
| MAD1L1 | chr7: 2082894-2083307 | 2.18 |
| hsa-mir-196a-1 | chr17: 44074360-44075233 | 2.17 |
| NXPH1 | chr7: 8449658-8450236 | 2.17 |
| chr18: | chr18: 5186244-5187389 | 2.12 |
| C10ORF114 | chr10: 21828640-21829594 | 2.1 |
| SIX3 | chr2: 45014932-45016562, chr2: 45013398-45013616 | 2.08 |
| TFAP2A | chr6: 10530308-10530634, chr6: 10498025-10498551 | 2.08 |
| ISL2 | chr15: 74414579-74414893, chr15: 74419318-74422570 | 2.05 |
| VAX2 | chr2: 70984709-70985764 | 2.04 |
| AMZ1 | chr7: 2724531-2724783 | 2.01 |
| CYB561 | chr17: 58865386-58865618 | 1.99 |
| HOXD3 | chr2: 176737660-176738187 | 1.97 |
| SIM1 | chr6: 101003802-101004342, chr6: 101002495-101002783 | 1.95 |
| EFNB2 | chr13: 105943410-105943788 | 1.91 |
| GAD1 | chr2: 171384799-171385226 | 1.91 |
| MSX1 | chr4: 4915358-4915735, chr4: 4910534-4911092 | 1.9 |
| FOXA1 | chr14: 37137198-37138958 | 1.88 |
| HDGFL1 | chr6: 22677564-22678684 | 1.85 |
| chr13: | chr13: 49595986-49600287 | 1.84 |
| chr16: | chr16: 87372445-87372706 | 1.84 |
| EVX1 | chr7: 27251165-27252762 | 1.83 |

TABLE 10-continued

Hypermethylated genes and CGIs in bladder cancer.

| Symbol | CGI | Fold Change |
|---|---|---|
| UNG2 (CCNO) | chr5: 54554812-54555385 | 1.83 |
| ONECUT2 | chr18: 53254153-53259851 | 1.81 |
| HSF2BP | chr21: 43902100-43904249 | 1.8 |
| chr1: | chr1: 119350668-119352843 | 1.8 |
| FOXD3 | chr1: 63554983-63563059 | 1.79 |
| FOXA2 | chr20: 22514822-22515055, chr20: 22510737-22514104, chr20: 22505518-22507240 | 1.77 |
| GRIK2 | chr6: 101953488-101953856 | 1.77 |
| chr2: | chr2: 45249374-45251690 | 1.77 |
| SIX1 | chr14: 60178708-60179539 | 1.76 |
| HOXA9 | chr7: 27170441-27172987 | 1.75 |
| FOXD2 | chr1: 47671713-47671985, chr1: 47682300-47683607, chr1: 47672249-47672972 | 1.73 |
| NKX2-8 | chr14: 36122886-36123441 | 1.72 |
| ZNF274 | chr19: 63420090-63420541 | 1.72 |
| TAF4 | chr20: 60061693-60062033 | 1.71 |
| SIX2 | chr2: 45085286-45086054 | 1.7 |
| chr8: | chr8: 145909302-145910517 | 1.7 |
| PCDH7 | chr4: 30330303-30333940 | 1.69 |
| PITX2 | chr4: 111774415-111774953 | 1.68 |
| TCF7L1 | chr2: 85213468-85216104 | 1.68 |
| chr6: | chr6: 10492952-10493478 | 1.68 |
| SOX7 | chr8: 10624024-10624296 | 1.66 |
| HOXC4 | chr12: 52726910-52727810 | 1.65 |
| PITX1 | chr5: 134390992-134393045 | 1.65 |
| PCDHGA12 | chr5: 140790679-140792801 | 1.64 |
| chr6: | chr6: 170422815-170423038 | 1.64 |
| EPN1 | chr19: 60907042-60907388 | 1.63 |
| DLX6 | chr7: 96469320-96469736 | 1.62 |
| hsa-mir-10b | chr2: 176723195-176723460, chr2: 176720618-176720921 | 1.62 |
| SIM2 | chr21: 36990064-36995761 | 1.61 |
| CACNA2D4 | chr12: 1844001-1845219 | 1.6 |
| HOXA5 | chr7: 27149139-27152087 | 1.6 |
| NCK2 | chr2: 105864220-105865009 | 1.6 |
| OSR1 | chr2: 19424445-19425131 | 1.58 |
| C17orf27 (RNF213) | chr17: 75936057-75936582 | 1.57 |
| chr6: | chr6: 169051743-169052507 | 1.56 |
| EVX2 | chr2: 176652334-176656692 | 1.53 |
| ZNF503 | chr10: 76825135-76839606 | 1.52 |
| chr5: | chr5: 92931996-92934631 | 1.52 |
| KIAA1303 | chr17: 76404186-76404427, chr17: 76390187-76390410 | 1.48 |

TABLE 11

| Genomic distribution of methylated probes in bladder cancer. | | |
|---|---|---|
| Probe location | % on array | % in bladder cancer |
| divergent promoter | 2.5 | 2.4 |
| downstream | 3.9 | 4.0 |
| inside | 52.4 | 52.3 |
| promoter | 26.0 | 25.9 |
| intergenic | 15.3 | 15.3 |

TABLE 12A

Overview of the CGIs differentientially methylated between tumor and control urine.

| Symbol | CGI | Fold Change |
|---|---|---|
| HOXA9 | chr7: 27170441-27172987 | 16.53 |
| PENK | chr8: 57520681-57521969 | 14.69 |
| PCDH7 | chr4: 30330303-30333940 | 12.00 |
| KCNA1 | chr12: 4888847-4891432 | 11.89 |
| HLX1 | chr1: 219134071-219134808 | 10.46 |
| POU4F2 | chr4: 147778656-147781351, chr4: 147777682-147778033 | 10.17 |
| LHX4 | chr1: 178464743-178471598 | 9.79 |
| FOXD2 | chr1: 47682300-47683607, chr1: 47672249-47672972 | 9.67 |
| LBX1 | chr10: 102986025-102986636 | 9.44 |
| chr11: 115956893-115956940 | chr11: 115955870-115957122 | 9.03 |
| LMX1A | chr1: 163590111-163590435 | 8.86 |
| BHLHB5 | chr8: 65662303-65662699, chr8: 65661156-65661382 | 8.61 |
| OTX1 | chr2: 63134539-63134851 | 8.22 |
| GADS | chr10: 26544390-26547440 | 8.02 |
| EVX2 | chr2: 176652334-176656692 | 8.02 |
| FLJ44006-BCL2L11 | chr2: 111591678-111597436 | 7.89 |
| ONECUT2 | chr18: 53254153-53259851 | 7.75 |
| ZIC1 | chr3: 148619591-148620015 | 7.33 |
| FOXA1 | chr14: 37137198-37138958 | 7.24 |
| DSC3 | chr18: 26875488-26877115 | 7.19 |
| SIM2 | chr21: 36990064-36995761 | 6.78 |
| MEIS1 | chr2: 66525936-66527140 | 6.74 |
| FEZF1 | chr7: 121727243-121727884 | 6.62 |
| ZNF503 | chr10: 76825135-76839606 | 6.57 |
| SLC35F3 | chr1: 232106922-232108080 | 6.34 |
| FEZF2 | chr3: 62331811-62332352 | 6.26 |
| NR4A2 | chr2: 156893804-156894601 | 6.20 |
| EN1 | chr2: 119329502-119332035 | 5.59 |
| PCDH10 | chr4: 134291113-134293078 | 5.53 |
| OSR1 | chr2: 19424445-19425131 | 5.23 |
| ZIC4 | chr3: 148591199-148594390 | 5.00 |
| CBLN1 | chr16: 47868915-47869809 | 4.92 |
| HMX2 | chr10: 124891898-124892607 | 4.89 |
| FOXB1 | chr15: 58083428-58085812, chr15: 58079172-58079459 | 4.76 |
| chr19: 057648585-057648629 | chr19: 57648469-57649057 | 4.58 |
| DPP10 | chr2: 115635208-115637235 | 4.55 |
| chr7: 032768257-032768301 | chr7: 32768010-32768497 | 4.48 |
| C10orf114 | chr10: 21828640-21829594 | 4.44 |
| FOXD3 | chr1: 63554983-63563059 | 4.39 |
| chr5: 092933638-092933682 | chr5: 92931996-92934631 | 4.25 |
| TCF7L1 | chr2: 85213468-85216104 | 4.21 |
| VAX2 | chr2: 70984709-70985764 | 3.99 |
| CBLN2 | chr18: 68359955-68362770 | 3.97 |
| PCDHGA12 | chr5: 140790679-140792801 | 3.94 |
| chr21: 037857850-037857894 | chr21: 37857725-37858416 | 3.89 |
| HOXA7 | chr7: 27164708-27165039 | 3.79 |
| GRIK2 | chr6: 101953488-101953856 | 3.77 |
| NKX2-8 | chr14: 36122886-36123441 | 3.65 |
| SOX9 | chr17: 67627870-67631593 | 3.64 |
| chr18: 005186349-005186393 | chr18: 5186244-5187389 | 3.50 |

TABLE 12A-continued

Overview of the CGIs differentientially methylated between tumor and control urine.

| Symbol | CGI | Fold Change |
|---|---|---|
| SOX21 | chr13: 94152191-94153185 | 3.43 |
| SNRPF | chr12: 94776152-94776377 | 3.39 |
| MSC | chr8: 72916429-72917309 | 3.18 |
| PITX1 | chr5: 134390992-134393045 | 3.05 |
| SOX7 | chr8: 10624024-10624296 | 2.99 |
| chr2: 042182832-042182879 | chr2: 42182944-42183157 | 2.97 |
| TBX15 | chr1: 119333515-119333719 | 2.96 |
| SIM1 | chr6: 101003802-101004342 | 2.91 |
| PFKFB1-APEX2 | chrX: 55043085-55043710 | 2.89 |
| GATA2 | chr3: 129688183-129694961 | 2.86 |
| chr5: 122462228-122462286 | chr5: 122461778-122463450 | 2.82 |
| GPR103 | chr4: 122521018-122521740 | 2.81 |
| SIX2 | chr2: 45085286-45086054 | 2.80 |
| SFMBT2 | chr10: 7489383-7495345 | 2.79 |
| NXPH1 | chr7: 8449658-8450236 | 2.73 |
| CA10 | chr17: 47590175-47591465 | 2.71 |
| CNTNAP5 | chr2: 124498723-124499725 | 2.66 |
| ZNF274 | chr19: 63420090-63420541 | 2.62 |
| HOXD3 | chr2: 176737660-176738187 | 2.61 |
| PITX2 | chr4: 111774415-111774953 | 2.55 |
| OLIG2 | chr21: 33316999-33322115 | 2.54 |
| FOXA2 | chr20: 22505518-22507240, chr20: 22510737-22514104 | 2.53 |
| DBC1 | chr9: 121170908-121172035 | 2.49 |
| PAX2 | chr10: 102497473-102499636 | 2.45 |
| MAB21L1 | chr13: 34950554-34951119 | 2.35 |
| CYP26B1 | chr2: 72224630-72228512 | 2.31 |
| CBLN4 | chr20: 54012011-54014085 | 2.26 |
| GAD1 | chr2: 171384799-171385226 | 2.25 |
| HHEX | chr10: 94441310-94441717 | 2.22 |
| chr9: 013268499-013268548 | chr9: 13268313-13269805 | 2.20 |
| FOXF2 | chr6: 1338049-1339169 | 2.17 |
| DLX5 | chr7: 96489900-96490182 | 2.08 |
| TBX3 | chr12: 113589232-113589931 | 2.04 |
| MEIS2 | chr15: 35174679-35174906 | 2.04 |
| PTGER3 | chr1: 71284813-71286392 | 2.04 |

TABLE 12B

Overview of CGIs associated with progression of NMI-BC.

| Symbol | CGI | FC |
|---|---|---|
| GPR103 | chr4: 122520930-122520974 | 1.81 |
| chr2: 042182832-042182879 | chr2: 042182832-042182879 | 1.96 |
| KCNA1 | chr12: 004890074-004890118 | 2.01 |
| HLX1 | chr1: 219134113-219134157 | 2.14 |
| DBC1 | chr9: 121171898-121171944 | 2.59 |
| GPR103 | chr4: 122521031-122521075 | 4.17 |
| TBX3 | chr12: 113609259-113609303 | 2.76 |
| GATA2 | chr3: 129693434-129693486 | 2.20 |
| TBX2 | chr17: 056833879-056833928 | 2.15 |
| TBX2 | chr17: 056835246-056835290 | 2.10 |
| ZNF577 | chr19: 057082979-057083023 | 2.08 |
| MSC | chr8: 072916695-072916739 | 1.82 |

EXAMPLES

Example 1

The CpG island hypermethylations as indicated in the Tables 1-5 are the result of comparative studies using well characterized patient samples. Both tumor samples and controls were analyzed. The DNA was extracted directly from the tumor and control tissue. DNA samples were analyzed using a CpG island microarray comprising 200.000

CpG islands (Agilent Technologies Inc.). The results obtained are indicated in the various Tables 1-5 as listed herein.

Example 2

Materials & Methods

Patient Samples, Ethics Statement and DNA Isolation

Samples from 44 fresh frozen bladder cancer tissues were collected, representing 29 non-muscle invasive tumors (19 with FGFR3 mutation (NMI-mt) and 10 without (NMI-wt)) and 15 muscle-invasive tumors (MI). Tumor tissue of patients was obtained from the Department of Urology of the Erasmus MC, Rotterdam. The medical-ethical committee of the Erasmus MC Rotterdam approved the project. All patients gave written informed consent. For validation, 90 formalin-fixed, paraffin-embedded (FFPE) bladder cancer samples (27 Ta NMI-mt, 13 Ta NMI-wt, 10 T1-mt, 14 T1-wt, 26 MI) were collected from the Department of Pathology. Usage of these samples was performed according to standards presented in "The Code for Proper Secondary Use of Human Tissues in The Netherlands" (http://www.federa.org). Tumor samples were included only if at least 80% of the sample consisted of cancer cells, as verified by H&E staining. DNA from tumor tissue was isolated with the DNeasy Tissue kit (Qiagen, Hilden, Germany), according to the instructions of the manufacturer. Commercially available normal human genomic blood DNA (Promega, Madison, WI, USA) was used as a reference in the genome wide analysis and the GGMA. DNA isolated from cells present in normal urine of four healthy persons of more than 50 years old was used as reference DNA in the GGMA validation assay.

Differential Methylation Hybridization (DMH) and Data Analysis

DNA amplicons were prepared for hybridization according to the DMH (differential methylation hybridization) protocol described by Yan et al [Yan et al. 2002.) Methods Mol Biol 200: 87-100]. Briefly, 0.5 μg of genomic DNA was digested with the four base (T^TAA) restriction enzyme MseI, which restricted genomic DNA into fragments less than 250 bp in length, while leaving the GC-rich CGIs relatively intact. Subsequently, the sticky ends of the fragments were ligated to linker primers. Samples were then digested with the methylation-sensitive restriction enzymes HpaII and BstUI to increase the genome coverage and to ensure complete digestion. Reference samples were treated in the same way to generate amplicons. PCR reactions (20 cycles) were performed using the purified, digested, linker ligated DNA as template to generate final target amplicons, followed by coupling to fluorescent dyes (Cy3 in case of human genomic reference DNA and Cy5 in case of tumor samples) before hybridizing to the Agilent 244K CpG island microarray. The pooled amplicons were co-hybridized on the array. Using this approach, genomic DNA fragments containing unmethylated CpG sites in one sample (e.g. the human genomic reference DNA) were degraded by restriction digestion and not amplified. However, corresponding DNA fragments in the other sample (the bladder tumor) that contain methylated restriction sites were protected from digestion and subsequently amplified by PCR. Differentially methylated sequences were identified by comparing hybridization signals between fluorescently labeled tumor (Cy5) and reference (Cy3) amplicons.

All microarray data generated are compliant with current MIAME standards according to Brazma et al [Brazma 2009. Scientific World J 9:420; Brazma et al. 2001. Nat Genet 29:365]. Normalization, preprocessing of raw data and statistical analysis were done using Bioconductor packages in an R programming environment (http://www.r-project.org/). Raw hybridization signals were normalized by applying the within-array global "lowess" normalization method [Yang et al. 2002. Nucleic Acids Res 30: e15], which assumes that the bulk of the probes on the array are not differentially expressed. The normalization also includes a pre-processing step, as a result of which the normalized intensities were log2-transformed. The log2-transformed intensities were then subjected to further statistical testing to determine which loci were differentially methylated. The linear model "limma" was applied [Smyth 2004. Stat Appl Genet Mol Biol 3: Article3]. We performed the following comparisons: All tumors vs. Blood, NMI-mt vs. NMI-wt, NMI-mt vs. MI, and NMI-wt vs. MI, to find genes that have different methylation profiles across the groups compared. These comparisons are analogous to a classical two sample t-test analysis.

The p-value threshold was calculated using the Benjamini and Hochberg method [Benjamini et al. 2001. Behav Brain Res 125: 279]. The loci corresponding to p-values less than 0.05 and a log fold change of either greater than 0.5 or less than −0.5 with more than 2 probes representing the same CGI were classified as differentially methylated. We left chromosome Y probes out of the subsequent analyses.

Illumina Custom Golden Gate Methylation Assay and Statistical Analysis

We designed a custom Golden Gate Methylation assay interrogating 384 CpG containing probes representing 238 CGIs, 184 genes, and 46 intergenic regions. The selection of the probes was based on the differentially methylated loci in the genome-wide analysis. Probes were included to detect methylation in all bladder subgroups, but also probes that appeared to be specific for a certain subgroup compared to others, and some probes specific for progression or death of disease. The methylation assay is an adaptation from the Illumina high-throughput SNP genotyping assay described by Fan et al. [Fan et al. 2003. Cold Spring Harb Symp Quant Biol 68: 69]. In short, non-methylated cytosines (C) were converted to uracil (U) by treatment with bisulfite. Sodium bisulfite modification of genomic DNA was carried out using the EZ DNA Methylation Gold Kit (Zymo Research Corp, Orange, CA, USA) according to the manufacturer's protocol, using 0.8 μg of FFPE DNA. The conversion efficiency was monitored by PCR with universal BS specific primers provided with the kit. Arrays were run at Service XS, Leiden, the Netherlands according to the manufacturer's protocol and as described by Bibikova et al. [Bibikova et al. 2006. Genome Res 16: 383].

Data were analyzed with Illumina's BeadStudio Methylation module software. All array data points were represented by fluorescent signals from both methylated (M) and unmethylated (U) alleles. The average methylation value β was derived from approximately 30 replicate methylation measurements for each locus. The methylation level was given by $\beta=(\max(M, 0))/(|U|+|M|+100)$. The β-value $(0<\beta<1)$ reflects the methylation level of each CpG site where 1 represents fully methylated and 0 represents unmethylated. At each locus for each sample, the detection p-value was defined as 1-p-value computed from the background model characterizing the chance that the signal was distinguishable from negative controls. Using this as a metric for quality control for sample performance, 6 FFPE samples (6%) were dropped from the analysis, because they either had very low overall signal intensities or >25% of loci failed. The significant differences were assessed by comparing the average β value per locus per group. Significant loci were selected on the basis of an average β value ratio larger than 1.4 and a difference between the average β value (Δβ) larger than 0.3.

Validation of Methylation of Individual CGIs

We used the MS-SNAPSHOT method described in [Gonzalgo and Liang 2007. Nat Protoc 2: 1931; Lurkin et al. 2010. PLoS One 5: e8802] to investigate methylation in urine DNA quantitatively. The method involves the bisulfite conversion of genomic DNA and the subsequent amplification of interested genomic region. This is followed by the methylation specific single nucleotide primer extension with CpG specific probes and finally the fragments are visualized on a ABI sequencer. To test the method, methylation of MEIS1 gene was investigated using normal, patient urine samples along with bladder cancer cell lines. In vitro methylated DNA was used as a positive control. A list of primers and probes used is given in Table 6.

Results

A Genome Wide Methylation Profile for Bladder Cancer

To investigate global DNA methylation in bladder cancers, we analyzed 44 bladder tumors on Agilent 244K human CpG island microarrays using differential methylation hybridization. We found that 729 different probes were significantly more methylated in bladder tumors compared to blood with a log fold change greater than 0.5 and a p value of <0.05. To select the most hypermethylated CGIs, we used as an additional criterion that 3 or more CpG dinucleotides should be highly methylated in a specific CGI. This selection generated a list of 82 CGIs representing 71 genes and 11 CGIs not directly associated with a gene according to the Agilent information file. These are shown in Table 10. The gene showing the highest degree of methylation was MEIS1 with a log fold change of 4.8 for the most highly methylated probe and an average log fold change of 2.2 across the 10 probes that were present on the array for this CGI (FIG. 1). We observed that for most of the significantly methylated CGIs, the adjacent CpG dinucleotides within a CGI were co-methylated. In contrast, CGIs neighboring a methylated island were usually not methylated.

Methylation of Intronic CGIs is Associated with Reduced Gene Expression

The 244k array contains probes for CGIs as displayed in the UCSC genome browser (http://genome.ucsc.edu/cgi-bin/, build 19). Of the CGIs represented on the array, 26% is located in promoter regions. Many studies have shown that aberrant methylation of CGIs in promoter regions represents one of the most frequent epigenetic events associated with gene silencing in cancer. In our analysis we observed that there was no specific preference for methylation of promoter regions. Instead, methylation was distributed proportionally over CGIs in promoter regions, within genes and in intergenic regions (Table 11). Examples are shown for CGIs in two of the selected genes, MEIS1 and NR4A2 (FIG. 1). To investigate whether methylation outside promoter regions also repressed gene expression, we next compared genes with methylated CGIs with available genome-wide expression profiles of bladder cancer using the Oncomine database [Blaveri et al. 2005. Clin Cancer Res 11: 4044; Dyrskjot et al. 2004. Cancer Res 64: 4040; Dyrskjot et al. 2003. Nat Genet 33: 90; Lindgren et al. 2006. Oncogene 25: 2685; Modlich et al. 2004. Clin Cancer Res 10: 3410; Sanchez-Carbayo et al. 2006. J Clin Oncol 24: 778]. This information could be obtained for 54 genes. Out of these 54 genes, 22 showed promoter CGI methylation and a positive correlation with low expression was observed in 17 genes (77.3%). The remaining 32 genes showed methylation of CGIs within introns. Interestingly, 23 of these genes also showed low expression (71.9%) in bladder cancers. These data suggest that not only promoter CGI methylation but also methylation of intronic CGIs leads to reduced gene expression. The expression profile box plots of MEIS1, NR4A2 and HOXA9 are shown in FIG. 1.

Figure 2A:
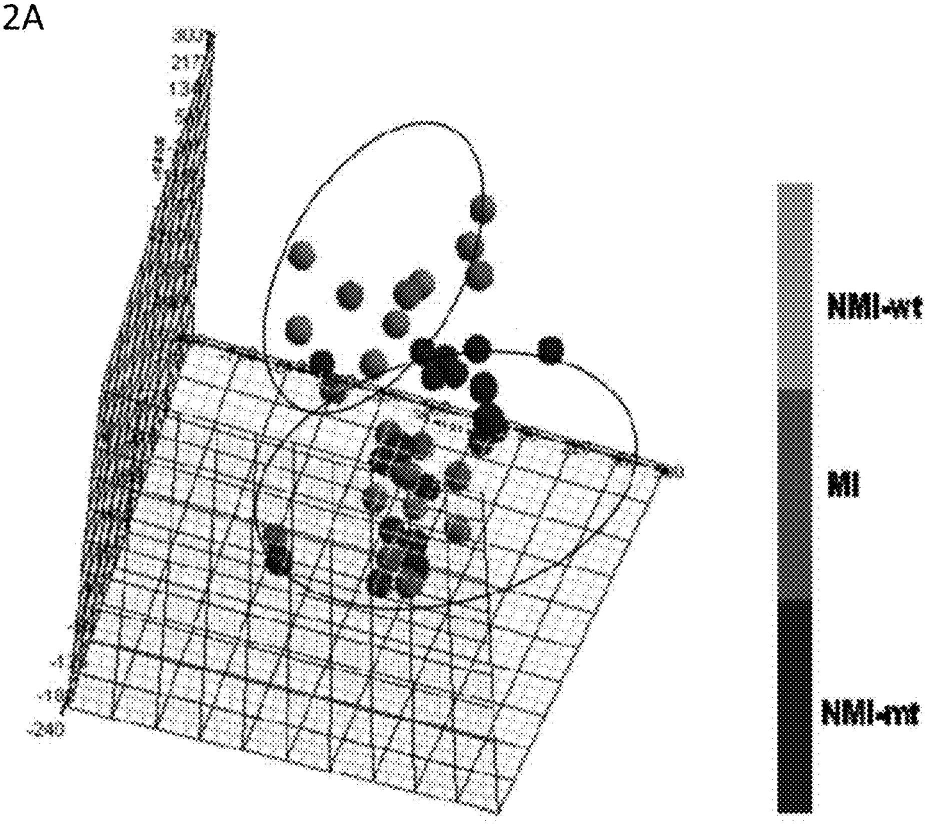
Figure 2B:
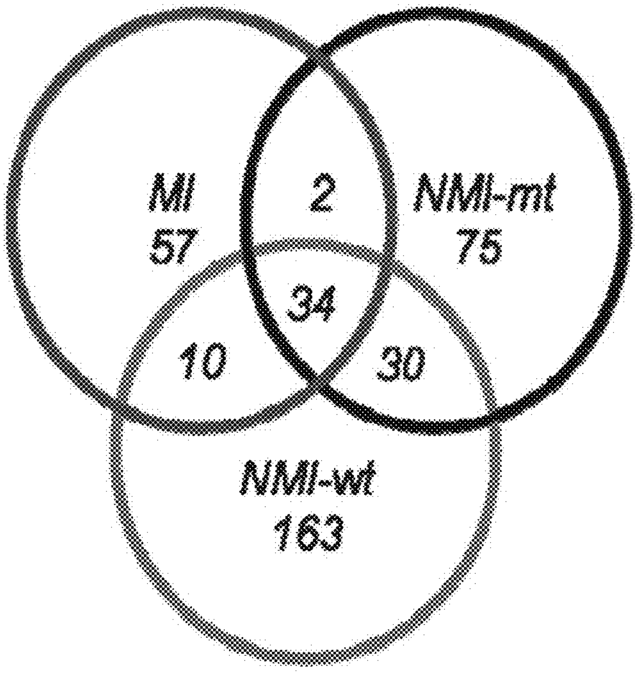
Figure 3A:
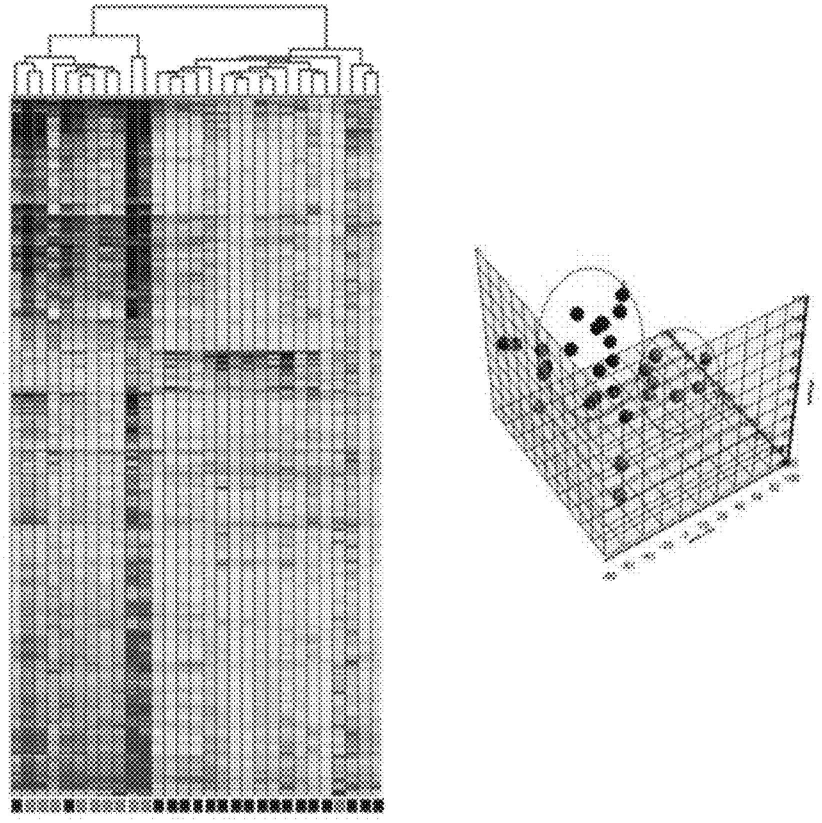
Figure 3B:
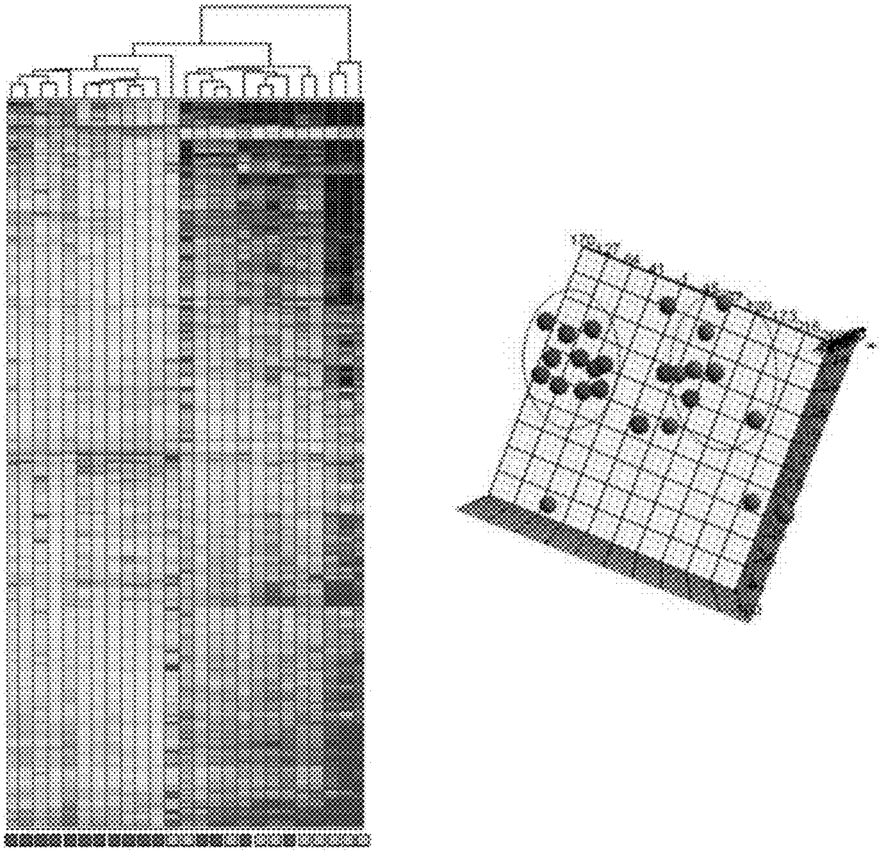
Figure 3C:
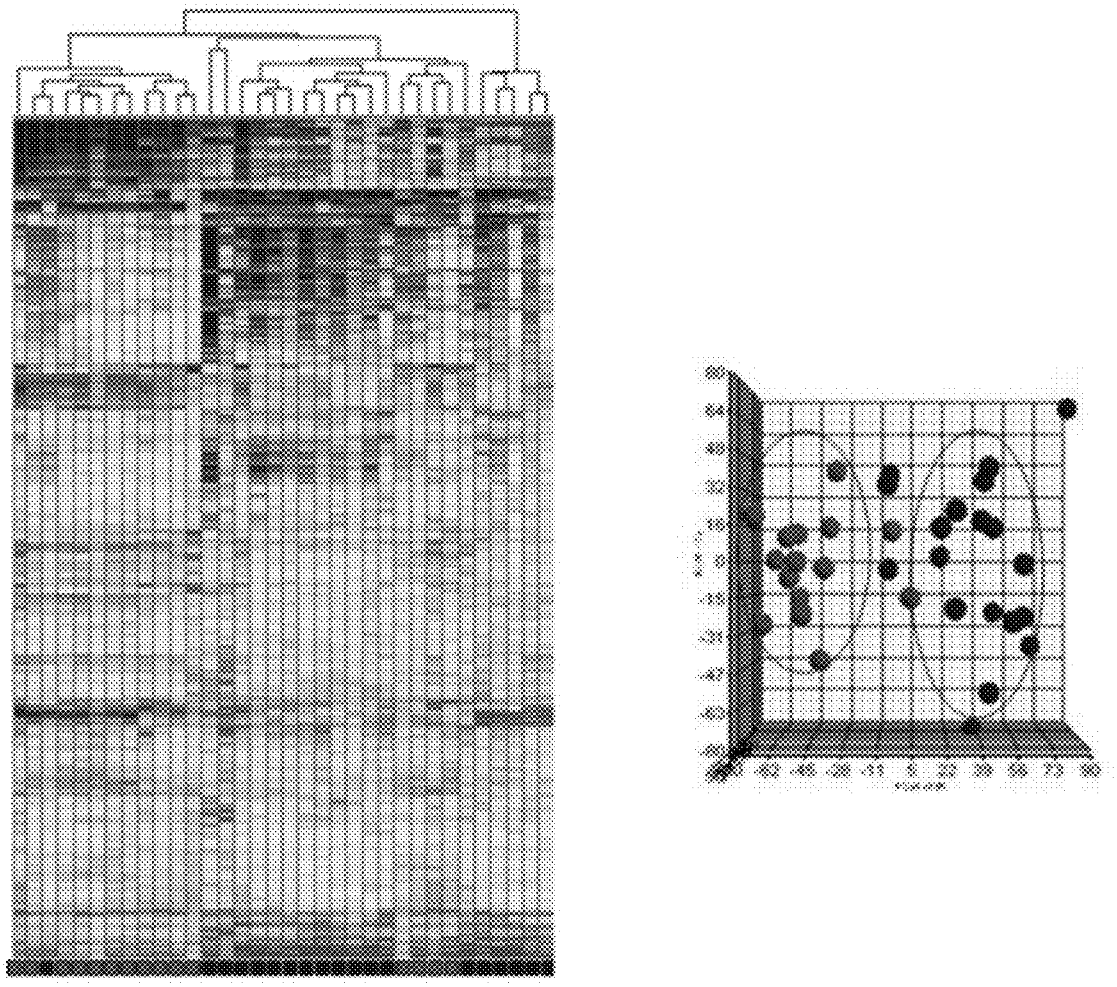

Analysis of Individual Subgroups Shows NMI-wt Tumors to have a Highly Methylated Profile To explore whether global DNA methylation can identify subgroups of bladder cancer, we performed an unsupervised analysis by means of a principal component analysis (PCA) using all probes on the array (244K) (FIG. 2A). The first three components of the PCA explained 42.4% of the variability between the samples suggesting that there is a reasonable discrimination between the subgroups. This unsupervised analysis indicates the presence of two clusters of bladder cancer patients. The NMI-wt tumors (in green) clustered closely together and separate from the NMI-mt (in blue) and MI tumors (in red). Furthermore, we looked at the individual subgroups of bladder tumors. NMI-wt tumors showed a 2.7 to 4.6 times higher number of hypermethylated probes compared to the NMI-mt and MI groups (FIG. 2B). A list of genes differentially methylated between subgroups is given in Table 12.

We next clustered the different subgroups of bladder tumors based on all probes that were differentially methylated between two groups with a p value of <0.05, regardless of the log fold change. For clustering of probes differing between NMI-mt and MI tumors, we had to use a p-value <0.5 because not many differences exist between these two groups. We employed a hierarchical clustering algorithm choosing Euclidian distance and complete linkage to organize the three different comparisons (FIG. 3). We then performed principal component analysis on the same data. The probes along with gene names and p-values are listed in Table 12. These semi-supervised analyses showed clearly that the different bladder cancer subgroups can be identified based on their methylation pattern.

Genes Hypermethylated in Bladder Cancer Often are PcG Target Genes

Polycomb group (PcG) proteins function as transcriptional repressors of genes that have been implicated in stem cell self renewal and differentiation. These PcG target genes have been shown to be particularly prone to DNA methylation in cancers [Ohm et al. 2007. Nat Genet 39: 237; Widschwendter M et al. 2007. Nat Genet 39: 157; Schlesinger et al. 2007. Nat Genet 39: 232]. We investigated whether DNA hypermethylation in bladder cancer was more present in PcG target genes by matching our list of 71 genes from Table 10 with recent studies showing that 8-14% of all genes in the genome to be PcG regulated [Bracken et al. 2006. Genes Dev 20: 1123; Lee et al. 2006. Cell 125: 301]. Notably, we found that 63.3% of the hypermethylated genes in bladder cancer were PcG target genes, with a representation factor of more than 3 (http://elegans.uky.edu/MA/progs/representation.stats.html) (FIG. 4A). This was approximately the same for all different tumor subsets. Twenty-two PcG regulated genes were methylated in all three subtypes, while a striking 81 genes were specific to NMI-wt tumors (FIG. 4B). A list of the PcG target genes methylated in bladder cancer is given in Table 8.

Genes Methylated in Blood Compared to Bladder Cancer

We also observed 21 CGIs that were methylated in blood but not in bladder tumors. These are listed in Table 9. We compared our results with a study based on methylated DNA immunoprecipitation (MeDIP), in which the genome-wide methylation pattern in blood was investigated [Rakyan et al. 2008. Genome Res 18: 1518]. We found a 90% correlation with their study.

Validation of Hypermethylation and Markers for Diagnosis and Progression

Next we set out to validate the selected significant CGIs on a custom Illumina platform based on bisulfite conversion of tumor DNA. The following CGIs were included in the custom array:

1) Differential methylation between tumors and blood (Tables 9 and 10);
2) Probes that could be of use as biomarkers to distinguish the subgroups. There were 7 CGIs representing 6 genes found to differentiate between NMI-mt and NMI-wt tumors. In the MI versus NMI-wt comparison, we found 17 CGIs representing 13 genes to be significant. No significant probes were found between the MI versus NMI-mt subgroups at a p-value <0.05. Therefore we decided to include probes from 6 CGIs representing 6 genes with a p-value <0.5;
3) CGIs that were associated with progression and survival. In all cases the CGI to be validated had at least 3 CpGs that were highly methylated.

Figure 5A:
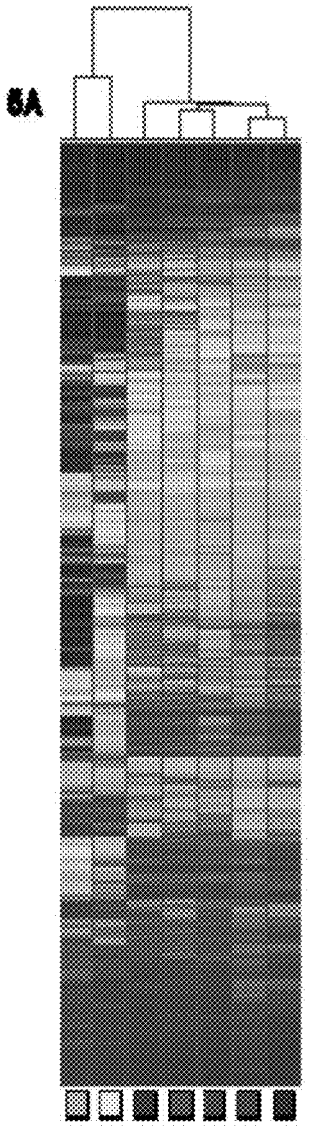
Figure 5B:
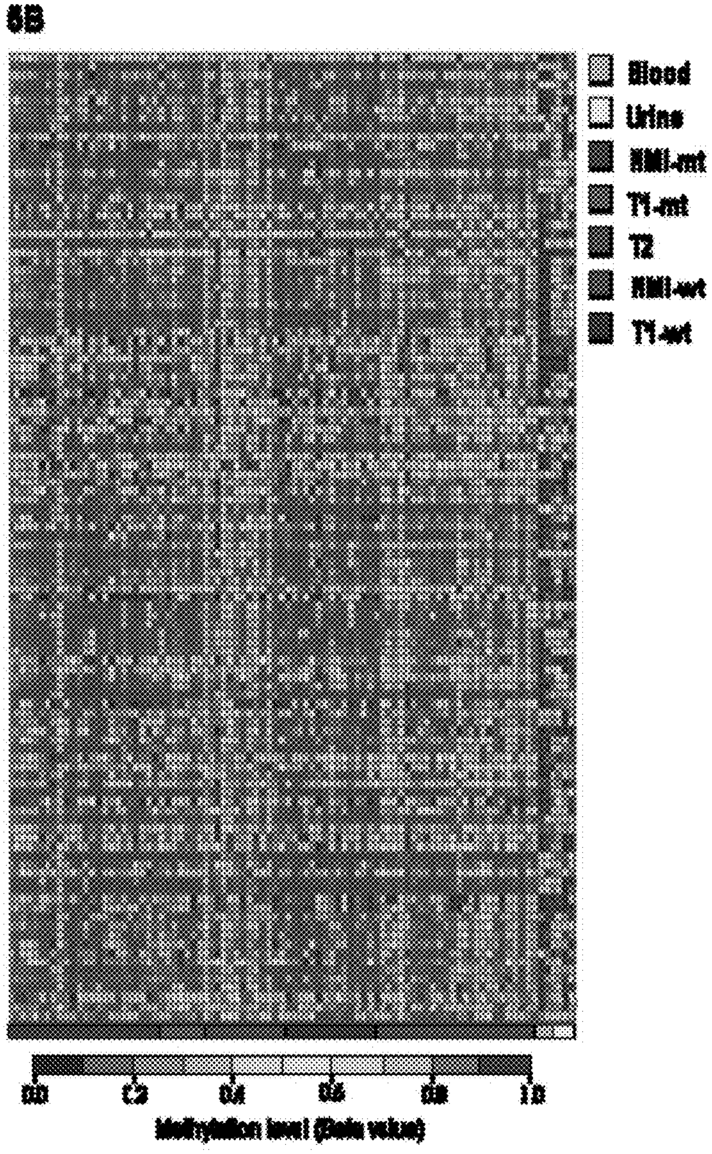

We employed a hierarchical clustering algorithm on the average beta values per subgroup with all 384 probes on the array choosing Euclidian distance and complete linkage. The analysis clearly separated the bladder tumors from normal urine and blood (FIG. 5A). We were able to validate more than 70% of the probes hypermethylated in all bladder tumors. For example, in the custom 384-plex GGMA, there were 205 probes which were methylated in bladder cancer but not in blood based on our Agilent array data. Of these, 147 probes were also methylated in bladder cancer but not in blood in the GGMA. These probes are shown in the heat map (FIG. 5B). We also included DNA isolated from cells present in urine of healthy individuals, which most likely are derived from normal urothelial cells. Eighty % of the probes validated against blood were also not methylated in urine. For the different subgroups of bladder tumors, the number of probes validated varied between 65-75% of probes compared to blood and 76-83% compared to urine.

Figure 5C:
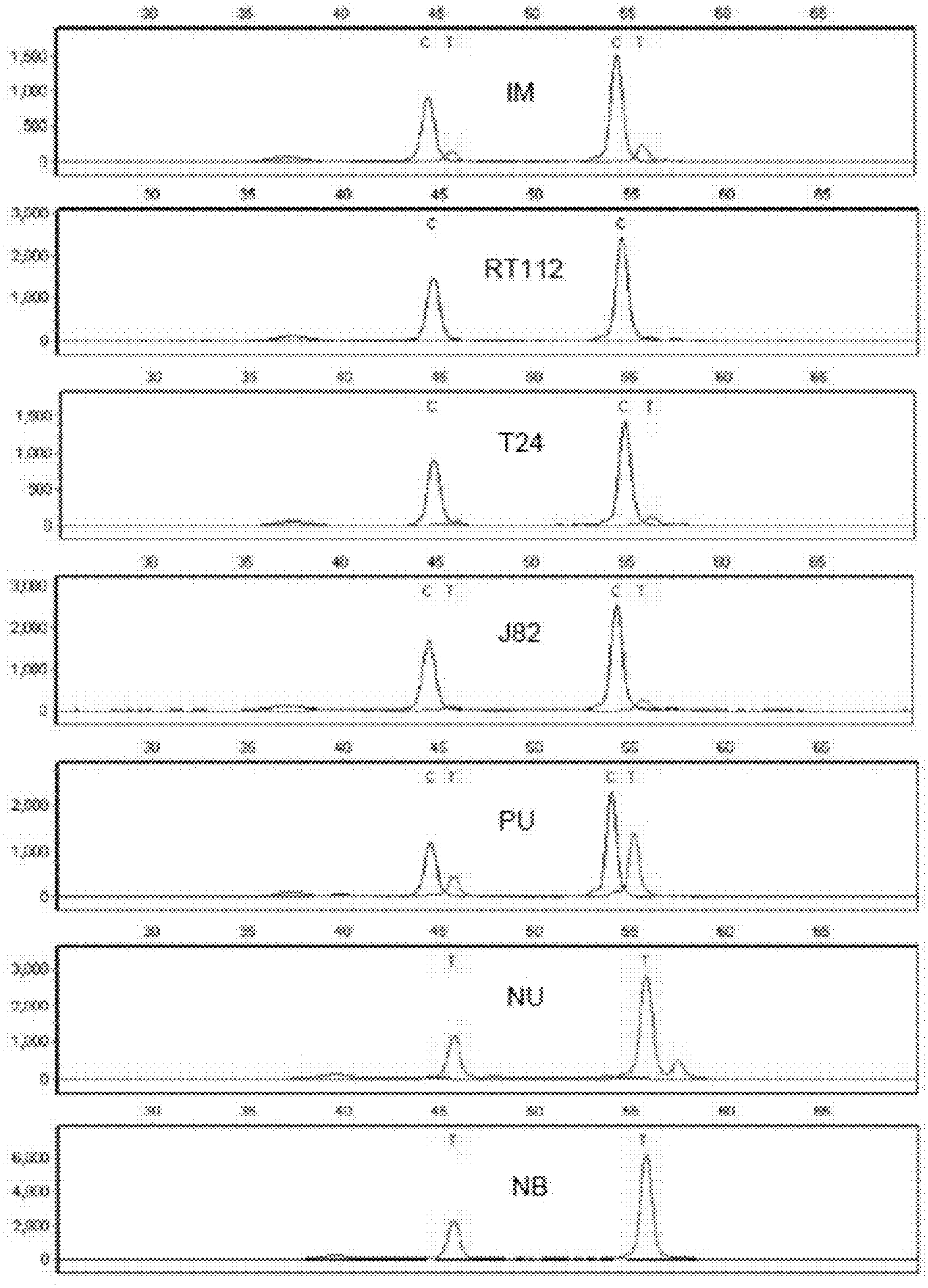

CGIs that are differentially methylated between tumors and urine from non-bladder cancer controls represent potential biomarkers for urine tests (Table 12). We validated several of these using a bisulfite specific PCR followed by a Snapshot assay for the CpG. The results of these analyses are shown in FIG. 5C. We were able to detect methylation in urine DNA quantitatively using this method. We investigated MEIS1 gene methylation at two CpG sites using different probes (MEIS1 A and B). The black peak (Cytosine) represents methylation and red peak (Thymine) represents no methylation. In vitro-methylated DNA (IM), BC patient urine sample (PU) and bladder cancer cell lines (RT112, T24, J82) showed a strong methylation signal while normal urine (NU) and blood DNA (NB) were not methylated.

Figure 5D:
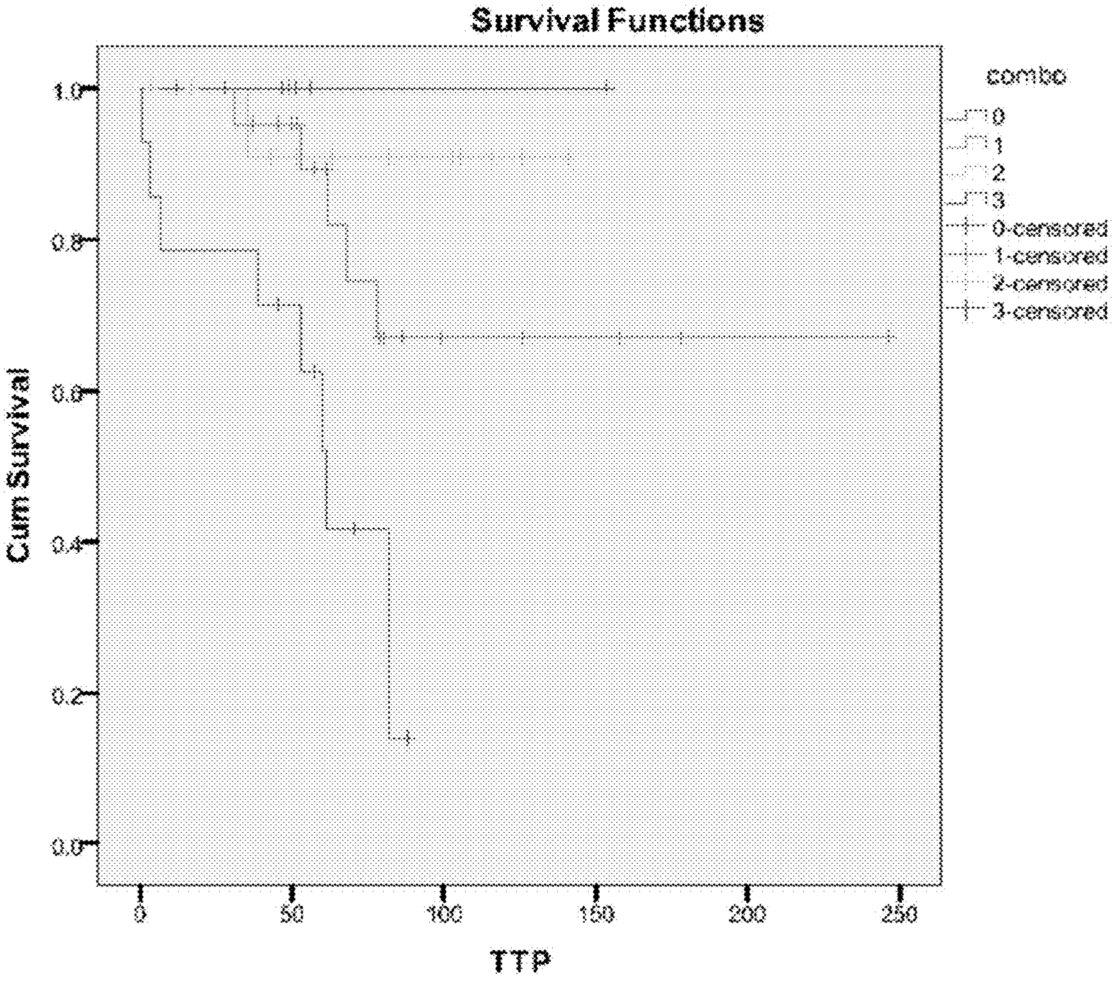

Next we analyzed the CGIs that were included on the GGMA as potential markers for progression. To this end the 6 best CGIs that were methylated in non-progressors vs progressors and similarly, 6 CGIs that were methylated in progressors vs. non-progressors were analyzed separately and in several combinations (Table 12B). The Kaplan-Meier curves depicted in FIG. 5D show that a combination of CGIs in the GPR103, DBC1 and GATA2 genes can significantly predict progression (p=0.001). Interestingly, methylation of the GPR103 and DBC1 CGIs was inversely correlated with progression and methylation of GATA2 was strongly indicative for progression. The DBC1 associated CGI overlaps with the promoter of this gene, whereas the GATA2 and GPR103 CGIs are located in introns.

Discussion

We report an investigation of bladder cancer-associated aberrant DNA methylation. To our knowledge this is the first study that addresses genome-wide methylation in bladder cancer. The major goal of this work was the identification and validation of methylated CGIs that could serve as biomarkers for the early detection of primary and recurrent tumors as well as markers that are predictive of disease course. The genome-wide screen resulted in the selection of 177 CGIs that significantly differed in methylation in tumors when compared to blood. About 70% of these CGIs could be validated in a custom GGMA assay. This analysis also showed that most of these CGIs were not methylated in urine-derived DNA from age matched non-bladder cancer controls. This group of CGIs represents markers for urine based assays. Methylation of some of these markers was confirmed on urine samples. Another important finding is that a combination of CGIs from the GRP103, DBC1 and GATA2 genes is able to predict progression to muscle-invasive disease. Loss of heterozygosity or homozygous deletions of DBC1 (also called DBCCR1) gene (deleted in bladder cancer 1) have been observed in many bladder tumors, as well as methylation of the promoter. Methylation has so far not been correlated to disease course. In our study methylation of the promoter CGI of the DBC1 gene was associated with a decreased risk of progression. The role of the GATA 2 transcription factor in cancer is contradictory. Decreased expression was found to be correlated with proliferation in monocyte progenitors, whereas high expression seems to poise prostate cancers for a more aggressive phenotype and gain-of-function point mutations have been found in chronic myeloid leukemia. In bladder tumors a lower expression of this protein has been observed in MI vs. NMI-BC, which correlates with methylation and the positive association with progression. The GPR103 (QRFPR) gene encodes a G protein-coupled receptor and hence the protein is involved in signal transduction, however, but no further data about the gene or its product can be found in the literature.

Most genes discovered in the present study have never been shown to be methylated in bladder cancer or in other types of cancer. Some of the previously described methylated CGIs in bladder cancer that are associated with the SOX9, CDKN2A, TERT, DAPK1, EDNRB, and LAMB3 genes were also found to be methylated in our study, although only SOX9 and CDKN2A made it to the list of our 177 highly methylated CGIs.

To our surprise we observed that NMI-BCs with a wild-type FGFR3 gene have more methylated CGIs and the intensity of methylation is more profound than in the FGFR3 mutant NMI-BC and MI-BC groups. The difference in methylation presents additional evidence that the two subgroups of NMI-BC develop along different pathogenesis pathways. WT NMI-BCs also have more wide spread chromosomal aberrations than FGFR3 MT NMI-BCs. The extensive methylation in WT NMI-BC is reminiscent of the CpG island methylator phenotype (CIMP) that characterizes a subset of colorectal cancers (CRC). CIMP in CRC also identifies a subset of CRCs as it is associated with BRAF mutations, microsatellite instability and occurs more often in elderly females. No large-scale genome-wide study on DNA methylation has been performed for CRC, however, CIMP has been studied using a 1536-plex GGMA array.

When comparing the genes methylated in this study with those found by us, there was hardly any overlap. This confirms that CGI methylation is tissue and tumor type specific.

In line with previous reports in solid tumors, a high proportion of the genes we find de novo methylated in bladder cancer are repressed by polycomb complexes (PcG) in embryonic stem cells. PcG target genes are as much as 12 times as likely to be silenced by DNA methylation in cancer as non-PcG target genes. The association between DNA methylation and PcG has further been substantiated by the finding of interactions between DNMT1, DNMT3A, DNMT3B and several PcG complex subunits like EZH2 and BMI1. Another recent study showed that 49% of the genes methylated in colon cancer are polycomb targets in embryonic stem cells, agreeing with other reports showing that genes prone to tumor specific hypermethylation in colon cancer were more likely to be marked by H3K27 methylation in normal tissues than genes lacking H3K27 methylation. Another study reported that many genes hypermethylated in a prostate cancer cell line were bound by PcG in normal cells but lost PcG binding upon acquiring DNA methylation in cancer. In this perspective we found that 60% of the hypermethylated genes in bladder cancer are PcG targets in embryonic stem cells. These epigenetic alterations occurring in early development specifically in stem or progenitor cells might be bladder cancer specific and this strengthens the further understanding of bladder cancer tumorigenesis. Besides finding 92 commonly PcG regulated genes in bladder cancer subgroups, a group of 336 genes regulated by PcG complexes are found to be specific to NMI-wt tumors. Besides a possible CIMP phenotype being the cause for the extensive methylation in this group, another possible explanation for this finding could be that the cell from which the WT NMI-BCs originate is more closely related to the embryonic or bladder stem cell than the founder cells of the MT NMI and MI-BCs. In general it is thought that lineage-specific genes are activated during subsequent differentiation steps and during this process the PcG complexes will be replaced by cell fate specific transcription factors. Hence, fewer possible methylation targets will remain after every differentiation step.

Our data clearly shows that adjacent loci within a certain CGI are co-methylated, while neighbouring CGIs of a certain gene can have a very different methylation level. Significant association among the methylation states of adjacent CpG sites and a high frequency of short-range co-methylation was reported previously. Another interesting finding in this study is that our data shows no preference for methylation of CGIs in promoter regions compared to gene bodies, since the location of the significant CGIs is distributed over the genome in accordance to the distribution of CGIs on the array. The effects of promoter methylation on chromatin organization and gene expression have been well documented in various types of cancer. In our study, besides promoter methylation, we found more than 50% of all significant probes to be located in CGIs located within gene bodies. The influence of this on gene expression in not fully known. Previous reports in Arabidopsis have shown that gene body methylation was low in genes transcribed at low levels, higher in highly transcribed genes, and absent in genes that were not transcribed. By comparing our methylation results with gene expression studies, we show that for 70% of our genes there is an inverse correlation with gene expression, suggesting that intragenic methylation also contributes to gene silencing.

In summary we have identified hypermethylated CGIs in bladder cancer. The aberrant DNA methylation in bladder cancer seems to be very selective and could be the first step in tumor initiation, especially for the WT NMI-BCs. The study also illustrates an interesting biological finding: besides the promoter methylation intragenic methylation observed to the same extent in bladder cancer and it also appear to influence the gene expression. Many discovered methylated CGIs represent putative biomarkers for early detection in urine-based assays. The combination of CGIs from the GRP103, DBC1 and GATA2 genes predicts progression to muscle-invasive disease. Thus, the CGIs identified in this study will be of considerable interest for further investigation of their clinical and functional relevance and will provide advance insights into the pathogenesis of bladder cancer.

We claim:

1. A method comprising:
  a. obtaining a nucleic acid sample isolated from a urine cell fraction of a subject at risk of or suffering from non-muscle invasive (NMI) bladder cancer; and
  b. detecting an increased level of methylation of at least one CpG island of ONECUT2 in the sample located between chr18:53259508 and chr 18:53259552.

2. The method of claim 1, wherein detecting comprises detecting the level of methylation of at least three CpG dinucleotides in the at least one CpG island of ONECUT2.

3. A method for diagnosing non-muscle invasive (NMI) bladder cancer in a subject at risk of, or suffering from, NMI bladder cancer comprising:
  a. measuring DNA methylation levels of at least one CpG island in ONECUT2 in a urine sample from the subject;
  b. comparing the level of methylation of the at least one CpG island from the urine sample of the subject to the level of methylation of the at least one CpG sequence of ONECUT2 from a urine sample from a healthy control subject; and
  c. detecting an increase in the level of methylation of the at least one CpG island in the urine sample of the subject relative to the urine sample from the healthy control subject, thereby diagnosing the subject as having NMI bladder cancer and performing a cystoscopy and/or transurethral resection on the subject.

4. The method of claim 3, wherein the step of measuring DNA methylation levels is preceded by the step of extracting DNA from a urine cell fraction obtained from the urine sample.

5. The method of claim 4, wherein the urine cell fraction is obtained by filtration or centrifugation of the urine sample.

6. The method of claim 4, wherein the method further comprises the step of obtaining the cell fraction by filtration or centrifugation of the urine sample.

7. The method of claim 3, wherein the subject is tested for the presence or absence of an FGFR3 gene mutation.

8. A method for predicting the recurrence or progression of a non-muscle invasive (NMI) bladder cancer in a subject at risk of, or suffering from NMI bladder cancer comprising:
  a. measuring DNA methylation levels of at least one CpG island in ONECUT2 in a urine sample from the subject;
  b. comparing the level of methylation of the at least one CpG island from the urine sample of the subject to the level of methylation of the at least one CpG sequence of ONECUT2 from a urine sample from a healthy control subject; and
  c. detecting an increase in the level of methylation of the at least one CpG island in the urine sample of the subject relative to the urine sample from the healthy control subject, whereby an increase in the level of methylation of the at least one CpG island in the urine sample of the subject relative to the urine sample from the healthy control subject indicates that the NMI bladder cancer in the subject is likely to progress or recur and performing a cystoscopy and/or transurethral resection on the subject.

9. The method of claim 8, wherein the urine sample is a urine cell fraction.

10. The method of claim 9, wherein the urine cell fraction is obtained by filtration or centrifugation.

11. The method of claim 8, wherein the subject is tested for the presence or absence of an FGFR3 gene mutation.

12. The method of claim 1, wherein the urine cell fraction is obtained by filtration or centrifugation.

13. The method of claim 3, wherein the at least one CpG island of ONECUT2 is located between chr18:53254153 and chr 18:53259851.

14. The method of claim 3, wherein the at least one CpG island of ONECUT2 is located between chr18:53259508 and chr 18:53259552.

15. The method of claim 1, wherein detecting an increased level of methylation of the at least one CpG island of ONECUT2 comprises treating the nucleic acid sample with sodium bisulfite under conditions whereby unmethylated cytosines are converted to uracil, and methylated cytosines remain unchanged and performing methylation-specific PCR (MSP) on the treated nucleic acid using at least two distinct methylation-specific primer sets for the sequence of ONECUT2.

16. The method of claim 1, wherein detecting an increased level of methylation of the at least one CpG island of ONECUT2 comprises reacting the nucleic acid sample with reagents for detecting the level of methylation of at least one CpG island of ONECUT2 and performing a polymerase chain reaction (PCR).

17. A method comprising:

a. obtaining a nucleic acid sample isolated from a bladder biopsy of a subject at risk of or suffering from non-muscle invasive (NMI) bladder cancer; and b. detecting an increased level of methylation of at least one CpG island of ONECUT2 in the sample located between chr18:53259508 and chr 18:53259552.

18. The method of claim 17, wherein detecting an increased level of methylation comprises treating the nucleic acid sample with sodium bisulfite under conditions whereby unmethylated cytosines are converted to uracil, and methylated cytosines remain unchanged and performing methylation-specific PCR (MSP) on the treated nucleic acid using at least two distinct methylation-specific primer sets for the sequence of ONECUT2.

19. The method of claim 17, wherein detecting an increased level of methylation of the at least one CpG island of ONECUT2 comprises reacting the nucleic acid sample with reagents for detecting the level of methylation of at least one CpG island of ONECUT2 and performing a polymerase chain reaction (PCR).

* * * * *

SEQUENCE LISTING

<160> NUMBER OF SEQ ID NOS: 329

<210> SEQ ID NO 1
<211> LENGTH: 550
<212> TYPE: DNA
<213> ORGANISM: Homo sapiens

<400> SEQUENCE: 1
cggatgtgcg tggactctgc gggcggggcg cccgtagtct ccctccttcg caccccgggc 60
gcctgggaac ctcctcgcgc gtttggccac tcgctgctcc tggcagtagg ggcttcgggc 120
cccgccgtgt ccccacccag gtatggggat gcggagttga tgggtgcggg gcgctgggag 180
ggggcagatg aaaggggcag tcgaaagggg gccatgcgcg ccgagcgcag ccgggtcatt 240
agccgcgggt gtgagcggcg gggcaggctt atcgcccatc caggcctggc gggcgggcgg 300
tccccgacgc ggctgccgcc gccgcccgcg gcagagggca cggcggttcc cacgctcggg 360
ccctggttcg ggggcgttct cgggacggcg tggccgcgct caccaccacc gcggaggccg 420
ggctgtaatt aggataattg cgctgctccc agcctggggc agctcaggac ccggctgcac 480
cgcgctggcc cgggacgggc gggggcaggg ggtggcgggg cccgagcgat acagcccctg 540
gcgcagtccg 550

<210> SEQ ID NO 2
<211> LENGTH: 1209
<212> TYPE: DNA
<213> ORGANISM: Homo sapiens

<400> SEQUENCE: 2
cgcccagacc ggccgtggcg gggccccggc gccacgtgct gctcatggcc accacgcgca 60
ccggctcctc gttcgtgggc gagttcttca accagcaggg caacatcttc tacctcttcg 120
agccgcttgg cacatcgagc gcacagtgtc cttcgagccg gggggcgcca acgccgcggg 180
ctcggccctg gtgtaccgcg acgtgctcaa gcagctcttc ctgtgcgacc tgtacgtgct 240
ggagcacttc atcacgccgc tgcccgagga ccacctgact cagttcatgt tccgccgggc 300
tccagccgct ccctgtgcga ggaccccgtc tgtacgccct tcgtcaagaa ggtcttcgag 360
aagtaccact gcaagaaccg ccgctgcggc cccctcaacg tgacgctggc cgcagaggcc 420
tgccgccgca aggagcacat ggccctcaag gcggtgcgca tccggcagct gagttcctgc 480
agccgctggc cgaggacccc cgcctggacc tgcgcgtcat ccagctggtg cgcgaccccc 540
gggccgtgct ggcctcgcgc atggtggcct tcgccggcaa gtataagacc tggaagaagt 600
ggctggacga cgagggccag gacggcctga gggaagagga ggtcagcggc tgcggggcaa 660
ctgcgagagc atccgcctgt ccgcggagct ggggctgcgg cagcccgcct ggctgcgggg 720
ccgctacatg ctggtgcgct acgaggacgt ggcacgcggg ccgctgcaga aggcccgcga 780
gatgtaccgc ttcgccggca tccccctgac cccgcggtgg aagactggat ccaaaagaac 840
acgcaggcgg cccacgacgg cagcggcatc tactccacgc agaagaactc ctcggagcag 900
ttcgagaagt ggcgcttcag catgcccttc aagctggccc aggtggtgca ggccgcctgc 960
ggccctgcca tgcgcctctt cggctacaac tggcgcggga cgccgccgcc ctcaccaacc 1020
gctcagtcag cctgctggag gagaggggca ccttctgggt cacgtagggg ggccggggcc 1080
ccgtatgccc ctcctcgtga aaggcctgcc ccgtctttct gccgcagccc tcgcagaggg 1140
cgggtgcaca gcgccatgac gggcagcgcc tcctgtagca gtagggcccc cagccagcgc 1200
tccagccaa 1209

<210> SEQ ID NO 3
<211> LENGTH: 316
<212> TYPE: DNA
<213> ORGANISM: Homo sapiens

<400> SEQUENCE: 3
cggggtcctc acggctcccg caggcagccg gcccctgctg ctgtcttcaa acagcctccc 60
gggggaccgc tctctccgcg tgctgagcat ccggccgggg gacttctctc gctccagggg 120
gcggccagag acttgtccct gcgcagctcg gtccgcccct cgcggtagcg gtggggtgtg 180
cttggctctc gcgggtggct ggggccttcg ggcggcgctg ggctggaggc cacgcgcttg 240
gtgatgtgct cgttgtacgt gggtgggcct cgcttgttgg ggctgctggc gacacaagag 300
aacgtaggga gctgcg 316

<210> SEQ ID NO 4
<211> LENGTH: 1209
<212> TYPE: DNA

<213> ORGANISM: Homo sapiens

<400> SEQUENCE: 4
cgagaggacc cggaccccgg cggggaaggg cgccctcccc cggcctcgcg gccgccccaa 60
agcacatccc cttctgccgg ccccaagtcc ccgcgcgtcc acggcgcccc tgtgcccacg 120
ggagagcacc cccgcccaga tggaaaaggg ggtagaccgg gcagagcgag aggcggcttt 180
ggctcgtggg gagcggcgac ccaacccagc gcgcatcccg caagccctcc cggctgcccc 240
ggaccttccc cctcgctacc tcggaacagg gtctgcccgg gggctgctgc acaaagaggg 300
gtggtcgagg gagacgccaa atcgttaaga cggggagccc gtttcggcca tcttggaaga 360
gaggaaaggg aaaaagggac agaaaaaagg gagaaagaaa ggcggacggg gcaagctggg 420
ctagggactg acggggcgcg gggggtgcga aggcaggatc ggctcagagc ccccctccc 480 atcggggctt gcgaagaacg gccggccccc atcccaatcc ccagagggtt acaggccagg 540
agagggaaag gcagggggag tccgctccgc ttacctgggt tcggggtccg gtgggtctcg 600
gggagggggg gatgggaggg agggagggaa gggaggggag ggggccgcag ccgtgtcgct 660
cgcccgggcg gcgggagggg agaaacctac ggtaagaaag gagtttgtga aagcggcttg 720
gggtgggagg gagaggggag gggaggggac cgagggggga ggggagggac cggagtgtgg 780
gggggagaca aaatggcttt tttcctccag acaaggtagg tcccgcccac cactcaccca 840
cgtgacctca ttccttcagg atgctggcag agacgggaag aggaggggga ggctggcgcg 900
gccgctcccc gccaccggct gccgggtccc tagccaggac gagacccctc ccttcccatg 960
cggccgcccc gaccccggag gatggatctc ttatgttacc ttccgcagtt agccccctc 1020 ccttcaaaat atgggttccc cccactgaca ctgtgatgcc catccctaac tggggcgcct 1080
ggaaaatggt gaaatgggga ctgggctgaa aggtggctcg tggtcctcca cgccccggcc 1140
tagaccaaag ggcgcggggt ccggcggggg acgcgacgcc ttcagccagg cgtccgagcg 1200
attttcatt 1209

<210> SEQ ID NO 5
<211> LENGTH: 1209
<212> TYPE: DNA
<213> ORGANISM: Homo sapiens

<400> SEQUENCE: 5
cggaggcggc acagctggag cccggattgt ggcacgccgt caccgtgctg ctccggggaa 60
tcccgacccg ctccctgcga aagcgtttcc gaacgcgaac ccagagcctg tgaacgcgcc 120
ggcaagcccc cactccccca ccgccgcccg tcgcaggtgg gcccgtccta ggggtccttc 180
ctgcgctcta ccccgtctct caagtcactc agtcgatcgc cccgttcacg ctcccgtgat 240
cccagacatc cataaccacg atctcgcctc catgcacatc caacgcacga cggtgcacaa 300
cgtgcacctg acttctgcgg accaggtgtc tcaagcgtac agcggccacc cgcggaaccg 360
cggcccgggg ccagtgagtc gtctgcagct ccccgggtta ggggattccc cagaactccg 420
ggaaagtcac ccgaagtcca tccgggatgc ggccttggtt ctcggccgcg tatctcgccc 480
ttaggtgcag aacgacgccc ttccagggcc cacagctgcc aggctgggcc ttgccctcgc 540
atcccccggg aagaccaggg acggggccac acaggccgtg gctgcggaga cgcttccccg 600
ggccaccccg cgaccaggag ggagtcgagc cgcccgctct cccgcgtccc ccgccccatc 660
ccagccagtt ggccccaccc tgcgcgggat aattgggacg ggagggaggc gacgggaggg 720
cggcggctcc agagagactg cgcgcctgtc agcggcaatt tgtttaagtg gacgggacgg 780
gccgggccgc tgcgggctgg ggtcaccgag gccgcgcccc caccccaacc agacctggga 840
ccgcggggga gcccggtccg gccgctaaac cgggctggct ggcgccaggg ctccgggagg 900
tgcggtccgg cggggaagcc gtgatgggaa gcgactctgt ccagggagtg tccttcacca 960
ccacactcct cacgtccagg cagtgatgac ggcctggcgg caccctcaca gcgggcccat 1020
agcacggggc cacacacgtc ccctgagctt agcctgggca cattcgtctg ccaccgaggg 1080
cttaagccag tctgcagccc gcgccccgtc actcggacgc aagtccgtcg tccgctctgc 1140
cacgcggccg cacagcccgg cttcctgctg cccactgccc gcggggtcac gcaaccccgg 1200
ccctgcaca 1209

<210> SEQ ID NO 6
<211> LENGTH: 688
<212> TYPE: DNA
<213> ORGANISM: Homo sapiens

<400> SEQUENCE: 6
cgatttccgc agatttcctg ctggaacgtt ctctcgggcc tcaagttttc ctgagaggac 60
gacgtggaga gtggagacaa agatgctcaa aagccaggaa atcgcaggct cggaagcccc 120
cacgcatcct ctgaacgcag cgccatctcg gggctgcggc gggaccaagc gggacgcttg 180
caggctgtcg gcggcggggg ccgcgagccg ccggcgtagg ccgctccagc tggaagaccc 240
caccgctagg gttccagggg gctgcggacg cttccgaggg gcccaaggcg aaagaacgcg 300
cccgcttgtc ggccacgtga ccgtccccgt ccgcgtccgc agcgaccacg tgactgtgcg 360
tccgcggcgt cgattgactg ggagctccct ggccacgccc taagcgccag ccccgggctt 420
cggggggcgg tgctgctgcg gttgccatgg cgtcttccga gcgcgcaggc ggggcccaga 480
gtagcttttc gggtatttgc taccggctct cggtagggct ggtcaccttt gcttgctgag 540
cttcgcgccc tgcgtccttt ggtccccagc aacttgcagg gcagccgtcc ctcatgaggc 600
cctccagcga atgccctaaa gctccgaagt tgctccggag gaaacaggct tgctccgagg 660
gtgcacgtcc ttactgcccg tgacgtcg 688

<210> SEQ ID NO 7
<211> LENGTH: 511
<212> TYPE: DNA
<213> ORGANISM: Homo sapiens

<400> SEQUENCE: 7
ctgctgcact tgtaaagtgg gtgcttctca gcttcatggt ttgaggggtg cagccagctt 60
cggcctaagt ggtgttgagg gtcgaggacc cagcaccccc acacgggaag cgcggtgtcc 120
cgccttcagg ctggagtact ctggcaccct ctggggtccc gaagtgcctg agtacctgtt 180
tgagccgcgt gtaggtgact gcgcacctgt ttgaactgcg tgtaggtgac cgcgcacctg 240
tttgagctgc ctgtagctga ccgggcacct gtttgagctg cctgtaggtg accgcgcact 300
gtttgagctg cctgtaggtg actgggcacc cgtttgagct gcctgtaggt gaccgcgcac 360
ccgtttgagc tgcctgtagg tgaccgggca cccgtttgag ctgcctgtag gtgaccgggc 420
acccgtttga gctgcctgta ggtgactggg cacccgtttg agctgcctgt agtgaccgcg 480
cacccgcttg agctgcctgt agctgaccgc g 511

<210> SEQ ID NO 8
<211> LENGTH: 1078
<212> TYPE: DNA

<213> ORGANISM: Homo sapiens

<400> SEQUENCE: 8

```
cgcgttgtag gggtagccgt agtaggccag tgtgtagggg tcgcaggagt acacgtagct     60
gggctgctgc gctgcctcag ccgcgccgcc gcccctggct gccttctggt agcgcgagta    120
ctgctcctgt ccacgggctt ggccagcgtg acctccaggc acgagccctc cagctcagtg    180
ccgttgaggt tgttcatggc atgcacggca tcctcgcggc tggtgaagtg cacgaaggcg    240
tagtcgcgga tcttcttgac gcgctccacg cagccggggt tgaactggcc gaagctcttt    300
tgatggtgtc ctcggtggtc tcgatcatga ggttgcgcac gtagaggatc ttcacggtct    360
ccatcacgtc ctcgtccacg tcgatctcag gttcggccca gtccacggcg atctggtggc    420
cccacagctg gatgcggcca ggcatgagct tgcggcgagc catggcagcc ggcggtggct    480
ctcgtactcc acgaaggcga agccgcggtt cttcatcttg tcggccgcgc tggcgtagac    540
gatcacgtcc agcacgccct cggtgacctt ggcaatctcc tccaggattt cctcgcgctt    600
cttcatcttg gggatcccgc cgatgaagag gcggcagttg tcccgctgca gcacacgccg    660
agcaggcggc ccgggcggat ctcgtagttg ttgagctcac gcactgcgcg cttggcctcg    720
tgcttgtggc agtacatgac gaaggcgtag ccgcggttct tgccgtcaaa gtccatcatg    780
aggcgcagct cgtagatgcg gcccacggcc tcgaaacggg caccagctcg tcctcgtaca    840
cgtcgcgcgg gatcttgccc acgaagacct cgcagccacg ctgcgggtgc gggccctccc    900
agccgggcgg tgggccgccg tacttgcgct gcccgttctc ttgcaccatg ctgtagcccg    960
tgcgctccat cagcgccagc agtgctgctc gttgggcgcg cccgccacgc cctcgggcac   1020
cttggcggag gacccggcgg ccgagtcact gctcatggct gcggtggaat cctctgcg     1078
```

<210> SEQ ID NO 9
<211> LENGTH: 1167
<212> TYPE: DNA
<213> ORGANISM: Homo sapiens

<400> SEQUENCE: 9

```
aagtctggag ataattatgt cgtacagtcg caaacattat tccgttctta ctgtaaacgg     60
ccccggccac ctttacgaga aaccaggaaa cttctgagag ttactagcag cgtttacgcg    120
ggcaaacgag ttctttttct ttctctcccg gattgttcga agtatctatc gggcggcttc    180
gatgccaggt tcagaggcgc gccagggaga gggcgccccg cagaggagcg cagcggagag    240
gcctacgcag gtccccggtg cccgcggccc tcggaggccg ggccctgcgt cttggccagc    300
actgggtggc agctgaggct ggtggcccgg agccctcgcg gccgcgggca ggccccttct    360
tgggcagggt cgggcactcc cgctgtccag ggctcttcgg caccctcctt ccaatcaggt    420
cgctctcccc tgctccccag actcaactcc tccgaagctg ctccaggttg aatgtgaccg    480
ctaggccgac tccctgggcc cgcgagcagt tctcgaaagg tgcggactga gccctttctg    540
gggtggggtg cgggttggtt ctcgcaagtg tgacccaggg tgaacttgct atttcgggtc    600
ccgggtgctg cagggccagg agaacagctg ggatggggga ccccgcctcc accctcgggc    660
cggcacgtcc gcgccctgtc aggtccccct ccctcctcta tgatggccaa ggcgtgcgcc    720
agggctatcc gggaaccttg taaggcctcg tgctggcacc taaccccact cgcggcacac    780
ttcctctatg tagtctgcgg ccccgcctgc caaatagagt gaccagtgca gggacagaat    840
gccaggctgg tggccgaccg cctgagggac aaaggcgagc attcacaagc caacagcaga    900
cccctgcccc ccatatttcc atttcgctca ggcttttagg acaaaatcaa caaggccgca    960
```

```
gagtggtgca ggcgctcacc ccgggtgcag cctggggagc cactggttcc gcgaccctgg   1020

gcatgaaact cctcaagggc ggccctcgag acgcagggga gaggatgctg ccggcgcctg   1080

cccgagggct tctctgcggg aagcgggcag gcaccccacc ggagtcattg ccgggaccct   1140

cagcgcaacg cgggcctgtt cctctcg                                       1167
```

<210> SEQ ID NO 10
<211> LENGTH: 751
<212> TYPE: DNA
<213> ORGANISM: Homo sapiens

<400> SEQUENCE: 10

```
cggagatggc gcgtctggat tcagggagat cgtgcggcca gcttccctcc ctctgctctg     60

gatgggggcc ggccgccgcc gctcactcac ggctctctct ctcccgctgt gcctgcaggt    120

gtggccgcga cgatgccctc gctgaggagc gcatgcggag aggccagaac gccctgccag    180

cccagcctgc cggcctccgc ccgccgaagc cgccccggcc tgcctcgctg ctgagacacg    240

cgcctcactg tctctctgag gaggagggcg agcaggaccg acctcgggca cccgggcccg    300

ggaccccctc gcgtccgcag caggtgtgca aagggaggca gccgtggagc aggcgcagag    360

tgagacttct ctgggtgcca gaggacagcg aggacacaaa ccgcgcctgg gctgctgtgt    420

tctgacctga gcgggcgtgg gcggtcgggc ggggcgggag gaggtagcct cctctgctcc    480

tctcccgctc gcggcgcccc acgccacggt ggctccgggc cccccaccgt taaaacgggg    540

tccgcgtgtc ctgtacgcag cgtgttgctc cgcaaaggat gacagagctg ccacggcagt    600

gcgaggtgct gcttttaccg tagacgtgcc ttttcgtagc tttagcgtag agcttgaggc    660

ctgtggctta ggccgggtgg tctcgtgctg gtggggtctg cgtttgcccc tgcccctccg    720

tcagcttcac cttctcgtgc cttcttctgc g                                   751
```

<210> SEQ ID NO 11
<211> LENGTH: 734
<212> TYPE: DNA
<213> ORGANISM: Homo sapiens

<400> SEQUENCE: 11

```
cgtaacgggc gtgggtcgtc cgtcgcgccg cccggcgagg agtgggctgg cggcggtagc     60

tgtcgcccgc ttggttgcgt gaccgcgggg tccgcgtccg ctccctccac ccttcgccct    120

tcgccctcgc ctcgttccgg cctccgcggc ccagcaacgg ccgtcatggt gccgtcggcg    180

ctccctgcgc ggccccgctg agcctcggtg cggcggcgag cgcggtcgag atcgccatgc    240

ctacccgtga gtggccggcc gagggccggg ggcgttggga ggcgactgcc tgcgcgacgg    300

cttgggccgg gtactcctcc cgggcggctg gggaggctgg gccgcgctga gcagagccag    360

gaagtgtctg cgagcggcgg agttagtttc gtttcggctt agccttccgg agatggcgtg    420

agcccgttgc acggatcggg aaactgaggc ccgaacgtta agggaactgc gggacgcgct    480

gttaggaggc ggcagagctg gtggtaacct gacccgtggg atttcaaagt taaagccctt    540

ttcccacggc cacacggctt cgtgggactt tatggaaata ttgaaaataa ctgcggtacc    600

attgtcagtc ccttctcacc tcgggccgga cgtcgctagt ggagcgccgg ccccgagtcc    660

cttcccgcgg ccgccagaca gacccccgac agcctaactc ggcgtccgta tcgccgtcgg    720

ggcggctgaa gtcg                                                      734
```

<210> SEQ ID NO 12

<211> LENGTH: 279
<212> TYPE: DNA
<213> ORGANISM: Homo sapiens

<400> SEQUENCE: 12
cggaggcacg aaccaagcag cctagaagac aaatgcgctg ctcggagaga ctgccgcggc 60
aaccaactgg acaccccaag agctcactcc tccgcggttt tatattccga cttgcgcaca 120
ggagcgggtg cgggggcgca gggagtgtgg gtaacaggca tagattccgc ttgcgcaata 180
cgtggtaaga aaccagctgt gaggggctgg cccaacgcag agcggcgcga ggtccgcttg 240
gcatctacaa caatcgaggg gctagtccag aagttcaag 279

<210> SEQ ID NO 13
<211> LENGTH: 1209
<212> TYPE: DNA
<213> ORGANISM: Homo sapiens

<400> SEQUENCE: 13
gctcagctag taagtgagga gctcagctct gaagctgtaa ccaagaccgc gcgggcagga 60
ggaaaggaca cttcagcgct ctgcggttgc aaacacaccc ctgcgggtgc tgccacttag 120
caaagtctag gttcccgctt actcgcacac gcatcctgac ttcccccaac cctggaacta 180
cctaccagga gcggagacca gcagaccgac agcacgcaca tgatccccat aagctgaatg 240
gccgtctcgg tcgtgatgcg gccccactgg gcactggact gagatgccgt ggccttggcc 300
ggcagcggga caccagggcc ttaatggtgg ccaggttgca ggaaaaggtg actgtcagcg 360
ccaagagccc caggaaggca aaggcagagg cgaagaaaag gttgccccag ttatgcgaag 420
agctagtccc gttgcccccct cgcccggtgc tgatgaagca ccacgtcccg gccactggac 480
ggtgtactgg cccacgccca gcaccggcag cagggcgaag gcgagcacgg ccagccacac 540
gccgagcagc acagcgcggg tggcacgcgt cttcatgtgg ctcgcatacc agtgcggcgc 600
cctgatggcc agcgcccgct cgacggccat ggcgctggcg atgacaacga ggagagcccg 660
aaaacagtca tggtcagccc gaaaaaggtg cagagccgcc ccgacgggtc gatgtgctcc 720
caacgctgct tggacaggta cacgacgatg acgaccgggg tggtgagaag ctgcccgacc 780
aggtcggtga gcgccagcca gccgatgcac agcagaagga cttcttgcgc ttgctctccc 840
ggcgccggta gctgcgcgac acgagcagca tggccagtgc gttgcccacg aaaccagtga 900
gcagcatggt gatcgggaag gccacggaca ccgatccgca atcctcgcca gaccctggag 960
ggcgcgtgag gttgccccgc gcctcgggga acgctcgggc gcccacatgc ctgtgtagga 1020
gtggttgagg cgggtgcaga agggggcatc ccctccgtag ccccgggtct ccttcatgtt 1080
ggcttcgagg tgaggagggg atggcgtcca gagagccgca gcgggagggg gcagacgcgg 1140
cgcgggcggc ggcggaggtg gcgtttaccg cggctggggc tgggctgccc cccatggtgc 1200
ggggcgcag 1209

<210> SEQ ID NO 14
<211> LENGTH: 235
<212> TYPE: DNA
<213> ORGANISM: Homo sapiens

<400> SEQUENCE: 14
attcttaatt cccacacctc ttcccaagtt acgccaccgg tcgaggacgg caggagaccc 60
ccgagtgcag agaaagctca aaccggcagc gaagtcggtc ctagccaagc tgaaaaaacg 120
tctcggattc gcggacagcg gcctagacac agcccgatct tccagtccta gtgccctggt 180
cgagacggtt ctatcctttt gcaaagaagc cggaaagagc tgggtcccgg gggcg 235

<210> SEQ ID NO 15
<211> LENGTH: 1209
<212> TYPE: DNA
<213> ORGANISM: Homo sapiens

<400> SEQUENCE: 15
cggggtgggc ttcccgcgcc tgcagcccgg aggcgtcgag cgcctgatgg agcgtcagag 60
gagacctcgt cccagcgttg ggccttctgt tgtatttctg ccagaaactc gcgttgagga 120
gaatttgttt aagcgtttct ctacctgtcc atgcatctcg taaatacagt aagcatggca 180
agccctttcg ctggttaacc ccggcgtccg tgtgctcact gccgccctgc acgcacgagg 240
tcgcggatgg ttcaaagcac ccgcggtggc agccggagag gcagagcggg ctctagggac 300
taagacaggg ccgagctgga cgactggtgg cagggcggcc ggggaggccc cgccgcgggg 360
aggtttgggc cccctaccct gcggaactgg aggcaagtgc ggactccggc tgcaggccgc 420
ggtctgcggg gacgcgcgcg gggggcctgc gtcccgccac ctccgcgcac acccctggtc 480
cccttcccca gcccgggccg gcgccgcccg ccgcgtgact cgcgcgttcc gggccgagta 540
cgggctgtcc cttggcccag cctcagccag acgcggggga gagagagcag gggctgggaa 600
gtgccggcag gaaaggaatt ggccagggga aagaggagga ggagatagat ggagtcatcg 660
gttacggagc gcgctccgtc cggcggagcg aagccgggga ccgagagcgc gcaaggcgaa 720
gacacagcga cgcagccccg tccccggcct ccggaccgcc tgccccgctc ggccccggct 780
cggctccgcc ccgcccctgg gtccgaacgg aggaggagga ggacacgagc cgcgcgggct 840
tggaacccac gaagacccgc aaacccaggg cgccgccgtc tccgaccacc tgctgccgcg 900
gcaggccatc agcagaattt atacccaggg cgcgagcccg ccacggctgg gcggaggcgg 960
aggcggaggc ggggaggggg ggggggtccg gcttgcgagg ccccgccccg ctccctgccg 1020
ccccgccccc ctccgccccg ccggcctcac tcggggcgcc gggaccccca ctccctccgg 1080
ggtcggctgc ccgccgccgg gttgggggat gtgccgaagg gcgggcctcc ctgcggaaag 1140
cgacgtcacg gccgctcctc agtgtgaatg aatcaaaacg cccgggtgac cgcggcctcc 1200
cgggcggcc 1209

<210> SEQ ID NO 16
<211> LENGTH: 313
<212> TYPE: DNA
<213> ORGANISM: Homo sapiens

<400> SEQUENCE: 16
aaaccactct gaaagaactg tgagaccttt gcactaagac cattagggat tctacgcaag 60
gttctctctg ctccttgcaa aattacaggc gtcatgaagg atggcggctc gtaaatcgaa 120
gcctttgaac aggggctcac cgtccggcgg catcaacacc ttgttgttct gtgtgcacca 180
ccccacgggg tgcaaatccg cgatgactac gtcacaccag aagtcggccc tgcggtcctc 240
cccgtaaccg cagtagcgca gaagcagcag ctgcccgcac gtggtaatga tcgtggccac 300
cagtacgtgt ccg 313

<210> SEQ ID NO 17
<211> LENGTH: 1209
<212> TYPE: DNA

<213> ORGANISM: Homo sapiens

<400> SEQUENCE: 17

```
cggcaaccga gccagatcca agaggggtcg gcctcgtcta aattggtttc ccaccaatgg      60
cctcggatca gccgcggctg tgctgcggga gccctcagga cgcggctggg gttggtgcgc     120
ggggcccgga accccaaacc cggctcggtt cggcaaggtt cagggagaca aggtagagaa     180
ggctggggtg agcgagaagt cgggcggccg atcgtcaggg ccacgagcct cgccttgcct     240
tcttggaatc ccacccaact ttaaaggccc aaagatcctg aaaattccga aagcgaaacg     300
cgagctggtc tccagaagtt tgagaacggt ctcccaggct ttccagcgtc gtcccgggat     360
tctcggacac cacaaacgcc atcaaccacg agcaccggtg tccgtggcta ttgccccgaa     420
tggtccccat ccgcgtcccc gggaactccc tcggcttttc gcgcatccag gccccagccc     480
cagctactgg tgcgccccga gcccctaggt gccagagcgg tggtcggccg ggctcctgcc     540
cagtctcggc tcctccctcc tccccaccag aaggaaaaac ttgggccctt cgagaaccct     600
gtggaatgtt ctttgtaatc aactgtacat ccgcttccac ggccggcctc gtgcaaaatc     660
gcgggtttcg gggccttgga gcaaattgcg cttgtcagcg gcgacgtcag gaggacaagg     720
ggaggggttc gcggctgaaa ctgcagcttc gcagcacaga gccattttag gctgctcccc     780
acctcgcggg gcccatggga aagccggccc cgggaggcgc gcccaaacgc aggctggagg     840
agccacggac gcgtcctggc cggcgtgtcg ccatcgttca gcctcgctgc ccaggtggga     900
ggggtcacct gccgcggggt ctccaagcca gtgccgcttg ctcccggccc ccacccactg     960
acagcacggc gtccgagtga ccctgtcagc ctcgttctgc gctcctgcaa accacgttgc    1020
tgcgctaact acaaacctgg ccaacatgtc tttgtaaccc tatcatttaa aaacgcttcc    1080
aggcacctgg ccgctgccag atcaggttcg cgggcccgga ggaggtcctc ccacctgccc    1140
ccgccagccc cggggaccgg cgcggcctcc gtgtggcccc cgcccacgag gtccctcggg    1200
caggaaccg                                                            1209
```

<210> SEQ ID NO 18
<211> LENGTH: 630
<212> TYPE: DNA
<213> ORGANISM: Homo sapiens

<400> SEQUENCE: 18

```
cggaaaaact cgaatgtcgc cctgccgttc ctggggttgg tgacaggtct ggtcatcgca      60
cggcggcagc tcctcacctg gatttagaag agctggcgtc cccgcccgcc caagccttta     120
aactctctct gccagaaccc gccaactctc cagggtacaa agtacagcag ggacgcgggt     180
ggagcccttc caagcggcgc agccttatct ttcccgagtg aacacctagg tggattccca     240
acaccgcgcc tggcacgttt ctggagggag tctcaagctc ctccagagct cccagctgcc     300
gtcctcgttt ctgcagtcga tattcctgtg ggagacacgg ggggctctga gcgctacgag     360
ctttattaag agatttgcga atggttcact caggtccctg aacactccca atagcctaag     420
ctgcctgctg tgttatagcg cagaagcccc taacgcacgg tggttgtcct tcttctcata     480
acgctcgcag cttagggcca gtttccgcga ttctaagagt aattgcgtgg gcacctgtgc     540
tggggccagg cgcaaagaag ggagttggtc tgcgcgaaga tcgtcaacct gctaacagac     600
cgcacatgca ctttgcaccg accatctacg                                      630
```

<210> SEQ ID NO 19
<211> LENGTH: 272

<212> TYPE: DNA
<213> ORGANISM: Homo sapiens

<400> SEQUENCE: 19
cggtaaagat cccgcatgta gtccggaatg acggcactct tgctaggctg cgggcggcgg 60
cgcagcccaa acatctgcag aagtgtcgcc tcgaagtccc gcaggagctc atggctctgc 120
cctgagcgcg tcctcccgcg tggccctgaa tctcggcgac ttttttcttc cccgtctcag 180
gtatcaaact agcatggctc gcgcctccta gcaggacttg gcataataaa acgaccatca 240
gcattcggtt accaggaatc atggtgtctc tg 272

<210> SEQ ID NO 20
<211> LENGTH: 1209
<212> TYPE: DNA
<213> ORGANISM: Homo sapiens

<400> SEQUENCE: 20
cgcgaggatg ggcgggctcc acgtctgggg gcgctgtgag cagggccaga gcgaaacctc 60
agtctgagtt tacgaactgg gaaggagcct gaaccccaga aacaccgtta acaaagaggg 120
cgaacgcagg gagccgagga gacgtctcct tggcctctgg ggaaggggct ggaggagcga 180
gccagctgag aagcggcttt gccgggtgtc cactagcggt tcgccagccc tctgtgcgcc 240
cgcagagtga cgcagaggcc gacacagtcc cctccccact cgcccctggg gcgccgccga 300
ccttgatcac cccccttcgcg gagggaactc ccaaggcgcg gcgctggccg ctgggtccgc 360
atggcccagt cctgtcgggc tccgctctgc tgccgccgag cttcgaaggt gtgcagtgtt 420
gagccgtgtc ttgttccgtg gcttcgaggg gtgtgcgcgc ttcctatacc tcccggaacg 480
cgcgagatag tcacacgcgc cactttgagg gtcaaacacc ccgcatctgg ccacactgta 540
cctttactaa cgtggggagg gggcaaaaaa atgtgtctct ccttcttacc ccgaggtgtc 600
actcgcccaa acactcccta caacttcttc aagtcaaact tggcaaggtt ggctggctga 660
ctgcgagagg aaaaagaggg cgcggagggg gcgcggcgcg cggccgggtg tagaggccac 720
ggaggcgagg cgccgagcgt cccctttgtc ctgtagaggg agctccagcc ccaaatttcc 780
ctgctgcctc ccccggcccg cccaccccag gcccgctgga gccggaatcc cggctggaaa 840
ggtgcggcgg tctgacaccc ccgcaacccc cgcgccgggg ccttagcagg atgcctcttc 900
tagggcacgt gggaaaaccc accagggtgc caagacgcac agatgctccc aggacccggg 960
ctccccaact ctcaactaga gctgggcgtc acacatcatc tagaggatta tgtacccccta 1020 ggcgaccctc ttctccatat ccgcctccac cgtcacccca caccctggca tctataaaga 1080
gggaaggggg gcaaccgggt tggaaggagg atggaatctg ggcttgcaca gcctcttata 1140
ggtaacagtg agaaagccta actgtgtcga tcaaagaatg gggacgaagg gagtgatgag 1200
aacacgacc 1209

<210> SEQ ID NO 21
<211> LENGTH: 1209
<212> TYPE: DNA
<213> ORGANISM: Homo sapiens

<400> SEQUENCE: 21
cacacacaca cacacaaaag ttgggagaga atgtgagaat gcttgtgttc gtggacgcgt 60
gcgcacgtat ggagcggcgg tacctatgat tatttgcgcg tggcgcctgg ctatgcgtgg 120
gcgaacggca gtggagaaca tgtgggcgtg catgaagtgt gcacttaaac caaagtgtgc 180
cctccccgtt gggcaggcct gtgtgttggt ccaagggttg ggagcgcctg agctgtgtga 240
gggtcgctgg gaagggtgtt tgaggccgtg ggcggtgcgg agcgtgtctg tgtgcgcggg 300
gctgagctgg ttgtgtgaag tggtagcggg tctgccagag agcgtttacc tgcgtgaatg 360
cacaaccaca cactacgggt cacgtcccac actcattctt tccctaggcg ggccaggctg 420
tctgcacgcg gagacccaga gaggccagcg gaagggcagc gcgggaaggc gctctcttct 480
cccgcgagcg cagatctggc ggaggaggcg gcgactgccc ggcaggctgc gccggcgagc 540
cccccagctc ctctcaccga cgtgccaggc gccccgaagg cgacaggcgt ctcccgccga 600
aaatgaaggc gtccgagcca ggaaggtggg ggcgggtagt taggggagac aaggagtccg 660
gagaaaaccg agaggcgggt aggctttgaa cgcgccgcgc cgcgggccgt gctgcgagcc 720
cggcacacgc ctctcgcccc agctcgcgct ggggcttggc ctctaggctc ttcgcgatga 780
cccgcgaaaa cacccctcgc ccccctcttc tcaaccggaa ccctggaggg agaggccgcg 840
cccggccagc agtcgctgcg agagcagcac tcacctgggt ctgtgcgcgc cgcgatgcgc 900
cggggctcct gcgctgtcct gcgctccgct ctcggcacca cctttcgtgg ctccaccgcc 960
cccagcccgc acccgagcgc tgaggtgcaa gggcaggtct gcgtgcgagc cccctgcggg 1020
ctggcagcca ggtgcgcgag ggccgccctt gccggcgctc ccagcccgcg ctgtctgctc 1080
tcaggaacct ggcctggcgc gcagtgtcag aggccccgcg gcggcggcag gccgagccca 1140
caggggcatt aggccaactc cccctcccgc cctgcgcacg cggaattctc tattattatt 1200
attaaagaa 1209

<210> SEQ ID NO 22
<211> LENGTH: 1209
<212> TYPE: DNA
<213> ORGANISM: Homo sapiens

<400> SEQUENCE: 22
cgagcaggag caggcgcggc cccggatgtg gagccaggct ttcgggagag cccatttcta 60
cagggattcg gcccgacggg tgccgggccg agctcgctcg gcctttgtta gtttcggcgc 120
cgctgattga tcgcctaatc cagtggaccc tgagaagaac agactgggct gccaatggcc 180
cgaccccacg ccgccgcgac ctgcccgagg gcaccgggag cgatgggtgc ggaggggctg 240
ggaggacggt catccgggcg gctggacctc tccttcctcc cctccgcctt cgtggctcgg 300
cgccgggcct cagggaggac gcagaggggg cgcccgtggc ggtgggcgcc cagcggtacc 360
tttgggtcgg ggggaggtaa ggctttctca gctcgggttc ggaaccagaa agccaccggc 420
cccccggggg taaggggtgg gcgccggcga cccgggccga cgccgccacc tcagagggcg 480
cgcgcgtccc accaaggtcg gccgccggcc cttcggacgg acgagggaaa agccagccgc 540
ggctccaggg tgcccgagac tcaatcgcac cacctgcacc ccggccacct ccgcctccga 600
agtctcagga ggaaagcccc gacccagccc gcagcctctc tcgcgcgttc aggacccgag 660
gctgcgggca gccgccttcc acgacggaca gcacggagtc ccgccgggcc ccgagccacg 720
ccagtctcgg acttcagctg ggtccgaggc tcctctgggc ctggagggct tttagaggag 780
aagaggaaac cagcacagga gccccagagg gccggacagg tctgtgcgcc agcggcccgg 840
gcgcatggca cagtgcctgg atcaggattg gtgcgaagcc agcatcaaac ggacagaaaa 900
tgaatccgat ccgacactct aggaagagca tgaaccttcc aatccaacca atgtttgtgc 960
gaggccaggt tccccgccgc ggtggcccac aagccagccc tgtcctcggg acgcaaggta 1020
accagtccgg ctggaggccg ccacgcacgc ctggtctctg cagttgtggc ggattcccag 1080
ggactctgcc caggaaatgg aaacccgtga gggcgctcct caaagccgag ggtggtgatg 1140
gccagcgaac ccgaaaaagg gcagggtggg cgccctccca tccgcttaag cagtagccca 1200
ttccactgc 1209

<210> SEQ ID NO 23
<211> LENGTH: 1209
<212> TYPE: DNA
<213> ORGANISM: Homo sapiens

<400> SEQUENCE: 23
cgcgcgcgca ggtccccgcc cctctccccg ggctgggggc ggggtgggca ggccgacggc 60
tgacctggtc gaaatagatg gtcatggtgc ggttgctcat ctcggacggc tcgtggttgg 120
tgctccggtg gcggagaagg ccaccttggc gctgccggag cgcacggaga tgcctaggga 180
ggaggtgacg gcgccgtccg ccgacgggct ggagtcgcac accaccaggc acttgccctc 240
cagcacgatg ggctccgtgt cgttctgcgc ccgcacgggg cagcaggcgg gcagtagcac 300
aacagcaggg ccagcgccac ccccaggcag gatccgcagc cgcccggctc gcgcagcgcc 360
ccccggcgcc cgggcatcat cagccgcagc ccgagtggcc cccggccggg cgcctgcatc 420
gggactggtg ggaggcggcg cgcgggggtg gaggccggcg ccggcgcgag cgcgcggaag 480
ggcgcgaagg aacgcgcgga gctcgcagca gcctccgggg gccttcgtcc ccggctctga 540
cgttcaaggc cagggtcgtt ctcagaagaa aggcgcctgt gaacctgtca gggcacagaa 600
cccaaagcct tacaccggga ggtggagcca ccgggaagaa ggggactggg agcaggtgcc 660
tgcggctcgg gggttctccc cgaaggccac cccccttggtc ccgcgcacag ccaacccgct 720
ttccgatctg gcacaacagg tccggagaaa cgcccgggcg cagctggcag cgcatccctg 780
aaggctcccg agcagcgcgc ggggctgcga cgaggagggg gccgcgcttc tgcaggtcct 840
cgtcgctaag acgggccccg agaccctcag aaggcgtcac cgccaccccg cccattcacc 900
agcgcggagg gggctaagac gcaggcaaag aaaaacctac gaatgcttgc cttctcgcct 960
tcatctcaca gcatttcctt ggagcagacc aaggaaccct tttcctatcc cttgtttccc 1020
tgctatcctc tatttttcaa tcctcgagat gtttttaaag tccatttaag tccctttggt 1080
acagatttta tctgttttcc acccacagaa caaatcccag gaatctcctt ggggcgaata 1140
agattactag gggggaaata caccacacac acacacacac acacacacac acacacacac 1200
acacacaca 1209

<210> SEQ ID NO 24
<211> LENGTH: 538
<212> TYPE: DNA
<213> ORGANISM: Homo sapiens

<400> SEQUENCE: 24
ggaagtatct tggcctgcac gcggtttaca tcattgggag cacaggcctc gccctccgaa 60
ctacgaggcc cagagccctt cgcgccgagc gtttcccgcc tttcccctgt ctcaagtcat 120
tgcccagggc cactgcgggc cgttcctgcc tgtccgtgga gctgcggccc ccgtgttccc 180
agggtgaacg agcacgtgcg aggcggtggt gcttgtatcc gggataacca ggtagggcgg 240
ctgcatgctt catagaggcc agcctgtgcc gaccgggagc tgtaggacgg tctgtgtctg 300
ggctgcttat gggtattcgc gtgcgtctgc cggtgcgcgg tccgagccta ctcacgagag 360
cgtgtgtgtg tcttctgtct cgtgttgcta tgaggtttgc atctgtgtgg ctggaatagc 420
ttgtttgtgg gggcccgcgc gtgacctgtg tgtgcgttac tgtgtgtgtc taggcaggat 480
agtgacgggc cgtgtgactg tgacgccatc atcaggttgg tgagatggcg tgaccgcg 538

<210> SEQ ID NO 25
<211> LENGTH: 450
<212> TYPE: DNA
<213> ORGANISM: Homo sapiens

<400> SEQUENCE: 25
cgagggagga cgacaagcgg ggacgttggc ggaggggtta atggcggagt cgcgatccag 60
ccgagcccac aactctggga ggctggttct gcctctctcc cgaagcgtcg cccggctaag 120
cttcgagacc aggacacaca accgccgact attccagagc ccacagtcgg cttcacgctg 180
gaggccggaa acgacacgtc cccaaagccc gcgcgcgcgg cccgccagaa ctgacctacc 240
caatcaccgc accgctgcga tcaagcggcg acacacgttg ccgggtaaga gtcacgcttg 300
gcaaataagc aacctgcctc atccaatcag cgtctcgcct gcccggttag ttccttgtct 360
tgcccaacca gattcttgcc tcctccatac cgctacttgc gtgtgccggt gcctggccca 420
atcagcgtct tgcgcctctt ctcgctcccg 450

<210> SEQ ID NO 26
<211> LENGTH: 1209
<212> TYPE: DNA
<213> ORGANISM: Homo sapiens

<400> SEQUENCE: 26
cgcttgttgc ggtggatgtc gccaatggaa ttggacaccg tgttggggcc cagcaacatg 60
cgggtgctgc gaggccactc ggtgctcacg aggtggtgct cgcccatgag gatcttgcgc 120
acgttctcgc gccggtcacg cgtatcagcg gccgccccaa caaatgcgtc ttgaacacgt 180
tgccatactt ctccctccgc gacgactgga agccagaacc ctgcgggagc cacacccggg 240
tctctctcag ggtgcacttc tgcagagggc ccgcgaggga ggggcggcgg accccaaccg 300
gggtacagtc acctgccccc tctccccacc aaacacactc acacagacga gcacgcaggt 360
tttatttttc atagcgtgca caagaactgc gaagtagggc ctagaggata ataaataatg 420
caaggaggcg gaggcccagg ggcaccccca ggaggctgtt ttttggtaat gctttcgaga 480
ggaaagaggt atcccggaca gctggacccg aagcgggagt ctccgccccc acccccaccc 540
ccacaccccc accccgcgct cgggagcctc tcggaataaa tatttccagg ctccgggcca 600
cgggctggcg agaccccgcg gggtggccgc aggccaaaga ttattatagc ggtaagcggt 660
cggtgcccgg aggcagcaac tacagatggg ggttggagtt tcctccgctc tccggtgtgg 720
cccgcgcagg gacccggcgg ccctcggagg actctgcagg gcggggtcac gggcccagag 780
ccgcgatttt cctaatgcat tttgccctgg aaatacggag acggactttg gttgccgccc 840
tggagtttgg aacccgagcg cggggcgggg cgggaccggg cagggcgacc cgcgcaggta 900
accagatccc cggtggtggc ggcgcaagcc gaggatggcg gggccggggc cggccggact 960
ctcgaaacgg ctggcggagc cggccggcgc gggtaccgga aaccgtggag acctcagagg 1020
ggcgggggca agggcgtccc gctcaccttt gacgtcggca ctagttaccc caccccacgt 1080
taacccttct cctgccgggg cagcacccgg cgcaaagggg aggggcgcca cctgtctagc 1140
cgccccgcct gccagcccag agcgtaccga ctcgggctcc agatctaccc gctcctgcac 1200
ccccgaggg 1209

<210> SEQ ID NO 27
<211> LENGTH: 1209
<212> TYPE: DNA
<213> ORGANISM: Homo sapiens

<400> SEQUENCE: 27
cgctcggcag aggcacgata cagcgggaga gaagggcagg cccgttcaca ttttaatcgg 60
agcgcaccgg cggccgctcc tcggctgcgt cctgggctgc cgctcgggct cgggactgcc 120
agatgcagct ctggctgggg gcggcgggcg caagcgggcg cacccgcagc taggggtgcg 180
gggtgcacgc acacgcacgc tcattaagag ccatgtattt attgaatgtc cgagttgggt 240
tagttcattg gaaatccccg aggagggctc aatttgccct tgttttcgtt gccactttcc 300 tttttcttg gttcgctgag gttcctctgt gcagcgtttc cgcttggccg cgtcccccca 360
ccccacccca ccccaccccc gcttctctcg cctaccgggt gcactccccc tcccatcccc 420
cttaactctt tcagctgggt tagagctgag aaagcatttg tcgccgccag cccatccacc 480
acgcaaatcc atctgagaca gaaaggaaag aaaaaaaagc accaccatgc ctaagaatag 540
agagcgagca aaccccccca ccgctaatca cacacacaca cacacacaca cacacacaca 600
cacacgagga agcggtggag cagagaaggg cgcggctagc cgacccggtt ctttcgcccg 660
gctcctgctg ccacagggaa ttcctaaagc cattggggtc gaatacactt acgatgaatc 720
tatgggggaa ggtcggactg attgcttttc aaatacatcg cacggctccg ctgaccggca 780
ccctccaaac tcacaagggc acgcacgcta cttgccgaat cccagaggag ggaggaggga 840
ggaagggagg gagagcgaag gagggagaga gggggtggag gagccaggga gcggcggcag 900
cgagcggtcc gtctcgcacg cgcgggcacc gcgctggtcc tgggctgcag gtttcccaga 960
tgatggcatc cgagaactta aacaaagggg ctgccgccgg cgcgcaacgg ctgcggaaag 1020
ttgcggtggc ggatttccaa ggagcgtggc cacgaccaga gctcttggcg atgcgagccc 1080
ccgcttccca cccccgccga tcagagaagg gggccggctg gtgaagggaa gaggaaactt 1140
tgaaaccact ggggacacac tgtctatagg tattagcttg aatggtacat ccgtgccgcg 1200
cgctttaca 1209

<210> SEQ ID NO 28
<211> LENGTH: 1109
<212> TYPE: DNA
<213> ORGANISM: Homo sapiens

<400> SEQUENCE: 28
gactctcatc actaccacac ccatgtgtct ttcctctctc cgtctccctg agacgccagt 60
gaaccacctg ggcttggaat ccagagcccc ggaacacctt gcagtacttg cccgaagcaa 120
cgcgccacag cgggagggag acgcagacgc gaagaccggc gagaggatgt gcggtgggag 180
tagctgcggg gtctgcaagc aggggagcgc gcacaacgtt aaaccttgaa accagaaatc 240
ccgatcctat cgagacccat cagcttttcc catttgggaa cgagcgcagg ggaaattaat 300
gcgtaattca agctctgttt tcccctcccc tccaaaggtg aggtggggga acgcgtctcg 360
ttagctcatt acaaagcttt ccgtgggaaa ttccctcttc ctaatgcgtc tgtcttgcaa 420
ctcctattag catccttcga cagcggcctt tgaaaatctc ctttaaattt catacctcta 480
ctcgtttccc aaatgggggg aagggaagag aaagccgggg ggtagagaga atttccttcc 540
cctttccctc ccaggtagcc aaagcgcacc gcagcggctt ggcttcctgg aggaaaagcg 600
cccgagcggg gcaaagaccc gcccaggctg ctcttatagg cgacgcgggg cgggcctggc 660
tgggggcggt gccgcgcggc cccgctcgcc tataaggagc tgtccgccac ccgggtgctg 720
attccagctc tcgcgcccga cgaggtggat ttggctgtcc accgagctcc ggcgcctgtc 780
gttctaattg ggtttggatt tgcaccgtta aggaggggga agagaaggaa gaggcgggcg 840
aggaaggcga gtccagctag cggctgttgc ggggaccgta gccccagctg cagctccgaa 900
gaatcccccg ccacggtttc ggtggagcgt ctgggcacgg gatggagtga aagagcgagt 960
gcctctccaa gcgggggtgg gagggggcag gctgtgcaga ggagagagac agcgagaaga 1020
agccgcggct ggctactgcg aatttgggat tcgattggga gggaccgctc actcggggga 1080
aatggattct ttaccacggc tgaccagcg 1109

<210> SEQ ID NO 29
<211> LENGTH: 1209
<212> TYPE: DNA
<213> ORGANISM: Homo sapiens

<400> SEQUENCE: 29
cgtacccggc tctcaaaggc acggcacctt tgaattaggt tgcggagtgg cctgggcgag 60
gggacccggg gccatcaaag gcccgaggga aggccgtggg gcgacacccg tctaatgaca 120
agtaattaag gattcgacgc cgcgcattac cagcggaacg ggaggcatta attatttaaa 180
aacgattagc cttgccgtgt gtcctgcagg cgtcccatca tgttcagcga agataaccag 240
ccacccgagg cgagccgggg ctcggagggc ggcgggcgcg ctccccagca ggcttcgggg 300
cggtggacac gggcgcacag cccaaggcac cagggaagga gaggaggggc caccaagggt 360
ccccacacag gaaggtgact acataacact gaccctgctg aacaacgaaa cagatttctg 420
cccacttggg ttcgaagtct ggtgactgcg gcgcagatgg gaaaagcttt cggtcggggg 480
tggtgggcaa tttccatgtg ccagttccct gtcgcatcag accaaagacc caaagtaacc 540
cagccaggca cgggcctctc acagtgcctg ctacccaggc gtttaaagaa aagaccccag 600
agagaatgtg gatctggcgt gggggcaggg attggggggg ggcctggtag acacctgggg 660
aaatacaact ttatgaggtt tcaaggggca gcagcagaac tactattttt ccgaggtcca 720
cgcctttccg caggcggcgg aaagacgcgg ctggttctgt tgggtcctac aaactcgcgt 780
cctccggaat tcccgagggc aagcccggca cgcgcagcgt gctcctgccc gtggaagggg 840
ggaaatcggc gactgggttg cagggagaat gcgatgataa atggccctgc gtctgctttc 900
tgactttctc tcctggaccc agctcgtaac cccagaggct ccccaacctg cctgccgcca 960
agcacggctg tgcgcaaaag gccaccaccg cttcctgcag ccagagctaa ggttcactcg 1020
cctcttagaa aggcgcggcc cctcccctgc tgctgcttga tgacgatccc catcgtctcc 1080
tcggcctgcc tgtgtccgag aaagagttga gactggactc gaacccctgc gcgccaaggg 1140
gagggcgtca ccatgctccg cctcagcctc ttcaaactcc catgcaccac gcacatcatt 1200
ttctgctga 1209

<210> SEQ ID NO 30
<211> LENGTH: 1209
<212> TYPE: DNA
<213> ORGANISM: Homo sapiens

<400> SEQUENCE: 30
cgacgtccag ggaccaggtg cccttcggct cccgccgacc tgttgctcga aacttgccct 60
gagctctcgc tgccgggctc tgggctccca agcctctccc ccgccgccgc agcagcctct 120
tttagggccc ggaagaaatg ggagccgggg ctggtgagag gggtaggaag agggacggta 180
gaagtttcag acccaggcat atttgggaag gcgagtgctt tacatgattc cccatttccc 240
aatcggacca gcttagcctg ggcaggcagc ctcgtgctga ggtgcctgga gaccgcccac 300
ccctaggtgc tcgcttcccc ccgggtctga cctgatcgaa gtaaatgatg cgcgtcttgt 360
tgctcatctc ggatggctcg tggttggtgc tccgcaccgc cgagaaggcg accttggagt 420
tggccgcccg gaccgatatc cccagcgggg aggaagagga gcccttggag tcgtggccgg 480
gttcgagtcg cacaccacca gacacttgcc ctccagcacg atgggctccg tgtcgttctg 540
tgcccagacg ggcagccccg gcagcgtgag gaccagcagc acggccggca ccgcggacag 600
cgcccggcgc ccggagccca tggtgagccg tgtgggcagc cgcgccggct ggcgctggtg 660
ctcgcccgcg tcgcctccta ccccgggatc ccggtgctcg ggaagatgct agcggctagg 720
tcgacagcgc tgcaggagcg acggcggcgg cggcgcgcac acttccacca attctgtggc 780
ttgaagtcaa agtctcccct cgagctctct cgctgctctg ttacctttgt cctttaagga 840
gctcatgcag caccctttac cctactctcc tccgcccaag aatcagccct gcctggggcc 900
cctgcaccca ctctggttcc tagacatctg aaagtcatca aaccctcaca ttcacacctc 960
aaggcaaaaa ataataataa taataaatct caccccaaac tcaagcacca ccagctaaac 1020
cacggagcag gaacaaaaag aggggactca aagagaagcc acaagggtgg cgggtgccca 1080
gcggcgcggg tgccagtcct gtctggcttg cggcagggac gagttacaga ggcagaaggt 1140
ccttcccagg ctgagaagac gcgaggctgt gttcatggcc aggacgccag cgactcccac 1200
tttcgcctg 1209

<210> SEQ ID NO 31
<211> LENGTH: 1209
<212> TYPE: DNA
<213> ORGANISM: Homo sapiens

<400> SEQUENCE: 31
cggtgccggg agccttgcct cccgccgcca cccctggtca gctctgcgca agaacgtcgt 60
tctgtttggc agccaggccg agacgcagcc tgaatgtgag caggaactcg gagaagggaa 120
gggagagatc agaaagaagg cccgggaggg acccgggaag cagtgggagg tctgcgccct 180
ggagccccgc gagagcccgc cggtttggca cgggctcctc ccgggccgcc cggcggtcca 240
acaaaggccg gccccgacac gcacccggtc ttttgtggga gagaaacaca aagaagagga 300
aaaacacgga ggaggccaac agcaccagga cgcgggggcc aaccaggaac tcccggagcc 360
ggggcccatt agcctctgca aatgagcact ccattcccca ggaaggggcc ccagctgcgc 420
gcgctggtgg gaaccgcagt gcctgggacc cgcccaggtc gcccaccccg gcgccgggcg 480
caggacccgg acaagtcctg ggacgcctcc caggacgcac cagggcaagc ttgggcaccg 540
ggatctaatt tctagttatt cctgggacgg ggtggggagg cataggagac acaccgagag 600
gtactcagca tccgattggc accagggcca agggagccca gggcgacaca gacctccccg 660
acctcccaag ctactccggc gacgggagga tgttgaggga agcctgccag gtgaagaagg 720
ggccagcagc agcacagagc ttccgacttt gccttccagg ctctagactc gcgccatgcc 780
aagacgggcc cctcgacttt cacccctgac tcccactcca gccactggac cgagcgcgca 840
aagaacctga gaccgcttgc tctcaccgcc gcaagtcggt cgcaggacag acaccagtgg 900
gcagcaacaa aaaaagaaac cgggttccgg gacacgtgcc ggcggctgga ctaacctcag 960
cggctgcaac caaggagcgc gcacgttcgc ctgctggtgt ttattagcta cactggcagg 1020
cgcacaactc cgcgccccga ctggtggccc cacagcgcgc accacacatg gcctcgctgc 1080
tgttggcggg gtaggcccga aggaggcatc tacaaatgcc cgagcccttt ctgatcccca 1140 ccccccgct ccctgcgtct ccgagtgaca gattctacta attgaacggt tatgggtcat 1200
ccttgtaac 1209

<210> SEQ ID NO 32
<211> LENGTH: 1209
<212> TYPE: DNA
<213> ORGANISM: Homo sapiens

<400> SEQUENCE: 32
ggccggccgg ccttccttcc ttccgccctc gccctcttca tgcctcagaa acgtggccta 60
ctctgcattc ggtgtgtgcg gaagcagcaa tcacagaggc agccctaata ccggaggcgg 120
cggcggcgca gcagggccag gtggtagctc ggggctgagg atcgcggcgg gggcagccgc 180
tatggggccc aagccctgac acacgtacca ttcgctcaag tcggcggtac gcgccgccac 240
cgccgccgag gaggccacct gggacttgtg gccgcagtcc gacgagggcg acacgaggga 300
gacggtgtag ccgaatcgta gccagagctg ggcggcggcg agcgcccgtg caccttcatg 360
tgcttacgca gcgagctggg gtgcgtgtag cacttgtcgc agccccgcac cttgcacgtg 420
tatggcttgt cgctagtgtg cacgtgcgaa tgcttcttac ggtcgctgct gtggcgaagc 480
gccgctcgca gccctcgaac tcgcatctga agggcttctc gcctggcgga ggcaacgcag 540
agacattagt gcttgtgggt cgtgttcccg tcaggtgctt gccaccctcc cccattcgtc 600
tctcattttc tggaaaagaa ctacaaaata ttttcagaaa tcctttccac ggcgcctcag 660
gtcgagcacc cctttccctc gtgcagagag cgcccccggt gccctctctt gaacgcctcc 720
atccctcccg ccttcctcct ctgggctcat ggggagggta tggaggagga gcgacagtga 780
ctccatctta gtcgagtttc catcctcgaa aatccgatcc actcgggttg tttcctccaa 840
attttctcca cttggaacca gaagcacctc tgctcggaaa tacattaacg gaggagctca 900
caatatagtt aacggggaag ctcacatctg ctcgatttaa agttgctgtt tcagactaac 960
ttctctgccg ctaccccgcc cagccgtcat cccccccacc caccccccatc ctggcccaaa 1020 ttgtttccta aagtaggttt tgcgcaaacg ccaaagcgat gaaataattt aaggatgcgc 1080
agccgatgca cattgtgtgt gcataaagtg gattcgtgct gcagggagag gtattctgag 1140
caatgattca cttcagaagg atttttacag gaatggagcc ccctccctct ttccttctac 1200
cccctgagg 1209

<210> SEQ ID NO 33
<211> LENGTH: 807
<212> TYPE: DNA
<213> ORGANISM: Homo sapiens

<400> SEQUENCE: 33
gaaatgttct ggagcatggt gacgggaatg cagaagaagg tgatgagcag gtcactgagc 60
gccaaggagc agataaagat gttggtgacg gtgcgcatgg ccttgctgcg ggtcaccacg 120
tagaacacag agcattgcca aagagcgcca gggcgaagat gagcacgccg gtgagcacga 180
gggccagctt ggcgcgtccc ggcagctctg gggtgtagac gagcggtcgc agccggtaca 240
gagcgatgaa ctgctcccgc gtcaggttgt ggtcccgcag cagccgagag aactgctccg 300
ggtaatgtta agcgcctgca ttgctgtgcg ctcccgggac gcggggccac cgcccgctac 360
tggctggcca tccgcatctg cggggcagcg agggcttcgg gggaccagcc ggaggccgcc 420
tcccttcctc tactctggag tcagccgcgc gggagggctc taggctgcac ccgggaggtt 480
cgggaaagga gagcagctca gggatcaaac ccacgataaa gaggcgggaa gccaaagcac 540
tgggagactc gatctcagtg accaaaaaat gttcgcggtt caaataaagt tcttcccttg 600
ctcttcccta aggcgaggcg ccgccacggt ctggggtgct ggacgccacg cgagggtcct 660
ggcgcctctg gctccccgcc ttctggccat gcgatgcgga cgccggaccc gcttggggag 720
cggtggaggg tggggctgaa ctcggtgacg cctccctcac acccagcttc agtggcgcca 780
acgccgcttc cccgcaccct cagggcg 807

<210> SEQ ID NO 34
<211> LENGTH: 349
<212> TYPE: DNA
<213> ORGANISM: Homo sapiens

<400> SEQUENCE: 34
gaagatgagg tgcagaagta agctgggacc tgtgagcctc aatttcggcc tcttctgcgc 60
tgagacccaa gcggatcttg cttggcctgt atgcgttact gggggaaatg gacgtgggcc 120
tgagcgcgca ggtgcgaggg cgctgccccg gggccgacca ccctgcgggg acactgtagc 180
tgtcattcct tcttctgcag gcgggtaggg gaagcggtgg ccaaagtggg agtcgaccgc 240
tcagcacagt ctgtctgagt gttgaccagg aaagtccagg ctctttctaa atctcgccgc 300
agacctggtg acgcattcgc atgtatttaa ggcgtttgca cgcagaacg 349

<210> SEQ ID NO 35
<211> LENGTH: 457
<212> TYPE: DNA
<213> ORGANISM: Homo sapiens

<400> SEQUENCE: 35
ctttactctt ggagaaatcc ctcacaacaa aggacaaggg agaagcaagg gggaggggcg 60
cccagtggac ttggctggaa gaagtgagcg ggctggggtt ggaagagtaa ctcgggctgc 120
gggctgacgc agtcggcaac cgcggaagag cagcatctcc cctgcgcctg tggatacgcc 180
agtccaggga tggcgagtgc tttctcctcc ccagcttctc cctcgctctt cgaggtgact 240
cgtgggaccc tgcgtcctag tgctgggtgt gaatcggcta tttcacaccc agttcttccc 300
ccctccgcca cacgcagtca cattcctgga gctattccaa gctgcctccg ctaagcaccg 360
aataagcgga ccctgcctgg aaacttgagc gaagctgaac tgcgccgaac tccaccgtcc 420
agtgacccga gccagtgtgg acgccctttt aatcacg 457

<210> SEQ ID NO 36
<211> LENGTH: 677
<212> TYPE: DNA
<213> ORGANISM: Homo sapiens

<400> SEQUENCE: 36
cgctgtgcga gccaggatcc gggcagatcc gctactcgat gccggaggag ctggacaaag 60
gctccttcgt cggcaacata gccaaggacc ttgggctgga gccccaggag ctggcggagc 120
gcggagtcgc atcgtctcca gaggtaggac gcagcttttt gccctgaacc cgcgaagcgg 180
cagcttggtc accgcgggca ggatagaccg ggaggagctc tgcgctcaga gcccactgtg 240
tgtggtgaac tttaacatct tggttgagaa caaaatgaaa atttatggag tagaagtaga 300
ataatcgata ttaatgataa cttcccgcgt ttccgggatg aagagttaaa agtaaaagtt 360
aatgaaaatg cggctgcagg gacacggtta gtgcttccct tcgcgcggga tgcggatgtg 420
ggtgtgaact ctctccggag ttaccagctc agctccaatc tgcacttctc ttggatgtgg 480
taagcggaac tgatggacaa aagtatccgg agctggtgtt ggaacagccc ctagaccgcg 540
agaaagagac tgttcacgac ctcctcctca cagctttaga tggcggagac ccggtactct 600
ccggcaccac gcacatccgt gttacggtcc tcgacgcaaa cgaaatgcgc ccctgttcac 660
cccatccgag tacagcg 677

<210> SEQ ID NO 37
<211> LENGTH: 415
<212> TYPE: DNA
<213> ORGANISM: Homo sapiens

<400> SEQUENCE: 37
cgaatcggga attggcattc cgtaagggag cggagggcct caggccacta ggcagctccg 60
aacgcgggga agcgggagca aagatgagct cagagcgagg gttgccggcg ccaccctggg 120
ctgcgcatga ggggccgtgg acccgccccg agactcagtg acagtcgcag cttaaccccg 180
ttgggggcgc cgccccgctg aggtggttgc gtctccaagt cgtgagcctc caatagctgc 240
tcccgctttc gcgtcgcaac cccaggaccc cgggaaatta ccactgtgct cgtctgggcg 300
gagacccggt gcttcggaag cctggggcac atgcctgggt cccaccctag actcaccgcc 360
tctgggcccg agacatggga atctgccctt gaatatctgg gcgcctttgc tgtta 415

<210> SEQ ID NO 38
<211> LENGTH: 639
<212> TYPE: DNA
<213> ORGANISM: Homo sapiens

<400> SEQUENCE: 38
cgctccacaa cccggaagga gctcaggccg gacttggcgt gagggtccct gcggggctgg 60
gtcacctacc cgtccgcgat caccccacag gggctgttag taatctccct gcttcctagg 120
ccgttgaaag cactcaggtc acccactctc ggtgaccaga gcggtcagtc tttccccgcc 180
atgaaatgtg agttcgggtg gcagccgccg cgcccctgca gtgtcccctg cacatctccg 240
gtctcggtct cgcctttctc agctccgcgc cgccttttcc tgggcgccgc aggactcatg 300
aagtgaggcg gggccacaga tttaagttta ttccccgcaa ctgtcggggc ggtcccggag 360
ctggtgagga cgcgctacgg tgggtgcaga aaggagatcc ctggactctg tagaacctgg 420
gcccgcggtg tggaccgatg gtggattctc cgcgacaaca gccctggagg ggagagtggg 480
ccgggggagg ggccacgggg cccctgaggc ctgcggggct ggccgcactg gccccgggcc 540
tggcggggtg gtggagtccg aagcggcgag gcgaggaccc cggggcccgc tccccccagt 600
cgccctcccg ggatgtggcc ccgctgcagt agcactacg 639

<210> SEQ ID NO 39
<211> LENGTH: 888
<212> TYPE: DNA
<213> ORGANISM: Homo sapiens

<400> SEQUENCE: 39
cgggctccgg tgcgggacag gcagccggag ggagctccag acccctcccc tcgcgcccgc 60
ggccgctgcg cggaggtctg cggagggcgc ctggctcggt cggtcgctcc ttccttggcg 120
ggccctcccg acccacggtg ctcagccagc cccattcttg gcattcaccg cgtgccttaa 180
ttgtatggac atttaaatca aggtccgctg tgaacacgga gagagaggcc tttctcctga 240
ggaaggaaag gaggaaggaa ggaaggaaag gtgaaagaaa ggaagagggg tgggtagaaa 300
tggaataaga aaaccaggaa aaagaaataa aaagcggcgc gtgtgcgtgc gcactgacag 360
cggggagagg gatgggggtg gggaacgccg gaggaaggga ccacagcatc ctccccgccg 420
cagctccccc aatcacacag acaatgagat aacagcgacg tcttccaaag gtctttgttc 480
tcccccatcc tttcgcatcc aggctttttc ctgcaaagcg gagggggtgg agggatgggg 540
gtgtgggtgg aagtgggaga cggaggggtg cctcccccgt gttaattacc ccggctcccc 600
tcgccccttt ccccgcgcct cgcctcccct gcagctccag acatgaaaaa acaacatcga 660
ccccacctcg ccccagcgca gcaacccacc cacccatgtc gccctctgct tcgcccagga 720
aactgaaggg gactaggagg aggaagaaga gagcgaagga caaggagagc agcggggact 780
cggcagcggc agccggggca gggcgcgcgg ccgcccctct ttacctccat cgctgagtgg 840
gggcgcagcc gggccgggcg tgccgcaggg gcgagttgcc gcggtccg 888

<210> SEQ ID NO 40
<211> LENGTH: 1209
<212> TYPE: DNA
<213> ORGANISM: Homo sapiens

<400> SEQUENCE: 40
cgcgcgcgcg cgcacccgca cgcagtctgc aatgccctca ccagtccccg cagctgggca 60
acccctccaa gaccctgtgt tacgcttaaa ttcctctccc tcctatcgta cccaccatcc 120
atccttaagc agggaggccg agactcacag aattcccttc tccaccaact cgcactcttg 180
gtctagcacg cggaaaccga acctttctac gcggcccgac cttgcgattg ctccagcatg 240
agtggcattg acttttccaa tgtaatgact tatgaaagat ataatcatgt gttaaattga 300
tcctccgttt aactgttaat ggtgtgctct gggcacattt acgtatttga tgctatggta 360
actaattacc actagaaaaa aggataatac acttcccaga ctttgaaaaa taatcatgag 420
ttcacttccc ggctcgcagc acatcgtggc ggccctgccg ggaggagcga gaaacgagtg 480
gaaacccgaa agtgtgctca tggaatgcag gaggtaatga atcctggtca ggtgagacta 540
cttagtcaaa cctttaatga aaacgtgatt cacatggaaa gcaggagtgg gagggaacaa 600
ctacacaaag gtgcctttaa acaaaattaa atggcaaaac ctgctatcag aaacatgaat 660
aggtttcttt caattaaaat gcaggtaaga ctaaattatc cacgtgccaa gcaactttac 720
atcaattaac atttttttgt tgtgtgggca aagtaaatga gcccggctcc tgtgctctct 780
gtattggcat atacaacttg aaagtctctg gatttccaag ccaatgagct gcaggtttat 840
ttaaattcgg ccttttaaat caaactttag acacagtagg tggaaggagg gaaagagaag 900
gaaaaacaag gagtcagtaa cttcagttta acagtagaaa caactcttac ggtgagagtc 960 tttttgccc ggcaaatctc tggctctctg atcgactggt gtttagaacc aaggttccag 1020
taaacagggc tgggtaggat aacgaggaga gtgtttgtgc tgggacctgg caggactgga 1080
ggaggaaagg agccgccttc cagcaggtcc agcatcccta ggttgcaaac acaccaaatg 1140
acgtccacgc agcactcgcc ccaccgcgct gtttttgctt gcgcagtgct cccgaaggga 1200
ttcgggatc 1209

<210> SEQ ID NO 41
<211> LENGTH: 1209
<212> TYPE: DNA
<213> ORGANISM: Homo sapiens

<400> SEQUENCE: 41
cgtcgggagc gcgcggggac acacacgcca ctcactcaaa cccgcaatta gccctttgag 60
ccccaggcac aggaaccccc tccctagaac tggagaagac ttggaggcgg cggggcggcc 120
aggtgaaagc ggacaagggt gccggtaggg ggaggggcag aggagcgcgg ggacgccccg 180
aatgcggccc ggggccgggt ccaagggcag cggggctgcg gggcgctgca cccggcgccg 240
ccttacctgg agtcaatgtc cgtctttggc ggagagctgc gggaggacgc tttttattcg 300
ctcggtggga acttgggaga gccctgcgtg cagctcgcat tccgggcacg gcgcggggac 360
tgcaggcgtg gggtacctg gctcctagca gcctggctca tactcagccg taaagtcccc 420
ttcgctggtc ccgaggacag gcatgaatcc cggctccgga aggcggtcac tctccctctg 480
cctcccggct ctctcgctct cgctctcgct gttgctcgct cgctctctcc ctctctcgcg 540
ggttcgctcg cctgcgctct cctcctcccc gcgcgccaga tcagtttgca gccgtggggt 600
ccgggagcga ggcggctggc gaatggagag ggaagtccaa gtggccgcgg tctccgggcg 660
gggagcggcg gaggccgggc tacgccgggg gagggactta gccggcgacg gccgaaaatg 720
aatgggggag cggcggccgg ggggcgggga gggaggagct gaacgccggg gttgcttccg 780
aggagtgttt tgtacatctt taggcggagg aggagagaag cgagaggagg agagacggga 840
ggccgcctcg agggaagggc ggcccgggtg ggctggggct gagccgtagg gagtttcgtg 900
ggtctggggc gtgtagggtg ttgtgtctat gcgcacgagc atccaaaggg accgcgcata 960
cgcgcaaacc cggaatcctg gtgccctaag cgtgactgta ctgtgtgtgt cgcgagtacc 1020
tgagtgtttc tggggcggca ggtgtttcca cggccgcgtg gatccatcga gtgtgggttt 1080
tgtctcggga gttgcccgtg tgggtccgtt tgtgtctgcg cgtctctctg tgagtgtttg 1140
acactgtttg tttctctcgt gtgtaggcga gagcccacgt aacctcccag aatgaagcaa 1200
gagcttctc 1209

<210> SEQ ID NO 42
<211> LENGTH: 340
<212> TYPE: DNA
<213> ORGANISM: Homo sapiens

<400> SEQUENCE: 42
gcgtgtcgca gctgtgcacg ctgattggtc ctctgctggc caatcaccac tgcacttcat 60
gacggctgta gttttcaaaa tcccaactgg gctggtggag ggtcgcaggt gtcaggttga 120
gacggaccga gtcgctatag taaggagctc cgttcatttc cttggcctct cctggtctag 180
gggtgcgtcg atggtctttg ctgtctgtcc tcgatctcgg tgtgaggtag gcgcctttgg 240
gcaagtactg ctggctccag cgtccggctc tgtcgcctgc cagtgggtcc ttgggcgtcc 300
tccagcccct tgctgaattc tgttgctggg atgcgcggcg 340

<210> SEQ ID NO 43
<211> LENGTH: 214
<212> TYPE: DNA
<213> ORGANISM: Homo sapiens

<400> SEQUENCE: 43
cgggcgcggg agctacgcca aggttctcct ggtgcggttg aagaagaatg accaaattta 60
cgccatgaaa gtggtgaaga aagagctggt gcatgatgac gaggtaggtg ccgcttctca 120
tggggccggg ggcccgggaa cgcgctgccc tggggcctcc tccgggcttt agcggaatta 180
atccatgcac gagagaccta gcctcacgtt gacg 214

<210> SEQ ID NO 44
<211> LENGTH: 420
<212> TYPE: DNA
<213> ORGANISM: Homo sapiens

<400> SEQUENCE: 44

```
cgaggagtcg gtgtgaggcc gcgtgcgtct ctgtcgtgga cacgcgtgat tgaccctta     60

actgtatcct taaccaccgc atatgcatgc caggctgggc acggctccga gggcggccag    120

ggacagagct tgcgccgaga ccgcagaggg aagcgtcagc gggcgctgct gggagcagaa    180

cagtccctca cacctgggcc cgggcaggcc agcttcgtgc tggaggaact tgctgctgtg    240

cctgcgtcgc ggcggatccg cgggaccctg ccgagggggc tgtcatgcgg tttccaaggt    300

gcacattttc cacggaaaca gaactcgatg cactgacctg ctccgccagg aaagtgagcg    360

tgtagcgtcc tgaggaataa aatgttccga tgatgtggag ctcctctgat gcctttttc    420
```

<210> SEQ ID NO 45
<211> LENGTH: 413
<212> TYPE: DNA
<213> ORGANISM: Homo sapiens

<400> SEQUENCE: 45

```
cggacgttaa gccgcgtcca gggctccgtg caggcgctgt actggttgcc atcgtgcatc     60

acgatgcagt agaagccgcg gctgggctgg atctggatgc tgcccttgcg gcttgcggct    120

tcgtgtgcag cccgatcacc cactgggtct tctccgccac caccacctcc cagtagtgga    180

cgccactact gaaggcttca gaacccagca ccgacacctc cacatcgaag cgctttggcg    240

agtcctgcag tggctgtggg tgcagttgcc gtaagccaca atggtgcagt cgtccgacag    300

gatcaggcgc tggtgggctg tgcccgggtc cagggttagg gcggctggca ctgtgggggt    360

tggaggaggg agagaagatg agtggggaga aggctgtggc ccaccatgca gtg           413
```

<210> SEQ ID NO 46
<211> LENGTH: 719
<212> TYPE: DNA
<213> ORGANISM: Homo sapiens

<400> SEQUENCE: 46

```
cgcgccggct ttgccgcttt ccctgagggt gtccagtttt gtgaataaaa ttagagaaat     60

ctgcgggcgt agttccccaa gcccagctca ggcttccgtt tgcagcccgg cgctggccga    120

gctcgaacgc tgaaaagggc cgcgtgcaat cgttccgctg tgcctcagga caaactccgc    180

ttcaagccag tgccgctctc cggcagtttc ctgattgact taattagatc cgcataatcg    240

ctggagggct tttctttccc agaccgagaa cagctcattt atggggacca aaaggaagag    300

agggagagac gacccggacg ccactgatag caacgtactc ttcgcaaaaa acactcagta    360

actagtggaa aagcccaaca ggcatccccc tccgcccgca acgcttcctc ccaattgttc    420

tgggctgcac gagggagatg gccgggccgt ggaacagatg cagaaggagg cccggcacga    480

ccagagacgc tgtaaccaag acccgcagag cctgtggctt cccgctcttt ggcggtgcag    540

caggcatggt gctggagccc aaggcttctg ggaaagagtc caggttttcg cggagggagc    600

gacggactca cgcgggatcg caggcactgc tgcaagacgc cgaacaggct gagccggtag    660

gcgaaagaag tagggtcaca gaagaagcaa agaaaacgaa ataaattccg aatcccgcg     719
```

<210> SEQ ID NO 47

<211> LENGTH: 999
<212> TYPE: DNA
<213> ORGANISM: Homo sapiens

<400> SEQUENCE: 47
cgtccgggag cctccgcaac tcgcatttcc cagtcgcaac cctgggtcat tcctgcctcc 60
gtcccagctc ccggacaatt cccaaagcca aaggcgtcga gcgtgttact ggctcccacc 120
agcccaatta ataatcagct taactcgtgg aggctttgag ccccagtgct ccgttccctg 180
aagcctccca gtgcggagcc cggctcctgc gaggacatcc ttggaggggg gccggggcgc 240
agggacggat ttcctgggaa aaatgtcgct ggcgtgttgc acctagaggg ctgtgggcaa 300
ggaggcacgc accaatgtcc cagttctggg ctctcagatc gggattcctc caaaatcgcg 360
acagccgctc aggtgctggg tgctcacgtt ggcagcacaa gcgccaaatg cacgaccccg 420
cgcgccgcgc gcgacctcca cgcacactta gagccgaggt gacaagggaa ggcggcgggg 480
gtggagccgc tctctggtgg agcatgatca atcactttaa agggttcaaa agttcaagtt 540
cccctttgga ggggagaggt aatgcttccc gcggcctgct tctctctgag acccgcgggt 600
tcccggcagc cgcgcaacca ctggggatct cggctgccgc ttgcgggagc cccttccggg 660
gaacacgctc tcgggccgcg cagccgggcg aggttgacgc agctgctagg gggcagtttg 720
gcttccccgg gagtaccgga gtcgctcggc aaaaacgtga tctcagcctg cagggcccgg 780
ggcgcgcgct tttccctttc tcagcaacgg gaaaggcctg ttggcagagg ccggcggagt 840
gctggcggcc tggcggctgg aggcttcggc ggaaacctga gctccctgcg acctgttctg 900
ctagcagggg cgggggagag ccccaataag ccgccccaga ggcgaccgtg caaattccta 960
agaaaaagcc ctctagaaaa caccaagccc ttccaaaag 999

<210> SEQ ID NO 48
<211> LENGTH: 1226
<212> TYPE: DNA
<213> ORGANISM: Homo sapiens

<400> SEQUENCE: 48
cgtcggcgct aagcagctct ggaaacgggc agacccagct gtgcagcgat gtccagtgtc 60
gccgcatctg ccccgcgggg tgcagcatga gtcttccttt gtggcgtgcg gctccatcgg 120
aacgcgcttg cgacgacaaa ttcctttttt cccccccgca gttaacagtt ctggggcaga 180
ggctggtgga gaggtccaga gcccactcag accgagatga agatgaggaa aagcatgagc 240
aggaagaggc tggcggctgc ggcgccacag ggaagagctc ggtgcgcggc gcagcctccc 300
gcgaccgcga ctcctgggct gcgtcgagga gccgcgttgc cataggaacc gtagcggcgc 360
cccagtgaaa ccctgcgttc ggacaggaga agctaaccgg gccgcccact cccacccgcg 420
cttcctcccc gcccccaccg gccgtgcgcg aaaagcagag atccgagaac cgcgtgcggt 480
acaaacggca aaagcttcgc gcgcattttc cgggagttga gcgcgcggcc gcaggcggga 540
acctaccgct ctcaggctcc cagcccgggc gctacgaccc tgtgggcgcc gcctgtgcag 600
cccctccttc cagcccgctc gggcgcatcc cccaggccgg gccagcgacg cgggcaccgg 660
gagcccctcc cccggtccgg gctttggccc acacccgggg accgcggagt gggaaaggaa 720
ccaaagcgcg gcgcctggcc gaccgcggac gaaattcgag gccggagggc gttttctttt 780
ttgcaaaatt gccccaaagc cagggcccat gtacctactg tctcctttgc cccacatgct 840
ccaagaaaat aagacacatt ctaccccgag tcctaattat tgggccattt ccttaacgcg 900
cggtctgtcc ccgtgggcag aaacatactg cgagatgcag tttggtaatt aacaaagaga 960
cgagacctaa ctgggcttcc gaaatgctgg atactgcggc cgggtcgccc cgcattcggg 1020
catcgcgcgg ttcccggcct tcgggacgtt ccggcccggc cggactttga ccgctggcga 1080
attaggagaa acgcagaagg cggacgctcc ccaatttccc catcgagcct tctcctcccg 1140
agtctgcgaa gcccctggct caggagacac cggctccgcg cctgggcctg caaatccgct 1200
tccagcgagc gcaggcctgt cgctcc 1226

<210> SEQ ID NO 49
<211> LENGTH: 332
<212> TYPE: DNA
<213> ORGANISM: Homo sapiens

<400> SEQUENCE: 49
gttacttccc aaagggcgtg ttctccaaga actgcattta gcatttcaga tcagagtgac 60
ccgaactcaa taggattacg acaaaaacta gtgagattca gataacaccg ttacatcgaa 120
agttttatcc gtgacagagg aaatattgct tacgccctta ggtaatttca aatgcacgta 180
tgaaggccgt gcgggtttct gcaggcgaag caaaagaaag gtggggccgg cagggtcgtg 240
gggcgggggt ggggcatgac acctatccca gacgcaactc gacctcgttt gcaagaaatt 300
ctgtatccaa ctctcttcag tgcgtttcgc cg 332

<210> SEQ ID NO 50
<211> LENGTH: 1226
<212> TYPE: DNA
<213> ORGANISM: Homo sapiens

<400> SEQUENCE: 50
gttcagtggt ttatagaaaa tttctttctc tctctcaggt ccactaagac cgagagagag 60
agagaagtcg actctggcac acccgggcga ggggctgccg ggattcggga gctggcgcgg 120
ttgatttttc cgagaatcct ccacttgggg tgacgtcggg cagcgcgcgc gggccgtgag 180
gttaatgccc aggcttttct ctaaagcgtc cgggaatgat ccggcgaata aaacgggtgt 240
ctgcaaagtt aatgaattgt acaggaggct gagggtgggg acttcgaccc ggggagccag 300
aggcggttct ggtggacgct tccccgtgcg cctaggggtg cgctgggctt tcccagccga 360
ggtctgcaga gcgcaccgcg tgagcttcat cgatctcatc ttcttccaag tgggaggagg 420
tggagatgct gggagagttg tggggagttg ggagtgggtt ggagggggac tgtctagatt 480
ctactctgga ggatccaatc acgtggtgct gttcccctgc ctagaacttc aaggtttcca 540
acggtttgaa taaaacccaa acgatgcccg atgtccaacg aacgaatgat ctagcctcgg 600
cctacttctc aggacttagc tttgtccctg cccgcgactt cccgctggga acgtcgtccc 660
cgccaccacc gctctgctta ggttcgaact ctgggccact cttcctactc cctctggttt 720
ccagcaggag aagcgcttcg gaggaggggg ctaggggcgc tcaacctccc gggttagagg 780
aaatgcaagt tgggccaatt tcgccctcca gactccgagg cggataggcc cagggggcag 840
cggccttgcc cggcggccac tgccctcctc ctcccccgcg cccccctggct aggctttgaa 900 gagctcattt taagaacttt tccattttcc ttttggaggc gtgttgttct tctcagtcac 960
ctcgcttttt ttttttttat gagcttcagc gctgatctgc acgttcttcc ctccgtgtaa 1020
tttcaatttg aactctcccc agagcggcct tttccctctt gttgcctgcc aagtcgttta 1080
aggctaagca aacattcttc ctccctcccg tccgcgcgag tctcggtcta cacccgcgag 1140
gggaggcgga ggcggttact ccgagagttc cggtgggttg gagcctttca gcagccgcct 1200
tcagactgtt tgggagccga aaagcg 1226

<210> SEQ ID NO 51
<211> LENGTH: 628
<212> TYPE: DNA
<213> ORGANISM: Homo sapiens

<400> SEQUENCE: 51
ctttgccgtc atcgcgggtg aatgcaccac taccttttgg cagttggagg ggagacccat 60
cagagccgga gaacctgcag ccacgacggc gaggatgtgc agtggtctct ggggaaacgc 120
cgccttcgcc ctcacccggc gcgtgtggcc ctgtgccgtc cgctcgccgc ctctctctcg 180
ctgctccgca ttcccgtgcc ctcttacttt cctctctggg ctcaagatcg ctacgcttta 240
tttctgcgtg agcttatttg aaaccttact tggtgtcccg gcttactctc cacgtctgct 300
ccagaccacg gtctgcccac gcacccctca gcctgcaccg cccacgtccg gcccaggtgt 360
ggtcgcagcc aagccccagc cgcgggcccc tgcgccctgg ctctctccct tgggttcagg 420
ccagagatgc ttgccccaag acctcgcccc ttgccttctt gggccacctg cagaacaccc 480
ttggttgtca aggacgtgag acagccgagg acggggaggc cccagggctg ttcggggacc 540
ttaagtgggt ccaacgggaa ggacgcgggc ctgcgaggga tgccggtcgg gcctggctgg 600
agccaggcgc gcaggtggcg catcttcg 628

<210> SEQ ID NO 52
<211> LENGTH: 1226
<212> TYPE: DNA
<213> ORGANISM: Homo sapiens

<400> SEQUENCE: 52
cgggcggacg aatggacgga ttcgagcgaa gcttatttcc cttctcctaa cgcatctacc 60
tataaatagc gctcaccgcg ctgagtcacc aaaaccccga gtttccccaa atagcgcgta 120
acgactgtgg gatcgcgtcc ctcggggctc tgtgacagac tccaaccaca cacccgctgg 180
gctggactgc gggcccacac ggcccagcgg gtctctcacc acccggcgcc ccagggacgc 240
gggcgaggcc gcggtgtccg gacgagtcga cagcgtcgga cttcccgcgc gcggacggcg 300
ctctggggaa ggaggagccg gcgggcggct ggacctggcc ttgactgcgc ggggtccgcc 360
cccgccccct cgggagcgca gagttgcggg gggccggcac agcctccgcc ctgcgccgcc 420
cgctcacaca atgggacgcg tcgggagggg gcggccgcgg ctcccattcc ggtcccaggg 480
cggggactcc gggcggcggg agaagcagtc gggctggggc cagaaggaaa acccccctctc 540 cctctgccca ctcaaactgc gaaagggctc cagccggcgg tgccaggggc tggggagcag 600
ctggggaggg agcggaagtg ccaccccctg cagtcaaggg tggtgacgtc accccctgcag 660 ccagcctgta ggggggtgtc tgtacatcac atgacccggc ccccctctcc ccgccgaagc 720
ccgcgcgcgc gctctctccc ccagccccga ctcccacctc tcccccgccc cctctcccca 780
actttcgccc tccccgctcc ggcaccgtgt caacagcgcc agctccgccc cctccccgcg 840
ccctgtggaa ccgccacggc ggcgcggcgg gcgctcgcgc tcaggtccga ggctccgaga 900
agcgagcgtg ccccggttcc accctgcccc ccagctcagt gctgctggct gcgtgggcac 960
cagagccagg gggcacggcg gcgtgcagcg acagcgcttc tctgctccat cctcccacag 1020
cagttagagg acgaagctga ggcgccgggt ccgagctcgg agggagcgag gcgcatgcac 1080
ggcctccggg ccctgacgcg tagcctccgg gggtcggccc acgggcgaga gaagcagccg 1140
ggagcccctc ctcgacccca gcaaggcggc ccgcgcctcc gctctcccta ccgcccgggt 1200
ggcgcacgcc agtccccgtc tttggc 1226

<210> SEQ ID NO 53
<211> LENGTH: 988
<212> TYPE: DNA
<213> ORGANISM: Homo sapiens

<400> SEQUENCE: 53
cggaagcctc atcccgccaa gccttcgcct cctcgctgag actctgagct gcgctggggt 60
tggcgggcac ccgattccgc cccggcccag accggtcact cagtgtgtgc atatgagagc 120
ggagagaagc gacctggagg ccatgggtgg gggcgggtgg tgaagctgcc gaagcctaca 180
catacactta gctttgacac ttctcgtagg ttccaaagac gaagacacgg tggcttcagg 240
gagacaagtc gcaagggcga ctttccaagc gggagatggt gaagtctttg gacgtgtagt 300
gggtaggtga tgatccccgc agccgcctgt aggcccgcag acttcagaaa acaagggcct 360
tctgtgagcg ctgtgtcctc cccggaatcc gcggcttaaa cattctttcc agctgcgggg 420
ccaggatctc caccccgcgc atccgtggac acacttaggg tcgcctttgt tttgcgcagt 480
gattcaagtt gggtaaccct tgctcaacac ttgggaaatg gggagaatct ccccccccgc 540
aacctcccgc accccaggtt cccaaaatct gaatctgtat cctagagtgg aggcagcgtc 600
tagaaagcaa agaaacggtg tccaaagacc ccggagagtt gagtgagcgc agatccgtga 660
cgcctgcggt agctagggca tccaggctag ggtgtgtgtg tgcgggtcgg ggggcgcaca 720
gagaccgcgc tggtttaggt ggacccgcag tcccgcccgc atctggaacg agctgcttcg 780
cagttccggc tcccggcgcc ccagagagtt cggggagcgg tgagcctagc cgccgcgcgc 840
tcatgtttat tcacgcggcc ttgagcagcc gagctccaat ccatattaat caaccgctcg 900
acctacacaa gtctaagttt acgggagaaa acctagtccc cgaaaggaag aacagcaatc 960
cggacaagca gttggcgcct ttgtcccg 988

<210> SEQ ID NO 54
<211> LENGTH: 603
<212> TYPE: DNA
<213> ORGANISM: Homo sapiens

<400> SEQUENCE: 54
cgacccagcc cccgaggaga acccagaacc gacccagccc ccgaggagaa cccagaaccg 60
acccagcccc cgaggagatc ccagaaccga cccagccccc gaggagaacc cagaaccgac 120
ccagccccga ggagatccca gaaccgaccc agcccccaat gagatcccac aaccgaccca 180
gcccccgagg agatcccaga accgacccag cccccgagga gaccccagaa ccgacccagc 240
ccccgaggag accccagaac cgaccagccc ccgaggagat cccagaaccg acccagcccc 300
cgaggagatc ccacaaccga cccagccccc gaggagaccc cagaaccgac ccagcccccg 360
aggagatccc agaaccgacc cagcccccga ggagatcccc aaccgaccca gcccccgagg 420
agatcccaca accgacccag cccccgagga gaccccagaa ccgacccagc ccccgaggag 480
atcccacaac cgacccagcc cccgaggaga ccccagaacc gacccagccc ccgagagatc 540
ccacaaccga cccagccccc acggagaacc cagaaccgac ccagcacctg ggcaacattc 600
tgc 603

<210> SEQ ID NO 55
<211> LENGTH: 902
<212> TYPE: DNA
<213> ORGANISM: Homo sapiens

<400> SEQUENCE: 55
tcagagaatt tggaaaggcc tactctgagg ggagtaaaac ttcaccaggc cctgggctgg 60
aagcacagga ggtcgcggct gggcccagcg ccctcgggag gccaagggca gggagccgac 120
ccaaggttaa gccctccagc tctccgtcgc gggtttgggt cccgtctcaa gagtggggcg 180
cgcgggctgg gcctccggcc tgacaccctc tcttctctcc atcagtgagc gacagctccc 240
cctaccacag ccccaaggtg gagagtggag cagcctgggc cgcaacaact tccccgccgc 300
cgccccgcac gcggtgaacg ggttggagaa gggagccctg gagcaggaag ccaagtacgg 360
tcaggtgagg aggcgagggt caggccaggt gggccgcgtg cggcggggat ttaggcgatg 420
gaacactttg tgatgggtcc ctttctgagc ttcccgcgag agaagcccag gctggcgtcc 480
ctttgctgct acgagccaga tccttcgtgg actggggcga agcagaggcc tgagcttgga 540
aggcggagct ggggcctcga cccccgccag gggccgggag cgctcgtcag ggcgctgggg 600
gtctggggcg gcagctcccc ggggcgaggc tctgggaagc gcctccaggc ctgtcggcct 660
ccgggagctt gggaggcggc tcccgaagcc ctttcggcgg ctctcgttgg gggtagagtt 720
aaccaaagaa ggcgcttctg aagggccgag cggagcagcc ctggggcctc agagccgcgc 780
cttcacgccc gcgaaacgcg cgccccggtc tcggccccac ggtgcgactg cggctgcggg 840
gtcctcacgt tcggactttc tctccggtgg ctctcggaca aacacgcttg gccaatcctg 900
cg 902

<210> SEQ ID NO 56
<211> LENGTH: 332
<212> TYPE: DNA
<213> ORGANISM: Homo sapiens

<400> SEQUENCE: 56
cgctacgaat gtaagatgaa tttagtggcg cggctgcctc cctgaatccg aacggtaatg 60
atggatttat caacggggat tcgccttcag cccagcgagg gaggtttact cagcaaatat 120
gtcggcggca cccacccaaa tgcaatcatt tgaccccctg cggacgatag ctgccgtgcc 180
ccttcccacc gctggtcctg cttggccagg gtcgctgggg gccagaggcc ggcccggatg 240
accagagagg tggcctcacg gatccttggc ctctcgcccc ctcctctgtt tcctcctctc 300
agcttgaggc tctcctggca agggggatcg at 332

<210> SEQ ID NO 57
<211> LENGTH: 527
<212> TYPE: DNA
<213> ORGANISM: Homo sapiens

<400> SEQUENCE: 57 cggggggtg gggcgtggag ggcggcctga gtgccgcgcc tggcccctgc cctgggtgcg 60
caccaggccg cgaaagccgg gggccgcctt ctcggctgct gaagcccggg agtcagtcaa 120
gcgcccttgg caccgcgagg gaggcgcacc tcgcctggtg cagagttgcc gcgacccgag 180
cgggaggagg cacaggacgc agggctcctg gcctggctgt gggcttggcc ttggcgcact 240
aagcgctccc catctgcccg agctggcctc cgcggccctc tcggcccagt ctacgttcgt 300
ttaaggactt cagcgcgaag aagagcgaac gtggctagaa cctgttgacc tctcctctgg 360

```
cctggaagtc cgcacagctc gtggcaacac tggacggacg gttgtcaggg gacgaccgcg    420

ggcaggtggg gaggaggcct tggtctggct cctggattcc accctgggac ggaaggggaa    480

gcggaaacct tgacctcagc cacacaagga cacctatctg gctgtct                  527


<210> SEQ ID NO 58
<211> LENGTH: 326
<212> TYPE: DNA
<213> ORGANISM: Homo sapiens

<400> SEQUENCE: 58

cgcctgctgc ctgccgtggg gccgctccga ggtgccagga actccggtaa gggtcccggc     60

ggcggcagcc cgggagtggg caaagaggga acatgcgtgt atttcaaaga aaccagcgcg    120

gtctctgact tccctgtctt cgctctccac ccccgctccc cctcaacaca cacataatat    180

aacagacgcg aagataatcc tgccatctgg caaatcccaa atttggtgac caagctcgga    240

aagcaacagc gacggctcat cccggagtag gtggctggtc ctgccggact ctccggagct    300

ggggcaaggg ccgtgggctc tgcccg                                          326


<210> SEQ ID NO 59
<211> LENGTH: 331
<212> TYPE: DNA
<213> ORGANISM: Homo sapiens

<400> SEQUENCE: 59

taggacctga aattgcagag acatagaaaa tcaatacgtg gtcgggagtc aactgcgcgc     60

gaccaagggc tctgccctcc ctctctccgt tgatttggac gctgggaagc tgcccgccgt    120

ccttcccacc ccctttgccc agccttggca agacctctcc ggaaacatac tcgcgttaag    180

gaactgggaa agcttcctgg cccggagcta ggagcccgac gttggggctc cttgctgagt    240

gagacgctca gtcctgtgct cccgccccgc cccaggcgcc cagtcccgct gggatccatc    300

tcctcagccc cggtttcccg ctctgcgagc g                                    331


<210> SEQ ID NO 60
<211> LENGTH: 1226
<212> TYPE: DNA
<213> ORGANISM: Homo sapiens

<400> SEQUENCE: 60

cgcgaggatg ggcgggctcc acgtctgggg gcgctgtgag cagggccaga gcgaaacctc     60

agtctgagtt tacgaactgg gaaggagcct gaaccccaga aacaccgtta acaaagaggg    120

cgaacgcagg gagccgagga gacgtctcct tggcctctgg ggaaggggct ggaggagcga    180

gccagctgag aagcggcttt gccgggtgtc cactagcggt tcgccagccc tctgtgcgcc    240

cgcagagtga cgcagaggcc gaccagtccc ctcccactc gcccctgggg cgccgccgca     300

ccttgatcac cccctcgcg gagggaactc ccaaggcgcg gcgctggccg ctgggtccgc      360

atggcccagt cctgtcgggc tccgctctgc tgccgccgac ttcgaaggtg tgcagtgttg    420

agccgtgtct tgttccgtgg cttcgagggg tgtgcgcgct tcctatacct ccccggaacg    480

cgcgagatag tcacacgcgc cactttgagg gtcaaacacc ccgcatctgg ccacatgtac    540

ctttactaac gtggggaggg ggcaaaaaaa tgtgtctctc cttcttaccc cgaggtgtca    600

ctcgcccaaa cactccctac aacttcttca agtcaaactt gggcaaggtt ggctggctga    660

ctgcgagagg aaaagagggc gcggaggggg cgcggcgcgc ggccgggtgt agaggccacg    720

gaggcgaggc gccgagcgtc ccctttgtcc tgtagaggga gctccagccc caaatttccc    780
```

tgctgcctcc cccggcccgc ccaccccggc ccgcctggag ccggaatccc ggctggaaag 840
gtgcggcggt ctgacacccc cgcaaccccc gcgccggggc cttagcagga tgcctcttct 900
agggcacgtg ggaaaaccca ccagggtgcc aagacgcaca gatctcccag gacccgggct 960
ccccaactct caactagagc tgggcagtca cacatcatct agaggattat gtacccctag 1020
gcgaccctct tctccatatc cgcctccacc gtcaccccac accctggcat ctataaagag 1080 gaagggggc aaccgggttg gaaggaggat ggaatctggg cttgcacagc ctcttatagg 1140
taacagtgag aaagcctcaa ctgtgtcgat caaagaatgg ggacgaaggg agtgatgaga 1200
acacgacccc gccaccgcgc aggcta 1226

<210> SEQ ID NO 61
<211> LENGTH: 254
<212> TYPE: DNA
<213> ORGANISM: Homo sapiens

<400> SEQUENCE: 61
cgtgtgacac tttggaacgc ttctctcgtt acaaaccagc gtctttactg aaggtccttc 60
cgctgcagag ctgcgcaatg gatgtgtgga cagagctagt cggcacgtgg aggctctcct 120
ggttttcagc aggaaacgtg ctgtgagcag gaatcgcgag tgagttccat ggcgtccccg 180
ggtcagcgcg cgtgcaggaa tcgcgagtga gttccatggc gtccccgggt cagcgcgcgt 240
ggggtcctgt ctcg 254

<210> SEQ ID NO 62
<211> LENGTH: 283
<212> TYPE: DNA
<213> ORGANISM: Homo sapiens

<400> SEQUENCE: 62
cggcggggaa tcgggtggcc acgcacgtcg gcctaagggg ccctggcagc gcccggcagg 60
acagccgtcc actgcacacc tcagagccgg cacccgggac ggtcagcgtc cccatgggcc 120
cggcaccgca gctgcccaga tcctcacccg cacacaggaa gggtccctgc aacccagcgt 180
ccaccgtgga gaaacatgaa cgtgagcaaa aatacggcct gcggtgggtg tgcgacccca 240
cacagaaggg cgagaggctc gtggccatcc cacacactgg gag 283

<210> SEQ ID NO 63
<211> LENGTH: 947
<212> TYPE: DNA
<213> ORGANISM: Homo sapiens

<400> SEQUENCE: 63
tttcgctaga tcatttgtta attgtgggaa ggaaggacgc atccggggag aggagatcca 60
gggctggaaa agtgggtgag cggcgctggc gcaggcggcc aggagagagc agatgaaccg 120
ttcgttagag cagcgaggta gtcgtgagcg ctgagatcca gagactagga cccactccct 180
ctctgagcag caaattggga agaagatgct cactcggtaa gggcgaggga gcccggcatg 240
gcgccccacc acgggctcgg tcttctgcgc gccaagatcc cgcttggggc gaggcgttgg 300
gtcagcgttt agagccactc cctgcgctgg tggctggaca tagcctccct atcccacctc 360
atcttccccc atccccgaca gaggaggttg tgaatctacg gcccttgacg ttgaggcgtc 420
ggagggcgca cctttgtaat tgcggcctcc cttcgcccct taagtgccgc ttctgggcgc 480
ctaggctgga tatgaaagcc ccgttcctaa tcctctgctc tggtcccctc ctctgactgc 540
tgggactcta agctaggccc tccccaggtt ccatcactgc ggcgccaacc cgcggctggg 600
ctgtccgcaa gagggagttg aaggcgcgcg gaatcccgag gtgcagctga ccctcctctc 660
aacgccgact cgccgctccc gcccggccac ctccctgtcg ggcagacttc ctgttctcct 720
gctcacagca gggaggcagt cgccgagccg gtcagcagcg tgcacggaga tcttcactct 780
gcgcccagcc ccgggacaca ggtgcagtct ccagcggagc actgcggagt gcgcgccgtc 840
gagcactagg gaatcctaga cggaggactt ggtccattcc acgcagtccc aggcaggtcc 900
gcagcggagg gacgcagcgg tctccaactc ctggtcacga cttggcg 947

<210> SEQ ID NO 64
<211> LENGTH: 289
<212> TYPE: DNA
<213> ORGANISM: Homo sapiens

<400> SEQUENCE: 64
agaggaggcg gagacctgac cccagaaagc agcactcaaa cagatgcagc tgcacccacg 60
cgcccgcctg ctgccagagc cactctccgg agcctgcagt cctgaagacg cctcagcagg 120
ggcaggcaga agacaccccg cgaacccccca gggccggccg ggcgcatcac tgggagccgg 180
ggctatctcc ctccgtcagc gtcttgaagt ccatggagag ggcctgctct tccgcctggg 240
aaggccgctt ccagtcggcc cggtcaagat gtagagcacc gccccaccg 289

<210> SEQ ID NO 65
<211> LENGTH: 368
<212> TYPE: DNA
<213> ORGANISM: Homo sapiens

<400> SEQUENCE: 65
cttctgcaga cagacaagag ccctccttac cttccatgaa gagtccgtac acgtaggagc 60
cctctcgcgg aggagcggtc atgtcctctc ggtttttctt ggtcacctcg acagacagac 120
acatctttcc aggggccact cgttcttcct ggccatggac tgcatgatgg ccgtgaggaa 180
cgactggggg ttgaagaagc cggccagcca cacggtggtg ggcagggcaa agtctgtcgt 240
ccaggcctcg agttcctgca aggcacacga gccgctagga ggagaggaca tagaatgaca 300
tgggaacgac cgggccttgg ccgttctgag caggggtcac gccagaacct tccacgggcc 360
actcagcg 368

<210> SEQ ID NO 66
<211> LENGTH: 265
<212> TYPE: DNA
<213> ORGANISM: Homo sapiens

<400> SEQUENCE: 66
cgcctcacgg ggcctgccag caacgcgctg tgtgcagcag gaagcccacg ccaggtcctg 60
acggctgcat cctgtgtgct ctccggcctg gccgcctcaa gacacgccac ctttgatgca 120
cacgcgctcc ggaggcacag gaaggacggg ggcactggga agtccatgtt tagtctcctg 180
acgtcgacca cacaaaccag acggaacggt gtccccggcc caggctgagc ggagcacacc 240
atgagggcag aggctacagg tgatc 265

<210> SEQ ID NO 67
<211> LENGTH: 1138
<212> TYPE: DNA
<213> ORGANISM: Homo sapiens

<400> SEQUENCE: 67
cgtcggacgt tcacaacgac cacgcttttc cccgcttcct cgattagcct ggcctccctt 60
gctccagtgg ggcggactca aatgcgcacg cacgcacacg ccgccaagcc ggtcaaccgc 120
agacaaactg actcttcgcc aactagtagc cacggagagc agcaaaggga ccaaggtcct 180
tcaccgcctg ctccaaaaag acacggcaac ctccagcggc gccgcagtag ctgcctctgt 240
gctgcagcct ccggtcggag tttaggtcta attccttaag aagtatcgct cctctgccct 300
tcgtcctact ccccttggct tcgcccactt cgcctccttc tcctcgggag gccaggagga 360
cccgggtcac tttgccaatt ctgcggaggg ggaagtagcg tgagggagat tcccacgcaa 420
gtagcccgaa gcccactact ctttgcccca cctctccact ctcttgcccg tgtaggtgcc 480
ggtgctgctg gcgaaagtcc cagttcttaa ggctcctgag ctcggaaggg gtgtgaggag 540
ccagatggga agagaagcag cgggacgagg gcgaggaagg gctggagatt gttagaggac 600
agatggggcg ggactgggga gaggggcgaa ggcgacgcgc cgaggcactc ctccgcccca 660
tgagcacaga cgtaactccg aaacgcgcag atgggccgta aggtaaagag gccttttttc 720
cctctcctct ccgtcctcta ccctgctccc ctcctagaca cttggtgaaa aagcaaggtg 780
cggtgtacct ggagcgaaca ccatgattct tccagccgct acgcccccag attaagagag 840
aaagacaggc agacggagga tgggaagaag gccggacttg gcggggtccg gtgcaggagg 900
gcgcgctggg cgggcggcgg gcggggcggt cagcaccccg gacgctcccg ccgctagatc 960
ctggggccgc agctccagcc gccgccgcgc gctctgcctc cacaatgcgg ccacagcggc 1020
ggcgggagga ggagggtgaa tccccgctca gtccatccct cattcctgtg ccagctcggg 1080
acgtacactg ctgcttaggg agcaaagcac ttccaccgct ttcacgcgac gaaggtcg 1138

<210> SEQ ID NO 68
<211> LENGTH: 315
<212> TYPE: DNA
<213> ORGANISM: Homo sapiens

<400> SEQUENCE: 68
gaccacaaag cgcttcctca tcctttcctc gccctttgat gccgccggca acgtgactct 60
gcgagcagcg gggcagacgc caggtctccc tcgcaggcgg gaaaggggct ccaaggcggg 120
tgctgcctgc tcgggtcaca tggctacgtg ggggccttgc tcaaattcac ttcctgcctt 180
cattacaaaa ctgtcaaagg ggatcgcacg tttgcagggt gtcacccaag cattctggtt 240
ttgcaaacga cgctgtgcgg cagcggtctg atacctgatg agctcggtgt ggcggggtcg 300
gcagcatttc ctccg 315

<210> SEQ ID NO 69
<211> LENGTH: 578
<212> TYPE: DNA
<213> ORGANISM: Homo sapiens

<400> SEQUENCE: 69
cggtgtctgg aggaagcggc gcggacagtc tcccgctcca ccgtgtcggg cctgaagagg 60
ccgctgaacg ctcgcgatta ctgaggcatc tggtaggatc gcaaggccat caacctacag 120
gtgaagccga ggcgctgtgg cgctttgaag ccggagagaa gctcagtaga atcgggaagg 180
cgctggggct gtccaactcc accttggcca ccattcgtga caacaaggaa aagatctggg 240
cgagttccca ggaggccaca ctgaggcggc caccaagttg acgcgtggcc gcagcctggt 300
gatggagaac atggagcagc tgctgagcat gcggatggag gaccagagcc agcgcaacat 360
gcccctcagt gtggtgctca ttcgggagaa agcccacagc cgttcgagaa ccgcaagcag 420
gagcagggcg agggcgccta gcccgagagc ttcggggccg gtcgagggtg attcgctggc 480
tttaaggcgc gccacagctt gagcagcatc ggggccagcg gcccaagaac gcagctgcaa 540
gaatccagcg ttaatgcgca gggtgatccc ggagggcg 578

<210> SEQ ID NO 70
<211> LENGTH: 682
<212> TYPE: DNA
<213> ORGANISM: Homo sapiens

<400> SEQUENCE: 70
cggccgttcg gtgctgcggt atcccatccc ccgcctgttt aagagaaatt gatcacgtta 60
agcgggccct gcgtcgctgc gcagtgcccg gactaccgct tggatggatt gacaagggaa 120
ggacgcagac acctaagagc aacaagggta ctttttaagc gaggttacat gtgtttagga 180
ctcgcgagga cgtcacgttt cgaatttggt aaaagtcctc ggtagctagg acccaacagt 240
tctgccctcc tggaaaccca atgaggtgac aaaactccca tctcattact gggagtccag 300
cgcactccgc caccgcggct gcagcttctg ctagctcgga gcctgcggac tccagccggc 360
gcgaactccg ccgcgactct ttctggctct ctcgctcacg ccttcggggc ggaaccgcgg 420
gcgccggagt ggtcccagac tcggctggga ccgggcagcc tagaagaagg gtcccctcag 480
tagagaccag gcctccagct ctccgtccgg cgctccgctc cacaacccgc cagtcatgtg 540
aggtccgtca agggagcgat ccctccgtct gcccgggctt ccgggctgtg gaccgcactg 600
aacccagtcc cgcagcaagc cctgctgccg ccttttcctg ggcacgcctg cggtggtgac 660
ggcccgctgc tatgtctcca cg 682

<210> SEQ ID NO 71
<211> LENGTH: 265
<212> TYPE: DNA
<213> ORGANISM: Homo sapiens

<400> SEQUENCE: 71
aaacacagtg ccgcagtgaa agtgggacaa acgcgcctgt gtgcatcctg gccgaggtgc 60
cggaggaagc gtggtcgggg cagaagtgtt aatgggcctc cttcctgccg tgccctgccc 120
gtgccagtcc tcggtgctca tcccggctcc ctgaaatgct cgcttccact cagggccagc 180
gcactccctc cacgtccctg gccgcagatc tgtcctgctt tgacaaataa cccgctcagc 240
cttcgggttt atggtttttc cgtcg 265

<210> SEQ ID NO 72
<211> LENGTH: 1226
<212> TYPE: DNA
<213> ORGANISM: Homo sapiens

<400> SEQUENCE: 72
cgctcccttt cccgcacacg cattgctgcc tcctctcggg cttggttaat gagtctgtgc 60
gccaagccag gtcgctccgg gcagttcgcg cttccgcgcc tcggcactcg gatgaccgtg 120
tcctattgtc tctctcgtga atgtcgctga aaaaaaataa aagtttgttc taagcccgtg 180
gcatttccgc gcgcagatgg aaaggcaagt gggagaggag ggtgcaggtg cggggcgggc 240
gcggcggccc cttcaggcgc cggggctggg ctgcccccgg ccgggagcag ctccgctccg 300
cgcacgtggc tgtgggcgct gcggacgggg gacggcaggc gggggacggc aggcggggag 360

```
tggagggtgc agtgcccgca ggtgccgacg gcttcctcca gagcccttcg cgccgcgcct    420

tgcctggctg gtggcgcggg gaaaccatgg cagcattgcg gctccggcgg gcgggctctg    480

cgcggggccc caccgagctt tccgggagcc tctcccgcag ccgatgggca tctagggcgc    540

agaacgaaga gtgggcgccg aaacgggtgt aggcgctgga ggccgacggg gaggcccggg    600

gcggtcaggc ttctcggtag agagggccgt gcacctcgcg gcctgcgggc taaggcgggg    660

agccgctcct gggcggccgg gcgcgcggac tggagggagg gaagcgccac ggactgggga    720

accggggtga cggggagacg gggggctgg tggggtgagg tcggcgggca gcagccaagt     780

gttctgcagc tccgaacccc gccacccctg ggcgaacgga atggcacccg cggagacggg    840

cggggacggg cgaaagcggg tttgctccga cccgaagctg agcccgggtt ggagggcgag    900

accgtaggcg agaatggccg cgcgggctgg gagacccggg ccgtatggag tgagtggagc    960

cgcccgaggt agggtagttg gggatggtag ttgtgaagac agtcggagtc tagctccggg   1020

cagacgaaac accggggcgc gccagggtcc gtttcctcct tctctctgct ttcccaccac   1080

cctgtagata cggagccagc agtcgggcta gagcggaggc tgagggtcgc ggttccaagg   1140

gcggtctctc gccccgggtc aggccccacc ccgcggtggc ggtcgcgtgg cgctgtcctg   1200

gagttgagct gtcccgcgcc gcggcc                                        1226
```

<210> SEQ ID NO 73
<211> LENGTH: 461
<212> TYPE: DNA
<213> ORGANISM: Homo sapiens

<400> SEQUENCE: 73

```
ctcgaatctt ggagacactg gcttctagtc gcacatctgc actttctccc acctgtggcc     60

tctcaggctc ggccgcccga gggagtttct tttattccca gttcggcttt cttttgcgaa    120

ggccgagtct gggcctgcca ggggcctgcc cgagtcctct atcgcgggtc cacgtggcca    180

ccaatgaccc gcggcgcccc cgcgtgtccc cgcagccact ccgcggaagc agcggcggga    240

gcgcaccacc ttcacgcgtt cacgctggac gtgctcgagg cgctcttcgc caagactcgc    300

taccctgaca tcttcatgcg ggaggaggtg gcgctcaaga tcaacctgcc ggagtctaga    360

gtccaggtgc gcactccccg ggctccaggg tctgggtagg gagctgaggc tgctcgggga    420

aggtctagga aggctcttga gtagttcttg aggagaccat c                        461
```

<210> SEQ ID NO 74
<211> LENGTH: 1226
<212> TYPE: DNA
<213> ORGANISM: Homo sapiens

<400> SEQUENCE: 74

```
cggtttggag aggggagcgc aaagcgctgg acgcatgcgg tacagtgcca cggccgccgg     60

tgggctccac tgccctgggg agctgaggcg cgacgaatga agcaccaggg cgcctggtgg    120

gcgccagtct ccggtctgga gcctgctggc ctgtccctcc ggggcgctga acccctagtg    180

cggcgtcctg ggggccgggc aggaaggatg gcctctccac ctgtctgcga atgcagccca    240

gccagtttga gcctccgcag aggtgcgctc cgggactggg cgcttctcgt gctgtgagaa    300

cgctgggcct tgttagctca ttaacccctc tgtctctagg gcccgttggc ggcacggttt    360

attttatttt acctgttttc ctcggagggc gcgaagactc cacccgcgcg gggacctggg    420

atcgacgact ttgatactag gcggtatccc ggagggctaa gtcggcggaa atccacttga    480
```

```
ccttgtagcg ttagtccttt cttttccttt cctttccttt ttctttcttc tctcttccta    540

tttatttatt tattttaaaa ataggattaa gacaccagta gaagctgtaa tcccgttcct    600

tcccccactc ccagtcttcc gggccgcctg gaggtccctg ccggagagag ccactttggc    660

gggcgcaagc ccctgggcgc cctctcctga ccgccgcgct ctcggctcgg cttggctgtt    720

ccgggctccc agaggctagg ggaagcgagg ggcgccaggg gcttcccggc ctcagcgtgg    780

ggcgaggtcc cggctgcgac cccggagaga gggagagggg ggccatgatg ctaggcgtcg    840

aggcgagggt tgagcctgtt tggcttcaga gaacgatgcg ggttcgaccg gaagcggggc    900

gcgtgttcta ggggcccttg ggtggattag ggggcgccaa gagggttagg cgaggagagg    960

cctggccacc cagttgctag actttaggcc gcactccagg aaggagcagt cggcttcctt   1020

cctaggccgc ttctattgcg cgccactcct tgaatctaag cattttccac tccaagaacc   1080

gttgggagag aggggagagc ggagcagagt ctctaggccc ccagggccgc ctcccggggt   1140

ggccacgcct gccggtagcg agccgagatt agctaggtct gtgctcgggc ctcagcggtg   1200

gccctggctc ttccctaagc agcggg                                        1226
```

<210> SEQ ID NO 75
<211> LENGTH: 1049
<212> TYPE: DNA
<213> ORGANISM: Homo sapiens

<400> SEQUENCE: 75

```
cgggcgcata acaggcaccc cgcacatcgc accgcggacg cagcgatcct cccatttgta     60

ccctaaggcc tgagaaggcc gctccacacc tccgcgtgca cagtccctag accagtgagg    120

gcggggaggg gaaatccttt tgttttatat tggaaacctt acgccaaagg caggcaggaa    180

gcaaccaaag gaacaacagg ccgcctgagc cgtggctcaa acagcacagg gcagtggccg    240

agcaccaggc ttttcggtgg agcgggatac cagcaggcag aagaggtgga caactctgac    300

cgcagactcc ctacaacccc gcgatcgatg ctccacctgc acgctcaaac gcacctgttt    360

cccaaattaa tccagacgcg aatttaacga ccgattttgt agatccggga aattctgtcc    420

accagcgtca cccaacacag caacttttac agacaatgcg tggcgtccgt tcctgctcac    480

ccaaagcggc ctctctgggc tgacagccac ccctgcgggt cctcaaaccc cactcaaacc    540

ctccgaaccc ctgtgtctgg gagcagtagg gtgggatgac tgcaggatcc cttgaagaag    600

tgactcgctg caaccccacc accagcagca aaaacgcttt cacccgggag ctgcatggat    660

gcgcggatgg cgggggctga ggggacgcgt gaagcccagg cctcttgctt gggctgggcg    720

attcccgccg tgggacgggt gggattgacc ttagtggagt ccagtccttc ggagaatccg    780

cgggcagtcg ggacccacgc tccggaacac ccaagtccga actcgtacac acagcacaat    840

ggcgtgcagc cgccggggcc ctaactccca gagacgcgtc tgaagaagcc atacaagggg    900

gcgcagcttc ggggctctgg ctgggaggtt actgcaggga cagcgcctcg cctccagcag    960

ccgggtccag gctcagggcc ggccggcctc tgctcgcttt ctgcttggat taccaacagc   1020

cactgggctt ggggagatcg gccgggccg                                     1049
```

<210> SEQ ID NO 76
<211> LENGTH: 785
<212> TYPE: DNA
<213> ORGANISM: Homo sapiens

<400> SEQUENCE: 76

```
cggcaagacg cgcaggaaga ccagcgcgcg ggatgcgtcc cccacgccca gcacggacgc      60
cgagtacccc gccaatggca gcggcgccga ccgcatctac gacctcaaca tcccggcctt     120
cgtcaagtcg cctatgtggc cgagcgggag gatgagttgt ccctggtgaa ggggtcgcgc     180
gtcaccgtca tggagaagtg cagcgacggt tggtggcggg gcagctacaa cgggcagatc     240
ggctggttcc cctccaacta cgtttggagg aggtggacga ggcggctgcg gagtccccaa     300
gcttcctgag cctgcgcaag ggcgcctcgc tgagcaatgg ccagggctcc cgcgtgctgc     360
atgtggtcca gacgctgtac cccttcagct cagtcaccgg gaggagctca acttcgagaa     420
gggggagacc atggaggtga ttgagaagcc ggagaacgac cccgagtggt ggaaatgcaa     480
aaatgcccgg ggccaggtgg gcctcgtccc caaaaactac gtggtggtcc tcagtacggg     540
cctgccctgc accctgcgca cgccccacag ataagctaca ccgggccctc gtccagcggg     600
cgcttcgcgg gcagagagtg gtactacggg aacgtgacgc ggcaccaggc cgagtgcgcc     660
ctcaacgagc gggcgtggag ggcgacttcc tcattaggga cagcgagtcc tcggtaagtg     720
cgctgcgccc acagctccgg ctgcaggcag taaatgcgcc ttgcgcggtg ggtctgtgtg     780
ccgcg                                                                 785
```

<210> SEQ ID NO 77
<211> LENGTH: 1226
<212> TYPE: DNA
<213> ORGANISM: Homo sapiens

<400> SEQUENCE: 77

```
cgactcggtg aaggatgatg cccggagggt gatctcgacc tttaacattc cacacaccta      60
cctccacgca ccaatcgccg gaatctccaa cccgcgggcc gcgtgggctt tctaccctgc     120
accgctgagc cgcggccacg ggaagaggcg cgctcccggc ggcccaagct gggagccaag     180
ctctaacggg tgtggcggga agtgtggtgg cccgccagca gctgccacga cgctcgctcc     240
accgacgccc agagctgtgg ccgggccggg ggctggcacc cgctgggccg ccactctcgg     300
ggattttggt ggcaaagcgg aggtcccgcc gaggctggcg aggtgcgcgg ctggctgcta     360
ggaaagagat ccagacggtc gcctggtgcg ctggatcccg tgccctttcc ctgaaaccca     420
gcctggcctg actgcaacct ctcccaactt cagtgccgga tcccctagac aatcagggtg     480
ggctccccgc tgcgagcgcg ccccacagcc gggtgccgcc aaaggtctcc tgctgtagcg     540
gtgactcaca ttcccagtga tttagaaaaa ctgtggtgcc gagtgaaaga aaaaaaaaaa     600
agcaaacacc cttagacaaa agaaaaaagc tccactcttt ccgcgagcgg gaaaaaaggt     660
ttggttcagc agtgatgcta tttcagtgaa tcagacgctc tggggctctg caaggaaacg     720
cacggactgg gagaaggaag tgggagccta gagttttgct ctcggcaaaa caagaactcg     780
gcttgtcctc ccaggccggc ggtttcctac ggcaagacaa ggcgcggaaa acatttttac     840
catctgacgc tgtagtctgt cctttagaag agaataggtg aaaagtttaa taaagaaatt     900
aagcgatgtg gaagtcgttc ccgctgcttg cagagggtgg ggagcgggcc tgggcaattt     960
cggaactagg agagaccacg tcggcaaagc ctgtggtccc gaacaagggc catggatttc    1020
ccatttctca gatcccggct gcccgacttc attcttgttt ctttcagcac aagccatccc    1080
ccttctccct ccctccacgt ctcttggcag agacagaaag ggacaccgct ctgcccgcgt    1140
```

ccagcgcgaa ggaggtgacc taaaacccat gggcccttct cacactgcgt tctctgcgct 1200
ccggcccagt tccggaggac ctcccg 1226

<210> SEQ ID NO 78
<211> LENGTH: 242
<212> TYPE: DNA
<213> ORGANISM: Homo sapiens

<400> SEQUENCE: 78
cgggttggag tcgacatggg ccctgacgag ggcactgatc agactcaccg ggggcgaagg 60
gggagagggc tcctgtgggc tcttcggttt cgagggcaaa cgacctctcc ggccttttaa 120
actgtcttgc gaaccactgc aaaggaagag ccctgttagc gccgcttttc cgagcccagg 180
cccagctgct gcctcggtcc ctccccgggg aaggccgcag ccgcggggca ccaggctgag 240
cg 242

<210> SEQ ID NO 79
<211> LENGTH: 943
<212> TYPE: DNA
<213> ORGANISM: Homo sapiens

<400> SEQUENCE: 79
tcctaaccaa tttcattctg aacagggaag acagctccta gcacatgcaa atgaccctct 60
tccaactccg gctccagcaa cttcgggcgg gggccagccg ggtcggctga atgcgagggg 120
gatgcgacct ggcctcccag tctttctgct tccctttctc agacacccgg aagtccccgc 180
cgcagcccat ggtctcctgc agggcagctt cggcggaccc cggagagctg ggcagtcccg 240
ggagagctgg ggctgggcta ctgcaccaag gcagagggca cactccgagg tcccgggcac 300
taggggctcc ctacctgcct actccgctcc cgccattgct caccttaaag aagcctttgc 360
agccctcaca ggtgcgcacg ccgtagtgtt ggcaggccgg ttgtccccac acacagcgca 420
cagcccctcg ttggaggggg agccccgcga cggcggtgag ggcacctgcg tgtcgagcag 480
ctgagacgcg tggccgatct gcaggcccgg gaagcccatg gacgcgggct tgcgatgggg 540
ttgggcacag cgaaggtctg cccgtccacc acgtggtggc tgccggcggg ctccgggttc 600
atggggacgt gcaggggccc gtcgaagcgc atctggcaac tagacaccgg ggtgccaggg 660
ggcgattgct taaggagaag agggagaggc gggagactgg cgttttcctc tgctcgatca 720
tgtgcgtagt ggccacgtag ttctggtgga agttgtggag agatcccggg tcgtcccaca 780
tggggctgtg ctgcacctgg aagcccgggt ggtgggcgtc gggggcgagg agggcttgta 840
gtaaaccgac ccggagtgcg gcatcatctc ctcagactgg gggggcaggt ggctgtgttg 900
ctggtagttg tgcatctgaa tgtcttctac cttaatggag gac 943

<210> SEQ ID NO 80
<211> LENGTH: 495
<212> TYPE: DNA
<213> ORGANISM: Homo sapiens

<400> SEQUENCE: 80
atacaattac ccacacaaca aagagggcct cgggagagtc gccagccctg gtagcatatg 60
aaccaggcac cggcgttgga gctggccagg gcagggcggg aggaacgcga ggcctgcgcg 120
cctttgttgg tgctttcgcc ttgatggatt tcttttctga cgctttccac atttcccgct 180
cccttttgcc gcctgggggt gggggtgggg ggttagcggg cagttgtgtt aatttgccct 240

```
ccactcccgg cgcccttacg gaatcccggt ggccgccagt cgccggcgca aatgccaagt    300

caccggtagg agacacaaca gaggcgatga cctgaatccg cacgtggcct ggttcgcctg    360

gaagctgcca aagcgaaggc aagagagccc gggaccctgt gtaaaacagc aagcagcacg    420

tgtcccaggc acactgttgc gggcccttag cctagctacg catccgcacc ccaggcttca    480

aaggcgcgct gggcg                                                     495


<210> SEQ ID NO 81
<211> LENGTH: 574
<212> TYPE: DNA
<213> ORGANISM: Homo sapiens

<400> SEQUENCE: 81

gaaagagatc cgtgggcttc tgaccctggt ttaggcaaaa caggggggagg cgccgagacc    60

agctcgagca ctagcggatt ttgagagaaa ctgaccgcaa cctccatcgc cttccccctc    120

tctttcactt ggatgggctg actctacccg tcggtgattt acgacgattg cagcgctagt    180

cacagcctgg cgcctggtgt cccctccctt cccaagcccc ctcagctttt ccactgccac    240

cggcgtacaa gcaagtgccg agcggcctcc gcaagtcgga ctagcctccc ggcgtccgag    300

gccaccacgg gcagcagatt tttggtcccc agcgaggctg cgcgcgttcg tcccgcctcc    360

gaccgccgag cagagctgct agcagaagca ggcgccggta ctttatataa tcctgctgct    420

cgcagggtgc aagagcggga aaagtgcgga gtagggaatt cttttgctgc gctgcctcct    480

acgcggagcc tgctttccac tgctgaaaag tgccgggcct tgggaagtgt ttttctttca    540

ttccttaccg aagcgtttac tgccgccgtg gtcg                                574


<210> SEQ ID NO 82
<211> LENGTH: 1226
<212> TYPE: DNA
<213> ORGANISM: Homo sapiens

<400> SEQUENCE: 82

cggctggcta ccggtgcgcg gggaccacac tcacaaaccg cattccggtc ttcccgcccg     60

aaaatccgcg ctgtgcgagg gacccacaag actggcggtc taaaagggac ccgcctcact    120

tggaaacggg ctgcggtagc cacaaccctc cggtagcggt agcgtaaccc cgttcggtga    180

tccagccgca cagcgcaacg ggtacaaaga accccactgg ctaaggccga cctaccaggg    240

cttgggggag gggagcggaa gacgaggtcg aaacgacctg tccagcagaa aactatcccc    300

aagcatattc caaccacttc tccgtagagc tcattccttc cgtgcatacg aagggcgcca    360

atccttcctg tatccctcct acagataccg ggtgactacg cttttgcgcc caaagcgcag    420

tgctctggct cagctcccta cagtagcgac ctccaccgca gattctcatc tcctcgctac    480

cgtaagagag atgtaaagaa tcagacgggt tacgcgctca ggcaccctca tgaagagagg    540

acctgggctt aaaactcatt cagtatcagg aaaagagcgc cgagcacggg cctattatgc    600

caaagcttct gaaaggggca ccacgttttt tgctctatgg ggcagatgac ccctccctaa    660

tttcggtttt catccatccc caaggtaggc tttggagtgg caccggagac tgagctcaaa    720

tttgcaggcc agggactggg gagaagggcg ccacactaag agacctgcac ccccattctc    780

gccctgtact ctacccagag tcgtggtccc ctccatttta aagcaaaatc caaaagcaag    840

cacggcggaa tcttctggaa gggggctaag atggaactca ggaggcgggg gtcggtatgg    900

aaagagcaga tggattattt ttttcctctc ctggcgaatg agggcgcccc cagccacccc    960

tcctcataaa caccccccaa ggcgcgcatg cgcacttagg tggcgggcgg gtacttaagg   1020
```

cgcggccacc gcggctgcgg cagtgcgccc aacagcggac tccgagacca gcggatctcg 1080
caaaccctct ttctcgacca cccacctacc attcttggaa ccatggcggc agtggcggcg 1140
gcctcggctg aactgctcat catcggctgg tacatcttcc gcgtgctgct gcaggtaagt 1200
ctgacggggt ttcggtggga gagggt 1226

<210> SEQ ID NO 83
<211> LENGTH: 339
<212> TYPE: DNA
<213> ORGANISM: Homo sapiens

<400> SEQUENCE: 83
cgtctaatcg atggtggggc gaagggagag ccacggcggc cctgagtgca agcaccatcc 60
tgaaaccagg agcccatgag gccgcgggag ccggaggacc aggaccgccc tcgcactgcc 120
ctgtgacagc tcccggccca gctctctgcc gctctggatc cgtcactaag cagctccatt 180
aagtgcccgg tcaggcagga gcggcaggga aacactgggg cacccacatc tgaacagaga 240
agatgcccac cttgagaagg tacctggaga agggagccac gagcgacgtt tatgctgaga 300
agcggcatcc gtgcacctca cctccgcccg tccacgccg 339

<210> SEQ ID NO 84
<211> LENGTH: 292
<212> TYPE: DNA
<213> ORGANISM: Homo sapiens

<400> SEQUENCE: 84
cgctcgggtg gccgagttac acctggctat aagtcatccc gtgcacctga ctaaatgcat 60
cccgtgcacc tgactaaatg cgtcccgtgc acctgactaa atgcgtcccg tgcacctgac 120
taaatgctcc cgtgcacctg actaaatgcg tcccgtgcac ctgactaaat gcgtcccgtg 180
cacctgacta aatgcgtccc gtgcacctga ctaaatgcgt cccgtgcacc tgactaaatg 240
cgtcccgtgc acctgactaa atggtcccgt gcacctgact aaatgcgtcc cg 292

<210> SEQ ID NO 85
<211> LENGTH: 329
<212> TYPE: DNA
<213> ORGANISM: Homo sapiens

<400> SEQUENCE: 85
cgcggagaga cacagggaga gggaagggag ttgcgctgaa aagacgcaaa gatacgcgcg 60
tgcaactccc tcccctttca ggtttcagag gtttgcaaac cagggctgag aggaaggggc 120
tcgggaactc acgttcctct cgccccccttt ctgtctggag tctcgcccgc cagaggctgg 180
ttaaccccag tcccggccgc cgcagacact gcgctgagct tttgggtcct cgccttgccc 240
agcgccagtg cagctgaagt gagagctggt gggaaatgca aatggctcct ggagaaatag 300
aagatacaga atgattctca ttccctcct 329

<210> SEQ ID NO 86
<211> LENGTH: 416
<212> TYPE: DNA
<213> ORGANISM: Homo sapiens

<400> SEQUENCE: 86
cgcggctgcc gcggctgggc ttccgcttct gctgcagcgt tggggttgac tctggggtgg 60
ggagggccgt caggtccagg tggtgctggt ctgctttaat gagcatcttg gccgtgttgc 120

```
cgggagtgcg agcttgccgt tgtgcatgag tggcgtgagg atggcctccg gctttgggtc    180

tttggattga gtgtccccaa agaggccgct gagcttggtg acgctgctca tggagccccg    240

gcgcgagtgg gtgagctcct tctcttgcgc tgcaccacag ccacgtcttt gcgccgatga    300

tcacagacgc agtagacggt gatgcccgag aagacggccc ccatgacgaa agccaggatg    360

actgcaatgg ccaagagggt gacgggaacc agctggtcgg gcctttgagg taactt        416
```

<210> SEQ ID NO 87
<211> LENGTH: 1226
<212> TYPE: DNA
<213> ORGANISM: Homo sapiens

<400> SEQUENCE: 87

```
cggccaaggc tggcggcggc aggtacccgg gtgccccgag ggccacccgc cgccccgctc     60

tggcgcatcc atcagtggcc agctttcacc gtgtctgcca ggcgggactc gccaggtgtc    120

aggctcatgc cataagcctg acacttgcgc ggggtcgccg tggctcctca gggaagctgg    180

gccaaggagg ctgggtcgcg ccggcgggcg ccgaggccac cttctcgggg caggccatcc    240

gcgctgaggc gcagacacgg cggtcctcca ggcccattaa taacccggag ggcgctgcga    300

tccgacagcg cagtcgccac aggctctatt tcccgtggcc gcctgcctcc ttccagccca    360

gttcgagtgg agggatactg ggcgcccact accgcccggc cggagggtgg gggtccctct    420

cgcgcaggct gctttggaga gtgtcggaga gagacagctt tatctacagc ttcacccatt    480

gtatagcaca acagaatcgc atttagcctg gagaacagcc gtcggggcag gagttgtgcc    540

ttctctaaca attaggctga tcgttaaatt tgctattcct ttcttccggc gtctagggag    600

agcgtgcaca ccaaaccctc cagaacagca ccccggtccc ccaccccgcc ccacctgtcc    660

ccgccctgct tagtgcctgg agggagaact gactggtcgc ttgagggacc ccatttcggg    720

cgcgcccttg gagtcctggg gctgcggctc ctgctctacc gggctgcagg cttgctctgc    780

cccgtcccgt ggcgtttggg aggcagtgag gaagcctccg agtctctggg tcgaaggaag    840

tgcgaatggc acccgcgata gactggccgt ctcccccacc ccgccccgtc tggtgatttt    900

aaatcgtctc ctgtgtaatt gtaaaaagag gaaagctgaa taccagacga ccagtataga    960

atctcttcga gacagcagat tgggcaagag acgggctttt tttcgcaata caaggataaa   1020

cacatcctga aactccagat agaaacctca ggaatgggcg agagggtcag aaggaacgaa   1080

gacagtaggg aagagagaga gagagacaga gacagaggga gagatgcaga gagactgaaa   1140

cgggaggaag aagcctggaa ctgtcggttc cgtggagagc ggacatgcta tctgcgccca   1200

gatccgaagg cttttgggga gcctag                                         1226
```

<210> SEQ ID NO 88
<211> LENGTH: 1226
<212> TYPE: DNA
<213> ORGANISM: Homo sapiens

<400> SEQUENCE: 88

```
cacagaagaa aaggcaaccc caggcataaa gaggctctca gcagcccctg cccgaacgct     60

cctggcaggc aagggcccca tagcaccctg gggcctcgag ggtcaccgca gacccggcct    120

gggaagaacc cgtagagtcc cgcagccgcg gagggagggg gttctcgcta aggcgtcccg    180

cggacaacgc cgagaggcac agcttagcgg gtgcgcaccg gacaggctcg caacgcagga    240

cggtgccctc atgggagcca ggcgagcagg tcaagaatgg tggtggggaa gcggggtagg    300

cagacctcgg cgggggctgc ctcggcgctc tgctcctacc caaggggccc ggttcccttt    360
```

```
ctacccacag ttccctttct atccgcctcc ctcctcagcc aatgaagcag tcggggctca    420

gcagtgctta gcacgctcgg actatggttt taatagacgt acatggacaa gtcgatatag    480

acagatttat tacagtcagt ccaacataca cagggacgct gtaaacaggg gcgcggccgg    540

agagcgggtg tgcaaagtgg gcgcagggcc ctggggccgc gccccttgct ctgccggctc    600

gactcttgca cggcgggcgg tgaggagggg gctgttcgcc cagacagagg gccacctcct    660

agcccgggag cgagcagagg gcctgggcct gcagctaagc tcaaggctgg ggtgttctga    720

gatggacctc ccccacctcc cgccaggccc gcactgcccg ctgtcgctcc gtggccttaa    780

tatagggctc cggggcgcgg ggccagcagg ctctaccagg cgcgccgggg ccgtgtgcgg    840

ctccactgag tgcccgatcc tgggctgggg gcaccgtccc cccaaaccca acgcccgccc    900

caacacggat ccgactcgag ctaaggcgct ctcggccggg cctgctcgga gagggcaact    960

tggtttgtac ggggtcggga aatcctaggc aagtccaggc cccgcacatc cagtccgcag   1020

gcccggccac tcagtccgga tccagcgcgg cggggacgcg ggatacgagg tcgtcctccc   1080

cggccgctgg gcctcggcgc tcgcctaccg cgccgcgtgc cctccgcgga gtgggcctcc   1140

ggggcccgtg ggaacacaca caccacccgc gccatcccga gagaaattgc aactcatcca   1200

ttttttcgcg gcactttctc cgacgt                                        1226
```

<210> SEQ ID NO 89
<211> LENGTH: 237
<212> TYPE: DNA
<213> ORGANISM: Homo sapiens

<400> SEQUENCE: 89

```
cgcgcgggac cggaggcgca caccggaggg gaggtgcccc caccaaaatt taagtgcggc     60

gcaacatgca ccacaggtag gggcactacc agggcaaaaa gacttggtga atgcgagggc    120

cgggcctatc aaaggtgcgt atggtggtac cagagcaagg cggaacagct gctcagtggt    180

ccgcaaccgg gtcaagggac aagaagacga ttctggattg taggccgccc gagagcg       237
```

<210> SEQ ID NO 90
<211> LENGTH: 1042
<212> TYPE: DNA
<213> ORGANISM: Homo sapiens

<400> SEQUENCE: 90

```
cggtgactcg gaacagaggc agaaaggatg cgaggacttc ttgctgcgta aacagcgcgg     60

cgggcagatt ggcacctggc acctaccagg actggcgctt cgtcccgcgt ttccattgtg    120

cccgcaccac tttgaaagtg ggcgccggaa actccgtttt tcttatgggg ccggggtcgg    180

gcaacgtggt tcagaggttt cacaagctcc agcacagaag tgatccaaac cgaggggtcg    240

gctcgaagtc ggaggctgat ttttcttgct cagtcgctcc gccggagctg agccgctgga    300

acgacccaaa cctacctgaa agcgcgtctc tgcagtcccg ctggacttct ccggctcgaa    360

ctcctaatct cagcccggaa tccagccata ttcatttaag attgcgtttt ccaaaggcca    420

aagcctttcc cggtttcgtc atcagccgcc aggttgggtc cctaattagc ctgtccaccg    480

agcttccttc ccggcgccgc ttggaccccg cagccccggg cgatctcagc ccgggggga    540

atccggagac gccggctccg ggttaagact ctgctcgtcc ccaggaggac ggggtcgcga    600

tccagagtgc gatccggaga aaagggctgc atcttgcgtg gctggcgggt tagactggaa    660

tccgtctggg gactgcgcac catccccatc gctccagacg ccgaaacaaa acctgaggct    720
```

```
cggagagggg aaaaagagtt gttcaggctc gaacatacgc atcccagcct cataggtgga    780

tggggttacc gagctgagaa ccaagccgag gtccgcgaag ccgggccgcc cccttgctct    840

gggcctccct tcaagcctgc agtctgggga tgggttccga gtcaccgcgg tccgggcctc    900

ggtcaggctt ggtcgggcac acagggcgtt tcagaggcca gatgacaacc tgtggcggca    960

aaaggactct ccctcaccag ggacccgcga aggcgcgcat tgcaagatgt tagcgtgcgg   1020

gctttagata tccttgcgtc cg                                            1042
```

<210> SEQ ID NO 91
<211> LENGTH: 1226
<212> TYPE: DNA
<213> ORGANISM: Homo sapiens

<400> SEQUENCE: 91

```
cggggtccca cgcgggcggc gcggtcttcc ccaggcctcc ttctctggag acccggttcc     60

caggggacgc tgtgcgggga caggcggagc cggccccttgg agcccggcgc gggcagaggc   120

gccgcgggac aacgcctccg acggcagggg gcgctcgtag cacgcgcagt gcgcggtgcg    180

ggcgcccagg acggctgcct ggccccgggt tcccgaggcg cgggacctgc cggggtgagg    240

tgcccccagc ctgagagccc cagctgggtc ggccaagggg cctccgggct tccacatcgt    300

ccctttttct gctgacgctc gcggggaagc ggcgggaagc ctgtgagggg cggcctggga    360

gcagacggac caccaggtca ccggcgcgcg ctgccaggcc cgacccactc gcgaggacca    420

gcggttcccg gaggcgtcgg ccctcaggtc ctcgggggag gccggctgca ccgagccggg    480

tgtcggcctt gtccctgtcc tgagaggtgc aaacaccggc cccggcccag gccccggggc    540

tcctgcccag aaggctcaga gctgggggcc gaccgcgcct tacccgcagg aggcccggcg    600

gtgcgtccgc gttggtgcca ctccccggcc ggggtgaggg acgtcggaag gaaggtccca    660

gggcgcaggg tccgcgaagg gagcactcgg aaggaaggct ggctgcggcc ccggcgcctg    720

ggtccgctgc ggcgccgggc cggagacctg ggaacagcca gccacctgca aggttgcagc    780

ccacctcacc ccgccggcgg ctccgggctg tctgtgggtc tgtctcacgg ggcaaagcct    840

ttcttcccac acccacagcc aaggcgcgtc cgtgcagggg cacacgcctt ctgctccagc    900

cccaggaagg cgctttcgcc ctgcagtcct ccgacggccg gctccgccgc accgcgcacc    960

ctggctccgg cagactctgg ggcctgggga ctcgcccacc ctgcgcggcg cgccccccac   1020

atgagccgag gttgggaggc tgcggggcct ctgtcctccc aggccgtgga gtgcggcggc   1080

gctctgagtc cgctggggac ctggatggag agaaactggg gctcgttcgc gcacacatgc   1140

accatttgtt ctttccgatc atctatccct ttacgaattt tatttttatt ccggattgtt   1200

aatgcaagac gacagttgaa tctcca                                        1226
```

<210> SEQ ID NO 92
<211> LENGTH: 583
<212> TYPE: DNA
<213> ORGANISM: Homo sapiens

<400> SEQUENCE: 92

```
cggcctgcgg tggggaagcg ggtacgggag gcccagctct ccccaccagg gtcactggag     60

aggagcagac gcagccgtcc gccaagaccc gggcacgagt ccccagcagc tgtcactgcc    120

ccaaactaac gtgaccccac gtccaccagc aggtgaacag ataaaccaac ggccgatcca    180

cacaatggca ggccacccag tgcccacaac accacgactc tccagactgt gcgagcagag    240

cacccgcaag ctccctcggt ataaactcaa cgcagacaaa cccacagggc cacagggcgg    300
```

cgcggactgg gaaggggcaa gaggggtagc cggcgatggc catgtacact gtggcctccg 360
ccctccctcc ctgcccggcc agggcacctg ggacggcggg gggagcggca gagttgcgcc 420
ctcaccttgc agacgctgct gctggcagcc ccttcgctgt gcagtaggac ctcaggcacg 480
ggcacccgca gctccggccg ctgtaggtag agctgcagga gaaggtctcg gcagccctgc 540
ccagcacgct ggaagaggtg gagcagggct caccaggcgg acg 583

<210> SEQ ID NO 93
<211> LENGTH: 560
<212> TYPE: DNA
<213> ORGANISM: Homo sapiens

<400> SEQUENCE: 93
aacacagtta tgacacagtg agcccacagc acagttagcc tgcagcacag tgagcccgag 60
acacaggtat gacacagcga gcacatggca tggtgaccct gagacagggt tacgacttgg 120
tgagccccaa catggtgagc ccaagacggt tacgacatgg tgagctcacg gcacagtgag 180
cctgagatgg ttacgacacg atgagcccgc agcacggtca gcctgagacg gttacaacat 240
ggtgagcctg tggcacggtg agccaagaca gggttacgac atagtgagcc cacagcatgg 300
tcagcccgag acagttatgg cacagtgagc ccgcggcacg gtgagcccgc agcatggtga 360
gcccgagacg gttatgacac agtgagctca cggcacggta gcccgagaca gagttacgac 420
ttggtgagcc cgcggcatgg tgagcccaag acagagttac gacttggtga gcccgcggca 480
tggtgagccc gagatggtta cgacatggtg agctcgcagc acggtgagcc tgccatggcc 540
tcaagggtta agatgtaaac 560

<210> SEQ ID NO 94
<211> LENGTH: 336
<212> TYPE: DNA
<213> ORGANISM: Homo sapiens

<400> SEQUENCE: 94
cttctcagca aaggccaaca cgtctttctc gagtccaaga ccatctcccg ttcaagggcc 60
ctcaccgcgc tttgtgagtc tgtctcgtgg gcctccttca gtggtctgtg accagcggga 120
atgaatggga cgtgttttgt tcagccctga ctcttggacg ctggtggcag ccgcgggcgc 180
ccactcacct ggcacgtgga cgaaggtgat gagcgcggct gacggctccc gggggcagtg 240
tggggtccag tctgaagccg acgccctctc ggtcaggctt tcagcagcag aaggcagtgg 300
actcttcacc atttcttcca acactttctc acgtag 336

<210> SEQ ID NO 95
<211> LENGTH: 646
<212> TYPE: DNA
<213> ORGANISM: Homo sapiens

<400> SEQUENCE: 95
aaactgaggc aaccaactta ttcgcaagag taaaacccta tggggagaag cgattcctgc 60
ccctcttccc ccggcgagga acacggctgg agccacccag gcgccttcca ggctaaggcg 120
cctttagggc gcgcaggggt gagggagagg gtggggagag tcctaattat tatgaatttc 180
taaaggcgca gtaattattc acggggagca ggacaaacca tggctaggca gggaaatcga 240
tatatttgct atcgaaagtt cctgctcgcc tttaatgcag acgaatgggg gatgcagcct 300
cattattttc cgtggttagg ctcgccagcg tggggcctga tgcagcgtga aatctatcat 360

```
cattagaccc gggatggagc ggcggggggg agtttctctt acttaccaaa ccgcaacaac    420

aaacaaacaa cgacgaacaa ccgcccccta caaacactca ttctcacaca acgttgccct    480

acctccctcg ccgcttgccc tggccgctgt tgcacactcc cctgggggct gtctgacgcc    540

ctagagcaga cactgcggtc acttaaagtg cgcccagttc ctccaccgca gcggtcacac    600

cgttgatttg atccagaaat aagacggata gtaccgagcg ttggcg                   646


<210> SEQ ID NO 96
<211> LENGTH: 330
<212> TYPE: DNA
<213> ORGANISM: Homo sapiens

<400> SEQUENCE: 96

cgccgccgcc gtctgtctag actcaagcga ctgaaggggc caacagagct ggtgtttaaa     60

gtagaacctg cccagtccaa cagcccgagc agggagcgat ttcggggatc gcgggaagga    120

acgcactcgc caagggaggg ccgggtgccc tcgccaccgg ctcattcctg ctccggtttt    180

gcccgatgcg cgtccaggag gttctggcag gacgcactgc ccctctgccc cggccaagga    240

ggatgcggat actgcccgca aggttcggcc tttatggacc caagtcagcc aactgggccg    300

agtcctgcgg acaccgaaac ctccctttcg                                     330


<210> SEQ ID NO 97
<211> LENGTH: 1226
<212> TYPE: DNA
<213> ORGANISM: Homo sapiens

<400> SEQUENCE: 97

cgcctgtgct ctggactcgc tgtgcagggt ccggctccga ggcgctggtc ggcagtccga     60

acggagggag cgagaccccc aagagcaacg gcggcagtgg tgggggcggc tcgcaaggca    120

ccctggctgc agcgccagtg accagatgcg tcgttaccgc accgccttca cccgagagca    180

gattgcgcgg ctggagaagg aattctaccg ggagaactac gtatccaggc cgcggagatg    240

tgagctggcg gccgccctaa accgccggaa accaccatca aggtatgcgg ggtccaggct    300

ggggaggcgg gtgtgcacct atttagcggg aagtaaatgc caactgccaa ctccctgaaa    360

cgcaggccag gaatctgggc ctggggtctc cctgcccggg cgtgcagatt gaccctcgtg    420

acagctccta ggcaggcatt gctgccatgt ggctgactct gtccctttcc tggttaaata    480

gacaaggggt gggcgtgggg gaaggggata gagtgcctgt gcgggtgaca aggaatttct    540

ggggacacgc tctctgcggc cgcagaccaa ttgagtccat gtcctttcac tgctcctccc    600

atacacacac tggcctctgg caccccgggg gcctggccac ctgggcagaa ggaaggaggg    660

agcgggctgg atcactcccc aaacctctct cggagggatt ccagctccag gtggtggtgg    720

tggggtcggt ctctacccgg ctggtgtctg ctttggctgt tcctgccctg cgaacactgt    780

ccccggagcg ggaccagact actggccctg agcatcgggc caagtccagc tactgaacct    840

gctccgctcc tctccccagg tgtggttcca gaaccggcgc atgaaggaca agcggcagcg    900

cctggccatg acgtggccgc acccggcgga ccccgccttc taccttacat gatgagccat    960

gcggcggccg cgggcggcct gccctacccc ttcccatcgc acctgcccct gccctactac   1020

tcgccggtgg gcctgggcgc cgcatccgcc gcctccgccg ccgcctcgcc cttcagcggt   1080

cgctgcgccc gctcgacacg ttccgcgtgc tgtcgcagcc ctacccgcgg cccgaactgc   1140

tgtgcgcctt ccgccacccg ccgctctacc ccgggcccgc gcacggactg ggcgcctctg   1200

ccggcggccc ctgctctgcc tcgcct                                        1226
```

<210> SEQ ID NO 98
<211> LENGTH: 485
<212> TYPE: DNA
<213> ORGANISM: Homo sapiens

<400> SEQUENCE: 98
cggacttgtc cccgcagccc ttgcggacct cctggtcgtc atggcgactg tgaaatgtgg 60
ggtggggagc atgcgttcga agccatttgc gcgggcagtc cctgcgtgtc cccccacgtg 120
ctccccacac tcgcaggacc cccgcctccg agcttccctg agcgtgcagc ttccagtgag 180
ggcagcccca cgcacagccc cccacaccct ccccaacgcc ttcagccccc ggtgcgcgta 240
gtccccaagc ccacacgtgc acttccacct tgcggcagct gcacgtacag ccccccacac 300
gctcccagcc ccactggcgc agaacccatc accgctcgcc cttcacgcgc ttcactggga 360
gtgcagcccc caccccgagc gcgcagctcc acgcagcctt ccacactctc cccagcgcct 420
gcagcacccc cagtgcgcac agctctgcca gtcgcttccc cgcgtgccgc ccctgcacca 480
cttcg 485

<210> SEQ ID NO 99
<211> LENGTH: 564
<212> TYPE: DNA
<213> ORGANISM: Homo sapiens

<400> SEQUENCE: 99
cgagcacggc ctcggaggct gagaggcctg ggaggcaggg ccgcgtcctg cgggctccac 60
gagagccctg tgaaatgcca gtcagatcct ggcccagtgc cccaggtcct cccgcagcct 120
cggcaaaccc tcccccggcg ctggaaacct tcccctgcca ggcgcagaag gccgcgcgca 180
agcacgcagc tcacagtcac cgccacctgc tctgaaaccc caggttcagc gcaggatcag 240
agtcccccat ccccacccca cgcaagggac gcaggattga cagcgaccct gaagaaatgc 300
agtcgagagc tattgtgaaa gggcgctggc ccggaggccc cccagcccgc gcaggacagg 360
ccagttaatc gccttggtcc caggccccta ttagcgtgtc atctgcgaca gcaggacacg 420
ccttcccatg ccagccgctt tggggcccgt gcggcccttt ttccctcgca gctgctgcaa 480
caaatagcag ttcttttgag ggaaggaaca gtgtggtcct caaagttcat aatgaaaatc 540
ttggagaaaa gtcatagttg ctaa 564

<210> SEQ ID NO 100
<211> LENGTH: 1226
<212> TYPE: DNA
<213> ORGANISM: Homo sapiens

<400> SEQUENCE: 100
cgagcgggac gagccctggg gctcccacac cgctggagac tgcggcgagt tacacgccat 60
tgggtcgctg gagctgggac tgtgctccgg gggcatctcc ccgtttttca tgatcttctt 120
gatcttgatc ttttgttctg aaaccagatt ttcacctgag ttggggaaca aaggcacacg 180
ttaccgggac actcagaggt cgcccgcgcc ttccccgggg cggcgactgg aggcatcttc 240
ggacctctgg gcggcccagc cctcctggcg tctccccgcc gcttgcggcc taccgccaag 300
aagctatgcc ttaggcaaac catggagctc tggccccaga gggcgccctg gccggctcgg 360
ggcgccccgg cccagcgagg ccacgacccc aaggcttgtt tttgtttggg ctgggggtgg 420
gggacgccag cgcggcgggt gtgcgcccga gtgtcctcgg cggcggcgcg cctcgtgtaa 480
gcctgcgcag gacgcgcgga acgcggcgaa ggtctccaaa acaatcgcgc gagccggcgg 540
ggaaggggcg tggggcgggc tacgcgcgcc tgtggtcaga aaaaggagcg agctcccaac 600
ctcccgtcct actcccttca ctccctctgc agctcagaga ggccagaatc tgactgcagc 660
tcttggcggc gctcgaacat tctttatgct tccgtaggcc ccagctgggt tggaggagta 720
aaaggaatgg gacaatccag gaagacttct cacgtacaat agcgcccccc acctcgcgac 780
ccttcggtgg ccgtggcctg aagctccgta ggctcagggc acgacccttc agtttctccg 840
ctccaggcga cgttctcagc cttttcttag cctgagacca ccgcgagaac accaggcctt 900
gctcaccccc gaggaggctc tacattgtta agaaaaccag atactgctct gggctgccta 960
ggccgcccta gaaataaccc tccgcttgct ttcaacccgc gaaattggcc ccacagctcc 1020
ggaggcccgc tacggggtgg gggcgggggg cgcggttagt gggaggtatc tccagaccgt 1080
gatgaatacc atccccaccg tctcaaggcc tgactcaccg agttaaagca taggggctga 1140
tgtctttggg tctgttagtt tctcacgggt actgtcaaaa cagctccagt cccatcgaga 1200
ctgaaccgcg cgaccaacca gacgtg 1226

<210> SEQ ID NO 101
<211> LENGTH: 331
<212> TYPE: DNA
<213> ORGANISM: Homo sapiens

<400> SEQUENCE: 101
cgattcaaag atgccggcgt cccgcagtgt gcggttcgtg cccttaacca cccgcttctt 60
tgtttcccgc ccctctgctt tcgcaggagc tcttgtgctt gagttcagtg ttagtggtag 120
cgtggctact ccacttggag gtggcggccg tctgaccgtg tgttactgct ttgccgacgg 180
ggcctcccgg ccctgatgcg tgtacactct gcgggctgca ccgggtggct ctggttgggg 240
gcgaagctgt gttgactggg agacgttgga aattgagaca tggagagatg acgggagtgc 300
gtttctctgg gtttgatctc catcctgttt t 331

<210> SEQ ID NO 102
<211> LENGTH: 1226
<212> TYPE: DNA
<213> ORGANISM: Homo sapiens

<400> SEQUENCE: 102
cgcggtggcc cccgcacccg gagcgtcggc agcacctgga gcggttaggg ctactctgcc 60
gccgccgccc ccgcggtccc cgccgccgct gtccccgccg cggtccgtgc gcgcgggcgc 120
cagtgcacca ggagcgcgtg cgccaggcgg aagggcgcga aggcccggtg cgcccagctg 180
tgctcctcga tgaccgcgta gcacgaggcc agcacccggt tgatgagaat ggtgccctgg 240
gccgtgagcg gcgcgtaggc gccgcggcct cctcgcttag ggtcacgctg tgcacagcgg 300
cgggcaggag ccggcggtcc ccgtcacgct cggccaccac gtacacgcgc tggcccgggc 360
gcacgcggct ggcgaacagc gcccgaggcc ccagtgcgcc ccggaaggcg gccccgagcc 420
cgaggacgcc tcgggctccc cggtggccga gtcgttgtgc ggcgccacaa agagcaggtg 480
cgcggcggtg agcagcaggc gctcgcgcgg ctcccgcgtc tcgatcacgt agaagccttc 540
ttggcgccgt cgtcgcggtc caggaaagtg aggaagtcgc tgtagagcag ccggccctgg 600
tcgtccgccg ccagcacgcg gtccccgggg ctcaggtcct tcaccagctt ggtgccgccc 660
tgctccaggt gaccgtggcc gagcccggga agcagcctcc cgatttggcc gccaccgagt 720
tctctgcggg tgaggagaag ggaaagaaga gaggacaggg cattgagttc cgagagggag 780
gcgcgtctcg gggaggaggg cgcacgctgg tgcccgcgct cctaggccag gggtgcgcaa 840
ggcgcggggc ggggcgattg attccaggcg ggtcccgcac acacctccct cccccaaccc 900
cactgcccca gggacaggat tccgacacat tccttaacga ctcctaagtc tgggctggcg 960
gtcacagagg ttggctggcg tttcctgcag aggccggtga cactctttcc ttccgccttc 1020
ctccaacccc acccccagct ccgcacacac ccggcctcgc cgcgaatcca tccagagggg 1080
tttgctctgc acttggattc ctcaggaagc ctccttgagc tcccgcgggc gccgggcgca 1140
ccctccttcc ctcccgcccc ggcgcggggc gcggcgcctg ctcgcgcact cagcacccgg 1200
gctgcgcggc ggaaaccctg gcccgc 1226

<210> SEQ ID NO 103
<211> LENGTH: 337
<212> TYPE: DNA
<213> ORGANISM: Homo sapiens

<400> SEQUENCE: 103
cgcacggcct cctcgtccct ctcgggcaag gctatcagcc agagcacctc ccctttgaca 60
ctgaccggcg tccccagccc cgccttgtta ctgcatccgt ctgaggtaca aggttagaag 120
ccacagaacc cgagctgcag cctgacccac acaagctgcg ggcgcaatgg cgctttgcag 180
acaagacagc ctgcccgtct gcccttcttc tcggcttccc ttaagacaca aggtgacgac 240
acggacggtt tcaagtgagt gcatctggaa ataatctcag tgcaggggag gggttgaggc 300
caaagatgtc gtgacctggt ccccgctgtg gccaggc 337

<210> SEQ ID NO 104
<211> LENGTH: 1226
<212> TYPE: DNA
<213> ORGANISM: Homo sapiens

<400> SEQUENCE: 104
cgaggtataa agaccaacgc acgacgggcg ccggggcgcc gtcacctgcc tgggttaaca 60
gttcctgccg cgggggcagg gagaaaggcg ctagaggggc gcggggtgcc ggcggggccg 120
agcccgggcg cgggcgagcc ctgggtgcca ggccctgcgc cgcacgccac tctcgcagcg 180
ctgccgccgg gaaagtgccg gcgctggctc tccctcccct cccgggaata gcgggcgcag 240
gcacgcacat ccacacacat ccaacacaca cacacaccgc acactcacac acccgggtgg 300
ccgcgcgggg ctccgagccg cgcaggcctc cttggcagac atcttcctgt gggaggattt 360
caaacgagcc gtgaaagcca gaaactacac gggttacaac tccggaatcc ctggccggcc 420
tcggcctccc tccccacctc cggcccggcc ccctccgttc ggcccgtggc caggagcccc 480
accaaaggac aaagctcaca cgccgaaagc gcggggagat ccgggggcgc agagatgccc 540
cgacggccct tctaccttct gaccctggga cccacggcca agtgccgcgc agccgaggtc 600
ggccttgctg atctgtggtg gcccagggcg acccgaagcg caccggcttc agggtgcgcc 660
ctggccaggg ctggggtgga gggtcacata agccacctgg catccgaggg tggccgcctc 720
gccccctcaa cgccgctctc cagggaagga ggcggcgggg tcaccagggc gcagctgaca 780
gccccaggcc ccggccaggg cgcacccaaa gaagagggag gctgctgcct gaactggcct 840
gggggcagag ggaagtgggc cccgcgctgt ggaaggcccc aggctggagc gccggggaca 900
gctgtccaag cggcgagggc taggagtggc ctcgcctagc gctagccggc caggccctgg 960
aggtgctccg cgccttctcg gccaaaagcc agctccgcgc cgctggcgga gtgggaggga 1020

```
ggcggccagg cgagcgcccc gccttcgtcg cccgcggtca caggggcaat tacactcctg   1080

ctgcagacgg ttaccagctc gcccgcgcat ccctctctcg gctcccctct cctcccctct   1140

cctctcctcc cctcccctcc tccgcggaac tgctggctcc atattagcga gggtgccctg   1200

gcagcgcgac cgaggcaact acccct                                        1226
```

<210> SEQ ID NO 105
<211> LENGTH: 468
<212> TYPE: DNA
<213> ORGANISM: Homo sapiens

<400> SEQUENCE: 105

```
taggcaggag gaggaggagg aagagggcac ctgctgagat acttcactgg tctgagggcc     60

ccttctgccc cagctagcgc ttgggtgagg gttgggcttg cggagccgtc ctgtaaagcc    120

ggggatgcag gacgcattgt cacccccctcc tgccgctctt acgaaacact cttaattgag   180

tccgattctt ggtgaatcag ccttccaaga accgcgaccg cagcatcctg tgccgcttct    240

gtgttccgca tttttctctt tctgcagcgt ttcctctcat tctggatgga aagcctgttt    300

gtctccctca atctttggcg agggtggcag gcagccaggc ggccattacg ggccgcgcct    360

cccaccagcc agtcgctggc aggagcgtcc ggggagggag cagaccccgt tcaccctcac    420

cccagaactg aagcagcgag gggacccaga cgagctggaa tgcaggcg                 468
```

<210> SEQ ID NO 106
<211> LENGTH: 1324
<212> TYPE: DNA
<213> ORGANISM: Homo sapiens

<400> SEQUENCE: 106

```
cgcgctccgc cagcaagacc tggcgtctgc aaaacacagg cgtgaggggc gtgcttacta     60

atgcctggtg ttccagaagg cggctcccgc caggcctccc gagtaggaag gagagggctc    120

ggcccgccag acacacacac acccacctgc acacgctgct tctctgggct ctgcctcacg    180

gttctcacgc tgcagctccg gtctcgcgcc tccttttacg ttgtttaggt ttctttctga    240

catgactgag ggaagtgcgg ttcacaggca gagctgcctg gggagagagg tggcaggcgg    300

cccgttgttc accgggcccc ggcctcgcta aattcacacc tcggcggcgt ctggcagctt    360

ccgcggcgtg ggctttagca caacacaacc ccgtcggccc tcagagctgc agggttgccg    420

acgtgccctc ctgcgcgtgc cagtccctcg ccccagccgt cccccgccac tgttgtcctt    480

gattctggtt ggaggtgtga tttcccacat acatattcat gtggtgtgtt tgcagcgtgg    540

ggtgtgagtc acacggatat tttaatgggg agagtggggg ggcttgcgga ggcgccgggc    600

ggatggacgt gtccatctgg ctcgtgggga gacccggggc cctcagatgg tgcgatgtct    660

gaggctgccc tcctcacatt gatgggagcc agggcctact tggcttgctg cccccaaggg    720

gaacgtggcc ctagataccg ggggaggccc cgccgcagcc tcaagtgact gactcaggcc    780

cccaggttag cacagctgcc acaggcctgg cggaaactcc ggatgggggt ctgaaaagcc    840

tttgtggggt cggggcacca cacgggttgg gctgatggcg cgctgggggc ggggctccag    900

ggcacattgt cagatagatg accccacggg gtgggctgag gactgctggt caggtgaggg    960

gtgtgctggg accggctggg cagtgacccc gagccgcctc cggcccccag gagctggagt   1020

tcctacgcgt ggccaagaag gagaagctgc gggaggccac ggaggccaag cgtaacctgc   1080

ggaaggagat cgagcgtctc cgcgccgaga acgagaaaag atgaaagagg ccaacgagtc   1140

acggctgcgc ctgaagcggg agctggagca ggcgcggcag gcccgggtgt gcgacaaggg   1200
```

ctgcgaggcg ggccgcctgc gcgccaagta ctcggcccag gtatgcgggt ggggagactg 1260
aggcacgcag cacggtgggc gtgagccgcc gtgggccccg gtggccagtc ctgcccagcc 1320
ggaa 1324

<210> SEQ ID NO 107
<211> LENGTH: 1324
<212> TYPE: DNA
<213> ORGANISM: Homo sapiens

<400> SEQUENCE: 107
cgagtgcacg gctttgtgct gctccaggct caccgcgtgc ccgaaggtct tgccgcacat 60
ctcgcaggca aagggtctgg taccgctgtg ggacctgcgc acgtgcacct cgagcccgtg 120
cggcgtgaga acacctaagg cgggtggggc cagagagaag gccgctgaga ggggccgcgg 180
ggcgcaggcg aggcgcgggt aggggaagcg ggcgcacggc aggcgaggtg gtgagctcgg 240
gagcctcacc ttgctgcact tgatgcactt gtaggagccg ccgcccagca gcggcgggtg 300
cacagcagct ccgactccac cttgacgcca gcgcccttgt ctgcgtgcag cccgtggcca 360
cgctcggggt acagcaagcc cgccgctgcc gtgggcctct catacagccc ggctgccgca 420
gacccgaagt cgccgtagag ccctaggcca gggccagggt ggcaccggcc cctgcgctgc 480
agctccctgg cgccccggcc cccgcgccgc cggcagcccg cttcgggccg tacagcgcgg 540
ccgggtggcc aggctccggg gcgggttcgc agaagaggcc caggccagcg ccacgctcca 600
gggccccaca cggtcggtag cttgcaccag gtgccgcagg tcagaacccg ccaggccgct 660
ccatgagtac ggtttgaaag gcagggggaa gggctgggct tcgtccagcg atgggcacat 720
tgacttctcc gaggctgtgg aggcacaagg ggagcgtccg gtcaggcttc agacggcaga 780
gcggaggcgc cgggctgcgg ctgcgagcgt ggcgtgttcg cggactgcgg ggcacccagc 840
gcttgtagaa cactgcgtgc gccaggtgcc aggctcgccc cagggtaaaa cgtggcccgg 900
gccctggggc ctcgcaggcc actataggag gcagaacagt aaacagatca ttaaaagacc 960
tcgggagagg aggtcgtaaa ttctgtgcga gtgcagcgga ggcgctcggc gttccgagga 1020
tcttttctgg ctggacccgc gcacctggag atcctacagg gaagggcgca tctataaatg 1080
cccgtagttg agctgttaag aaggagaagg tggcggcgtt cggcccctca cagcactcaa 1140
gggcggaagg gtccagccac cagcgcaggc actctcccag cccctacatg ttcccattca 1200
attctttttc ttcccagaat ccaagaggaa ggagggagaa ggtccataaa tgcggccccg 1260
aactacccga aaggctgctg tcgaataaac ccgaaggtat taagatttca cgaagttaag 1320
tgcc 1324

<210> SEQ ID NO 108
<211> LENGTH: 323
<212> TYPE: DNA
<213> ORGANISM: Homo sapiens

<400> SEQUENCE: 108
cgagaggccc ggccaccggc tcgggagctg ggccggtcgc tttgggagcg gatgaggaag 60
gttaggagaa gcagcgagat agatcccaat tttacaattc tattttcttt cggtagggtc 120
tcggcgtctg ggccacgttg agagcgaacg tgggccgagc ggaggacaca gagtaaaaag 180
cgacgcccgc tgtatacata aatccgcacc cgctgcccgc ccgggtactg cctgctctgg 240
cttccgctct cttccgaggc tgggcaagtc caaaagttcc cgaaaggggg gtcaaagagg 300
ggcgctcagt gcacgtgatt tcg 323

<210> SEQ ID NO 109
<211> LENGTH: 770
<212> TYPE: DNA
<213> ORGANISM: Homo sapiens

<400> SEQUENCE: 109
ttcttccctc tttactccat tccctaactc ctgcctcgta ggcagcggtg gggagccgca 60
ggctgctccc cgagtcccaa cgctactagg gtgctgtaac agtgatgagg cggcgttgca 120
gtctggcagg cgctgcagcg ggcaccagct acgttttgct gtcggcggca gttacccgga 180
cgcaagttaa ggggtaggcg cgcagaggcg gttggaggcg ggcggccggc ccctgacctc 240
ggagagctgc gccgagcagg gcggaaaatt tatggtctgt gtacactttc tgctccagag 300
ccccgcgcac cagaaggatg gggccctgcg agcgcgcccc aggccgcgag ctggggccgc 360
aggcgccacg gccatgtata gtgcccaccc gactctgttc tgcagcgctg tggtcataaa 420
ccttccctta gagggcgcgg ctgtaaacga aagtccggcg agaggtggat gcaggccttg 480
ccgcccggac cctcaggtat aattctggaa acttgcacgg aagcctgggt cccgccatct 540
tccctgttgt ggtggggtaa gaggatagtt tatactggct gtttggaatc ccgcgcggtg 600
gatgcaaggt gggattccag ccagcgacgc gccgcgtggc cgggagtgca gacaggtcac 660
cggtccccgg gtgtctggac cgcgccgctt cctactgggc ttacttcggg atctagactt 720
cggcctccgt ccttgcaagg gcccagattt gattccggtt cgtcgaggcg 770

<210> SEQ ID NO 110
<211> LENGTH: 339
<212> TYPE: DNA
<213> ORGANISM: Homo sapiens

<400> SEQUENCE: 110
cgaaaccctc gaggagcgac cacatgaccc ccgcgctgtg agctgctggc ggccagcgcc 60
ctcgcctcga ttgtctgcag ccctgtagtg ggccgcgagg cacgcaagcc gcaactacag 120
ctcgccacgg ggcacacaga caggcatgca ccaccactac ccgtcgcccg gatacactga 180
actggttttg aagcctgaac tgcagagatc ctaatatagc aacgcaggac gtttacggcc 240
acccgccagt gacagccggt gatgtgatga caggagggcc tgggtgaaaa tgcaagacac 300
tcactctcag agaacgacga ctccacttga aattcatgt 339

<210> SEQ ID NO 111
<211> LENGTH: 218
<212> TYPE: DNA
<213> ORGANISM: Homo sapiens

<400> SEQUENCE: 111
cggccgggtg gggaccggcg tggcgtcctg cggaccgcgt ggagtttggg gtgtctgaca 60
tcgttctcca cgtggctatt ttcagcgttc tcccggggaa gtacttggaa gagatcgcca 120
cacagatcgc acgcacagca tcaacgcgct gctgatcatc ggtggattcg aggtacgtta 180
ccgtttctct cttgccggtc ttgcaggtgt gagccgcg 218

<210> SEQ ID NO 112
<211> LENGTH: 1324
<212> TYPE: DNA

<213> ORGANISM: Homo sapiens

<400> SEQUENCE: 112
cggcaaccga gccagatcca agaggggtcg gcctcgtcta aattggtttc ccaccaatgg 60
cctcggatca gccgcggctg tgctgcggga gccctcagga cgcggctggg gttggtgcgc 120
ggggcccgga accccaaacc cggctcggtt cggcaaggtt cagggagaca aggtagagaa 180
ggctggggtg agcgagaagt cgggcggccg atcgtcaggg ccacgagcct cgccttgcct 240
tcttggaatc ccacccaact ttaaaggccc aaagatcctg aaaattccga aacgaaactg 300
cgagctggtc tccagaagtt tgagaacggt ctcccaggct ttccagcgtc gtcccgggat 360
tctcggacac cacaaacgcc atcaaccacg agcaccggtg tccgtggcta ttgccccgaa 420
tggtccccat ccgcgtcccc gggaactccc tcggctttcg cgcatccagg tccccagccc 480
cagctactgg tgcgccccga gcccctaggt gccagagcgg tggtcggccg ggctcctgcc 540
cagtctcggc tcctccctcc tccccaccag aaggaaaaac ttgggccctt cgagaaccct 600
gtggaatgtt ctttgtaatc aatgtacatc cgcttccacg gcacggcctc gtgcaaaatc 660
gcgggtttcg gggccttgga gcaaattgcg cttgtcagcg gcgacgtcag gaggacaagg 720
ggaggggttc gcggctgaaa ctgcagcttc gcagcacaga gccattttag gctgctcccc 780
acctcgcggg cccatgggaa agccggcccc gggagggcgc gcccaaacgc aggctggagg 840
agccacggac gcgtcctggc cggcgtgtcg ccatcgttca gcctcgctgc ccaggtggga 900
ggggtcacct gccgcggggt ctccaagcca gtgccgcttg ctcccggccc cccccactga 960
cagcacggcg tccgagtgac cctgtctagc ctcgttctgc gctcctgcaa accacgttgc 1020
tgcgctaact acaaacctgg ccaacatgtc tttgtaaccc tatcatttaa aaacgcttcc 1080
aggcacctgg ccgctgccag atcaggttcg cgggcccgag gaggtcctcc cacctgcccc 1140
cgccagcccc ggggaccgtg cgcggcctcc gtgtggcccc cgcccacgag gtccctcggg 1200
caggaaccgc cgcgcgacct ctgttcagcg gccgcgtcct ggccacgggc gacccctgtc 1260
gggaaccctg ttcccggcta agtgcgttcc cgcattccgg tggctctcac ccgagctcgc 1320
gttt 1324

<210> SEQ ID NO 113
<211> LENGTH: 337
<212> TYPE: DNA
<213> ORGANISM: Homo sapiens

<400> SEQUENCE: 113
tacagttgat acccaccatc cccatcatcg ctattagaat tggggtcaat acccatcatc 60
actgttagac ttgaggccga tacccgtcat cactgttaga ctcggggtcg atatcatcat 120
cactgttgac tcggggtcaa tacccttcat cactgttaga ctcggggtcg atacccgtca 180
ccactgttag actcggggtc gatacccgtc atcactgtta gactcggggt cgatacccgt 240
catcactgtt agactcgggg tcgatacccg tcatcactgt tagacttggg gtgataccca 300
tcatcgctct tagactcggg gttgatactc gtcatcg 337

<210> SEQ ID NO 114
<211> LENGTH: 592
<212> TYPE: DNA
<213> ORGANISM: Homo sapiens

<400> SEQUENCE: 114
caacatctgt catcgctgtt agatttcggg tcaatatcca tcatcgctgt tagactcggg 60
gccgacatcc gtcatcgctg ttagactcgg ggtcgacacc catcatcgcc gttggactcg 120
gggctgaacc cgtcatcgct gttagatgcg gggtcgatat ccatcatcgc tgttaaattt 180
ggggtcgata tccgtcatga ctgttagatt tggggtcgat attcctcatg actgttagac 240
tcggggctga tatctgtcat gactgttaga ctcggggccg atatctgtca tcctgttaga 300
ctcgggtcaa tacccgtcat cactgttaca ctcggggccg atacccgtca ccgctgttgg 360
actcgggtcg atacccgtca ccgctgttgg actcgggttg atacccgtca ccgctgttgg 420
actcgggtcg atacccgtca ccgctgttgg actcgggcga tacccgtcat cgctgttgga 480
ctcgggtcga tacccgtcat cgctgttgga ctccggtcga tatccgtcat cagtgttggg 540
ctcaggtcga tacccgtcat cagtgttgga ctcgggtcga tacccatcat cg 592

<210> SEQ ID NO 115
<211> LENGTH: 780
<212> TYPE: DNA
<213> ORGANISM: Homo sapiens

<400> SEQUENCE: 115
cgacagcttc acagtaggat tattgtgata aaaatgactc aagcgatgca aaaagtttca 60
tctgttccca gaatccgagg gagaactgag gtgatcgtta gagcatagcg acatcacgtg 120
cggtttctaa tgtccctggt ggcggatacg ccgagtcctc ggaaggacat ctggacacca 180
ctttcagcca cctccttgca ggggcgacat ccgccaaagt catcctttat tccgagtaat 240
aactttaatt cctttctaac atttacacgg caaacaggaa tgcagtaaac gtcacgtccg 300
tcccacggct gggctgccgt tccgtttcct ccacgaacgg gtacgcgctt ccatgagaaa 360
ggatatttgg caattttata ttccacagtc aggtgggtct gcgatagctc atttaatgtt 420
aaacgccatc aggggcctct cctcccgttt ctgccagggc ttttcttgtc ttctccttgg 480
tcatcatcat catcgtcttc ctcttcctcg tgggcagatc ttctctggtg ggggctggct 540
gctggctccg agggggcatc cgcagtccgt ctggtcgtct cctcctgcag gctgggcagc 600
tggccaccac ttctccgact cgcccctcca acaagcatcg cagggcactg tcctcggggg 660
tacagaccgt ggtcccacat tcgctaccac tctgttccac gtcatccagg tacacgagct 720
gcgtgtaggc cgtgctgtct ggggctcgag gctctttctg ctggtgctct tggacgggcg 780

<210> SEQ ID NO 116
<211> LENGTH: 1324
<212> TYPE: DNA
<213> ORGANISM: Homo sapiens

<400> SEQUENCE: 116
cgtgaacgcc ctcgcctcgc acctgtggcg cctgccgcgg ggcccgaccg gaggcagtgg 60
ctgtggacaa gggcggcccc ggcgtaggcc aggatttccc cgcagccgga ccggcccagc 120
tccgctcttt cctgggcgaa cagcgcccac ctccggccca ggcggcggcg cctccgcccg 180
cggcgcggac agcgagagag aaaccggctc ctccaaacct ggtggaggag cgctgcagag 240
aagcgccggg ctgaggctct gggggccgcg gggcgcgaaa cgccgcgcct acaggttatg 300
cccgggagaa ggagacaggt cgggctccag ccgctgggcg ctcctcacct cgaagcgagg 360
aaaacaccgg gccactgaga tcaggggagg tgcgcccgat acaggtaccc ggcacgcaga 420

```
cacgcccacc cccaaacacc gagaaacaaa gactgcccga gccacgcacg cctgcgcggc    480

cagcgctggg cgcacacccg cgcccacaca gcccgaaggg cgccacgcaa cccgcaagaa    540

caccagctcc ccgcgctcgc aggctctccg tgccggcccg cagcgcagag cagtcccggc    600

gccgctgcct aggtgggccg ggaaggcgcg ccaccgcgca tggcaccgcg gctgccgagg    660

aacagagggt gccctgcgca gcccagctcg tcccaacccc tccggtgccc actgctgcga    720

cgcctcgcag gccgtgtccc agtgggccct gggcacagcg gtcactcacc ttcctgcaca    780

gcctggatgg gttgttggcc tcgatgacct tgatggagta ggtgatcttc tcgctctgca    840

ggatgtcatc gttgaggctc aggtcggata ccgccaactg gaacaccctg tcgtccttgg    900

ccgcgttctc ctcgaagatg gcacctggag gagagaaggg atcaagaccg gactggacaa    960

gaaccctctc cccgcttccc ttggcccgag ggtcaaggca ctcgcagacc gatgattgcc   1020

gggtggtggg aagtctgaac tgggatttca gcttggcggg gtagattaag gctctccgat   1080

ctccacctgc acaggaatat gttcccctcc ccccaccgcc ctcagcgcac acgtgcacac   1140

agttgacatg agttacacat gcacatccca caggctgcca ccaggtcaca cacgtgtctc   1200

acaaccaagg caccacatgt cctagccatg ctccacacaa gggactaagc caagctgggg   1260

tggccccagg cagcgcccaa atccttgaca tggttccata aatcccatcc caggagccag   1320

gaag                                                                1324
```

<210> SEQ ID NO 117
<211> LENGTH: 609
<212> TYPE: DNA
<213> ORGANISM: Homo sapiens

<400> SEQUENCE: 117

```
cgggggcgc cgggcgcagg ccgggcatgg ggcctgagct taggccaggt ggaaaggtgg     60

aaggacctag tggggacaga cgaagagacc gaggagccgc ccgcccggct aaatggacac    120

aggaaagcct gagtcaggct tctcataata aataaactgc acgtgaataa ttcagcagtc    180

gcgcggggc cggttgcatc agcgccgccg ccgccgcgcg gcgcccaatt ccccgcggag    240

gggagtagcc aattaaggca cttgaaaagg gagtcgggtg gaagatcccc cgccaccagt    300

atcctggatt tacccaggtc gagttcagag agcctccccg gtcccaaccc cctcgggccc    360

catgggtcag gggccgcct gctgggaagt gctacctcag ctaagccgct caggtgtccc    420

gagactccgg gcaagggaag acaggcggcg agacggacca gaataaggga tgcggacgtc    480

tgacctgtgg aaaacccagc atctgcagtg cccagccgca cagggaacgt gggcggcgtg    540

gttccaagca cagtgaagac gccaggctcg gatctgtgct cagagccggg atccctccgg    600

gctgcttcg                                                            609
```

<210> SEQ ID NO 118
<211> LENGTH: 298
<212> TYPE: DNA
<213> ORGANISM: Homo sapiens

<400> SEQUENCE: 118

```
cgtagcgacg acgtggtcct tgtaggacca agcattcttg gcattctgtc gagattgaga     60

ttccagagca tcggatgaac gggacttata gctaaggcgt actcacccac ccctcccttc    120

gtcttttacg cacgcagcaa ctcgtcctca cgtgcatagg ggtagtggac agtgttgact    180

tgaattgctg tccctcgttc caagcctttc ctgtgaatga acccgaaaac actcgacagg    240

tcgtgaataa tcgttttaat gagtgtgcaa agcgtgcgac ggggtgcacc gactgtcg      298
```

<210> SEQ ID NO 119
<211> LENGTH: 287
<212> TYPE: DNA
<213> ORGANISM: Homo sapiens

<400> SEQUENCE: 119
cgctggcggg ggtagggggt gtgggtgggt acggagtcct ttcactgccc gtcggcagtt 60
ggcaccagag cggaaagtgt gtcccctccc ccgcctctct cccttgggca gtttgatttc 120
ccgccagctc agtcggagtg gcctggaaga gcgggctcaa actccaaagg cagtcgtggg 180
agagtcgtag cggatacgtt tcccctgaca tgcgccgggt gctcgtctct gccccccacc 240
cgcccccaaa acccaaacct gcaagtcgat gttgtccggt gaccccg 287

<210> SEQ ID NO 120
<211> LENGTH: 1324
<212> TYPE: DNA
<213> ORGANISM: Homo sapiens

<400> SEQUENCE: 120
gtgcctaaag ttacctaacg atacaaaccg gatacaacgc agaggaaaca gaataccccca 60 gccaagcaat ttccatgtca aacatcatcc gcgcggctgc tccatctgtg aacgtgagtg 120
gtcgcctgct ccctcttccg cggcggccgc ttcctcatac cttcacacgg cgcacaccgg 180
ccggcgcgtc cagctgcctg cccagtggcc gaggctcttc cccctcgccc agtcttgagc 240
tggaagtgat tcctattggc caaggtgtcc atgtaaatag gtgtgaaaga aacagagctg 300
gccgggctct cccttctcgc tcagtcccct ccctctgcag cccccgctcc ccctcctctt 360
cctcctcctc ccaaggcgat tgtcatatga tagctaagaa gtggcacatt aatgaagcgc 420
cgctacaggg gtcttttctg ctcctgtcac cgcttaaact atcagatggt tcgagggagg 480
acatggaggc agccacctag ctcagcggag acgcggagcc cacagcagcg ccctccggag 540
ccctaacacg tcgctgccac catccgcgcc gggactccgc agccgagctc ggccgcccgc 600
aggacgctcc aggagcgtcg cgaccgggcg gcacgggacg ctgcggggct gagctcaaga 660
gcccaggttc gcgccgagtc caaccggacc cggacgctgc gcgcggagtg cgcgtcgagt 720
gcgcgccgag agagaagcgg cgcgcagcgg cgtcctcccg gatgcggacg cgcaacttga 780
agcaacttaa ggtgagcagc tctctgttcc gtccctgccc cctattctgg ccccagtacc 840
gacttacttc ccggctatcc tcgcgccgtt cgccggcttc ccctcccgcg cccactaagc 900
ccgcaaagtt gctggcgaaa gagtccgggc gctggctgat cgagcgccgc agccccaccc 960
ccgacccccg aagtctgtta ctcggtctgg ctgaccccgc cggtgtctct gtgcatccat 1020
gctacctttc cctattaccc accccccttcc cagatccgag cagtccgccg gcccgcgcgg 1080
acccagagca agaagagggc gaggaagaag atgcctcgcc cggccgcaac acgtacagcg 1140
accagaagcc gccctactcg tacatctcgc tgaccgctat ggccatccag agctctcccg 1200
agaagatgct gccgctgagc gagatctaca agttcatcat ggaccgcttc ccctactaca 1260
gggagaacac gcagcgctgg caaacagtct gcgccacaac ctctccttca acgactgctt 1320
catc 1324

<210> SEQ ID NO 121
<211> LENGTH: 1283
<212> TYPE: DNA
<213> ORGANISM: Homo sapiens

<400> SEQUENCE: 121
cgacgggaaa acggggggaa ggggggagcc cgacacggca cacacacata cacactcgca 60
cacacttccg agcgagtgca cactcgcact cccacccgac agccggccag ggacagtcac 120
ccccaagtca atatcgcagt ttgaattgtt ccggcaaatc tcccctcggg ctcgacggat 180
gtgcgcccca gatgtgctga cacatgtccg atgcctcgct gccttggagg tctccccgct 240
cgcgtgtctc ttctcttcgc accagcggcg gaaaccgcac tagcagcggc ggggcggcgg 300
cggcggcagc agccacctga agccaccaac actgggctct tccagcaaaa acgagacccc 360
gattcgtctg gcgccccaag aagacataga cgatagcccc ccgccgggct gcgccgtgca 420
attccgggct cccgggagcg cgtagctcgc tggctaaccc aggcagtccg cggcaagttg 480
ccctcgaagt ccgcccccct caccggggca tggtcggagg gtggctgctg cgctccgggg 540
cagttcttct cctgcttccg gggggcgggg aaggagcaga cacagcagac acacagagaa 600
agagaggcag ggattattgc ccaaaccgcc agccgccggc agcctccgcc gaccctccct 660
gctccccagg tccgcgcgca gcctgcagcc tctcagccgg gttccggcag tgcgtccagg 720
gcgccgaggg gaagggctgg gccccgggga ctggggcgcg gtgggggcac acagactctc 780
caggtcggcg cgcccttcct gctcctctgc tattttcctg aactccccag aacccccagt 840
tgcctggctt ccatcgcccg caactagcgc cgctgtcgag attttccgca atacaactgc 900
aggggtcgtt atttcctcgc ctacggatcc ctacgcttcc caactcagag agaggaggac 960
aggtgggggc gggaggggga ggaggagaag gaggcttggc caggtgagcg tcctcgccgc 1020
cgccgggcgt cccagcgtca gctccgcagc ccggcacccg ggggcggagg caggaggccc 1080
gggcggggag gtgaggctga gcgcggccat gaggagggga ggaggaggct gggtgtcaca 1140
gcttcaggcc accttggccg ccgcctcggc cccagtccct ggcagccgcc tccgcactcc 1200
gccccgccct ggctgcctct gttaccctcc aggattttcg agtttctctt cttaaaaaga 1260
acttcgtgct gcgggttcgg cgg 1283

<210> SEQ ID NO 122
<211> LENGTH: 327
<212> TYPE: DNA
<213> ORGANISM: Homo sapiens

<400> SEQUENCE: 122
cgtgggtccg cctaccccaa gcactttttg tgacgtcaca gctccgagga ccatccgggg 60
gctttactct cgcggaagcc caaaagttgg ggtttgacct catgaccttg gccttcccgg 120
ggggcggagg ccctcgggac aggacgcgct gtccccggag tccggagctc aggccagtgg 180
cagtcgaccc agcccccgag actccctcac gccgctccaa aaccaaaacg gagcccaaca 240
cgaagctggg tgaagccgta gcttgcagga gccagggaga tgcgctctgc ccggacttcc 300
cgggtcctgt tgagacggaa aggatcg 327

<210> SEQ ID NO 123
<211> LENGTH: 1324
<212> TYPE: DNA
<213> ORGANISM: Homo sapiens

<400> SEQUENCE: 123
cgactcggct gacgtttttg acccggccag gaggcaaaga ccaaaacgtc agagcagtag 60
ccctgttact gaggagcgtc ggcagggtcg cgggtagagg gggctggaga atgacttgtc 120
agagctcagg tcgatgtggc gcggggcggc ctcgagagcg ccgggctcct gcgtggccac 180
ggccgccgct gccaaccttc gcggggactt agctttgctt tccattgact ccctttgcaa 240
aagcgcagca gaatcctgac cagccgcacc agccccggcg aacccgagca tgtaatctat 300
ttatatggat tattacggag gaacagcggg cgttgagtca ccaaaacatt tgcttcaaaa 360
gactatttct aagcactttt gcaggcaggc aggctcgctc caggcgcgta aactcggcta 420
cgcattaaga agcggctgct tttcgaatac tgcaaaccca gctaagtccc cggtgccgcg 480
gagagagcag tgaaaagaaa tgtcggaggt gggggtagat cctagtctag acacacacac 540
ttgcgcgcac acacacacac acacacacaa gattcgcgcg gagaaggcac taaaattctg 600
gcattccgag agtacgacaa actacacact tggaagtccc gggtccccgg ccttccccgc 660
agcacccccc gcccccccac cctaccgtcc gccctttggc tgcgatcccc tcccctctcc 720
tcccctcccg cctcgtcacc cagcccagtg ccacaatcct cctccctccc caaaatcggg 780
tccaatcgct gcctgccaac cctgggactg ctgtgctgtg attggcgggt ggctctaagg 840
tgaggcggag tatttattaa agagaccctg ggctgggagt tggagagccg aaagcggagc 900
tcgaaactga ctggaaactt cagtggcgcg gagactcgcc agtttcaacc ccgaaacttt 960
tctttgcagg aggagaagag aaggggtgca agcgccccca cttttgctct ttttcctccc 1020
ctcctcctcc tctccaattc gcctcccccc acttggagcg ggcagctgtg aactggccac 1080
cccgcgcctt cctaagtgct cgccgcggta gccggccacg cgccagcttc cccgggagcc 1140
gcttgctccg catccgggca gccgagggga gaggagcccg cgcctcgagt ccccgagccg 1200
ccgcggcttc tcgcctttcc cggccaccag ccccctgccc cgggcccgcg tatgaatctc 1260
ctggacccct tcatgaagat gacgacgagc aggagaaggg cctgtccggc gcccccagcc 1320
ccac 1324

<210> SEQ ID NO 124
<211> LENGTH: 602
<212> TYPE: DNA
<213> ORGANISM: Homo sapiens

<400> SEQUENCE: 124
cgattggggc ctcagcctta gttcttccag ctggaccctg ggatggtgcg gggctgtggc 60
tctgggaagt atcttggcct gcacgcggtt tacatcattg ggagcacagg cctcgccctc 120
cgaactagag gcccagagcc cttcgcgccg agcgtttccc gcctttcccc tgtctcaagt 180
cattgcccag aggccactgc gggccgttcc tgcctgtccg tggagctgcg gcccccgtgt 240
tcccagggtg aacgagcacg tgcgaggcgg tggtgcttgt atccgggata acaggtaggg 300
cggctgcatg cttcatagag gccagcctgt gccgaccggg agctgtagga cggtctgtgt 360
ctggggctgc ttatgggtat tcgcgtgcgt ctgccggtgc gcggtccgag cctactcacg 420
agagcgtgtg tgtgtcttct gtctcgtgtt gctatgagtt tgcatctgtg tggctggaat 480
agcttgtttg tgggggcccg cgcgtgacct gtgtgtgcgt tactgtgtgt gtctcaggca 540
ggatagtgac gggccgtgtg actgtgacgc catcatcagg ttggtgagat ggcgtgaccg 600
cg 602

<210> SEQ ID NO 125
<211> LENGTH: 599
<212> TYPE: DNA
<213> ORGANISM: Homo sapiens

<400> SEQUENCE: 125
cagcagaccc ctttttaagt acgcatgtga taagcaatga acacgaactg cccagagcag 60
tctccaacac tgacacgatt cgcttcccca ccacgacgcc ctagcgctac tgtgcaacga 120
agacctccaa gcactggttc caatgcggag accatgggct cccagactct gggaactcca 180
acacgactgc gaaacgaact ccgagcgagg actccccgag agctccccgc aacacggacc 240
tcacgcgcta gcgaacaaca gaaaaaaaaa agcgcgctct ccctgcccct gaacattccc 300
agaagcccac gcagaccaga ccgatgacct gtctccactg ctggaggcga gtcagggacc 360
cgaagtctct aaacactcgc ctctacccgc cgcccgcga accccacaca ctgcagacgc 420
gacactcgca agtttcgggg atggcggccg gcgagggcat actgcgtctt tccggagaca 480
cggaatacgg caccagccgt ccctttatga tgcaatatgt ctgcgcccag gggacgcttg 540
ctgggagcag ccattttcaa ccctactgcc gtagagcagg cggagtccct cttttcgcg 599

<210> SEQ ID NO 126
<211> LENGTH: 1324
<212> TYPE: DNA
<213> ORGANISM: Homo sapiens

<400> SEQUENCE: 126
cgaggaggct gcagggacgc gcatggaaga gccggtgcgt gggagggttt gcggggggga 60
catcgcgccc cctaggggtg accccagtgg gtcccgtgtg ctctccgcgg agccggcgga 120
gccttgtctc tgcacccggc gcgcagcggc cccttaaaca gtggaaccgt gaggccgctc 180
taagccgaag ggctggaatc tgggtttctc gggttttatt ttagaccatt cggcaccaag 240
cccgagctcc cccgccgcac cgcttccagt cccctttctt tccatagagc gaccgaagcc 300
ggcggtggcg cagggagccg agtctgatga gctcgcgggc ggctgaaggc cggcttccct 360
gtggggaacg cgccacctgt cggcgccagt gagaactgcg tctgtgtggc gccctcgggg 420
tattcggggc tgcggggaga tgtgtgcctg aagccctcgc ttgcggtggg gacgtccggc 480
ctctttcctg gcaattgacc cctgaggcgg gagagacaac ggaattccca caaagggatc 540
cttctcggga tctccccacc tcaagacagc taaagctgga ggaaaagccc ctccgggggg 600
tggggggtgc gggtttgccc tggattccga aagcagaaaa tacccgagcc acacagggac 660
gggcgccgcg ttggtagtcg gggctacgtt cctactccct ctacctcccc cgcgctgtgt 720
gaccctgggc ggaaccccgc tgctctctgg gcctcagtgt tcttattcgt aaactgaggg 780
cgttggagag attggtcctc tcccaactct gaccttgaaa ctgatactga atctgagcag 840
cgtctgtaga cacctgtgcc ttgccttcta tttctagcct tgaataaatc ctggactttt 900
atgtgccatt tatatcctaa tctcatatat atttaatgta taactgctgc catattgttt 960
tctcaattgt ctaggttttc atttggatgg ggttaggatg gtccaaatta tcccgataag 1020
tgcccattaa cttaaacctt tttaaaaaat gaaaccagta aaacttcatt cactttgcag 1080
tgtggacact gctggagagc acccatgtcg tgggtccgcg aggacacaag gaggggctta 1140
gagacatgcg ggaggcttag atgagaagac agcacccggg cagcggtcag tgttagagag 1200
aggacccgta agaagggccg aggctagagg gagagcgaag actgagccaa cgacgcacct 1260
gagccctggg gtgggggtgg agcgtggctc ctaacccaaa tctccctgcc aggcagtgtc 1320
cgac 1324

<210> SEQ ID NO 127

<211> LENGTH: 1324
<212> TYPE: DNA
<213> ORGANISM: Homo sapiens

<400> SEQUENCE: 127
accatgagct tccagttcct acgggtgaga aaagaggtgt ctgtgtggag ggcaggtgcg 60
accccggggg ctagcagaga ggagaggctg cgggaggact cgctgcgaag ggcgaggggt 120
ggcgctggtg ggacgggcgc ctggggccgt gcagggtggc tcctgggtgc tgcccgggct 180
gcctgtcgcc cagtactggc gcaggaagac gggtccgcgc agcgtctggc aacagtggcc 240
tgctccacgc ctggaggcga ccaagttctg agttaaaggc gccgggctta gcgggaagtg 300
tatggcgacc cagaacacgg agcggagaag gcctcagggg acacgaggct accgccttag 360
tcctcgggcc tgcgctccga gcggttaggg tgcgtacgga tgggctccgg gatgttagtg 420
gagaggtgac aggagtctac catcccacgg ccaagcggtg aggcctccgg cgggcggggg 480 tccccccgg ggcagggcag ggggagagtc aggcatgtct ctaacgggct ccctagtaga 540
accgctagga aagtggcctt caaccctagg cacctttgtg gctttcaggt agttgggcga 600
ctaaaaattc acttttgcct gcgtgaaatg ggacaggtgg ttgtcaggtt agagactgtg 660
cccacgaagt ctcgtttggc gggccgggac tgacgtggac ccgggccctc ctcggaagct 720
tgggaacctg tgagcccctc agctcctcgc ctcactttgc ctgtttgaaa aaaggagttg 780
tttgagagaa gagttaaggc tcaaaaggtt ctaaacgaag agcatgcggc ctgacgcgga 840
gcgcaaagaa gcgagcagtg aactgaatct ggtgggactg agaccagagg cgtctgtatg 900
cggcggccgc ttcgcgccct attaaagcaa tctgttattt acgataatca ttttgtaatt 960
attttggagt ggctgtgact tgatgtctgt ggtgccccag ggcatgccct tactggacat 1020
agatacttca gggtgccctt tgacgccagt gtcggtccag tgggtgccag tgccgcgaag 1080
ggagggtggc gggcgtgaat gccccctcct cctgggttgc cgcaggcccc ggcctttcca 1140
ccttgcttga tcctggcggg tctgccactt actgaggtcc ctaccggcgc tcacgttgtc 1200
ccgagaggcg ggacaaacgt ccggcgcgtg gcgcggagtc tgcgaaagcg ctcgggggcc 1260
tccatcttct gctcgggagt ccctccctgg ggcgggaaga ggagtcgcag atctgcccga 1320
atct 1324

<210> SEQ ID NO 128
<211> LENGTH: 530
<212> TYPE: DNA
<213> ORGANISM: Homo sapiens

<400> SEQUENCE: 128
gagtgcgtaa agggaaattt ttgcattggt ggatttattg aaagcatgga aacagtcttc 60
gggggtaggt gtagggggtg caacagcgag acttccccac aacacctcca ccgaaggctg 120
ggtcgtcgcg tttgagggac cctcccgcca ccccgcagcc tggcggggcg ctttccaaat 180
cgtcgcggca ggctctggcc gggcagggcg agatgtgcgc atgcgcggcc tgtggcccga 240
ggttccacgt gctgatgaat atgcatgaga ctcccccgcc ctcgcgggct aggagagaac 300
caagcagagg ctccggcctg tgaaagtcgc tggctaggct cccaaaatag tgcggcgggg 360
tagctgcacg tgtttgtttt caaaccgcgc tggtttaagt gagttcacac tgcggagccg 420
acagcagagg gtagagcaac ctggggctgc tgccattgaa cggcgagttg agcgggcctg 480
tcagggcctc tccgccgagg gccgggggct gcatggtgct cgagccccag 530

<210> SEQ ID NO 129
<211> LENGTH: 1273
<212> TYPE: DNA
<213> ORGANISM: Homo sapiens

<400> SEQUENCE: 129
cgcgttgccc ctgcgcctcc ggaaggggca ctcacagctg gtcaagcgcg tccttcggaa 60
ctcggggagg ctccgttggg gcttacacag agctaagccc tgggccaggg aggatggatg 120
caagtacgtg catgtgcaaa cgtgttcgca gatacccgca gcggtgcaca ctcgggcccc 180
tcgtgtgcac gggccctgcc caccaccccg cccgcgttcg ccgccgcccc actgtcctca 240
tcccgcgggc tgaccccagg attggcagaa atcagtggtc taatctagca tgtgggtaaa 300
gggatcgatc tccaattgcc aaaaaaaaaa tagaaaatag ccggtgttcc cagccgctgc 360
gtggcacttg gccgcacaag gcgcagggat atcagaggcg ctttgcagcg cttggcggtg 420
ctgtgtgccg gatgccccag agcccggcgt taggatgcgg gcttgtagga agcggctcaa 480
atcaactcct cagtcactga tgaacgcgct cacggctcga agctaggtcc tcgagtgagt 540
taatctactt ggtaagtatt ttgtgaatat gtattttggg aggaaagaag cacgtcgaac 600
gcgtctgccc gtctgtaagc gcgtcatccc cacatccttt agcgtgaatt cctccgcttt 660
ttaggagtca cctccacccc ctactccgta tgcttcgcgc ctttcctcac ggccccgtca 720
gaccccctca cctttagatt gacacatgcc atataatact cacttttaaa atgccctgcc 780
agtctctcta gggtccctta attaggtaac ccttgccaat tagtgggccc tgcgctactt 840
tttcccttct cgatgattta tttccatgat gcgtattagg gaaaatacct taaaggaaaa 900
agaatgttag catcattgga aatcccgctc ctaggagagg atatcgcagc tgtgctatta 960
tgttttcgca tttgctgatg caaacagggg aacctctcta ttccctcccc attacctgcg 1020
gctggggact gggaactttc cgcggcattg tccccagcca gcgcctcggg acctgcgggg 1080
ctgttctcgc tctcacactc acactcaccc cggccgccgg gcgagagttc tgtcccgccc 1140
cgcccggctg ccgcgtgacg tgtctgtttg gcggccagtt tggccaatca tcggcagctc 1200
ggtgggtggt gctcctgggc gattggttgg cagaatgagg gcgctgcgca aaaacggaga 1260
agccgagcgc tcg 1273

<210> SEQ ID NO 130
<211> LENGTH: 1324
<212> TYPE: DNA
<213> ORGANISM: Homo sapiens

<400> SEQUENCE: 130
cggagccaga cctgacggtg gaaatctctg agagcgccac gccaggcact cgcttcccct 60
tggagagcgc attcgaccca gacgtgggca ccaactcctt gcgcgactac gagatcaccc 120
ccaacagtac ttctccctgg acgtgcagac ccagggggat ggcaaccgat tcgctgagct 180
ggtgctggag aagccactgg accgagagca gcaagcggtg caccgctacg tgctgaccgc 240
ggtggacgga ggaggtgggg gaggagtagg agaaggaggg ggaggtggcg gggagcaggc 300
ctgccccccc agcagcagcg caccggcacg gccctactca ccatccgagt gctggactcc 360
aatgacaatg tgcccgcttt cgaccaaccc gtctacactg tgtccctacc agagaactct 420
cccccaggca ctctcgtgat ccagctcaac gccaccgccc ggacgagggc cagaacggtg 480
aggtcgtgta ctccttcagc agccacattt cgccccgggc gcgggagctt ttcggactct 540
cgccgcgcac tggcagactg gaggtaagcg gcgagttgga ctatgaagag agcccagtgt 600

```
accaagtgta cgtgcaagcc aagacctggg ccccaacgcc gtgcctgcgc actgcaaggt    660

gctagtgcga gtactggatg ctaatgacaa cgcgccagag atcagcttca gcaccgtgaa    720

ggaagcggtg agtgagggcg cggcgcccgg cactgtggtg gccctttca gcgtgactga    780

ccgcgaccag aggagaatgg gcaggtgcag tgcgagctac tgggagacgt gcctttccgc    840

ctcaagtctt cctttaagaa ttactacacc atcgttaccg aagcccccct ggaccgagag    900

gcgggggact cctacaccct gactgtagtg gctcgggacc ggggcgagcc tggctctcca    960

ccagtaagtc gatccaggta caagtgtcgg atgtgaacga caacgcgccg cgtttcagcc   1020

agccggtcta cgacgtgtat gtgactgaaa acaacgtgcc tggcgcctac atctacgcgg   1080

tgagcgccac cgaccgggat gagggcgcca acgcccactt gcctactcta tcctcgagtg   1140

ccagatccag ggcatgagcg tcttcaccta cgtttctatc aactctgaga acggctactt   1200

gtacgccctg cgctccttcg actatgagca gctgaaggac ttcagttttc aggtggaagc   1260

ccgggacgct ggcagccccc agcgctggct ggtaacgcca ctgtcaacat cctcatagtg   1320

gatc                                                                1324
```

```
<210> SEQ ID NO 131
<211> LENGTH: 1324
<212> TYPE: DNA
<213> ORGANISM: Homo sapiens

<400> SEQUENCE: 131

cgagagaagg tgagctcggc gggcgcagcg ggttgggtgg gtgtggcccg cggctccggg     60

aacagaccca aggccccgcc accgccggct agcagcccga cagcccgccc gcctggcgag    120

cgcaggcctt cttccagaaa ctgcgaggat ccgagcgtac tgtttgtgca ccacaaggtc    180

aagtcgggaa gtggagccgg aggaggaggg gcgaggaggc gaagggtggg gagaggggcg    240

ccccgcttcc tcgccatgtg ccagcctttg gaagttaccc ctcggttttt aactttcggg    300

gtaatgggaa ggaagagcaa ggaggaaggg gtcgccccgg ggcaaaatcc tgctggggcc    360

aggatgtgca accacccacc cacccgctca tcactgcctt ctccaccccc cggaaatgcg    420

gggcagcgct aggcgccagg aggcacccgg gagggggagg gggcgacgag cccaatgggg    480

accctctcta cggaccgccc ctcttttctt gaggtcgcct acaatttcaa gttcccccgc    540

ccggaatgtt agttttccat ttggagtggg tgcggggagg agggccgcgc cccctcccca    600

agactcgcgt tcgcccctcc accccctcct gccagcactt tctgctcact tctggtgctg    660

caaaacgcca cgcaatttat tcgattcgca ttttaaaacc agcgattcag aagcagggcc    720

tagggcgagg gtcttccagc gctggagccc cggggggcgg ggtgctcagt gcaaacctcg    780

ttccctcgcg agtgtcgcct ccaggctgtt atttgcaaag aaacgtcttt ttgacgcagg    840

gagaaatggc aaattttaag tacgtcatta atatggcgcc aaaagatttt tttaagtata    900

agctcgcttt tttttttttt taaggttgcg gggggcgccg cccgggtctg ggcgcgtagg    960

gggcggggtg tgagcagaaa gtgtgagtga aagagtggag gggcggggta tgtgtgtgag   1020

tgtgtgaagt gtgagcagac ctgatgggac ttgcacgggc gcagccgccg ctcgggcccg   1080

gccctgggga cagggcgggc taggggcgcc ccagagtcat ggggagtccg ggcccagggt   1140

gccagcaggc gtggtggtgg ggctgcgagg gagggcaccc ttcccccacg gggcccgcaa   1200

cgctacctgg actccccgcc ggagccaaac aactgggcgg ggggttgggg gggcggcgac   1260

gggggtgtcg ggagcggaga tcgagtgaat aagaaaaaag tggctactcc ccctccctcg   1320

ctcc                                                                1324
```

<210> SEQ ID NO 132
<211> LENGTH: 762
<212> TYPE: DNA
<213> ORGANISM: Homo sapiens

<400> SEQUENCE: 132
atccctattc cttctccttc ctctcccttg gtaacggcac tcctagggct gtggagggtg 60
cggttcactc ctgggactgt ggagggtgcg gatcactccc gggactgtgg agggtgcgga 120
tcgctccggg gctgtggagg gtgcggatcg ctcccggggc tgtggagggt gcggatcgct 180
cccggggctg tggagggtgc ggatcgctcc cgggactgtg gagggtgcgg ttcactcccg 240
ggactgtgga gggtgcggat cgctcccggg actgtggagg gtgcggatcg ctccggggct 300
gtggagggtg cggttctctc ccggggctgt ggagggtgcg gttcactccc ggggctgtgg 360
agggtgcggt tcactcccgg ggctgtggag ggtgcggttc actcccggga ctgtggaggg 420
tgcggatcgc tcctggggct gtggagggtg cggttcatcc cgggactgtg gagggtgcgg 480
atcgctcccg ggactgtgga gggtgcggat cgctcccggg gctgtggagg gtgcggttct 540
ctcccggggc tgtggagggt gcggttcact cccggggctg tggagggtgc ggttcactcc 600
cgggactgtg gagggtgcgg atgctcctgg ggctgtggag ggtgcggttc actcccggga 660
ctgtggaggg tgcggatcgc tcctggggct gtggagggtg cggatcgctc caggtgtgat 720
tttcatggga atggaactgg ctccctaggt ggtgttcatt tc 762

<210> SEQ ID NO 133
<211> LENGTH: 270
<212> TYPE: DNA
<213> ORGANISM: Homo sapiens

<400> SEQUENCE: 133
cgaacgccgg gggagggacg gtgggagggg tgcggtgagc gaggggctgc cctgcatgta 60
aacagcctcg gggtcccaga cgagacaagt gggaccgctc aagcctgcag aacccccggt 120
ctcggtccag gcacaagagc ctcccgtagc cccgcctgat ctttctcagt ctttaggttc 180
caggacatcc aaaggagcgt aggtaaccga cgtctacgta gtatttctgt ccccggaaga 240
ctggatctca gggaattatt atggaagata 270

<210> SEQ ID NO 134
<211> LENGTH: 876
<212> TYPE: DNA
<213> ORGANISM: Homo sapiens

<400> SEQUENCE: 134
cggggcaagg gcgcgttccc tatcgcagga tcacttgcta tggtaagccg cccaccctgc 60
gcgctcctcc gcgcggggaa gaacctgcgc ggcaggacgt ggtgttggag ttggggcgcc 120
cggagcggga gtggggagac ctgatgcaga gagtctggag tcggagctgg gggtgctgca 180
ggtaggagca ggagcggggc ggagagggag gcccgaagaa gaccccacac aggttggcgc 240
agcggggctt ggggaggctt cagcccagaa gtggagaggg ttgacagacg ccgcctgatt 300
agaaaaagcc gggagcttgg gaaggagacg ggattgaaga agccacccgg cagggaggcc 360
gaacggccca gagctctccg ggtaaaaccc gcctgcggtg atctgggaag tgtgtctcca 420
cctagccctg cgagcagcgg ccttcctccc gcccgttgaa gggcgctgtg ctggagtacg 480
aacccggccc agagaagcca ctcgcccttc tttgtcactt aaaaccctgt cccgacgcgg 540

```
atctcacgtc tagacctctg tctttaaagc ggatgtagag cgcgttctaa ccgttcccta    600

accattgtgt caccgcgaaa ggcggggctg tgtggaaccg tcccgcacgt gtgcgatgaa    660

tctggctccg ctgagaacgg atccgtgggc tgtctggcgc gggctggggc agcagccgag    720

agttagtcta cagagctagg gcccgagggt ggacctgcgt ccgcgtctcg tcacgaaagg    780

aagctctttt ggagaggcaa aacgtggtcg cccagatccg gcgcagctgt agccgtgggc    840

gctgtgcagt gacagccaca cccgccacct gtcacg                              876


<210> SEQ ID NO 135
<211> LENGTH: 309
<212> TYPE: DNA
<213> ORGANISM: Homo sapiens

<400> SEQUENCE: 135

tttctcatca ggatacagtt ccagcgtcgc acaaacccga aggaggagta ccaagagatg     60

aaaaacaggc agcccacgcc ggccatgccg gtgactgctc tcgcggagac agagaagaaa    120

ccgcaggctg gccggcagcc agggtgagaa tccccagcgc caggaactgg gtgtaacccc    180

agagctgcgc cctcagggcg gcgtccactt cggggggcct gcctgggtca cagtcgtttg    240

tgagcgtgaa gggcatgccg tagaaatagt caaatccgtg gttcaggggg tgtggcagtg    300

atccccgcg                                                            309


<210> SEQ ID NO 136
<211> LENGTH: 1209
<212> TYPE: DNA
<213> ORGANISM: Homo sapiens

<400> SEQUENCE: 136

aaaaaagaaa tgagtatcag agtcttatca tcattacagt tcttatggtt tttaaccgac     60

ctttaggagt tccaccgacg tgacccaagc agctggtagg agaatctggg ctggattcgg    120

aaggcgcgct acaggacgcc cgctgccccg gatcggaagg cgcagcacct caggccacaa    180

tctcagacac gccctcgggt cccgacaggt gttgcccgcc tcccacgggg ctccgggacc    240

ccggtccccg ggctgccccc tgccttctgg ggcgctggag cgcgcgcagt ggcggagctg    300

agccacccag tgcttcgcac gggcgcgctc cgcttctccg ggttttagcg gaagcctgcg    360

gggggcgggg taaccgcgga agccggcggc cgtgggcgcg cgggttgggg gctctcgcgc    420

cgctccgggc tctccccccc cccggctgcg gttgccgaag agaggccgga ggcggcgccc    480

ggctgctcca cctggcgcgc tgagcaccgc gcggggagcc cccgggggcg ggcggtgggg    540

ggcgcggact gcgggaagaa ggcacgaggc gtcgccgcag ctcggtcagg ggccggggcc    600

ccgccgctcg ccgctgcact aacttgccgc ttggtctcgc ctcccgccgc ggctcgctgc    660

gctttgggtg gcggggggcg gggagagcgg ggagtcagag ggtctgcggt ggccgaggga    720

gggaccctac gacggggagc ccgcccggtg ccgctcttct tcccctcccc gcccctccgc    780

tccccccacc ccgtcccttc cgccgattcc gggaggacgg gcgcccgtga cctgcgaacg    840

ctgccaagtg acggtccccg agtctgaagc gcccgcgagg aagcgagcgc cagcgcgggc    900

cgccggcgat gacggccgcg aagcaggagc cgcagcccac cccgggggcc agggcgagcc    960

aggcgcagcc ggcggaccag gtgagagcgg cagccgcggc caggccctcc cgggaggggt   1020

ggctccagtg cgcgctccgc ccgcctcccg cttcccaggc tgggctcccg cgcctccctc   1080

ttctcaccct cccccgcccc gccccagttc caggctctcc tgcttctcca cggactctgc   1140
```

gggaagttag agcctctgct gcgctccggg gcccggcgag aggatgcgca aggtggagag 1200
ccgcgggga 1209

<210> SEQ ID NO 137
<211> LENGTH: 327
<212> TYPE: DNA
<213> ORGANISM: Homo sapiens

<400> SEQUENCE: 137
aaaattggtg catttaggaa ggaaatgcta taaacgccta attccttctc gttctttggg 60
gttgctgagc tgacctcgcc gcgaggggag agggggaaaa aaacgcgcac taatgattct 120
gtttattagt tatatatgta tatattccgt gttcgcttgt acaggaggat ttacatggct 180
gtataaagat ggctaggggc gccgcgctct tctggggcgc tcacggtgac aggctggggt 240
taaaactggc tgccccagga gaagcggagg cctggaatta aatacgtttc ggcgcactga 300
tttaaataag tttcctgaat atacaaa 327

<210> SEQ ID NO 138
<211> LENGTH: 629
<212> TYPE: DNA
<213> ORGANISM: Homo sapiens

<400> SEQUENCE: 138
agagcttccc cctacaccag gcacaacccg attctaaaga aatgctgcgc ccgcgcctgc 60
agatttcgcc ttctctctcc agatccctct ttgccttcct gccagccagc cgcgacccga 120
gtcctgagtg aggtgagaag agaaggcctc gcctggcacg ttaccttttt ggtgaaagcc 180
tttgccgcaa aattcgcaga cgaagggctt gtagcccgcg tggatgcgga tatgcgtgtt 240
gagcgtggag ctgcggttga acgctttgcc gcactggttg catttatgtg gcttttccta 300
ggaaaggggc gagtgcacag taaggagagg ccacctcggg aacacctgga agggacatcc 360
cccccacccc cactcaaccc tagagggtaa gggataatct ttggccatcg tatccccggt 420
gttatcacta agattctggg ggttgcgcgc gggctaggcc cgacccgggg gcacgtacct 480
gggtgtggat aattttgtgc ctgcagagcg tgctggcctg gcgaaagcct ttgccgcaga 540
ctttgcacac gaacggtctg gctccggtgt ggaccggcat gtggcgggtg agattatagt 600
gagcgttaaa cacctatgga aagacatgg 629

<210> SEQ ID NO 139
<211> LENGTH: 385
<212> TYPE: DNA
<213> ORGANISM: Homo sapiens

<400> SEQUENCE: 139
atcttttgct gctgaaatgc agatggtttg gacacttcat aaagagggca ttaataagcc 60
cgccgagtga gcgccagggc gggattctcc cacaaattca aggtctgtat ctccgcggaa 120
gccgtgctat cggtcccccg agtgctgaag gctcccacga ggggcaggcc agcccggtgc 180
gccagggaag gagcttgatg gtgtgtacgg ctacgtagtg aacgtggagg tgtgcgcagc 240
ggagtcagag gggctagatc cccagcattt cccacggggt cccacctagc gcgtggatgg 300
agcaacttca tcactccacc gagggcaggg aaagaggagt aagcattgga gctcaaagaa 360
tgagcaattt ttcaaagctt tctcc 385

<210> SEQ ID NO 140

<211> LENGTH: 1209
<212> TYPE: DNA
<213> ORGANISM: Homo sapiens

<400> SEQUENCE: 140
cgggtggttg aaggcgtagt ggtgttccgg cttcaggtgg gcctcaggcg gcaggcccgg 60
gtggtggggc gggcccagca ggtgggccgc ggcctgctgc tgctgcccgg gagagggcgc 120
cggctctggg ggctcagcgc cgcagccggc gtccccttca gctctcccag gccccctcgc 180
ttgtgctcct ggcacgggga ggcgctcgag tgaggcgact cggtgcccgc cggagtctcg 240
gaggccggcc cggcggcctc cccgagttga gcctgtgagg cctgggctcc ggcggccgct 300
tcttgccgct gccggcggcg cctgcggcct ccttcagcgc cagctgcttc tcgcacttga 360
agcgcttctg gcggcgcagg tagcagccgt tctcgaacat gttgcccgag tcagggtgca 420
gggtccagaa ggagcccttg ccgggcttgt cgggcgagcg gggcaccttc agaaacagtc 480
gttgaaggag agcgagtggc ggatggagtt ctgccagcgc tgctggttct gccggtagaa 540
ggggaagagg tccatgatcc actggtagat ctcgctcagc gtcagcatct tgttggggct 600
ctgctggatg gccatggtga tgagcgagat gtacgagtag ggcgctttgc gtgcgtgtag 660
ctgcgcctgt aggtcttggg gtcgcgggcg cggctcaggc ccgcctgccc gtacatgggg 720
ctcatggagt tcatgttggc gtagggggcc aggccgccca tggccccggc cgcctgcccc 780
ccgagcgggc tcaggctggg actcaagtgc ggcccatgcc cgccacgccg gccgccccgg 840
ccgagccgcc catgcccgcc atggcgcccg cgccggggga catccccgcc agggacgggc 900
tcatgccagc gcccacgtac gacgacatgt tcatggagcc cgcgctcatg ttgcccgagc 960
cgctgcccat ggcggccgcc gacatgccat gtacgtgttc atgccgttca tccccaggcc 1020
ggcgttcatg ttgctcacgg aggagtagcc ctgcggacag agccccggga gggaggcgac 1080
agcgttagca ccgcggctgg agggtgccca gacctcccac ccaccgccca ggcctccgcg 1140
tccggggagg cctccggggg ccctttcgtc cccgatggcc cagtctccgg actccgagtc 1200
tgtttcatt 1209

<210> SEQ ID NO 141
<211> LENGTH: 1209
<212> TYPE: DNA
<213> ORGANISM: Homo sapiens

<400> SEQUENCE: 141
acagaggact tctcggggtt cccgaattcc cagggttaaa acaaacttgg tttgtgcggc 60
gacaccgcta cccttaccgg tccccagata gtcgcggatc cccgaagcta agagccaggg 120
caggactcag tcagtgttcc aggaacagct gagacaccca ggtcaccacg ggctcgcgcc 180
gctgcggctc cgacccggtg cgaaccgcca tacgcgccgc gcggtgggcc ggaggcagtc 240
cgcgtactgt tgcggaaact ctgtctcaca aggtgcgcaa cactcgccgc gcgcaacacc 300
accaggaagt tgatgtcggc cgggcgcact aggcggtagc tgcacgtcgc gcaatcctgg 360
ctgcattcgg cccgcacggt cgccaggagc ccggggccga gcaacagcag ccaagtgcaa 420
agtgtcagga accgcgccat ggactgcgag gagagaggga cgcgtgcttc ggcctgcctg 480
ggcgcagaac ggggtccctc ggcaggaccc tcgccgcgac agcctcagca ggggatcgtc 540
gagcaaaagc ccgcaggaat gctcctttct ggggccccgc cctcccggcc gacagctttt 600
aggtagacgt ggaggcgact cagatcgcct cgcggttccc gggtggcgcg gtcgccccca 660
acgcgaggct gcctggggca cccggctctt ttcctgggcg tccgcggccc agggcaagat 720

```
tccggagaga acgccgcaga ccaggggcga gagagcggga gccgggggag gcaggacatt    780

gactggggtc acaaagaaga accagggaac gctgtgggga acccatgcaa tgaaatgtga    840

agggaaagag ggcgggcaga cgtccccaaa cccgctcagc aaagacaagc ttcgggcaaa    900

ttcactcacg ttgacgctgt tcggatggag caggccaatt ggaaaagccg ggttcagaca    960

cgactctaga gggaagagaa gaaggcagtg tgaggagggc gggcgtcggg gagaagcggg   1020

cccgggtgtg ctggcggacg tagggcctca ccgtcgcggt cctcagcgtc tctgcggggt   1080

cacgggccag gctgcggggc tctgagcgcc tgcctcgccg tcccggggct taacggctgc   1140

tggagccact ttataattac cccaaaccga aggaggcgcg cgcgccccaa tcgccggcgg   1200

gctgcagct                                                           1209
```

<210> SEQ ID NO 142
<211> LENGTH: 476
<212> TYPE: DNA
<213> ORGANISM: Homo sapiens

<400> SEQUENCE: 142

```
gatctgctct tcaagaggaa gcctaaagtg gagagtttgt aatcctgaca acgcccagct     60

acctgcgtac cccggactcc aactcccagt ttgcaacgcc aaagggtcta aagggcgaac    120

gggggcgatt gcatcctggg agcaagaatc gcgataggtc tgatggattg tgggaactgt    180

agttccatgt gcgtgcgatg cactctatgg taggatagac ccggggaaga gtcatttgcc    240

ggccaggaag ggatactttt gagagcgtca gtgctgcatg ccgggatttg tagtctgagg    300

cccgcctcgc attctgggcg gggattcatg ctccttttca gggcgcccgc tcctcccctt    360

ggtattgccg tcagagatgg gcggttggtt attgctgcct gatggtggat gaagcagtgg    420

aaaagagaat tgtatcgttg tgcttgacac taggggttta gttggaattg tgcttc        476
```

<210> SEQ ID NO 143
<211> LENGTH: 679
<212> TYPE: DNA
<213> ORGANISM: Homo sapiens

<400> SEQUENCE: 143

```
taggattact gcatgttcag ctacgacctc atcaacatgg ctgctggaag tcgtctacag     60

gaaaaagaaa gaaatgacac tgaaggatca cttccgcttc cgttggcgca agcgctttca    120

ttttttcgct accgtgacta agatggaagc gtttttgggg tcgcggtccg gactttgggc    180

ggggggtccg gccccaggac agttttaccg cattccgtcc actcccgatt ccttcatgga    240

tccggcgtct gcactttaca gaggtccaat cacgcggacc cagtaagttc tcggcgcttc    300

gtttgcgtag cgggagggac cgtggggcct ggtgctgccg gctggttttg agagcccggg    360

aaggtgaggc ggggaccccg ggggcgcgcg aacggcaggg gagctcaggg cgcggagtcc    420

tggagaatgc agaataattg gaaggaatta tagaaaatca gaagcgcagc tagtgcgcgg    480

aaagagggcg cagtccatcc cccctctcag ctcccaccgt tctcactctt taggaacccc    540

atggtgaccg ggacctcagt cctcggcgtt aagttcgagg gcggagtggt gattgccgca    600

gacatgctgg gatcctacgg ctccttggct cgtttccgca acactctcgc attatgcgag    660

tcaacaacag taccatgct                                                 679
```

<210> SEQ ID NO 144
<211> LENGTH: 1209
<212> TYPE: DNA

<213> ORGANISM: Homo sapiens

<400> SEQUENCE: 144
tccttagtga caaggtctct gatctcctgc tgccactgca atagcctctc ccatcccgcg 60
gggaacggcc ggagttcttc ccttgatctc tcccgagtcg gcttccgctg ggatggatc 120 gcaggtagcg ccggcgcggc ctggggaaga acagttgcgg agcatctgaa gcggaaaatc 180
caagcagatg tgaggcgatc cggcccgcc tcgttcctct tggggcctga atttcttcca 240
gataagtttc ctaatggaac atttctaaga ggtggggtac gaggcggctt gctcgcacgg 300
cagtgggaca gactgcgggt ggggacgtac tgagaggtcc ggacctcaat gcgtccgacc 360
cgtctccaca ccgccctttt ccagcccca gtctcctttc attccctact cttcaggctc 420
ctttggggcc agtgggtgaa ccgccattta gaacggtgcc tcggactcgg ggtcgtgcgc 480
tccatctctg cctcccccct ggggcccgcg aggctggtcc gggctttctg agctgggcgt 540
tcggctttag gcccaatacc tggaccagga atttcttctc cccgcgccag aagggaaaga 600
cataggaggt gtcccaatct gcggtcaccg ccgatgctcc tgacactcta gtgagcacct 660
gcccggtact tttccattcc aacagagctt ccagcttcat actaactatc ccacatacgg 720
cctgtgggta ttagctctaa gtgtcctttt ccgagggccc gaggctcccc ctccagcagg 780
gagagctccg ggacggcccc caccaagggt tgggttcttc cttcacaatt ccacagaggc 840
atccctgtcc ttcctacctg ggaaacctcg aggtgcggtg cccgtgtact tctggtactt 900
tgcgtggtgc catcagggac cccagagcca cagctgcgtg tgtgtgtgga tgtgtgtgtg 960
tgtgtgcgcg cgcgcgcgtg tacggcgaag gatgtgcttg gggagccgga gtacacaacg 1020
tctgcttggg cagctgctgg gcaggcgttg ggcctggagg tatctcacac ccacgtatct 1080
tccagtcttc aaacacggca ttgctctgcc tcccgtagcg cgcttcgaac ctgcctcgcg 1140
gacacgtgaa cagaggctgc cctgggaaga taagtgcgct ttcccgtaaa atccgggaaa 1200
tttgccttg 1209

<210> SEQ ID NO 145
<211> LENGTH: 1209
<212> TYPE: DNA
<213> ORGANISM: Homo sapiens

<400> SEQUENCE: 145
aagtactgaa ctgggagcgg cagggtttga gtcaaaagag aagggtggag gagcgcgtcc 60
ggtgccccaa ggcttccagg cggagcgcgg gcgcgaggtg cgggctccgg ggcggagcgc 120
acgcccggag gcgggaagtg ggcagcagcg cccccgcctg gcccctgtgc gccccgaccc 180
gacgcctccc cgcccgacca ggtgcctcga gagcgcacag ctgggagggc tctcccggtc 240
gcggcgagac tcacgcctgc ggtgtgctag ggcggcggcg acggtgacgg gcgtggggcc 300
ggcgctgcct cggctgccgg gtcgttgcgg cgagcgcgcg ggccggcctg gagtcaccgg 360
gctgaaccgc cgcgcctgca tcgtgccgca cgccgcggag gcgctcgggt acagaccgcg 420
cgggcgcgca caaagcggcc cggggcggcc ggcgcggcgc agaccctcgg tggcagcgca 480
ctccagtctt cccaggctag cggctgcagg gagctccggc ccgcggcccc tccgcctcaa 540
gtctgggagc tgccggtccc actctgtctt tgcctatggg gattcgagag tttcccagcg 600
gcgcacccag gggcaagagc attgccgtgt gagtagcgcc ccggcgtggg tgagcgagcc 660
ggcgggcggg aggccggagc gccggggtag cccttttgcag ctgggacact gggcagtctg 720
aggctcgggg aagggcggcg cgcgcggtgg agctgctcgg gaagtttcag tcattctttc 780

```
cctcgccact cgccccaacc cgcactgccc cgagagccca ggatagggca ctggggacag    840

ctgcccgggg aagtgggtga gtggcggcgg gaagggagga gcgcgggctc tgccgcggcg    900

ctcgcccccg gagggccccg gccgcgctct tgctctcgcc ctgggatctg ctcctcacga    960

atcccctcct ctctgtccat gctcccctgc ccacccacct gcccgtggcg cctgcgaccg   1020

cagtggcatg aggaggtcac cggacgtcag cccccggaga ctgtccgaca tcagccccca   1080

gctccggcag ctcaagtact tggtggtgga cgaggcgatt aaggaggatc tgaaatggtc   1140

gcgctccgtg gaggatctcc cagcgggccg gtggggctca cgtccatcga ggagcggatc   1200

ctgcgcatc                                                           1209
```

```
<210> SEQ ID NO 146
<211> LENGTH: 475
<212> TYPE: DNA
<213> ORGANISM: Homo sapiens

<400> SEQUENCE: 146

tgcatcacca ccttggtttt gttttatttt gcttcttggt caagaaagga ggggagaacc     60

cagcgcaccc ctcccccccct ttttttaaac gcgtgatgaa gacagaaggc tccggggtga   120

cgaatttgcc gatggcagat gttttggggg aacgccggga ctgagagact ccacgcaggc    180

gaattcccgt ttggggcttt tttttcctcc ctcttttccc cttgcccccct ctgcagccgg   240

aggaggagat gttgagggga ggaggccagc cagtgtgacc ggcgctagga aatgacccgg    300

aaccccgttg gaagcgcagc agcgggagct aggggcgggg gcggaggagg acacgaactg    360

gaagggggtt cacggtcaaa ctgaaatgga tttgcacgtt ggggagctgg cggcggcggc    420

tgctgggcct ccgccttctt ttctacgtga aatcagtgag gtgagacttc cagac         475
```

```
<210> SEQ ID NO 147
<211> LENGTH: 551
<212> TYPE: DNA
<213> ORGANISM: Homo sapiens

<400> SEQUENCE: 147

ttggggttgt agtctatctg ggtcgtatag gaatactcat tctcgaacag cagcctgggg     60

acgatctgtg tgttggtgtg ggtgtcgaaa gcgtaggaga tgttggcatt ccgctggttg    120

tagctatcac ggcatacagc accccacaga tgacgaagca gttgccgtag aaattcctcc    180

ggagccccgt gcgccatgtg gtctccttct gtgtgctcag gtccgcggca ttgagcttgc    240

tcaggacaat gacctcctgg ctgaagccct catcgtccag ggccgggtag atgagccatg    300

gccattctcg tccacagcaa agtccacgtc tgagtggccc tgccatcgcc agggggtggc    360

ctcctcgtag gccacgtcat gcagcatggc ccaggcagcc acgtagcgct gcttcaggtc    420

gtacttgatg atgttgcggg tgaaggcgcg attgtagtag aaggcgccat ttataccacg    480

tggcctgtgc cgatccagct gtacgggagc ttgtaggaat tgctccagcg acctgcaggt    540

ggggagaaaa c                                                         551
```

```
<210> SEQ ID NO 148
<211> LENGTH: 1209
<212> TYPE: DNA
<213> ORGANISM: Homo sapiens
```

<400> SEQUENCE: 148

```
tcacaggcca gctggaagtg ggcagaaacc ctgtgggtcc cagaccctcc ccaatcggcc     60
gctgctccca cctctcccgc cccaattttt cagcagctcg attcctgcgg atcctacatc    120
cgggaagaag cagacgggcc ctcctcccct ccctcgcctg gcgcgcggcg cctgggttct    180
catcaccacg ggcccagtgc tcaccgtgcg cggggctgta ggagacgcgc gcccgcgcgt    240
gagcggggtt ggcatagtag gggttgccct gcgagtcgag gtgattgaag aagacgtccc    300
ctcgtctgga ggcagcagct gcgcgggttc catgtagttg tgcgccaggc ccgggtggtg    360
tgagtcgggg tgctgcgcat tcagcacggc cgggtgcgcc atccagcgcg gctgctcggg    420
cgccacctcc atggccggcg gcggcggctc agggtctggg tgcagacggc acggccctgc    480
gcgaggaagg gggagtgagg cgtgccgcca gcgcctgaca ccccccaaag tcccaccacg    540
aggtgtcccg cacgccacgg agccccagcc cagatccggc gagaaagagc accagtcccg    600
ggtgggagga aagcccaagg ctcaaaacga aaggaaggcg gggagggggt tcagccacgc    660
acactcacgt ggtgacccgc ggctccagaa tcacacaccc gtgcacatgg ggtcacgccc    720
ggggacgggt cccgacacca gtgaccccaa caaacgcaca gagcagcact tcagtcagac    780
actcacactg agccccccg cccggtagac aaacaatgaa cacagactca aaagttggag    840
acaggcgccc gggcacccag tgtggcactt gatcccagcg acacgcacac acccacactt    900
ggcgccagat acacatactg atctcaaccc cgaaaacatg cacacgcagc cccctgagcg    960
cagtactaag cggcacaatc aggaccttca acaaagcaca ccaaagcagt cgcccgcagc   1020
ctggccccc gccctaagtc cccccagagt cccctcaaag ctaggagcgc cccaggcccc   1080
cagccggctc tcaaacccca aacttacaca cgcagccgtg gggaggggag ggactcggcc   1140
tctgagagtg aaggagttcg gcgggagccc cgagggcgac gggcccaggg acagcacgtc   1200
cggaggctg                                                           1209
```

<210> SEQ ID NO 149
<211> LENGTH: 601
<212> TYPE: DNA
<213> ORGANISM: Homo sapiens

<400> SEQUENCE: 149

```
gtctgatctg tgaagggtag ggccagcagg cagcaccaaa gttcccgtat gcgcgttttc     60
agtcttcatt taggtccgaa ttcccggcat ataagaatac taccgtcgct tgtttttcag    120
atttttgggc tattttcgtt ggtgtgttgg tcatgtctgg tcgcggcaaa ggcggaaagg    180
gactgggtaa aggaggcgct aagcgtcacc gtaaggtcct gcgagataac atccagggca    240
ttaccaagcc tgccatccgg cgccttgctc gtcgcggggg tgtcaagcgc atttctggtt    300
catctacgag gagactcgcg gggttctgaa ggtgtttctg gaaaacgtga ttcgtgatgc    360
tgtgacttac acggagcacg ccaaacgcaa gacagtgaca gcgatggatg tggtctacgc    420
gctgaagaga cagggacgca ctctttacgg cttcggcggc taatgctacc gttaaacgac    480
tcagcatctc gacttcccaa atcaaaggcc cttttcaggg ccgcccacag ttttccgcaa    540
aagagctcat gacttgttag acgattggtt ggtctcttta taagttaatt gttcctgtca    600
a                                                                    601
```

<210> SEQ ID NO 150
<211> LENGTH: 22
<212> TYPE: DNA

<213> ORGANISM: Artificial
<220> FEATURE:
<223> OTHER INFORMATION: primer

<400> SEQUENCE: 150
gggtttttag aggttagggg aa 22

<210> SEQ ID NO 151
<211> LENGTH: 25
<212> TYPE: DNA
<213> ORGANISM: Artificial
<220> FEATURE:
<223> OTHER INFORMATION: primer

<400> SEQUENCE: 151
caactaaata accaaacctc tcctc 25

<210> SEQ ID NO 152
<211> LENGTH: 24
<212> TYPE: DNA
<213> ORGANISM: Artificial
<220> FEATURE:
<223> OTHER INFORMATION: probe

<400> SEQUENCE: 152
ggagaggggg gttatgatgt tagg 24

<210> SEQ ID NO 153
<211> LENGTH: 20
<212> TYPE: DNA
<213> ORGANISM: Artificial
<220> FEATURE:
<223> OTHER INFORMATION: probe

<400> SEQUENCE: 153
gtttgtttgg ttttagagaa 20

<210> SEQ ID NO 154
<211> LENGTH: 8077
<212> TYPE: DNA
<213> ORGANISM: Homo sapiens

<400> SEQUENCE: 154
cgggcaggcc caagctgcga tgtggagaat tcgatgtccg agcgacctcc tcggaggagt 60
gggtcgagtt aaatataacc gcgcgaatgg aatggcgcta aaaataaggc agcagctggc 120
ctgtccacag ccctgtcccg ggaggggcgg gggccccagt ggtcttgggc aggaaggccg 180
cgtccggccc aggggcgaga aggctgcggc gtccgcagcc agggctggaa ggcctgggag 240
gccgcgctct gtgggccccg gggcctccat tcgggctggg tcgcgggcct ggacggggac 300
tgtccagagg catccgaaag ccaggccaac ttgcctggac gtaacaagac ggaagggctg 360
ggcgctgagg tcctgccagc ccggccgcca gagggagctg agcgccagag gaggacaagc 420
cgaacccttc aggaggccgg gcgtctccgg agaccgaagc gccggaggac ccgaggaggt 480
ctgccccgcg cgctgctctg gagactcccg gggcgggtgg cgctcggcct ttccgctccc 540
ttccttccca caagtccctt cccgcgcgcg ccccacggcc ctgcccgccc tcccgcgtca 600
gcgccccaac cgtcaagcca gcaattgaaa cgtttccaaa acggtctatt tatttgctcc 660
caataaatcg atcggcggtg attaaagaat cgatgtggcc tgggtgggcg agtcgcttga 720
ggggagggat tgggggcttt cgcccggcgc ctgcagggag gccgagggcg ggcgcgggcc 780
tgagggaggc gtgtcccgcc cgggccacac ccgaggaccc gacacctggg ctggcaggcc 840

```
ccggcaggca gcgttccctc cggcggagag gggcgcgcgc ccgccgcctg ctttcctcgg    900
cccctctcgc ctttctcgcg cgccggggag gctgtggccg ccagtggctg cggagctgct    960
cagaggcttt tgttgctcct cggccggctg aatggggatt ttgtaaagcg ggacagataa   1020
aaatgagcag catcatattg tttgacagaa tgatctcgca tgatgaagtg tcggctccga   1080
agggggtgaa aatggtgaat tcctaaaaac ccagccctgg gctcctcctc gagctgccgg   1140
tagcctggag ggacccagcg gacagccggg cctggccgca tcgctccaaa cggtgtcaga   1200
aagactccgg ctttcaatgc caagtcattt ttaagccccg atcctgtcca ggacctttct   1260
cctcgtggat gaaaagaaca attttcgaga gaaaggctcg tttttattaa atccgacatg   1320
ctgctgataa ctccatgcta atgtgaaata attaacataa tagccataat taaaagcacg   1380
ctaacaatgc cataaattta tcacacaatt ttactagctt tctgccccta actgctctct   1440
catcgttaat taaacgtgtt gccttttaca gaatggatgt ttatatattt ccaatataaa   1500
taaattcgaa accatcctct ctctcttcct ctttctctcc tcctttcctt ttggtctctc   1560
gccatttaca ggcacgcctt ggcgtggacc ctgagtggca gacatcttga aaataaatga   1620
agttttgaga tgcaaatcca aacaagaaca ttaaaatagc ctcttttttt ccaccccgaa   1680
aagatccgga gaggtataca agggggtagt ggtgggtaag agagttgaaa atcccccgct   1740
ttgggaaatg gaagtaatct gggtgggttg gggccttggg taccacctct gccctttccc   1800
accttccttg gtggcggcca tccagacaaa gaggccggta atagtttaac aaatctatga   1860
agattttcaa gaagcagcag actttgattg ttgcgggcgc gggggtgttg gggagaaagg   1920
aggggaattt ttctaatagt cccacccacg ttttgctccc tcttggacaa agagtaacta   1980
ctcttggtgg gggacgcgcc cttcactccg cggaacctgg tcccaactcc ccgtattgta   2040
agaaaagtgc acccgcgcgc gggcatgatg attctatctc acatcgcgcc aacgacttat   2100
tcaagccact ggcactgtct ctgacttaaa agaggagaaa agaggcatat gggttcactt   2160
gggcctggtg aggggtaggt gggcaattcc cgccttccgc actctaaccg tgcccctcct   2220
ccagtgttga ccacctaaga acccaaaatg agctgtaatt aatttccctt tctccatcat   2280
aaatttttct atccatttct tccccccat cccccactg gacgcacaca ctaaatctcc   2340
cctcccctgg agacgtctca atttccttcc tatcgatccg gactccattc ttcttgcctc   2400
ctgttgctag aacctagatc ccccactcccc gcacccctca ttcccaccgc gtccaggtgg   2460
ctttcccagc ggggtaccat gtactctgcc cgctccagag gaaccgaagg ggtttcattc   2520
cattctcctt tggttgaaac atttcaaaca tttgagcagg tgaggcagct ggctgccatc   2580
ttccttttta aatctctcct gggaagttcg cttgttgaga ctcaaagagt cactcaaact   2640
cataattgcg tgtgtgtgtc tactcattct ccctctatct ctccaataac cctttgagac   2700
tcagaaactt tttatccaca tacacccttt atcacatttt cttcccccca ctacatgtgt   2760
ctcactttct ctctgtatct gtctcgcttc ttccgtctct gtcctacagc ttggcggtaa   2820
ctgacgacct gtgagctttt agctgcaaac tgcaactacg cggcaaacaa tttatttagc   2880
ccgacatcta gccggtctcc ggcaggaccc tgcaccgcgt cgggatcgga cccttccgct   2940
ggggcggcct cctgcgtcaa ggccagcagg aaccttcctg tcgccctccc cggccgccgc   3000
ttcgcctcct tcccgccccc ggaggttgtg caggcgctat ggtccgcctg gagggagaaa   3060
gccggcggcc ggttcctgag ccgagagcgg ccgcggaaaa atcctctgcc tccgctggaa   3120
atcgatatta ggccggcgcg ggcgcgggac gtcggggccg cagccagtag gttgtgcacg   3180
```

-continued

```
tctcatcatt tagctaatcg agtcgaaaag tttctgtaag ggccggaccc agcatcagat   3240
ggtaacactg attgaacaag agattagcac aatagatctc taaccgaggg gaagcgttgc   3300
ttttcacgct acgcgccgta attaatggta tgaatcaatt aatttgactt ttattgtgtc   3360
gaaggaaaaa agcgcaacaa atggaaccgg cagctgggag ttgttcgtcc tccaccccct   3420
tccccaggga ggttccaagg agacaccggg gaatggacgg atcaggctgg gccgtggcag   3480
agggagggta ggaggcagcg accagcagcg tggagggagt ccagagagct agcctctgcg   3540
gacggcggaa tcgaaattag gctcatttgg agactacttc gagaccggtg aggggagccc   3600
tgtagccacc atcctccggc gcgcatccac acatactagt ccacgcgggc ccagccacca   3660
aggccgcggc agggccagcg ctgcgccccg ggcccctgcc tttagggctg ggcaacccaa   3720
gcagagcaaa ggaggttcct gaatgtgtaa atttccgctt tttagctttt tttttttttt   3780
tttttggacc ttccgacact tcggttgctg aggcagttgc agacgcgacc tctgcagtcc   3840
tgggcgatgg ccagccagct cagctcgggt cggtttcgcg gaaagctgtc tagacggcat   3900
tgtaaacggt tcggagcctg cgggccacaa agctgtggag ctacggaaat caactctgag   3960
atgcgtttta gggccgtgtg caacctcggg atcatttaga taaagaaaaa ctgtggaggt   4020
tggcgggcgt ctcaggatag tgtcaccacc ccctaccctg ctcccagcct cagatgagta   4080
gtgttatatc ctgggaaact gtctaatggg gatgaaagtc aatctgtgtg tctcaatgcc   4140
tgtaatgaag caagtttaca gatttttaaa tttttatttt tattttattg aattattttt   4200
ggtgtgtcta ggccaaggaa agaggagatc gtgggtgggg aaacagactg agggaatcag   4260
aagcaccact gtccatccgg aattaaatcc acatcccagc atcttctgca aatatttcac   4320
taattatttc ctctcggaac tcctcccctc gtgctccttc ctctggtgag gccggcgctc   4380
ccctcccagg ccgcagcgga cagacaggga ttgggttccg tgtgcctgcc acaccaggca   4440
ggctcttgcg gctcccaact aggcggccta aatgagggag gaaagaggag gcgcatcgct   4500
gattcaccgc gtcaagagca ctgactttcc ttggaggtgt gaggtccacg caccccagcc   4560
acgcacttgg gggtcggttt gcggtgcctc cccctccagt cccagtgaaa tccccacagt   4620
ttttcctact atcactgact tgccttgcac tccgcgtgca ttggccacac atcctcgcct   4680
cctccacccg ctccgccgcc ggttttcttg gaagttaaat cttggaggat ttgtccacac   4740
cttaagagaa gaaaatccac gttagctggc agcaacggag atcccagcat gctggcatgc   4800
ccaagtctgc ccaggttccc ccaaggccat gcccgccgcc cgggaagtca ctgcccgcac   4860
ccctcacgtt tcttcagccg cccctgggcg ctgcgtctaa cctgaagaca ccaggcctct   4920
tcccggatcc actcgactta cccaggccgc tgccaatccc agctccttcc ccagcgcctc   4980
atttccgatt ttttcatatg ctaagtcgtt taacaactcc aagtagccag ttatggcttc   5040
tttatttata ggttccctgc tattttacgt cgtttttatt tctctcggca actattctag   5100
tagattaatc aatagccatt ttctgacctt cgggaacccc agctgatgct ttttgtggcc   5160
gcacgaaaaa atacatacag gaaaacacgc ccgcatcaag ccgggaaaga gcaggtagga   5220
cctgagtggt ttggttgggg gagggggaaa aagacatctc agcaggtgtc ttccccggaa   5280
tgagcactga ggccagaggg gaatctgaaa tctaattagc aggagggagc cgggtgcgct   5340
gctcttactc tttaaagcta aaaacaatga aacaaaaagc aaaacagaga ctaagttttg   5400
ctttttaaaa cacgatatgg gaacctcgtt ctaggtcgcc cagtccctgt ctaaggagtg   5460
tgacaaagtg ggggggagaa gggcggaagg gagagggggc ggggaaggca gggcagcgac   5520
agtcgcacag tcccgcggac gctcccaggc ccacgccctg actcgctcac acccacccac   5580
```

actcacaccc acccgctccc tggccccag ggcccggatc cagcctgggt gggggggtct 5640
ccgggcgggc cgcagcgccc tccgtgcccc ggggatgctg gcgcacagtg cggagcggag 5700
ttgcgcgtct ctcgtccctt tgttgacaat tccctgaacc aacttgagtt tggccggctc 5760
ggccgcggcc ctgacgtcac gcacggtcac gtggccccgc ctcccgctgg atctttaagt 5820
agaaagtaat ctatcaggcc agtccttaaa acgggacttt cgactaccgg ggcttcggcg 5880
tccctgacac ccagcccccct gcccccccgc tactgtccct gcccgcgccc tcccgagctg 5940
ctcggcgccc ggcgtcccgc gcccgcctgg accgctcctg cgccccacgc cagggccaga 6000
ggccgaggaa ggcgggctaa gtgagggggc gcggcgtgga gaaccgccgg ggccgggagc 6060
ggtagcgagc gcctagtacc gagcgccagg gacggcagga gttcgcggag cgcggccgct 6120
gggggcggac ggcagagccc gcgccacgcg atgcggggcc gccgagtgtg agctgagccc 6180
agcgggcccc aagccacctg cggcccctc ccctctccct gccccccatc tttcgggggc 6240
actcaaaccc tcttcccctg agctccgtgg cagcccccga acaccctcat cgcccgctgc 6300
cccctccccg ccgccgctac caaccccgag gagggatgac cctctccggc ggcggcagcg 6360
ccagcgacat gtccggccag acggtgctga cggccgagga cgtggacatc gatgtggtgg 6420
gcgagggcga cgacgggctg gaagagaagg acagcgacgc aggttgcgat agccccgcgg 6480
ggccgccgga gctgcgcctg gacgaggcgg acgaggtgcc cccggcggca ccccatcacg 6540
gacagcctca gccgccccac cagcagcccc tgacattgcc caaggaggcg gccggagccg 6600
gggccggacc ggggggcgac gtgggcgcgc cggaggcgga cggctgcaag ggcggtgttg 6660
gcggcgagga gggcggcgcg agcggcggcg ggcctggcgc gggcagcggt tcggcgggag 6720
gcctggcccc gagcaagccc aagaacagcc tagtgaagcc gccttactcg tacatcgcgc 6780
tcatcaccat ggccatcctg cagagcccgc agaagaagct gaccctgagc ggcatctgcg 6840
agttcatcag caaccgcttc ccctactaca gggagaagtt ccccgcctgg cagaacagca 6900
tccgccacaa cctctcactc aacgactgct tcgtcaagat cccccgcgag ccgggcaacc 6960
cgggcaaggg caactactgg accctggacc cgcagtccga ggacatgttc gacaacggca 7020
gcttcctgcg gcgccggaaa cgcttcaagc gccaccagca ggagcacctg cgcgagcaga 7080
cggcgctcat gatgcagagc ttcggcgctt acagcctggc ggcggcggcc ggcgccgcgg 7140
gaccctacgg ccgcccctac ggcctgcacc ctgcggcggc ggccggtgcc tattcgcacc 7200
cggcagcggc ggcggccgcg gctgctgcgg cggcgctcca gtacccgtac gcgctgccgc 7260
cggtggcacc ggtgctgcct cccgctgtgc cgctgctgcc ctcgggcgag ctgggccgca 7320
aagcggccgc cttcggctca cagctcggcc cgggcctgca gctgcagctc aatagcctgg 7380
gcgccgccgc ggccgctgcg ggcacagcgg gcgccgcggg caccaccgcg tcgctcatca 7440
agtccgagcc aagcgcgcgg ccgtcgttca gcatcgagaa catcataggt gggggccccg 7500
cggctcctgg gggctcggcg gtgggcgctg ggtcgccgg cggcactggg ggttcagggg 7560
gcggcagcac ggcgcagtcg tttctgcggc cacccgggac cgtgcagtcg gcagcgctca 7620
tggccaccca ccaaccgctg tcgctgagcc ggacgactgc caccatcgcg cccattctta 7680
gcgtgccact ctccggacag tttctgcagc ccgcagcctc ggccgccgcc gctgctgcgg 7740
ccgccgctca agccaaatgg ccggcgcaat agggacgcgc caatggccgg gacccagggt 7800
ccggcggcgg cctcgagcaa caaatgcacc tccaggctgc gcgccctgtc ccaagcccgg 7860
tcccggtccc gctgcccaat cctggactct gcctctcccc aatttccttt cccctgagcc 7920
cccaacgcct accttccgcg gcctccatcc cctcgcgcac acctaagctg gtcgagcaaa 7980
ctcaccgcgc gcccgccggg gatagctttc catacaggta aaaccgaaaa ccgaattttc 8040
caaaaatgca ccccgacggc gcctgctctt agtaccg 8077

<210> SEQ ID NO 155
<211> LENGTH: 348
<212> TYPE: DNA
<213> ORGANISM: Homo sapiens

<400> SEQUENCE: 155
cgcgtctgct accagatgcg gctccggggg ctccatggtg actgagatag gagaagaagg 60
cgccgtccct acggtatcaa tctccgaaca gggagatggg gtggcctgac tcctaaaatc 120
cgcggtcctg gcctcaccga gcgggcggaa atctccattc atcatgcctg ggctgcctga 180
actggcactg gacaaaatcg tgtctattcc aaaactcgac ccgctggccc cttccattgt 240
cattgctaca tgaggtccac gccactccgc cgttcagcag ccgccccgaa ccagcgaaga 300
aagctatcga tcgtaaaaca aaataaacac caaacaatgt tgccgccg 348

<210> SEQ ID NO 156
<211> LENGTH: 325
<212> TYPE: DNA
<213> ORGANISM: Homo sapiens

<400> SEQUENCE: 156
cgagaggccc ggccaccggc tcgggagctg ggccggtcgc tttgggagcg gatgaggaag 60
gttaggagaa gcagcgagat agatcccaat tttacaattc tattttcttt cggtagggtc 120
tcggcgtcct gggccacgtt gagagcgaac gtgggccgag cggaggacac agagtaaaaa 180
gcgacgcccg ctgtatacat aaatccgcac ccgctgcccg cccgggtact gcctgctctg 240
gcttccgctc tcttccgagg ctgggcaagt ccaaaagttc ccgaaagggg ggttcaaaga 300
ggggcgctca gtgcacgtga tttcg 325

<210> SEQ ID NO 157
<211> LENGTH: 431
<212> TYPE: DNA
<213> ORGANISM: Homo sapiens

<400> SEQUENCE: 157
cgcggaagag ggcggaagga gaacccctgg actggtcctc accgagcact acaggtggca 60
gagccgtggg ggacccgtgg gttatgagat tcagcggtga ggggtagcgg tgtggataaa 120
agtagaggcc tgacctgctt gaacgtccgc agcagcgagc ccagcatgaa ggccgccatg 180
ttgtccgcta caaactacaa accgctgaaa ctttattgac actgccgaat agcgcaggac 240
acgaggggcg gggcctgggc cgcctggggc ggagctggga ggtgggtggg aatgtggcct 300
acaggaaagc ggggttagtt ttgggatcgg agctctcgcg atatttcacg gaacttgggc 360
aaatgacaaa tctgaaggcg ccgcgttgat gctgatggcg cagccagacc cgccccgtgt 420
gttgcagccc g 431

<210> SEQ ID NO 158
<211> LENGTH: 703
<212> TYPE: DNA
<213> ORGANISM: Homo sapiens

<400> SEQUENCE: 158
cgtctggcca aaggcgccca gctcaacggc cgcgacgcgg taaggaaggg ctccgccgcg 60
gcggtagccg ggcacccctg cgccctctgt taaaccaagc cgactccctg gccggtggag 120
aaccggagcg gcgggtcgta gagacgtccg cttgagggtg gcgggtgagt tttctcccgt 180
ccacctatgc ctacagggct aagaaacggt cgtttttctg aatcgaaatg tctgcagctg 240
gctatcctcc gtcgcagctg attccgaaag agcagggaga ggaactggga ggaggtggga 300
tggggggtgg tggcattctc ttctacagac ctcaaggttc ccttgattcc ggggcaggcg 360
tctccccggc gaggatccgc agctccgagg gcaagctggg cataagcaat aggaggacgg 420
cgcgctgccg aggcgtccga gccaagcagg agcccaggtg gccttagtct ctgggcctga 480
tgaccggacc tgtggagtag attccgacgc gactgggtca tttccagttc tctagacgct 540
cggggcttgg gacccctaac cgagagaatc tcagggtttc tggcatcccg actcagtccc 600
tctaaggaga cagcactacg tttagcgcca ggacccggcg ggtgtcatgt gtaggggaa 660 atcaaataaa acatacggag gagcgcggca cccagtcgaa acg 703

<210> SEQ ID NO 159
<211> LENGTH: 416
<212> TYPE: DNA
<213> ORGANISM: Homo sapiens

<400> SEQUENCE: 159
cggcgggggt cgctccaaag acttgtattt cgcgtttgcc tccgggagct gggagtaagg 60
ccttggatgg cgccgacgcg gttgcgagga agctgaggcc tgggagagca aggggcgcgc 120
aggcgaagtt gcaacttgca ctccagccgc gggcctggcg gagaaaggga ggctcgcggc 180
gccgcgagga gtcggcgggc ctcggggcct cgctttcgcc gcatctgccc agcgctccgg 240
gccttgaatc tcggcagatg cgagttgtgg gcacctaggg aaccctgagg actcgcattc 300
ccccgggtct gtatcccgtg cccaccccgg agcgtcgcaa accttggaaa gggtgaaagc 360
tgatagggga gtcttatttc ttaagagaga gggtgagggc gcgcggcgct gcctcg 416

<210> SEQ ID NO 160
<211> LENGTH: 332
<212> TYPE: DNA
<213> ORGANISM: Homo sapiens

<400> SEQUENCE: 160
cggaagaggt ggaccggctg cggacccagg tactgtgcag aacgcggcgc aggtgggagt 60
ccttgggcgg gcgtctacag gtggatcttt tatgcacctc aacaggccgg ctttctcacg 120
gatcacatcg gttagcagta agctgggagg gaggtcccga agactgtgct gggcacagtg 180
caggacccag agaagcggag ccatgggccc gtcctggtga gggagttaaa gtccgtgcag 240
gtgaacagac cccggcccgc gaatcaacga accacaccga gtgccaagtt gcgccgtgca 300
ggctgcggag ggtgcgagag cagggagaag cg 332

<210> SEQ ID NO 161
<211> LENGTH: 1475
<212> TYPE: DNA
<213> ORGANISM: Homo sapiens

<400> SEQUENCE: 161
cgaacgcaac atcaagggcg aaaagaggct gcacaaatca cgtagaaaat tagaccgcct 60
ctttccatgg cgataatcga attagcctca aattaaacgt gaaattggcc ctctccggct 120
gtggagacaa agcccctatt gtcctgctcg ggtagcggca gcagcagtgc ccaccccgcc 180
ccggccagcc tggtcggtcc ccgccgctgg gaggatgagg tccgggctgg acccgggaag 240
agcctcagct ggagaggacg tggacgcgcc cgaggctcgg ctccctgggc ggctgcgggg 300
ctccgggcag gaggagaggg cgggcgaagc agagggagcg ggcgggagtg gggagggagg 360
agtgcggagg gcggagggcg tgcgggaggg atcccgggag tgcgcttgtg tgtgtgtgcg 420
cgcgcgcccg ccccgcgcgc tcctctcccc gcccctcgcc ccctccctgc gagcgccctc 480
ctctcctcct ccccccgccc cccgcgctcc cgcccagccc ccggaatcag tgccgctgtt 540
gccgtgcagg ctgcggattc ctccagtccc tccctcggcc gcctctcctc ccggagcgag 600
cgcgcagccc tgcgcagcag cgcccactgg tcccgtcctg tgagccccgg ccccagccgc 660
ggacagaccc gcggagtcgc ctcccggccc acccgcccgg ccgccgagga gcgggaggag 720
gacgggaccc cggcgccccc accccatccc cgggaggtag gtagggggcc cgaggcaggg 780
agatgccaac tcactggggc tgcctcccgg gtgggctccg cggcggcgga cgggcgggag 840
gaggggcgcg ggcccagggc cggaggacgc cgctgcccgc ctgccctgcg cccggggagc 900
cgcgtggggg cagggaggct gcaaagcccg ggcgggggcg gcgcggggag cccgggtcgc 960
gggtgctcat tggtactcgg atgatgcggg acgaggggcg gcaggctctg cggtgaggcg 1020
gcagcagacc cgccgtgcgc accgctgccg tccggcccca gccccggcgc ggcgcggcga 1080
ttcctcctcc ctgcctccgc cggcgcctcc ctgcagccgg gcgcggcggc ccctgacgcg 1140
gaggcccctg gcgcggaggt gggtgcggag cggacagcgg acagccggag ggtctatttt 1200
caggtgccct ctctgtggcc ccgcgggtgg ggagcggggg cggcggtgac agggccgggc 1260
tctgcgcgta gcggtgcagg ggatgcggcc aggcgtggtc ccggctgcgc cgcgctgcag 1320
ctgagccgga ggcggcggcc ccgcgccccc acctccgccc catccctgcg cttgctaccc 1380
tcgtgcgccc gcccccccccc cgccctttct gccgtcccca ctctcccagg gctgggcgtg 1440
agccgcctcc gggcgccgag ccgccgctgc gcccg 1475

<210> SEQ ID NO 162
<211> LENGTH: 860
<212> TYPE: DNA
<213> ORGANISM: Homo sapiens

<400> SEQUENCE: 162
cgcgttcccc cgcggagtgg ctctcgagtg cggggaggtg ttgcggaggg gagtggactt 60
agggaagggg cggcaaaagg gcaaagggag aaatggcgtg tgtgtgcgtg tcaaggaatg 120
gagagggcag ggcgcttggg agcagggcgc gaggccaggc tctgttgggc cccggctcac 180
ggcgcccctt ctctctgtct gtacctgcgt gtgttgccgt cggcggcggg gccgcagcca 240
gcgacgtgcc ccaggacggg ctgcttctgc acggcccctt cgcacgcaag cccaagcgga 300
tccgcacggc cttctcgccc tcgcagctgc tgcggctgga gcgcgccttc gagaagaacc 360
actacgtggt gggcgccgag cggaagcagc tggccggcag tctcagcctc tccgagacgc 420
aggtaatcac ccccggtcgc ggcctgccct gcgcccggag cccgggtgga ggtgagggtg 480
cgcgggtgca ggagaggccc tgagcccgcc ccagcccagc cctgctgggt tccaaaaggc 540

```
ccccattccc cgcggcgctg cggtcaagcc cgtctttaga gcctcttcct cgagactgcg    600

tgcagcctgc tgagcccgca ggacttttgt caagcgctaa agacctagca ggaggcagag    660

taaatgcaaa ctgtatcccg agcccggctc ccaaagctcc tcacgggggg accaggttcc    720

ctggaggaag cgggtcgcct cgggagcggg cagcgcaggc agcaccgagg ccactggagc    780

tggctccagc cctggcattc ctgcagccct tttcccgcca ctgtgtcggg gcgctcatag    840

tcctgcgggg agccggtccg                                                860
```

<210> SEQ ID NO 163
<211> LENGTH: 2637
<212> TYPE: DNA
<213> ORGANISM: Homo sapiens

<400> SEQUENCE: 163

```
cgggggtcgc gttggaaccc cacaggaaaa aggcgcggaa agccgccggg cattttccgg     60

ggttccatag atgtccccag tgtcctagtc cgtgcatcag ctcgcgcact cggagggact    120

ctaggcaggg ggagggcccc gcggccagta tgtgcgtccg aggctttccc gcagggggca    180

gtgccgcccg cccgcgcgcc gatacggtgg gagggggtgg gaacctgcgc ggagttctgg    240

aggttctttg ggagaaagtt aggggatgcg gaggggtggg cgcaagactt ccaggactcc    300

agggaggccg tggggagggc cgccgagggt gcagtgtgag gcgcaggagg gggttggggg    360

cggtgcacgt tgcagggaga cgcagcccct ggaagatgcg agtgtgaacg tgtgagtgtg    420

agtgcgtgtg tatgtgtgtg tgtgcgcgcg caccgcagct ctccgggttc cgcgaggcgc    480

gcgggtgtca gcttgcagcc ggggctcctc cctccggccc ccctgcccag cccggcggtc    540

cctcctccct ccctccccgc tcgcccctcc ccggcgggcc aggggctggg acgccccggc    600

ggagcaggcg gcggcggtgg cgagttgggg agccctaggc tcggcgctgc cggaggggcc    660

cgagccgagc cgcctgcgcc ccggccgggc agcgccgggc ccgcttcccg cggggccacg    720

ccctgtcaaa ctttgttgcg gcggctagcg cagcgggccc gcaagcgggc gggaggggcg    780

ccgggccggg ccgggcaggg cgcgggcggc taggggctcc gagagcggcg gccccggccc    840

gcggccccac catgccccag ctcggcggcg ggggcggcgg cggcggcggc ggcagcgggg    900

gaggcggcgg ctccagcgcc ggggcggccg gcggagggga cgacctcggg gcgaacgacg    960

agctgatccc cttccaggac gaggggggcg aggagcagga gccgagcagc gatagcgcct   1020

cggcgcagcg ggacctagac gaggtcaagt cgtccctggt caacgagtcg gagaaccaga   1080

gcagcagctc ggactcggag gtaaggaagc accgcggcca cccccggggg atcccggccc   1140

tgcgtccgct cacccgctct tgcctttgtg tctcctccgc aggcggagag gcgcccgcag   1200

cccgtccggg acactttcca gaagccgcgg gactatttcg ccgaaggtat gtgcccgctg   1260

ggacagcccc ccactctcga ttcccgctgc gctccgctgc tcagcccggg cggcccaccg   1320

tccccctgc ttgggtggac gcacccttgc cctccgcctt tattggcggc agcccccgtg   1380

gggcgcgcgt ggggggcgct ggggtcccca gctcccgcct cgagcccct gccgcggcgc   1440

tgtcagtccc gggggcctgg gcctcacctc gccttggtct tgttcgcagt gagaaggcct   1500

caggacagcg cgttctttaa aggaccccg taccctgggt accccttcct gatgatcccg   1560

gacctgagca gcccgtacct ctccaacgga cccctgtctc ccggaggagc gcgcaccgtg   1620

agtgcccgtc gggcgcgccg gggagggtgg gaggccgcgg cccgcaggat gcgcccccgg   1680

gcttggccat ggagtggggg atggggcctt ctgcgccgat cccaagcaga acttgtttgc   1740

ggagttgaac tactctctgg cggccgagcg cgaggctgcg ctggccagtg cctggatgaa   1800
```

```
agtaaagtta ctttaacttt tcccctcttg cgggttgagg ttttggagtc cacctctggg   1860
atcttccttg gcctccagaa ttcttcgcct gcaccgaagg aaacttggat ttgtgcccgc   1920
tttggggggg tctcgctttc cttcttggaa atcggtcagc tttctctggc agtggggcaa   1980
ggggcctagg gagctgggtt ggcgacgttg tcctccgact ccgggttcac tgggcggctg   2040
caggctggtt cctaagaaac ccagttttcg tggcgggtta ttcacagccc ccgttcccac   2100
ccccagccct cgcaccgggg cctcagcttt tctgcggagc tagctccgaa ttttaaactc   2160
gcgtagatga tttcgaggcg acccaaggca ttcttcaagt tgaggaactt ggctttttcc   2220
ccctttttgtc gcctgctttt ctcatttaaa gcgagcgctg cgacacttta aacctgttaa   2280
tgggcgcgta ttgtgtgctg cccgctggca tttagagcgg tgattaagca aattgaccgg   2340
gccccagacg acgtgcaaat gagggcggat tccttcgccc cctctctctg gctctaaact   2400
cccgcccccc gcgttgcgag gggcgcagct gggggctggc gaggcctttg tgtcccccaa   2460
gccgccactc caccccctagg ctccctgccc aggtgctggg tccgatgaca gatgttgggt   2520
gaacgcctac ctactgtgtg ccaggttccc gcgtgctgct gcttgggcgc gatgtgaatc   2580
gtagtagttc tttgcttccc gcccagattc ccattgcctg ccacttcgct gtcgacg      2637
```

<210> SEQ ID NO 164
<211> LENGTH: 2534
<212> TYPE: DNA
<213> ORGANISM: Homo sapiens

<400> SEQUENCE: 164

```
cgaggaggct gcagggacgc gcatggaaga gccggtgcgt gggagggttt gcgggggga     60
catcgcgccc cctaggggtg accccagtgg gtcccgtgtg ctctccgcgg agccggcgga    120
gccttgtcct ctgcacccgg cgcgcagcgg ccccttaaac agtggaaccg tgaggccgct    180
ctaagccgaa gggctggaat ctgggtttct cgggttttat tttagaccat tcggcaccaa    240
gcccgagctc ccccgccgca ccgcttccag tccccttttct ttccatagag cgacccgaag   300
ccggcggtgg cgcagggagc cgagtctgat gagctcgcgg gcggctgaag gccggcttcc    360
ctgtggggaa cgcgccacct gtcggcgcca gtgagaactg cgtctgtgtg gcgccctcgg    420
ggtattcggg gctgcgggga gatgtgtgcc tgaagccctg cgcttgcggt ggggacgtcc    480
ggcctctttc ctggcaattg acccctgagg cgggagagac aacggaattc ccacaaaggg    540
atccttctcg ggatctcccc acctcaagac agctaaagct ggaggaaaag cccctccggg    600
gggtgggggg tgcgggtttg ccctgcgatt ccgaaagcag aaaataccg agccacacag     660
ggacgggcgc cgcgttggta gtcggggcta cgttcctact ccctctacct cccccgcgct    720
gtgtgaccct gggcggaacc ccgctgctct ctgggcctca gtgttcttat tcgtaaactg    780
agggcgttgg atgagattgg tcctctccca actctgacct tgaaactgat actgaatctg    840
agcagcgtct gtagacacct gtgccttgcc ttctatttct agccttgaat aaatcctgga    900
cttttatgtg ccatttatat cctaatctca tatatattta atgtataact gctgccatta    960
ttgttttctc aattgtctag gttttcattt ggatggggtt aggatggtcc aaattatccc   1020
gataagtgcc cattaactta aacctttta aaaaatgaaa ccagtaaaac ttcattcact    1080
ttgcagtgtg gacactgctg gagagcaccc atgtcgtggg tccagcgagg acacaaggag   1140
gggcttagag acatgcggga ggcttagatg agaagacagc acccgggcag cggtcagtgt   1200
tagagagagg acccgtaaga agggccgagg ctagagggag agcgaagact gagccaacga   1260
```

cgcacctgag ccctggggtg ggggtggaga cgtggctcct aacccaaatc tccctgccag 1320
gcagtgtccg acgagcatcg acggcaggcg tcgagaccag tgcagggtag ctcagacctc 1380
aagccacgct tgacctttcc atgaaatgaa taaaactcga aagccaggga aaggggacag 1440
tactttgatc cggagatcgc ttataacctc tgcttggagt tccgagttcg tgcggctcaa 1500
gggaggctac agtccagcaa gctctgggct ccaagcgtgg ggacggcagc ccccaagctt 1560
ggcgcacccc tcgggaagcc ccggaacggt cctcgccaga catagccggc tgtcctggtc 1620
cttagcttca ggctggcggc gcaaggccag agcggctgcc ttctaggcac ctgggtggag 1680
gtctcgcata gcattccctg agaagcgaaa ctgcccttgg ggccgcagcg agcctgccac 1740
atcgaactgg agaccctctg ctttcgggat agatgggacg tttctgctct gtccttcttg 1800
gagtcccgga atcgttctgg ggccgcgtgc tgcctggagg cggtgaattt cagggtcttg 1860
agaagccgcg cacacacggg attctgggcg agcgtcccgt ctcttaattc ctattaagag 1920
acgggaaaat cgagggactg gaggtcccat cattgtcgcg tgagcagcct cctgaacacc 1980
aagcgagacc tgagggttcc gctggggcct cgccctgaca cccgggccct ccgtgtggtc 2040
gagagtttgc gcccgctccc gctagggcag cgaggtccca cttgcggccg gctggggcat 2100
ggtggcaccg gttgtctact ccccacttgt gacaccgaca gcttccaact cctcagaccc 2160
accccgtgga attctggact ttgtgagggc cgccggggtc ctggccctgg ggtcagctgc 2220
catctgacta agccaggacg gcggagctcc aggccttgct ccagcactgc cggtgcgtcg 2280
gggcccgcgg agagcccagg gcgggagctg tgggctgagc cgggtggccg cgtggacaca 2340
gatgcccggc cggactgagc ggcagccaag actctccgtc catcccgccg ctggactcga 2400
ctctcccaga cccgccacgg aacccagatt tgagcacgca agataaagac gccagaggcg 2460
agtgcgcggc ggagaactgg ccgcgacacg ggaagcttct ggggcgcaga acgctggctc 2520
cgactcgcgc ggcg 2534

<210> SEQ ID NO 165
<211> LENGTH: 396
<212> TYPE: DNA
<213> ORGANISM: Homo sapiens

<400> SEQUENCE: 165
cgacggcgcg cttgtggccc ggccggagct tgcgtgcgcg ttctgacggc tgggtgctgt 60
gttacaggtc ggcgcagttc gagcacacgg ttctgatcac gtcgaggggc gcgcagatcc 120
tgaccaaact accccatgag gcctgaggag ccgcccgaag gtcgcggtga cctggtgcct 180
ttttaaataa attgctgaaa tttggctgga gaacttttag aagaaacagg gaaatgaccg 240
gtggtgcggt aacctgcgtg gctcctgata gcgtttggaa gaacgcgggg gagactgaag 300
agcaactggg aactcggatc tgaagccctg ctggggtcgc gcggctttgg aaaaacaaat 360
cctggccctg gactcggttt cccagcgcgg tcaacg 396

<210> SEQ ID NO 166
<211> LENGTH: 3176
<212> TYPE: DNA
<213> ORGANISM: Homo sapiens

<400> SEQUENCE: 166
cgccctcgcc cccccccgc aagtatcccc cactactccc ccccaccccc gcggccctag 60
ctagctgact tgactggcac gcgccgggag cccgggctcg ggcccctcgg agcgtctgat 120
tggctgcggg gcagctccgg tctgctctgc ctgcgccctc attgggcgag aggcgcagcc 180

```
agcggcactt caaagcgggt gctcctcgca cttaggctga gtttagccgg cgggagcctg    240
gagtccgctc ggcacgagcg cggggacgcg ggagccgcgc gggacccaag cagtttttcc    300
gagcagccgc caggctcagc cccgctccca gcctcgctgc gcagccagag acctgctatg    360
gccacgtcta tactcggggt aagtcgcaag cgcggcaacg catttgcttg ttttaaccgg    420
agtaattttt cgttatggct tctggggtct gcggctccgg agaaactgtt gctgctagac    480
tgcagcttca gcttctatta gcactttcca catttctggg actgattttt ccccaagttt    540
ttggaaccca gaaagatgcc tttgcaagaa aaggccttct taatcaagtc ctttttcatt    600
tggtttcaaa aaaaagctag aggtttcttt tcttcccctc gtgatttata ccccatcccc    660
cgcattgctt tggggatttt gttgcaatta tgcgacaatg gtgtttccag aaaacagtct    720
taatcgtttt gcagtccatc tagtcacgct aataaacatt tacatttccg cggctcccca    780
attcgcccat gactttgaaa tctgtctctg gccgcttatc ctcggattat tgttttcata    840
atcgctgttt ttgtgtgtat gtaaacttta aaaccaaacg ttttctatta aaaaagaaaa    900
gtcaagtcgt agccaccctg ggagagctgc aagtttcgcc cgtccctggc agctgtttcg    960
gccgcctccg ccctcacccg gtgtttgttg tctctggtct ctgtgtttac cttcgcgctt   1020
caccccgaag ggcgacttgg ggtcttctgg gagatgagcc ggtttacggc gacaacccaa   1080
gtccggttgt aggcagggtt gcagcgggga acacggaggc atctttgatt tatagcctca   1140
gcgaagtgca actttccggc gcctggacct tcgcccgggt gatcgcccct gctccgcgcc   1200
cggtgcggcg actcctccgc gggcgcgtgg ggaggaggcg cgaggcgggg agccaggacc   1260
ccccgggagc agccgcaggg gacgaggctg ctcacgggtg cactttgttt cttcccccac   1320
ttcctcttgc cctcctcctt cttgctccct cccccatccc acccactcta ggaagagccg   1380
cgcttcggaa cgaccccgtt ggccatgctg gcggcgacct gcaacaagat cggcaacacg   1440
agcccgctga cgacgctgcc agagtcgagc gccttcgcca aaggcggctt tcacccctgg   1500
aagcgctcct cgtccagctg caacctcggc tccagcctct cgggcttcgc ggtggccacc   1560
gggggccgtg gctcgggcgg cctggcgggc ggctcgggcg ccgccaacag cgccttctgc   1620
ctggcctcca cgtcgcccac gtcgtccgcc ttcagcagcg actacggcgg cctcttctcc   1680
aactcggcgg ctgccgcggc ggcagcggcc ggggtgtccc cgcaggaggc gggtggccag   1740
tcggccttca tttccaaggt gcacacgacg gcagccgacg ggctgtaccc gcgcgtgggc   1800
atggcgcacc cgtacgagtc ctggtacaag tcgggcttcc attcgacgct ggcggccggc   1860
gaggtgacca acggcgcggc gtcgtcgtgg tgggacgtgc acagcagccc gggctcgtgg   1920
ctggaagtgc agaaccccgc tggggggctc cagagctcgc tgcactcggg cgccccccag   1980
gcctcgctgc actcgcagct gggcacctac aaccccgact tcagctcgct cacgcactcc   2040
gccttcagct ccacgggcct cggctcctcc gccgccgccg cctcccacct gctctccacc   2100
agccagcacc tgctggccca ggacggcttc aagccggtgt tgccctccta ttcggactcc   2160
agcgccgccg tggcagccgc cgccgccagc gccatgatat cgggcgccgc ggctgccgcc   2220
gccgggggga gctcggcacg ctctgcccgc cgctactcgg gccgcgccac ctgcgactgc   2280
cccaactgcc aggaggcgga gcggctgggc ccggccgggg cgagcctgcg gcgcaagggc   2340
ctgcacagct gccacattcc gggctgcggc aaggtgtacg ggaagacgtc gcacctgaag   2400
gcgcacctgc gctggcacac gggcgagcgg cccttcgtgt gcaactggct cttctgcggc   2460
aagcgcttca cgcgctcgga cgagctgcag cggcatctgc ggactcacac gggcgagaag   2520
```

```
cgcttcgcct gtccggtgtg caacaagcgc ttcatgcgca gcgaccacct gagcaaacac   2580

attaagacgc acaacggggg cggcgggggc aaaaagggca gcgacagtga cacggacgcc   2640

agcaacctgg agacgccccg ttccgaatcc cccgacctca tcctgcatga ctccggcgtc   2700

agtgccgccc gggcggcggc agcggcggcg gcggcagcgg cggcggcggc ggcggcggcc   2760

tccgcgggag gcaaggaagc agcgtctggc cccaacgact cttagaggcc gggcgagagg   2820

cgcgagcaca caagcgagta gagacaccga gaacgaacga gaggttcgga gggcgagcga   2880

gcgggaggcg ggagggcagg ggcttcagtg acgcccccag ggcccgggct gggcgcgagg   2940

tggagccgct cagggctccc gggctgcggt tcgcccgctg tgcgaggagc tcccctctgc   3000

cttccgcgcc cggataagaa tcgaacgcgt ggtccggaaa caaaagcgaa ccatcctccg   3060

acacaaacac tttaaaaact gtactcccag acgtacacat acaccggaga cctacaacca   3120

caagcacgca cactcgcgcg cgcacacaca taccactcgc ccaaacttct cgagcg       3176
```

<210> SEQ ID NO 167
<211> LENGTH: 4359
<212> TYPE: DNA
<213> ORGANISM: Homo sapiens

<400> SEQUENCE: 167

```
cgaaaaggag gcggcgcaac ggccacccct tccagcacct cggctttgtc cttcccgggg     60

aaggcggcca catccctacc cgccttgctc ctgaacgtag taaacaatct cacaaacaac    120

caccgctgcc cacgctctcc atccgtcctc ccggccttat cagacctccg ttctcccgca    180

ctcttcgggc agggtcccta ataagctcag gctgaaagaa cgtttgccac ctcccccacc    240

ctcgttgaaa gaaaaggaag aaaaacagca gcagcgagaa acctccgggg cgactcctcc    300

cccgccccca agcaccagcg cacagcatcc ccctctgtct ttgttgtggt tctccgttgc    360

ttcgggccac gccgttcagc caagcaaccc ggacctgaga gtgcacagcc aggactagct    420

tagggggcga ggggttggtc tttgggaaac caagcgctca ggacagaggt ggaaagtggg    480

tcccgggagc cagaaaagag agagaagggc agacggctgg gtggcaaata caaaaataga    540

aataatttag gggatgcccc gccaggcttt tgcgcctgct ccttctcccc caattcggag    600

caggttccct tcggcctccc gcgccccggg gcgccccctg gcggcagcgg cagcagcggg    660

caacgcgcgg agggctcagg gggcgcacag gggactcccg ggcacactca gagaggcggg    720

cgcggccccc tggcggtggc gacgtagtta tctggtgagc ggagcctcgt ccctctggtc    780

cggcgggctc acggccgtct tactaagcac cgcggccgag tagggcagga agccgctctc    840

ggaacgcggc gccgccgcgc tgcagccgaa gtccgagcct cccccggccc cggcgccccc    900

gccgccgccg ccaccaccac caccgccgcc gccaccgcca ccccgggaac ccagggctgc    960

ggcagctgct gccgcggctg ccgccgccga ctgactgctg tggcaactga ggcacgagca   1020

gggtgcagag ccgccgctgg ggggcgcgcc ggccgccgcc gccgaggagg ccgcagccgc   1080

tgcggctgcc gcggctgccg cggcagaggc cgcgctgttg agccccgcgg cggccgcggg   1140

agcctggtag agaccagggt ggcggaagct acacagcagc tccggccgag agtaggggtg   1200

cgagagggcg cggaaggtgt ccagtggccg gatggaagta gcgaagggcg acgaagccgc   1260

ggccgccgcg cctgaggctg cagccgcggc cgccgccgcc gtgacgccca cgtgcgggta   1320

gtagtgcagc ggcacgtgcg agtggaaggg gtagggcagg cttccggtgg cggccgcgtg   1380

cgtcatcatg taggtgtaga agctggggtc ggctgggtgc ggccaggaca tggccaggcg   1440

ctgccgcttg tccttcatgc gccggttctg gaaccacacc tgcggggaga gacgcgccgc   1500
```

agcctgggtt agggagcgcc ccgtgttccc agctcctgtc ccaggacctc tgccccttcc 1560
ggacctctga atggcttggt ctacttctct ccgaccaagc ccaaccccga gtaccctgtg 1620
gtctcccagc tgggaaagtg tggacggcag tgtgtggacc gccgtgggca caccgtcctc 1680
aacgaagagg gtcctctccc ccgcgtccgg ctgctgctgc tcctcaggct tttattccct 1740
tacttcttgc tgcacttttt tgtcccaatc caacctttcc tctccctccc gccacccacc 1800
agtgccggtc tcgctgagca cccgtctctc aatcccagga tttgtacggg gattctgggc 1860
agcctttgaa gagaggctgc cgctcagctt ttctgagagg tcgccgcgcg aagtcttgag 1920
ccctccgaac tgcaaggacc tgcccctagg ggcacgggtc cgattttgat attgaaggga 1980
tgattttgtt ggaatcgttt gccttaaatg agtgggtaga gcaatgtctc cataaacggg 2040
gaaggggacg tttccacccc tcccaacact atctaataaa gacatcattc gtcacaactc 2100
taaattaaag aaagcccgat caaaccagag ggagacttcc acactcctcc cctaccccgt 2160
ggagattttt tcttttttct gcagtgtcga acgctccatg aagggctcac caaatcgcct 2220
aacctcccgg ctatctctcc cagacgtata ataaaattaa taacctaaag ttatatataa 2280
ataaggacaa tttcgttgca tttttccccg caggaggttg ccctttttttc gttgcccaag 2340
aggaaaatgt tcaggaaact actgtctcaa accaatcgat tttaaagata cagtatcctt 2400
ttctccgtgt aacgatttat gcggaaaata aatctccaag ctcaagagca aatgaaaagt 2460
ttcacctctg gttcctgctt gaggaacaaa gaccaactgg gcttgccgcc taggggaaag 2520
tggggccgtg ggtatgggcg agggggcatc tggccaggcg ttgggcacaa tggagcaggg 2580
gcgagtgctt tcagcattgg agtcaccatt cgggggcctt cttagatccg tcaggccgga 2640
caaccgttcg gattcggtgg ccgggaaata aataagccaa ttcctttggt gactaccccc 2700
cgcggatttc cagaccctta gctaaatcta gccacccaga aaggggaaag gggaaaaaga 2760
aacaatcaac ccagatgccc ccggggaggc cagagcaggc atgcactgga attgatacct 2820
tgatggtggt ttcgggcagg ttgagtgccg cggccagctc gcaccggcgg ggccgcgaca 2880
catagttctc ccggtagaac tccttctcca ggcgcgcgat ctgctcgcgg gtgaacgccg 2940
tacggtagcg ccgcacttga tccgcgccag agccggagcc acccagcgcc gcgctcccgc 3000
cgctgcctcc gctgcctcca tgcaggcttc cgaggcctga gcccgacgcc gacgtcgtgg 3060
tgccggcagc cgagccgctc tctgcgtacc ctggcaaaca aacgaccaac agcgcatgag 3120
tggctgtagg accaacagcc cggcgctggc gctgcgcgcg gatcggggaa gccccgtcag 3180
gaaggagagt cgctgccgga attgatgggg tctgtcatgc ttacaaattg ctgccgttaa 3240
tggaatcaat aaagtttggg gagcccttca taagcaaata atagaaacgg aattaggaga 3300
tttctttttt aataattaga aattttcaac caaggaggaa aagtggccga gggaaaatgc 3360
ctacctctgg gcgcagtttg ggaagctctg ggtttcccat ggtctggaga ccgcagggca 3420
gctttttata cggcctctaa cctttatctg agtcttcggg gtttcaaata ttttaagagt 3480
tccaacacag cagtagctca aacccaagcc aatagggggt gaaatatact tttcaactct 3540
ttctcccgct gacctaaaca gagacgccgg cgaggcttcc tccgacttac ccagaagaat 3600
gccccctcca gccctgaggg cacaggggca ggggagttca gagtagttgc ccagggtacc 3660
tttcccaaaa gcaactcggc tgctgactag gggtctaccg gctcgctcgg gctcttagac 3720
acgagcgcag aaacattttc tcggactcag gagcgagggc gggtgggcct ggtgttccag 3780
gctccgcagg cctgagcctg gcgggaaagc tcaaggagca gaactggaag gcacggtccc 3840
agacatgcgt cccgcccccg cccgtgctag ctcggtgtag cttgcctgtg gagggtctga 3900
gaggggaaaa ggcaccggga aaggctggcg ggggccgcgg aggagcaaag aggatgggac 3960
tggagagcgc ggtgcggccg gcgcggttac ctttgccatt gttttcctta agctgagcgg 4020
cgccgaggcc cccgggggag cgaagcgcgg agcagcccac ctccacgtcg ctgctcatgt 4080
cggcctcagc ggccgcctct gaataatggc ccggcttctt gcggctctcg gcggcggagg 4140
agatttcgga ggagacggtg ctttcgctgc ccgtgtgctg caggttgaac aaagtgtcta 4200
tttcgaattt gcccttggcg gggagttctc ccagagcgct gtgcaggggg gcagacggca 4260
ggcgcgggct taggcgagcc gggtgctgcg aattttccag ggcctcgagc acagcattgc 4320
cagccgagtt ggacaaattg gagaatctct tgcccgccg 4359

<210> SEQ ID NO 168
<211> LENGTH: 304
<212> TYPE: DNA
<213> ORGANISM: Homo sapiens

<400> SEQUENCE: 168
cgccgctgta agtaccttcc cgcttcttcc gaatcgcgaa gagacggtac tgatcgcggg 60
gaagtggtgg gctaaggggc caagccagcg gagtgggcgg atagaagaaa ggccctgcct 120
cccccacccc acccccaccc tccacccccg gcctcgctct gcgaggttag cccgcttcgg 180
gaggtggagg cgctaaatcg aggtcccgga aagcttttct ggggcctggt tcacagacac 240
ctgcctgaga gaacggtccg cggggtctcg cccttgtctc cttgggcctc cctagacctt 300
cgcg 304

<210> SEQ ID NO 169
<211> LENGTH: 201
<212> TYPE: DNA
<213> ORGANISM: Homo sapiens

<400> SEQUENCE: 169
cgaatccagt cccggccggc gctttgaagc ctgtgctgtg cgattttctc agcagtgagg 60
taggaataga cgcggctaat gacaggaagg tcgcgcgggt gagctgacct gtgtgtggcg 120
cagccttggg ttccgcaaat agggcaccca cagtaacacg tgtggcgccg accccgccgt 180
gcgcaatcgg ggctttatac g 201

<210> SEQ ID NO 170
<211> LENGTH: 247
<212> TYPE: DNA
<213> ORGANISM: Homo sapiens

<400> SEQUENCE: 170
cgatgggacc gcggcttgac acgcattaag gagccactga aaactccatc taagcagaaa 60
agcggcttag tcatccatgc gttctgggca agttatcctg gccgcaccac gtggaacgga 120
gtagatagag ctcgggaagc tgagcgcagg gcggacaacg ggaaggccag agccgtgggc 180
aagcacgcgg agggcagcga ggggcactgg caccggagcc gcggggaggc aggaaaacgc 240
agaggcg 247

<210> SEQ ID NO 171
<211> LENGTH: 562
<212> TYPE: DNA
<213> ORGANISM: Homo sapiens

<400> SEQUENCE: 171
cgctcctgtc ccaagggcgc gtctctctct cccacgcaca aactcgggtc ctgtttgctc 60
ttctctcacc caaacccaca gtctggcgga cgcaccccgc cccgcaggca gctttctctc 120
gcacgccggg cgcccggtcc cgacggtcac ccgcactccc gcacaggcat ccccacagcc 180
tgcgccagcc caccgctcag cacccgggaa ggccgctcgc cccgcgccgc gccctcaccc 240
gctgtcaagc tctagctcca gaagggactg ggtcctctcc gagttgcagt gcaggcacca 300
catggcggcc gcagtgggag cgggccgggc cgggagccgg gacccaggcc cagcagaggc 360
cgccgactcc cgccagcgag ccgccggatc ccggggccga cacccggcca cccggagacc 420
cgaccacccg ccacgcgatc acgtcggggc tcctggtcca gcgtccgccg gctcccgcgg 480
ctccggcccc aagtccgagc cccaggccag ccaagcccgc ccctccgccg ccgcccgctt 540
ggcgcagcgc gaggccgggc cg 562

<210> SEQ ID NO 172
<211> LENGTH: 1014
<212> TYPE: DNA
<213> ORGANISM: Homo sapiens

<400> SEQUENCE: 172
cgcggggagc gggctggagg attctgcaag cacaggcccc tatggagcgc ccgttcgggg 60
gacgggattt ccctcccttt cccctccccc gcccgttcgg aattccgccc ccgccgcggg 120
cccggaacaa tgcagccgcc cgtcccgggg accagccact taccacccag gtcagtgccc 180
cgttgccgcc gcccacgccg gctcccgcgc cgcagccacc cgacttggcc atggcgagtg 240
cctccagctc acaggccctg aggccgcagc cgccgctccc gcctccctgc gggccgctgg 300
gccccgccgc tccgcaccca ccgctccact cgccgcactc ctagccgcgc cgaccccccgc 360 gccccatcgc gaagatccgg agcggacgtc cagccgagcc cgctgaggag gccgcgccgc 420
cggctgccct caaactcgag gcgcggcgtc cgcgtcgccc gggcctagcg cggcggctga 480
ggagaaagca gggagcgacc ggcggcggcc gagcggcggc gttgccttct cgcccgcccg 540
cgggcgccgc tgcaggccgg gctgaagccc gggcgtgcga gccgcgaggg cggccgggga 600
gcccgaggcg ctcggacgtg gcgaggacgc agaggtgcct tgtccttctc acactccgcg 660
aaggccagcc actcgagtcg ccagagtagt cgtcccggtc gccgccgctg cttcaaaggc 720
agccttagcc tcgctgcagc cccgatttcc tcacacacac acaccgagag ggacaataaa 780
cagagccgcc gccgccgccg ccacggtcac ctccctcttg tccggcataa caccgcacac 840
acacatttgc acaccgggga gagagggagg gcgcggcggc cgccccccgct gtcagtcagc 900 gccatgctgt ccaatccggg ccttgtcgcc acagcctctc ggccaatccc aaaattccaa 960
gccccctgga ggggcgggac ccgagggggg aaacgtcatt gcgggtagca accg 1014

<210> SEQ ID NO 173
<211> LENGTH: 235
<212> TYPE: DNA
<213> ORGANISM: Homo sapiens

<400> SEQUENCE: 173
gaccggcgct tcgctaacag cagcgaccgc aagaagcaca tgcacgtgca cacgagcgac 60
aagccctatc tttgcaagat gtgcgacaag tcctacacgc atcccagttc gctgcgcaaa 120

```
cacatgaagg taatcgccgc actctcgtcg cccccttga ggcaggagct ctcttggctc    180

tcggcttggg gtcgggcggc gagtggcaga caggcggtgg cgggagccag aggaa        235
```

<210> SEQ ID NO 174
<211> LENGTH: 559
<212> TYPE: DNA
<213> ORGANISM: Homo sapiens

<400> SEQUENCE: 174

```
cgggcaaacc tccggaggcc ccggtgcacc gcgcgtccag ccggcccaac tcgagctaga     60

agccccaacc actgcccagt gcctgagttg cagtcttggg tcctttagaa acctggagat    120

gtgcgtaaaa ttcagatgcc ggtattcccg aacttcccca ggcctcagca tatctcggcg    180

gcctgtggac agatgggagg ctaccaatcg ctccggcgtc cgcagcccga cccctgccgc    240

cagaccccgg acgtcttccg gataataaag ttcccgctct aattcatttt ccctaatctg    300

gacgccccta atctacagct tttattgcgc ccagttaaaa gtcgagggaa ttcgctgtcc    360

ctccgcgctc ggataattac ccctaaatgg ccacggcagc cccttgtgtt tcctggagat    420

tagaaccccg cagtcatcaa tggcagggcc gagtgagccg ccaatcacct ccgctcactc    480

cctgagagcc gctggcctgg gccgcaggag gagaggccat aaagcgacag gcgcagaaaa    540

tggccaagcc ccgaccccg                                                 559
```

<210> SEQ ID NO 175
<211> LENGTH: 3638
<212> TYPE: DNA
<213> ORGANISM: Homo sapiens

<400> SEQUENCE: 175

```
cgagcgcggc ggctggctga cgctccctcc cgcctcctta tcccgggccc tcctccctcg     60

ctctctccta gtgtgtagtt tcggcggctc ggctgctact gccgccgccg ctgcagcagc    120

agcgtcaggg acaagcctga tccgtgagcg agcgagcacc cagcagcaac caccactttg    180

ggcaacttgc gggtttcctg ctcgcgggta gcgaacggga gattcccact agcggttcag    240

tgtctccgag ccgctgcagc ccgaggggcg gcgggagcgc ccgcaccaga ctctcccaga    300

cgcgaaaagg gacgagacaa ctgcggaatt caccagccgt gccagggcac ttccgaggcc    360

acaaccgact gacacttttt ctccccttgg caaactggat ttttttttt aagctacttg      420

gcagctgtct ctgactccac ctccccctcc acccccgccc gaaagccttt ggcttttctt    480

cggaaatcca gacagaattg ggcatctttg ttaattgccg ttggggacgc ccggccgtgc    540

gctttcgccg gctaacgtcg cctgtgctcc gagcctggtt tgctcacctt tgaactgcaa    600

agggatcaag ttcagcttga gttccctgca ttgggaagga gagagagcgt gcaagagagc    660

gagtgggaga gggggaaagg ggaaaggaga ggagggagga gagagaggag ggaggagaga    720

gaaagggagg gagggagggg agggatcgag agagagcggg gagagagagg ctgcaatctc    780

ctccctgaat cgcgcacagc gctgcagatc ccactgctcc gacatgcggg ccgaatgcag    840

gtgagaaaag gcacggactc tgcggctgcg aacccaaact tgggcaccgc acggtgcgca    900

ctgctcagcc ttcgcccccg tgggcgaaag gctgctgcgg tttcaggcgg ctgcttcgtg    960

actaatgacc ttgcgcagag ttgttaagaa aaaagagaaa cccgcgctct ccggggtgag   1020

aagggactga ctctgggcgt ctctgaagat ggctcgggct tctctttggc gcgccggggg   1080

gaccctgaca ctgaccgctc tgtgacgcga gtagtctccc ctgcaccgtg cccgaagcga   1140
```

cgtgccgggg gatttttcat tctcgatctg ttgactggct cccccgctgc atgagcagag 1200
tcggagttga gactggcttg ttgctggccc cagcgcctgg tgcaggaagc gactcacgtt 1260
tgtctgggtg gccggagccg gagcagagcc tgggtttgga gtgagtgcct ggaacgtgaa 1320
ttggactcaa ctcgagtagc agcaaagacc agcgggctgg caggcggggg aggctgcagg 1380
ctcattcccc acctcttccc agccccactg cccgtctgcc ggagcggttc tggccccttc 1440
cgacagagcg gggactagag ccggggattc tccgcccgct gaggggatga ctctgggttg 1500
ggggagcgcc gaacccgcgg cgcgcagtgt cccgtgaact gtgagtactg cgactgaacg 1560
gcggcaggcg agcgggcgat tagcacccat tgcatgaatt atgaaacaat aactttcgga 1620
agaagcagga ggaaaaaaag aagcatctat cgctgccctc ccacccccat tcccggccaa 1680
ctctccacgc cgcttttgcc ccctccctcc cctccctctc gctccttcct ttccgggaga 1740
ggggagagga ctcgggggag ggcaggcggc cggccccgga ggagggggc gccgaggggg 1800 ctgtggttag aaggagcagt agcagcagca gcaggagaag atgctgagga tgcggaccgc 1860
gggatgggcg cgcggctggt gcttgggctg ctgcctcctc ctgccgctct cgctcagcct 1920
ggcggccgcc aagcagctcc tccggtaccg gctggccgag gagggccccg ccgacgtccg 1980
catcggcaac gtggcttcag acctgggcat cgtgaccgga tcgggtgagg tgactttcag 2040
cctggagtcc ggttccgagt acctgaagat cgacaacctc actggcgagc tgagcacgag 2100
cgagcggcgc atcgaccgcg agaagctgcc ccagtgtcag atgatcttcg acgagaacga 2160
gtgcttcctg gacttcgagg tgtcggtgat cgggccctcg cagagctggg tggacctgtt 2220
tgagggtcag gtcatcgtgc ttgacatcaa cgacaacacg cccaccttcc cgtcgcccgt 2280
gctcacgctc acggtggagg agaatcggcc ggtgggcaca ctttacctgc tgcccacagc 2340
caccgaccgc gacttcggcc gcaacggcat cgagcgctac gagctgctcc aggagcccgg 2400
aggcggcggc agcggcggcg agagccggcg cgccgggggcg gccgacagcg ccccctaccc 2460
cgggggcggc gggaacggcg cgagcggcgg cggctcggga ggctccaagc ggcggctgga 2520
cgcatcagag ggcggcggcg gcaccaaccc cggcggccgc agcagcgtgt tcgagctgca 2580
ggtggcggac accccggacg gcgagaagca gccgcagctg atcgtgaagg gggcgctgga 2640
ccgcgagcag cgcgactcct acgagctgac cctgcgagtg cgcgacggcg gcgacccgcc 2700
tcgctcctcg caggccatcc tacgggtcct catcaccgac gtgaacgaca acagcccccg 2760
cttcgagaag agcgtgtacg aggccgactt ggctgagaac agcgccccgg ggacccccat 2820
cctgcaactg cgcgcagccg acttggacgt gggggtcaac gggcagatcg aatacgtgtt 2880
cggggcggcc accgagtcgg tgaggcggct gctgcgcctt gacgagacgt ccggctggct 2940
cagcgtcctg caccggatcg accgcgagga ggtgaaccag ctgcgcttca cggtcatggc 3000
ccgcgaccgc gggcagcccc ccaagaccga caaggccacc gtggtcctta acatcaaaga 3060
cgagaacgac aacgtgccgt ccattgaaat ccgcaagatt gggcgcatcc ccctcaagga 3120
cggggtggcc aacgtggccg aggacgttct ggtcgacacc cccatcgctc tggtgcaggt 3180
gtccgaccga gaccaaggcg agaacggggt ggtcacctgc accgtggtgg gcgacgtgcc 3240
cttccagctc aagccagcca gcgacaccga gggcgaccag aacaagaaaa agtacttctt 3300
gcacacctcg accccctctgg actatgaggc cacccgggag ttcaacgtgg tcatcgtggc 3360
ggtggactca ggcagcccca gcctctcgag caacaactcc ctgattgtca aggtgggaga 3420
caccaacgac aacccgccca tgttcggcca gtcggtggtg gaggtttact tccctgagaa 3480
caacatcccg ggcgagaggg tggccacggt gctggcgaca gacgcagaca gcggtaagaa 3540
cgccgagatc gcctactcgc tggactcctc tgtgatgggg atctttgcca tcgatcccga 3600
ttctggggac atcctggtca ataccgtgct ggaccgcg 3638

<210> SEQ ID NO 176
<211> LENGTH: 261
<212> TYPE: DNA
<213> ORGANISM: Homo sapiens

<400> SEQUENCE: 176
cgtcaccagt tactcccgtt tagccaacga gctgcgtgtg agctgcatgg agcggaaaaa 60
ggtccaaatt cggagcttgg atccctcctc tttggcgagc gaccgattta acttcattct 120
ggcgagtacc aacagcgacc agctcttcgt agtgaaccag gtcgaagtcg aaggctccaa 180
gtacggcatc atcagcctgc gaactctgaa gatcccttcg ttccacgtgt acgtgctcag 240
aaacctctac gtccccaacc g 261

<210> SEQ ID NO 177
<211> LENGTH: 3140
<212> TYPE: DNA
<213> ORGANISM: Homo sapiens

<400> SEQUENCE: 177
cgcaacttcc cgcagttact gccgctcagc cgcactaagg aggtccggag acttggaaga 60
aacttcggag actcgctgaa aggcgaagaa ctgagcgaga aaaggacccc aggctgggcc 120
ctgaagtcca cctggaaggc tgggagcctc cgcggcgctg cggcctacta ccccgaagac 180
tagcgtgatc ttggggcaac tcagtttgcc tcaagcaagg tctttgcggg atggtacatt 240
ttccccaggc cgtgtccctt catctcactc ttctcctggc tcgctcttgt gttagggtgt 300
tgagctccac gatgtcccca aatgtgcccg gacgcagcgt gtgccagccc ccagagtgga 360
ggcaggtggg aaagcgcggg cccagcgctg gtgagcggct ggaagcgctc gccctgccct 420
ggggacgctg gactgtcttc aatgggctca cccaggccga gtgtactcgg gcggcgaggg 480
cgaagaggtg aggtggggac accccaggcg gagacgtgca tgcaaataca ctcacttccc 540
gggcggtgga gggctcaccg ctgccgggcc tcactgcttc gaagagaggc agcgggttag 600
gctggcgaag gcggaatggg gcgctggacg acagggagga gccgggaaag cagagatgca 660
gtggcctctc ctcccctctc ctccccatct ttctaatcca ggccaggcct gcggtcctgg 720
ccaggccgtt tcaggaacag ccagggcctc ggacgagaca cacgtccctc accgcgttgt 780
ggtccacacg aacacacaca caccggctca gcccaggcgt actcaagact tagagagagg 840
gaggcgcttg gatacagcca cgcgagctca gaaaagcgag aatccctttc tggaagccct 900
ggcccaacct aactggtgtg attccggcgc tgtcaaacta ctggggcggg ccacaggatg 960
gactgagcgg catgcacacc aggggccgcg acccgggagt gggcagaaca ggcacggcag 1020
gcaggcatcg gggcgcgggt ggtagtactc acgaggggta caggccaggc gtgcgtccct 1080
ccagggcggg ctctgcatca ctccgggcca gaagatgggc gtccggccag gcagctcagc 1140
cagcggcttg gggtaccggc ccacggcggc cacggccgcg gcgctggggc tgaagtagag 1200
cccgggcggc ggcggcggcg ggctcaggct gctaaagcgt ggcagtccgg ccagcagccc 1260
cgccggggat gaggcggcgg ctgcggccgc ggcagcagcc gcggcggcgg cagaggcgga 1320
ggaggcagag gcggacgagg aagaggagga ggaggaaccg gagggcgagg cggagggcag 1380
ggcggccccc gaggccacgg gcatggaggg ccggctcagg atatcgttga tgccgtgtgg 1440
ggtggcggcc gagagctgct gcggggggct gccgagggat gagagccccc ccgtggccgg 1500
gggcttcagg ccgcctgggt tgtgggtgcc cagaggcggg gagggcgacg aggaggacga 1560
cgacgaggac gaggaggagg gggggccggc aggcagcggg ggatacgcgg cagggtacag 1620
cggggtcttc atctcggcca tgctgtgcag ggcggccagg ggagggctgc tgagcaggaa 1680
tgcgctctgc cgggtgccct ccattgcccc caccgctaac atcccacggc cacgccggag 1740
accgtagcct tgcagcgagg gcgctggctg gtgccccccg cggggctcag aggagccgga 1800
agcgccgagg gcgcgagcgg agaggcactc ggcgcgcccg gaggcgagct gccaactgaa 1860
ccaaaaatgc cgctgccggg agttgctcgc ctagctgcgc agcagagatg tccaaaccct 1920
ccacgcggga ggcggcagct cgccgagaaa agcaggcgtc ccggcgggct aggcagtcct 1980
ttcgttccgc gagtcctaga ttcgatccct ggctattctc tcttcctcac ttttcctagc 2040
tgttcaaagt gcgctacttc tcatcttctg cccccgggaa ataagcaaaa caaaacccag 2100
gctggctccg gagagtttgt agcaaagtta gttgccgaat ctccactttg aagttggagg 2160
gtgggggtgg cttgctttct ttggggaggt tcaaaggacg ccttgtgcag cccgtggcgc 2220
tcctctgatc ttactgggat gctctgctct ttcggtcgcg cggctgattc gcattcgacg 2280
ctcactgtgc ccggggagaa agcgcatcca gcccgcggga gatctagcct ctgtgcgggc 2340
ttcctccgcc cacgctgccc cgggctgctg cgccagaaag ggcagtgcca cggatccccg 2400
cggctcccag gtcctcacct ccacccgcct tgccctctgg cccacggggc actggagttg 2460
caatattgaa aagaaaaagg gggaggaaaa acacagaaaa acaaaagact aagtgtgaaa 2520
agtctgacgg ctgggtttcg gcgccgctcg tcagtccact tctgcaaacg ggcccggcga 2580
cccccgcccc accccgctc cctctctccc tctcactctc agcctttgac tctcctctct 2640
ggcattttct tcgcggcttc ccaggcttcg gtcttctaag tcctgtcctc tggccaaact 2700
gaccctctcc gcggctcctc cgctctttct ctcctttcct ctctccctcc gggcctgaca 2760
gttcagatga agctctcaaa ggtaataaaa catttgcatc actccctacc cctctttagc 2820
tgggggacga aagggagggg gaagtggggg accaaaatga gaactttgag ggacgtcact 2880
ccgaggctgc gggggccggc gagccgggcg caggccgggg gcgtaaccac cgtgtccaat 2940
agctcgccgc ctcgatcctt gcgtcgcccc tggggctcgc ccactcgggg gcgccgcacc 3000
ctctgattgg ctgaggcggg ccaggcgtag ggccgcgccc gcctagtccc ctcccgctcc 3060
ctacttcttt ctcctgtggg cggggccagg aggggcggga gctggtgagt ggtgcggttc 3120
cgcgctgggg ccagtggccg 3140

<210> SEQ ID NO 178
<211> LENGTH: 524
<212> TYPE: DNA
<213> ORGANISM: Homo sapiens

<400> SEQUENCE: 178
cgcggtgcgg agcgtctgga gcggagcacg cgctgtcagc tggtgagcgc actctccttt 60
caggcagctc cccggggagc tgtgcggcca catttaacac catcatcacc cctccccggc 120
ctcctcaacc tcggcctcct cctcgtcgac agccttcctt ggccccccac cagcagagct 180
cacagtagcg agcgtctctc gccgtctccc gcactcggcc ggggcccctc tcctccccca 240
gctgcgcagc gggagccgcc actgcccact gcacctccca gcaaccagcc cagcacgcaa 300
agaagctgcg caaagttaaa gccaagcaat gccaagggga ggggaagctg gaggcggcag 360
aggcggcggc gggagagctg tggggttgtt caggaaaagt tgggctgggg gctgaggcac 420
ctgaagcagt gaaccaggac taggtaggaa gcaagagcat cctcctgcgc aagcggagac 480
gcaaacgcgc tcctgaaccc atgcaaccgc ccggcccagc gccg 524

<210> SEQ ID NO 179
<211> LENGTH: 1966
<212> TYPE: DNA
<213> ORGANISM: Homo sapiens

<400> SEQUENCE: 179
cggagccaga cctgacggtg gaaatctctg agagcgccac gccaggcact cgcttcccct 60
tggagagcgc attcgaccca gacgtgggca ccaactcctt gcgcgactac gagatcaccc 120
ccaacagcta cttctccctg gacgtgcaga cccaggggga tggcaaccga ttcgctgagc 180
tggtgctgga gaagccactg gaccgagagc agcaagcggt gcaccgctac gtgctgaccg 240
cggtggacgg aggaggtggg ggaggagtag gagaaggagg gggaggtggc gggggagcag 300
gcctgccccc ccagcagcag cgcaccggca cggccctact caccatccga gtgctggact 360
ccaatgacaa tgtgcccgct ttcgaccaac ccgtctacac tgtgtcccta ccagagaact 420
ctcccccagg cactctcgtg atccagctca acgccaccga cccggacgag ggccagaacg 480
gtgaggtcgt gtactccttc agcagccaca tttcgccccg ggcgcgggag cttttcggac 540
tctcgccgcg cactggcaga ctggaggtaa gcggcgagtt ggactatgaa gagagcccag 600
tgtaccaagt gtacgtgcaa gccaaggacc tgggccccaa cgccgtgcct gcgcactgca 660
aggtgctagt gcgagtactg gatgctaatg acaacgcgcc agagatcagc ttcagcaccg 720
tgaaggaagc ggtgagtgag ggcgcggcgc ccggcactgt ggtggccctt ttcagcgtga 780
ctgaccgcga ctcagaggag aatgggcagg tgcagtgcga gctactggga gacgtgcctt 840
tccgcctcaa gtcttccttt aagaattact acaccatcgt taccgaagcc cccctggacc 900
gagaggcggg ggactcctac accctgactg tagtggctcg ggaccggggc gagcctgcgc 960
tctccaccag taagtcgatc caggtacaag tgtcggatgt gaacgacaac gcgccgcgtt 1020
tcagccagcc ggtctacgac gtgtatgtga ctgaaaacaa cgtgcctggc gcctacatct 1080
acgcggtgag cgccaccgac cgggatgagg gcgccaacgc ccagcttgcc tactctatcc 1140
tcgagtgcca gatccagggc atgagcgtct tcacctacgt ttctatcaac tctgagaacg 1200
gctacttgta cgccctgcgc tccttcgact atgagcagct gaaggacttc agttttcagg 1260
tggaagcccg ggacgctggc agcccccagg cgctggctgg taacgccact gtcaacatcc 1320
tcatagtgga tcaaaatgac aacgcccctg ccatcgtggc gcctctacca gggcgcaacg 1380
ggactccagc gcgtgaggtg ctgccccgct cggcggagcc gggttacctg ctcacccgcg 1440
tggccgccgt ggacgcggac gacggcgaga acgcccggct cacttacagc atcgtgcgtg 1500
gcaacgaaat gaacctcttt cgcatggact ggcgcaccgg ggagctgcgc acagcacgcc 1560
gagtcccggc caagcgcgac ccccagcggc cttatgagct ggtgatcgag gtgcgcgacc 1620
atgggcagcc gcccctttcc tccaccgcca ccctggtggt tcagctggtg gatggcgccg 1680
tggagcccca gggcgggggc gggagcggag gcggagggtc aggagagcac cagcgcccca 1740
gtcgctctgg cggcggggaa acctcgctag acctcaccct catcctcatc atcgcgttgg 1800
gctcggtgtc cttcatcttc ctgctggcca tgatcgtgct ggccgtgcgt tgccaaaaag 1860
agaagaagct caacatctat acttgtctgg ccagcgattg ctgcctctgc tgctgctgct 1920
gcggtggcgg aggttcgacc tgctgtggcc gccaagcccg ggcgcg 1966

<210> SEQ ID NO 180
<211> LENGTH: 3844
<212> TYPE: DNA
<213> ORGANISM: Homo sapiens

<400> SEQUENCE: 180

```
cggattacgc agccacttct ccctgcaaag tgcacgctcc cgcgccgcgg ccgcacgccg     60
agcacggcaa gcggtgcccc gccgcgcgcc cctacacacc tgcctcggcc ggggtccgtc    120
tctcgccgtc tacctgttgc agcgcttgcc accgccacga aacccctgct gcggagcccc    180
cctaaatcca accacatcca ggccagcgag tgccgctctc cctgcagcgg gagagcccga    240
ggcagcaacg ctcttgcacc caggtgactg actgcacggg cttcctctga gcagcctgaa    300
gttggctccc gtctcccggg cccaatgaca ccccgggcgc ggaggggctg agaggagggg    360
gcaggggcag gggcagggcc agggcgggca aaaaagggag ggagagaggg cgggcgaaag    420
cccggagggg gagtgggcca gctggagggc tggccctttt aaaagcgggt cacatgtcca    480
gataaagttc aggttgctat cccgcccccc tgaacccttc ctattggccc gaagagaagc    540
aaggctccac gccgcacggg tcaggcgggc ttcttattgg acaatccagg ctgtcagtca    600
ccaggcgggc gacatgactg atacaaagtt gctgcgacac agcctggact cggcagcttc    660
cttaaagccg cagccgcggc gggagcttgg ggtgccgggc ggtggctaca tcaggcggcc    720
tccgcacgct gcccccaccc ccatcgctcg gccgccccaa acttgcttac gtccaccctg    780
ctctccttct gaccgacccc aggatatctg gagagatgtg aaaagtgtgc tgacgcggaa    840
gaagtcggtt tttccgcgag caaagtgtcg tcccctcacg ctctccacct gcagctccag    900
gtgagctgca gcccagaccc tggcgccgcc caacagcgtc cgcgcgcggg gaggactctg    960
ggtgggcttc acccgaccct cgaggttcct ctcccagccc ctttccactg tctccagagt   1020
tacctctcag cagagcagca gcagccttcg ctgccagcga gcaagacgat cacgttcact   1080
cgatttgaat ttagttgttt taaccgtgct ggaaaaaccc tttaaacaca gctttcctcc   1140
catcccttag accectaaca ccaaaaaaaa aaaaaaaaaa aaaaaaaaaa aaaagagaga   1200
gagagaaaga taaatgaaag aagtggcagg gtcaagagct gctcctctac ttccttataa   1260
ttttgtcact gtacttacta ctttagtatt ggatttttcc actagttcaa tttgaaagca   1320
agcttaccat cgaggatatt cacgttataa tgggtggagg gggtgggtca cataagtggg   1380
agaaacagac aggagggggg aaggaaccaa actgttttct aaggatcggt tgtctgcatg   1440
aagaaatttc ggtttccctc caaccgcccc ctcctcgatt ctcctcccgc ccacccaaat   1500
gctgcagtta ctaagcaaaa ggatggggtt cctaactttg atttctaagg acttttaggc   1560
ttctcatgta aggccccgtt ttaggctccc cgctggcccg gagtcagcat cagtgacgta   1620
tacacctaaa tctggtcccc cggccctcgg cgacccgcag cccggcggcg gcagctgtgc   1680
ggcctcccgc ctcaccctcg cttcgcgccc gccaaagccc gaggcggggg accgggggac   1740
accctgtgcc caaaggcccc tcctctcctt aacagttagt taagctccgg gattccggac   1800
ccctaaccca gggctgagac ttgaactctc agccgctcca gtcaggaact ccctggagat   1860
aggggcgaca gcggcagcgc cgcgagctgg tcctgacccc agactctaat gcccctcggt   1920
ccccagcttg gagctgcccc cggcgtcccc gcagccagga gtccccgccg agcgtcccaa   1980
ctttcccgcg gggcccaccg tcacgcgcac tctcccggcc cagcgaactg ggcatcgatc   2040
tcacgtcggc agagcgcggg cggcgggcgg gagcaagggg agtcccggac ctagagcctg   2100
ggcacgcgag gcggcggcgg ctccgcaagc gttgccgaat tattcattat taaaggaatg   2160
```

gacgtgtctc ttttactaag tttttatctc ctttgaggag ggccggtctt gccctggatc 2220
tcagcttctt gcaaaatcta ggttagaacc gtgcaggggc agccgccgcg atcactcgcc 2280
cgccacccag caccccttgcc ccagggccgc cagcgggcaa ctcgtctcct gcccgcatcc 2340
cacctccgct cgccaacccg cgccctctgc cctgggcgcg caacctgcct tgcccggggc 2400
cgcccctgcg ctctccggac cccctctcgc cgctgtcagc gcaaagtgac tgtcgctgca 2460
ctcacctttt ctaggacatg gtggggaggc tggggcgggg gaaggggaac ggctagactc 2520
ccgccgccgc tgctgccgcc gccaccagca agtccaatat tggctgatcg gcggtgagga 2580
tggagaggat gataatcccg gcagtggcag tcgccctgct gacggtgggt agagcaatag 2640
tgctgttacc ctacaagagg cggcgaggca gcggcgccaa atcgcgcaga gggggacgcg 2700
ggcacccgcc cgcccccagc ggcggcggcc gggcctctgg cgggcccctc tcccggggct 2760
gcgcgtccgc tcggcgttga cagcggcgtc cctgggagcc gggaagtccg gcaggaggat 2820
cccgcgcccg ccgctccgca gcgccactct ccgcgccccc tccccgggcc ctgggtggcc 2880
ggtgacagct ccggcggccg agcgcgtgtg tgagggggcg gtcgcagggg gagcctgcgc 2940
ccccctcccc gggtcacgcc ctcacgagcg ggaggaggcg gcaccgcgtc cggccacccg 3000
cgggtgggaa acgggcaggg gcgccggcag ccgccctccc actacggcca ctgacaacct 3060
ggaggccaaa ggaaaactga gcccaaatgc acgcaccccc ttcagccctg cccgcagccc 3120
tccaaagtcc ggccctgacc tcgcgcccgg cttcaggtgc agttcccacc tgcgggggga 3180
ggcgagggct ggggacctcg cgcgggggc gggagggaaa agttttcttt tcctgctcct 3240
cggctgccca ccccgccagg ctgctcctct ccccgcccct ctcgggctcg ccgcgcctct 3300
gccccacccc cgccgtgggg gggcgccgag gagggagcgg gcgtctgtgc gcggaggcgt 3360
gcggggagct ggctggggcg ctgcggtcgc gaccggtccc ctcgctctga cggcggctca 3420
gacgcccgcg gaggcggctc ggcggggcaa gccgaggaag gggccgagag ccgggacccc 3480
tcctcctccg ctcgcggcgc gccgcgcgcc cccgcgtctc ctggcgcgcc cccgcgccct 3540
cgtgcccgct cgggcagaca cctacgcaga cgcgaaagtg aaagggggc gactgggccc 3600 ggcaggcggg cggccggcgg cgcgcgggca cgcggcaggg gacagaggat ggatgggtga 3660
acccggatcc cgggattctc ccgcgcccgc tgcccctctg cggagcctcc ccggagtccc 3720
acgcccccac cccggccacg gagatcacca cgtcaggaga tatgtatgcg tgtgcatgtg 3780
tgtgcgcgcg tgttcacgcg cgtgtgcgag gtacgcttct gccccagact cttcccccgc 3840
accg 3844

<210> SEQ ID NO 181
<211> LENGTH: 623
<212> TYPE: DNA
<213> ORGANISM: Homo sapiens

<400> SEQUENCE: 181
cgagaagctg aacgagctgg ccgaccagga cttccccttg cacccgcggg agaacgacca 60
gctggatttc atcgtggaaa ccgaggggct gaagaagtcc atccacaacc tcgggacgat 120
cttaaccacc aacgccgttg cctcagagac agtggccacg ggcgaggggc tgcggcagac 180
catcatcggg cagcccatgt ccgtcaccat caccaccaag gacaaagacg gtgagctgtg 240
caaaaccggc aacgcctacc tcaccgccga actgagcacc cccgacggga gcgtggcaga 300
cggggagatc ctggacaaca agaacggcac ctatgagttt ttgtacactg tccagaagga 360

```
aggggacttt accctgtctc tgagactcta tgaccagcac atccgaggca gcccgtttaa    420

gctgaaagtg atccgatccg ctgatgtgtc tcccaccaca gaaggcgtga agaggcgcgt    480

taagtccccg gggagcggcc acgtcaagca gaaagctgtg aaaagacccg caagcatgta    540

cagcactgga aaacgaaaag agaatcccat cgaagacgat ttgatctttc gagtgggtaa    600

ggagagggct tctgtgcccg acg                                            623


<210> SEQ ID NO 182
<211> LENGTH: 1423
<212> TYPE: DNA
<213> ORGANISM: Homo sapiens

<400> SEQUENCE: 182

cggcgggtac gttggggatg cactcgcgca gttcggcgaa ggcgctgttg atgctctgag     60

tcctgcgccg ctccttgcgg ttggcggtgc ctcggcgctt caccgggcgc ggccccccca    120

ggcccggggg cccggcgccc ggcggcaccc ccccgtaatg ggagtggtcc aggccggcgg    180

cgccgctggc atactcgggg ctgtaggaca gggccatgct gtagtcgggg ggcgacatct    240

cggggtggcc gatgagccag ccatggaagt aggggttctc ctcatggctg cagcggctgg    300

cggcggcggc ggcagctgcg gcggcggcgg cggcaaacgg gtagccctcg tggtgcacca    360

ccgggtggtg gggaaaacca cctaccagac tcatttcgcc ctccgcgccc ctccacgcgc    420

cccagcgtgc gcgcagcccc gccgcgccct cggcccgggc ccctgcctca gcgctcggcg    480

tcctccccca ccccccaccc cccagccccc gggcgcccgg gcccgcccgg cagccgcaga    540

gggggctgct gcagcccggg ccccgtcccc ccgcctggcc agccgggccc gcctcagcag    600

cgctgcggcc gccggctccc catggggcgc ggcgagctgg tcctggcacc gtgcgcccct    660

ggccgccgcc gccgccgcct ccggttcccg ccttgctcca cggcccgcgc ttcggctcct    720

gcttcccggg ctgctgcgcg gaggcagaat cctctcgtgc tcatacaaag gtgccggggc    780

tcccgcgagg ctggtacgcg gagtctcggg aatccaagcc cgggccgcgg tcctggcacc    840

gaagctaacc cggaatccag gggcgagtct gagccgcggc tggaggagcc ggtccagctg    900

tgccgggggg cggcggggtc gactgctcac tgcaaagcta cctccgtgcg accctcccct    960

tcccgcctct tcccctcccc ccaccagccc gatctgggtt cttgggcgct tattgtttta   1020

atgaaatttt tggttgttgt tgttttggtc cttaaatgtg attttagctg cgagtaacgt   1080

gtcctcgctc ctctcgcgct ctctcggagg gttttcagag aggtctcagt gcatccattt   1140

tctcagatcc tctcctttcg gggcaaggat ctggggccct gaatgagcct tggagctcga   1200

agaccgcggc tcgggctctc ggagggctct gcgcggtggc cgaggaagct ccggggtgac   1260

ggcggtggtt ctcctgggct ggacgacgtg aggggagcaa gcggattttc ccagcaagat   1320

ctccatgtac agctacatct ttagggccgc tcgggttaat atatgtcgtc agaggctcct   1380

cacgccaatc ccggggcggc aggggcggcg cctcgagctc tcg                     1423


<210> SEQ ID NO 183
<211> LENGTH: 2549
<212> TYPE: DNA
<213> ORGANISM: Homo sapiens

<400> SEQUENCE: 183

cgagattggc cgcagatgcc ccgacgggat ggcctgggga gccgaaagct gtccccagcc     60

ccggacagct actgcccacg ccgcgcaggc cagcctcaca cagtagcgaa tctccttcac    120

gcgacttcct cgcaggcctg tgaacccgca ggggaggcgg aggtcggttc aaaccctgcg    180
```

```
agagcccctg cccagcgcgg agtcctgcac acggtggaaa gtccttacgc attagcgggc    240
aggattaaac gacttcacac cacgaggtgc aagactgggc ttcggggcct tcctcggtgt    300
tgctatttta aaagaagctg ctcagtaacc cagaagaaga tgacggggga cggtggtgta    360
gacccggctg gagaggagtc cagggcctgg gaggcgcccc ctctgactga ggggctgggg    420
accctgaagc ttggcgtcca ggccccgcca gcgctgcacc cggcattgtc ccgcctgggg    480
caggcgtccg gtccctcggc agtgcgggcc agcacgtacg tagtagctgc tgaataaata    540
aatgcctatg caacagggaa cgtcccggcc caccccggcc gggccagggc ctaggaaggg    600
cgggcgtccg gcgccgccgt gggtccctcc ggcgtggccg cccacacctc ctggccacgg    660
cggggctgcg gtggggggac atcctggggc gggcggctgg acggaaggga ctagagtcgg    720
ggcgcgtcca cggccaaccg ccccgaacca agcaggggag gccagggacc aggagcttcc    780
ggggccccgc ggctggagcg cccggacgcg aaggggcggc gggtgacggg gcgcggtgcg    840
ggcggctaca gggccggacg ggagttcctc cgctttccgc cgcgcggctc gcggtctcag    900
ccgaggtcat cgagggccag gagccctggc ggaggccccg ccgtcccgga cccaccgacg    960
cactcccagg gcttggcgct ttcccaccac cccggaccgc ccttggggtg ccggaggggc   1020
tcggggcgcg gcgtggggag cctttgtgcc ctctccgctt gttgaggttt tttctccgga   1080
ggagagctcc ccgcccgcca cccctttcct ctcgaaagtt ttgtggtttc cctagaagac   1140
gaaagaggtt gagaaggttg cggagacttt tgcaatcttc cccgtccaga aactctaaaa   1200
cctctcggcg tttggcccag gggagctatc tggggtcaag gggagggagc tggccgcaca   1260
ttccttcgcc cgccttcctc ccacctggag ccgcggcccc gcggggcagt gcgtccgagc   1320
tggtgcggcg acgccggcag cggcggggtt aagctcagga atgcggcgcg aggaatgcgc   1380
atgcagatga ggcgggcggg cgcatgctaa tcgcatgcaa atgaggggcc cgccgctgcc   1440
gcggcagcgc cgcagcttcc cggatccgag cccagacggc ggcggctccg gcagcctggg   1500
cgccgcgacc ctcggcggcc agagggggac ggggcggagg aggaggaaga ggcggaggca   1560
gcggcggcga gggggaggag ggttcgctcg ccggctccga cgcagacatg gtggactgat   1620
ccgcagcggg gccgcgaaca gcgtttcctg aggcacctcc cgcgcgtggt tccgccgcgc   1680
cccgcgccct gcgcccctca gcccctcgcc ggcgcccgcg tcgcgggttg gcagcctagc   1740
ccggcagccg cgttcccgcc gcgtcccgcg cccggtacct atggaggcgc cgctcgccgg   1800
cgaggccgcc gaccatgcct aggagggccg ggagcggtca gctgccgctg ccccggggct   1860
gggaggaggc cagggactac gacggcaagg tcttctacat tgaccacaac accaggagga   1920
ccagctggat cgacccccgg gacaggtggg cgccggccgc gggggcgcgg gcccgttcgg   1980
acacggcggc tgttgtcccg gagacccggc cgcgcggggg gctggggcgg cgccggcccg   2040
cggtgccccg aggggtcccg ggagggatgt ggggctggct gctccggcgg ggccgaggag   2100
ccgcccgtac ccgggctcct ccgcccaccg gcttcccgac gcccctccgg ggacccggcc   2160
ccgaggcaag gctggagtcg ctgccccggg ccgacgccgc gcgccaggct aacggacccg   2220
aggggccacc tgagccctgt taggaacttc cctaggcttc gaggtgccca cgtggaggct   2280
gcaggacacc ttcggcctct gggcggcggg ggtgggctag ggcctcactg ccagttgggg   2340
aacgagccct ccgggccacc tgtggcatcc ctcaggccgt ccttggcgcg ggagcctggg   2400
ctgcgagctc ttggcggggg cgcccagact ggccggaggt cccgagctgg gaaggggctc   2460
```

ccgccccccg ccgggccctg ctagtgggtg tgactgactt tgcccctcag agtttaaaaa 2520
cgcgcgtttg gggtttcgc tgtctgtcg 2549

<210> SEQ ID NO 184
<211> LENGTH: 306
<212> TYPE: DNA
<213> ORGANISM: Homo sapiens

<400> SEQUENCE: 184
cgtgcgcctc agaaggggcg ttaggcagaa cgcgtgccca ttctcaggtg tgctcggcgt 60
gtgtgtgctc ggcgtgtgtg tgctcggcgt gtgtgtgcac acgtgtgccg tgcgcctcag 120
aaggggcgtt aggcagaacg cgtgcccatt ctcaggtgtg ctcggcgtgt gtgtgctcgg 180
cgtgtgtgtg cacacgtgtg ccgtgcgcct cagaaggggc gttaggcaga acgcgtgccc 240
attctcaggt gcgctcagcg tgtgtgtgct tgacgcgtgt gcacacacac atgtgacggt 300
gtgccg 306

<210> SEQ ID NO 185
<211> LENGTH: 249
<212> TYPE: DNA
<213> ORGANISM: Homo sapiens

<400> SEQUENCE: 185
cgaccggcgt gcaccgtctc gccattccca agggcagtgc agagcatggc acccagcacc 60
cgacaggcga ggacggccca ggacaaagcg gcagctctag ctgtcctcag attttgggag 120
ggggctccca acacggacac ggtaggtagt tggagcagga gggacggcca ggccactgac 180
cacgcaaccg ggcctctgtc agcggccagg ggcagaggga ggcaggaccg cccctggaca 240
accgacacg 249

<210> SEQ ID NO 186
<211> LENGTH: 8587
<212> TYPE: DNA
<213> ORGANISM: Homo sapiens

<400> SEQUENCE: 186
cgaggctccg tgaagagagg gaagcgaggc agggggtgaa gggaccgcct ggccggtgtc 60
caggatacgg gtggctcaaa ccaccagcag aacagcatgc cgactctggc ccgatggccg 120
ccttcatccc gtagccccaa cccggcctaa agccgagaag acgccagagt gcgctgctga 180
aattcccgcg gagtccggtg tgctggagag ccgcagcggg gtgaactccc ggccccgtct 240
ctgcgtagga ggtggttcgc aaagtggccc cgggagccgg gactggtacc cggttcccca 300
cggcaccgtc cggagctctc cagccacgag gcgcagaagt ggcctgccag cgccttccca 360
ggctcaggga ggcgaggagg cccgtgcact tggcatcttc tcccgggagc cgcacggcca 420
gggccgcggc gaaacggagc ccatctcaag tgcgccgcgc ctggccgcgt cctgtagccc 480
gacgaggctg aggatggaga ggggagacgc agggagaaga gggacgcggg acttggaccc 540
aagaggccgc tccgttgccg gtctggcggc ggcgccgact cgggttcgcg cgttccacac 600
aagtttcctg tctgcctctg cacacctggt ggacaaaccg ggcgtccagg ccacaccgtc 660 ttccccccttc gcgggggcgc gggggatgtt tccctccggc tgccaggggg ctttctgggt 720
gaagagaaag cccctccccc cgcgtctccc ccacccctcc ctccgagaac ccgcggcgcc 780
gactgcgcct gcttcccccg agctggcgac ttctccgcgg gatttgccct cgctcaaagt 840

-continued

```
ttgcacaatt gaaagagccc gcagagctcg gccgctcccc gcttccccaa gggcggcgag     900
gccggtcatt ggcagacgat cggttactac ccagtagggg cccacgggaa cccgcatctg     960
gagtcggggg tgtcacgcca cgccggttca gtggctcgcg gagagcgtcc gggtgcactt    1020
ctgccaaaga tgtcccctgg aggcccccggc cgcgcgggac tcgggggaga ggccgctccc   1080
ccctcgctgt caccagcgtc caggccgccg gccccttccc cgctgcccaa acagtagaaa    1140
agcaggcgcc aagttgtttt tgttaaaaag gggacacacc tcggccgcga aactgcaaac    1200
ccggtgtcag acagctgtaa acccgtgtcg acaggttgtc agacagctgc gggggctggt    1260
cgggaaggag cccacggcct ccgggcccac accccgccgc cccgacgcgc gcgcccaccg    1320
cgagagtagc tggccgggcc ggcacggggc accacgtgct cgcgggaggg gcgggagcgg    1380
ccggcgaggg cgggcgggag gcagggaggg ggcgggaggg gagccagggg cggggcctgc    1440
gctcaagggg atgccaatca aagcatcaac ttcaaattgt gtctgaaagc cccgccgccg    1500
agcggagggc ggccgccgca gtcggcgcgc gattgcggat ccgggcgcag ccgggagccg    1560
ggcgcctgcg agcaccgggc agaggagccg cgaccggcct ccatctcccg gcccgcccga    1620
gcgcgcccgg ccggccgccc gctcctccct agacccctcg cggcgccccc tgcaaccccc    1680
tccggccggc ctccgcctcc ctccccgcgc ctttaatact cgcccgctgc ggcggtcgcc    1740
gagtccgcgg acatgtcctt cccgcagctg ggctacccgc agtacctgag cgccgcgggg    1800
ccgggcgcct acggcggcga gcgcccgggg gtgctggccg cggccgctgc ggcggctgcc    1860
gccgcctcgt cgggccgacc gggggccgcg gagctgggcg gcggggcagg cgcggctgca    1920
gtcacctcgg tgctgggcat gtacgcggcg gcggggccgt acgcgggcgc gcccaactac    1980
agcgccttcc tgccctacgc cgcggatctc agcctcttct cgcagatggt gagtgcgccc    2040
ggcctccccc gcttctcctc tgtctcaccc gcgccagggc aagggtggcg ggtcgcccgg    2100
gagggagaga ctacgggtgg acctggtccg gaagaggaac tagaaaggtc cgggggcagg    2160
ttcccggtgg ccgaggccgc ggcccccggg gacgcaagag ggctgggagg ccgggcgggt    2220
gacggctggg ccatctcggc ctgggaaagc ggaaggcccg ggccagggag cgggtagcga    2280
gtgaattcag agaggccgca gaagcaggcc cgtggagcgg tgcccgcgct ggaggtcggg    2340
ggcaaactcg cctggctcgg ccagggcgcc cgggcaggcc cacggggttc ctgcaggtcg    2400
gcccggcgta gcgtagcagg acttcccttc ctggccgcgg gttccactcg cgcggcctct    2460
ttagttttcg aaccgagtct ggaaaacttg gttttctccc tctttagcag ctccgagata    2520
gttgtatccg agtttgccag acagacccct tctaagcctg gtagagtcaa tcaaaataat    2580
cttaacaata gaggtccaaa gggatggaga ggtctctcca cggcgtgagt gcgaatttga    2640
gattaaacaa aaattaagtt gcagtaatgt gctggtgtct gaaacggtgt ttgattttac    2700
ttttgtaagt tgcccaagtt ttcatttcat ttgcacagaa agaaaagcac ttttcttcct    2760
gcgttacata atggaggatt aaagaaaaca gtgtcccttg gcttaaaaca aatggtgtcc    2820
tcttagtctc ccgtcccagt gggcgttaga tgtcggggca ggcggctgca cacttaattc    2880
tccgcggggg cattggcctg tctgccggtc caaatcatcc attttccttg gtctgactgc    2940
aaggtcggtg cttaaacttc ggacggctgg tgaattgtgc ggcgggcgcg gggccctggg    3000
aggcagcccc ctcctgggtc gctgcccgcg ggataaagca atttccaagc acccgcgata    3060
tctccccgct ccccgcagga gaagcgggga gtaaacgccc ctcaagtgtg cacaagcaaa    3120
gagcgggttt ccctgtaact tttcttgtag ttttgaaaga aagcggcccg gctgcctttc    3180
aggtctctta ctatcgaaaa agatcagccc ccattttgtt caggcggcgg ggaggccggg    3240
```

acgcgatgag agatttacaa ggtgtccttt caaaaagaat tcccagtgga gacgaggctg 3300
aaacgtcttc tttacaatta caaccaaaat aattagaaaa gcgcaaagta cattttggaa 3360
cgattgggca aaaacgaaat ctagccgcag aaatgttttc tctgcggcct cagtcaccaa 3420
actaattagt ccaagaaatc ttctggtctt tacaactttc tcagagtccg gaactccctt 3480
tgctaacatt gcaactagac cattttttca gaggatgaat atttttaca gaaattgcga 3540
atgcagttgt gtgccatttg ggaaccctgc ctgtgtttgc gggggaggga gagagcttca 3600
gtgtgaggac ctgcaccctt tgtggagagc tggggaaggg agatgtttgc tgttctgagt 3660
tgtttttccc acctagaggg ataaatatgta aaaattattc ccacccaaaa ggtgtgtgtt 3720
tctccagctc tcccactggt tctgagagag taaactcaaa cccaaaccct gattctaggc 3780
ctaggtttcc aagccattat aattgggtgt ttggaagtca aaagataaaa ttgtatttga 3840
atgtctgtct gcgcaattta tggtaataat gaggcctaat gaggttgtta gaaagataaa 3900
atgttattta ccaaaaaacc tgatgggata atttgacttg ctgtgtttta ctactgatta 3960
taaaaagaat atcgattgca aataaatcag cgcctctaaa tgcctgcaaa cagctagtgt 4020
ttgctccctc cagatcaaag tcaaacttaa gagatgaagt aactgagaag aggcctagga 4080
tactgaaccg gttcccctcc tggccgccgg tggctcccag cccttgcgtt aatattttac 4140
aggctaagcc ttccttttgt attaaaaaaa aaaatggtgt tttgttatt gttgtcgatg 4200
atggccggga ttaaaatttt aaattacctg tcacctctaa agacctttta atgtgggtaa 4260
accattatat gcagattaat ttggaaggca aaggactgtg ctttcgtttt aaattgctgg 4320
cggatttaga ccggtagaaa acccgggatg gtttattttg attgagcccc ctctgggtgg 4380
cagagaggag gcttgggctc tgggcccttt acgtttggag aaatggcttt atcagctcag 4440
ttgaaaggtt tttccctcta gctagtgaaa gataaacttg gaaatgcagg tttctccagc 4500
ggttggtggt ggggacaggg gtcgcctagg gaacttgcag gggccgcggc ctctgttgtg 4560
ctcttctgga gagtgcactg tttgtggaac ttttctagag tggcaaaaac gatctccact 4620
gtcggtgaaa gggcagttcc tgaagtcagc tcatggtcct ggctcccctt ctccccagca 4680
gtgaactggg ggtgacttcc tgatctgccc agcacaggag agccccgcaa agcgcctggg 4740
aggccctcga gtccattgaa gcggctgctt cccactctcc cgtcttgggg actcatgtct 4800
ctctctctct ctccctttct ctctccactt ccctcctctc tctcctcgat ggatctgccc 4860
tgtggcttca gggctcgcag tatgaactga aggacaaccc tggggtgcac cccgccacct 4920
tcgcagccca cacggcgccg gcttattacc cctacggcca gttccaatac ggggaccccg 4980
ggcggcccaa gaacgccacc cgcgagagca ccagcacgct caaggcctgg ctcaacgagc 5040
accgcaagaa tccctacccc accaagggcg agaagatcat gctggccatc atcaccaaga 5100
tgaccctcac gcaggtctcc acctggttcg ccaacgcgcg ccggcgcctc aagaaggaga 5160
acaaggtgac atggggagcg cgcagcaagg accaggaaga tggagcgctc ttcggcagcg 5220
acaccgaggg cgacccggag aaggccgagg acgacgagga gatcgacctg gaaagcatcg 5280
acattgacaa gatcgacgag cacgatggcg accagagcaa cgaggatgac gaggacaagg 5340
ccgaggctcc gcacgcgccc gcagcccctt ctgctcttgc ccgggaccaa ggctcgccgc 5400
tggcagcagc cgacgttctc aagccccagg actcgccctt gggcctggca aaggaggccc 5460
cagagccggg cagcacgcgc ctgctgagcc ccggcgctgc agcgggcggc ctgcagggtg 5520
cgccgcacgg caagcccaag atctggtcgc tggcggagac agccacgagc cccgacggtg 5580

-continued cgcccaaggc ttcgccacca ccacccgcgg gccaccccgg cgcgcacggg ccctccgccg 5640
gggcgccgct gcaacacccc gccttcctgc ctagccacgg actgtacacc tgccacatcg 5700
gcaagttctc caactggacc aacagcgcat tcctcgcaca gggctccctg ctcaacatgc 5760
gctccttcct gggcgttggc gctccccacg ccgcgcccca tggccctcac cttcctgcac 5820
ctccaccacc gcagccgccg gtcgctattg ccccgggggc actcaatgga gacaaggcct 5880
cggtccgcag cagccccacg ctcccaggta cagctccagg ccgcgtccac ctgtccccta 5940
gctgggaatg cagaggcctg gctaggtgtg gtagcgtggg gtgcagcatg agccgggagg 6000
gtaccaggca gtggccgctg agccctgggg ctgcgcttaa tccctgcttc aatttagaaa 6060
gccagacaag gccctagggc tctcccaaga gagctttgcc ctaccggcgg gcctgctacg 6120
gggtggtggt ggggtgaggg gtgacgtttt tcggcgaatc tgcctgggca gccggcagaa 6180
gttggtggga aggaggcctg ggacctctcc cgcccgtctc tccgtcctaa ctctgcctct 6240
tccgatctct cgcagagaga gacctcgtcc ccaggccaga ttcgccggca cagcagttaa 6300
agtcgccctt ccagccggta cgcgacaagt gagtgctgtt tgcttttgct atgggagaag 6360
gcggtgggga ggggggagga ggagtggtcg ggacccgggc ggagctggct gggtggcggt 6420
gggggtcgcg cagtcctagt tgaaggagcg ctccccgcca gccctgggcg ccgggcgagc 6480
cgaggagact ggagtttctc cccagccggg agccgcgctg gctgtcgacc ccgcccccag 6540
ggctccgcta ctggaaccgg cgtcgcccgg cgctgcgtcc ccccactcaca gtgcccctgt 6600
cttcttgtct cgctgtgttt cccatgcagc tctctggccc cgcaggaggg aacgccgcgg 6660
atcctagcag ccctcccgtc cgcctgatta agggtcttct tttacttttg cgggggggag 6720
gggggaggag ttggggaggg agggaatgtg ggaggaatta agacaaatat ttcagactgg 6780
tgtaaaggac aaatatgaca acgacgtcaa ggactcgcat ccgtcgcttt ctgcagaaag 6840
gggcttcttc ggtcccgagc tcgcgtccag gtggccaggc ctctgccggc ggctccagtg 6900
gctgcgatta tcgggttcgg taaatgcccc cacgtgcttg tgtctctttc ccccctttc 6960
tgtatataga gtggtttcag attgtaaata gcgcgtcagc gaacttgtct aaatcatata 7020
tttttgtcta ataaactaaa tgaaatgaca cccccctcccc gctcctgctg ctgtgtgcct 7080
gtccagcgtg tgtgtgagtg tgtgtttgtg tgtgaatgtg tgtgtgtgag tgtctgtgtg 7140
gcagaaacag agacagagag agagaagtgg gggatacagg gatcctggaa ccctgggtgg 7200
gacccaaggg tctgtggctg gggagatgg gcttctcaat gggggccttt agagactgtt 7260
gccacccaag acgcaggtgc tttaaacatc tcttcgttgt ttgtggttgt tgttgaattt 7320
ttaaatattg tcactgtggc agtttcttgc tggcagttca attgctttca cgaacatttt 7380
tctgagacat aattttctca ggacataaat aagttcaatt tgaggcagtt ttacaaaacg 7440
attttataac gtcggtaaaa acagaggaaa aagaattttt attgcgaccc cagaggagaa 7500
cttcggatta gaaaccagtt tacaactagt tgtctcaacg gcgcatcgtg gcgcctggtc 7560
gttttctgag ttgagtgtga aaataatgga gtatcgcttt gcatgtattt ttagtgattc 7620
ggttaaatca aacacgggaa gaaattggaa ggctctttaa aactccacag atgggccagc 7680
cgggatgcgg tgcggggctt ctctgcggtg tgaggtgtga acgaggggct gaggctgtgg 7740
tgggaagcga gaaagaggag gtggctttgg tctcccaggg aagccccttt acacttgggc 7800
tccacggact gcgtcctttg ccctcaggcg cgcgcaccgc gggagtccag agcaaattgc 7860
ccttagatgg ccgcggccgg gcagcgggga ggcagctggg agcagcgatg ttgggaaaca 7920
ctcgcagcgg ggctggcctc gggcgcgcgc gagtggggaa aggcctagga gcctggacat 7980
cgctgcggat ccgggacatc agcatcagtg ggttcggagc gggacgcgcg ccacgcgccg 8040
cagcaggcac cttcaggagg ctttgcggac ccggcgcggg gccttcaggg cgcaggcgac 8100
tcagcgttga atgcgtgaaa actgagccag caaacatttc caaaactgcc agcgaggatg 8160
tgggctgccg ggaaaaacgg tctagtgggg acagggccga gtcccgaagt cagagccgag 8220
tcccgaggtc agagcggccg tcctccgctc gcaccccag cctgtgaccc gcccttcccg 8280
gcttgctcga gacccactgg cgccagtgct gcgcgtgggg actccgtgca tggccgaagc 8340
gagggggaaa gtcggggcgc tggtgtcttt tcagaggttc caggaaagag ggaggctcgc 8400
gttaggacta ggaggtgcca gtccacggct cctacccgct cccgacgccc gcatccttct 8460
acagccctcc accccgttcc tggtccctgt agaggggaag gtcctctccc tgccccgagg 8520
cgggaggaaa agcggcgaag aggaggctcg aagggcgccg cgtagggcaa gtgggccgag 8580
gacaccg 8587

<210> SEQ ID NO 187
<211> LENGTH: 1500
<212> TYPE: DNA
<213> ORGANISM: Homo sapiens

<400> SEQUENCE: 187
cgtgtactcg cgcacacgca gtcaggtgtg gatgtacacc cgcgcacacc caggcacatg 60
tacacccgcg cgctcacaca ccccatccag ctacagcaga attctggcca ggctgttgac 120
cgcacacctg ctgcctcctt ggccaccctg tccacacagt agcccgatcg acccccgtgg 180
cggccgagac ccaggcccat ccgcagccct gagacctccc tagggattgc acccagcagc 240
cagtcaccgg cctccgcggc ctggccagtt gagggtggcc gtgaccgcgg ggccaggagc 300
gccgccacat ctcggggcaa atggcgcggg ggaagagttt cctcctcagc ctccccgtct 360
ccgatcgctc cgcaaactcc agagcgaggc acgcgccttt aaaggcaggt ccgcggctct 420
cccacgtcct ggcgcccggt tttccgcacc cagtgtcccc acagctgtgc ccgggcacag 480
aggcgcggcc agaccgcact ccgcgggctg caggtgtccc ggcctctggc ggcgccggtg 540
cggcccggag gtgggagccc gcggagccac tgcagtagct ggagtcccgc cgagtcccca 600
gccccaaggc agggcaggag cgcgcaccgg ccggaggtcc atgctgagca tcgcccgcgc 660
cggtgcccgg cagcctctcc aactgtgtgg tccccgcgcg ggcagagagg cacggactgc 720
aggccgtggg cagctccatc ttcccgcgtc ctcctcctct ggcgctgccc gctgtctccc 780
gccttccctc tgctccccgc tcgcctccgc ctcagcgccc cgctgacctc gcctcctccc 840
ctctgctctt tgtccctgca ctctcccctc ctcggtcctc tgaccccccc gccctcacct 900
cctcccctcc tctctcccct gcccgccccg cgctctccca ccgctcccgc cgcccccgcc 960
gccgcggctg ccactccgcc ccccgcgccg cacggagctt cagtaataac cccggcgcgg 1020
cggcggagtc gctgtgggga atcctcccgc gctctgcctg ggtcgggtcc tccctgcccg 1080
ctcgcacgct gccggccggg gaccctccgg tggcccctag cccctcggag cgctcctgga 1140
tgaagccccg cgcgcgcgga tggcggggct tggcggcgct gtggatgctg ttggcgcagg 1200
tggccgagca ggtgagtccc gggcgctccc accagcgcgg aaaccgcggg tccggacagc 1260
tggaggcgag tcccccgcgg ctcctctccc gcggaccccg ccgtctcacc gcgatgtcgc 1320
cgctgttttc cgcaggcacc tgcgtgcgcc atggacccg cagcggcagc gcctgggagc 1380
ccgagcgtcc cgcgtcctcc tccacccgcg gagcggccgg gctggatgga aaagggcggt 1440
aagtccgtga ggtgggggct tctaatcctt gccatttagc agctcgtaat ctccgtgccg 1500

<210> SEQ ID NO 188
<211> LENGTH: 300
<212> TYPE: DNA
<213> ORGANISM: Homo sapiens

<400> SEQUENCE: 188
cggatcgaaa ctgtggtgaa agacctttgg ccgacggctg atgtgagtat gttctttgga 60
gttctgtgtc gcacgtcacg tgcgagtaaa tttaaatacc ctgtgatgat gatgtgtcgg 120
ctagatccac acagaccttt tctcgttggc ccgaggcagc agttctccaa gtgtgctttg 180
agaaggcctc cgttgcctgg aatgcatggc ccccggcgca cctgcacctg ctgtcttaga 240
cacctgcggt ggccgcacat cttcgtgatg ctggcgcgca ctcaagtgcg aagaccatcg 300

<210> SEQ ID NO 189
<211> LENGTH: 574
<212> TYPE: DNA
<213> ORGANISM: Homo sapiens

<400> SEQUENCE: 189
cgggctcggc ggcggtctgc tcgcacttac gtcgccagcc cagtctcgta cccgaaaatt 60
caagccccat ccgagacagg gaacccagca ggcttgcact gccacggtgg ggagcgggac 120
gcacggagca cgacactgac tgggggaagg gggcagcagt tcgcggctcc tgcagagcag 180
ctgcgtggcg ggaatgggtc cttccaccgg cggtgcggcg gccctgcgcc ggctccgggc 240
agccgagtag cccgccaccc accaactagc taagcagccg cctctgtgaa gctcggcggt 300
tccctgtgcg cctgcgaaat tttgactccg actcaccagc gaccggccac cgagccgccg 360
ctgtaggagc tgagagcacg tcttgaacac cggatctttc cacccaagac ccgacagcgt 420
gcaggggcct cgagcagtaa tttgaggccg cgtttcccgc caaggtttgg ccccagctaa 480
ccgccccacc catgcaaccg agcgggaaga aagctgtgat tcgaggggcc aggagaatac 540
gggaaaagct tctgttctgc gcacagccag tgcg 574

<210> SEQ ID NO 190
<211> LENGTH: 1504
<212> TYPE: DNA
<213> ORGANISM: Homo sapiens

<400> SEQUENCE: 190
cgcgcacagg gagtcgagtg ctcctttgtg ccatcacctc ttctcgaagc tccaggcgca 60
gagggcaaac gctgacgccc tttcccgcct tctctccgtc tgcgagttcc ggagggcagt 120
gcactgtgca gcctccgtac ttcccgacac gttccgcctg caaaccactt aggagcttct 180
gccggcaatt tctcggatgc agcgcggagc ccagcctccc gcactgactc aggcccggca 240
ccaccccgcc tgctgagggc gtcgtcgcgg gcgccaccga cggcgccagc ctgcgttcct 300
aaaggctcca ggacaggtgt ggggctgaaa tcccgctcct ccagcatctt cccctcccta 360
ccaaaagaag gctgctttaa atattcccgg cctggagcag cagcagctaa ggacctggaa 420
agaggcccga aaaggccagg gcagggcgaa cgaacgtgct gtccctattt accggccaca 480
cgctctgact gcgggctgac cctgatcgca cacttcgagc ctgttcactc gctgggcgga 540
ccctccctcc acgctccgcg cccaggcagg cgaggtcacc cactcgaagt caccacgttt 600

```
gagtagccct ggttggtggg gcagcgcccc cttggccaac gccccgccct cctctccatc    660
ttccgacgct gggctctcgc ccttcggcgt ccgagagccc ctattgctgc ccagctggcc    720
ccaaaagcgt ccgaaagtcc cctcttggct tatttcagag atgccacgca ataaagaaaa    780
ggcggctact ttgcattccg cagctgctgg gacgcccggg ctgcgagcgc ggctcctgga    840
ttccagcctc ccgcccttcc caggcgctgg aatggacacg gacgcccaca gtggcgggcc    900
aggtagtgcc ggagtcgggg gcccaggccg cggcgccccg cgcctcatca cttaccttgc    960
ctttagctat caattccatg atgtagccaa attcactcat ctccccagac tccgacatgt   1020
ttacacccct tcacaaactc tggaggaccg acgcgggtgt atcgaatttg tcctttcttt   1080
tctctttttc tgtttttagt ctgagttttg ccgagctccc cgcccataag ctgttaacca   1140
ggaaaagagg ggaagcgccg gggaaagcaa gaagcgggct tgggtgaaat gaaggccatc   1200
gagggctccc gggcagcctc gcccggcttg ctaggatccg ggtgcagcgg tcggggctgc   1260
gcgatctaac ggaacaaacg agggcggcgg cggcggcagc agaggccgtg aaaccctcac   1320
caggcggagc cgggcgcgcg gaggccccgc ctcctcgggg gtcgcggcag cggttcggac   1380
cgcagcggag acaaacaaac gcgcacacaa agcgggtccg cactcggctc agcgcggccc   1440
cagctagaca ttccccggcc tttatcgcat gccggcaggt tggccgtccc cggctctcgg   1500
cgcg                                                                1504
```

<210> SEQ ID NO 191
<211> LENGTH: 305
<212> TYPE: DNA
<213> ORGANISM: Homo sapiens

<400> SEQUENCE: 191

```
cgcgtcccga ttatcagtgc aatgtgatca cttgatttta aacgcaacta tgcgtccaaa     60
tggctgagtg caagaggtcg gccggagata gggccgagtg cgctgcccca agctgcgatc    120
cctgccaagc actcacggac aatgcactgg tttcctccag ggagcgtctt ccatccaggg    180
cagcagtagg agtggaatct ggagccgcac acgttgggcc tgtgatggac aagcgcggtc    240
acgtaacaga taggtagagg gatgcagcaa catataaacg gtcttcgtaa gcaatgcccc    300
gagcg                                                                305
```

<210> SEQ ID NO 192
<211> LENGTH: 645
<212> TYPE: DNA
<213> ORGANISM: Homo sapiens

<400> SEQUENCE: 192

```
cgccagtcct ttgtaggcgt tcatgcgcga gcgcgagtgg ctgaaggagt ctttccgctg     60
tttctcggtg cactcattgc acttgcagaa gtagtcgtgg ggccgctcga tgcgggcgcc    120
cttgagcagc aggatgtgca cgatctcata ctcctggcag tgcgccgcca ggatgatggg    180
cgtgatgtcg tgggagaagc gcgtgccgtc ctcgtcgtag gcatagaagt cgtcgtcgcg    240
cagctcctgt tccagcgggc tgagcgtcag gcgctggccc tgcgcgaagg ccgggtggtt    300
gaggatggcc tccacgatgc gcacatagcc cttgctgatg gccagcagca gcgcgtcccc    360
cacccgtgcc aggttctcct tcttcagcag cagctccgtg acctctaggt gctcgttgcc    420
cacggccagc tgcagagcgt tctgccccat gtagtccaca cagttgaagt taagggtctt    480
ggactcctcc agcattttcc ggaccaccgg gatgttgcca tactcagccg agtccaggaa    540
```

gcgctcctcc tcgggcgtca gactggtgcc cttctcgttg aacatgtagg cgggaccccg 600
gatggcctgg cgacggccct tctccctcag cgttgtgtgc cggcg 645

<210> SEQ ID NO 193
<211> LENGTH: 312
<212> TYPE: DNA
<213> ORGANISM: Homo sapiens

<400> SEQUENCE: 193
cgagaaaccg cggaatatcg gcttagagcc tgccatggcg aatcggctac agcgcgggga 60
ccgcagtcgg ctgctgctgc tgctgtgcat tttcctgggg acgctgcggg ggttccgggc 120
caggcagatc cgatattcgg tgccagaaga gaccgaaaag ggctccttcg tgggcaatat 180
ctccaaggac ctggggctgg agccccggga gctggcgaag cgcggagtcc gcatcgtctc 240
cagagggaag acacagcttt tcgctgtgaa tccgcgaagc ggcagcttga tcacggcagg 300
caggatagac cg 312

<210> SEQ ID NO 194
<211> LENGTH: 2404
<212> TYPE: DNA
<213> ORGANISM: Homo sapiens

<400> SEQUENCE: 194
cgcggcgtct tcctgcacga agcgacccaa gcagccccag tccgcaccgc cttggtcagc 60
gggcgctccc agcacacacc cagcgcgcgg agcgactcct cccagaggac gccgagtgtg 120
tgtgtgtgtt gcggagatta gggggtggcg ggggggacgg cggcagtttc ttgggctctg 180
gcggccccac ccccaccccg gcagcgccca gcctccagga acccaaggca aggctagggc 240
gcggcgtggt gagaacgcgc ttcggctagt gggggggagcc cttgcgcccc ccgcacccag 300
gccaccgcgg ggaatccctc ctccccggca tctccggcct cggcctaggg tcccccgcaa 360
gccggagccg gcgcgagcgg cgcagcgggc gccaggaggg ggcggggagg gagccggcgc 420
cggaatcaca aagccgcgaa cccggctagg cggggacatt ctcataaaac cgaccctctc 480
gtggcgagca gagggggttt tttgccctac gctcaatcct ccaaggcctc agtgccgccc 540
ccagtctttc ctggcagaag aaatagtagc cgaccactgt tggggaaact gaggccagaa 600
ttctgactta cagagggtag ctggggggaa ggggtgcgag accacctcgc ctacaaattc 660
tgctcctatg cctgccgcga tctccgttct ggctccaggg cctgcccgcg cacacactgg 720
cctacagcgg ggaccaggcg gagggggcgc tcaggtgtga gacgaaccca ggtgtgcggg 780
acccaccaag gtgtgtggga cccaggtgtg ctggagaccc aggtggctca gaaaactcag 840
ctaaatggct ggaagagggt cgcaatcacc gtcccaggct agcaccctct acaaaggaac 900
ctggggcccc agagctccgg ggaggcggga tggcttggcc agccaggtcc agcttgttcc 960
cggaacacca gccggttcgg cccgggagtg ggggttgggg aggcgccgac tgggaagccg 1020
gcaggccggc ccagccttcc cgctgtgccg atatttacaa taataatgtc gcgattaacg 1080
tggcggggcg cttggggctc gccgaacgac cccggcggct tctcctgcct gaatctggac 1140
tccgagagag aggaacggag tgtgtgtgtt tgtgtgtatg cgctgcaggg tgtaatgtaa 1200
tgtgacactg ttggtttaag gtgtgtgtga cacccagtgt taagatgggt gaagcagtgg 1260
attctgtgtt tgtgaccgtg aggcgctgct gtaggtgcca attcctgtgt tagagtgtgt 1320
gccatcaagc gtgtgctgag atactgggtt gtgtgtttgt gtgggtgcag tagaggggtg 1380

-continued caaggagacc tgtgctgtgt acctatgttc tggccaagaa gtgggtaaga tgatatatgc 1440
tagggtgtgt tccttaaagg aatgtggggg gtggctaggt tttgagggtt catctagtga 1500
actgtggctg tgacactcgt acatgagggc acgagattgt gtttgtgtgt ccacgtcgcg 1560
gggtgtcaca cccggttgtg ttattgctct gtaaagccac gggttgtgtg tcggtgctgc 1620
tgatcgtgca gacactgaag cggattctga gctggcgacg gtgccccagt gggcgctggt 1680
gtgcgggagg tatgtctgtg tgcacatatg cagggatgta tgtatgtgtg tatatatgtc 1740
cacggtctgg ccctctgggt gcccgcgaga agctggaagc ggctgagtga gccgaggtag 1800
ttgcccaaca agtgtgtatg tatgtgttgt ggacaacggt ccttgcttgc tccgtcctcc 1860
gggagacccc caccaaactg ggggccgcgc gcttccccaa acccatcctc cacgccgcgc 1920
gctcctggag tctccttatc cccgtctctc cgagcgcgcc caggtttggg acgcggggac 1980
tagggttctg ctcagcaccc cctcccctcc ctcggcttct cgccgcggac ctgggaggac 2040
ggaatccctc agccgcatcc cctgctatgg gctcccagca gcccccacct cagcccccctc 2100
gcgccgagct cgtgttgggc ccccgcggcc tcgctccgcc gagcgcccct ccctcagctc 2160
ccgccggcca tgaccgcttc gggccccaag ccgctgctgc ctccaccgcc gccggatcct 2220
tacccgcctc cgggcagcgc cggccgcccg ccccgctgtc catgagccgc cgccggcccc 2280
ggcctgggct gcggctccgc acggctgggg ctggagctgc agttcgggct ccggctccgg 2340
ctccggctgg ctctgggcgc agcagcccgg cggctttgcg tccgcgccgc gctcccgctc 2400
cccg 2404

<210> SEQ ID NO 195
<211> LENGTH: 3468
<212> TYPE: DNA
<213> ORGANISM: Homo sapiens

<400> SEQUENCE: 195
cgccgcgcag agtcggccga atccagcttc tccaagggcg ggcgggtggg atgatttgtt 60
gatttgcttg ttttccacca aaccgcaggg cacctccagg agctccggga caacttacaa 120
atgaagacac agagcccccg tcccttgctt cagagaacca aataacggaa ctgaatgatc 180
gtttcttcag caaagcctaa agacgcttgc gtcccgcgga gaggtgccca cgcgcgactc 240
ggctgccccc tcttcttgcg ggtccgggta gggtagggcg ggaacgcggg acgtgcccta 300
agcgggccag ccgagcgcga gacaggcgat gctgcagaag cctgcccgcc tgcgggtcac 360
acaccggccg gcctcggctg caggggttgc ggggccacgg gtcgcggggc gccgggagcc 420
gcgagcaggt gacggccgcg ccgggcagcc ccgcgggccg cgattcccga gagcctggcg 480
ccacccccgcg gaagccggag gaactgcggc ttcttcccgc tcccgcgcgg aggggagagg 540
gaggcgcagc gcggaggggga gagggaggcg cagcgcggag gggagaggga ggcgcagcgc 600
ggaggggaga gggaggcgca gcccgcaccg cgcaatcccg gggctctggc gggagggaag 660
gtgacttgcg tgggacgact ccaagaggcc aggcccggcc ttcgcagttc acccacgagg 720
ataccgcgac caagccacca aagcactctc tggccaggcc gagacccctt ttcccccggg 780
ccccaagaga aaaaagcact ttctcctaaa acacgaactc cccgcggagg ggcccggggc 840
tgcctggcac ggggcagggt gtgcggctgc cgtgcgggcg cgggccagag tcacgtggag 900
gcaggcggag agggcgaggg ggcccccgta aatcatcctg agggattttt ggcccaagtc 960
cctgtttccg aaaggttgcg ggacggcttt gacgttgatt atgtagctgt tctcttttca 1020
agtgcgcgcc cctccccacc gcagcccgtc tggtgtgcga ggattgtgtt tgaaagggag 1080

```
gaagcatcct tgaagtggtg ggtgatggat tgtctaaacc cttctgggac gttctgggtg   1140
ggggttttcg aggcagctca tcaataaaga cccccctgga gagaaggggc ggctggagac   1200
cagcccccgc cgcgcagccc cgaggcccca ggcctggaac acagtcctcg gtgtggggca   1260
cagggcgtga ggggaggatg agctcccccct gagcagatgg agatttctcc ttgcctgggc   1320
cgtttgaccc ccaaagcctt gcagactggc cgcgtgggtg ccatggggcg atttcttggg   1380
aaaggagggc agcagaaagg cccgtgggct ctcagcgcct tggagtcagg ggagcaggaa   1440
ggggagtgga ggtgcggaca cgcctccagc caccgtgctc ccctaggagg atctcccttc   1500
agcccctgta gaaccctgca tctcaaccac cctcgtgcat gtggtttacc ttggcataga   1560
tttccaagcc gctacagaaa acctgtccac ctcccccaag gtggaggcgg gagttgggag   1620
gcaggggtgc tggaaagggt cacctggctc aagccgaccc caggtctgac gggcggagag   1680
cctcgagggc cacgccccag gccagtggtg tcctctgagg ccgcaaagcc gactggcttc   1740
tggaggagca gcagcctcgg cctcagcctc ggctgggaaa agacgcagtc ggggccctcc   1800
gtgctccaaa cttgaactac tctgggtccc cacgaggagg aggctgccct ggggtcagaa   1860
actccgacgg aaatgaaggg gagggggcgt aggttccctg gcacagctcg gcctggagag   1920
gcagcctggg ggcccaaact catctagggc gcgcccggag cttccccggc ctctcttggc   1980
ccatcgcgaa cgagctcccc tccccgactg ggtcggcctc gggcgccttt cgccttcgca   2040
ggccgccggg gttccgcgga gggcttgtgt ccctccctcc cgccgccgca gcccgcccga   2100
aggtcaggcc gcatccgggg cccggggcct ttggccaggc tgcggggagg ggtggggttg   2160
gggggctccc caaagcagct tctcggaggc ggcgtcgggg cgccctgagg tccctagtcg   2220
gcctctgggc gccgagcacg ttttatttat ccccacagag gatgctggag gacaaaagaa   2280
atatttggac gtcagagctg atttatattt ttggaagagc tacgtttcct tttctgaaga   2340
gaagcgagcg cgccccatat cctgagctcg gcggggagga cgagagggga gttttgatgc   2400
gccaggaagt tcatctatcg cccaggcgct caggacccgg cgccccgccg agttcgccgc   2460
cctcggaaat atttatttat ttgggggaag ggagggcagc ggggaggaga ccagccagac   2520
gggagaagaa agccctgccc gggctgggtt gggacctcca gggcgcttcc ccgcgcggcc   2580
gcagccggcc agcctctggt ctcggttgga gggcatcgca ggcgcggcct ggcgacctcc   2640
gggcgccttt ggctggtgtc ttccgtagcc ctcggcgcgc accctcccgc gtgcagtgcc   2700
cggagtgacc tcttcaggcc ccgcgggcgc ctcctgggtg ggccccgcgg cccctccaac   2760
cctgcccagc gtgtgtgcgc ggcctagcca tctttctccc cagcctggga aggcgggcgg   2820
gaggagggga tccgaggccg ggggccgcgg agcaaaaggc acgcggaccc ctaaacgacc   2880
cccgagcgtt gccacagccg ggagggcgga gggaaggtgt gcagagctcg ggggtctccc   2940
aggacgcagc ttggctccta ccggtttcca aggcatctgc aagctctgtc ctgcgaccta   3000
aagcatgggg acgtcccttc cagcagcatc agtgggcgaa aagttaacat gctgagggcc   3060
accggcaccc acacttgctt ccaggaatac ttgcggtaca ggcttcctga cttattttct   3120
ttagccgctg ggtgcccccc cttcttcccc cgttgggaga cgcagaccga ctctgttcca   3180
acctaagccc cttctctctg ccttttggac aaagcgggcc gcctctgctc tccactcact   3240
ccccgcaacc ccgcaactcg ccacccctaa acgcagcggg ctgtaggcga agtcgaagag   3300
gtgctccgcc tggtaccgcg gcctgcgcac tgggatcggg gcctgcaggc cgctgggctg   3360
```

gctcctggga tcatcccaag gttttggtct cgcaaccgag gggacccgcg cccggcaatt 3420
tgggaagtgc ggaaatgggg tgaggccggt cttcgcttga gggtctcg 3468

<210> SEQ ID NO 196
<211> LENGTH: 2654
<212> TYPE: DNA
<213> ORGANISM: Homo sapiens

<400> SEQUENCE: 196
cgatgcggat tcgcgctggc gctgaacgct gagcgcaggc ggggaggctc ggcactctcc 60
gacctcagta gcgcccccaa aaccgaagtc cagccggcca gagaggacac ttacgtgcac 120
acggtcttga tgttcgtctt gtcgtccagg ccctgcgggt agttggccat gctgtcgccc 180
agcttgagca aacagtccga aaagcccttg aagaccgcat cgcacttgcc cgctgctctc 240
acggcctgca ccagatacgc tgcggggagg agggaacacc ggtcagcagc gccacgaccc 300
cgccctgccg cccactgccc tttcctgcga gaccctggct ccgcgcggcc tcatcgcatc 360
gggcggcctc tcccagcgcc cagcctcggg gctcgccagt gttaaaggtg aatgaaagac 420
gtgacccagg aatgcccgac ctgcagctaa cgctgcgtct agtgcaaatt gtcggtgtgt 480
gagcaggtgt gggtgggtgg gaggtaggtg agtccattcc tttcctccag ctccctcccg 540
catctcgctc cgtatctttt tctgtttcca tcgcccccctc ttctcacctc cctcatccct 600
tttatttctc tttctcctcg ctccctcctt cgtctcccaa cacttcccca gcaagccctg 660
tcacagctct cgcaatgcga tcttccattt tgaggtgaca gaaggggtct cggctgcagc 720
gtgcgggggc gagaacgggg tggggagacg acagggcgtg gggtcacgca gctgaaccca 780
acgccacatc acgagaataa gcctcaggct tggcgctctg tccttggtgg gcgctcagca 840
aacactgctg aatgaatgaa cgaatatagt ccctggaagc caccagcagt taccgaaatg 900
gattgtttca ttataaaacc gattgcctac cgtggactct gtattccgag tgagaccctc 960
ggatgcaccc tctcccgccc cgctggaaag agggcagcct ggacgtcctg agacctggcg 1020
cggatgatga gtggtctgga gaggagaagg ccagaggccg ggcggggtca cggatgagtc 1080
tgcctgggtc acctccgcaa aggccaaatc cacgaacctc gggcctcttt ctctcctcct 1140
cccctgtccg ccactcggct ccccagacac ccttaacaac ccacccgccc gccaaaaagc 1200
ccgcctacac tccggacggc agcggggaga ggctgttctt ctccaggtgc cagccctgct 1260
gctgaaagtg agctcgccgc ggcccggggc tcctggcccc agctcaggac tccctgcaga 1320
gagcaggcag ggataaaagc tgagcggcgg gaggaggagg aggaggagga aacacaggcc 1380
gcacgaaggt ccaagcccca agcccccaag cccccggcct ctggacggcc aaaccccgag 1440
gcgcgggact ggaaggacag gtaccaggct gcgggcgcgc ggctgtggcc atctctttcc 1500
gccctgaggc cgacgaaccc ggctggaagc tgagtgccta gcggcccaaa gcagcccggg 1560
cgccgggagg gcgccagaga agcacagcgt tagggcgggg aagaaagggt gaatctcaga 1620
atcgaaatcc gcactggcgc ccacgaccct gggcgccggc ctggtcctcg gcagctttct 1680
ggcggctgcg cttgtgtgtg aatgtgtccc gggaggaccg gacacctcaa tcccccggcc 1740
cccaacgcgg gcgcctgtcc gcgagcgccg ggccagacgc cgaagaggaa ggtgaccgaa 1800
cccgtagcag cttccgagag cgtacccgtt tgcaaattgc tgcaggaaga gcgaggcggg 1860
ccttgcgctt tttaatccgg aacgggaagc actggggaag ggaccgaggt taacttcgac 1920
ctccgctggg gcagatacgt aaaccttctc aaacctccga gttcacctta cagcgaacat 1980
taaataccct tgcgactaca atactaacaa atcgaacact gacgtaaaat cttaagaata 2040
aacgaatctt tgttctgata gagctcgttc aaaatggaaa tacactccac acatcttcct 2100
ctataacgca tgtcacaaat acagctttgc agagaagaaa cgaaataaaa taaagtccaa 2160
tctccccgtc cacgtctctc cccacccctt gcctacaccc ccaaaactca gtggcgaaag 2220
aagcccctaa aatgcattga catttttaa ggggaattgg ggctcgccgg gggcgggagc 2280
gctcttgtca cgttatcttc ccaggcgctg ctggagaaga ccctgcacac cgcgcatgtg 2340
tgagtgtgtg ctgtgtaaaa taagtcgtga acatttctgt cttttaaaac tgtgactcct 2400
tggactctag ccttctctgg gaggccggga ggctgcgcgc gggacggatt ttgcaggcgc 2460
acgcgtccca gcaggtcgca gcccgtgggt ccctcgctgt ccttcctgaa ccccgcttag 2520
gcgagactct agcgggtgac cctggctcct tccctgtcct ctctgccgtc cccttcttgt 2580
gcggtttcca tccgttcatt cattcgttcg acctctcatt cattccgaac ttcctcctgc 2640
tgcgtcttct ttcg 2654

<210> SEQ ID NO 197
<211> LENGTH: 527
<212> TYPE: DNA
<213> ORGANISM: Homo sapiens

<400> SEQUENCE: 197
cgtttcgggt gcggggtgct gatgctgctt ttttgttgtt cgtttgcgct cgcgctcgct 60
ctcgctctct ctctgcatcc ccctcacccc ctttctcgga gactgaacta agtgaaaagt 120
tgtttcaata atcgcagctc tctgctccgc cagggccgag ggaggcgggc ggaacacgga 180
gggtgttttg ttaaatgctc ccgtcgttcg caggggctgg gacttgataa aaggagacag 240
ttttctgaaa agatttgatt gaaatggcgt gtgccagggc tgatgggagc cagcgaggga 300
caaagcgccg agaatccatg gacactcgag caattatgcc tccacgctga aggtggatta 360
gcgcgctgga aagaagcata tgtttggccc ggggcgacac ttccccccgg ctgagcttag 420
agaatgggag cgcggagagc ggctggaccc ggaatatcaa ctatctgcga agcccccct 480 tctagcccaa ctccgccagc ctccccgccc ccgccgggga aaagtcg 527

<210> SEQ ID NO 198
<211> LENGTH: 1121
<212> TYPE: DNA
<213> ORGANISM: Homo sapiens

<400> SEQUENCE: 198
cgtccgaggg tgggtccaac gggcttcgag tgttcgggag ataatgcaca cttcgcagtg 60
gatcttctcg gggccccgag cgttgcccgc ccattaggtg gcgccggtcc cctcgaacag 120
gtcgctcaac aactcccgcc cagcagccgc ccttactgcg cgcgcgcaga cttcggcgtc 180
tacttccggt gtggcccagg cggggtccgc agaaccagct atgtcggcct acggcatgcc 240
catgtacaag agcggggacc tggtgtttgc caagttaaag ggctatgccc actggccggc 300
gaggatagag cacatgaccc agcccaaccg ctaccaggtg tttttcttcg ggacccacga 360
gacggccttc ctgagtccca aacgcctgtt cccgtacaag gagtgcaagg agaagttcgg 420
caagcccaac aagaggcgcg gcttcagcgc ggggctgtgg gaaatcgaga acaaccccac 480
ggtccaggcc tccgactgcc cattagcctc agagaagggc agcggagacg ggccttggcc 540
ggagcccgag gccgcagagg gcgacgagga caagccgacc cacgctggtg gcggcggcga 600
cgaattgggg aagccggacg acgacaagcc cactgaggag gagaaggggc cgctgaagag 660
gagcgcgggg gacccgccgg aggacgcccc caaacgaccc aaggaggcag cccccgacca 720
agaggaggag gcggaggcgg agagggcggc ggaagcggag agggcggcgg cggcggcggc 780
ggcgacggcc gtcgacgagg agagtccgtt cctcgtggcg gtggagaacg gcagcgcccc 840
tagcgagccg ggcctggtct gcgagccgcc tcagccagag gaggaggagc tccgggagga 900
agaagtcgcg gacgaggagg cctcccagga gtggcatgcc gaggcaccgg gcggcggaga 960
tcgcgacagc ctgtagttac cagcgtttcc agaagagccc ctgccccgtt cctgctgcgg 1020
cctggccgtt cttggggaat ctgaccacgg cgtgcaaact gggactgcct ttccctctcc 1080
tcagcccgtc ctcctccaac ccgcgctcct ttgccctgcc g 1121

<210> SEQ ID NO 199
<211> LENGTH: 268
<212> TYPE: DNA
<213> ORGANISM: Homo sapiens

<400> SEQUENCE: 199
cgccgcccaa aagcttattg agttcctcat cattgcggat cgctagctgc aggtggcggg 60
gaataatgcg agttttttg ttatcgcgag acgcattgcc tgccagctca aggatttctg 120
ctgtgagata ctctaacact gccgccaaat acactggtgc gcctgcccct atccgctctg 180
catagtttcc cttacgaagc agacgatgga tccggcctac gggaaactgc aaacccgctc 240
tagaagagcg agacttagac ttggcgcg 268

<210> SEQ ID NO 200
<211> LENGTH: 873
<212> TYPE: DNA
<213> ORGANISM: Homo sapiens

<400> SEQUENCE: 200
cggctttatc gtaggagcgt cttcgcctcc cccgtttcca gtagaaaaga cagctttgct 60
cctttgaaag cgcagaccgc cgcacctcca gccccttctc cccggggaag taggccccgc 120
taagaatgtg ggaaggtggt ggggcggcga ctgaagtcgc ttccgattgg cgttgtccca 180
aggaagcctg cgcggattga tcggcggcag gcctccaata gagcctgcta ggcggattgg 240
ctgctacgcg gctgggccct gtttccggta cctaggcggg cagccatggt gaccggcgag 300
cggcatgcga cgccgcctct gtggcctgtg gaggcccgct tggcggcgct gcttcccgac 360
ctactggtct ttcggaagcc tcggggatgg gaacccgagc tcgccacggc ccagggcgtc 420
ctcctaggcg tccatgtgac gggtgagggc gacggccggc acttgcactt aagtctcctg 480
gcctgcggga gaggcggccg ttgggtctaa gcccctggag gcctcgacgg ttacaggcct 540
agcctcccgc gagctaaggc acagtttaac ttcgtgctgc ggcttcctta ggaaactttg 600
agtatcttcg ttttagcgtg ggaggacatc ttttgggatg aaccggctca gtccttgagc 660
tcaccccaaa gatgatgaaa ttgaaactca gaggaaagga tttttacagg accacgcccc 720
gggctttgaa cccgtttttc ccaaccccga gcattttcta ttaagcgttc tgtttcaatt 780
attttattcg ttcagttaat tcgttcttgg cgtcataagt atatgcccgc cgttgttctg 840
gccgtagcta tctagcagcc actccgcgag tcg 873

<210> SEQ ID NO 201
<211> LENGTH: 805
<212> TYPE: DNA
<213> ORGANISM: Homo sapiens

<400> SEQUENCE: 201
cgtccgaaca gaaatcgcag ccgcctcctg tgtgggcatc tttcacggaa atttctgccc 60
acgttcaatg cgtacgggtc tctagcactg aggctagctc aactcttcgg ggcaggagaa 120
gttgcgccca gccaggagga cgccagccgc ctccggggcc cggaccgcgc tcgccaaagc 180
ccttttccgg ctcgggcgag ggctgacgcg gccagacggc tccgctactc gcgggcgagg 240
cggactaggc ggacgaggcg gccgaggcgg gcgaggtggg agaggcgggc gaggtgggag 300
aggcggccga ggcgggcgag gcgcggggcg cgcggcgggc caggctgggg accgggaagc 360
ccgcggagcc tcgcttttaa gcggaatggt ctgggacagc cccaggtggt tgccagggga 420
agggaggaag ggaaggttct gctgagacgt cgaggttgga aataaaaact tcggaaaggc 480
gaagcggatt tagaaaagga gggaagtcga ggcgggcgaa gcgggccatg gagattgcta 540
agaggaaaag ttggagagaa aaggaaggaa gagaagcaga ctcccgggtg gcgggcgcgg 600
gccgctaggt cagacgaaag gtggagggat gcagaggctc cccaaagagc cgagaaagac 660
acgcgacccc tccggatcgg gacagctcct gaaagcccgg cgcagagccg cctcgaagat 720
cctaagagtg ggcgactcac aggcgcggcc ggcaagctcc tgggggactc gggctcggac 780
gagcgcccac aggcagcgcc tggcg 805

<210> SEQ ID NO 202
<211> LENGTH: 554
<212> TYPE: DNA
<213> ORGANISM: Homo sapiens

<400> SEQUENCE: 202
cggcgccgtt ttggaaaccc atctcggagc gccccactgc ctccgcggga aggtccgacg 60
cacccggctg tccctgaggg aggcaggatg gagcaagggc aggacactgg aggtggtgcc 120
cagcaactcc ggcgcgcgct tgcttcccag gctggaaacc ttggcccagg ctcaacctgt 180
ctgagctgga ccagtccagg ccacgcgcct tggagccctg ctaaccaaca gggacagccg 240
cgaccctagg tcgtgcgaac acctggggtc ccggatctcc gcttgcctgc catcatcccc 300
caggctgctt ggctgctggc tcatctgccc gcaccgtccg ccccgccgac tgagctcccc 360
acaaagcaca cagaggcgca gagccagcgc tgttggagtc ttttattgtg ttctgtcacc 420
gaggtcgcag ccccgagcca ggtggttggt taccagccaa gcgagcgagt gcgcccgctc 480
ttcggggctc ctgggtgcca cccggaggtg tcctgttggt tgcgctgatt agagccgtcg 540
ccccctctcg ggcg 554

<210> SEQ ID NO 203
<211> LENGTH: 369
<212> TYPE: DNA
<213> ORGANISM: Homo sapiens

<400> SEQUENCE: 203
cgccttttgt gccgggctgt ggctcgctat cgacatctcg tccgttacca aggctgggtt 60
tcctactgat ttccctcctc ctctgctttc acaggctcgc gcggccggac attgtgggtg 120
tgcgtgctgg atttctcccg gatgctctcc gactaacatg gatgtcccac cattccttgc 180
agtggaaggt tgttccttgg cgcagtgagt gaagaacatg cagcgattgc taatgggttt 240
gggaagcgga gactccttcc tctctctatg accatgccgt gatcgtgtct gcggtcacca 300
ctcgacgcat cctcatttct acccgaaccc aggagccgaa cgctagatcg gggaagtggg 360
tgccgtgcg 369

<210> SEQ ID NO 204
<211> LENGTH: 4868
<212> TYPE: DNA
<213> ORGANISM: Homo sapiens

<400> SEQUENCE: 204

```
cgccgagttc gagaaagcgc tacgccgccg gtcgggctag ctccacaagc ggctgtacaa     60
gttggctgtc aaaaaacgct gatttctcct cctgtcacct aataaacccc tacgcgctta    120
tggcctcgtc ccacaatccc ccaatctcgt cccaattcga aaaaccgagg aggagggaat    180
aaactgagag ataaagatcc ccccatcttg ctctttcccc gggaccccag ccttggtcgc    240
ggcgccccac taaggaggac acaggctctg gtgtgtgtgg tgtgcgagac cccgagctcg    300
aggccgagcc aaggctgggc agaaagttgc aatcacgtgc tgtcggagcc cactggagcg    360
cacagcccgc tccccctggg acgcccaggc ggaggacctg ctgcgccctc ccagggctcg    420
ggggactcca gcattcactt gcacgcacag gcgaactctg attgaaagcc cgggatgaca    480
ccgagtctgg agaaagaggg accgggggt gggctggcgg aattgcagag cgccggccac    540
agctcccctc cccgcgaacg tcgagcggag ggcgggaggt gtaacctctg acctctggcc    600
gggtccacgc cctgaggagg gactggcaag ctcttgttcg acaagttcaa gctgccgaga    660
gagcttaaat agaattaatc tcttagagat cggggatcat cgctccctcg gcatgcgctc    720
tcccagcgcc gcgcacagag caaggcgcga gagagctcag gaatcgcggg aaggcaagcg    780
gaatggggag ggggtagggg atgagggcct ctcttcacta ttcctccgcc cggagagcgg    840
gagcccgcaa cgcccgccga ggacgagcgg cgggagggaa cgctctgccc tccagccgcc    900
ccggtgcaga taatggaggc gacaagagat tcgctcagcg tcggatgggc cagctctgct    960
tggggaagct ggcggcatcc tcccctcggc tggtgcccaa acccactgcg cgaaggccga   1020
aggaacgcgg aacctccaga agaccccatc ctcagccctg actttccgta gatatgtgca   1080
aaatgagtaa attactcacc tcgggccaga tccaagtttt acccaacaga aggggcaccg   1140
gaccaagaat gaaccaactc acatggccat gtccggcgcg cacaatcaca cgccagcaca   1200
cagccaccca atttcttccg cgaatctatc tggcactctg gagagagggg gaaaagcgtt   1260
ttgagaaagc cccgtcaccc ctccccttcc ttcttgccgt gaaatatacg aattcatttt   1320
tattacgagc cgcaccgtcc tcaccatcac gcacgcacag agccacactc ccatattcac   1380
actttctaac tcgtaagctc cgacagcgcc tgcattttct ttgggagccg cttggaggtt   1440
cattaatatc attagcattt aacccccctcc ctcttcccat cccctccccg cacatggctg   1500
acgtcagacc ccgccaggag ttgggggaaa agctaagtgg gccagggacg ccctattccc   1560
ctccccgcgg ctgcctgtca gagcgcttct ggagatatta caggggaccc agcccgcagc   1620
gacaggcaca aagtcacggg gtaatgaact tcggggaccc ttcgccgctg cgtgcgcggc   1680
tctccccgga aacccggacc tggccgcctc ttccctcgga agatttccca gcaatctagt   1740
tttcccactc tgcgcttggg ttccggcagc gcggagcccg tctgcctctg agactgcggt   1800
agtgttttcc ttctttcctt gggagaccag cggtcggcag agattgccca cactctgcat   1860
gcctatgtag agggagagat cgaagactga gtgacaggaa tggggaaaaa gagggatttc   1920
gctccgtagg aaggccattt tcgtgtctcc atctctgtct ttcaacatcc ctctcttgct   1980
gttcttcctt cttcctcagt cttcctgtcc atctctccat ctgtctgtcc atgtgtgtgt   2040
ccatatcaag cagcattccc agcagctgcg gttttgcaag agccgggaag aaacttaagg   2100
```

atgcttaaat ttccactgtt ggacgaattc tgagcgccca gggagcagcg cagcgcgcga 2160
ctgacaccca cctgtcccgc ccaggagcct tgcaggctgg agggcagctg gagagcggcg 2220
gcgcccggcg gcgaggcggg cgctgccggc cgggactcgg gcagcgccca ccaaccgctc 2280
cgccccggga cagccagcat gagcaagcca gccggatcaa caagtgggta cctctcgggc 2340
cgccgtgggg cctaggcgcg cagcctgggg cgagcgagcg gggaggctgg gggaggtcct 2400
gcctggagcg ctgcgaatct gagcccctga gagggattcc agcgggcgtg tgcgttcggc 2460
ccagacctgt agaccgtgag ttggagcatt tcgtggagag gggagagccg tttcgttgcc 2520
tctggattgc ttgatccccc ctgtctggtg cggtgagaag gttacgaccc gcgcagccca 2580
ccagtcggat gagttgtctc catttagccg ccaggtgctg gatgggggg ccatgggggc 2640
gggaactggg ccgcagctcc aggcggtagc acaataacac actcgctcaa aactccgagc 2700
tccagcgcgc aaaagcaact ctgtgcaaag cggattttga atggaatgct ttgcaccccg 2760
tttctagcta tttcaaataa tcctgcaaac tgggaagcag aaacaattta aaagtcacat 2820
tttccttaat cctaaatccg cgtaggtcat aactggggaa tttaaagtat ggcgaaccac 2880
tctagcaaag agaggaccaa atccctaatc ccaaggactt ttcgagccgg agcccagcag 2940
aggcaggagt gcgcggcctg ctccctccgt gcgcttctct ccttcctcga acttccttag 3000
ctgccggctc tccgaacgcc aggccgcagc tgacctctca ccaccccgag actcacgagc 3060
gcagggctaa gtgtgtgtgc gagggcattt gcttgcaccc tgcctgcgga acccaagaat 3120
gtgcaggccc gagccagcgt tgagcaggcg cggtcacggt gctcagatct cccgggggca 3180
tttcagttcc cgccatccag tggcccacgg ctgcgggctc cagggtctga ggctggggac 3240
taccgttgcc gccgcagtcc ccatatcccg aagttgcctt gctgcttgtg ttgttttcgc 3300
agatagcatt tttggcgctc tgtgcgttcc ttccctcccc ctcccccttt cactcgccct 3360
cattgtcctg agtctttgaa agttgggaga atcggagata cttctgagga ctggtaatga 3420
agtctcactt aagtgggatg caattcccgc cctcctaccc ccctccaaga aggaggttgt 3480
gttttcattt tgttttgctt tgggtgctga cctttaaaaa attagagcaa aatgaacgtg 3540
aacaaaaaga aaaggagaaa tgtttcgagc tggggcagag ggagcagaga aggagccctc 3600
accgcggccg gaatgcagag cggaccctgg cccaggactg ggtttccctt taggctcggg 3660
cctaccctgg ccctcgctgt tggaatctcc aggaggtaaa gcgacctcga tttttgttgc 3720
ccgcattccc gggcgtgagt gtccttccca ggaggctcag gaggccgttt ctgttgcatt 3780
ctgagcctcc gttgcaaaaa ctgaagcccg tgggtctcgg caggcctcct agctcgctcg 3840
ccccgggaca ggccctcgcc tacacccctg gaagtaagga gccccgggct ctttcgtcct 3900
tttcggggtg tggagcccct ggggcccttg aaaggtgagg cctcagaggc gagggagggg 3960
tgagcgggga gctctgcccg cctgcggctg cgccccccgct gtggactagg aggcaggcca 4020
accctccgga ctttggggga aaaaccacag cgggctcctt gcggaaactt tggccgttct 4080
aacttgccaa gagcctgagt gaggccttgg aagcctccag ccccggctca ggtcgggacg 4140
cggctgctga gctttctcag gcccgcagga cagcggcccc cgccggtggc gccgctgcat 4200
ttaggccctt tccagaccgg tggcggcagc caacccgaga cttgcgtccc tcgggcccgg 4260
ggcagctagg aggtcggcgc gcagcgggcc gggtcaggac tgggtcgagc agacagagct 4320
gcagcccccg ccttgcccgg cttctcgcgg ctggagagca gagcgatgtc acccggagcc 4380
ccgcctgggt ggtaacgaga ccctggccag tcacccctgc agcccagact aacttctttc 4440
aacagcctct gatggtaatt acagtaatcg aagctgccat atatctttag gcaattatga 4500
cacacaaaaa gccccgaggg gaccccctgg cgagggaagt taagaacggt tttccagctt 4560
caggaaactc cggctcgcct cacgtcggag ctcgctcggc ttgctaaatg agaggagctt 4620
tgcaacgggg tcaaccagct tgtctcgtga ccccaagtca ccttaacgtg gctgggtggc 4680
ggagtctgag gcacaggccc gctatgcccc ggaattttcg cgtccctccc tcctgggccc 4740
cgccccagcc cggttgcctg tttctaatct gccccgggag ccgcggctca gaggtctgct 4800
cagaggcagg actcgcactg gtggtggcct agagggcaac agtccggaag ctcgggcggg 4860
ggaatccg 4868

<210> SEQ ID NO 205
<211> LENGTH: 497
<212> TYPE: DNA
<213> ORGANISM: Homo sapiens

<400> SEQUENCE: 205
cgcggtacct gagctccgtg gaaggcctgg actcctcgga tccgctgcgg gtgcggcttg 60
tgtctcatct cagcacttgc gccacccagc gggaggcggc ggccatgaca tcctccatgg 120
cccaccacca tcatccgctc cacccgcatc actgggccgc cgccttccac cacctgcccg 180
cagccctgct ccagcccaac ggcctccatg cctcagagtc aaccccttgt cgcctctcca 240
caacttcaga agtgcctcct gcccacggct ctgctctcct cacggccacg tttgcccatg 300
cggattcagc cctccgaatg ccatccacgg gcagcgtcgc cccctgcgtg ccacctctct 360
ccacctctct cttgtccctc tctgccaccg tccacgccgc agccgcagca gccaccgcgg 420
ctgcacacag cttccctctg tccttcgcgg gggcattccc catgcttccc ccaaacgcag 480
cagcagcagt ggccgcg 497

<210> SEQ ID NO 206
<211> LENGTH: 3450
<212> TYPE: DNA
<213> ORGANISM: Homo sapiens

<400> SEQUENCE: 206
cgtcgcctcc cgttcaagca gcgtcccttc ccacaacccc cgtgcagaag gcgcagcgcg 60 gcccccctcct cgctggtccc agacctggcg ggctcctcac acctacctgg ccccctccgt 120
tgagcttgtt ggtgagcttg actttgctga aggagacggg agccttcatc cagtgggccc 180
cgaagttggg cgagtcgggg tggatgtaga cgcagctggg cgcctgcggc tccggcttgc 240
cccccggcac ccattccccg ttcacgtact tccagcggtg gttgtccgcc gccacgaagt 300
ccagcaggaa ggagtacatg gcgttggggt ccaggccaga cacgttcacc ttcagcaccg 360
gaaacatcct cctggaaaac acggggcggg cgcaggagga ccccgacact gaccaggtag 420
gccggaggca gaagctgggc acagaggcct cagttatttc ggggcacaga ggagccccct 480
ggggaacgtc cgagggtgac tcccaagctc cccccttcccc gagccctgcc aggtccaggt 540
ggcctcctca ccatctccac ggcctcggga gggaggggag gagaggacct ggcgaagggt 600
ttcagtgcag gaggccacat cccgcgggga caggcgggga ccagggcgcg cctcgcgggt 660
cccgggatgc ctccgaggtc gggacaccga agtgcgcgtt cctcctcccc aagcttccgc 720
ggagaaagcc ccagaagagg ggcttgtaga aatgcactcg agggagttaa ccagagcggg 780
aacaaacaca aagccctcct ccaggagaaa aagggttcga cctccgggaa cttgccaggt 840
cccccaggct gcccaggcgc tggagagcgc ggcgcgcgcg ggctccggac gcgcacccac 900

```
ctgccgttct tggtcacgat catctcattg gtgagctcct tgaagcgcag ccacagctcg    960
ctctcctcca ggcccacgcg cagttcgcgc tctgtggggt cgcccttctc gctgcccgcc   1020
tgcagctcat tctccacggc gctcagcagg tggtccactc ggtactgcag gctctttccc   1080
gcgctctcgg tgccagggga gctcatcctc ccgtccggct cccctccccg ccgtccccga   1140
agcccagact cgctacctga gatccacctt ccctgctctt ggccgccgcc cttccgagaa   1200
aaggggcccc ttggaccgag acctgcgacg gctcccgggt cccgggtccc ggcacagacc   1260
cgggaggagg gcgcggacca agacttgggg ggaggggacg ggggcagagg ggtggggaga   1320
agttattcca cttgaactcc ccaaggctct actagtgtag gtctctgggg accgaaattc   1380
agtgccctcc ccataaatag agccgcggcg gcagcgctgg ggtgctcggc ggattgggcc   1440
gcgcacgctt tgaagtgccg ggcagcctcc cattggccga gagcggccat atcagaccca   1500
gccgggcggg tctgggaggc cgggggccaa caatgggctc ccgcacgcct gtttcatgta   1560
aatccggggc cccagccctg cgagccccgg cccagcccct acacccccgc ccttctccaa   1620
atgtttgcac ctccatcaaa gcggcggggc aagccccgga ggaaggtaag ctggacgccc   1680
cggcctgccc cagcccgccc cagcccgccc cagcccgcac ttccgcgagg ggctgcccgg   1740
cagcctgcga tgctccctga ttcccgcgcg gggtcctcct cgctttccca gcgcgcccgg   1800
atcccgcagc cgcgccaggc tggaacgttc gcgcggcctc acctgtcccc gctccaggcg   1860
cgcctccctc ccctcccagg gacgagcgca tttggccggg ctttgggatg cgccgcgctc   1920
gtctcgccgc agtagtagtg ctgttctcgc gcctccgatg cctcaactct ccagtctggc   1980
agtttccggt gcacctgtcc ccacacgtcc ctcgcccacg gagccccagg cggcgttacg   2040
cacacccagg atcgtggatc agcctgcccc ggcgtcgggt gtccccgcgg ctctcaccat   2100
ctggaaaagg aaggtccgcg cgcagagagg gaaatggacg gaaataagca aaagcaaaac   2160
aaccccttct gagaagtgtc ctcctcgctc tcttataaaa acaggacttg ttgccgaggt   2220
cagcgcgcgc atcgagtgtg ccaggcgtgt gcgtggtttc tgctgtgtca ttgctttcac   2280
ggaaggtggg agaaggtcgg ggctggcggg gtggtccgga ctagtgggac tcggggcgct   2340
ttccccgccc ggcccagcgc caagcggtgt cggcagcggt tgttttatta cctttcggtg   2400
agaacttacg cgaggagagc gaaggagagg tgacaatgag caggaaatag ttcagtgggg   2460
tctctttaaa cagtaacatt cctcctaaaa cgggagccca ggaagggggga aggaggcaga   2520
agctccccct tccaaggcct ggctttgcgc ttctgcacac ctcgcccatt cgctggacga   2580
gggcctgcct cgggtagcag cctctgtttc ccggtctcct gagcgggcac cccagcccca   2640
acccctctag agaaagcctg cgcatcgggt ggggcagcga gttcagagga gtcttgcgcc   2700
ctagcaaggg ggctttcccg cggacatggt atctgcgccc cgcgctaagt ctcccctgcc   2760
ccctgccccc tgcccctcgc ccctcgccca gccgggctcg ctccggggtc gggaattgct   2820
ggggaagccg aaggagggat ccccgcccgg gactcgaggg atcgacccgc ctcgcggtat   2880
gcggagggct gccaggagcc agtcccgggg aagggtgcct gccgcccgtg ggggacaggg   2940
ctccttctct cccttctcca acttacaccg acgagtcagg aagccggagc gtctagtccc   3000
tgtccgcatt tctcagtgtc ttttgatgtc tgggatgcat ggatattccc agggggctga   3060
cccgaggtgg ggaagtttcc ttctagaaag aggcaccaaa aggacctcat ttgctcctga   3120
cgccggaccc tcctgacacg ccttcactgg ctcatcgggt cctgggcttt gggggagagc   3180
gtggtgcgtg ttactctcct tactccgggt attaaaatgt ctaagaggtc atcgctttgg   3240
cccaaggcct cccgaggata agataaaagg gaaaagtgga ggggaggtga aggaggaacg   3300
```

agggtgggtc ccaggcaatt gagggcctcg gaaccctagg cacgggagcg aaacctctcc 3360
tgcggcttca gggcaaagga gtcccgaagg ctggatccct cccctgcgct cggacggcgt 3420
cgcggccgct tttcccacag tcgggaagcg 3450

<210> SEQ ID NO 207
<211> LENGTH: 349
<212> TYPE: DNA
<213> ORGANISM: Homo sapiens

<400> SEQUENCE: 207
cgcggccggg ttgatctcca acacggcaat cttcccgcca aagagggagg ccagcaagca 60
cagcacctgc agggacgcgg tttcaacatc gttagcgaca ccacccagta aaagcagacg 120
aaacgtgcat ccgcacacgt atcctaacag ctgcttcatt ctcatagcag cgacatcgcc 180
ctgtcactcc taaaacgttt ttacacacaa aatcccgttt actcagccag tcgttacagg 240
atcactctga agaaagaaga aatcagaggc acgtctcata gacagggagg gccgcgtctc 300
aggactgacc ttttgatccg cagtgcggtt cctcagggca cacgatccg 349

<210> SEQ ID NO 208
<211> LENGTH: 470
<212> TYPE: DNA
<213> ORGANISM: Homo sapiens

<400> SEQUENCE: 208
cgcatacgag tccaggggct gctacaaagc gcggcgacgt ctccgcggcg agctggccac 60
tccatggtcc cggcgcagac actggggcag gcgccggctc tgtcgtcgag gcgctcacag 120
gcaggcacac gtgagctcct ggaggacagg gagagcggcc gccccgcccc tgcggagcac 180
aggacgcttc ctgccacccc tgcagagcat gggacgcttc ctgccatggt gccgtggcaa 240
tgggtggcac ctgcctgtgg ccccttctca gaaggacgtt ttaaacgcgt gaggtctgat 300
gcacagccac agggagacac agacgagcag atgtgggcat ccgagtattt acaaggtctg 360
gtggctcctg cagccgcgac acgggctgag cgcaagtgat gtgtgaggtg tccccaacag 420
atggcacggg gagcgcccac acccgccacc gcggggtctg cggaagctcg 470

<210> SEQ ID NO 209
<211> LENGTH: 385
<212> TYPE: DNA
<213> ORGANISM: Homo sapiens

<400> SEQUENCE: 209
cgcttctaaa cccaatacgc ttttctggag tcctcggaac agctggccgg ggcttttagc 60
acacgggacg ggaccttcgc ctttgcctgt tttttttcg accaggagaa gcaggtgcga 120
gagtctgggg cttaggaggt ggaaggcggg gaaagagaat ccactaggtc ctcgtgtaga 180
gaacaacagt cgctccttag atattactcc aggacggaaa cctgattgca aaccgctgtt 240
ccttcgaaac ttgcaaaacc cggaacagaa aactcccgcc cagccaattt tagctctcgc 300
tgaactctcc cgcctgcgtt acgtttgcac agcaactctt tgtaaatgtc cgagtcctct 360
cggaggaaag atcgttaggg cgacg 385

<210> SEQ ID NO 210
<211> LENGTH: 2949
<212> TYPE: DNA
<213> ORGANISM: Homo sapiens

<400> SEQUENCE: 210
cgagagccgc gtccccgcgg tcgcgtggat ttagaaaaag gctggcttta ccatgactta 60
tgtgcagctt gcgcatccag ggtagatct ggggttgggc gggcggcgcc gggctcggct 120
cgctctgcgc actcgcctgc tcgctgctgg caggggcgtc ctcctcggct ccggacgccg 180
tgccaacccc ctctctgctg ctgatgtggg tgctgccggc gtcggccgag gcgccgctgg 240
agttgcttag ggagtttttc ccgccgtggt ggctgtcgct gccgggcgag ggggccacgg 300
cggagcaggg cagcggatcg ggctgaggag agtgcgtgga cgtggccggc tggctgtacc 360
tgggctcggc gggcgccgcg ctggcgctgg cagcgtagct gcgggcgcgc tctccggagc 420
caaagtggcc ggagcccgag cggccgacgc tgagatccat gccattgtag ccgtagccgt 480
acctgccgga gtgcatgctc gccgagtccc tgaattgctc gctcacggaa ctatgatctc 540
cataattatg caactggtag tccgggccat ttggatagcg accgcaaaat gagtttacaa 600
aataagagct catttgtttt ttgatatgtg tgcttgattt gtggctcgcg gtcgtttgtg 660
cgtctatagc acccttgcac aatttatgat gaattatgga aatgactggg acatgtactt 720
ggttccctcc tacgtaggca cccaaatatg gggtacgact tcgaatcacg tgcttttgtt 780
gtccagtcgt aaatcctgcc tgatgacctc tagaggtaaa ctcgtgcact aatagggag 840
ttgggtggag gcgagggggg tggcgcgcgc gccccgggcg cgtgcccgcc gccagttgcc 900
gccgttcagc cggactcgag cgccacccgc tggaggcagg gctcatcgcc cagcttccga 960
ccgggggctg caagggccgg ggtcgaattg aggttacagc ccattatggc aaaattattg 1020
catttccctc gcagttccat taggatgtac caattgttag gccgtcagct gccgatcgcg 1080
cgcccggcga ggatgcagag gattgggggg aggtggtgac ttgcatttta tttacaacaa 1140
ctttatttcc cccgttttgc agcccctctt atttttgtgt cgaggttggg gtcggtactg 1200
accgtcctgc cagcagctct gaattttgaa aatacagata tcaccttcgg ggaaggggga 1260
aagccattta gccaattgga gaaataaatc ctgcccgcag cagcagcagc tacaattacg 1320
gctctgtttt tgcgagcgca tgagggacag tgtccctgcc gctcttaaat gacaggcgtc 1380
tattaaagat agcttttgtg tagtgtttct ccaaggcgag gtcaaattcc atacactttt 1440
ataaccgtag tcgatttttc tttcgtgtga atatggtttt cgtgtcatta gtttgcgatt 1500
tgatttgctt acgtatccag cctggaaaat cttcatcaca gggtccggtt cctcgagcca 1560
gccgggcccc aagtcggagg gttctccttg aacccagcga gtgggcccag gctccctgca 1620
gccacagagg ctgcctgggg tctggggatc cgtggggcgg gttactgggg tcttgcttag 1680
acctccagga gtaaaatgag ggcgataatg gaagcattcc ttggcagtgc ctagtatctc 1740
tgtagttatt ttccacggct ccgaaagact caagtaaatc acaaatatag ctgagaggca 1800
agtggagtct ccccgctgga ggcccggcgt tgcaggcgcc cctggcacgt ctggaagcca 1860
ggactctggc ggctcccatg gccctgggcc cctcgttggg tcctgaacgc tgctgtggcg 1920
gcgacgcggg cgctatcgga ggctgggagc gggaatccgg agccgggagc ctaccccggg 1980
ctgtaatgtt ccacccgcgc ccaggttaac tcgcctcggc tgaggctgct tctcttccac 2040
tgacggttgc acacgcggga ccgagagact gggctctgtt ggggccccct ttgttcctcg 2100
agcttccttc ctgttctggg aggcggcttg ggaggccgcg acaaggccgg gctccagctc 2160
ttagaccccc tctttccact ggccagagat gatttgatga tgcccttcgg gacttactgg 2220
cgagggactt aggcagagac gcccagacac gaaacggggc tcggcccagg gctctttcct 2280
ccccagcagc cccgcgtccc gaggtcgggg agctcagaga cactagcaca ggagccccag 2340
acgcattcag ggcgcacccc agaactccgg agccggtttg ggcatccttg tggagcggga 2400
ctgggtgtgt gcagtgcgcc ccgctccacc gctggtattg gctgtgtgtg aggttttgtt 2460
ttgttttgtt ttgttttgtt ttgttttgtt ttgttttgtt ttgtaagaaa taaatgcaca 2520
gacgcttgca aagctccggg ctcccctgaa gctgcggaag cccccagatg ggagcaggcg 2580
gggagaaaag ttggggaaca ggcgagggca agggggcaaa gccgaaggag gttgcagcgc 2640
tggcctggtc cctgcccagg catctactcg cccgcctttg cctctgagtc ctccccgctg 2700
ggctgcgtgg aattgatgag cttgttttcc tttttccact tcatgcggcg gttctggaac 2760
cagatcttga tctggcgctc ggtgaggcag agcgcgttgg cgatctcgat gcggcggcgc 2820
cgtgtcaggt agcggttgaa gtggaactcc ttctccagct ccagtgtctg gtagcgcgtg 2880
taggtctggc ggcctcggcg cccatggctc ccatacacag cacctacgag cagaaacggc 2940
cgggcgccg 2949

<210> SEQ ID NO 211
<211> LENGTH: 2547
<212> TYPE: DNA
<213> ORGANISM: Homo sapiens

<400> SEQUENCE: 211
cggagctggg caagccgtca gggcgcccta aggccgctga tcacgtctgt ggcttatttg 60
aataatctgt catggggacc cttgtggccc gggtcgcccg cagcctcatc ttggcaggat 120
ttacgccgcc actggccgaa ggcaagaagt ggaaggaatc ggccgtctcc cccagcgtcc 180
cagctccggc tgccctggct gccgccgctc acggacaatc tagttgtaca aaaggctctc 240
tgggctgcac tgctttcgaa gaacggccca aagtatctcg gtcctgggcc tgggcagcca 300
aggagagggg cggccagtct tggctcgtcc cgaagtgccc gccccgcccc ctctcgctgc 360
agcagccgcc tcctctcccg tagccctgcg ggccgctctt cactgctctc cagacttggg 420
gccctatctg aggcgtccca aacaccaact tctggctcct ggccccaact cgagaggctt 480
ccagcgagga cgaaggcagg ctcgagagaa acctggcggg ccagcagatc cgggaggccg 540
gcgtggaggc ggcggcggat ttgaagggag gagacactta ctgggatcga tggggggctt 600
gtctccgccg ctctcattct cagcattgtt ttcagagaag gcgccttcgc tgggttgttt 660
ttctctatca actggaggag aaccacaagc atagtcagtc agggacaaag tgtgagtgtc 720
aagcgtggga cagtcacccc ttctggccga cagcggttca ggtttaatgc cataaggccg 780
gctggagggc aagcccgcga aggagagcgc accgggcgtg ggctccagcc aggagcgcat 840
gtacctgccg tccggcgccg ccgccgccac gggcgcctgg gggtgcacgt aggggtggtg 900
gtgatggtgg tggtacaccg cagcgggtac agcgttggcg cccgccgcgt gcactgggtt 960
ccacgaggcg ccaaacaccg tcgccttgga ctggaagctg cacgggctga agtcggggtg 1020
ctcggccagc gtcgccgcct gccggggagg ctggcccagg gtccccggcg catagcggcc 1080
aacgctcagc tcatccgcgg cgtcggcgcc cagcaggaac gagtccacgt agtagttgcc 1140
cagggcccca gtggtggcca tcaccgtgcc cagcgcctgg cccgcccggc ccgacccacg 1200
gaaattatga aactgcagat ttcatgtaac aacttggtgg caccgggggg gaagtacagt 1260
cacctaataa gttgccggcg cccgcgcccc cattggccgt gcgcgtcacg tgcccgtcca 1320
gcagaacaat aacgcgtaaa tcactccgca cgctattaat ggtccgatgt tttgcagtca 1380
taatttttat agcaaaagcc atatgttttt atgtaaaggg atcgtgccgc tctacgatgg 1440

```
ggtttgtttt aattgtggcc aacgacgatt aaaagatcaa atctagcctt gtctctgtac   1500
tctcccgtct cccccccat acacacactt cttaagcgga ctattttata tcacaattaa   1560
tcacgccatc aagaaggcgc gggtcccgcg tgcgagtgcg gccagcggag cccctcacat   1620
aaaattagac aataattgaa gccataaaaa agcagccaaa tcgcattgtc gctctactgt   1680
atttaaatct atatttatga tatttcataa ggagttattg tttcagaagc cacacaggct   1740
ggcgggaagt cggaaacgac caacagattc gtttgcctcg ccgtggctcc cagctgtaaa   1800
aatttacgag gacttggaaa ggttagactg ttgtgtttgg ttggcgagct ccctgtaaat   1860
aatccctgcg gtccccggga gaggcgagtt tacccgcggc cgccctcgaa aagtcaaatt   1920
caacgcagga tccgtcccaa acggagccgc cgccggccct accagggcac tccaggcagg   1980
gaccggccgc tcagggagta ccgcgggtgt aggtccccac agctacccgc ctggagcgag   2040
gggcgcccgg gcaaccctta aattcgcctt tgctacgagg accccacgga ggagctggcc   2100
aggagggagc ggccagccgc caccagggcg aaggttttga gggcctggtt ggttgtgcgg   2160
cgcgctcggt ccccggccct cgaccccacg cacacgcgcg cccagcccgc ctttctcatc   2220
agctggcaat caggattccc aggcgcaggc ggctggcgac ccagccctgt gctccagcct   2280
cagaggctct aaccatgagc gctgcaagcc tggttgcgct ccgtgaatcc cagctgggga   2340
aaaaactaca agtggcatga atggaaggca agttcggttt gggaaaaggc agcctcgcct   2400
aagagacccc gcagctccgg aacctgggag gcccgcaccg atgtggcctg tcccggggcc   2460
gcgtgagcct ttcagggctc cttcctccct ttccagctgc tactccgggc ctcgccttgg   2520
ttacctacgg ggcccggaga ctcggcg                                       2547
```

<210> SEQ ID NO 212
<211> LENGTH: 1292
<212> TYPE: DNA
<213> ORGANISM: Homo sapiens

<400> SEQUENCE: 212

```
cggcggcagc gatcggccct gaccatagag gcggccgtgg cgcggaggac ttgaccttta     60
cggcacgaga ggagggcgct ggctgagccg cagggagggg gacgctgctc tctccagcct    120
cctccaccca atagcagtcc gctcgaccca cgccagctgc gcgctcaccc cctttccccc    180
tccattttgt gcagtgtccg cagacccgcg gccggaaaca aagcccccag ccctgctctc    240
accacccttc ttgcaagctg ctgtcgccaa ccccccagac cagaggctca gagctaacgc    300
taagcccctt aaggccctct ccagggccct cttctctcgc cagccgccct cagccagctc    360
ctgaccccag ccgccctcag ccagctcctg ggtaccactc tgggtgccaa ccgggacctg    420
ccggtgccac ggtcccgtgc gccgggtccc ggcctcgggc tgcgggcggc ttcggggcct    480
acagcccagc ggcgcggagc gtggcagagg cgcggggcgc agcgcagccc gaggctgcct    540
cccgcccggg cggacggcgc ggccgctggg gtgcacagcg tagccccgcg tgcccggctc    600
gctctccgtt ccctcggata gctcccaccg ctcggctccg ggctcagaaa gcggaagtat    660
ttggtagaga aaaacacggt ttcttttcag ctcgtctcaa aatccctttt agagaaaatg    720
ctcctgtcaa gttttatttc ccgttgcaaa ccaccttcca cgctgccaag aattaagacc    780
gggagagatt aaatacccga ttattctcct ggggagggcg gggcggggcc gggaagtggg    840
cacccacacc aaacattcct tgaagtaggc ttgtcctgat ccagccgcgc ccggggagcc    900
ccacgaaggc ccgcgcggcc tgcggtgacg tcagcctgca gttgcggggc cactcacccg    960
cacagacacg gcccttgctg ttccgcgccg ggacctccgc cagccgtcct gccgcagccc   1020
```

cgactggccc gcgtgccgtc agagggaggc ccgctttaca ccggcctgag cctccatttt 1080
gagtaggggg ttcttgtaga agcgtggagg gtttggggcc gcgcctctgt ccccgagggg 1140
cgcgacatca ggtagctctc cgagttcaca ccccagtacc tgggggagga cctatgtcgc 1200
cgcataaccg cccgcagagg tttggaaatc tctgagaccc gttgtaatta tttctgccca 1260
gtggatccgg ctcttcagcg tcacgagagc cg 1292

<210> SEQ ID NO 213
<211> LENGTH: 1297
<212> TYPE: DNA
<213> ORGANISM: Homo sapiens

<400> SEQUENCE: 213
cggtttccgg cttttggaca atggtccctc gcttaacgaa tgctaacgaa tgctccctta 60
gctgggagct gcagggaccg gtcccggcag gtctaaccaa ccgtccgcag gcgccgtggt 120
cgagagcaga gccgagacgg cggggcaggg tgccaagcgg agggcacagc ctggcagcca 180
ccgttggcgg caggagagaa tgggagaagg gagacccgct tctcagcaca agggcatctg 240
tctactcccg aacatggccg gagattcctg tccacagcct ccctccagct ctttctggta 300
gacactttaa aagcgacatt aacgggcttc ggtgcctttg gattcctaaa ttaggtttac 360
ggaaaaggaa agacttccca agaacagtga gaagaggaac tgcagcccct ccaaggccgc 420
tgcggcgcgt tcccggggcg cgccgagagc agcgcgcggc tccgtgcccc gtggggagcg 480
cgcggcgcgg ccttggattt caccgcgagt cgggagggcg ggtctgagcc ttgcctccca 540
ggatccttcc gacgaacacc ccgcgggttt tagtttatcg agccaaagtg gtcccggaga 600
agcgctccct cgcagccaag ctgcaagaag tggccgggaa cctacaggcc tcgggccgac 660
ccaggaagcc tccgcaccag aaagctcgag gagcccttac ccaagtcttg ctcgaagggc 720
aaagcaaaga gccagcaccc ctgagtgtca ctgaagttcc tggatggggt gtgagtgcgc 780
gcgttccgtc cgagacctca gtctcgccca gctatagagc cgataaaggg atgtcttgtg 840
ggcgtaaggc gcttcgcgcc catctccaag gccgatgtgg tcaggaggtg aggggaaatg 900
tccttctggc agaagcccgc ggtgctgcga cgttgacccg cctggcctca ggctcagggc 960
ggcgggcagc ccagggcaca tgtagtttca gcagccgcgc tacgtgggcg ggggacccca 1020
ggccacccca cgtgtccgcc ctgggcctcc tccgggtccc aaggcgcggc gcctccaggc 1080
cttgtagcgt cttccccggg tccccgcgcg ccaggccccg cagcctgctc acaggacagc 1140
cctcggggct gcgaccctct cgctcctccc cgcggccact cgctccccgt tcatccccca 1200
cgagctcact accgcaggga ccggccctca gagccccggg cctcctcccg gcagtggaag 1260
aatcagcgtg ctaacattgt gtgcaaaact cgcagcg 1297

<210> SEQ ID NO 214
<211> LENGTH: 417
<212> TYPE: DNA
<213> ORGANISM: Homo sapiens

<400> SEQUENCE: 214
cgagggcctt gcccgccctc ctcctcccac ccgcaagggt tggcccgcgt tcccctgcgg 60
gcgagacaaa gaagcaggag ccaggacccg gctggcgcct aacccggcgc cggggccttg 120
agcccctgag gtgtgcgcct tcctgcaagg ccccaaagaa cccgagtttt tgccccttgc 180
tgaagggttg gaagtgcggg ctggactagt gcaaacaaga gtgactccaa ccgccttact 240
tcagctcatt accgtcaccc atgaaaacgg aatgaaggac tgggaagcca atctgccgcg 300
ttcaattgga gagaaatgac tgtcggaaga ggccctgcgg taaatagcct ctgagccgcg 360
aactctatgc gccgtggccg gtggcagagg ccacacctgg cagccactcg tggcgcg 417

<210> SEQ ID NO 215
<211> LENGTH: 423
<212> TYPE: DNA
<213> ORGANISM: Homo sapiens

<400> SEQUENCE: 215
cggaaatcat cggcgactgc tgttatgagg agtacaagga tcgcaggcga gagaacgccg 60
agcgcctgca ggacgacgcg gataccgaca ccgctgggga gagcgccttg cccaccatga 120
ctgcaaggca gagggtctgg agggccttcg agaaccccca caccagcacg atggccctgg 180
tgttctacta tgtcacgggg tttttcattg ccgtctctgt catcgcgaat gtggtggaaa 240
cagtgccgtg cggatcaagc ccaggtcaca ttaaagaact gccctgtgga gagcggtatg 300
ctgtggcctt cttctgcttg gacacggcct gcgtcatgat cttcacagtt gagtatttgc 360
ttcgcctggc tgcagcgcct agtcgttacc gttttgtgcg tagtgtcatg agtatcatcg 420
acg 423

<210> SEQ ID NO 216
<211> LENGTH: 454
<212> TYPE: DNA
<213> ORGANISM: Homo sapiens

<400> SEQUENCE: 216
cgtcctccga cgcgagatgg ctgtgtgcca ccgactgtcc aaatgccctg ccaatgccat 60
cgtgaagcat ccgtgtgaag gaaaaagtcc accttaccgt gcgctgtggc atcgatcagg 120
cgtgtggaca gtcgcaggca cgcagcggtc tcccaacatc agggcacacc gcgatcaggt 180
gtgtggacag tcgcaggcac gcagcggtcc tgcagcagca gggcgcaccg cgatcaggtg 240
tgtggacagt tgcaggcacg cagcggtctc ccagcatcag ggcacaccgc gatcaggtgt 300
gtggacagtc gcaggcacga agcggtcctg cagcagcagg gcgcaccgcg atcaggtgtg 360
tggacagttg caggcacgca gcggtctccc agcgtcaggg cgcaccgcga tcaggtgtgt 420
ggacagtcgg tgggcacgca gcggtctccc agcg 454

<210> SEQ ID NO 217
<211> LENGTH: 273
<212> TYPE: DNA
<213> ORGANISM: Homo sapiens

<400> SEQUENCE: 217
cgcaggaggg ctcggcctgg gaccccctct gcgggcctgc ggctttagcc agcagaaaga 60
ggggcgtcag tcctatcccc aaagttccgc ctcgggaaag agccctgagc tctgaactcc 120
gacgaaaaaa ggaagggctc tgttccggac cgggtggggt ttgggaaggg tagagccggc 180
ctcgggtgcc cttcttacag ggcctgtctc ccgctgcgtg caccaagtgc tttgaaagtt 240
tttcgcggat taaaacgaat aaaaaacctcg tcg 273

<210> SEQ ID NO 218
<211> LENGTH: 3360
<212> TYPE: DNA
<213> ORGANISM: Homo sapiens

<400> SEQUENCE: 218
cgagggtgaa ggatcgccgc aaggcaccgc acctcccgct gcagcccatc ccgcactact 60
aggagaagcc ggcgtaggag cgccgcctgt gtccttggct gtggggagga cgtcagatgg 120
caccccgcca gacactaagc cccaagcccc tggcttgttg ctaagaaaat tcactgcccg 180
gtccagactc agccctttc gccctttaag ggtcgcgcgt gggaggcagc tctgagaccc 240
cgggtagcgc tggagccaca gatttcctcc gagaaaagaa aggccgggat agcttcccgc 300
tcgcccaagc ccagattttc cactctccag gaaggccttg caggtccctg ccgcaggcct 360
tggcttcgcg cctctctcgc tcgcccccca cgaagatgat tgccggtttc aaaccgggag 420
cagggagtct gcttccttct ccgctgagtc cgaaggatcg cagattggag cgtgctccgg 480
agaccgcttt tccgcagcgc cggcctccga gatccccagc accccttcag ccttaagttc 540
ccacgtttcg ggtccgtggc gccaattctg ctaagtagca ggctaggaat tgggggaagt 600
cggagaagaa accctaagtg tgtcgccccc agcttccggg atgcaggccc gccggggtct 660
agaggggcgg ctgccgtgcg tccagcctgt gcgcaggcct ttcgccgctc ggcgccccag 720
gcagcctcag tttcctttcc tctgtttgcg ccccagtgaa cctccgcacc tctcattcag 780
ggaagagaat tccccgcgca gccgcgctcg tttcttcctc tgggattttc ctgagaatcc 840
ccaggagttg gccacgatcc catggggggt ttccttctac ccagccccgc gtcctggcct 900
cgtccttaac ccccgggttg ccttcactca ggctgggaat ccacgattga tttcctacta 960
cggaagcggg tggcgttccc agcctgcttt cggagcagca cgggtttcgt gcagggtgtt 1020
atcccgaccc cttcccccat ccctctaatc tggcttgaga agcccgtgct ggagagaaaa 1080
acgcggcctt aaaaaaaaaa aaaagtttaa ccgaaagcgt gagagccacc cgccggctgt 1140
tatctggggc tgaaggctgc ggtaatcgat gggttatttt tacgcggtaa tagggccctg 1200
tgattgctct attaaccttt agacctgtct gagggactct ccggctcgca gccccgctgc 1260
gctggggcct ccaggctctg acgccgactc ccaactcagg cctgacacat tcccctcccc 1320
cataccctgg aagagccccc tccatgaaga agctcccctg gaccgcctgg ctccccagcc 1380
cttgccacgt cccttggatt ggtgcagagc cgccgcaggc tgcagaaaaa agggggaaag 1440
attagaagag aggaggccac aggagatggg aagtgtcgcc aggaagggat gcagattgca 1500
taaatacata aaattgaggc tgaggcctgg gctcccgacc atctccctgg gattttggga 1560
aggcaaaagg gaggcttcgg tctctacgct ctgattttag gaggcagtct gggtgtctcc 1620
tgaacctcca aggaatccgg ggctgggagg atccccacta cccctgccca ggaactagca 1680
tccagccggg caccccgggt gacccagtgc cccacacaag atcgagagtt gagcccaaga 1740
ggtcaccttc ttctctactg gccccgcccc tcgcccgccg ctgcgggatg aggaccacag 1800
gaaggggggg cggggaggga gaaagggaac tcattaataa agctgaccct gggcaccaca 1860
gcgaacccaa tcgacctccg gctgggttgc gggtgattcc ccgctccctg gcggtagcac 1920
ttgggcattt tccgcggaga ccccagagcc tggactttgc ctgctggggg agctttccgc 1980
acagtcccgc agcctgcgcc cagcggaggt gtagccgggg ccgcgcaccc ccgccccgcc 2040
cttgcacgtg actcccacag gccagtcagc gccctagggc cgagttgctg ggccggggac 2100
ccgagccgcg agctggggac ttggaggcgg ccggcgcagg ggccgcgaga ggcttcgtcg 2160
ccgctgcagc tccgggggct cccaggggag cgtgcgcgga acctccaggc ccagcaggta 2220
gggctttttt cttccctttc tttgctcctt cccgcggtcc cccaaactcg gagcttctcc 2280
gcctttgctt gtctggaggt agagaggtag ctagtgggag gaaaagagac gtgcgctact 2340
cacttcaccg aaattgccca acccctgctc tgcttttgac tttgccttag caacttcttt 2400
aagtcaaagt aagacttggg ggcaaaacag agaaatattg gaagcgcctt tggattcttt 2460
ccgtgtgaac ttgaacgctt tcaatccctg tccccgtgtg cacattctcc aacccttgtt 2520
tgcatatcgc aggccggggc ctgggtggtg atggtggccg cgtgaagtta ccgggactga 2580
cgggcccggg acaggctgca cggcagctcg cacatggagg gaagtagacg gaggcttgtc 2640
gcccaccagc gactccgggg acgcagggtg gcagtgccag gcagctccgc tgggcctcag 2700
gggcccccgg gagccgctct gaggtgcgga gaggctgctg agtggcggaa ctattcatgc 2760
cctttctggc cggcctcctc gccctcgggg ctggggtcca gggactgaat gctcctctgg 2820
aagctcacca ccccacctgc ccgcgctgct tctacctgaa actggccaag ggcccgagcc 2880
cggaccggag ccgtgacttc cctccgccgg ccacggggct gcccggatcc gccgggttat 2940
gtcgcttggc tttgggctca ggggtcaccg tgggcagagg ggggtgccgg ggtcgcggac 3000
tgccaccagg ttgaggaaag gaggggcctt ttggctgggg aaagagcgtg gtgggggacc 3060
cgcggccgat ggaatccctg gggcagcgcg gcccgcaccg tggaggttgg ggaagcgcct 3120
cggggaagtg tttcctgtgt tcccagaaaa ggaagacaac cgagagcagg tttcaggctt 3180
ttaaagaaag cctggggtgt ggaggtgatg ctccgcacac gtctgtgtct cctcccctgc 3240
tgcggccggc ttggttgtgc cggctagcgt gcgaccgtcc tcctcgctgc aggccgagag 3300
cggaggcgta aacccaggcc agcgaggagt gtcctataaa gggacgggga cttttcggcg 3360

<210> SEQ ID NO 219
<211> LENGTH: 357
<212> TYPE: DNA
<213> ORGANISM: Homo sapiens

<400> SEQUENCE: 219
cgtttgctcc gccgtcagtc cataaccagg cgctactaag gcctccaggc tcggtgcgca 60
gagccgggag cgctcctcca gctccaggtt gggggagtcg gggtgggagg aggttcggga 120
aatcgactga tttagaggct gggggtgagt agcctcgatt tatcatccct gatggtgaga 180
gtggaaaagt gtcgcgagag tgacagatgg aatctttagt gcttcgcaag agggagttat 240
taggccgcgg ggtttggggg gtactttccg cttactttgt cattctccac aaagtccacg 300
aaggccgtcc gctcgatctc caccggctgg ccctgcctgt catagagcgc caggacg 357

<210> SEQ ID NO 220
<211> LENGTH: 2355
<212> TYPE: DNA
<213> ORGANISM: Homo sapiens

<400> SEQUENCE: 220
cgctcggtat gttcatctaa acgaccttgg gcaagtacgt cgattccaag gtacaatcag 60
ccctcccaga cggcttttcg agtctcccta accccggtgg gagaggacgc ggcgccagag 120
cccagctccg gctagttttc ccgggggcag gtgtagcctt gggcgcgggg ccgggggagg 180
ggcaaggggc gggcgtgggg ttggactggg acgtgggact cggaccacgg cctgggcgtg 240
ggcctaacga cgcgggaccg gcccgccctc gccgctccat tggccacatc tgtgcagaaa 300
aggccccgcg gcccaggggc gcccgcagtg tcactaggcc ggctgggggc cctgggtacg 360
ctgtagacca gaccgcgaca ggccagaaca cgggcggcgg cttcgggccg ggagacccgc 420
gcagccctcg gggcatctca gtgcctcact ccccaccccc tcccccgggt cgggggaggc 480

```
ggcgcgtccg gcggagggtt gaggggagcg gggcaggcct ggagcgccat gagcagcccg    540

gatgcgggat acgccagtga cgaccagagc cagacccaga gcgcgctgcc cgcggtgatg    600

gccgggctgg gcccctgccc ctgggccgag tcgctgagcc ccatcgggga catgaaggtg    660

aagggcgagg cgccggcgaa cagcggagca ccggccgggg ccgcgggccg agccaagggc    720

gagtcccgta tccggcggcc gatgaacgct ttcatggtgt gggctaagga cgagcgcaag    780

cggctggcgc agcagaatcc agacctgcac aacgccgagt tgagcaagat gctgggtgag    840

tccgagtcgc agacccaggc ggccgggcgc gctggcgcga atcgctaggc cgatttctta    900

aaccccaaac tgttctttgc gagcctgacg cccaaaacca ggggtgtgta gcggccacgt    960

cctttcttaa ggctctgggt tcccttcccg cttcccgccc tccgaccctc caaagcagct   1020

ttccgccttg ctctccggct cccggattcc ccaggtggcc gggggcgcgg gtccaacggc   1080

tctgggaagg cgacttcccg gcacctccgg gcggcgcgag agcacccttg gccctgaact   1140

gggccggttg tgtccatccc tcgacccctt ccctagttag gtgtcctttt ctgtttttcg   1200

aacgaccggg tgatgggtga gcggaaagcc gcttccagga gaccaaaaga aaggggtgcc   1260

tttagaggac gggtgttccc caagggctcg gactcaggag tcccagatct ccctctttaa   1320

cttcaccccg gttgcgcaat tcaaagtctg aggggggagg tgcgtccagg tggggccagg   1380

tggggcctgg agcgggagcg cagccgataa gccctgcgcc cctctccccc ttccttccac   1440

tgtgcaggca agtcgtggaa ggcgctgacg ctggcggaga agcggccctt cgtggaggag   1500

gcagagcggc tgcgcgtgca gcacatgcag gaccacccca actacaagta ccggccgcgg   1560

cggcgcaagc aggtgaagcg gctgaagcgg gtggagggcg gcttcctgca cggcctggct   1620

gagccgcagg cggccgcgct gggccccgag ggcggccgcg tggccatgga cggcctgggc   1680

ctccagttcc ccgagcaggg cttccccgcc ggcccgccgc tgctgcctcc gcacatgggc   1740

ggccactacc gcgactgcca gagtctgggc gcgcctccgc tcgacggcta cccgttgccc   1800

acgcccgaca cgtccccgct ggacggcgtg gaccccgacc cggctttctt cgccgccccg   1860

atgcccgggg actgcccggc ggccggcacc tacagctacg cgcaggtctc ggactacgct   1920

ggcccccegg agcctcccgc cggtcccatg cacccccgac tcggcccaga gcccgcgggt   1980

ccctcgattc cgggcctcct ggcgccaccc agcgcccttc acgtgtacta cggcgcgatg   2040

ggctcgcccg gggcgggcgg cgggcgcggc ttccagatgc agccgcaaca ccagcaccag   2100

caccagcacc agcaccaccc cccgggcccc ggacagccgt cgccccctcc ggaggcactg   2160

ccctgccggg acggcacgga ccccagtcag cccgccgagc tcctcgggga ggtggaccgc   2220

acggaatttg aacagtatct gcacttcgtg tgcaagcctg agatgggcct cccctaccag   2280

gggcatgact ccggtgtgaa tctccccgac agccacgggg ccatttcctc ggtggtgtcc   2340

gacgccagct ccgcg                                                    2355
```

```
<210> SEQ ID NO 221
<211> LENGTH: 881
<212> TYPE: DNA
<213> ORGANISM: Homo sapiens

<400> SEQUENCE: 221

cggggcaagg gcgcgttccc tatcgcagga tcacttgcta tggtaagccg cccaccctgc     60

gcgctcctcc gcgcggggaa gaacctgcgc ggcaggacgt ggtgttggag ttggggcgcc    120

cggagcgtgg agtggggaga cctgatgcag agagtctgga gtcggagctg gggtgctgc    180
```

aggtaggagc aggagcgggg cggagaggga ggcccgaaga agaccccaca caggttggcg 240
cagcggggct tggggaggct tcagcccaga agtggagagg gttgacagac gcctgcctga 300
ttagaaaaag ccgggagctt gggaaggaga cgggattgaa gaagccaccc ggcagggagg 360
ccgaacggcc cagagctctc cgggtaaaac ccgcctgcgg tgatctggga agtgtgtctc 420
cacctagccc tgcgagcagc ggccttcctc ccgcccgtta gaagggcgct gtgctggagt 480
acgaacccgg cccagagaag ccactcgccc ttctttgtca cttaaaaccc tgtcccgacg 540
cggatctcac gtctagacct ctgtctttaa agcggatgta gagcgcgttc taaccgttcc 600
ctaaccattg tgtcaccgcg aaaggccggg gctgtgtgga accgtcccgc acgtgtgcga 660
tgaatctggc tccgctgaga acggatccgt gggctgtctg gcgcgggctg gggcagcagc 720
cgagagttag tctacagagc tagggcccga gggtggacct gcgtccgcgt ctcgtcacga 780
aaggaagctc tttttggaga ggcaaaacgt ggtcgcccag atccggcgca gctgtagccg 840
tgggcgctgt gcagtgacag ccacacccgc cacctgtcac g 881

<210> SEQ ID NO 222
<211> LENGTH: 236
<212> TYPE: DNA
<213> ORGANISM: Homo sapiens

<400> SEQUENCE: 222
cggccgcccc gatgcacagc gtccccatgc aggagaagaa gcccacagtc accatgttct 60
ccatagacac gtcagtgttg cgcatgccac agcacttctt aatgcgcttc agcaggtagc 120
gcacgaaggt gttcatgcgc tcgcccaggc tctggaacat gaccagtgtc agcgggatgc 180
ccagcacggc gtagaacatg cagaaggcct tgcccgcatc ggtgccaggt gcagcg 236

<210> SEQ ID NO 223
<211> LENGTH: 288
<212> TYPE: DNA
<213> ORGANISM: Homo sapiens

<400> SEQUENCE: 223
cgctgaccac ctgccgcagg gccgcagccc tcccagaccg acagagtgcc accagctccc 60
gccgcttgtc agcgccaacg tattcggaga gcagcaggtc ccagagtgac acgctacacc 120
ccttaaacct ccctgtgctg acgggcacct tcatggccct cagagccacc gcggtgtggt 180
cgtccacctc aagcactgtg tctgagggca gtggcaacag caacaatccg gtctcggagt 240
cgcacacgca gcgctccctg agctgctggt aggtcacctg gtcccgcg 288

<210> SEQ ID NO 224
<211> LENGTH: 3747
<212> TYPE: DNA
<213> ORGANISM: Homo sapiens

<400> SEQUENCE: 224
cgtgtgccct tcggcgggcg gctgtagctg tagctgttgt gacggctacg gcggaggctg 60
cggccgcgcg gggaatggag ccggaccgcg gagtcgtcac ctccaaggtg tttctagtgg 120
cctcctggaa gatgatcccg cgcccacctt gccggcgtgt tcgcgggccc ctgcccactg 180 cccccccctct ttctttaggt ctggcttttg aggatcccgg agtcttgcag ctcccgccat 240
tccgcagata acctccgcac acttaattgt gacccgcggg gtggtcggag aagctccgca 300
cgcgtcctca gtgggaaagt gtcccctctc agcactgccc ccttcagtcc ccctgcattt 360
ctggaaagtc aggcaaggcc caggtaggct gccagtgcac tctcagcctt gactgagcac 420

-continued

```
ctttcgggcc tctggtgagc cccgagagcc aggtttggct cggcagagcg ggcttgggct    480

gcgcaagcaa tgcgcatcgt ggccgcctgc accctgggaa ctaggcctgt ccagtgggca    540

gcatcctcat ttttgaaaag gcccttctaa acccaccggc ctcgcctaac gccgtttggt    600

gctgcatccg agcggcctca cgcggtcccc tggaagggcc actcccagcg ggagggcggg    660

gcccgggacc tgcgctggcc acgcagggtc tcaagctgac cggaagaccc ggcttttggc    720

ctgtgtccaa tagccccaga agagaggggt ctggagcctt cctcccacgc gtagtgacgc    780

tcaggtgtcc tcgggttgtt agtcttgacc caggagagtg caagacaggc ccaaggcctg    840

gggggattgc gttatgaatg tccaattcta aacacaaggt agagcacaga cagtacatcc    900

tcacggctgg attttaaccg tattttaata aacacattcg agggggtgtc agtttcccca    960

agctctgccc ccttccgcgg gcgggatcca tggtgtgtgc agtgtaagag tgcgcagaac   1020

gcgtgtgttc aagtgtgggc gtggcaggcg tcgtgtgctc gccccgcgca ctgtgcggat   1080

cgcccagaca gccttgacag gtttttgcag atgtttgggt gctacggtgt ggggaaaccc   1140

aggcaggagc gccaggccta attctcctgg actcttggtg agcggccgct actccacgag   1200

gggctagaag caaagggggc acgcgctttt ccccaggccg cctcttgctg ccgcagtggc   1260

tgagggcgct gatgacccct ccccgcttcc agcggacttg acccgcgggc tgacaaccca   1320

ccgcgacaag caggcggctg ggttcgcgcc gccgccccgg ggcccttggc tcaaatttca   1380

cctcgagtcc tgcagaccct gcgccactga attggggccc aggacgccct tggtgacact   1440

cgccttcttg ctgccacaac caccgtcata cccgcagccg gggctccctc cgctaaccac   1500

gcttggagac cccaatcggg gacagaggtg ggagtcagac ccccccctggc ctgcactgcc   1560

gtttccctcg attcttgcgg aaacaagact cccgcccaca cataaaaatg cagctcccgg   1620

ccaccgggcg ccggtggctc acgcctgtaa tcccaacacc ttgggaggcc gaggcgggcg   1680

gatcacttga ggtcaggagt tcgagagcag cctgaccgac tactaaaaat acaaaaatta   1740

gccaggagta gtggtgcatg cctgtaatcc cagctactcg ggaggctgag gcacaagaat   1800

cgtctgaacc cgggaagcgg agggaagcag cgagtcgaga tcgcgccact gcactccagc   1860

ctgggcgaca gaatgagatt ccgtctcaac aaataaatag aaataaaaat atgcagcccc   1920

ctccgctcca cttgaacttt aatgctgaac cggtttccca cgtatacgtg tatcgcaccg   1980

cattttgacg ctttgcatcg agtcgcatta atggcgcttt tgagaacgcg tcgtcgcgct   2040

ttacagagaa accctacggg cagcctgtgg aggggtaggg gatattcatt ggctttccct   2100

gctgggcccc gtccgccggg cgggttaggg tcgtggcagc ctgcccgcgc gccgctgact   2160

ctggaatttt gtccgggaaa ctggcgtagg gccctggctc tcccttcgcc ctccgcgcac   2220

acgcggacga ggccttagat ccacagcctt ttctaggccc tgcgcctttg aagctgggcc   2280

actgccaacc gctcgcgatt ctcaccttca acagtcgccc ccttacccct cccccacccg   2340

cctgccctcg ggagcgggtc gcctccactc caccacctgt ttaagttcct ccccctcggc   2400

gcccctccag tccccacccc ggccccggtc caaaaaacca gcaaacggaa cttttccaca   2460

gttgaaagcc gcggcccgcg aggccgggct gggaggggaa agcggggcgt gtctgggggg   2520

cggggccccg agcactccgg aagttgcccc gcccaggagg ctcctgggaa agtgaggaga   2580

gggcccgggc ctactttcgt cctggtgtgg cgcccctcag cctcccctcc tcccagttcc   2640

cgcgcctccg cagggcgcct cggcctggcc tccaggcaaa gttcgcgccc cctgttcctg   2700

gggtgtcggc cgcgcgggcc gtttcccttc attactcccg ggcccctgaa tccgaacgct   2760
```

ttcccagaag cgcgcaaatc cgcttgcttt ccccgcggct gggctttgtt cagggacagc 2820
aaaggaggag gcgggaggct ggtgaggttt tctggaaaag gggcttgtcc cgaggaggaa 2880
gtgccccaga tccctgagag ccaacgctct ggggagaaga aactttcctt ctcccttgaa 2940
tgttgctcag attacctaaa attatttttt cagcccttgt gttctaaagt cgcagggtaa 3000
aggttatctt aagacttaac atcagcgctg ctcatttgta cgttggtgga gacgtgcctt 3060
ttttcctttg cacttaaggt ggacagggtc tgcgacgctc ccttccagga cggtgtgggg 3120
aagcggccga cgtccccagc cggactcacg ccctcctact actgggcgtc ggctccgccg 3180
cgggcgctcc cgacagggag ctggagtcgg acgagcggct gcccccaggg cctccaggaa 3240
ccgcggccca gcggggagcg ccccaggcta gcgcttttcc agttcccttc gaaagcgcgg 3300
ggctgaggtc gcggcgctgg gccctcggat gaagccgtgc tgtagctaca cctgaacccc 3360
gcgaaaggct ggcgcggtcg tgtatccagg ctgggtctga ggaatccgca agcgggagag 3420
cgctaactcc taggcgtgag ccgctgctgg cttcgagagt tcgagaacat gaaggacctg 3480
gcttctcccg cccggtcggc ttagggccag cgaggtcaca ggccgttctg ctctccctgt 3540
ttgtccccaa aggcctcggc acgtggggat ctggagcagg cctcaggctg cgacccgtct 3600
cttcccctac caaaattatg tgggaacagc ggtccaggac cttcccctgt tcagcggtat 3660
ccccgggccg gtgaccccgg ggttcagtcg tctccccgac cccaagcggc ctctgctttc 3720
cacccctcgc cccggagggc ggcttcg 3747

<210> SEQ ID NO 225
<211> LENGTH: 335
<212> TYPE: DNA
<213> ORGANISM: Homo sapiens

<400> SEQUENCE: 225
cgcggccagt gaaatcccaa tcgtcttcca cgtggaaccc caggtccgca gttatgataa 60
cggatcacat cgctcctgcg gaaagtgcgc gcggtggagt gataattgga cctagcgtct 120
aaattcttgt tggaggacct cgttccagct gccagttaag cctctgggat ccgcagcgtc 180
tctaggaatt gagagagtgg ggaagttagg atccaggagg aggatggtgg gggctgagga 240
gtggaggagc agcgtgcatc tcatctcttg tcgccgggcg ggcgctcttt cgggtccagg 300
gcccttgcac ccccagcgtg gctccggagg cggcg 335

<210> SEQ ID NO 226
<211> LENGTH: 255
<212> TYPE: DNA
<213> ORGANISM: Homo sapiens

<400> SEQUENCE: 226
cgactatgca aacgcttgcc gctagccgca tccttctatc gccccccaac tcaagacccg 60
aaatggccaa ctcttcaccg agggggcgtc ccatcgctgc cttgccttgg cccgcccctt 120
cgccaagctc aatccctttt ccccagaaaa acctgtgcct gtcctcagac ccggccccac 180
ggctggaagt caaaacccac cccggagcca cgcggctgga gcacgttttt acacctgctc 240
ggccgcttaa ttacg 255

<210> SEQ ID NO 227
<211> LENGTH: 4206
<212> TYPE: DNA
<213> ORGANISM: Homo sapiens

<400> SEQUENCE: 227
cgctcacagg tcggaataat tcaagccttc cgctcccccg ccgagctggg gtagctgatc 60
actgagctga aactaaacgt tttaggtgga aaaaaagcgt ccgaaggcac cgtgaaatga 120
ttaaggaact aaagagcttc tcgccatgtg agatcatgtc ctgttctcgc caacatcaca 180
agatgtcccc agacacgccg cgcccccagc gcgccgcccc acactgccgg cccggagcga 240
ggaaagggta ggcgctgcgc ggccgggcct gctcagcgcg ccagacgtgg cggacccggc 300
ccggccggag tagagcggga agccgggaga gcagcagtgc tgctgccgcg ccgccccaga 360
cttttatagg ggttgggggg agggaaggaa ggcttcagcc tgcgccgggc gctagccagc 420
gcacctacgg gaaggggcag accgaagcgg agcccgggag cccgggtctt ccagccgcac 480
cttctattaa gacatgcgct tgggggtcgc ggccctctgc gctgtgcgcg gggcctgtga 540
catctccatg tgcaaacccc gctgcttaga cgagcgcagg ccgggttttt gtttttgaag 600
aaattaactg ctcggccaag caggtgcttt tgaaaggggt tgcaaaggct ggcagtgttg 660
ccaggcaccg aggcgacgtt ccggtttact ccgattcacc cctagggcgg cgcccgaccc 720
cagggttccc agccatccaa cccccacccc aatttgttgg ggtcctgact attgctgggc 780
ccctgaccct agggcagcgc cagatcccta aagcccccag gtcccatcca gtcttctagt 840
cccagaaccc ctccccacat caagttccat tctggcccag agcatggagg ttaagctgtg 900
aaatactgga gatgaaatcc gggcttccgc tttggagcac ccgggcagag cagaacatct 960
cagtagtttc tggagattgg cgggagttcc agacacctta ccccggccca taagtggaat 1020
cgcattgccc tcgagccctg agacgttgtg gagtcccaga gccccaggac ttgattccag 1080
agaggaaatc agatccacag agaccgagca gaggtgtggc atgtccagcc ctctctcttc 1140
gggccagact caagcctccc ctccctgttc ccctccccag ccttgagtta gttcagctgc 1200
tgggcctagc cactgaaagc ctgtggggcc ctgcagcggg gtggtcgcag gggaaaggtt 1260
ctccagggcg ggggagcgct ccgtaggagg actcctggcc cgccggacaa tggcagtttt 1320
ggagagtgaa tcgtcctcag caagagtgtt gtttgttttt tggagggggt ggtcacgagg 1380
ctgggtcgca acctaggggg aagagcctag agctcgagga aaggggggcc cccggcggca 1440
actggacatc acatatccac tgagcagatt tcgccacaat cggaaatgtg gctgtggatt 1500
cccgggcggc ccccccacca agtggtctgc gcagttcccc agcgccgcct cctccctgca 1560
gcctgcgggc ccgtgtccct accccgagat ttgatttttg gccatctccg agtgctcgac 1620
tctttccctc cgcagcccag ccccagccca ggcttcccgc cctcccgcct cgcccgcgcc 1680
gggaggcagc gcctgggagg agcggcctgt ccgcgcctgg agatcaaaag ccctcccgga 1740
attgacattt caccccgggc tgggggcggg gggtgttggt gttttgttgt tgttgttgtt 1800
tccatttaga gggcttgttt tgtttttgtt tgttttctgt gagttttcat ttttccatgg 1860
gatattcttt tgtttcgggt gttttgcgtg ttgttttttc gtgggattga ttttagcggg 1920
ttttgctctg taagtcctgg tctttggggt gagttttgat tttgtgtaat tttgtacttt 1980
gtccttgtag gctgtctttt tgtgtgtcgt ttgtaaggct tttccttctc cgcggtgttt 2040
agatgtgttt tgatttggtg tgagtgggtg tcgtctgtgt gtgtgttgcc ttagggaatt 2100
tcgtgttgtg tgtgttttgt ttccttcgat ttgaatttta ttttttgaa ctgtacgttt 2160
tggtggggga tcgggttata ttttcatgtg ttgtctttag tttttgtgtt tgtgagatgc 2220
gctggtgaga gtttgcgtgt gtattttggc ttttgtgggg ctttgggatt agggagggga 2280

```
catcagccgc tactccgttc ctgcccgcac ccatgaaggg cagaggatta ggccaagcat   2340

cacgaatcgt aggttcgccg tgctccgccg cttcgcgctc tggacgctcg agaccagcgg   2400

gaaacaaatg tggttcccga gggggcgccc gctggtcgtc aaaacctcgc gggcccggag   2460

gcgccgctgc tgggtcagaa tcgcagagcc cccctcgcgg ggtaccgagg cccagccgcc   2520

gtccccttgc ccaccctctc ccctgtgagt cggtctcccc ttgcgcctgg ccagcatgct   2580

tcggaccgtc cggactcccg cagcgttggc ccaaggggcg gctcccctcg gcggagcagg   2640

tgacgaacca cttcggagga cacggaattg acactgcggc cctagagata cgggacaagg   2700

ggccagaacg cggggagtct aggctcagat cggagtcggg atcccgggaa aatcccccat   2760

ctcccttgcc cgcagcccta gaatcccaga aacccaactc cgcgcagctt tcggtttgga   2820

gagcccgccc tggtttgcaa gcacagatac atgtgcccac acccgaacac acgcagacac   2880

cgccagagag cgagacagcg agcgggcgcc tccgtagcag cggcctgcgg ggcggaaccg   2940

gagctggcgc cgcctcaagg ggaaaccgaa ctgtagtgac cggaaatgtc cccaggacag   3000

aataagccat tccttctgtc cacgttgcca ggacttctcc agctcaacac accttggttt   3060

gtttaatgtt acacgaggga gaagatttag aggcagagac acatgctggc tcaatcggcg   3120

aggaaatacg agcagagtct aaacagaaag aaatatggaa cggggggaga ctagactgtg   3180

gggaaggcaa attggaggcc cagaaaaggg gctggtgcgg aagctcctcc aggcccctgg   3240

gcgctctggc attctgtgag aaggagaaag cagaagccga gaacagagag tgacaggaaa   3300

agaaaagaga cgcagaaggg gttggcctag gcacgctgcg agctgccctc cagctaagac   3360

gctgcgggca agggaggggg aggccgacat cgccaggcga ggggccaagg tcgggctctt   3420

taactcagcc aggaaacatc gttgggggct ccagggctcg tggagcccga actggggctc   3480

atttccggcc cgatgcccct cttccccaga cccctagccc ggaatccagc aaaggctggg   3540

ccatcgccgt ccgccactgg gcctccctct gtgcgagccc tgggagaagc ctcagggaac   3600

gactctggca ctggggctcg gccccggagc tagcgcagag cgtgggtggg agtcgacatc   3660

caggcaggag gcaaagaaga ggccccgccc taaagccgag ggcccagttc ttcgaaagcc   3720

tgtggccgga gctggactca caggattcgg ggtccgtaca gcgcgcacgt ggtaccgcat   3780

cttcggcagg cggcgcccct aatgcccagc cccgccctgc ttcgtttgcc gggcctgaac   3840

tgtgtcagca ttgagggtgg acgccgagtc gcggcgagtt ggtcccttgc ggtataaact   3900

tggggcttcc ctaggggcgg tgccgggatg gatgggggcg cctctccacc tgcaactccc   3960

ccagcgcaga gcgcaaaaag tgcacatcgc gggccagccg tcgcctcggg gtttcaggcg   4020

gcgcccgggg caaaaaggag ctgaggattg gtttgggtca aaacacccat ttcagttggc   4080

agtggggtcc tctgcgccta cagggcttcg agctccgggt gcgggctcac tggggcacca   4140

tgtgccagcg actcgccacc cggaaatact tgggttgcgc tagaatacgc aatgggtctg   4200

tgttcg                                                              4206
```

<210> SEQ ID NO 228
<211> LENGTH: 5770
<212> TYPE: DNA
<213> ORGANISM: Homo sapiens

<400> SEQUENCE: 228

```
cgggccgcca ccgccgcctc ggctcctccg tgacgtccgg gaagggtatc cccggcactc     60

aggaagtggt ggccgcgggc agctccgccc ccacgcgact cggggctggc cgagctgccg    120

ggtggtagaa ccgccgggcc ttccgcaggg cgggcgggga tcaccgtctc cccacctccg    180
```

```
tgcgcacaca catgcacggg cctcgcgccc cgctgtcgcc cgcgcctcgc cctgctcact    240
tctcacagcc cgcgccggac gaagagagcc gccagcgccc cccctctctc ccacggctcg    300
cacccactca ccccgacccc cggcgccgag cccggcccct cgtcgccggt caccagacct    360
ggtcgaaccg agtccaagat ggcgactccg cccccgcccc ctccgcactc ccggcggggt    420
cagggcgccc cctcacgcgg cgggctcgcg cccgagaccc ggctaaaaat agccaggccc    480
gactatattt ggttcggccg gatcctggcg cggccgcgcg ctccccgccc cgccccgccc    540
cgccccgcgc gccctgcccc gccccgcgcg gcgttgaatg gagaaggggc gggggtgacc    600
gaggggaacc tactccgcta tctgcggcgc gcgccggcgg cgggtcccgg ccaaccgccg    660
aatttagtaa catcgcctgc gtcaatcacg cgcctcgcgt gcgtcagcgc cgcgcggctc    720
caggtcctgc tcccccccctt caagcctttg aatggataca atgtagcagc gccctccttc    780
cttccgaggc tggattggaa cccgccgcag tgcagagact cggttgctct cggctgggtc    840
aactttcggg gcattctccc acgatcctct ccgcaccacc gtgtctgaat tggaagtgga    900
ggcgaagaaa gatatacatg ccatatttac ctatatgtag tttgttttca agtttctggt    960
cctagctcga accttcttcg attctgaaat gtgtgctgtc tacaaaggaa tcttgtatct   1020
cccctcggcg cagcgccccc cgcccccgcc acacacacac aaattgggac aggtcaaaca   1080
tataaaacgg tatttgtgat tcaagcggac cacatgggga ccactctatc tgcattgttt   1140
cactcaaata ttttctcctg tccaaaaatt catttctgaa agagactgcg ttcactcagc   1200
agcaaccttt gggactaggg gtctttaact ctgataaatt ttgttttcat caagaaattt   1260
acacttaaat ttatcatttc caggaagaaa ttgctctcct tcatacagtc acccaggctt   1320
tcggcacacc atttcatgac aaatgtgtcc gaggagacca aagcaaatcc cctagcgagg   1380
gactgactaa taagtcctgt tgattgattt cgaaatgttt aatttgggag atgtgggcgg   1440
agggcatcta caaccatcaa aaagtgaaag tgctagttga gagttccatt tctgacccgg   1500
tgccggggag gaggaatgat ttgcaatagt cagacccgct cagctgttca acacgtgtgt   1560
gtttgtttta cacacagagt agtttctgct gcagcgcgcg tgtgcatgat ggatgtgcac   1620
ttcgctgggt tataacgtgt ccagttaaga aacccacgcc gtacgtgtaa agaaatcaaa   1680
ccttatcccc ggaaccatct gcatccctgt gtgaaacacg cacccagtaa atgatgcggg   1740
gaggggggat tagcctgggc gcagaggacc ggagcaacgt aaacagcttt agaacctatg   1800
caagaggaaa gtgcagctgc acctcagggc gtcttcgggc tggtgccaga cgccttctgc   1860
accggctgcc aggtcactgg agctggtcag aagctggctg gcggagcctt ccctttcgga   1920
agagctgtcc tctcccttac ccccctcgcc ctggctccgt gcctcggggc agcctcggag   1980
gcgcgccagc agcactcctc caactctact ccacccgagc ctgacagctg ggcggtcccg   2040
cctgacccgt gggcaggccg ctgcaccctc ccgcagacgc acgccctggc gagcggttcc   2100
gctgcaaaaa gagaagcccc caggccgggg ccggccgtgc ggcggagttt ccattgtgcg   2160
gccgtgcgac tggccgagga acgcgcgcgc gcgcgcgcgc acacgaacac acacaccctc   2220
cctcgcacac gcggaaccgg ctgggccagg ggagggagga ggagggtgac gtagcgtccc   2280
atggcgtcac attgacgtct cgcattccag gcactctatg gagaggccgc tagggctcct   2340
gtggcataaa tgacgtgccg agagagcgag cgaacgcgca gccgggagag cggagtctcc   2400
tgcctcccgc cccccacccc tccagctcct gctcctcctc cgctccccat acacagacgc   2460
gctcacaccc gctccctcac tcgcacacac agacacaagc gcgcacacag gctccgcaca   2520
```

cacacttcgc tctcccgcgc gctcacaccc ctcttgccct gagcccttgc cggtgcagcg 2580
cggcgccgca gctggacgcc cctcccgggc tcactttgca acgctgacgg tgccggcagt 2640
ggccgtggag gtgggaacag cggcggcatc ctccccccctg gtcacagccc aagccaggac 2700
gcccgcggaa cctctcggct gtgctctccc atgagtcggg atcgcagcat cccccaccag 2760
ccgctcaccg cctccgggag ccgctgggct tgtacaccgc agcccttccg ggacagcagc 2820
tgtgactccc ccccagtgca gatttcggga cagctctcta gaaactcgct ctaaagacgg 2880
aaccgccaca gcactcaagt acgtatgaga ttcgcccagt taataagggg acttgctaaa 2940
aaagttggct tgctgggaag cgtcgctcct gaaattgaca actttgagtg tggggttccc 3000
tcccctgacc ttgccgcccg gctccggctt tgctagccca gcggcccgta ggttctgatc 3060
tgaaactttt cccctgtagt gggcccgcgg ggatctctgg agctcgtggg attcctcccc 3120
ccactcgaag aggcgaaaag cctctaacaa agaggaggac cgggatttgt gctatagcgg 3180
ctccagcgat gtaattcagg gtatttcggc tctagttgtc atggtaatga tgctctcggc 3240
ggcggcggcg gcggcggcag cggcagcggc agggagttgc agctccggtg atgaacggca 3300
gtaattttcc tgccttttaa gtaggattga aaataggagc tctggtgggt ccaagtaaat 3360
gttgctaatg gtggcaccga gctggttctc tggaaggaag cttaggaggg aagggcctag 3420
gcagcgacgg ccagagtttg cagacgcact cggaggacct caggaaagag ggcgtaattg 3480
taggaatgtg gcttattgta ttgaaatgag cctggggttc cactaggcac gtctgcctgt 3540
cgtcgctgac atgccggttt acacttttcc cttaggaggt aaatcgggtg taattggcga 3600
ctcccgcaca ctgacacgtg tggggacggt gtccctctcc tctggacgtt ggctcggtgt 3660
gggaaaggca tgctttttca cggacagaac tcgcgctttt ggagaagttg ctccgagtgt 3720
tttactctta gtagaaatga aagttctcgg tggtgagacg agagcggtca tgcgagcgca 3780
gcctgcggag actgacttcc aaaggcacct ctccaacctg ttggaagcct cggggcagtg 3840
gtgaggaaga acgcatttgt cccttgattt ccaaaaacgt tcttggagat tgccttttat 3900
ttatttatgc gtccggattc tccagaggga agagctgcga ggagttagta atcagaaatg 3960
tcgggctgtg atcccagggc cttgtggtgc tgggagagaa gaacagggag ccgtcattcc 4020
atcgcgagtc cagtgccgga tctccttttc ccacgaccgg gaaatatttt atagaatcaa 4080
gttagggaaa gaaaaagctg cctaacgtgg ctgatgggca caatgaatga agttacttta 4140
ttcgagttat tttcgctgaa caagatgctc gcagagttag tatcaaagcc tccttaggcc 4200
acagcaacct ccacgtccgc tccgcccccc accccccggc acccatccac ccctttgcct 4260
gggaccgtgc gctcacagaa attcttcccc gcggtttgtc tagtctccct cggtctttct 4320
gagaatctca gtctttccct ttctgtcagt ctctccctcg ctcctcttgc ccccgcccaa 4380
cctccgcccc cgctccccag ggttggaaac tccgcagagg agccccggtc acaatggtgc 4440
gtttcacggt ttcctccaca cacttcacca ccgggagggg aacacggggg tgttcctttc 4500
gtctgcccac gagaaagaaa ggggctttga cagaggtagt tatttcttcc taatttacaa 4560
ccccaaggct ctgtgctccc ggccccggcg gccgcaagca ggagcggcgg aacgtgtttc 4620
caggcactga ggctttgcct aggtaaccgg ccgcttgtgg ggtggagaga gcggcggggc 4680
gctgggctgg gctggaggaa aggctgtgtg ggtccctccc gcgaacgctg ggcgctcgag 4740
gggaactcct tcgttgggga gaggcggtcc ccgcccaccc gagttctgag gcctcctctc 4800
agagaacgac tccgcttgaa aggccctcag ggaatgcggg acgggaatgc gggcacccac 4860
tgaaggggcg ggtgggggat tgctggagac ccccattgaa gatgcgggga gacgggaagc 4920
acgtgctaca gccgtgggaa gatccgcttc tacccgcgct acatcgagcg caagctttcc 4980
gtccgagcag ctccagctgg ggctgggggt ggcaagggaa tcccccattt cctggtcgtc 5040
gagggtttcc tggacctggg agccccgagt ccctttctct cttcctgcag gcaagccccg 5100
ggctcagggg cgccaggaga tgaccctcgt ggccccgcgc acctcggagg tttttggttt 5160
ggtttgattt ggggtttttc ggtccctgtt cccactcttc gagctgcgcc caccccgggc 5220
aaagggggcg ctataggccg gagtttgggc acccagttcc ttccctgagg cctgctgagc 5280
tgcgctttca gctacaaagt ttcgctgagg ctgtgggctg agacgctggt cccggagctg 5340
cgctcggcgc cctcaggaat gtgcccccgc taggccgctg ggtggccagg agcctccaag 5400
ccgcccaccc tcgaagacac cgccctctgg gtgcagggga cctgcctccg ctcgtcccat 5460
cagccgctaa cgccgtccgc ttcgtcccct tgcttccagc gccagccttc tcatcgctgt 5520 gccctttgt ttgcttgacc cctggccctc gaaactcgcg gctaatagaa gcgaagctcc 5580
attagcattt agaatgaaaa gcgcagactt tcttaattcc tcggggcatt catgcattcg 5640
ttccggacct tgtgcatttc ctatgcaacg tgtaaaattt gtatttgagg ggtgggggcg 5700
ggcggagctg gaaaatggct tttttccgct ggtgaacact cactgacccc ccgtattcgg 5760
gcggagctcg 5770

<210> SEQ ID NO 229
<211> LENGTH: 582
<212> TYPE: DNA
<213> ORGANISM: Homo sapiens

<400> SEQUENCE: 229
cgctgttaga tttcgggtca atatccatca tcgctgttag actcggggcc gacatccgtc 60
atcgctgtta gactcggggt cgacacccat catcgccgtt ggactcgggg ctgatacccg 120
tcatcgctgt tagatgcggg gtcgatatcc atcatcgctg ttaaatttgg ggtcgatatc 180
cgtcatgact gttagatttg gggtcgatat tcctcatgac tgttagactc ggggctgata 240
tctgtcatga ctgttagact cggggccgat atctgtcatc actgttagac tcgggtcaat 300
acccgtcatc actgttacac tcggggccga tacccgtcac cgctgttgga ctcgggtcga 360
tacccgtcac cgctgttgga ctcgggttga tacccgtcac cgctgttgga ctcgggtcga 420
tacccgtcac cgctgttgga ctcgggtcga tacccgtcat cgctgttgga ctcgggtcga 480
tacccgtcat cgctgttgga ctccggtcga tatccgtcat cagtgttggg ctcaggtcga 540
tacccgtcat cagtgttgga ctcgggtcga tacccatcat cg 582

<210> SEQ ID NO 230
<211> LENGTH: 254
<212> TYPE: DNA
<213> ORGANISM: Homo sapiens

<400> SEQUENCE: 230
cgttagagca tagcgacatc acgtgcggtt tcttaatgtc cctggtggcg gatacgccga 60
gtcctcggaa ggacatctgg acaccacttt cagccacctc cttgcagggg cgacatccgc 120
caaagtcatc ctttattccg agtaataact ttaattcctt tctaacattt acacggcaaa 180
caggaatgca gtaaacgtcc acgtccgtcc cacggctggg ctgccgttcc gtttcctcca 240
cgaacgggta cgcg 254

<210> SEQ ID NO 231

<211> LENGTH: 14472
<212> TYPE: DNA
<213> ORGANISM: Homo sapiens

<400> SEQUENCE: 231
cgctcccaaa gccacgcgaa agtggaagcg cggggcctcg ggatgcccat ccagccggct 60
gcccgcgcgc tggccggggt tccaggactc cttcctgctc cgccgggctc tgcagcgccg 120
cctggtggac acgcggcgct ccgcccgggc tccagccgcc agccggcgcg ccggggatcc 180
cgcggctgtt cgggaaaaag ctggagagag tcgggggcg cgccttgggg aggggcattt 240
gtccctccga ggaggctcgc acctcggcct ggacacgcag cagatactgg cacccaccct 300
tcacttaccg cgcgcccggg gtgactcgga tccgtccaac acgtcgggga atcctttctg 360
tcctcacccc cgggcgcccc agcgccggaa cgctgctgcc tctgtgtagc tgctcccgga 420
aggagtttca tcaaactttt aaggggcttt ggttttgggt tgtgttgata aaataccaag 480
aaggggcatg aaggcacgaa cgtcccgggt tcgtctccct gctggtccca agcctgaatc 540
ccagggcggg ggaatgtcta ggtccttccg ggccggcaag gtgtggtcgc tcagggaccc 600
ctgtccgaag acgctaggga aaagaggcac agcctgtggg tcgcagtggc caggagcgcg 660
tggccgctgc tggtgagaga gtggtagacg cctggctttc aggtcctgag ctgcgggcac 720
cggagcgtgg gaccccggct gcagcaccgc cacgcgctcc cgccctccca cctgcagggc 780
gggggatgtc tgtccaagag gccggggcga caagcccgcc ggccaggatt ctcaaggaac 840
caggcccagc tcagcctctc tcggcgggac cagagtggga ccggggccgc ggcgtccgaa 900
gacgctgcgg gccaggggtc ctcctcggcg ccagctccgt ttcctggggt ctcgcgacgt 960
ccggacatca gggtcggggg tgtggagacg gcggcggagc cagagtcccc accaagtcag 1020
ttccaggagg cggcccgcgc gcttcccgca gtgtccggga ggtcgctggg ggtggctttg 1080
cgtgcaaccc gggtaaaggc cctgcagccg tgaggctggc gctgggagga gggtggaaaa 1140
tctcaaagtc accaatcccg gtgcaaatgg cggcaggggc cgcgggctgt cggacgcagg 1200
cgagaggcca aaggctgact tcgcgcggcc gtgagtcccc agaggcaaca ggggtacctg 1260
agcgccgagg ggatcccgag actcggagaa accggaagag cctgacccca gggagcggag 1320
agtttggggt gcgctctcag agctgtgact ccacggtccc ggaatccttg gaaagggcgc 1380
tctgggctca gagctcccaa ctagccggag gacctgggct agcgcccagg cctggagcgt 1440
ctgggagggg gcgctgggtc tcggcccccc tccccccaaa agggactgag actttttttct 1500 gcgtgcttcc ttcggcgctt cgggcagctc tgtcctgcgg cccaagctgg ggagaagaca 1560
gcggcccgcg ccacagggag ctgcgcccgg acccagactc ccgccgcgct tctgcagagc 1620
ggagccctag gtgcccacct ggtagcccca gaaaggccgg acctgggcgc cgggacgctc 1680
gcggggccgc acttggaggg gctttccggg tcctggccgg gcgggctctc ctgcggcgcg 1740
gaatggaata gagcgccggc tgcagagcca cccggacggg gaaaagcagc ggtggcgccg 1800
gccagccccg ggtcccgact ctggagggag gaaggagcgg gcgggtgggg gtgggggtga 1860
gggcgagggt tgcggggagc gtttagaagg ccctgggcag ccagaagaag aaaagaggac 1920
gcactctccc ctagggacca gagggtccct gcgtactccc cccaggcccg ggacacaggt 1980
tcccccagcg cccctccgcc tcccagtcta ttcggcttgc cccagcgcgc tgccccacgt 2040
ccccgaggcc ccggcccagg cccagccggc gagtcccggc ctgctccact ctgcacaaaa 2100
cgaaacccaa atgcccaaaa agctcaggag ggaaatttaa caaaaaccct gtcccccgcc 2160
ccacaccccc tttcactttt aacaagccag ctgccaagag aaaattgaaa taaaaacgaa 2220

```
atgatagata gcggaggaca ctattttcca aatggtgaaa tatcctctaa aaatatgttc   2280
cccaaggcca acttcgcggc tggtagcccc ttccgacgcc tttgcctccc agaaaatcac   2340
aacaaagcga tcggaaattc agccacggtc ccgggaagaa ggagtagcag tgaggccccg   2400
gaacccactg cggccgaaac tgccatgctc tctttaacca aaataaaaaa gataagaaga   2460
agaagtaaaa ccctttaata catcaaatat acggaatttt aatctttaaa gcgatacatt   2520
gtctattatt ttagtacatg acgtaaacct tgtccccttc tcagcgggtg gacttaaaaa   2580
ttaaaaatag ttaagtgttc cttttaaaga acaaaataag gcaaatgagg ttttggaata   2640
gaatttttc tttttctttt ttttttgtt gttttcttcc agaatacata caaaaaaata   2700
cccattctct tcgatggtat acaccttaaa aataattgca atttgaaatc agagctgaca   2760
aattgtgact ttttttttca tttttttgt aacaaacatg catgtaaatt tgtgtttcaa   2820
tcagacatta aataacgtac aatacaatca tagcaatttt aaagtaacat taaagagaag   2880
acctctagtt ctgtggcggt tttgctttta tttataatct acaagggatg ggagggtttg   2940
ttttccacat ttttaccctc aagttttaaa atttttccca cctccttttt acctacagag   3000
ctcaaactaa ataatgcact tttgaaccac cggtccgctt ggagctaaca taaataaata   3060
ccagtgtcca ccgatgcagt cctcagatga acactttctc aattattttt tcctttttt   3120
ttctataaaa agtcaaatga tattttttca acttttataa agtttgggtg gggaggtgaa   3180
agtggggaga aggggagtgt cccaccgggt ctcggtcgct gctgtcgggt agatagatac   3240
ggtatacatt tctttccttt cgtggcccga gtcctcccca cgcgcgggtg tcagcagcct   3300
gggccgtgat cccgcctctc cctggactcc tcccctcccc ctctccctcc tctccctcgc   3360
tcgccctccc ggccgccctc actgataccc cagcgccgag gcggtggtca gtctctgtcc   3420
gtagagggcg tagggggagt agtacggtcc ggtggcggcg ggcaccggca cgggggcgcc   3480
aggcgtggga agcgggctct tggagtaggg gtggtagcgg ctgctgagtc ccagcgcgtg   3540
gtgggggctg cgcagcgcca gcgtcccagg gctgcccggt gcgcccgagg tggggatgtg   3600
catgtggcaa gccatggcgg ccgcggcagc gctggccaga gacgacgagc tggggtagcc   3660
cgacagcagt ttgtctgtcc cgggaaatgc cgtatgggtc cgcaagtggc tcagcagctc   3720
ttcggacgtg gcgaagcgct tgtcgcacgg cccgttggcc gacacccagt tgcagatgtg   3780
ggggagtggg tcgttaggga gcataaagcc gtaggggtag agggggtggc cggccaggga   3840
gggcggtgtg gcgccagcag ccgcggcggc cgttagcgag gagtgcacac cgtgcagcgg   3900
gtgcgtgggg tacaccagcg ggtatccgga cttcagcgcc gcagccgcag cagccggatc   3960
atgtgcgcaa gaagcgctgg cggccgccgc ccctgccagg tggctagcgc agtggtagct   4020
gaggcagtaa gggtcccggc acaaactggc tgtcatcacg gacggcggag acgctccggc   4080
caaagggctg gagccggccg gcttactgca gcccagagac ccggccgcgg ccgccgccag   4140
ctgcgccccc accaggctgc ccggcttggt ggggtcaagt gccacgccgt gtggcaggaa   4200
ctggggcggg tagccggcgt aggccccggc caggctgcct gggtaggtca tacccgcggg   4260
aggcagaggg aacactgtct ggcccggctt gtagggtgac acgggagcca ccagcccaga   4320
gcccaacact gaggaggagg tgggcgcgct ggggccggag ccggagctgg agcccgatga   4380
accgccgcag tccgagccca gagccttgcc tcccgggccc ccatccggat gctggttcac   4440
atccacatta atcccgccgc cgcagctaat ccggccgtgt gccagccccg tgggtccccc   4500
ttcggccgag gcgcccccgg tgcccttgcc accgccgccc acgtcggtgt ctttcttgtc   4560
```

gtccttgccc tccggggcac ccccggccga ggacagcata cctcccggcg agcaggccga 4620
ggcgctggag ctcgggctgc ctgtcctggg cgtgaatggc tggcaggtgg cgctcggtac 4680
ccggaatccc gacttctccg acgaaacacc cccgccgccg cccccgccac cgccaccgcc 4740
tccaccgccg cctcccggct ccttcttatc cgagccgggt ttggagtacg gcttgaaact 4800
cgacttgtcc tccacgccga tgtcgctcag cttcaggggg cccgatttgg tgtccttgtc 4860
gcccgcagca ccgccgccgg caccgcccgc gccgcccccg ttggaggcaa ccgaggagag 4920
tttggaggag ggcgaggggt cgggcttccc gatctgcgaa catgtttgcg ccaacagcgc 4980
cagcgggctc ttcttggcat cgagctgcgg ggtcagacga tgggggggga gcgtcacaca 5040
gagaaagaag tggaaaccct ttagaatcct ggcttctggg gttcaaatgc ctctccgcaa 5100
cagcccacga agatcctccc agccccaagg cgcaattcta ggcggcaccc cctcttcaac 5160
acccactcac aaacattctc gccgttggga aaggcagcag attgctcccc ccgcccaacc 5220
accaccccca gcagcatctt tcctgccctc tctgagcgct aactagattt ttaaagagca 5280
aaatgttttg gttttcggtt cctagaccca gaactgtacc ccctccccac aaacactcct 5340
taattcttca gagtaagggc tcgggcggct ggcgcctcag aggctgtgtg cacacactgg 5400
cttctgcgga tacgaaggac ggcgactttg gaaccgtatt tcagacctcc gcctgccttc 5460
ggtgccgagt gaaggggcct gggtcggggt aggggctttc atatcgaaag gagaaacaag 5520
tattggcagc cttgctccct agcatgcacg ccccattcca cttcctcccc cttttccgcc 5580
ctagttttga ggtacggaag cagtagcctc ttcccccatt cgggagctga atcactccga 5640
cccccccacc tccgcccaga tcccgagaaa aagaaagccc tagggtggca gccagggtag 5700
tggtcccagt gcgatccaga gagagggtcc ttacctcgat ggggctgacc ggcgtggaag 5760
gcaggggctg caggtactcg gggtgcaaaa tgtggccagt tcgtgccgtc agcatcttca 5820
gcaccttgat tggcaggcgg ttggcctggc gcagggggtc agagggggc acggcgtgca 5880
caaaaggctt ggtgctgccg gccggggacg agcctgggcc ggggccggag ctatttccag 5940
agagcgcgct ggtccaggca gggtctgcac cgccgcctcc gcctccgccg ccgccgccgc 6000
cgctgtgctt actgcttctt agggcagaaa gcgagggcgc tgtgctcatg acccacccgc 6060
gcgcatggga gcagcggggg ggagggctcc gggaggcgcg gggcgggctc ggggctgcgc 6120
gctcgccccg ggagcaggag cagcgggagg aggaggagct ggcgcggcgg ccacgggcgc 6180
ccagcgcgcc ttctcggcgc ctggagccag acgcgagtaa tcctgggtgg cccgcagcgg 6240
agccgtggcc gggctagagg agccggctgg actgcgggag tgccgggcgg ctcgcggtgt 6300
ccgcctcggg ctgctcccct gcgctgcgtt ctcgcggccc cgcgccggcg ctgcgctctg 6360
cgatgcgagc cgctgcgtgt ccagccgggg ctctggcgag gaaactcact tcaaaagcag 6420
ctgcaccaag gggagatta aagcctttgc cgccttccaa tcaaatggga gcccgaggtg 6480
attggagggt caaggggatg tgacgcgtcc cgcgccgccg ccgccgccgc tgccaggact 6540
ctcagtgccg gttttaatgg gcagctccct cttcgccgcc cccctgtgtg tcccctccct 6600
cgatttcgct gggaggacga gatggacatt tattctacgt ttgccatccg ccgcctccct 6660
ctttttttcct cctcgtcgtt cttcctttcc ccagctcgaa aataaactga aaccttcttt 6720
tgaagggggg tgcgcgtgag gaacagactg cggggggtgt ccagaaggag caccggtggg 6780
agtgtggaca ccggccggac tgtcaactcc aggggcgaag ggaacctgca cacccagtgt 6840
tttttccttc gcagtaatcg agatcccgcg cggcgcagcg cagccaccag ggtaagaagg 6900
caaggtgggg agccggagct ggaagaagcc cgcccgcccg ctctaatttc ctcagattcc 6960
gcggcggaga aaccagaagc tagatgggca gtcgcagcgg cggcggctca acaccgcgag 7020
gagcgctggg ctctccgccc ttcccggcca cgtgacgccc ggggacgcgt agattggggc 7080
agcagcgggg gtcacatgtt tcctctgttt caccctcagt ctgtccccca accccccatt 7140
cttactctcc caccctgttt tcctccctcc ccccttcttt tgggcatctc cacccctcca 7200
tcaattgtca atgttcctcg accgcaatca atcagttatt tgtcagctct tgtcaatcct 7260
cccgtgattt atgtcagctt ttgttgctga ttacaaggcg ggtgcgactt gaagggaaaa 7320
agagagaggg agagagagac ggagaggaag gaggagattg agagggaact ggaggagggg 7380
aaaagaggag cggcctcctg ggatgggggt ggggtggggg ctctaagaaa aagaatgaaa 7440
gaggcgcacg gtgtcaggaa aatgaatagc gagagtaaag tgcgcaggtg cgcccagggc 7500
gccgagaggg gcgcgcaggc ctggagtgtg cgcctgccct ctcggtgtcg gagagacgcc 7560
cttccacctc tgggagcctc ggtctgttgg ggtcgcggag ttcgggcgcg gctccgggta 7620
cccgagacca gcggcggcaa cttctaacac gggagatttc ccgccacccc accccgccgc 7680
cgcgagtcct cgcggggcgt gttgcgtgcg gaggtcaggc tgccaccctc tgtagttccc 7740
taaccccaaa ctcggagact tctaagagcc acaccaccaa ggaacttcta gtcctggagg 7800
tcaatggtgg ggcaaacctc gcctcaattc tttgaccccc tcgggtcgta agcagggcta 7860
agaggctgcg aagaagaggc ctggccatgg gtgtatgggg gaagaaacat ctcaggctca 7920
ctcatgcccc ctccccgacc ttctcccacc tgccgccatc cccgcaggct ggggagccag 7980
ggtaactcgg ggctgctctc tcgaatttat tggaacgccg agtcggaatg agctgcgcta 8040
ggagagccga gggaaggagc gagagaggga gggggcggct gcctgtggga acgcgggttc 8100
ttccagggaa gcggagcggg actgccgcgt tcccctcgat ttgcaccgtc actcgggttg 8160
tttgggaaga aaaggggagg cgctgtgcgt gccaccgggt acctggacct ggatgcccag 8220
tgtgtatgca tgcctgtggc gctgcgtgag ttatcggggc tctgatagcg tccggagcgg 8280
gttcgagggt ctcctccagg aactcgcaga aattagaggg ggtggggagg aggacacacc 8340
cccttcctcg gaacgactta gaagactttg aatctcccct cctccgcttt tccgccccgg 8400
ctcttctttt gttgtcaagt ccttttgata aatggtgggg ctgggagctc tgggagtcgg 8460
gagccagtct gtgcccgcgt ggggggcggg ggccgagcct ggagacccgg tttcgaccgg 8520
cgcgcacctg ggctgagcc gggtgcgcgc gggggtcggg tctggaactg cccttggtat 8580
gctcgccctc tcctcttggc ccatctcact cccctccccc acctgactcc cctccccggc 8640
ttctttctct gtctcccact ccgcacgggt accgagaact ttccggggtg agttttagaa 8700
tttgctccta ggcattcttt ttctgcgttt ggattttatc ccttgattct ttgggttggt 8760
aaactttatg aaatggtaac ttgactgaag ctcatttgga gagaagaggg gagtgaggcg 8820
gtgtgtgctt ggggctggtg tttgtcagtg tgagcgtgta agagcacacc tgcattcaag 8880
ggggtttgta gtgtccgtgc gacatctgag ggaggtgagt cggcgagcgg gtggcgaggc 8940
cccacgctga gggaggcggt tgtctggtct ccggggagca agtcccaggt gcgcgtttcg 9000
gagggcggga cagtcctacg ctgtctctgc ggggcagcgc gtctgtgaag cactcttatc 9060
cttcgggtgt gtccatgtgt gcctggttac tgagtgcgcg gccgtctagg tgtcgaccca 9120
accaatggta gtgctcctaa cgccgcgagc ccacctttgg gccgctatcg ccgcggcctc 9180
cccgcgaggc ccgggcactg aaattctggg gcctgcgaca gggccggggg ggacgcagcc 9240
aagggcgtcc ctccccagcc tccagactca gctcttcccc ctctcctcta attccagcag 9300

```
cttattacgc cggcggctca ggggaggcag cctcagcacc tgaagcctgg gggggccgtg   9360
gagtggctcc tgcgtccccc ggtgtggcca cacacgctcg tggggctgcg ctgtgctgcg   9420
tgggtgcggg tcgtggtcag cgtgcgttcg cttttctcaa aactccactc cgagggtccg   9480
agcgcatggg ggcgcctggg ggcctgcgcg cccggggctt ttgggaggcg ccagcgtccg   9540
agcctgcgca cctcgcgcag gaggccaaac ccccgaaggc cggcgcgggc ccgggagtgg   9600
gggccattaa ttactctgcg ccaggcctaa agcctccaac cccagcagc agttggcgtg   9660
gatgtcctgc ggattttatt tgcaaacaat ggaaatgatt tgttttctct aaaaaaggag   9720
tgggcaaggc agatattgga ggagggggtg ggaggaggag aaggaagggg aaagagctga   9780
ggaaaaaagt ttgaaaatgc cttgaactat tcactgtcga gatggctaat cagtattgag   9840
gccggagggc aggcgggccg cctttcaccg ccgcttccct ttcatctcgg gctcggcgga   9900
ggcgctcaat taaaagccta tcagtttgta agtaaatcaa cgcctatcag agttgtcaca   9960
tcaaacaaaa cgattattat tgcagcccgc ctcccctatt aatctccctc gaagataatc  10020
cgcctgacag gtcaggcccg gcgagctgga aagcctggcc cagagcaccc aaacagtccc  10080
ggactggcgc gcgcccccgg gggcctcccc acccctgtcc tgccccgcct cgcggtccct  10140
gggagcgggg agagaaagcg cgcgcggagg cctctgcacc caggtccgcc ccacctgact  10200
gggagcaagg cccagattcg cggggccagt aggggacagt cccgcgcggc cctcgccgct  10260
gctcggggca ggggagaagc ctggcgtgca ggagccgcgg cccggcccgg ggtctcgcca  10320
cggcctgcgc tctcctcggc tctcatttat tttcttcctc ccttcttttt gttttctctc  10380
ccgcgtcttt ctgggctccc ccatcttttt ccttcatttc cttttccttt tcccttttt   10440
ttacttgcca gggagtattt cccattctgg ctctctcttc ttggtgtgcc gtataaacct  10500
ttcttgcgca gccacactgc ctggagtagg atgttctcag ggcccgggtt atttctcccg  10560
ggttgcccca ggagtgtgca gttcccagaa actcatggca aagtcctcta taatctcttt  10620
ccgagcaggg gctctgagaa gctctgcgcc tgtttaaggg ttgggtgggt ttggaggggt  10680
gaagaggaaa aagagggaga gagactggtg gacagttgtc ctattctgga attagtattt  10740
tgccttggaa tttcatagct gtaacgttgc cgacctcgct gttggcgttg cccgggcttt  10800
tcaaatatgt agataagact caagggggca tccaggcctc agtagtgact atgtgtgtgt  10860
gggtgggtgc ctgatacaag taaatacacc cagataactg cctctgtggc ctcaagttag  10920
tgtcccaaga gtttgggtgg ggcctcgctt ctagaaggcg caaaaatcgt ggccttcttc  10980
ccagtggcct ccggcttcct gctttgggat gcctcggaat cgagccggac ccgccttttt  11040
ctgcgctctt cctccacatc tgtaggccca aacggccact gccggagcca ggtggagcca  11100
ggattgaggg gtagctgaag tgtctgtgac gaaagggctg cccgagggag cccaggcctg  11160
ccacctcata tgtcgggttc agtgcgccgc gaaggctctc cgcgcctgta tctcggagga  11220
cccccagagc gctgcagtat tgggcgtcag ggccgagcct ctcgcagcag tcacgccgca  11280
gtccgaggcc acggacatcc aatagagccc acttcaactt gcatggtgca tggggtccag  11340
gaccggtggc ccccacacag ggtttcccaa agcctctcca tttgtctgca ctctccactg  11400
ccgaccttgt aggaaattta tttccatgcc cagaaatatt gtttggacac agtggctcgg  11460
ttatcttcgc gcctgctttt cttaaataca tttatttcac ctctgccacg ctgcagatat  11520
ttaaagatct gtagataccg taaccctcag cgatgcggga ctcactctgg ttatagataa  11580
tattctctgg gtggttattt gaacataagt tctatctcca gcccagatga cacccaagca  11640
ggggctgtaa aggacacttg ctctagaatg ttttcaactg aaatatatgt ccacacacgg  11700
```

```
agaatttaag agtattttta tatttctctc tagatctaaa tattcagatg tgttaattac  11760
atgccctaga agctggaagc gatcagtggt gttcacactg gacgtggagc tgtttgtata  11820
attttcatct ccctgcactt aaacatgact ctcagtctaa taaattcaac cttgtcattt  11880
ttagaatcga cgggatttct ctggctgtcg tttgcgctgc atttatccga atacatccag  11940
ctcgcaggca tcctgcaaga aacggctccc ggctcgcgtg tacgccgaca cctcggccca  12000
acgcaggact cgaggtggtt tctagtgccc gggtggctgc aagtctgccc tccgagggag  12060
gctggacaag cggcgccccc aggtcgagcg gcctctcgct gcctggcagt gcctggcagc  12120
ccccacctct gccagtgctt cggaaacccg cctggccagg ttcgcccgcg gtgaaaaatg  12180
aaagcaaatt ccccaacaga ggtagccgga actttcctcg acgaaggctc cctcctgcgc  12240
ctgtgtctgg agaaccccca gagcgctgca agttagcaag agagattcga tggcggctct  12300
ggaaggcgca cgaagggtgg ggcgggggag caaagaggcc actgggtgac ccagcctggt  12360
ccggggtgaa acgctagaga aggcgcctcg ccttccttat ttcaatgcaa ctcctcggcc  12420
ccagacggta aaaatagttt ccaagctgcc gcggacgccc aggatgtgtt tgcagagatc  12480
aaactgggga ggaggcagct ttgtaaaagt tgcagaaaga ttagccgaga agcgtccgcc  12540
cggcggggct caagaaagct tggggacagc tccatgttcc ttggggcgga atggcccaag  12600
aattggcctg ggtaaccccc tgcccagttc tctgtcctca cttcgagcca gtgcttaaat  12660
aacttcccgc cgcctgccct gcaaacttcc cggcgcggcg ccgttgaggc caggacacag  12720
caaaggctag caaaaccccg ccgcggcgcg ctcggccccg gccctgagag gctgcgcggg  12780
tgggaggacc agtgtggttt ctgctcccac tcggctgccc agaccctcaa gaccgatccc  12840
ccaactcctg ggagcgggtg cttccctctg ggagccgaga tcttgcgggg ccagcgaggg  12900
cgcaaagtgc gcgcgctggc ccgcgcgggg gcggccgcgc gtctctccgc ggggcctgtc  12960
gccaggccgg ccgcggcgcg tgagtgatga gggcagagaa gggcgcccat aaatcgcggg  13020
tgtcagggcg aaaaactctc tttattgtct gcgtgatgga tgggcccggg gacgagacac  13080
caaatacttc gtatcgcctt taaatgggaa cacattttcc gcggccataa ttcatgtttt  13140
ttaaatagaa agtttgaaat gttgcctata tttcaccagc cctgacatat ttatgaatcg  13200
ctccctgcat gcaaatatca ttacttaaag cgccggggag agcgcggggg aggggaggag  13260
gcgcggttcc cggggcgtgg gggtggtgaa ccggggaaat atcggtggag gggggccatc  13320
tccctaaagg gcagagggtg aggtgcggtg aatagccgta tccggaaacc gagcgtgccc  13380
cgggcttctt tcccgccgcc agaccccgca cagccgccct gggacgtttt tcgaggcttg  13440
ggacctaaga cgggtccccg gaccctgctg ggaaaccagg gggcgttttt cgtccctctc  13500
tgaggccatt atccaagctg aaaccacctt ttataagaaa aaagtttaaa gaaaaaaaat  13560
ttaacaaaca caaataataa taataaccca acatgtttcg cgttctttgc cactgcatcg  13620
attttattga ttttcattct gcaaacctgg gaatgtgcgc gctcgggagg ggaggctgtc  13680
aaaacccagt catcgcgggg actggatggg ggacaattct ccgacgccgc ggcctggacc  13740
cgcccccacc caaccggcgc accacctccc aggcaccacg gagcctgcgc aagctgcggg  13800
gccgtaaagg aaccggcccc caatctccgg ggcttcagtc ccgcccctct ctccccccag  13860
tgccctgcag cgctcccagg gtccgtgtct gccctcccca agcccccact gtcaatacaa  13920
tccctgttaa aaaaaaaaaa tctttttaga gccaggcacg tgccgtcggc ctctccccctg  13980
cccgcctggc ccaggaggcg cccacacctg cgccctcact tgccgagact tttacctgtg  14040
```

```
cagtccccgg cggcgcctgc agccgcgcag gtaaccgaga aatggaaggg agggctgggg  14100

agtgagaagg acagagagca ccgcccgaca caaccagacg cgcggacccg gggcctcctc  14160

tctggaccgg tgctggggcc ctggtagaac cagctccggg agccgaaatt gagccatgaa  14220

gagtgggccg agggaggggc gaggggaacg ggcctcagga gggaggggcg ggcccggcgg  14280

cacttccgtt gggggtgggg ctgcgggctg ccgcgccggt cccgcccctc cgccgcgcgg  14340

gcccgcccgc tccaggccag gctccgcccc caccgactcg gagctggatc tcaggccacg  14400

gcgccccccc agtcgcgccc ccaaccccgg aggcctcggg ctgaaccggg tttcgcagga  14460

gggcacaggg cg                                                      14472
```

<210> SEQ ID NO 232
<211> LENGTH: 4440
<212> TYPE: DNA
<213> ORGANISM: Homo sapiens

<400> SEQUENCE: 232

```
cgtgaacgcc ctcgcctcgc acctgtggcg cctgccgcgg ggcccgaccg gaggcagtgg     60

ctgtggacaa gggcggcccc ggcgtaggcc aggatttccc cgcagccgga ccggcccagc    120

tccgctcctt tcctgggcga acagcgccca cctccggccc aggcggcggc gcctccgccc    180

gcggcgcgga cagcgagaga gaaaccggct cctccaaacc tggtggagga gcgctgcaga    240

gaagcgccgg gctgaggctc tgggggccgc ggggcgcgaa acgccgcgcc taccaggtta    300

tgcccgggag aaggagacag gtcgggctcc agccgctggg cgctcctcac ctcgaagcga    360

ggaaaacacc gggccactga gatcagggga ggtgcgcccg atacaggtac ccggcacgca    420

gacacgccca cccccaaaca ccgagaaaca aagactgccc cgagccacgc acgcctgcgc    480

ggccagcgct gggcgcacac ccgcgcccac acagcccgaa gggcgccacg caacccgcaa    540

gaacaccagc tccccgcgct cgcaggctct ccgtgccggc ccgcagcgca gagcagtccc    600

ggcgccgctg cctaggtggg ccggggaagg cgcgccaccg cgcatggcac cgcggctgcc    660

gaggaacaga gggtgccctg cgcagcccag ctcgtcccaa cccctccggt gcccactgct    720

gcgacgcctc gcaggccgtg tcccagtggg ccctgggcac agcggtcact caccttcctg    780

cacagcctgg aatgggttgt tggcctcgat gaccttgatg gagtaggtga tcttctcgct    840

ctgcaggatg tcatcgttga ggctcaggtc ggataccgcc aactggaaca ccctgtcgtc    900

cttggccgcg ttctcctcga agatggcacc tggaggagag aagggatcaa gaccggacct    960

ggacaagaac cctctccccg cttcccttgg cccgagggtc aaggcactcg cagaccgatg   1020

attgccgggt ggtgggaagt ctgaactggg atttcagctt ggcggggtag attaaggctc   1080

tccgatctcc acctgcacag gaatatgttc ccctccccccc accagccctc agcgcacacg  1140

tgcacacagt tgacatgagt tacacatgca catcccacag gctgccacca ggtcacacac   1200

gtgtctcaca accaaggcac cacatgtcct agccatgctc cacacaaggg actaagccaa   1260

gctggggtgg ccccaggcag cgcccaaatg ccttgacatg gttccataaa tcccatccca   1320

ggagccagga agttccccgg gagggtggtg tcccccaccc aaatcccagg acagaatgat   1380

gggtccttct ccatgcacgt cccctgctga gtggagctga gcgaagcagg tctacagttg   1440

gctttcctgc gcagaggggt cttccttagg caggggcttc ggatggcctg cagcttggat   1500

gactgtgacg ctgcccggcc tggcgccctg agctcagcct cctactctcc atccttcccc   1560

actcccattt cctgtacgtc tgtcgagggg agtgggggaa ggggacttgt gtcctaggcg   1620

cctccacgtt cagatctagc ggagctgggg gtcccagaag gagctgctct tgaagggctt   1680
```

tctagaaccg cggacagctc ctccagggcg ccctccggct ggcgctttgt gcgcctagca 1740
cagcttccac ggaccctgcg cttccagccg agatcagtgc gaccagcccg agcctagtcc 1800
tgcaacctgg acagctctgg agtcagccac ccacatcccg cctcaccaag cctcgagggt 1860
ccctgaggtc ccggagctag gcccagtgat ccctcgagct gggggctggg taggaggagg 1920
gaggcccgga ttcctcacta cacccggagc cggcgccgca atgctgaccg cgagacccgc 1980
acccctccag ggcgggaagc aggtttggtc acgggcccct gaggaggaat cgtagctctc 2040
cgagcccagg cctagtcctc accaccccac tccaccaccc accctcccgc cttgtcccgt 2100
cctcctcgcc ttcaacacct cccaaccccc agtttccctg tgctcgctgg tctttcccaa 2160
cttccggaaa gacgactgcg gagggactcc cccaaagcga ccgctgtcag ccccccaact 2220
cggcccaact tcccgagatt cctcccgtgt tgctcccaac tcccacccac tccccctcgg 2280
cgcgcccact cccccctcggc gcgccccctc ctcctctgcg ctttcatctt ctctcccggt 2340
tctctctctc tatccatctc ttcccgctca gcatccccct accccccgct gcccacgctt 2400
cttccctcgg ctcccaccac ccagaccgtc tgggccccca agacttggac cacgcaaaac 2460
tctaggactg tccaggatgg ggatgcagtc gccacaacca gatacacacg cactcacaca 2520
tacaccaagg gctacacaga cacacaccgg agaagcaggc agacactgtg tccactctaa 2580
caggctgaca gacagtcgtg cacgcaccaa cacacgctca gatggcccca cacaccccaa 2640
caccctctca cagtaacacc gacaccgtgc caggcgcaca cagcgacaca cgctgacaac 2700
acgcacccac acacattcac acacggttcc ggtccggcct ctttgatctt gccctgccaa 2760
cttggcgagc cccccgctgt acctcccccct gccccccgct gctctgagct gcgcagaagg 2820
gccctcccga cccgccgacg gccccgctaa gggcgcgggt ctcgacgcgc gtccatcccg 2880
gtgttccccg aagcgtcggc cctaagtgtc ggtagaggcc gcggggcccc gcgcggagat 2940
cggagccccg gggagcggca agcagccagc gggagcgcgg cgcggccggt gcacagctcc 3000
tccgccgggc ggcgcggcgc ggcccttcgg gggagcaccg cccgccgagc ccctcggccc 3060
agggaaacgc caagtttgga cgccgcgcac cccctgcccc gttggggccc ccgcccagcc 3120
tcggcccggc ctccagccgc gcttaccgat gtggatgatg gagtcggccc gcaccgacac 3180
gcactggcat atccagggga gaagccacag cgtcagcgct tccatgtccc ccgggcgcgc 3240
ggctcatcca cccgggcccg gggcgaggcc gagggcagcg cgaagcgggg aggcgctggt 3300
cccggtgcag tcccgggccg ctccccggga gagccgagcc cgcccgtgcg tcttcccccg 3360
cgcgcccgcc cctgcgccct gcgcccgccc cagcccagcc cagcccagcc cagcgcggtc 3420
gggctcccgc tccggctccg gtggcggctg cggcggtgct ggcagcttga gcccaggccg 3480
gcgcggcggg ggcggcccgc ggctgtggca gcggcgcttc ccgcggctag agcggcttcg 3540
ggggaggctg aggcggtggc ggcggcggcc gggccggcgt ggcggctctg ggctggctgt 3600
gtgtctgagc cccggcgagg agcgaactgc ggaggacgcc ccctcccctc cccctccccc 3660
tcagctccgc tccccctccc ctccctgccc gcctccctcc cctccgcccg cctctctacc 3720
acgtgactgc ggagcctcag cctcgccgcg cggctctcgc ccgctcgcgg ctcggagggg 3780
gcgccgggtg ctccacgctc ccggctcggg ggacgctcgg agaccggcac agcggcgggg 3840
accggcctgg gctgcggcgc gccgagctct gacggttcgg gcctccttct ccggttcgcc 3900
aggggcggga gaatggagga gggccggccg ctaactgccc tcgaggggct cccgaagcgc 3960
cctggcgacc tcagcagccg cgcgtctcgg gtcatgtccc cggccgaaac agaccgttcc 4020
tcgtggagtg ggacctgggg agcaagaaga gagaccgggg cggggcgccg ggccaggccc 4080
caggacagct ggggagccag agggggccgg ccgccgcaag catctcagag tagagcccgg 4140
gccgtgggct cgaaccctgg ctggccgcgc ggacctcggc gggcgcccat cccccgctcc 4200
atgggcagcg cgctcagccg ggagtcgggc aagaggctcg gactctgaag cccaattcat 4260
ggccggaaac cagcgcagcc gtgaccgcgg cgcctggacg tgaggagcct tccaagcggc 4320
cggcgggctc agactccgac cctgcacgga gctttcatgt gcgagcccgg gcgaagagcc 4380
cgctcctcgc ggccacagcg gaacagggct ccctccgcct ccggtgcctg cctcgggccg 4440

<210> SEQ ID NO 233
<211> LENGTH: 408
<212> TYPE: DNA
<213> ORGANISM: Homo sapiens

<400> SEQUENCE: 233
cgagggtttg atgatgcggc ccgagcctgg ctgtggtcgc ctgtcggggc tggagcggga 60
ccctcagccg ggccgggcct gggggctaac gttttcacag tgcgccctga gtttccttgg 120
gttactgctg ggaccgcgca ggaggaagca aagagttttt cgagctagac caacaggaaa 180
cacattgacg gaaatgttgc catagcccat ggggtggctt taactggccg cccccgcggg 240
ctgggtgtga aatcagagga ggccgcggct cccccggcca ggattggagg ctcctcgcgc 300
aacctaatgc gggtgtccgg gcccgagcgc ttcccgcgca gccaggcctt gtcggtgcag 360
cagccccgct cctccccaac acgcacacac ccggtgttcg caagtgcg 408

<210> SEQ ID NO 234
<211> LENGTH: 2237
<212> TYPE: DNA
<213> ORGANISM: Homo sapiens

<400> SEQUENCE: 234
cgcgcccgac tgcgggagcc aggatcaggt ccccagggcg cccttgcaga cagcaccctg 60
agcgaaggag ctcagaaggc agtccggctt cacccagacc cccaatccca cagaagcgcc 120
gtcccccagc ggcacagcac cccctccccg gcgcggtggt agggcccgac gtgacgtcac 180
ccattgttta caaatcaacc cgagccggca ggattccggc tcccgcggct gcaggcgcgc 240
ggctagagtg cctggcgggc tccggcttcc gcgtccgccc cggccccggt ccagacttag 300
tcttcagctc cgcgcccgct ccgccgcggc ccaccgcgcc cgccggcagc cgagccccca 360
gcgacgcccg cacagctccg ggtgcccaga caggggggcca tgccgtgccg gagggaggag 420
gaagaggaag ccggcgagga ggcggagggg gaggaagagg aggaggacag cttcctccta 480
ctgcagcagt cagtggcgct gggcagctcg ggcgaggtgg accggctggt ggcccagatc 540
ggcgagacgc tgcagctgga cgcggcgcag cacagcccgg cctcgccgtg cgggcccccg 600
ggggcgccgc tgcgggcccc ggggcccctg gctgcggcgg tgccggcgga caaggccagg 660
tccccggcgg tgccgctgct gctgccgccc gcgttggcgg agactgtggg cccggcgccc 720
cctggggtcc tgcgctgcgc cctgggggac cgcggccgcg tgcggggccg cgctgcgccc 780
tactgcgtgg ccgagctcgc cacaggcccc agcgcgctgt ccccactgcc ccctcaggcc 840
gaccttgatg ggcctccggg agctggcaag cagggcatcc cgcagccgct gtcgggtccg 900
tgccggcgag gatggctccg gggcgccgcc gcctcccgcc gcctgcagca gcgacgcggg 960
tcccaaccag aaacccgcac aggcgacgac gacccgcacc ggcttctgca gcagctagtg 1020
ctctctggaa acctcatcaa ggaggccgtg cgaaggcttc attcgcgacg gctgcagtta 1080
cgtgcaaagc ttccccaacg cccgctcctg ggacctctgt cggccccggt gcatgaaccc 1140
ccttcgcctc gcagccctcg cgcggcctgc agtgaccctg gcgcctccgg gagggcgcag 1200
ctcagaactg gcgacggcgt tcttgtgcct ggcagctaac acgcccgggg tggccacagc 1260
gccagcctca gactggaggg caaggggttc ccttgagggc tgcagttcta ctcaggctgg 1320
tggagaactc tggcttttgg aagcgagagt aaaaagctaa tgacgaggaa ccgaaaaatc 1380
gcgagtgttt cgcgggtaac tggggttgag ggccaaaata tttggaatga aggactttgg 1440
ccctatttaa ggcagatttt acagagcgca cctcaaacgt acaagtcagt aggactcctt 1500
atttggcgtg acccgacctg gccgcggagc ctgcatttcc tcgcagcctc tcagtgccct 1560
ccagccccgc gaccatgtgg ccacaatcca cgcttctccg gatcgcggtg cgccggaacc 1620
acggaggatg atgccagtta cttgctttac cttttcaggg ctggctcctg atccactttg 1680
ggggaggaga acatgagtag ataatttcag ggtgcagccc aatctgccag acttaaaaaa 1740
accatcttgt gtctttggag gtgctgctta ataccaaaca tgcggtgcca tgaagggacc 1800
ctttgggggt tgaataggag ttaacccctg cgctctcttt gcaactgtct ctcttctcag 1860
agtggtgggg gaaggctgta cgacacgggt ggggaaagga ggtgggggcg gggagtattg 1920
aatggtggtg gaagggtaga gaggcgcgga gtgaacccca cgccctgtct aaagtgtatt 1980
ttcagagccg gcccgcctct cctcggttca aggtcactgt ttcctgggca cgcactgggt 2040
tgcgggacag agtagccagg ttctgccggt gctcggagaa gagcgcagtg ttttgcaagt 2100
gctggagtct cctgaggaca cgcgcgtcgc cgccaccgcg ggtgtgggaa agcgcggacg 2160
tgctgggcgg ctgtgcttcg gtaggcgacc accgcccctg gccgcgctcc gggctttcac 2220
ggaaactccc gagaccg 2237

<210> SEQ ID NO 235
<211> LENGTH: 758
<212> TYPE: DNA
<213> ORGANISM: Homo sapiens

<400> SEQUENCE: 235
cgtgcacggg cttggagacg gggcgccagt accaggcagg gcacaatgag gcttggggcc 60
cttacagtcg ctgcaacctg gaggtaccga accggggact ccgacctgac atgcaggcga 120
ggctgcgagg tccagagcct ggacctggtt cctagggagc gccactcctt ctgacccctg 180
tggcgtgcgt cctggcgcgc cgcacccgcc tggtgcctcg gccctctctg ctgttccctg 240
gctgattctg agcaaggcca gcagcccacg gccccacccg acccccacat ctccgcaggg 300
tcaggcgagc cgagcaggaa ctgcgccggg gcagtggtga tggctgggcg tccctgcagc 360
ttcaggggcc aagggcaatc ggggggctag gcccgcagac ctggccgtcc gctgacgcag 420
cgaaggtcta gcggaacctt ggggatcgct ctcccagtgc cgaccgaagg cccggacctc 480
caggctggac gcggcgaagg ccgcataaga cgttacttaa acatgttact taaacaagac 540
tgcagtaaac gtttctttcc aagtgagaaa ggtctttttc gttctcagac ggtttgaagg 600
tgtttgtgcc aacgtgaccc ccggggagat ttggaggaag ctttctacgt cctaggaggc 660
tgagatccca cggagccggt ttacggttga gagcagacag tttcgagtag atagcgctgg 720
aagagacacg aagaatctct cttgcttctt ggaacgcg 758

<210> SEQ ID NO 236
<211> LENGTH: 5881
<212> TYPE: DNA

<213> ORGANISM: Homo sapiens

<400> SEQUENCE: 236

```
cgctttaact agacgggcgg ataaatggcc ccgtttctcc tcagccccga cgcgcctgct     60
tagctgcgcg ccccgcgggc gccgcagctc gggtgggctc agccctgggg ccgccgcccc    120
cagcccaaag ggacccagcg gggccaggcc cagggccgcg aagcagagag cggccggagg    180
tgccagggcc gcttcattgg gattcatgag cgtgttgggc gggcggcctg gggcttcggg    240
cgcggggcgg gggccgagtg ggggggtgcg cacggcgggc gcagatgccc gggtgaccga    300
cccgccgtgg tccctgcgcc gcctttgtgc cgaggaggcg cgcgcgggga cctaatccat    360
caaattgtct acaaattgtg aagaaaattc aaaaaccata tggtcgccag cgccggcgcg    420
ctctgggctg cggagggccg cggccgtgcc cgcaccggga gccgcggggg gctgggcccg    480
gctattgtcg cctgtcagcg gccgcccagg cccattcgtc ccggccttca tggtccgcgc    540
tccgaattac agacccatcc atcctaagag agggcaattt ttgtcgcccg ggaggaacca    600
gccgcacgcc tgccccgctg ccctgccgtc tccttccttc tctgctcctt ctctctcttc    660
tcctctcttc ccattctttt tttctccctc tgtctctgtc tccctttctc cgtttctctg    720
tttctctctc tttttcctct ttttctccgt cctgtctctg tggctctccg ctttctctct    780
ctgcttttgg agtgtctttc tgtgctccta ttttttttc ctgtttctct ctgtctcttc    840
gtttcctcct ggacacgcac gttcctggct cgggcccggg ggccccatcg ccgcccgaga    900
ccagatgcgc atttctcaca tcaattttgc ggagaaagag agcccagcgg cccggaggcg    960
ggacccccact ccggtgacag cggctactcg ccagcccagc gacaacaaaa gcccggagag   1020
aaacccgctc tgtccaggaa agtgaaagcg gcctcagccc ccgcccccagc cggccttggg   1080
gcgccgcaga cccgagagag tccttgcaag atccatacct ctgcccccag cggtgtgccg   1140
gggtgtggag gcagaattgg ttaatgttgc cagaaattca caccagctcc cagacgcttg   1200
ggcttacagt tccaggtgcc cacattgaaa ttcagcctgg ccttgatgcc tttagccttt   1260
ggcccccgac tccccaagga tgaggccctc ggggctagaa tcgaaacttg ggaacccaag   1320
gctccacccc gcgtctgact gagtgatacc tgcagcgctc ccggggctca gccctgtttt   1380
cggggagtgc agggagaatg cccttgggtc tggggtggga tgcaggaaat gcagggcaag   1440
acccccctccc accctttgtt caacacaaat taatgttgta ctgtggtgtg cccccacata   1500
cacaggcatt ttctcccagc atttcacggc tcgtttttta ccccgacctg gcgaagcccg   1560
cttctctccc gatttagcag ctgcctcagg tttatgggca agaggcgcct cctcctgctg   1620
cttcccccctc gcccttcact cttaagcctg tcctgaaaat cccccccaaa tctccaaggc   1680
tagggcgacc ggcacgaaga gcggcaagaa gcccagcctg ccgctgcttc tcggaaacgg   1740
gcccaccact cagacacggt cgccgccggt tctagtaaaa tggcaaagac tttatttatt   1800
ggagaaagag gccttgggta cagtctaggg aggagagggg aagggaggag cagggaaggg   1860
gcactcgcag cccactcaca tccagccacc ctcctctggc caagtcgggt aggagtgggg   1920
tgttcgaagt ggcaagagag acccagagct gtggaggagg tgaggtgagg gcttgggtcg   1980
gcctcctctc tgtctctgtc acatgcaaaa aaattctaaa aagagtacaa aataattata   2040
gggctttggg ttctgttttc gatagttggt tggttggatt tccccctgca ttgtccctaa   2100
gagccggact ccaacagtca gtccgaggaa atgcgggagg gagggaggaa tcttaaaaac   2160
agcattagtg ggcattagga ggcagaaatg gcatcgaaaa cagacttttc tctcagaggg   2220
tggggaggaa agatcgattt tgaaacttgc aagtcaggac ctgactgccc acctcttccc   2280
```

```
ctcccacatg aggaaaaaag gcccgaggaa atagaagtca actgcaataa ggccgaggga   2340
ggcgaggaag gagcgggccg gtgcattcgc cacatgcaga gaaaaatcaa aacagccgga   2400
gctgccactc ccctagaccg cagggttagt gttccccgcc ctggtttctg tctcgccctc   2460
agcaaacccg gcagcccgag agctttgaaa acatcgaaat ctccgagatt taaaaaataa   2520
taataaaaga aaggaaaaat caggctgcgg tgggaagaac ccgctatata ggtttaaata   2580
tttatataga agccatacag aattgcacgg cgagggcttc cggggcggcg gaggccgctg   2640
gtggcggccg gcccggccgg ccagcctggg tttattgctt cgagagggaa gaggcggctg   2700
ccaggagccg agtccggggc cggggacagg ggaggaggcg ggagttggca gaggaggtcc   2760
cagctcccct cggcggtccg gtccgggagg cgttgggctt tcgagcgcta ggagcccagg   2820
gcggcggaag acccggggcg ccgctcaatc gtccacgtcg atctcttcgt cttcctcgtc   2880
ctccgagcag tcctggctgc tggccggctg gtccgtgagc ggagaggcag gcgagagctg   2940
cagggcgcca gcgcccgggg ccttcggggc gcctgggggg aggaccggag agccgggcct   3000
cgacttggcc ctgccgcagc cgccgccacc gccggctgtg gcctccgagt tctgctcgag   3060
ttcggccagc gccacgatgt ccatctgccc gctggggccc agtttcttgg cggactctac   3120
gtcggccttc atctcctcca ggtcccgctt gagcttagcg cgccgattct ggaaccaggt   3180
gatgacttgc gcgttggtga ggcccagctg ctgcgcgatt tggtcgcgat cggcggggga   3240
caggtacttc tggtatagaa agcgcttttc caattcatag atctggtggt tggtgaaggc   3300
cgtgcgcgac tttcgccgct tcttaggggt ctgccgctgc ccaaagatgg tcataccgtc   3360
gcggcctggg aggaaaggac agtgtaggct cgcgttggga gagaggaagc ccaccctggc   3420
tctcgccccc gtaactccgt aacccaccca ggcctgtccg gcctgcagtc taccaatgtt   3480
cccttctcag atttaattca gcctccagga ccagggcaag tcttggctat ggcaaaccat   3540
ctcctgtctt tggtctccca gaagtcccta ggaaaaattg ttttggtctc tgccccctac   3600
ctaagagttg gtttgaaaga cccaaagtct ctaagggtat gagaaagcca gacagagaca   3660
ccctaattgc ggtgtgaatg ttggttctcc atcccttccc aatcacttca actctaccct   3720
acccataagg tccccggcaa aagactctcg attccccacg ccgagtagcc gggctaagag   3780
cgcccaggac actgggaacg caagggagcc cggcaaagca agcagactgc ggaaagagct   3840
tggccaccct tctcctgcca ccccccagct ctggcctacc cagaggtccc tgggaaataa   3900
ggattgggtc ccgtcccaca tatcttcact cccataagca gctgctcagg ctggaaggcc   3960
ctggcggccg gagagggcag aggcgagcag aggcataggg gacgaagcgc gcagggcaca   4020
gggcgcgagg cgctgggtgc aggggaaccc agcagctgcg cctaccttcg gctgcctgca   4080
gaacgctgac ctccagcccc ttaaacgtct tgctggcgag ctcctccagc gcgcacagcg   4140
gcgaggtctg cgagagcagc gcgcggcccg ccaggggcaa gccgccctgc gcgtgcttgt   4200
ccgcggcggc cagcaggtgc gccgccccgc acagcgagta acttctccgc acagacggct   4260
tgttgaggat gtcctcgatg ctgaacggcg tcagtggctt gttggagttg gcaggcggag   4320
gcaggtggtc cagcgggctg cgccgccgct cctcccccgg cgccgccttg ccgtcctcct   4380
tggaagtcat ctcggccttg ttcggggtcc cggccggggc ggctcgggcc gcggggaccc   4440
agcccgcggg cagctcgggc gccggacggc gcgggcaggc agcggcgggt ggaaaggagg   4500
ccgcactggg cagggcgcgg gccgggcgcg gggccgatta gcgcggcggc tgaggagggg   4560
agaacagcgc ggggccccgg gaagagggcg ctgacgcggg cgccgctgct gctggggctt   4620
```

ccagcaatcc ggggccggag ccggggcgcg ctgcgcgggg ctccagtttc gccaaccccg 4680
gtgctattta aaggtgtcag gtggctcggc agtggctcct ggccccgggt cctggcggcc 4740
gcagttggaa gagccgaggc gagggcgccg atcccggact gcgagggagg cggagagacg 4800
gggcaattga ctattgctaa caagttagcc ttgatcgcgg tgtaatcaat tatctgcagc 4860
ggcacttctt tctctttctc tctcctttct cccttttttcc tctcttcttt gcctctgttc 4920
tctcctcctg ttctcgctct ccctccctcc ctctctcttc tctcttctct gctcccccct 4980
tctctctcct tctctccctc tccctcgccc tctctttcac tctctgtctg tccaatgcag 5040
gcggctgtaa gttgggaagc tcattaatta gcgggccggg ggtaggagga gccggctgga 5100
attagcctgc ctaatgcgcc tgtcagtccg ggcgctgcgc tgcgttcggc ccgagctgtt 5160
tgtaaattac attagctgct cctttattgc acccgaacct cgggcgactg aaaagccacc 5220
gcccccaccc caaactgcga gccgcgctcc tggcgcaccc gcctcccgcc ggcctagctg 5280
caatgaccgc accggcccga aggtctcggt ctctccgacc cgggatgtgg agcccgaaag 5340
agtggtggga accccagccc gggagggacg cggccgccgc tcgggccagg taggaccagg 5400
agcccgggtg ggccccgctg ccacccagag tggactttgc ggagctgaga tcaagagccc 5460
agcgcctcta cctctgaccc tcttgcccct caccccactg cctgggcgac gcgcctgggg 5520
agagggaatc tgaagccctc ctgcgctggc ccgcaggagg tcagagccgg ctgcgcagcc 5580
ttgggtgggc gacgcgggaa gggggtggag gaccccaggg gttgggggag ggggctagtc 5640
ggagagctca gccttctcca cgcggagagg cggaggaggg aattgttggc ggctctggac 5700
gcctctcccc ggcctgattc cgaagcggcc gccctacctc ctccggcaat cttgctcact 5760
ttcctccggc agccgctccc caggctggct ggggccacca acggcctgat gatgggcgtc 5820
tgaagagtag ccaggccagg tgccggggct aacggggccg gctccgtgcc tccctgctgc 5880
g 5881

<210> SEQ ID NO 237
<211> LENGTH: 3245
<212> TYPE: DNA
<213> ORGANISM: Homo sapiens

<400> SEQUENCE: 237
cggtcacgaa ggatctcagc tgcaccaagc gcgcaggcta cactcctgca gtagcggatt 60
ggggaccaga taagcccacg cggctcccgc ctgagtaccc tcttaactgg cggccgacac 120
tttgaaacaa ttgagtccgt tcagaaacgg actggggaga gtgagggcac gacctcaaaa 180
tcctaggcag caaaatgagg tctggatcct ccctggaaga acagacatct cgactactct 240
ctcgccccac ctctggccgg gaggtcgggg caaggagaat ccctcaaccg agaagatctg 300
gcaagtcccc gatcccaccg gggccttccg cctcttttcc ctcatcccct aggaggcttt 360
atcaggttct aaccgcttgt agtgggggcc gtgggtgctc ggggcgccaa gaggaggggg 420
ctgccgagag cggcctgcct agttctcagc attgcctctt tgaccactcg caggctcctg 480
gaaatgcaaa cacagcccgt gcgtgatccg cacgcgacca aaagccgagc gcacacctcc 540
cgcccccgcc ccacttgcca tcgctcacac taacgtgcac acatgctcgt gcaaacgcgc 600
acgcacggaa ccgcgcgccc cctcacaccc agccgcgctc ccggcccggc tcagccaggt 660
gcccccacgc ggcagcgccc ggtctgcccg ccggcccccct gcgaacccct cgcctcacgc 720
ccgcctgcct gcgcgcacgc acgcgcacgc acgcattccc cacgccccccg cgcgggggcg 780 caggccttgg gtggcggggt ttggccggga gccggccggg ccagggagcg gcgagcagag 840
tccagggtgc atcccgcgct tggcttccgt gcgcagcctc cccgcgcgga ggcacctggc 900
tccctctcgg ctctagaacg cgaacagttg gcgttgagca cacaactcct cctccttctc 960
ccccgagacc cctgtaccct ccccgcgcgc catctcccgc ccctcataac aggcccgaag 1020
agtaaacccc caaacgcgtc cagaagcggc tcccaactct tcgccgggag cacgttggag 1080
gctggatttc ggagagactc gggattgggg tctattgccg gcccctcctg gatccggctt 1140
gattttcata ttttaagaag attttcttat tacctttgat tactcctttt taccaaattt 1200
ctggaggagc tcagtgggga ggattggggg gaatctgatt ttaagaaaga aagcaccgaa 1260
ggggcaatta ttaattttcc tcgggtttgg aatcaccctc tggacaagag aacgggcgag 1320
cgggagctag gagggaagag tggagaggac cggcgaggcg cgccagccgg agccacctcc 1380
ttcccggccg ccccctcccc actcccccta cacacacacg ctcgctcgct cgccggcgcg 1440
cgcacacccc ccgcgccgga cccgcacctc ggcgggcgcc acacactcgg cagcccgagc 1500
cgcggtagcc gcagcgggat ggaggcggcg cgcacggagc gccccgcagg caggccgggg 1560
gcgccgcttg tccggacggg gctcctactc ttgtcgacgt gggtcctggc cggcgccgag 1620
atcacttggg acgcgacagg cggtcccgga cgcccggcgg ccccggcttc gcggccaccg 1680
gcgttgtctc cactctcgcc gcgggcagtg gccagccagt ggccggagga gctggcgtcg 1740
gcgcggagag ccgccgtgct ggggcgccgg gccggaccag agctgctgcc ccagcagggc 1800
ggcggcagag gcggtgagat gcaggtggaa gccggaggga catcaccggc aggcgagcgg 1860
cggggccggg gcatcccagc tcctgccaag cttggcggcg cgaggaggag tcgccgggcg 1920
cagcccccaa tcacccagga acgcggggac gcctgggcca ctgctccggc cgatggttcc 1980
agaggaagcc gtccccttgc taagggttcc cgggaggagg tgaaggcgcc gcgggctggg 2040
gggtcggcgg ctgaagacct ccggctgccc agcacctcct tcgcgctgac cggggactcg 2100
gcccacaacc aagccatggt gcactggtcg ggacacaaca gcagcgtgag tacccacccg 2160
gcggcgggtc cgcctgtttc ctgacaccga aggggaatgg gggggtgggt gggagcgagg 2220
gacagatagt tgctcggggg tcgaggcggg ggacgcctcg acttttcgag ataacaggtt 2280
tgtccgattc cccccacgcc cccaacaggt taacggagtt tgttgttaga cgctgtgtgt 2340
gtttgtttac tggagaccct aggcttcggc cgccgggagg ggagtggagg aaggggcttc 2400
ttaaagatga gtgggggagg gatctgtgct cactttctcc aatacttggc ttggagggtc 2460
agttttcctg tttgcggggt gcttgaattc ttggatgaga aaaagggctg acttggggcg 2520
ggagccgctg aacagaccga ttcctgcggc tgccgggctc cccctacccc caccccaccc 2580
ccaccccccc tcccgtcacg cgaaagggaa cccggaaggc cattcggact cccagcctcc 2640
tgctcgcctc ggggtcgctg ctatccgctc caggcgcgca gtcctccagc ccaagaggga 2700
ggctcggcca agtcggcccc cagccttggc cttcaggtaa ccccggttcc tccttcaaag 2760
tccagggagc ggccctggaa agccgtagca gaggccgtaa aaaaaagttt aaagcgtgaa 2820
gcgaaattcc acacccatcc agcgctcatg ccacaccgct cgccctcacg cacgcacagg 2880
cacacggaag tcgctcagca gaaaactctc gacttcacca ttgcgtcctg cgccacaaac 2940
ggctccctga gcggagttgg gtgcctgagc ttcctgcaca cctctccacc cgcttttccc 3000
cgccaccggg ttctcctgga caaggatgta ccgagaggtg gcgtcgttga gcccggtctg 3060
gcctactccg gcattccgaa ctgggcgccc gactgagcat cgcgcctgcc tggcagctgc 3120
agcggcccgc agcgcgtgcc cggaggggct ccccctacct cgccggcacc cagcgctgtg 3180
cagccaagca aagaaaaggc gggggacagg ttcccaccat ctccccgact tccctccctc 3240
ccgcg 3245

<210> SEQ ID NO 238
<211> LENGTH: 710
<212> TYPE: DNA
<213> ORGANISM: Homo sapiens

<400> SEQUENCE: 238
cgggcgctca ttctgagccg cgacgccccc tcaacaggct cccggcaccg cagagccaga 60
ggccacgcgg tgagaacccc agtgcgtgcg ctcttcttgt gtgagaggcc ggaggtagag 120
ttgggagaaa gaggagccgg cgaaaaggtt agtgggatct gctttccctt ctgcggcctt 180
ctgggccagc tagggcctgg gagatgggga ccagggtcgg aggcttgggg gcgggagggc 240
ggtgctgccg gctgcttcct gcaagcggtt tgaagaggca tcgcgttgtc cggccgcctg 300
cgcaagggcc acgcgctgct gctttcaccc ccttgcgccc gcggggcacc tggactcccc 360
ttaagagtcc ccgtggggcc tgagcttctg ctgggcgcta cgctgccctc cacgattcca 420
ttttgcccca tttactcggg tcgtccactt cccgcggctc agtgacccag ccagggggcg 480
tcttccgcta gcggtccaaa tgtagactcc gcaaagaggc taagaagacc tgtctacccg 540
ggtgcgcgcg atggggtcag ggtgtaagaa ccaggagcct catagaaacc tctgcttggg 600
gtccaaagcc cagccgggca ctcccagagg acaacatccg cccccgcatg tacacgtggc 660
cccgcaggac ccagccgcag ggctcccacg ctcggctccc cgccctctcg 710

<210> SEQ ID NO 239
<211> LENGTH: 474
<212> TYPE: DNA
<213> ORGANISM: Homo sapiens

<400> SEQUENCE: 239
cgaccacttc cgtatgaggc acgattcgtt ggcattcttc acctgcagca accgctgtgg 60
gactaggctg gttccccagc cccggcgggg tgtgagtctg cgacggctgc tcactacatt 120
cgggggacag gcactgcatc gggggtgagc aggccagggc agtttccgag ggcgcctgga 180
gcccgttgag atgtgtggct ctcctccgct cgtcatctgc cgggcagagt gaccactggc 240
tggcggctgc agagtctgac aaaccaggct cgggggccct ggcactgagg gcaggtgcgt 300
aaacggtggc aacctccgtt ttaaacaccc tcctgagggc aggtggagcg ggctcctcgg 360
agtttggcct cccccggtcc tgcttggccc tcccgagcag ctggtaatcg ggctcttcgg 420
atggaggccg agtggagttt tggagcgcag cttctccata gctgagcggc tccg 474

<210> SEQ ID NO 240
<211> LENGTH: 515
<212> TYPE: DNA
<213> ORGANISM: Homo sapiens

<400> SEQUENCE: 240
cgccgccgcc gcggccaagg gcacctgcag aatgtgagag agcctgggag gtcttgcagc 60
ttggtgtcac cccaccaccc taatccccga gggtgggggg aggtcgacgg ccctcctccc 120
aaccccgacg ggtcctgaaa aatgggaatg ggtcagcatc gggggtacct aagccgccaa 180
gtccttgact cgcccctgct ctgccgcgca gggtgctgga gaagaagcaa gacaccgggg 240
agacaatcga gctgacggag gatgggaagc ccctagaggt gcccgagagg aaggcgccgc 300
tgtgcgactg cacgtgcttc ggcctgcccc gccgctacat tatcgccatc atgagcggcc 360

```
tgggcttctg catctccttc ggtatccgct gcaacctggg cgtggccatt gtggacatgg    420

tcaacaacag caccatccac cgcgggggca aggtcatcaa ggaggtgggc aacgtctggc    480

cgccctggct cctgcccttc ggccatgcgg cctcg                               515
```

<210> SEQ ID NO 241
<211> LENGTH: 1356
<212> TYPE: DNA
<213> ORGANISM: Homo sapiens

<400> SEQUENCE: 241

```
cgggaacgtg aagcgaagct caccaccggt gcccgctacc cccacgccgg caactctgtg     60

cttcgtttgg cccacgtgtc ctccccacgc aactaggggc gacggtcctg tgcctgaggt    120

gacaatcacc ccccaaaaac ctcacttgcg ggtggggggg tggtgattgc cagttgaccc    180

agaattttct agcaactagg cgcgttaaag tgaaaagccc ctggactagc tccacctccg    240

gccccaacca tcacaggcgg accctagctg atttgactct cacttcccgc cctcagactg    300

ccggcgacga aaatccgccc gaatcgggcg ccacctctgg tggaagctgc tgtcctcggc    360

ttctgcccaa ctccaagaag cggaaggggg gtgtatcctg cgccccaagc tcatgggagc    420

ccacgcaccg gggagagccc ggagtggagg ctctgggctc agccctccca ggcctaggcc    480

accgtgccct gagtccctcc ccaagacttc tcggactaag tgggccagac tcttgtcagg    540

ggagggatca ccaggacctc agattgctgg gggcggaggg gtggacgctc gtgagtgcga    600

agttcgggtg tcacttgggt gtgtccagtg tctacaagtg ggaatcctac ggtttcaaaa    660

gtcaggcagg gatggggttg cctacactcg gtggggtcaa tcgctagtct caccagaggc    720

gggagcgggc ctgggggccc tctgagctcg cggaggcggc gggttcgggg cccgtgcggg    780

cggggtcgcc caggggagcc cggccccgc gcgtcaggag gcctccgccg gccgagcggc     840

cgcgctggga aacaagaagc gagcgctttg ctccctatct tcccagtgtc cgtcctatat    900

tgttttctgc tcttaaaact gacatgtcta attggcaatt ggtgccgaat cgtgtccaga    960

ggtctcttgt ggaacatttc tacagctgtc tccttcaact agacgcttat tcatgtcgcc   1020

ttaatgagaa acaaaacgtt ctctaatgag caattacaga gcgacaggat tgttcccata   1080

acaaattctt gcgagtgaca gaagcatcct ttgtaccaga tatttcgcat actgttaccg   1140

attttccctt ccctcgcccg actccatgga ggcgccgggc atccggagcc ggtccgagag   1200

ctcacggatg cgccggcagc ctcctcgcag tcccgcgcgc cgcccctggc cccgagcccc   1260

tcggctccgt tgtgctcctg ggagtgagac gccacgtccc attatcccgc atattatctc   1320

cttgtcacga ggacaacaaa taccgattaa tcttcg                             1356
```

<210> SEQ ID NO 242
<211> LENGTH: 512
<212> TYPE: DNA
<213> ORGANISM: Homo sapiens

<400> SEQUENCE: 242

```
cggacgcccg ggtgggaggc tccttccagg acccaggcgc ccaggggcaa caccgccggg     60

ctgcggtgcg cgggtagcag cgaggacagg aagtgcacgt tgcaggcggg cggctgcggg    120

gcctgcagga gcgcgacgtc ctccagcgcg ctgagctctg ggatcccggg gtactccccg    180

aggagctccc cgccgtcgct gtcgcccccc gcgagcttcg ccttgacctg gcccttgcag    240

tcggcgccca gcgcggggtt gaacgcgtgc aggacgggtt ccttggggtc cgccgggccc    300
```

aggtacgctt ctttgaagac gtggaactcg tcctcctcgt acttcacggg ggccttcagg 360
ccgatgttct ccgaagcgaa cggaccctcg gggcttaaga gctccgtcac catcgcatcc 420
tcggggctgg gcagcccgcc cggcagaggg ccctcctcca tggcgcaggg cggcggggcg 480
ggatggcggg ggccgcgcac ctgcaacacg cg 512

<210> SEQ ID NO 243
<211> LENGTH: 3661
<212> TYPE: DNA
<213> ORGANISM: Homo sapiens

<400> SEQUENCE: 243
cggacgggac gggggacggg ggcggggact ggcgggaggg gggcgggaca ggctcgctct 60
cctcctactt agcgagctcc cggggaaaag caacggtgtc ctcctaagcc tgaggccacc 120
gcgaccgagc cgagccaggc taagggacca gtgtctccct gccccccccc cacctctagg 180
taagagcgcc ccgtcccact acacttgcgg gtcccattcg ctgcggtgct aggactggat 240
aaggggaagt ccccggggcc tggcgagagc cctgagatca gctctaggct agggagctcg 300
gcagaaaccc gtgggggaga gagggcaccc caggtgagtg cgtgggggcg aaaggagcgt 360
tatggggagt tttcctgtga gcctcttgct tttgccttcc tcggccgctg ccaacgccac 420
cgccagaggg ggccgtgacg ctctcccccc cttggagaaa ctctgatcct ggccctatcc 480
agactctccc gccggcaccc aggcggccgg gcggacactc gcggggtatc gggcggcgag 540
cgcgcgcgcg ggttttcgtc ctccagcgcc ccacacctcc ccctctccgc ccacagcagg 600
accttggggc gggggtatct cctgtgacgt ctccccgcct gtccccaggc cggccgcctt 660
gatggaccag gaagggattc ggagtccggc tcagagtctt gagcgtctag gagggctgcc 720
tgggggtgtc caggagatgg gaagcccgcc tggggcctcc caggcactcc ccaaggcccc 780
acgtcctcgg gggccgggga ggccgcctgg ggcgccttgc cacgcccgcg cggtccctat 840
tggaatccct agcggagttc cccgagcgga ggctgaccca agtcatccgg gctcccccgg 900
gatagggaag tgcgggcggg cggctgggta ggggcgccgg cgcagggtgg ccgagtcgcc 960
cgctagcgct tccgccgagg caggctcgag tggggacttg gccgggcgac cgcacagccc 1020
tgccggggac ccacggctct ggggcggggc tgcattctgg gccgttagct cagcggtcct 1080
ggagcctccc gaggctgact catcgggcgg cgggctcacc ccccagccgt caaacgcaaa 1140
cgcaggcgcc ccaccacgcc gggctcccac gcggcacaca cgcacgcctc cgcgacactt 1200
cgcacaccta cgtccctgcg tcacgccacc cagacacacc cggacccgcc cacacgccga 1260
ggccttccca cgcactccat gccttacgcc tcacaggaaa gcgccccgcg ctcacgcagc 1320
ccctcacacc cgcagccccg cttacacgcg ccccagctca cacatgcacc ccagtcacac 1380
agcctacctc acacacgcac cccagtcaca cacacaaccc agctcacaca cgtacccgtc 1440
acacatgagg ccccagctca cacacgaagc ccagctcaca cacgcagtcc cagctctcac 1500
acacacaccc cagtcaaaca cgaggcccca gctcacacac gaagcccagc tcacacacac 1560
tgccccagtt acacagccca gctcatgcaa gcagcccgtc acacacacag cccagctcac 1620
acacacagcc cagctcacac aagcagcccg tcacacacac agcccagctc acacacacag 1680
ccccagttat acacacacag cccagctcac acacgcagcc cgtcacacac acagctcagc 1740
tcaatacaca gcccagctca cacacacagc cccagttaca cacacagccc agcttacaca 1800
cacagcccag ctcacacaca cagcccatca cacacacagc ctatcacaca cacagctcag 1860
ctcaatacac agcccagctg acacacgcag cccagctcac acatacactc cagctcacac 1920

```
acgcagcccg tcacacagcc ccagccacac acacagccca gctcacacac gcagcccagc   1980
tcacacatgc agccccctca cacatgcagc cccagtcaca cacacagccc agctcacacc   2040
gcagccccag ctcacacacg cggcccctca cacacattca gccgcccttc ccgcagctgc   2100
caggctcgga acgggcggtg tctgtggggg ccgccccgtt tcccggccgc gcaaacaagc   2160
ggctccttct ctctgccccg ccaaagaaag gccgcttgtc aggggcgggc gggcaggcgg   2220
cagcggcagg cgcccaacac tgcggccttg tcccacgcgg gcagcctggg caggagcagg   2280
ccgaggggtg caaggggccg ctaccttgcg gaaacctccc tccctcggcc ctgcggaccg   2340
cggagaggca cctttccacc accggacacc caagcaacag ccctcgctcc atccgcgctc   2400
tcccggctcc ccctctcctc gggccgccca tctctcctct cttccgcctt tggggtcccg   2460
gtgggcccca gcctccctct ccttcgcccc atctccccgc ccgtcagcct cccctccgct   2520
gccctcgcgc atccccagtg ttcccgtctg tcgtcgcctc cacttgagga cccgcctgtc   2580
ctttcttccc ccgacccctc cacctctgtg ttcttcagtc tccccgcatc ctctgccctc   2640
ggtcttcccc tccccagctt gcatttttc ccatctctta gtctgccttt cattttcccc   2700
ttcacatccc ggtggctccc cttccccgcc ccgtccctct gcacaccccc attcatctct   2760
gtcaggtttt tctcatcctt aagttctctc gtccccctcc ccactcgggc gtcccccgct   2820
gggctccccg cctcagtttc cttcccttcc tgactccttc ctctgacggc ggccctttct   2880
cgagggcgga tgtgcgcctg gagggcgaag gcggcggccg agaggacccc agctcggcct   2940
ggcgggcctc tggccacagc catgcaccgc ttgggccgag gccgaggccg acccccaggg   3000
acacaggtga ggccgggcga cccgcggggc tccggggagc gcccgagcag tggccccgcg   3060
aagggccggg tctggtgctc tggggctggc tttggacctc tcgtcctggg actccgtggg   3120
agcccgggag ctgtgtcagt gcccgttggt gctggagcca gtcggccctt ccttggcctc   3180
cttcaggcgg gggccaagac ccccgagagt tcactctggg tgctccactc ggcggagagg   3240
gcttcagact ggtgtcccgc gtggctgggg tgtcggcgca ttcccgcggg ggaggaggcc   3300
gagggcccgg gccggggtca cctgccggcg ccccggcctt gcgcacagag ggccttgcct   3360
gtcgctcgtc aaatccagac acctgggcct ccgccactcg gctgccgggg cggcactggg   3420
gcgtctgtac ccagcgtgcg ggagggcacc cagggccgga cgcgcaccgc aggggtcttt   3480
ttttggccgc ggggccgggc gggcgggtaa tgacagccgg gttgctgggg agccgcgggc   3540
cagatggaag cggggccgca ggtgagggac gtccctcgcg tagcgccact cagccgccgg   3600
ggccagagcg ggagtcaagg tgagggcgcc cccaggtggc cgctctcggc cgcggcgatc   3660
g                                                                   3661
```

<210> SEQ ID NO 244
<211> LENGTH: 1219
<212> TYPE: DNA
<213> ORGANISM: Homo sapiens

<400> SEQUENCE: 244

```
cgtgcgggtg actcctcttc ctgccgacaa ggtgggcgat gagaacgagg aggcccagtc     60
ccaccagggc gccgccgacg gcgatgggga tcggcgtgtt gttctcgccc agcagacgct    120
cctccgcaga tccgaactgg ttgccttcca ccttgaaagc ctggccccac actgggaata    180
tgttgattga aaacgccttc gtgccgcgga cacgctccgc tccggctgta gaattgccga    240
tggctgcccg caatgctcgc agggagtcgt tggcagcttt aaaagtgggg tctctggggt    300
```

caggaagagt cgtattcagc tggattcctc gtaggaaaat ccggctagaa cctgcattca 360
tccccaaccg gaagcccagg accgtggtgc cctcgccgcg ccgctcccgg gtctccaggt 420
gggcgccgcg ctcccgctgg ctgaggtcat gcccaggtca ccgtcgcgtg gtccctcctc 480
tctgggtgag gttcagctgc agtcccgcgc tggccggcag gcaggccccg tgggtgccgc 540
tcacgctgta cctggccacg gaggggagaa ggggctctcg gcgccgtggc ggggaaggcg 600
cgtcttgctc gtggcgcgtc tctcccttgc tgaagctgct gttggaaatc taggcctgga 660
tcggggcacc gcggagcctg atggtctcgc tgttcgtgcg gacctggggg ccttgatatc 720
tggtagagat tccacagtcc tgatttcctt ggagcttgca ctgaggaaaa tgtgtgtgtc 780
tgacaagttg taaacaaaac tcatgagctg gacgctgtca cgtgtcgcac ttcttgtgaa 840
atggaaggtc agtgtctgtc ttcctccaaa gcacaatcgc gtgcctgggg tcggaagtgt 900
tctctttact gcaagagcca ctgtcaagca cttccgcatt ggatggcagg tcaaaggtca 960
cattcttaga gccactctta gagtcgtagt tcatcgagaa ggcagcgaag ctggccatta 1020
cgcaggctgt cccgttgccc tttttcaccg catccgctgc ggctgcacca cgcacgaggc 1080
ccagcagcag cagcagcacc aggggcagcc gggggctcca ccagatgcag cccgggcggc 1140
aggcgcgagg ggagccggtg tgtggggaac cggggcgcgg ggaggcggtt gcggggcgct 1200
ggcctgaagg acggtggcg 1219

<210> SEQ ID NO 245
<211> LENGTH: 210
<212> TYPE: DNA
<213> ORGANISM: Homo sapiens

<400> SEQUENCE: 245
cgacgggaca cggtacatca caaagagacc cgtgcgagac cgaatcctga aggaacgtgc 60
cttaaagatc aaggaagagc ggagtggcat gaccacagac gatgacacca tgagcgagat 120
gaaaatgggg cgctactgga gcaaagagga gagaaagcag cacctggtta gggccaaaga 180
gcagcgccgt cgccgtgagt tcatgatgcg 210

<210> SEQ ID NO 246
<211> LENGTH: 901
<212> TYPE: DNA
<213> ORGANISM: Homo sapiens

<400> SEQUENCE: 246
cgtgttcccg ggcggaggtg cgcgcagcca ccccaggctg ctgccaggtg cccgctgggg 60
ctgccagggc gaggaggcct ctgggctgtg gagcgaaagt cagatccacc gcctactgcg 120
gggtaggggc cgcagtgggg accgccagcc ctgtggtccc tctcgcgctg actggcgtaa 180
agttgtggcc gaattcgcat ctcttctggt gcttctcgcc cgccagcgca gggcccaggt 240
gtttgaggcg aaggggctct agctccccgc aagcctggag ccaggcgtcg cgcttcctcc 300
gggcttaatc cagacctttc aacacacacc tcattcgggg gaggagaaaa gcacaggacc 360
gcggagagcc cagctttgag gccaggcctg aagggataac ccacacaggg aacgttttcc 420
tatcagagaa taatggagca caaaataatt cagaaagcga atgggcagga ccacagcctg 480
agagtcccgc gccgcggggc cgctgcagag ccggtctccc gagcaccgcg gcaggaccat 540
ttcgttggaa tgtagggcga ggccgaagcc cgccccggac ccaggccgcg aggtgcgcgc 600
cggccgccga ggggccgcct gtaaattaca gcccgccggg aggactcgga aatacacaaa 660
aggagccgaa agatttaaac agtcggaggc agaggcgtcc cgaggcggcc aaagcggaaa 720
tcaatcacgt aattaaaaca gggaggggac gaagcccaag gctgggggtc ccgggttcgg 780
aggaggcggc caaggtgcag gccgaggctg gcgagcggct tagggacgtg gctcgcccgc 840
caggaccaga gcgcgcggag gggcttcggg gaagtttata acacatcgct attgattccc 900
g 901

<210> SEQ ID NO 247
<211> LENGTH: 401
<212> TYPE: DNA
<213> ORGANISM: Homo sapiens

<400> SEQUENCE: 247
cggagcgaca gactagggag ctccgcccgg gatttgccca tcggcggagg cgccaggctc 60
ccgtttctcc ccatccctct cgctgccgtc caggtgcacc gcctgcctct cagcaggatg 120
gacgtgatgg atggctgcca gttctcacct tctgagtact tctacgacgg ctcctgcata 180
ccgtcccccg agggtgaatt tggggacgag tttgtgccgc gagtggctgc cttcggagcg 240
cacaaagcag agctgcaggg ctcagatgag gacgagcacg tgcgagcgcc taccggccac 300
caccaggctg gtcactgcct catgtgggcc tgcaaagcct gcaagaggaa gtccaccacc 360
atggatcggc ggaaggcagc cactatgcgc gagcggaggc g 401

<210> SEQ ID NO 248
<211> LENGTH: 370
<212> TYPE: DNA
<213> ORGANISM: Homo sapiens

<400> SEQUENCE: 248
cgcggtggag atcagccggg agagccttct gctgcaggac agcgactgca aggcgtctcc 60
ggagggccgc gaggcccaca aacacggcct ggccgccctc agaagcacga gccgcaacga 120
atacatccac tcaggcctgt actcgtcctt caccattaat tccctgcaga acccaccaga 180
cgccttcaag gccatcaaga cggagaagct ggaggagccg cccgaagaca gcccccccgt 240
ggaagaagtc aggactgtga tcaggtttgt gaccaataaa accgacaagc acgtcaccag 300
gccggtggtg tccctgcctt ccacgtcaga ggctgcggcg gcgtccgcct tcctggcctc 360
gtccgtctcg 370

<210> SEQ ID NO 249
<211> LENGTH: 423
<212> TYPE: DNA
<213> ORGANISM: Homo sapiens

<400> SEQUENCE: 249
cgcgcgaagc agagaacgag aggaaagttt gcggggttcg aatcgaaaat gtcgacatct 60
tgctaatggt ctgcaaactt ccgccaatta tgactgacct cccagactcg gccccaggag 120
gctcgtatta ggcagggagg ccgccgtaat tctgggatca aaagcgggaa ggtgcgaact 180
cctctttgtc tctgcgtgcc cggcgcgccc ccctcccggt gggtgataaa cccactctgg 240
cgccggccat gcgctgggtg attaatttgc gaacaaacaa aagcggcctg gtggccactg 300
cattcgggtt aaacattggc cagcgtgttc cgaaggcttg tgctgggcct ggcctccagg 360
agaacccacg aggccagcgc tccccggacc ccggcattag gcgccagctg ccggctatct 420
gcg 423

<210> SEQ ID NO 250

<211> LENGTH: 1267
<212> TYPE: DNA
<213> ORGANISM: Homo sapiens

<400> SEQUENCE: 250
cgcaataatg ctgcgtcacg aaactgcgca ttccaagaga aacttttctc aggcccagaa 60
ttaagtcgga gggatccgcc gcgcagctca atccctagga agcatgaaag aatgtattgt 120
aaagagtaaa atcacgcgca atccatccca atataaccgc agttgttcgt gggccttctt 180
gcagagaaag gctgcccaac cttgacgggg ccatgggcgc tgcgggaggg caaaagacca 240
cagagatctg cgaagccaaa gtaaacaacg ggttggggc ggcgagaatg atcaatagcg 300
atgctccgaa aggactccgc gataggaatc gagcgggaag gattccctcc atcctaacag 360
tccatgggtt aagaggccga agcttcccta aataccacac tcccgcgaga gaagggactg 420
agaacaactt ctcaaactat tctctctcga aatcgctccc ttcctcgaaa attccatctc 480
tgagactcgg atgaggtccc cacccctcc acccttgtcc cgtgaccgtc gcccgctcag 540
cctcccagcc gagtccgcgg ggcctggggc gcccaccccg cccacccaag ggaccgcgca 600
ggggtgaact cccccgcgcc ccacctgcgc cttccagacc tcgggcgccc cggcgttgcc 660
tcgagagctc cctgcgcggc cgccgcggca cggaccagct cccactccct tacactgggc 720
gccgctgcgc tcgccggggg ccggtcccga ggttcccaag gcctcgcgcg cgcgcttgcc 780
gtggcaacca agacgttcca cgacgcgcgc tctcgaacgc ttcgcgtcac gcggccgcgc 840
ggccccgccc gtcggcctcg ctcccgccac agagcccgca gcacgccgcc gccgcagcct 900
aggtcacgtg agtacccacg cgcgcgtctt gccagcggat tcatcaccgg cctgctcaga 960
ctaggttctg cccactctga ccttctaaat ggtacgtggg aggacgtccg tccccttcgg 1020
acccaagagt caccgtaaca ctctagaagg ggagaaaagg agcgagggcg gcaggcgaca 1080
gagaacctcg cgagtcagcg gccccgcgca gacccccca ggcacggtcc cctgcggcca 1140
cgtcggctgc tcggcgcctg cgcaatctct ttctctccag cgaaaccgag gcctccggag 1200
agcctagtag agagtgtggg cagtgagcgc ttgtagccgc tagagggagc gctgggcaca 1260
gtgcacg 1267

<210> SEQ ID NO 251
<211> LENGTH: 736
<212> TYPE: DNA
<213> ORGANISM: Homo sapiens

<400> SEQUENCE: 251
cgcggcatgt tcgtaccagc gcgggcagaa acgggctcac gagcgccctc gaattcacac 60
acactcaccg aaatacacat ctcagcccgt ggaagcgcat tcacacacac ccacgtacac 120
tcctccgcac ctcattcaga tgggtccacg cggagtcagg gctgcgcttc ccttggcatg 180
ggcgtgtgtg cggcgagggc gtgtgtgcgt gcgtgtgtga gagtgtgtgt agagaaaccc 240
tttaggcaga ccgcagctac gttattctgc aagcatactg cgattcccga ttccgtgtat 300
gtaggaccac aaaaaaatta aatcgctgtt aaactttttt ttgtaaattc tcttttccga 360
aggaaggcgc tggaagagct actcccggtg gttaaaggcc cgggagacct ggtggcgaat 420
cctggggcgc gtccgctttg gcggagcgct gggctccgct agccggactg gttccccatc 480
taactgatct aatcaatgac tccgaagagc cggggctcct ggccccgccc ccgccatcct 540
cttctccgcc tcccattgga cgcgggccga gaaggcaggg ccttgctcct cgctcggatt 600
ggctgacagg gaatcagtat caatgtttaa gcggcggcgt gaggtgaata gagtcagtca 660
gcaagagacg ctggggagag agcagggatc gcgagcccgg cggatgcggc agcggcggaa 720
ggcggctggg gagacg 736

<210> SEQ ID NO 252
<211> LENGTH: 379
<212> TYPE: DNA
<213> ORGANISM: Homo sapiens

<400> SEQUENCE: 252
cgccgggctc tgcgggggca tctcctggac gatgtacacc gggtgcccgt agtcgccgct 60
gaccttctcg tagtgagggc agaagacgct gtccgcagtc cttagcggga tgataatgtc 120
actgggctct gagccgttgt tgttgccgct gcgcttgggt gtggccagtg tgctgagcga 180
cagcgtggtc gtgtgctgcg gcgagtgctt cctgtgtctc ctccggtact tcagcaagag 240
gaccaccagc gtgatgatga tgacgatgaa gatgatgcat cctgaagcaa tccctgcaaa 300
taaggccact tcggaaccga ggatgttgtt ccccgaatgt ccggcgctgt tgccgtctgt 360
gctagaacct gcagacgcg 379

<210> SEQ ID NO 253
<211> LENGTH: 875
<212> TYPE: DNA
<213> ORGANISM: Homo sapiens

<400> SEQUENCE: 253
cgctcccagc cggcagccgc tctgggcgtg cacccgccac gcgaagccag aggttggacg 60
acgcagccgg ccaggcgcgg ctcccggggg accccgaaac cgcctgtggc tcaggcccta 120
cttggcaaga agagactggg gagtgagagg aggggtcact cttgctctct cgcacaatag 180
acttcccgca ggcgagtgcg aacggccttt tgcttcctcc ttcttttcca ggacccttag 240
cgacaggaga ggaagagaag cggcccggcg gtttaattgc caatttcctg atgcagccac 300
agggcccagc agcggctcag cctaggccac cgggtccagg cctctaggca ataggcccgg 360
cgccccctcc aagcaccgtt tcccgccgac cccgcagtca tcactgtgag ctcgagagta 420
tgggcagcct gtggtgccct gaggcgccgg gcgctcggcg catccgccgt gcccacagcg 480
ctgaggacca actagggctg ccctcggcca ggggcactgt gcccgtttga gtggcactcg 540
gacctggcga ggggtggaag cccaggtaga gctcgcgtct ttaagagcca cccgacagaa 600
ctgcgcgcta catctgcgcc agctgggctg ggtgggaaca gcgcagaaat actcccgtgc 660
cggggcgtac agggcaggta ggcccagcag agagtcttct cggaaagttt cccacaaaag 720
aagggccggg caggccgagc ggcaggaaaa gccggtgctc agcggcgagg cccgagaggt 780
ctggcatccg gcggcctccc agctttgctc gggtctcccg ccgcctctct ccagagccgc 840
ccgtagctcc gtggggcgga gggcgcaatg ccccg 875

<210> SEQ ID NO 254
<211> LENGTH: 221
<212> TYPE: DNA
<213> ORGANISM: Homo sapiens

<400> SEQUENCE: 254
cgattcctat cgaatcaaca cggccattaa ggacaaaaac gggcaggaca caaaagcaag 60
cctggatggc gcaccctaca aacgagttct gaaacaaagc gagtgccaga cgcgcgtggg 120
aaagacgcgc gtgggaaaga cgtgcatggg aaagtcgcgc gtgggaaagt cgcgcgtggg 180
aaagtcgcgc gtgggaaaga cgtgcgtggg aaagacgcgc g 221

<210> SEQ ID NO 255
<211> LENGTH: 1283
<212> TYPE: DNA
<213> ORGANISM: Homo sapiens

<400> SEQUENCE: 255
cgtgacgtaa gtccgccgcg ggttcgccag caccttgcca tcccgcacca cgcccacgcc 60
aatcttattg gcgctgcctt caaaacccag caccgccggc atggcggagg ctgggagaaa 120
acgccgacag gactcctggc aatgtcagga gctgtggagg tcctcactag tccgcgctgg 180
gccgcagctt tccggagcgc agaggaagct ggccagcctg cagatagcac tgggaaagac 240
accgcggaac tcccgcgagc ggagacccgc caaggcccct ccagggacct gtcttcctaa 300
ctgccaggga cgccgagcca actctgtgcc ttacattcgt atccgttttc ctatctcttt 360
cccgtggtcc agcccagcct tctccactgt ttttttccct cttgcacata gttagaatct 420
taagtcagtg tcacacaatg tgctgtgcat ctggcacaac gataaacagc ccgagggagg 480
gttggggacc taagtgtcct agagaattag aggagggagg cgaggctaag cgtctccgtc 540
acgtggtgtc agacagacca atcacgcgca ttcttcggcc acgacaagcg cgcctctgat 600
cacgtgacca ggtccgctac ccacgtgggg gctcagcgtg caccccttctt tgtgctcggg 660 ttaggaggag ctaggctgcc atcgggccgg tgcagatacg gggttgctct tttgctcata 720
agaggggctt cgctggcagt ctgaacggca agcttgagtc aggaccctta attaagatcc 780
tcaattggct ggagggcaga tctcgcgagt agggtacaag gcactatgaa atgatctagt 840
ttcgtgggtg aggggctgaa gggcctatga tgcacggagg cggggaaagg atttagagat 900
aacgtggttt gaaaggcggg acctggtgcg gggacgctct tgggaggagt cttctcccca 960
gccttagctg gtttcatgat ttctttgcgt ctgtaggcaa cgcggtaaaa atattgcttc 1020
ggtgggtgac gcggtacagc tgcccaaggg cgttcgtaac gggaatgccg aagcgtggga 1080
aaaagggagc ggtggcggaa gacggggatg agctcaggac aggtaaggga atgaaatcag 1140
cccttcttcc tagaagctgc ggcgggggtg tttgtcattc ccttgatgta cggtaagtac 1200
gggccgactc atttttgcag ggtttgtga agaagtcgca ggaaccgtag gctttcgttg 1260
ggtctatagt taacgccgga tcg 1283

<210> SEQ ID NO 256
<211> LENGTH: 1167
<212> TYPE: DNA
<213> ORGANISM: Homo sapiens

<400> SEQUENCE: 256
cgcctgttac tagaggcgag aaccggagcc cattggtcgg aacacctcac aatggacccc 60
agcggcgcgc aaaatcctta tgattggttt gctggctgcc tcgggagacc ctgttgccag 120
gatacttggc gttcccgacc cgaccccccgt tccccattgg ctgtcagggc aaaagccgcc 180
atctaatgag gagcgaggtg cggtgccccg aagcgctcgc ttcccgcggt gcgatctagt 240
cctgcagtag gcggcccggg gccacaccgc ggccgcccaa gccagtgcaa ggcccagggg 300
cctgacatcg ctcccagcgc tcgaggaccg aggcctgctg tggaggacac cgtgctccct 360
cgggacctgc tctggattcc ggcccggacg tccccttgga gctctgcatc tccaacctgg 420
aacccaaccc agaagtctca agtttgacgc atcacgtggc gtgcggatcc actgagggtc 480
cacagagagg ggcgcccatc tcctgcgtct cagttatcct ggtaattgtg tatctgccca 540
ttgttcgttg cctcattaac ttggctttct aggtgcaccc accttgccac cagagaagtc 600
caaatcctga cttctctcca aggtgttggg aattctgtgc cctaaagaat tccgactcag 660
atccgaacgg ggatctggtg gaatcgaggg tgaaagacca gagggacaat gttctactat 720
cccaacgtgc ttcagcgcca caccggctgc tttgccacca tctggtaagg gcggggcccg 780
ttggcgcgcg atggcggacg ctgcccggga tcccagcctg acagctcccc ctccatcccc 840
attctcccac cttccccacc cacttcaggc tggcggcgac tcgcggcagc cggttggtga 900
agcgcgaata cctgagggtg aatgtggtga aaacctggta aggcccagaa aagggaagga 960
gggcctggtg cggggggtga gttaggggat ggggtggcca agactgtggg cccactcctg 1020
gacgcagcgg taatcagggc gcattgttcc ccagcgagga aatcctcaat tacgtgctgg 1080
tacgagtgca accccgcag cccggcctgc cgcggccccg cttctccctc tatctctcag 1140
cccaacttca gatcggtgtg atccgcg 1167

<210> SEQ ID NO 257
<211> LENGTH: 300
<212> TYPE: DNA
<213> ORGANISM: Homo sapiens

<400> SEQUENCE: 257
cgtagcgacg acgtggtcct tgtaggacca agcattcttg gcattctgtc gagattgaga 60
ttccagagca tcggatgaac gggacttata gctaaggcgt actcacccac ccctcccttc 120
gtctttttac gcacgcagca actcgtcctc acgtgcatag gggtagtgga cagtgttgac 180
ttgaattgct gtccctcgtt ccaagccttt cctgtgaatg aacccgaaaa cactcgacag 240
gtcgtgaata atcgttttaa tgagtgtgca aagcgtgcga cggggtgcac cgagctgtcg 300

<210> SEQ ID NO 258
<211> LENGTH: 1492
<212> TYPE: DNA
<213> ORGANISM: Homo sapiens

<400> SEQUENCE: 258
cgagaactcc aagtccgacg agaaggggaa ccagtccgag aacagcgaag acccggagcc 60
cgaccggaag aagtcgggca acgcgtgtga caacgacatg aactgcaacg acgacggcca 120
cagctccagt aacccggaca gccgcgacag cgacgacagc ttcgagcact cggactttga 180
gaaccccaag gcgggcgagg acggcttcgg tgctctgggc gcgatgcaga tcaaggtgga 240
gcgctacgtg gagagcgagt cggacctgcg gctgcagaac tgcgagtcac tcacgtccga 300
cagcgccaag gactcggaca gcgcaggcga ggcgggcgcg caggcctcca gcaagcacca 360
gaagcgcaag aaaaggcgga aacggcaaaa gggcggcagc gccagccgcc ggcgcctgtc 420
cagcgcgtcg agcccaggcg gcctggacgc gggcctggtg gagccccgc ggctgctgtc 480 ctcccccaac agtgcctcgg tgctcaagat caagacggag atctcagaac ccatcaattt 540
cgacaatgac agcagcatct ggaactaccc gcccaaccgg gagatctcca ggaacgagtc 600
cccctacagc atgaccaagc cccccagctc tgagcacttc ccgtccccgc agggcggcgg 660
cggtgggggt ggcggtggcg gggggctgca cgtggccatt cccgactcgg tcctcacccc 720
gcccggcgcc gacggcgcgg ccgcccgcaa gactcagttc ggcgcctcgg ccaccgcggc 780
cctggccccc gtcgcctccg acccgctgtc acccccgctc tcggcgtccc cgcgggacaa 840
gcaccccggg aacggcggcg ggggcggggg cgggggcggc ggcgcggggg gcggcggccc 900
cagcgcgtcc aactccttgc tgtacactgg ggacctggag gcgctgcaga ggttgcaggc 960
gggcaacgtc gtgctcccgc tggtgcacag ggtgaccggg accctggccg ccaccagcac 1020
ggccgcgcag agggtctaca ccacgggcac catccgctac gcgcccgccg aggtgaccct 1080
ggccatgcag agcaacctgc tgcccaacgc gcacgctgtt aacttcgtgg acgttaacag 1140
ccccggcttt ggcctcgacc ccaagacgcc catggagatg ctctaccacc acgtgcaccg 1200
gctcaacatg tcaggaccgt tcggcggcgc agtgagcgca gctagcctga cgcagatgcc 1260
cgccggcaac gtgttcacca cggccgaggg actcttctcc acgctgccct tccccgtcta 1320
cagcaacggc atccacgcgg cacagactct ggagcgcaag gaggactgag gcgccgcccg 1380
tcctgggccc ggccaggccc cgcttggagg aggcatcgtc ggcattttcg tttagacctt 1440
taattctagc actttgaatt cgagcaggtc agcgtcttct ctcgccacga cg 1492

<210> SEQ ID NO 259
<211> LENGTH: 301
<212> TYPE: DNA
<213> ORGANISM: Homo sapiens

<400> SEQUENCE: 259
cgcccggccg ctgccgatct cggagctcgg aggccgagct ccacaaattt gggtccaggc 60
ccgctttaga gcccctgggc gggggcgctt ctcagggcat cctgtgaggg ctttgaggcc 120
tccttggagt cgccagatga actggtgccg cctgtgcgcc ttggccccat agcctcaacg 180
gcactctcac tgcctgggct ttggtctttg cccaggagcc tgcccatggc ctacgctccc 240
cgctcgcagc atggcagacc ctgacgaggc tgcccgcctt ggtccgggaa tggaccgatc 300
g 301

<210> SEQ ID NO 260
<211> LENGTH: 1761
<212> TYPE: DNA
<213> ORGANISM: Homo sapiens

<400> SEQUENCE: 260
cggggcaggg tacccgcgag ggcaggcacg tggcggctcc tgcggtgtcc cgggttaaac 60
ttgcctgtgt ttaagacggg tctgcgacag cttggggcgg tccaggtcgc ggggagggcg 120
ggctcctcaa gtgggggatc cgcggcagtg aggactgtag ggtgcgcggg tactccgggt 180
agccgccagc ggaggaagcg gctccgccct tcccggaagc tgcccttgct acacccgtgg 240
ggcctgctcc cggcgcagtc ccgcagtacc tgagcggcac tcggtccttt gaccacgctt 300
ggctgcctca gcttacactt cccagcagga tctggctggg agccccttcc tcagatattc 360
accaggcagg tagaagcaga gggagacgac ggcgaaaggt ggaaggagag gccgcggcct 420
cgggcctcgg gccccgggcc cagacggcgg cctctcgcgg cgacagggtc cttcctattt 480
agcaggaccg cagggttggc agacagcagg gcctgggccg gcggggctct gcggtgccca 540
ttcgagtctc tccagggctt ccctctgtgg ctgtccctcg cctgcccccct ttccttgcct 600 acccttccct ggacggggtt gttgtcaggt gacggcttca gcaacccagc catgcttggt 660
gtggagtggt tcgagttcct ccgcgggccc ccacccccca cccagataag aagcttaagt 720
cctccttctg caggggagaa tcggatgcaa tgaaactaag acctgtggtc gttaacgcgg 780
ttcaaagccg accccaactg ggacacggct cagcttagaa gtgaggaagg cctgggacgc 840
tggaaacaag gggtcacacg tgcgtgtgcc tggccttcgc aggtggatgt gtgcgccgag 900
ctggggaagg ggccagggag ccgcgagact gcggtccccc gcgagagaga agtatgggcc 960
tggccagggt tcgaactccg ttccttcgct gccttccttt tatttttctt cctcatcttc 1020
cttcctctct cccttggttc catcattaaa tctttaaggg attaattcac aactctgtag 1080
taggtagggg ccctgggacc acttgacggg cctttgcagg cagttctgta cagagtccta 1140
acccgtaacg ggcctcaacc ccggctgtgt gtgcgtgtgc ttgtgtctgt gtgtctttgt 1200
gtgtaaaagc aacgcataaa catacccagg gctttcactt attttattga agcaaacaaa 1260
caaaaacagc cactgggttt gtcttttccc ctactcctgc ctgagcgccg ccgggtttct 1320
gagctgctcc gggcgcggac ctagctcacc cgcagccgga tgtcggagcc ggagctgctc 1380
cccacccggc ctcgcccgcg ggcgacaaaa ccgtccctct ggccacggga gagcatcgcc 1440
ttgccaaaat caactcgcat tttcatgtat tcaaatgaga aagactgaga agggcgattt 1500
cccctgctgg gcagtcgaca gcgttggaag gaagaagtgc cccctagggc ctcgcggaaa 1560
cgggaacaaa cctccctcga ggcccccgga accgatatgg cgaccccgcc cagacctggg 1620
tccccgcggc cgcgcgcgtc tcccgccgtt gtggcccccg agttactgac ttttgttcac 1680
accggtcagc gcctgttgga ggacgtgctc agccccagcc ggtccctcct catccagccg 1740
atccccctcc tggggagcgc g 1761

<210> SEQ ID NO 261
<211> LENGTH: 219
<212> TYPE: DNA
<213> ORGANISM: Homo sapiens

<400> SEQUENCE: 261
cgggcctcga ggatgcgagt gtgaggtcga caagatatcg tggaagagag cgaacgaggg 60
aggcccccgt tggaaacagt ttctgtgtta gaacaaacgc caccaaacga ccgacactgc 120
gaggcctgga gctacctggg ctggcgccgc ccgagccccg ggctgcgagc ccagaggctg 180
ggaagtgatg ggacctgggg gcccgagccg gagagtgcg 219

<210> SEQ ID NO 262
<211> LENGTH: 2448
<212> TYPE: DNA
<213> ORGANISM: Homo sapiens

<400> SEQUENCE: 262
cggcgggcgc tgtcgagcac ggggaggtgc tgaaatagtc ctggcgtgct gattcaagct 60
ttgattggca gagccacccg gtgactgaca gggggtctcc atggcgcccg cgccgccaat 120
ccgcccaccc caatagcgga gccagctcgc ctgccggcgt gcctgagccg agccgagccc 180
gaaccccaag ccgcggagcc agcacctcct ccagtcgggg tcgtccgctc ccggccgttg 240
agccaccgcc gccacccggt agtgtgtccc gctgccccaa tccgcctcat caacaagcgc 300
ctggcacact cagccaggcc cgcgggcatc tgctgcgtgt cccgctccgg gctcagtgcc 360
ctcgccgccg ccggcactgc ctcgatgttc cagctgccca tcttgaattt cagcccccag 420
caagtggccg gggtatgtga gaccctggaa gagagcggcg atgtggagcg cctgggtcgc 480
ttcctctggt cgctgcccgt ggcccctgcg gcctgcgagg ccctcaacaa gaatgagtcg 540
gtgctacgcg cacgagccat cgtggccttt cacggtggca actaccgcga gctctatcat 600
atcctggaaa accacaagtt caccaaggag tcgcacgcca agctgcaggc gctgtggctt 660
gaagcacact accaggaggc tgagaagctg cgtggaagac ccctgggacc tgtggacaag 720
taccgagtaa ggaagaagtt cccgctgccg cgcaccattt gggacggcga acagaagaca 780
cactgcttca aggagcgcac gcggcacctg ctacgcgagt ggtacctgca ggatccatac 840
cctaacccca gcaaaaaacg tgagctcgcc caggcaaccg gactgacccc tacgcaggtg 900
ggcaactggt tcaaaaaccg ccgacaaagg gaccgagcgg ctgcagccaa gaacaggtcg 960
gtacctagag gcctccgcgc tttgagcgca ccggggagga ggcgggtgga ggcacctctg 1020
gcgcccttac ccagtccctg gcgactccaa ttcagcagga gttgggagcg cggtctgtct 1080
tgggttaaga gccctgcgtt ctgggctcct ggccgggagt tcccttgccg gctctgcttc 1140
cccacccgct ggctccccac gcctgcgggc agctgcagca gctggtcccg gtcaccaaac 1200
caaggcttca ctgggacgga gaggggaaga gaaataaaaa attaaaatcc tacaaacagt 1260
tagggacccc aagacccaaa gctaattctt gtcagcctgg gcacaggctc ctactattaa 1320
tcgaagcctg gcttattagc aatgtgtcgg tttcatgtta attatcattt tcaaagccca 1380
ggtatatccc tccctaatgc tttgaaaaca gttttcaatg gacttttgag aaatgggaag 1440
tcgagttttc ctcttcccat gcgctgcctg ccactcttgt ctcaaaacag caaactagtc 1500
cgtgggccga ggcttttcgt ttcccggagt gtggatctcg attagccaaa cattttgcgg 1560
aagagcccgg cctcatcccc caggcccaaa tgctccttac aatccttttt gcctttaggt 1620
cgggccgacc cgatccaacg cgatcgcggg agcacttgct caggcgtaag ccccaggcag 1680
acgcaccgtt agaaatggta tcccatgtcc ctgggaccga tctgtccttg tcacccacac 1740
ttcgtttatt tcctgacagt cctgtaaatc tcccaaaagt gcacaacaaa cagggaggac 1800
actgcaagcc cagtatataa aagacctggg agctgcggcg ctgagaaagg gcgcgaatca 1860
tggtggggca caacagtagg gacccgcgga ggggcggccg cggactcctg cccgacctct 1920
gtcgccttgc cgagtaatcc tcgccttaac tgctggggtc ttcggaagaa cctctagccg 1980
ccgggctgga gggacgcagg aggtggtggg ggcgggcgac gggcggctgt gttacgagct 2040
gtgacccgtg ttccctttct tccccgtaga ctccagcagc aggtcctgtc acagggttcc 2100
gggcgggcac tacgggcgga gggcgacggc acgccagagg tgctgggcgt cgccaccagc 2160
ccggccgcca gtctatccag caaggcggcc acttcagcca tctccatcac gtccagcgac 2220
agcgagtgcg acatctgagt tgcccatcca ggatgctcag aagcagattc cagtgtaaaa 2280
acgagaaaaa caaaatgaaa gaggggaaga agatgagaga cctgcaaatc cagcgccaca 2340
gaagccaggt gaccagggac ccgcgggctc gggttgccgt ttcccgcccc accccgcggc 2400
cggcctggct tcactggcgc cctttggccg cgaccacggg aaccagcg 2448

<210> SEQ ID NO 263
<211> LENGTH: 685
<212> TYPE: DNA
<213> ORGANISM: Homo sapiens

<400> SEQUENCE: 263
cggctaggct gcgcctgcat caggcgtggt gattggcagg cgcctacggc ccacgcagag 60
atggccgcgt gggggtcgga gcgccaactt ctcagctccc cttctcccat gaccctcacc 120
ccccacacca tcttcagccg cccactggga gcttcctcca cccctacccc ccagtgccgg 180
cgaggccccc tggcagatgg aagctgctga ctgatggggg ctgccgagcg cgagggagct 240
gagtgaggcc cttgcgccct aggcggttgc accccggacc cctgcagctg tggacgccgg 300
agctgtgcgc agtcatcctg agccagcccg cggggcccga tcggaaggga cgcctctcct 360
aagagctggc ctggagtcct ggagcctcca agcgggcaag taggggccgc aaaggctggg 420
ctgggcctcc gctgaggccc tcgggggcct ctgggccctc atggcctgga ggccgcgcgg 480
cccaagcccc tagagcagag gccgcgctag cctgcagggg tcgacgcagg gccggaggca 540
gcggcttttc cttcccactc cggttgacc ctaaagacac gatttaacgt ggcggcggca 600
gctgcccacg ctgtctggag gagcagggcg cctgggatgc ggcggcgaaa ctggcccgga 660
ggggggccca ggcctcacgc gcccg 685

<210> SEQ ID NO 264
<211> LENGTH: 1592
<212> TYPE: DNA
<213> ORGANISM: Homo sapiens

<400> SEQUENCE: 264
cggaggctcc ttccgtcccg gcctcacctg gatcccggga accgcccgct ctgtcccgcc 60
aaggtgggct gaggaagacg gcgccactca tcagggcaat ggcggcgggc ggaagaggga 120
tccccgtgcg cccccagcac ccgggacgaa tgccaccccg gcgaagcgac ccgaccggcg 180
cgcacggttt cggggagggg accacttcca cattccccat gcccgagaag gtcacccacc 240
cgggagagcg cccaagggcc agagaggagg cgactggtgg aggaggggcg gccccgtgcg 300
cacaaagggg cccggggccg gcaggctccc cgcccttgac cttgggtctc cgcctccatc 360
catctccgcc ggctgccagg gaagggggct ggcccggggc cagaggcgtg ctcgctgggc 420
tgctgctggg ctggggaccg acgggggcgg gggggaaagg agccgggaaa aaagactcca 480
gggctgcaga gtgctccgag gaagcctgca ttccaccacc ttcaggagcc ggtcccgagg 540
cggctccgat tcactgcatg ccccccgccc cccaaagcaa aagttgcacg gatgcacgag 600
ggaaacccct tcccaaagct agcccttcga ctcgcccacc ccccgccttc ctcggaccca 660
ggccgagtgg gggaggggag tgtcagggga ggaagaaagg agcgcgcctt cccagcgagg 720
ccagacgcgg gctgggtcag ctgcgcctcc gcccgcccct cgccgcccgg ctcaggcagc 780
tgctccatta agcccccgaa ttatgcatgg accttgagcc ctctcggccc tcccgcccca 840
ccaaggcaca atcaacgtgc gcagcgggcg cgggtcaaag agagagggaa ggaggtggac 900
gatgggcgca aggccgtggg cgaatcagag gccggcggcc aggcgggggc caggcgcgcc 960
cgcaggcctg ggaacagtgc cgaggagcct cccgacccgg ccagggccag ccgggaaagg 1020
ggcaccgctc gcaggggagg cccccgcgca gttttgaagt tgccaaagtg tccgcgccgt 1080
gccgggtgcg gggtccggga gatgcagccg cccccgcgga gctctgcgcc cctggcctcg 1140
gggaaggcca ttgtgttctc ctgtgtggca atgaaggggg ctatggaccc caaccattga 1200
gcccttggag ggaggggcct gaagacccct cgggcagggc gggggaggct gtcttgcggg 1260
cggcggagag gatgggtatg atttgctcgg gataggcacc gtcgcgggga ggggaggagg 1320
ccaagcttga ggaggggctg ctggagatgg aaggaagtga gaggagactt gcaagttgca 1380
aacgtcgggg aaaccggaaa attgcagtag cggggaggca ggtggcgccc agaggttcga 1440
aagcagaatt gggaggactt cgatgtccac ctcgcagaca gtgacccagg ccccagaggg 1500
ctccgcagcc tggagcctcg cgtcccgcct ccccgcaaca cgctgttttc agcgttccag 1560
accacagcgc tgcagtctac gctgccctga cg 1592

<210> SEQ ID NO 265
<211> LENGTH: 3241
<212> TYPE: DNA
<213> ORGANISM: Homo sapiens

<400> SEQUENCE: 265
cgccaaaaga atgagcgcgg gagggggtca cagcagccag ttcggccaaa catcgacgct 60
gctccggcac gctccagccc agcgcctggg atgtgtcaga ggtacctgcg aggaacattt 120
gcgtgcgatt ccacgcacgc gttgcatccc tcttcccaaa cccggatcgc tgaactgaga 180
ggtggcgcag agtgtctcac caggtgcggg gatttctctc cgcctcaggc cgtacgagct 240
tccctcgctg tccctgagcg caaatgagcc tcttcagtcg ccgaggcccg gccgcttagc 300
tctcggagcc ttccacagcc caacaccctg agccctggag taggcaattt gctcccacag 360
ccctgtgctg gcccttccag gcacagggag tccccccttct aggggtaggg gcgggcggga 420
tgaagcgcac ccagccctct ctcctaccct tcctcctttg gtcccttcgg ctttcgtgta 480
ccttatctcc cgcgcgccca gctccttggc cggctcacct gctaagcgga gcgcggacat 540
gcgctggaac tccggctcct gcagccactt ccacatcctc cggaaggtct cccggccgga 600
tttgagtttg ctccagggtt tggggttgcg cagcaggtcc gagagggtcc cctgggagcg 660
gcagagcacc ctctgcgcga agatggcctg tgggatgctg tagcgcttga gctcggtggt 720
gatacgctgc gccacctctt tggtattgat ctcttccatc tgccctgaat tacttccatt 780
gctgacctgc gcgccggtca ccgaagggtt gggctcccgg gctgtgccca ggagttgccc 840
gtggccctgg gcgttcaggt gggcgtgggg atggtgcgga ggaaggccgt tgatgggcac 900
catgccggcc gaggtgggcg tgaggtgctg ctccccgtgg cggccgagca tggccgggtg 960
gtgggcttcg aagccgttgg gggtgagcat cttgtcggtg ggcatggcgg cccccgggtg 1020
ggcatagtgg gggagccctt gctgggagtt gtggatgctg cccagaccgg agctggagag 1080
gggcgagagg ctctggccca tgccggccac gtccttgtgg tagggggtat agaggttatt 1140
catggaggcc agcccgcgct catcccgcat gagcgtgaag ctaccgctca cgttgcccgc 1200
caggcgctgg tggtggtgcg ggtggtggtg gtgatggtgg tggtggtgat ggtgggggaa 1260
cttgtccgag actgtggaga tgggaggcag cggctgcaga ggggtcaagg tggtgtaggt 1320
ggtgggcatg ctcatacctg ggggagtctc gcaggccatg gtcatggtgg gatgcagggg 1380
gccggccagg ctgtgctcag ggcccggtg gtggtggtgg taatctccgc cgccgctgcc 1440
gccgtccagc agggacgcca tgcccatgga gcgcgggtgc gcggggggca ggtggctgcc 1500
gcggtgcgcc acggagctgc gcgcgtgggg gctgccgccc agcaggtcgg caggggcggg 1560
caccggctca tggctcaccc cgtgcagctc gccgatcgct tccatggtca gctgcgcgtt 1620
catcgtgatc cgggcgagca ggcggcggac acaacatcga tgtggccagg cagaggcggc 1680
gaggggcgca cggagtccgg tcttcacatc ggctgctggc gactgttgcc ttccttcctc 1740
tcactgtggg gctctgtctc tctctctctc tctctccgtg tgtgtgtgtc cgtgtgtgcg 1800
tgtgcgtgtg tgtgtgtgtg tgtgtctcgc cttccctctt accccccacc ttcccctctg 1860
cgtcctcggc tttttttttt ttaatattaa tttccaaaga ggatccgcgc cgttgggaga 1920
gcgcagtgcc ccagcccgcc cgcctcggcc acctctcgcc cctctctttc ttaaaattct 1980
gaggtctccg gctcccctgc cgcggcccgc gcgcctgccg cgtctgctgc ctgcccgccc 2040
cgctggccag cttgagccat ggctctgtta ctgttacaga ctctgtggcc gcggttcggt 2100
agccgccgcc gccgccgccg cagcggcccg ccctcacgcc cgccaggcgc agcgcgcatg 2160
cgcgaggccc gcccccgccc cctaggtcgc ggcgcgccag gcccttggcg tcccggtaca 2220
aatgaaggag ggggcccagc gccttccctg cggcgctgga tggccaggga gctgcgggca 2280

```
cgtgcgaaag attggcgcag agcgcgacct ggggccgccg ctgcaatccc aggagactcg   2340
cgcctggctc gctcgcctcc cttgcttgag tgggctctgt cctcccagcc cggggacgct   2400
cgtgtcgggc ttctagcggc tggagtgctg tgcttggaga catcgcccct ctctctccag   2460
ttgctgcttc ccggtgcagc ttgcccgggg agctggggac tgtgtcatca ccccttcggc   2520
tctagcccac taagctttat ttcccggggg gctgctggga gtgcgctttc ccacccttga   2580
attcacggcc tattggggga tgggggttgg ggtggggtgg ggtgcagatt gcttaaaggg   2640
ctgggtccgt ttggcggccg ttgacccggc acccttcgtc ctcccagata catacttgcc   2700
cacccttct catccatgcc ctggggagag gagtaatcag tgccaagaat cccagttcgg   2760
gccatacctc actgtccccc gccgcctggc tccttctccc gctcagctca taattaaggc   2820
tgtgcgtccg cttcgccgat gactcggcct gtggaggggg gcgagggaga gcggagggag   2880
tgccctggag ggtacccatg ttaacttccg ggtgctggtg gggccgtgga ggctcgggcc   2940
gtccctgcgg ttactcccaa ggccctcctg ctaaagcacc cggaggcggt tgctttccag   3000
aagtactgac gcagacaggg tggacgccgg cgcgcgggtc tccgcttggc ccctagggac   3060
gccctttcc cggcgtcccc gagagacgcc tccagatttg aaaatcaatt cagcttcggg   3120
agtaatttcg cccttcccac agtcacgctc caatctggaa tcgaacctgg tctttgggcc   3180
tggtggggac gtgtgcggag gcccccagtt tgagacgtac acccggccgc cacatgccgc   3240
g                                                                   3241
```

<210> SEQ ID NO 266
<211> LENGTH: 2385
<212> TYPE: DNA
<213> ORGANISM: Homo sapiens

<400> SEQUENCE: 266

```
cgcgcggctg ctccatctgt gaacgtgagt ggtcgcctgg ctccctcttc cgcggcggcc     60
gcttcctcat accttcacac ggcgcacacc ggccggcgcg tccagctgcc tgcccagtgg    120
ccgaggctct tccccctcgc ccagtcttga gctggaagtg attcctattg gccaaggtgt    180
ccatgtaaat aggtgtgaaa gaaaccagag ctggccgggc tctcccttct cgctcagtcc    240
cctccctctg cagcccccgc tccccctcct cttcctcctc ctcccaaggc gattgtcata    300
tgatagctaa gaagtggcac attaatgaag cgccgctaca ggggtctttt ctgctcctgt    360
caccgcttaa aactatcaga tggttcgagg gaggacatgg aggcagccac ctagctcagc    420
ggagacgcgg agcccacagc agcgccctcc ggagccctaa cacgtcgctg ccaccatccg    480
cgccgggact ccgcagccga gctcggccgc ccgcaggacg ctccaggagc gtcgcggacc    540
gggcggcacg ggacgctgcg gggctgagct caagagccca ggttcgcgcc gagtccaacc    600
ggacccggac gctgcgcgcg gagtgcgcgt cgagtgcgcg ccgagagaga agcggcgcgc    660
agcggcgtcc tcccggatgc ggacgcgcaa cttgaagcaa ctttaaggtg agcagctctc    720
tgttccgtcc ctgcccccta ttctggcccc agtaccgact tacttcccgg ctatcctcgc    780
gccgttcgcc ggcttcccct cccgcgccca ctaagcccgc aaagttgctg gcgaaagagt    840
ccgggcgctg gctgatcgag cgccgcaggc cccacccccg acccccgaag tctgttactc    900
ggtctggctg accccgccgg tgtctctgtg catccatgct acctttccct attacccacc    960
cccttcccag atccgagcag tccgccggcc cgcgcggacc cagagcaaga agagggcgag   1020
gaagaagatg cctcggcccg gccgcaacac gtacagcgac cagaagccgc cctactcgta   1080
catctcgctg accgctatgg ccatccagag ctctcccgag aagatgctgc cgctgagcga   1140
```

gatctacaag ttcatcatgg accgcttccc ctactacagg gagaacacgc agcgctggca 1200
gaacagtctg cgccacaacc tctccttcaa cgactgcttc atcaagatcc cgcggcggcc 1260
ggaccagcca ggcaagggca gcttctgggc gctgcaccca agctgcgggg acatgttcga 1320
gaacggcagc ttcctgcggc gccgcaagcg cttcaaggtg cttaagtccg accacctggc 1380
gcccagcaag ccagccgacg cggcgcagta cctgcagcag caggccaagc tgcggctcag 1440
cgcgctggcg gcctcgggca cgcacctgcc acagatgccc gccgccgcct acaacttggg 1500
cggcgtggcg cagccctcgg gcttcaagca ccccttcgcc atcgagaaca tcatcgcgcg 1560
ggaatacaag atgcctgggg ggctggcctt ctccgccatg cagccggtgc ccgctgccta 1620
cccgctcccc aaccagttga ctaccatggg cagctcgctg ggcaccggct ggccacacgt 1680
gtatggctcc gccggcatga tcgactcggc caccccccatc tccatggcga gtggcgacta 1740
cagcgcctac ggcgtgccgt tgaagccgct gtgccacgcg gcgggccaaa cgctgcccgc 1800
catccccgtg cccattaagc ccacgccggc cgccgtgccc gcgctgcctg cgctgccagc 1860
gcccatcccc accttgctct cgaactcgcc gccctcgctc agccccacgt cctcgcaaac 1920
agccaccagc caaagcagcc ccgccacccc cagcgaaacg ctcaccagcc cggcctccgc 1980
cttgcactcg gtggcggtgc actgacccgc aggagcccac gccccctctc gttctcctcc 2040
ccaccacctc actcgccttc cctggctccc agtcctgccg gcccccacct gggaccgcca 2100
ccctaacttg ttcatttcac cttcggccaa cccgccttgc cccaagagaa ctttgttttg 2160
gacccaggag accaaacaca aacttgcaga tgggccgaga ggcgcgtggg agttgtcctc 2220
gcccccacat caaggaaggc cggggccacc tgagccgaac catcccctcc ctgaggcccc 2280 gaaacccccct cctatttgac cggcgggggga aaccctgtca ccccctcttc gccgagaaaa 2340
gcgcgtcttc cctccgccca gatcggcgga gccccgaact ctgcg 2385

<210> SEQ ID NO 267
<211> LENGTH: 264
<212> TYPE: DNA
<213> ORGANISM: Homo sapiens

<400> SEQUENCE: 267
cgcgcccctc tggcctccat cactgtcgtg ccggtcgtgg ggacagatgg gagggaatta 60
cggtatttac agctgctctt cgccggctct tgctccccccg cgtgtcgaca accgaaactg 120
cagcgaggcc cagaggcctc tgcccactcc cctcggagtt ccaggaggac gctaagcgcg 180
agaagccagg ctcagggaaa ctgaacgccc atacgctcct agtccctctc acctggatcc 240
tctgcgtcag gttacgtgct tgcg 264

<210> SEQ ID NO 268
<211> LENGTH: 7090
<212> TYPE: DNA
<213> ORGANISM: Homo sapiens

<400> SEQUENCE: 268
cgggacgcag gtgcagggtg ctggacgcag gtgtgcggcc gcttacctgg ggcgtgcagg 60
ccttgggctg cggggaggcg gcgggcgccg cgcgtggccc gcgggcgggc ggacccgggg 120
agggcgctag cgactgcgcg ggcggtgggt gtggcgcccc ggctctcagc tgtcaggcgc 180
gcctgccccg ccactcgggc tgtgaccgcg ccgtccccgc cgccgcgcca tgcgctccag 240
gcttcggcct cttcttccgg ccagtccccg gcctcggggt caacggctca gggttcgcat 300

```
ctccgcgccc ggggtcccgg cgccccgtgc ccgctgagag cgggaggggc cgcgggtggg    360
agcgcggaga accagggagc acggctgtgc gcgcgcgcgg ggaggggccg cgccgtcacc    420
cggagagccc ggcggatccc ggactcccgc ccgccgctcc tcccgccgcg cacctccgct    480
caccgctcgc ccggctccag ccgccgccgc actgtgagta cccacgtccg gtagcccgcc    540
gcccccgcgc tctgctcctg cagctttttt ttcgtttagt tctgatttgg gctcctgtgg    600
ctgttgtttt tatgattata cctaaagaca ccaccgcctc gctcccacca ctgccagtct    660
cccgcttcgc tgccctcccc aagctcgtcc atctagctcc gggagccgac gggggttcct    720
caagctgctc tggctgctgc tccttgtcgc tgcatatggc tcttcgcctg tgctttccgc    780
tttggccccc gaaattccgt tcctttccta gggaccccct tcttctgact ccgggcccgg    840
acccccctcc tctcactcag ggaaaaccgc gcagggaccc aggaccctca actggggtac    900
gctctcggct cgggcgctgt cttcactgta tgcgggccag gcatagttgc cgatttcgag    960
aaaccgagaa gctgtcattt cccagcgctg cgcgccctcc agccacctcc aggagggcgc   1020
gaggcttgtc agccggggag ttaggacagt gtttttgcct cctacaatga tataaaggac   1080
ttcaacgcga aataagggtc aacttatttt agttcgatcc tcggagataa agatgaaaca   1140
gacagataat acataaatag cttgatactt gaagaaggta caaaacagat gagagaaaga   1200
ggaacgagcc ggcagagaca gctcagggac agataagatc gacaaatgag ggtctcctag   1260
acaaatagag aagaagggag agagacagat aaacagaaga ttccagtctc cttgctgaag   1320
gcttttgaac tgggatcccc tgtctggagc tgcccctctg aaaacggagt tacattcagg   1380
gccgactgca ggggaggagc cctcagggtt gggctgccct ggccgcagga gcgcctgcag   1440
ccttgggccg gatgggagcc tggcttgtct gaggacatgt ggctgggtca ggcgacctag   1500
agggccccaa acatcagtcc ccaagtaccc ccgctgctga ggtctgcctg cacagctccc   1560
tccctgcctc agccagaaag caaagtgcaa ggaccagcag caacttgtgt gcctggagcc   1620
ttgcaatggc tacgaagatg gctgagattc cttctagccc atatgagccg ggacagcgag   1680
gcatgaagga tactcagaga ggtgatgccc ctcaaagagg aagcccagag ccccgaatcc   1740
tgcagttggc ccgagtggga aacgtatatc tgaaggagga aagctcaagg agtgggcgac   1800
tggaagctaa gaagtggatc ccaacaaagt tccttgagaa cctctctgtc ccacacgttg   1860
acctcggtgg aaaccagctt tggtctggaa tacagctaaa aatgcagaaa atgtggttag   1920
aactgcagga tcctggtctc actaatagct ggaaagaaaa cggtttatat atccagccga   1980
aatctttctg ctcaacgaac gcgggcgcca gccgtgagag gagaagctcg ggtttgtgga   2040
aactggcaat gttgtcccct gaagccggct cgggcaccaa gctgggtgcg gtgggggccg   2100
cgctaggtcc gggtgcgcac cgagcgcttt ggagagggtc aggttcagca ccgcgaacag   2160
cggtagcctc cgcctctctc cttccctggc agacacggtt ccctcctcct tctcctcacc   2220
cccctccttc tcttcacccc cctctacccc ctgctgtctg gagatgggca gtgaccgccc   2280
ctcccccctc cccacccctc cttgcactgc ccccgcccgc ccgcgtgcat gcgcgactga   2340
gcagaggggc ggccgatccc cgaagtccgg gcttcaggac ccgggccggc agcaccggct   2400
gcgagggttg ccgaaggcgc acggatctgg gcgctgaaaa agccaggatt tggcaatggc   2460
tttgctgtgt ggccttgggc aagtcactct gcgtatctgg gtttcacttc cttcccaatc   2520
cgaaaacggg attgggttcc ttgcagcccg ggcattcctg aggtctcctt taccccttct   2580
cctcccccaa gccccgggggg ctgttgttaa cggcgccaac atgggtctga gtaacaaaag   2640
acgcctgtcc agggggtgaa tgagtttgga ctccccactg ccaagtatcc cccgcgcgcc   2700
```

caactcggag cgccctgctg ggcgggcccg agcctcggcg gcggcgctga aaatggctca 2760
tctgctctct gctttctcta tttcgcagga gcggcggcat ggaggctctc accactcagc 2820
tggggccggg gcgcgagggc agttcctcgc ccaactccaa gcaggagctg cagccgtact 2880
cgggctccag cgctctcaaa cccaaccagg tgggcgagac gtcgctgtac ggggtgccca 2940
ttgtgtcgct ggtcatcgac ggccaggagc gcctatgcct ggcgcagatc tccaacaccc 3000
tcctcaagaa ctacagctat aatgagatcc acaaccgccg cgtggccctg ggcatcacgt 3060
gcgtgcagtg cacgccggta cagctggaga ttctgcgtcg ggccggggcc atgcccatct 3120
cgtcgcgccg ctgcggcatg atcactaagc gagaggccga acgcctgtgc aagtcgttcc 3180
tgggcgagca caaaccaccc aagctgcccg agaacttcgc cttcgatgtg gtgcacgagt 3240
gcgcgtgggg ctcgcgtggt agcttcatcc ctgcgcgtta caacagctct cgtgccaagt 3300
gcatcaagtg cggctactgc agcatgtact tctcgcccaa caagttcatc ttccactcgc 3360
accgaacacc cgacgccaag tacacgcagc ccgatgccgc caacttcaac tcctggcgtc 3420
gtcacctcaa actcagtgac aagtcggcca cagacgaact gagccatgct tgggaggacg 3480
tcaaggccat gtttaatggc ggcacgcgca agcggacctt ctccctacaa ggaggcggcg 3540
gaggcggtgc caatggcggg tcgggtgggc aggggaaggg tggtgctggc ggcggtggcg 3600
gcggtggccc agggtgcggt gcagagatgg ccccaggccc gccgccccac aaaagcctgc 3660
gctgtggcga agatgaggct gccgggcctc cggggccacc tccaccccac ccgcagcgcg 3720
gacttggcct ggcgactgga gctagtggcc cggcgggccc aggagggccc ggtggcggcg 3780
ccggcgtacg aagctacccg gtgatcccgg tgcccagcaa aggctttggg ctcctgcaaa 3840
agctgccccc accacttttc ccccatcctt acggcttccc tacggccttc ggcctatgcc 3900
ccaaaaagga cgacccggtt ttaggcgcgg gcgagccaaa gggcggtcct ggcactggga 3960
gcggcggcgg cggcgcgggg acaggcgggg gtgcgggggg cccgggagcc agccacttgc 4020
ccccgggggc aggggcgggc ccgggcggcg gcgccatgtt ctgggggcat caaccctccg 4080
gggcagccaa ggacgcagcg gcagtggctg cagcggccgc cgccgccact gtgtacccga 4140
cgtttcccat gttctggcca gcagcaggca gcctcccggt accgtcctac cccgctgctc 4200
agagccaagc caaggccgtg gcggcagccg tggcggcggc agcggcggcg gcagcggcag 4260
ctgctggcag cggtgcccca gagcccctgg acggtgccga gccagccaaa gagagtggcc 4320
tcggcgcgga ggagcgctgc ccgagcgctc tgtcccgcgg gcccctggac gaagacggca 4380
cggacgaggc gctgccaccg cccctggccc cgttgccccc gccgcccccg ccgcccgcac 4440
gcaaaggctc ctacgtgtcg gccttccggc cggtggtcaa ggacaccgag agcatcgcta 4500
agctctacgg gagcgcccgg gaggcgtacg gcgcggggcc tgctcggggg ccgggacccg 4560
gcgctgggag cggcggctac gtgagcccgg actttctgag cgagggcagc tccagctaca 4620
attccgcctc gcccgacgtg gacaccgcgg acgagcccga ggtggacgtg gaatccaacc 4680
gcttccccga cgacgaggac gcccaagagg agaccgagcc cagcgcaccc agcgcagggg 4740
gcggcccaga cggtgaacag cccactggac ccccttccgc cacctcctct ggcgcggacg 4800
gtcccgcaaa ctctcccgac ggcggcagcc cccgcccccg gcgccgcctc gggccacccc 4860
cagctggccg gcccgcattt ggggacttgg cagccgaaga cttggtgcgg agacctgaga 4920
ggagcccgcc aagcggcggc ggcggctacg agctgcgaga gccttgcggg cccctaggag 4980
gccccgcgcc ggccaaggtg agccccgcgc ccgccccgcc agtggcgcct tcccacctac 5040
cctgtgcgcg gcagggctgc ggggccgggc ggagaacggg aattttgttc cgcgcaggcg 5100
tgggagcagc aggcctcggc cactctccgc aggcccagcc ttgggcgcgc tgcgaaactg 5160
ggcccacccg caccctccag tgagggtttc gaagggaagg gaagctgggg gcggcgggag 5220
gactggggaa cttgtgtgct ttgtttttgt tgatgggaat ggggaggaga ccggctgaga 5280
ctgccagaca cagagacaga aaaggggtgt ggagaaagaa agaggaggta agaaaggaac 5340
ccagagccag agaaaagcgc tcgcccgggt gggcatcaga gccccaagga agaggagaag 5400
agaggacagt gtggcctctc cctgagtcgg gccccagcag taccgggtcc ccggaatctc 5460
ccaccacccc aactcgcagt tttccgagtc tcttcgcact cccgccttgg gaaccacagg 5520
gttcgttgct gggaagctgt ctcgggaccg cgtgcggagc gggagggggg ctctcaagct 5580
ggcagggccg gggcttgagg ggcaggatgc agccaggctg gagtcgttgg ccattttgaa 5640
agtgagtgcg catacctgta cattcggttc attaaaacac gaatcattaa ccggatgcga 5700
aaggcgtcat ttatgccgcg gacggggcac tggcgggagg gaaaatgcct aaaaggaggc 5760
gggtgcagag ggtggaggac actttgaacg cccctcggct tgggagccgc tttgtgttta 5820
gagtaatttt cccgagggcg ctaacaatta ccctgaatct acaagggggc aagggtgcgc 5880
cgcgtgcgtc actgtgcccg ctcaagtcca gcgggcgcac caacctttgc cactccgtcg 5940
gctttccctc ttggccgcgg ggtagggctg ggcgtctttg ggccgccgca gggcgccacc 6000
ctaatcgcct gtcatttctc ggccgtcgca ggtgttcgcg cccgagaggg atgagcacgt 6060
gaagagcgcg gcggtggcgc tggggcccgc ggcctcctac gtctgcaccc ccgaggccca 6120
cggtaacgcc tgtcgcggcc gctggccact gtaatggggg aaccgcagac agagggccgg 6180
ggtcaaggaa ggcctgcgaa ggaagacaag gagagagacg cagagaaaga gggagaggga 6240
aagaaaaata atgaaaacaa ggaagctaag ctagtactcc caacaacttc caatctttag 6300
ttacttaaaa acaacagtga caacgccctc tccaccacac gcacacacat gctgcagtac 6360
acccagacac ggcgttaaac ccttaacaaa atcacgcccg acacggcctt caaatcctct 6420
catttattca gcaagtgtgt ttggccgcgg ggtccccttt ggctaggccg gatcggggcg 6480
gaggatgggg gcacatggcc gcgcgcttgg gtaccccaga agcgccaggg tagctgaggc 6540
ccatcgcggg gtggtggggg ccgccctgca cttgcgcgcc ttaccaggtt cctcacagag 6600
gaggggttgg gggcagcgga aaatcgggca ggtcgaggca gccgaacccc ggacgatgtc 6660
cccccaccca ccccgaaggt cgcagcctgg gccgcgttct cagcaggagt cgggcggaca 6720
gacccggcgg ccacgcgcgc tcgcggtgcc ccagtatctg cgcgcgatgt aggtcgctcg 6780
tccctggtgg gctcggctgc tcgcctagct cttttccaag ggctggggc gggggcctga 6840 agcccggaga tgagcagacc aggcgcgggg gtggggggtg cccggcccaa agcctcaggg 6900
cgcgctcctg ggcgcacagc cgggaaccag aggcggccac gacgctttta attagggctg 6960
gggcgccccg accgcggcag ctccggcagt atccgggtca cggtttcttt gcctctcttg 7020
aaattcggtt tgttgccttc aagagccaga taaggaagac aatcactcgc ccgccgatga 7080
tttggaaacg 7090

<210> SEQ ID NO 269
<211> LENGTH: 3174
<212> TYPE: DNA
<213> ORGANISM: Homo sapiens

<400> SEQUENCE: 269
cgggaagtaa agcctcggga ctttggttaa gcgcgcccca ctggcgtatc gcgccgcggg 60
actgcagagc cgtgagcagc ggtcgccttg gtgcagggtt ccagccacat cttcctcgcc 120
cagccagcac cctctgccgt tgacccgcct ctgcgcccgg caagcggctt ccagcagggg 180
gcgcgcgcgg accaggcttg ggccctagaa cagcgcggat ggagtcgctg gagcaagtcc 240
ccagatccaa ccggtttcaa ccctccccac cctcccgacg ctccgggttc gcgacgttga 300
agttaagggt cgatccgcag aaagcggcca ggggctccag ctctccattc ctgggtctgt 360
ctggggtcgg ctccagcctg gttagaagcc ttagtctgga ttcggcagat tctgaatctg 420
ggaccctctg cgctagcggc ttggaacctt gtcaccctcc cctcccccac ccctacttcc 480
acacacctga ttagttgtct gtttctttaa tgatcaaaga cgtgggcggc ggcgggatga 540
ggtcttggtt cccggctcca cagccctccc taactgtcat tattaacgtt ataaacatta 600
gacccgcttc tgcgcgccgg acggcgccgg acgaggtgcg cgcagtcttc tagctgagct 660
cggaggcaga tccagaagtc gcggctccca ccccaggcct cggcggactc tgcctggggc 720
gactcgggct ccagccctgc ccgggcgggc actgggctct ccagggtcga aggcaggggt 780
aaggggcgtc tttcccccag ggcagcctcc gggaacaaaa gcatttgctg tagagtgagc 840
tagagcctcc gggcccgcgg gagtcagctc ccgcccaggg gtggtcaccg cgtccttaac 900
caccccagga gccccgtctc cctgccgaac tccttggctt ctgcaaccct gtcaagacag 960
caaggaaagg gggtcttccc tggtcctcgg gccccgaagt ttcggggttg cttataggac 1020
gggttcctgc agtccaggga agctctgggc agatagcgag cccattctcc cttccattac 1080
ccagattctg cctccctgcg gaaggcaaaa aagaaagaaa gaaaataggt aaaaaccggc 1140
ggagggcctt gagcctcccc gcctggcgcc cctcactcag tcccgaaaag tcccctggac 1200
acgccatgcc ggaccggact cagctcccgc tgctgggccc ctgcctccaa atatccttcc 1260
caggcacagg ctcccaagac cgccccctca gggttcccaa cacccggaca actgcccaag 1320
acgccgctcc ccgcccccac ccccaccttg ttcggcagac aaagaagggt gtgctggccc 1380
cgccgtctgc ctccttctcc cgaccccaca aggcctagaa acctcaggga ctcaccccgg 1440
gctagggacc caatcctggc tgtcccacca caggatcccc ggcagggacg ggtcacagtg 1500
ctctcacccc tcgaccattt tcgaagacac cttccctgaa aggcgccttg cgccctcccc 1560
atgggtcggc ggggggggac tccaggcccg agcaggcggt gtgaagttct gtgttctgaa 1620
ctggggctga gcaagatgcg atggtctcag cccgctgggc cgcccgtagc gacggcagga 1680
gtaggggaga gggagggacg cttggagtgt gagcgcacca gtctgttcat atttaattta 1740
caaagcagcc tcggaacccc gggccgggtg gtctctttag acgctgcgct cttagcctgt 1800
ctctcttccc cacccccctcc cctagctcat taagatgctc aacactcaaa tcggggtatt 1860
gatctccacg gaagccccaa accctcgcca tcgagagacc cccatggccc ggggtgatgg 1920
ctgtggggct tggtgctccc agagagctca gtggctacag aatgggtggg gattctgcgt 1980
gtctcccgga gcctgaaccc ctttcctggt tatggccggt agctgtctcc agggctaacg 2040
tgggcagcgc aggggggcgg aaaccgggtt ttagccaaat gcctcgacat cgccgcgcct 2100
ccgcctcctc gtcgctgaaa gaaatgtcgg ggtttcatca gagctaggga gcgacagtcg 2160
ggaacagcga gtctgccgaa gccggctgtt gtgtgagggt gtgagacggc ggggcggtga 2220
ggggccaccg cggcttgggg gatagtgcgt gtggggttga ccgtgtgtct gcttgagagg 2280
ctgtgaagat atggggggca gatatgggag aaatgctcgg gcctgaagtc cccagcccac 2340
cgtgctcaag agtagcggac gttttgccac catccttgtc tgtgctactg tctgctgcag 2400
cttccgtgcc ccgttctcct ggagcaggca agacctggag tgaggtgctt gggtgcgctc 2460
gagagagctt cccccctgctc cacctgtccc gcggtgcgcg caggccaacg cgtcgggcag 2520
tgggcttcaa gcgctggttt agccacaaaa gaccagaagt aaagagttcc ggcttaagag 2580
gctgggcagg gctgcggtgg gctggggagg ggggtgtccc ttcccagcac gccctgcagg 2640
gctgtgcgtt ctggtgtcgg gttagactag caggcggggc gggggggttg gggcggcggg 2700
gcgggggaga ctagggctta tatcagccca gatccaggca aaaatggtag ggagggtgcg 2760
gcgctctgct aacactatca attatgcatc atgttgaacg tggcttcggg gaggaggcgg 2820
ctagcagcgg ggggtgcggg agggaagggt ccgcgcgagc tcggctgcgc gcagctcagc 2880
gggtcccgct cgaagtctgt cggtgccacc gcctgcattt gcaaaaagag tttaaaggca 2940
aagacacgcc ttcccccccc acttcagccg cgcgcctttc cttcccccaa attcctcaaa 3000
gatggtttgt ctcacgtgtt gcagggcgta aaagcggctt gcattcaatt agcagcgaag 3060
ctcgcgggcg ctggcgggac aggcgcgtga gggtgagttc gcgtgaatgt gtgtatgcgt 3120
gtgcgagagg agaacggtaa gtgtcccggg tgcaggtgtg cccgtgaaaa tgcg 3174

<210> SEQ ID NO 270
<211> LENGTH: 315
<212> TYPE: DNA
<213> ORGANISM: Homo sapiens

<400> SEQUENCE: 270
cggagctcaa aagccggacg ctactggacg aggcttaaag cgctcgcccc agcgcggggc 60
cggtgaggaa cgttcaccgt ggaccatggt cgaataatgt tagcgtgcac tcggggcctc 120
gccctagcct tctgcaaagc ctcggcctgc gccctcggct gcatccgttt cgacgccaac 180
caacctcatg ctcttagtag aacggcagta gcgaccgcgc cctcaggccc acaagcccga 240
aggtctgggc agggtctgga atggcggtgg agacacttta tccgcaggcg tttcacctcg 300
cgccccaccc aggcg 315

<210> SEQ ID NO 271
<211> LENGTH: 1171
<212> TYPE: DNA
<213> ORGANISM: Homo sapiens

<400> SEQUENCE: 271
cggcatcttg gccgggttgt aggagcgagg gagaacgcga ctgtaacgcg ggcgttgagc 60
acctagagtt ccccttcctc ttcactgaga gctgcggcgg aggctttaga ccgaggagcg 120
agatctaagg ttaaagaaag ggcctctgag cccagtgttg gccagagacc ccacaggcgg 180
gccgggttcg ccctttgcct tcggccgcgc cccacccacc agggacagag tggccgcggc 240
cgagccgggt ccacccgccg cagcttagct ccgctccgcc gccctccccg tccgtcctcc 300
ccaggctccc gtcgccctcg cccaccctgg ggccccctcc ccagatggga gcccctccga 360
cccctgcgag gcccgctggg gacccacttg accgcgagat cgtagtggga gctcggccaa 420
aagaattctt cgctttccct ggccctcagt ttacccatct gggaagaggg gcgtcgcggc 480
cgcagaagtc cagctccgca cgcgccaagc gctgggtctg cagctccctc ggttcccgcg 540
cacccaactg ccccacgacc cctacccgcg cccgcagccc ccgccctccc gccccacttg 600
cctgggccgc cgggcgctgg aacctggacc ctggaccctg gcgggttccg agctgcgccg 660

```
ccgccgtccc tgcccctcca gcactggact cctcctttcc cgtcttttta aagggaagta    720

accggacccg accactactc cacccgattc acccctagcg ggccgcccgc ccgcagctcc    780

gcccgggctc ctcccccgtc cgcccgcggc ttcccgggag ccccccaggg ctcctccgct    840

cctccgacgg cccggccttc cccccggggc ctgggatgca ccagggctcc tgctgccccc    900

gacggggtcc ctgtcgccgc agcccgcggg acccgccggc cacatctgga cggcatctgc    960

cgcgggggag gggctcagag cctcgccctg agtgtcccgc agggagcctt gtgcatccgg   1020

ggcaggaagc cagcgcatcc cgtgcagacg ggtggtgcag ataacggacc cgccacagca   1080

cgcaattcaa ctttcttggt acctgggact cgtagttcag aaggcgcagt agcacgacct   1140

tgcgaaaaag caccggagtc gggaacacgc g                                  1171
```

<210> SEQ ID NO 272
<211> LENGTH: 257
<212> TYPE: DNA
<213> ORGANISM: Homo sapiens

<400> SEQUENCE: 272

```
cgccacccgc acgacggacg tcggcaccac acgagctgcc cttggcaaaa cgcgttgtcg     60

gctgctggga tggatttcag gttaaagcag agtcaccagg ccgaccactg cttaccttgt    120

tagcatctag aaccttcttc agctcctcgt ggctctgctg ggtgataagc acggtctctg    180

cggaggtgat gcagccgctg cacgccaggc agtcgtttag cgagaccttg gccttctcca    240

gcctccgggt cccgccg                                                   257
```

<210> SEQ ID NO 273
<211> LENGTH: 895
<212> TYPE: DNA
<213> ORGANISM: Homo sapiens

<400> SEQUENCE: 273

```
cgggtccact cctcactcgc gaagtcccta tctatctctg tgggtcccgg aggcacaggg     60

ctgcaagggc gcccgctaga gctgctccac ggcttaccgg attgcatgcg gagaagaaac    120

gggcccgggt ttcaacagag gccccgtgct ccgtgaattt ctaactcgaa ccagccgctg    180

ggataaatcc gagaaacgtt gtttattgtg ctattattaa ctttcccttc tccccacgcc    240

cctagaggaa ataaaattca ttcctgaata ttgggccagg aaaacgtttc tctgaaagga    300

accacaactg caggggacca cccggctgca gctcccagct cccggccctt cgccctaggc    360

tgcccactcg ctccggctcc cgacctcccc gctgccgaag caactgggtc agcctttcag    420

acttaaaacg aagtcgttta tttcattttt gctttcacat tatgttccga tacaatcaaa    480

actcctggac gaacctcttg aataaagtcc tgtgaatgag cggaatcata ggtcctgggc    540

gcccgagtat gcggcgggtg gactccggat tcagaggcgg tgtataaaac atacgctgct    600

tcgggaactg cgagggggac gcggtgggag acatccgggg acagaaggcc tgaggagtct    660

gccgctccag gcagggtcgt ttgggtcctc aaactgggac tattcctgat gcatttggaa    720

tgcaaagaaa aaaatcaaac ttcgctcctg ggccggcggc cgcgcctggc ctagcaagat    780

ttcggccaca tttcttacgt ttccgccaaa gctgtgaaca caggcgaatg cagtgctggt    840

ccccggcctg gcgcaggaag gagcgcaagg ccggctttgc aaggaagccc tcgcg         895
```

<210> SEQ ID NO 274
<211> LENGTH: 2545
<212> TYPE: DNA

<213> ORGANISM: Homo sapiens

<400> SEQUENCE: 274

```
cgcgaaggct cggggctgcg agccgaatgc ccgccgagct gcctgggaac gggaaccgcg     60
cacccgggaa cgccaggcgt ttctcttcat ccaggaacgg cgcggagagc ctccggctgg    120
ggagctaaac cgctggggac tccgcggctg ctgcctgagt cgctgtccgc tgcccgcatc    180
ccttccgccc tgggcctctg cacggtctgc ggttttctgt gcgcacttgg tcttcagtac    240
tagcacccaa ttacgtctgg gtttttcttc tttacagagc tgggtttcgg tggccaccag    300
cttttctggt gtttagtgac tctgagtttg gaggtggcct accaggcaaa cggggattca    360
gggcatttag gaaacgtctt ccgcgcttaa tcccagaagt ggttgcgtgt ccgtacgatc    420
ccaagttcct cccggagcct cttctttgct gcgtctcggg ccctccagca ggcgaagcct    480
cttagacgcg ctggggaaac ttccggcgtg ttcggggctc agggtttctt ctcaggcatg    540
gattggggcg cagaagttgc gcgaggcagc gcctaaggtc ccgaggtgct gagactgtgc    600
tggcgtttgc cacctgcccc tggctaggcc gtttctgggc cccaagaaac gcctaccttg    660
gcacttaggg accagaagcc tctggatgtc tagcaacagg ggtcacggga tcactgcgtg    720
gggtctctgt aagcagtccc ctgaggcagt gcaaaaccgg aaacctgctc tgtgcggggc    780
cgaatcagtt catgggattt gggagtcagg agagacgtct ttctcctccc agctcctaca    840
ctccgggtac caaggcccga aatgccgttc ccccagcccg ggtgcggggt ctgcagcaag    900
gcctcctgat ttgcaaaccc ctccgggctg cttattcctg gtgccatgcg cagcccttgg    960
gacctagaag attgtggggg agggaaggtc gcacgtgcgg ttttggcacc gaccgtgcct   1020
cctagtccac ctgtccccca cagctagctg ccaactcgga cggaagcgcg gaacagcgca   1080
atgcaaaccg cccaaagtga aaggaatgta attgcgctcc catgacagag ccagacgcgg   1140
atgcagttta ggaagggcgc cgcctaccgg cccctgggag ccatgcgatt cgaagggagg   1200
gggacctaga ggagaccccc gctatccccc cacccaccgt ggggccttag ctttgaactc   1260
cggcccggac aaacttaaac tgcttcgcca ccccaacgcg ccacagccct ggacctaaga   1320
cccagttagc attgggaatt tggggagcag ggcccacgac tagaacaaag ttaaccctac   1380
cggttcccgc cacggcttcg gcacatttca aaaaaccagg cgcaggcaat tgagaaatac   1440
gctgccggct gaaacagcct gcgggtgggg gctgcagccg tgcgcgcccg gcagttcccg   1500
tcccgcatca ggtgtacgca cttccactcc tgcgggccct tccacgctcc aactctggac   1560
cccgcgcagt tttaatctgc ggtttgggaa atgggggtgc taccgtgcaa ccgcgccctg   1620
aaagaccgtt ttggtcttaa gagcttttgg cctgtggggt ggacatctgt agaaaaagga   1680
aaaacaaaac aaaagtaacc tcccattgcg tcgaaccctc ctattccgaa aagaacttta   1740
atgaggttgg cttggcaagg cctgcggtgc ttacctcggc ttcgccctac cccgccagaa   1800
gccctcatag gttgtatcca ctggtctccc ccaggtgcag ggttattagg ggaaaggggg   1860
gcgcgccctc gggctggatc tttgtttccc tcgtcgcccg gtcatcaaac aggagggaaa   1920
tcgggcccga ctgggacctt gctgcccgcc ttccccttaa actggctaaa gcttcaggac   1980
tgtccctaga cccaccccgc gggtcttcct ttgtgtccag ggcatagccg atctcctttt   2040
cgttttcacg agaactgcga cttgggcctc gggcactagg cgagcccagg ttgtggccta   2100
acagcagatc gcctcgggag cttggctgca gctctgcccg cacctccagc gctgggcggc   2160
ctctcggggc cagtggggat ctctggcctc gtgtaggcca cgggccccag ccctgggtcc   2220
ccaaggccgc tcgccgggca gcgctcgttt ccggcaccgg gacgagccca gcgcgctcag   2280
```

acaccacttt cccggtgaaa tctgctttta tttgctccga gcaaacctcg ggctctcagc 2340
gctcccgcct gatggatgca aatgtaaatg tgcacttatt taattggatc aggccccaag 2400
ataaaagaga taaacggctc cccgcttgct aacttatttt cctaggcatg cagcgccgcg 2460
tggaggggaa gctaatgaag gagcagcgcg gtgctgggca ctcgagctct ccgcagccgt 2520
ggcacgctgg ccggccggcc ccgcg 2545

<210> SEQ ID NO 275
<211> LENGTH: 947
<212> TYPE: DNA
<213> ORGANISM: Homo sapiens

<400> SEQUENCE: 275
cgcaggccaa cgcgaagaca cgatgatccc aaagacctta gtgtcttggc ggggggaggg 60
ggaagaggtg ggggactttt ccgcttagct tccctaaggg ttgctacgcg acagctctcg 120
ggctacgtca gggtaaagag gtttgtatgg ccacacctcg caccgaccaa ctacccccga 180
aacaccccct cctcccaaac tgcagggtga gcacagcgag agaaaaggtg gcccaagcag 240
aggcgaacaa ctgcggttct taaagccttg tttgagtttg ggcccgcgcc gagccacagc 300
tagaggtaga tcccgctcct gcgcgtccgc tatcagcccc aggattccca gagaggcctc 360
tcaggccctt caagaccccc ccttccggct tcccggccta cacctctgaa ccctcaggcc 420
ccggacagcc tctatccccg cctttcgcgg ccccggctca ccctctagcg tctcgcactg 480
caccaggttg aggtagtcgg cctggctgag caccccggcc ttcaggccgc gcaccagtcc 540
ctccaagtag ccattgtcca cgttaaagta aagctccggg aagaacgaca tggctgctgc 600
gggagcggcg ggaccggaga accaggaccg gccggcacga atcgcgactc cccaggtcag 660
ctgacgctgc gtcctcagcg ggctgtcaag tgcgtcaggt gacgcgcaag cgcctcacgt 720
gaccataagg gggcgtggct ctgagcggtg cccggcttcc gggtggctgc gcggaagcgc 780
ggtgcaggcg tgggctggcc ctgcggcgcc tgcgcgctaa aaagaggaag tttgaggccg 840
gccgcttggt ggcgcctgtg gccgcaggga tttgactggg ccttctctag ctttccccgg 900
tttgctgcac ttgacgctgc agggcgggcg gggtaaagaa gggagcg 947

<210> SEQ ID NO 276
<211> LENGTH: 536
<212> TYPE: DNA
<213> ORGANISM: Homo sapiens

<400> SEQUENCE: 276
cgggggttgg gggcacggaa ggggaagctt cggtcgctaa gtgggccggc ctttggaagg 60
gtctgggagg ggccagcgct gactaacagt cggtttccct accctagacg gctgcgacga 120
ggagctggtg ggtcccctgt atgcacgctc cctgggcgcc tcctcctact acagtctcct 180
tactgcgccg agattcgcca ggctgcacgg tgagctccgc ggaacatcag ctgccaactg 240
gcagcgcacc gcggaagggt gggggcctcc ggaggacttc ggggagaggg atagccggtt 300
aaagctcctg tcctttctat aggcataagc gggtggtcac cacggattgg ggatccgaat 360
ccctggctcc agatagactt aatgaagaag caccggatcc gggccgtggc cacacagggc 420
tcctttaatt cttgggactg ggtcacacgt tacatgctac tctacggcga ccgagtggac 480
agctggacac cgttctacca gcgagggcac aactcggtac tctgggcgcc aaggcg 536

<210> SEQ ID NO 277

<211> LENGTH: 874
<212> TYPE: DNA
<213> ORGANISM: Homo sapiens

<400> SEQUENCE: 277
cggcgctggc gcaggcggcc aggagagagc agatgaaccg ttcgttagga gcagcgaggt 60
agtcgtgagc gctgagatcc agagactagg acccactccc tctctgagca gcaaattggg 120
aagaagatgc tcactcggta agggcgaggg agcccggcat ggcgccccac cacgggctcg 180
gtctatctgc gcgccaagat cccgcttggg gcgaggcgtt gggtcagcgt ttagagccac 240
tccctgcgct ggtggctgga catagcctcc ctatcccacc tcatcttccc ccatccccga 300
cagaggaggt tgtgaatcta caggcccttg acgttgaggc gtcggagggc gcacctttgt 360
aattgcggcc tcccttcgcc ccttaagtgc cgcttctggg cgcctaggct ggatatgaaa 420
gccccgttcc taatcctctg ctctggtccc ctcctctgga ctgctgggac tctaagctag 480
gccctcccca ggttccatca ctgcggcgcc aacccgcggc tgggctgtcc gcaagaggga 540
gttgaaggcg cgcggaatcc cgaggtgcag ctgaccctcc tctcaacgcc gactctgccg 600
ctcccgcccg gccacctccc tgtcgggcag acttcctgtt ctcctgctca cagcagggag 660
gcagtcgccg agccggtcag cagcgtgcac ggagatcttc actctgcgcc cagccccggg 720
acacaggtgc agatctccag cggagcactg cggagtgcgc gccgtcgagc actagggaat 780
cctagacgga ggacttggtc cattccacgc agtcccaggc aggtccgcag cggagggacg 840
cagcggtctc caactcctgg tcacgacttc ggcg 874

<210> SEQ ID NO 278
<211> LENGTH: 3724
<212> TYPE: DNA
<213> ORGANISM: Homo sapiens

<400> SEQUENCE: 278
cgactcggct gacgtttttg acccggccag gaggcaaaga ccaaaacgtc agagcagtag 60
ccctgttact gaggagcgtc ggcagggtcg cgggtagagg gggctggaga atgacttgtc 120
agagctcaag gtcgatgtgg cgcggggcgg cctcgagagc gccgggctcc tgcgtggcca 180
cggccgccgc tgccaacctt cgcggggact tagctttgct ttccattgac tccctttgca 240
aaagcgcagc agaatcctga ccagccgcac cagccccggc gaacccgagc atgttaatct 300
atttatatgg attattacgg aggaacagcg ggcgttgagt caccaaaaca tttgcttcaa 360
aagactattt ctaagcactt ttgcaggcag gcaggctcgc tccaggcgcg taaactcggc 420
tacgcattaa gaagcggctg cttttcgaat actgcaaact ccagctaagt ccccggtgcc 480
gcggagagag cagtgaaaag aaatgtcgga ggtgggggta gatcctagtc tagacacaca 540
cacttgcgcg cacacacaca cacacacaca caagattcgc gcggagaagg cactaaaatt 600
ctggcattcc gagagtacga caaacttaca cacttggaag tcccgggtcc cccgccttcc 660
ccgcagcacc ccccgccccc ccaccctacc gtccgccctt tggctgcgat cccctcccct 720
ctcctcccct cccgcctcgt cacccagccc agtgccacaa tcctcctccc tccccaaaat 780
cgggtccaat cagctgcctg ccaaccctgg gactgctgtg ctgtgattgg cgggtggctc 840
taaggtgagg cggagtattt attaaagaga ccctgggctg ggagttggag agccgaaagc 900
ggagctcgaa actgactgga aacttcagtg gcgcggagac tcgccagttt caaccccgga 960
aacttttctt tgcaggagga gaagagaagg ggtgcaagcg cccccacttt tgctcttttt 1020
cctcccctcc tcctcctctc caattcgcct ccccccactt ggagcgggca gctgtgaact 1080

```
ggccaccccg cgccttccta agtgctcgcc gcggtagccg gccgacgcgc cagcttcccc   1140
gggagccgct tgctccgcat ccgggcagcc gaggggagag gagcccgcgc ctcgagtccc   1200
cgagccgccg cggcttctcg cctttcccgg ccaccagccc cctgccccgg gcccgcgtat   1260
gaatctcctg gaccccttca tgaagatgac cgacgagcag gagaagggcc tgtccggcgc   1320
ccccagcccc accatgtccg aggactccgc gggctcgccc tgcccgtcgg gctccggctc   1380
ggacaccgag aacacgcggc cccaggagaa cacgttcccc aagggcgagc ccgatctgaa   1440
gaaggagagc gaggaggaca agttccccgt gtgcatccgc gaggcggtca gccaggtgct   1500
caaaggctac gactggacgc tggtgcccat gccggtgcgc gtcaacggct ccagcaagaa   1560
caagccgcac gtcaagcggc ccatgaacgc cttcatggtg tgggcgcagg cggcgcgcag   1620
gaagctcgcg gaccagtacc cgcacttgca caacgccgag ctcagcaaga cgctgggcaa   1680
gctctggagg taggacccgg cgggggcggc gcggcagggt gggcatcgcg gcggctgggg   1740
gcgctggtca gggctgattt gccccgcccc gcctcccatc gcccgggagt tgccgttccg   1800
ggagccggcg ggatggggtt gggagtggga atggggtgta actgtggctc agagtttgac   1860
aaagttcttg ggctgctcgc ggggacgcgg aggagggggg tggtaagtgg aagaggtgag   1920
ggaggtagct ggaggatgga cgaagactgg tgggagacgg aaggaggggg ctgccagcct   1980
gctctccagt cgcctggaag ctcaatcggg gcggggaagt gaaacttgcc tccctcctac   2040
ccggcctctt aaaactgcac tctctcgtgc agccccactg tccacggaga tggggcaagg   2100
gagaaaccga ggttggagga gacccttggc aggaactggg aggcgggagg agggaggcta   2160
ctggaaatag gtgggagtgt atggtggggg gtgagaattg gggaccttct tgcagcttaa   2220
gtaatttggg ggaaagtttt caaagggggt tggggttggg ggcggtaagt cgagcagcaa   2280
aggcgtttag ggggcagcac cgggagtcgt tttcatctcc agcgtttcca aaatagaaat   2340
agaaggggag gggagggagg gggcggggag tgaccgctca ggtcagactg caataactta   2400
tttatttatt tatttttaag aaaagttatg agctgtggtt gcaggcagga gggaagatgg   2460
agttgtgtgc agaggaagcc gagtggtctg ggtcgccgcc tcctccccgc cgacctgaca   2520
gtttggcgga tttcactgac ccctctccct ctttttctct gtgccccccg ccccgccccg   2580
agcagacttc tgaacgagag cgagaagcgg cccttcgtgg aggaggcgga gcggctgcgc   2640
gtgcagcaca agaaggacca cccggattac aagtaccagc cgcggcggag gaagtcggtg   2700
aagaacgggc aggcggaggc agaggaggcc acggagcaga cgcacatctc ccccaacgcc   2760
atcttcaagg cgctgcaggc cgactcgcca cactcctcct ccggcatgag cgaggtgcac   2820
tcccccggcg agcactcggg tgagtcgccc ctcgacccca ccggacaagc tatctccgtc   2880
ccgcctggca cacccctgc cctccgcctg ggagattctt cgtggggact ttatgcttcc    2940
cgggagggac acactgccct ttgcgcccgt cccgctcccc tctctaccca gagcctaaga   3000
ggcatccaaa caacacacac acaaacacac acaccccaac tcaatcccag catccgaaga   3060
gattaacttt tttattggga ggtaaaatgc ccttaacagc cttacaagac ctctcccttc   3120
ttctctgctc ccccacccca aaagcacaca cagggctctt acacaagtag caattaggtc   3180
ttccggaccc tccgggcccc agaccctccc ctgataaaag ggggctgtcc agtgtgtacc   3240
ggcgggttaa tcattgggcg acttatctcc ggtgcagcgc gcctcttgcg cgggtgcggg   3300
cccttattac actttagcag cgagggaggg tccccggagg gtgcctaaga ctagggcgtc   3360
tgcacagccc ttgttgattt tctcgtgctt gttcttttat tgtccacagg gcaatcccag   3420
```

```
ggcccaccga ccccacccac cacccccaaa accgacgtgc agccgggcaa ggctgacctg   3480

aagcgagagg ggcgcccctt gccagagggg ggcagacagc cccctatcga cttccgcgac   3540

gtggacatcg gcgagctgag cagcgacgtc atctccaaca tcgagacctt cgatgtcaac   3600

gagtttgacc agtacctgcc gcccaacggc cacccggggg tgccggccac gcacggccag   3660

gtcacctaca cgggcagcta cggcatcagc agcaccgcgg ccaccccggc gagcgcgggc   3720

cacg                                                                3724
```

<210> SEQ ID NO 279
<211> LENGTH: 3126
<212> TYPE: DNA
<213> ORGANISM: Homo sapiens

<400> SEQUENCE: 279

```
cgcctccgcc ccgcgtttcc tccccccgat ctcccagggg tcctcttttg agggcacccc     60

agcccctcga cggtcccggg atatcctgca cccctgccag gctgcaggga agcgccgagg    120

cgcgcggagt gcgaggtccg tgctccctgc ggcgcggcgc acacgcaggg tccggggtcg    180

acccctccac cgctccggcg tctgccgggg aagtcagtcc gcctggtcag cccagaaccc    240

ccgactgcgg gggctggagc tcggaagcag gtacaagcgc cactctccgc ctgcgccgtg    300

gaatgcgcgc cgggaccact ccgcagccct tcccccagcg ccgccggccg ctgctgggga    360

caacctcgcc ctcctgtctc ttgctcctcc tcctgacccc agcgcacccc catccccgcc    420

ccagatgagg caaggctccc tccgccttca gcccggcaga gtcgcactag gagttgcagc    480

ggccgcagcc ccgggagctt cccgctcgcg gagacccaga cggctgcagg agcccgggca    540

gcctcggggt cagcggcacc atgaacgtct cgggctgccc aggggccggg aacgcgagcc    600

aggcgggcgg cgggggaggc tggcaccccg aggcggtcat cgtgcccctg ctcttcgcgc    660

tcatcttcct cgtgggcacc gtgggcaaca cgctggtgct ggcggtgctg ctgcgcggcg    720

gccaggcggt cagcactacc aacctgttca tccttaacct gggcgtggcc gacctgtgtt    780

tcatcctgtg ctgcgtgccc ttccaggcca ccatctacac cctggacggc tgggtgttcg    840

gctcgctgct gtgcaaggcg gtgcacttcc tcatcttcct caccatgcac gccagcagct    900

tcacgctggc cgccgtctcc ctggacaggt gagccagcgc cttggcctcc ctgggagatg    960

ggcatccacg cgggggatgg agcgggaggc gggactgggg accaagaagg gacgcgcaga   1020

gtgggacagg acactaagaa ggcagtggaa gacaagcggg cgcggaggag gaaaaagagg   1080

aataagaatg ggggaccgtg gtgtccctcg gttagatgcg tcctggggcc tggaagcctg   1140

gagaatgtgg ctctccagcg ccgcccgtgc ctgacaacgc gcagcgtttc ccagtacgac   1200

gcgtttgtgc gcgttcatct cgcttgagct taatgccctc cgtgagggtg ggataggaca   1260

aagtgcccaa tatacagaag agttgagttc ctaagtaact cgctcagagt cgccagccag   1320

ggatcgggtg cgtgaagtga ccgtctgtct cctgcagcca acttcaggcg cctccactgc   1380

gctcgcctcc aagccacggt ttggttggtt ggtgcagctg gctcaggtcc aggctgtgga   1440

tcttgggtcc tttgcaagga tccactccgg agtcccagcg agcgtgccta aaggtcccta   1500

gctcagtccc agcccactct gcctctcgcc tccaaacaaa acaaaacaaa ataaaatcca   1560

aaacaagtcg gggccgggag aggagcgtgc cctggggttc ttcctcccca gccagaggag   1620

agcgagagac gcacattcgg gagagcgcgg gactcaggtg gagcttgaaa ggacactggg   1680

atggttcctg gggaggaaat ccgggtattt cccctctcca tcctctggaa aaacagagag   1740

gcgaggccag actgccccca cacctcctgt agccactgag cgcgaagtgc gttggttccg   1800
```

agcgcgctgg tgggatccac aaagctcgca ttctctcagg aatcccctga gaaattaact 1860
gtcccttgcc caacatgtct tctccaggct gtctgctaga gcctcaggcg cctccgccct 1920
ccctcccgcg gcaccgtcac cagtgggtag tcacagcctc ccggagccca tagccggttc 1980
tccaaccttt agtcttcagt ggctttgggg tgccctctca gtggagactg tggttgcagt 2040
ccccgggggc agcgggagaa tggcttgaag gcacaccttt cctgctgccg ggcccgcccc 2100
atttccaggc tccgctgagt gtctgggaca cgctgggagg cccccacctc cgccctcacg 2160
ccgagcctca cccccacctc ctctgtgtgc ggtgtaacca tgcgctaagg accttcctcg 2220
agagcagcct tgggaccgag gtgcaggggt cgcggccctc cagcatgaat gtgcccgctc 2280
agccgacgtc tcccttcccg gtctgaccgc aggtatctgg ccatccgcta cccgctgcac 2340
tcccgcgagc tgcgcacgcc tcgaaacgcg ctggcagcca tcgggctcat ctgggggctg 2400
tcgctgctct tctccgggcc ctacctgagc tactaccgcc agtcgcagct ggccaacctg 2460
accgtgtgcc atcccgcgtg gagcgcccct cgccgccgcg ccatggacat ctgcaccttc 2520
gtcttcagct acctgcttcc tgtgctggtt ctcggcctga cctacgcgcg caccttgcgc 2580
tacctctggc gcgccgtcga cccggtggcc gcgggctcgg gtgcccggcg cgccaagcgc 2640
aaggtgacac gcatgatcct catcgtggcc gcgctcttct gcctctgctg gatgccccac 2700
cacgcgctca tcctctgcgt gtggttcggc cagttcccgc tcacgcgcgc cacttatgcg 2760
cttcgcatcc tctcgcacct ggtctcctac gccaactcct gcgtcaaccc catcgtttac 2820
gcgctggtct ccaagcactt ccgcaaaggc ttccgcacga tctgcgcggg cctgctgggc 2880
cgtgccccag gccgagcctc gggccgtgtg tgcgctgccg cgcggggcac ccacagtggc 2940
agcgtgttgg agcgcgagtc cagcgacctg ttgcacatga gcgaggcggc gggggccctt 3000
cgtccctgcc ccggcgcttc ccagccatgc atcctcgagc cctgtcctgg cccgtcctgg 3060
cagggcccaa aggcaggcga cagcatcctg acggttgatg tggcctgaaa gcacttagcg 3120
ggcgcg 3126

<210> SEQ ID NO 280
<211> LENGTH: 526
<212> TYPE: DNA
<213> ORGANISM: Homo sapiens

<400> SEQUENCE: 280
cgagagcctc tacgacgcac tcaaccagta ctacgtccac ctcggcggcc agaagtacgt 60
ggacctcggt ctggggaccc accgcgtcaa atgtcgggtt caccccaact tccgcctgat 120
tgtcattgaa gagaaagacg tcgtgtacaa acactttccc atccccctca ttaaccggct 180
ggagaagcac tatctggata tcaacacggt gctggagaaa tggcagaaga gcatcgtgga 240
ggagctctgt gcgtgggtgg agaagttcat caatgtcaaa gcacatcatt tccagaagag 300
gcacaaatac agcccctctg acgtcttcat cggctaccac tcggacgcct gcgcgtctgt 360
ggtgctgcag gtcatagaga ggcagggtcc ccgggccttg acggaggaac ttcaccagaa 420
ggtgtctgag gaggccaaat cgatcctgct gaactgcgct acgcccgatg ccgtggtccg 480
gctgagcgcc tactcgctgg gcgggttcgc agcggagtgg ctgtcg 526

<210> SEQ ID NO 281
<211> LENGTH: 242
<212> TYPE: DNA
<213> ORGANISM: Homo sapiens

<400> SEQUENCE: 281
cgtcacgtgc agagcatcct cccgactggc gaggtggctt ccacgtgccc cgtcaatcag 60
ggctggacag tccgtcacgt gcagagcatc ctcccgactg gcgaggtggc ttccacgtgc 120
cccgtcaatc agggctggac agtccatcac gtgcagagca tcctcccgac tggcgaggtg 180
gcttccacgg agcgattctc gagacccgag gggcgtggac acagcttcta cgcaggcagt 240
cg 242

<210> SEQ ID NO 282
<211> LENGTH: 724
<212> TYPE: DNA
<213> ORGANISM: Homo sapiens

<400> SEQUENCE: 282
cgcgcgtcgg gcgctgggaa ggtgactgtg cgttgggcgc gcttggtggc cccagggctg 60
ggcctgctcc cgtctgacag tagtgccgcg ctgcatggca cgggtgttgc gttcgtgggt 120
gagagcgctg aggtctgcac gtcgggtctc agtggtcatg gggatggaag ccaccccagt 180
ggctgtcggg gtgaatggag gcccctggag atggcagcgg gttaagcacg agcacggaat 240
tctccctccc aaaacggaac tcagacaaca gtgacggagc ctaagagcaa agccaaagcc 300
acgggcaggg gtgagcggga cccgaggcag gagatgacgg agcctaagag caaagcgaag 360
ccacgggcag gggtgagcgg gacccgaggc aggaggtgac agagcctaag agcaaagcga 420
agccacgggc aggggtgagc gggacccgag gcaggagatg acggagcctg agagcaaagc 480
gaagccacgg gcaggggtga gcgggacccg agccaggagt ggcgccgggc agggaggcag 540
gcagccccag gcgctgtgtg ggcactgggt gagaagcagg gatcccggcg ccctggctct 600
gtgctgcttc ctgagacgag agtggcagag ggcaagaaga aaaccaaaca gcgcggggaa 660
cagaagtcag gaaagatgaa cgtctggaag gaaatgcccc tgggccgggc ggtgcccccg 720
ggcg 724

<210> SEQ ID NO 283
<211> LENGTH: 4996
<212> TYPE: DNA
<213> ORGANISM: Homo sapiens

<400> SEQUENCE: 283
cggagagacc tcggagcaga gaaggcgccg ccgaccctcg cggctgcctg gcccgcggct 60
cctacaaagg cgggctagcc gcccgccctc tcccttgcct tcctcccctt cttttctgac 120
tttccctctt tcccttaatc gcctgcttct tcctccgggt ggacttacgg ccaccttgct 180
cctccgcgct tcacctcatc gccccctctt tctttcttct gcctctctct ctgcgccccc 240
ttctctccgt gtcacgctcc ctcctggttc tgcgcgtcta caaacttttg agcagaacac 300
gagcctcggc aaacgagtcc cgcagctcct cctgctgctc ccgctggttc ctgcggcttc 360
tgctcagaca ccaacgccag acggcgatgc ctctcgggtg gtgactccag cgcaggaact 420
tgaagaagcg ctttgcccgc cgtcctacct ggcagctctc ctggcagcgg gaggagttga 480
agggtaaggg agggaaaatc ttaccaaagc gaccggctca ctcgactgct gattctttcg 540
cttggcatcg cgtcagggga gttagctttc cttcagccgg gtctggctag ttattgggcg 600
ccgggtagat gcatatatat atattttttt ctaactatag caagcaagaa gtggcagggc 660
gcgcaccggc tgtcgccaag tgctgttcaa ctcagggagc cggggcttcg ctccgtccct 720
cccccggctt ccagagcttt ttggggttgg agggtgggag gccaggggcg ttctcacagc 780

-continued tgtgtgtcct ctttcccatc ctgcgcagaa tgaccatgtg tagcggagcg aggctggccc 840
tgctggtcta tgggataatc atgcacagca gcgtctacag ctcacctgcc gccgccggac 900
tccggttccc cgggatcagg taggtgctgg ctgcctggcc caagcaggag ctggggcttc 960
ccaggcacag acgcttcctc acggtctcct tcctgcagtc ctttgggtcc agactactag 1020
catcgccctc tgcgcccccg gtgcgcctcc gccagcctcg gctggacagc gggtccccat 1080
tctagccgag ggtctggcag gctccgcgac tgctcggacg cctcccccag ccctaggcag 1140
ctcagggtcc cgggtagagc cagtgagctt ctggccgctg gagaaccccc cctcccccaa 1200
cccggcccac aggatggggg cagggcacgg cccctagctt ggtttctttt acctattctt 1260
gggacgagtt aggagaactt cagctctgga gcctggccgg gggttgagcg tgaagctccc 1320
tcggactttg ctttgttact gcttgttctg gactatccgg gtggggtctc tctctctcct 1380
ccaccctttc ttttcatttc attccaattc tttcccctga agagctttct ttcaagtgat 1440
ccgtgttcca actgcatttt gaatcccagg ctgtcttggg gggcgtgcgg tggggagggt 1500
gttggcccgg tgtgattgag gaaaagcgac ttaagagagg gaagaacaag gacgagactg 1560
cgaaggaggg ggaaaaacag gcgcaaagga ggaggaaggg aaagccagca ggcaggcagg 1620
accgggagag cagccctgcc tggcccggga tggaggaacc ttggcttttt tcttaacccc 1680
gggtttctaa ccggcaggcg cggcccaggt tcccggaggc agccccagag tcgcggaccg 1740
atgtgccagg ctgtggatga gccctgggta ggggagggtt cgtaccagcg gcgcctgggg 1800
cagcgaggag cgcgcgttct gcctgcgaag ctgccttctc cgagccccgc ccaggaacat 1860
tagctctggg gggccgctga tcattgattt ggacggagag atgggttctg ggttctgtat 1920
taggattcca gcatctgggc tcgaggcagg gcaatatcca gaaagacccc agggttcggg 1980
gtacccgggc cagggctgag gcgcatcgcc gagcaaaggc tgggtgcgag gcgtgcggaa 2040
tgatgcgctt gccttgcccg ggcctctcca aggatggaga aaaggcgagt gaagcagcga 2100
agtacgactc caaccccgcc cagagagtgc tactagcgct ggctgcacgc caagtctctc 2160
caggggtcca aagcgagagg gatttgtttt aacccatctc tacccgtcct gtgtcaagaa 2220
cggaggctgt agagggcgac tgcgaagtcg ccaggcactc gctggatctc ggtccccctc 2280
ctcgtgctct ggggttgaga tggggcaccg ccatcgataa cagatcagcg cgaactattc 2340
gtttagtggc cttaaaacac cctggtttca ccctcagcta ttttcaagtt cccgtgtgcc 2400
tggcactttc tccgtgcgag aagcaccgga gggtgcggac gcgccacagt ctgagccgcc 2460
gccgaactgg ctaagtttag gggcatttat tattcatgtt cctgccagat cctcgcctgc 2520
ccaaaataga aaccgaggtt ctccgtgacc tacatctgct cggagaaggg ctcccctggg 2580
ctcggaggct ggggtggggg tggctgagga gttggccccc gcacgcccca cgcatcctct 2640
cctttgcttt ctgggcctcc ccattcgggt cttcgcgtgg gtcagcgccc ggtctcccag 2700
ggcctttctc gtccccgccc gttgctgctt tggggaggct cgggagccag gcggggaggg 2760
gggcggtcct tttccgtaga caggtgtgcg cgatcggcgg agacgcctcg gtttcccagc 2820
gcttgttgag gccgtggccc gcaggacgac cctttacccg cgaagggggg gtgggcgggc 2880
cgcccggcgg ggtaggagtg gttgggtgtc gttgcctcct ccttacctct gctcccaccc 2940
ccagtcctgg gagaagagac aattctcagc ggaggacttt tatcacctgt gaaaatccgc 3000
gcgagcccct tactttggat cctcgccgag ctggggagga acttgcactg accacacctt 3060
ctgtccccgg ccaccccgca ggccagagga agaggcgtac ggcgaggacg gaaacccgct 3120
gccagacttc gatggctcgg agccgccggg cgcagggagc cccgcctccg cgccgcgcgc 3180
cgccgccgcc tggtaccgcc cggccgggag aaggtgagat tcgcgcggcc tcgcgcacac 3240
ccgcggctgg gagctcggga ctgcggtgac gggaggggca gtgtggtgac ccacccagga 3300 ttttttttt tttcccgtga aagtcctcaa gcctgtcctc tccctggccc gatcctattg 3360
cagcgacaga aaatcagcag cgggcgggtc tgtgtggacc tgagggccgc gtggggaccg 3420
aggggggctg tggcccaaag agtggcagtg agtggcgtca aggaacccac actccgcatc 3480
tgccactcct agagccggga ctagctcccg atcctagcag ttgctctcga gatcatcccg 3540
ggagttattg gcgagttctg ggcctctgga ggtttccctg tcagcctccc cggccgccga 3600
gggggcgcgc gcccaacaag gggtctcta gcggccacct ggggacagaa acagtgaccc 3660
tgggcgcgca ctttgcctcc ccgttagaga tgtcgcccac gggatcctta acgaggccta 3720
ccgcaaagtg ctggaccagc tgtccgccgg gaagcacctg cagtcgctcg tggcccgggg 3780
cgtggggtaa gagtttgtgg aaggattaac ctgcgcgcgc cggggtgggt gcctgtgcgg 3840
ggcgcgcggg gcgggcggcg gtgggtgccc gtgggggcca gggtgagtct gcgcccctgg 3900
gtctggggtg ggcatccgcc acgggtcgca gttggagatt ttgaagtggc actttaaatt 3960
tgcccagaga gctctggaag aggcaaaaag ggaacgcgag ccagggagtt tgatccgttt 4020
tgaatgaaaa gaaagagaaa ccaaaccaaa cctctcagtc atccaaaacc ttcaggcttc 4080
cagggaggtt ttgctataat tttctctaag catgactgtt tctgggggag gggaaagggg 4140
tggttgtatt tactgaaaat tcaaatcgaa ataataaatg gccaaatgtg gacacttatg 4200
gacccaaaca gttttgctca cgccagagaa actgagagca cagggcttgt gtgaagccta 4260
tctcggcaga aggcaacatt ctaataaagc ccgtgggaaa acagattaca ttttcgccat 4320
gaataagtca tgcagtgaaa aatattgcct acagcctgtc gacttatatt attatcacgt 4380
ttttcaactc ggcgtgagga gggagaggag tgttcatatt tgactaggaa ttgcaggatc 4440
gatgcaaact ccagggcagc agccagactg gcatatgtag ggctctccgg ttactttctc 4500
tgtatgtcgc gggtgagagg aacagcgagg acaatttagc gcaaacacac gaagggtcgg 4560
atctcaaggg ggcagcgctg ggagaaaggt taggcttgaa gcgcgcgtcg cctgcccgga 4620
tcttatcccg ggccccctcc gcagggtttg gtgccaggag atcctgcgtg gggagggggg 4680
catcgagggg ctgccgtctc ggccctcccc acggctgctt ccaggcagag gcgggcgacg 4740
cggtgggcag tgcgagcccc gggccctccc cgaaggctcc cgcgtggggt ggggcccgcc 4800
tgctccccgc ggcgattgaa cctgtgtctc ccgccccgcc accctcttcc cgaccccttt 4860
gcttgcagtg ggagcctcgg cggcggcgcg ggggacgacg cggagccgct ctccaagcgc 4920
cactcggacg ggatcttcac ggacagctac agccgctacc ggaaacaaat ggctgtcaag 4980
aaatacttgg cggccg 4996

<210> SEQ ID NO 284
<211> LENGTH: 4239
<212> TYPE: DNA
<213> ORGANISM: Homo sapiens

<400> SEQUENCE: 284
cgcagaaatt actcgtgcgc accatttccg ctgtgggggc attcgtacaa gtttccgctg 60
cacacacagc ctcccgggcc ctctcctcca aggctctgcc ggatcttcca acgaaatccc 120
agagcagcct gcgctgggga gcccgcaagt ctctccagat ctctgcaccc cgcaccgccc 180
ggaatctggg acggcgccca cgcagggctg ggccaagggc agagctcgca ccctgccttc 240

```
acgcccggtt cacttgcgtc cacgaaagca gcgtgccggc ctcctccatc ttcccactcg    300
cgcaacgcac ggcgacccgc gcgacacttc tgcaatctga aggcttgctt cttacaaata    360
aagggccaga gtctcacact tgccttcgtt ggagggactt agaagatcct ccccacgtcc    420
acaccttgta ggaaatgcaa aacagatcga tgaaattaaa cagttgcatt tggaagcccc    480
agaaagacct aaagacatcg tgccggtttg ttggagagag ggttgcggga caggggggagc   540
gggccttacg caacagaaaa ggtgggcaca gcgcgctcaa aatgacccag tgaggagttg    600
gtgccgccgg gccagaggct gcgagtccag ctggctctgg acttgctccg caggcgtcag    660
acgccgtggg aacctgtgtc tgcttcttct ctccaaagtg tatcggttaa aaaaaaataa    720
aagtagtagt agtagtagtg gtaaggaaaa aaataaaaat aaaaaggaga cacaattaac    780
caggtcataa aagctagggc accttcgacc agggctctgg ccctccagcg atcgttttgc    840
gttgtttctc ttctcaaaag tagtctcaga cccctgcctt tccgctgcag ctctgcgact    900
tccccaaact ccttaatcct gtaaattctg caagaaactc ccatcctgca agctgctttt    960
ccccctcccc cctgcgttcc ttttttctct ccccacccgc gccgcctctc tatgcccctc   1020
tcttctcaga aaaattcctg ccccccgcgc gccccaaagc ccgggctgca aacttttccc   1080
cgccgggcgc ctctgcgcca gatgccggag cgtctccaca aagcctgagc atctgcacaa   1140
gttcgcagcc taactgcggg ataaagacgt ttcccccgta gcttaactag aaaagcgcca   1200
tcgatgggtg tgttaaacgg gataactaga gatttcaaac accttttatt tgcctgtctt   1260
gaaaaaaaaa tctaaatgaa tacgcccgct accaaaaggc aaaataaaac caaccttaag   1320
ggtttttgtt gttttttttt tttttcaaaa gtggcgatag ggactgtttg gacctgactc   1380
caacctgcgc cctcccttcc tctatgaccc tcctgcgctt ttcctggaac ccaaagctct   1440
gacttcgtca aacttacaca attaaaggca ggcggaagaa cgcgggctgg gaagcaagcg   1500
ggaagattct agaatggaag ggagcccgcc gagcgccgcg agccgcgcca ggccgggtcc   1560
gatggagcag gcggggattc ctcccccagg cggacccccg ccaccagccc tgccgggagc   1620
tcgcggcctg cggagcgccc gggctggccg ctcaccgccc gcttccccca gcgaacgact   1680
cggggaagct ccaggaggcc atctgtgctg acggttcaca ccagacagga ccacttgcaa   1740
ggacaaaaat aagaaattta ggaaacgaaa aaagacgtac tggggcgagg ggcgcgggcg   1800
cggcgacgac ggggccgggg gcacatcctg gcggccgctc ggggagagag gacacgcgcg   1860
ggaaggagcg cggcgggtgc acggccgcgg gtgggagtac gcgcctgtgc gcgcggggcg   1920
agggcgaggg cgcgtgcgtg tgaccgcggg gagggggcgg gcgcgtgtgc ggggagcgcg   1980
ccgcgccagg ggccgagtgt gtggggccga tccagaagtg cgcagccccc tcacctggcc   2040
cccgtgtcat ccccgaaatc ccgggaaagg gtgggccgcg cgcgggagtt tggtggagtt   2100
ggaactttcg gtcgcgctcg ctgcccactc cgctggcgcc cggtggcccg tggtgaaggg   2160
ggactagggt ggggaacacc ggggccctgc ggtcccctcc ctttcctgta tttaagaagc   2220
cgccggcggc gcagaggccc aggcgggctg gcgcgggggc gaggcggccc ggtggcagca   2280
gcgggcgggg cgggcgctcc ggagtcggtg gggcccgcgg gttgggggc ggggagaggg    2340
gggagtggaa gggagggggga acgcagggga gggagaggag gggaggagcc gcgcggcccg   2400
cgccgcttcc gaaccggaaa gttggtcttg ccgaagtcct gccaccccgg cgtgcgcact   2460
ccgctccgct ccggccgcga gcctccgagc ccggccggcc gccgggggaa gcccgcggag   2520
gggacgcggg gccgggcgag aaggtccgga gagcgggggg cacctgagcc cgggcgggcc   2580
```

cgccgcgctg agcggcgctg agagccgcgg cggagcagcg aaggcggccg gccgaccccg 2640
cgcgcccgga acaggaggcg cggcgcccga gcggcccggg cgagacaaag gcgccgggtc 2700
ggagccctgc ccgcggccgc tcgctccggg aggggccgcc cggcggcggc ggcggggggg 2760
gcgcgggcgg cggcgcagac actctataaa ggggcgagcc cggcgcgccg gcggagacgg 2820
cgccgcgcgg acgccgccaa agtttgctgc ctgcgccctg cggagggacg gccaccgcgg 2880
cccgcgccgc acccgggccc cgccacagcc gcacccgggg cggccgagga gcgcggcgcc 2940
ggagcccgcg atgtgaggcg gcgccgggca gcgcgcgccc cggtcccgag gcgccgcggc 3000
cccctcctcg tcggcgcggc cgctaattgc gagcgcggcc tcatttgcat aggccgccgg 3060
agtccgctgg agcccggcca atcggcgcgg ccctccgcta atggccatgc attattcacc 3120
agcctaattg ctcagcccca tgcgcggccc gcgcagccgc cgccgccccg cgccccgcgc 3180
cgcgcgcccg ccaggccgcc ccgcgccgtc cccgccggcc gccccgctga tgccgctgcc 3240
ccgcgcgggg cccgagcgcc gctagcagca tgtctcggcg caagcaggcc aagccccagc 3300
acctcaagtc ggacgaggag ctgctgccgc ctgacggggc tcccgagcac ggtgagggcc 3360
ggggctgcgg ggtggccggg gggtctgggg ctgcccgtcc gggctgggga agcgcgtgcg 3420
gcgggagcgg atgcgcgcgt ccgggagcgg gagaaagttc cctgcttcct gcgggcaagc 3480
gtccgccccg cgccaggccg gccgcggggc cccgggtact tcgccggagc gcgcgcggcc 3540
gccgagagag ttgtgggcga agtaaacttg gctcctctcc tcggagtcgg ggagctgccc 3600
gcgaagggcg ccgaggccgc ggccggctcg aggacggctc ggaggccggg gcgggaggga 3660
gtccacggtg cctccgccgc cgcgccgccc cccagggtct ctgcgccagg acgctgaggc 3720
cggcggcggc ggggaaggcg accgcagccc acctaccgct ggacgcgggt tggggacccc 3780
gccgcccggc cagctttgtt cgggggcccg cggcccctcc cgggccccccg caccgcctcg 3840 ggtgacccgc ggtgtcccag cgcgttgacg cagcctgtga tccctcgcga ggcgaggaga 3900
aggtcggggg cttggctctg cctaatggcc gcccggggaa ttaagctggg ggtgagcgca 3960
gcggcggcgg cctgggcctg gcccctgctc gcggcgtgtt tccggggcgt tcgttgcagc 4020
gtctgcgcgg gccttttctc tcccgtcttt ttggatccgc cgaggccggg cgctggagac 4080
ctcggctttg cagtcatttc gctggtagga gcgtcctctt cgaaacatcc aagagcaaag 4140
ggcaggcgcc gcgaaagtta agagactggc aaagggctgg acttcccaga gtggcgcctt 4200
agccccgcaa agtttggggc gcccccaccc ccttcgtcg 4239

<210> SEQ ID NO 285
<211> LENGTH: 621
<212> TYPE: DNA
<213> ORGANISM: Homo sapiens

<400> SEQUENCE: 285
cgggtgcaaa cgcatcctct gtcccacgtg gagtggtgtg tccacacgca tgtcctctgt 60
cccatgccca cgtggagggg cgtgtacaca cgcatgtcct ctgtcccgtg tggaggggcg 120
tgtacacgca cacgtgtcct ctgtcccgtg tggaggggcg tgtacatgct cacatgtgtc 180
ctctgtcccg tgtggagggg cgtgtacatg caaacgtgta tcctctgtcc catgtggagg 240
gatgggcaca tgtgtgtctt caggacgcct gtctcaggca cccgtgtgtc ttcaggacgc 300
ctgtcgggca cacgcgtgtc ttcagaacgc ttgtctgggg cacacgtgtg ttctcaggat 360
gcctgtctcg ggcacacagg ttgcgggggc ggccggggct cctcaggcct tttctcccga 420
ctgttgctac tattcttttt agggcatctt tcacttccag ctgggccggg gtgagcccat 480
gctgcacacg cgcctgcgtc cacactgcaa ggacttcctg gagaagatcg ccaagctgta 540
cgagctgcac gtcttcacct tcggcagccg gctgtacgca cacaccatcg caggtcagtc 600
aagccgcagc cgaagaggcc g 621

<210> SEQ ID NO 286
<211> LENGTH: 434
<212> TYPE: DNA
<213> ORGANISM: Homo sapiens

<400> SEQUENCE: 286
cgggaccgtt tcacagatga gaagaccgag gtgccagggt ggcgatcgca cgaagggccc 60
gtcacgggag aatgaggagg gtctggcgtc agcaagctcc cccggaatct cgtgatctgg 120
aaatccacag agaagcacct tcaccacgcc agcttcccgg gccgcgcttc attgtcattt 180
ctggagagtg ttattaatat ccgccccgtg ggtgcggcgc tgtgtatttc cagagagggg 240
actcggggcc catcagggcc gggggagtgg agccggcaga tgttcggccc tgcccagaat 300
cacttcccca atttccccac gcccggcggg gctctcagca tctgcatccg ccgaggcctg 360
gctgtgctga cgggaattga aaggacctcg tggcttaggc aggcggggga gccccccggc 420
tggtcaggtg cacg 434

<210> SEQ ID NO 287
<211> LENGTH: 1012
<212> TYPE: DNA
<213> ORGANISM: Homo sapiens

<400> SEQUENCE: 287
cgccgcgact atggggtagc gttcaagggc aggccgcacc tcactcagca catgagcatg 60
tacgacggga gaaaaatgca tgaatgtcat cagtgccaaa aagccttcac cacgagcgcg 120
tccctcacac ggcacaggag aatccacacc ggggagaagc cttacgagtg cagcgactgc 180
gggaaagcct tcaacgaccc ttcagccctt aggagccacg caagaactca cctcaaagag 240
aagccctttg actgcagtca gtgtggaaat gcattccgga ccctctcggc cctgaaaatc 300
cacatgcgag ttcacactgg cgagaggcct tacaagtgtg atcagtgcgg gaaggcttac 360
ggccggagct gccacctcat cgcacacaag agaacgcaca ccggagagag gccctacgag 420
tgtcacgact gtgggaaagc tttccagcac ccctcccacc tcaaagagca cgtgaggaat 480
cacacggggg agaagcccta cgcgtgcacg cagtgcggca aagccttccg ctggaagtcc 540
aactttaatt tgcacaagaa gaaccacatg gtggagaaga cctacgaatg taaagaatgc 600
gggaaatcct ttggcgatct cgtgtcccgg aggaaacaca tgaggattca catcgtcaag 660
aaacccgtgg aatgtcggca gtgcgggaag accttccgaa accagtccat ccttaagact 720
cacatgaact ctcacactgg agagaaacca tacgggtgcg atctctgcgg gaaagctttc 780
agcgcgagtt caaacctcac cgcacacagg aagatacaca cgcaagagag acgctacgaa 840
tgcgccgcct gcgggaaagt cttcggtgac tatttatccc ggcggaggca catgagcgtt 900
caccttgtaa agaaacgagt tgagtgtagg cagtgtggca aggccttcag gaaccagtca 960
acgctgaaga cgcacatgcg aagccacacg ggggagaaac cgtacgaatg cg 1012

<210> SEQ ID NO 288
<211> LENGTH: 300
<212> TYPE: DNA
<213> ORGANISM: Homo sapiens

<400> SEQUENCE: 288
cggaaagcgc gcttttcggc agagctggtt agtttttaat gcgggctttt tttttctcac 60
ccgccgttcc ctccgctccg gtctgattcg caaatcccca aactggcaca aaccgggaaa 120
cttgcggccg gccgttcttc tccccgagtt ggagacagcc ctctcctctt ccctcccccg 180
cctctgggcc ctgacccact gcctggtttg cgctagagcc gtttaaaaaa gaaagaaagg 240
aagaaaggag ccgggctctg gtaccccgat gccagccgag ggcgcgtttc ccaggcggcg 300

<210> SEQ ID NO 289
<211> LENGTH: 310
<212> TYPE: DNA
<213> ORGANISM: Homo sapiens

<400> SEQUENCE: 289
cgcgaccacc cgctgcgcat gcgcttcact tgggcgtcac ccggggaact gcgcctgcgc 60
agtctctccc catccgaggt ccgctccgcg agtgcgagcg cgcgccaggc ccacccgggc 120
gctgctcttc atgtccccgc ggtcgaagac ggccacatac gtccccaaga agacgtcacc 180
gaggatccag aagggccctg caggcggagg gacatccagg gcctggaaac cggacaagca 240
gaggcggacg ccatttcgag tagtctgcaa ggcaacaaga cgacaactgg gtgtcgcggc 300
cacaaggacg 310

<210> SEQ ID NO 290
<211> LENGTH: 527
<212> TYPE: DNA
<213> ORGANISM: Homo sapiens

<400> SEQUENCE: 290
cgattcgctt ccccaccacg acgccctagc gctactgtgc aacgaagacc tcccaagcac 60
tggttccaat gcggagacca tggctcccca gactctggga actccaacac gactgcgaaa 120
cgaactccga gcgaggactc cccgagagct ccccgcaaca cggacctcac gcgctagcga 180
acaacagaaa aaaaaaagcg cgctctccct gcccctgaaa cattcccaga agcccacgca 240
gaccagaccg atgacctgtc tccactgctg gaggcgagtc agggacccga agtctctaaa 300
cactcgcctc tacccgccgc cccgcgaacc ccacacactg cagacgcgac actcgcaagt 360
ttcggggatg gcggccggcg agggccatac tgcgtctttc cggagacacg gaatacggca 420
ccagccgtcc ctttatgatg caatatgtct gcgcccaggg gacgcttgct gggagcagcc 480
attttcaacc ctactgccgt agagcaggcg gagtccctct tttcgcg 527

<210> SEQ ID NO 291
<211> LENGTH: 2075
<212> TYPE: DNA
<213> ORGANISM: Homo sapiens

<400> SEQUENCE: 291
cgaggtgggg gcgaggaacc acccggactg ggtctccatg ggcggggtcg tggcttaggg 60
cagggacagg tgtagggcga ggggtgagtt cggggcgtgg acgtgcgtgg gttcacaggt 120
gtgaacggta gccgcacgtg ggctgggact gagctgaaaa atcggccagg ggcgaggccc 180
gggtaggaag tgggtgcggc gtggggaggc gtggcctgac ggtgtgattg gcaggcggag 240
ctgatccgag aggacatcca gggggctctg cacaattacc gctcgggccg cggggagcgc 300
agggcggcgg cgctcaggtg agagggaaga agttggcagg gtctctggga agccggtttc 360
ccctccttgt gcctcagtct acaacaccag cctggaacag aacaagagtt ttgcatggag 420
tcaagcacac cctagtcgag tcttgtctgt acctcccaga cgagctgacc ccttctccag 480
aactctgctt cttttctctg ttccctgtcc aggccctcag tttcactcta gagaggtgct 540
atccctccgt atatcggatt tctccctacc tcgttgaact tgttcactcc ctttgagcct 600
tttgagcctg tgtgtctcgt tctgcgccct ggatttcccc ctccctggac ccctcagtgg 660
acccagtctt ggtgtccccg tcgccctccg cagggccacg caggaggagt tgcagcgcga 720
ccgctcgccc gccgctgaga ccccgcccct gcagcgccgc ccgtcagtcc gcgcagtgat 780
cagcaccgta gagcggggcg cgggccgcgg acgaccccag gcgaagccca ttcccgaggc 840
agaggaggcg cagaggcctg agccggtggg gacctcgagc aacgctgact cggcctcccc 900
ggacctgggt ccccggggtc ctgacctggc ggttctgcag gcggagcggg aagtggtgag 960
ccgctaagga aggggtctgg gggcagggcc aggcgactgg aggcggggct agggcgtgga 1020
agggcggggc cggctgcggg acgggcgttc tctggtcaga cttctgcgtt atggaagagg 1080
ggctgggtcg ggggcggggc ttggttgtgg ggcgtggcca ggtgtttggg gcgtggcctg 1140
atctggggaa gtgtataggt gctcaggttc agggcttcga cggggatggt tttggaactc 1200
gggagccctg agcgtccccc tcctctgtcc cctaggacat cctgaaccac gtgttcgacg 1260
acgtagagag ctttgtatcg aggctgcaga agtcggcgga ggcggccagg gtgctggagc 1320
accgggaacg cggccgcagg agccggcgcc gggcggctgg gggtaagggg caccctggcg 1380
tgggatctga accccctccc gatctcttcc aaatgtcccc gctctcccca ggctctcccc 1440
tcccgccact tgccagggct gacctcaccg ccatcttaac cgggtgtcca cctctctctg 1500
cctgcctggt gctggccccg cgtccccatc gccgcgcccg tctgctcccc tcagagggct 1560
tgctgacgct gcgggccaag ccgccctcgg aggccgagta caccgacgtg ctgcagaaga 1620
tcaagtacgc cttcagcctg ctggtgagga cgcgcccgcc cctgggccgg ggcgcgggca 1680
cgacgaacct gtcccgtccc cgcacccacg ccaaccacct ccctccccac gccccaggcc 1740
cggctgcgcg gcaacatcgc cgacccctcc tctccggagc tgttgcactt ccttttcggg 1800
cctctgcaga tggtgagacc cgccccaggc cctcgggccc ccctgcagcg ggaggaatcg 1860
ggttcgactt gtagaaggtg tggcggcaca gcctgcccct cctgctcccc tgacagattg 1920
tgaacacgtc gggggggccg gagttcgcga gcagtgtgcg gcggccgcat ctgacatcgg 1980
atgccgtggc gctgctgcgg gacaacgtca ctccacgtga aaacgagctc tggacctcgc 2040
tgggggactc gtggacccgc cccgggtgag gggcg 2075

<210> SEQ ID NO 292
<211> LENGTH: 347
<212> TYPE: DNA
<213> ORGANISM: Homo sapiens

<400> SEQUENCE: 292
cgctcccctg cgtttcggct gctggcccag cagagggcgc cggagagcgg acggagccgc 60
aggcggggtt gtgggaagac gctgggatcc cgtgcgcgct tgtgctcctt ccttctgggc 120
cagcgcgcag actatcaacc gaggtattca gtccctcgga aacccagttc ctccgtttcc 180
aggcttctcg cccacacgga gacagtcgct ctcacacgta cctctcgcgg gctcttactc 240
gtggtcccgg tctcctcctg gtccccacct tccagcccag cgcgcacact agacggcacg 300
tgctctccac gctctttctc cagcgcccct tgctcacccg ccccccg 347

<210> SEQ ID NO 293

<211> LENGTH: 712
<212> TYPE: DNA
<213> ORGANISM: Homo sapiens

<400> SEQUENCE: 293
cgcagcaagc ctcagccgcc cttatttaag ataccgcccg agagggcggg gaaagaaaac 60
ccctacaggc aggacagccc ttcgcccctc ccaccaccac tgcggcaaac aagccccgcc 120
cccagagggt agccgggcac gccggcgccg cgaggccgat ggcaccccgc aggaaggggc 180
attttcgcag cccccagacc cagcccagga ggcccagggc tcccgagagc cgcattccgc 240
cgtggcaaca gggatagcat tggtgtcgac cttgctggac ttgccgtggc agagcccccg 300
gctgtctgcc ctaatgcccc cggtttgctg cggtggcccc cggccagtca gaaaggcgcg 360
gagaccctgc agcagcccct cagaccccgg actgcaagat ggcggcacca acgcagcagc 420
ccgggctgcg cccacccctg ccccaaaaag gcaccaacca tccacagcct ggccgccact 480
gtgcccactc tcggactggg cagcgggcgg ccaagtacca tgtccgccag cccgccctgc 540
cacaagggtc gctggcttgc cgcggggtct tgggcttgcg gcaagacggc cactctggcc 600
cagagccgtc gcgacaccaa ggtcccgcgg gcaggaggcg cgcggggcgg ccgaaggcgc 660
actcacctca cctcagtgct gcgcagcctc gggcacgaac agccgcctag cg 712

<210> SEQ ID NO 294
<211> LENGTH: 932
<212> TYPE: DNA
<213> ORGANISM: Homo sapiens

<400> SEQUENCE: 294
cgcccaacga agaggaggga gtaggggtcc gcgccccacc acgaaaggag agtagagggc 60
tcgcgccctg cggggagagg cgttaggggg tccgcgcccg gcgaggagat gcgcgtacca 120
gccccgcacg ccaaggggag aagacacgcg ggacggtccg cgcctggcgg agagagttcc 180
tcacgcccgc cccgccggga accacaagcc agcgccccta acaagcccct gcccagagca 240
gggctgccgc gtaccctcac agacagaaag agcgaccacg cagccaccgc ccagccccag 300
ccgctctgga gtccttgacc ccaccctcac taggccttgg ctccgcgacc ggtgggcggg 360
aacggaggaa acagacccga gaggccgcga gaggacggaa ctcacttccc gccgccgtag 420
cgtcctcgtc agctcgccct ccgactctcc gcatgggcgc gcagagttcc cggatgcgat 480
attccggtga caccggacgc tgggggcggg gcctagtgcg acgagggcgg ggccggggcc 540
ggcccggggc ggggccgtgg ccgcagctgc ctggcagcca gaacctggga gcgctcgcag 600
tgctgccttt cggggttctt tgtccttcgc ttctgctggt aggtgaggtt taacagacgg 660
aaagacgccg ggagcgcacg tgggctgcct tgagccgctg cggacgagca ccttgtctct 720
caggttgacc agccgtatat ccgcttgcga gcctgcacca ccctgggcgc gcgtggtctc 780
ggcagaatct cgttcacacg ggtcccactc gtaggctgct gtgtctcctt cctctcacgg 840
cgtcggggac tggggcctgg agtcactcct ctacaggggt gtggaacgcg ccaatggacg 900
ctgacacctt catgcggtcg tttaacgctc cg 932

<210> SEQ ID NO 295
<211> LENGTH: 422
<212> TYPE: DNA
<213> ORGANISM: Homo sapiens

<400> SEQUENCE: 295
cgcttcccta tcggggctgc acgtagagca tctaaccgca tgttcccgga acctgggatg 60
cgcgcgcgca aaggagcgcc caagcgtgca acccagagtt tggacgcgcc gccctttaca 120
gcccccgccc cggggccggg cgagctgagg gggcgcgggg cgtctgtgtt cccagctgat 180
cacagaacag gccgatatcg cattgacccg gggagctgag gtgaagggcc gctgtggcca 240
cagccagtcg gagctgcaag tgttctgggt ggatcgcgca tatgcactca aaatgctctt 300
tgtaaaggta actccgagcc cagcgggcag aggggccgca ggctccgcgt gggtgtggga 360
agtggcggcc cctaggttta agaacccaga cgctgcgggg acgattgaag cgcacctccc 420
cg 422

<210> SEQ ID NO 296
<211> LENGTH: 10782
<212> TYPE: DNA
<213> ORGANISM: Homo sapiens

<400> SEQUENCE: 296
cgcggagaca tctcgagtcc cgcaggtgtc tgagctgcgc tgcgcgcccc agccgggaag 60
ccttttctta tccaaccgcg ccgcccccgcg gaaagcctgg gtactgcaga cgccctcacc 120
ggcccaccga cagctggttt tgaagcgggg gcttagaaaa gtaaagggga cagtgtttgg 180
agccacgatg cctttgatgt gaggcggttc cacccaacaa tcaacgaatc aagctggaac 240
tgcaggccct acttttgttg gggggaggac cttaaggaat gtcacccccct tgtcccctac 300 cctctgcccc acgcccagcc tctcagaagg caccaggcgt gagtagagtg cgaggcgtcc 360
acaccctcgt gtcccttcca ttcccggaca cctttgcacc ctagccgagg cctcagcacg 420
gagtgagggt tgcctggggt gccctgctgt gtgtggggcg ttcttgcctc ccgggccctg 480
accccacggt ctgggtcggc gaggcgtctc tccctggcgt ctggactgtg cgcctgcccc 540
gcttccaggc gacgaacggc aggagccggg ggtccggcgg gacccggatc cagggcgggc 600
ggaaggcgag ggtctctcct tcccggaacc cccgcccccgg aaacctgcaa ccaaaccggg 660
tccctcctcc gcatcgctcc cgcgctcccg ggccgcctcc ccacgcgggc acccactctc 720
cgggccctcg cagcaccgcc ctctccgcgt ccacccgcgc ggccgacgcc gccaggggcc 780
ctgagatcgc ggagacagcg cgccctggcg cctggtgggg ccctcccagt ggccagagcg 840
ctcctggacc agtcggctgt ggtctgtgcc caaacacgat ggaaaccggg gctgggacgg 900
gcggtggtac gcacgtggag gagaagaggc atggcgggaa aaccacagcc gaacacaggt 960
cgactcgcac ctcccaggca cccgccgccg tctgactcgc ggctctcccc aaggttccga 1020
ctcgccgcca cctcttggca ccactcaccg ggctccgacc cgggccgcga gtccgctgat 1080
gcgcagctgc ctccggcggc tcccgggctc tgcccggacc cgcgcgcaga gacgctcggg 1140
aacgctgggc tcgggcgcct cctggcggcg gcagcacgcg gcacacgctc ggttctccgg 1200
cccgaggggg cgcgtggagc gtacgcggga tccgcgcgcg ggcctgggct gctggcccac 1260
atttccccgc ttgctcggat ggcggcgctg aggcctattc gcctctttat taataacgat 1320
gcctcgggag ggaaaaaata gagcctttaa aaatcagagt gcgagagagg agtgtgtgtg 1380
tgtgtgtgtg tgtgtgtgtg tgtgtgtgtc tcggggcgtt ggtgaaagca ataaaactca 1440
gatcgcttcc ttggcgagat agcggcggct ataatgcgcc ggggggatca ggggtttatt 1500
tgcagatcct ggataaaaga tgatatatcg acacggttta gagtgtcact gcgcttggcc 1560

```
tctcagggag ccacaagtac atatttcctg aaataccgcc cagcacagta tctaatccgc   1620
ccgccactta acaccgggag gggaacttca gcagcgcaca agcgcgctcc cggtttcctg   1680
gttctgggtg gggagagccc aaatgagaag gatctggtat gcctagacgc cccctcccct   1740
ggcctttgtc ttcagtccaa gtaatcactt agcgatgggc cttaataaat acgtctgaga   1800
actgtcctta tgctcggtaa atattggatt agcttttcaa tgaccaggct cttgaaaagg   1860
ctcgagaaat acacaccagg tctcaactaa gcccaacagt caataggtaa ggaaataagt   1920
tatttcccca tctgaggtgg ggaatgttgg gaagggggac ttccactctt accaaattat   1980
ctgattctac taaatatgac cgttgtacta aataggaaag gggcgcatc caagtttccc   2040
attagtcgga atttccacca gctcagttct gctcattaag ggccgagtga ctttgtgggg   2100
aacatatctg ggttccagtt tttatttcca cagagctcag cataaactat ttttgtttag   2160
tacatatggt ttatttgggg actgcttatg ggagttttga cctggcaatt gcaggggaga   2220
aggcatgacc caaattattt ccgactgcct cgcgccaatt tggaccgctt agaggaggca   2280
aaaaatgggc aaattccttg gaagccctgc tgtgtctccc tggtactgaa ttttgtaagc   2340
acgcgataca ggagacattg aaaattaaag aggaagtatc tccctcctcc aacatgggga   2400
gagacgctgt tggaagaagt ttctgaagtg gtttcccatc gcaccaagag gccagtggga   2460
tggatccccg cgcataattc aaaggaacgc gcgcgtcttt agctcttcgg ggttggtaac   2520
caagtggtcc ggccgggcgc aagtcgcctt ggaaccggct gcagcccaag tctagctggg   2580
cccgggactg agcggcaccc ttggcctctc agaacctttc tcgcggtgag tggaagggcg   2640
gctccgcgcg cgggcgcttc ggggccggtc ggttgcgaaa tcaggggggtg gattttcatc   2700
tacccaggag ccgctaagcc cgtaggggac cgagcatcac ccaggccctg ggtaccctga   2760
gttgcctcct gagccccagg acggtccgat ggtgcagagc tcccaggcag aagttagttt   2820
cctgatacac acacagcagt gagcaaagtg cgcacaagtg agccaaaccc tgaagacgca   2880
ggttcgcgga ctcccatccc agcgttagag tcaaggagac agaagagagg aaggagagaa   2940
gtgaggaagg gagagagatt atgagaaaaa gagattatga aagtagagaa agagattatg   3000
agagcgagat tatgagaaga gagaaaaaga gagattttga gagagagaga cagaatgaga   3060
gagatccaac tttcagtgtc acggggccta ggcggggcaa gcgccctccg aagccatcaa   3120
agacaggggt ggctttttct cccctcctcc agcctcctcc ccaatagata tagcacgaat   3180
ttttaatgcg tcttcctttc acagacaaca atacagggtt tgaaagccgg acacaattta   3240
ggttttgtgc gggtccctcc tcgcgctccc tcggcccagc tggccatatg gaatccagca   3300
tggagcccgt ggatgacaaa gggacccagt gacaggccca acaaaacccc aaggagactt   3360
ctgcctgact ccgggattca ctgccggcga taagcgcgct gaatggtgcg gggtggggcg   3420
gggggtgggg ggcgggcccc ttctccttct tcccctctct ctgtccccgc gatcctttct   3480
ctgtcccttt ttaatatgca cgcctctaac atctccggct cccagctttc ccattgtgcg   3540
gttttgtacc gcccgctgta gattgggcga agatagactg ctgaagcgga ccccgcgccg   3600
ggtgcgctcc cagggcgctg gggttagggc cacacagggc tccgcaggcg cttttattga   3660
ctccatgggg acccgaggac agagagaggc gggcgccggg tccacctccc gggctcccgg   3720
ccggccacag gagcgcacac ccagattgca ggcccgcggt cctggccaca gctccaaatt   3780
tgtcctcaat gagcaagtgg tggaagcctg ccagggtgag gaccttccac gcttccccct   3840
tcctctctgg aaacctgagg gtctcttgtg atcattctca ccctggaagc cctggggcct   3900
ggaaaagtca aaatggcctc aggccttctg acagctccgc tccaagagac ttgaaaccct   3960
```

cacctttcct cccaagagga ttttgggatt aggggaagtt gcaagtggat gttgagtggt 4020
tagtaccagg gcaggttggg cgttcaatta ttgcacaaca aactatttgg gagaaattcg 4080
ttggccttta aaaacagtaa gacataagcc cccaaacatt gccaagctag tgtggagaac 4140
aaagggagac cttttagcat ttagaaaaac tgccctttcc ccgaggatga gcccggagat 4200
gggaaaggac ctttactggg gtattagaaa gacttccgag ccctcaatta tccaggggcg 4260
gtgtggaacg cgggaataaa gtgtcatcgc gtccctgggc tgctgcgcag agtgctatcg 4320
acgcacagat ttggtcgcac ggataatcat gtttgcttta gatattgaat taaacctgat 4380
catcaactac agggagcgag aaagtcagct gggaccgctc cttttgcccg gcctcctcac 4440
tgccacccaa ccccccagcc ttgatggtgc agcttcggag agaacagaga tacaatttcc 4500
aaatgcgccg acgttcagtc cctcagcgtc tgcagcaccc gctgggctct gagctagagt 4560
cccaagtatt tttagaaacc cgcgagatag aggagaaagg ctcatcctcc agttggccag 4620
gcttcctaag acgctccccc gcgtggccaa gtgtgcgcca gcatctgcca aggagatctt 4680
cctccagcaa caagggtggg acggaatccg ttccccgccg gaaagatgga tgcgcccttc 4740
ccgggcgtgc ccggggctgt gtgcccactt cccatccggg gagctcaccc cacccccaaa 4800
cctctacttc ctagcaatcc acccagttcc acgctcaagg gctgacctgg ggggaccgca 4860
caccctggtt cggaccgccg aacgctggag ggaaggaggc ccgggatcca gtccccggag 4920
agaggcctgg aagcccggaa aggatgggag cgtaagggaa gggagaggca tggtttgctg 4980
ggattgccaa agattctcgc tccctggctt cctggggcca aagatcctag ggagggctgc 5040
agtatcccct ccctccccg agcccagaac cccgcgtact tcccccaagc cccctaagcc 5100
aaagcctcgc gcgccctgac cgttcccacc cccagcctta gcggtctcct aggtcagcac 5160
cagcccgcag attttgaaaa ggagtgggga gtggggagaa ggcagccagt cttaacctca 5220
gacccccacc cacccacttt cttagcgtga ggtaagtcaa atgtaacaaa gtgaaagtca 5280
tcgagtgtag tggcttcaac agcttctcag gctgaaggag ccactcatag atttgggcca 5340
gcgagggggg tttgctctcc tcgcctttgc ggctcccgaa gtcacttttc ctcccgtagc 5400
cggacgctgc cgcccggggt tcagacagcg cgcgagacca ggggagatgc gggggagggt 5460
gggcggccct gggcttccgg ccgaccgctc gcaggccgga ggccgagcgt tctcctcccc 5520
gccccaatcc taggcgcggg gtgcagcctg tggtcggagg ggcctgcacc gggagccccg 5580
cccgccccag ggccccggta cccccggcct ccccgcccga gaggaaccgc ctgtgggagc 5640
cccgcgggcg gccgggcccg gctcccaggc ccaggcctcc ggcccggcgc agtaggacaa 5700
acgggagggc agggattttt tctttttttc ttttttaaac acaggatttt tattaaaatt 5760
cttatttaaa aaatcgaaag ctttctgcgc ccggcgctgt tggggaaccg cgccgaatag 5820
ctgagctcca agttcggggc tgaaggcccg gaggacaggg cagagggctc cctgcctaca 5880
gggttttctt ttccatattt gagaaatgtt tgcacaataa aataaaaaga gaaaggaaga 5940
aagcagggga aaacgcaaaa acaaaaacaa aacaaaaaac aaacccaaac aagccacaaa 6000
gaaaggagtt ggacccagac gggaaacagg ccggtcctga aggtcatttt ggcaacaatc 6060
accaccgata tttacaacga aaagcgaaat ctgccaccag ttgtcagaac gtttacatgg 6120
ccataaatat ttagcatttt cttatttttt tttaaaaaaa ggaagaaatt ctctgtattt 6180
ttaaagtgtt ctccacttgc tttagaagac ggctgacaat atcgctactc acacaaacat 6240
attttacaaa atgcacgaaa gcaggggtgg ggggtcggtc tttttctcgt tttcaagtga 6300
cgacattaac gctgggacgg tttggtcccc ccggggagag gcaaagaagc gaagctgcgc 6360
aaacattctg taaacacggc gtagagttca gccctctccc aaggttcaga aggagaggca 6420
tgggcagagc tgggtgggtg gaatctgcca ctccaaggag acgcaggcaa cctcccggcg 6480
cctccctagt ggagccgaga gtcaactcga ctccataata ataattataa taataataat 6540
aaccaccata aggaccgagg cctcctcgcc gccaccgccg ccggggtggg gcctgggcct 6600
ggggccgcga gtctcgttgg ggcggcgctc accaagtcca ctgctgggcc tggaccaggg 6660
ggtgtgctgt cgggtactgg ggggtgctgg ccgagctgta ctgggcgttg tactgcatgt 6720
gctgcagcga ctgcgcgctg taggcagaaa agggaatgcc cgcctggaag gtggcggctg 6780
ccaggtcctg ggctttgagc gcgtgacatg gtttgccgtc cctgaccaag acgggcacgg 6840
ccacccggcg cggcgagggc aggggcgtca cctccatacc tttctcggcc cgggcgcgct 6900
tcatcttgta gcggtggttc tggaaccaga tcttgacctg cgtgggcgtg aggcggatga 6960
ggctggccag gtgttcgcgc tcgggcgccg acaggtaccg ctgctgccga aagcgccgct 7020
ccagctcgta ggtctgcgcc ttggagaaaa gcactcgccg ctttcgcttc ttgccggcgt 7080
ccccccgcc gcccggggtc tccttgtcat tgtccggtga ctcgtcggcc gagggctccg 7140
gggacttgga gcttgagtcc tgaggggcg ccccggcagc cagaccgtgc actgggggga 7200
gggggagaga gaagcgcgtc aggcgtctgg aggccgcgcg cagcctgcac cagactcgga 7260
gcaccctgga tcctccgtgc gaccctggac ctccgcgcct ggcagcccag ccccgctgcc 7320
tttgccatga cccctgcctt cctctacgcc tgacgaagac gtcgggacct cccagggtaa 7380
agagggaaat ccgtaggagt gggggctagg ggctcgcctt tcaaggggct cacatagtgt 7440
gggtgagaat ttgggggggg aagtggcact gaagatcatc gcgggttaag ggctccggcg 7500
cccttaagcg gtttcctctc cggcgagacg tgggcagatt tttaaaagaa ataccccaca 7560
atcccagcat tgatcggctc ggccatttaa ggcaggtttt tgggggcttt cgtttctgct 7620
ttcgggcctt ctagacaccc cctgcactgc acaaagcgtc ctctatgatc gcgcaggggg 7680
cagggtgagc tatttatacc cggccaccc gaagcctccc caccctccac ccgtacccgg 7740
acgaggctcg ctggctacct ccagggcgcc aggccagtcc ctcccagcgg ccggagtccg 7800
ggggctgcgg ctggagccat cggtccgggt tgacatcata taccagcccc tgggaggtat 7860
agcccttctc cctctttctc cttaacttct cgcattgaaa aaaattttgg agaccaagtt 7920
ctttcccgga actaaggagg cttgaagagg agggcagagg acatcctata caggtgttaa 7980
aaatctttct acggatccga gtgagggggt ccgggcttac atggcccctt cccctttcac 8040
tcccagcgtc caacccgggc tgcggctgca ggaatggagg ggaccacggc ctcggcagcc 8100
aagttttgct acttacggga gtactgaagg ccctcggtgc tggccagcca gcgcgtgtac 8160
gggttgtcgc tgctgtcgta gaaggggttc ttcaggggca ggctctgcac cgcgtccagg 8220
gcgccctgcc ccagcggccc ggccctcttg gctggctcgg gcccctcgtt ctcttcctcc 8280
ggaccttcgg ccacagagcc ctcctcatcg ttggtgtccg gcaggtctaa gatgtccttg 8340
accgaaaacc ccgtctttgt gttggtcagc gacatggttc gagaccccaa aatttatgtc 8400
gcaaagttgt agcttcactt ggtcaattcg tggcgctccc ctgccccggc gggcggggga 8460
ggggggagtt ggggggaggg actgggggag gggagggggg aattggcttt aattattggg 8520
ataattatta tttttaaaaa gagaaagaaa ctggggatgg ggaggaaaaa aatgaagccc 8580
aacccagtgc ctctctctgt cttctttgaa agcacgcgga aatggacgca ggaagccggg 8640
cggcctgcgc gccgagcgcc gcgggccccg gccttagttt ctaactccag gaggggtgcc 8700

```
aaggcggcgt cagctcgggc tccggcggcc gctcggcgcg cggtggcggc tggtggcgag   8760
gaaaaaatgg gccattgccc gagcgatcag tccatataag gctgggctcc actcacgaac   8820
ctggggaggc ggggagaggg ggagaaagag agggagggag ggaaagaaag agggagggag   8880
ggggagcgag agagggagcg ggagaagggt ggaaaaaagg gggaagagac attaaaaacg   8940
caaaggttgg ccacgtgtgg gcgggtcttg ggagtcaagt ggatgaagac agtatttgca   9000
gatgtgaaat tgtgggtttt ggggagctcc gcgctcccag ccaacggccc tctagagcaa   9060
gatgagaggt gtaacgtgtc aattaattgc aaagacgggg cgagcctttt tttttttaaa   9120
cccagtattt acatacaaag ggccaccgcg tcgctcgcga gtccacacac ttgaaagggc   9180
cgttttaaca aattgcatct taaaaaaggt gggggtgggg aggaggaggg gagaaaacaa   9240
aacagaaacc aggaggaggg aaaaaatcct ctttaacatt caccggttcc tacctccccg   9300
cccccgcgcg cccacccccg gcaagccgga aaattggcga tttgtggcgc ctttggaaaa   9360
gggggagggg gcgaaggccg agctgcggaa atctctcctt tccatcgttg gtggttgcct   9420
aaacaagatc cggttcaaat ggcaagagcc caacttctgt aagcctccta ggtcaatatt   9480
ttggttgagg cttaaggatg agtgctagaa atgacaaggc aagtaattga ttccagttaa   9540
ccgcgagaga gcccaaaacc caggagagag ctccgctccg ggccggccag agccaccacc   9600
aagcgacccg ccccccttcca gccgcccttt atttgctaaa gactcattta tttccttcac   9660
tccgcctccc cccacctccc acccccaacc ccccgcctcc acctctctgc ggccaaggag   9720
gacgcgcagt tcactttctg ctttgcgggc ggtcccgggg agggcggggt aagagtgagg   9780
agctccaact tcgtctgggg tcggaccctg gccctgctgc ctctgggctc tgcgggcctc   9840
tttccccggg tggaggaaag ggcagacggc cctgctcttt cctgccctct attatccctc   9900
cctctccggc cccctccctc tccagcctct ggctagaggt ggagcagcgg gaaggcggcg   9960
gggcgggatt gcgggggtgg gggtgggggt tgtgtctcca gcctgggtga agacccagaa  10020
agctgcgggg gaggggggtc gctgggtggc ccgacgatgc ctcgttttct ccccagtttt  10080
cttctcccac gcgagttctt tagtgtggtc tctttttgga cgccttgggt gcgttcggag  10140
tacgcgctcc acgtttccag gttaagtcag gttagtgtga agtttccagc cactctcggc  10200
tctgggaact gaactttccc gggacttgca cttcctcctc ggcgctgggg ttggaaaaga  10260
ccacgccgca tttgccaccc cttcttctag ttaaaacttt tttggggggg gggtgcaggg  10320
gtgtagattg gctacctgat gctcgttcgc cccagaggag tgtcaggaag gagctttgtc  10380
tgggggcggg gaggggcaca gaaggccacc cctgcggggt ccaggtctag tcttcccaca  10440
acctgggctc ctccgcgcgg gccaagctga gcgcgcgggc accgggtcct cctcgcgcgc  10500
agctgcagcg gacgccgccg cgccccagct gcccccgggt tgccagcgct gggtgagggc  10560
acctctcccc gagccgctcg gcggctttct gcagccctag ctgcctcgcc cccagtatgt  10620
gacgtgggtg acaatggccc aggttagagc aagcccctcg tcggcgcgtc ctgggtggtc  10680
ggacccgggc aaacacaaat acaaaccgat tgctaagctg cggacaatga gcgaaatgta  10740
gacaaatgtc ccgctcccgt tggaagcctt tgtcccggct cg                      10782
```

<210> SEQ ID NO 297
<211> LENGTH: 616
<212> TYPE: DNA
<213> ORGANISM: Homo sapiens

<400> SEQUENCE: 297
cgccacggcg tggccaccga ggtggtgtac cgctgcgaca cctgcggcca gaccttcgcc 60
aaccgctgca acctgaagag ccaccagcgc cacgtgcaca gcagcgagcg ccatttccca 120
tgcgagctgt gcgggaagaa gttcaagcgc aagaaggacg tgaagcggca cgtgctgcag 180
gtgcatgagg gcggcggcga gcggcaccgc tgcggccagt gcggcaaggg cctgagttcc 240
aagacagcgc tgcggctgca cgagcgcaca cacacgggag accggcccta cggctgcacc 300
gagtgcggcg ccaggttctc gcagccgtcc gcgctcaaga cgcacatgag gtacgcgggg 360
agccgtccgg aggggtccct gcgcactgga agggtgtgtc aagcactgag gtcgtcctgg 420
gatttgatgt ctcactgctt aatttctccg ctccaaacct gggggcttat ttcgagacag 480
cgtttagttc tctgtcaagg tacaggggct gcgagtgatg gctctgctcc cttgttctga 540
gacccctggg gcgcccctgc tggccgggac gtccctctgg tgggaccgcg acagcggccg 600
cgggctcgcc ccaccg 616

<210> SEQ ID NO 298
<211> LENGTH: 1687
<212> TYPE: DNA
<213> ORGANISM: Homo sapiens

<400> SEQUENCE: 298
cgcgctttga acccaaccag ccctcatcgc tcggagccct gcgtcccccg cttcccaatc 60
ccagaacccc ggaagcagat ctcctcagtc ccactccctg agggtcctac agtccgaggt 120
cccgcagcga gggaggagca aacgcctgag ctccgcggga acccggcgcg gctgcctgcg 180
cgcacgcagg gaccggagcc cgagcctggg ccctgcaaag tgggtctccc actcgctgcg 240
cgttcgagtg gggcctccgc taaacatgca gattaaacaa ggggcttccg ataaggataa 300
ttacaggagg ctgcgcattg actttccgtt actaaaggaa gacccaaatc tccccccttgc 360 aagctgttcc cgggattacc aaaacaatca ctttcttttg agatcattgt cttttgaacc 420
actccagctc ggggcagaac gctttagacg ctggcgttgt tttccgctcc gcgaggaatt 480
ttcccccaga tttatctctg ggtttaggga aggcgttggg cattcgggac tgcgtagtcg 540
tttgtaaatc cgaatttggg gtagcagtta agtgagatac ctacgcttcc acacagtttg 600
tagcccgaga ccagtcaggc aggcagggta gtcgattcta aggtggcccg accggggtcg 660
cccgcgaatg gaaagcctaa ggggcgaggg cggacgcggg cgccgtgcct gcagccccgg 720
gtgccgacca agtggcctca cctgggacag gtcttggggt ctccctcccc taggtctccc 780
tggaaggtag gcgatcacgg gagtgacaga ccccgagtag atagccagtg atccaaagac 840
accaaaaggc caggcggtag gagcccagcc tcagacactc tctatagtga ccgcggcgcc 900
tcgggaagga tcgtcttaaa ctcattttgc aggtgagagc aactgggact tattaaccca 960
gtcacatcgg acacagagac gtggcgaggg cgacacagag caggagactc aatcaaggag 1020
cccgtattgg agctctaagg ggactcagag atgcagaagg aacgaacttc taaggggtct 1080
tgcaattcct ggactggggc gttcctaatg catcccggga ccccaatgcc agggaggggc 1140
ctgcaggacc ccagcggtgg gcgagttgtg tcctgggtca ccttgtgttt cgcagcgtgg 1200
cggtggcagg agcccagcgc gggaggacat tttcatagcc tcctacagtg agaaacgccc 1260
cccacccgac gctgcgctca tctgtgtccc cgctgttgcc ggggctctgg tatccacttg 1320
cgcgccctat gtggtgggga tccacccaga gcccagcgtc aagttatacg ggcgcttcac 1380
tcagcgtcag ccaagaccag ggaagcgctt cttgccgttt aggagacgtc tgcaagagat 1440
aaaaagctag cccacgatcc acccacaatc ctcgtgtccc cggggtgccc tcgcagttgc 1500
caaacctacg ggccgcgttt aggggaagcc tccgcgtcct ggcggccaaa agaatgggct 1560
ccttccagct tcccccctacc ggataccacc tgcaaatcta ttgccagagg cgcagctccc 1620
gcgaacgttc ccgccccggg cggcccccag gagtcgtttt gggtccctaa atccgttgag 1680
ggttccg 1687

<210> SEQ ID NO 299
<211> LENGTH: 5242
<212> TYPE: DNA
<213> ORGANISM: Homo sapiens

<400> SEQUENCE: 299
cggccgtcgg agcagggccc cagcgcaccg cgagcctctg cttcctccgc cttgcagcgc 60
cgcgagccct tctttcctcc gcgcctggcc ccgtctgcgc ccctctcggc gtgggcattc 120
gcagacccgc taggaggctg acgagaggtg tcctcataga gtcctgcctt cttccagacc 180
cccaaacgaa aagaaagaga aaagccaacc tttcgcctcc attctgcacg catttggaga 240
gcggctggtg gcgagcgatc cgcacaatcg cttccctcgc ggcgtccctg gacgggcgga 300
gagaacccgg gtgactgagc ctgaggctga gcttccttgg gagcgatcca tgccagccac 360
ttctaccttc aagggggact cgcggccggg tttacgcgcg aaggatgggt gccagggaaa 420
ctgacttata gacgacccgc tccgcgagag actgacaact cagtcctgcg ggctttcggg 480
gcgcccagac cagtccttag ccagaggatc tggggctgca cagctcccgg accctggagg 540
gggtggtccg ggggtgggag actgcgagca tcagcccacg ccggcccccct cccaccctgc 600 ggcggcgagg tgggaagggc caggatgcga gcttagcacc tcccctagaa atgcagcact 660
tcgccccccc acctcccctg ccctcggcgc tccctctttc acgcgctccc tcccgcctcc 720
ttcccaaggg cgcccttctt ctgcccccag ctcacgtctg aatccctcgg cgcccccttt 780
ctcttctcct agccccttcc tcacgtcccc tgcctccggg tatttcctct ctccaatccc 840
ccacccccgc accgcctgat tccgaggggc gggagcgcat tgggctgcgc acgggtgggg 900
gcgccgcgcc agcttcgcgt agctgctctg acgccgctgc cgccgccgcc gccgccgccg 960
ccctccgcag cccagctcgc gccccgcggc agctccgcag tgcactagcc accaccgccg 1020
ccgccgccgc tccgccagac ctgctgccag cttgcccggt ccagccctga gagagcctcg 1080
aacgccagct gcgagggtca tgagccagag agccccgggg cgccgcgcgg agagcaagcg 1140
gagatagcga ctttgcgccc cccagccctc gccttcttgc atcgcgttcc ccgcatcctc 1200
gggtccttct gtcctttccg ctgtccccac cgccgccatg gccaccttgc tccgcagcaa 1260
gctgtccaac gtggccacgt ccgtgtccaa caagtcccag gccaagatga gcggcatgtt 1320
cgccaggatg ggttttcagg cggccacgga tgaggaggcg gtgggcttcg cgcattgcga 1380
cgacctcgac tttgagcacc gccagggcct gcagatggac atcctgaaag ccgagggaga 1440
gccctgcggg gacgagggcg ctgaagcgcc cgtcgaggga gacatccatt atcagcgagg 1500
cagcggagct cctctgccgc cctccggctc caaggaccag gtgggaggtg gtggcgaatt 1560
cgggggccac gacaagccca aaatcacggc gtgggaggca ggctggaacg tgaccaacgc 1620
catccaggta agcgcgggat tcccagttct gcctgtcctc ccccctccca gctcagcgtg 1680
ccgggctctg cccccgacag tcgcccggtg atctcggcct ggagaccccc tcctgtaccc 1740
aggaatctcc ctttctccat ccctcccagc cctgcgcggg gacctacgcc cccaggcggt 1800
gttttccgcc ctaacccacg ctccctccca acggcaccag ctgcaagacc gctaggctga 1860
agttcggtct gagacacctg tccggagaca ctgcaaaagt gaaggaaatg gggggaggga 1920
gcaggaagcg atgagaaaga aagaaaatca ggattggagg gcacggtttg gtcttggact 1980
ctggaacgga ttcacagctg catttttggg aggaaagaag aaggggaaat cgctgaggtc 2040
ggagtctcct ccccccgcac acacgcatag acacgcacac gtatataggc aggcacacca 2100
catgcccaca gcccccctte ccacgaacaa aggcgcaggc acaggcgcac acgacatgta 2160
tctatatata gaccacagta ctatccccaa atgcacctgc gtacacccct acagctccac 2220
aaacaaaagc atatacctgc acataccaaa cacacgaata ttcgtttgaa catatgcaca 2280
cacacatgca cagatgcatg cagacaggaa ccagcctgct cccttgggtg cggccctgtt 2340
ggagacatac aggtatacac acacgaaagc acacacatgc tcccacacaa acacatttag 2400
tccgcaataa tccagcatta cctgtgcaca gactcgcccc tctcgcccga aatcccggct 2460
gcaccgcaaa gaggcggcca gctcctcccc gtgtgaccct ggcgaagccc tctccagagg 2520
ctaagaatgg cccctgctct ctaggccctc tcccccttatt cctaaccccc cactccccac 2580
caggcggcgc aggactccta catagggagc aggtttggag tcttggcaac gacctccgag 2640
ctagcagggg ctggcaggcc gcagctttct gggccgaagg agacttcagc tctaggcaac 2700
cccggtccct tacagcttgg ccccgcggcg tccctggagc gcactatcac tggggccacg 2760
gaaggcaggt tttctgggag cagaggcctc ccaggggttg ttccatgtat cggggtaagc 2820
aggactccac cgggccccga acaccagatg gcccgaccca aggcgctttc cgctccgggg 2880
cccggcgaga cggccttgct ggatcacgga cccggggctg ctcccgcctt cgctgtgccc 2940
cgcgacttcc cggggcgtct ttcaaggctc cgtttgatag gccccaaggg aggccagggc 3000
aggaggctgg aggctcgtag gcctccggga ccctggattt cgttagctct tagtccccgt 3060
gtggattcta aaccctacag ccctgtccgc ctgaccctga agcttctggt tctagactct 3120
tgctcggttc ggctttctgg cctccctggc gccttcccgc caagctcctc ctcctgcttg 3180
cctccccagc ctccacttag tccccttcct taggtctcgc cctcgcctca ctctaactcc 3240
agccttgtcc taagactctc aatttccagc cctgcttcct cctccccgcg cgctgctccc 3300
caagcgtctt cacattgtct ctgttcttgc ctcccagggg ctttgcccca ccttcagccc 3360
ctctccctct ctaccctatt tccttttcgc ctcacaactg cagcctttaa cgtttcctcc 3420
tctggtctga gcctgagacg cccgagtttt cctctttagc tcccgtgccc cattccagcc 3480
ccaccacaaa tcccgtgccc actctttcca ctggcccagg cccagctcac tacctttctt 3540
agagcccctt tccgactacg ctcccttctg tcccttctca tctcctcccc caactcctca 3600
ttctgttcct gtccccagaa accatcccga agtatctccc ttccctcctg tggcttctcc 3660
ctattctcag ccctctccca ccctagccct ctcgctatca ccagccatta gcgcaccttt 3720
ccttctcaga tccgtccata catccctccc tctccatctc tggctcgaca cccgggctca 3780
ctattagttc ccctacatcc accccgcagc ctgctcttaa cctctcctcc ccggcggctc 3840
agacccaatt ctcagtgtcc ttagcgcccc cttcgggcca cagcgttaag ccacgccccc 3900
cgggcccctc atccgttgcc aagttcgctg agcgtccgcg tctggttgcc tctccgcccc 3960
acagggcatg ttcgtgctgg gcctacccta cgccatcctg cacggcggct acctggggtt 4020
gtttctcatc atcttcgccg ccgttgtgtg ctgctacacc ggcaagatcc tcatcgcgtg 4080
cctgtacgag gagaatgaag acggcgaggt ggtgcgcgtg cgggactcgt acgtggccat 4140
agccaacgcc tgctgcgccc cgcgcttccc aacgctgggc ggccgagtgg tgaacgtagc 4200
gcagatcatc gagctggtga tgacgtgcat cctgtacgtg gtggtgagtg gcaacctcat 4260
gtacaacagc ttcccggggc tgcccgtgtc gcagaagtcc tggtccatta tcgccacggc 4320
cgtgctgctg ccttgcgcct tccttaagaa cctcaaggcc gtgtccaagt tcagtctgct 4380
gtgcactctg gcccacttcg tcatcaatat cctggtcata gcctactgtc tatcgcgggc 4440
gcgcgactgg gcctgggaga aggtcaagtt ctacatcgac gtcaagaagt tccccatctc 4500
cattggcatc atcgtgttca gctacacgtc tcagatcttc ctgccttcgc tggagggcaa 4560
tatgcagcag cccagcgagt tccactgcat gatgaactgg acgcacatcg cagcctgcgt 4620
gctcaagggc ctcttcgcgc tcgtcgccta cctcacctgg gccgacgaga ccaaggaggt 4680
catcacggat aacctgcccg gctccatccg cgccgtggtc aacatctttc tggtggccaa 4740
ggcgctgttg tcctatcctc tgccattctt tgccgctgtc gaggtgctgg agaagtcgct 4800
cttccaggaa ggcagccgcg ccttttttccc ggcctgctac agcggcgacg ggcgcctgaa 4860
gtcctggggg ctgacgctgc gctgcgcgct cgtcgtcttc acgctgctca tggccattta 4920
tgtgccgcac ttcgcgctgc tcatgggcct caccggcagc ctcacgggcg ccggcctctg 4980
tttcttgctg cccagcctct ttcacctgcg cctgctctgg cgcaagctgc tgtggcacca 5040
agtcttcttc gacgtcgcca tcttcgtcat cggcggcatc tgcagcgtgt ccggcttcgt 5100
gcactccctc gagggcctca tcgaagccta ccgaaccaac gcggaggact agggcgcaag 5160
ggcgagcccc cgccgcgctt ctgcgctctc tcccttctcc cctcaccccg cccccaccag 5220
cccagtgcgc cctgccgccg cg 5242

<210> SEQ ID NO 300
<211> LENGTH: 3437
<212> TYPE: DNA
<213> ORGANISM: Homo sapiens

<400> SEQUENCE: 300
cgctggtgga gcccgcctcc ctgaagccgg agttggcgag tttctcgcac ttgaccttgt 60
aggcgtctct ctcgcgggcc agccgggaca cctcctgctt aagctgctcc acctgctgaa 120
tgagctgcgt cttctcattc tccaggtggt gcttctgctg gacgcgttta tacctgcaag 180
actgggcgta gccccggttc ttcagggtcc gccgcttctg cttcaggcgg atcacctcgt 240
ccttggtgaa gccccgcagg tggcggttca gctcgcgcac ggacatggac acgagctggt 300
cgtcggagaa gcggtcctcc acgctgccgt tgccgcccgc cgccgtcgcc gaggccgtcg 360
cgtgcggccc gggcccgggg tggctagtgg gcagctgttg cgccgggcta gcggcgctgg 420
acggcggcgg cgacgcttgg tgatgatggt gatggtgcgg gtgagcgtgc gggcccagct 480
cgtcgtgggc cacgccggcg cccgggtacg cgtggtgcgg gtgagggtgg tggtgatggt 540
ggtggtggtg agcgccgcga aagctgtcga agctttgcag cggctgtggc actgggtgcg 600
agccgatgag cgcttccacc gcgtcctcgg gcgtcaggtt gagcgcctcg gggttcatct 660
gctggtagtt gctcgccatc cagtacagat cctcgaggtg tgtcttctgt tcggtcgggc 720
tgaagctggg cgacgagggc acggagctac acggagtgct gagcggtgtg gaggacaccg 780
agccggctgg ctgcaggcgt gtgcagggcc tgcccggacg ctccgcgcgc cccagtggct 840
ccttcttcac gtcgaacttg agcaggtcga agtcgttgac atactccatg gccagcgggc 900
tggtgggcag ctctggcccc atgctcagct ccgcggccat cgctgaagcg aggcgcagcc 960
gccgctgccg cccgggaaac tttgcggccg gccggagcgc gccgagccaa gcgcgggggg 1020

```
gaagagcgga gaagagctgg ggaggcgggg agcgagggcg cagcgggccg gggccgccgg   1080
ccaagccttt gtctggggac gcggcggcgc gccggagagt cccgaggctg cctgcaccgc   1140
cccagagctc tgggctgtgc ccgcgcaggg accgggccgg gtagagtcgg gcggggtgga   1200
gaggcaagcg gagcgcgcgg tggggctgag gggaggcgtg gggcgagtgc ccgttgctcg   1260
ctctctagct ctcttgctct tacgctctct cgctcgcagc cgctcgcagc tcggcggtgc   1320
agctgtgctg gatccggcgg cgccgcagcc ttttatcgcc tcctgatgtc actggggtgc   1380
gggggcccgg gcggcccggt gcgcgggcca atagctgcac ggcctccgcg gcccagcggc   1440
gcagggcggg gcgcgcctga cagctccccc gccccccgcg tcagctgact ggcggcccga   1500
gcggccccgg agcggcggag gcctggcgga gcgctggagc ggagtgggac ggccagcctg   1560
ggcccacccc cgtaccctgc aggtcccggc ccacgcacgc tcgcctggag tgcgcgcccc   1620
acctctaggc caaatcaccg ctttcccctc ctcgcgcact ctcctccctc agttcccttt   1680
gcaccccacc cccatcccgt gtcaccccca aggaggctca gaatgagcgc cgggacaacg   1740
cctcctgggc cctttgttcc caagcggccc ccgcccagtg ggcgacgctc tgtgtgtcct   1800
cgcggcttct ggccgtgtgt gtcgtgcgtt cctgtttctg gagatctgcg cgtatttgta   1860
tgttggggag ggcgggctcg aggctccgag agttgtgttc agacccaact cttaacctca   1920
ggggaccttt ctcaggccaa gcgagggccc ctcctggcgg gtgcagtcgc agagccctga   1980
ggttcgactc cactggcccc gccgctcccc gcgttcaccc caccgcacaa tgttcacagt   2040
gaaggcgacg ggaaaagcag cagcccaaag gctctgaatt cctcttcccc gccacacgca   2100
cggaatcctg agcccccgga gcctcggggc cgaggccggc ccgggacggt gctccgagta   2160
gctctccact gctggggagc cggccctgtt tttgtttgaa cgttttgtaa cgattaagca   2220
gatcccggcg tcagcccgcc gcggagaggc tcaaacaggc ataaagtgcg accccaagtg   2280
gccactgtgc gcaaaggcgc cgcgaccgcc cggcccacgg ccggaaggct tggacggcgc   2340
ctcgtaccca gccaggtctc ccctacctgg cccaacccaa gccagcccag aacgcatact   2400
atgtgtgcac cagagcccag gacaggttcc cctcgagcga tgtacaggtc ctcgggtccc   2460
gtcttcgtac tcagccgcga gcctcgagcc gcgagctccg ctctggtcgc cccgttgaaa   2520
ttccgtgccc cagcgttcgg gggtgcccgt cggctgctcc ctgggccgga aggtcctggg   2580
cggaggaagg ccggtagcca aaagtggaag cgccacagtg aagcggccca gggccaccgg   2640
gtgagaaacc tccccggagg gcagacgggg agaccgaagc acaccgcact aggcatccag   2700
actgggcttg ggagccgcgc accctcccta cccagatcca ggatggctag aattaacggg   2760
ttctttctga gacctcggct caggcgccga aaccggatag atcgcgaatt cgctggaccc   2820
ggagacccga cccgcctccc gcgtcacctt cttctttcta gctttgggcg cgcgcagcga   2880
aaggcaggag aggcgcgcac tgggtgagtg agtcccggcc gctgtctgcg ctggaccagc   2940
ccgactgacc tcgcgcgtag ggtcgcgtg agccacaccg gtgcagacgc gcctagatta   3000
tttttaaatg ttagaaggta aaatatttgc ctccaattaa tctgaaaact ctctattctc   3060
ttgcgccctc ggagaggctg gggtacggcg tggtattggg ccgcctattt ttaataaaat   3120
gagtgtattt taactaaaac ttaactcaat cttgtggggt ggcaaattaa atgctggaag   3180
agcgcgtcta caaccctctt cgagaagcgt gctctccgca gaaatgagtc ggccgcctgg   3240
agagagagcc tgggcggtgc cgctgcgcag cccctgccag tagctggggg ttggggactc   3300
gcaccttgta aatgtcctcg tcttgtttga acgcagtgag agcacactcg tttccagatc   3360
```

actcgggacc gggtgtctcg gatctgtgca gactatgtat ggctccggcc tcaggcggcc 3420
agggcgggac aagcacg 3437

<210> SEQ ID NO 301
<211> LENGTH: 661
<212> TYPE: DNA
<213> ORGANISM: Homo sapiens

<400> SEQUENCE: 301
cgctggcacc accgagcccc gccgcacccc gccgctattc tcaggacgac ctgggcagcc 60
ccccagcttc tagaaaagac acagaggaga ctgcgcaatc aacaggcagg agtgtgcgtg 120
agtgcggcat gacatgggca cgccacccca gagaagtggg cgcctgctgc gctaaacgtc 180
atccgtcatc ctttcgctga aaagttggaa aacaaacaac aaaaaccccg cccagcctca 240
tttaatgcga accaaacaca aaagccacag gggaaagctt ttcctctctg tgcttccctt 300
ttccggccga ggaacaccac cagccaagat aaggggactg tgcggggccc tctgcgcggc 360
ttcaaagggc tggcacccgc ccgggcccgc tcccactccc actggctaat gggctccccg 420
ctccagccct tggggagcag gaggcggccg gggctccatg ccaggcgact tggaagaggt 480
ttaaggctca cgccacacaa gggaggaagc tcggcctgtc aagaggcgtg ataaagcagc 540
cccttatcgc agttttcctt tcaactgcct ccaagtgagc gccggccggg gctgggcctg 600
tcaaggccaa gcgtgttcct ttcatgtcgc cctgggttcc tcggtcagcg acgtatccac 660
g 661

<210> SEQ ID NO 302
<211> LENGTH: 247
<212> TYPE: DNA
<213> ORGANISM: Homo sapiens

<400> SEQUENCE: 302
cgcgggttta agtggacgcc aggtgcaccg gacacaggct gtgtttaacc acaccgagga 60
ctatgtgttg ctgcccgacg agaggacgat cagtctttgc tgctgggact cgaggacagc 120
cgagcggaga aacctgctgt cgttggggca caacaatatt gtacgctgca tagtgcactc 180
ccccaccaac cccgggttca tgacgtgcag cgatgacttc agagcgcggt tttggtaccg 240
gagatcg 247

<210> SEQ ID NO 303
<211> LENGTH: 402
<212> TYPE: DNA
<213> ORGANISM: Homo sapiens

<400> SEQUENCE: 303
cgcacgcgca cgtgtgtgcc tgcatgcact cacatgtgtg tttccaaccg gccgacagtg 60
acgcacgtat gccctcgcca ctcggcaagc acctcgtgct ccttggtaac cagcagatgt 120
ttctctcaat tactgatttt caagagcctg gtgtttcctg acatgagcca ggatggcggg 180
cggcgcccag gggaggggaa gtgaaccggg gctccgtttc caaggctctt ggacaaaaag 240
cgaagccctg gatcaggaag cacaatgcgg ctggtattta gccgcttctc aatagtgcct 300
cattcaatcc ccggggcctc attgatgccc gccgcgtgct ggagagcctc tgagggtcag 360
tcggcgacgg gcaccgtctg gaggggtctc gccgctaacc cg 402

<210> SEQ ID NO 304
<211> LENGTH: 318

<212> TYPE: DNA
<213> ORGANISM: Homo sapiens

<400> SEQUENCE: 304
cgcagcatgg tagcgggagc gcagctgcgc gggcaaccgc cgggtttgtg gccggttggc 60
gggctcagtg ccgcctcagt gggctctagc agtagaaaag taaagcgact accctaagat 120
acccagagcg agaggagagg ggctagaagg gtgctggagg caggctgtag tggggctaaa 180
ggagctgact gaccagcgct gcggccggtg cccgaagcag cgagcagcgc acctcagctc 240
cggttgccgc gcggcatggt atttatctgt gggttcagtg cgcacagcgt tgtccagtct 300
cgaaaccacc ctaaaccg 318

<210> SEQ ID NO 305
<211> LENGTH: 215
<212> TYPE: DNA
<213> ORGANISM: Homo sapiens

<400> SEQUENCE: 305
cgtgagtgag ggcgtgcacg gtgtggggtc ctgtgagtgc gggtgtgcac ggtgtggggt 60
cgtaagttca ggcgtgcacg gtatggggtt gtgtgagtgc atggcgtggg gtcttgtgag 120
tgcgggcgtg cacggtgtgg ggtcttgagt tcaggcgtgc acggtatggg gtcgtgtgag 180
tgcatggtgt ggggtcgtca gtgcgggcat gcacg 215

<210> SEQ ID NO 306
<211> LENGTH: 214
<212> TYPE: DNA
<213> ORGANISM: Homo sapiens

<400> SEQUENCE: 306
cgcagggccc acgctcccgg cctctgggac gctcacggca gccccacgag aatgatcaca 60
cgagggccca cgctcccggc ctcggggacg ctcacggcag ccccacaaga acgatcacac 120
gagggcccat gctcccagcc ttggggacgc tcatggcagc cccacgagaa tgatcacacg 180
agggcccacg ctcccggcct cggggacgct cacg 214

<210> SEQ ID NO 307
<211> LENGTH: 291
<212> TYPE: DNA
<213> ORGANISM: Homo sapiens

<400> SEQUENCE: 307
cgcggcctag agcggtgagt ggggtctcga gcgcatcccg ggtgtttgtg ccgaggctgg 60
tgacgtccga ggtggcctct gagtgtgctg acttgtgacc ctgagctgtt gggggctcac 120
cggtgactcc atggtcttgt tgagcaccct gcacgtgggg ctcagggtcg gtaaaatagc 180
agtgcgtgga gaccgcgtgc tagaggccgt ggcgcccgcg tacaatgagt cgcagacagc 240
acagacggga gtagggcaga atagacaata tcccgtgaat tgcgtggggc g 291

<210> SEQ ID NO 308
<211> LENGTH: 568
<212> TYPE: DNA
<213> ORGANISM: Homo sapiens

<400> SEQUENCE: 308
cgccagcgca cagcgcggca ggacgcgccc gggtctcagc ggacttgtgc atgttagctg 60
tgtagattta tgtgagggct tgtaaaactc tggtcttgta aactagtctt aagcgctttt 120
aatatggaga cagatgagag cccctctccg ctcccgtgtg ggcccgcagg agaagcggtg 180
atggagagcc gagctcgccc cttccaagcg ctgccccgtg agcagtctcc accacctccc 240
ctgcaaacgt ccagtggtgc agaggtaatg gacgttggct ctggtggtga tggacagtcc 300
gaactccctg ctgaggaccc cttcaacttc tacggagctt ctcttctctc caaaggatcc 360
ttctctaagg gccgcctcct catagacccg aactgtagtg gccacagccc gcgcaccgcc 420
cggcacgcac ctgcggtccg gaagttctcc cctgacctta agttgcttaa ggatgtaaag 480
attagcgtga gctttaccga gagctgcagg agtaaggaca ggaaggtgct gtacacagga 540
gcagagcgcg acgtgcgggc ggagtgcg 568

<210> SEQ ID NO 309
<211> LENGTH: 386
<212> TYPE: DNA
<213> ORGANISM: Homo sapiens

<400> SEQUENCE: 309
cgtgcggggc tggggcggcg gttacctggg cgtcctggta gccctggagc agcaggaagt 60
aggggcggtt gctgggggcc tggatgaggc actgagtcaa ctgatcgaag tccccggggt 120
ctgcagttcc gatttgggcg tcggctgccc ctggggccat gctaagtgcc tgctgtctcc 180
gctcctgctg ccgccgccgc cgcccctgaa ggctaagctc cgacacgctg cgccgcaaag 240
acaagttttc tgagcgctcc ttgcctccag acccagctgg ggcccctgat ccggtccccg 300
ggccaggact ggccagcgct gccccacccg acgccgcccg ggagcggttc ttctgtggcc 360
gccacgaagg ggcgccggtg cctgcg 386

<210> SEQ ID NO 310
<211> LENGTH: 611
<212> TYPE: DNA
<213> ORGANISM: Homo sapiens

<400> SEQUENCE: 310
cgaacgttaa gtccgtcccc agcgcttgga atcctacggc ccccacagcc ggatcccctc 60
agccttccag gtcctcaact cccgtggacg ctgaacaatg gcctccatgg ggctacaggt 120
aatgggcatc gcgctggccg tcctgggctg gctggccgtc atgctgtgct gcgcgctgcc 180
catgtggcgc gtgacggcct tcatcggcag caacattgtc acctcgcaga ccatctggga 240
gggcctatgg atgaactgcg tggtgcagag caccggccag atgcagtgca aggtgtacga 300
ctcgctgctg gcactgccgc aggacctgca ggcggcccgc gccctcgtca tcatcagcat 360
catcgtggct gctctgggcg tgctgctgtc cgtggtgggg ggcaagtgta ccaactgcct 420
ggaggatgaa agcgccaagg ccaagaccat gatcgtggcg ggcgtggtgt tcctgttggc 480
cggccttatg gtgatagtgc cggtgtcctg gacggcccac aacatcatcc aagacttcta 540
caatccgctg gtggcctccg ggcagaagcg ggagatgggt gcctcgctct acgtcggctg 600
ggccgcctcc g 611

<210> SEQ ID NO 311
<211> LENGTH: 5799
<212> TYPE: DNA
<213> ORGANISM: Homo sapiens

<400> SEQUENCE: 311
cgccaacgtc ttgtcgtcgt ccgcgctgtc caccagggcc ttgtcagcgg gcatgtacca 60
ggcagcgctg tgctctgcca tcagcgagtc caggtcaatg gtgctcatgg cgctcttgac 120

```
cgcctcggag cagcagctgc ccagctcgct gtcgccattc tgcgcccctg aggccccgac    180
ggcgcactca cccttcttgc caccccttcag ccccagaggc tggtcctcgg agatgctgaa    240
ctgctgcctc tgtagctgga tctgcgcctg aaggatctcc agggggtgga tctcgtcggg    300
tggcggggcg ccgctgctgc tcgtcggggt gcggacctgc tccaggcccg gagtgcccgg    360
atggcccggg cccccaccgc cgccgtagct gtcaggggtc gaggtagagt tagacatgat    420
gcccaggccg agggcgggcg ggggcgcctt cggtccgtgt tccccggcgc ctaccccacg    480
gggagggagt ttgggcgagc cggtcaccag gggactcctg ctcgctttaa ctagtgcctg    540
ggggttgtca gagctggacg acacctcgtc ctcattggcg tagctcgtgc tcacctcgtc    600
cgaggcgaac tcacccacgt ttggcgaact actgtccgac ttggccccgc cgtccaggga    660
cccaatgagg tccggctgat cccccaggag caactcagcc cccttccccc aggatggcga    720
cgtgagcgcc ttttcgtggg gcgtcggtgc cccgcgcgtc tcgcctgcgg agcttccccc    780
gacggctgcg cctgacgctt gctgctgccc tgggctcacc ccaggtgcgc ccccgctgtc    840
cggagccgcc gagtacttgt caaagaaggt gccagggctc acgtgaccac tgtccctttt    900
tctgcgaccc cgtccccggc cgccgccccc ggagaccggc ttgccgtcat tccccgacgt    960
ggattccagg gtgtagttgg gggagaggct ggtgccgtcc ccctgggctg gagggttggg   1020
cggccccgag gctttggagc cgctgctact ggtcccggac gggcctccgg gtcctggggc   1080
cccaggagca gtccctcctg ggaagtaatc cgagcccggg ttgccggcca ctgccgcgcc   1140
gtcggtctcg ttctggctca gtttcctctt gccctctggc gggttcttct tgttgaaggt   1200
cacgttgagg ttgggggccc cgaggctggc gatcatgttc tggcaagcgg tggagagcgc   1260
agccaggcag ctctggccga acaggttgtc cttggagctg ggcttgttga aggagcccag   1320
cgagagcgcg cccaatttac tggccgaggt gcgctggctg ggctggaaat caggctgcgg   1380
cgggtaggca cccccgccac cgccgccacc agagctgcca ccgccccctc ccgcgctggg   1440
gggcgagttc acgcctggac cgctgtgcgg cgtggactgc cggccggctg caccaaacgg   1500
aaagcccggc tggcccccga gcgcagacgt agcaaagtcc ggcggcgggg gccggcgctc   1560
cgaagcagcg ctggggagcc ccacgcccgc cccgggcgac tgcagctgac ccaggcctcc   1620
cagactgccc ccgaactgca ggcccggtga aggcagcgcg ggcacgtggc cctctccggg   1680
catcctcatc ggctcctgca gagggccccg gaacagcacc cccgagccac caggcggagg   1740
agggggcgcc aggctggggt cgtgcgggcc acagtcagcg ggcagacccg agccgcccat   1800
cctacggggc agcaggtctc cgggcggcgg atgcggacct gagaaccacg cgctctcttg   1860
cgccaagtgc ggcgcctgct gctcgaaggt gcccagacgc ccggcgcccg tgctgccgcc   1920
ttcgcgctca aagttcggct gggccaagcc gcccaccggg ccgccatgca ccaggccgcc   1980
ctggcccacg tccccggggt ggcctagctg agccaggttg ggctggcgca gccgctgctg   2040
ctgattccgc gacgccatct gcttaatcat gagggccgcg ttttggcgct gctgctgctg   2100
ctgctgttgc tgttgctgtt gctgctgctg ctgctgctgt tgctgctgct gctgctgctg   2160
ctgctgctgt tgcagggact ggtggtccgg ggccggatgc tgcaggggcg gccccgaagg   2220
gaagctgtcg ggcacaggcg gtgtgaactc gccgggtagg cctgggtagg cggaagggga   2280
gaggtgatta tccagagcgc cgttgtgcat gctgccgttc cacgaagcgc agcggtccac   2340
tcccgcgctg cccggaaagt cgaagcgcgg cctcttggcc acgttcatgt agggggggcgc   2400
gtcgaaatgc tgcagccgct ggttgggcgc ctgctgcgga ggaggatgct gcatgctgaa   2460
```

```
aacaggctcg gaataagggt gcatgctccg gttctccagc cggtggatgg gatactcgaa   2520
ttgcgcgtgc tggctgggca gcatggggcc tccgtcctgc aggccgccgc tgggcgtgcc   2580
cgcctcgccc tgctggggcc gagggagcgc aggcgggcac gaattttgtc ggactagaag   2640
cccgggtggc ggcggcggct gctgctgtgg cggctgctgc gggggctgct gctgaggggg   2700
tggcggggcc tgctggggag gctgcattaa cgggtgcctg gagcccactg agggctccag   2760
acccacaggc atctttctgg ccccactgaa cctctcaaag aacacaccat gctgctgctg   2820
ctgctgctgg ggctgctgct gctgctgggg ctgctgctgc ggtggctggg cgtgcatttt   2880
ggacaagccc accatgcccg cagctctggg catggccgag gcgcccggga aagcgccccc   2940
aggaacctgg cgacccgctg cataatgagg cagctgccct tcggagtcag agggcgaaaa   3000
catgtcaaaa tgtcccgagg gcgcctcgcc cgggtaattg tattccagcg agtcgacggc   3060
tccttggttc gtcaccctcc gtggctccag actgtgggaa tcggagccgc tggaggacgg   3120
caggccgtgg aaggaggcgg ctcggttagg gctctggtcc agcggcaggc atggggccgg   3180
cacggcgtgg ctggaggcac ctgaactgtg gaagtccggg aggttccccg gtcgctgcgg   3240
gccgaagctc tcaggcccct ggctctccgc catgtgctca tagccctcgg cgaagggcgg   3300
ctggctgccc aggcctccgg ctgcgccgcc gtagccgagc aggcgacccc cgtgcaggca   3360
cgaggccccg gggtccgggc caccgaagtt gcccccaaag tgggggtgat gctggtgggg   3420
atgatgactt cccgggtggc cgtggtgagg ctgctggccg ccaaagaagc cgtgcacagg   3480
ctgcgcttgc agccccccctg cgtgcaactc cgagtggccg cgcgcgtgga agccgtaggg   3540
ctccatgttc atgcccaaga tcgggggttc gcccagcgcg ctcatagcag gatccacagg   3600
gccaggggc cccccagtgt ggaaagccgg ggccttaaag tgggtgttca tgctcagtcc   3660
ggtctcgtta aagttcctct cgccctggcc agcgttcctg ctgttgacct ggggctcgaa   3720
ttggtccagc ccaaacatac ttggcggggg gcagaggggg atcaataggg catgacagcc   3780
ggctctccgc ggcgcgcctc cggccagcta ctcgttccag cccaggattg ggcgctccgg   3840
gacgctcagc accgcggggg ctcagcgcgc acctccaccc cgcctgatgt gagggacggg   3900
gggcggggta ttagctcctc tcctgaagct ccgattctgc ccggggaggg cctctcacat   3960
cttgcgaggc cgcggggcct ctaggagccg tgttgggggg cccatgcccc gggcggttgt   4020
cacagccgcg ggtgggtctg cggggagggg acgaagccgc ggatgaacgg agacaaaaag   4080
ttaagtgggg ggaatgggga gggaaggggg ttgggagagc agagcgatca ccttctcaag   4140
tccgattggg tctgctgggg agccctcagg acgccgcccg cagcctcccg gagtccgtgg   4200
cagagctgct aagggcaggg gagggagacc cttcaaagcc gcggctggcg ccgggcaccg   4260
acagagcggt ccctccccc gccccccgga gtccccgcgc cccgcagccc gagcctccac   4320
cgagcacgat ccgctcgcac aatccccgta ggctccgggc gagcggctgc tgcttcttca   4380
gcgggtcgga ggactggagg ctccgctcgg catcgccggt gccggccccc gagccgagga   4440
cgcagagggg ctgcgaggcg gcaggcgccg ggggctggag ccgagggtcg gggaaaggcg   4500
cggctcctct gctcggcagc gggtgcgctg cgttcggcgc gcagcttcgc ggccacgtcc   4560
gccgcctgcc gcttctgttc tccgccgttg ggtgtctgag ttcgccggag tctccgcgca   4620
ccgttgcagg cgcgggaggg cagcgagacg aggggttggg tcgctccaag gctccggttc   4680
cctgcctccg cgctgaggtg cttcgcgagt ccctctcgga cctgagggag gggggcgtac   4740
gcgggtcggg gggccacgcc gggcgagcag gctaaggcgt tcccgctgcg ctctcagagc   4800
ccggaatggg gggaggggg cgcgggggca gctctggggg gtctgcgcac ccctctcccg   4860
```

```
actagcgggg gggctctgcg tggggcgttc cgagggtctc ggctcccctc tctgtgtctg   4920
cctctcgccc agcgccggga gaagcagcaa caagttttgc atttcagcaa tcaatttcag   4980
ccattacatt tgcaccaatc agcgccgccc aagttccggg ctcggggcgg ggctcgctct   5040
taaggtggtc cggggtcctg gctgccgaag cccccgccac gaacccgcac taccccagct   5100
ctggggtccc ctgcgcccgc ctctcctcgg ggtccggcgt cagtgcgctg gggcgcgcc    5160
ccggcctccg ggcgcatcga gctggagagg gtgcaggcgg aggagaatgg cgggagcttg   5220
gctttgttca ccccctccc attcacactg ttcccaactc cccaccccca actggagcga   5280
gacccaccgg gtgggcaggg ggcggggagg tgggcggtga gcggtacggg gcgctcagac   5340
aatgaggtcg ccaggcaaag accctagact cgccacggaa agtcgctaag tgtctactgc   5400
acttcggctc cggggtgaac actccgttct ccgctagcgg cgcccaagtt agccggccct   5460
gggattttct tggagggtaa agcagacggg gaacctcgaa gttagggttc tcctcgagag   5520
acctgggcgc ttgctcactc ctccgtcact agggcgttca caattgttcc ccttccccac   5580
tgcctggggt tcccggttct caccggccgg cgtgggctcc aaggagtcac agtcactcag   5640
ccactttatg ggggagcaca tcggttgagc ccagtaaccg gagcgacttg cgaggcggct   5700
gggaaccccg agaagacacg cacgaagagg gcgcacccgc cgggccgcac accttgccct   5760
gggccacccg gtccaagacc cagaccctct gcgggtgcg                          5799
```

<210> SEQ ID NO 312
<211> LENGTH: 327
<212> TYPE: DNA
<213> ORGANISM: Homo sapiens

<400> SEQUENCE: 312

```
cgcctaccac gtggccgaga ttcccgaggc tgcagccaat gagcagcata gtccgatggg     60
ggaggctgga agggccgttc acgagatctc tcgggaggaa tcggtaggag ctgcccaact    120
gaaagggacg ggggaataac ccggggcgag ggacctgccc aggccctgcc ctctgggggg    180
aagccaggcc aggggccggg ggcatctctg gggtcccagg tgagatgcgg gtcgagggag    240
ccaggccacg gttctccaga ctcgcgtgga ggccacgagc gtcttctgga ggagcgggca    300
ctgcgcggac cggcagactc tggggcg                                        327
```

<210> SEQ ID NO 313
<211> LENGTH: 1949
<212> TYPE: DNA
<213> ORGANISM: Homo sapiens

<400> SEQUENCE: 313

```
cgtcctaacg tactgtcgtt cctgaatctc gcaggcaccg acactgccct ggacactgtg     60
agggggtgct ccgtgggggg atggatgacc ggcagggcgg actggagggc gggacgggga    120
gggctcggtc cccccgcggg tgtagccaac agcctccccc cgcagctctt cgcagcggta    180
tcccgaggct gctgcaccag ccttacccac ctcgacgctt cgaggaacgt cttctcccgc    240
acgtaagggg gacctgtcgg ggccggggga ggctgctgga agccgcctcc ttgcggcccc    300
aggcccacct tcccacttcc cccaggaagt cccgcgccgc gccggccgcg ctgcagctct    360
tcctcagccg cgcgcggacg ctgcggcacc tgggcctggc gggctgcaag ctgccgcccg    420
acgcgctcag gtcagtgtcg gaccccggcc acgcccccgc gggcgctccc accctgccct    480
ggccttcgcc cctccccgct cctgcttctg tcgctcccac aacctccccc agatcctggc    540
```

cctgcctcct tcgttcgcac cctggagccc cctgtcccag ctcccgccac cccgtgtaac 600
gtcctctccc agagcccttt tggatggcct cgcgctcaac acgcacctcc gcgacctgca 660
cctggacctc agcgcttgcg aggtgagcgc cggcccccag aagagaccac acattgggag 720
aggcgctggg aggcggaagg gcagggccgt gggccgcctg cccctcccca ctcgcggcct 780
aagtgggtcc cacttcccac ctcccacctc ccacatacag ctgcgctcgg ccggcgccca 840
ggtgatacaa gacttagtgt gcgacgcagg cgctgtgagc tccctggatc tggcggataa 900
cggtgaggct gcaggagagc ccatcctcgc atcatccact cgattcccaa tccccaccct 960
acccttgcaa cttcgcctcg tgcgtgaccc gagtcacccc caggcttcgg ctcagacatg 1020
gtgactctgg tgctggccat cgggagaagc cggtccctga gacatgtggc gcttggaagg 1080
aacttcaacg tccggtgcaa gtgagccccc accctactcc tgggcctccc agacaacacc 1140
ccaccacccc tgtcccccac aactgcggcc cctgcccaca gggagaccct ggacgacgtc 1200
ctgcaccgga ttgtccagct catgcaggac gacgattgtg tgagttcacg ggaccttgca 1260
gggcctcggg caattagacc actttggtcc tcctttctct tgttccctca gaccctgtga 1320
cctgccctca ctgacccctg actccagcca tcaatggctt tctcttaacc ccagcctctt 1380
cagtctctgt cggtggctga gtctcggctg aagctgggtg ccagcgtcct actccgggcc 1440
ctagccacca atcctaacct gaccgcgctg gatatcagcg gcaacgccat gggggacgcg 1500
ggcgccaagt tgctggccaa ggcgctgcgg gtcaactcga ggctccggtg ggcggggtca 1560
gaggggtggg accagcgggc agggggcgcg gtggagagga gggcaccggg ctaaggggag 1620
ggactgaatg aggcggagca aatggagcag gctgacgagg cgaatggact aggccgaggg 1680
ttgggtgggg cgttgggaag ctccgtcccc gactgaagcc aggcccggcc caggtctgtg 1740
gtctgggacc ggaaccacac atctgctttg ggtctgctgg acgtggcgca ggcgctggag 1800
cagaaccaca gcctgaaggc catgcctctg ccactgaacg acgtggccca ggcgcagcgc 1860
agccgcccgg aactgacagc acgtgcagtc catcaggtgg gcgtccccct cttcccttgc 1920
ccttctctgc acggtaactc cgtccctcg 1949

<210> SEQ ID NO 314
<211> LENGTH: 319
<212> TYPE: DNA
<213> ORGANISM: Homo sapiens

<400> SEQUENCE: 314
cggatgccgg cctcctgcct cggccaccgc cctcctcttc aaggatgctg ttttgcctct 60
ggtcgctcta tcttatcttt tttctccgca ctcctggacg tctctcggac ctttcgctct 120
gacagtggct tgagcctcgg ccgccacttc cgcccctgct acttcggggc cacgtctcgg 180
tccgacgctg aggggtgctg ccaaccgtgt cttctctgtg aacgtcctca cgatgaacgc 240
ccccgttcca cttcccaccc tggagctgct gcttccgtga ctcacattcc ggccatttcc 300
gtggtgtgag gtacgggcg 319

<210> SEQ ID NO 315
<211> LENGTH: 776
<212> TYPE: DNA
<213> ORGANISM: Homo sapiens

<400> SEQUENCE: 315
cgttacattg cgattcattc aggaacccac gagacctctc ccgcagcgtc cccgctgctc 60
accgggctgc agacgagtgc gtcgcggtac cccccgaaga gcagggcctg ggctttgagg 120
aagagacggg acaccccttc cccgggggcc agggcgacct tcctgagccg gagcctcagc 180
agggacacct gaagcacaag ggagtggccc tgagtgggca ggtgtgggcc cctcgcctcc 240
cggggcagga aggtgggagg ggcgacactg accacgtctg gaggcagcgc ctgcacgtcg 300
ttaaaggtcg tctccaaggt attggcgtcc acgttcagca ccacgacgtc ctccagggct 360
ttttctcgta ctctctgcgg aaaagcgggg tcggccgctc agagcccggg agtccttggc 420
agaggagggc atctggggat gtagaggaag ggggaaccct cacgtccccg tcgtctgggt 480
agatccacgc tcacctcggc gagactggcg tgcactccaa tgaggtaggg catgggcgcg 540
ctgcggaccg aggggacggg gtcatgcagg caccgccccc agggcctgcc cacaggccct 600
gcccctccca gctgccctcg ctcaccagca gtagtccagc aggtgtgggg gcagcgtggg 660
gatcagcacg tgctcccagc gcatggggta caggagcgcg caggacgcgt ggacgcacga 720
ggtcagctgg ggagcgatgg cggggcgtgg agtcagggcc tggaccctct agcgcg 776

<210> SEQ ID NO 316
<211> LENGTH: 288
<212> TYPE: DNA
<213> ORGANISM: Homo sapiens

<400> SEQUENCE: 316
cgtgaaatcg ccgttcgtgg gcccacggct gcaccccgag atagaagcgg aataaaggga 60
cgacgttacc ttcaccagcc tgagtctctt gggccgcgcc cgcctgcccc gactccaagc 120
cctacaggaa ccggtttccc tggttaggag gtatccaccc ggctcaacca gggtctcgac 180
ttccttggaa aagaccaagg cagccgtacg ctgctggaac gccggagtgc aaaggctttt 240
agggctacat tgcaaccctc gggctcgatt tcgccctttg ggctgtcg 288

<210> SEQ ID NO 317
<211> LENGTH: 482
<212> TYPE: DNA
<213> ORGANISM: Homo sapiens

<400> SEQUENCE: 317
cgttgccgcc tttttcgtac tgagcgcgca gggcactacg cccaccactc cccttgaccc 60
actcctcaag ccctgatacc ggggcgaggc cccttccttt tctagtcctt ctacgcgcca 120
ggtgggtggg tttcgcggtg acgaggcgac acctctttcc cctctggcga gcacgttaac 180
tggggaagct accaaattct cacgccttag ctgccctgcc tccacctccc gcaagtccgg 240
ttgcccctct aggcttctgc gcctgcagtg gttccgaccc tcgcctttag aactctgccg 300
cttccgcctc ttatttcgcg cctttgtttt tagttttgga aggggcggag ttgaaatggc 360
tgcgccgcgg ttgccgaagc aacgctttgg ttacttccgt tggtttcaat gcttccgggt 420
tggcgctgca gtggcgtttc cgactgtggg agcctcagct tcccagtcgt ccgatgagcc 480
cg 482

<210> SEQ ID NO 318
<211> LENGTH: 3343
<212> TYPE: DNA
<213> ORGANISM: Homo sapiens

<400> SEQUENCE: 318
cgaggcccag gcgagtggcc aagacgcggc aggacaggag gatgcgcctg gctgctctcg 60
gctgctggac gcggcctgca gtagggagag cgcagcccgg ggtaatccca ctcagggctc 120

-continued

```
cgggtgccca gttctcccac ttcccatcct ggcggcctaa aggcaaggcc tagaccctgg    180
agaggccaaa gtcgggccaa aacaacagcg aagctgggac tggaacaggc gctgggggcc    240
tgcgcatgac cccaggctca gaatgcgaca ctccagtgac gccggggaat gagttgagat    300
ggagccggag acagaggttg gggttcagga cgaggcgctt gggtatggga tcggatctga    360
gacggttgcg gcgctggtgc tttgggctgg accagactcg aacccagagc ggagcgaggg    420
tcagagccag ggcaagagtc cgaagcccag ctcagcgtcc agcccgcgag agaccccacc    480
atgaatgacg tccgagtagg gttggaactc gaagcccgaa cgcactggaa atgcagccgg    540
acgacggctg ggatccgagt gggtccgggc cagaaatggg gacctcagag ctccaccgag    600
gcgctcgagg tcagaactga agcctgagac ttaggcagga cccgagacag agccagagac    660
gataccgaaa cccaatggac cgcgaggacc gaaggcagat ccggggcgca aacctgtgca    720
ggcactggcg cgctgcctgg agctctgggt tcgcgccgct gagcgccggc aggttggacc    780
agcgctgcgc gccggaagtg cactcgggac gccggggttc tggaggagag accacacgcc    840
gcaaaagtgg cctccgaatg cgcccggggc ctgccctcgg cgacactgct ggctcggcgg    900
ccgcagccta cctgaagtag tccatcttgc agaagatctc cttgttcttg atgtagcagc    960
tgttctgctg cctcagcgac gtgcgacaca cggagcactc gaggcaccgc acgtgccaga   1020
tgaggttgtt gacctgggga cggggcgggg acggaggtcg gctcagcgcg ggcctctttc   1080
actccgggcc ccagccttcc cggtctcatt tacagtcaga ggcgctgaag ctcagaaggt   1140
gcatgcgatt cccctatttt tctcccgtaa tactgagact cagggaaatg gaaataaact   1200
cttcttattt ttcagacgga acccgggggc tcaggcagac cctaagtctt gcccaaagct   1260
tcgcagtcgg gcagcagtgg agccaggatt tggaagtaag aggacctgcg gtgcttccct   1320
gcagtctcct gcgctgcgtc ccacgccccg acaacacgca cgcaacacct acccctgtct   1380
caccttgagc agatatcggt ccaggatctc gaggccgcag ctggagcaga tgttcttgcc   1440
tgcagacggc acggaggagg cggcagaggg cggtgagcag acagatggcg tgctgggcgt   1500
acatggggag gcctgaccct cgtccttgtc cagagctcct gccagggcct cggcgtcaga   1560
ctgagcctgc ggcgggggag agaaggagag gagcgctgat ccgggcaccc agagttgggg   1620
ctgccttgga gacaaatctg ggccccccga gcaccaattg acaacgaaat ctccccagga   1680
caatgcgccg tagactgaag gacagggatg gaagggccta ttggagagga agggacggcc   1740
ccaactttta acacgcgcat tctgggtgct gggagcggtt aaagccaaca ttccctgccg   1800
gaaaaccgag gctcagagag gggcggcgcc cgccgggagt cccccagagc gtgagcagca   1860
gttcgtggcc ggaaaacctg gccaggtccc cagggccggg ccgctggagg actgggcacc   1920
gcaggcaggg ccaaacggac tcaccatggc gggcggcgcg gtcccttcaa gacagcgggt   1980
ggtcgctttg cagccggacc ctggctgggc catcacctgg gggagggggg gagggaacgc   2040
aggcggcggc ggctgctgaa ctggctccgc acagcctgag cccagcgcct ccccgcgcct   2100
gttatataaa ccggcgccga acaatgagtc ctaactttgt agtgggcatt taaagccctt   2160
ccccacaaaa gcggtgtctc tctaatgaag caatttgaat ttggattgga ttttttccct   2220
ctctctcccc ctctccctgc acttaacccg tggctcttga agtaatcgct tagttccctt   2280
gcaatccaag cctctgaggg gggaagaaaa acacgcgcac acacacacaa actacctgca   2340
attagaaatt gtcgtgaatg cccaagataa gaggtagcca gagtgtcaat tccaactgtc   2400
aatcagtgag atccatcagg ccgcccaaag aattgcaaat ttgatttttt aatggtagta   2460
attaaaaatc gaattttttc tctctccacc cgcccccccca ccccactccc cttcctcgct   2520
```

cccttctcct ctcggcacaa aatgcaaaaa ggagaaaaga gagaaagaaa gaaaataaaa 2580
aagagatggg tgaggggcgg agggtggttg aagaaaagaa aaccccgagc gcggtgagca 2640
cccgcccgcc cgcccgcctg acacgcgcgg cgaaattgaa gcagctatat tgacacggat 2700
tcaggcgcct ttcgagggcc agtcggaggg aaacccggag caaaaagaga gcgagatcgg 2760
ggcgaaacgg gaccaaaaag agaaaagaga ggcgctcaag ggaggaaaa agcaccctcc 2820 agcccctcgg cgcgccgggt accggccccg cgtcgggatt ctcagcgctg cgccggcaca 2880
acccccggcg catcggcgct atcagcgcct attcagacgg acaataccgg cctcgcctcc 2940
tcttgattcg cctgtgtctt tactaaatcg ctttttgaga aattcctcca acatttgcat 3000
aatgtgttcc cgctttccgc gacccccccc ccccgctcgc gcgcgcgctc ccacactcac 3060
aagcacacac tcacaggcgc accctcgtac ccctccttcc tgcaaccgcc cgccaccctg 3120
ctcggcccgg ctgggtcccg gaccctgccc gaccccggcc cgggccgctc acccagtcgt 3180
tcgccggctc acctggtcgg tggcggggcc gccctcggcc ggcagccggc agccctcggg 3240
caacgccggg gcggcgttct catgcttcca gtacatgggc cggggaacct cgggctcagc 3300
gggcgcgcag cgcggagagc tgcgccgagg gggaccacag ccg 3343

<210> SEQ ID NO 319
<211> LENGTH: 2956
<212> TYPE: DNA
<213> ORGANISM: Homo sapiens

<400> SEQUENCE: 319
cgcctctttc gcacaggtgc ccgactcgga gtccgggagg cgggccctct ttccaggtac 60
ccagcccagc gtcagcctgg gtccatcctc cgccacccca cagcgcgggg agcaggggag 120
gccgaaagcc gggcagcttg gggggccggg ataacccggg ctgcagcaac cccgggcggc 180
agcaggactg gagagctggt gtcggacgca ctgcagagac gtccctgttt tcggcgcgtc 240
ctccgacacc cagcagagag cttggcgctc tccgctctgc gcgcccgagg tcacagcgcg 300
gagaaacctg gcggggcccc ggactccccg gcttgggaaa agcgatgact gccctgaact 360
gctggggcgt tcgaaatttc cagggtcccg accctccgtg gggtacgcgc gacttcggcg 420
cagatgtcag tccgctgcct tccgggttga gggagcgagg actccagacg accccagggc 480
cgctgtccag gcccagcccc gcgttctcca cctcgccacc tcgctctgcg gctccagcct 540
ggagatctac ggacttcatt gcgatctctt gcgcagtgta gtcgccctct atccctagcc 600
ccgagtcccg ggtaacccag gggccccggc gaggcgagtt tctttggggc gagatgtccc 660
gagccgagca aaggggccgc gcattggacg gggctcccaa gccacagccc tgggggcctt 720
gaggagtcgt ggtacggtcc agggcagtcg gggctgcggg gcccgtgaag ccagacgagg 780
ctacggactt agggtccctg caaccaagac cgcgagcgac tgtggactcg ggacggatcg 840
cacaaaggag gaagggggaa tcagagggc gtccggtcca ggacgtgtca ggcctgggcg 900
gggcggaaaa ctgacaccag ggcgaggaca aggatttcgc tcctccaggg ctgccagggg 960
aggggctcgc caccgtcact ctccatgggc tctggccccg acggtgttta aagggcggag 1020
ggctgggccg ggctggtcgc acccgggcgc tgctggcggc caagctggat gggtcgccag 1080
tgagtttcgg tgcggcaccg ctggcccagg cccgggcgcg gctggacatg gccacctact 1140
gcgacgacct gggcccctcc tcggccccgc ccggccaggc ccaggccacc gcgcaccccc 1200
cgggctatga gccaggggat ctgggcgcgg tgggcggggg cccccctcctg tgggtgaacg 1260

```
cgccagcgct cagccccaag tcctacgctt cgggtcccgg gcctgcgccg ccctacgcgg   1320
ccccgagcta cggggctccc ggcccgctcc tcggcgcccc gggcggcctg gcgggcgccg   1380
acctcgcctg gctgagcctc tccggccagc aggagctgct gaggctggtg cggccgccct   1440
actcctactc ggcgctcatc gccatggcca tccagagcgc gccgctgcgg aagctgacgc   1500
tcagccagat ctaccagtac gtggctggta acttcccttt ctacaagcgc agcaaggcgg   1560
gctggcagaa ctccatccgc cacaacctgt cgctcaacga ctgcttcaag aaggtgcccc   1620
gcgacgagga cgacccaggt aacagcggcg cgccggctcg ctccgtccag gactccccat   1680
cttcccgccg ggccgcgggc actccggggg tgggagcacc ttagacaacc taatttctcc   1740
ctgcgcggtt ggggataccc ggggaggagg gagaagggga agaagtgctt gggcatggac   1800
aggttctcag acagcggctg agcccaccac aggcccgcgt ttacagtgcg gcggtcccgg   1860
ggctctcaat ctctgtgcgc tccttcggag gaagaagcgg gagagccagc aagctgggtg   1920
accttgggag tgactcaact tccctgggcc tcagtgccct acctggtaaa atggggaaga   1980
cagcgcctac cccaaggatg ggcaaaacaa ataggatgcc cgtttggaaa gctctggagc   2040
ctacctgggg gcctggcgtg gtctgcgctg tccttggcag agcggctggc ggagtcccac   2100
cattagcatc tcgcaggcct tccttcacct taacggggct cggcctttcc cagggctccc   2160
ttcctcctcc tttctggatt gtcactttct tcccagtcct gctgtggagg cccatcgggt   2220
acagagtgcc cgtcaagggt ggaatggggg cgaggactca gaccctctgt aagggccagc   2280
aggggatctt tctgaagctg acctcctcgc tggctcacac cacggcccgt caaagctcga   2340
accttctgaa ctgggctgtt tcttcttctg caggtaaagg caattactgg accctggacc   2400
ccaactgcga gaagatgttt gacaacggga acttccgaag gaagaggaag aggagagctg   2460
aagccagcgc ggccgtgcgc tcgggagcca ggagcgtggg aggggccgag gcgccagcgc   2520
tggagccccc gagcgcggct tgcctggacc tgcaggcctc gccctctcca tccgcacccg   2580
aggccgccac ctgcttctcc ggtttcgctt ctgctatgag cgctctggct ggcggccttg   2640
gcaccttccc cgggggcctg gcgggcgact tttctttcgg gaggcggcca ccgacagtcg   2700
ccacccacgc tccccagacc cttaacccct cccctggctt cgcccctggc caccagaccg   2760
cggccgccgg cttccgcctc agtcacctcc tctacagccg ggaagggacc gaagtttgaa   2820
gggaggctgg aggctagccg ggtgcgggtc cagaggtgct gagctcaggc ctccggtttc   2880
ccctggtgac agccccacgt gttggcgttg aaggccttgg tgccctggga ggaagcgcag   2940
agccgggggc ggctcg                                                   2956
```

<210> SEQ ID NO 320
<211> LENGTH: 791
<212> TYPE: DNA
<213> ORGANISM: Homo sapiens

<400> SEQUENCE: 320

```
cggggtgcgg ggaggttgag agcgcggcgg ccgctgccag caatcgagga gccagcggcg     60
cgtgtgctga gggcccagct agcaaaataa agagggtttt cagcggagcg gcggctcagg    120
cgaggctggg ggagccgggg agcgcgtccc gccatttttc cagccgaggt cagcagcggg    180
tgaaggggcg gagtccgtgg tgttcccaac tgcccaggcg ggcggtgaga tggggcaggc    240
ggttccgcaa cgcggctcag gccccagcgc cctgcctgca ggaggccgct tctttctctg    300
ttgccatcgg gcgccggttt cctcttccgg ggatgcaggg cagctggggg ggctctgcct    360
ctgtgcggct cttccgtggt tccacgctgg gctccggggt gaccacagtc ctcagcagcc    420
```

cacaccctca gcccgaaggg ggcccaggcc ccgtgcccag aggatccaga gagacagccg 480
ggagcccagc agctgtggca gctgccccca ccaccacccc ggggctggcc aggtcccacc 540
tcctgacgcc acacggtatg actgggccct cctggtcagt gcgtcgcatg taacgccttc 600
aactattggg gccggtgttg gagcatccgt ctctgcgtcc ccacctgatg acaagctccg 660
gggagcagga gtgctggcca agcccacgca cggaccaagc ccacgtcaga ctccgccaga 720
aaggcaagaa gggcctccgc atggcgtgac ggatgggttt atgggggcat tccatcccac 780
ccggacgctc g 791

<210> SEQ ID NO 321
<211> LENGTH: 4184
<212> TYPE: DNA
<213> ORGANISM: Homo sapiens

<400> SEQUENCE: 321
cggagcttga gcgccagaac cacgcactga ggtcgcccag ggtggggaag tggggggccg 60
ggggaggggc ggggcatccg gcggggaggt ctcccccacc gcatgcaaga ccctttgccc 120
ccccacaaca tacactgagg ctaaaacggg gatgagagtc acacagagca ggagcgaaat 180
ctttcgctct ccgacccgaa cggcgcgttg ctcgaccccc cccttcctgg agccaggggc 240
tggccgagga aggtggctcc gttcttcccc cgtggccagt gcggggtctg cggctgcccg 300
gcgaggttcc ggcttccccg ggactggcag ggggagcccc gagaactgca ggcccgcccc 360
cccttcctcc tcctccttcc cctcctcccc cacgtgtcct ccctgagccc agcagcctga 420
tcccagcacc ccccgccacc tccctcctcc cgcttcgccc gcttccccgg cggcgtggag 480
aagagcaaag ttgcgacagc ggccgggggc tctgcccagg taaagggggc gccgtgaggc 540
gggggtggtg ggggaacggt gcggccctgc ggcgggggcg gggggaggat aaagaaactt 600
gcttcccgcg gcccccaccc cgcgtgggtt ccgatcttgc gtggaacgag cccgcgtggc 660
gagtcgcggc aacactgccg ggaccgaggc cggcacctgg acccggaccc ggaccgcgcg 720
cttgggccgg ctcggcgggc gcaggcagcg ggccaggcca gcacccaggc aagggcgggg 780
tgggtggccg tacaccggac cgaatcgggg actccggtgg cgtgggcgcg ggccgaaccc 840
cgaccgggcc gagttgggtg gcgaagtagg acgtggattc gggggcgggg cgcggcggga 900
gggggaaacc aggcctggcc agactggcct gggcgtgggg gcgggggggcg agttcggggc 960 acttgctggg ctctggaccg agcggtaggg cggggcggcg ctaggggctg ggccggaccc 1020
gcagggagag ggcgaggga gggagagccg ggggtggagt aggggcgtgg agttgtgagc 1080
ggggtctggc ctcggccggg ggcgaaggta gatcggcggg gccgcgagcg gagggaggga 1140
ggcccgcggc ggcgcggcgg cagcgaaggc cagcttccgc ggagtttgtg cccgggcttc 1200
ccgggctctg gccgcctcac gcgcacaaat ggggctaggg gactgagtgg taagcaactc 1260
cgagtgttag acggtgatcg ggcggcgatt ccgggaaaag cgaggaaaga cacagtctgc 1320
gattgtgccg caccccccac ccacctctta gcatctggat tctgctctcg tagtgggggc 1380
cgcggaccct ccccgccaca gtccttttac tctccagcac tcccaccgcc ttccccccttc 1440 ttcagccatc tgactctcct aggggtatgt gtttttgggg gtggacggcg acgggggtgg 1500
gggatacttt ccttcccgtg gcggcaacct agttcgtatc ttattcctac aaggtagcgt 1560
cgcttcgagt cgcatggaca ttggggttta gataatttac cccccaccca agcgatttaa 1620
tggcttttaa gcaaaaggcg aatacctgga tttccatggg agggatgagg tttgaagatt 1680

-continued

```
gggattcacc cctagctcac ttccactacc aacccctctt tcttgtgagc cacttccacg   1740
ggtattcaaa tctggggggg aggggggacg ggagtattaa tatgcttctc tatttctaca   1800
cagggtcggc gtggcgaagg acggctagcc ttggagggaa agtagccacc agtccaactc   1860
gggtcgcccc caccattatt tcggtgaggg ggcaacgcta agaaggggat actggtgggt   1920
aggggcccag tataagggag ggggctgggt agtcgtcccc agaaggactc cgtgtcttgg   1980
cggggagaga gagaggcgag ccccggcttc aggggagggg ttccggggag ggagatgggg   2040
gggtggcgac gacggtgggg gggggagcgg gaagaagggg gagtcacgcc ctgcctgcaa   2100
ggggagcctc cctcaggccc ctgggagaag gggactgaat gcgtctgttc tccgctgccc   2160
ggcagaggag atctggggtc tcgagatttg cacactggat cggcaccagt ggcctgagaa   2220
agtcaggtcg gggcataagg tggagaacgt tggaagaaag agagagaacc ctttggccgc   2280
ggctcactga ccctctccct tcctcaacct ccccccttcga ggggcgtcga ggtggggggg   2340
gacgtggggc tcctgcagcc ccgcagattg agcgcctccg cctctcccag gagtctagct   2400
ttttgcccgg cttgctgcag ccactgctgc ctccctctcc ggaatccgct cggtcctctc   2460
agcgatcccc tcctcctctc ctcccctccc agtgtcaccg gggctgcttg gctctgcccc   2520
cttcgccgcc gcttgctccc tgctttcgtc cctccctctc ttgctcgctc cctcccttcg   2580
cctcctcctc cccattcccc cccacccgcg taggccgcat tctgggagtt gtagtccggt   2640
ggagcggggg ttggcgccgc ccgcggaccc agccggactc cacttcccgt cgagccctgc   2700
gaccggcacc cactccacca ggcttcgctc gcacacagac acacacacac accgctctcc   2760
ccctcactct ttcgctcgcc gcggctgctg ccagtgtgtg gctctgtctc tcctccgctt   2820
tgctgagccc tcccttcttc ctctcagttc ctagagtccg accgccgccg ccgccgagag   2880
agaggagaag gaggtcggtg gcgataaggg gcggaggggg gcatcagatc ggggcagtat   2940
taggcgggtg gcggttaaga gggagtaaga gggagcccgg gtggcggcct gagcctcccc   3000
gcggagccga cccgggaaca ggtgcgtctt ttttctctct cccccaatcc ctccacccct   3060
tttgactccc cggctttttc gtatcccccc acccgcttct ttctatctta agcctttctc   3120
caaccctgtt ccttcttttc cctgcggccg ctcggcttgc cccccggggg cgccgtcctc   3180
ttcgtgtccc cggacgtagc gctccctgga gctgggtatg tcttcgcccc tcccttcggg   3240
acagctccct tccacttccc accttcgtac cccatcccct gacttgccct accccccttct  3300
cgaccccctt ctctcttagc caggtgagac tcgttcgcca cgatccaaga gagtcttctt   3360
cccggctggg cgggggtctc catggaaacg gggtcggtt gatcctgggg gggaaaccat    3420
aggaattacc ccactcctcg gaaagggagg tggaggctat ggtcttgtta actacctgac   3480
tccaaccccc gatccaagga tccgacgatc cgaagggagg ctggctagca gggcagggcg   3540
agaaaaggct ttttttttggg gggggggggt gtccgtgatg aagtgttgaa gagaccggga  3600
gaaaatgccc tccaacctca gaggggaggt gcgacgggtg ctcttcaggg ctgctttctt   3660
cccggcgctg gggtgcggga atcgtagggt aaggggtacc cctaggtggc ggcggggcct   3720
gggttcggga gtgggagtgc tgtgatgggg gcaggggcaa ttatccgagt ccctggaaaa   3780
aaggcggggg atgacttcgg agcgccctgg ctccgctgcc ctcgctctag gggcgggggc   3840
cgccgggccg ggcgcggcgg ggaggggct taaattgaag gaagatgaga tcgggggcaa    3900
ttcatactag caccggcaag ccagagggga gatccggcgt gcaagccctc cacccgcttc   3960
gcgccaggcc tggaggcaag ggtcggcga gcgaagccga gggctggaag gagggaggct    4020
ccggttacgg ggccgggttt cgggatcagg ggcaatcccc cggcccttgg agaaggaggg   4080
```

agagggatgg ccgcgaaccc cagggctccc ccaccccggg tcctaagggg cgtgagggac 4140
ggacagcagg cccagcggag ctggattcga gcggatcgcg gccg 4184

<210> SEQ ID NO 322
<211> LENGTH: 514
<212> TYPE: DNA
<213> ORGANISM: Homo sapiens

<400> SEQUENCE: 322
cgagttggtg cgggacgtgc cgcacggcgt gcttctgctg gacaccttcc acaggcttgc 60
ctcccgcgag gtgcggctgc cccgcggctt cctcggcttc ccgtcccgcg tgctttcctg 120
gagtccctcc ttccggaggc cctcctgcct ccacgtgtgc ccttctccat gtccagcatt 180
cgggcgcctc ttgtctttct tctgttccct ggcttcggcg tccccgggag tgtgactccc 240
gcagcggggt gcagctttcc tctgggatga gtgaccggag ggaacccgcc ttcccgggca 300
cgtcgccagc ctcttcctct tcttccctag gctatcaagc ggacttatga caagaaggcg 360
gtggatctct acatgctgtt caatagcgag ctggccctgg tgaaccgtga acggaacaag 420
aaatggccag acctggagcc ctacgtggcc cagtattccg gaaaggcgcg ctgggtgcac 480
atcctccggc gtcgcatcga cagagtcatg accg 514

<210> SEQ ID NO 323
<211> LENGTH: 2097
<212> TYPE: DNA
<213> ORGANISM: Homo sapiens

<400> SEQUENCE: 323
cgaggaggct gacccggagc tggagcccgc gtcgggggga gagcaggagc cgcggcccca 60
gcaagcccag gtaggcggga gtggcccgtg gctgctctca acatccggag cggactccgg 120
gcggggagcg ctcctgccca gggctgcgag ccgcccgcga cccagggcgc tcggggcagg 180
ggtggggaaa gaaggggcgc cccgtcactt gccccctctg cagaccaagg ccgcgtccca 240
gatcctggag aatggggagg aggccccggg gcccgacccc tctctcgacc gcatgctcag 300
cagcagctcc tcggtgtcca gccttaactc ctccacggtg aggcgggagg gaggggaccc 360
gggcggccgg ggggtggacc cgttccgatg cgtagcccct gcctgcccct ccctcgccgc 420
gggacccacc gctgcagccc cccagcctgc cacctatgac ccgggtctga agcctccgcg 480
ctgcccgcgg ccccgacgtg agccctgcga gcggccctga ctcccaccca ctcccgtccg 540
cagctgagcg gcagccagat gagcctgtca ggcgacgcgg aggcggtgca ggtccgcggc 600
tccgtgcact tcgcgctgca ctacgagccg ggcgccgccg agctgcgcgt gcacgtgatc 660
cagtgccagg gcctggccgc cgcccggcgc cgccgctcgg acccgtgagt gccccgccgg 720
ccaagcgggg cgcggctgtc acagcccagc ccaccattca cagggtctcg gcctcctcgt 780
cctcatcttc aaaatgggaa caacagcgtt attgggaggc gtgcgattaa gcgagacaat 840
ccctgtaaag cgcttagcac gaggcctggc acgtgttcgg gatggtggct gggggagccc 900
acaggcaggg gagaaggctc tgggagggcc cctcctcacc tcgggttctc acctccccag 960
ctacgtcaaa agctacctcc tcccggataa gcagagcaag cgcaagacgg cggtgaagaa 1020
acggaatctg aatccggttt tcaacgagac tctccgggtg aggctgtgac cacgatgcgg 1080
ttccccgtta atgaactgga cgcccccttc ctgcggggct aggtggcaag ggcagccagt 1140
aacgtcattg cccggaggat cggcggaggg ggcccattaa ctcgttatcc agtgttgtca 1200

```
gcctcgtggt gggcgtggtg atagtgcagg tccccattaa tgcccttagg ggctccccag   1260

aattccatca tggtaggaac gcggtaggac ctgcctcagc caactcgcgc agcatctacg   1320

cgggccacca gcagtgctcc actaaagctc acctcctgtc ctcagtactc cgtcccgcag   1380

gccgagcttc agggccgcgt gctgagcctg tctgtgtggc accgcgaaag cctgggtcgc   1440

aacatctttc tgggcgaagt tgaagtgccc ctggacacgt gggactgggg ctctgagccc   1500

acctggctcc ccctgcagcc ccgggtgagg cagccaggcc gcgtggggag acctgcggcc   1560

cgggtctcct gcatttaccc caccaggctc tcccgcagcc ccctcacacc ccgccttcga   1620

cagaacctcc cctcaacctc ttaacctcat ggccccaggc gaagcccggc cggccacggc   1680

cccttccccg agggcgctag gacccctagg ttctgcccct gcaggccccg ccgtctcttc   1740

tagccgcacc ccatccgggt ctgcagaccc caccctcctg aggcccottt ccattagccc   1800

ctgctccacg ataagcccgc ctctcgcagg tcccaccctc tcccgacgac cttccgagcc   1860

gcgggttact cgccctgtcc ctcaagtacg tccccgccgg ctccgagggt gagtgacagc   1920

cggagaggcc aagctggaca cgccctgaaa agcgggagac tccagtcccc gggtttgggg   1980

gcggtggact ccatccgtgt gcgggcctga gccgagcctc tccgcaggcg caggactgcc   2040

cccgagcggg gagctgcact tctgggtgaa ggaggctcgg gacctcctgc cgctgcg      2097


<210> SEQ ID NO 324
<211> LENGTH: 2334
<212> TYPE: DNA
<213> ORGANISM: Homo sapiens

<400> SEQUENCE: 324

cgccccttc cattccccgc ccgcttccat cacttggtgt cgcccaagcc tgtggtcgcc     60

cctagcaacg ccctccctca cttcgcagtc ggtttcccct ttcatcatcg ccccccacg    120

tcccgctctt ggtctctccc gatcccgcgt ggatccggtg cttgggcgcc cccgccaacg    180

acccccgcgc acctcagcgt tggtgtcgcc cggttccccc cgcgcacgcg caccgtggta    240

tttcccgcca cgctcctaca ccgccccccc caatacctgg ttggtcacgt cccccgggag    300

gccccggatc agtatcttgc ggcggttacg gaactggcgc tcggtgtgtt ccaggcgttt    360

ccggatctct tctggatcta gaggcggcag ctcttcttcc ggcgcccggc gctccgcggc    420

atcgccggct tcgacttcgg ccccagactt agggctcagc gggggccggt gagtaacgga    480

cacgtccgcc gccatcttgg gaaacccggc gccttctggg accagcgagc cggggcggag    540

cggcatagag cggcaacgag ggcgcgcccg tcgattggct gggagaaacc ccacctcctt    600

cccgcccccc ttgccccgtt ggctaagccc cagcccacct ctcaagagtt caagctgcgt    660

ctgcgcgcca caggccccgc ccccttccgt cgcagcgacg ctactcagtg gatgtgcacc    720

tgggtgggag agacttgcag cgcgggtgga atcaaaccac agattaggga gtttgaaggc    780

tttattggtg cggaatctga gggcacagcc aagcccccgc caactttgat cccggatccc    840

agcgtcactc agctctggac ggttcttccc ccattgcttc tgtcggctgc atagacgtga    900

ggggcagata ggtgctctcc tccctaacat ggtaactgcc gctccgttgg tgctccctga    960

agacgtacat taaggccagt acgatagtca ccacgcccag ggtcagtaac accgccacga   1020

agacggggac aaagtgggag ctcccagctg tgcagagaaa gcgctaagtc aatatgcgtc   1080

ccttctgtct ccaaccccc cgcccccgg cttaccggtc cagacccgca gccccgtgtt    1140

agctcaccct caatgtccat caccacgacc agggtgtatt tgcctcgtga gctggacgct   1200

tggcactgat aagtaccatt atgtgttacg ttgacgaaga acgggatccc caccggcacc   1260
```

```
tcccggctgg agccttcctt caaacaccgc agctcggggt acgggttgcc cctggcttgg   1320
cactgcagga cgtgtctcgt tttatctttc catttcaagt gctgggggca tgtggctcgg   1380
tcaattttgg gaccatctgt ggaaccacca tgtgtgatca gacacccaac acacccgagg   1440
cacagtggtg cagaggagcg tctaatcttt ccagggcagg ggtggaggga ttaaaggtca   1500
gggtgaccga ctcacacagg actcgcagct ggacgctact gttcctgtgc aagaactcgc   1560
cgtccacctc gagagtggca ctgcagaaga agctgcgtcc gtcgtcactc tcggtagcat   1620
ttagctgaag ttgagctggc tgccccgggg ccgcggccgg aactccgtcc agcgtgacct   1680
ggactcgagc cccagccatg caactcacgg tcactgtgga cccctcatgg gcggtgggct   1740
cgctgaggtt cacaatgggt cctaggaagc ctaaaggcgg ggcattgccc aggagcttaa   1800
tgaacaggac cttcctgtgg gtcaagccgc tccctccgcc ctcccctttc ctctcgggat   1860
atccgggcca cgctttcggc cgttcaagcc tcgccctctt tccgcgctgt gtccagcttc   1920
gggcactcag gcccaaccca cgttgcaact gctattgggg caagccaggc cccacctttt   1980
cggctagtct ccgcccccctc tgccacgccc ccagactgct gaggccgcgc cccccttccca   2040
cgcctcctct tactaaagac cgtcaagttc tcccgggcct cccgtctctc gcccccctagg   2100
gtcacgttgc agacgatctc ccgggcaccc tcctgatccg cgcgcgccgt ggctgtggct   2160
gtggccgtta gcgtgtcccc gtggttcatg actgtcgcat tcagcatctg gtcccccagc   2220
gccaggtaga cctgggcctc tgaggctgga aaaagcccgt ctagggtgca gtccaccggc   2280
cacgacgttt ccacctccaa gaaccggggg gccacgaggc gcggggggggt cacg         2334
```

<210> SEQ ID NO 325
<211> LENGTH: 1481
<212> TYPE: DNA
<213> ORGANISM: Homo sapiens

<400> SEQUENCE: 325

```
cgcggcgggc cttccccatt ggccagccaa acacaaccga ctgcggcagc caataggagc     60
cgctctcctg aacattcaga ggatgggtgc gcgtggtgtg ataaggggat gttggcgcct    120
ggtacgcgcc cccctacatc tggcaagtct gtaacagaaa cagttacacc ccctacacac    180
gcacacgcgt gcccgctggc tccctcctct cagctgtaca ggccccggac aacccactgc    240
gtgtcttggc agcggcctcc caggctgcct ggggcccgcg agtgcacctg ctcactcatt    300
aagacagagc atccctttat cccaaggcgc gggtcgggta gagggtgggg gtagagggga    360
cggggtagcg gggaccggga aggcgcggct cagctgcccg ctgctcccga ggtgaaagag    420
gtgcctccgc ccccacccca tccccgcaga gttgcgttgc tccagggagg ccgaagtgat    480
ccagtgatgt cttaaggtgc agctctttgt cctccccagc tgtgctccct gcccgctgac    540
cccgtgcgct cgagccagtg ggggtgggga gcccgaaacc tataacataa acgggggcaa    600
ggagaaagaa gtctatcccg gggtggcgtg tgccgctgtc cccaccccgt ctctttcctc    660
ctgaggcttc ttccctcggg tccgtcccgg gaatgcaggc aggggagggt gtgggccgag    720
gcgcggcggc ggctggagca gcgcggtagg gtccttcgcc agagcatccg gtccgagggc    780
gcacacaggc agaaggctcg cggctcgtcc actctcctcc ctctctcctc ctctccctgg    840
cttttgtgtt ggtgcctccg agctgcaagg agggtgcgct ggaggaggag gagggggcc     900
cggagtgaga ggcacccccct tcacgcgcgc gcgcgcacac ggtgccggcg cacgcacaca    960
cgggcggaca cacacacacg cgcgcacaca cacacgcaca gagctcgctc gcctcgagcg   1020
```

cacgaacgtg gacgttctct ttgtgtggag ccctcaaggg gggttggggc cccggttcgg 1080
tccgggggag atggcgcagc ccatcctggg ccatgggagc ctgcagcccg cctcggccgc 1140
tggcctggcg tccctggagc tcgactcgtc gctggaccag tacgtgcaga ttcgcatctt 1200
caaaataatc gtgattgggg actccaacgt gggcaagacc tgcctgacct tccgcttctg 1260
cgggggtacc ttcccagaca agactgaagc caccatcggc gtggacttca gggagaagac 1320
cgtggaaatc gagggcgaga agatcaaggt gatccagggg gtcaggtcca ggaagggtgg 1380
gacccgggag gggacctcgc ccgaggcata gctctagcgg ttgtcgtcgt ccagcgtcca 1440
gcgcgtggcg gtttcgcctc ttgctgagcc gaggaccctc g 1481

<210> SEQ ID NO 326
<211> LENGTH: 1703
<212> TYPE: DNA
<213> ORGANISM: Homo sapiens

<400> SEQUENCE: 326
cgcacgcccc tcctgtctcg cgtccgtccc tccgtgcagc cggggcagga ccctgcaggg 60
gccttgcggg ccggaggtgc cggcttcctc ctccgtcccg tcccccccgc ggtgactcta 120
ttcaaatctc ccccctcccc gctgccccac cggactcagg ggctggggtc gtagcccggc 180
gggcagcggt gttcaccttc cgcataaacc tgggcttcct cgcggggcag cccccgggcc 240
ctgtgctggg tcgcagcctc gggcggttcc ctcggggcgg gacgtgtccc cgtccgtcct 300
cgcccgtccc cgccgccccc gggtcccggc ccgccccgtc ctcgcagccg caggtccgct 360
gcggcgcccg ccccctctc ccctccccgg gccttgccct gctcgtcgct ccgccccctg 420
cccggcccct gcccggcccc gccccgcgcc cgccccctgc ccgcgcccgc cccgcccct 480 gcccggcccc tgcccggccc ctgcccgccc cctgcccggc ctcccagcgg cggcggctgc 540
agcgcggcgg tccgagcggg tgcaccgcgg cggaggaggc agcatcccgc ggcgctgacg 600
gtcctgggga gagcatggcg ccgaggtgag gccggggctg cgggcagggg ttgggggacg 660
ccaagatgcg gctgcggggg tcgcgggggt cgcggggctc ggccgggtcc tgcgggggtc 720
gcgggggtcc tgcggggtct gacccgtgcc tgtcccgcgc aggtgcccct ggccatggcc 780
gcggcggcgg cgcctcctgg acgtgctcgc gcccctggtc ctgctgctcg gggtccgcgc 840
ggcctccgcg gagccaggta agacccgggc gggacgggaa ggttcgcgcc ggtgcccgcc 900
ggcctcgccg ccctggctgg ggtccccgcc cggctccctc acccccgccc cggccgctct 960
gggttcagcc ccggccctgc ccacgcgcgc aggaggcgcc ggagccggac ggagcggggc 1020
ggggtggccg gagtcccgcc cattcattct ccccgcgggg tccgggccgg gaggggtgcg 1080
cggtgcgagc ggccggagtc cccgcgcggg gaccgaacct ccgcggccgg cggggtcgtc 1140
ggtgccggga gggctcgggg cggggccgcg gggtctcggg agacgcggcc tctgtcgccg 1200
tcacggcctc gtccccgcag cgccgggtcc cgggactgac cgcgggcgga aggcggcgga 1260
gcgcggggcg tcgtctccgc gtttccaacc tgttgaggct cctcgccgcg ggccgggcct 1320
tgtgcgcctc tgtccccgcc gccctcaggc ctctgtcccc gcgcccgccg tggtgtcggg 1380
ttgcgcggtc ccctttgatg ccaaccgagc gccgcgcggt ccgagaacaa tgcccagaag 1440
ccgctgcccc gccggcctcg ccgcttcccg tgcgcggcaa acggtgcgcg gggcccgtgg 1500
ggaccttcct gcctccaacc ccgggaccca gttccccacc acctgctaac cggggcctcc 1560
tgcctccagc cagcccagca gaggcccggg ggaggcggcg gggacgcgga ccccagggga 1620
gccccgccca aagggcctgg gtgccttgtc gcgggtggaa tcccacccgg gggtccacgc 1680
agccagcgcc tgcctccgac tcg 1703

<210> SEQ ID NO 327
<211> LENGTH: 699
<212> TYPE: DNA
<213> ORGANISM: Homo sapiens

<400> SEQUENCE: 327
cgaggacagg gcccggcccc accccggggc gagtacgagt ttggaagcag tgagggcgca 60
gagtggggct ccatctgggg agaggcctct ctctgtcacc cggccccgtg cggcagttca 120
gggtcccagc atctcccctg cactgggagg cggcagccgt gcccgggggg cgcccgtggt 180
gggcgggtgc aagagagaag ggcgtcgggt gtgcaagcac caccggcctc ccattaacag 240
cctgcccggg ctccgcccac aggagccact gtccacgtaa cctgcgtctc tttctttcaa 300
ggaaaagaga agccagccat ggccaggacc agcagcaggg ccccctgctc acccacctcg 360
gtgtcggatg tggactcgga cgcactgtca cggggaaact tcgaggtggg gtttcggcct 420
cagaggtccg taaaagccga gagagcgcag cagcctgagg ctggcgagga cagacggcca 480
gctggcgggg cctcagacgt ggaggcagtg acccgactgg ccaggtccaa aggggtcggc 540
ccagccttgt cccccggccc agccggattc cagagctgca gccccggctg gtgcagcgcc 600
ttctacgagg ccgactgctt cggggccgac gtccacaact acgtgaagga cctggggcgg 660
cagcaggcgg acggggccct gcccgacgcc cagagcccg 699

<210> SEQ ID NO 328
<211> LENGTH: 1442
<212> TYPE: DNA
<213> ORGANISM: Homo sapiens

<400> SEQUENCE: 328
cgaatgcagc atccctgcgc tcggcgccct gctattggcc agagatgatc tcaccgcctc 60
ccggcctgcg cgcgcctgat tggccggtgc ggggatgctg cgctccgccg ccggcggggc 120
agtccttcag gcgggctccg cgagcgtgtg tgagcctggg ggagcgaaga gccgacgcgc 180
ctggcatctc ccagggggct caggggcag gagcgcggag acccccggac agggtcttaa 240 cccctcccg ccagcccgag cccagcatcc cctccagctc ccctcggcgt cccaacccca 300
agcaaagcca tccccaaagg atgctccgca gagaggcggg gtccgggtcc tcccctccac 360
ccccttccgt ttaaccctct caccgccgcg gcgccgtcct gcactgcccg gccagctggg 420
ctgggagaga cccgcgcccc aggcatgtcc aagcccacct agagggcggg agggtggcgg 480
gcgctctggc cccaaccctg gcatccgaag catccccgc gtttcctgct cctcactcag 540
tcttcagatc ccagtccggc gccccggta caatggggag ccagggtgcc caggtcagcc 600
gcaagggcca gcgtaccagg cggaggaccg gcaggacgcc ggagacccca tctcccagtc 660 cccctgccc cagctctctc cctcctgcgg aggaggcaga aacggaccgg catctaccgc 720
agcccagagt cccaggagtg gccgccgaac cctcaccccg cggagcgcct gggcgcccag 780
aggtgaggct ggggtgaccc cgcccctcc ccgggtcggc cgggcccagc ccagcccgac 840
cctgccgggc gccgctgagc tgcagctccc cggctggctc tagggccccg ggcggagcgg 900
ccgggggtcc cagcccggcg cgcgtggcgg gggccgagcc gcccccctcac ctgcacctgc 960 acgaaggagc cgcggtagaa gcagcaggcg gcggccgaca gggcactcca caggctgcac 1020

-continued

```
cgctcggtca tggtggggcc aggctgccgg ggccgggacg gtgtgggggg gcggtggccg   1080

gcggggcagg ggcgcaggga ccaaccggct aggcaccggc tgcgcgtgcc tctcagcggc   1140

gcgattacct catcgccttg tcgggggagg agcggggagg cggggcgggg agaccccacc   1200

ctccagccgg ccaggggagg ggagggggcc attgttcctc cctccgcccg ccccccgctc   1260

ccagcccctc gccccccgcc ctccagttcc gcgcgctcgg gctgcctgga gctgcgggcg   1320

cggagcggag gacctgccaa ggagggtatt accgggggca gcgggatcgg gtggggaccc   1380

atgggccagc gaggggaggt tctgcctccc ccactcgccg cacctctaac agaccgggag   1440

cg                                                                  1442


<210> SEQ ID NO 329
<211> LENGTH: 690
<212> TYPE: DNA
<213> ORGANISM: Homo sapiens

<400> SEQUENCE: 329

cgcctgcgcg agtcaggacg agcgcttgcc ccagatcttg acgtttcagg cggcccctcc     60

taatccggaa cacgactcac attccgttgg tcttgccttg acagacgtga ccctgaccca    120

ataagggtgg aaggctgagt cccgcagagc caataacgag agtccgagag gcgacggagg    180

cggactctgt gaggaaacaa gaagagaggc ccaagatgga gacggcggcg gctgtagcgg    240

cgtgacaggt gagggcgggc ccgggagggc tcggtttctg gagcggctgc cgggcacggg    300

cagggagccc ggaccgaaag ctcagctcca ggatggctgc gcttgggccc cggcgttccc    360

tgcccggaac cggaggagtg gtttgacccg gggcgagacc atcgtcgaca gcgggggtgg    420

ggtgggtaac aggaataggc gggcaaggct gcgggtgatg gtttcgcccg ctgctagtgg    480

tggtgcgcct gcgcagagcc ggaagccctt tggtaggcgg gacccgaccg agtggtgccg    540

ggattccgtc ttaacccccg ctaaggtgtc caatgacctt tccttaccaa ctgcggggag    600

tgtgtggaaa cgcggttcac tccccggttt ccttattctg gatcagtgtc tgaccgcccc    660

cgccgggaga atgtcaggat tctcgcctct                                     690
```